US008741614B2

(12) United States Patent      (10) Patent No.: US 8,741,614 B2
Stephan et al.      (45) Date of Patent: Jun. 3, 2014

(54) CRYSTAL STRUCTURE OF ISOGLUTAMINYL CYCLASE

(75) Inventors: Anett Stephan, Halle/Saale (DE); Stephan Schilling, Halle/Saale (DE); Jens-Ulrich Rahfeld, Mansfelder Land (DE); Michael Wermann, Halle/Saale (DE); Christoph Parthier, Halle/Saale (DE); Hans-Ulrich Demuth, Halle/Saale (DE); David Ruiz-Carillo, Singapore (SG); Milton T. Stubbs, Halle/Saale (DE)

(73) Assignee: Probiodrug AG, Halle (Saale) (DE)

( * ) Notice: Subject to any disclaimer, the term of this patent is extended or adjusted under 35 U.S.C. 154(b) by 0 days.

(21) Appl. No.: 13/283,676

(22) Filed: Oct. 28, 2011

(65) Prior Publication Data

US 2012/0108449 A1    May 3, 2012

Related U.S. Application Data

(60) Provisional application No. 61/409,200, filed on Nov. 2, 2010.

(51) Int. Cl.
*C12N 9/00*      (2006.01)
*G01N 31/00*      (2006.01)

(52) U.S. Cl.
USPC .............................................. 435/183; 436/4

(58) Field of Classification Search
USPC .............................................. 435/183; 436/4
See application file for complete search history.

(56) References Cited

U.S. PATENT DOCUMENTS

| 7,572,614 | B2 | 8/2009 | Wang et al. |
| 2007/0202586 | A1 | 8/2007 | Wang et al. |
| 2009/0203045 | A1 | 8/2009 | Wang et al. |

FOREIGN PATENT DOCUMENTS

| WO | WO 2008/034891 | 3/2008 |
| WO | WO 2008/087197 | 7/2008 |
| WO | WO 2010/026209 | 3/2010 |

OTHER PUBLICATIONS

McPherson, A. Current Approaches to Macromolecular Crystallization. European Journal of Biochemistry. 1990. vol. 189, pp. 1- 23.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Moon et al., "A synergistic approach to protein crystallization: Combination of a fixed-arm carrier with surface entropy reduction", Protein Science, 2010, 19:901-913.*
Balbes et al., A Perspective of Modern Methods in Computer-Aided Drug Design, in Reviews in Computational Chemistry, 1994, pp. 337-380, vol. 5, Lipkowitz and Boyd, Eds., VCH, New York.
Bateman et al., Evidence for Essential Histidines in Human Pituitary Glutaminyl Cyclase, Biochemistry, 2001, pp. 11246-11250, vol. 40.
Bockers et al., Glutaminyl-Cyclase Expression in the Bovine/Porcine Hypothalamus and Pituitary, J Neuroendocrinol, 1995, pp. 445-453, vol. 7.
Böhm, The Computer Program LUDI: A New Method for the De Novo Design of Enzyme Inhibitors, in Journal of Computer-Aided Molecular Design, 1992, pp. 61-78, vol. 6.
Bricogne, Bayesian Statistical Viewpoint on Structure Determination: Basic Concepts and Examples, in Methods in Enzymology, 1997, pp. 361-423, vol. 276.
Brunger et al., Crystallography & NMR System: A New Software Suite for Macromolecular Structure Determination, Acta Cryst, 1998, pp. 905-921, vol. 54.
Busby et al., An Enzyme(s) That Converts Glutaminyl-peptides into Pyroglutamyl-peptides, in the Journal of Biological Chemistry, 1987, pp. 8532-8536, vol. 262, No. 18.
Cohen et al., Molecular Modeling Software and Methods for Medicinal Chemistry, Journal of Medicinal Chemistry, 1990, pp. 883-894, vol. 33, No. 3.
Consalvo et al., A Rapid Fluorometric Assay for N-Terminal Glutaminyl Cyclase Activity Using High-Performance Liquid Chromatography, Analytical Biochemistry, 1988, pp. 131-138, vol. 175.
Dahl et al., *Carica papaya* Glutamine Cyclotransferase Belongs to a Novel Plant Enzyme Subfamily: Cloning and Characterization of the Recombinant Enzyme, Protein Expression and Purification, 2000, pp. 27-36, vol. 20.
Eisen et al., HOOK: A Program for Finding Novel Molecular Architectures that Satisfy the Chemical and Steric Requirements of a Macromolecule Binding Site, Proteins: Structure, Function, and Genetics, 1994, pp. 199-221, vol. 19.
El Moussaoui et al., Revisiting the enzymes stored in the laticifers of *Carica papaya* in the context of their possible participation in the plant defence mechanism, CMLS Cellular and Molecular Life Sciences, 2001, pp. 556-570, vol. 56.
Fischer et al., Identification of a mammalian glutaminyl cyclase converting glutaminyl into pyroglutamyl peptides, Pro. Natl. Acad. Sci. USA, 1987, pp. 3628-3632, vol. 84.
Gillet et al., SPROUT: A Program for Structure Generation, Journal of Computer-Aided Molecular Design, 1993, pp. 127-153, vol. 7.
Goodford, A Computational Procedure for Determining Energetically Favorable Binding Sites on Biologically Important Macromolecules, in Journal of Medicinal Chemistry, 1985, pp. 849-857, vol. 28.
Goodsell et al., Automated Docking of Substrates to Proteins by Simulated Annealing, Proteins: Structure, Function, and Genetics, 1990, pp. 195-202, vol. 8.

(Continued)

*Primary Examiner* — Suzanne M Noakes
(74) *Attorney, Agent, or Firm* — Dentons US LLP

(57) ABSTRACT

A crystal comprising human isoglutaminyl cyclase having a characterized space group of P1211 and unit cell dimensions of +/−5% of a=126.51 Å, b=109.68 Å, c=159.53 Å, α=90.0°, β=104.9° and γ=90.0°.

10 Claims, 412 Drawing Sheets

(56) References Cited

OTHER PUBLICATIONS

Guida, Software for Structure-Based Drug Design, Current Opinion in Structural Biology, 1994, pp. 777-781, vol. 4.

Hannig et al., Strategies for optimizing heterologous protein expression in *Escherichia coli*, Trends in Biotechnology, 1998, pp. 54-60, vol. 16.

Huang et al., Crystal structures of human glutaminyl cyclase, an enzyme responsible for protein N-terminal pyroglutamate formation, PNAS, Sep. 2005, pp. 13117-13122, vol. 102, No. 37.

Huang et al., Cloning, expression, characterization, and crystallization of a glutaminyl cyclase from human bone marrow: a single zinc metalloenzyme, Protein Expression & Purification, 2005, pp. 65-72, vol. 43.

Huang et al., Structures of Human Golgi-resident Glutaminyl Cyclase and Its Complexes with Inhibitors Reveal a Large Loop Movement upon Inhibitor Binding, Journal Biological Chemistry, Apr. 2011, pp. 12439-12449, vol. 286, No. 14.

Johnson et al., Phylogenetic Relationships from Three-Dimensional Protein Structures, Methods in Enzymology, 1990, pp. 670-690, vol. 183.

Kuntz et al., A Geometric Approach to Macromolecule-Ligand Interactions, Journal of Molecular Biology, 1982, pp. 269-288.

Lattman, Use of the Rotation and Translation Functions, in Methods in Enzymology, 1985. pp. 55-77, vol. 115.

Lauri et al., CAVEAT: A Program to Facilitate the Design of Organic Molecules, Journal of Computer-Aided Molecular Design, 1994, pp. 51-66, vol. 8.

Martin, 3D Database Searching in Drug Design, Journal of Medicinal Chemistry, 1992, pp. 2145-2154, vol. 35, No. 12.

McPherson, Current approaches to macromolecular crystallization, Eur J Biochem 1990, pp. 1-23, vol. 189.

Meng et al., Automated Docking with Grid-Based Energy Evaluation, Journal of Computational Chemistry, 1992, pp. 505-524, vol. 13, No. 4.

Messer, Enzymatic Cyclization of L-Glutamine and L-Glutaminyl Peptides, Nature, 1963, p. 1299, vol. 197, No. 4874.

Miranker et al., Functionality Maps of Binding Sites: a Multiple Copy Simultaneous Search Method, Proteins: Structure, Function and Genetics, 1991, pp. 29-34, vol. 11.

Murshudov et al., Refinement of Macromolecular Structures by the Maximum-Likelihood Method, Acta Cryst., 1997, pp. 240-255, vol. D53.

Navia et al., Use of Structural Information in Drug Design, Current Opinions in Structural Biology, 1992, pp. 202-210, vol. 2.

Nishibata et al., Automatic Creation of Drug Candidate Structures based on Receptor Structure. Starting Point for Artificial Lead Generation, in Tetrahedron, 1991, pp. 8985-8990, vol. 47, No. 43.

Pohl et al, Primary structure and functional expression of a glutaminyl cyclase, Proc in Natl Acad Sci USA, 1991, pp. 10059-10063, vol. 88.

Ruiz-Carrillo et al., Structures of Glycosylated Mammalian Glutaminyl Cyclases Reveal Conformational Variability near the Active Center, Biochemistry, 2011, pp. 6280-6288, vol. 50.

Song et al., Molecular cloning, sequence analysis and expression of human pituitary glutaminyl cyclase, in Journal of Molecular Endocrinology, 1994, pp. 77-86, vol. 13.

Stephan et al., Mammalian glutaminyl cyclases and their isoenzymes have identical enzymatic characteristics, FEBS J, 2009, pp. 6522-6536, vol. 276.

Tronrud et al., An efficient general-purpose least-squares refinement program for macromolecular structures, Acta Cryst, 1987, pp. 489-501, vol. A43.

Weber, Physical Principles of Protein Crystallization, Adv Protein Chem, 1991, pp. 1-36, vol. 41.

Yu et al., Substrate and Inhibitor Specificity of Glutamine Cyclotransferase (QC), Biol. Chem. Hoppe-Seyler, 1996, pp. 395-398, vol. 377.

* cited by examiner

FIGURE 1 (CO-ORDINATES)

```
ATOM      1  CB  GLN A  87     -27.792 -43.643 -50.760  1.00 50.17           C
ATOM      2  CG  GLN A  87     -27.496 -44.445 -52.009  1.00 47.30           C
ATOM      3  CD  GLN A  87     -26.008 -44.582 -52.271  1.00 45.41           C
ATOM      4  NE2 GLN A  87     -25.219 -44.709 -51.197  1.00 44.63           N
ATOM      5  OE1 GLN A  87     -25.565 -44.567 -53.427  1.00 45.44           O
TER       6      GLN A  87
ATOM      7  CB  ALA A 261     -29.285 -18.883 -61.734  1.00 36.70           C
TER       8      ALA A 261
ATOM      9  CB  ASN A 303     -43.642 -51.929 -47.362  1.00 50.93           C
ATOM     10  CG  ASN A 303     -44.018 -52.189 -45.930  1.00 49.98           C
ATOM     11  ND2 ASN A 303     -43.094 -52.795 -45.184  1.00 48.99           N
ATOM     12  OD1 ASN A 303     -45.134 -51.871 -45.493  1.00 49.14           O
TER      13      ASN A 303
ATOM     14  CB  VAL A 312     -53.025 -38.721 -49.206  1.00 53.79           C
TER      15      VAL A 312
ATOM     16  CB  PHE A 321     -56.041 -18.643 -50.071  1.00 46.64           C
ATOM     17  CG  PHE A 321     -56.083 -17.458 -50.949  1.00 46.03           C
ATOM     18  CD1 PHE A 321     -55.572 -17.518 -52.235  1.00 45.21           C
ATOM     19  CD2 PHE A 321     -56.630 -16.270 -50.499  1.00 45.52           C
ATOM     20  CE1 PHE A 321     -55.581 -16.402 -53.051  1.00 45.17           C
ATOM     21  CE2 PHE A 321     -56.647 -15.148 -51.315  1.00 45.32           C
ATOM     22  CZ  PHE A 321     -56.120 -15.215 -52.592  1.00 45.13           C
TER      23      PHE A 321
ATOM     24  CB  GLN B  87     -24.551   2.001   4.265  1.00 50.21           C
ATOM     25  CG  GLN B  87     -23.753   2.758   3.182  1.00 47.95           C
ATOM     26  CD  GLN B  87     -24.420   2.762   1.811  1.00 45.96           C
ATOM     27  NE2 GLN B  87     -23.714   3.284   0.801  1.00 44.50           N
ATOM     28  OE1 GLN B  87     -25.550   2.295   1.660  1.00 45.74           O
TER      29      GLN B  87
ATOM     30  CB  ALA B 261     -50.120  -2.244  -4.127  1.00 36.66           C
TER      31      ALA B 261
ATOM     32  CB  ASN B 303     -14.138 -12.880   5.964  1.00 50.73           C
ATOM     33  CG  ASN B 303     -13.709 -11.862   7.067  1.00 45.24           C
ATOM     34  ND2 ASN B 303     -12.699 -11.033   6.764  1.00 41.14           N
ATOM     35  OD1 ASN B 303     -14.289 -11.822   8.164  1.00 42.59           O
TER      36      ASN B 303
ATOM     37  CB  VAL B 312     -26.195 -23.787   4.746  1.00 53.80           C
TER      38      VAL B 312
ATOM     39  CB  PHE B 321     -45.784 -29.291   5.640  1.00 46.31           C
ATOM     40  CG  PHE B 321     -46.854 -29.454   4.631  1.00 35.66           C
ATOM     41  CD1 PHE B 321     -48.090 -30.011   4.954  1.00 28.69           C
ATOM     42  CD2 PHE B 321     -46.634 -28.972   3.337  1.00 27.86           C
ATOM     43  CE1 PHE B 321     -49.092 -30.114   3.978  1.00 23.92           C
ATOM     44  CE2 PHE B 321     -47.611 -29.061   2.374  1.00 23.64           C
ATOM     45  CZ  PHE B 321     -48.848 -29.638   2.687  1.00 22.22           C
TER      46      PHE B 321
ATOM     47  CB  GLN C  87     -77.736 -23.835 -17.805  1.00 50.19           C
ATOM     48  CG  GLN C  87     -79.000 -24.543 -18.238  1.00 47.62           C
ATOM     49  CD  GLN C  87     -79.515 -24.031 -19.550  1.00 44.96           C
ATOM     50  NE2 GLN C  87     -80.691 -23.419 -19.529  1.00 44.19           N
ATOM     51  OE1 GLN C  87     -78.867 -24.190 -20.579  1.00 44.12           O
TER      52      GLN C  87
ATOM     53  CB  ALA C 261     -59.474 -38.467 -31.584  1.00 36.67           C
TER      54      ALA C 261
ATOM     55  CB  ASN C 303     -73.645  -6.174 -15.322  1.00 50.98           C
TER      56      ASN C 303
ATOM     57  CB  VAL C 312     -58.089  -7.196 -19.889  1.00 53.79           C
TER      58      VAL C 312
ATOM     59  CB  PHE C 321     -40.859 -17.542 -23.339  1.00 46.58           C
ATOM     60  CG  PHE C 321     -40.015 -18.444 -24.197  1.00 44.35           C
ATOM     61  CD1 PHE C 321     -40.463 -18.890 -25.440  1.00 42.02           C
ATOM     62  CD2 PHE C 321     -38.751 -18.834 -23.774  1.00 42.22           C
ATOM     63  CE1 PHE C 321     -39.678 -19.729 -26.228  1.00 39.81           C
ATOM     64  CE2 PHE C 321     -37.964 -19.668 -24.566  1.00 40.34           C
ATOM     65  CZ  PHE C 321     -38.431 -20.110 -25.792  1.00 39.16           C
```

FIGURE 1 (cont'd)

```
TER      66          PHE C  321
ATOM     67    CB    GLN D   87    -54.317  -76.878  -14.273  1.00 50.23           C
ATOM     68    CG    GLN D   87    -55.420  -77.208  -13.275  1.00 49.08           C
ATOM     69    CD    GLN D   87    -55.184  -76.654  -11.891  1.00 48.74           C
ATOM     70    NE2   GLN D   87    -56.024  -77.072  -10.939  1.00 48.37           N
ATOM     71    OE1   GLN D   87    -54.262  -75.860  -11.671  1.00 48.35           O
TER      72          GLN D   87
ATOM     73    CB    ALA D  261    -37.076  -57.542   -5.793  1.00 36.67           C
TER      74          ALA D  261
ATOM     75    CB    ASN D  303    -46.682  -92.906  -18.655  1.00 50.99           C
TER      76          ASN D  303
ATOM     77    CB    VAL D  312    -31.268  -87.719  -18.808  1.00 53.83           C
TER      78          VAL D  312
ATOM     79    CB    PHE D  321    -17.015  -73.193  -19.993  1.00 46.67           C
ATOM     80    CG    PHE D  321    -16.170  -72.349  -19.096  1.00 46.13           C
ATOM     81    CD1   PHE D  321    -16.484  -72.238  -17.742  1.00 44.75           C
ATOM     82    CD2   PHE D  321    -15.058  -71.679  -19.581  1.00 45.54           C
ATOM     83    CE1   PHE D  321    -15.727  -71.460  -16.902  1.00 44.11           C
ATOM     84    CE2   PHE D  321    -14.283  -70.899  -18.728  1.00 44.89           C
ATOM     85    CZ    PHE D  321    -14.623  -70.792  -17.390  1.00 44.37           C
TER      86          PHE D  321
ATOM     87    CB    GLN E   87    -47.415   11.135  -75.093  1.00 50.22           C
ATOM     88    CG    GLN E   87    -47.247   12.388  -75.922  1.00 48.19           C
ATOM     89    CD    GLN E   87    -48.038   12.335  -77.194  1.00 46.45           C
ATOM     90    NE2   GLN E   87    -47.379   12.645  -78.303  1.00 46.35           N
ATOM     91    OE1   GLN E   87    -49.231   12.018  -77.191  1.00 45.62           O
TER      92          GLN E   87
ATOM     93    CB    ALA E  261    -66.971   -4.309  -86.044  1.00 36.69           C
TER      94          ALA E  261
ATOM     95    CB    ASN E  303    -30.739    3.766  -74.582  1.00 50.97           C
TER      96          ASN E  303
ATOM     97    CB    VAL E  312    -35.333  -11.490  -78.110  1.00 53.81           C
TER      98          VAL E  312
ATOM     99    CB    PHE E  321    -49.210  -26.431  -79.419  1.00 46.68           C
TER     100          PHE E  321
ATOM    101    CB    GLN F   87     -3.679  -43.800    3.912  1.00 50.26           C
TER     102          GLN F   87
ATOM    103    CB    ALA F  261      3.303  -67.707   14.833  1.00 36.75           C
TER     104          ALA F  261
ATOM    105    CB    ASN F  303    -21.391  -39.534    4.659  1.00 51.02           C
TER     106          ASN F  303
ATOM    107    CB    VAL F  312    -26.692  -54.331    8.971  1.00 53.83           C
TER     108          VAL F  312
ATOM    109    CB    PHE F  321    -24.701  -74.585   10.553  1.00 46.67           C
TER     110          PHE F  321
ATOM    111    CB    GLN G   87    -35.103  -51.762   35.910  1.00 50.29           C
ATOM    112    CG    GLN G   87    -35.307  -53.006   35.044  1.00 50.35           C
ATOM    113    CD    GLN G   87    -34.938  -52.805   33.592  1.00 51.24           C
ATOM    114    NE2   GLN G   87    -35.895  -53.043   32.701  1.00 50.87           N
ATOM    115    OE1   GLN G   87    -33.800  -52.461   33.271  1.00 51.76           O
TER     116          GLN G   87
ATOM    117    CB    ALA G  261    -24.018  -31.224   21.829  1.00 36.69           C
TER     118          ALA G  261
ATOM    119    CB    ASN G  303    -52.606  -49.589   40.719  1.00 51.01           C
TER     120          ASN G  303
ATOM    121    CB    VAL G  312    -53.624  -33.745   37.194  1.00 53.83           C
TER     122          VAL G  312
ATOM    123    CB    PHE G  321    -45.453  -15.381   33.693  1.00 46.67           C
ATOM    124    CG    PHE G  321    -44.880  -14.439   32.669  1.00 46.71           C
ATOM    125    CD1   PHE G  321    -44.451  -13.167   33.036  1.00 46.58           C
ATOM    126    CD2   PHE G  321    -44.758  -14.811   31.344  1.00 45.95           C
ATOM    127    CE1   PHE G  321    -43.915  -12.281   32.089  1.00 45.37           C
ATOM    128    CE2   PHE G  321    -44.210  -13.931   30.410  1.00 45.61           C
ATOM    129    CZ    PHE G  321    -43.799  -12.668   30.788  1.00 44.88           C
TER     130          PHE G  321
```

FIGURE 1 (cont'd)

```
ATOM    131  CB  GLN H  87      -4.973 -89.608 -50.822  1.00 50.31           C
ATOM    132  CG  GLN H  87      -3.825 -89.469 -49.830  1.00 50.78           C
ATOM    133  CD  GLN H  87      -4.105 -90.090 -48.483  1.00 52.28           C
ATOM    134  NE2 GLN H  87      -3.210 -89.843 -47.535  1.00 52.63           N
ATOM    135  OE1 GLN H  87      -5.100 -90.796 -48.293  1.00 52.45           O
TER     136      GLN H  87
ATOM    137  CB  ALA H 261     -27.434 -90.901 -35.536  1.00 36.71           C
TER     138      ALA H 261
ATOM    139  CB  ASN H 303       0.362 -72.886 -55.834  1.00 50.99           C
TER     140      ASN H 303
ATOM    141  CB  VAL H 312     -13.289 -65.191 -51.495  1.00 53.82           C
TER     142      VAL H 312
ATOM    143  CB  PHE H 321     -33.184 -64.718 -46.938  1.00 46.70           C
TER     144      PHE H 321
ATOM    145  CB  GLN I  87       3.557 -45.752 -32.209  1.00 50.27           C
TER     146      GLN I  87
ATOM    147  CB  ALA I 261      22.212 -34.275 -48.307  1.00 36.69           C
TER     148      ALA I 261
ATOM    149  CB  ASN I 303     -10.435 -35.081 -27.214  1.00 51.03           C
TER     150      ASN I 303
ATOM    151  CB  VAL I 312      -3.902 -21.012 -32.116  1.00 53.85           C
TER     152      VAL I 312
ATOM    153  CB  PHE I 321      11.943  -9.252 -37.490  1.00 46.70           C
TER     154      PHE I 321
ATOM    155  CB  GLN J  87     -23.847  -5.527 -87.859  1.00 50.27           C
TER     156      GLN J  87
ATOM    157  CB  ALA J 261     -16.377 -28.976 -99.404  1.00 36.71           C
TER     158      ALA J 261
ATOM    159  CB  ASN J 303     -11.260   7.789 -87.973  1.00 51.05           C
TER     160      ASN J 303
ATOM    161  CB  VAL J 312       1.347  -1.551 -92.321  1.00 53.85           C
TER     162      VAL J 312
ATOM    163  CB  PHE J 321      10.748 -19.559 -94.336  1.00 46.68           C
TER     164      PHE J 321
ATOM    165  CB  GLN K  87      35.258  -4.588 -70.113  1.00 50.43           C
ATOM    166  CG  GLN K  87      36.029  -4.400 -71.387  1.00 54.98           C
ATOM    167  CD  GLN K  87      35.157  -3.896 -72.502  1.00 60.03           C
ATOM    168  NE2 GLN K  87      35.148  -4.621 -73.616  1.00 61.00           N
ATOM    169  OE1 GLN K  87      34.500  -2.862 -72.371  1.00 61.15           O
TER     170      GLN K  87
ATOM    171  CB  ALA K 261       9.857   1.578 -77.337  1.00 36.73           C
TER     172      ALA K 261
ATOM    173  CB  ASN K 303      38.672 -22.259 -66.666  1.00 51.03           C
TER     174      ASN K 303
ATOM    175  CB  VAL K 312      23.111 -27.031 -66.196  1.00 53.83           C
TER     176      VAL K 312
ATOM    177  CB  PHE K 321       3.110 -23.499 -64.086  1.00 46.70           C
TER     178      PHE K 321
ATOM    179  ZN  ZN  L 121     -39.948 -19.657 -36.121  1.00 13.08          ZN
ATOM    180  ZN  ZN  M 121     -45.246 -14.153  20.542  1.00 10.95          ZN
ATOM    181  ZN  ZN  N 121     -49.388 -29.145  -7.384  1.00  4.73          ZN
ATOM    182  ZN  ZN  O 121     -32.404 -64.639 -32.240  1.00 18.99          ZN
ATOM    183  ZN  ZN  P 121     -56.702 -15.549 -62.975  1.00  7.27          ZN
ATOM    184  ZN  ZN  Q 121     -13.489 -70.900  -7.041  1.00 15.72          ZN
ATOM    185  ZN  ZN  R 121     -31.545 -23.306  47.399  1.00 36.87          ZN
ATOM    186  ZN  ZN  S 121     -32.794 -80.764 -60.838  1.00 27.72          ZN
ATOM    187  ZN  ZN  T 121      21.103 -22.133 -23.209  1.00 59.72          ZN
ATOM    188  ZN  ZN  U 121      -0.876 -23.160 -76.847  1.00 42.26          ZN
ATOM    189  ZN  ZN  V 121      11.335  -8.672 -51.172  1.00 80.71          ZN
TER     190      ZN  V 121
ATOM    191  CA  MBI W   1     -49.115 -17.258 -38.943  1.00 74.42           C
ATOM    192  NA  MBI W   1     -46.798 -16.971 -40.479  1.00 69.48           N
ATOM    193  OA  MBI W   1     -51.726 -19.241 -37.243  1.00 79.05           O
ATOM    194  CB  MBI W   1     -50.279 -17.486 -38.173  1.00 73.43           C
ATOM    195  NB  MBI W   1     -48.596 -16.073 -39.267  1.00 73.00           N
```

FIGURE 1 (cont'd)

```
ATOM    196  OB   MBI W    1     -50.024 -21.243 -38.411  1.00 87.42          O
ATOM    197  CG   MBI W    1     -50.631 -18.844 -37.964  1.00 76.80          C
ATOM    198  CD   MBI W    1     -47.479 -15.936 -40.007  1.00 70.67          C
ATOM    199  ND   MBI W    1     -42.290 -17.721 -39.699  1.00 68.01          N
ATOM    200  CE   MBI W    1     -48.376 -18.293 -39.454  1.00 78.27          C
ATOM    201  CH   MBI W    1     -48.723 -19.598 -39.247  1.00 81.26          C
ATOM    202  CI   MBI W    1     -41.019 -17.403 -39.426  1.00 73.28          C
ATOM    203  CJ   MBI W    1     -45.603 -16.753 -41.270  1.00 70.15          C
ATOM    204  CK   MBI W    1     -52.049 -18.922 -35.911  1.00 80.98          C
ATOM    205  CL   MBI W    1     -49.837 -19.882 -38.511  1.00 81.14          C
ATOM    206  CM   MBI W    1     -49.555 -22.263 -39.325  1.00 89.39          C
ATOM    207  CN   MBI W    1     -43.403 -16.862 -40.155  1.00 67.43          C
ATOM    208  CC   MBI W    1     -40.406 -18.576 -39.041  1.00 75.02          C
ATOM    209  CF   MBI W    1     -42.472 -19.013 -39.500  1.00 67.43          C
ATOM    210  CO   MBI W    1     -44.481 -17.703 -40.838  1.00 68.27          C
ATOM    211  NC   MBI W    1     -41.330 -19.572 -39.093  1.00 70.88          N
ATOM    212  S    MBI W    1     -46.934 -14.499 -40.343  1.00 70.77          S
ATOM    213  CA   MBI X    1     -46.364 -22.951  18.369  1.00 74.42          C
ATOM    214  NA   MBI X    1     -49.083 -20.750  17.659  1.00 69.46          N
ATOM    215  OA   MBI X    1     -43.739 -24.373  16.196  1.00 79.04          O
ATOM    216  CB   MBI X    1     -45.657 -23.182  17.166  1.00 73.46          C
ATOM    217  NB   MBI X    1     -47.444 -22.184  18.524  1.00 73.00          N
ATOM    218  OB   MBI X    1     -43.126 -25.466  18.786  1.00 87.42          O
ATOM    219  CG   MBI X    1     -44.533 -24.043  17.263  1.00 76.82          C
ATOM    220  CD   MBI X    1     -48.009 -21.512  17.504  1.00 70.69          C
ATOM    221  ND   MBI X    1     -47.106 -17.290  17.008  1.00 68.03          N
ATOM    222  CE   MBI X    1     -45.982 -23.526  19.553  1.00 78.27          C
ATOM    223  CH   MBI X    1     -44.898 -24.354  19.634  1.00 81.29          C
ATOM    224  CI   MBI X    1     -47.668 -16.110  16.722  1.00 73.30          C
ATOM    225  CJ   MBI X    1     -49.646 -20.051  16.520  1.00 70.14          C
ATOM    226  CK   MBI X    1     -42.336 -24.306  16.107  1.00 80.95          C
ATOM    227  CL   MBI X    1     -44.175 -24.616  18.507  1.00 81.17          C
ATOM    228  CM   MBI X    1     -42.180 -25.364  19.875  1.00 89.39          C
ATOM    229  CN   MBI X    1     -47.628 -18.659  16.811  1.00 67.42          C
ATOM    230  CC   MBI X    1     -46.757 -15.150  17.105  1.00 75.00          C
ATOM    231  CF   MBI X    1     -45.914 -17.092  17.539  1.00 67.45          C
ATOM    232  CO   MBI X    1     -49.111 -18.618  16.441  1.00 68.28          C
ATOM    233  NC   MBI X    1     -45.666 -15.783  17.614  1.00 70.89          N
ATOM    234  S    MBI X    1     -47.395 -21.615  16.059  1.00 70.75          S
ATOM    235  CA   MBI Y    1     -43.184 -23.028 -12.385  1.00 74.40          C
ATOM    236  NA   MBI Y    1     -43.592 -25.664 -11.611  1.00 69.48          N
ATOM    237  OA   MBI Y    1     -43.736 -21.758  -8.961  1.00 79.05          O
ATOM    238  CB   MBI Y    1     -43.464 -23.102 -11.001  1.00 73.42          C
ATOM    239  NB   MBI Y    1     -43.114 -24.048 -13.240  1.00 72.99          N
ATOM    240  OB   MBI Y    1     -43.206 -19.374 -10.479  1.00 87.42          O
ATOM    241  CG   MBI Y    1     -43.482 -21.867 -10.303  1.00 76.81          C
ATOM    242  CD   MBI Y    1     -43.312 -25.325 -12.862  1.00 70.68          C
ATOM    243  ND   MBI Y    1     -46.822 -28.789 -11.144  1.00 68.01          N
ATOM    244  CE   MBI Y    1     -42.945 -21.831 -13.009  1.00 78.25          C
ATOM    245  CH   MBI Y    1     -42.964 -20.647 -12.328  1.00 81.28          C
ATOM    246  CI   MBI Y    1     -47.703 -27.884 -11.587  1.00 73.28          C
ATOM    247  CJ   MBI Y    1     -43.795 -27.057 -11.266  1.00 70.15          C
ATOM    248  CK   MBI Y    1     -43.346 -20.729  -8.085  1.00 80.97          C
ATOM    249  CL   MBI Y    1     -43.229 -20.654 -10.989  1.00 81.17          C
ATOM    250  CM   MBI Y    1     -44.213 -18.347 -10.637  1.00 89.40          C
ATOM    251  CN   MBI Y    1     -45.384 -28.938 -11.451  1.00 67.43          C
ATOM    252  CC   MBI Y    1     -48.905 -28.197 -10.990  1.00 75.01          C
ATOM    253  CF   MBI Y    1     -47.426 -29.624 -10.319  1.00 67.44          C
ATOM    254  CO   MBI Y    1     -44.859 -27.693 -12.167  1.00 68.28          C
ATOM    255  NC   MBI Y    1     -48.713 -29.288 -10.201  1.00 70.89          N
ATOM    256  S    MBI Y    1     -43.215 -26.482 -13.923  1.00 70.77          S
ATOM    257  CA   MBI Z    1       5.978 -16.477 -54.051  1.00 74.42          C
ATOM    258  NA   MBI Z    1       5.604 -13.830 -53.294  1.00 69.56          N
ATOM    259  OA   MBI Z    1       8.003 -17.232 -51.057  1.00 79.08          O
ATOM    260  CB   MBI Z    1       6.630 -16.216 -52.824  1.00 73.46          C
```

FIGURE 1 (cont'd)

```
ATOM    261  NB   MBI Z   1       5.273 -15.612 -54.780  1.00 73.00           N
ATOM    262  OB   MBI Z   1       7.942 -19.737 -52.468  1.00 87.42           O
ATOM    263  CG   MBI Z   1       7.320 -17.311 -52.242  1.00 76.83           C
ATOM    264  CD   MBI Z   1       5.093 -14.330 -54.411  1.00 70.72           C
ATOM    265  ND   MBI Z   1       8.213 -10.405 -54.431  1.00 68.10           N
ATOM    266  CE   MBI Z   1       6.014 -17.716 -54.638  1.00 78.27           C
ATOM    267  CH   MBI Z   1       6.682 -18.763 -54.069  1.00 81.29           C
ATOM    268  CI   MBI Z   1       8.488  -9.243 -55.034  1.00 73.37           C
ATOM    269  CJ   MBI Z   1       5.375 -12.439 -52.951  1.00 70.17           C
ATOM    270  CK   MBI Z   1       8.517 -18.286 -50.280  1.00 80.98           C
ATOM    271  CL   MBI Z   1       7.331 -18.573 -52.883  1.00 81.18           C
ATOM    272  CM   MBI Z   1       9.006 -20.455 -53.135  1.00 89.40           C
ATOM    273  CN   MBI Z   1       6.942 -11.158 -54.364  1.00 67.45           C
ATOM    274  CC   MBI Z   1       9.821  -8.992 -54.788  1.00 75.10           C
ATOM    275  CF   MBI Z   1       9.301 -10.864 -53.841  1.00 67.50           C
ATOM    276  CO   MBI Z   1       6.691 -11.656 -52.940  1.00 68.35           C
ATOM    277  NC   MBI Z   1      10.313 -10.016 -54.041  1.00 70.98           N
ATOM    278  S    MBI Z   1       4.248 -13.362 -55.319  1.00 70.90           S
ATOM    279  CA   MBI a   1     -53.038 -23.644 -67.376  1.00 74.40           C
ATOM    280  NA   MBI a   1     -55.246 -22.184 -66.534  1.00 69.50           N
ATOM    281  OA   MBI a   1     -51.303 -23.211 -64.146  1.00 79.09           O
ATOM    282  CB   MBI a   1     -52.859 -23.195 -66.048  1.00 73.44           C
ATOM    283  NB   MBI a   1     -54.097 -23.425 -68.156  1.00 73.00           N
ATOM    284  OB   MBI a   1     -49.451 -24.777 -65.693  1.00 87.43           O
ATOM    285  CG   MBI a   1     -51.637 -23.562 -65.427  1.00 76.83           C
ATOM    286  CD   MBI a   1     -55.165 -22.717 -67.745  1.00 70.69           C
ATOM    287  ND   MBI a   1     -56.990 -17.935 -66.356  1.00 68.04           N
ATOM    288  CE   MBI a   1     -52.085 -24.389 -68.021  1.00 78.26           C
ATOM    289  CH   MBI a   1     -50.911 -24.736 -67.415  1.00 81.30           C
ATOM    290  CI   MBI a   1     -55.717 -17.565 -66.539  1.00 73.27           C
ATOM    291  CJ   MBI a   1     -56.424 -21.431 -66.149  1.00 70.17           C
ATOM    292  CK   MBI a   1     -50.396 -23.850 -63.280  1.00 80.99           C
ATOM    293  CL   MBI a   1     -50.680 -24.333 -66.131  1.00 81.19           C
ATOM    294  CM   MBI a   1     -48.150 -24.261 -66.059  1.00 89.38           C
ATOM    295  CN   MBI a   1     -57.602 -19.278 -66.416  1.00 67.45           C
ATOM    296  CC   MBI a   1     -55.687 -16.198 -66.371  1.00 75.01           C
ATOM    297  CF   MBI a   1     -57.722 -16.870 -66.089  1.00 67.47           C
ATOM    298  CO   MBI a   1     -56.663 -20.264 -67.112  1.00 68.29           C
ATOM    299  NC   MBI a   1     -56.951 -15.780 -66.090  1.00 70.92           N
ATOM    300  S    MBI a   1     -56.382 -22.495 -68.717  1.00 70.83           S
ATOM    301  CA   MBI b   1      17.457 -12.788 -26.931  1.00 74.57           C
ATOM    302  NA   MBI b   1      19.649 -14.366 -27.583  1.00 69.51           N
ATOM    303  OA   MBI b   1      18.949 -11.731 -23.722  1.00 79.13           O
ATOM    304  CB   MBI b   1      18.433 -12.726 -25.910  1.00 73.54           C
ATOM    305  NB   MBI b   1      17.530 -13.488 -28.063  1.00 73.10           N
ATOM    306  OB   MBI b   1      16.416 -10.370 -23.760  1.00 87.52           O
ATOM    307  CG   MBI b   1      18.117 -11.904 -24.797  1.00 76.93           C
ATOM    308  CD   MBI b   1      18.593 -14.252 -28.376  1.00 70.75           C
ATOM    309  ND   MBI b   1      21.116 -18.575 -27.472  1.00 68.06           N
ATOM    310  CE   MBI b   1      16.278 -12.093 -26.845  1.00 78.37           C
ATOM    311  CH   MBI b   1      15.983 -11.305 -25.769  1.00 81.39           C
ATOM    312  CI   MBI b   1      21.039 -19.904 -27.614  1.00 73.31           C
ATOM    313  CJ   MBI b   1      20.765 -15.205 -27.976  1.00 70.21           C
ATOM    314  CK   MBI b   1      18.969 -10.666 -22.803  1.00 80.97           C
ATOM    315  CL   MBI b   1      16.887 -11.204 -24.750  1.00 81.27           C
ATOM    316  CM   MBI b   1      15.360 -10.644 -22.809  1.00 89.44           C
ATOM    317  CN   MBI b   1      21.420 -17.533 -28.474  1.00 67.46           C
ATOM    318  CC   MBI b   1      20.726 -20.405 -26.369  1.00 75.04           C
ATOM    319  CF   MBI b   1      20.867 -18.253 -26.216  1.00 67.49           C
ATOM    320  CO   MBI b   1      20.270 -16.529 -28.566  1.00 68.29           C
ATOM    321  NC   MBI b   1      20.622 -19.358 -25.508  1.00 70.95           N
ATOM    322  S    MBI b   1      18.613 -15.052 -29.730  1.00 70.92           S
ATOM    323  CA   MBI c   1     -35.277 -72.458 -58.134  1.00 74.44           C
ATOM    324  NA   MBI c   1     -36.039 -74.964 -55.710  1.00 69.50           N
ATOM    325  OA   MBI c   1     -32.994 -69.558 -58.018  1.00 79.08           O
```

FIGURE 1 (cont'd)

```
ATOM    326  CB   MBI c   1     -34.328 -71.573 -57.572  1.00 73.48           C
ATOM    327  NB   MBI c   1     -35.816 -73.527 -57.548  1.00 72.99           N
ATOM    328  OB   MBI c   1     -34.137 -69.402 -60.653  1.00 87.43           O
ATOM    329  CG   MBI c   1     -33.906 -70.504 -58.405  1.00 76.85           C
ATOM    330  CD   MBI c   1     -35.502 -73.901 -56.293  1.00 70.70           C
ATOM    331  ND   MBI c   1     -34.210 -78.286 -56.944  1.00 68.07           N
ATOM    332  CE   MBI c   1     -35.756 -72.288 -59.408  1.00 78.29           C
ATOM    333  CH   MBI c   1     -35.344 -71.256 -60.200  1.00 81.30           C
ATOM    334  CI   MBI c   1     -34.606 -79.558 -56.815  1.00 73.31           C
ATOM    335  CJ   MBI c   1     -37.004 -75.775 -56.427  1.00 70.15           C
ATOM    336  CK   MBI c   1     -31.715 -69.317 -58.553  1.00 80.98           C
ATOM    337  CL   MBI c   1     -34.428 -70.367 -59.714  1.00 81.18           C
ATOM    338  CM   MBI c   1     -33.215 -69.507 -61.763  1.00 89.42           C
ATOM    339  CN   MBI c   1     -34.886 -77.039 -56.529  1.00 67.43           C
ATOM    340  CC   MBI c   1     -33.605 -80.328 -57.367  1.00 75.04           C
ATOM    341  CF   MBI c   1     -33.033 -78.250 -57.540  1.00 67.47           C
ATOM    342  CO   MBI c   1     -36.363 -77.075 -56.923  1.00 68.35           C
ATOM    343  NC   MBI c   1     -32.630 -79.493 -57.815  1.00 70.94           N
ATOM    344  S    MBI c   1     -34.462 -73.065 -55.461  1.00 70.82           S
ATOM    345  CA   MBI d   1     -38.139 -17.527  45.053  1.00 74.41           C
ATOM    346  NA   MBI d   1     -34.846 -17.125  43.738  1.00 69.48           N
ATOM    347  OA   MBI d   1     -41.139 -19.178  43.671  1.00 79.07           O
ATOM    348  CB   MBI d   1     -38.908 -18.245  44.108  1.00 73.45           C
ATOM    349  NB   MBI d   1     -36.859 -17.174  44.936  1.00 73.00           N
ATOM    350  OB   MBI d   1     -42.034 -18.195  46.222  1.00 87.43           O
ATOM    351  CG   MBI d   1     -40.257 -18.498  44.469  1.00 76.81           C
ATOM    352  CD   MBI d   1     -36.119 -17.476  43.853  1.00 70.70           C
ATOM    353  ND   MBI d   1     -32.414 -20.618  43.776  1.00 68.01           N
ATOM    354  CE   MBI d   1     -38.671 -17.104  46.244  1.00 78.25           C
ATOM    355  CH   MBI d   1     -39.971 -17.354  46.581  1.00 81.27           C
ATOM    356  CI   MBI d   1     -31.313 -21.343  44.004  1.00 73.27           C
ATOM    357  CJ   MBI d   1     -34.101 -17.479  42.545  1.00 70.14           C
ATOM    358  CK   MBI d   1     -42.384 -19.728  44.028  1.00 80.98           C
ATOM    359  CL   MBI d   1     -40.764 -18.042  45.710  1.00 81.17           C
ATOM    360  CM   MBI d   1     -42.418 -18.913  47.418  1.00 89.37           C
ATOM    361  CN   MBI d   1     -32.549 -19.191  43.417  1.00 67.43           C
ATOM    362  CC   MBI d   1     -31.748 -22.617  44.300  1.00 75.02           C
ATOM    363  CF   MBI d   1     -33.481 -21.382  43.918  1.00 67.45           C
ATOM    364  CO   MBI d   1     -33.776 -18.976  42.530  1.00 68.29           C
ATOM    365  NC   MBI d   1     -33.107 -22.622  44.241  1.00 70.92           N
ATOM    366  S    MBI d   1     -36.762 -18.276  42.661  1.00 70.77           S
ATOM    367  CA   MBI e   1     -21.017 -74.268  -1.668  1.00 74.41           C
ATOM    368  NA   MBI e   1     -18.550 -75.165  -2.580  1.00 69.49           N
ATOM    369  OA   MBI e   1     -22.135 -73.346  -5.064  1.00 79.06           O
ATOM    370  CB   MBI e   1     -20.922 -74.117  -3.071  1.00 73.45           C
ATOM    371  NB   MBI e   1     -20.084 -74.764  -0.855  1.00 72.99           N
ATOM    372  OB   MBI e   1     -24.379 -72.642  -3.409  1.00 87.43           O
ATOM    373  CG   MBI e   1     -22.058 -73.561  -3.713  1.00 76.83           C
ATOM    374  CD   MBI e   1     -18.890 -75.197  -1.299  1.00 70.68           C
ATOM    375  ND   MBI e   1     -14.364 -73.652  -3.324  1.00 68.05           N
ATOM    376  CE   MBI e   1     -22.141 -73.897  -0.976  1.00 78.25           C
ATOM    377  CH   MBI e   1     -23.229 -73.362  -1.605  1.00 81.28           C
ATOM    378  CI   MBI e   1     -13.219 -73.067  -2.953  1.00 73.30           C
ATOM    379  CJ   MBI e   1     -17.247 -75.647  -2.997  1.00 70.17           C
ATOM    380  CK   MBI e   1     -23.289 -73.271  -5.866  1.00 80.98           C
ATOM    381  CL   MBI e   1     -23.198 -73.191  -2.959  1.00 81.18           C
ATOM    382  CM   MBI e   1     -24.816 -71.269  -3.276  1.00 89.40           C
ATOM    383  CN   MBI e   1     -14.861 -75.017  -3.050  1.00 67.44           C
ATOM    384  CC   MBI e   1     -13.256 -71.791  -3.473  1.00 75.03           C
ATOM    385  CF   MBI e   1     -15.082 -72.802  -4.034  1.00 67.48           C
ATOM    386  CO   MBI e   1     -16.132 -74.962  -2.201  1.00 68.31           C
ATOM    387  NC   MBI e   1     -14.428 -71.644  -4.146  1.00 70.92           N
ATOM    388  S    MBI e   1     -17.835 -75.771  -0.283  1.00 70.77           S
ATOM    389  CA   MBI f   1     -23.979 -68.735 -31.177  1.00 74.42           C
ATOM    390  NA   MBI f   1     -24.477 -65.350 -30.160  1.00 69.50           N
```

FIGURE 1 (cont'd)

```
ATOM    391  OA   MBI f   1     -23.944 -71.886 -29.253  1.00 79.08           O
ATOM    392  CB   MBI f   1     -24.066 -69.558 -30.031  1.00 73.45           C
ATOM    393  NB   MBI f   1     -24.109 -67.409 -31.218  1.00 73.01           N
ATOM    394  OB   MBI f   1     -23.453 -72.748 -31.953  1.00 87.42           O
ATOM    395  CG   MBI f   1     -23.891 -70.949 -30.251  1.00 76.83           C
ATOM    396  CD   MBI f   1     -24.348 -66.669 -30.119  1.00 70.72           C
ATOM    397  ND   MBI f   1     -28.492 -64.471 -29.165  1.00 68.01           N
ATOM    398  CE   MBI f   1     -23.740 -69.255 -32.423  1.00 78.25           C
ATOM    399  CH   MBI f   1     -23.573 -70.595 -32.624  1.00 81.27           C
ATOM    400  CI   MBI f   1     -28.968 -65.581 -28.588  1.00 73.30           C
ATOM    401  CJ   MBI f   1     -24.735 -64.608 -28.942  1.00 70.16           C
ATOM    402  CK   MBI f   1     -24.212 -73.262 -29.370  1.00 80.98           C
ATOM    403  CL   MBI f   1     -23.646 -71.442 -31.556  1.00 81.17           C
ATOM    404  CM   MBI f   1     -24.247 -73.504 -32.896  1.00 89.39           C
ATOM    405  CN   MBI f   1     -27.100 -63.988 -29.281  1.00 67.42           C
ATOM    406  CC   MBI f   1     -30.334 -65.547 -28.764  1.00 75.03           C
ATOM    407  CF   MBI f   1     -29.493 -63.778 -29.676  1.00 67.46           C
ATOM    408  CO   MBI f   1     -26.162 -64.856 -28.443  1.00 68.28           C
ATOM    409  NC   MBI f   1     -30.644 -64.412 -29.446  1.00 70.90           N
ATOM    410  S    MBI f   1     -24.486 -67.367 -28.716  1.00 70.80           S
ATOM    411  O    HOH g   1     -23.465 -18.944-102.549  1.00  2.00           O
ATOM    412  O    HOH g   2     -25.776 -12.459  -3.978  1.00  2.29           O
ATOM    413  O    HOH g   3     -37.034  -7.663 -67.028  1.00  2.00           O
ATOM    414  O    HOH g   4     -27.354 -52.256 -18.806  1.00132.22           O
ATOM    415  O    HOH g   5     -42.142 -37.631  -0.182  1.00  2.39           O
ATOM    416  O    HOH g   6     -51.882 -14.397  28.624  1.00  2.53           O
ATOM    417  O    HOH g   7     -42.903 -15.874 -62.148  1.00 74.99           O
ATOM    418  O    HOH g   8     -48.148 -31.870 -36.109  1.00  2.03           O
TER     419       HOH g   8
ATOM    420  O    HOH g  10     -75.225 -26.513 -12.716  1.00 75.61           O
ATOM    421  O    HOH g  11     -20.623 -64.351 -43.524  1.00  2.00           O
ATOM    422  O    HOH g  12      29.584 -18.882 -56.056  1.00 78.26           O
ATOM    423  O    HOH g  13     -56.880 -79.849 -18.672  1.00 46.09           O
ATOM    424  O    HOH g  14     -14.912  -0.540 -99.355  1.00113.26           O
ATOM    425  O    HOH g  15      -4.047 -70.400 -64.259  1.00 56.83           O
ATOM    426  O    HOH g  16     -30.375 -43.527 -60.944  1.00  2.73           O
ATOM    427  O    HOH g  17     -27.879 -11.343 -30.152  1.00 27.39           O
ATOM    428  O    HOH g  18     -50.792 -53.015 -19.213  1.00100.03           O
ATOM    429  O    HOH g  19     -15.829 -14.698  13.910  1.00  2.58           O
ATOM    430  O    HOH g  20     -59.040 -10.386  -2.968  1.00  5.16           O
TER     431       HOH g  20
ATOM    432  O    HOH g  22     -43.811 -41.136 -30.550  1.00 32.98           O
ATOM    433  O    HOH g  23      34.013 -18.354 -41.804  1.00  8.10           O
ATOM    434  O    HOH g  24     -24.747-104.402 -52.735  1.00 95.30           O
ATOM    435  O    HOH g  25       6.890 -33.329 -47.047  1.00 35.86           O
ATOM    436  O    HOH g  26     -24.530 -81.919 -13.484  1.00 16.39           O
ATOM    437  O    HOH g  27     -23.244 -26.545  57.944  1.00  9.05           O
ATOM    438  O    HOH g  28     -22.388 -40.158 -34.646  1.00 73.20           O
TER     439       HOH g  28
ATOM    440  O    HOH g  30     -51.991 -29.838 -54.044  1.00128.82           O
ATOM    441  O    HOH g  31      -3.185 -41.426 -40.805  1.00 13.47           O
TER     442       HOH g  31
ATOM    443  O    HOH g  33     -42.104 -27.159 -21.440  1.00  2.91           O
ATOM    444  O    HOH g  34     -57.143 -33.330 -35.155  1.00  2.00           O
ATOM    445  O    HOH g  35     -47.568 -37.049  25.080  1.00  2.57           O
ATOM    446  O    HOH g  36      -7.933 -28.717-102.269  1.00  2.08           O
ATOM    447  O    HOH g  37     -29.055 -96.582 -21.451  1.00  4.12           O
ATOM    448  O    HOH g  38      -3.310 -51.952  13.096  1.00107.36           O
ATOM    449  O    HOH g  39      -1.199 -31.452 -41.619  1.00 13.94           O
ATOM    450  O    HOH g  40     -16.304 -76.175 -69.205  1.00  4.57           O
ATOM    451  O    HOH g  41      -8.220 -80.189 -16.999  1.00 77.59           O
ATOM    452  O    HOH g  42     -54.729  13.219 -87.440  1.00 43.64           O
ATOM    453  O    HOH g  43     -28.034  -5.160 -96.513  1.00  2.93           O
ATOM    454  O    HOH g  44     -46.585 -39.532 -39.055  1.00  2.00           O
TER     455       HOH g  44
```

FIGURE 1 (cont'd)

```
ATOM    456  O   HOH g  46     -13.492 -71.879 -61.830  1.00  2.00          O
ATOM    457  O   HOH g  47      -2.204 -46.012  -1.132  1.00106.25          O
ATOM    458  O   HOH g  48     -44.214 -34.583  23.707  1.00 27.32          O
ATOM    459  O   HOH g  49     -14.854 -63.124 -53.788  1.00 58.51          O
ATOM    460  O   HOH g  50     -10.295 -72.656 -38.447  1.00  3.39          O
ATOM    461  O   HOH g  51      -0.172  -0.825 -64.682  1.00 70.51          O
ATOM    462  O   HOH g  52     -52.788 -15.462  -4.819  1.00  5.22          O
TER     463      HOH g  52
ATOM    464  O   HOH h   1     -12.059  -1.219 -76.416  1.00289.28          O
ATOM    465  O   HOH h   2     -11.118  -0.959 -73.889  1.00337.23          O
ATOM    466  O   HOH h   3     -11.715  -1.216 -80.604  1.00268.93          O
ATOM    467  O   HOH h   4     -14.143  -1.179 -81.558  1.00261.60          O
ATOM    468  O   HOH h   5     -12.192  -0.740 -83.207  1.00255.02          O
ATOM    469  O   HOH h   6     -40.862  -0.614 -85.155  1.00  2.00          O
ATOM    470  O   HOH h   7     -62.736 -41.486 -29.567  1.00  2.00          O
ATOM    471  O   HOH h   8     -52.523 -52.930 -13.163  1.00  2.00          O
ATOM    472  O   HOH h   9     -24.657 -47.364 -50.020  1.00  3.76          O
ATOM    473  O   HOH h  10     -34.940 -43.005  -8.220  1.00  3.89          O
ATOM    474  O   HOH h  11      14.061 -41.773 -50.898  1.00 28.48          O
ATOM    475  O   HOH h  12     -24.896 -10.612 -12.483  1.00 13.75          O
ATOM    476  O   HOH h  13     -58.110 -71.212 -14.918  1.00 10.58          O
ATOM    477  O   HOH h  14     -31.253 -80.966 -33.682  1.00  3.00          O
ATOM    478  O   HOH h  15     -24.006 -44.065   2.273  1.00 12.23          O
ATOM    479  O   HOH h  16     -62.941 -20.022 -55.080  1.00  2.00          O
ATOM    480  O   HOH h  17      -2.947 -21.896 -56.753  1.00 27.25          O
ATOM    481  O   HOH h  18      10.104  12.104 -52.454  1.00 26.16          O
ATOM    482  O   HOH h  19     -55.919 -63.251 -24.038  1.00  2.00          O
ATOM    483  O   HOH h  20       5.796 -66.723  12.060  1.00  8.63          O
ATOM    484  O   HOH h  21     -30.915   4.010  -7.686  1.00 21.96          O
ATOM    485  O   HOH h  22     -52.538  13.227 -72.628  1.00  8.87          O
ATOM    486  O   HOH h  23      13.397 -52.160 -46.155  1.00 21.68          O
ATOM    487  O   HOH h  24      27.279 -20.536 -56.076  1.00  5.54          O
ATOM    488  O   HOH h  25     -40.416 -40.542 -30.209  1.00  2.27          O
ATOM    489  O   HOH h  26     -22.505   5.904  -2.361  1.00  9.91          O
ATOM    490  O   HOH h  27     -35.247 -23.661   1.195  1.00 11.74          O
ATOM    491  O   HOH h  28      37.401  -8.470 -65.523  1.00 21.55          O
ATOM    492  O   HOH h  29       2.088 -46.825 -40.200  1.00 21.30          O
ATOM    493  O   HOH h  30     -20.604   2.459  13.169  1.00 13.52          O
ATOM    494  O   HOH h  31     -72.349 -29.779   1.823  1.00  7.01          O
ATOM    495  O   HOH h  32       2.881 -47.282 -27.919  1.00 19.65          O
ATOM    496  O   HOH h  33      34.316   2.924 -60.300  1.00 16.52          O
ATOM    497  O   HOH h  34     -21.188 -10.518 -40.173  1.00  2.00          O
ATOM    498  O   HOH h  35     -25.637 -50.409 -18.294  1.00  2.14          O
ATOM    499  O   HOH h  36     -34.844 -82.087  -6.262  1.00  2.00          O
ATOM    500  O   HOH h  37     -45.152 -49.487  -3.570  1.00  9.00          O
ATOM    501  O   HOH h  38      22.569   6.222 -50.346  1.00 21.56          O
ATOM    502  O   HOH h  39     -45.623 -60.741   1.632  1.00  2.00          O
ATOM    503  O   HOH h  40      17.614 -17.568 -79.472  1.00 20.31          O
ATOM    504  O   HOH h  41     -43.465 -80.254 -43.257  1.00  3.78          O
ATOM    505  O   HOH h  42       2.475  -1.298 -84.530  1.00 21.99          O
ATOM    506  O   HOH h  43     -63.601 -22.686 -70.445  1.00  3.94          O
ATOM    507  O   HOH h  44       9.510 -64.937  17.883  1.00  5.60          O
ATOM    508  O   HOH h  45     -39.302 -63.285 -51.412  1.00  6.28          O
ATOM    509  O   HOH h  46      35.141 -22.610 -60.672  1.00 22.16          O
ATOM    510  O   HOH h  47     -55.351 -29.521 -36.536  1.00  2.45          O
ATOM    511  O   HOH h  48     -50.735 -22.910   7.540  1.00 19.87          O
ATOM    512  O   HOH h  49     -39.847 -49.335 -44.197  1.00  3.68          O
ATOM    513  O   HOH h  50     -25.142 -18.060  15.412  1.00  2.00          O
ATOM    514  O   HOH h  51     -33.555 -77.304  -4.775  1.00  2.84          O
ATOM    515  O   HOH h  52      -8.206-101.185 -41.191  1.00 19.40          O
ATOM    516  O   HOH h  53     -30.082 -16.030  49.007  1.00  2.64          O
ATOM    517  O   HOH h  54     -61.590 -13.762   3.422  1.00  3.13          O
ATOM    518  O   HOH h  55     -54.907  -9.825 -89.722  1.00  6.96          O
ATOM    519  O   HOH h  56      17.443  -5.221 -32.440  1.00 27.22          O
ATOM    520  O   HOH h  57     -42.069 -31.389  -4.330  1.00  3.34          O
```

FIGURE 1 (cont'd)

```
ATOM    521  O   HOH h  58     -71.459 -18.930 -75.793  1.00  6.41           O
ATOM    522  O   HOH h  59       5.327 -81.374  -0.221  1.00  9.14           O
ATOM    523  O   HOH h  60     -21.697 -14.766  32.210  1.00 16.78           O
ATOM    524  O   HOH h  61     -35.696 -14.298  -7.139  1.00  9.05           O
ATOM    525  O   HOH h  62     -64.135  -3.612 -22.446  1.00  2.04           O
ATOM    526  O   HOH h  63     -21.464 -75.063 -32.471  1.00 10.10           O
ATOM    527  O   HOH h  64      19.665  13.295 -58.730  1.00 26.25           O
ATOM    528  O   HOH h  65     -41.760 -43.682 -14.634  1.00  4.31           O
ATOM    529  O   HOH h  66     -29.752 -15.813-101.681  1.00 16.27           O
ATOM    530  O   HOH h  67     -13.453  -2.687 -99.536  1.00 14.13           O
ATOM    531  O   HOH h  68     -70.179 -16.514 -86.043  1.00  9.66           O
ATOM    532  O   HOH h  69     -47.601 -26.178 -62.741  1.00  2.98           O
ATOM    533  O   HOH h  70     -32.001  -5.608 -55.445  1.00  2.23           O
ATOM    534  O   HOH h  71     -76.868 -11.505 -57.830  1.00 22.23           O
ATOM    535  O   HOH h  72     -15.881   1.675 -98.351  1.00 24.60           O
ATOM    536  O   HOH h  73     -30.816 -22.795 -70.930  1.00 15.18           O
ATOM    537  O   HOH h  74     -52.926 -41.185  29.326  1.00 26.20           O
ATOM    538  O   HOH h  75     -31.169 -30.338  19.249  1.00 13.92           O
ATOM    539  O   HOH h  76     -19.928 -14.636 -55.902  1.00  4.90           O
ATOM    540  O   HOH h  77     -52.721 -21.373  23.403  1.00  2.34           O
ATOM    541  O   HOH h  78     -15.386 -46.647  34.097  1.00 17.80           O
ATOM    542  O   HOH h  79      21.009  -1.907 -83.315  1.00  6.87           O
ATOM    543  O   HOH h  80      -2.678 -26.094 -62.168  1.00 11.02           O
ATOM    544  O   HOH h  81     -43.209 -48.307  47.020  1.00  9.42           O
ATOM    545  O   HOH h  82     -26.505 -87.477 -30.996  1.00  7.40           O
ATOM    546  O   HOH h  83     -28.670 -66.484 -42.945  1.00 10.23           O
ATOM    547  O   HOH h  84     -45.960  11.479   6.989  1.00  2.12           O
ATOM    548  O   HOH h  85      16.149 -20.545 -50.689  1.00 26.25           O
ATOM    549  O   HOH h  86      23.701 -22.426 -12.245  1.00 18.33           O
ATOM    550  O   HOH h  87       7.701 -10.994 -78.639  1.00 17.20           O
ATOM    551  O   HOH h  88     -34.094 -49.285 -49.371  1.00  2.00           O
ATOM    552  O   HOH h  89     -53.375 -15.957  -7.324  1.00  2.22           O
TER     553      HOH h  89
ATOM    554  O   HOH h  91     -14.082 -39.663  37.685  1.00  6.47           O
ATOM    555  O   HOH h  92      28.570 -17.706 -50.285  1.00 23.27           O
ATOM    556  O   HOH h  93      13.042  -3.899 -74.239  1.00 16.46           O
ATOM    557  O   HOH h  94      11.773   9.154 -81.068  1.00 24.24           O
ATOM    558  O   HOH h  95     -15.535 -92.274 -38.826  1.00  2.00           O
ATOM    559  O   HOH h  96     -19.320 -22.306 -69.000  1.00 18.04           O
ATOM    560  O   HOH h  97     -22.662-106.533 -48.518  1.00 19.06           O
ATOM    561  O   HOH h  98     -12.172 -27.767  33.353  1.00  3.22           O
ATOM    562  O   HOH h  99     -16.866 -33.387  28.737  1.00  9.35           O
ATOM    563  O   HOH h 100     -36.692 -29.824 -18.169  1.00  6.79           O
ATOM    564  O   HOH h 101      24.348   7.004 -85.004  1.00 21.29           O
ATOM    565  O   HOH h 102     -73.993 -12.124 -12.597  1.00  7.10           O
ATOM    566  O   HOH h 103     -71.028 -12.092 -55.723  1.00  7.15           O
ATOM    567  O   HOH h 104     -25.404 -98.470 -65.571  1.00 16.81           O
ATOM    568  O   HOH h 105     -19.353 -28.671  11.526  1.00 19.56           O
ATOM    569  O   HOH h 106      26.989 -15.853 -44.056  1.00 18.91           O
ATOM    570  O   HOH h 107     -76.959  -5.160 -24.849  1.00  6.28           O
ATOM    571  O   HOH h 108      -7.517 -60.972  20.487  1.00 12.57           O
ATOM    572  O   HOH h 109      25.340 -17.570 -76.737  1.00 18.72           O
ATOM    573  O   HOH h 110     -54.668  -0.955 -53.394  1.00  8.11           O
ATOM    574  O   HOH h 111     -16.393 -22.275   2.887  1.00 11.70           O
ATOM    575  O   HOH h 112     -15.737 -22.591 -45.823  1.00 17.90           O
ATOM    576  O   HOH h 113     -26.412 -15.633  32.825  1.00  2.57           O
ATOM    577  O   HOH h 114      17.848  -8.659 -36.244  1.00 20.24           O
ATOM    578  O   HOH h 115     -45.873   3.743 -68.606  1.00  2.08           O
ATOM    579  O   HOH h 116     -23.199 -46.708  -7.981  1.00 15.05           O
ATOM    580  O   HOH h 117     -63.395 -16.197   1.297  1.00 13.22           O
ATOM    581  O   HOH h 118     -54.359 -33.246  28.371  1.00 35.19           O
ATOM    582  O   HOH h 119     -27.571 -70.426  13.798  1.00 18.71           O
ATOM    583  O   HOH h 120      29.124 -19.194 -17.591  1.00 15.65           O
ATOM    584  O   HOH h 121      18.690  14.949 -63.442  1.00 25.47           O
ATOM    585  O   HOH h 122     -53.560 -57.296  -5.837  1.00 11.14           O
```

FIGURE 1 (cont'd)

```
ATOM    586  O   HOH h 123      17.646 -21.399 -46.231  1.00  8.93           O
ATOM    587  O   HOH h 124     -10.427 -79.702 -15.637  1.00  7.48           O
ATOM    588  O   HOH h 125      29.912 -31.836 -61.405  1.00 15.66           O
ATOM    589  O   HOH h 126       9.254  -3.204 -37.532  1.00 29.90           O
ATOM    590  O   HOH h 127      32.556 -31.070 -60.967  1.00 26.55           O
ATOM    591  O   HOH h 128     -31.865  -9.447  32.296  1.00  8.95           O
ATOM    592  O   HOH h 129     -30.981 -47.818  12.773  1.00  8.42           O
TER     593      HOH h 129
ATOM    594  O   HOH h 131      11.244  -7.158 -35.610  1.00 31.38           O
ATOM    595  O   HOH h 132     -29.961 -32.027 -28.256  1.00  2.38           O
ATOM    596  O   HOH h 133     -41.931 -14.711 -64.291  1.00  2.90           O
ATOM    597  O   HOH h 134     -60.668 -43.780 -41.796  1.00  2.48           O
ATOM    598  O   HOH h 135     -23.058 -24.457  56.568  1.00 13.53           O
ATOM    599  O   HOH h 136     -50.093 -50.834 -18.309  1.00  3.72           O
ATOM    600  O   HOH h 137     -24.142 -46.322 -37.997  1.00  2.42           O
ATOM    601  O   HOH h 138      20.806 -17.590 -13.944  1.00 21.44           O
ATOM    602  O   HOH h 139     -22.342 -21.989 -68.442  1.00  3.24           O
ATOM    603  O   HOH h 140      -3.664 -89.510 -44.019  1.00 20.61           O
ATOM    604  O   HOH h 141     -50.133 -21.955 -67.840  1.00  5.85           O
TER     605      HOH h 141
ATOM    606  O   HOH h 143     -60.492 -66.834 -16.379  1.00  6.09           O
ATOM    607  O   HOH h 144     -39.935   3.019 -63.718  1.00  4.40           O
ATOM    608  O   HOH h 145     -28.735 -13.586  37.929  1.00  6.18           O
TER     609      HOH h 145
ATOM    610  O   HOH h 147     -43.319 -41.415 -21.969  1.00 12.44           O
ATOM    611  O   HOH h 148     -32.673  -1.554 -83.752  1.00  7.05           O
ATOM    612  O   HOH h 149     -49.057 -11.818  38.771  1.00 13.94           O
ATOM    613  O   HOH h 150     -16.734 -22.442  19.160  1.00 40.22           O
ATOM    614  O   HOH h 151     -49.943 -88.294 -65.087  1.00 32.92           O
ATOM    615  O   HOH h 152     -53.517 -31.084 -55.756  1.00  3.52           O
ATOM    616  O   HOH h 153     -43.656  -4.124 -14.876  1.00  2.09           O
ATOM    617  O   HOH h 154      19.700 -27.649 -47.931  1.00 20.15           O
ATOM    618  O   HOH h 155       9.235 -44.722 -28.932  1.00 21.38           O
ATOM    619  O   HOH h 156      -3.616 -82.909   4.770  1.00  4.97           O
ATOM    620  O   HOH h 157     -37.612 -25.987 -21.334  1.00  6.94           O
ATOM    621  O   HOH h 158      25.246 -21.444 -50.198  1.00 18.81           O
ATOM    622  O   HOH h 159      -8.497 -33.147 -68.934  1.00 40.02           O
ATOM    623  O   HOH h 160     -29.872 -56.844  -9.119  1.00  4.04           O
ATOM    624  O   HOH h 161     -51.510 -59.895 -32.099  1.00  6.14           O
ATOM    625  O   HOH h 162     -27.805 -73.627  -6.161  1.00  9.59           O
ATOM    626  O   HOH h 163     -61.888 -14.459 -89.512  1.00  5.49           O
ATOM    627  O   HOH h 164      -1.415 -16.305 -27.135  1.00 16.57           O
ATOM    628  O   HOH h 165       9.228  10.111 -77.959  1.00 30.42           O
ATOM    629  O   HOH h 166     -45.500 -29.064 -67.050  1.00  2.91           O
ATOM    630  O   HOH h 167     -38.164 -84.874 -29.302  1.00 16.62           O
ATOM    631  O   HOH h 168     -29.351 -23.682  63.005  1.00  9.74           O
ATOM    632  O   HOH h 169     -33.214 -35.053  61.001  1.00 12.34           O
ATOM    633  O   HOH h 170     -19.853 -29.996 -97.266  1.00  4.94           O
ATOM    634  O   HOH h 171     -56.956 -64.696 -21.864  1.00 10.56           O
ATOM    635  O   HOH h 172     -14.728 -63.393 -56.758  1.00 10.60           O
ATOM    636  O   HOH h 173     -27.228 -93.861 -37.452  1.00 18.48           O
ATOM    637  O   HOH h 174     -18.670 -31.827 -41.117  1.00  5.20           O
ATOM    638  O   HOH h 175     -53.860 -10.166 -52.234  1.00  4.27           O
ATOM    639  O   HOH h 176     -45.078 -88.179 -72.257  1.00 19.94           O
ATOM    640  O   HOH h 177     -43.516 -26.507 -62.882  1.00  6.03           O
ATOM    641  O   HOH h 178      24.194 -16.844 -44.110  1.00 15.58           O
ATOM    642  O   HOH h 179      16.728 -27.853 -27.617  1.00 13.63           O
ATOM    643  O   HOH h 180      25.353 -12.878 -28.347  1.00 17.18           O
ATOM    644  O   HOH h 181     -38.951 -54.982 -51.721  1.00  3.07           O
ATOM    645  O   HOH h 182     -24.667 -19.635  22.030  1.00 36.00           O
ATOM    646  O   HOH h 183       6.466 -49.830 -21.385  1.00 39.31           O
ATOM    647  O   HOH h 184     -81.846 -15.448 -18.054  1.00 13.01           O
ATOM    648  O   HOH h 185     -30.863 -11.450  39.318  1.00 10.08           O
ATOM    649  O   HOH h 186     -21.645 -23.182-102.874  1.00 33.87           O
ATOM    650  O   HOH h 187     -58.672 -17.162   5.967  1.00 10.78           O
```

FIGURE 1 (cont'd)

```
ATOM    651  O   HOH h 188     -16.203 -54.440  20.195  1.00 48.65           O
ATOM    652  O   HOH h 189     -29.373 -12.277-100.039  1.00 26.96           O
ATOM    653  O   HOH h 190       9.194 -24.303 -89.089  1.00 13.59           O
ATOM    654  O   HOH h 191      11.280 -14.444 -36.818  1.00  7.86           O
ATOM    655  O   HOH h 192      24.657 -41.394 -40.418  1.00 28.02           O
ATOM    656  O   HOH h 193     -50.630  -4.345 -52.782  1.00  8.55           O
ATOM    657  O   HOH h 194     -22.717 -52.928  -2.185  1.00  7.35           O
ATOM    658  O   HOH h 195     -42.685 -54.011  -1.133  1.00 11.64           O
ATOM    659  O   HOH h 196      33.069   0.114 -78.841  1.00 22.96           O
ATOM    660  O   HOH h 197     -33.010 -19.507 -86.589  1.00 19.97           O
ATOM    661  O   HOH h 198       1.231 -46.025   5.069  1.00 20.34           O
ATOM    662  O   HOH h 199     -50.872 -35.786 -58.986  1.00  9.49           O
ATOM    663  O   HOH h 200      28.334 -43.967 -40.562  1.00 51.16           O
ATOM    664  O   HOH h 201     -38.636 -11.701 -70.315  1.00  5.62           O
ATOM    665  O   HOH h 202     -21.357 -25.678  12.616  1.00  5.24           O
ATOM    666  O   HOH h 203     -28.927 -14.674  30.884  1.00  5.32           O
ATOM    667  O   HOH h 204     -60.113 -10.435   8.271  1.00  2.64           O
ATOM    668  O   HOH h 205     -42.632 -15.993 -81.488  1.00  4.24           O
ATOM    669  O   HOH h 206     -21.843 -72.587 -34.875  1.00  2.85           O
ATOM    670  O   HOH h 207       8.777 -29.721 -86.770  1.00 37.91           O
ATOM    671  O   HOH h 208      -7.130 -37.555 -40.292  1.00 15.61           O
ATOM    672  O   HOH h 209     -57.540  13.146 -70.387  1.00 48.76           O
ATOM    673  O   HOH h 210      -4.403 -72.302 -56.660  1.00 12.00           O
ATOM    674  O   HOH h 211     -72.805 -16.967  -9.025  1.00  4.48           O
ATOM    675  O   HOH h 212     -66.680 -14.263 -33.785  1.00  8.61           O
ATOM    676  O   HOH h 213     -41.586 -42.807 -24.023  1.00  3.77           O
ATOM    677  O   HOH h 214     -73.284 -17.786  -5.334  1.00  8.54           O
ATOM    678  O   HOH h 215     -76.962 -15.100  -4.782  1.00 32.02           O
ATOM    679  O   HOH h 216     -56.071 -21.800  10.351  1.00  7.38           O
ATOM    680  O   HOH h 217     -26.123 -20.099  -4.471  1.00 17.58           O
ATOM    681  O   HOH h 218     -29.833 -84.697 -10.368  1.00 16.98           O
ATOM    682  O   HOH h 219     -19.479 -36.563  12.269  1.00 12.76           O
ATOM    683  O   HOH h 220     -30.156 -53.404 -40.654  1.00  8.78           O
ATOM    684  O   HOH h 221       8.883 -35.108 -48.176  1.00 19.53           O
ATOM    685  O   HOH h 222     -72.704 -12.043 -34.275  1.00  9.30           O
ATOM    686  O   HOH h 223     -11.362 -50.445  21.797  1.00 18.42           O
ATOM    687  O   HOH h 224     -24.019 -61.840  15.386  1.00 16.72           O
ATOM    688  O   HOH h 225     -17.985 -17.840  35.228  1.00 16.78           O
ATOM    689  O   HOH h 226      35.790  -0.629 -72.791  1.00 15.89           O
ATOM    690  O   HOH h 227     -23.624 -20.833-103.857  1.00 22.47           O
ATOM    691  O   HOH h 228     -30.071 -68.959  -3.208  1.00  8.22           O
ATOM    692  O   HOH h 229     -27.638 -19.588  65.222  1.00 23.30           O
ATOM    693  O   HOH h 230     -44.007 -53.978 -11.937  1.00  5.37           O
ATOM    694  O   HOH h 231       0.969 -77.446  17.377  1.00  2.02           O
ATOM    695  O   HOH h 232     -40.601 -52.978 -11.220  1.00  9.85           O
ATOM    696  O   HOH h 233     -65.799 -29.106 -37.565  1.00 20.44           O
ATOM    697  O   HOH h 234      34.604  -0.551 -69.964  1.00 17.42           O
ATOM    698  O   HOH h 235     -35.123 -25.168  -0.928  1.00 18.26           O
ATOM    699  O   HOH h 236     -79.265 -15.646 -16.693  1.00 16.53           O
ATOM    700  O   HOH h 237     -39.815 -99.154 -46.719  1.00 16.77           O
ATOM    701  O   HOH h 238     -38.329   6.669 -90.361  1.00 25.12           O
ATOM    702  O   HOH h 239      23.948 -25.512 -53.325  1.00  4.51           O
ATOM    703  O   HOH h 240     -33.952 -14.534  -9.306  1.00 19.13           O
ATOM    704  O   HOH h 241     -63.020  -4.143 -27.254  1.00 11.86           O
ATOM    705  O   HOH h 242      17.131 -10.062 -33.929  1.00 12.74           O
ATOM    706  O   HOH h 243     -67.058  13.826 -74.156  1.00 15.40           O
ATOM    707  O   HOH h 244     -22.223   3.129  -7.595  1.00 19.79           O
ATOM    708  O   HOH h 245     -37.940 -19.624 -75.140  1.00 12.82           O
ATOM    709  O   HOH h 246     -41.292 -80.376 -36.670  1.00 17.56           O
TER     710      HOH h 246
ATOM    711  O   HOH h 248     -17.774  -9.155  49.729  1.00 16.75           O
ATOM    712  O   HOH h 249     -70.065   9.105 -74.300  1.00 17.62           O
ATOM    713  O   HOH h 250     -45.644 -43.546 -27.903  1.00 11.76           O
ATOM    714  O   HOH h 251     -61.281  -9.929  10.537  1.00 21.75           O
ATOM    715  O   HOH h 252      13.555 -40.954 -20.414  1.00 17.85           O
```

FIGURE 1 (cont'd)

```
ATOM    716  O    HOH h 253     -43.400 -35.739  21.326  1.00 26.02           O
ATOM    717  O    HOH h 254     -36.511 -24.879 -26.675  1.00 17.54           O
ATOM    718  O    HOH h 255     -21.824 -22.204  61.860  1.00 13.32           O
ATOM    719  O    HOH h 256     -29.997 -78.826 -33.092  1.00 25.53           O
ATOM    720  O    HOH h 257     -40.573 -16.969 -63.953  1.00 10.51           O
ATOM    721  O    HOH h 258     -49.225 -40.566 -59.212  1.00 19.92           O
ATOM    722  O    HOH h 259     -78.728 -36.750 -31.907  1.00  8.82           O
ATOM    723  O    HOH h 260      26.810 -31.925 -58.598  1.00  3.11           O
ATOM    724  O    HOH h 261     -31.330 -73.611 -49.321  1.00 10.26           O
ATOM    725  O    HOH h 262     -47.900  13.437 -81.242  1.00 15.18           O
ATOM    726  O    HOH h 263     -22.581 -17.252  54.181  1.00 19.70           O
ATOM    727  O    HOH h 264     -40.951  12.127  -6.684  1.00 16.92           O
ATOM    728  O    HOH h 265     -17.210 -64.414   8.233  1.00 12.19           O
ATOM    729  O    HOH h 266      -0.408 -60.002 -15.182  1.00 14.54           O
ATOM    730  O    HOH h 267     -27.359  -6.010 -94.256  1.00 16.81           O
ATOM    731  O    HOH h 268     -30.179 -21.222  -5.182  1.00  3.91           O
ATOM    732  O    HOH h 269     -82.288 -23.148 -17.063  1.00 13.65           O
ATOM    733  O    HOH h 270      38.940  -9.667 -66.893  1.00  9.43           O
ATOM    734  O    HOH h 271     -28.375 -11.860 -85.717  1.00 14.41           O
ATOM    735  O    HOH h 272     -51.276 -88.397 -53.603  1.00 17.18           O
ATOM    736  O    HOH h 273     -37.549 -72.248 -50.761  1.00 28.31           O
ATOM    737  O    HOH h 274      25.486 -11.797 -30.998  1.00  8.70           O
ATOM    738  O    HOH h 275      18.064 -22.934 -62.214  1.00 11.04           O
ATOM    739  O    HOH h 276     -37.561 -29.598  -3.010  1.00 17.05           O
ATOM    740  O    HOH h 277      23.932 -11.054 -34.784  1.00 19.03           O
ATOM    741  O    HOH h 278     -31.266 -18.818-101.717  1.00 16.17           O
ATOM    742  O    HOH h 279      -1.142 -67.710 -18.709  1.00 17.88           O
ATOM    743  O    HOH h 280       0.434 -44.910   2.768  1.00 12.64           O
ATOM    744  O    HOH h 281      23.501 -30.796 -57.870  1.00 17.38           O
ATOM    745  O    HOH h 282      24.758 -16.777 -47.345  1.00 29.41           O
TER     746       HOH h 282
ATOM    747  C1   PEG i   1     -28.045 -63.373 -52.873  1.00 55.79           C
ATOM    748  O1   PEG i   1     -27.017 -63.355 -51.880  1.00 53.07           O
ATOM    749  C2   PEG i   1     -29.304 -64.054 -52.347  1.00 57.58           C
ATOM    750  O2   PEG i   1     -29.421 -65.379 -52.870  1.00 58.86           O
ATOM    751  C3   PEG i   1     -30.439 -66.141 -52.218  1.00 59.85           C
ATOM    752  C4   PEG i   1     -30.027 -67.610 -52.165  1.00 60.64           C
ATOM    753  O4   PEG i   1     -30.927 -68.381 -51.351  1.00 60.29           O
ATOM    754  C1   PEG j   1     -43.475 -23.730 -74.842  1.00 38.65           C
ATOM    755  O1   PEG j   1     -42.911 -22.792 -75.773  1.00 38.35           O
ATOM    756  C2   PEG j   1     -45.002 -23.835 -74.951  1.00 38.10           C
ATOM    757  O2   PEG j   1     -45.701 -23.066 -73.954  1.00 36.74           O
ATOM    758  C3   PEG j   1     -46.806 -22.330 -74.498  1.00 34.35           C
ATOM    759  C4   PEG j   1     -48.127 -23.027 -74.182  1.00 32.77           C
ATOM    760  O4   PEG j   1     -49.231 -22.178 -74.512  1.00 31.47           O
ATOM    761  C1   PEG k   1     -51.274 -34.238  28.119  1.00 46.37           C
ATOM    762  O1   PEG k   1     -52.371 -34.645  28.955  1.00 45.70           O
ATOM    763  C2   PEG k   1     -51.106 -35.169  26.916  1.00 46.52           C
ATOM    764  O2   PEG k   1     -51.222 -36.536  27.318  1.00 46.38           O
ATOM    765  C3   PEG k   1     -52.487 -37.114  26.985  1.00 45.47           C
ATOM    766  C4   PEG k   1     -53.060 -37.831  28.201  1.00 44.71           C
ATOM    767  O4   PEG k   1     -52.892 -39.232  27.992  1.00 43.75           O
ATOM    768  O1   SO4 l   1     -50.788 -40.544 -57.437  1.00 80.56           O
ATOM    769  O2   SO4 l   1     -51.835 -39.011 -58.928  1.00 80.65           O
ATOM    770  O3   SO4 l   1     -51.780 -38.522 -56.590  1.00 80.43           O
ATOM    771  O4   SO4 l   1     -49.772 -38.443 -57.873  1.00 80.75           O
ATOM    772  S    SO4 l   1     -51.047 -39.130 -57.702  1.00 80.65           S
TER     773       SO4 l   1
ATOM    774  N    GLY A  74     -42.920 -41.920 -66.467  1.00 42.06         A N
ATOM    775  CA   GLY A  74     -43.076 -41.716 -64.990  1.00 42.28         A C
ATOM    776  C    GLY A  74     -41.897 -40.965 -64.378  1.00 42.05         A C
ATOM    777  O    GLY A  74     -41.809 -39.727 -64.476  1.00 42.42         A O
ATOM    778  N    SER A  75     -41.017 -41.720 -63.713  1.00 41.01         A N
ATOM    779  CA   SER A  75     -39.643 -41.306 -63.388  1.00 39.93         A C
ATOM    780  C    SER A  75     -39.075 -42.214 -62.319  1.00 40.70         A C
```

FIGURE 1 (cont'd)

```
ATOM    781  O   SER A  75     -39.752 -42.528 -61.353  1.00 40.32      A    O
ATOM    782  CB  SER A  75     -39.537 -39.836 -62.968  1.00 39.16      A    C
ATOM    783  OG  SER A  75     -39.473 -38.978 -64.097  1.00 37.16      A    O
ATOM    784  N   LEU A  76     -37.834 -42.641 -62.532  1.00 42.67      A    N
ATOM    785  CA  LEU A  76     -37.057 -43.471 -61.607  1.00 45.28      A    C
ATOM    786  C   LEU A  76     -37.681 -44.827 -61.262  1.00 48.87      A    C
ATOM    787  O   LEU A  76     -38.730 -44.879 -60.640  1.00 48.84      A    O
ATOM    788  CB  LEU A  76     -36.693 -42.690 -60.339  1.00 44.07      A    C
ATOM    789  CG  LEU A  76     -35.371 -43.101 -59.698  1.00 42.71      A    C
ATOM    790  CD1 LEU A  76     -35.223 -42.441 -58.360  1.00 40.99      A    C
ATOM    791  CD2 LEU A  76     -34.193 -42.747 -60.612  1.00 42.18      A    C
ATOM    792  N   PRO A  77     -37.013 -45.927 -61.654  1.00 54.09      A    N
ATOM    793  CA  PRO A  77     -37.425 -47.323 -61.469  1.00 55.33      A    C
ATOM    794  C   PRO A  77     -37.063 -47.932 -60.103  1.00 55.72      A    C
ATOM    795  O   PRO A  77     -36.073 -47.544 -59.487  1.00 55.66      A    O
ATOM    796  CB  PRO A  77     -36.678 -48.047 -62.587  1.00 56.05      A    C
ATOM    797  CG  PRO A  77     -35.457 -47.234 -62.816  1.00 55.88      A    C
ATOM    798  CD  PRO A  77     -35.757 -45.823 -62.416  1.00 54.78      A    C
ATOM    799  N   GLU A  78     -37.867 -48.891 -59.656  1.00 55.87      A    N
ATOM    800  CA  GLU A  78     -37.715 -49.511 -58.345  1.00 55.75      A    C
ATOM    801  C   GLU A  78     -36.272 -49.829 -57.938  1.00 57.02      A    C
ATOM    802  O   GLU A  78     -35.871 -49.552 -56.808  1.00 57.24      A    O
ATOM    803  CB  GLU A  78     -38.541 -50.790 -58.293  1.00 53.76      A    C
ATOM    804  CG  GLU A  78     -39.818 -50.735 -57.493  1.00 51.01      A    C
ATOM    805  CD  GLU A  78     -40.110 -52.119 -56.904  1.00 42.90      A    C
ATOM    806  OE1 GLU A  78     -39.724 -52.375 -55.740  1.00 39.68      A    O
ATOM    807  OE2 GLU A  78     -40.677 -52.973 -57.628  1.00 41.36      A    O
ATOM    808  N   ALA A  79     -35.507 -50.418 -58.854  1.00 58.26      A    N
ATOM    809  CA  ALA A  79     -34.133 -50.834 -58.577  1.00 58.92      A    C
ATOM    810  C   ALA A  79     -33.262 -49.671 -58.104  1.00 58.69      A    C
ATOM    811  O   ALA A  79     -32.574 -49.786 -57.090  1.00 58.83      A    O
ATOM    812  CB  ALA A  79     -33.519 -51.501 -59.802  1.00 59.74      A    C
ATOM    813  N   ARG A  80     -33.301 -48.560 -58.841  1.00 57.97      A    N
ATOM    814  CA  ARG A  80     -32.534 -47.364 -58.493  1.00 56.98      A    C
ATOM    815  C   ARG A  80     -33.145 -46.690 -57.270  1.00 56.71      A    C
ATOM    816  O   ARG A  80     -32.425 -46.226 -56.387  1.00 56.75      A    O
ATOM    817  CB  ARG A  80     -32.443 -46.390 -59.678  1.00 55.27      A    C
ATOM    818  N   LEU A  81     -34.472 -46.664 -57.208  1.00 56.41      A    N
ATOM    819  CA  LEU A  81     -35.172 -46.036 -56.095  1.00 55.83      A    C
ATOM    820  C   LEU A  81     -34.747 -46.653 -54.776  1.00 55.87      A    C
ATOM    821  O   LEU A  81     -34.316 -45.943 -53.874  1.00 55.52      A    O
ATOM    822  CB  LEU A  81     -36.690 -46.132 -56.281  1.00 55.66      A    C
ATOM    823  CG  LEU A  81     -37.608 -45.343 -55.336  1.00 54.88      A    C
ATOM    824  CD1 LEU A  81     -38.838 -44.846 -56.072  1.00 54.70      A    C
ATOM    825  CD2 LEU A  81     -38.020 -46.174 -54.141  1.00 54.76      A    C
ATOM    826  N   ARG A  82     -34.849 -47.978 -54.682  1.00 56.34      A    N
ATOM    827  CA  ARG A  82     -34.511 -48.709 -53.454  1.00 56.78      A    C
ATOM    828  C   ARG A  82     -33.018 -48.581 -53.112  1.00 56.70      A    C
ATOM    829  O   ARG A  82     -32.628 -48.612 -51.940  1.00 56.66      A    O
ATOM    830  CB  ARG A  82     -34.950 -50.181 -53.549  1.00 57.34      A    C
ATOM    831  CG  ARG A  82     -34.988 -50.913 -52.203  1.00 58.28      A    C
ATOM    832  CD  ARG A  82     -35.742 -52.233 -52.271  1.00 59.64      A    C
ATOM    833  NE  ARG A  82     -37.143 -52.106 -51.866  1.00 59.76      A    N
ATOM    834  CZ  ARG A  82     -38.159 -51.894 -52.699  1.00 59.81      A    C
ATOM    835  NH1 ARG A  82     -37.948 -51.769 -54.005  1.00 59.99      A    N
ATOM    836  NH2 ARG A  82     -39.393 -51.801 -52.221  1.00 59.57      A    N
ATOM    837  N   ARG A  83     -32.202 -48.415 -54.147  1.00 56.45      A    N
ATOM    838  CA  ARG A  83     -30.770 -48.196 -53.997  1.00 55.91      A    C
ATOM    839  C   ARG A  83     -30.495 -46.797 -53.455  1.00 55.48      A    C
ATOM    840  O   ARG A  83     -29.605 -46.612 -52.634  1.00 55.65      A    O
ATOM    841  CB  ARG A  83     -30.081 -48.445 -55.345  1.00 54.94      A    C
ATOM    842  CG  ARG A  83     -28.777 -47.702 -55.627  1.00 54.46      A    C
ATOM    843  CD  ARG A  83     -28.552 -47.702 -57.145  1.00 54.57      A    C
ATOM    844  NE  ARG A  83     -27.490 -46.806 -57.610  1.00 53.98      A    N
ATOM    845  CZ  ARG A  83     -27.677 -45.681 -58.313  1.00 51.87      A    C
```

FIGURE 1 (cont'd)

```
ATOM    846  NH1 ARG A  83     -28.893 -45.275 -58.667  1.00 51.08      A  N
ATOM    847  NH2 ARG A  83     -26.633 -44.954 -58.676  1.00 51.11      A  N
ATOM    848  N   VAL A  84     -31.282 -45.829 -53.908  1.00 54.69      A  N
ATOM    849  CA  VAL A  84     -31.143 -44.444 -53.474  1.00 53.62      A  C
ATOM    850  C   VAL A  84     -31.651 -44.280 -52.046  1.00 52.96      A  C
ATOM    851  O   VAL A  84     -30.917 -43.821 -51.185  1.00 52.80      A  O
ATOM    852  CB  VAL A  84     -31.845 -43.451 -54.453  1.00 53.49      A  C
ATOM    853  CG1 VAL A  84     -31.035 -43.306 -55.727  1.00 53.53      A  C
ATOM    854  CG2 VAL A  84     -32.054 -42.076 -53.814  1.00 52.77      A  C
ATOM    855  N   VAL A  85     -32.896 -44.672 -51.797  1.00 52.15      A  N
ATOM    856  CA  VAL A  85     -33.468 -44.602 -50.463  1.00 51.25      A  C
ATOM    857  C   VAL A  85     -32.557 -45.313 -49.481  1.00 51.74      A  C
ATOM    858  O   VAL A  85     -32.512 -44.960 -48.306  1.00 51.95      A  O
ATOM    859  CB  VAL A  85     -34.864 -45.210 -50.429  1.00 49.75      A  C
ATOM    860  CG1 VAL A  85     -35.255 -45.601 -49.018  1.00 49.95      A  C
ATOM    861  CG2 VAL A  85     -35.856 -44.231 -51.011  1.00 49.70      A  C
ATOM    862  N   GLY A  86     -31.813 -46.298 -49.980  1.00 52.06      A  N
ATOM    863  CA  GLY A  86     -30.844 -47.034 -49.174  1.00 52.01      A  C
ATOM    864  C   GLY A  86     -29.590 -46.243 -48.857  1.00 51.61      A  C
ATOM    865  O   GLY A  86     -28.884 -46.547 -47.907  1.00 51.86      A  O
ATOM    866  N   GLN A  87     -29.310 -45.222 -49.652  1.00 50.94      A  N
ATOM    867  CA  GLN A  87     -28.098 -44.436 -49.484  1.00 50.13      A  C
ATOM    868  C   GLN A  87     -28.185 -43.483 -48.297  1.00 49.54      A  C
ATOM    869  O   GLN A  87     -27.164 -43.019 -47.805  1.00 49.51      A  O
ATOM    870  N   LEU A  88     -29.402 -43.181 -47.852  1.00 48.72      A  N
ATOM    871  CA  LEU A  88     -29.613 -42.308 -46.702  1.00 48.02      A  C
ATOM    872  C   LEU A  88     -29.273 -43.080 -45.442  1.00 48.37      A  C
ATOM    873  O   LEU A  88     -29.772 -44.177 -45.252  1.00 48.60      A  O
ATOM    874  CB  LEU A  88     -31.069 -41.840 -46.631  1.00 47.28      A  C
ATOM    875  CG  LEU A  88     -31.631 -40.948 -47.736  1.00 45.85      A  C
ATOM    876  CD1 LEU A  88     -33.081 -41.276 -47.956  1.00 43.96      A  C
ATOM    877  CD2 LEU A  88     -31.440 -39.489 -47.459  1.00 43.98      A  C
ATOM    878  N   ASP A  89     -28.418 -42.513 -44.594  1.00 48.71      A  N
ATOM    879  CA  ASP A  89     -28.094 -43.109 -43.290  1.00 49.11      A  C
ATOM    880  C   ASP A  89     -28.833 -42.391 -42.165  1.00 49.18      A  C
ATOM    881  O   ASP A  89     -28.461 -41.279 -41.789  1.00 48.98      A  O
ATOM    882  CB  ASP A  89     -26.580 -43.114 -43.022  1.00 49.28      A  C
ATOM    883  CG  ASP A  89     -26.211 -43.718 -41.657  1.00 49.42      A  C
ATOM    884  OD1 ASP A  89     -25.089 -44.253 -41.524  1.00 48.52      A  O
ATOM    885  OD2 ASP A  89     -27.018 -43.635 -40.703  1.00 48.81      A  O
ATOM    886  N   PRO A  90     -29.876 -43.038 -41.610  1.00 49.43      A  N
ATOM    887  CA  PRO A  90     -30.724 -42.447 -40.582  1.00 49.32      A  C
ATOM    888  C   PRO A  90     -29.955 -41.971 -39.357  1.00 49.26      A  C
ATOM    889  O   PRO A  90     -30.234 -40.892 -38.853  1.00 49.02      A  O
ATOM    890  CB  PRO A  90     -31.677 -43.587 -40.221  1.00 49.46      A  C
ATOM    891  CG  PRO A  90     -31.745 -44.409 -41.460  1.00 49.73      A  C
ATOM    892  CD  PRO A  90     -30.347 -44.384 -41.987  1.00 49.80      A  C
ATOM    893  N   GLN A  91     -28.983 -42.743 -38.893  1.00 49.44      A  N
ATOM    894  CA  GLN A  91     -28.250 -42.335 -37.715  1.00 49.53      A  C
ATOM    895  C   GLN A  91     -27.261 -41.211 -38.036  1.00 48.96      A  C
ATOM    896  O   GLN A  91     -26.952 -40.397 -37.171  1.00 49.05      A  O
ATOM    897  CB  GLN A  91     -27.632 -43.549 -37.014  1.00 50.12      A  C
ATOM    898  CG  GLN A  91     -26.252 -43.953 -37.446  1.00 50.80      A  C
ATOM    899  CD  GLN A  91     -25.278 -43.749 -36.312  1.00 46.14      A  C
ATOM    900  NE2 GLN A  91     -23.987 -43.853 -36.600  1.00 45.31      A  N
ATOM    901  OE1 GLN A  91     -25.689 -43.497 -35.179  1.00 45.29      A  O
ATOM    902  N   ARG A  92     -26.811 -41.136 -39.285  1.00 48.12      A  N
ATOM    903  CA  ARG A  92     -25.963 -40.027 -39.735  1.00 47.09      A  C
ATOM    904  C   ARG A  92     -26.748 -38.721 -39.706  1.00 46.63      A  C
ATOM    905  O   ARG A  92     -26.264 -37.716 -39.183  1.00 46.53      A  O
ATOM    906  CB  ARG A  92     -25.402 -40.308 -41.140  1.00 46.97      A  C
ATOM    907  CG  ARG A  92     -24.684 -39.137 -41.843  1.00 45.17      A  C
ATOM    908  CD  ARG A  92     -24.127 -39.551 -43.214  1.00 43.07      A  C
ATOM    909  NE  ARG A  92     -25.181 -39.918 -44.164  1.00 41.61      A  N
ATOM    910  CZ  ARG A  92     -24.995 -40.615 -45.280  1.00 37.06      A  C
```

FIGURE 1 (cont'd)

```
ATOM    911  NH1 ARG A  92     -23.790 -41.074 -45.600  1.00 36.17    A    N
ATOM    912  NH2 ARG A  92     -26.026 -40.875 -46.067  1.00 35.34    A    N
ATOM    913  N   LEU A  93     -27.961 -38.759 -40.261  1.00 46.06    A    N
ATOM    914  CA  LEU A  93     -28.868 -37.614 -40.287  1.00 45.44    A    C
ATOM    915  C   LEU A  93     -28.986 -37.048 -38.885  1.00 45.51    A    C
ATOM    916  O   LEU A  93     -28.762 -35.857 -38.652  1.00 45.43    A    O
ATOM    917  CB  LEU A  93     -30.254 -38.046 -40.776  1.00 45.05    A    C
ATOM    918  CG  LEU A  93     -31.191 -37.102 -41.532  1.00 43.87    A    C
ATOM    919  CD1 LEU A  93     -31.232 -35.702 -40.965  1.00 42.72    A    C
ATOM    920  CD2 LEU A  93     -32.583 -37.689 -41.598  1.00 43.10    A    C
ATOM    921  N   TRP A  94     -29.301 -37.936 -37.949  1.00 45.70    A    N
ATOM    922  CA  TRP A  94     -29.629 -37.562 -36.583  1.00 45.73    A    C
ATOM    923  C   TRP A  94     -28.420 -37.138 -35.760  1.00 45.70    A    C
ATOM    924  O   TRP A  94     -28.517 -36.226 -34.946  1.00 45.61    A    O
ATOM    925  CB  TRP A  94     -30.365 -38.710 -35.885  1.00 45.92    A    C
ATOM    926  CG  TRP A  94     -31.236 -38.221 -34.794  1.00 46.40    A    C
ATOM    927  CD1 TRP A  94     -30.867 -37.963 -33.511  1.00 47.12    A    C
ATOM    928  CD2 TRP A  94     -32.625 -37.889 -34.885  1.00 46.45    A    C
ATOM    929  CE2 TRP A  94     -33.031 -37.444 -33.614  1.00 46.68    A    C
ATOM    930  CE3 TRP A  94     -33.566 -37.930 -35.915  1.00 46.24    A    C
ATOM    931  NE1 TRP A  94     -31.939 -37.502 -32.791  1.00 47.07    A    N
ATOM    932  CZ2 TRP A  94     -34.339 -37.043 -33.344  1.00 46.58    A    C
ATOM    933  CZ3 TRP A  94     -34.866 -37.529 -35.642  1.00 46.15    A    C
ATOM    934  CH2 TRP A  94     -35.238 -37.094 -34.367  1.00 46.29    A    C
ATOM    935  N   SER A  95     -27.284 -37.789 -35.984  1.00 45.74    A    N
ATOM    936  CA  SER A  95     -26.132 -37.637 -35.106  1.00 45.72    A    C
ATOM    937  C   SER A  95     -25.035 -36.737 -35.658  1.00 45.14    A    C
ATOM    938  O   SER A  95     -24.508 -35.909 -34.931  1.00 45.12    A    O
ATOM    939  CB  SER A  95     -25.561 -39.008 -34.766  1.00 46.25    A    C
ATOM    940  OG  SER A  95     -25.240 -39.092 -33.397  1.00 47.20    A    O
ATOM    941  N   THR A  96     -24.689 -36.901 -36.930  1.00 44.43    A    N
ATOM    942  CA  THR A  96     -23.652 -36.086 -37.543  1.00 43.76    A    C
ATOM    943  C   THR A  96     -24.159 -34.708 -37.952  1.00 42.88    A    C
ATOM    944  O   THR A  96     -23.385 -33.749 -37.931  1.00 42.99    A    O
ATOM    945  CB  THR A  96     -23.054 -36.750 -38.780  1.00 43.97    A    C
ATOM    946  OG1 THR A  96     -23.077 -38.167 -38.622  1.00 44.70    A    O
ATOM    947  N   TYR A  97     -25.444 -34.612 -38.323  1.00 41.59    A    N
ATOM    948  CA  TYR A  97     -26.011 -33.367 -38.866  1.00 40.20    A    C
ATOM    949  C   TYR A  97     -27.021 -32.649 -37.989  1.00 39.80    A    C
ATOM    950  O   TYR A  97     -26.965 -31.433 -37.883  1.00 39.61    A    O
ATOM    951  CB  TYR A  97     -26.601 -33.575 -40.262  1.00 39.64    A    C
ATOM    952  CG  TYR A  97     -25.621 -34.127 -41.249  1.00 38.59    A    C
ATOM    953  CD1 TYR A  97     -24.359 -33.570 -41.387  1.00 37.57    A    C
ATOM    954  CD2 TYR A  97     -25.955 -35.199 -42.047  1.00 34.99    A    C
ATOM    955  CE1 TYR A  97     -23.452 -34.082 -42.275  1.00 37.35    A    C
ATOM    956  CE2 TYR A  97     -25.055 -35.718 -42.945  1.00 33.76    A    C
ATOM    957  CZ  TYR A  97     -23.805 -35.150 -43.051  1.00 34.07    A    C
ATOM    958  OH  TYR A  97     -22.882 -35.641 -43.931  1.00 33.98    A    O
ATOM    959  N   LEU A  98     -27.947 -33.378 -37.375  1.00 39.58    A    N
ATOM    960  CA  LEU A  98     -28.988 -32.736 -36.563  1.00 39.43    A    C
ATOM    961  C   LEU A  98     -28.512 -32.255 -35.191  1.00 39.65    A    C
ATOM    962  O   LEU A  98     -28.651 -31.083 -34.857  1.00 39.53    A    O
ATOM    963  CB  LEU A  98     -30.215 -33.643 -36.407  1.00 39.23    A    C
ATOM    964  CG  LEU A  98     -31.347 -33.053 -35.549  1.00 39.00    A    C
ATOM    965  CD1 LEU A  98     -31.900 -31.772 -36.157  1.00 38.44    A    C
ATOM    966  CD2 LEU A  98     -32.469 -34.040 -35.322  1.00 39.13    A    C
ATOM    967  N   ARG A  99     -27.972 -33.179 -34.403  1.00 40.00    A    N
ATOM    968  CA  ARG A  99     -27.535 -32.893 -33.038  1.00 40.08    A    C
ATOM    969  C   ARG A  99     -26.535 -31.748 -32.939  1.00 40.21    A    C
ATOM    970  O   ARG A  99     -26.680 -30.901 -32.064  1.00 40.38    A    O
ATOM    971  CB  ARG A  99     -27.054 -34.160 -32.297  1.00 39.51    A    C
ATOM    972  CG  ARG A  99     -28.044 -34.626 -31.235  1.00 39.38    A    C
ATOM    973  CD  ARG A  99     -27.530 -35.744 -30.352  1.00 39.90    A    C
ATOM    974  NE  ARG A  99     -28.225 -37.003 -30.618  1.00 39.62    A    N
ATOM    975  N   PRO A 100     -25.539 -31.688 -33.840  1.00 40.19    A    N
```

FIGURE 1 (cont'd)

```
ATOM    976  CA   PRO A 100     -24.656 -30.540 -33.790  1.00 40.11      A  C
ATOM    977  C    PRO A 100     -25.410 -29.223 -33.944  1.00 39.74      A  C
ATOM    978  O    PRO A 100     -25.004 -28.221 -33.368  1.00 39.96      A  O
ATOM    979  CB   PRO A 100     -23.729 -30.767 -34.985  1.00 40.23      A  C
ATOM    980  CG   PRO A 100     -23.679 -32.215 -35.136  1.00 40.46      A  C
ATOM    981  CD   PRO A 100     -25.066 -32.676 -34.822  1.00 40.33      A  C
ATOM    982  N    LEU A 101     -26.511 -29.238 -34.689  1.00 39.09      A  N
ATOM    983  CA   LEU A 101     -27.279 -28.031 -34.971  1.00 38.47      A  C
ATOM    984  C    LEU A 101     -28.146 -27.544 -33.811  1.00 38.44      A  C
ATOM    985  O    LEU A 101     -28.594 -26.394 -33.797  1.00 38.29      A  O
ATOM    986  CB   LEU A 101     -28.155 -28.266 -36.190  1.00 38.08      A  C
ATOM    987  CG   LEU A 101     -27.717 -27.705 -37.543  1.00 37.77      A  C
ATOM    988  CD1  LEU A 101     -26.223 -27.807 -37.761  1.00 38.20      A  C
ATOM    989  CD2  LEU A 101     -28.485 -28.384 -38.679  1.00 37.49      A  C
ATOM    990  N    LEU A 102     -28.374 -28.412 -32.833  1.00 38.52      A  N
ATOM    991  CA   LEU A 102     -29.323 -28.128 -31.760  1.00 38.58      A  C
ATOM    992  C    LEU A 102     -28.731 -27.324 -30.599  1.00 38.92      A  C
ATOM    993  O    LEU A 102     -28.752 -27.763 -29.448  1.00 39.21      A  O
ATOM    994  CB   LEU A 102     -29.961 -29.433 -31.269  1.00 38.52      A  C
ATOM    995  CG   LEU A 102     -30.885 -30.165 -32.252  1.00 38.07      A  C
ATOM    996  CD1  LEU A 102     -31.278 -31.533 -31.722  1.00 38.26      A  C
ATOM    997  CD2  LEU A 102     -32.137 -29.347 -32.546  1.00 37.55      A  C
ATOM    998  N    VAL A 103     -28.210 -26.140 -30.913  1.00 39.07      A  N
ATOM    999  CA   VAL A 103     -27.697 -25.214 -29.902  1.00 39.36      A  C
ATOM   1000  C    VAL A 103     -28.270 -23.823 -30.090  1.00 39.07      A  C
ATOM   1001  O    VAL A 103     -28.702 -23.484 -31.181  1.00 38.82      A  O
ATOM   1002  CB   VAL A 103     -26.180 -25.116 -29.935  1.00 39.69      A  C
ATOM   1003  CG1  VAL A 103     -25.688 -24.843 -31.340  1.00 39.55      A  C
ATOM   1004  CG2  VAL A 103     -25.570 -26.389 -29.386  1.00 40.63      A  C
ATOM   1005  N    VAL A 104     -28.276 -23.026 -29.024  1.00 39.02      A  N
ATOM   1006  CA   VAL A 104     -28.749 -21.650 -29.096  1.00 38.70      A  C
ATOM   1007  C    VAL A 104     -27.875 -20.940 -30.111  1.00 38.90      A  C
ATOM   1008  O    VAL A 104     -26.657 -21.037 -30.045  1.00 39.21      A  O
ATOM   1009  CB   VAL A 104     -28.662 -20.929 -27.744  1.00 38.04      A  C
ATOM   1010  CG1  VAL A 104     -29.706 -19.834 -27.678  1.00 37.50      A  C
ATOM   1011  CG2  VAL A 104     -28.848 -21.900 -26.592  1.00 38.08      A  C
ATOM   1012  N    ARG A 105     -28.503 -20.248 -31.057  1.00 38.76      A  N
ATOM   1013  CA   ARG A 105     -27.806 -19.741 -32.242  1.00 38.51      A  C
ATOM   1014  C    ARG A 105     -28.424 -18.469 -32.840  1.00 38.50      A  C
ATOM   1015  O    ARG A 105     -28.337 -18.226 -34.046  1.00 38.21      A  O
ATOM   1016  CB   ARG A 105     -27.689 -20.848 -33.308  1.00 38.34      A  C
ATOM   1017  CG   ARG A 105     -29.017 -21.365 -33.860  1.00 37.70      A  C
ATOM   1018  CD   ARG A 105     -28.875 -22.739 -34.460  1.00 37.34      A  C
ATOM   1019  NE   ARG A 105     -30.097 -23.121 -35.152  1.00 37.00      A  N
ATOM   1020  CZ   ARG A 105     -31.047 -23.900 -34.648  1.00 36.78      A  C
ATOM   1021  NH1  ARG A 105     -30.924 -24.401 -33.430  1.00 36.90      A  N
ATOM   1022  NH2  ARG A 105     -32.122 -24.183 -35.374  1.00 36.40      A  N
ATOM   1023  N    THR A 106     -29.035 -17.655 -31.985  1.00 38.71      A  N
ATOM   1024  CA   THR A 106     -29.572 -16.364 -32.393  1.00 38.91      A  C
ATOM   1025  C    THR A 106     -28.504 -15.554 -33.143  1.00 38.98      A  C
ATOM   1026  O    THR A 106     -27.321 -15.679 -32.841  1.00 38.99      A  O
ATOM   1027  CB   THR A 106     -30.077 -15.581 -31.179  1.00 39.09      A  C
ATOM   1028  OG1  THR A 106     -28.981 -15.306 -30.304  1.00 39.78      A  O
ATOM   1029  N    PRO A 107     -28.918 -14.733 -34.133  1.00 39.10      A  N
ATOM   1030  CA   PRO A 107     -28.000 -13.970 -34.992  1.00 39.39      A  C
ATOM   1031  C    PRO A 107     -26.819 -13.325 -34.259  1.00 39.94      A  C
ATOM   1032  O    PRO A 107     -26.991 -12.746 -33.182  1.00 40.11      A  O
ATOM   1033  CB   PRO A 107     -28.902 -12.891 -35.585  1.00 39.28      A  C
ATOM   1034  CG   PRO A 107     -30.236 -13.530 -35.665  1.00 38.87      A  C
ATOM   1035  CD   PRO A 107     -30.326 -14.487 -34.505  1.00 38.98      A  C
ATOM   1036  N    GLY A 108     -25.630 -13.453 -34.848  1.00 40.37      A  N
ATOM   1037  CA   GLY A 108     -24.398 -12.857 -34.319  1.00 41.00      A  C
ATOM   1038  C    GLY A 108     -23.922 -13.318 -32.950  1.00 41.36      A  C
ATOM   1039  O    GLY A 108     -23.117 -12.648 -32.312  1.00 41.83      A  O
ATOM   1040  N    SER A 109     -24.421 -14.456 -32.489  1.00 41.33      A  N
```

FIGURE 1 (cont'd)

```
ATOM   1041  CA   SER A 109     -23.972 -15.027 -31.233  1.00 41.37      A   C
ATOM   1042  C    SER A 109     -22.837 -16.017 -31.500  1.00 41.56      A   C
ATOM   1043  O    SER A 109     -22.495 -16.249 -32.658  1.00 41.35      A   O
ATOM   1044  CB   SER A 109     -25.138 -15.728 -30.553  1.00 41.26      A   C
ATOM   1045  OG   SER A 109     -25.553 -16.844 -31.315  1.00 40.68      A   O
ATOM   1046  N    PRO A 110     -22.235 -16.591 -30.436  1.00 41.91      A   N
ATOM   1047  CA   PRO A 110     -21.234 -17.632 -30.621  1.00 41.84      A   C
ATOM   1048  C    PRO A 110     -21.810 -18.884 -31.249  1.00 41.27      A   C
ATOM   1049  O    PRO A 110     -21.144 -19.520 -32.049  1.00 41.10      A   O
ATOM   1050  CB   PRO A 110     -20.769 -17.926 -29.196  1.00 42.31      A   C
ATOM   1051  CG   PRO A 110     -20.999 -16.680 -28.467  1.00 42.76      A   C
ATOM   1052  CD   PRO A 110     -22.271 -16.136 -29.035  1.00 42.32      A   C
ATOM   1053  N    GLY A 111     -23.038 -19.232 -30.886  1.00 40.81      A   N
ATOM   1054  CA   GLY A 111     -23.715 -20.391 -31.471  1.00 40.15      A   C
ATOM   1055  C    GLY A 111     -24.007 -20.234 -32.955  1.00 39.59      A   C
ATOM   1056  O    GLY A 111     -23.793 -21.159 -33.734  1.00 39.40      A   O
ATOM   1057  N    ASN A 112     -24.501 -19.055 -33.336  1.00 39.19      A   N
ATOM   1058  CA   ASN A 112     -24.751 -18.698 -34.734  1.00 38.59      A   C
ATOM   1059  C    ASN A 112     -23.505 -18.900 -35.575  1.00 38.81      A   C
ATOM   1060  O    ASN A 112     -23.572 -19.477 -36.649  1.00 38.63      A   O
ATOM   1061  CB   ASN A 112     -25.236 -17.244 -34.840  1.00 38.28      A   C
ATOM   1062  CG   ASN A 112     -25.538 -16.816 -36.272  1.00 37.16      A   C
ATOM   1063  ND2  ASN A 112     -25.046 -15.642 -36.654  1.00 36.45      A   N
ATOM   1064  OD1  ASN A 112     -26.215 -17.516 -37.013  1.00 36.01      A   O
ATOM   1065  N    LEU A 113     -22.368 -18.439 -35.065  1.00 39.29      A   N
ATOM   1066  CA   LEU A 113     -21.087 -18.613 -35.743  1.00 39.75      A   C
ATOM   1067  C    LEU A 113     -20.572 -20.059 -35.669  1.00 39.77      A   C
ATOM   1068  O    LEU A 113     -19.986 -20.548 -36.622  1.00 39.70      A   O
ATOM   1069  CB   LEU A 113     -20.051 -17.629 -35.186  1.00 40.18      A   C
ATOM   1070  CG   LEU A 113     -18.849 -17.278 -36.065  1.00 40.89      A   C
ATOM   1071  CD1  LEU A 113     -18.468 -15.819 -35.891  1.00 41.44      A   C
ATOM   1072  CD2  LEU A 113     -17.668 -18.186 -35.773  1.00 41.76      A   C
ATOM   1073  N    GLN A 114     -20.787 -20.732 -34.541  1.00 39.88      A   N
ATOM   1074  CA   GLN A 114     -20.383 -22.128 -34.385  1.00 39.87      A   C
ATOM   1075  C    GLN A 114     -21.097 -22.993 -35.410  1.00 39.60      A   C
ATOM   1076  O    GLN A 114     -20.464 -23.819 -36.056  1.00 39.70      A   O
ATOM   1077  CB   GLN A 114     -20.650 -22.643 -32.961  1.00 40.05      A   C
ATOM   1078  N    VAL A 115     -22.407 -22.787 -35.570  1.00 39.05      A   N
ATOM   1079  CA   VAL A 115     -23.220 -23.540 -36.548  1.00 38.30      A   C
ATOM   1080  C    VAL A 115     -22.819 -23.223 -37.994  1.00 38.63      A   C
ATOM   1081  O    VAL A 115     -22.543 -24.133 -38.780  1.00 38.79      A   O
ATOM   1082  CB   VAL A 115     -24.742 -23.344 -36.330  1.00 36.87      A   C
ATOM   1083  CG1  VAL A 115     -25.530 -23.831 -37.535  1.00 36.69      A   C
ATOM   1084  CG2  VAL A 115     -25.174 -24.104 -35.103  1.00 36.66      A   C
ATOM   1085  N    ARG A 116     -22.779 -21.931 -38.323  1.00 38.85      A   N
ATOM   1086  CA   ARG A 116     -22.310 -21.445 -39.624  1.00 39.06      A   C
ATOM   1087  C    ARG A 116     -21.001 -22.112 -40.052  1.00 39.49      A   C
ATOM   1088  O    ARG A 116     -20.864 -22.529 -41.198  1.00 39.48      A   O
ATOM   1089  CB   ARG A 116     -22.137 -19.926 -39.582  1.00 38.97      A   C
ATOM   1090  CG   ARG A 116     -21.548 -19.295 -40.838  1.00 39.20      A   C
ATOM   1091  CD   ARG A 116     -21.225 -17.819 -40.603  1.00 40.25      A   C
ATOM   1092  NE   ARG A 116     -22.399 -17.067 -40.151  1.00 40.90      A   N
ATOM   1093  CZ   ARG A 116     -22.360 -15.872 -39.563  1.00 41.48      A   C
ATOM   1094  NH1  ARG A 116     -21.200 -15.263 -39.340  1.00 41.96      A   N
ATOM   1095  NH2  ARG A 116     -23.492 -15.282 -39.194  1.00 41.63      A   N
ATOM   1096  N    LYS A 117     -20.055 -22.210 -39.120  1.00 40.07      A   N
ATOM   1097  CA   LYS A 117     -18.754 -22.817 -39.363  1.00 40.51      A   C
ATOM   1098  C    LYS A 117     -18.905 -24.312 -39.637  1.00 40.17      A   C
ATOM   1099  O    LYS A 117     -18.204 -24.856 -40.489  1.00 40.28      A   O
ATOM   1100  CB   LYS A 117     -17.831 -22.562 -38.171  1.00 41.11      A   C
ATOM   1101  CG   LYS A 117     -16.353 -22.660 -38.476  1.00 42.50      A   C
ATOM   1102  CD   LYS A 117     -15.483 -22.213 -37.284  1.00 43.87      A   C
ATOM   1103  CE   LYS A 117     -15.028 -20.745 -37.406  1.00 44.08      A   C
ATOM   1104  NZ   LYS A 117     -15.700 -19.744 -36.541  1.00 44.59      A   N
ATOM   1105  N    PHE A 118     -19.832 -24.963 -38.930  1.00 39.55      A   N
```

FIGURE 1 (cont'd)

```
ATOM   1106  CA   PHE A 118     -20.092 -26.392 -39.120  1.00 38.91      A    C
ATOM   1107  C    PHE A 118     -20.717 -26.662 -40.470  1.00 39.16      A    C
ATOM   1108  O    PHE A 118     -20.401 -27.660 -41.117  1.00 39.39      A    O
ATOM   1109  CB   PHE A 118     -20.993 -26.944 -38.020  1.00 37.65      A    C
ATOM   1110  CG   PHE A 118     -21.432 -28.370 -38.240  1.00 36.12      A    C
ATOM   1111  CD1  PHE A 118     -20.502 -29.399 -38.330  1.00 35.85      A    C
ATOM   1112  CD2  PHE A 118     -22.779 -28.684 -38.331  1.00 34.57      A    C
ATOM   1113  CE1  PHE A 118     -20.914 -30.715 -38.524  1.00 35.47      A    C
ATOM   1114  CE2  PHE A 118     -23.203 -29.991 -38.520  1.00 33.86      A    C
ATOM   1115  CZ   PHE A 118     -22.268 -31.008 -38.616  1.00 34.28      A    C
ATOM   1116  N    LEU A 119     -21.608 -25.774 -40.890  1.00 39.15      A    N
ATOM   1117  CA   LEU A 119     -22.205 -25.891 -42.201  1.00 39.15      A    C
ATOM   1118  C    LEU A 119     -21.143 -25.755 -43.284  1.00 39.66      A    C
ATOM   1119  O    LEU A 119     -20.973 -26.658 -44.094  1.00 39.82      A    O
ATOM   1120  CB   LEU A 119     -23.356 -24.905 -42.372  1.00 38.70      A    C
ATOM   1121  CG   LEU A 119     -24.637 -25.303 -41.619  1.00 37.90      A    C
ATOM   1122  CD1  LEU A 119     -25.605 -24.151 -41.569  1.00 37.42      A    C
ATOM   1123  CD2  LEU A 119     -25.331 -26.509 -42.192  1.00 36.66      A    C
ATOM   1124  N    GLU A 120     -20.397 -24.655 -43.268  1.00 40.15      A    N
ATOM   1125  CA   GLU A 120     -19.295 -24.447 -44.221  1.00 40.59      A    C
ATOM   1126  C    GLU A 120     -18.427 -25.681 -44.388  1.00 41.29      A    C
ATOM   1127  O    GLU A 120     -18.193 -26.117 -45.509  1.00 41.56      A    O
ATOM   1128  CB   GLU A 120     -18.403 -23.286 -43.797  1.00 39.83      A    C
ATOM   1129  CG   GLU A 120     -18.994 -21.915 -44.016  1.00 39.53      A    C
ATOM   1130  CD   GLU A 120     -17.986 -20.817 -43.742  1.00 40.12      A    C
ATOM   1131  OE1  GLU A 120     -16.975 -20.734 -44.472  1.00 40.87      A    O
ATOM   1132  OE2  GLU A 120     -18.199 -20.034 -42.790  1.00 41.92      A    O
ATOM   1133  N    ALA A 121     -17.965 -26.235 -43.264  1.00 41.84      A    N
ATOM   1134  CA   ALA A 121     -17.062 -27.391 -43.243  1.00 42.19      A    C
ATOM   1135  C    ALA A 121     -17.686 -28.665 -43.836  1.00 42.13      A    C
ATOM   1136  O    ALA A 121     -17.087 -29.312 -44.700  1.00 42.45      A    O
ATOM   1137  CB   ALA A 121     -16.569 -27.637 -41.838  1.00 42.51      A    C
ATOM   1138  N    THR A 122     -18.888 -29.014 -43.383  1.00 41.55      A    N
ATOM   1139  CA   THR A 122     -19.580 -30.184 -43.888  1.00 40.83      A    C
ATOM   1140  C    THR A 122     -19.736 -30.106 -45.399  1.00 41.30      A    C
ATOM   1141  O    THR A 122     -19.423 -31.062 -46.100  1.00 41.71      A    O
ATOM   1142  CB   THR A 122     -20.937 -30.358 -43.231  1.00 39.40      A    C
ATOM   1143  CG2  THR A 122     -21.677 -31.496 -43.872  1.00 39.47      A    C
ATOM   1144  OG1  THR A 122     -20.742 -30.671 -41.855  1.00 38.49      A    O
ATOM   1145  N    LEU A 123     -20.195 -28.959 -45.891  1.00 41.38      A    N
ATOM   1146  CA   LEU A 123     -20.457 -28.764 -47.308  1.00 41.45      A    C
ATOM   1147  C    LEU A 123     -19.176 -28.891 -48.129  1.00 42.12      A    C
ATOM   1148  O    LEU A 123     -19.164 -29.498 -49.199  1.00 42.36      A    O
ATOM   1149  CB   LEU A 123     -21.125 -27.406 -47.544  1.00 40.99      A    C
ATOM   1150  CG   LEU A 123     -22.592 -27.154 -47.168  1.00 39.78      A    C
ATOM   1151  CD1  LEU A 123     -23.532 -27.758 -48.163  1.00 39.19      A    C
ATOM   1152  CD2  LEU A 123     -22.948 -27.666 -45.827  1.00 39.55      A    C
ATOM   1153  N    ARG A 124     -18.092 -28.334 -47.611  1.00 42.73      A    N
ATOM   1154  CA   ARG A 124     -16.812 -28.374 -48.305  1.00 43.41      A    C
ATOM   1155  C    ARG A 124     -16.249 -29.776 -48.347  1.00 44.07      A    C
ATOM   1156  O    ARG A 124     -15.636 -30.160 -49.337  1.00 44.46      A    O
ATOM   1157  CB   ARG A 124     -15.799 -27.428 -47.661  1.00 43.39      A    C
ATOM   1158  CG   ARG A 124     -15.970 -25.994 -48.081  1.00 42.80      A    C
ATOM   1159  CD   ARG A 124     -14.917 -25.068 -47.502  1.00 42.34      A    C
ATOM   1160  NE   ARG A 124     -15.164 -23.714 -47.981  1.00 41.53      A    N
ATOM   1161  CZ   ARG A 124     -14.877 -23.292 -49.211  1.00 40.14      A    C
ATOM   1162  NH1  ARG A 124     -14.298 -24.101 -50.095  1.00 39.46      A    N
ATOM   1163  NH2  ARG A 124     -15.170 -22.050 -49.563  1.00 40.65      A    N
ATOM   1164  N    SER A 125     -16.474 -30.543 -47.283  1.00 44.55      A    N
ATOM   1165  CA   SER A 125     -15.914 -31.892 -47.161  1.00 45.11      A    C
ATOM   1166  C    SER A 125     -16.605 -32.966 -48.023  1.00 45.23      A    C
ATOM   1167  O    SER A 125     -16.396 -34.161 -47.816  1.00 45.54      A    O
ATOM   1168  CB   SER A 125     -15.902 -32.319 -45.690  1.00 45.28      A    C
ATOM   1169  OG   SER A 125     -17.220 -32.530 -45.211  1.00 45.00      A    O
ATOM   1170  N    LEU A 126     -17.418 -32.546 -48.987  1.00 45.10      A    N
```

FIGURE 1 (cont'd)

```
ATOM   1171  CA   LEU A 126     -18.132 -33.494 -49.839  1.00 45.11           A  C
ATOM   1172  C    LEU A 126     -17.337 -33.850 -51.094  1.00 45.64           A  C
ATOM   1173  O    LEU A 126     -16.567 -33.034 -51.586  1.00 45.90           A  O
ATOM   1174  CB   LEU A 126     -19.528 -32.970 -50.200  1.00 44.59           A  C
ATOM   1175  CG   LEU A 126     -20.562 -32.805 -49.083  1.00 43.77           A  C
ATOM   1176  CD1  LEU A 126     -21.951 -32.720 -49.669  1.00 42.93           A  C
ATOM   1177  CD2  LEU A 126     -20.489 -33.927 -48.078  1.00 43.53           A  C
ATOM   1178  N    THR A 127     -17.539 -35.063 -51.610  1.00 46.14           A  N
ATOM   1179  CA   THR A 127     -16.758 -35.593 -52.743  1.00 46.60           A  C
ATOM   1180  C    THR A 127     -16.912 -34.779 -54.024  1.00 46.67           A  C
ATOM   1181  O    THR A 127     -15.925 -34.501 -54.703  1.00 47.15           A  O
ATOM   1182  CB   THR A 127     -17.112 -37.057 -53.046  1.00 46.84           A  C
ATOM   1183  CG2  THR A 127     -15.995 -37.747 -53.840  1.00 45.62           A  C
ATOM   1184  OG1  THR A 127     -17.358 -37.748 -51.818  1.00 47.07           A  O
ATOM   1185  N    ALA A 128     -18.150 -34.426 -54.363  1.00 46.32           A  N
ATOM   1186  CA   ALA A 128     -18.405 -33.467 -55.437  1.00 46.09           A  C
ATOM   1187  C    ALA A 128     -17.882 -32.115 -54.986  1.00 45.97           A  C
ATOM   1188  O    ALA A 128     -17.959 -31.778 -53.813  1.00 45.94           A  O
ATOM   1189  CB   ALA A 128     -19.878 -33.387 -55.738  1.00 45.78           A  C
ATOM   1190  N    GLY A 129     -17.332 -31.342 -55.905  1.00 45.95           A  N
ATOM   1191  CA   GLY A 129     -16.666 -30.109 -55.514  1.00 45.72           A  C
ATOM   1192  C    GLY A 129     -17.614 -28.960 -55.242  1.00 45.14           A  C
ATOM   1193  O    GLY A 129     -17.766 -28.071 -56.078  1.00 45.52           A  O
ATOM   1194  N    TRP A 130     -18.248 -28.960 -54.075  1.00 44.25           A  N
ATOM   1195  CA   TRP A 130     -19.221 -27.918 -53.746  1.00 43.26           A  C
ATOM   1196  C    TRP A 130     -18.552 -26.555 -53.595  1.00 42.94           A  C
ATOM   1197  O    TRP A 130     -17.581 -26.401 -52.869  1.00 43.12           A  O
ATOM   1198  CB   TRP A 130     -20.002 -28.263 -52.473  1.00 42.93           A  C
ATOM   1199  CG   TRP A 130     -21.155 -29.235 -52.638  1.00 42.39           A  C
ATOM   1200  CD1  TRP A 130     -21.105 -30.593 -52.516  1.00 42.60           A  C
ATOM   1201  CD2  TRP A 130     -22.525 -28.912 -52.910  1.00 41.94           A  C
ATOM   1202  CE2  TRP A 130     -23.240 -30.124 -52.954  1.00 41.83           A  C
ATOM   1203  CE3  TRP A 130     -23.218 -27.715 -53.127  1.00 41.71           A  C
ATOM   1204  NE1  TRP A 130     -22.347 -31.136 -52.715  1.00 42.21           A  N
ATOM   1205  CZ2  TRP A 130     -24.617 -30.173 -53.204  1.00 41.34           A  C
ATOM   1206  CZ3  TRP A 130     -24.589 -27.770 -53.384  1.00 41.32           A  C
ATOM   1207  CH2  TRP A 130     -25.267 -28.988 -53.418  1.00 41.08           A  C
ATOM   1208  N    HIS A 131     -19.080 -25.571 -54.303  1.00 42.53           A  N
ATOM   1209  CA   HIS A 131     -18.578 -24.215 -54.218  1.00 42.32           A  C
ATOM   1210  C    HIS A 131     -19.300 -23.507 -53.073  1.00 41.92           A  C
ATOM   1211  O    HIS A 131     -20.302 -22.803 -53.282  1.00 41.70           A  O
ATOM   1212  CB   HIS A 131     -18.766 -23.492 -55.561  1.00 42.47           A  C
ATOM   1213  CG   HIS A 131     -18.099 -22.156 -55.628  1.00 42.79           A  C
ATOM   1214  CD2  HIS A 131     -18.621 -20.904 -55.609  1.00 40.85           A  C
ATOM   1215  ND1  HIS A 131     -16.729 -21.997 -55.653  1.00 40.53           A  N
ATOM   1216  CE1  HIS A 131     -16.437 -20.707 -55.674  1.00 39.52           A  C
ATOM   1217  NE2  HIS A 131     -17.567 -20.023 -55.650  1.00 39.26           A  N
ATOM   1218  N    VAL A 132     -18.786 -23.717 -51.861  1.00 41.67           A  N
ATOM   1219  CA   VAL A 132     -19.358 -23.142 -50.640  1.00 41.28           A  C
ATOM   1220  C    VAL A 132     -18.873 -21.708 -50.455  1.00 41.32           A  C
ATOM   1221  O    VAL A 132     -17.698 -21.413 -50.673  1.00 41.58           A  O
ATOM   1222  CB   VAL A 132     -19.004 -24.002 -49.425  1.00 41.25           A  C
ATOM   1223  CG1  VAL A 132     -20.066 -23.873 -48.371  1.00 40.99           A  C
ATOM   1224  CG2  VAL A 132     -18.912 -25.474 -49.850  1.00 40.82           A  C
ATOM   1225  N    GLU A 133     -19.782 -20.821 -50.067  1.00 41.18           A  N
ATOM   1226  CA   GLU A 133     -19.513 -19.387 -50.096  1.00 41.39           A  C
ATOM   1227  C    GLU A 133     -20.343 -18.624 -49.071  1.00 41.12           A  C
ATOM   1228  O    GLU A 133     -21.564 -18.744 -49.049  1.00 40.98           A  O
ATOM   1229  CB   GLU A 133     -19.802 -18.853 -51.500  1.00 41.63           A  C
ATOM   1230  CG   GLU A 133     -19.441 -17.391 -51.741  1.00 42.98           A  C
ATOM   1231  CD   GLU A 133     -19.869 -16.917 -53.126  1.00 44.70           A  C
ATOM   1232  OE1  GLU A 133     -19.506 -17.577 -54.125  1.00 45.50           A  O
ATOM   1233  OE2  GLU A 133     -20.573 -15.888 -53.217  1.00 45.17           A  O
ATOM   1234  N    LEU A 134     -19.670 -17.837 -48.232  1.00 41.05           A  N
ATOM   1235  CA   LEU A 134     -20.321 -17.021 -47.202  1.00 40.72           A  C
```

FIGURE 1 (cont'd)

```
ATOM   1236  C   LEU A 134     -20.846 -15.709 -47.755  1.00 40.48      A  C
ATOM   1237  O   LEU A 134     -20.293 -15.175 -48.706  1.00 40.67      A  O
ATOM   1238  CB  LEU A 134     -19.346 -16.720 -46.064  1.00 40.91      A  C
ATOM   1239  CG  LEU A 134     -19.359 -17.595 -44.818  1.00 41.05      A  C
ATOM   1240  CD1 LEU A 134     -18.159 -17.269 -43.960  1.00 41.90      A  C
ATOM   1241  CD2 LEU A 134     -20.617 -17.349 -44.034  1.00 41.13      A  C
ATOM   1242  N   ASP A 135     -21.916 -15.199 -47.157  1.00 40.02      A  N
ATOM   1243  CA  ASP A 135     -22.444 -13.890 -47.504  1.00 39.82      A  C
ATOM   1244  C   ASP A 135     -22.544 -13.051 -46.243  1.00 39.73      A  C
ATOM   1245  O   ASP A 135     -23.615 -12.923 -45.665  1.00 39.73      A  O
ATOM   1246  CB  ASP A 135     -23.809 -14.005 -48.198  1.00 39.60      A  C
ATOM   1247  CG  ASP A 135     -24.444 -12.639 -48.486  1.00 39.86      A  C
ATOM   1248  OD1 ASP A 135     -23.716 -11.702 -48.881  1.00 40.64      A  O
ATOM   1249  OD2 ASP A 135     -25.675 -12.494 -48.319  1.00 39.58      A  O
ATOM   1250  N   PRO A 136     -21.423 -12.470 -45.807  1.00 39.71      A  N
ATOM   1251  CA  PRO A 136     -21.462 -11.719 -44.570  1.00 40.00      A  C
ATOM   1252  C   PRO A 136     -22.035 -10.340 -44.825  1.00 40.62      A  C
ATOM   1253  O   PRO A 136     -21.886  -9.830 -45.937  1.00 40.88      A  O
ATOM   1254  CB  PRO A 136     -19.984 -11.600 -44.187  1.00 39.27      A  C
ATOM   1255  CG  PRO A 136     -19.209 -12.260 -45.302  1.00 38.92      A  C
ATOM   1256  CD  PRO A 136     -20.122 -12.340 -46.466  1.00 39.24      A  C
ATOM   1257  N   PHE A 137     -22.694  -9.759 -43.819  1.00 41.09      A  N
ATOM   1258  CA  PHE A 137     -23.169  -8.372 -43.878  1.00 41.58      A  C
ATOM   1259  C   PHE A 137     -23.661  -7.860 -42.539  1.00 42.03      A  C
ATOM   1260  O   PHE A 137     -24.073  -8.639 -41.696  1.00 42.01      A  O
ATOM   1261  CB  PHE A 137     -24.264  -8.195 -44.939  1.00 41.45      A  C
ATOM   1262  CG  PHE A 137     -25.571  -8.842 -44.591  1.00 41.09      A  C
ATOM   1263  CD1 PHE A 137     -25.764 -10.204 -44.788  1.00 40.77      A  C
ATOM   1264  CD2 PHE A 137     -26.624  -8.080 -44.101  1.00 40.98      A  C
ATOM   1265  CE1 PHE A 137     -26.980 -10.800 -44.476  1.00 40.24      A  C
ATOM   1266  CE2 PHE A 137     -27.839  -8.666 -43.787  1.00 40.51      A  C
ATOM   1267  CZ  PHE A 137     -28.018 -10.028 -43.972  1.00 40.16      A  C
ATOM   1268  N   THR A 138     -23.612  -6.545 -42.359  1.00 42.73      A  N
ATOM   1269  CA  THR A 138     -24.183  -5.887 -41.195  1.00 43.36      A  C
ATOM   1270  C   THR A 138     -25.531  -5.265 -41.560  1.00 43.43      A  C
ATOM   1271  O   THR A 138     -25.711  -4.783 -42.676  1.00 43.57      A  O
ATOM   1272  CB  THR A 138     -23.202  -4.833 -40.635  1.00 43.76      A  C
ATOM   1273  CG2 THR A 138     -23.883  -3.493 -40.340  1.00 44.42      A  C
ATOM   1274  OG1 THR A 138     -22.624  -5.324 -39.424  1.00 44.27      A  O
ATOM   1275  N   ALA A 139     -26.480  -5.285 -40.628  1.00 43.45      A  N
ATOM   1276  CA  ALA A 139     -27.821  -4.761 -40.891  1.00 43.55      A  C
ATOM   1277  C   ALA A 139     -28.474  -4.113 -39.679  1.00 43.92      A  C
ATOM   1278  O   ALA A 139     -28.235  -4.496 -38.536  1.00 43.99      A  O
ATOM   1279  CB  ALA A 139     -28.723  -5.843 -41.452  1.00 43.17      A  C
ATOM   1280  N   SER A 140     -29.323  -3.136 -39.964  1.00 44.36      A  N
ATOM   1281  CA  SER A 140     -29.998  -2.332 -38.958  1.00 44.76      A  C
ATOM   1282  C   SER A 140     -31.265  -3.027 -38.421  1.00 44.46      A  C
ATOM   1283  O   SER A 140     -32.235  -3.245 -39.158  1.00 44.32      A  O
ATOM   1284  CB  SER A 140     -30.322  -0.963 -39.566  1.00 45.20      A  C
ATOM   1285  OG  SER A 140     -31.301  -0.268 -38.816  1.00 46.13      A  O
ATOM   1286  N   THR A 141     -31.248  -3.375 -37.136  1.00 44.27      A  N
ATOM   1287  CA  THR A 141     -32.379  -4.058 -36.499  1.00 44.03      A  C
ATOM   1288  C   THR A 141     -32.906  -3.226 -35.334  1.00 44.32      A  C
ATOM   1289  O   THR A 141     -32.244  -2.289 -34.910  1.00 44.79      A  O
ATOM   1290  CB  THR A 141     -31.996  -5.480 -35.983  1.00 43.70      A  C
ATOM   1291  CG2 THR A 141     -31.268  -6.289 -37.053  1.00 43.38      A  C
ATOM   1292  OG1 THR A 141     -31.177  -5.371 -34.814  1.00 43.73      A  O
ATOM   1293  N   PRO A 142     -34.099  -3.562 -34.812  1.00 44.27      A  N
ATOM   1294  CA  PRO A 142     -34.622  -2.900 -33.618  1.00 44.48      A  C
ATOM   1295  C   PRO A 142     -33.753  -3.094 -32.371  1.00 44.68      A  C
ATOM   1296  O   PRO A 142     -34.013  -2.480 -31.336  1.00 45.11      A  O
ATOM   1297  CB  PRO A 142     -35.986  -3.565 -33.421  1.00 44.37      A  C
ATOM   1298  CG  PRO A 142     -36.387  -3.968 -34.774  1.00 44.10      A  C
ATOM   1299  CD  PRO A 142     -35.121  -4.415 -35.439  1.00 43.99      A  C
ATOM   1300  N   LEU A 143     -32.738  -3.945 -32.470  1.00 44.50      A  N
```

FIGURE 1 (cont'd)

```
ATOM   1301  CA   LEU A 143     -31.767  -4.132 -31.394  1.00 44.52      A  C
ATOM   1302  C    LEU A 143     -30.457  -3.435 -31.750  1.00 44.77      A  C
ATOM   1303  O    LEU A 143     -29.439  -3.623 -31.088  1.00 45.00      A  O
ATOM   1304  CB   LEU A 143     -31.524  -5.627 -31.147  1.00 44.16      A  C
ATOM   1305  CG   LEU A 143     -32.304  -6.441 -30.106  1.00 44.06      A  C
ATOM   1306  CD1  LEU A 143     -31.939  -5.994 -28.696  1.00 45.10      A  C
ATOM   1307  CD2  LEU A 143     -33.809  -6.409 -30.306  1.00 43.66      A  C
ATOM   1308  N    GLY A 144     -30.493  -2.628 -32.806  1.00 44.89      A  N
ATOM   1309  CA   GLY A 144     -29.296  -1.958 -33.309  1.00 45.00      A  C
ATOM   1310  C    GLY A 144     -28.525  -2.843 -34.268  1.00 44.82      A  C
ATOM   1311  O    GLY A 144     -28.987  -3.931 -34.594  1.00 44.46      A  O
ATOM   1312  N    PRO A 145     -27.348  -2.380 -34.735  1.00 44.95      A  N
ATOM   1313  CA   PRO A 145     -26.510  -3.119 -35.676  1.00 44.59      A  C
ATOM   1314  C    PRO A 145     -26.272  -4.552 -35.250  1.00 43.79      A  C
ATOM   1315  O    PRO A 145     -25.872  -4.791 -34.117  1.00 44.01      A  O
ATOM   1316  CB   PRO A 145     -25.198  -2.343 -35.653  1.00 44.96      A  C
ATOM   1317  CG   PRO A 145     -25.623  -0.959 -35.429  1.00 45.66      A  C
ATOM   1318  CD   PRO A 145     -26.818  -1.028 -34.505  1.00 45.50      A  C
ATOM   1319  N    VAL A 146     -26.548  -5.485 -36.162  1.00 42.50      A  N
ATOM   1320  CA   VAL A 146     -26.339  -6.918 -35.946  1.00 41.05      A  C
ATOM   1321  C    VAL A 146     -25.615  -7.534 -37.138  1.00 41.24      A  C
ATOM   1322  O    VAL A 146     -25.951  -7.263 -38.283  1.00 41.29      A  O
ATOM   1323  CB   VAL A 146     -27.668  -7.677 -35.738  1.00 39.29      A  C
ATOM   1324  CG1  VAL A 146     -27.398  -9.079 -35.222  1.00 37.83      A  C
ATOM   1325  CG2  VAL A 146     -28.570  -6.944 -34.774  1.00 40.00      A  C
ATOM   1326  N    ASP A 147     -24.621  -8.368 -36.855  1.00 41.32      A  N
ATOM   1327  CA   ASP A 147     -23.797  -8.984 -37.898  1.00 41.09      A  C
ATOM   1328  C    ASP A 147     -24.361 -10.338 -38.355  1.00 40.66      A  C
ATOM   1329  O    ASP A 147     -24.435 -11.283 -37.566  1.00 40.62      A  O
ATOM   1330  CB   ASP A 147     -22.346  -9.158 -37.410  1.00 41.31      A  C
ATOM   1331  CG   ASP A 147     -21.520  -7.873 -37.481  1.00 41.21      A  C
ATOM   1332  OD1  ASP A 147     -21.642  -7.096 -38.438  1.00 40.44      A  O
ATOM   1333  OD2  ASP A 147     -20.692  -7.665 -36.579  1.00 38.07      A  O
ATOM   1334  N    PHE A 148     -24.738 -10.427 -39.632  1.00 40.12      A  N
ATOM   1335  CA   PHE A 148     -25.345 -11.636 -40.202  1.00 39.52      A  C
ATOM   1336  C    PHE A 148     -24.426 -12.341 -41.178  1.00 39.31      A  C
ATOM   1337  O    PHE A 148     -23.399 -11.789 -41.573  1.00 39.49      A  O
ATOM   1338  CB   PHE A 148     -26.624 -11.283 -40.942  1.00 39.30      A  C
ATOM   1339  CG   PHE A 148     -27.674 -10.662 -40.086  1.00 39.33      A  C
ATOM   1340  CD1  PHE A 148     -28.593 -11.449 -39.420  1.00 39.10      A  C
ATOM   1341  CD2  PHE A 148     -27.771  -9.291 -39.974  1.00 39.77      A  C
ATOM   1342  CE1  PHE A 148     -29.586 -10.872 -38.644  1.00 39.25      A  C
ATOM   1343  CE2  PHE A 148     -28.757  -8.710 -39.200  1.00 39.81      A  C
ATOM   1344  CZ   PHE A 148     -29.665  -9.497 -38.538  1.00 39.55      A  C
ATOM   1345  N    GLY A 149     -24.815 -13.551 -41.580  1.00 38.93      A  N
ATOM   1346  CA   GLY A 149     -24.044 -14.320 -42.548  1.00 38.79      A  C
ATOM   1347  C    GLY A 149     -24.737 -15.542 -43.112  1.00 38.50      A  C
ATOM   1348  O    GLY A 149     -24.947 -16.517 -42.404  1.00 38.48      A  O
ATOM   1349  N    ASN A 150     -25.079 -15.483 -44.395  1.00 38.26      A  N
ATOM   1350  CA   ASN A 150     -25.717 -16.591 -45.092  1.00 37.92      A  C
ATOM   1351  C    ASN A 150     -24.668 -17.592 -45.525  1.00 38.09      A  C
ATOM   1352  O    ASN A 150     -23.505 -17.239 -45.664  1.00 38.34      A  O
ATOM   1353  CB   ASN A 150     -26.487 -16.079 -46.313  1.00 37.66      A  C
ATOM   1354  CG   ASN A 150     -27.688 -15.222 -45.942  1.00 37.26      A  C
ATOM   1355  ND2  ASN A 150     -27.739 -14.007 -46.460  1.00 37.26      A  N
ATOM   1356  OD1  ASN A 150     -28.565 -15.658 -45.219  1.00 36.75      A  O
ATOM   1357  N    VAL A 151     -25.075 -18.841 -45.728  1.00 38.13      A  N
ATOM   1358  CA   VAL A 151     -24.187 -19.872 -46.271  1.00 38.43      A  C
ATOM   1359  C    VAL A 151     -24.764 -20.363 -47.590  1.00 38.63      A  C
ATOM   1360  O    VAL A 151     -25.824 -20.982 -47.614  1.00 38.49      A  O
ATOM   1361  CB   VAL A 151     -23.981 -21.045 -45.281  1.00 38.35      A  C
ATOM   1362  CG1  VAL A 151     -23.214 -20.580 -44.063  1.00 38.72      A  C
ATOM   1363  CG2  VAL A 151     -23.238 -22.182 -45.929  1.00 38.48      A  C
ATOM   1364  N    VAL A 152     -24.068 -20.063 -48.684  1.00 39.16      A  N
ATOM   1365  CA   VAL A 152     -24.537 -20.376 -50.039  1.00 39.66      A  C
```

FIGURE 1 (cont'd)

```
ATOM   1366  C   VAL A 152     -23.696 -21.479 -50.676  1.00 40.23      A  C
ATOM   1367  O   VAL A 152     -22.474 -21.349 -50.790  1.00 40.61      A  O
ATOM   1368  CB  VAL A 152     -24.518 -19.129 -50.934  1.00 39.61      A  C
ATOM   1369  CG1 VAL A 152     -25.685 -18.222 -50.593  1.00 39.11      A  C
ATOM   1370  CG2 VAL A 152     -24.556 -19.510 -52.397  1.00 39.97      A  C
ATOM   1371  N   ALA A 153     -24.359 -22.559 -51.087  1.00 40.64      A  N
ATOM   1372  CA  ALA A 153     -23.680 -23.734 -51.625  1.00 41.25      A  C
ATOM   1373  C   ALA A 153     -24.208 -24.107 -53.003  1.00 41.76      A  C
ATOM   1374  O   ALA A 153     -25.406 -24.308 -53.173  1.00 41.72      A  O
ATOM   1375  CB  ALA A 153     -23.815 -24.900 -50.670  1.00 41.07      A  C
ATOM   1376  N   THR A 154     -23.310 -24.198 -53.981  1.00 42.50      A  N
ATOM   1377  CA  THR A 154     -23.691 -24.528 -55.341  1.00 43.14      A  C
ATOM   1378  C   THR A 154     -22.702 -25.515 -55.957  1.00 43.97      A  C
ATOM   1379  O   THR A 154     -21.515 -25.227 -56.058  1.00 44.39      A  O
ATOM   1380  CB  THR A 154     -23.756 -23.263 -56.204  1.00 43.05      A  C
ATOM   1381  CG2 THR A 154     -24.603 -23.486 -57.433  1.00 42.97      A  C
ATOM   1382  OG1 THR A 154     -24.324 -22.198 -55.443  1.00 42.53      A  O
ATOM   1383  N   LEU A 155     -23.188 -26.691 -56.344  1.00 44.66      A  N
ATOM   1384  CA  LEU A 155     -22.425 -27.585 -57.205  1.00 45.53      A  C
ATOM   1385  C   LEU A 155     -22.383 -26.951 -58.572  1.00 46.34      A  C
ATOM   1386  O   LEU A 155     -23.410 -26.471 -59.055  1.00 46.57      A  O
ATOM   1387  CB  LEU A 155     -23.131 -28.928 -57.339  1.00 45.34      A  C
ATOM   1388  CG  LEU A 155     -22.609 -30.144 -56.590  1.00 45.36      A  C
ATOM   1389  CD1 LEU A 155     -23.182 -31.399 -57.226  1.00 45.19      A  C
ATOM   1390  CD2 LEU A 155     -21.097 -30.178 -56.617  1.00 45.87      A  C
ATOM   1391  N   ASP A 156     -21.216 -26.935 -59.205  1.00 47.22      A  N
ATOM   1392  CA  ASP A 156     -21.118 -26.452 -60.594  1.00 48.05      A  C
ATOM   1393  C   ASP A 156     -21.720 -25.039 -60.760  1.00 47.89      A  C
ATOM   1394  O   ASP A 156     -22.812 -24.891 -61.315  1.00 47.68      A  O
ATOM   1395  CB  ASP A 156     -21.804 -27.464 -61.545  1.00 48.58      A  C
ATOM   1396  CG  ASP A 156     -21.412 -27.284 -63.020  1.00 50.21      A  C
ATOM   1397  OD1 ASP A 156     -20.744 -26.283 -63.364  1.00 51.16      A  O
ATOM   1398  OD2 ASP A 156     -21.784 -28.160 -63.842  1.00 51.70      A  O
ATOM   1399  N   PRO A 157     -21.013 -23.995 -60.270  1.00 48.01      A  N
ATOM   1400  CA  PRO A 157     -21.508 -22.620 -60.421  1.00 48.06      A  C
ATOM   1401  C   PRO A 157     -21.705 -22.207 -61.878  1.00 48.38      A  C
ATOM   1402  O   PRO A 157     -22.512 -21.323 -62.153  1.00 48.25      A  O
ATOM   1403  CB  PRO A 157     -20.394 -21.774 -59.798  1.00 48.04      A  C
ATOM   1404  CG  PRO A 157     -19.665 -22.694 -58.896  1.00 48.06      A  C
ATOM   1405  CD  PRO A 157     -19.725 -24.032 -59.548  1.00 48.14      A  C
ATOM   1406  N   ARG A 158     -20.973 -22.845 -62.794  1.00 48.92      A  N
ATOM   1407  CA  ARG A 158     -21.078 -22.528 -64.218  1.00 49.41      A  C
ATOM   1408  C   ARG A 158     -22.352 -23.001 -64.921  1.00 49.25      A  C
ATOM   1409  O   ARG A 158     -22.704 -22.472 -65.977  1.00 49.57      A  O
ATOM   1410  CB  ARG A 158     -19.832 -22.929 -65.014  1.00 49.90      A  C
ATOM   1411  CG  ARG A 158     -19.256 -24.309 -64.790  1.00 50.24      A  C
ATOM   1412  CD  ARG A 158     -17.796 -24.254 -65.235  1.00 48.48      A  C
ATOM   1413  NE  ARG A 158     -17.330 -22.861 -65.340  1.00 48.02      A  N
ATOM   1414  CZ  ARG A 158     -17.177 -22.017 -64.316  1.00 47.53      A  C
ATOM   1415  NH1 ARG A 158     -17.452 -22.394 -63.068  1.00 47.71      A  N
ATOM   1416  NH2 ARG A 158     -16.763 -20.777 -64.543  1.00 47.32      A  N
ATOM   1417  N   ALA A 159     -23.040 -23.985 -64.349  1.00 48.73      A  N
ATOM   1418  CA  ALA A 159     -24.287 -24.473 -64.930  1.00 48.33      A  C
ATOM   1419  C   ALA A 159     -25.302 -23.349 -65.021  1.00 48.00      A  C
ATOM   1420  O   ALA A 159     -25.370 -22.501 -64.132  1.00 48.77      A  O
ATOM   1421  CB  ALA A 159     -24.836 -25.615 -64.122  1.00 48.23      A  C
ATOM   1422  N   ALA A 160     -26.078 -23.354 -66.101  1.00 47.86      A  N
ATOM   1423  CA  ALA A 160     -26.955 -22.240 -66.435  1.00 47.60      A  C
ATOM   1424  C   ALA A 160     -28.097 -22.051 -65.443  1.00 47.11      A  C
ATOM   1425  O   ALA A 160     -28.492 -20.911 -65.168  1.00 47.04      A  O
ATOM   1426  CB  ALA A 160     -27.491 -22.393 -67.845  1.00 48.01      A  C
ATOM   1427  N   ARG A 161     -28.620 -23.160 -64.915  1.00 46.52      A  N
ATOM   1428  CA  ARG A 161     -29.724 -23.140 -63.939  1.00 45.91      A  C
ATOM   1429  C   ARG A 161     -29.511 -24.158 -62.824  1.00 45.12      A  C
ATOM   1430  O   ARG A 161     -28.764 -25.118 -62.996  1.00 45.27      A  O
```

FIGURE 1 (cont'd)

```
ATOM   1431  CB  ARG A 161     -31.062 -23.411 -64.626  1.00 46.15      A    C
ATOM   1432  CG  ARG A 161     -31.705 -22.194 -65.282  1.00 47.55      A    C
ATOM   1433  CD  ARG A 161     -32.335 -22.556 -66.626  1.00 50.40      A    C
ATOM   1434  NE  ARG A 161     -32.821 -23.937 -66.640  1.00 52.62      A    N
ATOM   1435  CZ  ARG A 161     -32.680 -24.793 -67.659  1.00 53.88      A    C
ATOM   1436  NH1 ARG A 161     -32.061 -24.431 -68.778  1.00 54.67      A    N
ATOM   1437  NH2 ARG A 161     -33.155 -26.030 -67.559  1.00 54.15      A    N
ATOM   1438  N   HIS A 162     -30.167 -23.944 -61.684  1.00 44.05      A    N
ATOM   1439  CA  HIS A 162     -30.067 -24.862 -60.544  1.00 43.01      A    C
ATOM   1440  C   HIS A 162     -31.357 -24.980 -59.739  1.00 41.93      A    C
ATOM   1441  O   HIS A 162     -32.096 -24.014 -59.593  1.00 41.67      A    O
ATOM   1442  CB  HIS A 162     -28.909 -24.478 -59.610  1.00 43.24      A    C
ATOM   1443  CG  HIS A 162     -28.895 -23.032 -59.211  1.00 43.88      A    C
ATOM   1444  CD2 HIS A 162     -28.085 -22.014 -59.588  1.00 44.45      A    C
ATOM   1445  ND1 HIS A 162     -29.785 -22.495 -58.305  1.00 44.04      A    N
ATOM   1446  CE1 HIS A 162     -29.535 -21.208 -58.156  1.00 44.23      A    C
ATOM   1447  NE2 HIS A 162     -28.507 -20.892 -58.921  1.00 44.50      A    N
ATOM   1448  N   LEU A 163     -31.619 -26.184 -59.238  1.00 40.86      A    N
ATOM   1449  CA  LEU A 163     -32.658 -26.409 -58.248  1.00 39.65      A    C
ATOM   1450  C   LEU A 163     -32.095 -25.898 -56.965  1.00 38.96      A    C
ATOM   1451  O   LEU A 163     -30.956 -26.199 -56.626  1.00 39.00      A    O
ATOM   1452  CB  LEU A 163     -32.974 -27.895 -58.088  1.00 39.54      A    C
ATOM   1453  CG  LEU A 163     -33.776 -28.297 -56.852  1.00 38.87      A    C
ATOM   1454  CD1 LEU A 163     -35.175 -27.735 -56.914  1.00 38.45      A    C
ATOM   1455  CD2 LEU A 163     -33.819 -29.791 -56.693  1.00 38.84      A    C
ATOM   1456  N   THR A 164     -32.892 -25.126 -56.245  1.00 38.01      A    N
ATOM   1457  CA  THR A 164     -32.417 -24.538 -55.007  1.00 37.04      A    C
ATOM   1458  C   THR A 164     -33.325 -24.829 -53.809  1.00 36.43      A    C
ATOM   1459  O   THR A 164     -34.505 -24.490 -53.789  1.00 36.20      A    O
ATOM   1460  CB  THR A 164     -32.043 -23.028 -55.176  1.00 36.99      A    C
ATOM   1461  CG2 THR A 164     -33.144 -22.238 -55.853  1.00 36.92      A    C
ATOM   1462  OG1 THR A 164     -31.748 -22.449 -53.903  1.00 36.66      A    O
ATOM   1463  N   LEU A 165     -32.749 -25.524 -52.838  1.00 35.84      A    N
ATOM   1464  CA  LEU A 165     -33.405 -25.801 -51.573  1.00 35.29      A    C
ATOM   1465  C   LEU A 165     -32.883 -24.836 -50.511  1.00 34.97      A    C
ATOM   1466  O   LEU A 165     -31.726 -24.416 -50.544  1.00 35.02      A    O
ATOM   1467  CB  LEU A 165     -33.155 -27.249 -51.132  1.00 35.23      A    C
ATOM   1468  CG  LEU A 165     -33.528 -28.397 -52.067  1.00 35.31      A    C
ATOM   1469  CD1 LEU A 165     -33.356 -29.734 -51.374  1.00 35.42      A    C
ATOM   1470  CD2 LEU A 165     -34.945 -28.250 -52.546  1.00 35.12      A    C
ATOM   1471  N   ALA A 166     -33.742 -24.491 -49.562  1.00 34.51      A    N
ATOM   1472  CA  ALA A 166     -33.370 -23.557 -48.518  1.00 34.06      A    C
ATOM   1473  C   ALA A 166     -33.990 -23.877 -47.159  1.00 33.81      A    C
ATOM   1474  O   ALA A 166     -35.106 -24.393 -47.064  1.00 33.66      A    O
ATOM   1475  CB  ALA A 166     -33.719 -22.150 -48.939  1.00 34.08      A    C
ATOM   1476  N   CYS A 167     -33.221 -23.581 -46.119  1.00 33.62      A    N
ATOM   1477  CA  CYS A 167     -33.670 -23.573 -44.742  1.00 33.48      A    C
ATOM   1478  C   CYS A 167     -33.036 -22.344 -44.102  1.00 33.47      A    C
ATOM   1479  O   CYS A 167     -32.141 -21.743 -44.684  1.00 33.55      A    O
ATOM   1480  CB  CYS A 167     -33.172 -24.818 -44.027  1.00 33.49      A    C
ATOM   1481  SG  CYS A 167     -31.379 -24.855 -43.771  1.00 33.67      A    S
ATOM   1482  N   HIS A 168     -33.484 -21.968 -42.908  1.00 33.48      A    N
ATOM   1483  CA  HIS A 168     -32.788 -20.935 -42.129  1.00 33.49      A    C
ATOM   1484  C   HIS A 168     -32.116 -21.556 -40.902  1.00 33.42      A    C
ATOM   1485  O   HIS A 168     -32.710 -22.372 -40.202  1.00 33.35      A    O
ATOM   1486  CB  HIS A 168     -33.731 -19.803 -41.726  1.00 33.59      A    C
ATOM   1487  CG  HIS A 168     -34.631 -20.146 -40.583  1.00 33.98      A    C
ATOM   1488  CD2 HIS A 168     -35.883 -20.656 -40.553  1.00 34.31      A    C
ATOM   1489  ND1 HIS A 168     -34.253 -19.983 -39.270  1.00 34.33      A    N
ATOM   1490  CE1 HIS A 168     -35.235 -20.371 -38.478  1.00 34.37      A    C
ATOM   1491  NE2 HIS A 168     -36.237 -20.784 -39.231  1.00 34.31      A    N
ATOM   1492  N   TYR A 169     -30.875 -21.164 -40.646  1.00 33.48      A    N
ATOM   1493  CA  TYR A 169     -30.086 -21.801 -39.601  1.00 33.63      A    C
ATOM   1494  C   TYR A 169     -30.034 -21.022 -38.297  1.00 33.72      A    C
ATOM   1495  O   TYR A 169     -29.572 -21.527 -37.284  1.00 33.74      A    O
```

FIGURE 1 (cont'd)

```
ATOM   1496  CB   TYR A 169     -28.676 -22.123 -40.098  1.00 33.72      A    C
ATOM   1497  CG   TYR A 169     -27.725 -20.956 -40.132  1.00 33.93      A    C
ATOM   1498  CD1  TYR A 169     -27.717 -20.070 -41.206  1.00 33.85      A    C
ATOM   1499  CD2  TYR A 169     -26.810 -20.752 -39.104  1.00 34.39      A    C
ATOM   1500  CE1  TYR A 169     -26.835 -18.997 -41.248  1.00 33.94      A    C
ATOM   1501  CE2  TYR A 169     -25.920 -19.684 -39.137  1.00 34.60      A    C
ATOM   1502  CZ   TYR A 169     -25.939 -18.810 -40.210  1.00 34.21      A    C
ATOM   1503  OH   TYR A 169     -25.061 -17.754 -40.248  1.00 34.29      A    O
ATOM   1504  N    ASP A 170     -30.504 -19.786 -38.316  1.00 33.85      A    N
ATOM   1505  CA   ASP A 170     -30.622 -19.026 -37.087  1.00 34.18      A    C
ATOM   1506  C    ASP A 170     -31.726 -19.617 -36.223  1.00 34.43      A    C
ATOM   1507  O    ASP A 170     -32.570 -20.364 -36.731  1.00 34.26      A    O
ATOM   1508  CB   ASP A 170     -30.877 -17.540 -37.377  1.00 34.23      A    C
ATOM   1509  CG   ASP A 170     -32.226 -17.281 -38.022  1.00 34.14      A    C
ATOM   1510  OD1  ASP A 170     -32.516 -17.868 -39.079  1.00 33.79      A    O
ATOM   1511  OD2  ASP A 170     -32.991 -16.460 -37.484  1.00 34.54      A    O
ATOM   1512  N    SER A 171     -31.692 -19.312 -34.922  1.00 34.91      A    N
ATOM   1513  CA   SER A 171     -32.765 -19.668 -33.981  1.00 35.33      A    C
ATOM   1514  C    SER A 171     -33.337 -18.402 -33.374  1.00 35.60      A    C
ATOM   1515  O    SER A 171     -32.597 -17.452 -33.157  1.00 35.92      A    O
ATOM   1516  CB   SER A 171     -32.247 -20.597 -32.877  1.00 35.39      A    C
ATOM   1517  OG   SER A 171     -31.662 -19.882 -31.807  1.00 35.80      A    O
ATOM   1518  N    LYS A 172     -34.639 -18.380 -33.094  1.00 35.76      A    N
ATOM   1519  CA   LYS A 172     -35.266 -17.167 -32.553  1.00 36.19      A    C
ATOM   1520  C    LYS A 172     -34.661 -16.743 -31.213  1.00 36.90      A    C
ATOM   1521  O    LYS A 172     -34.203 -17.580 -30.437  1.00 37.18      A    O
ATOM   1522  CB   LYS A 172     -36.785 -17.314 -32.427  1.00 35.92      A    C
ATOM   1523  CG   LYS A 172     -37.510 -15.983 -32.262  1.00 35.68      A    C
ATOM   1524  CD   LYS A 172     -38.999 -16.145 -32.052  1.00 35.07      A    C
ATOM   1525  CE   LYS A 172     -39.668 -14.807 -31.761  1.00 35.07      A    C
ATOM   1526  NZ   LYS A 172     -39.808 -13.923 -32.957  1.00 35.03      A    N
ATOM   1527  N    LEU A 173     -34.657 -15.436 -30.967  1.00 37.68      A    N
ATOM   1528  CA   LEU A 173     -34.123 -14.858 -29.743  1.00 38.56      A    C
ATOM   1529  C    LEU A 173     -35.251 -14.577 -28.768  1.00 39.09      A    C
ATOM   1530  O    LEU A 173     -36.190 -13.848 -29.093  1.00 39.20      A    O
ATOM   1531  CB   LEU A 173     -33.386 -13.561 -30.066  1.00 38.63      A    C
ATOM   1532  CG   LEU A 173     -32.912 -12.700 -28.904  1.00 39.21      A    C
ATOM   1533  CD1  LEU A 173     -31.484 -13.021 -28.528  1.00 39.56      A    C
ATOM   1534  CD2  LEU A 173     -33.056 -11.252 -29.260  1.00 39.38      A    C
ATOM   1535  N    PHE A 174     -35.157 -15.147 -27.573  1.00 39.75      A    N
ATOM   1536  CA   PHE A 174     -36.172 -14.929 -26.554  1.00 40.31      A    C
ATOM   1537  C    PHE A 174     -35.593 -14.158 -25.373  1.00 40.08      A    C
ATOM   1538  O    PHE A 174     -34.405 -14.298 -25.085  1.00 41.33      A    O
ATOM   1539  CB   PHE A 174     -36.780 -16.256 -26.134  1.00 40.57      A    C
ATOM   1540  CG   PHE A 174     -37.769 -16.789 -27.125  1.00 40.46      A    C
ATOM   1541  CD1  PHE A 174     -39.079 -16.318 -27.136  1.00 40.59      A    C
ATOM   1542  CD2  PHE A 174     -37.391 -17.749 -28.070  1.00 40.06      A    C
ATOM   1543  CE1  PHE A 174     -40.009 -16.801 -28.062  1.00 40.09      A    C
ATOM   1544  CE2  PHE A 174     -38.315 -18.244 -28.999  1.00 39.56      A    C
ATOM   1545  CZ   PHE A 174     -39.628 -17.766 -28.990  1.00 39.66      A    C
ATOM   1546  N    PRO A 175     -36.404 -13.283 -24.728  1.00 37.08      A    N
ATOM   1547  CA   PRO A 175     -35.843 -12.493 -23.640  1.00 35.47      A    C
ATOM   1548  C    PRO A 175     -34.971 -13.366 -22.750  1.00 35.06      A    C
ATOM   1549  O    PRO A 175     -35.380 -14.495 -22.413  1.00 34.51      A    O
ATOM   1550  CB   PRO A 175     -37.082 -12.000 -22.871  1.00 35.02      A    C
ATOM   1551  CG   PRO A 175     -38.251 -12.756 -23.440  1.00 35.19      A    C
ATOM   1552  CD   PRO A 175     -37.851 -13.035 -24.861  1.00 36.64      A    C
ATOM   1553  N    PRO A 176     -33.764 -12.861 -22.393  1.00 35.47      A    N
ATOM   1554  CA   PRO A 176     -32.856 -13.655 -21.574  1.00 36.48      A    C
ATOM   1555  C    PRO A 176     -33.505 -13.758 -20.206  1.00 38.35      A    C
ATOM   1556  O    PRO A 176     -33.228 -12.951 -19.295  1.00 38.65      A    O
ATOM   1557  CB   PRO A 176     -31.580 -12.812 -21.541  1.00 36.11      A    C
ATOM   1558  CG   PRO A 176     -32.071 -11.383 -21.664  1.00 35.36      A    C
ATOM   1559  CD   PRO A 176     -33.326 -11.450 -22.508  1.00 35.15      A    C
ATOM   1560  N    GLY A 177     -34.462 -14.685 -20.119  1.00 40.37      A    N
```

FIGURE 1 (cont'd)

```
ATOM   1561  CA  GLY A 177     -35.086 -15.003 -18.835  1.00 43.03      A  C
ATOM   1562  C   GLY A 177     -34.244 -16.236 -18.651  1.00 44.72      A  C
ATOM   1563  O   GLY A 177     -33.194 -16.160 -18.016  1.00 45.04      A  O
ATOM   1564  N   SER A 178     -34.646 -17.400 -19.157  1.00 47.00      A  N
ATOM   1565  CA  SER A 178     -35.950 -18.112 -19.166  1.00 46.88      A  C
ATOM   1566  C   SER A 178     -35.480 -19.495 -19.491  1.00 46.88      A  C
ATOM   1567  O   SER A 178     -34.826 -20.088 -18.646  1.00 47.49      A  O
ATOM   1568  CB  SER A 178     -36.969 -17.691 -20.174  1.00 45.24      A  C
ATOM   1569  OG  SER A 178     -36.986 -16.254 -20.165  1.00 44.55      A  O
ATOM   1570  N   THR A 179     -35.803 -20.060 -20.651  1.00 45.46      A  N
ATOM   1571  CA  THR A 179     -35.233 -21.376 -20.880  1.00 42.96      A  C
ATOM   1572  C   THR A 179     -34.673 -21.386 -22.293  1.00 43.46      A  C
ATOM   1573  O   THR A 179     -35.307 -20.850 -23.192  1.00 44.44      A  O
ATOM   1574  CB  THR A 179     -36.235 -22.544 -20.539  1.00 37.62      A  C
ATOM   1575  CG2 THR A 179     -37.569 -22.037 -19.905  1.00 39.18      A  C
ATOM   1576  OG1 THR A 179     -36.513 -23.318 -21.707  1.00 34.56      A  O
ATOM   1577  N   PRO A 180     -33.478 -21.968 -22.491  1.00 42.23      A  N
ATOM   1578  CA  PRO A 180     -32.822 -21.906 -23.798  1.00 41.26      A  C
ATOM   1579  C   PRO A 180     -33.747 -22.403 -24.916  1.00 42.04      A  C
ATOM   1580  O   PRO A 180     -34.519 -23.344 -24.702  1.00 42.94      A  O
ATOM   1581  CB  PRO A 180     -31.635 -22.859 -23.632  1.00 36.48      A  C
ATOM   1582  CG  PRO A 180     -32.076 -23.838 -22.574  1.00 34.98      A  C
ATOM   1583  CD  PRO A 180     -32.846 -22.970 -21.613  1.00 41.02      A  C
ATOM   1584  N   PHE A 181     -33.689 -21.768 -26.083  1.00 41.81      A  N
ATOM   1585  CA  PHE A 181     -34.544 -22.158 -27.209  1.00 40.93      A  C
ATOM   1586  C   PHE A 181     -33.748 -22.611 -28.429  1.00 40.22      A  C
ATOM   1587  O   PHE A 181     -33.051 -21.803 -29.055  1.00 40.02      A  O
ATOM   1588  CB  PHE A 181     -35.481 -21.018 -27.594  1.00 40.98      A  C
ATOM   1589  CG  PHE A 181     -36.238 -21.266 -28.860  1.00 40.73      A  C
ATOM   1590  CD1 PHE A 181     -37.266 -22.209 -28.904  1.00 40.88      A  C
ATOM   1591  CD2 PHE A 181     -35.925 -20.562 -30.011  1.00 40.49      A  C
ATOM   1592  CE1 PHE A 181     -37.974 -22.439 -30.077  1.00 40.28      A  C
ATOM   1593  CE2 PHE A 181     -36.623 -20.787 -31.196  1.00 40.00      A  C
ATOM   1594  CZ  PHE A 181     -37.651 -21.725 -31.228  1.00 39.77      A  C
ATOM   1595  N   VAL A 182     -33.877 -23.893 -28.770  1.00 39.41      A  N
ATOM   1596  CA  VAL A 182     -33.085 -24.492 -29.855  1.00 38.69      A  C
ATOM   1597  C   VAL A 182     -33.825 -24.675 -31.180  1.00 37.93      A  C
ATOM   1598  O   VAL A 182     -33.194 -24.935 -32.211  1.00 37.76      A  O
ATOM   1599  CB  VAL A 182     -32.409 -25.830 -29.453  1.00 38.74      A  C
ATOM   1600  CG1 VAL A 182     -31.210 -25.563 -28.592  1.00 39.11      A  C
ATOM   1601  CG2 VAL A 182     -33.376 -26.758 -28.748  1.00 39.08      A  C
ATOM   1602  N   GLY A 183     -35.152 -24.554 -31.149  1.00 37.22      A  N
ATOM   1603  CA  GLY A 183     -35.978 -24.669 -32.355  1.00 36.24      A  C
ATOM   1604  C   GLY A 183     -35.606 -25.834 -33.241  1.00 35.55      A  C
ATOM   1605  O   GLY A 183     -34.990 -25.658 -34.283  1.00 35.38      A  O
ATOM   1606  N   ALA A 184     -35.975 -27.030 -32.817  1.00 35.03      A  N
ATOM   1607  CA  ALA A 184     -35.607 -28.219 -33.539  1.00 34.44      A  C
ATOM   1608  C   ALA A 184     -36.315 -28.271 -34.886  1.00 33.88      A  C
ATOM   1609  O   ALA A 184     -35.691 -28.548 -35.901  1.00 33.72      A  O
ATOM   1610  CB  ALA A 184     -35.905 -29.441 -32.707  1.00 34.78      A  C
ATOM   1611  N   THR A 185     -37.612 -27.984 -34.894  1.00 33.34      A  N
ATOM   1612  CA  THR A 185     -38.385 -27.959 -36.134  1.00 32.80      A  C
ATOM   1613  C   THR A 185     -38.143 -26.651 -36.864  1.00 32.55      A  C
ATOM   1614  O   THR A 185     -38.493 -26.516 -38.033  1.00 32.53      A  O
ATOM   1615  CB  THR A 185     -39.908 -28.046 -35.885  1.00 32.74      A  C
ATOM   1616  CG2 THR A 185     -40.262 -29.180 -34.919  1.00 32.98      A  C
ATOM   1617  OG1 THR A 185     -40.376 -26.796 -35.362  1.00 32.40      A  O
ATOM   1618  N   ASP A 186     -37.532 -25.697 -36.167  1.00 32.33      A  N
ATOM   1619  CA  ASP A 186     -37.526 -24.302 -36.599  1.00 32.10      A  C
ATOM   1620  C   ASP A 186     -36.136 -23.644 -36.524  1.00 32.15      A  C
ATOM   1621  O   ASP A 186     -35.918 -22.769 -35.678  1.00 32.48      A  O
ATOM   1622  CB  ASP A 186     -38.534 -23.534 -35.725  1.00 32.00      A  C
ATOM   1623  CG  ASP A 186     -38.840 -22.133 -36.237  1.00 31.48      A  C
ATOM   1624  OD1 ASP A 186     -39.670 -21.470 -35.577  1.00 31.32      A  O
ATOM   1625  OD2 ASP A 186     -38.277 -21.693 -37.270  1.00 30.63      A  O
```

FIGURE 1 (cont'd)

```
ATOM   1626  N   SER A 187     -35.201 -24.017 -37.403  1.00 31.90      A   N
ATOM   1627  CA  SER A 187     -35.405 -24.959 -38.501  1.00 31.63      A   C
ATOM   1628  C   SER A 187     -34.233 -25.940 -38.593  1.00 31.61      A   C
ATOM   1629  O   SER A 187     -33.755 -26.248 -39.685  1.00 31.52      A   O
ATOM   1630  CB  SER A 187     -35.549 -24.197 -39.828  1.00 31.54      A   C
ATOM   1631  OG  SER A 187     -36.769 -23.486 -39.902  1.00 31.71      A   O
ATOM   1632  N   ALA A 188     -33.771 -26.429 -37.446  1.00 31.72      A   N
ATOM   1633  CA  ALA A 188     -32.645 -27.352 -37.391  1.00 31.79      A   C
ATOM   1634  C   ALA A 188     -32.828 -28.562 -38.299  1.00 31.81      A   C
ATOM   1635  O   ALA A 188     -31.967 -28.836 -39.134  1.00 31.81      A   O
ATOM   1636  CB  ALA A 188     -32.411 -27.789 -35.979  1.00 31.98      A   C
ATOM   1637  N   VAL A 189     -33.951 -29.267 -38.136  1.00 31.76      A   N
ATOM   1638  CA  VAL A 189     -34.298 -30.442 -38.954  1.00 31.62      A   C
ATOM   1639  C   VAL A 189     -34.286 -30.137 -40.451  1.00 31.60      A   C
ATOM   1640  O   VAL A 189     -33.606 -30.832 -41.196  1.00 31.70      A   O
ATOM   1641  CB  VAL A 189     -35.645 -31.079 -38.537  1.00 31.55      A   C
ATOM   1642  CG1 VAL A 189     -36.054 -32.142 -39.517  1.00 31.35      A   C
ATOM   1643  CG2 VAL A 189     -35.556 -31.670 -37.146  1.00 31.76      A   C
ATOM   1644  N   PRO A 190     -35.027 -29.098 -40.899  1.00 31.51      A   N
ATOM   1645  CA  PRO A 190     -34.908 -28.673 -42.293  1.00 31.52      A   C
ATOM   1646  C   PRO A 190     -33.465 -28.565 -42.774  1.00 31.74      A   C
ATOM   1647  O   PRO A 190     -33.136 -29.115 -43.818  1.00 31.75      A   O
ATOM   1648  CB  PRO A 190     -35.581 -27.308 -42.288  1.00 31.32      A   C
ATOM   1649  CG  PRO A 190     -36.649 -27.458 -41.292  1.00 31.30      A   C
ATOM   1650  CD  PRO A 190     -36.136 -28.391 -40.231  1.00 31.45      A   C
ATOM   1651  N   CYS A 191     -32.617 -27.883 -42.005  1.00 32.12      A   N
ATOM   1652  CA  CYS A 191     -31.211 -27.714 -42.365  1.00 32.67      A   C
ATOM   1653  C   CYS A 191     -30.460 -29.038 -42.359  1.00 32.98      A   C
ATOM   1654  O   CYS A 191     -29.635 -29.304 -43.239  1.00 33.16      A   O
ATOM   1655  CB  CYS A 191     -30.525 -26.689 -41.464  1.00 32.72      A   C
ATOM   1656  SG  CYS A 191     -31.102 -25.001 -41.747  1.00 33.25      A   S
ATOM   1657  N   ALA A 192     -30.768 -29.879 -41.379  1.00 33.24      A   N
ATOM   1658  CA  ALA A 192     -30.154 -31.200 -41.279  1.00 33.45      A   C
ATOM   1659  C   ALA A 192     -30.422 -32.045 -42.526  1.00 33.39      A   C
ATOM   1660  O   ALA A 192     -29.528 -32.732 -43.020  1.00 33.65      A   O
ATOM   1661  CB  ALA A 192     -30.630 -31.911 -40.015  1.00 33.57      A   C
ATOM   1662  N   LEU A 193     -31.649 -31.964 -43.030  1.00 32.98      A   N
ATOM   1663  CA  LEU A 193     -32.058 -32.717 -44.201  1.00 32.60      A   C
ATOM   1664  C   LEU A 193     -31.263 -32.286 -45.425  1.00 33.19      A   C
ATOM   1665  O   LEU A 193     -30.761 -33.128 -46.181  1.00 33.59      A   O
ATOM   1666  CB  LEU A 193     -33.557 -32.550 -44.453  1.00 31.28      A   C
ATOM   1667  CG  LEU A 193     -34.540 -33.244 -43.514  1.00 29.67      A   C
ATOM   1668  CD1 LEU A 193     -35.932 -32.741 -43.762  1.00 28.71      A   C
ATOM   1669  CD2 LEU A 193     -34.511 -34.740 -43.726  1.00 27.61      A   C
ATOM   1670  N   LEU A 194     -31.137 -30.975 -45.609  1.00 33.38      A   N
ATOM   1671  CA  LEU A 194     -30.365 -30.440 -46.721  1.00 33.53      A   C
ATOM   1672  C   LEU A 194     -28.942 -30.988 -46.721  1.00 34.45      A   C
ATOM   1673  O   LEU A 194     -28.383 -31.246 -47.782  1.00 34.78      A   O
ATOM   1674  CB  LEU A 194     -30.364 -28.915 -46.717  1.00 32.43      A   C
ATOM   1675  CG  LEU A 194     -31.712 -28.258 -46.992  1.00 31.24      A   C
ATOM   1676  CD1 LEU A 194     -31.481 -26.897 -47.587  1.00 30.88      A   C
ATOM   1677  CD2 LEU A 194     -32.591 -29.093 -47.911  1.00 29.95      A   C
ATOM   1678  N   LEU A 195     -28.371 -31.187 -45.535  1.00 35.24      A   N
ATOM   1679  CA  LEU A 195     -27.026 -31.745 -45.412  1.00 36.05      A   C
ATOM   1680  C   LEU A 195     -27.018 -33.207 -45.767  1.00 36.76      A   C
ATOM   1681  O   LEU A 195     -26.194 -33.639 -46.556  1.00 37.08      A   O
ATOM   1682  CB  LEU A 195     -26.480 -31.567 -43.999  1.00 36.00      A   C
ATOM   1683  CG  LEU A 195     -26.122 -30.156 -43.546  1.00 35.80      A   C
ATOM   1684  CD1 LEU A 195     -25.741 -30.173 -42.098  1.00 36.02      A   C
ATOM   1685  CD2 LEU A 195     -25.001 -29.580 -44.375  1.00 35.81      A   C
ATOM   1686  N   GLU A 196     -27.947 -33.955 -45.176  1.00 37.40      A   N
ATOM   1687  CA  GLU A 196     -28.077 -35.399 -45.392  1.00 38.01      A   C
ATOM   1688  C   GLU A 196     -28.328 -35.744 -46.851  1.00 38.10      A   C
ATOM   1689  O   GLU A 196     -27.684 -36.644 -47.396  1.00 38.32      A   O
ATOM   1690  CB  GLU A 196     -29.178 -35.984 -44.501  1.00 38.17      A   C
```

FIGURE 1 (cont'd)

```
ATOM   1691  CG   GLU A 196     -29.624 -37.411 -44.846  1.00 39.28           A  C
ATOM   1692  CD   GLU A 196     -28.582 -38.477 -44.553  1.00 40.75           A  C
ATOM   1693  OE1  GLU A 196     -27.516 -38.173 -43.986  1.00 41.39           A  O
ATOM   1694  OE2  GLU A 196     -28.836 -39.642 -44.896  1.00 41.48           A  O
ATOM   1695  N    LEU A 197     -29.257 -35.024 -47.473  1.00 38.08           A  N
ATOM   1696  CA   LEU A 197     -29.528 -35.177 -48.891  1.00 38.33           A  C
ATOM   1697  C    LEU A 197     -28.258 -35.010 -49.723  1.00 38.83           A  C
ATOM   1698  O    LEU A 197     -27.962 -35.833 -50.591  1.00 39.14           A  O
ATOM   1699  CB   LEU A 197     -30.584 -34.175 -49.338  1.00 37.91           A  C
ATOM   1700  CG   LEU A 197     -32.008 -34.669 -49.501  1.00 37.70           A  C
ATOM   1701  CD1  LEU A 197     -32.699 -34.716 -48.186  1.00 37.57           A  C
ATOM   1702  CD2  LEU A 197     -32.738 -33.730 -50.403  1.00 37.65           A  C
ATOM   1703  N    ALA A 198     -27.507 -33.950 -49.432  1.00 39.30           A  N
ATOM   1704  CA   ALA A 198     -26.299 -33.601 -50.174  1.00 40.01           A  C
ATOM   1705  C    ALA A 198     -25.227 -34.663 -50.030  1.00 40.75           A  C
ATOM   1706  O    ALA A 198     -24.377 -34.814 -50.898  1.00 41.08           A  O
ATOM   1707  CB   ALA A 198     -25.766 -32.260 -49.716  1.00 39.84           A  C
ATOM   1708  N    GLN A 199     -25.275 -35.394 -48.925  1.00 41.34           A  N
ATOM   1709  CA   GLN A 199     -24.294 -36.418 -48.632  1.00 41.99           A  C
ATOM   1710  C    GLN A 199     -24.747 -37.734 -49.201  1.00 42.93           A  C
ATOM   1711  O    GLN A 199     -23.954 -38.454 -49.778  1.00 43.57           A  O
ATOM   1712  CB   GLN A 199     -24.124 -36.582 -47.133  1.00 40.91           A  C
ATOM   1713  CG   GLN A 199     -22.706 -36.438 -46.638  1.00 40.40           A  C
ATOM   1714  CD   GLN A 199     -21.716 -37.462 -47.162  1.00 40.13           A  C
ATOM   1715  NE2  GLN A 199     -20.574 -36.989 -47.637  1.00 40.57           A  N
ATOM   1716  OE1  GLN A 199     -21.931 -38.654 -47.056  1.00 40.43           A  O
ATOM   1717  N    ALA A 200     -26.023 -38.056 -49.032  1.00 43.60           A  N
ATOM   1718  CA   ALA A 200     -26.561 -39.323 -49.508  1.00 44.32           A  C
ATOM   1719  C    ALA A 200     -26.520 -39.437 -51.029  1.00 44.88           A  C
ATOM   1720  O    ALA A 200     -26.199 -40.494 -51.573  1.00 45.32           A  O
ATOM   1721  CB   ALA A 200     -27.969 -39.518 -48.998  1.00 44.10           A  C
ATOM   1722  N    LEU A 201     -26.837 -38.340 -51.709  1.00 45.23           A  N
ATOM   1723  CA   LEU A 201     -26.824 -38.304 -53.165  1.00 45.76           A  C
ATOM   1724  C    LEU A 201     -25.502 -37.784 -53.716  1.00 46.48           A  C
ATOM   1725  O    LEU A 201     -25.396 -37.505 -54.904  1.00 46.75           A  O
ATOM   1726  CB   LEU A 201     -27.966 -37.437 -53.677  1.00 45.30           A  C
ATOM   1727  CG   LEU A 201     -29.360 -37.929 -53.345  1.00 45.06           A  C
ATOM   1728  CD1  LEU A 201     -30.366 -36.815 -53.543  1.00 44.76           A  C
ATOM   1729  CD2  LEU A 201     -29.716 -39.162 -54.152  1.00 45.34           A  C
ATOM   1730  N    ASP A 202     -24.497 -37.668 -52.856  1.00 47.23           A  N
ATOM   1731  CA   ASP A 202     -23.217 -37.046 -53.203  1.00 48.06           A  C
ATOM   1732  C    ASP A 202     -22.578 -37.620 -54.467  1.00 48.68           A  C
ATOM   1733  O    ASP A 202     -22.146 -36.868 -55.336  1.00 48.93           A  O
ATOM   1734  CB   ASP A 202     -22.254 -37.133 -52.012  1.00 48.20           A  C
ATOM   1735  CG   ASP A 202     -20.885 -36.570 -52.306  1.00 48.60           A  C
ATOM   1736  OD1  ASP A 202     -20.783 -35.388 -52.668  1.00 48.43           A  O
ATOM   1737  OD2  ASP A 202     -19.908 -37.316 -52.138  1.00 49.35           A  O
ATOM   1738  N    LEU A 203     -22.536 -38.944 -54.582  1.00 49.08           A  N
ATOM   1739  CA   LEU A 203     -21.853 -39.584 -55.703  1.00 49.26           A  C
ATOM   1740  C    LEU A 203     -22.601 -39.444 -57.012  1.00 49.53           A  C
ATOM   1741  O    LEU A 203     -21.997 -39.121 -58.019  1.00 49.97           A  O
ATOM   1742  CB   LEU A 203     -21.547 -41.045 -55.404  1.00 48.33           A  C
ATOM   1743  CG   LEU A 203     -20.279 -41.262 -54.576  1.00 48.06           A  C
ATOM   1744  CD1  LEU A 203     -20.608 -41.511 -53.103  1.00 47.97           A  C
ATOM   1745  N    GLU A 204     -23.908 -39.685 -57.001  1.00 49.33           A  N
ATOM   1746  CA   GLU A 204     -24.743 -39.460 -58.185  1.00 48.96           A  C
ATOM   1747  C    GLU A 204     -24.789 -37.981 -58.576  1.00 49.41           A  C
ATOM   1748  O    GLU A 204     -24.877 -37.654 -59.760  1.00 49.75           A  O
ATOM   1749  CB   GLU A 204     -26.157 -40.044 -58.023  1.00 47.46           A  C
ATOM   1750  CG   GLU A 204     -26.665 -40.130 -56.593  1.00 45.81           A  C
ATOM   1751  CD   GLU A 204     -26.083 -41.317 -55.825  1.00 45.08           A  C
ATOM   1752  OE1  GLU A 204     -26.538 -42.454 -56.048  1.00 45.20           A  O
ATOM   1753  OE2  GLU A 204     -25.178 -41.125 -54.984  1.00 45.64           A  O
ATOM   1754  N    LEU A 205     -24.712 -37.096 -57.584  1.00 49.60           A  N
ATOM   1755  CA   LEU A 205     -24.609 -35.655 -57.826  1.00 49.74           A  C
```

FIGURE 1 (cont'd)

```
ATOM   1756  C    LEU A 205     -23.260 -35.303 -58.418  1.00 50.47      A    C
ATOM   1757  O    LEU A 205     -23.142 -34.366 -59.205  1.00 50.57      A    O
ATOM   1758  CB   LEU A 205     -24.798 -34.861 -56.535  1.00 49.19      A    C
ATOM   1759  CG   LEU A 205     -26.191 -34.366 -56.173  1.00 48.21      A    C
ATOM   1760  CD1  LEU A 205     -26.196 -33.969 -54.726  1.00 47.82      A    C
ATOM   1761  CD2  LEU A 205     -26.601 -33.202 -57.041  1.00 47.58      A    C
ATOM   1762  N    SER A 206     -22.243 -36.059 -58.025  1.00 51.33      A    N
ATOM   1763  CA   SER A 206     -20.884 -35.807 -58.465  1.00 52.23      A    C
ATOM   1764  C    SER A 206     -20.719 -36.127 -59.938  1.00 52.71      A    C
ATOM   1765  O    SER A 206     -20.293 -35.272 -60.711  1.00 52.76      A    O
ATOM   1766  CB   SER A 206     -19.888 -36.614 -57.630  1.00 52.47      A    C
ATOM   1767  OG   SER A 206     -18.579 -36.089 -57.761  1.00 53.15      A    O
ATOM   1768  N    ARG A 207     -21.063 -37.352 -60.327  1.00 53.23      A    N
ATOM   1769  CA   ARG A 207     -20.891 -37.750 -61.710  1.00 53.74      A    C
ATOM   1770  C    ARG A 207     -21.629 -36.808 -62.647  1.00 53.74      A    C
ATOM   1771  O    ARG A 207     -21.018 -36.263 -63.562  1.00 54.15      A    O
ATOM   1772  CB   ARG A 207     -21.211 -39.223 -61.971  1.00 53.99      A    C
ATOM   1773  CG   ARG A 207     -22.481 -39.777 -61.414  1.00 53.40      A    C
ATOM   1774  CD   ARG A 207     -22.308 -41.297 -61.562  1.00 47.61      A    C
ATOM   1775  NE   ARG A 207     -22.390 -42.089 -60.333  1.00 42.52      A    N
ATOM   1776  CZ   ARG A 207     -21.405 -42.864 -59.888  1.00 39.15      A    C
ATOM   1777  NH1  ARG A 207     -20.262 -42.931 -60.572  1.00 38.29      A    N
ATOM   1778  NH2  ARG A 207     -21.558 -43.571 -58.770  1.00 37.21      A    N
ATOM   1779  N    ALA A 208     -22.916 -36.584 -62.404  1.00 53.25      A    N
ATOM   1780  CA   ALA A 208     -23.661 -35.608 -63.184  1.00 52.87      A    C
ATOM   1781  C    ALA A 208     -23.101 -34.223 -62.899  1.00 52.61      A    C
ATOM   1782  O    ALA A 208     -23.602 -33.505 -62.064  1.00 52.38      A    O
ATOM   1783  CB   ALA A 208     -25.140 -35.682 -62.863  1.00 52.56      A    C
ATOM   1784  N    LYS A 209     -22.034 -33.880 -63.604  1.00 52.67      A    N
ATOM   1785  CA   LYS A 209     -21.245 -32.670 -63.386  1.00 52.20      A    C
ATOM   1786  C    LYS A 209     -19.874 -32.984 -63.920  1.00 51.25      A    C
ATOM   1787  O    LYS A 209     -18.979 -32.170 -63.939  1.00 52.58      A    O
ATOM   1788  CB   LYS A 209     -21.083 -32.358 -61.905  1.00 52.38      A    C
ATOM   1789  CG   LYS A 209     -20.491 -30.989 -61.628  1.00 52.69      A    C
ATOM   1790  CD   LYS A 209     -19.611 -31.015 -60.400  1.00 53.55      A    C
ATOM   1791  CE   LYS A 209     -19.153 -29.621 -60.038  1.00 53.73      A    C
ATOM   1792  NZ   LYS A 209     -18.215 -29.624 -58.890  1.00 53.89      A    N
ATOM   1793  N    LYS A 210     -19.650 -34.240 -64.208  1.00 44.23      A    N
ATOM   1794  CA   LYS A 210     -18.433 -34.547 -64.864  1.00 38.09      A    C
ATOM   1795  C    LYS A 210     -18.848 -34.623 -66.323  1.00 36.09      A    C
ATOM   1796  O    LYS A 210     -18.012 -34.548 -67.226  1.00 35.83      A    O
ATOM   1797  CB   LYS A 210     -17.807 -35.799 -64.267  1.00 36.91      A    C
ATOM   1798  CG   LYS A 210     -17.395 -35.573 -62.820  1.00 31.82      A    C
ATOM   1799  CD   LYS A 210     -16.199 -36.403 -62.463  1.00 26.58      A    C
ATOM   1800  CE   LYS A 210     -15.847 -36.202 -61.006  1.00 23.92      A    C
ATOM   1801  NZ   LYS A 210     -14.904 -37.248 -60.500  1.00 23.32      A    N
ATOM   1802  N    GLN A 211     -20.165 -34.698 -66.529  1.00 33.78      A    N
ATOM   1803  CA   GLN A 211     -20.793 -34.527 -67.849  1.00 32.05      A    C
ATOM   1804  C    GLN A 211     -21.376 -33.114 -67.963  1.00 31.62      A    C
ATOM   1805  O    GLN A 211     -22.220 -32.833 -68.824  1.00 31.47      A    O
ATOM   1806  CB   GLN A 211     -21.907 -35.558 -68.067  1.00 31.33      A    C
ATOM   1807  CG   GLN A 211     -21.856 -36.728 -67.110  1.00 28.82      A    C
ATOM   1808  CD   GLN A 211     -21.115 -37.936 -67.659  1.00 26.84      A    C
ATOM   1809  NE2  GLN A 211     -19.938 -37.717 -68.268  1.00 25.57      A    N
ATOM   1810  OE1  GLN A 211     -21.606 -39.065 -67.534  1.00 27.60      A    O
ATOM   1811  N    ALA A 212     -20.903 -32.233 -67.086  1.00 31.07      A    N
ATOM   1812  CA   ALA A 212     -21.428 -30.884 -66.955  1.00 30.44      A    C
ATOM   1813  C    ALA A 212     -22.933 -30.877 -67.159  1.00 29.80      A    C
ATOM   1814  O    ALA A 212     -23.427 -30.422 -68.201  1.00 29.78      A    O
ATOM   1815  CB   ALA A 212     -20.749 -29.951 -67.918  1.00 30.60      A    C
ATOM   1816  N    ALA A 213     -23.638 -31.427 -66.166  1.00 28.79      A    N
ATOM   1817  CA   ALA A 213     -25.088 -31.371 -66.097  1.00 27.87      A    C
ATOM   1818  C    ALA A 213     -25.484 -29.906 -66.142  1.00 27.61      A    C
ATOM   1819  O    ALA A 213     -24.825 -29.082 -65.508  1.00 27.54      A    O
ATOM   1820  CB   ALA A 213     -25.578 -32.013 -64.829  1.00 27.72      A    C
```

FIGURE 1 (cont'd)

```
ATOM   1821  N    PRO A 214     -26.543 -29.576 -66.909  1.00 27.80      A    N
ATOM   1822  CA   PRO A 214     -26.952 -28.195 -67.212  1.00 28.95      A    C
ATOM   1823  C    PRO A 214     -27.858 -27.597 -66.158  1.00 31.23      A    C
ATOM   1824  O    PRO A 214     -28.008 -26.376 -66.088  1.00 31.29      A    O
ATOM   1825  CB   PRO A 214     -27.735 -28.344 -68.506  1.00 28.38      A    C
ATOM   1826  CG   PRO A 214     -28.329 -29.731 -68.423  1.00 27.87      A    C
ATOM   1827  CD   PRO A 214     -27.448 -30.567 -67.525  1.00 27.50      A    C
ATOM   1828  N    VAL A 215     -28.479 -28.462 -65.368  1.00 35.82      A    N
ATOM   1829  CA   VAL A 215     -29.266 -28.012 -64.233  1.00 36.04      A    C
ATOM   1830  C    VAL A 215     -28.621 -28.531 -62.953  1.00 36.41      A    C
ATOM   1831  O    VAL A 215     -28.573 -29.741 -62.716  1.00 36.72      A    O
ATOM   1832  CB   VAL A 215     -30.743 -28.466 -64.296  1.00 35.41      A    C
ATOM   1833  CG1  VAL A 215     -31.566 -27.646 -63.353  1.00 34.51      A    C
ATOM   1834  CG2  VAL A 215     -31.305 -28.327 -65.688  1.00 35.72      A    C
ATOM   1835  N    THR A 216     -28.117 -27.613 -62.133  1.00 36.12      A    N
ATOM   1836  CA   THR A 216     -27.361 -27.979 -60.938  1.00 35.57      A    C
ATOM   1837  C    THR A 216     -28.217 -27.966 -59.680  1.00 35.08      A    C
ATOM   1838  O    THR A 216     -29.441 -27.924 -59.757  1.00 35.04      A    O
ATOM   1839  CB   THR A 216     -26.141 -27.075 -60.746  1.00 35.57      A    C
ATOM   1840  OG1  THR A 216     -25.010 -27.895 -60.441  1.00 35.45      A    O
ATOM   1841  N    LEU A 217     -27.557 -28.021 -58.524  1.00 34.50      A    N
ATOM   1842  CA   LEU A 217     -28.222 -27.990 -57.220  1.00 33.70      A    C
ATOM   1843  C    LEU A 217     -27.598 -26.939 -56.312  1.00 33.30      A    C
ATOM   1844  O    LEU A 217     -26.379 -26.802 -56.242  1.00 33.53      A    O
ATOM   1845  CB   LEU A 217     -28.166 -29.363 -56.551  1.00 33.58      A    C
ATOM   1846  CG   LEU A 217     -28.662 -29.467 -55.110  1.00 33.05      A    C
ATOM   1847  CD1  LEU A 217     -30.159 -29.311 -55.035  1.00 32.84      A    C
ATOM   1848  CD2  LEU A 217     -28.247 -30.787 -54.521  1.00 33.15      A    C
ATOM   1849  N    GLN A 218     -28.452 -26.208 -55.612  1.00 32.53      A    N
ATOM   1850  CA   GLN A 218     -28.015 -25.130 -54.740  1.00 31.89      A    C
ATOM   1851  C    GLN A 218     -28.636 -25.255 -53.356  1.00 31.29      A    C
ATOM   1852  O    GLN A 218     -29.838 -25.463 -53.227  1.00 31.22      A    O
ATOM   1853  CB   GLN A 218     -28.383 -23.782 -55.359  1.00 31.94      A    C
ATOM   1854  CG   GLN A 218     -27.873 -22.582 -54.596  1.00 32.15      A    C
ATOM   1855  CD   GLN A 218     -28.421 -21.284 -55.122  1.00 32.78      A    C
ATOM   1856  NE2  GLN A 218     -29.729 -21.114 -55.055  1.00 32.81      A    N
ATOM   1857  OE1  GLN A 218     -27.672 -20.444 -55.589  1.00 33.64      A    O
ATOM   1858  N    LEU A 219     -27.815 -25.125 -52.321  1.00 30.72      A    N
ATOM   1859  CA   LEU A 219     -28.306 -25.216 -50.949  1.00 30.05      A    C
ATOM   1860  C    LEU A 219     -28.094 -23.904 -50.217  1.00 29.78      A    C
ATOM   1861  O    LEU A 219     -26.976 -23.405 -50.133  1.00 29.91      A    O
ATOM   1862  CB   LEU A 219     -27.632 -26.370 -50.203  1.00 29.91      A    C
ATOM   1863  CG   LEU A 219     -27.825 -27.764 -50.802  1.00 29.63      A    C
ATOM   1864  CD1  LEU A 219     -26.979 -28.769 -50.076  1.00 29.42      A    C
ATOM   1865  CD2  LEU A 219     -29.283 -28.185 -50.767  1.00 29.20      A    C
ATOM   1866  N    LEU A 220     -29.177 -23.336 -49.707  1.00 29.25      A    N
ATOM   1867  CA   LEU A 220     -29.099 -22.053 -49.040  1.00 28.81      A    C
ATOM   1868  C    LEU A 220     -29.435 -22.198 -47.581  1.00 28.94      A    C
ATOM   1869  O    LEU A 220     -30.499 -22.690 -47.239  1.00 29.01      A    O
ATOM   1870  CB   LEU A 220     -30.034 -21.038 -49.691  1.00 28.11      A    C
ATOM   1871  CG   LEU A 220     -29.838 -20.770 -51.185  1.00 27.42      A    C
ATOM   1872  CD1  LEU A 220     -30.718 -19.623 -51.643  1.00 26.95      A    C
ATOM   1873  CD2  LEU A 220     -28.378 -20.555 -51.563  1.00 27.42      A    C
ATOM   1874  N    PHE A 221     -28.509 -21.773 -46.732  1.00 29.07      A    N
ATOM   1875  CA   PHE A 221     -28.703 -21.740 -45.298  1.00 29.02      A    C
ATOM   1876  C    PHE A 221     -28.723 -20.285 -44.883  1.00 29.07      A    C
ATOM   1877  O    PHE A 221     -27.682 -19.650 -44.787  1.00 29.18      A    O
ATOM   1878  CB   PHE A 221     -27.571 -22.482 -44.598  1.00 29.07      A    C
ATOM   1879  CG   PHE A 221     -27.441 -23.915 -45.015  1.00 29.12      A    C
ATOM   1880  CD1  PHE A 221     -28.026 -24.927 -44.265  1.00 29.20      A    C
ATOM   1881  CD2  PHE A 221     -26.729 -24.261 -46.151  1.00 29.22      A    C
ATOM   1882  CE1  PHE A 221     -27.912 -26.260 -44.647  1.00 29.22      A    C
ATOM   1883  CE2  PHE A 221     -26.606 -25.592 -46.534  1.00 29.47      A    C
ATOM   1884  CZ   PHE A 221     -27.199 -26.591 -45.780  1.00 29.33      A    C
ATOM   1885  N    LEU A 222     -29.915 -19.758 -44.650  1.00 29.13      A    N
```

FIGURE 1 (cont'd)

```
ATOM   1886  CA  LEU A 222     -30.087 -18.330 -44.414  1.00 29.40      A  C
ATOM   1887  C   LEU A 222     -29.995 -17.960 -42.940  1.00 29.74      A  C
ATOM   1888  O   LEU A 222     -30.495 -18.682 -42.082  1.00 29.74      A  O
ATOM   1889  CB  LEU A 222     -31.415 -17.860 -45.005  1.00 29.23      A  C
ATOM   1890  CG  LEU A 222     -31.605 -18.243 -46.474  1.00 29.04      A  C
ATOM   1891  CD1 LEU A 222     -31.179 -17.122 -47.389  1.00 29.13      A  C
ATOM   1892  CD2 LEU A 222     -33.038 -18.614 -46.736  1.00 28.71      A  C
ATOM   1893  N   ASP A 223     -29.339 -16.835 -42.663  1.00 30.29      A  N
ATOM   1894  CA  ASP A 223     -29.219 -16.283 -41.311  1.00 30.88      A  C
ATOM   1895  C   ASP A 223     -30.368 -15.309 -41.050  1.00 30.91      A  C
ATOM   1896  O   ASP A 223     -31.073 -14.895 -41.979  1.00 30.82      A  O
ATOM   1897  CB  ASP A 223     -27.866 -15.568 -41.132  1.00 31.31      A  C
ATOM   1898  CG  ASP A 223     -27.462 -15.382 -39.659  1.00 32.37      A  C
ATOM   1899  OD1 ASP A 223     -28.115 -15.945 -38.751  1.00 33.27      A  O
ATOM   1900  OD2 ASP A 223     -26.465 -14.664 -39.413  1.00 33.08      A  O
ATOM   1901  N   GLY A 224     -30.561 -14.978 -39.776  1.00 31.05      A  N
ATOM   1902  CA  GLY A 224     -31.546 -13.998 -39.336  1.00 31.24      A  C
ATOM   1903  C   GLY A 224     -32.855 -14.006 -40.091  1.00 31.19      A  C
ATOM   1904  O   GLY A 224     -33.162 -13.065 -40.805  1.00 31.42      A  O
ATOM   1905  N   GLU A 225     -33.623 -15.072 -39.948  1.00 30.99      A  N
ATOM   1906  CA  GLU A 225     -34.934 -15.108 -40.542  1.00 30.92      A  C
ATOM   1907  C   GLU A 225     -35.960 -14.725 -39.490  1.00 30.98      A  C
ATOM   1908  O   GLU A 225     -36.889 -13.983 -39.758  1.00 30.93      A  O
ATOM   1909  CB  GLU A 225     -35.209 -16.492 -41.104  1.00 30.80      A  C
ATOM   1910  CG  GLU A 225     -36.587 -16.657 -41.707  1.00 31.11      A  C
ATOM   1911  CD  GLU A 225     -37.638 -17.019 -40.691  1.00 31.86      A  C
ATOM   1912  OE1 GLU A 225     -37.343 -17.804 -39.769  1.00 32.62      A  O
ATOM   1913  OE2 GLU A 225     -38.765 -16.517 -40.820  1.00 32.32      A  O
ATOM   1914  N   GLU A 226     -35.782 -15.245 -38.288  1.00 31.29      A  N
ATOM   1915  CA  GLU A 226     -36.668 -14.934 -37.176  1.00 31.79      A  C
ATOM   1916  C   GLU A 226     -36.434 -13.498 -36.713  1.00 32.42      A  C
ATOM   1917  O   GLU A 226     -35.295 -13.029 -36.691  1.00 32.59      A  O
ATOM   1918  CB  GLU A 226     -36.430 -15.895 -36.003  1.00 31.69      A  C
ATOM   1919  CG  GLU A 226     -36.585 -17.377 -36.323  1.00 30.95      A  C
ATOM   1920  CD  GLU A 226     -37.966 -17.918 -36.048  1.00 30.24      A  C
ATOM   1921  OE1 GLU A 226     -38.933 -17.134 -36.018  1.00 30.20      A  O
ATOM   1922  OE2 GLU A 226     -38.084 -19.148 -35.871  1.00 29.67      A  O
ATOM   1923  N   ALA A 227     -37.517 -12.823 -36.328  1.00 32.99      A  N
ATOM   1924  CA  ALA A 227     -37.484 -11.430 -35.898  1.00 33.73      A  C
ATOM   1925  C   ALA A 227     -36.688 -11.248 -34.615  1.00 34.40      A  C
ATOM   1926  O   ALA A 227     -36.416 -12.221 -33.910  1.00 34.50      A  O
ATOM   1927  CB  ALA A 227     -38.893 -10.923 -35.710  1.00 33.72      A  C
ATOM   1928  N   LEU A 228     -36.318 -10.006 -34.308  1.00 35.19      A  N
ATOM   1929  CA  LEU A 228     -35.628  -9.726 -33.056  1.00 35.90      A  C
ATOM   1930  C   LEU A 228     -36.502  -9.070 -31.981  1.00 36.63      A  C
ATOM   1931  O   LEU A 228     -36.476  -9.494 -30.838  1.00 36.90      A  O
ATOM   1932  CB  LEU A 228     -34.338  -8.948 -33.301  1.00 35.87      A  C
ATOM   1933  CG  LEU A 228     -33.072  -9.675 -33.781  1.00 35.19      A  C
ATOM   1934  CD1 LEU A 228     -32.795  -9.374 -35.218  1.00 34.74      A  C
ATOM   1935  CD2 LEU A 228     -33.107 -11.165 -33.550  1.00 34.60      A  C
ATOM   1936  N   LYS A 229     -37.265  -8.041 -32.341  1.00 37.37      A  N
ATOM   1937  CA  LYS A 229     -38.245  -7.458 -31.418  1.00 38.18      A  C
ATOM   1938  C   LYS A 229     -39.589  -8.129 -31.708  1.00 38.17      A  C
ATOM   1939  O   LYS A 229     -39.914  -9.137 -31.077  1.00 38.13      A  O
ATOM   1940  CB  LYS A 229     -38.302  -5.914 -31.515  1.00 38.69      A  C
ATOM   1941  CG  LYS A 229     -39.053  -5.187 -30.369  1.00 39.48      A  C
ATOM   1942  CD  LYS A 229     -38.153  -4.835 -29.192  1.00 40.02      A  C
ATOM   1943  N   GLU A 230     -40.361  -7.599 -32.654  1.00 38.32      A  N
ATOM   1944  CA  GLU A 230     -41.507  -8.354 -33.150  1.00 38.54      A  C
ATOM   1945  C   GLU A 230     -41.614  -8.355 -34.666  1.00 38.26      A  C
ATOM   1946  O   GLU A 230     -41.226  -7.400 -35.330  1.00 38.31      A  O
ATOM   1947  CB  GLU A 230     -42.837  -7.975 -32.463  1.00 38.97      A  C
ATOM   1948  CG  GLU A 230     -43.963  -9.089 -32.541  1.00 39.91      A  C
ATOM   1949  CD  GLU A 230     -43.553 -10.522 -32.045  1.00 40.11      A  C
ATOM   1950  OE1 GLU A 230     -43.076 -11.375 -32.845  1.00 38.74      A  O
```

FIGURE 1 (cont'd)

```
ATOM   1951  OE2 GLU A 230     -43.795 -10.825 -30.856  1.00 40.56      A    O
ATOM   1952  N   TRP A 231     -42.131  -9.461 -35.185  1.00 37.92      A    N
ATOM   1953  CA  TRP A 231     -42.251  -9.707 -36.605  1.00 37.66      A    C
ATOM   1954  C   TRP A 231     -42.892  -8.567 -37.375  1.00 37.99      A    C
ATOM   1955  O   TRP A 231     -43.943  -8.057 -37.004  1.00 38.32      A    O
ATOM   1956  CB  TRP A 231     -43.059 -10.980 -36.833  1.00 37.34      A    C
ATOM   1957  CG  TRP A 231     -43.006 -11.450 -38.251  1.00 36.76      A    C
ATOM   1958  CD1 TRP A 231     -43.802 -11.042 -39.278  1.00 36.73      A    C
ATOM   1959  CD2 TRP A 231     -42.095 -12.405 -38.802  1.00 36.12      A    C
ATOM   1960  CE2 TRP A 231     -42.399 -12.525 -40.169  1.00 35.88      A    C
ATOM   1961  CE3 TRP A 231     -41.053 -13.176 -38.271  1.00 35.80      A    C
ATOM   1962  NE1 TRP A 231     -43.445 -11.682 -40.437  1.00 36.37      A    N
ATOM   1963  CZ2 TRP A 231     -41.701 -13.383 -41.012  1.00 35.26      A    C
ATOM   1964  CZ3 TRP A 231     -40.354 -14.024 -39.113  1.00 35.06      A    C
ATOM   1965  CH2 TRP A 231     -40.682 -14.121 -40.465  1.00 34.80      A    C
ATOM   1966  N   GLY A 232     -42.250  -8.200 -38.470  1.00 38.12      A    N
ATOM   1967  CA  GLY A 232     -42.723  -7.133 -39.325  1.00 38.50      A    C
ATOM   1968  C   GLY A 232     -41.841  -7.014 -40.554  1.00 38.70      A    C
ATOM   1969  O   GLY A 232     -40.788  -7.643 -40.624  1.00 38.43      A    O
ATOM   1970  N   PRO A 233     -42.267  -6.207 -41.541  1.00 39.14      A    N
ATOM   1971  CA  PRO A 233     -41.505  -6.011 -42.773  1.00 39.30      A    C
ATOM   1972  C   PRO A 233     -40.060  -5.576 -42.539  1.00 39.51      A    C
ATOM   1973  O   PRO A 233     -39.166  -6.015 -43.263  1.00 39.22      A    O
ATOM   1974  CB  PRO A 233     -42.289  -4.911 -43.488  1.00 39.49      A    C
ATOM   1975  CG  PRO A 233     -43.692  -5.119 -43.031  1.00 39.62      A    C
ATOM   1976  CD  PRO A 233     -43.565  -5.505 -41.587  1.00 39.41      A    C
ATOM   1977  N   LYS A 234     -39.836  -4.732 -41.533  1.00 40.11      A    N
ATOM   1978  CA  LYS A 234     -38.489  -4.234 -41.224  1.00 40.68      A    C
ATOM   1979  C   LYS A 234     -37.740  -5.068 -40.170  1.00 40.45      A    C
ATOM   1980  O   LYS A 234     -36.543  -4.860 -39.972  1.00 40.59      A    O
ATOM   1981  CB  LYS A 234     -38.521  -2.736 -40.854  1.00 41.29      A    C
ATOM   1982  CG  LYS A 234     -38.492  -1.773 -42.083  1.00 42.35      A    C
ATOM   1983  CD  LYS A 234     -39.138  -0.373 -41.814  1.00 43.54      A    C
ATOM   1984  CE  LYS A 234     -38.154   0.668 -41.267  1.00 43.74      A    C
ATOM   1985  N   ASP A 235     -38.437  -6.011 -39.522  1.00 40.08      A    N
ATOM   1986  CA  ASP A 235     -37.830  -6.930 -38.537  1.00 39.57      A    C
ATOM   1987  C   ASP A 235     -38.173  -8.385 -38.823  1.00 39.04      A    C
ATOM   1988  O   ASP A 235     -39.029  -8.966 -38.155  1.00 39.04      A    O
ATOM   1989  CB  ASP A 235     -38.256  -6.558 -37.107  1.00 39.83      A    C
ATOM   1990  CG  ASP A 235     -37.654  -7.475 -36.042  1.00 39.53      A    C
ATOM   1991  OD1 ASP A 235     -38.332  -7.687 -35.013  1.00 39.26      A    O
ATOM   1992  OD2 ASP A 235     -36.520  -7.974 -36.219  1.00 39.16      A    O
ATOM   1993  N   SER A 236     -37.504  -8.950 -39.826  1.00 38.42      A    N
ATOM   1994  CA  SER A 236     -37.659 -10.352 -40.250  1.00 37.78      A    C
ATOM   1995  C   SER A 236     -36.991 -10.587 -41.595  1.00 37.48      A    C
ATOM   1996  O   SER A 236     -36.966  -9.712 -42.446  1.00 37.54      A    O
ATOM   1997  CB  SER A 236     -39.127 -10.771 -40.356  1.00 37.65      A    C
ATOM   1998  OG  SER A 236     -39.761 -10.141 -41.447  1.00 37.60      A    O
ATOM   1999  N   LEU A 237     -36.465 -11.785 -41.789  1.00 37.17      A    N
ATOM   2000  CA  LEU A 237     -35.917 -12.194 -43.078  1.00 37.07      A    C
ATOM   2001  C   LEU A 237     -34.727 -11.330 -43.499  1.00 37.25      A    C
ATOM   2002  O   LEU A 237     -34.668 -10.864 -44.631  1.00 37.41      A    O
ATOM   2003  CB  LEU A 237     -37.005 -12.156 -44.169  1.00 36.90      A    C
ATOM   2004  CG  LEU A 237     -38.419 -12.678 -43.918  1.00 36.54      A    C
ATOM   2005  CD1 LEU A 237     -39.360 -12.136 -44.956  1.00 36.63      A    C
ATOM   2006  CD2 LEU A 237     -38.440 -14.186 -43.930  1.00 36.08      A    C
ATOM   2007  N   TYR A 238     -33.784 -11.110 -42.591  1.00 37.36      A    N
ATOM   2008  CA  TYR A 238     -32.592 -10.335 -42.920  1.00 37.46      A    C
ATOM   2009  C   TYR A 238     -31.702 -11.069 -43.924  1.00 37.14      A    C
ATOM   2010  O   TYR A 238     -31.197 -10.459 -44.863  1.00 37.26      A    O
ATOM   2011  CB  TYR A 238     -31.798  -9.960 -41.660  1.00 37.80      A    C
ATOM   2012  CG  TYR A 238     -32.573  -9.141 -40.651  1.00 38.38      A    C
ATOM   2013  CD1 TYR A 238     -32.801  -7.789 -40.850  1.00 39.32      A    C
ATOM   2014  CD2 TYR A 238     -33.078  -9.723 -39.497  1.00 38.50      A    C
ATOM   2015  CE1 TYR A 238     -33.519  -7.044 -39.926  1.00 39.70      A    C
```

FIGURE 1 (cont'd)

```
ATOM   2016  CE2 TYR A 238     -33.793  -8.983 -38.574  1.00 38.96      A   C
ATOM   2017  CZ  TYR A 238     -34.009  -7.654 -38.795  1.00 39.34      A   C
ATOM   2018  OH  TYR A 238     -34.713  -6.940 -37.872  1.00 39.62      A   O
ATOM   2019  N   GLY A 239     -31.526 -12.373 -43.735  1.00 36.70      A   N
ATOM   2020  CA  GLY A 239     -30.653 -13.152 -44.602  1.00 36.44      A   C
ATOM   2021  C   GLY A 239     -31.185 -13.266 -46.013  1.00 36.25      A   C
ATOM   2022  O   GLY A 239     -30.451 -13.075 -46.986  1.00 36.31      A   O
ATOM   2023  N   SER A 240     -32.475 -13.570 -46.115  1.00 35.99      A   N
ATOM   2024  CA  SER A 240     -33.121 -13.775 -47.408  1.00 35.72      A   C
ATOM   2025  C   SER A 240     -33.300 -12.488 -48.186  1.00 35.71      A   C
ATOM   2026  O   SER A 240     -33.018 -12.446 -49.376  1.00 35.82      A   O
ATOM   2027  CB  SER A 240     -34.463 -14.481 -47.235  1.00 35.59      A   C
ATOM   2028  OG  SER A 240     -35.094 -14.069 -46.039  1.00 35.89      A   O
ATOM   2029  N   ARG A 241     -33.770 -11.441 -47.519  1.00 35.70      A   N
ATOM   2030  CA  ARG A 241     -33.899 -10.140 -48.155  1.00 35.93      A   C
ATOM   2031  C   ARG A 241     -32.566  -9.621 -48.697  1.00 36.00      A   C
ATOM   2032  O   ARG A 241     -32.524  -8.962 -49.738  1.00 36.22      A   O
ATOM   2033  CB  ARG A 241     -34.513  -9.119 -47.198  1.00 36.04      A   C
ATOM   2034  CG  ARG A 241     -36.030  -9.108 -47.217  1.00 36.67      A   C
ATOM   2035  CD  ARG A 241     -36.614  -7.847 -46.582  1.00 38.01      A   C
ATOM   2036  NE  ARG A 241     -36.583  -7.880 -45.118  1.00 39.19      A   N
ATOM   2037  CZ  ARG A 241     -35.705  -7.215 -44.365  1.00 40.16      A   C
ATOM   2038  NH1 ARG A 241     -34.770  -6.456 -44.923  1.00 41.14      A   N
ATOM   2039  NH2 ARG A 241     -35.757  -7.297 -43.043  1.00 40.47      A   N
ATOM   2040  N   HIS A 242     -31.478  -9.917 -47.999  1.00 35.92      A   N
ATOM   2041  CA  HIS A 242     -30.178  -9.466 -48.452  1.00 36.03      A   C
ATOM   2042  C   HIS A 242     -29.646 -10.307 -49.608  1.00 35.71      A   C
ATOM   2043  O   HIS A 242     -29.190  -9.753 -50.615  1.00 35.93      A   O
ATOM   2044  CB  HIS A 242     -29.179  -9.449 -47.304  1.00 36.32      A   C
ATOM   2045  CG  HIS A 242     -27.805  -8.996 -47.702  1.00 37.15      A   C
ATOM   2046  CD2 HIS A 242     -27.277  -7.754 -47.827  1.00 37.93      A   C
ATOM   2047  ND1 HIS A 242     -26.793  -9.877 -48.029  1.00 37.30      A   N
ATOM   2048  CE1 HIS A 242     -25.702  -9.197 -48.333  1.00 37.97      A   C
ATOM   2049  NE2 HIS A 242     -25.969  -7.906 -48.220  1.00 38.41      A   N
ATOM   2050  N   LEU A 243     -29.695 -11.634 -49.457  1.00 35.13      A   N
ATOM   2051  CA  LEU A 243     -29.252 -12.553 -50.512  1.00 34.64      A   C
ATOM   2052  C   LEU A 243     -30.009 -12.310 -51.818  1.00 34.72      A   C
ATOM   2053  O   LEU A 243     -29.403 -12.255 -52.878  1.00 34.92      A   O
ATOM   2054  CB  LEU A 243     -29.373 -14.017 -50.077  1.00 34.19      A   C
ATOM   2055  CG  LEU A 243     -28.825 -15.055 -51.061  1.00 33.48      A   C
ATOM   2056  CD1 LEU A 243     -27.340 -14.896 -51.254  1.00 33.26      A   C
ATOM   2057  CD2 LEU A 243     -29.128 -16.443 -50.573  1.00 32.87      A   C
ATOM   2058  N   ALA A 244     -31.326 -12.151 -51.729  1.00 34.74      A   N
ATOM   2059  CA  ALA A 244     -32.135 -11.809 -52.883  1.00 35.01      A   C
ATOM   2060  C   ALA A 244     -31.606 -10.543 -53.567  1.00 35.49      A   C
ATOM   2061  O   ALA A 244     -31.417 -10.533 -54.781  1.00 35.67      A   O
ATOM   2062  CB  ALA A 244     -33.594 -11.661 -52.486  1.00 34.75      A   C
ATOM   2063  N   GLN A 245     -31.342  -9.494 -52.786  1.00 36.03      A   N
ATOM   2064  CA  GLN A 245     -30.789  -8.241 -53.316  1.00 36.62      A   C
ATOM   2065  C   GLN A 245     -29.452  -8.480 -54.019  1.00 36.93      A   C
ATOM   2066  O   GLN A 245     -29.241  -8.011 -55.133  1.00 37.20      A   O
ATOM   2067  CB  GLN A 245     -30.644  -7.175 -52.211  1.00 36.69      A   C
ATOM   2068  N   LEU A 246     -28.572  -9.235 -53.369  1.00 37.05      A   N
ATOM   2069  CA  LEU A 246     -27.214  -9.476 -53.859  1.00 37.31      A   C
ATOM   2070  C   LEU A 246     -27.158 -10.402 -55.072  1.00 37.74      A   C
ATOM   2071  O   LEU A 246     -26.244 -10.307 -55.892  1.00 38.03      A   O
ATOM   2072  CB  LEU A 246     -26.336 -10.007 -52.724  1.00 37.04      A   C
ATOM   2073  CG  LEU A 246     -24.828 -10.258 -52.831  1.00 36.44      A   C
ATOM   2074  CD1 LEU A 246     -24.579 -11.738 -52.862  1.00 35.20      A   C
ATOM   2075  CD2 LEU A 246     -24.063  -9.521 -53.946  1.00 34.76      A   C
ATOM   2076  N   MET A 247     -28.132 -11.298 -55.184  1.00 38.06      A   N
ATOM   2077  CA  MET A 247     -28.241 -12.179 -56.353  1.00 38.46      A   C
ATOM   2078  C   MET A 247     -28.790 -11.448 -57.576  1.00 39.25      A   C
ATOM   2079  O   MET A 247     -28.454 -11.800 -58.701  1.00 39.45      A   O
ATOM   2080  CB  MET A 247     -29.113 -13.397 -56.052  1.00 37.97      A   C
```

FIGURE 1 (cont'd)

```
ATOM   2081  CG   MET A 247     -28.477 -14.419 -55.130  1.00 37.32      A  C
ATOM   2082  SD   MET A 247     -29.434 -15.946 -55.088  1.00 36.49      A  S
ATOM   2083  CE   MET A 247     -28.638 -16.883 -56.384  1.00 36.92      A  C
ATOM   2084  N    GLU A 248     -29.636 -10.442 -57.350  1.00 40.15      A  N
ATOM   2085  CA   GLU A 248     -30.158  -9.595 -58.427  1.00 41.16      A  C
ATOM   2086  C    GLU A 248     -29.062  -8.720 -59.027  1.00 42.18      A  C
ATOM   2087  O    GLU A 248     -29.116  -8.385 -60.206  1.00 42.72      A  O
ATOM   2088  CB   GLU A 248     -31.301  -8.713 -57.916  1.00 41.00      A  C
ATOM   2089  CG   GLU A 248     -32.219  -8.147 -59.007  1.00 39.92      A  C
ATOM   2090  CD   GLU A 248     -33.250  -7.148 -58.474  1.00 39.02      A  C
ATOM   2091  OE1  GLU A 248     -33.394  -6.062 -59.072  1.00 38.50      A  O
ATOM   2092  OE2  GLU A 248     -33.919  -7.441 -57.463  1.00 38.77      A  O
ATOM   2093  N    SER A 249     -28.074  -8.358 -58.212  1.00 43.02      A  N
ATOM   2094  CA   SER A 249     -26.986  -7.503 -58.659  1.00 43.98      A  C
ATOM   2095  C    SER A 249     -25.822  -8.291 -59.223  1.00 44.46      A  C
ATOM   2096  O    SER A 249     -24.856  -7.709 -59.701  1.00 44.92      A  O
ATOM   2097  CB   SER A 249     -26.495  -6.607 -57.521  1.00 44.14      A  C
ATOM   2098  OG   SER A 249     -25.643  -7.309 -56.638  1.00 44.12      A  O
ATOM   2099  N    ILE A 250     -25.916  -9.610 -59.167  1.00 44.75      A  N
ATOM   2100  CA   ILE A 250     -24.837 -10.473 -59.622  1.00 45.30      A  C
ATOM   2101  C    ILE A 250     -25.173 -11.098 -60.988  1.00 46.10      A  C
ATOM   2102  O    ILE A 250     -26.021 -11.990 -61.075  1.00 45.87      A  O
ATOM   2103  CB   ILE A 250     -24.515 -11.546 -58.548  1.00 44.84      A  C
ATOM   2104  CG1  ILE A 250     -23.074 -12.043 -58.674  1.00 44.80      A  C
ATOM   2105  CD1  ILE A 250     -22.956 -13.432 -59.289  1.00 44.42      A  C
ATOM   2106  N    PRO A 251     -24.514 -10.615 -62.060  1.00 47.21      A  N
ATOM   2107  CA   PRO A 251     -24.784 -11.086 -63.409  1.00 47.90      A  C
ATOM   2108  C    PRO A 251     -24.391 -12.525 -63.623  1.00 48.32      A  C
ATOM   2109  O    PRO A 251     -23.447 -13.043 -63.014  1.00 48.33      A  O
ATOM   2110  CB   PRO A 251     -23.911 -10.188 -64.285  1.00 48.26      A  C
ATOM   2111  CG   PRO A 251     -23.648  -8.994 -63.452  1.00 48.26      A  C
ATOM   2112  CD   PRO A 251     -23.512  -9.540 -62.073  1.00 47.58      A  C
ATOM   2113  N    HIS A 252     -25.138 -13.146 -64.516  1.00 48.76      A  N
ATOM   2114  CA   HIS A 252     -25.049 -14.549 -64.737  1.00 49.10      A  C
ATOM   2115  C    HIS A 252     -25.656 -14.776 -66.083  1.00 49.67      A  C
ATOM   2116  O    HIS A 252     -26.369 -13.947 -66.628  1.00 49.92      A  O
ATOM   2117  CB   HIS A 252     -25.772 -15.334 -63.633  1.00 47.94      A  C
ATOM   2118  CG   HIS A 252     -25.647 -16.821 -63.751  1.00 47.73      A  C
ATOM   2119  CD2  HIS A 252     -26.546 -17.759 -64.135  1.00 47.57      A  C
ATOM   2120  ND1  HIS A 252     -24.492 -17.505 -63.433  1.00 48.04      A  N
ATOM   2121  CE1  HIS A 252     -24.683 -18.799 -63.625  1.00 48.04      A  C
ATOM   2122  NE2  HIS A 252     -25.921 -18.979 -64.053  1.00 47.80      A  N
ATOM   2123  N    SER A 253     -25.509 -16.028 -66.429  1.00 50.10      A  N
ATOM   2124  CA   SER A 253     -24.873 -16.621 -67.557  1.00 50.12      A  C
ATOM   2125  C    SER A 253     -25.521 -16.739 -68.883  1.00 50.23      A  C
ATOM   2126  O    SER A 253     -24.775 -16.822 -69.807  1.00 50.68      A  O
ATOM   2127  CB   SER A 253     -24.652 -18.012 -67.114  1.00 49.26      A  C
ATOM   2128  OG   SER A 253     -23.428 -18.519 -67.465  1.00 48.78      A  O
ATOM   2129  N    PRO A 254     -26.770 -17.195 -68.972  1.00 49.79      A  N
ATOM   2130  CA   PRO A 254     -27.890 -16.486 -69.553  1.00 49.42      A  C
ATOM   2131  C    PRO A 254     -28.928 -16.417 -68.507  1.00 49.04      A  C
ATOM   2132  O    PRO A 254     -29.958 -17.051 -68.658  1.00 49.22      A  O
ATOM   2133  CB   PRO A 254     -28.434 -17.428 -70.624  1.00 48.67      A  C
ATOM   2134  CG   PRO A 254     -27.423 -18.378 -70.879  1.00 48.82      A  C
ATOM   2135  CD   PRO A 254     -26.560 -18.490 -69.659  1.00 49.07      A  C
ATOM   2136  N    GLY A 255     -28.596 -15.745 -67.415  1.00 48.43      A  N
ATOM   2137  CA   GLY A 255     -29.542 -15.095 -66.546  1.00 47.57      A  C
ATOM   2138  C    GLY A 255     -30.467 -14.153 -67.280  1.00 47.10      A  C
ATOM   2139  O    GLY A 255     -31.248 -14.594 -68.104  1.00 47.40      A  O
ATOM   2140  N    PRO A 256     -30.372 -12.835 -67.081  1.00 46.61      A  N
ATOM   2141  CA   PRO A 256     -29.538 -11.694 -66.731  1.00 46.33      A  C
ATOM   2142  C    PRO A 256     -28.784 -11.777 -65.428  1.00 45.74      A  C
ATOM   2143  O    PRO A 256     -27.558 -11.695 -65.430  1.00 45.95      A  O
ATOM   2144  CB   PRO A 256     -30.557 -10.543 -66.670  1.00 46.53      A  C
ATOM   2145  CG   PRO A 256     -31.741 -11.029 -67.432  1.00 46.55      A  C
```

FIGURE 1 (cont'd)

```
ATOM   2146  CD   PRO A 256     -31.793 -12.442 -67.096  1.00 46.58      A    C
ATOM   2147  N    THR A 257     -29.519 -11.916 -64.329  1.00 44.73      A    N
ATOM   2148  CA   THR A 257     -28.934 -11.971 -62.996  1.00 43.64      A    C
ATOM   2149  C    THR A 257     -28.992 -13.386 -62.443  1.00 42.92      A    C
ATOM   2150  O    THR A 257     -29.632 -14.252 -63.028  1.00 42.81      A    O
ATOM   2151  CB   THR A 257     -29.668 -11.030 -62.040  1.00 43.47      A    C
ATOM   2152  OG1  THR A 257     -31.069 -11.313 -62.090  1.00 43.07      A    O
ATOM   2153  N    ARG A 258     -28.325 -13.617 -61.314  1.00 42.06      A    N
ATOM   2154  CA   ARG A 258     -28.328 -14.943 -60.685  1.00 41.07      A    C
ATOM   2155  C    ARG A 258     -29.705 -15.356 -60.167  1.00 40.55      A    C
ATOM   2156  O    ARG A 258     -29.937 -16.527 -59.880  1.00 40.51      A    O
ATOM   2157  CB   ARG A 258     -27.271 -15.053 -59.574  1.00 40.16      A    C
ATOM   2158  CG   ARG A 258     -25.932 -15.601 -60.058  1.00 40.10      A    C
ATOM   2159  CD   ARG A 258     -25.193 -16.366 -58.974  1.00 40.04      A    C
ATOM   2160  NE   ARG A 258     -23.969 -16.975 -59.492  1.00 40.30      A    N
ATOM   2161  N    ILE A 259     -30.613 -14.394 -60.057  1.00 39.83      A    N
ATOM   2162  CA   ILE A 259     -31.962 -14.683 -59.612  1.00 38.86      A    C
ATOM   2163  C    ILE A 259     -32.671 -15.562 -60.606  1.00 38.81      A    C
ATOM   2164  O    ILE A 259     -33.454 -16.430 -60.230  1.00 38.82      A    O
ATOM   2165  CB   ILE A 259     -32.759 -13.407 -59.337  1.00 38.00      A    C
ATOM   2166  CG1  ILE A 259     -32.899 -13.238 -57.834  1.00 37.65      A    C
ATOM   2167  CG2  ILE A 259     -34.162 -13.482 -59.906  1.00 37.75      A    C
ATOM   2168  CD1  ILE A 259     -32.858 -11.833 -57.389  1.00 38.53      A    C
ATOM   2169  N    GLN A 260     -32.366 -15.352 -61.877  1.00 38.50      A    N
ATOM   2170  CA   GLN A 260     -32.991 -16.106 -62.954  1.00 37.91      A    C
ATOM   2171  C    GLN A 260     -32.406 -17.490 -63.023  1.00 37.75      A    C
ATOM   2172  O    GLN A 260     -32.866 -18.322 -63.798  1.00 38.17      A    O
ATOM   2173  CB   GLN A 260     -32.747 -15.407 -64.288  1.00 37.09      A    C
ATOM   2174  CG   GLN A 260     -32.530 -13.918 -64.140  1.00 36.67      A    C
ATOM   2175  CD   GLN A 260     -33.849 -13.315 -63.852  1.00 36.30      A    C
ATOM   2176  NE2  GLN A 260     -34.835 -13.789 -64.618  1.00 35.92      A    N
ATOM   2177  OE1  GLN A 260     -34.065 -12.547 -63.000  1.00 36.70      A    O
ATOM   2178  N    ALA A 261     -31.377 -17.728 -62.220  1.00 37.14      A    N
ATOM   2179  CA   ALA A 261     -30.714 -19.023 -62.208  1.00 36.49      A    C
ATOM   2180  C    ALA A 261     -31.475 -20.049 -61.366  1.00 35.72      A    C
ATOM   2181  O    ALA A 261     -31.328 -21.258 -61.566  1.00 35.67      A    O
ATOM   2182  N    ILE A 262     -32.290 -19.561 -60.435  1.00 34.72      A    N
ATOM   2183  CA   ILE A 262     -33.128 -20.425 -59.609  1.00 33.64      A    C
ATOM   2184  C    ILE A 262     -34.288 -20.925 -60.440  1.00 33.57      A    C
ATOM   2185  O    ILE A 262     -35.228 -20.175 -60.710  1.00 33.77      A    O
ATOM   2186  CB   ILE A 262     -33.698 -19.678 -58.391  1.00 32.71      A    C
ATOM   2187  CG1  ILE A 262     -32.590 -18.915 -57.668  1.00 32.14      A    C
ATOM   2188  CD1  ILE A 262     -33.092 -17.806 -56.773  1.00 31.74      A    C
ATOM   2189  N    GLU A 263     -34.213 -22.181 -60.869  1.00 33.22      A    N
ATOM   2190  CA   GLU A 263     -35.314 -22.790 -61.613  1.00 32.81      A    C
ATOM   2191  C    GLU A 263     -36.487 -23.054 -60.674  1.00 32.18      A    C
ATOM   2192  O    GLU A 263     -37.643 -22.932 -61.072  1.00 32.28      A    O
ATOM   2193  CB   GLU A 263     -34.866 -24.078 -62.315  1.00 33.01      A    C
ATOM   2194  CG   GLU A 263     -35.858 -24.605 -63.344  1.00 33.02      A    C
ATOM   2195  CD   GLU A 263     -35.299 -25.715 -64.191  1.00 32.64      A    C
ATOM   2196  OE1  GLU A 263     -35.497 -26.911 -63.858  1.00 32.94      A    O
ATOM   2197  OE2  GLU A 263     -34.692 -25.366 -65.216  1.00 33.82      A    O
ATOM   2198  N    LEU A 264     -36.169 -23.408 -59.427  1.00 31.33      A    N
ATOM   2199  CA   LEU A 264     -37.166 -23.647 -58.385  1.00 30.34      A    C
ATOM   2200  C    LEU A 264     -36.592 -23.420 -57.002  1.00 29.74      A    C
ATOM   2201  O    LEU A 264     -35.609 -24.059 -56.619  1.00 29.78      A    O
ATOM   2202  CB   LEU A 264     -37.732 -25.067 -58.468  1.00 30.25      A    C
ATOM   2203  CG   LEU A 264     -38.781 -25.447 -57.425  1.00 29.81      A    C
ATOM   2204  CD1  LEU A 264     -40.009 -24.558 -57.510  1.00 29.71      A    C
ATOM   2205  CD2  LEU A 264     -39.164 -26.886 -57.606  1.00 29.61      A    C
ATOM   2206  N    PHE A 265     -37.233 -22.518 -56.260  1.00 28.90      A    N
ATOM   2207  CA   PHE A 265     -36.879 -22.218 -54.876  1.00 27.89      A    C
ATOM   2208  C    PHE A 265     -37.772 -23.040 -53.957  1.00 27.60      A    C
ATOM   2209  O    PHE A 265     -38.906 -22.662 -53.703  1.00 27.50      A    O
ATOM   2210  CB   PHE A 265     -37.058 -20.723 -54.616  1.00 27.61      A    C
```

FIGURE 1 (cont'd)

```
ATOM   2211  CG   PHE A 265     -36.479 -20.248 -53.320  1.00 26.24      A  C
ATOM   2212  CD1  PHE A 265     -35.207 -19.714 -53.273  1.00 25.31      A  C
ATOM   2213  CD2  PHE A 265     -37.222 -20.296 -52.154  1.00 25.15      A  C
ATOM   2214  CE1  PHE A 265     -34.676 -19.266 -52.077  1.00 22.95      A  C
ATOM   2215  CE2  PHE A 265     -36.700 -19.849 -50.962  1.00 22.62      A  C
ATOM   2216  CZ   PHE A 265     -35.424 -19.331 -50.922  1.00 21.98      A  C
ATOM   2217  N    MET A 266     -37.263 -24.169 -53.473  1.00 27.29      A  N
ATOM   2218  CA   MET A 266     -38.032 -25.041 -52.605  1.00 27.11      A  C
ATOM   2219  C    MET A 266     -37.607 -24.841 -51.159  1.00 27.07      A  C
ATOM   2220  O    MET A 266     -36.594 -25.371 -50.733  1.00 27.15      A  O
ATOM   2221  CB   MET A 266     -37.853 -26.489 -53.034  1.00 27.07      A  C
ATOM   2222  CG   MET A 266     -38.677 -27.495 -52.249  1.00 26.78      A  C
ATOM   2223  SD   MET A 266     -38.346 -29.229 -52.656  1.00 26.38      A  S
ATOM   2224  CE   MET A 266     -39.755 -30.036 -51.906  1.00 24.81      A  C
ATOM   2225  N    LEU A 267     -38.397 -24.071 -50.413  1.00 26.99      A  N
ATOM   2226  CA   LEU A 267     -38.083 -23.701 -49.027  1.00 26.90      A  C
ATOM   2227  C    LEU A 267     -38.622 -24.692 -47.998  1.00 26.98      A  C
ATOM   2228  O    LEU A 267     -39.824 -24.941 -47.935  1.00 27.06      A  O
ATOM   2229  CB   LEU A 267     -38.622 -22.298 -48.723  1.00 26.82      A  C
ATOM   2230  CG   LEU A 267     -38.485 -21.754 -47.305  1.00 26.52      A  C
ATOM   2231  CD1  LEU A 267     -37.036 -21.684 -46.898  1.00 26.53      A  C
ATOM   2232  CD2  LEU A 267     -39.105 -20.390 -47.232  1.00 26.43      A  C
ATOM   2233  N    LEU A 268     -37.726 -25.233 -47.182  1.00 27.04      A  N
ATOM   2234  CA   LEU A 268     -38.086 -26.227 -46.179  1.00 27.21      A  C
ATOM   2235  C    LEU A 268     -38.187 -25.593 -44.803  1.00 27.45      A  C
ATOM   2236  O    LEU A 268     -37.225 -24.976 -44.329  1.00 27.60      A  O
ATOM   2237  CB   LEU A 268     -37.037 -27.322 -46.142  1.00 27.14      A  C
ATOM   2238  CG   LEU A 268     -37.207 -28.532 -47.042  1.00 27.18      A  C
ATOM   2239  CD1  LEU A 268     -36.893 -28.196 -48.481  1.00 27.48      A  C
ATOM   2240  CD2  LEU A 268     -36.278 -29.608 -46.533  1.00 27.06      A  C
ATOM   2241  N    ASP A 269     -39.341 -25.750 -44.154  1.00 27.67      A  N
ATOM   2242  CA   ASP A 269     -39.561 -25.128 -42.848  1.00 27.96      A  C
ATOM   2243  C    ASP A 269     -40.516 -25.879 -41.959  1.00 27.90      A  C
ATOM   2244  O    ASP A 269     -41.418 -26.549 -42.443  1.00 28.11      A  O
ATOM   2245  CB   ASP A 269     -40.087 -23.713 -43.020  1.00 28.23      A  C
ATOM   2246  CG   ASP A 269     -39.494 -22.755 -42.016  1.00 29.36      A  C
ATOM   2247  OD1  ASP A 269     -38.241 -22.652 -41.948  1.00 30.27      A  O
ATOM   2248  OD2  ASP A 269     -40.285 -22.094 -41.311  1.00 30.11      A  O
ATOM   2249  N    LEU A 270     -40.312 -25.746 -40.653  1.00 27.78      A  N
ATOM   2250  CA   LEU A 270     -41.161 -26.375 -39.647  1.00 27.79      A  C
ATOM   2251  C    LEU A 270     -41.419 -27.854 -39.925  1.00 27.89      A  C
ATOM   2252  O    LEU A 270     -42.549 -28.331 -39.847  1.00 27.93      A  O
ATOM   2253  CB   LEU A 270     -42.476 -25.608 -39.490  1.00 27.70      A  C
ATOM   2254  CG   LEU A 270     -42.410 -24.094 -39.319  1.00 27.71      A  C
ATOM   2255  CD1  LEU A 270     -43.742 -23.563 -38.853  1.00 27.65      A  C
ATOM   2256  CD2  LEU A 270     -41.334 -23.692 -38.342  1.00 28.00      A  C
ATOM   2257  N    LEU A 271     -40.356 -28.573 -40.259  1.00 27.99      A  N
ATOM   2258  CA   LEU A 271     -40.439 -30.010 -40.472  1.00 28.28      A  C
ATOM   2259  C    LEU A 271     -39.784 -30.753 -39.313  1.00 28.69      A  C
ATOM   2260  O    LEU A 271     -38.761 -30.322 -38.784  1.00 28.73      A  O
ATOM   2261  CB   LEU A 271     -39.759 -30.400 -41.780  1.00 28.08      A  C
ATOM   2262  CG   LEU A 271     -40.313 -29.831 -43.077  1.00 27.69      A  C
ATOM   2263  CD1  LEU A 271     -39.174 -29.187 -43.820  1.00 27.64      A  C
ATOM   2264  N    GLY A 272     -40.377 -31.871 -38.918  1.00 29.23      A  N
ATOM   2265  CA   GLY A 272     -39.820 -32.674 -37.833  1.00 29.89      A  C
ATOM   2266  C    GLY A 272     -40.847 -33.184 -36.828  1.00 30.46      A  C
ATOM   2267  O    GLY A 272     -40.642 -34.234 -36.202  1.00 30.65      A  O
ATOM   2268  N    ALA A 273     -41.946 -32.443 -36.675  1.00 30.82      A  N
ATOM   2269  CA   ALA A 273     -43.010 -32.792 -35.736  1.00 31.21      A  C
ATOM   2270  C    ALA A 273     -43.790 -33.982 -36.263  1.00 31.55      A  C
ATOM   2271  O    ALA A 273     -43.696 -34.277 -37.450  1.00 31.62      A  O
ATOM   2272  CB   ALA A 273     -43.935 -31.607 -35.527  1.00 31.18      A  C
ATOM   2273  N    PRO A 274     -44.547 -34.681 -35.388  1.00 31.93      A  N
ATOM   2274  CA   PRO A 274     -45.442 -35.731 -35.864  1.00 32.22      A  C
ATOM   2275  C    PRO A 274     -46.618 -35.187 -36.663  1.00 32.35      A  C
```

FIGURE 1 (cont'd)

```
ATOM   2276  O   PRO A 274     -47.023 -34.040 -36.475  1.00 32.27      A    O
ATOM   2277  CB  PRO A 274     -45.947 -36.369 -34.570  1.00 32.47      A    C
ATOM   2278  CG  PRO A 274     -45.730 -35.370 -33.539  1.00 32.42      A    C
ATOM   2279  CD  PRO A 274     -44.491 -34.662 -33.919  1.00 32.11      A    C
ATOM   2280  N   ASN A 275     -47.146 -36.013 -37.554  1.00 32.56      A    N
ATOM   2281  CA  ASN A 275     -48.321 -35.662 -38.351  1.00 32.95      A    C
ATOM   2282  C   ASN A 275     -48.353 -34.251 -38.941  1.00 32.54      A    C
ATOM   2283  O   ASN A 275     -49.287 -33.497 -38.664  1.00 32.77      A    O
ATOM   2284  CB  ASN A 275     -49.603 -35.911 -37.556  1.00 33.41      A    C
ATOM   2285  CG  ASN A 275     -49.681 -37.313 -37.028  1.00 34.78      A    C
ATOM   2286  ND2 ASN A 275     -49.415 -37.461 -35.741  1.00 35.90      A    N
ATOM   2287  OD1 ASN A 275     -49.968 -38.260 -37.762  1.00 35.79      A    O
ATOM   2288  N   PRO A 276     -47.344 -33.890 -39.763  1.00 32.05      A    N
ATOM   2289  CA  PRO A 276     -47.439 -32.621 -40.472  1.00 31.80      A    C
ATOM   2290  C   PRO A 276     -48.401 -32.739 -41.637  1.00 31.80      A    C
ATOM   2291  O   PRO A 276     -48.607 -33.831 -42.147  1.00 31.91      A    O
ATOM   2292  CB  PRO A 276     -46.023 -32.406 -40.987  1.00 31.62      A    C
ATOM   2293  CG  PRO A 276     -45.461 -33.754 -41.129  1.00 31.60      A    C
ATOM   2294  CD  PRO A 276     -46.101 -34.609 -40.089  1.00 31.88      A    C
ATOM   2295  N   THR A 277     -49.012 -31.633 -42.029  1.00 31.83      A    N
ATOM   2296  CA  THR A 277     -49.826 -31.616 -43.235  1.00 31.91      A    C
ATOM   2297  C   THR A 277     -49.334 -30.503 -44.165  1.00 31.83      A    C
ATOM   2298  O   THR A 277     -49.131 -29.360 -43.742  1.00 31.80      A    O
ATOM   2299  CB  THR A 277     -51.351 -31.515 -42.936  1.00 31.99      A    C
ATOM   2300  CG2 THR A 277     -51.899 -32.844 -42.521  1.00 32.10      A    C
ATOM   2301  OG1 THR A 277     -51.578 -30.602 -41.863  1.00 32.28      A    O
ATOM   2302  N   PHE A 278     -49.118 -30.854 -45.427  1.00 31.78      A    N
ATOM   2303  CA  PHE A 278     -48.616 -29.905 -46.404  1.00 31.80      A    C
ATOM   2304  C   PHE A 278     -49.609 -29.654 -47.535  1.00 32.13      A    C
ATOM   2305  O   PHE A 278     -50.329 -30.554 -47.948  1.00 32.24      A    O
ATOM   2306  CB  PHE A 278     -47.306 -30.413 -46.988  1.00 31.57      A    C
ATOM   2307  CG  PHE A 278     -46.258 -30.721 -45.964  1.00 31.31      A    C
ATOM   2308  CD1 PHE A 278     -45.617 -29.701 -45.276  1.00 31.27      A    C
ATOM   2309  CD2 PHE A 278     -45.892 -32.028 -45.702  1.00 31.18      A    C
ATOM   2310  CE1 PHE A 278     -44.628 -29.986 -44.336  1.00 31.20      A    C
ATOM   2311  CE2 PHE A 278     -44.916 -32.315 -44.771  1.00 30.99      A    C
ATOM   2312  CZ  PHE A 278     -44.284 -31.294 -44.086  1.00 30.99      A    C
ATOM   2313  N   TYR A 279     -49.629 -28.426 -48.038  1.00 32.51      A    N
ATOM   2314  CA  TYR A 279     -50.495 -28.052 -49.147  1.00 33.06      A    C
ATOM   2315  C   TYR A 279     -49.699 -27.250 -50.158  1.00 33.66      A    C
ATOM   2316  O   TYR A 279     -48.585 -26.833 -49.869  1.00 33.63      A    O
ATOM   2317  CB  TYR A 279     -51.674 -27.239 -48.633  1.00 32.95      A    C
ATOM   2318  CG  TYR A 279     -52.513 -27.988 -47.628  1.00 32.43      A    C
ATOM   2319  CD1 TYR A 279     -53.566 -28.785 -48.049  1.00 32.35      A    C
ATOM   2320  CD2 TYR A 279     -52.240 -27.921 -46.260  1.00 30.63      A    C
ATOM   2321  CE1 TYR A 279     -54.343 -29.476 -47.148  1.00 30.96      A    C
ATOM   2322  CE2 TYR A 279     -53.009 -28.614 -45.350  1.00 29.69      A    C
ATOM   2323  CZ  TYR A 279     -54.060 -29.390 -45.808  1.00 29.94      A    C
ATOM   2324  OH  TYR A 279     -54.848 -30.099 -44.940  1.00 30.68      A    O
ATOM   2325  N   SER A 280     -50.251 -27.049 -51.348  1.00 34.58      A    N
ATOM   2326  CA  SER A 280     -49.565 -26.243 -52.351  1.00 35.42      A    C
ATOM   2327  C   SER A 280     -49.985 -24.776 -52.275  1.00 35.94      A    C
ATOM   2328  O   SER A 280     -51.089 -24.412 -52.677  1.00 36.26      A    O
ATOM   2329  CB  SER A 280     -49.793 -26.800 -53.754  1.00 35.57      A    C
ATOM   2330  OG  SER A 280     -48.976 -26.126 -54.695  1.00 35.77      A    O
ATOM   2331  N   HIS A 281     -49.096 -23.934 -51.765  1.00 36.39      A    N
ATOM   2332  CA  HIS A 281     -49.412 -22.520 -51.581  1.00 37.12      A    C
ATOM   2333  C   HIS A 281     -49.089 -21.668 -52.815  1.00 37.47      A    C
ATOM   2334  O   HIS A 281     -49.357 -20.456 -52.823  1.00 37.65      A    O
ATOM   2335  CB  HIS A 281     -48.718 -21.971 -50.334  1.00 37.19      A    C
ATOM   2336  CG  HIS A 281     -49.029 -22.743 -49.096  1.00 37.78      A    C
ATOM   2337  CD2 HIS A 281     -50.076 -22.671 -48.242  1.00 38.67      A    C
ATOM   2338  ND1 HIS A 281     -48.220 -23.756 -48.628  1.00 37.79      A    N
ATOM   2339  CE1 HIS A 281     -48.750 -24.271 -47.533  1.00 38.21      A    C
ATOM   2340  NE2 HIS A 281     -49.876 -23.629 -47.276  1.00 38.94      A    N
```

FIGURE 1 (cont'd)

```
ATOM   2341  N   PHE A 282     -48.523 -22.304 -53.846  1.00 37.83           A    N
ATOM   2342  CA  PHE A 282     -48.309 -21.654 -55.151  1.00 38.18           A    C
ATOM   2343  C   PHE A 282     -48.735 -22.551 -56.303  1.00 38.50           A    C
ATOM   2344  O   PHE A 282     -48.105 -23.579 -56.547  1.00 38.48           A    O
ATOM   2345  CB  PHE A 282     -46.850 -21.189 -55.326  1.00 38.08           A    C
ATOM   2346  CG  PHE A 282     -46.403 -20.237 -54.268  1.00 37.99           A    C
ATOM   2347  CD1 PHE A 282     -46.895 -18.947 -54.242  1.00 38.46           A    C
ATOM   2348  CD2 PHE A 282     -45.528 -20.639 -53.275  1.00 37.84           A    C
ATOM   2349  CE1 PHE A 282     -46.516 -18.069 -53.252  1.00 38.44           A    C
ATOM   2350  CE2 PHE A 282     -45.139 -19.767 -52.285  1.00 37.94           A    C
ATOM   2351  CZ  PHE A 282     -45.633 -18.479 -52.271  1.00 38.22           A    C
ATOM   2352  N   PRO A 283     -49.810 -22.165 -57.015  1.00 38.88           A    N
ATOM   2353  CA  PRO A 283     -50.303 -22.913 -58.168  1.00 39.02           A    C
ATOM   2354  C   PRO A 283     -49.296 -22.925 -59.310  1.00 38.89           A    C
ATOM   2355  O   PRO A 283     -49.374 -23.777 -60.182  1.00 38.97           A    O
ATOM   2356  CB  PRO A 283     -51.570 -22.156 -58.572  1.00 39.26           A    C
ATOM   2357  CG  PRO A 283     -51.944 -21.380 -57.391  1.00 39.29           A    C
ATOM   2358  CD  PRO A 283     -50.653 -20.995 -56.744  1.00 39.04           A    C
ATOM   2359  N   ARG A 284     -48.351 -21.994 -59.291  1.00 38.63           A    N
ATOM   2360  CA  ARG A 284     -47.280 -21.979 -60.269  1.00 38.51           A    C
ATOM   2361  C   ARG A 284     -46.497 -23.287 -60.257  1.00 38.72           A    C
ATOM   2362  O   ARG A 284     -46.175 -23.833 -61.316  1.00 38.99           A    O
ATOM   2363  CB  ARG A 284     -46.326 -20.831 -59.990  1.00 38.26           A    C
ATOM   2364  CG  ARG A 284     -45.755 -20.175 -61.246  1.00 37.49           A    C
ATOM   2365  CD  ARG A 284     -44.799 -21.045 -62.058  1.00 35.78           A    C
ATOM   2366  NE  ARG A 284     -43.809 -20.194 -62.715  1.00 34.88           A    N
ATOM   2367  CZ  ARG A 284     -42.862 -20.594 -63.554  1.00 33.81           A    C
ATOM   2368  NH1 ARG A 284     -42.755 -21.872 -63.922  1.00 33.34           A    N
ATOM   2369  NH2 ARG A 284     -42.022 -19.689 -64.034  1.00 33.61           A    N
ATOM   2370  N   THR A 285     -46.192 -23.784 -59.061  1.00 38.76           A    N
ATOM   2371  CA  THR A 285     -45.427 -25.016 -58.911  1.00 38.87           A    C
ATOM   2372  C   THR A 285     -46.289 -26.217 -58.501  1.00 39.25           A    C
ATOM   2373  O   THR A 285     -45.756 -27.240 -58.077  1.00 39.17           A    O
ATOM   2374  CB  THR A 285     -44.244 -24.825 -57.921  1.00 38.50           A    C
ATOM   2375  OG1 THR A 285     -44.702 -24.216 -56.709  1.00 38.13           A    O
ATOM   2376  N   VAL A 286     -47.610 -26.106 -58.660  1.00 39.86           A    N
ATOM   2377  CA  VAL A 286     -48.544 -27.139 -58.172  1.00 40.36           A    C
ATOM   2378  C   VAL A 286     -48.181 -28.544 -58.600  1.00 41.02           A    C
ATOM   2379  O   VAL A 286     -48.482 -29.498 -57.885  1.00 41.06           A    O
ATOM   2380  CB  VAL A 286     -50.040 -26.938 -58.583  1.00 40.29           A    C
ATOM   2381  CG1 VAL A 286     -50.867 -26.340 -57.456  1.00 39.91           A    C
ATOM   2382  CG2 VAL A 286     -50.195 -26.232 -59.921  1.00 40.38           A    C
ATOM   2383  N   ARG A 287     -47.550 -28.676 -59.763  1.00 41.86           A    N
ATOM   2384  CA  ARG A 287     -47.225 -29.988 -60.300  1.00 42.75           A    C
ATOM   2385  C   ARG A 287     -46.008 -30.618 -59.617  1.00 42.52           A    C
ATOM   2386  O   ARG A 287     -45.866 -31.840 -59.615  1.00 42.72           A    O
ATOM   2387  CB  ARG A 287     -47.059 -29.937 -61.821  1.00 43.48           A    C
ATOM   2388  CG  ARG A 287     -45.886 -29.097 -62.300  1.00 45.25           A    C
ATOM   2389  CD  ARG A 287     -45.705 -29.197 -63.810  1.00 48.26           A    C
ATOM   2390  NE  ARG A 287     -44.458 -28.572 -64.270  1.00 49.98           A    N
ATOM   2391  CZ  ARG A 287     -43.299 -29.211 -64.444  1.00 50.48           A    C
ATOM   2392  NH1 ARG A 287     -43.191 -30.518 -64.200  1.00 50.53           A    N
ATOM   2393  NH2 ARG A 287     -42.238 -28.533 -64.869  1.00 50.74           A    N
ATOM   2394  N   TRP A 288     -45.140 -29.795 -59.033  1.00 42.16           A    N
ATOM   2395  CA  TRP A 288     -44.034 -30.321 -58.243  1.00 41.87           A    C
ATOM   2396  C   TRP A 288     -44.506 -30.773 -56.870  1.00 41.64           A    C
ATOM   2397  O   TRP A 288     -43.913 -31.655 -56.261  1.00 41.71           A    O
ATOM   2398  CB  TRP A 288     -42.892 -29.316 -58.137  1.00 41.77           A    C
ATOM   2399  CG  TRP A 288     -42.128 -29.204 -59.400  1.00 42.45           A    C
ATOM   2400  CD1 TRP A 288     -41.947 -28.090 -60.141  1.00 42.95           A    C
ATOM   2401  CD2 TRP A 288     -41.461 -30.261 -60.091  1.00 43.18           A    C
ATOM   2402  CE2 TRP A 288     -40.887 -29.705 -61.244  1.00 43.56           A    C
ATOM   2403  CE3 TRP A 288     -41.290 -31.627 -59.844  1.00 43.42           A    C
ATOM   2404  NE1 TRP A 288     -41.197 -28.374 -61.249  1.00 43.37           A    N
ATOM   2405  CZ2 TRP A 288     -40.153 -30.462 -62.155  1.00 44.07           A    C
```

FIGURE 1 (cont'd)

```
ATOM   2406  CZ3 TRP A 288     -40.560 -32.384 -60.751  1.00 43.92      A    C
ATOM   2407  CH2 TRP A 288     -40.000 -31.797 -61.890  1.00 44.27      A    C
ATOM   2408  N   PHE A 289     -45.586 -30.173 -56.392  1.00 41.47      A    N
ATOM   2409  CA  PHE A 289     -46.233 -30.641 -55.180  1.00 41.29      A    C
ATOM   2410  C   PHE A 289     -46.848 -32.011 -55.439  1.00 41.40      A    C
ATOM   2411  O   PHE A 289     -46.740 -32.922 -54.626  1.00 41.26      A    O
ATOM   2412  CB  PHE A 289     -47.293 -29.640 -54.717  1.00 41.20      A    C
ATOM   2413  CG  PHE A 289     -47.789 -29.890 -53.326  1.00 41.07      A    C
ATOM   2414  CD1 PHE A 289     -47.034 -29.513 -52.224  1.00 40.67      A    C
ATOM   2415  CD2 PHE A 289     -49.007 -30.505 -53.119  1.00 41.40      A    C
ATOM   2416  CE1 PHE A 289     -47.486 -29.748 -50.949  1.00 40.53      A    C
ATOM   2417  CE2 PHE A 289     -49.461 -30.739 -51.845  1.00 41.51      A    C
ATOM   2418  CZ  PHE A 289     -48.696 -30.363 -50.760  1.00 41.07      A    C
ATOM   2419  N   HIS A 290     -47.466 -32.149 -56.600  1.00 41.73      A    N
ATOM   2420  CA  HIS A 290     -48.059 -33.391 -57.019  1.00 42.18      A    C
ATOM   2421  C   HIS A 290     -47.032 -34.485 -57.020  1.00 42.28      A    C
ATOM   2422  O   HIS A 290     -47.334 -35.613 -56.671  1.00 42.52      A    O
ATOM   2423  CB  HIS A 290     -48.628 -33.208 -58.404  1.00 42.46      A    C
ATOM   2424  CG  HIS A 290     -50.052 -32.769 -58.414  1.00 43.15      A    C
ATOM   2425  CD2 HIS A 290     -50.795 -32.014 -57.567  1.00 43.70      A    C
ATOM   2426  ND1 HIS A 290     -50.918 -33.202 -59.382  1.00 43.98      A    N
ATOM   2427  CE1 HIS A 290     -52.135 -32.803 -59.123  1.00 44.47      A    C
ATOM   2428  NE2 HIS A 290     -52.084 -32.013 -58.062  1.00 43.62      A    N
ATOM   2429  N   ARG A 291     -45.810 -34.146 -57.399  1.00 42.33      A    N
ATOM   2430  CA  ARG A 291     -44.726 -35.103 -57.380  1.00 42.58      A    C
ATOM   2431  C   ARG A 291     -44.499 -35.647 -55.983  1.00 42.21      A    C
ATOM   2432  O   ARG A 291     -44.343 -36.851 -55.788  1.00 42.49      A    O
ATOM   2433  CB  ARG A 291     -43.435 -34.518 -57.933  1.00 42.82      A    C
ATOM   2434  CG  ARG A 291     -43.417 -34.489 -59.429  1.00 44.47      A    C
ATOM   2435  CD  ARG A 291     -43.526 -35.893 -59.983  1.00 46.61      A    C
ATOM   2436  NE  ARG A 291     -42.210 -36.472 -60.182  1.00 47.67      A    N
ATOM   2437  CZ  ARG A 291     -41.604 -36.513 -61.357  1.00 48.72      A    C
ATOM   2438  NH1 ARG A 291     -42.200 -36.024 -62.439  1.00 49.26      A    N
ATOM   2439  NH2 ARG A 291     -40.405 -37.050 -61.449  1.00 49.25      A    N
ATOM   2440  N   LEU A 292     -44.505 -34.741 -55.013  1.00 41.60      A    N
ATOM   2441  CA  LEU A 292     -44.265 -35.103 -53.631  1.00 40.93      A    C
ATOM   2442  C   LEU A 292     -45.375 -36.006 -53.126  1.00 40.90      A    C
ATOM   2443  O   LEU A 292     -45.098 -37.013 -52.474  1.00 40.95      A    O
ATOM   2444  CB  LEU A 292     -44.105 -33.855 -52.768  1.00 40.55      A    C
ATOM   2445  CG  LEU A 292     -42.838 -33.045 -53.043  1.00 39.84      A    C
ATOM   2446  CD1 LEU A 292     -42.949 -31.662 -52.447  1.00 39.38      A    C
ATOM   2447  CD2 LEU A 292     -41.616 -33.766 -52.509  1.00 39.40      A    C
ATOM   2448  N   ARG A 293     -46.622 -35.672 -53.455  1.00 40.86      A    N
ATOM   2449  CA  ARG A 293     -47.743 -36.559 -53.149  1.00 40.98      A    C
ATOM   2450  C   ARG A 293     -47.497 -37.932 -53.799  1.00 41.29      A    C
ATOM   2451  O   ARG A 293     -47.600 -38.964 -53.132  1.00 41.40      A    O
ATOM   2452  CB  ARG A 293     -49.081 -35.955 -53.598  1.00 40.88      A    C
ATOM   2453  CG  ARG A 293     -50.306 -36.556 -52.908  1.00 40.64      A    C
ATOM   2454  CD  ARG A 293     -51.632 -36.128 -53.537  1.00 40.43      A    C
ATOM   2455  NE  ARG A 293     -51.824 -34.679 -53.505  1.00 39.71      A    N
ATOM   2456  CZ  ARG A 293     -51.954 -33.918 -54.590  1.00 38.73      A    C
ATOM   2457  NH1 ARG A 293     -51.943 -34.480 -55.795  1.00 38.46      A    N
ATOM   2458  NH2 ARG A 293     -52.108 -32.599 -54.474  1.00 37.96      A    N
ATOM   2459  N   SER A 294     -47.128 -37.928 -55.081  1.00 41.43      A    N
ATOM   2460  CA  SER A 294     -46.900 -39.190 -55.835  1.00 41.67      A    C
ATOM   2461  C   SER A 294     -45.758 -39.977 -55.268  1.00 42.08      A    C
ATOM   2462  O   SER A 294     -45.827 -41.198 -55.256  1.00 42.61      A    O
ATOM   2463  CB  SER A 294     -46.640 -38.839 -57.303  1.00 40.71      A    C
ATOM   2464  N   ILE A 295     -44.710 -39.317 -54.793  1.00 42.17      A    N
ATOM   2465  CA  ILE A 295     -43.565 -40.016 -54.217  1.00 42.23      A    C
ATOM   2466  C   ILE A 295     -43.940 -40.653 -52.880  1.00 42.51      A    C
ATOM   2467  O   ILE A 295     -43.567 -41.793 -52.613  1.00 42.71      A    O
ATOM   2468  CB  ILE A 295     -42.338 -39.084 -54.088  1.00 41.96      A    C
ATOM   2469  CG1 ILE A 295     -41.754 -38.785 -55.467  1.00 41.88      A    C
ATOM   2470  CG2 ILE A 295     -41.266 -39.706 -53.210  1.00 41.83      A    C
```

FIGURE 1 (cont'd)

```
ATOM   2471  CD1 ILE A 295     -41.047 -37.460 -55.550  1.00 41.61      A    C
ATOM   2472  N   GLU A 296     -44.689 -39.917 -52.058  1.00 42.67      A    N
ATOM   2473  CA  GLU A 296     -45.168 -40.423 -50.782  1.00 42.96      A    C
ATOM   2474  C   GLU A 296     -46.029 -41.644 -51.034  1.00 43.52      A    C
ATOM   2475  O   GLU A 296     -45.815 -42.696 -50.439  1.00 43.81      A    O
ATOM   2476  CB  GLU A 296     -45.969 -39.355 -50.047  1.00 42.69      A    C
ATOM   2477  CG  GLU A 296     -46.363 -39.741 -48.625  1.00 42.90      A    C
ATOM   2478  CD  GLU A 296     -47.355 -38.776 -47.982  1.00 43.11      A    C
ATOM   2479  OE1 GLU A 296     -47.540 -37.650 -48.505  1.00 42.81      A    O
ATOM   2480  OE2 GLU A 296     -47.949 -39.148 -46.943  1.00 43.37      A    O
ATOM   2481  N   LYS A 297     -46.989 -41.490 -51.939  1.00 44.10      A    N
ATOM   2482  CA  LYS A 297     -47.872 -42.564 -52.371  1.00 44.81      A    C
ATOM   2483  C   LYS A 297     -47.051 -43.801 -52.747  1.00 45.45      A    C
ATOM   2484  O   LYS A 297     -47.275 -44.871 -52.196  1.00 45.73      A    O
ATOM   2485  CB  LYS A 297     -48.699 -42.076 -53.562  1.00 44.73      A    C
ATOM   2486  CG  LYS A 297     -50.197 -42.271 -53.462  1.00 44.59      A    C
ATOM   2487  CD  LYS A 297     -50.911 -41.193 -54.269  1.00 43.73      A    C
ATOM   2488  CE  LYS A 297     -52.320 -41.596 -54.682  1.00 43.74      A    C
ATOM   2489  NZ  LYS A 297     -53.184 -40.378 -54.805  1.00 44.35      A    N
ATOM   2490  N   ARG A 298     -46.080 -43.632 -53.650  1.00 45.96      A    N
ATOM   2491  CA  ARG A 298     -45.228 -44.726 -54.149  1.00 46.48      A    C
ATOM   2492  C   ARG A 298     -44.401 -45.411 -53.056  1.00 47.02      A    C
ATOM   2493  O   ARG A 298     -44.392 -46.635 -52.956  1.00 47.61      A    O
ATOM   2494  CB  ARG A 298     -44.313 -44.222 -55.276  1.00 45.49      A    C
ATOM   2495  CG  ARG A 298     -43.461 -45.290 -55.983  1.00 45.44      A    C
ATOM   2496  CD  ARG A 298     -42.698 -44.688 -57.174  1.00 45.12      A    C
ATOM   2497  NE  ARG A 298     -41.773 -45.632 -57.798  1.00 44.97      A    N
ATOM   2498  N   LEU A 299     -43.710 -44.622 -52.240  1.00 47.23      A    N
ATOM   2499  CA  LEU A 299     -42.881 -45.163 -51.165  1.00 47.45      A    C
ATOM   2500  C   LEU A 299     -43.719 -45.911 -50.135  1.00 47.87      A    C
ATOM   2501  O   LEU A 299     -43.261 -46.886 -49.538  1.00 48.13      A    O
ATOM   2502  CB  LEU A 299     -42.070 -44.056 -50.490  1.00 47.12      A    C
ATOM   2503  CG  LEU A 299     -40.890 -43.476 -51.266  1.00 46.95      A    C
ATOM   2504  CD1 LEU A 299     -40.459 -42.190 -50.623  1.00 46.53      A    C
ATOM   2505  CD2 LEU A 299     -39.727 -44.443 -51.330  1.00 47.42      A    C
ATOM   2506  N   HIS A 300     -44.948 -45.450 -49.936  1.00 48.20      A    N
ATOM   2507  CA  HIS A 300     -45.892 -46.134 -49.067  1.00 48.75      A    C
ATOM   2508  C   HIS A 300     -46.247 -47.514 -49.617  1.00 49.23      A    C
ATOM   2509  O   HIS A 300     -46.155 -48.507 -48.897  1.00 49.55      A    O
ATOM   2510  CB  HIS A 300     -47.153 -45.290 -48.861  1.00 48.70      A    C
ATOM   2511  CG  HIS A 300     -48.272 -46.030 -48.200  1.00 49.34      A    C
ATOM   2512  CD2 HIS A 300     -49.487 -46.403 -48.661  1.00 50.12      A    C
ATOM   2513  ND1 HIS A 300     -48.201 -46.482 -46.902  1.00 49.65      A    N
ATOM   2514  CE1 HIS A 300     -49.322 -47.103 -46.590  1.00 50.28      A    C
ATOM   2515  NE2 HIS A 300     -50.120 -47.067 -47.640  1.00 50.71      A    N
ATOM   2516  N   ARG A 301     -46.638 -47.564 -50.890  1.00 49.68      A    N
ATOM   2517  CA  ARG A 301     -46.953 -48.820 -51.566  1.00 50.20      A    C
ATOM   2518  C   ARG A 301     -45.791 -49.803 -51.439  1.00 50.85      A    C
ATOM   2519  O   ARG A 301     -46.007 -50.998 -51.256  1.00 51.40      A    O
ATOM   2520  CB  ARG A 301     -47.262 -48.599 -53.053  1.00 50.07      A    C
ATOM   2521  CG  ARG A 301     -48.277 -47.511 -53.385  1.00 49.11      A    C
ATOM   2522  CD  ARG A 301     -49.727 -47.997 -53.381  1.00 48.44      A    C
ATOM   2523  NE  ARG A 301     -50.645 -46.864 -53.576  1.00 47.67      A    N
ATOM   2524  CZ  ARG A 301     -51.706 -46.557 -52.819  1.00 46.82      A    C
ATOM   2525  NH1 ARG A 301     -52.056 -47.327 -51.789  1.00 46.11      A    N
ATOM   2526  NH2 ARG A 301     -52.437 -45.477 -53.112  1.00 45.77      A    N
ATOM   2527  N   LEU A 302     -44.564 -49.291 -51.526  1.00 51.23      A    N
ATOM   2528  CA  LEU A 302     -43.360 -50.120 -51.469  1.00 51.83      A    C
ATOM   2529  C   LEU A 302     -42.926 -50.447 -50.051  1.00 52.16      A    C
ATOM   2530  O   LEU A 302     -41.812 -50.910 -49.843  1.00 52.49      A    O
ATOM   2531  CB  LEU A 302     -42.208 -49.436 -52.200  1.00 51.73      A    C
ATOM   2532  CG  LEU A 302     -42.358 -49.335 -53.708  1.00 52.21      A    C
ATOM   2533  CD1 LEU A 302     -41.587 -48.150 -54.231  1.00 51.85      A    C
ATOM   2534  CD2 LEU A 302     -41.905 -50.616 -54.368  1.00 53.47      A    C
ATOM   2535  N   ASN A 303     -43.806 -50.207 -49.085  1.00 52.26      A    N
```

FIGURE 1 (cont'd)

```
ATOM   2536  CA  ASN A 303     -43.503 -50.436 -47.681  1.00 52.16          A    C
ATOM   2537  C   ASN A 303     -42.109 -49.915 -47.312  1.00 52.66          A    C
ATOM   2538  O   ASN A 303     -41.228 -50.688 -46.942  1.00 53.17          A    O
ATOM   2539  N   LEU A 304     -41.909 -48.607 -47.440  1.00 52.83          A    N
ATOM   2540  CA  LEU A 304     -40.612 -47.985 -47.129  1.00 52.73          A    C
ATOM   2541  C   LEU A 304     -40.744 -46.749 -46.233  1.00 52.44          A    C
ATOM   2542  O   LEU A 304     -39.781 -46.005 -46.037  1.00 52.15          A    O
ATOM   2543  CB  LEU A 304     -39.844 -47.632 -48.412  1.00 52.79          A    C
ATOM   2544  CG  LEU A 304     -39.070 -48.717 -49.165  1.00 53.24          A    C
ATOM   2545  CD1 LEU A 304     -38.555 -48.182 -50.479  1.00 52.92          A    C
ATOM   2546  CD2 LEU A 304     -37.921 -49.258 -48.345  1.00 53.82          A    C
ATOM   2547  N   LEU A 305     -41.942 -46.543 -45.694  1.00 52.35          A    N
ATOM   2548  CA  LEU A 305     -42.211 -45.433 -44.798  1.00 52.16          A    C
ATOM   2549  C   LEU A 305     -42.679 -45.973 -43.454  1.00 52.57          A    C
ATOM   2550  O   LEU A 305     -43.682 -46.672 -43.387  1.00 53.03          A    O
ATOM   2551  CB  LEU A 305     -43.273 -44.509 -45.403  1.00 51.73          A    C
ATOM   2552  CG  LEU A 305     -43.055 -43.923 -46.804  1.00 51.05          A    C
ATOM   2553  CD1 LEU A 305     -44.288 -43.208 -47.280  1.00 50.39          A    C
ATOM   2554  CD2 LEU A 305     -41.871 -42.987 -46.837  1.00 50.63          A    C
ATOM   2555  N   GLN A 306     -41.940 -45.661 -42.392  1.00 52.72          A    N
ATOM   2556  CA  GLN A 306     -42.310 -46.042 -41.027  1.00 53.01          A    C
ATOM   2557  C   GLN A 306     -43.574 -45.337 -40.553  1.00 52.92          A    C
ATOM   2558  O   GLN A 306     -43.871 -44.239 -41.001  1.00 52.62          A    O
ATOM   2559  CB  GLN A 306     -41.184 -45.676 -40.070  1.00 53.15          A    C
ATOM   2560  CG  GLN A 306     -40.174 -46.768 -39.815  1.00 54.04          A    C
ATOM   2561  CD  GLN A 306     -39.260 -46.434 -38.649  1.00 54.72          A    C
ATOM   2562  OE1 GLN A 306     -38.665 -45.355 -38.607  1.00 54.91          A    O
ATOM   2563  N   SER A 307     -44.308 -45.966 -39.640  1.00 53.25          A    N
ATOM   2564  CA  SER A 307     -45.493 -45.362 -39.034  1.00 53.47          A    C
ATOM   2565  C   SER A 307     -46.338 -44.576 -40.027  1.00 53.33          A    C
ATOM   2566  O   SER A 307     -46.689 -43.421 -39.772  1.00 53.10          A    O
ATOM   2567  CB  SER A 307     -45.085 -44.450 -37.887  1.00 53.50          A    C
ATOM   2568  OG  SER A 307     -44.113 -45.077 -37.081  1.00 54.25          A    O
ATOM   2569  N   HIS A 308     -46.667 -45.213 -41.150  1.00 53.45          A    N
ATOM   2570  CA  HIS A 308     -47.354 -44.544 -42.245  1.00 53.42          A    C
ATOM   2571  C   HIS A 308     -48.562 -45.358 -42.662  1.00 53.70          A    C
ATOM   2572  O   HIS A 308     -48.523 -46.020 -43.695  1.00 53.98          A    O
ATOM   2573  CB  HIS A 308     -46.398 -44.359 -43.429  1.00 53.26          A    C
ATOM   2574  CG  HIS A 308     -46.798 -43.272 -44.381  1.00 52.94          A    C
ATOM   2575  CD2 HIS A 308     -46.727 -41.924 -44.278  1.00 52.52          A    C
ATOM   2576  ND1 HIS A 308     -47.330 -43.530 -45.625  1.00 53.23          A    N
ATOM   2577  CE1 HIS A 308     -47.575 -42.389 -46.243  1.00 52.89          A    C
ATOM   2578  NE2 HIS A 308     -47.220 -41.400 -45.446  1.00 52.34          A    N
ATOM   2579  N   PRO A 309     -49.647 -45.310 -41.864  1.00 53.91          A    N
ATOM   2580  CA  PRO A 309     -50.829 -46.136 -42.106  1.00 54.40          A    C
ATOM   2581  C   PRO A 309     -51.863 -45.587 -43.110  1.00 54.67          A    C
ATOM   2582  O   PRO A 309     -53.068 -45.753 -42.897  1.00 54.94          A    O
ATOM   2583  CB  PRO A 309     -51.451 -46.266 -40.706  1.00 54.66          A    C
ATOM   2584  CG  PRO A 309     -50.421 -45.752 -39.764  1.00 54.41          A    C
ATOM   2585  CD  PRO A 309     -49.731 -44.691 -40.540  1.00 53.74          A    C
ATOM   2586  N   GLN A 310     -51.390 -44.931 -44.172  1.00 54.71          A    N
ATOM   2587  CA  GLN A 310     -52.169 -44.673 -45.405  1.00 54.87          A    C
ATOM   2588  C   GLN A 310     -51.343 -44.013 -46.513  1.00 54.98          A    C
ATOM   2589  O   GLN A 310     -50.139 -43.808 -46.366  1.00 54.83          A    O
ATOM   2590  CB  GLN A 310     -53.512 -43.955 -45.164  1.00 54.91          A    C
ATOM   2591  CG  GLN A 310     -53.512 -42.874 -44.088  1.00 54.53          A    C
ATOM   2592  CD  GLN A 310     -54.841 -42.774 -43.333  1.00 54.51          A    C
ATOM   2593  NE2 GLN A 310     -54.817 -43.070 -42.033  1.00 53.25          A    N
ATOM   2594  OE1 GLN A 310     -55.864 -42.396 -43.909  1.00 54.48          A    O
ATOM   2595  N   GLU A 311     -51.997 -43.694 -47.624  1.00 55.36          A    N
ATOM   2596  CA  GLU A 311     -51.308 -43.244 -48.824  1.00 55.70          A    C
ATOM   2597  C   GLU A 311     -51.020 -41.766 -48.714  1.00 55.00          A    C
ATOM   2598  O   GLU A 311     -49.864 -41.371 -48.676  1.00 54.83          A    O
ATOM   2599  CB  GLU A 311     -52.141 -43.544 -50.077  1.00 56.49          A    C
ATOM   2600  CG  GLU A 311     -52.684 -44.979 -50.174  1.00 58.90          A    C
```

FIGURE 1 (cont'd)

```
ATOM   2601  CD   GLU A 311     -54.011 -45.226 -49.426  1.00 61.43           A C
ATOM   2602  OE1  GLU A 311     -54.734 -46.167 -49.818  1.00 62.81           A O
ATOM   2603  OE2  GLU A 311     -54.335 -44.503 -48.449  1.00 62.01           A O
ATOM   2604  N    VAL A 312     -52.077 -40.959 -48.661  1.00 54.44           A N
ATOM   2605  CA   VAL A 312     -51.949 -39.525 -48.441  1.00 53.71           A C
ATOM   2606  C    VAL A 312     -52.010 -39.238 -46.935  1.00 53.21           A C
ATOM   2607  O    VAL A 312     -53.062 -39.358 -46.305  1.00 53.54           A O
ATOM   2608  N    MET A 313     -50.859 -38.896 -46.364  1.00 52.17           A N
ATOM   2609  CA   MET A 313     -50.757 -38.511 -44.964  1.00 51.18           A C
ATOM   2610  C    MET A 313     -50.192 -37.103 -44.894  1.00 50.19           A C
ATOM   2611  O    MET A 313     -50.802 -36.220 -44.298  1.00 50.07           A O
ATOM   2612  CB   MET A 313     -49.833 -39.464 -44.205  1.00 51.39           A C
ATOM   2613  CG   MET A 313     -50.295 -40.913 -44.117  1.00 51.99           A C
ATOM   2614  SD   MET A 313     -50.717 -41.456 -42.447  1.00 52.37           A S
ATOM   2615  CE   MET A 313     -49.153 -41.269 -41.585  1.00 52.14           A C
ATOM   2616  N    TYR A 314     -49.034 -36.913 -45.529  1.00 49.09           A N
ATOM   2617  CA   TYR A 314     -48.257 -35.681 -45.437  1.00 47.99           A C
ATOM   2618  C    TYR A 314     -48.646 -34.636 -46.473  1.00 47.47           A C
ATOM   2619  O    TYR A 314     -49.018 -33.516 -46.123  1.00 47.26           A O
ATOM   2620  CB   TYR A 314     -46.758 -35.979 -45.547  1.00 47.81           A C
ATOM   2621  CG   TYR A 314     -46.209 -36.893 -44.471  1.00 47.53           A C
ATOM   2622  CD1  TYR A 314     -46.687 -36.833 -43.167  1.00 47.54           A C
ATOM   2623  CD2  TYR A 314     -45.192 -37.799 -44.749  1.00 47.36           A C
ATOM   2624  CE1  TYR A 314     -46.183 -37.665 -42.175  1.00 47.60           A C
ATOM   2625  CE2  TYR A 314     -44.685 -38.631 -43.757  1.00 47.41           A C
ATOM   2626  CZ   TYR A 314     -45.187 -38.554 -42.479  1.00 47.31           A C
ATOM   2627  OH   TYR A 314     -44.700 -39.362 -41.496  1.00 47.28           A O
ATOM   2628  N    PHE A 315     -48.544 -34.996 -47.747  1.00 47.04           A N
ATOM   2629  CA   PHE A 315     -48.823 -34.058 -48.817  1.00 46.67           A C
ATOM   2630  C    PHE A 315     -50.272 -34.158 -49.252  1.00 46.91           A C
ATOM   2631  O    PHE A 315     -50.635 -34.959 -50.095  1.00 47.00           A O
ATOM   2632  CB   PHE A 315     -47.843 -34.264 -49.965  1.00 46.38           A C
ATOM   2633  CG   PHE A 315     -46.414 -34.062 -49.567  1.00 45.24           A C
ATOM   2634  CD1  PHE A 315     -45.850 -32.796 -49.589  1.00 44.51           A C
ATOM   2635  CD2  PHE A 315     -45.640 -35.129 -49.155  1.00 44.52           A C
ATOM   2636  CE1  PHE A 315     -44.538 -32.603 -49.217  1.00 43.98           A C
ATOM   2637  CE2  PHE A 315     -44.331 -34.945 -48.782  1.00 43.99           A C
ATOM   2638  CZ   PHE A 315     -43.777 -33.680 -48.814  1.00 43.76           A C
ATOM   2639  N    GLN A 316     -51.099 -33.334 -48.634  1.00 47.17           A N
ATOM   2640  CA   GLN A 316     -52.532 -33.393 -48.827  1.00 47.72           A C
ATOM   2641  C    GLN A 316     -52.932 -32.783 -50.157  1.00 48.09           A C
ATOM   2642  O    GLN A 316     -52.239 -31.908 -50.668  1.00 47.93           A O
ATOM   2643  CB   GLN A 316     -53.252 -32.660 -47.692  1.00 47.78           A C
ATOM   2644  CG   GLN A 316     -53.220 -33.377 -46.364  1.00 48.22           A C
ATOM   2645  CD   GLN A 316     -53.946 -34.691 -46.403  1.00 48.96           A C
ATOM   2646  NE2  GLN A 316     -53.228 -35.776 -46.148  1.00 49.07           A N
ATOM   2647  OE1  GLN A 316     -55.143 -34.733 -46.651  1.00 49.80           A O
ATOM   2648  N    PRO A 317     -54.058 -33.246 -50.727  1.00 48.67           A N
ATOM   2649  CA   PRO A 317     -54.620 -32.599 -51.899  1.00 48.94           A C
ATOM   2650  C    PRO A 317     -55.350 -31.318 -51.502  1.00 48.99           A C
ATOM   2651  O    PRO A 317     -55.658 -31.109 -50.324  1.00 48.95           A O
ATOM   2652  CB   PRO A 317     -55.606 -33.637 -52.418  1.00 49.25           A C
ATOM   2653  CG   PRO A 317     -56.057 -34.337 -51.204  1.00 49.41           A C
ATOM   2654  CD   PRO A 317     -54.856 -34.412 -50.314  1.00 48.95           A C
ATOM   2655  N    GLY A 318     -55.625 -30.471 -52.483  1.00 49.04           A N
ATOM   2656  CA   GLY A 318     -56.256 -29.193 -52.223  1.00 48.99           A C
ATOM   2657  C    GLY A 318     -55.244 -28.095 -52.404  1.00 48.82           A C
ATOM   2658  O    GLY A 318     -54.065 -28.264 -52.082  1.00 48.65           A O
ATOM   2659  N    GLU A 319     -55.708 -26.970 -52.935  1.00 48.82           A N
ATOM   2660  CA   GLU A 319     -54.869 -25.791 -53.116  1.00 48.61           A C
ATOM   2661  C    GLU A 319     -55.450 -24.601 -52.339  1.00 48.74           A C
ATOM   2662  O    GLU A 319     -56.133 -23.757 -52.921  1.00 49.12           A O
ATOM   2663  CB   GLU A 319     -54.740 -25.444 -54.608  1.00 48.50           A C
ATOM   2664  CG   GLU A 319     -54.165 -26.546 -55.493  1.00 47.90           A C
ATOM   2665  CD   GLU A 319     -54.209 -26.195 -56.975  1.00 45.68           A C
```

FIGURE 1 (cont'd)

```
ATOM   2666  OE1 GLU A 319     -53.902 -25.044 -57.352  1.00 45.95          A  O
ATOM   2667  OE2 GLU A 319     -54.537 -27.082 -57.777  1.00 45.00          A  O
ATOM   2668  N   PRO A 320     -55.204 -24.537 -51.016  1.00 48.61          A  N
ATOM   2669  CA  PRO A 320     -55.699 -23.389 -50.263  1.00 48.64          A  C
ATOM   2670  C   PRO A 320     -54.903 -22.116 -50.522  1.00 48.52          A  C
ATOM   2671  O   PRO A 320     -53.777 -22.174 -51.023  1.00 48.33          A  O
ATOM   2672  CB  PRO A 320     -55.545 -23.836 -48.800  1.00 48.71          A  C
ATOM   2673  CG  PRO A 320     -55.507 -25.321 -48.856  1.00 48.68          A  C
ATOM   2674  CD  PRO A 320     -54.725 -25.593 -50.110  1.00 48.47          A  C
ATOM   2675  N   PHE A 321     -55.495 -20.988 -50.144  1.00 48.33          A  N
ATOM   2676  CA  PHE A 321     -54.998 -19.676 -50.488  1.00 47.94          A  C
ATOM   2677  C   PHE A 321     -53.559 -19.328 -50.007  1.00 48.16          A  C
ATOM   2678  O   PHE A 321     -52.686 -19.017 -50.835  1.00 48.52          A  O
ATOM   2679  N   GLY A 322     -53.295 -19.395 -48.702  1.00 48.00          A  N
ATOM   2680  CA  GLY A 322     -51.988 -18.952 -48.157  1.00 47.43          A  C
ATOM   2681  C   GLY A 322     -51.905 -17.428 -47.958  1.00 47.08          A  C
ATOM   2682  O   GLY A 322     -52.941 -16.767 -47.861  1.00 47.62          A  O
ATOM   2683  N   SER A 323     -50.707 -16.845 -47.849  1.00 46.11          A  N
ATOM   2684  CA  SER A 323     -49.445 -17.558 -47.700  1.00 45.02          A  C
ATOM   2685  C   SER A 323     -48.931 -17.337 -46.287  1.00 43.86          A  C
ATOM   2686  O   SER A 323     -49.509 -16.566 -45.521  1.00 43.98          A  O
ATOM   2687  CB  SER A 323     -48.402 -17.035 -48.692  1.00 45.22          A  C
ATOM   2688  OG  SER A 323     -48.852 -17.156 -50.024  1.00 46.06          A  O
ATOM   2689  N   VAL A 324     -47.841 -18.018 -45.955  1.00 42.28          A  N
ATOM   2690  CA  VAL A 324     -47.162 -17.836 -44.685  1.00 40.74          A  C
ATOM   2691  C   VAL A 324     -45.841 -17.167 -44.995  1.00 39.98          A  C
ATOM   2692  O   VAL A 324     -45.058 -17.693 -45.766  1.00 39.88          A  O
ATOM   2693  CB  VAL A 324     -46.923 -19.184 -43.984  1.00 40.50          A  C
ATOM   2694  CG1 VAL A 324     -48.245 -19.792 -43.548  1.00 40.40          A  C
ATOM   2695  CG2 VAL A 324     -45.991 -19.018 -42.797  1.00 40.05          A  C
ATOM   2696  N   GLU A 325     -45.600 -16.006 -44.403  1.00 39.17          A  N
ATOM   2697  CA  GLU A 325     -44.395 -15.235 -44.692  1.00 38.49          A  C
ATOM   2698  C   GLU A 325     -43.133 -15.945 -44.217  1.00 37.59          A  C
ATOM   2699  O   GLU A 325     -43.007 -16.276 -43.051  1.00 37.46          A  O
ATOM   2700  CB  GLU A 325     -44.488 -13.858 -44.053  1.00 38.87          A  C
ATOM   2701  CG  GLU A 325     -45.727 -13.077 -44.442  1.00 40.45          A  C
ATOM   2702  CD  GLU A 325     -45.706 -11.644 -43.920  1.00 42.59          A  C
ATOM   2703  OE1 GLU A 325     -44.653 -11.203 -43.382  1.00 43.00          A  O
ATOM   2704  OE2 GLU A 325     -46.750 -10.954 -44.053  1.00 43.85          A  O
ATOM   2705  N   ASP A 326     -42.200 -16.175 -45.133  1.00 36.77          A  N
ATOM   2706  CA  ASP A 326     -40.961 -16.900 -44.842  1.00 36.00          A  C
ATOM   2707  C   ASP A 326     -39.883 -16.457 -45.832  1.00 35.74          A  C
ATOM   2708  O   ASP A 326     -40.099 -15.531 -46.609  1.00 35.86          A  O
ATOM   2709  CB  ASP A 326     -41.203 -18.413 -44.932  1.00 35.73          A  C
ATOM   2710  CG  ASP A 326     -40.283 -19.232 -44.022  1.00 35.11          A  C
ATOM   2711  OD1 ASP A 326     -39.175 -18.776 -43.657  1.00 34.81          A  O
ATOM   2712  OD2 ASP A 326     -40.679 -20.363 -43.682  1.00 34.55          A  O
ATOM   2713  N   ASP A 327     -38.733 -17.124 -45.803  1.00 35.30          A  N
ATOM   2714  CA  ASP A 327     -37.561 -16.728 -46.581  1.00 34.97          A  C
ATOM   2715  C   ASP A 327     -37.767 -16.633 -48.088  1.00 34.57          A  C
ATOM   2716  O   ASP A 327     -36.926 -16.066 -48.796  1.00 34.63          A  O
ATOM   2717  CB  ASP A 327     -36.416 -17.687 -46.308  1.00 35.13          A  C
ATOM   2718  CG  ASP A 327     -35.815 -17.506 -44.937  1.00 36.03          A  C
ATOM   2719  OD1 ASP A 327     -35.221 -16.429 -44.675  1.00 36.74          A  O
ATOM   2720  OD2 ASP A 327     -35.924 -18.460 -44.131  1.00 36.69          A  O
ATOM   2721  N   HIS A 328     -38.869 -17.194 -48.575  1.00 34.07          A  N
ATOM   2722  CA  HIS A 328     -39.146 -17.199 -50.005  1.00 33.72          A  C
ATOM   2723  C   HIS A 328     -39.623 -15.840 -50.512  1.00 33.63          A  C
ATOM   2724  O   HIS A 328     -39.420 -15.503 -51.671  1.00 33.82          A  O
ATOM   2725  CB  HIS A 328     -40.170 -18.271 -50.343  1.00 33.57          A  C
ATOM   2726  CG  HIS A 328     -41.548 -17.953 -49.865  1.00 33.84          A  C
ATOM   2727  CD2 HIS A 328     -42.634 -17.483 -50.520  1.00 34.43          A  C
ATOM   2728  ND1 HIS A 328     -41.928 -18.104 -48.553  1.00 34.07          A  N
ATOM   2729  CE1 HIS A 328     -43.194 -17.754 -48.421  1.00 34.33          A  C
ATOM   2730  NE2 HIS A 328     -43.646 -17.370 -49.599  1.00 34.56          A  N
```

FIGURE 1 (cont'd)

```
ATOM   2731  N    ILE A 329     -40.243 -15.060 -49.636  1.00 33.49      A   N
ATOM   2732  CA   ILE A 329     -40.858 -13.792 -50.025  1.00 33.62      A   C
ATOM   2733  C    ILE A 329     -39.978 -12.884 -50.886  1.00 33.61      A   C
ATOM   2734  O    ILE A 329     -40.400 -12.493 -51.966  1.00 33.90      A   O
ATOM   2735  CB   ILE A 329     -41.449 -13.023 -48.806  1.00 33.70      A   C
ATOM   2736  CG1  ILE A 329     -42.629 -13.798 -48.195  1.00 33.93      A   C
ATOM   2737  CG2  ILE A 329     -41.866 -11.602 -49.190  1.00 34.16      A   C
ATOM   2738  CD1  ILE A 329     -43.837 -14.014 -49.127  1.00 34.44      A   C
ATOM   2739  N    PRO A 330     -38.756 -12.553 -50.434  1.00 33.53      A   N
ATOM   2740  CA   PRO A 330     -37.977 -11.621 -51.252  1.00 33.61      A   C
ATOM   2741  C    PRO A 330     -37.405 -12.242 -52.540  1.00 33.52      A   C
ATOM   2742  O    PRO A 330     -36.867 -11.524 -53.382  1.00 33.78      A   O
ATOM   2743  CB   PRO A 330     -36.855 -11.181 -50.311  1.00 33.69      A   C
ATOM   2744  CG   PRO A 330     -36.657 -12.330 -49.423  1.00 33.52      A   C
ATOM   2745  CD   PRO A 330     -38.009 -12.976 -49.240  1.00 33.44      A   C
ATOM   2746  N    PHE A 331     -37.520 -13.561 -52.687  1.00 33.13      A   N
ATOM   2747  CA   PHE A 331     -37.204 -14.222 -53.951  1.00 32.88      A   C
ATOM   2748  C    PHE A 331     -38.439 -14.250 -54.832  1.00 32.86      A   C
ATOM   2749  O    PHE A 331     -38.359 -14.080 -56.047  1.00 32.96      A   O
ATOM   2750  CB   PHE A 331     -36.667 -15.634 -53.717  1.00 32.66      A   C
ATOM   2751  CG   PHE A 331     -35.294 -15.654 -53.130  1.00 32.77      A   C
ATOM   2752  CD1  PHE A 331     -35.107 -15.861 -51.776  1.00 32.78      A   C
ATOM   2753  CD2  PHE A 331     -34.184 -15.434 -53.930  1.00 33.31      A   C
ATOM   2754  CE1  PHE A 331     -33.837 -15.862 -51.235  1.00 33.02      A   C
ATOM   2755  CE2  PHE A 331     -32.908 -15.429 -53.399  1.00 33.50      A   C
ATOM   2756  CZ   PHE A 331     -32.733 -15.641 -52.050  1.00 33.22      A   C
ATOM   2757  N    LEU A 332     -39.588 -14.444 -54.198  1.00 32.81      A   N
ATOM   2758  CA   LEU A 332     -40.853 -14.452 -54.897  1.00 32.95      A   C
ATOM   2759  C    LEU A 332     -41.121 -13.082 -55.502  1.00 33.41      A   C
ATOM   2760  O    LEU A 332     -41.516 -12.997 -56.658  1.00 33.66      A   O
ATOM   2761  CB   LEU A 332     -41.979 -14.887 -53.959  1.00 32.65      A   C
ATOM   2762  CG   LEU A 332     -43.392 -14.866 -54.518  1.00 32.38      A   C
ATOM   2763  CD1  LEU A 332     -43.705 -16.129 -55.247  1.00 31.98      A   C
ATOM   2764  CD2  LEU A 332     -44.357 -14.661 -53.397  1.00 32.36      A   C
ATOM   2765  N    ARG A 333     -40.876 -12.012 -54.739  1.00 33.82      A   N
ATOM   2766  CA   ARG A 333     -41.155 -10.645 -55.221  1.00 34.37      A   C
ATOM   2767  C    ARG A 333     -40.321 -10.320 -56.471  1.00 34.13      A   C
ATOM   2768  O    ARG A 333     -40.688  -9.452 -57.262  1.00 34.48      A   O
ATOM   2769  CB   ARG A 333     -41.032  -9.587 -54.095  1.00 34.71      A   C
ATOM   2770  CG   ARG A 333     -39.816  -8.667 -54.143  1.00 36.60      A   C
ATOM   2771  CD   ARG A 333     -39.979  -7.410 -53.240  1.00 39.91      A   C
ATOM   2772  NE   ARG A 333     -39.287  -7.515 -51.939  1.00 42.26      A   N
ATOM   2773  CZ   ARG A 333     -38.131  -6.911 -51.616  1.00 42.97      A   C
ATOM   2774  NH1  ARG A 333     -37.590  -7.080 -50.405  1.00 42.55      A   N
ATOM   2775  NH2  ARG A 333     -37.508  -6.130 -52.494  1.00 43.83      A   N
ATOM   2776  N    ARG A 334     -39.230 -11.061 -56.652  1.00 33.56      A   N
ATOM   2777  CA   ARG A 334     -38.381 -10.928 -57.820  1.00 33.14      A   C
ATOM   2778  C    ARG A 334     -38.739 -11.914 -58.913  1.00 32.66      A   C
ATOM   2779  O    ARG A 334     -38.097 -11.947 -59.952  1.00 32.82      A   O
ATOM   2780  CB   ARG A 334     -36.914 -11.074 -57.434  1.00 33.14      A   C
ATOM   2781  CG   ARG A 334     -36.309  -9.807 -56.888  1.00 33.59      A   C
ATOM   2782  CD   ARG A 334     -35.323 -10.117 -55.795  1.00 33.74      A   C
ATOM   2783  NE   ARG A 334     -34.484  -8.974 -55.448  1.00 34.76      A   N
ATOM   2784  CZ   ARG A 334     -34.615  -8.242 -54.346  1.00 35.53      A   C
ATOM   2785  NH1  ARG A 334     -35.560  -8.509 -53.448  1.00 35.20      A   N
ATOM   2786  NH2  ARG A 334     -33.789  -7.230 -54.142  1.00 36.57      A   N
ATOM   2787  N    GLY A 335     -39.763 -12.720 -58.684  1.00 32.06      A   N
ATOM   2788  CA   GLY A 335     -40.263 -13.618 -59.734  1.00 31.49      A   C
ATOM   2789  C    GLY A 335     -39.779 -15.068 -59.735  1.00 30.83      A   C
ATOM   2790  O    GLY A 335     -40.027 -15.810 -60.694  1.00 31.10      A   O
ATOM   2791  N    VAL A 336     -39.101 -15.479 -58.663  1.00 29.95      A   N
ATOM   2792  CA   VAL A 336     -38.622 -16.851 -58.542  1.00 29.07      A   C
ATOM   2793  C    VAL A 336     -39.802 -17.767 -58.244  1.00 28.64      A   C
ATOM   2794  O    VAL A 336     -40.586 -17.497 -57.345  1.00 28.60      A   O
ATOM   2795  CB   VAL A 336     -37.547 -16.988 -57.438  1.00 28.87      A   C
```

FIGURE 1 (cont'd)

```
ATOM   2796  CG1 VAL A 336     -37.028 -18.403 -57.368  1.00 28.79          A C
ATOM   2797  CG2 VAL A 336     -36.402 -16.053 -57.701  1.00 29.03          A C
ATOM   2798  N   PRO A 337     -39.951 -18.844 -59.019  1.00 28.42          A N
ATOM   2799  CA  PRO A 337     -40.912 -19.888 -58.688  1.00 28.17          A C
ATOM   2800  C   PRO A 337     -40.626 -20.485 -57.308  1.00 27.74          A C
ATOM   2801  O   PRO A 337     -39.483 -20.856 -57.011  1.00 27.76          A O
ATOM   2802  CB  PRO A 337     -40.664 -20.942 -59.770  1.00 28.32          A C
ATOM   2803  CG  PRO A 337     -40.090 -20.194 -60.908  1.00 28.71          A C
ATOM   2804  CD  PRO A 337     -39.274 -19.098 -60.301  1.00 28.65          A C
ATOM   2805  N   VAL A 338     -41.655 -20.577 -56.473  1.00 27.26          A N
ATOM   2806  CA  VAL A 338     -41.478 -21.065 -55.112  1.00 26.71          A C
ATOM   2807  C   VAL A 338     -42.301 -22.327 -54.852  1.00 26.56          A C
ATOM   2808  O   VAL A 338     -43.434 -22.448 -55.317  1.00 26.74          A O
ATOM   2809  CB  VAL A 338     -41.831 -19.977 -54.061  1.00 26.58          A C
ATOM   2810  CG1 VAL A 338     -41.652 -20.501 -52.649  1.00 26.36          A C
ATOM   2811  CG2 VAL A 338     -40.980 -18.733 -54.260  1.00 26.59          A C
ATOM   2812  N   LEU A 339     -41.701 -23.275 -54.133  1.00 26.22          A N
ATOM   2813  CA  LEU A 339     -42.437 -24.356 -53.499  1.00 25.92          A C
ATOM   2814  C   LEU A 339     -42.192 -24.281 -51.995  1.00 25.76          A C
ATOM   2815  O   LEU A 339     -41.093 -24.527 -51.519  1.00 25.76          A O
ATOM   2816  CB  LEU A 339     -42.042 -25.721 -54.073  1.00 25.85          A C
ATOM   2817  CG  LEU A 339     -42.846 -26.913 -53.525  1.00 25.71          A C
ATOM   2818  CD1 LEU A 339     -44.355 -26.711 -53.694  1.00 26.02          A C
ATOM   2819  CD2 LEU A 339     -42.426 -28.206 -54.164  1.00 25.48          A C
ATOM   2820  N   HIS A 340     -43.232 -23.923 -51.257  1.00 25.60          A N
ATOM   2821  CA  HIS A 340     -43.100 -23.659 -49.835  1.00 25.41          A C
ATOM   2822  C   HIS A 340     -43.464 -24.899 -49.040  1.00 25.29          A C
ATOM   2823  O   HIS A 340     -44.637 -25.204 -48.868  1.00 25.34          A O
ATOM   2824  CB  HIS A 340     -43.988 -22.477 -49.448  1.00 25.47          A C
ATOM   2825  CG  HIS A 340     -43.601 -21.817 -48.164  1.00 25.61          A C
ATOM   2826  CD2 HIS A 340     -42.479 -21.904 -47.414  1.00 25.65          A C
ATOM   2827  ND1 HIS A 340     -44.431 -20.940 -47.506  1.00 26.01          A N
ATOM   2828  CE1 HIS A 340     -43.838 -20.514 -46.406  1.00 25.95          A C
ATOM   2829  NE2 HIS A 340     -42.652 -21.084 -46.327  1.00 25.87          A N
ATOM   2830  N   LEU A 341     -42.448 -25.614 -48.567  1.00 25.13          A N
ATOM   2831  CA  LEU A 341     -42.643 -26.875 -47.867  1.00 25.08          A C
ATOM   2832  C   LEU A 341     -42.663 -26.669 -46.353  1.00 25.06          A C
ATOM   2833  O   LEU A 341     -41.779 -27.120 -45.632  1.00 25.08          A O
ATOM   2834  CB  LEU A 341     -41.549 -27.861 -48.259  1.00 25.09          A C
ATOM   2835  CG  LEU A 341     -41.928 -29.301 -48.601  1.00 25.29          A C
ATOM   2836  CD1 LEU A 341     -40.680 -30.109 -48.882  1.00 25.55          A C
ATOM   2837  CD2 LEU A 341     -42.721 -29.955 -47.500  1.00 25.07          A C
ATOM   2838  N   ILE A 342     -43.695 -25.979 -45.893  1.00 25.12          A N
ATOM   2839  CA  ILE A 342     -43.903 -25.669 -44.486  1.00 25.19          A C
ATOM   2840  C   ILE A 342     -45.223 -26.307 -44.036  1.00 25.53          A C
ATOM   2841  O   ILE A 342     -46.233 -26.219 -44.744  1.00 25.77          A O
ATOM   2842  CB  ILE A 342     -43.920 -24.127 -44.263  1.00 25.01          A C
ATOM   2843  CG1 ILE A 342     -44.093 -23.770 -42.790  1.00 24.85          A C
ATOM   2844  CG2 ILE A 342     -45.003 -23.448 -45.104  1.00 24.97          A C
ATOM   2845  CD1 ILE A 342     -43.767 -22.338 -42.492  1.00 24.62          A C
ATOM   2846  N   SER A 343     -45.233 -26.959 -42.878  1.00 25.79          A N
ATOM   2847  CA  SER A 343     -46.471 -27.573 -42.413  1.00 26.21          A C
ATOM   2848  C   SER A 343     -47.469 -26.527 -41.940  1.00 26.37          A C
ATOM   2849  O   SER A 343     -47.120 -25.595 -41.236  1.00 26.28          A O
ATOM   2850  CB  SER A 343     -46.216 -28.618 -41.333  1.00 26.32          A C
ATOM   2851  OG  SER A 343     -45.772 -28.014 -40.143  1.00 26.99          A O
ATOM   2852  N   THR A 344     -48.704 -26.676 -42.392  1.00 26.74          A N
ATOM   2853  CA  THR A 344     -49.818 -25.882 -41.916  1.00 27.07          A C
ATOM   2854  C   THR A 344     -50.874 -26.883 -41.467  1.00 27.52          A C
ATOM   2855  O   THR A 344     -51.366 -27.653 -42.289  1.00 27.64          A O
ATOM   2856  CB  THR A 344     -50.384 -24.960 -43.001  1.00 26.98          A C
ATOM   2857  OG1 THR A 344     -49.758 -25.245 -44.251  1.00 26.75          A O
ATOM   2858  N   PRO A 345     -51.222 -26.881 -40.163  1.00 27.84          A N
ATOM   2859  CA  PRO A 345     -50.827 -25.890 -39.163  1.00 27.88          A C
ATOM   2860  C   PRO A 345     -49.402 -26.058 -38.651  1.00 27.68          A C
```

FIGURE 1 (cont'd)

```
ATOM   2861  O   PRO A 345     -48.753 -27.060 -38.939  1.00 27.45      A    O
ATOM   2862  CB  PRO A 345     -51.822 -26.127 -38.023  1.00 28.15      A    C
ATOM   2863  CG  PRO A 345     -52.693 -27.289 -38.459  1.00 28.23      A    C
ATOM   2864  CD  PRO A 345     -51.969 -27.982 -39.543  1.00 27.98      A    C
ATOM   2865  N   PHE A 346     -48.922 -25.067 -37.908  1.00 27.68      A    N
ATOM   2866  CA  PHE A 346     -47.589 -25.125 -37.305  1.00 27.83      A    C
ATOM   2867  C   PHE A 346     -47.535 -26.196 -36.226  1.00 28.03      A    C
ATOM   2868  O   PHE A 346     -48.567 -26.546 -35.646  1.00 28.40      A    O
ATOM   2869  CB  PHE A 346     -47.190 -23.770 -36.691  1.00 27.88      A    C
ATOM   2870  CG  PHE A 346     -47.060 -22.648 -37.689  1.00 28.02      A    C
ATOM   2871  CD1 PHE A 346     -46.989 -22.897 -39.052  1.00 27.85      A    C
ATOM   2872  CD2 PHE A 346     -46.982 -21.342 -37.257  1.00 28.60      A    C
ATOM   2873  CE1 PHE A 346     -46.863 -21.871 -39.954  1.00 27.78      A    C
ATOM   2874  CE2 PHE A 346     -46.850 -20.313 -38.161  1.00 28.48      A    C
ATOM   2875  CZ  PHE A 346     -46.794 -20.580 -39.507  1.00 28.02      A    C
ATOM   2876  N   PRO A 347     -46.336 -26.713 -35.939  1.00 28.00      A    N
ATOM   2877  CA  PRO A 347     -46.166 -27.707 -34.886  1.00 28.40      A    C
ATOM   2878  C   PRO A 347     -46.747 -27.234 -33.556  1.00 28.99      A    C
ATOM   2879  O   PRO A 347     -46.656 -26.059 -33.241  1.00 29.16      A    O
ATOM   2880  CB  PRO A 347     -44.650 -27.819 -34.773  1.00 28.19      A    C
ATOM   2881  CG  PRO A 347     -44.145 -27.416 -36.090  1.00 27.71      A    C
ATOM   2882  CD  PRO A 347     -45.061 -26.367 -36.580  1.00 27.68      A    C
ATOM   2883  N   ALA A 348     -47.340 -28.135 -32.784  1.00 29.64      A    N
ATOM   2884  CA  ALA A 348     -47.881 -27.762 -31.488  1.00 30.31      A    C
ATOM   2885  C   ALA A 348     -46.815 -27.071 -30.640  1.00 30.60      A    C
ATOM   2886  O   ALA A 348     -47.108 -26.108 -29.928  1.00 30.75      A    O
ATOM   2887  CB  ALA A 348     -48.429 -28.977 -30.779  1.00 30.61      A    C
ATOM   2888  N   VAL A 349     -45.578 -27.552 -30.761  1.00 30.68      A    N
ATOM   2889  CA  VAL A 349     -44.437 -27.053 -30.005  1.00 30.88      A    C
ATOM   2890  C   VAL A 349     -43.816 -25.784 -30.602  1.00 30.96      A    C
ATOM   2891  O   VAL A 349     -42.667 -25.453 -30.302  1.00 31.12      A    O
ATOM   2892  CB  VAL A 349     -43.326 -28.148 -29.840  1.00 30.86      A    C
ATOM   2893  CG1 VAL A 349     -43.828 -29.317 -29.027  1.00 31.42      A    C
ATOM   2894  CG2 VAL A 349     -42.816 -28.641 -31.184  1.00 30.46      A    C
ATOM   2895  N   TRP A 350     -44.572 -25.058 -31.415  1.00 31.03      A    N
ATOM   2896  CA  TRP A 350     -44.003 -23.945 -32.169  1.00 31.10      A    C
ATOM   2897  C   TRP A 350     -43.728 -22.725 -31.310  1.00 31.46      A    C
ATOM   2898  O   TRP A 350     -44.545 -22.357 -30.469  1.00 31.72      A    O
ATOM   2899  CB  TRP A 350     -44.897 -23.579 -33.348  1.00 30.92      A    C
ATOM   2900  CG  TRP A 350     -44.315 -22.544 -34.247  1.00 30.51      A    C
ATOM   2901  CD1 TRP A 350     -43.247 -22.697 -35.084  1.00 30.22      A    C
ATOM   2902  CD2 TRP A 350     -44.763 -21.187 -34.411  1.00 30.17      A    C
ATOM   2903  CE2 TRP A 350     -43.919 -20.582 -35.362  1.00 29.92      A    C
ATOM   2904  CE3 TRP A 350     -45.791 -20.426 -33.844  1.00 30.17      A    C
ATOM   2905  NE1 TRP A 350     -42.999 -21.521 -35.752  1.00 29.99      A    N
ATOM   2906  CZ2 TRP A 350     -44.072 -19.260 -35.755  1.00 29.61      A    C
ATOM   2907  CZ3 TRP A 350     -45.935 -19.121 -34.235  1.00 29.97      A    C
ATOM   2908  CH2 TRP A 350     -45.081 -18.550 -35.181  1.00 29.62      A    C
ATOM   2909  N   HIS A 351     -42.567 -22.114 -31.542  1.00 31.78      A    N
ATOM   2910  CA  HIS A 351     -42.114 -20.918 -30.824  1.00 32.36      A    C
ATOM   2911  C   HIS A 351     -42.289 -21.036 -29.306  1.00 32.92      A    C
ATOM   2912  O   HIS A 351     -42.807 -20.132 -28.652  1.00 33.16      A    O
ATOM   2913  CB  HIS A 351     -42.793 -19.653 -31.371  1.00 32.36      A    C
ATOM   2914  CG  HIS A 351     -42.160 -19.100 -32.619  1.00 32.42      A    C
ATOM   2915  CD2 HIS A 351     -41.331 -19.666 -33.532  1.00 32.06      A    C
ATOM   2916  ND1 HIS A 351     -42.360 -17.799 -33.040  1.00 32.53      A    N
ATOM   2917  CE1 HIS A 351     -41.689 -17.593 -34.160  1.00 32.27      A    C
ATOM   2918  NE2 HIS A 351     -41.056 -18.710 -34.480  1.00 31.85      A    N
ATOM   2919  N   THR A 352     -41.846 -22.171 -28.767  1.00 33.39      A    N
ATOM   2920  CA  THR A 352     -41.882 -22.453 -27.336  1.00 33.91      A    C
ATOM   2921  C   THR A 352     -40.705 -23.355 -26.949  1.00 34.19      A    C
ATOM   2922  O   THR A 352     -40.227 -24.120 -27.788  1.00 33.99      A    O
ATOM   2923  CB  THR A 352     -43.216 -23.107 -26.926  1.00 34.02      A    C
ATOM   2924  CG2 THR A 352     -43.717 -24.021 -27.981  1.00 33.52      A    C
ATOM   2925  OG1 THR A 352     -43.015 -23.892 -25.752  1.00 34.82      A    O
```

FIGURE 1 (cont'd)

```
ATOM   2926  N    PRO A 353     -40.237 -23.273 -25.679  1.00 34.70      A   N
ATOM   2927  CA   PRO A 353     -39.143 -24.109 -25.158  1.00 34.79      A   C
ATOM   2928  C    PRO A 353     -39.320 -25.580 -25.480  1.00 34.58      A   C
ATOM   2929  O    PRO A 353     -38.346 -26.331 -25.486  1.00 34.59      A   O
ATOM   2930  CB   PRO A 353     -39.250 -23.917 -23.652  1.00 35.21      A   C
ATOM   2931  CG   PRO A 353     -39.819 -22.581 -23.500  1.00 35.51      A   C
ATOM   2932  CD   PRO A 353     -40.733 -22.344 -24.650  1.00 34.95      A   C
ATOM   2933  N    ALA A 354     -40.563 -25.966 -25.756  1.00 34.30      A   N
ATOM   2934  CA   ALA A 354     -40.926 -27.338 -26.047  1.00 34.03      A   C
ATOM   2935  C    ALA A 354     -40.325 -27.862 -27.349  1.00 33.77      A   C
ATOM   2936  O    ALA A 354     -40.102 -29.062 -27.488  1.00 33.76      A   O
ATOM   2937  CB   ALA A 354     -42.413 -27.471 -26.064  1.00 34.04      A   C
ATOM   2938  N    ASP A 355     -40.054 -26.968 -28.297  1.00 33.55      A   N
ATOM   2939  CA   ASP A 355     -39.430 -27.344 -29.579  1.00 33.33      A   C
ATOM   2940  C    ASP A 355     -37.968 -27.803 -29.414  1.00 33.49      A   C
ATOM   2941  O    ASP A 355     -37.031 -27.073 -29.759  1.00 33.36      A   O
ATOM   2942  CB   ASP A 355     -39.517 -26.187 -30.583  1.00 33.02      A   C
ATOM   2943  CG   ASP A 355     -39.189 -26.607 -32.000  1.00 32.50      A   C
ATOM   2944  OD1  ASP A 355     -38.840 -27.782 -32.211  1.00 32.66      A   O
ATOM   2945  OD2  ASP A 355     -39.284 -25.758 -32.910  1.00 31.63      A   O
ATOM   2946  N    THR A 356     -37.796 -29.015 -28.885  1.00 33.75      A   N
ATOM   2947  CA   THR A 356     -36.488 -29.613 -28.695  1.00 33.96      A   C
ATOM   2948  C    THR A 356     -36.466 -31.008 -29.312  1.00 34.41      A   C
ATOM   2949  O    THR A 356     -37.503 -31.509 -29.769  1.00 34.31      A   O
ATOM   2950  CB   THR A 356     -36.131 -29.691 -27.210  1.00 33.36      A   C
ATOM   2951  OG1  THR A 356     -37.152 -30.415 -26.515  1.00 33.33      A   O
ATOM   2952  N    GLU A 357     -35.278 -31.621 -29.327  1.00 35.03      A   N
ATOM   2953  CA   GLU A 357     -35.074 -32.963 -29.879  1.00 35.55      A   C
ATOM   2954  C    GLU A 357     -36.126 -33.960 -29.358  1.00 35.90      A   C
ATOM   2955  O    GLU A 357     -36.685 -34.743 -30.125  1.00 35.84      A   O
ATOM   2956  CB   GLU A 357     -33.647 -33.449 -29.585  1.00 35.70      A   C
ATOM   2957  CG   GLU A 357     -33.345 -34.842 -30.099  1.00 36.33      A   C
ATOM   2958  CD   GLU A 357     -31.907 -35.247 -29.913  1.00 37.39      A   C
ATOM   2959  OE1  GLU A 357     -31.124 -34.452 -29.361  1.00 38.16      A   O
ATOM   2960  OE2  GLU A 357     -31.556 -36.373 -30.321  1.00 37.76      A   O
ATOM   2961  N    VAL A 358     -36.406 -33.888 -28.059  1.00 36.40      A   N
ATOM   2962  CA   VAL A 358     -37.324 -34.792 -27.368  1.00 36.80      A   C
ATOM   2963  C    VAL A 358     -38.712 -34.892 -27.992  1.00 36.60      A   C
ATOM   2964  O    VAL A 358     -39.408 -35.887 -27.807  1.00 36.83      A   O
ATOM   2965  CB   VAL A 358     -37.482 -34.369 -25.889  1.00 37.17      A   C
ATOM   2966  CG1  VAL A 358     -37.059 -35.496 -24.953  1.00 37.99      A   C
ATOM   2967  N    ASN A 359     -39.108 -33.862 -28.730  1.00 36.21      A   N
ATOM   2968  CA   ASN A 359     -40.476 -33.765 -29.236  1.00 35.91      A   C
ATOM   2969  C    ASN A 359     -40.653 -33.959 -30.752  1.00 35.34      A   C
ATOM   2970  O    ASN A 359     -41.752 -33.792 -31.293  1.00 35.22      A   O
ATOM   2971  CB   ASN A 359     -41.109 -32.445 -28.792  1.00 36.12      A   C
ATOM   2972  CG   ASN A 359     -41.379 -32.397 -27.306  1.00 37.11      A   C
ATOM   2973  ND2  ASN A 359     -41.126 -33.502 -26.615  1.00 38.09      A   N
ATOM   2974  OD1  ASN A 359     -41.815 -31.374 -26.783  1.00 37.72      A   O
ATOM   2975  N    LEU A 360     -39.570 -34.304 -31.432  1.00 34.82      A   N
ATOM   2976  CA   LEU A 360     -39.627 -34.655 -32.841  1.00 34.30      A   C
ATOM   2977  C    LEU A 360     -40.118 -36.081 -32.980  1.00 34.34      A   C
ATOM   2978  O    LEU A 360     -40.004 -36.865 -32.055  1.00 34.84      A   O
ATOM   2979  CB   LEU A 360     -38.237 -34.537 -33.455  1.00 34.02      A   C
ATOM   2980  CG   LEU A 360     -37.467 -33.235 -33.238  1.00 33.44      A   C
ATOM   2981  CD1  LEU A 360     -36.086 -33.328 -33.835  1.00 32.90      A   C
ATOM   2982  CD2  LEU A 360     -38.229 -32.095 -33.860  1.00 33.11      A   C
ATOM   2983  N    HIS A 361     -40.673 -36.419 -34.130  1.00 34.05      A   N
ATOM   2984  CA   HIS A 361     -41.054 -37.795 -34.397  1.00 33.88      A   C
ATOM   2985  C    HIS A 361     -40.020 -38.332 -35.368  1.00 34.19      A   C
ATOM   2986  O    HIS A 361     -40.145 -38.133 -36.571  1.00 34.05      A   O
ATOM   2987  CB   HIS A 361     -42.465 -37.875 -34.996  1.00 33.53      A   C
ATOM   2988  CG   HIS A 361     -43.129 -39.208 -34.823  1.00 32.68      A   C
ATOM   2989  CD2  HIS A 361     -44.033 -39.640 -33.913  1.00 32.21      A   C
ATOM   2990  ND1  HIS A 361     -42.884 -40.281 -35.649  1.00 31.50      A   N
```

FIGURE 1 (cont'd)

```
ATOM   2991  CE1 HIS A 361     -43.605 -41.314 -35.257  1.00 31.55           A   C
ATOM   2992  NE2 HIS A 361     -44.313 -40.953 -34.207  1.00 31.79           A   N
ATOM   2993  N   PRO A 362     -38.979 -38.999 -34.856  1.00 34.64           A   N
ATOM   2994  CA  PRO A 362     -37.904 -39.492 -35.708  1.00 34.83           A   C
ATOM   2995  C   PRO A 362     -38.376 -40.237 -36.960  1.00 34.83           A   C
ATOM   2996  O   PRO A 362     -37.842 -39.973 -38.025  1.00 34.74           A   O
ATOM   2997  CB  PRO A 362     -37.113 -40.409 -34.782  1.00 35.18           A   C
ATOM   2998  CG  PRO A 362     -37.360 -39.858 -33.439  1.00 35.32           A   C
ATOM   2999  CD  PRO A 362     -38.762 -39.348 -33.445  1.00 34.99           A   C
ATOM   3000  N   PRO A 363     -39.363 -41.161 -36.849  1.00 34.97           A   N
ATOM   3001  CA  PRO A 363     -39.903 -41.750 -38.078  1.00 34.97           A   C
ATOM   3002  C   PRO A 363     -40.326 -40.702 -39.112  1.00 34.63           A   C
ATOM   3003  O   PRO A 363     -39.835 -40.722 -40.234  1.00 34.62           A   O
ATOM   3004  CB  PRO A 363     -41.114 -42.534 -37.577  1.00 35.25           A   C
ATOM   3005  CG  PRO A 363     -40.725 -42.967 -36.233  1.00 35.64           A   C
ATOM   3006  CD  PRO A 363     -39.881 -41.865 -35.658  1.00 34.91           A   C
ATOM   3007  N   THR A 364     -41.205 -39.780 -38.733  1.00 34.30           A   N
ATOM   3008  CA  THR A 364     -41.660 -38.732 -39.636  1.00 33.92           A   C
ATOM   3009  C   THR A 364     -40.478 -38.058 -40.310  1.00 33.84           A   C
ATOM   3010  O   THR A 364     -40.506 -37.832 -41.509  1.00 33.69           A   O
ATOM   3011  CB  THR A 364     -42.536 -37.703 -38.914  1.00 33.82           A   C
ATOM   3012  CG2 THR A 364     -43.068 -36.688 -39.888  1.00 33.45           A   C
ATOM   3013  OG1 THR A 364     -43.642 -38.373 -38.296  1.00 34.08           A   O
ATOM   3014  N   VAL A 365     -39.427 -37.776 -39.542  1.00 33.98           A   N
ATOM   3015  CA  VAL A 365     -38.205 -37.146 -40.066  1.00 34.08           A   C
ATOM   3016  C   VAL A 365     -37.609 -37.940 -41.226  1.00 34.27           A   C
ATOM   3017  O   VAL A 365     -37.419 -37.412 -42.320  1.00 34.10           A   O
ATOM   3018  CB  VAL A 365     -37.128 -36.943 -38.963  1.00 34.09           A   C
ATOM   3019  CG1 VAL A 365     -37.566 -35.887 -37.967  1.00 34.00           A   C
ATOM   3020  CG2 VAL A 365     -35.791 -36.571 -39.576  1.00 33.93           A   C
ATOM   3021  N   HIS A 366     -37.333 -39.213 -40.980  1.00 34.68           A   N
ATOM   3022  CA  HIS A 366     -36.713 -40.070 -41.976  1.00 35.15           A   C
ATOM   3023  C   HIS A 366     -37.587 -40.213 -43.220  1.00 35.33           A   C
ATOM   3024  O   HIS A 366     -37.100 -40.116 -44.347  1.00 35.42           A   O
ATOM   3025  CB  HIS A 366     -36.350 -41.425 -41.365  1.00 35.35           A   C
ATOM   3026  CG  HIS A 366     -35.360 -41.323 -40.255  1.00 35.43           A   C
ATOM   3027  CD2 HIS A 366     -35.421 -41.735 -38.971  1.00 33.86           A   C
ATOM   3028  ND1 HIS A 366     -34.123 -40.739 -40.415  1.00 35.49           A   N
ATOM   3029  CE1 HIS A 366     -33.471 -40.776 -39.268  1.00 35.48           A   C
ATOM   3030  NE2 HIS A 366     -34.234 -41.383 -38.378  1.00 34.14           A   N
ATOM   3031  N   ASN A 367     -38.879 -40.416 -43.001  1.00 35.39           A   N
ATOM   3032  CA  ASN A 367     -39.834 -40.463 -44.079  1.00 35.41           A   C
ATOM   3033  C   ASN A 367     -39.639 -39.276 -45.000  1.00 35.24           A   C
ATOM   3034  O   ASN A 367     -39.492 -39.445 -46.211  1.00 35.38           A   O
ATOM   3035  CB  ASN A 367     -41.249 -40.468 -43.525  1.00 35.49           A   C
ATOM   3036  CG  ASN A 367     -41.640 -41.795 -42.952  1.00 36.08           A   C
ATOM   3037  ND2 ASN A 367     -42.909 -41.928 -42.614  1.00 36.19           A   N
ATOM   3038  OD1 ASN A 367     -40.819 -42.696 -42.817  1.00 36.99           A   O
ATOM   3039  N   LEU A 368     -39.610 -38.080 -44.416  1.00 34.94           A   N
ATOM   3040  CA  LEU A 368     -39.464 -36.846 -45.188  1.00 34.73           A   C
ATOM   3041  C   LEU A 368     -38.176 -36.827 -46.012  1.00 34.90           A   C
ATOM   3042  O   LEU A 368     -38.141 -36.296 -47.133  1.00 35.00           A   O
ATOM   3043  CB  LEU A 368     -39.526 -35.621 -44.278  1.00 34.35           A   C
ATOM   3044  CG  LEU A 368     -40.883 -35.258 -43.682  1.00 33.74           A   C
ATOM   3045  CD1 LEU A 368     -40.729 -34.148 -42.652  1.00 33.46           A   C
ATOM   3046  CD2 LEU A 368     -41.880 -34.860 -44.757  1.00 32.87           A   C
ATOM   3047  N   ALA A 369     -37.126 -37.426 -45.455  1.00 34.17           A   N
ATOM   3048  CA  ALA A 369     -35.844 -37.484 -46.129  1.00 33.51           A   C
ATOM   3049  C   ALA A 369     -35.875 -38.459 -47.296  1.00 34.49           A   C
ATOM   3050  O   ALA A 369     -35.298 -38.194 -48.350  1.00 35.68           A   O
ATOM   3051  CB  ALA A 369     -34.773 -37.855 -45.159  1.00 24.53           A   C
ATOM   3052  N   ARG A 370     -36.555 -39.585 -47.102  1.00 35.14           A   N
ATOM   3053  CA  ARG A 370     -36.735 -40.549 -48.171  1.00 34.80           A   C
ATOM   3054  C   ARG A 370     -37.498 -39.883 -49.312  1.00 34.22           A   C
ATOM   3055  O   ARG A 370     -37.080 -39.973 -50.466  1.00 34.13           A   O
```

FIGURE 1 (cont'd)

```
ATOM   3056  CB  ARG A 370     -37.426 -41.818 -47.660  1.00 35.08      A  C
ATOM   3057  CG  ARG A 370     -36.584 -42.615 -46.660  1.00 35.40      A  C
ATOM   3058  CD  ARG A 370     -37.232 -43.929 -46.246  1.00 35.72      A  C
ATOM   3059  NE  ARG A 370     -36.333 -44.754 -45.441  1.00 35.84      A  N
ATOM   3060  CZ  ARG A 370     -36.381 -46.082 -45.393  1.00 36.00      A  C
ATOM   3061  NH1 ARG A 370     -37.293 -46.738 -46.096  1.00 35.97      A  N
ATOM   3062  NH2 ARG A 370     -35.519 -46.764 -44.655  1.00 35.98      A  N
ATOM   3063  N   ILE A 371     -38.579 -39.175 -48.977  1.00 33.46      A  N
ATOM   3064  CA  ILE A 371     -39.388 -38.473 -49.970  1.00 32.84      A  C
ATOM   3065  C   ILE A 371     -38.570 -37.415 -50.690  1.00 32.76      A  C
ATOM   3066  O   ILE A 371     -38.626 -37.317 -51.918  1.00 32.86      A  O
ATOM   3067  CB  ILE A 371     -40.651 -37.865 -49.361  1.00 32.50      A  C
ATOM   3068  CG1 ILE A 371     -41.599 -38.977 -48.923  1.00 32.47      A  C
ATOM   3069  CG2 ILE A 371     -41.347 -36.971 -50.359  1.00 32.00      A  C
ATOM   3070  CD1 ILE A 371     -42.746 -38.513 -48.052  1.00 32.22      A  C
ATOM   3071  N   LEU A 372     -37.792 -36.642 -49.936  1.00 32.57      A  N
ATOM   3072  CA  LEU A 372     -36.959 -35.596 -50.543  1.00 32.44      A  C
ATOM   3073  C   LEU A 372     -35.869 -36.138 -51.446  1.00 32.74      A  C
ATOM   3074  O   LEU A 372     -35.696 -35.648 -52.556  1.00 32.68      A  O
ATOM   3075  CB  LEU A 372     -36.339 -34.670 -49.499  1.00 32.08      A  C
ATOM   3076  CG  LEU A 372     -37.359 -33.738 -48.868  1.00 31.33      A  C
ATOM   3077  CD1 LEU A 372     -38.305 -32.948 -49.761  1.00 30.79      A  C
ATOM   3078  CD2 LEU A 372     -36.900 -33.051 -47.643  1.00 30.89      A  C
ATOM   3079  N   ALA A 373     -35.138 -37.140 -50.963  1.00 33.15      A  N
ATOM   3080  CA  ALA A 373     -34.039 -37.750 -51.712  1.00 33.55      A  C
ATOM   3081  C   ALA A 373     -34.502 -38.276 -53.076  1.00 33.86      A  C
ATOM   3082  O   ALA A 373     -33.813 -38.103 -54.085  1.00 33.99      A  O
ATOM   3083  CB  ALA A 373     -33.387 -38.858 -50.901  1.00 33.67      A  C
ATOM   3084  N   VAL A 374     -35.672 -38.911 -53.101  1.00 34.04      A  N
ATOM   3085  CA  VAL A 374     -36.265 -39.379 -54.346  1.00 34.26      A  C
ATOM   3086  C   VAL A 374     -36.577 -38.171 -55.210  1.00 34.18      A  C
ATOM   3087  O   VAL A 374     -36.163 -38.125 -56.358  1.00 34.49      A  O
ATOM   3088  CB  VAL A 374     -37.532 -40.226 -54.108  1.00 34.34      A  C
ATOM   3089  CG1 VAL A 374     -38.285 -40.454 -55.399  1.00 34.56      A  C
ATOM   3090  CG2 VAL A 374     -37.167 -41.555 -53.494  1.00 34.79      A  C
ATOM   3091  N   PHE A 375     -37.275 -37.184 -54.651  1.00 33.91      A  N
ATOM   3092  CA  PHE A 375     -37.619 -35.974 -55.391  1.00 33.74      A  C
ATOM   3093  C   PHE A 375     -36.391 -35.320 -56.001  1.00 34.05      A  C
ATOM   3094  O   PHE A 375     -36.364 -35.032 -57.189  1.00 34.16      A  O
ATOM   3095  CB  PHE A 375     -38.334 -34.978 -54.489  1.00 33.33      A  C
ATOM   3096  CG  PHE A 375     -38.699 -33.691 -55.174  1.00 32.62      A  C
ATOM   3097  CD1 PHE A 375     -40.000 -33.456 -55.587  1.00 32.45      A  C
ATOM   3098  CD2 PHE A 375     -37.739 -32.711 -55.403  1.00 32.10      A  C
ATOM   3099  CE1 PHE A 375     -40.339 -32.273 -56.210  1.00 32.37      A  C
ATOM   3100  CE2 PHE A 375     -38.075 -31.525 -56.028  1.00 32.23      A  C
ATOM   3101  CZ  PHE A 375     -39.377 -31.305 -56.430  1.00 32.31      A  C
ATOM   3102  N   LEU A 376     -35.376 -35.090 -55.179  1.00 34.43      A  N
ATOM   3103  CA  LEU A 376     -34.136 -34.482 -55.638  1.00 34.87      A  C
ATOM   3104  C   LEU A 376     -33.563 -35.268 -56.810  1.00 35.65      A  C
ATOM   3105  O   LEU A 376     -33.189 -34.684 -57.820  1.00 35.78      A  O
ATOM   3106  CB  LEU A 376     -33.113 -34.404 -54.499  1.00 34.54      A  C
ATOM   3107  CG  LEU A 376     -32.384 -33.070 -54.344  1.00 33.78      A  C
ATOM   3108  CD1 LEU A 376     -31.567 -33.059 -53.097  1.00 32.58      A  C
ATOM   3109  CD2 LEU A 376     -31.542 -32.710 -55.540  1.00 32.71      A  C
ATOM   3110  N   ALA A 377     -33.517 -36.590 -56.670  1.00 36.55      A  N
ATOM   3111  CA  ALA A 377     -33.026 -37.469 -57.725  1.00 37.43      A  C
ATOM   3112  C   ALA A 377     -33.877 -37.388 -58.992  1.00 37.90      A  C
ATOM   3113  O   ALA A 377     -33.340 -37.287 -60.083  1.00 38.23      A  O
ATOM   3114  CB  ALA A 377     -32.930 -38.905 -57.230  1.00 37.59      A  C
ATOM   3115  N   GLU A 378     -35.197 -37.421 -58.848  1.00 38.20      A  N
ATOM   3116  CA  GLU A 378     -36.083 -37.352 -60.004  1.00 38.62      A  C
ATOM   3117  C   GLU A 378     -35.967 -35.998 -60.704  1.00 38.57      A  C
ATOM   3118  O   GLU A 378     -35.786 -35.946 -61.910  1.00 38.89      A  O
ATOM   3119  CB  GLU A 378     -37.538 -37.694 -59.626  1.00 38.72      A  C
ATOM   3120  CG  GLU A 378     -37.831 -39.208 -59.494  1.00 39.88      A  C
```

FIGURE 1 (cont'd)

```
ATOM   3121  CD  GLU A 378     -39.318 -39.544 -59.289  1.00 41.28      A  C
ATOM   3122  OE1 GLU A 378     -40.185 -38.648 -59.420  1.00 41.76      A  O
ATOM   3123  OE2 GLU A 378     -39.628 -40.720 -58.993  1.00 41.93      A  O
ATOM   3124  N   TYR A 379     -36.029 -34.913 -59.940  1.00 38.39      A  N
ATOM   3125  CA  TYR A 379     -35.964 -33.564 -60.501  1.00 38.39      A  C
ATOM   3126  C   TYR A 379     -34.684 -33.348 -61.304  1.00 38.94      A  C
ATOM   3127  O   TYR A 379     -34.712 -32.795 -62.397  1.00 39.07      A  O
ATOM   3128  CB  TYR A 379     -36.095 -32.496 -59.396  1.00 37.82      A  C
ATOM   3129  CG  TYR A 379     -36.251 -31.065 -59.906  1.00 37.03      A  C
ATOM   3130  CD1 TYR A 379     -37.488 -30.427 -59.904  1.00 36.33      A  C
ATOM   3131  CD2 TYR A 379     -35.158 -30.351 -60.392  1.00 36.81      A  C
ATOM   3132  CE1 TYR A 379     -37.626 -29.121 -60.379  1.00 36.15      A  C
ATOM   3133  CE2 TYR A 379     -35.293 -29.052 -60.869  1.00 36.51      A  C
ATOM   3134  CZ  TYR A 379     -36.522 -28.451 -60.856  1.00 36.16      A  C
ATOM   3135  OH  TYR A 379     -36.641 -27.175 -61.320  1.00 35.88      A  O
ATOM   3136  N   LEU A 380     -33.563 -33.787 -60.754  1.00 39.63      A  N
ATOM   3137  CA  LEU A 380     -32.268 -33.590 -61.390  1.00 40.40      A  C
ATOM   3138  C   LEU A 380     -31.857 -34.736 -62.322  1.00 41.15      A  C
ATOM   3139  O   LEU A 380     -30.700 -34.811 -62.743  1.00 41.77      A  O
ATOM   3140  CB  LEU A 380     -31.195 -33.366 -60.322  1.00 40.13      A  C
ATOM   3141  CG  LEU A 380     -30.671 -31.965 -60.038  1.00 39.72      A  C
ATOM   3142  CD1 LEU A 380     -31.722 -30.895 -60.176  1.00 39.37      A  C
ATOM   3143  CD2 LEU A 380     -30.078 -31.930 -58.654  1.00 39.49      A  C
ATOM   3144  N   GLY A 381     -32.794 -35.616 -62.664  1.00 38.54      A  N
ATOM   3145  CA  GLY A 381     -32.473 -36.799 -63.463  1.00 36.22      A  C
ATOM   3146  C   GLY A 381     -31.154 -37.474 -63.097  1.00 34.86      A  C
ATOM   3147  O   GLY A 381     -30.365 -37.780 -63.971  1.00 34.67      A  O
ATOM   3148  N   LEU A 382     -30.912 -37.698 -61.806  1.00 34.03      A  N
ATOM   3149  CA  LEU A 382     -29.723 -38.405 -61.325  1.00 33.58      A  C
ATOM   3150  C   LEU A 382     -29.917 -39.908 -61.384  1.00 33.69      A  C
ATOM   3151  O   LEU A 382     -29.125 -40.651 -60.785  1.00 33.86      A  O
ATOM   3152  CB  LEU A 382     -29.425 -38.042 -59.871  1.00 33.34      A  C
ATOM   3153  CG  LEU A 382     -29.255 -36.589 -59.461  1.00 33.25      A  C
ATOM   3154  CD1 LEU A 382     -28.773 -36.527 -58.024  1.00 32.68      A  C
ATOM   3155  CD2 LEU A 382     -28.288 -35.878 -60.405  1.00 33.76      A  C
ATOM   3156  OXT LEU A 382     -30.868 -40.413 -61.992  1.00 33.68      A  O
TER    3157      LEU A 382
ATOM   3158  N   GLY B  74     -27.302  -9.879 -12.166  1.00 37.08      A  N
ATOM   3159  CA  GLY B  74     -28.418 -10.211 -11.242  1.00 37.13      A  C
ATOM   3160  C   GLY B  74     -28.199  -9.582  -9.880  1.00 37.19      A  C
ATOM   3161  O   GLY B  74     -28.915  -8.664  -9.480  1.00 37.22      A  O
ATOM   3162  N   SER B  75     -27.191 -10.073  -9.169  1.00 37.19      A  N
ATOM   3163  CA  SER B  75     -26.912  -9.634  -7.804  1.00 37.48      A  C
ATOM   3164  C   SER B  75     -25.859  -8.524  -7.765  1.00 38.87      A  C
ATOM   3165  O   SER B  75     -25.288  -8.200  -8.792  1.00 38.82      A  O
ATOM   3166  CB  SER B  75     -26.490 -10.836  -6.962  1.00 36.96      A  C
ATOM   3167  OG  SER B  75     -25.604 -11.669  -7.680  1.00 36.63      A  O
ATOM   3168  N   LEU B  76     -25.613  -7.944  -6.588  1.00 41.51      A  N
ATOM   3169  CA  LEU B  76     -24.648  -6.852  -6.415  1.00 44.72      A  C
ATOM   3170  C   LEU B  76     -23.214  -7.270  -6.678  1.00 48.69      A  C
ATOM   3171  O   LEU B  76     -22.818  -8.377  -6.315  1.00 48.63      A  O
ATOM   3172  CB  LEU B  76     -24.688  -6.322  -4.986  1.00 43.85      A  C
ATOM   3173  CG  LEU B  76     -25.864  -5.535  -4.422  1.00 43.02      A  C
ATOM   3174  CD1 LEU B  76     -25.651  -5.357  -2.937  1.00 42.46      A  C
ATOM   3175  CD2 LEU B  76     -26.015  -4.178  -5.086  1.00 42.94      A  C
ATOM   3176  N   PRO B  77     -22.419  -6.376  -7.286  1.00 54.08      A  N
ATOM   3177  CA  PRO B  77     -20.979  -6.617  -7.337  1.00 55.33      A  C
ATOM   3178  C   PRO B  77     -20.290  -6.234  -6.024  1.00 55.74      A  C
ATOM   3179  O   PRO B  77     -20.755  -5.327  -5.320  1.00 55.67      A  O
ATOM   3180  CB  PRO B  77     -20.513  -5.712  -8.471  1.00 56.04      A  C
ATOM   3181  CG  PRO B  77     -21.505  -4.606  -8.514  1.00 55.88      A  C
ATOM   3182  CD  PRO B  77     -22.802  -5.132  -7.979  1.00 54.78      A  C
ATOM   3183  N   GLU B  78     -19.188  -6.922  -5.715  1.00 55.90      A  N
ATOM   3184  CA  GLU B  78     -18.458  -6.762  -4.445  1.00 55.76      A  C
ATOM   3185  C   GLU B  78     -18.276  -5.319  -3.971  1.00 57.04      A  C
```

FIGURE 1 (cont'd)

```
ATOM   3186  O    GLU B  78     -18.461  -5.026  -2.786  1.00 57.25      A    O
ATOM   3187  CB   GLU B  78     -17.095  -7.452  -4.511  1.00 53.73      A    C
ATOM   3188  CG   GLU B  78     -17.079  -8.852  -3.929  1.00 50.93      A    C
ATOM   3189  CD   GLU B  78     -15.729  -9.231  -3.352  1.00 40.91      A    C
ATOM   3190  OE1  GLU B  78     -15.235  -8.476  -2.488  1.00 38.47      A    O
ATOM   3191  OE2  GLU B  78     -15.165 -10.282  -3.744  1.00 38.08      A    O
ATOM   3192  N    ALA B  79     -17.916  -4.431  -4.902  1.00 58.30      A    N
ATOM   3193  CA   ALA B  79     -17.655  -3.016  -4.606  1.00 58.94      A    C
ATOM   3194  C    ALA B  79     -18.858  -2.327  -3.965  1.00 58.70      A    C
ATOM   3195  O    ALA B  79     -18.720  -1.662  -2.928  1.00 58.83      A    O
ATOM   3196  CB   ALA B  79     -17.220  -2.274  -5.871  1.00 59.75      A    C
ATOM   3197  N    ARG B  80     -20.028  -2.499  -4.585  1.00 57.98      A    N
ATOM   3198  CA   ARG B  80     -21.278  -1.938  -4.072  1.00 57.00      A    C
ATOM   3199  C    ARG B  80     -21.736  -2.687  -2.820  1.00 56.73      A    C
ATOM   3200  O    ARG B  80     -22.205  -2.071  -1.858  1.00 56.77      A    O
ATOM   3201  CB   ARG B  80     -22.372  -1.943  -5.149  1.00 55.27      A    C
ATOM   3202  N    LEU B  81     -21.578  -4.009  -2.830  1.00 56.42      A    N
ATOM   3203  CA   LEU B  81     -21.969  -4.840  -1.700  1.00 55.83      A    C
ATOM   3204  C    LEU B  81     -21.252  -4.409  -0.425  1.00 55.88      A    C
ATOM   3205  O    LEU B  81     -21.897  -4.126   0.578  1.00 55.54      A    O
ATOM   3206  CB   LEU B  81     -21.711  -6.314  -2.005  1.00 55.65      A    C
ATOM   3207  CG   LEU B  81     -22.252  -7.379  -1.047  1.00 54.88      A    C
ATOM   3208  CD1  LEU B  81     -22.662  -8.624  -1.811  1.00 54.68      A    C
ATOM   3209  CD2  LEU B  81     -21.239  -7.722   0.032  1.00 54.76      A    C
ATOM   3210  N    ARG B  82     -19.927  -4.336  -0.480  1.00 56.32      A    N
ATOM   3211  CA   ARG B  82     -19.129  -3.958   0.681  1.00 56.76      A    C
ATOM   3212  C    ARG B  82     -19.416  -2.523   1.119  1.00 56.68      A    C
ATOM   3213  O    ARG B  82     -19.336  -2.198   2.301  1.00 56.66      A    O
ATOM   3214  CB   ARG B  82     -17.636  -4.166   0.406  1.00 57.34      A    C
ATOM   3215  CG   ARG B  82     -16.762  -4.190   1.666  1.00 58.28      A    C
ATOM   3216  CD   ARG B  82     -15.371  -4.781   1.418  1.00 59.66      A    C
ATOM   3217  NE   ARG B  82     -15.270  -6.208   1.756  1.00 59.77      A    N
ATOM   3218  CZ   ARG B  82     -15.445  -7.209   0.896  1.00 59.79      A    C
ATOM   3219  NH1  ARG B  82     -15.745  -6.964  -0.375  1.00 60.00      A    N
ATOM   3220  NH2  ARG B  82     -15.325  -8.462   1.309  1.00 59.54      A    N
ATOM   3221  N    ARG B  83     -19.760  -1.677   0.157  1.00 56.44      A    N
ATOM   3222  CA   ARG B  83     -20.125  -0.290   0.423  1.00 55.90      A    C
ATOM   3223  C    ARG B  83     -21.472  -0.223   1.143  1.00 55.50      A    C
ATOM   3224  O    ARG B  83     -21.646   0.613   2.036  1.00 55.67      A    O
ATOM   3225  CB   ARG B  83     -20.129   0.495  -0.900  1.00 54.93      A    C
ATOM   3226  CG   ARG B  83     -20.973   1.777  -0.971  1.00 54.46      A    C
ATOM   3227  CD   ARG B  83     -21.805   1.773  -2.241  1.00 54.49      A    C
ATOM   3228  NE   ARG B  83     -21.737   2.907  -3.114  1.00 53.68      A    N
ATOM   3229  CZ   ARG B  83     -21.017   2.853  -4.260  1.00 41.83      A    C
ATOM   3230  NH1  ARG B  83     -20.400   1.704  -4.643  1.00 38.56      A    N
ATOM   3231  NH2  ARG B  83     -20.921   3.920  -5.056  1.00 39.45      A    N
ATOM   3232  N    VAL B  84     -22.396  -1.116   0.760  1.00 54.71      A    N
ATOM   3233  CA   VAL B  84     -23.756  -1.189   1.333  1.00 53.63      A    C
ATOM   3234  C    VAL B  84     -23.748  -1.793   2.741  1.00 52.97      A    C
ATOM   3235  O    VAL B  84     -24.258  -1.186   3.686  1.00 52.77      A    O
ATOM   3236  CB   VAL B  84     -24.742  -1.955   0.398  1.00 53.49      A    C
ATOM   3237  CG1  VAL B  84     -25.133  -1.084  -0.786  1.00 53.54      A    C
ATOM   3238  CG2  VAL B  84     -25.993  -2.413   1.151  1.00 52.79      A    C
ATOM   3239  N    VAL B  85     -23.157  -2.980   2.873  1.00 52.17      A    N
ATOM   3240  CA   VAL B  85     -22.972  -3.620   4.173  1.00 51.34      A    C
ATOM   3241  C    VAL B  85     -22.282  -2.673   5.143  1.00 51.74      A    C
ATOM   3242  O    VAL B  85     -22.510  -2.732   6.343  1.00 51.91      A    O
ATOM   3243  CB   VAL B  85     -22.152  -4.915   4.058  1.00 49.78      A    C
ATOM   3244  N    GLY B  86     -21.451  -1.788   4.602  1.00 52.09      A    N
ATOM   3245  CA   GLY B  86     -20.755  -0.771   5.385  1.00 52.03      A    C
ATOM   3246  C    GLY B  86     -21.645   0.362   5.848  1.00 51.62      A    C
ATOM   3247  O    GLY B  86     -21.321   1.047   6.810  1.00 51.86      A    O
ATOM   3248  N    GLN B  87     -22.770   0.555   5.169  1.00 50.97      A    N
ATOM   3249  CA   GLN B  87     -23.694   1.644   5.491  1.00 50.19      A    C
ATOM   3250  C    GLN B  87     -24.553   1.366   6.742  1.00 49.59      A    C
```

FIGURE 1 (cont'd)

```
ATOM   3251  O    GLN B  87     -25.134   2.288   7.333  1.00 49.51      A   O
ATOM   3252  N    LEU B  88     -24.625   0.099   7.142  1.00 48.74      A   N
ATOM   3253  CA   LEU B  88     -25.319  -0.272   8.363  1.00 48.03      A   C
ATOM   3254  C    LEU B  88     -24.456   0.131   9.547  1.00 48.40      A   C
ATOM   3255  O    LEU B  88     -23.273  -0.199   9.578  1.00 48.64      A   O
ATOM   3256  CB   LEU B  88     -25.562  -1.783   8.405  1.00 47.33      A   C
ATOM   3257  CG   LEU B  88     -26.515  -2.483   7.440  1.00 45.94      A   C
ATOM   3258  CD1  LEU B  88     -26.147  -3.967   7.400  1.00 44.84      A   C
ATOM   3259  CD2  LEU B  88     -27.956  -2.309   7.874  1.00 45.74      A   C
ATOM   3260  N    ASP B  89     -25.034   0.850  10.509  1.00 48.73      A   N
ATOM   3261  CA   ASP B  89     -24.333   1.171  11.757  1.00 49.12      A   C
ATOM   3262  C    ASP B  89     -24.833   0.277  12.886  1.00 49.19      A   C
ATOM   3263  O    ASP B  89     -25.960   0.457  13.351  1.00 48.98      A   O
ATOM   3264  CB   ASP B  89     -24.489   2.652  12.132  1.00 49.28      A   C
ATOM   3265  CG   ASP B  89     -23.709   3.037  13.400  1.00 49.42      A   C
ATOM   3266  OD1  ASP B  89     -23.430   4.236  13.577  1.00 48.61      A   O
ATOM   3267  OD2  ASP B  89     -23.364   2.163  14.224  1.00 48.76      A   O
ATOM   3268  N    PRO B  90     -23.987  -0.682  13.335  1.00 49.44      A   N
ATOM   3269  CA   PRO B  90     -24.328  -1.660  14.376  1.00 49.35      A   C
ATOM   3270  C    PRO B  90     -24.751  -1.049  15.710  1.00 49.29      A   C
ATOM   3271  O    PRO B  90     -25.704  -1.538  16.327  1.00 49.02      A   O
ATOM   3272  CB   PRO B  90     -23.031  -2.463  14.548  1.00 49.46      A   C
ATOM   3273  CG   PRO B  90     -22.360  -2.361  13.242  1.00 49.76      A   C
ATOM   3274  CD   PRO B  90     -22.636  -0.939  12.801  1.00 49.81      A   C
ATOM   3275  N    GLN B  91     -24.064   0.007  16.149  1.00 49.47      A   N
ATOM   3276  CA   GLN B  91     -24.453   0.670  17.394  1.00 49.56      A   C
ATOM   3277  C    GLN B  91     -25.738   1.507  17.235  1.00 48.98      A   C
ATOM   3278  O    GLN B  91     -26.490   1.671  18.194  1.00 49.05      A   O
ATOM   3279  CB   GLN B  91     -23.285   1.450  18.035  1.00 50.16      A   C
ATOM   3280  CG   GLN B  91     -23.032   2.856  17.508  1.00 50.93      A   C
ATOM   3281  N    ARG B  92     -25.997   2.006  16.027  1.00 48.13      A   N
ATOM   3282  CA   ARG B  92     -27.247   2.712  15.726  1.00 47.09      A   C
ATOM   3283  C    ARG B  92     -28.432   1.757  15.821  1.00 46.65      A   C
ATOM   3284  O    ARG B  92     -29.429   2.071  16.469  1.00 46.55      A   O
ATOM   3285  CB   ARG B  92     -27.181   3.372  14.344  1.00 46.95      A   C
ATOM   3286  CG   ARG B  92     -28.490   3.982  13.830  1.00 45.16      A   C
ATOM   3287  CD   ARG B  92     -28.321   4.589  12.433  1.00 43.08      A   C
ATOM   3288  NE   ARG B  92     -27.817   3.591  11.486  1.00 41.71      A   N
ATOM   3289  CZ   ARG B  92     -27.696   3.750  10.173  1.00 40.22      A   C
ATOM   3290  NH1  ARG B  92     -28.035   4.897   9.609  1.00 40.68      A   N
ATOM   3291  NH2  ARG B  92     -27.224   2.757   9.421  1.00 39.08      A   N
ATOM   3292  N    LEU B  93     -28.309   0.593  15.180  1.00 46.07      A   N
ATOM   3293  CA   LEU B  93     -29.323  -0.464  15.234  1.00 45.45      A   C
ATOM   3294  C    LEU B  93     -29.714  -0.731  16.680  1.00 45.52      A   C
ATOM   3295  O    LEU B  93     -30.895  -0.687  17.030  1.00 45.42      A   O
ATOM   3296  CB   LEU B  93     -28.782  -1.755  14.606  1.00 45.07      A   C
ATOM   3297  CG   LEU B  93     -29.676  -2.793  13.913  1.00 43.90      A   C
ATOM   3298  CD1  LEU B  93     -31.022  -3.014  14.560  1.00 42.73      A   C
ATOM   3299  N    TRP B  94     -28.701  -0.971  17.512  1.00 45.69      A   N
ATOM   3300  CA   TRP B  94     -28.886  -1.402  18.889  1.00 45.72      A   C
ATOM   3301  C    TRP B  94     -29.341  -0.297  19.837  1.00 45.70      A   C
ATOM   3302  O    TRP B  94     -30.125  -0.537  20.746  1.00 45.61      A   O
ATOM   3303  CB   TRP B  94     -27.598  -2.028  19.410  1.00 45.94      A   C
ATOM   3304  CG   TRP B  94     -27.849  -3.005  20.499  1.00 46.41      A   C
ATOM   3305  CD1  TRP B  94     -28.005  -2.732  21.825  1.00 47.12      A   C
ATOM   3306  CD2  TRP B  94     -27.987  -4.418  20.361  1.00 46.43      A   C
ATOM   3307  CE2  TRP B  94     -28.225  -4.940  21.645  1.00 46.67      A   C
ATOM   3308  CE3  TRP B  94     -27.929  -5.294  19.276  1.00 46.25      A   C
ATOM   3309  NE1  TRP B  94     -28.231  -3.889  22.521  1.00 47.07      A   N
ATOM   3310  CZ2  TRP B  94     -28.406  -6.298  21.876  1.00 46.61      A   C
ATOM   3311  CZ3  TRP B  94     -28.113  -6.644  19.502  1.00 46.16      A   C
ATOM   3312  CH2  TRP B  94     -28.348  -7.133  20.794  1.00 46.34      A   C
ATOM   3313  N    SER B  95     -28.854   0.915  19.618  1.00 45.75      A   N
ATOM   3314  CA   SER B  95     -29.056   1.994  20.573  1.00 45.74      A   C
ATOM   3315  C    SER B  95     -30.166   2.976  20.182  1.00 45.17      A   C
```

FIGURE 1 (cont'd)

```
ATOM   3316  O    SER B  95     -31.004   3.321  21.003  1.00 45.15      A    O
ATOM   3317  CB   SER B  95     -27.741   2.735  20.801  1.00 46.25      A    C
ATOM   3318  OG   SER B  95     -27.499   2.917  22.182  1.00 47.21      A    O
ATOM   3319  N    THR B  96     -30.167   3.427  18.936  1.00 44.46      A    N
ATOM   3320  CA   THR B  96     -31.181   4.367  18.472  1.00 43.79      A    C
ATOM   3321  C    THR B  96     -32.516   3.699  18.189  1.00 42.87      A    C
ATOM   3322  O    THR B  96     -33.552   4.329  18.368  1.00 42.99      A    O
ATOM   3323  CB   THR B  96     -30.745   5.103  17.196  1.00 44.00      A    C
ATOM   3324  OG1  THR B  96     -29.322   5.255  17.195  1.00 44.75      A    O
ATOM   3325  N    TYR B  97     -32.491   2.437  17.750  1.00 41.60      A    N
ATOM   3326  CA   TYR B  97     -33.707   1.743  17.289  1.00 40.23      A    C
ATOM   3327  C    TYR B  97     -34.196   0.588  18.172  1.00 39.83      A    C
ATOM   3328  O    TYR B  97     -35.395   0.457  18.401  1.00 39.62      A    O
ATOM   3329  CB   TYR B  97     -33.555   1.260  15.840  1.00 39.67      A    C
ATOM   3330  CG   TYR B  97     -33.240   2.353  14.836  1.00 38.67      A    C
ATOM   3331  CD1  TYR B  97     -33.935   3.563  14.860  1.00 37.62      A    C
ATOM   3332  CD2  TYR B  97     -32.271   2.160  13.832  1.00 36.46      A    C
ATOM   3333  CE1  TYR B  97     -33.656   4.569  13.945  1.00 37.43      A    C
ATOM   3334  CE2  TYR B  97     -31.987   3.157  12.899  1.00 35.41      A    C
ATOM   3335  CZ   TYR B  97     -32.688   4.361  12.967  1.00 35.86      A    C
ATOM   3336  OH   TYR B  97     -32.443   5.377  12.074  1.00 35.52      A    O
ATOM   3337  N    LEU B  98     -33.288  -0.252  18.656  1.00 39.59      A    N
ATOM   3338  CA   LEU B  98     -33.701  -1.417  19.439  1.00 39.43      A    C
ATOM   3339  C    LEU B  98     -34.057  -1.094  20.885  1.00 39.69      A    C
ATOM   3340  O    LEU B  98     -35.151  -1.430  21.329  1.00 39.61      A    O
ATOM   3341  CB   LEU B  98     -32.660  -2.536  19.392  1.00 39.23      A    C
ATOM   3342  CG   LEU B  98     -33.018  -3.769  20.222  1.00 38.99      A    C
ATOM   3343  CD1  LEU B  98     -34.265  -4.449  19.691  1.00 38.42      A    C
ATOM   3344  CD2  LEU B  98     -31.866  -4.741  20.256  1.00 39.15      A    C
ATOM   3345  N    ARG B  99     -33.134  -0.454  21.611  1.00 40.03      A    N
ATOM   3346  CA   ARG B  99     -33.332  -0.120  23.034  1.00 40.09      A    C
ATOM   3347  C    ARG B  99     -34.571   0.724  23.335  1.00 40.22      A    C
ATOM   3348  O    ARG B  99     -35.287   0.421  24.280  1.00 40.38      A    O
ATOM   3349  CB   ARG B  99     -32.069   0.472  23.677  1.00 39.54      A    C
ATOM   3350  CG   ARG B  99     -31.366  -0.516  24.614  1.00 39.41      A    C
ATOM   3351  CD   ARG B  99     -30.194   0.099  25.377  1.00 39.91      A    C
ATOM   3352  NE   ARG B  99     -28.908  -0.412  24.912  1.00 39.60      A    N
ATOM   3353  N    PRO B 100     -34.846   1.763  22.529  1.00 40.19      A    N
ATOM   3354  CA   PRO B 100     -36.095   2.480  22.729  1.00 40.12      A    C
ATOM   3355  C    PRO B 100     -37.321   1.575  22.665  1.00 39.74      A    C
ATOM   3356  O    PRO B 100     -38.290   1.818  23.375  1.00 39.95      A    O
ATOM   3357  CB   PRO B 100     -36.120   3.463  21.560  1.00 40.25      A    C
ATOM   3358  CG   PRO B 100     -34.715   3.691  21.247  1.00 40.48      A    C
ATOM   3359  CD   PRO B 100     -34.031   2.389  21.477  1.00 40.32      A    C
ATOM   3360  N    LEU B 101     -37.264   0.540  21.830  1.00 39.10      A    N
ATOM   3361  CA   LEU B 101     -38.382  -0.382  21.624  1.00 38.50      A    C
ATOM   3362  C    LEU B 101     -38.624  -1.371  22.779  1.00 38.48      A    C
ATOM   3363  O    LEU B 101     -39.719  -1.945  22.890  1.00 38.35      A    O
ATOM   3364  CB   LEU B 101     -38.175  -1.155  20.320  1.00 38.09      A    C
ATOM   3365  CG   LEU B 101     -38.922  -0.742  19.055  1.00 37.77      A    C
ATOM   3366  CD1  LEU B 101     -39.050   0.759  18.916  1.00 38.22      A    C
ATOM   3367  CD2  LEU B 101     -38.235  -1.348  17.831  1.00 37.48      A    C
ATOM   3368  N    LEU B 102     -37.617  -1.564  23.634  1.00 38.54      A    N
ATOM   3369  CA   LEU B 102     -37.659  -2.597  24.676  1.00 38.59      A    C
ATOM   3370  C    LEU B 102     -38.396  -2.179  25.961  1.00 38.94      A    C
ATOM   3371  O    LEU B 102     -37.829  -2.205  27.054  1.00 39.22      A    O
ATOM   3372  CB   LEU B 102     -36.243  -3.089  24.990  1.00 38.52      A    C
ATOM   3373  CG   LEU B 102     -35.508  -3.860  23.891  1.00 38.07      A    C
ATOM   3374  CD1  LEU B 102     -34.059  -4.098  24.265  1.00 38.25      A    C
ATOM   3375  CD2  LEU B 102     -36.186  -5.180  23.625  1.00 37.55      A    C
ATOM   3376  N    VAL B 103     -39.664  -1.797  25.812  1.00 39.10      A    N
ATOM   3377  CA   VAL B 103     -40.539  -1.459  26.940  1.00 39.39      A    C
ATOM   3378  C    VAL B 103     -41.861  -2.222  26.853  1.00 39.10      A    C
ATOM   3379  O    VAL B 103     -42.262  -2.655  25.775  1.00 38.83      A    O
ATOM   3380  CB   VAL B 103     -40.837   0.061  27.018  1.00 39.73      A    C
```

FIGURE 1 (cont'd)

```
ATOM   3381  CG1 VAL B 103     -41.345   0.598  25.681  1.00 39.57      A  C
ATOM   3382  CG2 VAL B 103     -39.601   0.832  27.488  1.00 40.65      A  C
ATOM   3383  N   VAL B 104     -42.529  -2.385  27.992  1.00 39.03      A  N
ATOM   3384  CA  VAL B 104     -43.846  -2.997  28.023  1.00 38.72      A  C
ATOM   3385  C   VAL B 104     -44.755  -2.163  27.140  1.00 38.92      A  C
ATOM   3386  O   VAL B 104     -44.798  -0.938  27.275  1.00 39.22      A  O
ATOM   3387  CB  VAL B 104     -44.411  -3.077  29.448  1.00 38.05      A  C
ATOM   3388  CG1 VAL B 104     -45.314  -4.298  29.591  1.00 37.51      A  C
ATOM   3389  N   ARG B 105     -45.452  -2.836  26.221  1.00 38.80      A  N
ATOM   3390  CA  ARG B 105     -46.179  -2.166  25.132  1.00 38.53      A  C
ATOM   3391  C   ARG B 105     -47.413  -2.922  24.628  1.00 38.49      A  C
ATOM   3392  O   ARG B 105     -47.778  -2.819  23.457  1.00 38.21      A  O
ATOM   3393  CB  ARG B 105     -45.225  -1.844  23.969  1.00 38.35      A  C
ATOM   3394  CG  ARG B 105     -44.585  -3.061  23.321  1.00 37.70      A  C
ATOM   3395  CD  ARG B 105     -43.311  -2.711  22.565  1.00 37.36      A  C
ATOM   3396  NE  ARG B 105     -42.869  -3.839  21.743  1.00 36.99      A  N
ATOM   3397  CZ  ARG B 105     -41.927  -4.711  22.091  1.00 36.78      A  C
ATOM   3398  NH1 ARG B 105     -41.296  -4.592  23.250  1.00 36.93      A  N
ATOM   3399  NH2 ARG B 105     -41.611  -5.702  21.274  1.00 36.38      A  N
ATOM   3400  N   THR B 106     -48.053  -3.664  25.526  1.00 38.70      A  N
ATOM   3401  CA  THR B 106     -49.317  -4.334  25.237  1.00 38.91      A  C
ATOM   3402  C   THR B 106     -50.342  -3.348  24.662  1.00 38.99      A  C
ATOM   3403  O   THR B 106     -50.327  -2.174  25.025  1.00 39.02      A  O
ATOM   3404  CB  THR B 106     -49.881  -4.985  26.500  1.00 39.12      A  C
ATOM   3405  OG1 THR B 106     -50.191  -3.966  27.458  1.00 39.81      A  O
ATOM   3406  N   PRO B 107     -51.226  -3.818  23.756  1.00 39.10      A  N
ATOM   3407  CA  PRO B 107     -52.170  -2.967  23.021  1.00 39.39      A  C
ATOM   3408  C   PRO B 107     -52.872  -1.917  23.875  1.00 39.93      A  C
ATOM   3409  O   PRO B 107     -53.284  -2.205  24.996  1.00 40.10      A  O
ATOM   3410  CB  PRO B 107     -53.189  -3.970  22.490  1.00 39.29      A  C
ATOM   3411  CG  PRO B 107     -52.400  -5.200  22.264  1.00 38.89      A  C
ATOM   3412  CD  PRO B 107     -51.336  -5.226  23.328  1.00 38.99      A  C
ATOM   3413  N   GLY B 108     -52.981  -0.703  23.342  1.00 40.37      A  N
ATOM   3414  CA  GLY B 108     -53.670   0.398  24.017  1.00 41.00      A  C
ATOM   3415  C   GLY B 108     -53.114   0.863  25.358  1.00 41.37      A  C
ATOM   3416  O   GLY B 108     -53.816   1.531  26.116  1.00 41.84      A  O
ATOM   3417  N   SER B 109     -51.864   0.511  25.654  1.00 41.34      A  N
ATOM   3418  CA  SER B 109     -51.198   0.963  26.868  1.00 41.37      A  C
ATOM   3419  C   SER B 109     -50.400   2.233  26.575  1.00 41.58      A  C
ATOM   3420  O   SER B 109     -50.330   2.657  25.418  1.00 41.35      A  O
ATOM   3421  CB  SER B 109     -50.274  -0.130  27.378  1.00 41.25      A  C
ATOM   3422  OG  SER B 109     -49.219  -0.331  26.462  1.00 40.65      A  O
ATOM   3423  N   PRO B 110     -49.815   2.861  27.620  1.00 41.93      A  N
ATOM   3424  CA  PRO B 110     -48.903   3.987  27.393  1.00 41.88      A  C
ATOM   3425  C   PRO B 110     -47.648   3.595  26.598  1.00 41.31      A  C
ATOM   3426  O   PRO B 110     -47.211   4.356  25.732  1.00 41.11      A  O
ATOM   3427  CB  PRO B 110     -48.530   4.425  28.810  1.00 42.33      A  C
ATOM   3428  CG  PRO B 110     -49.676   3.998  29.644  1.00 42.76      A  C
ATOM   3429  CD  PRO B 110     -50.136   2.707  29.052  1.00 42.30      A  C
ATOM   3430  N   GLY B 111     -47.088   2.420  26.887  1.00 40.80      A  N
ATOM   3431  CA  GLY B 111     -45.951   1.897  26.133  1.00 40.14      A  C
ATOM   3432  C   GLY B 111     -46.249   1.692  24.653  1.00 39.61      A  C
ATOM   3433  O   GLY B 111     -45.468   2.104  23.793  1.00 39.42      A  O
ATOM   3434  N   ASN B 112     -47.385   1.054  24.362  1.00 39.19      A  N
ATOM   3435  CA  ASN B 112     -47.863   0.854  22.995  1.00 38.59      A  C
ATOM   3436  C   ASN B 112     -47.905   2.177  22.227  1.00 38.82      A  C
ATOM   3437  O   ASN B 112     -47.454   2.257  21.091  1.00 38.64      A  O
ATOM   3438  CB  ASN B 112     -49.242   0.189  23.016  1.00 38.27      A  C
ATOM   3439  CG  ASN B 112     -49.801  -0.060  21.626  1.00 37.18      A  C
ATOM   3440  ND2 ASN B 112     -49.588  -1.263  21.118  1.00 37.39      A  N
ATOM   3441  OD1 ASN B 112     -50.444   0.812  21.029  1.00 37.03      A  O
ATOM   3442  N   LEU B 113     -48.430   3.215  22.867  1.00 39.30      A  N
ATOM   3443  CA  LEU B 113     -48.522   4.527  22.246  1.00 39.76      A  C
ATOM   3444  C   LEU B 113     -47.151   5.198  22.176  1.00 39.79      A  C
ATOM   3445  O   LEU B 113     -46.834   5.849  21.182  1.00 39.75      A  O
```

FIGURE 1 (cont'd)

```
ATOM   3446  CB   LEU B 113     -49.549   5.406  22.980  1.00 40.18      A    C
ATOM   3447  CG   LEU B 113     -50.152   6.593  22.213  1.00 40.90      A    C
ATOM   3448  CD1  LEU B 113     -51.627   6.779  22.556  1.00 41.45      A    C
ATOM   3449  CD2  LEU B 113     -49.366   7.890  22.445  1.00 41.76      A    C
ATOM   3450  N    GLN B 114     -46.342   5.031  23.219  1.00 39.86      A    N
ATOM   3451  CA   GLN B 114     -45.001   5.607  23.249  1.00 39.87      A    C
ATOM   3452  C    GLN B 114     -44.159   5.064  22.097  1.00 39.61      A    C
ATOM   3453  O    GLN B 114     -43.502   5.833  21.399  1.00 39.69      A    O
ATOM   3454  CB   GLN B 114     -44.330   5.325  24.597  1.00 40.05      A    C
ATOM   3455  CG   GLN B 114     -42.903   5.854  24.764  1.00 39.60      A    C
ATOM   3456  CD   GLN B 114     -42.081   5.016  25.743  1.00 38.60      A    C
ATOM   3457  NE2  GLN B 114     -42.551   4.914  26.991  1.00 38.10      A    N
ATOM   3458  OE1  GLN B 114     -41.043   4.453  25.373  1.00 38.03      A    O
ATOM   3459  N    VAL B 115     -44.195   3.745  21.900  1.00 39.03      A    N
ATOM   3460  CA   VAL B 115     -43.476   3.092  20.798  1.00 38.28      A    C
ATOM   3461  C    VAL B 115     -44.030   3.555  19.442  1.00 38.64      A    C
ATOM   3462  O    VAL B 115     -43.271   4.005  18.589  1.00 38.82      A    O
ATOM   3463  CB   VAL B 115     -43.498   1.536  20.904  1.00 36.86      A    C
ATOM   3464  CG1  VAL B 115     -42.582   0.902  19.869  1.00 36.44      A    C
ATOM   3465  CG2  VAL B 115     -43.047   1.096  22.258  1.00 37.17      A    C
ATOM   3466  N    ARG B 116     -45.350   3.461  19.261  1.00 38.86      A    N
ATOM   3467  CA   ARG B 116     -46.029   3.906  18.042  1.00 39.05      A    C
ATOM   3468  C    ARG B 116     -45.561   5.291  17.613  1.00 39.48      A    C
ATOM   3469  O    ARG B 116     -45.279   5.533  16.440  1.00 39.45      A    O
ATOM   3470  CB   ARG B 116     -47.538   3.913  18.269  1.00 38.94      A    C
ATOM   3471  CG   ARG B 116     -48.359   4.467  17.118  1.00 39.19      A    C
ATOM   3472  CD   ARG B 116     -49.833   4.566  17.498  1.00 40.25      A    C
ATOM   3473  NE   ARG B 116     -50.368   3.279  17.960  1.00 40.92      A    N
ATOM   3474  CZ   ARG B 116     -51.502   3.118  18.644  1.00 41.49      A    C
ATOM   3475  NH1  ARG B 116     -52.250   4.166  18.966  1.00 41.96      A    N
ATOM   3476  NH2  ARG B 116     -51.888   1.902  19.014  1.00 41.65      A    N
ATOM   3477  N    LYS B 117     -45.474   6.191  18.584  1.00 40.05      A    N
ATOM   3478  CA   LYS B 117     -45.066   7.568  18.344  1.00 40.54      A    C
ATOM   3479  C    LYS B 117     -43.616   7.640  17.878  1.00 40.18      A    C
ATOM   3480  O    LYS B 117     -43.287   8.438  17.001  1.00 40.26      A    O
ATOM   3481  CB   LYS B 117     -45.275   8.405  19.614  1.00 41.16      A    C
ATOM   3482  CG   LYS B 117     -45.370   9.923  19.392  1.00 42.53      A    C
ATOM   3483  CD   LYS B 117     -45.817  10.677  20.669  1.00 43.87      A    C
ATOM   3484  CE   LYS B 117     -47.355  10.788  20.794  1.00 44.11      A    C
ATOM   3485  NZ   LYS B 117     -48.035  11.370  19.576  1.00 45.10      A    N
ATOM   3486  N    PHE B 118     -42.762   6.798  18.465  1.00 39.57      A    N
ATOM   3487  CA   PHE B 118     -41.333   6.735  18.111  1.00 38.93      A    C
ATOM   3488  C    PHE B 118     -41.115   6.207  16.690  1.00 39.17      A    C
ATOM   3489  O    PHE B 118     -40.238   6.683  15.960  1.00 39.35      A    O
ATOM   3490  CB   PHE B 118     -40.569   5.871  19.123  1.00 37.68      A    C
ATOM   3491  CG   PHE B 118     -39.130   5.607  18.749  1.00 36.17      A    C
ATOM   3492  CD1  PHE B 118     -38.228   6.662  18.621  1.00 35.85      A    C
ATOM   3493  CD2  PHE B 118     -38.676   4.298  18.546  1.00 34.60      A    C
ATOM   3494  CE1  PHE B 118     -36.907   6.427  18.289  1.00 35.46      A    C
ATOM   3495  CE2  PHE B 118     -37.354   4.051  18.213  1.00 33.88      A    C
ATOM   3496  CZ   PHE B 118     -36.466   5.121  18.100  1.00 34.65      A    C
ATOM   3497  N    LEU B 119     -41.912   5.213  16.314  1.00 39.18      A    N
ATOM   3498  CA   LEU B 119     -41.866   4.684  14.973  1.00 39.17      A    C
ATOM   3499  C    LEU B 119     -42.261   5.782  13.987  1.00 39.70      A    C
ATOM   3500  O    LEU B 119     -41.469   6.108  13.108  1.00 39.84      A    O
ATOM   3501  CB   LEU B 119     -42.741   3.439  14.845  1.00 38.71      A    C
ATOM   3502  CG   LEU B 119     -42.078   2.180  15.396  1.00 37.92      A    C
ATOM   3503  CD1  LEU B 119     -43.093   1.075  15.565  1.00 37.42      A    C
ATOM   3504  N    GLU B 120     -43.450   6.376  14.164  1.00 40.19      A    N
ATOM   3505  CA   GLU B 120     -43.918   7.493  13.321  1.00 40.61      A    C
ATOM   3506  C    GLU B 120     -42.825   8.534  13.080  1.00 41.31      A    C
ATOM   3507  O    GLU B 120     -42.543   8.902  11.934  1.00 41.58      A    O
ATOM   3508  CB   GLU B 120     -45.130   8.190  13.946  1.00 39.85      A    C
ATOM   3509  CG   GLU B 120     -46.436   7.432  13.831  1.00 39.53      A    C
ATOM   3510  CD   GLU B 120     -47.646   8.281  14.204  1.00 40.09      A    C
```

FIGURE 1 (cont'd)

```
ATOM   3511  OE1 GLU B 120     -47.894   9.334  13.567  1.00 40.82      A  O
ATOM   3512  OE2 GLU B 120     -48.374   7.871  15.126  1.00 41.00      A  O
ATOM   3513  N   ALA B 121     -42.213   8.989  14.172  1.00 41.84      A  N
ATOM   3514  CA  ALA B 121     -41.199  10.031  14.126  1.00 42.21      A  C
ATOM   3515  C   ALA B 121     -39.953   9.597  13.367  1.00 42.13      A  C
ATOM   3516  O   ALA B 121     -39.503  10.317  12.481  1.00 42.46      A  O
ATOM   3517  CB  ALA B 121     -40.843  10.483  15.525  1.00 42.54      A  C
ATOM   3518  N   THR B 122     -39.416   8.422  13.706  1.00 41.55      A  N
ATOM   3519  CA  THR B 122     -38.212   7.893  13.054  1.00 40.85      A  C
ATOM   3520  C   THR B 122     -38.398   7.804  11.542  1.00 41.32      A  C
ATOM   3521  O   THR B 122     -37.556   8.282  10.779  1.00 41.72      A  O
ATOM   3522  CB  THR B 122     -37.800   6.513  13.626  1.00 39.41      A  C
ATOM   3523  CG2 THR B 122     -36.679   5.904  12.825  1.00 39.12      A  C
ATOM   3524  OG1 THR B 122     -37.336   6.670  14.965  1.00 38.49      A  O
ATOM   3525  N   LEU B 123     -39.513   7.205  11.126  1.00 41.43      A  N
ATOM   3526  CA  LEU B 123     -39.850   7.034   9.712  1.00 41.48      A  C
ATOM   3527  C   LEU B 123     -39.988   8.377   8.987  1.00 42.15      A  C
ATOM   3528  O   LEU B 123     -39.508   8.525   7.863  1.00 42.37      A  O
ATOM   3529  CB  LEU B 123     -41.138   6.212   9.562  1.00 41.04      A  C
ATOM   3530  CG  LEU B 123     -41.127   4.738   9.973  1.00 39.80      A  C
ATOM   3531  CD1 LEU B 123     -40.601   3.905   8.836  1.00 39.19      A  C
ATOM   3532  N   ARG B 124     -40.628   9.350   9.638  1.00 42.73      A  N
ATOM   3533  CA  ARG B 124     -40.813  10.676   9.052  1.00 43.41      A  C
ATOM   3534  C   ARG B 124     -39.503  11.424   8.862  1.00 44.07      A  C
ATOM   3535  O   ARG B 124     -39.306  12.103   7.855  1.00 44.42      A  O
ATOM   3536  CB  ARG B 124     -41.795  11.503   9.878  1.00 43.37      A  C
ATOM   3537  CG  ARG B 124     -43.230  11.175   9.550  1.00 42.82      A  C
ATOM   3538  CD  ARG B 124     -44.204  12.075  10.253  1.00 42.36      A  C
ATOM   3539  NE  ARG B 124     -45.581  11.668   9.998  1.00 41.59      A  N
ATOM   3540  CZ  ARG B 124     -46.631  12.449  10.202  1.00 40.99      A  C
ATOM   3541  NH1 ARG B 124     -46.468  13.694  10.640  1.00 41.01      A  N
ATOM   3542  NH2 ARG B 124     -47.846  11.989   9.953  1.00 41.32      A  N
ATOM   3543  N   SER B 125     -38.601  11.268   9.827  1.00 44.60      A  N
ATOM   3544  CA  SER B 125     -37.328  11.991   9.849  1.00 45.12      A  C
ATOM   3545  C   SER B 125     -36.299  11.462   8.861  1.00 45.25      A  C
ATOM   3546  O   SER B 125     -35.128  11.799   8.983  1.00 45.59      A  O
ATOM   3547  CB  SER B 125     -36.725  11.967  11.258  1.00 45.28      A  C
ATOM   3548  OG  SER B 125     -36.261  10.665  11.593  1.00 44.96      A  O
ATOM   3549  N   LEU B 126     -36.722  10.648   7.894  1.00 45.10      A  N
ATOM   3550  CA  LEU B 126     -35.793  10.118   6.891  1.00 45.12      A  C
ATOM   3551  C   LEU B 126     -35.680  11.015   5.646  1.00 45.66      A  C
ATOM   3552  O   LEU B 126     -36.634  11.703   5.290  1.00 45.88      A  O
ATOM   3553  CB  LEU B 126     -36.156   8.681   6.508  1.00 44.60      A  C
ATOM   3554  CG  LEU B 126     -36.051   7.580   7.570  1.00 43.79      A  C
ATOM   3555  CD1 LEU B 126     -36.039   6.193   6.911  1.00 42.93      A  C
ATOM   3556  CD2 LEU B 126     -34.830   7.768   8.457  1.00 43.53      A  C
ATOM   3557  N   THR B 127     -34.511  10.995   4.998  1.00 46.15      A  N
ATOM   3558  CA  THR B 127     -34.205  11.887   3.870  1.00 46.63      A  C
ATOM   3559  C   THR B 127     -35.094  11.680   2.651  1.00 46.68      A  C
ATOM   3560  O   THR B 127     -35.564  12.643   2.063  1.00 47.15      A  O
ATOM   3561  CB  THR B 127     -32.741  11.787   3.439  1.00 46.86      A  C
ATOM   3562  OG1 THR B 127     -31.925  11.587   4.599  1.00 47.11      A  O
ATOM   3563  N   ALA B 128     -35.311  10.429   2.259  1.00 46.32      A  N
ATOM   3564  CA  ALA B 128     -36.344  10.117   1.278  1.00 46.09      A  C
ATOM   3565  C   ALA B 128     -37.699  10.422   1.910  1.00 45.98      A  C
ATOM   3566  O   ALA B 128     -37.883  10.224   3.106  1.00 45.95      A  O
ATOM   3567  CB  ALA B 128     -36.260   8.673   0.879  1.00 45.78      A  C
ATOM   3568  N   GLY B 129     -38.643  10.915   1.122  1.00 45.95      A  N
ATOM   3569  CA  GLY B 129     -39.904  11.394   1.684  1.00 45.72      A  C
ATOM   3570  C   GLY B 129     -40.898  10.300   2.013  1.00 45.15      A  C
ATOM   3571  O   GLY B 129     -41.851  10.095   1.263  1.00 45.53      A  O
ATOM   3572  N   TRP B 130     -40.689   9.602   3.132  1.00 44.26      A  N
ATOM   3573  CA  TRP B 130     -41.561   8.485   3.524  1.00 43.27      A  C
ATOM   3574  C   TRP B 130     -42.970   8.961   3.865  1.00 42.97      A  C
ATOM   3575  O   TRP B 130     -43.145   9.881   4.660  1.00 43.12      A  O
```

FIGURE 1 (cont'd)

```
ATOM   3576  CB  TRP B 130     -40.976   7.700   4.704  1.00 42.91      A  C
ATOM   3577  CG  TRP B 130     -39.894   6.694   4.354  1.00 42.40      A  C
ATOM   3578  CD1 TRP B 130     -38.550   6.912   4.345  1.00 42.62      A  C
ATOM   3579  CD2 TRP B 130     -40.072   5.312   4.000  1.00 41.96      A  C
ATOM   3580  CE2 TRP B 130     -38.789   4.766   3.779  1.00 41.82      A  C
ATOM   3581  CE3 TRP B 130     -41.191   4.488   3.839  1.00 41.73      A  C
ATOM   3582  NE1 TRP B 130     -37.877   5.760   4.000  1.00 42.22      A  N
ATOM   3583  CZ2 TRP B 130     -38.594   3.438   3.406  1.00 41.35      A  C
ATOM   3584  CZ3 TRP B 130     -40.993   3.163   3.466  1.00 41.35      A  C
ATOM   3585  CH2 TRP B 130     -39.703   2.654   3.257  1.00 41.11      A  C
ATOM   3586  N   HIS B 131     -43.966   8.338   3.242  1.00 42.55      A  N
ATOM   3587  CA  HIS B 131     -45.371   8.664   3.488  1.00 42.35      A  C
ATOM   3588  C   HIS B 131     -45.832   7.800   4.650  1.00 41.90      A  C
ATOM   3589  O   HIS B 131     -46.412   6.732   4.462  1.00 41.68      A  O
ATOM   3590  CB  HIS B 131     -46.219   8.438   2.214  1.00 42.52      A  C
ATOM   3591  CG  HIS B 131     -47.646   8.912   2.307  1.00 42.86      A  C
ATOM   3592  CD2 HIS B 131     -48.475   9.054   3.374  1.00 41.60      A  C
ATOM   3593  ND1 HIS B 131     -48.410   9.228   1.199  1.00 42.13      A  N
ATOM   3594  CE1 HIS B 131     -49.630   9.571   1.578  1.00 41.10      A  C
ATOM   3595  NE2 HIS B 131     -49.697   9.474   2.894  1.00 40.77      A  N
ATOM   3596  N   VAL B 132     -45.536   8.270   5.854  1.00 41.65      A  N
ATOM   3597  CA  VAL B 132     -45.918   7.579   7.079  1.00 41.31      A  C
ATOM   3598  C   VAL B 132     -47.374   7.870   7.411  1.00 41.34      A  C
ATOM   3599  O   VAL B 132     -47.833   9.002   7.273  1.00 41.60      A  O
ATOM   3600  CB  VAL B 132     -45.033   8.010   8.255  1.00 41.29      A  C
ATOM   3601  CG1 VAL B 132     -44.791   6.846   9.196  1.00 41.01      A  C
ATOM   3602  N   GLU B 133     -48.094   6.845   7.859  1.00 41.21      A  N
ATOM   3603  CA  GLU B 133     -49.551   6.917   7.982  1.00 41.42      A  C
ATOM   3604  C   GLU B 133     -50.089   5.945   9.036  1.00 41.16      A  C
ATOM   3605  O   GLU B 133     -49.817   4.739   8.967  1.00 41.04      A  O
ATOM   3606  CB  GLU B 133     -50.186   6.612   6.625  1.00 41.62      A  C
ATOM   3607  CG  GLU B 133     -51.686   6.787   6.558  1.00 42.98      A  C
ATOM   3608  CD  GLU B 133     -52.247   6.382   5.200  1.00 44.72      A  C
ATOM   3609  OE1 GLU B 133     -51.804   6.946   4.167  1.00 45.51      A  O
ATOM   3610  OE2 GLU B 133     -53.135   5.496   5.166  1.00 45.21      A  O
ATOM   3611  N   LEU B 134     -50.855   6.469   9.999  1.00 41.08      A  N
ATOM   3612  CA  LEU B 134     -51.473   5.648  11.056  1.00 40.75      A  C
ATOM   3613  C   LEU B 134     -52.770   4.989  10.598  1.00 40.50      A  C
ATOM   3614  O   LEU B 134     -53.493   5.528   9.757  1.00 40.66      A  O
ATOM   3615  CB  LEU B 134     -51.765   6.486  12.299  1.00 40.93      A  C
ATOM   3616  CG  LEU B 134     -50.742   6.508  13.428  1.00 41.08      A  C
ATOM   3617  CD1 LEU B 134     -51.124   7.606  14.426  1.00 41.93      A  C
ATOM   3618  N   ASP B 135     -53.054   3.821  11.160  1.00 40.03      A  N
ATOM   3619  CA  ASP B 135     -54.320   3.147  10.931  1.00 39.82      A  C
ATOM   3620  C   ASP B 135     -54.987   2.876  12.283  1.00 39.76      A  C
ATOM   3621  O   ASP B 135     -54.912   1.764  12.811  1.00 39.76      A  O
ATOM   3622  CB  ASP B 135     -54.108   1.846  10.145  1.00 39.61      A  C
ATOM   3623  CG  ASP B 135     -55.394   1.043   9.969  1.00 39.82      A  C
ATOM   3624  OD1 ASP B 135     -56.453   1.649   9.704  1.00 40.61      A  O
ATOM   3625  OD2 ASP B 135     -55.342  -0.198  10.099  1.00 39.52      A  O
ATOM   3626  N   PRO B 136     -55.644   3.891  12.857  1.00 39.74      A  N
ATOM   3627  CA  PRO B 136     -56.272   3.688  14.147  1.00 39.99      A  C
ATOM   3628  C   PRO B 136     -57.588   2.956  13.977  1.00 40.60      A  C
ATOM   3629  O   PRO B 136     -58.219   3.078  12.930  1.00 40.84      A  O
ATOM   3630  CB  PRO B 136     -56.540   5.113  14.637  1.00 39.27      A  C
ATOM   3631  CG  PRO B 136     -56.085   6.030  13.528  1.00 38.95      A  C
ATOM   3632  CD  PRO B 136     -55.987   5.202  12.302  1.00 39.53      A  C
ATOM   3633  N   PHE B 137     -57.978   2.188  14.991  1.00 41.10      A  N
ATOM   3634  CA  PHE B 137     -59.288   1.528  15.031  1.00 41.59      A  C
ATOM   3635  C   PHE B 137     -59.562   0.891  16.386  1.00 42.04      A  C
ATOM   3636  O   PHE B 137     -58.632   0.543  17.113  1.00 42.00      A  O
ATOM   3637  CB  PHE B 137     -59.428   0.478  13.921  1.00 41.43      A  C
ATOM   3638  CG  PHE B 137     -58.584  -0.757  14.122  1.00 41.09      A  C
ATOM   3639  CD1 PHE B 137     -57.238  -0.768  13.770  1.00 40.77      A  C
ATOM   3640  CD2 PHE B 137     -59.145  -1.919  14.640  1.00 40.97      A  C
```

FIGURE 1 (cont'd)

```
ATOM   3641  CE1 PHE B 137     -56.465  -1.909  13.946  1.00 40.23      A  C
ATOM   3642  CE2 PHE B 137     -58.377  -3.061  14.815  1.00 40.51      A  C
ATOM   3643  CZ  PHE B 137     -57.035  -3.055  14.469  1.00 40.14      A  C
ATOM   3644  N   THR B 138     -60.842   0.752  16.718  1.00 42.76      A  N
ATOM   3645  CA  THR B 138     -61.258   0.055  17.932  1.00 43.36      A  C
ATOM   3646  C   THR B 138     -61.757  -1.325  17.568  1.00 43.45      A  C
ATOM   3647  O   THR B 138     -62.360  -1.500  16.515  1.00 43.61      A  O
ATOM   3648  CB  THR B 138     -62.364   0.807  18.674  1.00 43.76      A  C
ATOM   3649  OG1 THR B 138     -61.816   1.386  19.864  1.00 44.27      A  O
ATOM   3650  N   ALA B 139     -61.504  -2.307  18.427  1.00 43.46      A  N
ATOM   3651  CA  ALA B 139     -61.874  -3.684  18.118  1.00 43.55      A  C
ATOM   3652  C   ALA B 139     -62.323  -4.465  19.337  1.00 43.93      A  C
ATOM   3653  O   ALA B 139     -61.875  -4.207  20.454  1.00 44.00      A  O
ATOM   3654  CB  ALA B 139     -60.738  -4.399  17.418  1.00 43.17      A  C
ATOM   3655  N   SER B 140     -63.215  -5.424  19.094  1.00 44.38      A  N
ATOM   3656  CA  SER B 140     -63.827  -6.262  20.131  1.00 44.78      A  C
ATOM   3657  C   SER B 140     -62.914  -7.439  20.521  1.00 44.46      A  C
ATOM   3658  O   SER B 140     -62.648  -8.320  19.705  1.00 44.34      A  O
ATOM   3659  CB  SER B 140     -65.198  -6.753  19.639  1.00 45.18      A  C
ATOM   3660  OG  SER B 140     -65.663  -7.860  20.385  1.00 46.08      A  O
ATOM   3661  N   THR B 141     -62.422  -7.438  21.760  1.00 44.26      A  N
ATOM   3662  CA  THR B 141     -61.541  -8.504  22.243  1.00 44.01      A  C
ATOM   3663  C   THR B 141     -62.158  -9.197  23.453  1.00 44.32      A  C
ATOM   3664  O   THR B 141     -63.125  -8.689  24.017  1.00 44.81      A  O
ATOM   3665  CB  THR B 141     -60.142  -7.977  22.619  1.00 43.68      A  C
ATOM   3666  CG2 THR B 141     -59.587  -7.064  21.538  1.00 43.35      A  C
ATOM   3667  OG1 THR B 141     -60.209  -7.278  23.863  1.00 43.74      A  O
ATOM   3668  N   PRO B 142     -61.614 -10.366  23.850  1.00 44.29      A  N
ATOM   3669  CA  PRO B 142     -62.076 -11.040  25.069  1.00 44.49      A  C
ATOM   3670  C   PRO B 142     -61.867 -10.215  26.337  1.00 44.69      A  C
ATOM   3671  O   PRO B 142     -62.347 -10.598  27.408  1.00 45.14      A  O
ATOM   3672  CB  PRO B 142     -61.210 -12.300  25.118  1.00 44.37      A  C
ATOM   3673  CG  PRO B 142     -60.896 -12.580  23.694  1.00 44.11      A  C
ATOM   3674  CD  PRO B 142     -60.722 -11.235  23.059  1.00 44.00      A  C
ATOM   3675  N   LEU B 143     -61.150  -9.100  26.215  1.00 44.49      A  N
ATOM   3676  CA  LEU B 143     -60.985  -8.164  27.318  1.00 44.51      A  C
ATOM   3677  C   LEU B 143     -61.909  -6.957  27.136  1.00 44.78      A  C
ATOM   3678  O   LEU B 143     -61.786  -5.959  27.855  1.00 45.03      A  O
ATOM   3679  CB  LEU B 143     -59.519  -7.714  27.423  1.00 44.15      A  C
ATOM   3680  CG  LEU B 143     -58.491  -8.422  28.333  1.00 44.09      A  C
ATOM   3681  CD1 LEU B 143     -58.780  -8.220  29.833  1.00 45.10      A  C
ATOM   3682  CD2 LEU B 143     -58.318  -9.903  28.014  1.00 43.70      A  C
ATOM   3683  N   GLY B 144     -62.838  -7.058  26.183  1.00 44.89      A  N
ATOM   3684  CA  GLY B 144     -63.696  -5.935  25.797  1.00 44.98      A  C
ATOM   3685  C   GLY B 144     -63.038  -5.020  24.772  1.00 44.81      A  C
ATOM   3686  O   GLY B 144     -61.972  -5.336  24.263  1.00 44.46      A  O
ATOM   3687  N   PRO B 145     -63.673  -3.878  24.457  1.00 44.96      A  N
ATOM   3688  CA  PRO B 145     -63.139  -2.906  23.503  1.00 44.59      A  C
ATOM   3689  C   PRO B 145     -61.696  -2.502  23.803  1.00 43.81      A  C
ATOM   3690  O   PRO B 145     -61.392  -2.092  24.931  1.00 44.03      A  O
ATOM   3691  CB  PRO B 145     -64.065  -1.700  23.690  1.00 44.99      A  C
ATOM   3692  CG  PRO B 145     -65.366  -2.295  24.074  1.00 45.65      A  C
ATOM   3693  CD  PRO B 145     -65.018  -3.489  24.928  1.00 45.51      A  C
ATOM   3694  N   VAL B 146     -60.824  -2.629  22.796  1.00 42.52      A  N
ATOM   3695  CA  VAL B 146     -59.409  -2.221  22.885  1.00 41.03      A  C
ATOM   3696  C   VAL B 146     -59.015  -1.360  21.677  1.00 41.24      A  C
ATOM   3697  O   VAL B 146     -59.381  -1.666  20.546  1.00 41.29      A  O
ATOM   3698  CB  VAL B 146     -58.462  -3.436  23.007  1.00 39.25      A  C
ATOM   3699  CG1 VAL B 146     -57.072  -2.983  23.284  1.00 37.82      A  C
ATOM   3700  CG2 VAL B 146     -58.875  -4.335  24.144  1.00 39.13      A  C
ATOM   3701  N   ASP B 147     -58.284  -0.279  21.929  1.00 41.31      A  N
ATOM   3702  CA  ASP B 147     -57.903   0.670  20.884  1.00 41.07      A  C
ATOM   3703  C   ASP B 147     -56.550   0.320  20.278  1.00 40.64      A  C
ATOM   3704  O   ASP B 147     -55.539   0.293  20.977  1.00 40.57      A  O
ATOM   3705  CB  ASP B 147     -57.897   2.108  21.422  1.00 41.30      A  C
```

FIGURE 1 (cont'd)

```
ATOM   3706  CG   ASP B 147     -59.282   2.731  21.461  1.00 41.23      A    C
ATOM   3707  OD1  ASP B 147     -59.886   2.802  22.543  1.00 39.38      A    O
ATOM   3708  OD2  ASP B 147     -59.770   3.162  20.402  1.00 39.78      A    O
ATOM   3709  N    PHE B 148     -56.547   0.056  18.970  1.00 40.13      A    N
ATOM   3710  CA   PHE B 148     -55.345  -0.364  18.233  1.00 39.53      A    C
ATOM   3711  C    PHE B 148     -54.894   0.690  17.244  1.00 39.32      A    C
ATOM   3712  O    PHE B 148     -55.617   1.643  16.977  1.00 39.50      A    O
ATOM   3713  CB   PHE B 148     -55.604  -1.649  17.450  1.00 39.32      A    C
ATOM   3714  CG   PHE B 148     -55.985  -2.823  18.297  1.00 39.34      A    C
ATOM   3715  CD1  PHE B 148     -55.016  -3.647  18.837  1.00 39.06      A    C
ATOM   3716  CD2  PHE B 148     -57.320  -3.119  18.525  1.00 39.80      A    C
ATOM   3717  CE1  PHE B 148     -55.367  -4.731  19.601  1.00 39.21      A    C
ATOM   3718  CE2  PHE B 148     -57.680  -4.203  19.289  1.00 39.84      A    C
ATOM   3719  CZ   PHE B 148     -56.699  -5.012  19.828  1.00 39.57      A    C
ATOM   3720  N    GLY B 149     -53.703   0.492  16.685  1.00 38.95      A    N
ATOM   3721  CA   GLY B 149     -53.149   1.403  15.696  1.00 38.78      A    C
ATOM   3722  C    GLY B 149     -51.928   0.865  14.979  1.00 38.49      A    C
ATOM   3723  O    GLY B 149     -50.867   0.720  15.571  1.00 38.48      A    O
ATOM   3724  N    ASN B 150     -52.089   0.574  13.693  1.00 38.26      A    N
ATOM   3725  CA   ASN B 150     -50.989   0.155  12.832  1.00 37.93      A    C
ATOM   3726  C    ASN B 150     -50.161   1.332  12.336  1.00 38.12      A    C
ATOM   3727  O    ASN B 150     -50.663   2.454  12.216  1.00 38.36      A    O
ATOM   3728  CB   ASN B 150     -51.530  -0.612  11.626  1.00 37.67      A    C
ATOM   3729  CG   ASN B 150     -52.194  -1.916  12.009  1.00 37.27      A    C
ATOM   3730  ND2  ASN B 150     -53.433  -2.093  11.578  1.00 37.28      A    N
ATOM   3731  OD1  ASN B 150     -51.599  -2.759  12.672  1.00 36.76      A    O
ATOM   3732  N    VAL B 151     -48.893   1.069  12.042  1.00 38.13      A    N
ATOM   3733  CA   VAL B 151     -48.028   2.073  11.445  1.00 38.46      A    C
ATOM   3734  C    VAL B 151     -47.629   1.640  10.030  1.00 38.64      A    C
ATOM   3735  O    VAL B 151     -46.862   0.697   9.853  1.00 38.45      A    O
ATOM   3736  CB   VAL B 151     -46.800   2.376  12.339  1.00 38.34      A    C
ATOM   3737  CG1  VAL B 151     -47.250   3.003  13.629  1.00 38.72      A    C
ATOM   3738  CG2  VAL B 151     -45.842   3.320  11.648  1.00 38.49      A    C
ATOM   3739  N    VAL B 152     -48.166   2.339   9.033  1.00 39.17      A    N
ATOM   3740  CA   VAL B 152     -47.937   2.026   7.622  1.00 39.67      A    C
ATOM   3741  C    VAL B 152     -47.019   3.049   6.934  1.00 40.25      A    C
ATOM   3742  O    VAL B 152     -47.313   4.249   6.910  1.00 40.62      A    O
ATOM   3743  CB   VAL B 152     -49.275   1.932   6.870  1.00 39.63      A    C
ATOM   3744  CG1  VAL B 152     -49.981   0.650   7.238  1.00 39.10      A    C
ATOM   3745  CG2  VAL B 152     -49.069   2.022   5.362  1.00 40.00      A    C
ATOM   3746  N    ALA B 153     -45.914   2.562   6.369  1.00 40.66      A    N
ATOM   3747  CA   ALA B 153     -44.910   3.426   5.755  1.00 41.25      A    C
ATOM   3748  C    ALA B 153     -44.638   3.017   4.316  1.00 41.76      A    C
ATOM   3749  O    ALA B 153     -44.347   1.855   4.039  1.00 41.73      A    O
ATOM   3750  CB   ALA B 153     -43.628   3.402   6.571  1.00 41.09      A    C
ATOM   3751  N    THR B 154     -44.733   3.977   3.401  1.00 42.53      A    N
ATOM   3752  CA   THR B 154     -44.527   3.712   1.984  1.00 43.17      A    C
ATOM   3753  C    THR B 154     -43.743   4.852   1.339  1.00 43.97      A    C
ATOM   3754  O    THR B 154     -44.187   5.992   1.340  1.00 44.37      A    O
ATOM   3755  CB   THR B 154     -45.887   3.536   1.245  1.00 43.09      A    C
ATOM   3756  CG2  THR B 154     -45.703   2.815  -0.086  1.00 42.99      A    C
ATOM   3757  OG1  THR B 154     -46.806   2.800   2.069  1.00 42.58      A    O
ATOM   3758  N    LEU B 155     -42.561   4.545   0.815  1.00 44.67      A    N
ATOM   3759  CA   LEU B 155     -41.875   5.455  -0.097  1.00 45.55      A    C
ATOM   3760  C    LEU B 155     -42.664   5.475  -1.391  1.00 46.34      A    C
ATOM   3761  O    LEU B 155     -43.067   4.423  -1.891  1.00 46.57      A    O
ATOM   3762  CB   LEU B 155     -40.464   4.949  -0.410  1.00 45.37      A    C
ATOM   3763  CG   LEU B 155     -39.241   5.589   0.226  1.00 45.36      A    C
ATOM   3764  CD1  LEU B 155     -38.010   5.233  -0.587  1.00 45.17      A    C
ATOM   3765  CD2  LEU B 155     -39.424   7.089   0.274  1.00 45.85      A    C
ATOM   3766  N    ASP B 156     -42.893   6.660  -1.940  1.00 47.23      A    N
ATOM   3767  CA   ASP B 156     -43.530   6.769  -3.262  1.00 48.07      A    C
ATOM   3768  C    ASP B 156     -44.868   5.996  -3.344  1.00 47.90      A    C
ATOM   3769  O    ASP B 156     -44.925   4.939  -3.971  1.00 47.67      A    O
ATOM   3770  CB   ASP B 156     -42.544   6.277  -4.346  1.00 48.58      A    C
```

FIGURE 1 (cont'd)

```
ATOM   3771  CG  ASP B 156     -42.929   6.712  -5.759  1.00 50.20      A  C
ATOM   3772  OD1 ASP B 156     -44.036   7.259  -5.964  1.00 51.16      A  O
ATOM   3773  OD2 ASP B 156     -42.104   6.491  -6.674  1.00 51.69      A  O
ATOM   3774  N   PRO B 157     -45.946   6.522  -2.712  1.00 48.03      A  N
ATOM   3775  CA  PRO B 157     -47.258   5.851  -2.742  1.00 48.07      A  C
ATOM   3776  C   PRO B 157     -47.804   5.692  -4.150  1.00 48.37      A  C
ATOM   3777  O   PRO B 157     -48.637   4.821  -4.380  1.00 48.24      A  O
ATOM   3778  CB  PRO B 157     -48.168   6.795  -1.950  1.00 48.02      A  C
ATOM   3779  CG  PRO B 157     -47.255   7.580  -1.107  1.00 48.07      A  C
ATOM   3780  CD  PRO B 157     -45.995   7.755  -1.903  1.00 48.16      A  C
ATOM   3781  N   ARG B 158     -47.326   6.521  -5.076  1.00 48.90      A  N
ATOM   3782  CA  ARG B 158     -47.791   6.491  -6.468  1.00 49.42      A  C
ATOM   3783  C   ARG B 158     -47.222   5.336  -7.320  1.00 49.24      A  C
ATOM   3784  O   ARG B 158     -47.810   4.968  -8.339  1.00 49.55      A  O
ATOM   3785  CB  ARG B 158     -47.645   7.865  -7.174  1.00 49.93      A  C
ATOM   3786  CG  ARG B 158     -46.303   8.570  -7.031  1.00 50.25      A  C
ATOM   3787  N   ALA B 159     -46.100   4.760  -6.905  1.00 48.75      A  N
ATOM   3788  CA  ALA B 159     -45.551   3.591  -7.598  1.00 48.34      A  C
ATOM   3789  C   ALA B 159     -46.556   2.436  -7.619  1.00 48.01      A  C
ATOM   3790  O   ALA B 159     -47.257   2.186  -6.637  1.00 47.78      A  O
ATOM   3791  CB  ALA B 159     -44.250   3.152  -6.957  1.00 48.23      A  C
ATOM   3792  N   ALA B 160     -46.611   1.738  -8.748  1.00 47.87      A  N
ATOM   3793  CA  ALA B 160     -47.629   0.719  -8.999  1.00 47.60      A  C
ATOM   3794  C   ALA B 160     -47.564  -0.488  -8.067  1.00 47.09      A  C
ATOM   3795  O   ALA B 160     -48.599  -1.063  -7.735  1.00 47.01      A  O
ATOM   3796  CB  ALA B 160     -47.569   0.270 -10.448  1.00 48.02      A  C
ATOM   3797  N   ARG B 161     -46.349  -0.868  -7.667  1.00 46.53      A  N
ATOM   3798  CA  ARG B 161     -46.108  -2.011  -6.777  1.00 45.91      A  C
ATOM   3799  C   ARG B 161     -44.994  -1.721  -5.765  1.00 45.11      A  C
ATOM   3800  O   ARG B 161     -44.147  -0.869  -6.005  1.00 45.26      A  O
ATOM   3801  CB  ARG B 161     -45.750  -3.248  -7.597  1.00 46.16      A  C
ATOM   3802  CG  ARG B 161     -46.947  -4.000  -8.164  1.00 47.55      A  C
ATOM   3803  CD  ARG B 161     -46.652  -4.563  -9.551  1.00 50.40      A  C
ATOM   3804  NE  ARG B 161     -45.230  -4.874  -9.734  1.00 52.64      A  N
ATOM   3805  CZ  ARG B 161     -44.501  -4.558 -10.810  1.00 53.89      A  C
ATOM   3806  NH1 ARG B 161     -45.047  -3.928 -11.851  1.00 54.67      A  N
ATOM   3807  NH2 ARG B 161     -43.214  -4.895 -10.851  1.00 54.15      A  N
ATOM   3808  N   HIS B 162     -45.001  -2.431  -4.638  1.00 44.05      A  N
ATOM   3809  CA  HIS B 162     -43.959  -2.286  -3.620  1.00 43.00      A  C
ATOM   3810  C   HIS B 162     -43.602  -3.597  -2.928  1.00 41.95      A  C
ATOM   3811  O   HIS B 162     -44.462  -4.447  -2.709  1.00 41.72      A  O
ATOM   3812  CB  HIS B 162     -44.373  -1.260  -2.565  1.00 43.23      A  C
ATOM   3813  CG  HIS B 162     -45.756  -1.464  -2.036  1.00 43.85      A  C
ATOM   3814  CD2 HIS B 162     -46.903  -0.786  -2.267  1.00 44.45      A  C
ATOM   3815  ND1 HIS B 162     -46.075  -2.471  -1.152  1.00 44.02      A  N
ATOM   3816  CE1 HIS B 162     -47.363  -2.410  -0.870  1.00 44.26      A  C
ATOM   3817  NE2 HIS B 162     -47.887  -1.393  -1.529  1.00 44.53      A  N
ATOM   3818  N   LEU B 163     -42.323  -3.756  -2.597  1.00 40.86      A  N
ATOM   3819  CA  LEU B 163     -41.882  -4.799  -1.677  1.00 39.66      A  C
ATOM   3820  C   LEU B 163     -42.315  -4.368  -0.299  1.00 38.98      A  C
ATOM   3821  O   LEU B 163     -42.116  -3.218   0.090  1.00 39.03      A  O
ATOM   3822  CB  LEU B 163     -40.364  -4.942  -1.692  1.00 39.55      A  C
ATOM   3823  CG  LEU B 163     -39.725  -5.722  -0.543  1.00 38.90      A  C
ATOM   3824  CD1 LEU B 163     -40.126  -7.182  -0.601  1.00 38.46      A  C
ATOM   3825  CD2 LEU B 163     -38.204  -5.577  -0.547  1.00 38.87      A  C
ATOM   3826  N   THR B 164     -42.911  -5.288   0.443  1.00 37.99      A  N
ATOM   3827  CA  THR B 164     -43.405  -4.940   1.754  1.00 37.02      A  C
ATOM   3828  C   THR B 164     -42.868  -5.835   2.857  1.00 36.45      A  C
ATOM   3829  O   THR B 164     -43.095  -7.047   2.850  1.00 36.23      A  O
ATOM   3830  CB  THR B 164     -44.948  -4.785   1.776  1.00 36.98      A  C
ATOM   3831  CG2 THR B 164     -45.628  -5.925   1.112  1.00 36.92      A  C
ATOM   3832  OG1 THR B 164     -45.412  -4.701   3.125  1.00 36.66      A  O
ATOM   3833  N   LEU B 165     -42.121  -5.222   3.779  1.00 35.86      A  N
ATOM   3834  CA  LEU B 165     -41.616  -5.896   4.973  1.00 35.29      A  C
ATOM   3835  C   LEU B 165     -42.501  -5.575   6.163  1.00 34.98      A  C
```

FIGURE 1 (cont'd)

```
ATOM   3836  O    LEU B 165     -43.043   -4.469    6.259  1.00 35.03    A    O
ATOM   3837  CB   LEU B 165     -40.188   -5.474    5.271  1.00 35.20    A    C
ATOM   3838  CG   LEU B 165     -39.145   -5.702    4.180  1.00 35.31    A    C
ATOM   3839  CD1  LEU B 165     -37.749   -5.409    4.701  1.00 35.45    A    C
ATOM   3840  CD2  LEU B 165     -39.196   -7.107    3.630  1.00 35.09    A    C
ATOM   3841  N    ALA B 166     -42.647   -6.549    7.063  1.00 34.52    A    N
ATOM   3842  CA   ALA B 166     -43.515   -6.396    8.228  1.00 34.09    A    C
ATOM   3843  C    ALA B 166     -42.984   -7.038    9.510  1.00 33.80    A    C
ATOM   3844  O    ALA B 166     -42.324   -8.083    9.486  1.00 33.61    A    O
ATOM   3845  CB   ALA B 166     -44.916   -6.900    7.920  1.00 34.10    A    C
ATOM   3846  N    CYS B 167     -43.275   -6.360   10.617  1.00 33.64    A    N
ATOM   3847  CA   CYS B 167     -43.060   -6.843   11.977  1.00 33.52    A    C
ATOM   3848  C    CYS B 167     -44.273   -6.404   12.784  1.00 33.49    A    C
ATOM   3849  O    CYS B 167     -45.048   -5.559   12.326  1.00 33.58    A    O
ATOM   3850  CB   CYS B 167     -41.810   -6.203   12.582  1.00 33.51    A    C
ATOM   3851  SG   CYS B 167     -41.968   -4.425   12.929  1.00 33.64    A    S
ATOM   3852  N    HIS B 168     -44.450   -6.965   13.974  1.00 33.45    A    N
ATOM   3853  CA   HIS B 168     -45.465   -6.450   14.881  1.00 33.48    A    C
ATOM   3854  C    HIS B 168     -44.796   -5.754   16.073  1.00 33.42    A    C
ATOM   3855  O    HIS B 168     -43.817   -6.251   16.635  1.00 33.35    A    O
ATOM   3856  CB   HIS B 168     -46.432   -7.552   15.320  1.00 33.60    A    C
ATOM   3857  CG   HIS B 168     -45.878   -8.456   16.376  1.00 34.01    A    C
ATOM   3858  CD2  HIS B 168     -45.195   -9.621   16.286  1.00 34.34    A    C
ATOM   3859  ND1  HIS B 168     -45.983   -8.181   17.723  1.00 34.38    A    N
ATOM   3860  CE1  HIS B 168     -45.395   -9.140   18.417  1.00 34.39    A    C
ATOM   3861  NE2  HIS B 168     -44.908  -10.026   17.570  1.00 34.31    A    N
ATOM   3862  N    TYR B 169     -45.324   -4.596   16.449  1.00 33.50    A    N
ATOM   3863  CA   TYR B 169     -44.684   -3.779   17.459  1.00 33.64    A    C
ATOM   3864  C    TYR B 169     -45.300   -3.898   18.844  1.00 33.72    A    C
ATOM   3865  O    TYR B 169     -44.712   -3.456   19.816  1.00 33.75    A    O
ATOM   3866  CB   TYR B 169     -44.613   -2.318   17.002  1.00 33.73    A    C
ATOM   3867  CG   TYR B 169     -45.890   -1.540   17.146  1.00 33.93    A    C
ATOM   3868  CD1  TYR B 169     -46.872   -1.588   16.171  1.00 33.80    A    C
ATOM   3869  CD2  TYR B 169     -46.103   -0.732   18.254  1.00 34.42    A    C
ATOM   3870  CE1  TYR B 169     -48.041   -0.860   16.301  1.00 33.91    A    C
ATOM   3871  CE2  TYR B 169     -47.275   -0.001   18.392  1.00 34.64    A    C
ATOM   3872  CZ   TYR B 169     -48.240   -0.071   17.413  1.00 34.20    A    C
ATOM   3873  OH   TYR B 169     -49.399    0.651   17.562  1.00 34.27    A    O
ATOM   3874  N    ASP B 170     -46.479   -4.496   18.935  1.00 33.87    A    N
ATOM   3875  CA   ASP B 170     -47.081   -4.795   20.234  1.00 34.20    A    C
ATOM   3876  C    ASP B 170     -46.265   -5.872   20.965  1.00 34.45    A    C
ATOM   3877  O    ASP B 170     -45.465   -6.574   20.345  1.00 34.29    A    O
ATOM   3878  CB   ASP B 170     -48.553   -5.219   20.085  1.00 34.25    A    C
ATOM   3879  CG   ASP B 170     -48.723   -6.568   19.384  1.00 34.17    A    C
ATOM   3880  OD1  ASP B 170     -48.273   -6.723   18.232  1.00 33.79    A    O
ATOM   3881  OD2  ASP B 170     -49.339   -7.475   19.979  1.00 34.55    A    O
ATOM   3882  N    SER B 171     -46.436   -5.963   22.284  1.00 34.92    A    N
ATOM   3883  CA   SER B 171     -45.829   -7.022   23.091  1.00 35.33    A    C
ATOM   3884  C    SER B 171     -46.960   -7.787   23.768  1.00 35.63    A    C
ATOM   3885  O    SER B 171     -47.991   -7.201   24.093  1.00 35.96    A    O
ATOM   3886  CB   SER B 171     -44.838   -6.445   24.124  1.00 35.38    A    C
ATOM   3887  OG   SER B 171     -45.470   -5.920   25.280  1.00 35.79    A    O
ATOM   3888  N    LYS B 172     -46.789   -9.086   23.983  1.00 35.78    A    N
ATOM   3889  CA   LYS B 172     -47.841   -9.874   24.626  1.00 36.18    A    C
ATOM   3890  C    LYS B 172     -48.184   -9.394   26.039  1.00 36.92    A    C
ATOM   3891  O    LYS B 172     -47.320   -8.910   26.775  1.00 37.20    A    O
ATOM   3892  CB   LYS B 172     -47.482  -11.358   24.659  1.00 35.92    A    C
ATOM   3893  CG   LYS B 172     -48.688  -12.269   24.896  1.00 35.70    A    C
ATOM   3894  CD   LYS B 172     -48.325  -13.736   25.000  1.00 35.07    A    C
ATOM   3895  CE   LYS B 172     -49.532  -14.578   25.389  1.00 35.06    A    C
ATOM   3896  NZ   LYS B 172     -50.483  -14.783   24.275  1.00 35.00    A    N
ATOM   3897  N    LEU B 173     -49.456   -9.538   26.403  1.00 37.70    A    N
ATOM   3898  CA   LEU B 173     -49.954   -9.175   27.725  1.00 38.57    A    C
ATOM   3899  C    LEU B 173     -49.985  -10.386   28.662  1.00 39.08    A    C
ATOM   3900  O    LEU B 173     -50.605  -11.406   28.360  1.00 39.17    A    O
```

FIGURE 1 (cont'd)

```
ATOM   3901  CB  LEU B 173     -51.351  -8.579  27.580  1.00 38.63      A    C
ATOM   3902  CG  LEU B 173     -52.142  -8.290  28.850  1.00 39.24      A    C
ATOM   3903  CD1 LEU B 173     -51.956  -6.859  29.307  1.00 39.57      A    C
ATOM   3904  CD2 LEU B 173     -53.615  -8.611  28.643  1.00 39.40      A    C
ATOM   3905  N   PHE B 174     -49.320 -10.264  29.801  1.00 39.74      A    N
ATOM   3906  CA  PHE B 174     -49.282 -11.349  30.775  1.00 40.35      A    C
ATOM   3907  C   PHE B 174     -49.982 -10.935  32.095  1.00 40.18      A    C
ATOM   3908  O   PHE B 174     -50.076  -9.735  32.373  1.00 41.34      A    O
ATOM   3909  CB  PHE B 174     -47.828 -11.787  30.998  1.00 40.61      A    C
ATOM   3910  CG  PHE B 174     -47.280 -12.650  29.898  1.00 40.46      A    C
ATOM   3911  CD1 PHE B 174     -47.571 -14.011  29.859  1.00 40.59      A    C
ATOM   3912  CD2 PHE B 174     -46.483 -12.107  28.893  1.00 40.03      A    C
ATOM   3913  CE1 PHE B 174     -47.070 -14.824  28.835  1.00 40.11      A    C
ATOM   3914  CE2 PHE B 174     -45.974 -12.913  27.865  1.00 39.54      A    C
ATOM   3915  CZ  PHE B 174     -46.268 -14.273  27.839  1.00 39.65      A    C
ATOM   3916  N   PRO B 175     -50.491 -11.913  32.908  1.00 37.99      A    N
ATOM   3917  CA  PRO B 175     -51.265 -11.523  34.110  1.00 36.69      A    C
ATOM   3918  C   PRO B 175     -50.429 -10.596  35.010  1.00 36.56      A    C
ATOM   3919  O   PRO B 175     -49.194 -10.766  35.052  1.00 36.26      A    O
ATOM   3920  CB  PRO B 175     -51.565 -12.872  34.803  1.00 36.29      A    C
ATOM   3921  CG  PRO B 175     -50.490 -13.805  34.320  1.00 36.29      A    C
ATOM   3922  CD  PRO B 175     -50.236 -13.377  32.888  1.00 37.67      A    C
ATOM   3923  N   PRO B 176     -51.091  -9.649  35.737  1.00 37.04      A    N
ATOM   3924  CA  PRO B 176     -50.496  -8.426  36.308  1.00 38.15      A    C
ATOM   3925  C   PRO B 176     -48.998  -8.576  36.502  1.00 40.08      A    C
ATOM   3926  O   PRO B 176     -48.528  -8.883  37.608  1.00 40.09      A    O
ATOM   3927  CB  PRO B 176     -51.223  -8.264  37.656  1.00 37.71      A    C
ATOM   3928  CG  PRO B 176     -52.160  -9.454  37.770  1.00 36.98      A    C
ATOM   3929  CD  PRO B 176     -52.396  -9.909  36.368  1.00 36.71      A    C
ATOM   3930  N   GLY B 177     -48.278  -8.370  35.397  1.00 42.34      A    N
ATOM   3931  CA  GLY B 177     -46.868  -8.725  35.249  1.00 44.61      A    C
ATOM   3932  C   GLY B 177     -46.033  -8.969  36.495  1.00 46.04      A    C
ATOM   3933  O   GLY B 177     -45.092  -8.208  36.744  1.00 46.54      A    O
ATOM   3934  N   SER B 178     -46.412  -9.965  37.317  1.00 47.15      A    N
ATOM   3935  CA  SER B 178     -45.420 -10.920  37.736  1.00 46.93      A    C
ATOM   3936  C   SER B 178     -44.038 -10.445  37.416  1.00 46.88      A    C
ATOM   3937  O   SER B 178     -43.361  -9.983  38.302  1.00 47.44      A    O
ATOM   3938  CB  SER B 178     -45.640 -12.149  36.927  1.00 45.26      A    C
ATOM   3939  OG  SER B 178     -46.898 -12.637  37.246  1.00 44.56      A    O
ATOM   3940  N   THR B 179     -43.582 -10.575  36.176  1.00 45.46      A    N
ATOM   3941  CA  THR B 179     -42.387  -9.827  35.815  1.00 42.95      A    C
ATOM   3942  C   THR B 179     -42.590  -9.239  34.422  1.00 43.47      A    C
ATOM   3943  O   THR B 179     -43.152  -9.906  33.550  1.00 44.43      A    O
ATOM   3944  CB  THR B 179     -41.042 -10.619  35.984  1.00 37.59      A    C
ATOM   3945  CG2 THR B 179     -41.191 -11.946  36.757  1.00 39.39      A    C
ATOM   3946  OG1 THR B 179     -40.431 -10.831  34.713  1.00 34.52      A    O
ATOM   3947  N   PRO B 180     -42.139  -7.989  34.211  1.00 42.25      A    N
ATOM   3948  CA  PRO B 180     -42.461  -7.254  32.976  1.00 41.29      A    C
ATOM   3949  C   PRO B 180     -41.989  -8.038  31.748  1.00 42.07      A    C
ATOM   3950  O   PRO B 180     -40.941  -8.691  31.803  1.00 42.96      A    O
ATOM   3951  CB  PRO B 180     -41.663  -5.949  33.118  1.00 36.48      A    C
ATOM   3952  CG  PRO B 180     -40.501  -6.311  33.992  1.00 34.99      A    C
ATOM   3953  CD  PRO B 180     -40.960  -7.428  34.903  1.00 41.00      A    C
ATOM   3954  N   PHE B 181     -42.761  -8.001  30.664  1.00 41.83      A    N
ATOM   3955  CA  PHE B 181     -42.401  -8.746  29.456  1.00 40.94      A    C
ATOM   3956  C   PHE B 181     -42.203  -7.817  28.270  1.00 40.23      A    C
ATOM   3957  O   PHE B 181     -43.161  -7.194  27.790  1.00 40.03      A    O
ATOM   3958  CB  PHE B 181     -43.446  -9.825  29.133  1.00 41.01      A    C
ATOM   3959  CG  PHE B 181     -43.241 -10.496  27.792  1.00 40.75      A    C
ATOM   3960  CD1 PHE B 181     -42.209 -11.414  27.594  1.00 40.86      A    C
ATOM   3961  CD2 PHE B 181     -44.081 -10.204  26.727  1.00 40.50      A    C
ATOM   3962  CE1 PHE B 181     -42.023 -12.016  26.357  1.00 40.25      A    C
ATOM   3963  CE2 PHE B 181     -43.892 -10.811  25.487  1.00 39.99      A    C
ATOM   3964  CZ  PHE B 181     -42.864 -11.716  25.306  1.00 39.72      A    C
ATOM   3965  N   VAL B 182     -40.961  -7.749  27.788  1.00 39.45      A    N
```

FIGURE 1 (cont'd)

```
ATOM   3966  CA   VAL B 182     -40.606  -6.844  26.682  1.00 38.70      A    C
ATOM   3967  C    VAL B 182     -40.475  -7.498  25.305  1.00 37.92      A    C
ATOM   3968  O    VAL B 182     -40.438  -6.792  24.300  1.00 37.75      A    O
ATOM   3969  CB   VAL B 182     -39.324  -6.031  26.970  1.00 38.76      A    C
ATOM   3970  CG1  VAL B 182     -39.632  -4.910  27.923  1.00 39.12      A    C
ATOM   3971  CG2  VAL B 182     -38.213  -6.923  27.512  1.00 39.11      A    C
ATOM   3972  N    GLY B 183     -40.396  -8.829  25.267  1.00 37.24      A    N
ATOM   3973  CA   GLY B 183     -40.320  -9.587  24.010  1.00 36.26      A    C
ATOM   3974  C    GLY B 183     -39.314  -9.027  23.019  1.00 35.59      A    C
ATOM   3975  O    GLY B 183     -39.687  -8.393  22.026  1.00 35.41      A    O
ATOM   3976  N    ALA B 184     -38.035  -9.254  23.298  1.00 35.07      A    N
ATOM   3977  CA   ALA B 184     -36.966  -8.726  22.466  1.00 34.47      A    C
ATOM   3978  C    ALA B 184     -36.994  -9.352  21.081  1.00 33.91      A    C
ATOM   3979  O    ALA B 184     -36.937  -8.650  20.077  1.00 33.74      A    O
ATOM   3980  CB   ALA B 184     -35.620  -8.934  23.134  1.00 34.79      A    C
ATOM   3981  N    THR B 185     -37.105 -10.674  21.031  1.00 33.35      A    N
ATOM   3982  CA   THR B 185     -37.187 -11.376  19.761  1.00 32.81      A    C
ATOM   3983  C    THR B 185     -38.591 -11.250  19.203  1.00 32.58      A    C
ATOM   3984  O    THR B 185     -38.819 -11.522  18.027  1.00 32.60      A    O
ATOM   3985  CB   THR B 185     -36.890 -12.884  19.896  1.00 32.72      A    C
ATOM   3986  CG2  THR B 185     -35.645 -13.132  20.710  1.00 32.99      A    C
ATOM   3987  OG1  THR B 185     -37.999 -13.531  20.524  1.00 32.39      A    O
ATOM   3988  N    ASP B 186     -39.528 -10.823  20.042  1.00 32.33      A    N
ATOM   3989  CA   ASP B 186     -40.938 -10.974  19.738  1.00 32.08      A    C
ATOM   3990  C    ASP B 186     -41.724  -9.675  19.981  1.00 32.16      A    C
ATOM   3991  O    ASP B 186     -42.476  -9.601  20.950  1.00 32.49      A    O
ATOM   3992  CB   ASP B 186     -41.472 -12.116  20.613  1.00 31.98      A    C
ATOM   3993  CG   ASP B 186     -42.859 -12.586  20.219  1.00 31.47      A    C
ATOM   3994  OD1  ASP B 186     -43.358 -13.525  20.876  1.00 31.34      A    O
ATOM   3995  OD2  ASP B 186     -43.456 -12.039  19.272  1.00 30.66      A    O
ATOM   3996  N    SER B 187     -41.591  -8.655  19.124  1.00 31.90      A    N
ATOM   3997  CA   SER B 187     -40.779  -8.673  17.912  1.00 31.63      A    C
ATOM   3998  C    SER B 187     -39.977  -7.382  17.777  1.00 31.61      A    C
ATOM   3999  O    SER B 187     -39.886  -6.806  16.690  1.00 31.48      A    O
ATOM   4000  CB   SER B 187     -41.671  -8.855  16.686  1.00 31.55      A    C
ATOM   4001  OG   SER B 187     -42.136 -10.190  16.589  1.00 31.72      A    O
ATOM   4002  N    ALA B 188     -39.393  -6.939  18.891  1.00 31.77      A    N
ATOM   4003  CA   ALA B 188     -38.614  -5.696  18.943  1.00 31.84      A    C
ATOM   4004  C    ALA B 188     -37.473  -5.673  17.925  1.00 31.82      A    C
ATOM   4005  O    ALA B 188     -37.357  -4.742  17.138  1.00 31.83      A    O
ATOM   4006  CB   ALA B 188     -38.090  -5.456  20.345  1.00 31.97      A    C
ATOM   4007  N    VAL B 189     -36.647  -6.712  17.939  1.00 31.75      A    N
ATOM   4008  CA   VAL B 189     -35.555  -6.849  16.983  1.00 31.64      A    C
ATOM   4009  C    VAL B 189     -36.053  -6.771  15.539  1.00 31.63      A    C
ATOM   4010  O    VAL B 189     -35.537  -5.955  14.770  1.00 31.73      A    O
ATOM   4011  CB   VAL B 189     -34.725  -8.144  17.224  1.00 31.58      A    C
ATOM   4012  CG1  VAL B 189     -33.726  -8.389  16.097  1.00 31.35      A    C
ATOM   4013  CG2  VAL B 189     -34.002  -8.067  18.550  1.00 31.79      A    C
ATOM   4014  N    PRO B 190     -37.047  -7.613  15.162  1.00 31.52      A    N
ATOM   4015  CA   PRO B 190     -37.613  -7.501  13.818  1.00 31.52      A    C
ATOM   4016  C    PRO B 190     -37.956  -6.074  13.431  1.00 31.76      A    C
ATOM   4017  O    PRO B 190     -37.550  -5.622  12.363  1.00 31.78      A    O
ATOM   4018  CB   PRO B 190     -38.869  -8.353  13.906  1.00 31.33      A    C
ATOM   4019  CG   PRO B 190     -38.468  -9.451  14.813  1.00 31.34      A    C
ATOM   4020  CD   PRO B 190     -37.525  -8.840  15.831  1.00 31.48      A    C
ATOM   4021  N    CYS B 191     -38.665  -5.361  14.304  1.00 32.16      A    N
ATOM   4022  CA   CYS B 191     -39.029  -3.960  14.041  1.00 32.69      A    C
ATOM   4023  C    CYS B 191     -37.822  -3.037  13.973  1.00 32.95      A    C
ATOM   4024  O    CYS B 191     -37.778  -2.141  13.135  1.00 33.11      A    O
ATOM   4025  CB   CYS B 191     -40.045  -3.454  15.064  1.00 32.75      A    C
ATOM   4026  SG   CYS B 191     -41.645  -4.288  14.934  1.00 33.29      A    S
ATOM   4027  N    ALA B 192     -36.843  -3.283  14.842  1.00 33.23      A    N
ATOM   4028  CA   ALA B 192     -35.592  -2.525  14.861  1.00 33.45      A    C
ATOM   4029  C    ALA B 192     -34.851  -2.619  13.529  1.00 33.43      A    C
ATOM   4030  O    ALA B 192     -34.344  -1.606  13.034  1.00 33.69      A    O
```

FIGURE 1 (cont'd)

```
ATOM   4031  CB   ALA B 192     -34.702   -2.987   16.005  1.00 33.58      A  C
ATOM   4032  N    LEU B 193     -34.812   -3.828   12.958  1.00 33.02      A  N
ATOM   4033  CA   LEU B 193     -34.181   -4.068   11.662  1.00 32.61      A  C
ATOM   4034  C    LEU B 193     -34.857   -3.279   10.543  1.00 33.19      A  C
ATOM   4035  O    LEU B 193     -34.189   -2.639    9.738  1.00 33.61      A  O
ATOM   4036  CB   LEU B 193     -34.189   -5.551   11.325  1.00 31.27      A  C
ATOM   4037  CG   LEU B 193     -33.278   -6.425   12.165  1.00 29.71      A  C
ATOM   4038  CD1  LEU B 193     -33.546   -7.886   11.846  1.00 28.75      A  C
ATOM   4039  CD2  LEU B 193     -31.843   -6.035   11.863  1.00 28.45      A  C
ATOM   4040  N    LEU B 194     -36.184   -3.307   10.500  1.00 33.39      A  N
ATOM   4041  CA   LEU B 194     -36.918   -2.557    9.488  1.00 33.53      A  C
ATOM   4042  C    LEU B 194     -36.565   -1.079    9.519  1.00 34.44      A  C
ATOM   4043  O    LEU B 194     -36.488   -0.435    8.476  1.00 34.77      A  O
ATOM   4044  CB   LEU B 194     -38.422   -2.749    9.645  1.00 32.44      A  C
ATOM   4045  CG   LEU B 194     -38.979   -4.146    9.366  1.00 31.24      A  C
ATOM   4046  CD1  LEU B 194     -40.407   -4.036    8.908  1.00 30.85      A  C
ATOM   4047  CD2  LEU B 194     -38.176   -4.892    8.336  1.00 30.56      A  C
ATOM   4048  N    LEU B 195     -36.333   -0.551   10.717  1.00 35.25      A  N
ATOM   4049  CA   LEU B 195     -35.904    0.836   10.876  1.00 36.08      A  C
ATOM   4050  C    LEU B 195     -34.483    1.056   10.367  1.00 36.79      A  C
ATOM   4051  O    LEU B 195     -34.241    1.943    9.548  1.00 37.10      A  O
ATOM   4052  CB   LEU B 195     -36.005    1.270   12.335  1.00 35.99      A  C
ATOM   4053  CG   LEU B 195     -37.397    1.412   12.936  1.00 35.80      A  C
ATOM   4054  CD1  LEU B 195     -37.281    1.704   14.411  1.00 36.05      A  C
ATOM   4055  CD2  LEU B 195     -38.211    2.489   12.245  1.00 35.81      A  C
ATOM   4056  N    GLU B 196     -33.552    0.239   10.857  1.00 37.41      A  N
ATOM   4057  CA   GLU B 196     -32.138    0.312   10.481  1.00 38.02      A  C
ATOM   4058  C    GLU B 196     -31.922    0.179    8.975  1.00 38.12      A  C
ATOM   4059  O    GLU B 196     -31.159    0.945    8.398  1.00 38.32      A  O
ATOM   4060  CB   GLU B 196     -31.338   -0.756   11.230  1.00 38.17      A  C
ATOM   4061  CG   GLU B 196     -29.935   -0.996   10.700  1.00 39.29      A  C
ATOM   4062  CD   GLU B 196     -28.995    0.163   10.956  1.00 40.78      A  C
ATOM   4063  OE1  GLU B 196     -29.401    1.151   11.608  1.00 41.39      A  O
ATOM   4064  OE2  GLU B 196     -27.837    0.082   10.503  1.00 41.53      A  O
ATOM   4065  N    LEU B 197     -32.594   -0.794    8.360  1.00 38.11      A  N
ATOM   4066  CA   LEU B 197     -32.570   -0.988    6.923  1.00 38.32      A  C
ATOM   4067  C    LEU B 197     -33.022    0.265    6.208  1.00 38.84      A  C
ATOM   4068  O    LEU B 197     -32.370    0.718    5.270  1.00 39.17      A  O
ATOM   4069  CB   LEU B 197     -33.481   -2.134    6.526  1.00 37.92      A  C
ATOM   4070  CG   LEU B 197     -32.829   -3.465    6.199  1.00 37.72      A  C
ATOM   4071  CD1  LEU B 197     -32.525   -4.248    7.448  1.00 37.61      A  C
ATOM   4072  CD2  LEU B 197     -33.773   -4.247    5.325  1.00 37.69      A  C
ATOM   4073  N    ALA B 198     -34.133    0.833    6.663  1.00 39.29      A  N
ATOM   4074  CA   ALA B 198     -34.708    2.014    6.031  1.00 40.04      A  C
ATOM   4075  C    ALA B 198     -33.765    3.216    6.085  1.00 40.77      A  C
ATOM   4076  O    ALA B 198     -33.806    4.104    5.234  1.00 41.07      A  O
ATOM   4077  CB   ALA B 198     -36.039    2.347    6.675  1.00 39.85      A  C
ATOM   4078  N    GLN B 199     -32.905    3.210    7.088  1.00 41.34      A  N
ATOM   4079  CA   GLN B 199     -32.023    4.310    7.360  1.00 42.00      A  C
ATOM   4080  C    GLN B 199     -30.711    4.082    6.633  1.00 42.93      A  C
ATOM   4081  O    GLN B 199     -30.189    4.985    5.995  1.00 43.54      A  O
ATOM   4082  CB   GLN B 199     -31.853    4.373    8.877  1.00 40.94      A  C
ATOM   4083  CG   GLN B 199     -31.718    5.745    9.576  1.00 40.39      A  C
ATOM   4084  CD   GLN B 199     -31.095    6.833    8.730  1.00 40.12      A  C
ATOM   4085  NE2  GLN B 199     -31.801    7.291    7.700  1.00 41.05      A  N
ATOM   4086  OE1  GLN B 199     -29.947    7.197    8.971  1.00 40.43      A  O
ATOM   4087  N    ALA B 200     -30.194    2.861    6.708  1.00 43.63      A  N
ATOM   4088  CA   ALA B 200     -28.923    2.509    6.065  1.00 44.36      A  C
ATOM   4089  C    ALA B 200     -28.978    2.620    4.540  1.00 44.91      A  C
ATOM   4090  O    ALA B 200     -28.024    3.077    3.909  1.00 45.35      A  O
ATOM   4091  CB   ALA B 200     -28.480    1.109    6.482  1.00 44.12      A  C
ATOM   4092  N    LEU B 201     -30.097    2.205    3.958  1.00 45.23      A  N
ATOM   4093  CA   LEU B 201     -30.291    2.290    2.517  1.00 45.77      A  C
ATOM   4094  C    LEU B 201     -31.043    3.556    2.107  1.00 46.50      A  C
ATOM   4095  O    LEU B 201     -31.459    3.692    0.955  1.00 46.72      A  O
```

FIGURE 1 (cont'd)

```
ATOM   4096  CB   LEU B 201     -31.051    1.067    2.030  1.00 45.33      A    C
ATOM   4097  CG   LEU B 201     -30.355   -0.271    2.235  1.00 45.08      A    C
ATOM   4098  CD1  LEU B 201     -31.346   -1.432    2.101  1.00 44.78      A    C
ATOM   4099  CD2  LEU B 201     -29.182   -0.417    1.281  1.00 45.37      A    C
ATOM   4100  N    ASP B 202     -31.202    4.477    3.055  1.00 47.26      A    N
ATOM   4101  CA   ASP B 202     -32.001    5.683    2.863  1.00 48.08      A    C
ATOM   4102  C    ASP B 202     -31.667    6.440    1.580  1.00 48.70      A    C
ATOM   4103  O    ASP B 202     -32.572    6.779    0.808  1.00 48.93      A    O
ATOM   4104  CB   ASP B 202     -31.867    6.598    4.083  1.00 48.20      A    C
ATOM   4105  CG   ASP B 202     -32.609    7.910    3.929  1.00 48.63      A    C
ATOM   4106  OD1  ASP B 202     -33.826    7.910    3.654  1.00 48.48      A    O
ATOM   4107  OD2  ASP B 202     -31.965    8.952    4.108  1.00 49.39      A    O
ATOM   4108  N    LEU B 203     -30.378    6.685    1.347  1.00 49.10      A    N
ATOM   4109  CA   LEU B 203     -29.945    7.493    0.197  1.00 49.29      A    C
ATOM   4110  C    LEU B 203     -30.140    6.812   -1.162  1.00 49.55      A    C
ATOM   4111  O    LEU B 203     -30.650    7.425   -2.093  1.00 49.94      A    O
ATOM   4112  CB   LEU B 203     -28.511    7.993    0.378  1.00 48.32      A    C
ATOM   4113  CG   LEU B 203     -28.461    9.197    1.319  1.00 48.02      A    C
ATOM   4114  CD1  LEU B 203     -27.925    8.805    2.683  1.00 47.94      A    C
ATOM   4115  CD2  LEU B 203     -27.699   10.371    0.740  1.00 46.22      A    C
ATOM   4116  N    GLU B 204     -29.746    5.546   -1.265  1.00 49.38      A    N
ATOM   4117  CA   GLU B 204     -29.996    4.743   -2.472  1.00 48.99      A    C
ATOM   4118  C    GLU B 204     -31.492    4.527   -2.700  1.00 49.42      A    C
ATOM   4119  O    GLU B 204     -31.943    4.454   -3.844  1.00 49.73      A    O
ATOM   4120  CB   GLU B 204     -29.235    3.400   -2.457  1.00 47.46      A    C
ATOM   4121  CG   GLU B 204     -28.884    2.852   -1.077  1.00 45.82      A    C
ATOM   4122  CD   GLU B 204     -27.717    3.602   -0.456  1.00 45.06      A    C
ATOM   4123  OE1  GLU B 204     -26.558    3.231   -0.739  1.00 45.22      A    O
ATOM   4124  OE2  GLU B 204     -27.948    4.622    0.257  1.00 45.22      A    O
ATOM   4125  N    LEU B 205     -32.250    4.434   -1.607  1.00 49.61      A    N
ATOM   4126  CA   LEU B 205     -33.707    4.361   -1.673  1.00 49.76      A    C
ATOM   4127  C    LEU B 205     -34.306    5.679   -2.129  1.00 50.50      A    C
ATOM   4128  O    LEU B 205     -35.356    5.703   -2.784  1.00 50.58      A    O
ATOM   4129  CB   LEU B 205     -34.296    4.004   -0.312  1.00 49.22      A    C
ATOM   4130  CG   LEU B 205     -34.581    2.539    0.015  1.00 48.23      A    C
ATOM   4131  CD1  LEU B 205     -34.825    2.403    1.502  1.00 47.82      A    C
ATOM   4132  CD2  LEU B 205     -35.769    2.021   -0.772  1.00 47.60      A    C
ATOM   4133  N    SER B 206     -33.637    6.771   -1.765  1.00 51.36      A    N
ATOM   4134  CA   SER B 206     -34.108    8.110   -2.093  1.00 52.25      A    C
ATOM   4135  C    SER B 206     -33.966    8.403   -3.577  1.00 52.70      A    C
ATOM   4136  O    SER B 206     -34.942    8.752   -4.229  1.00 52.74      A    O
ATOM   4137  CB   SER B 206     -33.374    9.162   -1.265  1.00 52.47      A    C
ATOM   4138  OG   SER B 206     -34.113   10.368   -1.232  1.00 53.14      A    O
ATOM   4139  N    ARG B 207     -32.757    8.242   -4.106  1.00 53.23      A    N
ATOM   4140  CA   ARG B 207     -32.511    8.522   -5.517  1.00 53.76      A    C
ATOM   4141  C    ARG B 207     -33.472    7.734   -6.405  1.00 53.76      A    C
ATOM   4142  O    ARG B 207     -34.211    8.333   -7.192  1.00 54.14      A    O
ATOM   4143  CB   ARG B 207     -31.026    8.349   -5.924  1.00 54.05      A    C
ATOM   4144  CG   ARG B 207     -30.403    6.981   -5.662  1.00 53.55      A    C
ATOM   4145  N    ALA B 208     -33.489    6.409   -6.251  1.00 53.28      A    N
ATOM   4146  CA   ALA B 208     -34.447    5.578   -6.964  1.00 52.88      A    C
ATOM   4147  C    ALA B 208     -35.853    5.954   -6.497  1.00 52.66      A    C
ATOM   4148  O    ALA B 208     -36.417    5.322   -5.603  1.00 52.42      A    O
ATOM   4149  CB   ALA B 208     -34.157    4.107   -6.737  1.00 52.57      A    C
ATOM   4150  N    LYS B 209     -36.376    7.014   -7.116  1.00 52.71      A    N
ATOM   4151  CA   LYS B 209     -37.644    7.662   -6.798  1.00 52.27      A    C
ATOM   4152  C    LYS B 209     -37.635    9.103   -7.387  1.00 51.51      A    C
ATOM   4153  O    LYS B 209     -38.321    9.936   -6.845  1.00 52.66      A    O
ATOM   4154  CB   LYS B 209     -37.845    7.733   -5.264  1.00 52.40      A    C
ATOM   4155  CG   LYS B 209     -39.252    8.069   -4.777  1.00 52.70      A    C
ATOM   4156  CD   LYS B 209     -39.199    8.816   -3.446  1.00 53.58      A    C
ATOM   4157  CE   LYS B 209     -40.593    9.130   -2.905  1.00 53.76      A    C
ATOM   4158  NZ   LYS B 209     -40.570    9.992   -1.684  1.00 53.87      A    N
ATOM   4159  N    LYS B 210     -36.981    9.467   -8.509  1.00 47.08      A    N
ATOM   4160  CA   LYS B 210     -36.763    8.730   -9.772  1.00 43.11      A    C
```

FIGURE 1 (cont'd)

```
ATOM   4161  C    LYS B 210     -37.867   7.768 -10.192  1.00 40.43     A    C
ATOM   4162  O    LYS B 210     -37.680   6.975 -11.114  1.00 39.99     A    O
ATOM   4163  CB   LYS B 210     -35.373   8.100  -9.850  1.00 43.11     A    C
ATOM   4164  CG   LYS B 210     -34.804   7.987 -11.256  1.00 42.14     A    C
ATOM   4165  CD   LYS B 210     -33.437   7.329 -11.230  1.00 41.68     A    C
ATOM   4166  CE   LYS B 210     -33.509   5.940 -10.609  1.00 41.28     A    C
ATOM   4167  NZ   LYS B 210     -32.171   5.411 -10.240  1.00 41.59     A    N
ATOM   4168  N    GLN B 211     -39.019   7.875  -9.527  1.00 37.25     A    N
ATOM   4169  CA   GLN B 211     -40.182   6.979  -9.690  1.00 34.20     A    C
ATOM   4170  C    GLN B 211     -39.881   5.610 -10.296  1.00 33.70     A    C
ATOM   4171  O    GLN B 211     -39.617   5.507 -11.499  1.00 33.47     A    O
ATOM   4172  CB   GLN B 211     -41.321   7.666 -10.466  1.00 33.09     A    C
ATOM   4173  CG   GLN B 211     -42.525   8.109  -9.601  1.00 28.93     A    C
ATOM   4174  CD   GLN B 211     -43.787   7.211  -9.740  1.00 24.62     A    C
ATOM   4175  NE2  GLN B 211     -44.921   7.755  -9.309  1.00 23.60     A    N
ATOM   4176  OE1  GLN B 211     -43.742   6.062 -10.227  1.00 23.91     A    O
ATOM   4177  N    ALA B 212     -39.944   4.574  -9.454  1.00 33.04     A    N
ATOM   4178  CA   ALA B 212     -39.714   3.200  -9.882  1.00 32.44     A    C
ATOM   4179  C    ALA B 212     -41.025   2.435 -10.095  1.00 32.04     A    C
ATOM   4180  O    ALA B 212     -41.068   1.434 -10.811  1.00 31.23     A    O
ATOM   4181  CB   ALA B 212     -38.827   2.498  -8.888  1.00 32.29     A    C
TER    4182       ALA B 212
ATOM   4183  N    VAL B 215     -41.133  -0.031  -8.762  1.00 36.34     A    N
ATOM   4184  CA   VAL B 215     -41.327  -0.884  -7.587  1.00 36.19     A    C
ATOM   4185  C    VAL B 215     -40.759  -0.258  -6.300  1.00 36.41     A    C
ATOM   4186  O    VAL B 215     -39.542  -0.114  -6.152  1.00 36.65     A    O
ATOM   4187  CB   VAL B 215     -40.684  -2.282  -7.763  1.00 35.47     A    C
ATOM   4188  CG1  VAL B 215     -41.373  -3.294  -6.844  1.00 34.56     A    C
ATOM   4189  CG2  VAL B 215     -40.699  -2.736  -9.226  1.00 35.85     A    C
ATOM   4190  N    THR B 216     -41.651   0.085  -5.369  1.00 36.12     A    N
ATOM   4191  CA   THR B 216     -41.284   0.809  -4.150  1.00 35.58     A    C
ATOM   4192  C    THR B 216     -41.070  -0.087  -2.941  1.00 35.08     A    C
ATOM   4193  O    THR B 216     -41.010  -1.300  -3.064  1.00 35.09     A    O
ATOM   4194  CB   THR B 216     -42.332   1.872  -3.789  1.00 35.57     A    C
ATOM   4195  OG1  THR B 216     -41.661   3.089  -3.445  1.00 35.46     A    O
ATOM   4196  N    LEU B 217     -40.951   0.518  -1.770  1.00 34.46     A    N
ATOM   4197  CA   LEU B 217     -40.758  -0.232  -0.539  1.00 33.70     A    C
ATOM   4198  C    LEU B 217     -41.779   0.193   0.520  1.00 33.33     A    C
ATOM   4199  O    LEU B 217     -42.053   1.385   0.696  1.00 33.55     A    O
ATOM   4200  CB   LEU B 217     -39.327  -0.052  -0.022  1.00 33.60     A    C
ATOM   4201  CG   LEU B 217     -38.977  -0.614   1.357  1.00 33.08     A    C
ATOM   4202  CD1  LEU B 217     -38.884  -2.128   1.305  1.00 32.85     A    C
ATOM   4203  CD2  LEU B 217     -37.688  -0.011   1.876  1.00 33.15     A    C
ATOM   4204  N    GLN B 218     -42.331  -0.791   1.223  1.00 32.54     A    N
ATOM   4205  CA   GLN B 218     -43.343  -0.540   2.231  1.00 31.87     A    C
ATOM   4206  C    GLN B 218     -42.979  -1.203   3.563  1.00 31.31     A    C
ATOM   4207  O    GLN B 218     -42.567  -2.365   3.601  1.00 31.23     A    O
ATOM   4208  CB   GLN B 218     -44.695  -1.031   1.728  1.00 31.91     A    C
ATOM   4209  CG   GLN B 218     -45.863  -0.688   2.632  1.00 32.13     A    C
ATOM   4210  CD   GLN B 218     -47.147  -1.388   2.217  1.00 32.80     A    C
ATOM   4211  NE2  GLN B 218     -47.136  -2.710   2.216  1.00 32.86     A    N
ATOM   4212  OE1  GLN B 218     -48.133  -0.744   1.892  1.00 33.63     A    O
ATOM   4213  N    LEU B 219     -43.124  -0.453   4.653  1.00 30.74     A    N
ATOM   4214  CA   LEU B 219     -42.805  -0.956   5.981  1.00 30.05     A    C
ATOM   4215  C    LEU B 219     -44.047  -0.965   6.854  1.00 29.79     A    C
ATOM   4216  O    LEU B 219     -44.644   0.079   7.111  1.00 29.87     A    O
ATOM   4217  CB   LEU B 219     -41.678  -0.140   6.623  1.00 29.90     A    C
ATOM   4218  CG   LEU B 219     -40.328  -0.160   5.895  1.00 29.62     A    C
ATOM   4219  CD1  LEU B 219     -39.338   0.766   6.557  1.00 29.41     A    C
ATOM   4220  CD2  LEU B 219     -39.752  -1.573   5.797  1.00 29.21     A    C
ATOM   4221  N    LEU B 220     -44.432  -2.163   7.293  1.00 29.29     A    N
ATOM   4222  CA   LEU B 220     -45.609  -2.342   8.133  1.00 28.83     A    C
ATOM   4223  C    LEU B 220     -45.258  -2.728   9.559  1.00 28.95     A    C
ATOM   4224  O    LEU B 220     -44.609  -3.745   9.795  1.00 28.97     A    O
ATOM   4225  CB   LEU B 220     -46.544  -3.385   7.530  1.00 28.09     A    C
```

FIGURE 1 (cont'd)

```
ATOM   4226  CG   LEU B 220     -47.026  -3.109   6.107  1.00 27.41      A    C
ATOM   4227  CD1  LEU B 220     -48.067  -4.124   5.729  1.00 26.95      A    C
ATOM   4228  CD2  LEU B 220     -47.572  -1.700   5.910  1.00 27.47      A    C
ATOM   4229  N    PHE B 221     -45.689  -1.890  10.499  1.00 29.10      A    N
ATOM   4230  CA   PHE B 221     -45.541  -2.141  11.931  1.00 29.06      A    C
ATOM   4231  C    PHE B 221     -46.929  -2.370  12.512  1.00 29.10      A    C
ATOM   4232  O    PHE B 221     -47.677  -1.417  12.751  1.00 29.20      A    O
ATOM   4233  CB   PHE B 221     -44.870  -0.949  12.623  1.00 29.12      A    C
ATOM   4234  CG   PHE B 221     -43.520  -0.605  12.076  1.00 29.11      A    C
ATOM   4235  CD1  PHE B 221     -42.373  -1.087  12.686  1.00 29.18      A    C
ATOM   4236  CD2  PHE B 221     -43.397   0.202  10.959  1.00 29.19      A    C
ATOM   4237  CE1  PHE B 221     -41.126  -0.779  12.187  1.00 29.23      A    C
ATOM   4238  CE2  PHE B 221     -42.159   0.516  10.455  1.00 29.45      A    C
ATOM   4239  CZ   PHE B 221     -41.016   0.029  11.069  1.00 29.34      A    C
ATOM   4240  N    LEU B 222     -47.271  -3.636  12.722  1.00 29.14      A    N
ATOM   4241  CA   LEU B 222     -48.631  -4.018  13.071  1.00 29.40      A    C
ATOM   4242  C    LEU B 222     -48.857  -4.024  14.574  1.00 29.74      A    C
ATOM   4243  O    LEU B 222     -47.983  -4.429  15.323  1.00 29.77      A    O
ATOM   4244  CB   LEU B 222     -48.961  -5.378  12.459  1.00 29.21      A    C
ATOM   4245  CG   LEU B 222     -48.769  -5.437  10.944  1.00 29.03      A    C
ATOM   4246  CD1  LEU B 222     -50.051  -5.124  10.190  1.00 29.12      A    C
ATOM   4247  CD2  LEU B 222     -48.264  -6.776  10.554  1.00 28.70      A    C
ATOM   4248  N    ASP B 223     -50.027  -3.553  15.001  1.00 30.29      A    N
ATOM   4249  CA   ASP B 223     -50.409  -3.553  16.410  1.00 30.86      A    C
ATOM   4250  C    ASP B 223     -51.168  -4.830  16.690  1.00 30.87      A    C
ATOM   4251  O    ASP B 223     -51.612  -5.505  15.764  1.00 30.79      A    O
ATOM   4252  CB   ASP B 223     -51.289  -2.325  16.735  1.00 31.35      A    C
ATOM   4253  CG   ASP B 223     -51.353  -1.992  18.251  1.00 32.40      A    C
ATOM   4254  OD1  ASP B 223     -50.597  -2.608  19.039  1.00 33.34      A    O
ATOM   4255  OD2  ASP B 223     -52.161  -1.109  18.654  1.00 33.05      A    O
ATOM   4256  N    GLY B 224     -51.291  -5.158  17.971  1.00 31.01      A    N
ATOM   4257  CA   GLY B 224     -52.137  -6.255  18.439  1.00 31.26      A    C
ATOM   4258  C    GLY B 224     -52.080  -7.521  17.602  1.00 31.24      A    C
ATOM   4259  O    GLY B 224     -53.072  -7.930  16.981  1.00 31.44      A    O
ATOM   4260  N    GLU B 225     -50.910  -8.141  17.569  1.00 31.05      A    N
ATOM   4261  CA   GLU B 225     -50.777  -9.422  16.903  1.00 30.96      A    C
ATOM   4262  C    GLU B 225     -50.953 -10.527  17.935  1.00 31.01      A    C
ATOM   4263  O    GLU B 225     -51.687 -11.479  17.702  1.00 30.93      A    O
ATOM   4264  CB   GLU B 225     -49.425  -9.509  16.204  1.00 30.80      A    C
ATOM   4265  CG   GLU B 225     -49.180 -10.809  15.493  1.00 31.07      A    C
ATOM   4266  CD   GLU B 225     -48.568 -11.854  16.385  1.00 31.84      A    C
ATOM   4267  OE1  GLU B 225     -47.779 -11.500  17.274  1.00 32.64      A    O
ATOM   4268  OE2  GLU B 225     -48.868 -13.039  16.199  1.00 32.29      A    O
ATOM   4269  N    GLU B 226     -50.285 -10.370  19.076  1.00 31.30      A    N
ATOM   4270  CA   GLU B 226     -50.368 -11.313  20.178  1.00 31.77      A    C
ATOM   4271  C    GLU B 226     -51.765 -11.275  20.793  1.00 32.42      A    C
ATOM   4272  O    GLU B 226     -52.355 -10.204  20.960  1.00 32.59      A    O
ATOM   4273  CB   GLU B 226     -49.322 -10.983  21.248  1.00 31.67      A    C
ATOM   4274  CG   GLU B 226     -47.877 -10.916  20.761  1.00 30.94      A    C
ATOM   4275  CD   GLU B 226     -47.136 -12.232  20.858  1.00 30.24      A    C
ATOM   4276  OE1  GLU B 226     -47.783 -13.301  20.873  1.00 30.22      A    O
ATOM   4277  OE2  GLU B 226     -45.889 -12.192  20.912  1.00 29.64      A    O
ATOM   4278  N    ALA B 227     -52.276 -12.455  21.132  1.00 33.01      A    N
ATOM   4279  CA   ALA B 227     -53.592 -12.621  21.743  1.00 33.74      A    C
ATOM   4280  C    ALA B 227     -53.717 -11.947  23.117  1.00 34.41      A    C
ATOM   4281  O    ALA B 227     -52.715 -11.567  23.741  1.00 34.48      A    O
ATOM   4282  CB   ALA B 227     -53.906 -14.091  21.861  1.00 33.73      A    C
ATOM   4283  N    LEU B 228     -54.954 -11.799  23.588  1.00 35.21      A    N
ATOM   4284  CA   LEU B 228     -55.186 -11.185  24.891  1.00 35.92      A    C
ATOM   4285  C    LEU B 228     -55.602 -12.175  25.973  1.00 36.68      A    C
ATOM   4286  O    LEU B 228     -55.066 -12.135  27.084  1.00 36.96      A    O
ATOM   4287  CB   LEU B 228     -56.156  -9.995  24.805  1.00 35.86      A    C
ATOM   4288  CG   LEU B 228     -55.654  -8.613  24.346  1.00 35.20      A    C
ATOM   4289  CD1  LEU B 228     -56.176  -8.277  22.974  1.00 34.75      A    C
ATOM   4290  CD2  LEU B 228     -54.130  -8.455  24.396  1.00 34.62      A    C
```

FIGURE 1 (cont'd)

```
ATOM   4291  N    LYS B 229     -56.550 -13.057  25.663  1.00 37.40       A  N
ATOM   4292  CA   LYS B 229     -56.895 -14.142  26.585  1.00 38.18       A  C
ATOM   4293  C    LYS B 229     -56.087 -15.371  26.161  1.00 38.17       A  C
ATOM   4294  O    LYS B 229     -54.998 -15.588  26.680  1.00 38.11       A  O
ATOM   4295  CB   LYS B 229     -58.414 -14.397  26.615  1.00 38.69       A  C
ATOM   4296  CG   LYS B 229     -58.929 -15.305  27.758  1.00 39.50       A  C
ATOM   4297  CD   LYS B 229     -59.209 -14.543  29.062  1.00 40.09       A  C
ATOM   4298  CE   LYS B 229     -59.877 -13.180  28.849  1.00 41.78       A  C
ATOM   4299  NZ   LYS B 229     -59.418 -12.198  29.912  1.00 42.12       A  N
ATOM   4300  N    GLU B 230     -56.605 -16.157  25.217  1.00 38.35       A  N
ATOM   4301  CA   GLU B 230     -55.794 -17.181  24.565  1.00 38.52       A  C
ATOM   4302  C    GLU B 230     -55.962 -17.226  23.044  1.00 38.25       A  C
ATOM   4303  O    GLU B 230     -57.042 -16.972  22.510  1.00 38.29       A  O
ATOM   4304  CB   GLU B 230     -55.956 -18.565  25.211  1.00 38.95       A  C
ATOM   4305  CG   GLU B 230     -54.730 -19.499  24.975  1.00 39.92       A  C
ATOM   4306  CD   GLU B 230     -53.357 -18.864  25.343  1.00 40.11       A  C
ATOM   4307  OE1  GLU B 230     -52.581 -18.414  24.451  1.00 38.75       A  O
ATOM   4308  N    TRP B 231     -54.857 -17.551  22.376  1.00 37.92       A  N
ATOM   4309  CA   TRP B 231     -54.739 -17.559  20.930  1.00 37.65       A  C
ATOM   4310  C    TRP B 231     -55.883 -18.284  20.253  1.00 38.00       A  C
ATOM   4311  O    TRP B 231     -56.229 -19.399  20.628  1.00 38.34       A  O
ATOM   4312  CB   TRP B 231     -53.409 -18.193  20.527  1.00 37.31       A  C
ATOM   4313  CG   TRP B 231     -53.099 -18.011  19.081  1.00 36.74       A  C
ATOM   4314  CD1  TRP B 231     -53.510 -18.802  18.054  1.00 36.71       A  C
ATOM   4315  CD2  TRP B 231     -52.324 -16.963  18.494  1.00 36.12       A  C
ATOM   4316  CE2  TRP B 231     -52.312 -17.184  17.103  1.00 35.88       A  C
ATOM   4317  CE3  TRP B 231     -51.639 -15.856  19.007  1.00 35.79       A  C
ATOM   4318  NE1  TRP B 231     -53.044 -18.316  16.861  1.00 36.36       A  N
ATOM   4319  CZ2  TRP B 231     -51.644 -16.343  16.217  1.00 35.22       A  C
ATOM   4320  CZ3  TRP B 231     -50.976 -15.022  18.124  1.00 35.07       A  C
ATOM   4321  CH2  TRP B 231     -50.986 -15.272  16.743  1.00 34.77       A  C
ATOM   4322  N    GLY B 232     -56.458 -17.641  19.246  1.00 38.13       A  N
ATOM   4323  CA   GLY B 232     -57.562 -18.209  18.490  1.00 38.49       A  C
ATOM   4324  C    GLY B 232     -57.927 -17.298  17.344  1.00 38.69       A  C
ATOM   4325  O    GLY B 232     -57.449 -16.166  17.292  1.00 38.41       A  O
ATOM   4326  N    PRO B 233     -58.775 -17.783  16.414  1.00 39.13       A  N
ATOM   4327  CA   PRO B 233     -59.193 -16.996  15.242  1.00 39.31       A  C
ATOM   4328  C    PRO B 233     -59.803 -15.638  15.597  1.00 39.53       A  C
ATOM   4329  O    PRO B 233     -59.619 -14.672  14.854  1.00 39.23       A  O
ATOM   4330  CB   PRO B 233     -60.243 -17.891  14.578  1.00 39.49       A  C
ATOM   4331  CG   PRO B 233     -59.843 -19.274  14.961  1.00 39.61       A  C
ATOM   4332  CD   PRO B 233     -59.304 -19.160  16.361  1.00 39.39       A  C
ATOM   4333  N    LYS B 234     -60.518 -15.573  16.722  1.00 40.12       A  N
ATOM   4334  CA   LYS B 234     -61.148 -14.327  17.165  1.00 40.68       A  C
ATOM   4335  C    LYS B 234     -60.301 -13.528  18.179  1.00 40.47       A  C
ATOM   4336  O    LYS B 234     -60.631 -12.370  18.489  1.00 40.61       A  O
ATOM   4337  CB   LYS B 234     -62.578 -14.589  17.674  1.00 41.28       A  C
ATOM   4338  CG   LYS B 234     -63.639 -14.612  16.555  1.00 42.33       A  C
ATOM   4339  CD   LYS B 234     -64.888 -15.439  16.912  1.00 43.53       A  C
ATOM   4340  CE   LYS B 234     -65.982 -14.625  17.616  1.00 43.76       A  C
ATOM   4341  N    ASP B 235     -59.212 -14.133  18.668  1.00 40.07       A  N
ATOM   4342  CA   ASP B 235     -58.278 -13.455  19.577  1.00 39.58       A  C
ATOM   4343  C    ASP B 235     -56.827 -13.590  19.097  1.00 39.06       A  C
ATOM   4344  O    ASP B 235     -56.069 -14.402  19.622  1.00 39.07       A  O
ATOM   4345  CB   ASP B 235     -58.457 -13.969  21.021  1.00 39.83       A  C
ATOM   4346  CG   ASP B 235     -57.531 -13.278  22.030  1.00 39.54       A  C
ATOM   4347  OD1  ASP B 235     -57.133 -13.940  23.013  1.00 39.27       A  O
ATOM   4348  OD2  ASP B 235     -57.198 -12.088  21.851  1.00 39.17       A  O
ATOM   4349  N    SER B 236     -56.465 -12.798  18.085  1.00 38.44       A  N
ATOM   4350  CA   SER B 236     -55.100 -12.730  17.532  1.00 37.78       A  C
ATOM   4351  C    SER B 236     -55.083 -11.975  16.220  1.00 37.48       A  C
ATOM   4352  O    SER B 236     -56.042 -12.033  15.457  1.00 37.51       A  O
ATOM   4353  CB   SER B 236     -54.525 -14.120  17.281  1.00 37.67       A  C
ATOM   4354  OG   SER B 236     -55.217 -14.774  16.239  1.00 37.62       A  O
ATOM   4355  N    LEU B 237     -53.981 -11.288  15.948  1.00 37.16       A  N
```

FIGURE 1 (cont'd)

```
ATOM   4356  CA   LEU B 237     -53.787 -10.619  14.657  1.00 37.08      A   C
ATOM   4357  C    LEU B 237     -54.844  -9.541  14.399  1.00 37.26      A   C
ATOM   4358  O    LEU B 237     -55.455  -9.506  13.330  1.00 37.40      A   O
ATOM   4359  CB   LEU B 237     -53.808 -11.639  13.498  1.00 36.89      A   C
ATOM   4360  CG   LEU B 237     -53.104 -12.991  13.623  1.00 36.55      A   C
ATOM   4361  CD1  LEU B 237     -53.634 -13.940  12.600  1.00 36.65      A   C
ATOM   4362  CD2  LEU B 237     -51.617 -12.856  13.460  1.00 36.08      A   C
ATOM   4363  N    TYR B 238     -55.071  -8.671  15.375  1.00 37.37      A   N
ATOM   4364  CA   TYR B 238     -56.043  -7.596  15.206  1.00 37.46      A   C
ATOM   4365  C    TYR B 238     -55.554  -6.559  14.200  1.00 37.13      A   C
ATOM   4366  O    TYR B 238     -56.328  -6.091  13.375  1.00 37.25      A   O
ATOM   4367  CB   TYR B 238     -56.376  -6.928  16.544  1.00 37.80      A   C
ATOM   4368  CG   TYR B 238     -56.963  -7.857  17.569  1.00 38.35      A   C
ATOM   4369  CD1  TYR B 238     -58.288  -8.256  17.489  1.00 39.29      A   C
ATOM   4370  CD2  TYR B 238     -56.187  -8.337  18.622  1.00 38.48      A   C
ATOM   4371  CE1  TYR B 238     -58.829  -9.122  18.427  1.00 39.70      A   C
ATOM   4372  CE2  TYR B 238     -56.718  -9.200  19.570  1.00 38.96      A   C
ATOM   4373  CZ   TYR B 238     -58.036  -9.591  19.468  1.00 39.37      A   C
ATOM   4374  OH   TYR B 238     -58.553 -10.446  20.413  1.00 39.62      A   O
ATOM   4375  N    GLY B 239     -54.272  -6.214  14.265  1.00 36.71      A   N
ATOM   4376  CA   GLY B 239     -53.699  -5.217  13.367  1.00 36.45      A   C
ATOM   4377  C    GLY B 239     -53.667  -5.655  11.910  1.00 36.25      A   C
ATOM   4378  O    GLY B 239     -54.052  -4.906  11.010  1.00 36.33      A   O
ATOM   4379  N    SER B 240     -53.210  -6.879  11.686  1.00 35.99      A   N
ATOM   4380  CA   SER B 240     -53.063  -7.420  10.341  1.00 35.71      A   C
ATOM   4381  C    SER B 240     -54.398  -7.731   9.697  1.00 35.71      A   C
ATOM   4382  O    SER B 240     -54.590  -7.423   8.524  1.00 35.82      A   O
ATOM   4383  CB   SER B 240     -52.171  -8.661  10.353  1.00 35.61      A   C
ATOM   4384  OG   SER B 240     -52.403  -9.448  11.514  1.00 35.92      A   O
ATOM   4385  N    ARG B 241     -55.313  -8.339  10.454  1.00 35.72      A   N
ATOM   4386  CA   ARG B 241     -56.658  -8.642   9.947  1.00 35.94      A   C
ATOM   4387  C    ARG B 241     -57.401  -7.386   9.520  1.00 36.01      A   C
ATOM   4388  O    ARG B 241     -58.139  -7.401   8.531  1.00 36.21      A   O
ATOM   4389  CB   ARG B 241     -57.492  -9.427  10.963  1.00 36.03      A   C
ATOM   4390  CG   ARG B 241     -57.369 -10.927  10.810  1.00 36.66      A   C
ATOM   4391  CD   ARG B 241     -58.462 -11.680  11.541  1.00 37.98      A   C
ATOM   4392  NE   ARG B 241     -58.233 -11.708  12.984  1.00 39.21      A   N
ATOM   4393  CZ   ARG B 241     -58.926 -10.993  13.868  1.00 40.16      A   C
ATOM   4394  NH1  ARG B 241     -59.899 -10.193  13.460  1.00 41.11      A   N
ATOM   4395  NH2  ARG B 241     -58.652 -11.083  15.164  1.00 40.49      A   N
ATOM   4396  N    HIS B 242     -57.186  -6.299  10.258  1.00 35.97      A   N
ATOM   4397  CA   HIS B 242     -57.807  -5.017   9.939  1.00 36.05      A   C
ATOM   4398  C    HIS B 242     -57.150  -4.316   8.743  1.00 35.71      A   C
ATOM   4399  O    HIS B 242     -57.840  -3.898   7.808  1.00 35.92      A   O
ATOM   4400  CB   HIS B 242     -57.806  -4.105  11.157  1.00 36.32      A   C
ATOM   4401  CG   HIS B 242     -58.472  -2.793  10.916  1.00 37.12      A   C
ATOM   4402  CD2  HIS B 242     -59.779  -2.442  10.923  1.00 37.91      A   C
ATOM   4403  ND1  HIS B 242     -57.768  -1.654  10.598  1.00 37.30      A   N
ATOM   4404  CE1  HIS B 242     -58.613  -0.652  10.432  1.00 37.98      A   C
ATOM   4405  NE2  HIS B 242     -59.840  -1.104  10.625  1.00 38.39      A   N
ATOM   4406  N    LEU B 243     -55.825  -4.187   8.776  1.00 35.09      A   N
ATOM   4407  CA   LEU B 243     -55.104  -3.594   7.665  1.00 34.61      A   C
ATOM   4408  C    LEU B 243     -55.429  -4.315   6.371  1.00 34.71      A   C
ATOM   4409  O    LEU B 243     -55.726  -3.675   5.373  1.00 34.94      A   O
ATOM   4410  CB   LEU B 243     -53.596  -3.571   7.914  1.00 34.17      A   C
ATOM   4411  CG   LEU B 243     -52.749  -2.827   6.872  1.00 33.47      A   C
ATOM   4412  CD1  LEU B 243     -53.130  -1.380   6.774  1.00 33.24      A   C
ATOM   4413  CD2  LEU B 243     -51.283  -2.937   7.192  1.00 32.87      A   C
ATOM   4414  N    ALA B 244     -55.400  -5.641   6.395  1.00 34.72      A   N
ATOM   4415  CA   ALA B 244     -55.759  -6.426   5.227  1.00 35.02      A   C
ATOM   4416  C    ALA B 244     -57.141  -6.036   4.701  1.00 35.49      A   C
ATOM   4417  O    ALA B 244     -57.298  -5.775   3.507  1.00 35.65      A   O
ATOM   4418  CB   ALA B 244     -55.691  -7.910   5.543  1.00 34.78      A   C
ATOM   4419  N    GLN B 245     -58.128  -5.978   5.596  1.00 36.00      A   N
ATOM   4420  CA   GLN B 245     -59.479  -5.574   5.219  1.00 36.60      A   C
```

FIGURE 1 (cont'd)

```
ATOM   4421  C   GLN B 245     -59.471  -4.196   4.584  1.00 36.97      A  C
ATOM   4422  O   GLN B 245     -60.063  -4.002   3.522  1.00 37.25      A  O
ATOM   4423  CB  GLN B 245     -60.406  -5.559   6.422  1.00 36.66      A  C
ATOM   4424  CG  GLN B 245     -60.897  -6.899   6.837  1.00 37.25      A  C
ATOM   4425  CD  GLN B 245     -61.285  -6.942   8.304  1.00 38.16      A  C
ATOM   4426  NE2 GLN B 245     -61.748  -8.110   8.762  1.00 38.22      A  N
ATOM   4427  OE1 GLN B 245     -61.164  -5.940   9.026  1.00 39.22      A  O
ATOM   4428  N   LEU B 246     -58.780  -3.253   5.233  1.00 37.10      A  N
ATOM   4429  CA  LEU B 246     -58.753  -1.846   4.815  1.00 37.34      A  C
ATOM   4430  C   LEU B 246     -58.000  -1.626   3.505  1.00 37.74      A  C
ATOM   4431  O   LEU B 246     -58.320  -0.704   2.763  1.00 38.05      A  O
ATOM   4432  CB  LEU B 246     -58.178  -0.967   5.933  1.00 37.06      A  C
ATOM   4433  CG  LEU B 246     -58.190   0.553   5.786  1.00 36.46      A  C
ATOM   4434  CD1 LEU B 246     -56.768   1.051   5.721  1.00 35.19      A  C
ATOM   4435  N   MET B 247     -57.013  -2.470   3.221  1.00 38.02      A  N
ATOM   4436  CA  MET B 247     -56.265  -2.375   1.972  1.00 38.44      A  C
ATOM   4437  C   MET B 247     -57.060  -2.929   0.800  1.00 39.23      A  C
ATOM   4438  O   MET B 247     -56.887  -2.499  -0.338  1.00 39.42      A  O
ATOM   4439  CB  MET B 247     -54.915  -3.084   2.079  1.00 37.97      A  C
ATOM   4440  CG  MET B 247     -53.888  -2.337   2.911  1.00 37.33      A  C
ATOM   4441  SD  MET B 247     -52.245  -3.056   2.791  1.00 36.51      A  S
ATOM   4442  CE  MET B 247     -51.566  -2.113   1.432  1.00 36.93      A  C
ATOM   4443  N   GLU B 248     -57.931  -3.889   1.084  1.00 40.15      A  N
ATOM   4444  CA  GLU B 248     -58.788  -4.467   0.052  1.00 41.17      A  C
ATOM   4445  C   GLU B 248     -59.848  -3.469  -0.402  1.00 42.20      A  C
ATOM   4446  O   GLU B 248     -60.265  -3.480  -1.559  1.00 42.74      A  O
ATOM   4447  CB  GLU B 248     -59.461  -5.751   0.547  1.00 41.01      A  C
ATOM   4448  CG  GLU B 248     -59.997  -6.636  -0.580  1.00 39.59      A  C
ATOM   4449  CD  GLU B 248     -60.807  -7.818  -0.079  1.00 38.63      A  C
ATOM   4450  OE1 GLU B 248     -61.351  -8.553  -0.924  1.00 38.50      A  O
ATOM   4451  OE2 GLU B 248     -60.909  -8.022   1.152  1.00 38.14      A  O
ATOM   4452  N   SER B 249     -60.276  -2.607   0.511  1.00 43.03      A  N
ATOM   4453  CA  SER B 249     -61.306  -1.631   0.202  1.00 43.98      A  C
ATOM   4454  C   SER B 249     -60.735  -0.344  -0.384  1.00 44.45      A  C
ATOM   4455  O   SER B 249     -61.485   0.547  -0.760  1.00 44.88      A  O
ATOM   4456  CB  SER B 249     -62.123  -1.315   1.451  1.00 44.13      A  C
ATOM   4457  OG  SER B 249     -61.391  -0.488   2.347  1.00 44.14      A  O
ATOM   4458  N   ILE B 250     -59.412  -0.255  -0.463  1.00 44.76      A  N
ATOM   4459  CA  ILE B 250     -58.737   0.961  -0.908  1.00 45.28      A  C
ATOM   4460  C   ILE B 250     -58.199   0.776  -2.330  1.00 46.11      A  C
ATOM   4461  O   ILE B 250     -57.203   0.072  -2.526  1.00 45.91      A  O
ATOM   4462  CB  ILE B 250     -57.608   1.356   0.081  1.00 44.83      A  C
ATOM   4463  CG1 ILE B 250     -57.293   2.848   0.014  1.00 44.79      A  C
ATOM   4464  CD1 ILE B 250     -55.999   3.163  -0.728  1.00 44.43      A  C
ATOM   4465  N   PRO B 251     -58.868   1.395  -3.329  1.00 47.21      A  N
ATOM   4466  CA  PRO B 251     -58.512   1.265  -4.740  1.00 47.90      A  C
ATOM   4467  C   PRO B 251     -57.151   1.851  -5.052  1.00 48.33      A  C
ATOM   4468  O   PRO B 251     -56.697   2.786  -4.389  1.00 48.37      A  O
ATOM   4469  CB  PRO B 251     -59.597   2.073  -5.459  1.00 48.23      A  C
ATOM   4470  CG  PRO B 251     -60.719   2.115  -4.512  1.00 48.26      A  C
ATOM   4471  CD  PRO B 251     -60.070   2.226  -3.171  1.00 47.60      A  C
ATOM   4472  N   HIS B 252     -56.528   1.299  -6.085  1.00 48.78      A  N
ATOM   4473  CA  HIS B 252     -55.156   1.590  -6.472  1.00 49.11      A  C
ATOM   4474  C   HIS B 252     -55.064   0.808  -7.761  1.00 49.72      A  C
ATOM   4475  O   HIS B 252     -55.937  -0.006  -7.988  1.00 49.97      A  O
ATOM   4476  CB  HIS B 252     -54.233   0.921  -5.459  1.00 47.94      A  C
ATOM   4477  CG  HIS B 252     -52.784   1.174  -5.699  1.00 47.76      A  C
ATOM   4478  CD2 HIS B 252     -51.811   0.391  -6.220  1.00 47.56      A  C
ATOM   4479  ND1 HIS B 252     -52.186   2.371  -5.376  1.00 48.09      A  N
ATOM   4480  CE1 HIS B 252     -50.903   2.317  -5.686  1.00 48.06      A  C
ATOM   4481  NE2 HIS B 252     -50.652   1.126  -6.203  1.00 47.82      A  N
ATOM   4482  N   SER B 253     -54.161   1.012  -8.710  1.00 50.15      A  N
ATOM   4483  CA  SER B 253     -53.688   2.176  -9.365  1.00 50.15      A  C
ATOM   4484  C   SER B 253     -53.395   1.692 -10.801  1.00 50.25      A  C
ATOM   4485  O   SER B 253     -53.279   2.518 -11.642  1.00 50.67      A  O
```

FIGURE 1 (cont'd)

```
ATOM   4486  CB  SER B 253     -52.443   2.666  -8.700  1.00 49.29      A    C
ATOM   4487  OG  SER B 253     -51.672   3.496  -9.504  1.00 48.82      A    O
ATOM   4488  N   PRO B 254     -52.993   0.428 -11.021  1.00 49.85      A    N
ATOM   4489  CA  PRO B 254     -53.553  -0.789 -11.601  1.00 49.44      A    C
ATOM   4490  C   PRO B 254     -53.363  -1.896 -10.613  1.00 49.07      A    C
ATOM   4491  O   PRO B 254     -52.622  -2.823 -10.904  1.00 49.23      A    O
ATOM   4492  CB  PRO B 254     -52.631  -1.126 -12.773  1.00 48.68      A    C
ATOM   4493  CG  PRO B 254     -51.890   0.033 -13.052  1.00 48.82      A    C
ATOM   4494  CD  PRO B 254     -51.767   0.794 -11.769  1.00 49.09      A    C
ATOM   4495  N   GLY B 255     -53.932  -1.726  -9.424  1.00 48.45      A    N
ATOM   4496  CA  GLY B 255     -54.326  -2.803  -8.550  1.00 47.55      A    C
ATOM   4497  C   GLY B 255     -55.235  -3.780  -9.244  1.00 47.08      A    C
ATOM   4498  O   GLY B 255     -54.801  -4.456 -10.154  1.00 47.37      A    O
ATOM   4499  N   PRO B 256     -56.531  -3.838  -8.915  1.00 46.60      A    N
ATOM   4500  CA  PRO B 256     -57.724  -3.190  -8.378  1.00 46.34      A    C
ATOM   4501  C   PRO B 256     -57.599  -2.483  -7.037  1.00 45.75      A    C
ATOM   4502  O   PRO B 256     -57.847  -1.278  -6.955  1.00 45.92      A    O
ATOM   4503  CB  PRO B 256     -58.718  -4.360  -8.262  1.00 46.51      A    C
ATOM   4504  CG  PRO B 256     -58.201  -5.404  -9.141  1.00 46.53      A    C
ATOM   4505  CD  PRO B 256     -56.758  -5.286  -9.061  1.00 46.70      A    C
ATOM   4506  N   THR B 257     -57.255  -3.238  -5.997  1.00 44.74      A    N
ATOM   4507  CA  THR B 257     -57.120  -2.703  -4.644  1.00 43.63      A    C
ATOM   4508  C   THR B 257     -55.653  -2.606  -4.235  1.00 42.91      A    C
ATOM   4509  O   THR B 257     -54.779  -3.071  -4.953  1.00 42.83      A    O
ATOM   4510  CB  THR B 257     -57.877  -3.565  -3.623  1.00 43.46      A    C
ATOM   4511  OG1 THR B 257     -57.454  -4.925  -3.737  1.00 43.09      A    O
ATOM   4512  N   ARG B 258     -55.383  -2.007  -3.081  1.00 42.05      A    N
ATOM   4513  CA  ARG B 258     -54.008  -1.866  -2.605  1.00 41.05      A    C
ATOM   4514  C   ARG B 258     -53.371  -3.198  -2.216  1.00 40.56      A    C
ATOM   4515  O   ARG B 258     -52.153  -3.286  -2.066  1.00 40.54      A    O
ATOM   4516  CB  ARG B 258     -53.911  -0.858  -1.456  1.00 40.13      A    C
ATOM   4517  CG  ARG B 258     -53.642   0.557  -1.924  1.00 40.06      A    C
ATOM   4518  CD  ARG B 258     -52.959   1.383  -0.854  1.00 40.00      A    C
ATOM   4519  NE  ARG B 258     -52.246   2.541  -1.408  1.00 40.06      A    N
ATOM   4520  CZ  ARG B 258     -51.015   2.454  -1.958  1.00 33.05      A    C
ATOM   4521  NH1 ARG B 258     -50.391   1.272  -2.041  1.00 30.46      A    N
ATOM   4522  NH2 ARG B 258     -50.394   3.534  -2.437  1.00 30.69      A    N
ATOM   4523  N   ILE B 259     -54.194  -4.232  -2.065  1.00 39.85      A    N
ATOM   4524  CA  ILE B 259     -53.690  -5.564  -1.767  1.00 38.86      A    C
ATOM   4525  C   ILE B 259     -52.856  -6.115  -2.901  1.00 38.81      A    C
ATOM   4526  O   ILE B 259     -51.858  -6.796  -2.671  1.00 38.84      A    O
ATOM   4527  CB  ILE B 259     -54.812  -6.523  -1.415  1.00 37.98      A    C
ATOM   4528  CG1 ILE B 259     -54.784  -6.752   0.086  1.00 37.65      A    C
ATOM   4529  CG2 ILE B 259     -54.639  -7.874  -2.112  1.00 37.56      A    C
ATOM   4530  CD1 ILE B 259     -56.128  -6.931   0.687  1.00 38.52      A    C
ATOM   4531  N   GLN B 260     -53.245  -5.797  -4.126  1.00 38.47      A    N
ATOM   4532  CA  GLN B 260     -52.511  -6.277  -5.281  1.00 37.90      A    C
ATOM   4533  C   GLN B 260     -51.231  -5.466  -5.468  1.00 37.77      A    C
ATOM   4534  O   GLN B 260     -50.432  -5.766  -6.358  1.00 38.20      A    O
ATOM   4535  CB  GLN B 260     -53.361  -6.249  -6.559  1.00 37.05      A    C
ATOM   4536  CG  GLN B 260     -54.843  -6.000  -6.379  1.00 36.67      A    C
ATOM   4537  CD  GLN B 260     -55.531  -6.970  -5.443  1.00 36.32      A    C
ATOM   4538  NE2 GLN B 260     -56.237  -6.436  -4.476  1.00 37.24      A    N
ATOM   4539  OE1 GLN B 260     -55.438  -8.172  -5.585  1.00 36.69      A    O
ATOM   4540  N   ALA B 261     -51.038  -4.446  -4.630  1.00 37.14      A    N
ATOM   4541  CA  ALA B 261     -49.847  -3.608  -4.701  1.00 36.47      A    C
ATOM   4542  C   ALA B 261     -48.655  -4.259  -4.006  1.00 35.72      A    C
ATOM   4543  O   ALA B 261     -47.508  -3.918  -4.277  1.00 35.69      A    O
ATOM   4544  N   ILE B 262     -48.931  -5.201  -3.115  1.00 34.70      A    N
ATOM   4545  CA  ILE B 262     -47.885  -5.941  -2.449  1.00 33.61      A    C
ATOM   4546  C   ILE B 262     -47.355  -6.970  -3.429  1.00 33.55      A    C
ATOM   4547  O   ILE B 262     -48.033  -7.952  -3.713  1.00 33.75      A    O
ATOM   4548  CB  ILE B 262     -48.440  -6.663  -1.214  1.00 32.72      A    C
ATOM   4549  CG1 ILE B 262     -49.157  -5.678  -0.278  1.00 32.11      A    C
ATOM   4550  CG2 ILE B 262     -47.347  -7.497  -0.525  1.00 32.84      A    C
```

FIGURE 1 (cont'd)

```
ATOM   4551  CD1 ILE B 262     -50.184  -6.342   0.644  1.00 31.72      A    C
ATOM   4552  N   GLU B 263     -46.160  -6.733  -3.960  1.00 33.18      A    N
ATOM   4553  CA  GLU B 263     -45.489  -7.706  -4.812  1.00 32.78      A    C
ATOM   4554  C   GLU B 263     -44.960  -8.863  -3.966  1.00 32.17      A    C
ATOM   4555  O   GLU B 263     -45.003 -10.012  -4.389  1.00 32.28      A    O
ATOM   4556  CB  GLU B 263     -44.350  -7.040  -5.585  1.00 33.01      A    C
ATOM   4557  CG  GLU B 263     -43.840  -7.809  -6.812  1.00 33.03      A    C
ATOM   4558  CD  GLU B 263     -42.892  -6.981  -7.690  1.00 32.60      A    C
ATOM   4559  OE1 GLU B 263     -42.029  -6.260  -7.144  1.00 32.71      A    O
ATOM   4560  OE2 GLU B 263     -43.011  -7.037  -8.936  1.00 31.13      A    O
ATOM   4561  N   LEU B 264     -44.470  -8.549  -2.769  1.00 31.31      A    N
ATOM   4562  CA  LEU B 264     -44.034  -9.564  -1.816  1.00 30.34      A    C
ATOM   4563  C   LEU B 264     -44.205  -9.099  -0.372  1.00 29.74      A    C
ATOM   4564  O   LEU B 264     -43.691  -8.050   0.005  1.00 29.80      A    O
ATOM   4565  CB  LEU B 264     -42.580  -9.959  -2.073  1.00 30.24      A    C
ATOM   4566  CG  LEU B 264     -41.952 -10.996  -1.143  1.00 29.81      A    C
ATOM   4567  CD1 LEU B 264     -42.701 -12.321  -1.177  1.00 29.73      A    C
ATOM   4568  CD2 LEU B 264     -40.508 -11.198  -1.517  1.00 29.60      A    C
ATOM   4569  N   PHE B 265     -44.928  -9.889   0.418  1.00 28.89      A    N
ATOM   4570  CA  PHE B 265     -45.103  -9.672   1.854  1.00 27.89      A    C
ATOM   4571  C   PHE B 265     -44.082 -10.523   2.624  1.00 27.61      A    C
ATOM   4572  O   PHE B 265     -44.274 -11.718   2.844  1.00 27.48      A    O
ATOM   4573  CB  PHE B 265     -46.539 -10.045   2.252  1.00 27.64      A    C
ATOM   4574  CG  PHE B 265     -46.949  -9.599   3.641  1.00 26.28      A    C
ATOM   4575  CD1 PHE B 265     -47.639  -8.409   3.823  1.00 25.32      A    C
ATOM   4576  CD2 PHE B 265     -46.687 -10.388   4.759  1.00 25.19      A    C
ATOM   4577  CE1 PHE B 265     -48.033  -7.995   5.094  1.00 23.05      A    C
ATOM   4578  CE2 PHE B 265     -47.083  -9.974   6.032  1.00 23.20      A    C
ATOM   4579  CZ  PHE B 265     -47.757  -8.776   6.192  1.00 22.29      A    C
ATOM   4580  N   MET B 266     -42.987  -9.894   3.027  1.00 27.32      A    N
ATOM   4581  CA  MET B 266     -41.925 -10.582   3.748  1.00 27.14      A    C
ATOM   4582  C   MET B 266     -42.029 -10.274   5.237  1.00 27.09      A    C
ATOM   4583  O   MET B 266     -41.592  -9.219   5.691  1.00 27.18      A    O
ATOM   4584  CB  MET B 266     -40.565 -10.153   3.193  1.00 27.10      A    C
ATOM   4585  CG  MET B 266     -39.371 -10.900   3.747  1.00 26.77      A    C
ATOM   4586  SD  MET B 266     -37.855 -10.374   2.914  1.00 24.94      A    S
ATOM   4587  CE  MET B 266     -37.012  -9.641   4.321  1.00 24.25      A    C
ATOM   4588  N   LEU B 267     -42.613 -11.203   5.986  1.00 26.98      A    N
ATOM   4589  CA  LEU B 267     -42.857 -11.009   7.413  1.00 26.90      A    C
ATOM   4590  C   LEU B 267     -41.688 -11.461   8.294  1.00 26.99      A    C
ATOM   4591  O   LEU B 267     -41.267 -12.623   8.228  1.00 27.03      A    O
ATOM   4592  CB  LEU B 267     -44.150 -11.723   7.830  1.00 26.84      A    C
ATOM   4593  CG  LEU B 267     -44.570 -11.706   9.303  1.00 26.55      A    C
ATOM   4594  CD1 LEU B 267     -44.822 -10.291   9.796  1.00 26.52      A    C
ATOM   4595  CD2 LEU B 267     -45.799 -12.539   9.485  1.00 26.44      A    C
ATOM   4596  N   LEU B 268     -41.194 -10.536   9.124  1.00 27.06      A    N
ATOM   4597  CA  LEU B 268     -40.057 -10.779  10.010  1.00 27.22      A    C
ATOM   4598  C   LEU B 268     -40.507 -11.014  11.439  1.00 27.44      A    C
ATOM   4599  O   LEU B 268     -41.188 -10.171  12.025  1.00 27.57      A    O
ATOM   4600  CB  LEU B 268     -39.107  -9.595   9.974  1.00 27.15      A    C
ATOM   4601  CG  LEU B 268     -37.998  -9.568   8.931  1.00 27.19      A    C
ATOM   4602  CD1 LEU B 268     -38.529  -9.184   7.574  1.00 27.47      A    C
ATOM   4603  CD2 LEU B 268     -36.971  -8.569   9.367  1.00 27.08      A    C
ATOM   4604  N   ASP B 269     -40.120 -12.154  12.003  1.00 27.66      A    N
ATOM   4605  CA  ASP B 269     -40.575 -12.523  13.335  1.00 27.96      A    C
ATOM   4606  C   ASP B 269     -39.606 -13.419  14.055  1.00 27.89      A    C
ATOM   4607  O   ASP B 269     -38.885 -14.190  13.439  1.00 28.07      A    O
ATOM   4608  CB  ASP B 269     -41.922 -13.236  13.260  1.00 28.24      A    C
ATOM   4609  CG  ASP B 269     -42.854 -12.827  14.375  1.00 29.35      A    C
ATOM   4610  OD1 ASP B 269     -43.099 -11.607  14.501  1.00 30.26      A    O
ATOM   4611  OD2 ASP B 269     -43.350 -13.718  15.105  1.00 30.10      A    O
ATOM   4612  N   LEU B 270     -39.623 -13.321  15.376  1.00 27.80      A    N
ATOM   4613  CA  LEU B 270     -38.791 -14.149  16.253  1.00 27.81      A    C
ATOM   4614  C   LEU B 270     -37.328 -14.192  15.808  1.00 27.91      A    C
ATOM   4615  O   LEU B 270     -36.706 -15.259  15.755  1.00 27.98      A    O
```

FIGURE 1 (cont'd)

```
ATOM   4616  CB   LEU B 270     -39.370 -15.564  16.418  1.00 27.70      A   C
ATOM   4617  CG   LEU B 270     -40.847 -15.716  16.781  1.00 27.71      A   C
ATOM   4618  CD1  LEU B 270     -41.135 -17.131  17.218  1.00 27.63      A   C
ATOM   4619  CD2  LEU B 270     -41.273 -14.741  17.867  1.00 28.01      A   C
ATOM   4620  N    LEU B 271     -36.789 -13.022  15.484  1.00 27.99      A   N
ATOM   4621  CA   LEU B 271     -35.391 -12.904  15.118  1.00 28.28      A   C
ATOM   4622  C    LEU B 271     -34.635 -12.207  16.233  1.00 28.71      A   C
ATOM   4623  O    LEU B 271     -35.150 -11.271  16.851  1.00 28.73      A   O
ATOM   4624  CB   LEU B 271     -35.236 -12.107  13.831  1.00 28.09      A   C
ATOM   4625  CG   LEU B 271     -35.873 -12.657  12.562  1.00 27.71      A   C
ATOM   4626  CD1  LEU B 271     -36.734 -11.566  11.936  1.00 27.65      A   C
ATOM   4627  N    GLY B 272     -33.410 -12.666  16.484  1.00 29.25      A   N
ATOM   4628  CA   GLY B 272     -32.557 -12.063  17.499  1.00 29.88      A   C
ATOM   4629  C    GLY B 272     -31.827 -13.064  18.374  1.00 30.45      A   C
ATOM   4630  O    GLY B 272     -30.757 -12.756  18.895  1.00 30.66      A   O
ATOM   4631  N    ALA B 273     -32.403 -14.256  18.544  1.00 30.82      A   N
ATOM   4632  CA   ALA B 273     -31.800 -15.313  19.362  1.00 31.22      A   C
ATOM   4633  C    ALA B 273     -30.566 -15.894  18.670  1.00 31.55      A   C
ATOM   4634  O    ALA B 273     -30.371 -15.670  17.480  1.00 31.59      A   O
ATOM   4635  CB   ALA B 273     -32.826 -16.412  19.659  1.00 31.17      A   C
ATOM   4636  N    PRO B 274     -29.712 -16.615  19.417  1.00 31.96      A   N
ATOM   4637  CA   PRO B 274     -28.615 -17.337  18.769  1.00 32.24      A   C
ATOM   4638  C    PRO B 274     -29.104 -18.543  17.978  1.00 32.34      A   C
ATOM   4639  O    PRO B 274     -30.138 -19.123  18.299  1.00 32.25      A   O
ATOM   4640  CB   PRO B 274     -27.761 -17.813  19.950  1.00 32.50      A   C
ATOM   4641  CG   PRO B 274     -28.693 -17.822  21.123  1.00 32.45      A   C
ATOM   4642  CD   PRO B 274     -29.602 -16.661  20.887  1.00 32.14      A   C
ATOM   4643  N    ASN B 275     -28.351 -18.905  16.950  1.00 32.59      A   N
ATOM   4644  CA   ASN B 275     -28.618 -20.098  16.141  1.00 32.95      A   C
ATOM   4645  C    ASN B 275     -30.064 -20.276  15.658  1.00 32.53      A   C
ATOM   4646  O    ASN B 275     -30.675 -21.324  15.886  1.00 32.76      A   O
ATOM   4647  CB   ASN B 275     -28.119 -21.364  16.855  1.00 33.42      A   C
ATOM   4648  CG   ASN B 275     -26.654 -21.279  17.231  1.00 34.80      A   C
ATOM   4649  ND2  ASN B 275     -26.394 -21.082  18.522  1.00 35.89      A   N
ATOM   4650  OD1  ASN B 275     -25.762 -21.377  16.374  1.00 35.80      A   O
ATOM   4651  N    PRO B 276     -30.614 -19.265  14.972  1.00 32.05      A   N
ATOM   4652  CA   PRO B 276     -31.923 -19.495  14.404  1.00 31.80      A   C
ATOM   4653  C    PRO B 276     -31.807 -20.379  13.168  1.00 31.82      A   C
ATOM   4654  O    PRO B 276     -30.753 -20.409  12.530  1.00 31.89      A   O
ATOM   4655  CB   PRO B 276     -32.382 -18.089  14.024  1.00 31.62      A   C
ATOM   4656  CG   PRO B 276     -31.145 -17.337  13.778  1.00 31.58      A   C
ATOM   4657  CD   PRO B 276     -30.099 -17.922  14.655  1.00 31.87      A   C
ATOM   4658  N    THR B 277     -32.870 -21.117  12.865  1.00 31.86      A   N
ATOM   4659  CA   THR B 277     -32.962 -21.874  11.618  1.00 31.92      A   C
ATOM   4660  C    THR B 277     -34.230 -21.474  10.844  1.00 31.84      A   C
ATOM   4661  O    THR B 277     -35.335 -21.434  11.404  1.00 31.82      A   O
ATOM   4662  CB   THR B 277     -32.851 -23.421  11.829  1.00 32.00      A   C
ATOM   4663  CG2  THR B 277     -31.411 -23.818  12.093  1.00 32.14      A   C
ATOM   4664  OG1  THR B 277     -33.637 -23.830  12.952  1.00 32.26      A   O
ATOM   4665  N    PHE B 278     -34.057 -21.158   9.564  1.00 31.80      A   N
ATOM   4666  CA   PHE B 278     -35.155 -20.720   8.729  1.00 31.79      A   C
ATOM   4667  C    PHE B 278     -35.388 -21.681   7.592  1.00 32.12      A   C
ATOM   4668  O    PHE B 278     -34.442 -22.246   7.056  1.00 32.23      A   O
ATOM   4669  CB   PHE B 278     -34.860 -19.342   8.171  1.00 31.55      A   C
ATOM   4670  CG   PHE B 278     -34.589 -18.302   9.224  1.00 31.33      A   C
ATOM   4671  CD1  PHE B 278     -35.606 -17.836  10.050  1.00 31.25      A   C
ATOM   4672  CD2  PHE B 278     -33.319 -17.773   9.374  1.00 31.20      A   C
ATOM   4673  CE1  PHE B 278     -35.355 -16.870  11.008  1.00 31.18      A   C
ATOM   4674  CE2  PHE B 278     -33.063 -16.802  10.328  1.00 31.02      A   C
ATOM   4675  CZ   PHE B 278     -34.080 -16.354  11.147  1.00 31.01      A   C
ATOM   4676  N    TYR B 279     -36.659 -21.860   7.238  1.00 32.53      A   N
ATOM   4677  CA   TYR B 279     -37.072 -22.709   6.111  1.00 33.08      A   C
ATOM   4678  C    TYR B 279     -38.085 -21.969   5.236  1.00 33.68      A   C
ATOM   4679  O    TYR B 279     -38.625 -20.940   5.641  1.00 33.63      A   O
ATOM   4680  CB   TYR B 279     -37.646 -24.034   6.618  1.00 32.95      A   C
```

FIGURE 1 (cont'd)

```
ATOM   4681  CG  TYR B 279     -36.661 -24.819   7.468  1.00 32.44      A    C
ATOM   4682  CD1 TYR B 279     -35.784 -25.721   6.887  1.00 32.36      A    C
ATOM   4683  CD2 TYR B 279     -36.582 -24.641   8.849  1.00 31.15      A    C
ATOM   4684  CE1 TYR B 279     -34.863 -26.451   7.661  1.00 30.82      A    C
ATOM   4685  CE2 TYR B 279     -35.655 -25.357   9.628  1.00 30.16      A    C
ATOM   4686  CZ  TYR B 279     -34.800 -26.257   9.025  1.00 29.55      A    C
ATOM   4687  OH  TYR B 279     -33.882 -26.957   9.776  1.00 28.50      A    O
ATOM   4688  N   SER B 280     -38.325 -22.471   4.029  1.00 34.61      A    N
ATOM   4689  CA  SER B 280     -39.289 -21.828   3.139  1.00 35.43      A    C
ATOM   4690  C   SER B 280     -40.660 -22.437   3.335  1.00 35.95      A    C
ATOM   4691  O   SER B 280     -40.902 -23.573   2.918  1.00 36.26      A    O
ATOM   4692  CB  SER B 280     -38.866 -21.949   1.678  1.00 35.57      A    C
ATOM   4693  OG  SER B 280     -39.728 -21.185   0.865  1.00 35.76      A    O
ATOM   4694  N   HIS B 281     -41.552 -21.680   3.968  1.00 36.39      A    N
ATOM   4695  CA  HIS B 281     -42.888 -22.175   4.284  1.00 37.11      A    C
ATOM   4696  C   HIS B 281     -43.892 -21.903   3.170  1.00 37.44      A    C
ATOM   4697  O   HIS B 281     -45.043 -22.314   3.259  1.00 37.65      A    O
ATOM   4698  CB  HIS B 281     -43.372 -21.620   5.622  1.00 37.18      A    C
ATOM   4699  CG  HIS B 281     -42.442 -21.909   6.756  1.00 37.79      A    C
ATOM   4700  CD2 HIS B 281     -42.300 -23.006   7.538  1.00 38.66      A    C
ATOM   4701  ND1 HIS B 281     -41.484 -21.011   7.174  1.00 37.78      A    N
ATOM   4702  CE1 HIS B 281     -40.800 -21.535   8.174  1.00 38.21      A    C
ATOM   4703  NE2 HIS B 281     -41.275 -22.746   8.415  1.00 38.93      A    N
ATOM   4704  N   PHE B 282     -43.447 -21.220   2.120  1.00 37.80      A    N
ATOM   4705  CA  PHE B 282     -44.251 -21.052   0.912  1.00 38.17      A    C
ATOM   4706  C   PHE B 282     -43.430 -21.287  -0.346  1.00 38.50      A    C
ATOM   4707  O   PHE B 282     -42.536 -20.500  -0.654  1.00 38.44      A    O
ATOM   4708  CB  PHE B 282     -44.919 -19.676   0.875  1.00 38.07      A    C
ATOM   4709  CG  PHE B 282     -45.804 -19.415   2.048  1.00 37.99      A    C
ATOM   4710  CD1 PHE B 282     -47.008 -20.072   2.173  1.00 38.45      A    C
ATOM   4711  CD2 PHE B 282     -45.421 -18.535   3.036  1.00 37.87      A    C
ATOM   4712  CE1 PHE B 282     -47.816 -19.857   3.258  1.00 38.42      A    C
ATOM   4713  CE2 PHE B 282     -46.228 -18.308   4.122  1.00 37.96      A    C
ATOM   4714  CZ  PHE B 282     -47.429 -18.971   4.233  1.00 38.23      A    C
ATOM   4715  N   PRO B 283     -43.735 -22.374  -1.077  1.00 38.89      A    N
ATOM   4716  CA  PRO B 283     -43.074 -22.709  -2.337  1.00 39.01      A    C
ATOM   4717  C   PRO B 283     -43.309 -21.651  -3.411  1.00 38.89      A    C
ATOM   4718  O   PRO B 283     -42.541 -21.565  -4.359  1.00 38.97      A    O
ATOM   4719  CB  PRO B 283     -43.747 -24.017  -2.746  1.00 39.28      A    C
ATOM   4720  CG  PRO B 283     -44.336 -24.553  -1.499  1.00 39.31      A    C
ATOM   4721  CD  PRO B 283     -44.768 -23.363  -0.731  1.00 39.04      A    C
ATOM   4722  N   ARG B 284     -44.362 -20.855  -3.253  1.00 38.65      A    N
ATOM   4723  CA  ARG B 284     -44.631 -19.727  -4.135  1.00 38.51      A    C
ATOM   4724  C   ARG B 284     -43.437 -18.790  -4.206  1.00 38.70      A    C
ATOM   4725  O   ARG B 284     -43.075 -18.340  -5.282  1.00 38.97      A    O
ATOM   4726  CB  ARG B 284     -45.858 -18.941  -3.662  1.00 38.24      A    C
ATOM   4727  CG  ARG B 284     -46.685 -18.304  -4.782  1.00 37.48      A    C
ATOM   4728  CD  ARG B 284     -45.978 -17.143  -5.477  1.00 35.74      A    C
ATOM   4729  NE  ARG B 284     -46.791 -16.389  -6.439  1.00 34.86      A    N
ATOM   4730  CZ  ARG B 284     -47.671 -15.431  -6.161  1.00 33.66      A    C
ATOM   4731  NH1 ARG B 284     -47.946 -15.118  -4.914  1.00 34.44      A    N
ATOM   4732  NH2 ARG B 284     -48.318 -14.805  -7.132  1.00 32.50      A    N
ATOM   4733  N   THR B 285     -42.829 -18.497  -3.057  1.00 38.77      A    N
ATOM   4734  CA  THR B 285     -41.696 -17.569  -2.987  1.00 38.87      A    C
ATOM   4735  C   THR B 285     -40.357 -18.284  -2.773  1.00 39.26      A    C
ATOM   4736  O   THR B 285     -39.358 -17.661  -2.419  1.00 39.13      A    O
ATOM   4737  CB  THR B 285     -41.910 -16.488  -1.904  1.00 38.47      A    C
ATOM   4738  OG1 THR B 285     -42.278 -17.107  -0.673  1.00 38.12      A    O
ATOM   4739  N   VAL B 286     -40.339 -19.587  -3.039  1.00 39.86      A    N
ATOM   4740  CA  VAL B 286     -39.193 -20.426  -2.722  1.00 40.37      A    C
ATOM   4741  C   VAL B 286     -37.905 -19.859  -3.253  1.00 40.99      A    C
ATOM   4742  O   VAL B 286     -36.849 -20.085  -2.680  1.00 41.06      A    O
ATOM   4743  CB  VAL B 286     -39.357 -21.856  -3.250  1.00 40.29      A    C
ATOM   4744  N   ARG B 287     -37.992 -19.106  -4.338  1.00 41.85      A    N
ATOM   4745  CA  ARG B 287     -36.795 -18.597  -4.984  1.00 42.76      A    C
```

FIGURE 1 (cont'd)

```
ATOM   4746  C    ARG B 287     -36.246 -17.362  -4.302  1.00 42.51      A   C
ATOM   4747  O    ARG B 287     -35.068 -17.050  -4.448  1.00 42.71      A   O
ATOM   4748  CB   ARG B 287     -37.014 -18.347  -6.476  1.00 43.49      A   C
ATOM   4749  CG   ARG B 287     -38.024 -17.278  -6.789  1.00 45.21      A   C
ATOM   4750  CD   ARG B 287     -38.126 -17.057  -8.287  1.00 48.25      A   C
ATOM   4751  NE   ARG B 287     -38.969 -15.903  -8.594  1.00 49.97      A   N
ATOM   4752  CZ   ARG B 287     -38.514 -14.665  -8.773  1.00 50.48      A   C
ATOM   4753  NH1  ARG B 287     -37.210 -14.411  -8.692  1.00 50.56      A   N
ATOM   4754  NH2  ARG B 287     -39.364 -13.678  -9.045  1.00 50.73      A   N
ATOM   4755  N    TRP B 288     -37.086 -16.658  -3.556  1.00 42.15      A   N
ATOM   4756  CA   TRP B 288     -36.590 -15.530  -2.775  1.00 41.86      A   C
ATOM   4757  C    TRP B 288     -35.926 -16.006  -1.496  1.00 41.65      A   C
ATOM   4758  O    TRP B 288     -35.052 -15.336  -0.956  1.00 41.70      A   O
ATOM   4759  CB   TRP B 288     -37.688 -14.516  -2.484  1.00 41.76      A   C
ATOM   4760  CG   TRP B 288     -38.035 -13.725  -3.676  1.00 42.46      A   C
ATOM   4761  CD1  TRP B 288     -39.246 -13.660  -4.298  1.00 42.98      A   C
ATOM   4762  CD2  TRP B 288     -37.153 -12.902  -4.431  1.00 43.20      A   C
ATOM   4763  CE2  TRP B 288     -37.901 -12.354  -5.495  1.00 43.57      A   C
ATOM   4764  CE3  TRP B 288     -35.799 -12.564  -4.309  1.00 43.41      A   C
ATOM   4765  NE1  TRP B 288     -39.179 -12.833  -5.391  1.00 43.37      A   N
ATOM   4766  CZ2  TRP B 288     -37.342 -11.487  -6.430  1.00 44.09      A   C
ATOM   4767  CZ3  TRP B 288     -35.240 -11.703  -5.240  1.00 43.90      A   C
ATOM   4768  CH2  TRP B 288     -36.013 -11.171  -6.286  1.00 44.28      A   C
ATOM   4769  N    PHE B 289     -36.337 -17.175  -1.020  1.00 41.45      A   N
ATOM   4770  CA   PHE B 289     -35.676 -17.798   0.107  1.00 41.26      A   C
ATOM   4771  C    PHE B 289     -34.272 -18.208  -0.326  1.00 41.40      A   C
ATOM   4772  O    PHE B 289     -33.297 -18.009   0.390  1.00 41.24      A   O
ATOM   4773  CB   PHE B 289     -36.491 -18.996   0.601  1.00 41.19      A   C
ATOM   4774  CG   PHE B 289     -36.030 -19.540   1.923  1.00 41.07      A   C
ATOM   4775  CD1  PHE B 289     -36.362 -18.897   3.104  1.00 40.67      A   C
ATOM   4776  CD2  PHE B 289     -35.263 -20.694   1.984  1.00 41.39      A   C
ATOM   4777  CE1  PHE B 289     -35.933 -19.383   4.312  1.00 40.53      A   C
ATOM   4778  CE2  PHE B 289     -34.837 -21.188   3.191  1.00 41.49      A   C
ATOM   4779  CZ   PHE B 289     -35.167 -20.525   4.355  1.00 41.07      A   C
ATOM   4780  N    HIS B 290     -34.184 -18.755  -1.529  1.00 41.76      A   N
ATOM   4781  CA   HIS B 290     -32.926 -19.147  -2.127  1.00 42.21      A   C
ATOM   4782  C    HIS B 290     -31.957 -17.987  -2.204  1.00 42.30      A   C
ATOM   4783  O    HIS B 290     -30.758 -18.163  -2.041  1.00 42.52      A   O
ATOM   4784  CB   HIS B 290     -33.205 -19.705  -3.507  1.00 42.47      A   C
ATOM   4785  CG   HIS B 290     -33.398 -21.175  -3.516  1.00 43.13      A   C
ATOM   4786  CD2  HIS B 290     -33.744 -22.056  -2.547  1.00 43.42      A   C
ATOM   4787  ND1  HIS B 290     -33.078 -21.926  -4.613  1.00 43.98      A   N
ATOM   4788  CE1  HIS B 290     -33.179 -23.200  -4.334  1.00 44.48      A   C
ATOM   4789  NE2  HIS B 290     -33.652 -23.312  -3.102  1.00 43.83      A   N
ATOM   4790  N    ARG B 291     -32.482 -16.794  -2.438  1.00 42.35      A   N
ATOM   4791  CA   ARG B 291     -31.654 -15.600  -2.458  1.00 42.58      A   C
ATOM   4792  C    ARG B 291     -31.022 -15.381  -1.113  1.00 42.20      A   C
ATOM   4793  O    ARG B 291     -29.833 -15.086  -1.020  1.00 42.47      A   O
ATOM   4794  CB   ARG B 291     -32.462 -14.369  -2.852  1.00 42.82      A   C
ATOM   4795  CG   ARG B 291     -32.695 -14.286  -4.335  1.00 44.49      A   C
ATOM   4796  CD   ARG B 291     -31.376 -14.213  -5.073  1.00 46.62      A   C
ATOM   4797  NE   ARG B 291     -30.980 -12.829  -5.261  1.00 47.68      A   N
ATOM   4798  CZ   ARG B 291     -31.149 -12.166  -6.396  1.00 48.72      A   C
ATOM   4799  NH1  ARG B 291     -31.692 -12.766  -7.442  1.00 49.25      A   N
ATOM   4800  NH2  ARG B 291     -30.770 -10.906  -6.490  1.00 49.25      A   N
ATOM   4801  N    LEU B 292     -31.822 -15.555  -0.069  1.00 41.60      A   N
ATOM   4802  CA   LEU B 292     -31.344 -15.375   1.288  1.00 40.95      A   C
ATOM   4803  C    LEU B 292     -30.255 -16.391   1.614  1.00 40.92      A   C
ATOM   4804  O    LEU B 292     -29.213 -16.022   2.149  1.00 40.99      A   O
ATOM   4805  CB   LEU B 292     -32.501 -15.425   2.286  1.00 40.56      A   C
ATOM   4806  CG   LEU B 292     -33.477 -14.254   2.167  1.00 39.84      A   C
ATOM   4807  CD1  LEU B 292     -34.747 -14.558   2.912  1.00 39.39      A   C
ATOM   4808  CD2  LEU B 292     -32.851 -12.980   2.681  1.00 39.39      A   C
ATOM   4809  N    ARG B 293     -30.474 -17.656   1.261  1.00 40.86      A   N
ATOM   4810  CA   ARG B 293     -29.423 -18.661   1.405  1.00 40.98      A   C
```

FIGURE 1 (cont'd)

```
ATOM   4811  C    ARG B 293     -28.177 -18.201   0.652  1.00 41.28      A    C
ATOM   4812  O    ARG B 293     -27.076 -18.243   1.197  1.00 41.39      A    O
ATOM   4813  CB   ARG B 293     -29.885 -20.035   0.903  1.00 40.90      A    C
ATOM   4814  CG   ARG B 293     -29.073 -21.223   1.434  1.00 40.67      A    C
ATOM   4815  CD   ARG B 293     -29.433 -22.530   0.723  1.00 40.45      A    C
ATOM   4816  NE   ARG B 293     -30.820 -22.949   0.920  1.00 39.73      A    N
ATOM   4817  N    SER B 294     -28.370 -17.734  -0.585  1.00 41.46      A    N
ATOM   4818  CA   SER B 294     -27.275 -17.319  -1.459  1.00 41.68      A    C
ATOM   4819  C    SER B 294     -26.536 -16.109  -0.918  1.00 42.08      A    C
ATOM   4820  O    SER B 294     -25.314 -16.027  -1.042  1.00 42.60      A    O
ATOM   4821  CB   SER B 294     -27.769 -17.049  -2.881  1.00 40.73      A    C
ATOM   4822  OG   SER B 294     -27.851 -18.250  -3.631  1.00 40.95      A    O
ATOM   4823  N    ILE B 295     -27.272 -15.184  -0.309  1.00 42.16      A    N
ATOM   4824  CA   ILE B 295     -26.671 -13.986   0.280  1.00 42.24      A    C
ATOM   4825  C    ILE B 295     -25.833 -14.331   1.521  1.00 42.53      A    C
ATOM   4826  O    ILE B 295     -24.720 -13.832   1.690  1.00 42.74      A    O
ATOM   4827  CB   ILE B 295     -27.729 -12.916   0.592  1.00 41.92      A    C
ATOM   4828  CG1  ILE B 295     -28.226 -12.299  -0.705  1.00 41.89      A    C
ATOM   4829  CG2  ILE B 295     -27.153 -11.828   1.453  1.00 41.78      A    C
ATOM   4830  CD1  ILE B 295     -29.651 -11.792  -0.650  1.00 41.62      A    C
ATOM   4831  N    GLU B 296     -26.365 -15.197   2.375  1.00 42.70      A    N
ATOM   4832  CA   GLU B 296     -25.639 -15.678   3.549  1.00 42.99      A    C
ATOM   4833  C    GLU B 296     -24.358 -16.372   3.093  1.00 43.54      A    C
ATOM   4834  O    GLU B 296     -23.272 -16.057   3.576  1.00 43.81      A    O
ATOM   4835  CB   GLU B 296     -26.519 -16.634   4.362  1.00 42.72      A    C
ATOM   4836  CG   GLU B 296     -25.948 -17.049   5.708  1.00 42.89      A    C
ATOM   4837  CD   GLU B 296     -26.713 -18.192   6.357  1.00 43.08      A    C
ATOM   4838  OE1  GLU B 296     -27.858 -18.477   5.948  1.00 42.80      A    O
ATOM   4839  OE2  GLU B 296     -26.166 -18.812   7.288  1.00 43.35      A    O
ATOM   4840  N    LYS B 297     -24.504 -17.297   2.146  1.00 44.09      A    N
ATOM   4841  CA   LYS B 297     -23.400 -18.016   1.552  1.00 44.79      A    C
ATOM   4842  C    LYS B 297     -22.333 -17.012   1.106  1.00 45.44      A    C
ATOM   4843  O    LYS B 297     -21.183 -17.094   1.523  1.00 45.71      A    O
ATOM   4844  CB   LYS B 297     -23.925 -18.834   0.374  1.00 44.72      A    C
ATOM   4845  CG   LYS B 297     -23.572 -20.314   0.389  1.00 44.61      A    C
ATOM   4846  CD   LYS B 297     -24.591 -21.136  -0.407  1.00 43.75      A    C
ATOM   4847  CE   LYS B 297     -23.983 -22.433  -0.940  1.00 43.74      A    C
ATOM   4848  NZ   LYS B 297     -24.932 -23.199  -1.772  1.00 44.59      A    N
ATOM   4849  N    ARG B 298     -22.739 -16.035   0.299  1.00 45.97      A    N
ATOM   4850  CA   ARG B 298     -21.820 -15.041  -0.270  1.00 46.49      A    C
ATOM   4851  C    ARG B 298     -21.122 -14.220   0.797  1.00 47.01      A    C
ATOM   4852  O    ARG B 298     -19.907 -14.077   0.759  1.00 47.64      A    O
ATOM   4853  CB   ARG B 298     -22.546 -14.121  -1.268  1.00 45.49      A    C
ATOM   4854  CG   ARG B 298     -21.662 -13.115  -2.022  1.00 45.43      A    C
ATOM   4855  CD   ARG B 298     -22.444 -12.471  -3.164  1.00 45.06      A    C
ATOM   4856  NE   ARG B 298     -21.861 -11.235  -3.696  1.00 44.70      A    N
ATOM   4857  CZ   ARG B 298     -20.873 -11.134  -4.585  1.00 34.84      A    C
ATOM   4858  NH1  ARG B 298     -20.256 -12.212  -5.065  1.00 33.03      A    N
ATOM   4859  NH2  ARG B 298     -20.485  -9.924  -4.980  1.00 32.88      A    N
ATOM   4860  N    LEU B 299     -21.892 -13.684   1.740  1.00 47.24      A    N
ATOM   4861  CA   LEU B 299     -21.346 -12.830   2.796  1.00 47.47      A    C
ATOM   4862  C    LEU B 299     -20.387 -13.602   3.702  1.00 47.89      A    C
ATOM   4863  O    LEU B 299     -19.427 -13.036   4.242  1.00 48.14      A    O
ATOM   4864  CB   LEU B 299     -22.467 -12.198   3.618  1.00 47.12      A    C
ATOM   4865  CG   LEU B 299     -23.258 -11.065   2.972  1.00 46.95      A    C
ATOM   4866  CD1  LEU B 299     -24.497 -10.804   3.780  1.00 46.55      A    C
ATOM   4867  CD2  LEU B 299     -22.439  -9.798   2.862  1.00 47.44      A    C
ATOM   4868  N    HIS B 300     -20.651 -14.897   3.853  1.00 48.20      A    N
ATOM   4869  CA   HIS B 300     -19.773 -15.773   4.604  1.00 48.74      A    C
ATOM   4870  C    HIS B 300     -18.431 -15.919   3.894  1.00 49.23      A    C
ATOM   4871  O    HIS B 300     -17.390 -15.728   4.513  1.00 49.56      A    O
ATOM   4872  CB   HIS B 300     -20.432 -17.134   4.820  1.00 48.69      A    C
ATOM   4873  CG   HIS B 300     -19.495 -18.178   5.326  1.00 49.34      A    C
ATOM   4874  CD2  HIS B 300     -19.023 -19.307   4.749  1.00 50.13      A    C
ATOM   4875  ND1  HIS B 300     -18.913 -18.109   6.571  1.00 49.64      A    N
```

FIGURE 1 (cont'd)

```
ATOM   4876  CE1 HIS B 300     -18.126 -19.155   6.743  1.00 50.29      A    C
ATOM   4877  NE2 HIS B 300     -18.176 -19.900   5.652  1.00 50.73      A    N
ATOM   4878  N   ARG B 301     -18.470 -16.239   2.596  1.00 49.71      A    N
ATOM   4879  CA  ARG B 301     -17.270 -16.347   1.749  1.00 50.22      A    C
ATOM   4880  C   ARG B 301     -16.415 -15.087   1.852  1.00 50.85      A    C
ATOM   4881  O   ARG B 301     -15.196 -15.164   1.887  1.00 51.40      A    O
ATOM   4882  CB  ARG B 301     -17.636 -16.578   0.265  1.00 50.08      A    C
ATOM   4883  CG  ARG B 301     -18.644 -17.696  -0.049  1.00 49.11      A    C
ATOM   4884  CD  ARG B 301     -17.984 -19.072  -0.090  1.00 48.46      A    C
ATOM   4885  NE  ARG B 301     -18.910 -20.203  -0.294  1.00 47.67      A    N
ATOM   4886  CZ  ARG B 301     -19.776 -20.696   0.599  1.00 45.37      A    C
ATOM   4887  NH1 ARG B 301     -19.904 -20.144   1.798  1.00 44.46      A    N
ATOM   4888  NH2 ARG B 301     -20.534 -21.744   0.279  1.00 44.59      A    N
ATOM   4889  N   LEU B 302     -17.070 -13.933   1.908  1.00 51.22      A    N
ATOM   4890  CA  LEU B 302     -16.396 -12.649   1.947  1.00 51.83      A    C
ATOM   4891  C   LEU B 302     -15.967 -12.234   3.351  1.00 52.17      A    C
ATOM   4892  O   LEU B 302     -15.626 -11.069   3.567  1.00 52.51      A    O
ATOM   4893  CB  LEU B 302     -17.310 -11.579   1.355  1.00 51.75      A    C
ATOM   4894  CG  LEU B 302     -17.556 -11.671  -0.143  1.00 52.22      A    C
ATOM   4895  CD1 LEU B 302     -18.878 -11.022  -0.490  1.00 51.86      A    C
ATOM   4896  CD2 LEU B 302     -16.415 -11.022  -0.890  1.00 53.48      A    C
ATOM   4897  N   ASN B 303     -15.970 -13.179   4.293  1.00 52.26      A    N
ATOM   4898  CA  ASN B 303     -15.669 -12.895   5.707  1.00 52.01      A    C
ATOM   4899  C   ASN B 303     -16.339 -11.597   6.171  1.00 52.65      A    C
ATOM   4900  O   ASN B 303     -15.664 -10.603   6.449  1.00 53.17      A    O
ATOM   4901  N   LEU B 304     -17.668 -11.594   6.225  1.00 52.84      A    N
ATOM   4902  CA  LEU B 304     -18.399 -10.403   6.653  1.00 52.72      A    C
ATOM   4903  C   LEU B 304     -19.491 -10.748   7.656  1.00 52.44      A    C
ATOM   4904  O   LEU B 304     -20.318  -9.902   8.007  1.00 52.18      A    O
ATOM   4905  CB  LEU B 304     -18.983  -9.650   5.453  1.00 52.76      A    C
ATOM   4906  CG  LEU B 304     -18.102  -8.693   4.649  1.00 53.24      A    C
ATOM   4907  CD1 LEU B 304     -18.853  -8.184   3.443  1.00 52.94      A    C
ATOM   4908  CD2 LEU B 304     -17.618  -7.515   5.477  1.00 53.84      A    C
ATOM   4909  N   LEU B 305     -19.482 -11.997   8.116  1.00 52.36      A    N
ATOM   4910  CA  LEU B 305     -20.432 -12.462   9.125  1.00 52.19      A    C
ATOM   4911  C   LEU B 305     -19.704 -12.930  10.383  1.00 52.61      A    C
ATOM   4912  O   LEU B 305     -18.884 -13.856  10.321  1.00 53.02      A    O
ATOM   4913  CB  LEU B 305     -21.295 -13.601   8.577  1.00 51.74      A    C
ATOM   4914  CG  LEU B 305     -22.066 -13.386   7.275  1.00 51.09      A    C
ATOM   4915  CD1 LEU B 305     -22.722 -14.679   6.837  1.00 50.42      A    C
ATOM   4916  CD2 LEU B 305     -23.105 -12.279   7.402  1.00 50.67      A    C
ATOM   4917  N   GLN B 306     -20.001 -12.281  11.512  1.00 52.74      A    N
ATOM   4918  CA  GLN B 306     -19.428 -12.641  12.805  1.00 53.02      A    C
ATOM   4919  C   GLN B 306     -19.923 -14.002  13.249  1.00 52.93      A    C
ATOM   4920  O   GLN B 306     -21.021 -14.410  12.883  1.00 52.58      A    O
ATOM   4921  CB  GLN B 306     -19.806 -11.612  13.864  1.00 53.15      A    C
ATOM   4922  CG  GLN B 306     -18.800 -10.498  14.069  1.00 54.02      A    C
ATOM   4923  CD  GLN B 306     -19.093  -9.701  15.322  1.00 54.71      A    C
ATOM   4924  OE1 GLN B 306     -20.216  -9.240  15.528  1.00 54.91      A    O
ATOM   4925  N   SER B 307     -19.101 -14.695  14.037  1.00 53.27      A    N
ATOM   4926  CA  SER B 307     -19.467 -15.978  14.646  1.00 53.50      A    C
ATOM   4927  C   SER B 307     -20.246 -16.886  13.683  1.00 53.35      A    C
ATOM   4928  O   SER B 307     -21.302 -17.427  14.028  1.00 53.13      A    O
ATOM   4929  CB  SER B 307     -20.274 -15.749  15.933  1.00 53.55      A    C
ATOM   4930  OG  SER B 307     -19.706 -14.729  16.740  1.00 54.27      A    O
ATOM   4931  N   HIS B 308     -19.710 -17.052  12.479  1.00 53.47      A    N
ATOM   4932  CA  HIS B 308     -20.404 -17.772  11.421  1.00 53.46      A    C
ATOM   4933  C   HIS B 308     -19.509 -18.870  10.839  1.00 53.74      A    C
ATOM   4934  O   HIS B 308     -18.979 -18.721   9.734  1.00 54.00      A    O
ATOM   4935  CB  HIS B 308     -20.838 -16.780  10.335  1.00 53.29      A    C
ATOM   4936  CG  HIS B 308     -21.956 -17.270   9.471  1.00 52.96      A    C
ATOM   4937  CD2 HIS B 308     -23.281 -17.384   9.713  1.00 52.54      A    C
ATOM   4938  ND1 HIS B 308     -21.762 -17.705   8.178  1.00 53.24      A    N
ATOM   4939  CE1 HIS B 308     -22.922 -18.064   7.661  1.00 52.92      A    C
ATOM   4940  NE2 HIS B 308     -23.860 -17.881   8.573  1.00 52.38      A    N
```

FIGURE 1 (cont'd)

```
ATOM   4941  N    PRO B 309     -19.333 -19.979  11.584  1.00 53.94      A    N
ATOM   4942  CA   PRO B 309     -18.379 -21.017  11.187  1.00 54.40      A    C
ATOM   4943  C    PRO B 309     -18.892 -22.049  10.180  1.00 54.67      A    C
ATOM   4944  O    PRO B 309     -18.544 -23.227  10.286  1.00 54.94      A    O
ATOM   4945  CB   PRO B 309     -18.021 -21.693  12.520  1.00 54.66      A    C
ATOM   4946  CG   PRO B 309     -18.541 -20.763  13.586  1.00 54.43      A    C
ATOM   4947  CD   PRO B 309     -19.767 -20.181  12.972  1.00 53.93      A    C
ATOM   4948  N    GLN B 310     -19.720 -21.606   9.232  1.00 54.72      A    N
ATOM   4949  CA   GLN B 310     -19.996 -22.336   7.974  1.00 54.88      A    C
ATOM   4950  C    GLN B 310     -20.877 -21.545   6.993  1.00 54.99      A    C
ATOM   4951  O    GLN B 310     -21.206 -20.378   7.230  1.00 54.82      A    O
ATOM   4952  CB   GLN B 310     -20.497 -23.783   8.177  1.00 54.91      A    C
ATOM   4953  CG   GLN B 310     -21.439 -24.035   9.346  1.00 54.54      A    C
ATOM   4954  CD   GLN B 310     -21.255 -25.438   9.916  1.00 54.55      A    C
ATOM   4955  NE2  GLN B 310     -22.359 -26.081  10.289  1.00 54.63      A    N
ATOM   4956  OE1  GLN B 310     -20.132 -25.955   9.972  1.00 53.86      A    O
ATOM   4957  N    GLU B 311     -21.229 -22.188   5.883  1.00 55.38      A    N
ATOM   4958  CA   GLU B 311     -21.913 -21.529   4.780  1.00 55.73      A    C
ATOM   4959  C    GLU B 311     -23.398 -21.453   5.077  1.00 55.01      A    C
ATOM   4960  O    GLU B 311     -23.934 -20.363   5.252  1.00 54.84      A    O
ATOM   4961  CB   GLU B 311     -21.655 -22.266   3.456  1.00 56.49      A    C
ATOM   4962  CG   GLU B 311     -20.182 -22.590   3.169  1.00 58.90      A    C
ATOM   4963  CD   GLU B 311     -19.684 -23.891   3.808  1.00 61.44      A    C
ATOM   4964  OE1  GLU B 311     -18.697 -24.456   3.280  1.00 62.86      A    O
ATOM   4965  OE2  GLU B 311     -20.260 -24.353   4.828  1.00 62.00      A    O
ATOM   4966  N    VAL B 312     -24.051 -22.611   5.135  1.00 54.42      A    N
ATOM   4967  CA   VAL B 312     -25.452 -22.672   5.503  1.00 53.71      A    C
ATOM   4968  C    VAL B 312     -25.572 -22.852   7.020  1.00 53.21      A    C
ATOM   4969  O    VAL B 312     -25.273 -23.915   7.559  1.00 53.55      A    O
ATOM   4970  N    MET B 313     -25.978 -21.786   7.701  1.00 52.17      A    N
ATOM   4971  CA   MET B 313     -26.230 -21.809   9.137  1.00 51.19      A    C
ATOM   4972  C    MET B 313     -27.688 -21.422   9.369  1.00 50.22      A    C
ATOM   4973  O    MET B 313     -28.442 -22.170   9.993  1.00 50.10      A    O
ATOM   4974  CB   MET B 313     -25.324 -20.808   9.868  1.00 51.40      A    C
ATOM   4975  CG   MET B 313     -23.809 -21.073   9.793  1.00 52.03      A    C
ATOM   4976  SD   MET B 313     -22.952 -21.436  11.360  1.00 52.40      A    S
ATOM   4977  CE   MET B 313     -23.287 -19.959  12.312  1.00 52.13      A    C
ATOM   4978  N    TYR B 314     -28.076 -20.255   8.845  1.00 49.13      A    N
ATOM   4979  CA   TYR B 314     -29.384 -19.650   9.100  1.00 48.01      A    C
ATOM   4980  C    TYR B 314     -30.465 -20.137   8.149  1.00 47.48      A    C
ATOM   4981  O    TYR B 314     -31.464 -20.700   8.581  1.00 47.29      A    O
ATOM   4982  CB   TYR B 314     -29.296 -18.120   9.047  1.00 47.79      A    C
ATOM   4983  CG   TYR B 314     -28.339 -17.518  10.051  1.00 47.55      A    C
ATOM   4984  CD1  TYR B 314     -28.173 -18.084  11.317  1.00 47.54      A    C
ATOM   4985  CD2  TYR B 314     -27.611 -16.369   9.749  1.00 47.39      A    C
ATOM   4986  CE1  TYR B 314     -27.288 -17.529  12.247  1.00 47.63      A    C
ATOM   4987  CE2  TYR B 314     -26.724 -15.802  10.682  1.00 47.44      A    C
ATOM   4988  CZ   TYR B 314     -26.570 -16.388  11.923  1.00 47.34      A    C
ATOM   4989  OH   TYR B 314     -25.705 -15.833  12.837  1.00 47.28      A    O
ATOM   4990  N    PHE B 315     -30.271 -19.915   6.854  1.00 47.05      A    N
ATOM   4991  CA   PHE B 315     -31.286 -20.254   5.869  1.00 46.66      A    C
ATOM   4992  C    PHE B 315     -31.048 -21.641   5.340  1.00 46.91      A    C
ATOM   4993  O    PHE B 315     -30.290 -21.849   4.399  1.00 46.97      A    O
ATOM   4994  CB   PHE B 315     -31.333 -19.207   4.761  1.00 46.37      A    C
ATOM   4995  CG   PHE B 315     -31.671 -17.828   5.259  1.00 45.27      A    C
ATOM   4996  CD1  PHE B 315     -32.994 -17.431   5.400  1.00 44.51      A    C
ATOM   4997  CD2  PHE B 315     -30.668 -16.940   5.612  1.00 44.54      A    C
ATOM   4998  CE1  PHE B 315     -33.307 -16.177   5.873  1.00 43.97      A    C
ATOM   4999  CE2  PHE B 315     -30.975 -15.689   6.082  1.00 44.00      A    C
ATOM   5000  CZ   PHE B 315     -32.297 -15.306   6.215  1.00 43.75      A    C
ATOM   5001  N    GLN B 316     -31.701 -22.592   5.991  1.00 47.19      A    N
ATOM   5002  CA   GLN B 316     -31.506 -24.007   5.719  1.00 47.74      A    C
ATOM   5003  C    GLN B 316     -32.212 -24.452   4.450  1.00 48.08      A    C
ATOM   5004  O    GLN B 316     -33.253 -23.903   4.097  1.00 47.93      A    O
ATOM   5005  CB   GLN B 316     -31.996 -24.855   6.897  1.00 47.80      A    C
```

FIGURE 1 (cont'd)

```
ATOM   5006  CG   GLN B 316     -31.109 -24.819   8.140  1.00 48.23      A  C
ATOM   5007  CD   GLN B 316     -29.719 -25.380   7.898  1.00 48.97      A  C
ATOM   5008  NE2  GLN B 316     -28.714 -24.534   8.056  1.00 49.08      A  N
ATOM   5009  OE1  GLN B 316     -29.550 -26.557   7.578  1.00 49.78      A  O
ATOM   5010  N    PRO B 317     -31.648 -25.458   3.759  1.00 48.68      A  N
ATOM   5011  CA   PRO B 317     -32.342 -26.032   2.619  1.00 48.96      A  C
ATOM   5012  C    PRO B 317     -33.481 -26.934   3.099  1.00 49.00      A  C
ATOM   5013  O    PRO B 317     -33.535 -27.308   4.277  1.00 48.95      A  O
ATOM   5014  CB   PRO B 317     -31.248 -26.849   1.926  1.00 49.28      A  C
ATOM   5015  CG   PRO B 317     -30.343 -27.274   3.033  1.00 49.43      A  C
ATOM   5016  CD   PRO B 317     -30.348 -26.119   4.003  1.00 48.97      A  C
ATOM   5017  N    GLY B 318     -34.380 -27.274   2.187  1.00 49.05      A  N
ATOM   5018  CA   GLY B 318     -35.535 -28.074   2.533  1.00 49.01      A  C
ATOM   5019  C    GLY B 318     -36.759 -27.198   2.535  1.00 48.83      A  C
ATOM   5020  O    GLY B 318     -36.698 -26.020   2.900  1.00 48.65      A  O
ATOM   5021  N    GLU B 319     -37.873 -27.777   2.112  1.00 48.81      A  N
ATOM   5022  CA   GLU B 319     -39.146 -27.082   2.098  1.00 48.60      A  C
ATOM   5023  C    GLU B 319     -40.163 -27.848   2.951  1.00 48.75      A  C
ATOM   5024  O    GLU B 319     -40.994 -28.590   2.411  1.00 49.14      A  O
ATOM   5025  CB   GLU B 319     -39.653 -26.930   0.658  1.00 48.50      A  C
ATOM   5026  CG   GLU B 319     -38.739 -26.136  -0.270  1.00 47.88      A  C
ATOM   5027  CD   GLU B 319     -39.305 -25.997  -1.674  1.00 44.81      A  C
ATOM   5028  OE1  GLU B 319     -39.250 -26.977  -2.448  1.00 43.60      A  O
ATOM   5029  OE2  GLU B 319     -39.804 -24.901  -2.000  1.00 43.87      A  O
ATOM   5030  N    PRO B 320     -40.092 -27.695   4.288  1.00 48.62      A  N
ATOM   5031  CA   PRO B 320     -41.080 -28.375   5.121  1.00 48.64      A  C
ATOM   5032  C    PRO B 320     -42.460 -27.736   5.035  1.00 48.52      A  C
ATOM   5033  O    PRO B 320     -42.587 -26.586   4.606  1.00 48.32      A  O
ATOM   5034  CB   PRO B 320     -40.500 -28.244   6.537  1.00 48.70      A  C
ATOM   5035  CG   PRO B 320     -39.045 -28.020   6.322  1.00 48.68      A  C
ATOM   5036  CD   PRO B 320     -38.999 -27.148   5.105  1.00 48.46      A  C
ATOM   5037  N    PHE B 321     -43.470 -28.487   5.473  1.00 48.36      A  N
ATOM   5038  CA   PHE B 321     -44.870 -28.115   5.302  1.00 47.73      A  C
ATOM   5039  C    PHE B 321     -45.387 -26.783   5.912  1.00 48.15      A  C
ATOM   5040  O    PHE B 321     -45.945 -25.945   5.188  1.00 48.47      A  O
ATOM   5041  N    GLY B 322     -45.198 -26.587   7.218  1.00 48.01      A  N
ATOM   5042  CA   GLY B 322     -45.713 -25.393   7.906  1.00 47.42      A  C
ATOM   5043  C    GLY B 322     -47.195 -25.540   8.227  1.00 47.07      A  C
ATOM   5044  O    GLY B 322     -47.709 -26.660   8.274  1.00 47.61      A  O
ATOM   5045  N    SER B 323     -47.899 -24.439   8.489  1.00 46.13      A  N
ATOM   5046  CA   SER B 323     -47.323 -23.112   8.656  1.00 45.03      A  C
ATOM   5047  C    SER B 323     -47.462 -22.696  10.119  1.00 43.87      A  C
ATOM   5048  O    SER B 323     -48.082 -23.399  10.922  1.00 43.98      A  O
ATOM   5049  CB   SER B 323     -48.049 -22.093   7.764  1.00 45.23      A  C
ATOM   5050  OG   SER B 323     -48.092 -22.512   6.412  1.00 46.05      A  O
ATOM   5051  N    VAL B 324     -46.887 -21.544  10.447  1.00 42.30      A  N
ATOM   5052  CA   VAL B 324     -47.015 -20.930  11.758  1.00 40.74      A  C
ATOM   5053  C    VAL B 324     -47.881 -19.684  11.595  1.00 39.98      A  C
ATOM   5054  O    VAL B 324     -47.535 -18.783  10.842  1.00 39.88      A  O
ATOM   5055  CB   VAL B 324     -45.623 -20.568  12.325  1.00 40.49      A  C
ATOM   5056  CG1  VAL B 324     -44.831 -21.832  12.624  1.00 40.39      A  C
ATOM   5057  CG2  VAL B 324     -45.736 -19.707  13.560  1.00 40.04      A  C
ATOM   5058  N    GLU B 325     -49.013 -19.649  12.287  1.00 39.16      A  N
ATOM   5059  CA   GLU B 325     -49.953 -18.549  12.169  1.00 38.46      A  C
ATOM   5060  C    GLU B 325     -49.343 -17.239  12.639  1.00 37.60      A  C
ATOM   5061  O    GLU B 325     -48.898 -17.129  13.768  1.00 37.48      A  O
ATOM   5062  CB   GLU B 325     -51.197 -18.850  12.979  1.00 38.84      A  C
ATOM   5063  CG   GLU B 325     -51.860 -20.141  12.605  1.00 40.44      A  C
ATOM   5064  CD   GLU B 325     -53.231 -20.309  13.239  1.00 42.56      A  C
ATOM   5065  OE1  GLU B 325     -53.740 -19.370  13.891  1.00 42.95      A  O
ATOM   5066  OE2  GLU B 325     -53.810 -21.399  13.075  1.00 43.85      A  O
ATOM   5067  N    ASP B 326     -49.324 -16.242  11.763  1.00 36.77      A  N
ATOM   5068  CA   ASP B 326     -48.744 -14.939  12.081  1.00 36.00      A  C
ATOM   5069  C    ASP B 326     -49.445 -13.877  11.236  1.00 35.74      A  C
ATOM   5070  O    ASP B 326     -50.434 -14.173  10.574  1.00 35.84      A  O
```

FIGURE 1 (cont'd)

```
ATOM   5071  CB   ASP B 326     -47.233 -14.964  11.815  1.00 35.73      A   C
ATOM   5072  CG   ASP B 326     -46.444 -13.985  12.686  1.00 35.10      A   C
ATOM   5073  OD1  ASP B 326     -47.000 -12.998  13.192  1.00 34.82      A   O
ATOM   5074  OD2  ASP B 326     -45.232 -14.195  12.849  1.00 34.59      A   O
ATOM   5075  N    ASP B 327     -48.928 -12.650  11.262  1.00 35.31      A   N
ATOM   5076  CA   ASP B 327     -49.534 -11.490  10.593  1.00 34.97      A   C
ATOM   5077  C    ASP B 327     -49.755 -11.631   9.097  1.00 34.56      A   C
ATOM   5078  O    ASP B 327     -50.486 -10.841   8.512  1.00 34.66      A   O
ATOM   5079  CB   ASP B 327     -48.691 -10.245  10.830  1.00 35.11      A   C
ATOM   5080  CG   ASP B 327     -48.785  -9.745  12.245  1.00 36.03      A   C
ATOM   5081  OD1  ASP B 327     -49.892  -9.320  12.636  1.00 36.76      A   O
ATOM   5082  OD2  ASP B 327     -47.751  -9.763  12.962  1.00 36.70      A   O
ATOM   5083  N    HIS B 328     -49.115 -12.618   8.479  1.00 34.07      A   N
ATOM   5084  CA   HIS B 328     -49.237 -12.834   7.042  1.00 33.72      A   C
ATOM   5085  C    HIS B 328     -50.576 -13.474   6.649  1.00 33.64      A   C
ATOM   5086  O    HIS B 328     -51.065 -13.274   5.545  1.00 33.82      A   O
ATOM   5087  CB   HIS B 328     -48.085 -13.694   6.546  1.00 33.58      A   C
ATOM   5088  CG   HIS B 328     -48.176 -15.124   6.978  1.00 33.87      A   C
ATOM   5089  CD2  HIS B 328     -48.586 -16.230   6.317  1.00 34.41      A   C
ATOM   5090  ND1  HIS B 328     -47.830 -15.542   8.246  1.00 34.07      A   N
ATOM   5091  CE1  HIS B 328     -48.013 -16.845   8.343  1.00 34.29      A   C
ATOM   5092  NE2  HIS B 328     -48.470 -17.287   7.186  1.00 34.54      A   N
ATOM   5093  N    ILE B 329     -51.168 -14.233   7.558  1.00 33.48      A   N
ATOM   5094  CA   ILE B 329     -52.374 -14.981   7.258  1.00 33.59      A   C
ATOM   5095  C    ILE B 329     -53.467 -14.177   6.553  1.00 33.60      A   C
ATOM   5096  O    ILE B 329     -53.923 -14.594   5.505  1.00 33.87      A   O
ATOM   5097  CB   ILE B 329     -52.920 -15.694   8.510  1.00 33.69      A   C
ATOM   5098  CG1  ILE B 329     -51.939 -16.773   8.970  1.00 33.90      A   C
ATOM   5099  CG2  ILE B 329     -54.306 -16.284   8.253  1.00 34.17      A   C
ATOM   5100  CD1  ILE B 329     -51.707 -17.881   7.956  1.00 34.47      A   C
ATOM   5101  N    PRO B 330     -53.888 -13.027   7.108  1.00 33.53      A   N
ATOM   5102  CA   PRO B 330     -55.008 -12.354   6.454  1.00 33.61      A   C
ATOM   5103  C    PRO B 330     -54.615 -11.636   5.165  1.00 33.51      A   C
ATOM   5104  O    PRO B 330     -55.484 -11.143   4.450  1.00 33.77      A   O
ATOM   5105  CB   PRO B 330     -55.472 -11.348   7.506  1.00 33.71      A   C
ATOM   5106  CG   PRO B 330     -54.253 -11.030   8.268  1.00 33.51      A   C
ATOM   5107  CD   PRO B 330     -53.444 -12.295   8.307  1.00 33.43      A   C
ATOM   5108  N    PHE B 331     -53.320 -11.566   4.878  1.00 33.09      A   N
ATOM   5109  CA   PHE B 331     -52.863 -11.099   3.579  1.00 32.88      A   C
ATOM   5110  C    PHE B 331     -52.788 -12.275   2.613  1.00 32.85      A   C
ATOM   5111  O    PHE B 331     -53.118 -12.159   1.430  1.00 32.96      A   O
ATOM   5112  CB   PHE B 331     -51.512 -10.400   3.702  1.00 32.67      A   C
ATOM   5113  CG   PHE B 331     -51.594  -9.070   4.366  1.00 32.76      A   C
ATOM   5114  CD1  PHE B 331     -51.259  -8.927   5.700  1.00 32.76      A   C
ATOM   5115  CD2  PHE B 331     -52.033  -7.961   3.658  1.00 33.30      A   C
ATOM   5116  CE1  PHE B 331     -51.346  -7.700   6.319  1.00 33.01      A   C
ATOM   5117  CE2  PHE B 331     -52.130  -6.724   4.263  1.00 33.50      A   C
ATOM   5118  CZ   PHE B 331     -51.785  -6.592   5.600  1.00 33.23      A   C
ATOM   5119  N    LEU B 332     -52.371 -13.418   3.140  1.00 32.81      A   N
ATOM   5120  CA   LEU B 332     -52.295 -14.637   2.357  1.00 32.95      A   C
ATOM   5121  C    LEU B 332     -53.676 -15.053   1.882  1.00 33.40      A   C
ATOM   5122  O    LEU B 332     -53.843 -15.374   0.719  1.00 33.68      A   O
ATOM   5123  CB   LEU B 332     -51.630 -15.759   3.158  1.00 32.68      A   C
ATOM   5124  CG   LEU B 332     -51.552 -17.138   2.512  1.00 32.38      A   C
ATOM   5125  CD1  LEU B 332     -50.318 -17.250   1.663  1.00 31.98      A   C
ATOM   5126  CD2  LEU B 332     -51.561 -18.198   3.577  1.00 32.36      A   C
ATOM   5127  N    ARG B 333     -54.672 -15.030   2.768  1.00 33.81      A   N
ATOM   5128  CA   ARG B 333     -56.032 -15.450   2.389  1.00 34.36      A   C
ATOM   5129  C    ARG B 333     -56.583 -14.588   1.236  1.00 34.12      A   C
ATOM   5130  O    ARG B 333     -57.471 -15.010   0.508  1.00 34.47      A   O
ATOM   5131  CB   ARG B 333     -56.985 -15.539   3.610  1.00 34.71      A   C
ATOM   5132  CG   ARG B 333     -58.050 -14.440   3.745  1.00 36.60      A   C
ATOM   5133  CD   ARG B 333     -59.159 -14.787   4.785  1.00 39.91      A   C
ATOM   5134  NE   ARG B 333     -58.981 -14.159   6.116  1.00 42.25      A   N
ATOM   5135  CZ   ARG B 333     -59.692 -13.125   6.599  1.00 42.96      A   C
```

FIGURE 1 (cont'd)

```
ATOM   5136  NH1 ARG B 333     -59.425  -12.651    7.812  1.00 42.54      A  N
ATOM   5137  NH2 ARG B 333     -60.668  -12.557    5.885  1.00 43.83      A  N
ATOM   5138  N   ARG B 334     -56.014  -13.401    1.057  1.00 33.56      A  N
ATOM   5139  CA  ARG B 334     -56.394  -12.518   -0.032  1.00 33.15      A  C
ATOM   5140  C   ARG B 334     -55.473  -12.666   -1.231  1.00 32.70      A  C
ATOM   5141  O   ARG B 334     -55.619  -11.947   -2.221  1.00 32.84      A  O
ATOM   5142  CB  ARG B 334     -56.397  -11.069    0.433  1.00 33.17      A  C
ATOM   5143  CG  ARG B 334     -57.656  -10.670    1.166  1.00 33.62      A  C
ATOM   5144  CD  ARG B 334     -57.342   -9.675    2.263  1.00 33.76      A  C
ATOM   5145  NE  ARG B 334     -58.548   -9.039    2.777  1.00 34.79      A  N
ATOM   5146  CZ  ARG B 334     -59.128   -9.341    3.935  1.00 35.56      A  C
ATOM   5147  NH1 ARG B 334     -58.617  -10.275    4.733  1.00 35.21      A  N
ATOM   5148  NH2 ARG B 334     -60.223   -8.689    4.301  1.00 36.60      A  N
ATOM   5149  N   GLY B 335     -54.516  -13.580   -1.134  1.00 32.08      A  N
ATOM   5150  CA  GLY B 335     -53.691  -13.934   -2.279  1.00 31.45      A  C
ATOM   5151  C   GLY B 335     -52.346  -13.250   -2.389  1.00 30.80      A  C
ATOM   5152  O   GLY B 335     -51.703  -13.328   -3.427  1.00 31.13      A  O
ATOM   5153  N   VAL B 336     -51.905  -12.586   -1.331  1.00 29.89      A  N
ATOM   5154  CA  VAL B 336     -50.605  -11.932   -1.356  1.00 29.05      A  C
ATOM   5155  C   VAL B 336     -49.509  -12.984   -1.233  1.00 28.63      A  C
ATOM   5156  O   VAL B 336     -49.596  -13.856   -0.392  1.00 28.60      A  O
ATOM   5157  CB  VAL B 336     -50.471  -10.907   -0.219  1.00 28.88      A  C
ATOM   5158  CG1 VAL B 336     -49.128  -10.230   -0.265  1.00 28.78      A  C
ATOM   5159  CG2 VAL B 336     -51.568   -9.878   -0.305  1.00 29.03      A  C
ATOM   5160  N   PRO B 337     -48.484  -12.923   -2.090  1.00 28.41      A  N
ATOM   5161  CA  PRO B 337     -47.304  -13.767   -1.943  1.00 28.16      A  C
ATOM   5162  C   PRO B 337     -46.622  -13.486   -0.623  1.00 27.72      A  C
ATOM   5163  O   PRO B 337     -46.385  -12.331   -0.300  1.00 27.75      A  O
ATOM   5164  CB  PRO B 337     -46.393  -13.291   -3.070  1.00 28.28      A  C
ATOM   5165  CG  PRO B 337     -47.296  -12.708   -4.067  1.00 28.72      A  C
ATOM   5166  CD  PRO B 337     -48.444  -12.128   -3.325  1.00 28.64      A  C
ATOM   5167  N   VAL B 338     -46.308  -14.528    0.135  1.00 27.25      A  N
ATOM   5168  CA  VAL B 338     -45.705  -14.352    1.448  1.00 26.70      A  C
ATOM   5169  C   VAL B 338     -44.343  -15.018    1.538  1.00 26.54      A  C
ATOM   5170  O   VAL B 338     -44.154  -16.112    1.026  1.00 26.73      A  O
ATOM   5171  CB  VAL B 338     -46.609  -14.908    2.572  1.00 26.59      A  C
ATOM   5172  CG1 VAL B 338     -45.946  -14.746    3.928  1.00 26.38      A  C
ATOM   5173  CG2 VAL B 338     -47.948  -14.205    2.576  1.00 26.60      A  C
ATOM   5174  N   LEU B 339     -43.395  -14.337    2.177  1.00 26.21      A  N
ATOM   5175  CA  LEU B 339     -42.172  -14.973    2.649  1.00 25.93      A  C
ATOM   5176  C   LEU B 339     -42.098  -14.818    4.162  1.00 25.79      A  C
ATOM   5177  O   LEU B 339     -41.882  -13.718    4.680  1.00 25.83      A  O
ATOM   5178  CB  LEU B 339     -40.927  -14.391    1.973  1.00 25.85      A  C
ATOM   5179  CG  LEU B 339     -39.605  -15.049    2.371  1.00 25.65      A  C
ATOM   5180  CD1 LEU B 339     -39.634  -16.536    2.094  1.00 25.98      A  C
ATOM   5181  CD2 LEU B 339     -38.475  -14.419    1.641  1.00 25.46      A  C
ATOM   5182  N   HIS B 340     -42.283  -15.926    4.866  1.00 25.60      A  N
ATOM   5183  CA  HIS B 340     -42.383  -15.898    6.312  1.00 25.40      A  C
ATOM   5184  C   HIS B 340     -41.023  -16.128    6.970  1.00 25.30      A  C
ATOM   5185  O   HIS B 340     -40.554  -17.265    7.071  1.00 25.35      A  O
ATOM   5186  CB  HIS B 340     -43.403  -16.938    6.759  1.00 25.46      A  C
ATOM   5187  CG  HIS B 340     -43.922  -16.723    8.146  1.00 25.65      A  C
ATOM   5188  CD2 HIS B 340     -43.856  -15.649    8.971  1.00 25.67      A  C
ATOM   5189  ND1 HIS B 340     -44.604  -17.700    8.841  1.00 26.03      A  N
ATOM   5190  CE1 HIS B 340     -44.944  -17.234   10.030  1.00 25.97      A  C
ATOM   5191  NE2 HIS B 340     -44.496  -15.994   10.137  1.00 25.89      A  N
ATOM   5192  N   LEU B 341     -40.390  -15.045    7.414  1.00 25.14      A  N
ATOM   5193  CA  LEU B 341     -39.035  -15.122    7.949  1.00 25.10      A  C
ATOM   5194  C   LEU B 341     -39.044  -15.268    9.466  1.00 25.07      A  C
ATOM   5195  O   LEU B 341     -38.633  -14.369   10.190  1.00 25.10      A  O
ATOM   5196  CB  LEU B 341     -38.242  -13.892    7.528  1.00 25.08      A  C
ATOM   5197  CG  LEU B 341     -36.819  -14.106    7.025  1.00 25.28      A  C
ATOM   5198  CD1 LEU B 341     -36.202  -12.758    6.725  1.00 25.58      A  C
ATOM   5199  CD2 LEU B 341     -35.956  -14.876    8.000  1.00 25.04      A  C
ATOM   5200  N   ILE B 342     -39.517  -16.416    9.932  1.00 25.12      A  N
```

FIGURE 1 (cont'd)

```
ATOM   5201  CA   ILE B 342     -39.662 -16.711  11.355  1.00 25.19      A    C
ATOM   5202  C    ILE B 342     -38.838 -17.952  11.664  1.00 25.51      A    C
ATOM   5203  O    ILE B 342     -38.893 -18.928  10.921  1.00 25.77      A    O
ATOM   5204  CB   ILE B 342     -41.169 -16.924  11.724  1.00 25.03      A    C
ATOM   5205  CG1  ILE B 342     -41.363 -17.217  13.213  1.00 24.86      A    C
ATOM   5206  CG2  ILE B 342     -41.789 -18.030  10.879  1.00 25.01      A    C
ATOM   5207  CD1  ILE B 342     -42.797 -17.091  13.671  1.00 24.59      A    C
ATOM   5208  N    SER B 343     -38.059 -17.924  12.738  1.00 25.77      A    N
ATOM   5209  CA   SER B 343     -37.238 -19.088  13.074  1.00 26.23      A    C
ATOM   5210  C    SER B 343     -38.064 -20.251  13.587  1.00 26.40      A    C
ATOM   5211  O    SER B 343     -38.948 -20.079  14.419  1.00 26.32      A    O
ATOM   5212  CB   SER B 343     -36.151 -18.742  14.085  1.00 26.34      A    C
ATOM   5213  OG   SER B 343     -36.697 -18.449  15.355  1.00 26.96      A    O
ATOM   5214  N    THR B 344     -37.776 -21.427  13.052  1.00 26.71      A    N
ATOM   5215  CA   THR B 344     -38.383 -22.645  13.514  1.00 27.07      A    C
ATOM   5216  C    THR B 344     -37.222 -23.564  13.815  1.00 27.52      A    C
ATOM   5217  O    THR B 344     -36.480 -23.914  12.905  1.00 27.66      A    O
ATOM   5218  CB   THR B 344     -39.313 -23.276  12.462  1.00 27.00      A    C
ATOM   5219  OG1  THR B 344     -39.204 -22.558  11.234  1.00 26.74      A    O
ATOM   5220  N    PRO B 345     -37.062 -23.978  15.089  1.00 27.87      A    N
ATOM   5221  CA   PRO B 345     -38.012 -23.803  16.190  1.00 27.90      A    C
ATOM   5222  C    PRO B 345     -37.982 -22.399  16.755  1.00 27.69      A    C
ATOM   5223  O    PRO B 345     -37.112 -21.610  16.366  1.00 27.45      A    O
ATOM   5224  CB   PRO B 345     -37.533 -24.820  17.242  1.00 28.16      A    C
ATOM   5225  CG   PRO B 345     -36.299 -25.486  16.670  1.00 28.23      A    C
ATOM   5226  CD   PRO B 345     -35.820 -24.610  15.560  1.00 28.00      A    C
ATOM   5227  N    PHE B 346     -38.935 -22.097  17.639  1.00 27.67      A    N
ATOM   5228  CA   PHE B 346     -38.986 -20.803  18.315  1.00 27.82      A    C
ATOM   5229  C    PHE B 346     -37.833 -20.658  19.301  1.00 28.01      A    C
ATOM   5230  O    PHE B 346     -37.317 -21.661  19.789  1.00 28.35      A    O
ATOM   5231  CB   PHE B 346     -40.299 -20.635  19.076  1.00 27.88      A    C
ATOM   5232  CG   PHE B 346     -41.525 -20.620  18.209  1.00 28.02      A    C
ATOM   5233  CD1  PHE B 346     -41.436 -20.434  16.843  1.00 27.86      A    C
ATOM   5234  CD2  PHE B 346     -42.784 -20.763  18.780  1.00 28.59      A    C
ATOM   5235  CE1  PHE B 346     -42.578 -20.413  16.057  1.00 27.81      A    C
ATOM   5236  CE2  PHE B 346     -43.927 -20.740  18.005  1.00 28.46      A    C
ATOM   5237  CZ   PHE B 346     -43.822 -20.563  16.641  1.00 28.01      A    C
ATOM   5238  N    PRO B 347     -37.433 -19.410  19.609  1.00 28.00      A    N
ATOM   5239  CA   PRO B 347     -36.351 -19.147  20.560  1.00 28.42      A    C
ATOM   5240  C    PRO B 347     -36.599 -19.867  21.885  1.00 29.05      A    C
ATOM   5241  O    PRO B 347     -37.756 -19.977  22.291  1.00 29.21      A    O
ATOM   5242  CB   PRO B 347     -36.436 -17.632  20.776  1.00 28.16      A    C
ATOM   5243  CG   PRO B 347     -37.033 -17.121  19.570  1.00 27.71      A    C
ATOM   5244  CD   PRO B 347     -37.982 -18.160  19.067  1.00 27.70      A    C
ATOM   5245  N    ALA B 348     -35.541 -20.349  22.550  1.00 29.70      A    N
ATOM   5246  CA   ALA B 348     -35.682 -21.010  23.856  1.00 30.32      A    C
ATOM   5247  C    ALA B 348     -36.403 -20.110  24.849  1.00 30.57      A    C
ATOM   5248  O    ALA B 348     -37.224 -20.574  25.638  1.00 30.70      A    O
ATOM   5249  CB   ALA B 348     -34.334 -21.418  24.399  1.00 30.61      A    C
ATOM   5250  N    VAL B 349     -36.099 -18.815  24.760  1.00 30.70      A    N
ATOM   5251  CA   VAL B 349     -36.674 -17.761  25.604  1.00 30.90      A    C
ATOM   5252  C    VAL B 349     -38.075 -17.282  25.175  1.00 30.97      A    C
ATOM   5253  O    VAL B 349     -38.513 -16.203  25.575  1.00 31.09      A    O
ATOM   5254  CB   VAL B 349     -35.716 -16.521  25.714  1.00 30.84      A    C
ATOM   5255  CG1  VAL B 349     -34.430 -16.904  26.396  1.00 31.41      A    C
ATOM   5256  CG2  VAL B 349     -35.426 -15.891  24.343  1.00 30.43      A    C
ATOM   5257  N    TRP B 350     -38.786 -18.086  24.392  1.00 31.05      A    N
ATOM   5258  CA   TRP B 350     -40.017 -17.621  23.772  1.00 31.11      A    C
ATOM   5259  C    TRP B 350     -41.152 -17.553  24.764  1.00 31.46      A    C
ATOM   5260  O    TRP B 350     -41.317 -18.448  25.587  1.00 31.73      A    O
ATOM   5261  CB   TRP B 350     -40.396 -18.503  22.585  1.00 30.94      A    C
ATOM   5262  CG   TRP B 350     -41.589 -18.009  21.825  1.00 30.51      A    C
ATOM   5263  CD1  TRP B 350     -41.663 -16.885  21.048  1.00 30.20      A    C
ATOM   5264  CD2  TRP B 350     -42.879 -18.624  21.764  1.00 30.17      A    C
ATOM   5265  CE2  TRP B 350     -43.685 -17.819  20.932  1.00 29.92      A    C
```

FIGURE 1 (cont'd)

```
ATOM   5266  CE3 TRP B 350     -43.436 -19.778  22.334  1.00 30.19      A    C
ATOM   5267  NE1 TRP B 350     -42.917 -16.764  20.511  1.00 29.94      A    N
ATOM   5268  CZ2 TRP B 350     -45.021 -18.129  20.659  1.00 29.65      A    C
ATOM   5269  CZ3 TRP B 350     -44.761 -20.084  22.060  1.00 30.01      A    C
ATOM   5270  CH2 TRP B 350     -45.539 -19.260  21.232  1.00 29.66      A    C
ATOM   5271  N   HIS B 351     -41.928 -16.480  24.666  1.00 31.77      A    N
ATOM   5272  CA  HIS B 351     -43.086 -16.244  25.523  1.00 32.37      A    C
ATOM   5273  C   HIS B 351     -42.776 -16.479  27.006  1.00 32.94      A    C
ATOM   5274  O   HIS B 351     -43.529 -17.154  27.717  1.00 33.17      A    O
ATOM   5275  CB  HIS B 351     -44.292 -17.069  25.056  1.00 32.35      A    C
ATOM   5276  CG  HIS B 351     -45.055 -16.447  23.922  1.00 32.41      A    C
ATOM   5277  CD2 HIS B 351     -44.710 -15.483  23.032  1.00 32.06      A    C
ATOM   5278  ND1 HIS B 351     -46.352 -16.804  23.612  1.00 32.53      A    N
ATOM   5279  CE1 HIS B 351     -46.766 -16.096  22.576  1.00 32.26      A    C
ATOM   5280  NE2 HIS B 351     -45.789 -15.289  22.203  1.00 31.85      A    N
ATOM   5281  N   THR B 352     -41.652 -15.911  27.450  1.00 33.39      A    N
ATOM   5282  CA  THR B 352     -41.205 -15.962  28.847  1.00 33.93      A    C
ATOM   5283  C   THR B 352     -40.435 -14.691  29.204  1.00 34.18      A    C
ATOM   5284  O   THR B 352     -39.841 -14.075  28.322  1.00 33.97      A    O
ATOM   5285  CB  THR B 352     -40.325 -17.215  29.135  1.00 34.07      A    C
ATOM   5286  CG2 THR B 352     -39.483 -17.577  27.944  1.00 33.55      A    C
ATOM   5287  OG1 THR B 352     -39.454 -16.965  30.254  1.00 34.79      A    O
ATOM   5288  N   PRO B 353     -40.435 -14.305  30.501  1.00 34.70      A    N
ATOM   5289  CA  PRO B 353     -39.692 -13.139  31.011  1.00 34.81      A    C
ATOM   5290  C   PRO B 353     -38.242 -13.116  30.554  1.00 34.60      A    C
ATOM   5291  O   PRO B 353     -37.618 -12.057  30.553  1.00 34.60      A    O
ATOM   5292  CB  PRO B 353     -39.717 -13.347  32.520  1.00 35.23      A    C
ATOM   5293  CG  PRO B 353     -40.945 -14.105  32.763  1.00 35.53      A    C
ATOM   5294  CD  PRO B 353     -41.180 -14.980  31.580  1.00 34.96      A    C
ATOM   5295  N   ALA B 354     -37.729 -14.284  30.173  1.00 34.32      A    N
ATOM   5296  CA  ALA B 354     -36.359 -14.437  29.702  1.00 34.06      A    C
ATOM   5297  C   ALA B 354     -36.070 -13.665  28.408  1.00 33.80      A    C
ATOM   5298  O   ALA B 354     -34.932 -13.232  28.185  1.00 33.75      A    O
ATOM   5299  CB  ALA B 354     -36.032 -15.908  29.536  1.00 34.06      A    C
ATOM   5300  N   ASP B 355     -37.096 -13.482  27.570  1.00 33.56      A    N
ATOM   5301  CA  ASP B 355     -36.958 -12.768  26.289  1.00 33.34      A    C
ATOM   5302  C   ASP B 355     -36.667 -11.288  26.512  1.00 33.46      A    C
ATOM   5303  O   ASP B 355     -37.543 -10.432  26.351  1.00 33.33      A    O
ATOM   5304  CB  ASP B 355     -38.207 -12.962  25.406  1.00 33.04      A    C
ATOM   5305  CG  ASP B 355     -37.996 -12.517  23.953  1.00 32.51      A    C
ATOM   5306  OD1 ASP B 355     -36.895 -12.026  23.622  1.00 32.70      A    O
ATOM   5307  OD2 ASP B 355     -38.937 -12.661  23.138  1.00 31.60      A    O
ATOM   5308  N   THR B 356     -35.429 -11.006  26.898  1.00 33.71      A    N
ATOM   5309  CA  THR B 356     -34.983  -9.643  27.108  1.00 33.95      A    C
ATOM   5310  C   THR B 356     -33.691  -9.415  26.337  1.00 34.42      A    C
ATOM   5311  O   THR B 356     -33.159 -10.351  25.727  1.00 34.32      A    O
ATOM   5312  CB  THR B 356     -34.750  -9.327  28.601  1.00 33.36      A    C
ATOM   5313  CG2 THR B 356     -36.045  -9.307  29.373  1.00 33.52      A    C
ATOM   5314  OG1 THR B 356     -33.882 -10.309  29.167  1.00 33.35      A    O
ATOM   5315  N   GLU B 357     -33.204  -8.169  26.371  1.00 35.04      A    N
ATOM   5316  CA  GLU B 357     -31.979  -7.755  25.677  1.00 35.55      A    C
ATOM   5317  C   GLU B 357     -30.812  -8.678  26.020  1.00 35.89      A    C
ATOM   5318  O   GLU B 357     -30.079  -9.117  25.130  1.00 35.85      A    O
ATOM   5319  CB  GLU B 357     -31.647  -6.289  26.001  1.00 35.73      A    C
ATOM   5320  CG  GLU B 357     -30.353  -5.765  25.368  1.00 36.38      A    C
ATOM   5321  CD  GLU B 357     -30.139  -4.264  25.566  1.00 37.44      A    C
ATOM   5322  OE1 GLU B 357     -31.004  -3.601  26.185  1.00 38.19      A    O
ATOM   5323  OE2 GLU B 357     -29.099  -3.744  25.093  1.00 37.78      A    O
ATOM   5324  N   VAL B 358     -30.682  -8.988  27.308  1.00 36.39      A    N
ATOM   5325  CA  VAL B 358     -29.614  -9.827  27.843  1.00 36.81      A    C
ATOM   5326  C   VAL B 358     -29.428 -11.167  27.129  1.00 36.65      A    C
ATOM   5327  O   VAL B 358     -28.340 -11.734  27.176  1.00 36.91      A    O
ATOM   5328  CB  VAL B 358     -29.837 -10.111  29.339  1.00 37.16      A    C
ATOM   5329  CG1 VAL B 358     -28.664  -9.602  30.140  1.00 37.98      A    C
ATOM   5330  N   ASN B 359     -30.473 -11.674  26.472  1.00 36.24      A    N
```

FIGURE 1 (cont'd)

```
ATOM   5331  CA   ASN B 359     -30.434 -13.029  25.902  1.00 35.91      A  C
ATOM   5332  C    ASN B 359     -30.389 -13.095  24.375  1.00 35.34      A  C
ATOM   5333  O    ASN B 359     -30.467 -14.180  23.796  1.00 35.23      A  O
ATOM   5334  CB   ASN B 359     -31.593 -13.879  26.442  1.00 36.12      A  C
ATOM   5335  CG   ASN B 359     -31.471 -14.182  27.940  1.00 37.13      A  C
ATOM   5336  ND2  ASN B 359     -30.339 -13.827  28.537  1.00 38.11      A  N
ATOM   5337  OD1  ASN B 359     -32.391 -14.730  28.547  1.00 37.72      A  O
ATOM   5338  N    LEU B 360     -30.266 -11.938  23.733  1.00 34.81      A  N
ATOM   5339  CA   LEU B 360     -30.080 -11.871  22.291  1.00 34.31      A  C
ATOM   5340  C    LEU B 360     -28.627 -12.171  21.969  1.00 34.37      A  C
ATOM   5341  O    LEU B 360     -27.776 -12.002  22.824  1.00 34.89      A  O
ATOM   5342  CB   LEU B 360     -30.437 -10.479  21.788  1.00 34.02      A  C
ATOM   5343  CG   LEU B 360     -31.804  -9.907  22.163  1.00 33.47      A  C
ATOM   5344  CD1  LEU B 360     -31.944  -8.487  21.648  1.00 32.90      A  C
ATOM   5345  CD2  LEU B 360     -32.920 -10.776  21.627  1.00 33.10      A  C
ATOM   5346  N    HIS B 361     -28.340 -12.632  20.754  1.00 34.07      A  N
ATOM   5347  CA   HIS B 361     -26.956 -12.833  20.311  1.00 33.90      A  C
ATOM   5348  C    HIS B 361     -26.616 -11.708  19.349  1.00 34.21      A  C
ATOM   5349  O    HIS B 361     -26.891 -11.823  18.151  1.00 34.04      A  O
ATOM   5350  CB   HIS B 361     -26.784 -14.194  19.618  1.00 33.55      A  C
ATOM   5351  CG   HIS B 361     -25.373 -14.714  19.620  1.00 32.70      A  C
ATOM   5352  CD2  HIS B 361     -24.795 -15.725  20.317  1.00 31.82      A  C
ATOM   5353  ND1  HIS B 361     -24.385 -14.199  18.809  1.00 31.54      A  N
ATOM   5354  CE1  HIS B 361     -23.256 -14.854  19.022  1.00 31.56      A  C
ATOM   5355  NE2  HIS B 361     -23.476 -15.782  19.936  1.00 31.23      A  N
ATOM   5356  N    PRO B 362     -26.031 -10.604  19.863  1.00 34.70      A  N
ATOM   5357  CA   PRO B 362     -25.801  -9.404  19.035  1.00 34.91      A  C
ATOM   5358  C    PRO B 362     -25.144  -9.690  17.670  1.00 34.88      A  C
ATOM   5359  O    PRO B 362     -25.573  -9.113  16.663  1.00 34.73      A  O
ATOM   5360  CB   PRO B 362     -24.910  -8.523  19.925  1.00 35.21      A  C
ATOM   5361  CG   PRO B 362     -25.291  -8.911  21.309  1.00 35.32      A  C
ATOM   5362  CD   PRO B 362     -25.562 -10.400  21.245  1.00 35.00      A  C
ATOM   5363  N    PRO B 363     -24.130 -10.590  17.628  1.00 35.00      A  N
ATOM   5364  CA   PRO B 363     -23.605 -10.966  16.318  1.00 35.00      A  C
ATOM   5365  C    PRO B 363     -24.704 -11.445  15.383  1.00 34.65      A  C
ATOM   5366  O    PRO B 363     -24.865 -10.869  14.306  1.00 34.59      A  O
ATOM   5367  CB   PRO B 363     -22.630 -12.099  16.648  1.00 35.29      A  C
ATOM   5368  CG   PRO B 363     -22.130 -11.741  17.995  1.00 35.69      A  C
ATOM   5369  CD   PRO B 363     -23.367 -11.247  18.711  1.00 34.94      A  C
ATOM   5370  N    THR B 364     -25.466 -12.456  15.809  1.00 34.30      A  N
ATOM   5371  CA   THR B 364     -26.551 -13.009  15.002  1.00 33.94      A  C
ATOM   5372  C    THR B 364     -27.480 -11.906  14.496  1.00 33.87      A  C
ATOM   5373  O    THR B 364     -27.930 -11.955  13.352  1.00 33.74      A  O
ATOM   5374  CB   THR B 364     -27.358 -14.069  15.761  1.00 33.83      A  C
ATOM   5375  CG2  THR B 364     -28.410 -14.669  14.863  1.00 33.52      A  C
ATOM   5376  OG1  THR B 364     -26.488 -15.116  16.202  1.00 34.07      A  O
ATOM   5377  N    VAL B 365     -27.741 -10.906  15.335  1.00 33.97      A  N
ATOM   5378  CA   VAL B 365     -28.584  -9.771  14.953  1.00 34.07      A  C
ATOM   5379  C    VAL B 365     -28.008  -9.028  13.762  1.00 34.25      A  C
ATOM   5380  O    VAL B 365     -28.686  -8.842  12.766  1.00 34.08      A  O
ATOM   5381  CB   VAL B 365     -28.795  -8.783  16.122  1.00 34.10      A  C
ATOM   5382  CG1  VAL B 365     -29.672  -9.397  17.187  1.00 34.02      A  C
ATOM   5383  CG2  VAL B 365     -29.413  -7.488  15.629  1.00 33.94      A  C
ATOM   5384  N    HIS B 366     -26.749  -8.623  13.867  1.00 34.67      A  N
ATOM   5385  CA   HIS B 366     -26.111  -7.833  12.832  1.00 35.12      A  C
ATOM   5386  C    HIS B 366     -25.956  -8.601  11.535  1.00 35.32      A  C
ATOM   5387  O    HIS B 366     -26.208  -8.063  10.463  1.00 35.44      A  O
ATOM   5388  CB   HIS B 366     -24.774  -7.300  13.319  1.00 35.37      A  C
ATOM   5389  CG   HIS B 366     -24.892  -6.407  14.510  1.00 35.50      A  C
ATOM   5390  CD2  HIS B 366     -24.410  -6.528  15.770  1.00 35.49      A  C
ATOM   5391  ND1  HIS B 366     -25.591  -5.219  14.477  1.00 35.53      A  N
ATOM   5392  CE1  HIS B 366     -25.537  -4.647  15.667  1.00 35.54      A  C
ATOM   5393  NE2  HIS B 366     -24.820  -5.417  16.468  1.00 35.94      A  N
ATOM   5394  N    ASN B 367     -25.558  -9.864  11.635  1.00 35.38      A  N
ATOM   5395  CA   ASN B 367     -25.551 -10.759  10.485  1.00 35.42      A  C
```

FIGURE 1 (cont'd)

```
ATOM   5396  C    ASN B 367     -26.850 -10.679   9.707  1.00 35.23      A  C
ATOM   5397  O    ASN B 367     -26.839 -10.444   8.501  1.00 35.38      A  O
ATOM   5398  CB   ASN B 367     -25.312 -12.204  10.921  1.00 35.50      A  C
ATOM   5399  CG   ASN B 367     -23.886 -12.452  11.374  1.00 36.14      A  C
ATOM   5400  ND2  ASN B 367     -23.552 -13.721  11.609  1.00 36.24      A  N
ATOM   5401  OD1  ASN B 367     -23.091 -11.518  11.511  1.00 37.05      A  O
ATOM   5402  N    LEU B 368     -27.967 -10.855  10.408  1.00 34.94      A  N
ATOM   5403  CA   LEU B 368     -29.287 -10.814   9.793  1.00 34.71      A  C
ATOM   5404  C    LEU B 368     -29.551  -9.493   9.066  1.00 34.91      A  C
ATOM   5405  O    LEU B 368     -30.224  -9.468   8.040  1.00 35.06      A  O
ATOM   5406  CB   LEU B 368     -30.382 -11.088  10.822  1.00 34.32      A  C
ATOM   5407  CG   LEU B 368     -30.476 -12.506  11.378  1.00 33.72      A  C
ATOM   5408  CD1  LEU B 368     -31.450 -12.541  12.516  1.00 33.48      A  C
ATOM   5409  CD2  LEU B 368     -30.892 -13.511  10.328  1.00 32.89      A  C
ATOM   5410  N    ALA B 369     -29.010  -8.397   9.582  1.00 34.17      A  N
ATOM   5411  CA   ALA B 369     -29.236  -7.095   8.983  1.00 33.50      A  C
ATOM   5412  C    ALA B 369     -28.395  -6.931   7.737  1.00 34.47      A  C
ATOM   5413  O    ALA B 369     -28.838  -6.334   6.763  1.00 35.65      A  O
ATOM   5414  CB   ALA B 369     -28.927  -6.017   9.966  1.00 24.54      A  C
ATOM   5415  N    ARG B 370     -27.178  -7.462   7.779  1.00 35.15      A  N
ATOM   5416  CA   ARG B 370     -26.305  -7.479   6.612  1.00 34.82      A  C
ATOM   5417  C    ARG B 370     -26.980  -8.270   5.500  1.00 34.23      A  C
ATOM   5418  O    ARG B 370     -27.077  -7.790   4.375  1.00 34.14      A  O
ATOM   5419  CB   ARG B 370     -24.911  -8.037   6.954  1.00 35.11      A  C
ATOM   5420  CG   ARG B 370     -24.119  -7.141   7.923  1.00 35.43      A  C
ATOM   5421  CD   ARG B 370     -22.687  -7.630   8.144  1.00 35.74      A  C
ATOM   5422  NE   ARG B 370     -21.904  -6.691   8.949  1.00 35.85      A  N
ATOM   5423  CZ   ARG B 370     -20.582  -6.562   8.877  1.00 35.99      A  C
ATOM   5424  N    ILE B 371     -27.487  -9.457   5.831  1.00 33.46      A  N
ATOM   5425  CA   ILE B 371     -28.207 -10.291   4.868  1.00 32.84      A  C
ATOM   5426  C    ILE B 371     -29.440  -9.569   4.305  1.00 32.78      A  C
ATOM   5427  O    ILE B 371     -29.657  -9.550   3.097  1.00 32.88      A  O
ATOM   5428  CB   ILE B 371     -28.591 -11.664   5.466  1.00 32.51      A  C
ATOM   5429  CG1  ILE B 371     -27.333 -12.474   5.766  1.00 32.48      A  C
ATOM   5430  CG2  ILE B 371     -29.488 -12.436   4.514  1.00 32.01      A  C
ATOM   5431  CD1  ILE B 371     -27.553 -13.708   6.610  1.00 32.21      A  C
ATOM   5432  N    LEU B 372     -30.232  -8.958   5.178  1.00 32.60      A  N
ATOM   5433  CA   LEU B 372     -31.440  -8.257   4.759  1.00 32.44      A  C
ATOM   5434  C    LEU B 372     -31.131  -7.049   3.886  1.00 32.75      A  C
ATOM   5435  O    LEU B 372     -31.764  -6.867   2.854  1.00 32.69      A  O
ATOM   5436  CB   LEU B 372     -32.257  -7.842   5.978  1.00 32.07      A  C
ATOM   5437  CG   LEU B 372     -33.467  -8.670   6.399  1.00 31.32      A  C
ATOM   5438  CD1  LEU B 372     -33.535 -10.046   5.782  1.00 30.78      A  C
ATOM   5439  CD2  LEU B 372     -33.511  -8.755   7.905  1.00 30.91      A  C
ATOM   5440  N    ALA B 373     -30.154  -6.241   4.301  1.00 33.15      A  N
ATOM   5441  CA   ALA B 373     -29.779  -5.030   3.579  1.00 33.53      A  C
ATOM   5442  C    ALA B 373     -29.347  -5.335   2.158  1.00 33.85      A  C
ATOM   5443  O    ALA B 373     -29.672  -4.595   1.237  1.00 34.02      A  O
ATOM   5444  CB   ALA B 373     -28.684  -4.311   4.303  1.00 33.68      A  C
ATOM   5445  N    VAL B 374     -28.609  -6.425   1.986  1.00 34.02      A  N
ATOM   5446  CA   VAL B 374     -28.202  -6.873   0.663  1.00 34.26      A  C
ATOM   5447  C    VAL B 374     -29.438  -7.294  -0.114  1.00 34.18      A  C
ATOM   5448  O    VAL B 374     -29.660  -6.835  -1.228  1.00 34.47      A  O
ATOM   5449  CB   VAL B 374     -27.186  -8.032   0.734  1.00 34.34      A  C
ATOM   5450  CG1  VAL B 374     -27.024  -8.686  -0.618  1.00 34.58      A  C
ATOM   5451  CG2  VAL B 374     -25.841  -7.534   1.224  1.00 34.79      A  C
ATOM   5452  N    PHE B 375     -30.255  -8.147   0.495  1.00 33.92      A  N
ATOM   5453  CA   PHE B 375     -31.504  -8.595  -0.116  1.00 33.77      A  C
ATOM   5454  C    PHE B 375     -32.351  -7.413  -0.580  1.00 34.07      A  C
ATOM   5455  O    PHE B 375     -32.781  -7.373  -1.730  1.00 34.15      A  O
ATOM   5456  CB   PHE B 375     -32.312  -9.462   0.860  1.00 33.32      A  C
ATOM   5457  CG   PHE B 375     -33.610  -9.962   0.293  1.00 32.60      A  C
ATOM   5458  CD1  PHE B 375     -33.728 -11.266  -0.158  1.00 32.47      A  C
ATOM   5459  CD2  PHE B 375     -34.711  -9.125   0.199  1.00 32.08      A  C
ATOM   5460  CE1  PHE B 375     -34.924 -11.729  -0.684  1.00 32.39      A  C
```

FIGURE 1 (cont'd)

```
ATOM   5461  CE2 PHE B 375     -35.897  -9.574  -0.327  1.00 32.22      A  C
ATOM   5462  CZ  PHE B 375     -36.006 -10.882  -0.769  1.00 32.33      A  C
ATOM   5463  N   LEU B 376     -32.585  -6.461   0.324  1.00 34.43      A  N
ATOM   5464  CA  LEU B 376     -33.407  -5.290   0.035  1.00 34.87      A  C
ATOM   5465  C   LEU B 376     -32.847  -4.569  -1.179  1.00 35.67      A  C
ATOM   5466  O   LEU B 376     -33.601  -4.198  -2.078  1.00 35.83      A  O
ATOM   5467  CB  LEU B 376     -33.486  -4.350   1.243  1.00 34.53      A  C
ATOM   5468  CG  LEU B 376     -34.831  -3.662   1.491  1.00 33.82      A  C
ATOM   5469  N   ALA B 377     -31.522  -4.415  -1.216  1.00 36.56      A  N
ATOM   5470  CA  ALA B 377     -30.822  -3.743  -2.316  1.00 37.43      A  C
ATOM   5471  C   ALA B 377     -30.910  -4.507  -3.627  1.00 37.89      A  C
ATOM   5472  O   ALA B 377     -31.169  -3.915  -4.666  1.00 38.20      A  O
ATOM   5473  CB  ALA B 377     -29.379  -3.498  -1.955  1.00 37.58      A  C
ATOM   5474  N   GLU B 378     -30.693  -5.818  -3.573  1.00 38.21      A  N
ATOM   5475  CA  GLU B 378     -30.819  -6.669  -4.756  1.00 38.62      A  C
ATOM   5476  C   GLU B 378     -32.264  -6.702  -5.292  1.00 38.60      A  C
ATOM   5477  O   GLU B 378     -32.477  -6.469  -6.474  1.00 38.93      A  O
ATOM   5478  CB  GLU B 378     -30.270  -8.080  -4.496  1.00 38.70      A  C
ATOM   5479  CG  GLU B 378     -28.743  -8.164  -4.476  1.00 39.87      A  C
ATOM   5480  CD  GLU B 378     -28.192  -9.591  -4.418  1.00 41.26      A  C
ATOM   5481  OE1 GLU B 378     -28.957 -10.563  -4.554  1.00 41.76      A  O
ATOM   5482  OE2 GLU B 378     -26.967  -9.747  -4.245  1.00 41.91      A  O
ATOM   5483  N   TYR B 379     -33.245  -6.957  -4.424  1.00 38.42      A  N
ATOM   5484  CA  TYR B 379     -34.658  -7.027  -4.829  1.00 38.40      A  C
ATOM   5485  C   TYR B 379     -35.126  -5.750  -5.510  1.00 38.96      A  C
ATOM   5486  O   TYR B 379     -35.805  -5.806  -6.524  1.00 39.12      A  O
ATOM   5487  CB  TYR B 379     -35.571  -7.341  -3.634  1.00 37.83      A  C
ATOM   5488  CG  TYR B 379     -37.011  -7.648  -4.004  1.00 37.02      A  C
ATOM   5489  CD1 TYR B 379     -37.486  -8.950  -4.000  1.00 36.30      A  C
ATOM   5490  CD2 TYR B 379     -37.895  -6.634  -4.349  1.00 36.78      A  C
ATOM   5491  CE1 TYR B 379     -38.803  -9.233  -4.334  1.00 36.15      A  C
ATOM   5492  CE2 TYR B 379     -39.210  -6.903  -4.686  1.00 36.51      A  C
ATOM   5493  CZ  TYR B 379     -39.656  -8.201  -4.676  1.00 36.19      A  C
ATOM   5494  OH  TYR B 379     -40.960  -8.469  -5.011  1.00 35.92      A  O
ATOM   5495  N   LEU B 380     -34.760  -4.606  -4.947  1.00 39.62      A  N
ATOM   5496  CA  LEU B 380     -35.171  -3.315  -5.479  1.00 40.43      A  C
ATOM   5497  C   LEU B 380     -34.178  -2.701  -6.472  1.00 41.24      A  C
ATOM   5498  O   LEU B 380     -34.330  -1.537  -6.855  1.00 41.79      A  O
ATOM   5499  CB  LEU B 380     -35.417  -2.343  -4.326  1.00 40.16      A  C
ATOM   5500  CG  LEU B 380     -36.838  -2.020  -3.872  1.00 39.76      A  C
ATOM   5501  CD1 LEU B 380     -37.770  -3.202  -4.004  1.00 39.37      A  C
ATOM   5502  CD2 LEU B 380     -36.817  -1.503  -2.442  1.00 39.49      A  C
ATOM   5503  N   GLY B 381     -33.163  -3.463  -6.880  1.00 39.64      A  N
ATOM   5504  CA  GLY B 381     -32.133  -2.960  -7.809  1.00 38.31      A  C
ATOM   5505  C   GLY B 381     -31.486  -1.644  -7.395  1.00 37.58      A  C
ATOM   5506  O   GLY B 381     -30.996  -0.883  -8.232  1.00 37.11      A  O
ATOM   5507  N   LEU B 382     -31.491  -1.384  -6.092  1.00 37.42      A  N
ATOM   5508  CA  LEU B 382     -30.935  -0.167  -5.533  1.00 37.65      A  C
ATOM   5509  C   LEU B 382     -29.425  -0.177  -5.685  1.00 38.02      A  C
ATOM   5510  O   LEU B 382     -28.805   0.895  -5.803  1.00 38.38      A  O
ATOM   5511  CB  LEU B 382     -31.281  -0.048  -4.045  1.00 37.60      A  C
ATOM   5512  CG  LEU B 382     -32.732  -0.146  -3.564  1.00 37.58      A  C
ATOM   5513  CD1 LEU B 382     -32.802   0.001  -2.048  1.00 37.39      A  C
ATOM   5514  CD2 LEU B 382     -33.624   0.881  -4.245  1.00 38.00      A  C
ATOM   5515  OXT LEU B 382     -28.815  -1.259  -5.677  1.00 38.10      A  O
TER    5516      LEU B 382
ATOM   5517  N   GLY C  74     -70.262 -16.540 -35.749  1.00 39.61      A  N
ATOM   5518  CA  GLY C  74     -69.044 -17.058 -35.054  1.00 39.68      A  C
ATOM   5519  C   GLY C  74     -69.252 -17.248 -33.560  1.00 39.51      A  C
ATOM   5520  O   GLY C  74     -69.039 -18.348 -33.040  1.00 39.66      A  O
ATOM   5521  N   SER C  75     -69.668 -16.175 -32.876  1.00 39.22      A  N
ATOM   5522  CA  SER C  75     -69.939 -16.187 -31.417  1.00 38.94      A  C
ATOM   5523  C   SER C  75     -71.381 -16.594 -31.137  1.00 39.93      A  C
ATOM   5524  O   SER C  75     -71.977 -17.290 -31.944  1.00 39.59      A  O
ATOM   5525  CB  SER C  75     -69.615 -14.827 -30.782  1.00 38.39      A  C
```

FIGURE 1 (cont'd)

```
ATOM   5526  OG   SER C  75     -70.155 -13.775 -31.559  1.00 37.24      A    O
ATOM   5527  N    LEU C  76     -71.947 -16.179 -30.007  1.00 42.18      A    N
ATOM   5528  CA   LEU C  76     -73.337 -16.532 -29.726  1.00 45.28      A    C
ATOM   5529  C    LEU C  76     -74.173 -15.404 -29.122  1.00 49.00      A    C
ATOM   5530  O    LEU C  76     -73.633 -14.527 -28.436  1.00 48.66      A    O
ATOM   5531  CB   LEU C  76     -73.436 -17.838 -28.921  1.00 44.43      A    C
ATOM   5532  CG   LEU C  76     -73.029 -17.979 -27.456  1.00 43.25      A    C
ATOM   5533  CD1  LEU C  76     -74.153 -17.489 -26.611  1.00 43.02      A    C
ATOM   5534  CD2  LEU C  76     -72.739 -19.450 -27.118  1.00 42.33      A    C
ATOM   5535  N    PRO C  77     -75.502 -15.431 -29.379  1.00 54.13      A    N
ATOM   5536  CA   PRO C  77     -76.328 -14.258 -29.098  1.00 55.35      A    C
ATOM   5537  C    PRO C  77     -76.803 -14.152 -27.654  1.00 55.71      A    C
ATOM   5538  O    PRO C  77     -77.007 -15.161 -26.981  1.00 55.62      A    O
ATOM   5539  CB   PRO C  77     -77.519 -14.433 -30.044  1.00 56.07      A    C
ATOM   5540  CG   PRO C  77     -77.654 -15.918 -30.215  1.00 55.90      A    C
ATOM   5541  CD   PRO C  77     -76.299 -16.540 -29.950  1.00 54.80      A    C
ATOM   5542  N    GLU C  78     -76.992 -12.915 -27.209  1.00 55.90      A    N
ATOM   5543  CA   GLU C  78     -77.359 -12.603 -25.830  1.00 55.78      A    C
ATOM   5544  C    GLU C  78     -78.426 -13.515 -25.226  1.00 57.04      A    C
ATOM   5545  O    GLU C  78     -78.283 -13.980 -24.094  1.00 57.28      A    O
ATOM   5546  CB   GLU C  78     -77.810 -11.147 -25.720  1.00 53.80      A    C
ATOM   5547  CG   GLU C  78     -76.763 -10.192 -25.202  1.00 51.30      A    C
ATOM   5548  CD   GLU C  78     -77.409  -9.018 -24.510  1.00 51.83      A    C
ATOM   5549  OE1  GLU C  78     -78.229  -9.254 -23.592  1.00 51.89      A    O
ATOM   5550  OE2  GLU C  78     -77.102  -7.864 -24.877  1.00 51.71      A    O
ATOM   5551  N    ALA C  79     -79.489 -13.766 -25.981  1.00 58.27      A    N
ATOM   5552  CA   ALA C  79     -80.606 -14.578 -25.510  1.00 58.92      A    C
ATOM   5553  C    ALA C  79     -80.175 -15.971 -25.058  1.00 58.68      A    C
ATOM   5554  O    ALA C  79     -80.549 -16.409 -23.971  1.00 58.82      A    O
ATOM   5555  CB   ALA C  79     -81.669 -14.673 -26.590  1.00 59.75      A    C
ATOM   5556  N    ARG C  80     -79.390 -16.648 -25.898  1.00 57.94      A    N
ATOM   5557  CA   ARG C  80     -78.873 -17.989 -25.601  1.00 56.75      A    C
ATOM   5558  C    ARG C  80     -77.761 -17.918 -24.554  1.00 56.70      A    C
ATOM   5559  O    ARG C  80     -77.665 -18.780 -23.685  1.00 56.73      A    O
ATOM   5560  CB   ARG C  80     -78.388 -18.700 -26.885  1.00 55.03      A    C
ATOM   5561  CG   ARG C  80     -78.467 -20.257 -26.857  1.00 46.86      A    C
ATOM   5562  CD   ARG C  80     -78.980 -20.905 -28.195  1.00 34.17      A    C
ATOM   5563  NE   ARG C  80     -79.934 -22.017 -27.954  1.00 25.26      A    N
ATOM   5564  CZ   ARG C  80     -81.263 -21.985 -28.176  1.00 19.52      A    C
ATOM   5565  NH1  ARG C  80     -81.866 -20.895 -28.687  1.00 17.33      A    N
ATOM   5566  NH2  ARG C  80     -81.998 -23.064 -27.894  1.00 17.16      A    N
ATOM   5567  N    LEU C  81     -76.937 -16.876 -24.628  1.00 56.42      A    N
ATOM   5568  CA   LEU C  81     -75.836 -16.693 -23.683  1.00 55.84      A    C
ATOM   5569  C    LEU C  81     -76.356 -16.602 -22.258  1.00 55.88      A    C
ATOM   5570  O    LEU C  81     -75.925 -17.350 -21.389  1.00 55.52      A    O
ATOM   5571  CB   LEU C  81     -75.013 -15.453 -24.043  1.00 55.64      A    C
ATOM   5572  CG   LEU C  81     -73.684 -15.226 -23.328  1.00 54.85      A    C
ATOM   5573  CD1  LEU C  81     -72.679 -14.604 -24.262  1.00 54.69      A    C
ATOM   5574  CD2  LEU C  81     -73.876 -14.358 -22.123  1.00 54.75      A    C
ATOM   5575  N    ARG C  82     -77.304 -15.698 -22.038  1.00 56.32      A    N
ATOM   5576  CA   ARG C  82     -77.862 -15.472 -20.717  1.00 56.76      A    C
ATOM   5577  C    ARG C  82     -78.614 -16.701 -20.219  1.00 56.68      A    C
ATOM   5578  O    ARG C  82     -78.666 -16.966 -19.019  1.00 56.66      A    O
ATOM   5579  CB   ARG C  82     -78.757 -14.229 -20.720  1.00 57.33      A    C
ATOM   5580  CG   ARG C  82     -79.055 -13.681 -19.323  1.00 58.29      A    C
ATOM   5581  CD   ARG C  82     -79.629 -12.259 -19.345  1.00 59.67      A    C
ATOM   5582  NE   ARG C  82     -78.619 -11.222 -19.128  1.00 59.76      A    N
ATOM   5583  CZ   ARG C  82     -77.982 -10.576 -20.099  1.00 59.79      A    C
ATOM   5584  NH1  ARG C  82     -78.236 -10.854 -21.370  1.00 59.97      A    N
ATOM   5585  NH2  ARG C  82     -77.083  -9.650 -19.794  1.00 59.56      A    N
ATOM   5586  N    ARG C  83     -79.176 -17.457 -21.154  1.00 56.44      A    N
ATOM   5587  CA   ARG C  83     -79.863 -18.715 -20.855  1.00 55.91      A    C
ATOM   5588  C    ARG C  83     -78.866 -19.798 -20.422  1.00 55.50      A    C
ATOM   5589  O    ARG C  83     -79.139 -20.572 -19.502  1.00 55.67      A    O
ATOM   5590  CB   ARG C  83     -80.702 -19.133 -22.077  1.00 54.94      A    C
```

FIGURE 1 (cont'd)

```
ATOM   5591  CG   ARG C  83     -80.984 -20.616 -22.286  1.00 54.46      A  C
ATOM   5592  CD   ARG C  83     -81.376 -20.823 -23.743  1.00 54.56      A  C
ATOM   5593  NE   ARG C  83     -81.418 -22.219 -24.152  1.00 54.03      A  N
ATOM   5594  N    VAL C  84     -77.706 -19.820 -21.079  1.00 54.72      A  N
ATOM   5595  CA   VAL C  84     -76.649 -20.791 -20.795  1.00 53.61      A  C
ATOM   5596  C    VAL C  84     -75.968 -20.465 -19.478  1.00 52.96      A  C
ATOM   5597  O    VAL C  84     -75.919 -21.303 -18.593  1.00 52.79      A  O
ATOM   5598  CB   VAL C  84     -75.622 -20.875 -21.946  1.00 53.49      A  C
ATOM   5599  CG1  VAL C  84     -76.216 -21.646 -23.111  1.00 53.55      A  C
ATOM   5600  CG2  VAL C  84     -74.331 -21.536 -21.490  1.00 52.77      A  C
ATOM   5601  N    VAL C  85     -75.464 -19.243 -19.345  1.00 52.15      A  N
ATOM   5602  CA   VAL C  85     -74.856 -18.788 -18.098  1.00 51.25      A  C
ATOM   5603  C    VAL C  85     -75.802 -19.028 -16.926  1.00 51.73      A  C
ATOM   5604  O    VAL C  85     -75.366 -19.245 -15.796  1.00 51.90      A  O
ATOM   5605  CB   VAL C  85     -74.494 -17.299 -18.174  1.00 49.76      A  C
ATOM   5606  CG1  VAL C  85     -73.887 -16.823 -16.865  1.00 49.83      A  C
ATOM   5607  CG2  VAL C  85     -73.543 -17.042 -19.339  1.00 49.90      A  C
ATOM   5608  N    GLY C  86     -77.098 -19.000 -17.219  1.00 52.07      A  N
ATOM   5609  CA   GLY C  86     -78.131 -19.261 -16.230  1.00 52.03      A  C
ATOM   5610  C    GLY C  86     -78.258 -20.724 -15.866  1.00 51.62      A  C
ATOM   5611  O    GLY C  86     -78.771 -21.056 -14.801  1.00 51.85      A  O
ATOM   5612  N    GLN C  87     -77.791 -21.600 -16.748  1.00 50.95      A  N
ATOM   5613  CA   GLN C  87     -77.866 -23.038 -16.504  1.00 50.17      A  C
ATOM   5614  C    GLN C  87     -76.863 -23.557 -15.468  1.00 49.57      A  C
ATOM   5615  O    GLN C  87     -77.039 -24.654 -14.931  1.00 49.52      A  O
ATOM   5616  N    LEU C  88     -75.814 -22.782 -15.201  1.00 48.73      A  N
ATOM   5617  CA   LEU C  88     -74.838 -23.145 -14.178  1.00 48.03      A  C
ATOM   5618  C    LEU C  88     -75.445 -22.901 -12.810  1.00 48.40      A  C
ATOM   5619  O    LEU C  88     -75.971 -21.819 -12.563  1.00 48.63      A  O
ATOM   5620  CB   LEU C  88     -73.571 -22.308 -14.317  1.00 47.30      A  C
ATOM   5621  CG   LEU C  88     -72.723 -22.453 -15.572  1.00 45.90      A  C
ATOM   5622  CD1  LEU C  88     -72.101 -21.116 -15.878  1.00 45.17      A  C
ATOM   5623  CD2  LEU C  88     -71.680 -23.541 -15.436  1.00 44.62      A  C
ATOM   5624  N    ASP C  89     -75.383 -23.904 -11.929  1.00 48.74      A  N
ATOM   5625  CA   ASP C  89     -75.845 -23.754 -10.538  1.00 49.12      A  C
ATOM   5626  C    ASP C  89     -74.668 -23.588  -9.577  1.00 49.17      A  C
ATOM   5627  O    ASP C  89     -73.980 -24.555  -9.280  1.00 48.96      A  O
ATOM   5628  CB   ASP C  89     -76.738 -24.927 -10.105  1.00 49.28      A  C
ATOM   5629  CG   ASP C  89     -77.257 -24.786  -8.672  1.00 49.43      A  C
ATOM   5630  OD1  ASP C  89     -76.898 -23.823  -7.971  1.00 49.93      A  O
ATOM   5631  OD2  ASP C  89     -78.024 -25.662  -8.230  1.00 48.70      A  O
ATOM   5632  N    PRO C  90     -74.449 -22.355  -9.081  1.00 49.42      A  N
ATOM   5633  CA   PRO C  90     -73.305 -22.028  -8.237  1.00 49.32      A  C
ATOM   5634  C    PRO C  90     -73.195 -22.876  -6.985  1.00 49.26      A  C
ATOM   5635  O    PRO C  90     -72.100 -23.303  -6.647  1.00 49.03      A  O
ATOM   5636  CB   PRO C  90     -73.548 -20.563  -7.870  1.00 49.47      A  C
ATOM   5637  CG   PRO C  90     -74.332 -20.023  -9.021  1.00 49.75      A  C
ATOM   5638  CD   PRO C  90     -75.253 -21.153  -9.383  1.00 49.80      A  C
ATOM   5639  N    GLN C  91     -74.304 -23.134  -6.303  1.00 49.45      A  N
ATOM   5640  CA   GLN C  91     -74.242 -23.963  -5.101  1.00 49.54      A  C
ATOM   5641  C    GLN C  91     -74.028 -25.441  -5.442  1.00 48.97      A  C
ATOM   5642  O    GLN C  91     -73.466 -26.177  -4.638  1.00 49.03      A  O
ATOM   5643  CB   GLN C  91     -75.440 -23.729  -4.157  1.00 50.15      A  C
ATOM   5644  CG   GLN C  91     -76.735 -24.446  -4.517  1.00 50.94      A  C
ATOM   5645  N    ARG C  92     -74.453 -25.857  -6.638  1.00 48.15      A  N
ATOM   5646  CA   ARG C  92     -74.211 -27.221  -7.135  1.00 47.11      A  C
ATOM   5647  C    ARG C  92     -72.713 -27.439  -7.369  1.00 46.66      A  C
ATOM   5648  O    ARG C  92     -72.156 -28.445  -6.935  1.00 46.58      A  O
ATOM   5649  CB   ARG C  92     -75.028 -27.501  -8.413  1.00 46.95      A  C
ATOM   5650  CG   ARG C  92     -74.681 -28.798  -9.164  1.00 45.19      A  C
ATOM   5651  CD   ARG C  92     -75.556 -29.032 -10.407  1.00 43.09      A  C
ATOM   5652  NE   ARG C  92     -75.424 -27.970 -11.394  1.00 41.73      A  N
ATOM   5653  N    LEU C  93     -72.078 -26.483  -8.047  1.00 46.06      A  N
ATOM   5654  CA   LEU C  93     -70.639 -26.496  -8.306  1.00 45.44      A  C
ATOM   5655  C    LEU C  93     -69.895 -26.714  -7.007  1.00 45.51      A  C
```

FIGURE 1 (cont'd)

```
ATOM   5656  O    LEU C  93     -69.054 -27.609  -6.911  1.00 45.43      A    O
ATOM   5657  CB   LEU C  93     -70.199 -25.151  -8.906  1.00 45.08      A    C
ATOM   5658  CG   LEU C  93     -69.002 -24.997  -9.850  1.00 43.90      A    C
ATOM   5659  CD1  LEU C  93     -67.817 -25.871  -9.499  1.00 42.74      A    C
ATOM   5660  N    TRP C  94     -70.232 -25.898  -6.008  1.00 45.69      A    N
ATOM   5661  CA   TRP C  94     -69.514 -25.855  -4.740  1.00 45.73      A    C
ATOM   5662  C    TRP C  94     -69.805 -27.034  -3.819  1.00 45.71      A    C
ATOM   5663  O    TRP C  94     -68.912 -27.522  -3.126  1.00 45.60      A    O
ATOM   5664  CB   TRP C  94     -69.828 -24.553  -4.013  1.00 45.94      A    C
ATOM   5665  CG   TRP C  94     -68.749 -24.152  -3.082  1.00 46.40      A    C
ATOM   5666  CD1  TRP C  94     -68.593 -24.546  -1.787  1.00 47.11      A    C
ATOM   5667  CD2  TRP C  94     -67.656 -23.285  -3.373  1.00 46.45      A    C
ATOM   5668  CE2  TRP C  94     -66.875 -23.192  -2.206  1.00 46.68      A    C
ATOM   5669  CE3  TRP C  94     -67.259 -22.575  -4.508  1.00 46.25      A    C
ATOM   5670  NE1  TRP C  94     -67.468 -23.971  -1.250  1.00 47.07      A    N
ATOM   5671  CZ2  TRP C  94     -65.720 -22.417  -2.141  1.00 46.62      A    C
ATOM   5672  CZ3  TRP C  94     -66.111 -21.803  -4.442  1.00 46.15      A    C
ATOM   5673  CH2  TRP C  94     -65.355 -21.730  -3.268  1.00 46.32      A    C
ATOM   5674  N    SER C  95     -71.050 -27.495  -3.821  1.00 45.75      A    N
ATOM   5675  CA   SER C  95     -71.498 -28.472  -2.838  1.00 45.76      A    C
ATOM   5676  C    SER C  95     -71.537 -29.907  -3.367  1.00 45.15      A    C
ATOM   5677  O    SER C  95     -71.045 -30.809  -2.700  1.00 45.13      A    O
ATOM   5678  CB   SER C  95     -72.858 -28.054  -2.259  1.00 46.27      A    C
ATOM   5679  OG   SER C  95     -72.885 -28.174  -0.844  1.00 47.18      A    O
ATOM   5680  N    THR C  96     -72.118 -30.110  -4.548  1.00 44.41      A    N
ATOM   5681  CA   THR C  96     -72.228 -31.440  -5.135  1.00 43.77      A    C
ATOM   5682  C    THR C  96     -70.920 -31.943  -5.738  1.00 42.87      A    C
ATOM   5683  O    THR C  96     -70.666 -33.145  -5.737  1.00 42.98      A    O
ATOM   5684  CB   THR C  96     -73.300 -31.505  -6.232  1.00 43.97      A    C
ATOM   5685  OG1  THR C  96     -74.363 -30.607  -5.919  1.00 44.71      A    O
ATOM   5686  N    TYR C  97     -70.097 -31.031  -6.256  1.00 41.62      A    N
ATOM   5687  CA   TYR C  97     -68.876 -31.403  -6.997  1.00 40.22      A    C
ATOM   5688  C    TYR C  97     -67.557 -31.023  -6.334  1.00 39.82      A    C
ATOM   5689  O    TYR C  97     -66.631 -31.817  -6.341  1.00 39.60      A    O
ATOM   5690  CB   TYR C  97     -68.901 -30.856  -8.428  1.00 39.68      A    C
ATOM   5691  CG   TYR C  97     -70.125 -31.245  -9.212  1.00 38.67      A    C
ATOM   5692  CD1  TYR C  97     -70.518 -32.584  -9.326  1.00 37.60      A    C
ATOM   5693  CD2  TYR C  97     -70.887 -30.271  -9.842  1.00 36.55      A    C
ATOM   5694  CE1  TYR C  97     -71.646 -32.930 -10.044  1.00 37.37      A    C
ATOM   5695  CE2  TYR C  97     -72.004 -30.600 -10.557  1.00 35.04      A    C
ATOM   5696  CZ   TYR C  97     -72.383 -31.913 -10.655  1.00 34.75      A    C
ATOM   5697  OH   TYR C  97     -73.515 -32.155 -11.381  1.00 33.90      A    O
ATOM   5698  N    LEU C  98     -67.460 -29.816  -5.778  1.00 39.60      A    N
ATOM   5699  CA   LEU C  98     -66.200 -29.363  -5.189  1.00 39.43      A    C
ATOM   5700  C    LEU C  98     -65.917 -29.987  -3.832  1.00 39.68      A    C
ATOM   5701  O    LEU C  98     -64.880 -30.609  -3.652  1.00 39.61      A    O
ATOM   5702  CB   LEU C  98     -66.127 -27.839  -5.091  1.00 39.22      A    C
ATOM   5703  CG   LEU C  98     -64.836 -27.333  -4.446  1.00 38.98      A    C
ATOM   5704  CD1  LEU C  98     -63.628 -27.735  -5.267  1.00 38.40      A    C
ATOM   5705  CD2  LEU C  98     -64.877 -25.833  -4.243  1.00 39.16      A    C
ATOM   5706  N    ARG C  99     -66.832 -29.807  -2.881  1.00 40.04      A    N
ATOM   5707  CA   ARG C  99     -66.637 -30.300  -1.506  1.00 40.11      A    C
ATOM   5708  C    ARG C  99     -66.342 -31.798  -1.393  1.00 40.22      A    C
ATOM   5709  O    ARG C  99     -65.464 -32.179  -0.622  1.00 40.36      A    O
ATOM   5710  CB   ARG C  99     -67.777 -29.857  -0.566  1.00 39.56      A    C
ATOM   5711  CG   ARG C  99     -67.354 -28.749   0.407  1.00 39.41      A    C
ATOM   5712  CD   ARG C  99     -68.443 -28.442   1.412  1.00 39.86      A    C
ATOM   5713  NE   ARG C  99     -69.090 -27.168   1.136  1.00 39.31      A    N
ATOM   5714  CZ   ARG C  99     -69.101 -26.152   1.982  1.00 31.80      A    C
ATOM   5715  NH1  ARG C  99     -68.491 -26.270   3.157  1.00 30.48      A    N
ATOM   5716  NH2  ARG C  99     -69.719 -25.023   1.657  1.00 29.50      A    N
ATOM   5717  N    PRO C 100     -67.051 -32.646  -2.166  1.00 40.20      A    N
ATOM   5718  CA   PRO C 100     -66.715 -34.058  -2.140  1.00 40.12      A    C
ATOM   5719  C    PRO C 100     -65.274 -34.321  -2.557  1.00 39.75      A    C
ATOM   5720  O    PRO C 100     -64.668 -35.279  -2.087  1.00 39.97      A    O
```

FIGURE 1 (cont'd)

```
ATOM   5721  CB   PRO C 100     -67.667 -34.660  -3.169  1.00 40.24      A    C
ATOM   5722  CG   PRO C 100     -68.818 -33.781  -3.162  1.00 40.48      A    C
ATOM   5723  CD   PRO C 100     -68.267 -32.406  -2.959  1.00 40.34      A    C
ATOM   5724  N    LEU C 101     -64.731 -33.471  -3.421  1.00 39.11      A    N
ATOM   5725  CA   LEU C 101     -63.363 -33.633  -3.917  1.00 38.49      A    C
ATOM   5726  C    LEU C 101     -62.271 -33.231  -2.920  1.00 38.45      A    C
ATOM   5727  O    LEU C 101     -61.121 -33.624  -3.093  1.00 38.32      A    O
ATOM   5728  CB   LEU C 101     -63.177 -32.841  -5.216  1.00 38.10      A    C
ATOM   5729  CG   LEU C 101     -63.260 -33.537  -6.571  1.00 37.74      A    C
ATOM   5730  CD1  LEU C 101     -64.311 -34.618  -6.597  1.00 38.21      A    C
ATOM   5731  CD2  LEU C 101     -63.528 -32.526  -7.664  1.00 37.47      A    C
ATOM   5732  N    LEU C 102     -62.628 -32.461  -1.890  1.00 38.51      A    N
ATOM   5733  CA   LEU C 102     -61.651 -31.867  -0.976  1.00 38.56      A    C
ATOM   5734  C    LEU C 102     -61.194 -32.791   0.163  1.00 38.91      A    C
ATOM   5735  O    LEU C 102     -61.316 -32.468   1.338  1.00 39.18      A    O
ATOM   5736  CB   LEU C 102     -62.185 -30.547  -0.433  1.00 38.50      A    C
ATOM   5737  CG   LEU C 102     -62.364 -29.408  -1.429  1.00 38.04      A    C
ATOM   5738  CD1  LEU C 102     -63.094 -28.250  -0.791  1.00 38.24      A    C
ATOM   5739  CD2  LEU C 102     -61.024 -28.956  -1.945  1.00 37.53      A    C
ATOM   5740  N    VAL C 103     -60.656 -33.946  -0.203  1.00 39.08      A    N
ATOM   5741  CA   VAL C 103     -60.100 -34.896   0.757  1.00 39.37      A    C
ATOM   5742  C    VAL C 103     -58.701 -35.318   0.334  1.00 39.06      A    C
ATOM   5743  O    VAL C 103     -58.349 -35.226  -0.837  1.00 38.79      A    O
ATOM   5744  CB   VAL C 103     -60.980 -36.164   0.903  1.00 39.72      A    C
ATOM   5745  CG1  VAL C 103     -61.328 -36.749  -0.455  1.00 39.59      A    C
ATOM   5746  CG2  VAL C 103     -62.250 -35.866   1.683  1.00 40.64      A    C
ATOM   5747  N    VAL C 104     -57.908 -35.782   1.292  1.00 39.00      A    N
ATOM   5748  CA   VAL C 104     -56.588 -36.322   0.992  1.00 38.69      A    C
ATOM   5749  C    VAL C 104     -56.765 -37.469   0.000  1.00 38.91      A    C
ATOM   5750  O    VAL C 104     -57.582 -38.353   0.211  1.00 39.23      A    O
ATOM   5751  CB   VAL C 104     -55.852 -36.851   2.240  1.00 38.02      A    C
ATOM   5752  CG1  VAL C 104     -54.351 -36.698   2.065  1.00 37.47      A    C
ATOM   5753  CG2  VAL C 104     -56.326 -36.168   3.507  1.00 37.81      A    C
ATOM   5754  N    ARG C 105     -56.001 -37.446  -1.085  1.00 38.79      A    N
ATOM   5755  CA   ARG C 105     -56.239 -38.342  -2.213  1.00 38.50      A    C
ATOM   5756  C    ARG C 105     -54.977 -38.681  -3.018  1.00 38.50      A    C
ATOM   5757  O    ARG C 105     -55.042 -38.926  -4.231  1.00 38.24      A    O
ATOM   5758  CB   ARG C 105     -57.323 -37.747  -3.123  1.00 38.35      A    C
ATOM   5759  CG   ARG C 105     -56.990 -36.395  -3.754  1.00 37.69      A    C
ATOM   5760  CD   ARG C 105     -58.239 -35.673  -4.188  1.00 37.34      A    C
ATOM   5761  NE   ARG C 105     -57.904 -34.498  -4.981  1.00 37.02      A    N
ATOM   5762  CZ   ARG C 105     -57.812 -33.255  -4.502  1.00 36.82      A    C
ATOM   5763  NH1  ARG C 105     -58.036 -33.012  -3.217  1.00 36.91      A    N
ATOM   5764  NH2  ARG C 105     -57.496 -32.245  -5.314  1.00 36.44      A    N
ATOM   5765  N    THR C 106     -53.835 -38.702  -2.335  1.00 38.72      A    N
ATOM   5766  CA   THR C 106     -52.564 -39.091  -2.938  1.00 38.93      A    C
ATOM   5767  C    THR C 106     -52.696 -40.447  -3.636  1.00 38.99      A    C
ATOM   5768  O    THR C 106     -53.463 -41.291  -3.177  1.00 39.01      A    O
ATOM   5769  CB   THR C 106     -51.481 -39.184  -1.869  1.00 39.12      A    C
ATOM   5770  OG1  THR C 106     -51.824 -40.231  -0.952  1.00 39.79      A    O
ATOM   5771  N    PRO C 107     -51.949 -40.660  -4.743  1.00 39.10      A    N
ATOM   5772  CA   PRO C 107     -52.057 -41.870  -5.567  1.00 39.40      A    C
ATOM   5773  C    PRO C 107     -52.192 -43.177  -4.780  1.00 39.94      A    C
ATOM   5774  O    PRO C 107     -51.481 -43.387  -3.797  1.00 40.10      A    O
ATOM   5775  CB   PRO C 107     -50.748 -41.865  -6.358  1.00 39.28      A    C
ATOM   5776  CG   PRO C 107     -50.426 -40.433  -6.520  1.00 38.89      A    C
ATOM   5777  CD   PRO C 107     -50.931 -39.736  -5.284  1.00 38.97      A    C
ATOM   5778  N    GLY C 108     -53.119 -44.030  -5.219  1.00 40.39      A    N
ATOM   5779  CA   GLY C 108     -53.336 -45.354  -4.635  1.00 41.00      A    C
ATOM   5780  C    GLY C 108     -53.758 -45.394  -3.177  1.00 41.35      A    C
ATOM   5781  O    GLY C 108     -53.635 -46.434  -2.534  1.00 41.85      A    O
ATOM   5782  N    SER C 109     -54.244 -44.272  -2.648  1.00 41.32      A    N
ATOM   5783  CA   SER C 109     -54.766 -44.223  -1.278  1.00 41.38      A    C
ATOM   5784  C    SER C 109     -56.276 -44.509  -1.288  1.00 41.58      A    C
ATOM   5785  O    SER C 109     -56.864 -44.647  -2.369  1.00 41.38      A    O
```

FIGURE 1 (cont'd)

```
ATOM   5786  CB   SER C 109     -54.455 -42.866  -0.632  1.00 41.24      A    C
ATOM   5787  OG   SER C 109     -55.157 -41.822  -1.276  1.00 40.69      A    O
ATOM   5788  N    PRO C 110     -56.906 -44.627  -0.099  1.00 41.92      A    N
ATOM   5789  CA   PRO C 110     -58.367 -44.735  -0.042  1.00 41.85      A    C
ATOM   5790  C    PRO C 110     -59.083 -43.504  -0.613  1.00 41.28      A    C
ATOM   5791  O    PRO C 110     -60.113 -43.642  -1.275  1.00 41.08      A    O
ATOM   5792  CB   PRO C 110     -58.642 -44.870   1.456  1.00 42.31      A    C
ATOM   5793  CG   PRO C 110     -57.406 -45.477   2.005  1.00 42.75      A    C
ATOM   5794  CD   PRO C 110     -56.295 -44.870   1.221  1.00 42.31      A    C
ATOM   5795  N    GLY C 111     -58.526 -42.321  -0.354  1.00 40.81      A    N
ATOM   5796  CA   GLY C 111     -59.064 -41.062  -0.863  1.00 40.14      A    C
ATOM   5797  C    GLY C 111     -59.023 -40.974  -2.371  1.00 39.60      A    C
ATOM   5798  O    GLY C 111     -60.013 -40.587  -3.004  1.00 39.45      A    O
ATOM   5799  N    ASN C 112     -57.872 -41.335  -2.940  1.00 39.16      A    N
ATOM   5800  CA   ASN C 112     -57.683 -41.424  -4.389  1.00 38.59      A    C
ATOM   5801  C    ASN C 112     -58.751 -42.300  -5.037  1.00 38.82      A    C
ATOM   5802  O    ASN C 112     -59.349 -41.912  -6.034  1.00 38.66      A    O
ATOM   5803  CB   ASN C 112     -56.290 -41.963  -4.706  1.00 38.27      A    C
ATOM   5804  CG   ASN C 112     -55.937 -41.852  -6.161  1.00 37.13      A    C
ATOM   5805  ND2  ASN C 112     -55.096 -40.874  -6.476  1.00 35.51      A    N
ATOM   5806  OD1  ASN C 112     -56.386 -42.632  -6.991  1.00 37.74      A    O
ATOM   5807  N    LEU C 113     -59.000 -43.466  -4.452  1.00 39.29      A    N
ATOM   5808  CA   LEU C 113     -60.022 -44.365  -4.953  1.00 39.73      A    C
ATOM   5809  C    LEU C 113     -61.427 -43.832  -4.678  1.00 39.78      A    C
ATOM   5810  O    LEU C 113     -62.296 -43.952  -5.536  1.00 39.73      A    O
ATOM   5811  CB   LEU C 113     -59.830 -45.763  -4.369  1.00 40.16      A    C
ATOM   5812  CG   LEU C 113     -60.447 -46.939  -5.128  1.00 40.90      A    C
ATOM   5813  CD1  LEU C 113     -59.526 -48.152  -5.066  1.00 41.45      A    C
ATOM   5814  CD2  LEU C 113     -61.857 -47.281  -4.630  1.00 41.75      A    C
ATOM   5815  N    GLN C 114     -61.640 -43.242  -3.496  1.00 39.88      A    N
ATOM   5816  CA   GLN C 114     -62.934 -42.645  -3.137  1.00 39.86      A    C
ATOM   5817  C    GLN C 114     -63.331 -41.557  -4.154  1.00 39.62      A    C
ATOM   5818  O    GLN C 114     -64.457 -41.561  -4.659  1.00 39.71      A    O
ATOM   5819  CB   GLN C 114     -62.913 -42.082  -1.705  1.00 40.00      A    C
ATOM   5820  CG   GLN C 114     -64.285 -42.010  -1.001  1.00 38.94      A    C
ATOM   5821  CD   GLN C 114     -64.610 -40.635  -0.356  1.00 37.87      A    C
ATOM   5822  NE2  GLN C 114     -63.650 -40.069   0.382  1.00 37.68      A    N
ATOM   5823  OE1  GLN C 114     -65.717 -40.102  -0.526  1.00 37.18      A    O
ATOM   5824  N    VAL C 115     -62.399 -40.650  -4.463  1.00 39.04      A    N
ATOM   5825  CA   VAL C 115     -62.630 -39.584  -5.447  1.00 38.36      A    C
ATOM   5826  C    VAL C 115     -62.884 -40.157  -6.849  1.00 38.64      A    C
ATOM   5827  O    VAL C 115     -63.892 -39.830  -7.480  1.00 38.82      A    O
ATOM   5828  CB   VAL C 115     -61.480 -38.560  -5.478  1.00 36.84      A    C
ATOM   5829  N    ARG C 116     -61.987 -41.031  -7.309  1.00 38.85      A    N
ATOM   5830  CA   ARG C 116     -62.116 -41.740  -8.591  1.00 39.06      A    C
ATOM   5831  C    ARG C 116     -63.504 -42.333  -8.789  1.00 39.50      A    C
ATOM   5832  O    ARG C 116     -64.104 -42.195  -9.857  1.00 39.49      A    O
ATOM   5833  CB   ARG C 116     -61.073 -42.863  -8.678  1.00 38.99      A    C
ATOM   5834  CG   ARG C 116     -61.158 -43.755  -9.920  1.00 39.21      A    C
ATOM   5835  CD   ARG C 116     -60.161 -44.897  -9.836  1.00 40.23      A    C
ATOM   5836  NE   ARG C 116     -58.788 -44.429  -9.619  1.00 40.87      A    N
ATOM   5837  CZ   ARG C 116     -57.780 -45.194  -9.199  1.00 41.48      A    C
ATOM   5838  NH1  ARG C 116     -57.963 -46.484  -8.932  1.00 41.96      A    N
ATOM   5839  NH2  ARG C 116     -56.576 -44.667  -9.035  1.00 41.66      A    N
ATOM   5840  N    LYS C 117     -64.001 -42.993  -7.748  1.00 40.08      A    N
ATOM   5841  CA   LYS C 117     -65.322 -43.617  -7.760  1.00 40.55      A    C
ATOM   5842  C    LYS C 117     -66.419 -42.559  -7.900  1.00 40.18      A    C
ATOM   5843  O    LYS C 117     -67.408 -42.777  -8.596  1.00 40.29      A    O
ATOM   5844  CB   LYS C 117     -65.522 -44.453  -6.490  1.00 41.13      A    C
ATOM   5845  CG   LYS C 117     -66.581 -45.535  -6.594  1.00 42.52      A    C
ATOM   5846  CD   LYS C 117     -66.558 -46.479  -5.373  1.00 43.89      A    C
ATOM   5847  CE   LYS C 117     -65.641 -47.711  -5.568  1.00 44.10      A    C
ATOM   5848  N    PHE C 118     -66.224 -41.411  -7.255  1.00 39.54      A    N
ATOM   5849  CA   PHE C 118     -67.193 -40.329  -7.310  1.00 38.91      A    C
ATOM   5850  C    PHE C 118     -67.254 -39.724  -8.688  1.00 39.14      A    C
```

FIGURE 1 (cont'd)

```
ATOM   5851  O    PHE C 118     -68.330 -39.369  -9.166  1.00 39.39      A  O
ATOM   5852  CB   PHE C 118     -66.867 -39.243  -6.288  1.00 37.67      A  C
ATOM   5853  CG   PHE C 118     -67.730 -38.018  -6.410  1.00 36.14      A  C
ATOM   5854  CD1  PHE C 118     -69.120 -38.104  -6.278  1.00 35.86      A  C
ATOM   5855  CD2  PHE C 118     -67.150 -36.779  -6.652  1.00 34.57      A  C
ATOM   5856  CE1  PHE C 118     -69.914 -36.967  -6.395  1.00 35.49      A  C
ATOM   5857  CE2  PHE C 118     -67.924 -35.632  -6.769  1.00 33.87      A  C
ATOM   5858  CZ   PHE C 118     -69.306 -35.722  -6.649  1.00 34.81      A  C
ATOM   5859  N    LEU C 119     -66.097 -39.603  -9.320  1.00 39.15      A  N
ATOM   5860  CA   LEU C 119     -66.031 -39.084 -10.670  1.00 39.16      A  C
ATOM   5861  C    LEU C 119     -66.737 -40.012 -11.644  1.00 39.66      A  C
ATOM   5862  O    LEU C 119     -67.642 -39.588 -12.355  1.00 39.83      A  O
ATOM   5863  CB   LEU C 119     -64.589 -38.826 -11.079  1.00 38.71      A  C
ATOM   5864  CG   LEU C 119     -64.038 -37.513 -10.519  1.00 37.93      A  C
ATOM   5865  CD1  LEU C 119     -62.529 -37.495 -10.619  1.00 37.44      A  C
ATOM   5866  N    GLU C 120     -66.351 -41.283 -11.649  1.00 40.14      A  N
ATOM   5867  CA   GLU C 120     -67.025 -42.296 -12.464  1.00 40.60      A  C
ATOM   5868  C    GLU C 120     -68.552 -42.195 -12.384  1.00 41.30      A  C
ATOM   5869  O    GLU C 120     -69.232 -42.133 -13.410  1.00 41.59      A  O
ATOM   5870  CB   GLU C 120     -66.600 -43.705 -12.046  1.00 39.85      A  C
ATOM   5871  CG   GLU C 120     -65.211 -44.123 -12.484  1.00 39.52      A  C
ATOM   5872  CD   GLU C 120     -64.930 -45.587 -12.203  1.00 40.08      A  C
ATOM   5873  OE1  GLU C 120     -65.603 -46.448 -12.807  1.00 40.83      A  O
ATOM   5874  N    ALA C 121     -69.074 -42.176 -11.160  1.00 41.82      A  N
ATOM   5875  CA   ALA C 121     -70.514 -42.153 -10.915  1.00 42.21      A  C
ATOM   5876  C    ALA C 121     -71.197 -40.893 -11.451  1.00 42.14      A  C
ATOM   5877  O    ALA C 121     -72.198 -40.996 -12.173  1.00 42.47      A  O
ATOM   5878  CB   ALA C 121     -70.799 -42.329  -9.434  1.00 42.55      A  C
ATOM   5879  N    THR C 122     -70.653 -39.720 -11.105  1.00 41.55      A  N
ATOM   5880  CA   THR C 122     -71.201 -38.439 -11.556  1.00 40.88      A  C
ATOM   5881  C    THR C 122     -71.295 -38.381 -13.069  1.00 41.29      A  C
ATOM   5882  O    THR C 122     -72.337 -38.046 -13.621  1.00 41.68      A  O
ATOM   5883  CB   THR C 122     -70.382 -37.257 -11.056  1.00 39.40      A  C
ATOM   5884  OG1  THR C 122     -70.550 -37.140  -9.646  1.00 38.49      A  O
ATOM   5885  N    LEU C 123     -70.205 -38.738 -13.731  1.00 41.39      A  N
ATOM   5886  CA   LEU C 123     -70.136 -38.733 -15.186  1.00 41.48      A  C
ATOM   5887  C    LEU C 123     -71.156 -39.684 -15.827  1.00 42.17      A  C
ATOM   5888  O    LEU C 123     -71.795 -39.336 -16.831  1.00 42.39      A  O
ATOM   5889  CB   LEU C 123     -68.715 -39.089 -15.653  1.00 41.03      A  C
ATOM   5890  CG   LEU C 123     -67.573 -38.101 -15.412  1.00 39.79      A  C
ATOM   5891  CD1  LEU C 123     -67.578 -37.028 -16.471  1.00 39.17      A  C
ATOM   5892  N    ARG C 124     -71.300 -40.877 -15.248  1.00 42.76      A  N
ATOM   5893  CA   ARG C 124     -72.241 -41.874 -15.754  1.00 43.43      A  C
ATOM   5894  C    ARG C 124     -73.691 -41.428 -15.574  1.00 44.08      A  C
ATOM   5895  O    ARG C 124     -74.527 -41.670 -16.452  1.00 44.44      A  O
ATOM   5896  CB   ARG C 124     -71.999 -43.239 -15.103  1.00 43.39      A  C
ATOM   5897  CG   ARG C 124     -70.853 -44.003 -15.733  1.00 42.79      A  C
ATOM   5898  CD   ARG C 124     -70.681 -45.379 -15.134  1.00 42.35      A  C
ATOM   5899  NE   ARG C 124     -69.566 -46.097 -15.745  1.00 41.57      A  N
ATOM   5900  N    SER C 125     -73.972 -40.750 -14.459  1.00 44.55      A  N
ATOM   5901  CA   SER C 125     -75.335 -40.337 -14.120  1.00 45.12      A  C
ATOM   5902  C    SER C 125     -75.864 -39.139 -14.931  1.00 45.24      A  C
ATOM   5903  O    SER C 125     -76.873 -38.551 -14.565  1.00 45.56      A  O
ATOM   5904  CB   SER C 125     -75.442 -40.053 -12.620  1.00 45.27      A  C
ATOM   5905  OG   SER C 125     -74.770 -38.852 -12.302  1.00 44.98      A  O
ATOM   5906  N    LEU C 126     -75.203 -38.803 -16.032  1.00 45.09      A  N
ATOM   5907  CA   LEU C 126     -75.637 -37.669 -16.844  1.00 45.11      A  C
ATOM   5908  C    LEU C 126     -76.596 -38.093 -17.947  1.00 45.66      A  C
ATOM   5909  O    LEU C 126     -76.527 -39.234 -18.407  1.00 45.93      A  O
ATOM   5910  CB   LEU C 126     -74.435 -36.928 -17.431  1.00 44.61      A  C
ATOM   5911  CG   LEU C 126     -73.484 -36.205 -16.466  1.00 43.79      A  C
ATOM   5912  CD1  LEU C 126     -72.642 -35.174 -17.208  1.00 42.93      A  C
ATOM   5913  CD2  LEU C 126     -74.251 -35.542 -15.340  1.00 43.55      A  C
ATOM   5914  N    THR C 127     -77.474 -37.173 -18.370  1.00 46.15      A  N
ATOM   5915  CA   THR C 127     -78.560 -37.477 -19.327  1.00 46.63      A  C
```

FIGURE 1 (cont'd)

```
ATOM   5916  C    THR C 127     -78.072 -37.880 -20.707  1.00 46.69      A   C
ATOM   5917  O    THR C 127     -78.580 -38.845 -21.292  1.00 47.19      A   O
ATOM   5918  CB   THR C 127     -79.544 -36.323 -19.491  1.00 46.85      A   C
ATOM   5919  OG1  THR C 127     -79.699 -35.660 -18.235  1.00 47.11      A   O
ATOM   5920  N    ALA C 128     -77.103 -37.137 -21.235  1.00 46.31      A   N
ATOM   5921  CA   ALA C 128     -76.379 -37.583 -22.420  1.00 46.10      A   C
ATOM   5922  C    ALA C 128     -75.579 -38.846 -22.058  1.00 46.00      A   C
ATOM   5923  O    ALA C 128     -75.045 -38.953 -20.950  1.00 45.95      A   O
ATOM   5924  CB   ALA C 128     -75.474 -36.487 -22.919  1.00 45.78      A   C
ATOM   5925  N    GLY C 129     -75.507 -39.809 -22.972  1.00 45.97      A   N
ATOM   5926  CA   GLY C 129     -74.898 -41.095 -22.644  1.00 45.72      A   C
ATOM   5927  C    GLY C 129     -73.385 -41.077 -22.625  1.00 45.14      A   C
ATOM   5928  O    GLY C 129     -72.760 -41.563 -23.562  1.00 45.54      A   O
ATOM   5929  N    TRP C 130     -72.790 -40.531 -21.564  1.00 44.26      A   N
ATOM   5930  CA   TRP C 130     -71.324 -40.429 -21.470  1.00 43.28      A   C
ATOM   5931  C    TRP C 130     -70.652 -41.813 -21.400  1.00 42.96      A   C
ATOM   5932  O    TRP C 130     -71.028 -42.650 -20.592  1.00 43.13      A   O
ATOM   5933  CB   TRP C 130     -70.896 -39.563 -20.270  1.00 42.93      A   C
ATOM   5934  CG   TRP C 130     -70.960 -38.065 -20.472  1.00 42.39      A   C
ATOM   5935  CD1  TRP C 130     -72.010 -37.253 -20.187  1.00 42.63      A   C
ATOM   5936  CD2  TRP C 130     -69.919 -37.210 -20.961  1.00 41.93      A   C
ATOM   5937  CE2  TRP C 130     -70.421 -35.890 -20.952  1.00 41.82      A   C
ATOM   5938  CE3  TRP C 130     -68.615 -37.428 -21.409  1.00 41.72      A   C
ATOM   5939  NE1  TRP C 130     -71.701 -35.945 -20.478  1.00 42.23      A   N
ATOM   5940  CZ2  TRP C 130     -69.667 -34.793 -21.375  1.00 41.34      A   C
ATOM   5941  CZ3  TRP C 130     -67.862 -36.335 -21.834  1.00 41.35      A   C
ATOM   5942  CH2  TRP C 130     -68.395 -35.033 -21.813  1.00 41.12      A   C
ATOM   5943  N    HIS C 131     -69.669 -42.043 -22.262  1.00 42.51      A   N
ATOM   5944  CA   HIS C 131     -68.913 -43.274 -22.262  1.00 42.30      A   C
ATOM   5945  C    HIS C 131     -67.755 -43.098 -21.297  1.00 41.90      A   C
ATOM   5946  O    HIS C 131     -66.646 -42.731 -21.697  1.00 41.68      A   O
ATOM   5947  CB   HIS C 131     -68.408 -43.553 -23.671  1.00 42.46      A   C
ATOM   5948  CG   HIS C 131     -68.009 -44.978 -23.928  1.00 42.81      A   C
ATOM   5949  CD2  HIS C 131     -68.592 -45.943 -24.684  1.00 40.35      A   C
ATOM   5950  ND1  HIS C 131     -66.840 -45.532 -23.440  1.00 40.85      A   N
ATOM   5951  CE1  HIS C 131     -66.737 -46.782 -23.860  1.00 39.74      A   C
ATOM   5952  NE2  HIS C 131     -67.784 -47.054 -24.619  1.00 39.72      A   N
ATOM   5953  N    VAL C 132     -68.037 -43.346 -20.018  1.00 41.66      A   N
ATOM   5954  CA   VAL C 132     -67.047 -43.267 -18.941  1.00 41.30      A   C
ATOM   5955  C    VAL C 132     -66.210 -44.531 -18.885  1.00 41.31      A   C
ATOM   5956  O    VAL C 132     -66.736 -45.627 -18.985  1.00 41.57      A   O
ATOM   5957  CB   VAL C 132     -67.723 -43.061 -17.579  1.00 41.28      A   C
ATOM   5958  CG1  VAL C 132     -66.873 -42.166 -16.698  1.00 41.03      A   C
ATOM   5959  N    GLU C 133     -64.905 -44.374 -18.711  1.00 41.19      A   N
ATOM   5960  CA   GLU C 133     -63.974 -45.487 -18.875  1.00 41.40      A   C
ATOM   5961  C    GLU C 133     -62.702 -45.308 -18.036  1.00 41.15      A   C
ATOM   5962  O    GLU C 133     -62.035 -44.269 -18.133  1.00 41.05      A   O
ATOM   5963  CB   GLU C 133     -63.619 -45.602 -20.355  1.00 41.62      A   C
ATOM   5964  CG   GLU C 133     -62.739 -46.767 -20.718  1.00 42.98      A   C
ATOM   5965  CD   GLU C 133     -62.358 -46.762 -22.196  1.00 44.70      A   C
ATOM   5966  OE1  GLU C 133     -63.270 -46.690 -23.055  1.00 45.48      A   O
ATOM   5967  OE2  GLU C 133     -61.143 -46.837 -22.496  1.00 45.17      A   O
ATOM   5968  N    LEU C 134     -62.369 -46.311 -17.218  1.00 41.04      A   N
ATOM   5969  CA   LEU C 134     -61.166 -46.267 -16.373  1.00 40.73      A   C
ATOM   5970  C    LEU C 134     -59.917 -46.713 -17.126  1.00 40.48      A   C
ATOM   5971  O    LEU C 134     -59.992 -47.546 -18.023  1.00 40.65      A   O
ATOM   5972  CB   LEU C 134     -61.338 -47.143 -15.136  1.00 40.92      A   C
ATOM   5973  CG   LEU C 134     -61.817 -46.502 -13.841  1.00 41.05      A   C
ATOM   5974  CD1  LEU C 134     -62.127 -47.595 -12.838  1.00 41.92      A   C
ATOM   5975  N    ASP C 135     -58.774 -46.149 -16.751  1.00 40.02      A   N
ATOM   5976  CA   ASP C 135     -57.482 -46.558 -17.292  1.00 39.81      A   C
ATOM   5977  C    ASP C 135     -56.562 -46.969 -16.136  1.00 39.77      A   C
ATOM   5978  O    ASP C 135     -55.704 -46.189 -15.707  1.00 39.73      A   O
ATOM   5979  CB   ASP C 135     -56.857 -45.427 -18.121  1.00 39.61      A   C
ATOM   5980  CG   ASP C 135     -55.464 -45.765 -18.637  1.00 39.82      A   C
```

FIGURE 1 (cont'd)

```
ATOM   5981  OD1 ASP C 135     -55.230 -46.924 -19.026  1.00 40.63      A    O
ATOM   5982  OD2 ASP C 135     -54.603 -44.863 -18.658  1.00 39.52      A    O
ATOM   5983  N   PRO C 136     -56.746 -48.198 -15.614  1.00 39.78      A    N
ATOM   5984  CA  PRO C 136     -55.921 -48.625 -14.496  1.00 40.02      A    C
ATOM   5985  C   PRO C 136     -54.541 -49.028 -14.989  1.00 40.61      A    C
ATOM   5986  O   PRO C 136     -54.400 -49.451 -16.135  1.00 40.87      A    O
ATOM   5987  CB  PRO C 136     -56.673 -49.846 -13.940  1.00 39.26      A    C
ATOM   5988  CG  PRO C 136     -57.883 -50.040 -14.812  1.00 38.94      A    C
ATOM   5989  CD  PRO C 136     -57.631 -49.284 -16.069  1.00 39.81      A    C
ATOM   5990  N   PHE C 137     -53.531 -48.870 -14.138  1.00 41.12      A    N
ATOM   5991  CA  PHE C 137     -52.184 -49.372 -14.418  1.00 41.59      A    C
ATOM   5992  C   PHE C 137     -51.271 -49.261 -13.205  1.00 42.04      A    C
ATOM   5993  O   PHE C 137     -51.483 -48.423 -12.320  1.00 41.99      A    O
ATOM   5994  CB  PHE C 137     -51.561 -48.662 -15.627  1.00 41.43      A    C
ATOM   5995  CG  PHE C 137     -51.191 -47.221 -15.376  1.00 41.10      A    C
ATOM   5996  CD1 PHE C 137     -52.149 -46.215 -15.451  1.00 40.78      A    C
ATOM   5997  CD2 PHE C 137     -49.879 -46.867 -15.087  1.00 40.98      A    C
ATOM   5998  CE1 PHE C 137     -51.808 -44.890 -15.229  1.00 40.23      A    C
ATOM   5999  CE2 PHE C 137     -49.536 -45.549 -14.863  1.00 40.52      A    C
ATOM   6000  CZ  PHE C 137     -50.502 -44.558 -14.932  1.00 40.16      A    C
ATOM   6001  N   THR C 138     -50.259 -50.119 -13.173  1.00 42.74      A    N
ATOM   6002  CA  THR C 138     -49.230 -50.027 -12.158  1.00 43.35      A    C
ATOM   6003  C   THR C 138     -47.996 -49.384 -12.744  1.00 43.44      A    C
ATOM   6004  O   THR C 138     -47.711 -49.571 -13.919  1.00 43.59      A    O
ATOM   6005  CB  THR C 138     -48.872 -51.386 -11.594  1.00 43.76      A    C
ATOM   6006  OG1 THR C 138     -49.395 -51.466 -10.265  1.00 44.30      A    O
ATOM   6007  N   ALA C 139     -47.278 -48.611 -11.929  1.00 43.47      A    N
ATOM   6008  CA  ALA C 139     -46.097 -47.882 -12.395  1.00 43.56      A    C
ATOM   6009  C   ALA C 139     -44.983 -47.775 -11.354  1.00 43.92      A    C
ATOM   6010  O   ALA C 139     -45.233 -47.728 -10.146  1.00 43.98      A    O
ATOM   6011  CB  ALA C 139     -46.482 -46.520 -12.906  1.00 43.17      A    C
ATOM   6012  N   SER C 140     -43.753 -47.737 -11.857  1.00 44.35      A    N
ATOM   6013  CA  SER C 140     -42.552 -47.705 -11.045  1.00 44.74      A    C
ATOM   6014  C   SER C 140     -42.227 -46.273 -10.596  1.00 44.44      A    C
ATOM   6015  O   SER C 140     -41.937 -45.410 -11.422  1.00 44.30      A    O
ATOM   6016  CB  SER C 140     -41.405 -48.325 -11.851  1.00 45.18      A    C
ATOM   6017  OG  SER C 140     -40.141 -47.949 -11.346  1.00 46.13      A    O
ATOM   6018  N   THR C 141     -42.296 -46.027  -9.287  1.00 44.25      A    N
ATOM   6019  CA  THR C 141     -42.014 -44.700  -8.706  1.00 44.02      A    C
ATOM   6020  C   THR C 141     -40.861 -44.766  -7.701  1.00 44.33      A    C
ATOM   6021  O   THR C 141     -40.474 -45.860  -7.295  1.00 44.81      A    O
ATOM   6022  CB  THR C 141     -43.251 -44.093  -7.996  1.00 43.69      A    C
ATOM   6023  CG2 THR C 141     -44.491 -44.200  -8.869  1.00 43.39      A    C
ATOM   6024  OG1 THR C 141     -43.482 -44.763  -6.753  1.00 43.71      A    O
ATOM   6025  N   PRO C 142     -40.303 -43.600  -7.295  1.00 44.29      A    N
ATOM   6026  CA  PRO C 142     -39.250 -43.582  -6.265  1.00 44.47      A    C
ATOM   6027  C   PRO C 142     -39.718 -44.088  -4.908  1.00 44.66      A    C
ATOM   6028  O   PRO C 142     -38.916 -44.212  -3.998  1.00 45.09      A    O
ATOM   6029  CB  PRO C 142     -38.887 -42.106  -6.163  1.00 44.34      A    C
ATOM   6030  CG  PRO C 142     -39.220 -41.560  -7.488  1.00 44.10      A    C
ATOM   6031  CD  PRO C 142     -40.454 -42.279  -7.926  1.00 43.98      A    C
ATOM   6032  N   LEU C 143     -41.009 -44.363  -4.780  1.00 44.50      A    N
ATOM   6033  CA  LEU C 143     -41.567 -44.997  -3.590  1.00 44.52      A    C
ATOM   6034  C   LEU C 143     -41.921 -46.461  -3.875  1.00 44.77      A    C
ATOM   6035  O   LEU C 143     -42.619 -47.109  -3.086  1.00 45.01      A    O
ATOM   6036  CB  LEU C 143     -42.825 -44.254  -3.135  1.00 44.19      A    C
ATOM   6037  CG  LEU C 143     -42.815 -43.098  -2.127  1.00 44.09      A    C
ATOM   6038  CD1 LEU C 143     -42.511 -43.608  -0.723  1.00 45.11      A    C
ATOM   6039  CD2 LEU C 143     -41.883 -41.969  -2.530  1.00 43.67      A    C
ATOM   6040  N   GLY C 144     -41.445 -46.971  -5.009  1.00 44.89      A    N
ATOM   6041  CA  GLY C 144     -41.758 -48.332  -5.436  1.00 44.99      A    C
ATOM   6042  C   GLY C 144     -43.060 -48.393  -6.209  1.00 44.81      A    C
ATOM   6043  O   GLY C 144     -43.670 -47.363  -6.477  1.00 44.45      A    O
ATOM   6044  N   PRO C 145     -43.490 -49.604  -6.584  1.00 44.95      A    N
ATOM   6045  CA  PRO C 145     -44.729 -49.802  -7.331  1.00 44.59      A    C
```

FIGURE 1 (cont'd)

```
ATOM   6046  C    PRO C 145     -45.925 -49.074  -6.724  1.00 43.79      A  C
ATOM   6047  O    PRO C 145     -46.206 -49.231  -5.539  1.00 44.01      A  O
ATOM   6048  CB   PRO C 145     -44.933 -51.317  -7.252  1.00 45.01      A  C
ATOM   6049  CG   PRO C 145     -43.545 -51.865  -7.215  1.00 45.66      A  C
ATOM   6050  CD   PRO C 145     -42.746 -50.867  -6.406  1.00 45.50      A  C
ATOM   6051  N    VAL C 146     -46.607 -48.284  -7.548  1.00 42.48      A  N
ATOM   6052  CA   VAL C 146     -47.807 -47.573  -7.135  1.00 41.06      A  C
ATOM   6053  C    VAL C 146     -48.925 -47.773  -8.155  1.00 41.26      A  C
ATOM   6054  O    VAL C 146     -48.690 -47.699  -9.350  1.00 41.31      A  O
ATOM   6055  CB   VAL C 146     -47.530 -46.086  -6.963  1.00 39.26      A  C
ATOM   6056  CG1  VAL C 146     -48.678 -45.422  -6.247  1.00 37.82      A  C
ATOM   6057  N    ASP C 147     -50.137 -48.033  -7.674  1.00 41.35      A  N
ATOM   6058  CA   ASP C 147     -51.287 -48.302  -8.542  1.00 41.09      A  C
ATOM   6059  C    ASP C 147     -52.064 -47.026  -8.889  1.00 40.65      A  C
ATOM   6060  O    ASP C 147     -52.592 -46.329  -8.004  1.00 40.57      A  O
ATOM   6061  CB   ASP C 147     -52.215 -49.352  -7.913  1.00 41.33      A  C
ATOM   6062  CG   ASP C 147     -51.699 -50.765  -8.076  1.00 41.25      A  C
ATOM   6063  N    PHE C 148     -52.132 -46.741 -10.187  1.00 40.10      A  N
ATOM   6064  CA   PHE C 148     -52.784 -45.539 -10.688  1.00 39.51      A  C
ATOM   6065  C    PHE C 148     -54.051 -45.859 -11.450  1.00 39.30      A  C
ATOM   6066  O    PHE C 148     -54.333 -47.015 -11.728  1.00 39.46      A  O
ATOM   6067  CB   PHE C 148     -51.849 -44.779 -11.617  1.00 39.30      A  C
ATOM   6068  CG   PHE C 148     -50.575 -44.315 -10.970  1.00 39.36      A  C
ATOM   6069  CD1  PHE C 148     -50.511 -43.085 -10.324  1.00 39.11      A  C
ATOM   6070  CD2  PHE C 148     -49.428 -45.093 -11.034  1.00 39.81      A  C
ATOM   6071  CE1  PHE C 148     -49.328 -42.649  -9.736  1.00 39.23      A  C
ATOM   6072  CE2  PHE C 148     -48.244 -44.662 -10.449  1.00 39.83      A  C
ATOM   6073  CZ   PHE C 148     -48.196 -43.438  -9.804  1.00 39.55      A  C
ATOM   6074  N    GLY C 149     -54.800 -44.816 -11.795  1.00 38.94      A  N
ATOM   6075  CA   GLY C 149     -56.025 -44.956 -12.559  1.00 38.77      A  C
ATOM   6076  C    GLY C 149     -56.581 -43.636 -13.050  1.00 38.50      A  C
ATOM   6077  O    GLY C 149     -57.026 -42.809 -12.251  1.00 38.51      A  O
ATOM   6078  N    ASN C 150     -56.553 -43.445 -14.368  1.00 38.25      A  N
ATOM   6079  CA   ASN C 150     -57.163 -42.288 -15.015  1.00 37.91      A  C
ATOM   6080  C    ASN C 150     -58.660 -42.468 -15.235  1.00 38.11      A  C
ATOM   6081  O    ASN C 150     -59.152 -43.588 -15.333  1.00 38.35      A  O
ATOM   6082  CB   ASN C 150     -56.493 -42.036 -16.352  1.00 37.65      A  C
ATOM   6083  CG   ASN C 150     -55.044 -41.637 -16.211  1.00 37.27      A  C
ATOM   6084  ND2  ASN C 150     -54.171 -42.370 -16.879  1.00 37.27      A  N
ATOM   6085  OD1  ASN C 150     -54.711 -40.672 -15.526  1.00 36.77      A  O
ATOM   6086  N    VAL C 151     -59.388 -41.361 -15.301  1.00 38.15      A  N
ATOM   6087  CA   VAL C 151     -60.816 -41.404 -15.593  1.00 38.46      A  C
ATOM   6088  C    VAL C 151     -61.062 -40.685 -16.911  1.00 38.65      A  C
ATOM   6089  O    VAL C 151     -60.905 -39.465 -16.998  1.00 38.50      A  O
ATOM   6090  CB   VAL C 151     -61.658 -40.794 -14.447  1.00 38.35      A  C
ATOM   6091  CG1  VAL C 151     -61.562 -41.671 -13.226  1.00 38.69      A  C
ATOM   6092  CG2  VAL C 151     -63.111 -40.643 -14.858  1.00 38.48      A  C
ATOM   6093  N    VAL C 152     -61.436 -41.455 -17.929  1.00 39.16      A  N
ATOM   6094  CA   VAL C 152     -61.623 -40.943 -19.280  1.00 39.66      A  C
ATOM   6095  C    VAL C 152     -63.099 -40.910 -19.678  1.00 40.19      A  C
ATOM   6096  O    VAL C 152     -63.779 -41.927 -19.648  1.00 40.54      A  O
ATOM   6097  CB   VAL C 152     -60.800 -41.768 -20.292  1.00 39.62      A  C
ATOM   6098  CG1  VAL C 152     -59.322 -41.435 -20.174  1.00 39.09      A  C
ATOM   6099  CG2  VAL C 152     -61.286 -41.530 -21.713  1.00 40.01      A  C
ATOM   6100  N    ALA C 153     -63.578 -39.732 -20.062  1.00 40.62      A  N
ATOM   6101  CA   ALA C 153     -64.980 -39.534 -20.396  1.00 41.24      A  C
ATOM   6102  C    ALA C 153     -65.165 -38.919 -21.777  1.00 41.75      A  C
ATOM   6103  O    ALA C 153     -64.617 -37.853 -22.070  1.00 41.70      A  O
ATOM   6104  CB   ALA C 153     -65.639 -38.665 -19.348  1.00 41.10      A  C
ATOM   6105  N    THR C 154     -65.950 -39.591 -22.616  1.00 42.51      A  N
ATOM   6106  CA   THR C 154     -66.200 -39.122 -23.970  1.00 43.16      A  C
ATOM   6107  C    THR C 154     -67.667 -39.286 -24.334  1.00 43.98      A  C
ATOM   6108  O    THR C 154     -68.180 -40.403 -24.327  1.00 44.40      A  O
ATOM   6109  CB   THR C 154     -65.354 -39.912 -24.994  1.00 43.08      A  C
ATOM   6110  CG2  THR C 154     -65.205 -39.132 -26.290  1.00 42.98      A  C
```

FIGURE 1 (cont'd)

```
ATOM   6111  OG1 THR C 154     -64.056 -40.174 -24.454  1.00 42.60      A    O
ATOM   6112  N   LEU C 155     -68.343 -38.176 -24.630  1.00 44.67      A    N
ATOM   6113  CA  LEU C 155     -69.638 -38.222 -25.310  1.00 45.55      A    C
ATOM   6114  C   LEU C 155     -69.401 -38.695 -26.737  1.00 46.36      A    C
ATOM   6115  O   LEU C 155     -68.477 -38.216 -27.400  1.00 46.58      A    O
ATOM   6116  CB  LEU C 155     -70.265 -36.831 -25.379  1.00 45.35      A    C
ATOM   6117  CG  LEU C 155     -71.398 -36.469 -24.440  1.00 45.36      A    C
ATOM   6118  CD1 LEU C 155     -72.136 -35.264 -25.010  1.00 45.19      A    C
ATOM   6119  CD2 LEU C 155     -72.328 -37.650 -24.278  1.00 45.85      A    C
ATOM   6120  N   ASP C 156     -70.213 -39.632 -27.216  1.00 47.22      A    N
ATOM   6121  CA  ASP C 156     -70.144 -40.038 -28.618  1.00 48.03      A    C
ATOM   6122  C   ASP C 156     -68.720 -40.449 -29.035  1.00 47.87      A    C
ATOM   6123  O   ASP C 156     -68.048 -39.706 -29.749  1.00 47.65      A    O
ATOM   6124  CB  ASP C 156     -70.660 -38.889 -29.499  1.00 48.56      A    C
ATOM   6125  CG  ASP C 156     -70.993 -39.324 -30.909  1.00 50.21      A    C
ATOM   6126  OD1 ASP C 156     -70.693 -40.485 -31.270  1.00 51.20      A    O
ATOM   6127  OD2 ASP C 156     -71.555 -38.494 -31.662  1.00 51.70      A    O
ATOM   6128  N   PRO C 157     -68.258 -41.636 -28.590  1.00 47.98      A    N
ATOM   6129  CA  PRO C 157     -66.925 -42.118 -28.939  1.00 48.05      A    C
ATOM   6130  C   PRO C 157     -66.720 -42.277 -30.435  1.00 48.39      A    C
ATOM   6131  O   PRO C 157     -65.574 -42.267 -30.894  1.00 48.28      A    O
ATOM   6132  CB  PRO C 157     -66.866 -43.497 -28.289  1.00 48.02      A    C
ATOM   6133  CG  PRO C 157     -67.854 -43.452 -27.220  1.00 48.06      A    C
ATOM   6134  CD  PRO C 157     -68.952 -42.584 -27.704  1.00 48.13      A    C
ATOM   6135  N   ARG C 158     -67.818 -42.423 -31.179  1.00 48.93      A    N
ATOM   6136  CA  ARG C 158     -67.754 -42.624 -32.633  1.00 49.41      A    C
ATOM   6137  C   ARG C 158     -67.498 -41.348 -33.439  1.00 49.20      A    C
ATOM   6138  O   ARG C 158     -67.092 -41.422 -34.587  1.00 49.52      A    O
ATOM   6139  CB  ARG C 158     -68.962 -43.420 -33.171  1.00 49.91      A    C
ATOM   6140  CG  ARG C 158     -70.331 -42.942 -32.725  1.00 50.26      A    C
ATOM   6141  N   ALA C 159     -67.707 -40.187 -32.835  1.00 48.70      A    N
ATOM   6142  CA  ALA C 159     -67.385 -38.922 -33.493  1.00 48.35      A    C
ATOM   6143  C   ALA C 159     -65.898 -38.839 -33.842  1.00 48.02      A    C
ATOM   6144  O   ALA C 159     -65.055 -39.265 -33.052  1.00 47.81      A    O
ATOM   6145  CB  ALA C 159     -67.792 -37.748 -32.615  1.00 48.22      A    C
ATOM   6146  N   ALA C 160     -65.592 -38.278 -35.014  1.00 47.86      A    N
ATOM   6147  CA  ALA C 160     -64.236 -38.291 -35.562  1.00 47.59      A    C
ATOM   6148  C   ALA C 160     -63.218 -37.716 -34.747  1.00 47.09      A    C
ATOM   6149  O   ALA C 160     -62.051 -37.884 -34.671  1.00 47.03      A    O
ATOM   6150  CB  ALA C 160     -64.247 -37.820 -36.998  1.00 48.02      A    C
ATOM   6151  N   ARG C 161     -63.665 -36.393 -34.149  1.00 46.51      A    N
ATOM   6152  CA  ARG C 161     -62.812 -35.523 -33.329  1.00 45.90      A    C
ATOM   6153  C   ARG C 161     -63.552 -35.010 -32.092  1.00 45.12      A    C
ATOM   6154  O   ARG C 161     -64.780 -34.987 -32.072  1.00 45.27      A    O
ATOM   6155  CB  ARG C 161     -62.308 -34.343 -34.156  1.00 46.15      A    C
ATOM   6156  CG  ARG C 161     -61.093 -34.642 -35.030  1.00 47.54      A    C
ATOM   6157  CD  ARG C 161     -61.203 -33.928 -36.369  1.00 50.39      A    C
ATOM   6158  NE  ARG C 161     -61.972 -32.680 -36.263  1.00 52.63      A    N
ATOM   6159  CZ  ARG C 161     -62.883 -32.263 -37.149  1.00 53.87      A    C
ATOM   6160  NH1 ARG C 161     -63.162 -32.990 -38.229  1.00 54.67      A    N
ATOM   6161  NH2 ARG C 161     -63.529 -31.116 -36.954  1.00 54.13      A    N
ATOM   6162  N   HIS C 162     -62.806 -34.604 -31.064  1.00 44.05      A    N
ATOM   6163  CA  HIS C 162     -63.405 -34.070 -29.840  1.00 43.00      A    C
ATOM   6164  C   HIS C 162     -62.583 -32.966 -29.205  1.00 41.93      A    C
ATOM   6165  O   HIS C 162     -61.359 -32.990 -29.258  1.00 41.68      A    O
ATOM   6166  CB  HIS C 162     -63.663 -35.185 -28.813  1.00 43.24      A    C
ATOM   6167  CG  HIS C 162     -62.494 -36.093 -28.583  1.00 43.86      A    C
ATOM   6168  CD2 HIS C 162     -62.280 -37.376 -28.956  1.00 44.45      A    C
ATOM   6169  ND1 HIS C 162     -61.377 -35.709 -27.874  1.00 44.03      A    N
ATOM   6170  CE1 HIS C 162     -60.517 -36.710 -27.837  1.00 44.25      A    C
ATOM   6171  NE2 HIS C 162     -61.042 -37.735 -28.483  1.00 44.51      A    N
ATOM   6172  N   LEU C 163     -63.273 -31.991 -28.619  1.00 40.83      A    N
ATOM   6173  CA  LEU C 163     -62.636 -31.039 -27.715  1.00 39.66      A    C
ATOM   6174  C   LEU C 163     -62.361 -31.778 -26.422  1.00 38.99      A    C
ATOM   6175  O   LEU C 163     -63.231 -32.483 -25.905  1.00 39.02      A    O
```

FIGURE 1 (cont'd)

```
ATOM   6176  CB   LEU C 163     -63.537 -29.832 -27.434  1.00 39.56       A  C
ATOM   6177  CG   LEU C 163     -63.164 -28.919 -26.257  1.00 38.90       A  C
ATOM   6178  CD1  LEU C 163     -61.857 -28.182 -26.514  1.00 38.47       A  C
ATOM   6179  CD2  LEU C 163     -64.278 -27.941 -25.953  1.00 38.84       A  C
ATOM   6180  N    THR C 164     -61.156 -31.618 -25.896  1.00 38.01       A  N
ATOM   6181  CA   THR C 164     -60.794 -32.325 -24.685  1.00 37.02       A  C
ATOM   6182  C    THR C 164     -60.274 -31.407 -23.581  1.00 36.44       A  C
ATOM   6183  O    THR C 164     -59.272 -30.705 -23.734  1.00 36.24       A  O
ATOM   6184  CB   THR C 164     -59.882 -33.558 -24.977  1.00 36.97       A  C
ATOM   6185  CG2  THR C 164     -58.734 -33.203 -25.850  1.00 36.93       A  C
ATOM   6186  OG1  THR C 164     -59.361 -34.090 -23.762  1.00 36.65       A  O
ATOM   6187  N    LEU C 165     -61.017 -31.384 -22.483  1.00 35.84       A  N
ATOM   6188  CA   LEU C 165     -60.632 -30.658 -21.287  1.00 35.29       A  C
ATOM   6189  C    LEU C 165     -60.030 -31.634 -20.287  1.00 34.97       A  C
ATOM   6190  O    LEU C 165     -60.425 -32.799 -20.227  1.00 35.01       A  O
ATOM   6191  CB   LEU C 165     -61.837 -29.942 -20.673  1.00 35.22       A  C
ATOM   6192  CG   LEU C 165     -62.624 -28.957 -21.535  1.00 35.26       A  C
ATOM   6193  CD1  LEU C 165     -63.628 -28.229 -20.681  1.00 35.40       A  C
ATOM   6194  CD2  LEU C 165     -61.723 -27.972 -22.221  1.00 35.08       A  C
ATOM   6195  N    ALA C 166     -59.067 -31.154 -19.507  1.00 34.51       A  N
ATOM   6196  CA   ALA C 166     -58.390 -32.002 -18.532  1.00 34.10       A  C
ATOM   6197  C    ALA C 166     -58.011 -31.288 -17.225  1.00 33.81       A  C
ATOM   6198  O    ALA C 166     -57.678 -30.099 -17.225  1.00 33.63       A  O
ATOM   6199  CB   ALA C 166     -57.166 -32.676 -19.167  1.00 34.09       A  C
ATOM   6200  N    CYS C 167     -58.101 -32.040 -16.126  1.00 33.62       A  N
ATOM   6201  CA   CYS C 167     -57.596 -31.658 -14.818  1.00 33.48       A  C
ATOM   6202  C    CYS C 167     -56.956 -32.899 -14.237  1.00 33.47       A  C
ATOM   6203  O    CYS C 167     -57.155 -33.998 -14.761  1.00 33.56       A  O
ATOM   6204  CB   CYS C 167     -58.741 -31.235 -13.916  1.00 33.48       A  C
ATOM   6205  SG   CYS C 167     -59.854 -32.567 -13.474  1.00 33.74       A  S
ATOM   6206  N    HIS C 168     -56.190 -32.743 -13.161  1.00 33.45       A  N
ATOM   6207  CA   HIS C 168     -55.700 -33.920 -12.436  1.00 33.49       A  C
ATOM   6208  C    HIS C 168     -56.386 -34.039 -11.082  1.00 33.42       A  C
ATOM   6209  O    HIS C 168     -56.539 -33.054 -10.364  1.00 33.36       A  O
ATOM   6210  CB   HIS C 168     -54.174 -33.917 -12.293  1.00 33.62       A  C
ATOM   6211  CG   HIS C 168     -53.670 -32.999 -11.233  1.00 33.97       A  C
ATOM   6212  CD2  HIS C 168     -53.288 -31.704 -11.286  1.00 34.33       A  C
ATOM   6213  ND1  HIS C 168     -53.531 -33.386  -9.922  1.00 34.31       A  N
ATOM   6214  CE1  HIS C 168     -53.082 -32.371  -9.210  1.00 34.37       A  C
ATOM   6215  NE2  HIS C 168     -52.923 -31.339 -10.014  1.00 34.32       A  N
ATOM   6216  N    TYR C 169     -56.800 -35.251 -10.736  1.00 33.50       A  N
ATOM   6217  CA   TYR C 169     -57.606 -35.451  -9.535  1.00 33.67       A  C
ATOM   6218  C    TYR C 169     -56.805 -35.908  -8.308  1.00 33.75       A  C
ATOM   6219  O    TYR C 169     -57.288 -35.834  -7.179  1.00 33.75       A  O
ATOM   6220  CB   TYR C 169     -58.809 -36.374  -9.828  1.00 33.73       A  C
ATOM   6221  CG   TYR C 169     -58.502 -37.850  -9.889  1.00 33.92       A  C
ATOM   6222  CD1  TYR C 169     -58.012 -38.434 -11.047  1.00 33.83       A  C
ATOM   6223  CD2  TYR C 169     -58.726 -38.665  -8.789  1.00 34.39       A  C
ATOM   6224  CE1  TYR C 169     -57.736 -39.788 -11.100  1.00 33.92       A  C
ATOM   6225  CE2  TYR C 169     -58.450 -40.016  -8.834  1.00 34.59       A  C
ATOM   6226  CZ   TYR C 169     -57.956 -40.571  -9.990  1.00 34.18       A  C
ATOM   6227  OH   TYR C 169     -57.683 -41.912 -10.030  1.00 34.24       A  O
ATOM   6228  N    ASP C 170     -55.583 -36.374  -8.524  1.00 33.86       A  N
ATOM   6229  CA   ASP C 170     -54.724 -36.717  -7.408  1.00 34.18       A  C
ATOM   6230  C    ASP C 170     -54.372 -35.464  -6.615  1.00 34.43       A  C
ATOM   6231  O    ASP C 170     -54.534 -34.351  -7.118  1.00 34.28       A  O
ATOM   6232  CB   ASP C 170     -53.467 -37.454  -7.890  1.00 34.24       A  C
ATOM   6233  CG   ASP C 170     -52.539 -36.586  -8.725  1.00 34.16       A  C
ATOM   6234  OD1  ASP C 170     -52.983 -36.042  -9.752  1.00 33.81       A  O
ATOM   6235  OD2  ASP C 170     -51.344 -36.476  -8.371  1.00 34.56       A  O
ATOM   6236  N    SER C 171     -53.937 -35.646  -5.369  1.00 34.89       A  N
ATOM   6237  CA   SER C 171     -53.395 -34.553  -4.556  1.00 35.33       A  C
ATOM   6238  C    SER C 171     -51.959 -34.891  -4.165  1.00 35.62       A  C
ATOM   6239  O    SER C 171     -51.637 -36.062  -3.979  1.00 35.94       A  O
ATOM   6240  CB   SER C 171     -54.254 -34.327  -3.308  1.00 35.39       A  C
```

FIGURE 1 (cont'd)

```
ATOM   6241  OG   SER C 171     -53.923 -35.228  -2.269  1.00 35.81      A   O
ATOM   6242  N    LYS C 172     -51.097 -33.884  -4.034  1.00 35.79      A   N
ATOM   6243  CA   LYS C 172     -49.691 -34.148  -3.690  1.00 36.20      A   C
ATOM   6244  C    LYS C 172     -49.525 -34.855  -2.351  1.00 36.88      A   C
ATOM   6245  O    LYS C 172     -50.316 -34.666  -1.436  1.00 37.14      A   O
ATOM   6246  CB   LYS C 172     -48.843 -32.867  -3.714  1.00 35.95      A   C
ATOM   6247  CG   LYS C 172     -47.323 -33.125  -3.795  1.00 35.70      A   C
ATOM   6248  CD   LYS C 172     -46.502 -31.852  -3.753  1.00 35.06      A   C
ATOM   6249  CE   LYS C 172     -45.027 -32.156  -3.690  1.00 35.05      A   C
ATOM   6250  NZ   LYS C 172     -44.512 -32.607  -5.000  1.00 35.04      A   N
ATOM   6251  N    LEU C 173     -48.487 -35.677  -2.261  1.00 37.68      A   N
ATOM   6252  CA   LEU C 173     -48.162 -36.418  -1.051  1.00 38.56      A   C
ATOM   6253  C    LEU C 173     -47.083 -35.681  -0.250  1.00 39.10      A   C
ATOM   6254  O    LEU C 173     -46.004 -35.396  -0.775  1.00 39.21      A   O
ATOM   6255  CB   LEU C 173     -47.680 -37.814  -1.440  1.00 38.61      A   C
ATOM   6256  CG   LEU C 173     -47.103 -38.712  -0.352  1.00 39.24      A   C
ATOM   6257  CD1  LEU C 173     -48.165 -39.603   0.260  1.00 39.57      A   C
ATOM   6258  CD2  LEU C 173     -45.940 -39.537  -0.885  1.00 39.38      A   C
ATOM   6259  N    PHE C 174     -47.374 -35.374   1.012  1.00 39.75      A   N
ATOM   6260  CA   PHE C 174     -46.421 -34.686   1.883  1.00 40.36      A   C
ATOM   6261  C    PHE C 174     -46.026 -35.596   3.064  1.00 40.30      A   C
ATOM   6262  O    PHE C 174     -46.759 -36.534   3.371  1.00 41.38      A   O
ATOM   6263  CB   PHE C 174     -47.020 -33.364   2.360  1.00 40.58      A   C
ATOM   6264  CG   PHE C 174     -46.989 -32.286   1.327  1.00 40.44      A   C
ATOM   6265  CD1  PHE C 174     -45.824 -31.568   1.100  1.00 40.58      A   C
ATOM   6266  CD2  PHE C 174     -48.122 -31.987   0.571  1.00 40.01      A   C
ATOM   6267  CE1  PHE C 174     -45.783 -30.565   0.133  1.00 40.11      A   C
ATOM   6268  CE2  PHE C 174     -48.089 -30.983  -0.392  1.00 39.53      A   C
ATOM   6269  CZ   PHE C 174     -46.919 -30.270  -0.610  1.00 39.64      A   C
ATOM   6270  N    PRO C 175     -44.869 -35.353   3.730  1.00 39.20      A   N
ATOM   6271  CA   PRO C 175     -44.511 -36.333   4.770  1.00 38.40      A   C
ATOM   6272  C    PRO C 175     -45.626 -36.446   5.819  1.00 38.19      A   C
ATOM   6273  O    PRO C 175     -46.265 -35.430   6.139  1.00 37.89      A   O
ATOM   6274  CB   PRO C 175     -43.230 -35.757   5.375  1.00 38.27      A   C
ATOM   6275  CG   PRO C 175     -42.692 -34.822   4.319  1.00 38.37      A   C
ATOM   6276  CD   PRO C 175     -43.906 -34.234   3.682  1.00 38.99      A   C
ATOM   6277  N    PRO C 176     -45.862 -37.669   6.357  1.00 38.45      A   N
ATOM   6278  CA   PRO C 176     -47.169 -37.856   6.990  1.00 38.68      A   C
ATOM   6279  C    PRO C 176     -47.261 -37.002   8.232  1.00 39.42      A   C
ATOM   6280  O    PRO C 176     -48.363 -36.709   8.698  1.00 39.50      A   O
ATOM   6281  CB   PRO C 176     -47.192 -39.355   7.347  1.00 38.34      A   C
ATOM   6282  CG   PRO C 176     -45.758 -39.752   7.493  1.00 38.08      A   C
ATOM   6283  CD   PRO C 176     -44.904 -38.735   6.738  1.00 38.32      A   C
ATOM   6284  N    GLY C 177     -46.096 -36.575   8.718  1.00 40.43      A   N
ATOM   6285  CA   GLY C 177     -45.965 -35.961  10.025  1.00 42.54      A   C
ATOM   6286  C    GLY C 177     -46.757 -34.693  10.313  1.00 44.17      A   C
ATOM   6287  O    GLY C 177     -46.590 -34.105  11.395  1.00 44.22      A   O
ATOM   6288  N    SER C 178     -47.628 -34.255   9.391  1.00 46.97      A   N
ATOM   6289  CA   SER C 178     -47.875 -32.819   9.374  1.00 46.87      A   C
ATOM   6290  C    SER C 178     -49.205 -32.152   9.377  1.00 46.86      A   C
ATOM   6291  O    SER C 178     -49.743 -31.936  10.452  1.00 47.48      A   O
ATOM   6292  CB   SER C 178     -47.055 -32.199   8.294  1.00 45.24      A   C
ATOM   6293  OG   SER C 178     -45.722 -32.540   8.587  1.00 44.57      A   O
ATOM   6294  N    THR C 179     -49.718 -31.733   8.222  1.00 45.44      A   N
ATOM   6295  CA   THR C 179     -51.091 -31.275   8.274  1.00 43.01      A   C
ATOM   6296  C    THR C 179     -51.656 -31.669   6.941  1.00 43.49      A   C
ATOM   6297  O    THR C 179     -50.965 -31.556   5.926  1.00 44.44      A   O
ATOM   6298  CB   THR C 179     -51.206 -29.766   8.617  1.00 37.56      A   C
ATOM   6299  OG1  THR C 179     -51.955 -29.094   7.615  1.00 34.48      A   O
ATOM   6300  N    PRO C 180     -52.899 -32.184   6.940  1.00 42.29      A   N
ATOM   6301  CA   PRO C 180     -53.468 -32.795   5.733  1.00 41.30      A   C
ATOM   6302  C    PRO C 180     -53.479 -31.799   4.567  1.00 42.04      A   C
ATOM   6303  O    PRO C 180     -53.753 -30.613   4.768  1.00 42.89      A   O
ATOM   6304  CB   PRO C 180     -54.895 -33.157   6.166  1.00 36.48      A   C
ATOM   6305  CG   PRO C 180     -55.224 -32.169   7.243  1.00 34.99      A   C
```

FIGURE 1 (cont'd)

```
ATOM   6306  CD   PRO C 180     -53.930 -31.926   7.970  1.00 41.22      A  C
ATOM   6307  N    PHE C 181     -53.155 -32.274   3.371  1.00 41.80      A  N
ATOM   6308  CA   PHE C 181     -53.104 -31.411   2.203  1.00 40.91      A  C
ATOM   6309  C    PHE C 181     -54.146 -31.814   1.176  1.00 40.21      A  C
ATOM   6310  O    PHE C 181     -54.069 -32.901   0.597  1.00 40.01      A  O
ATOM   6311  CB   PHE C 181     -51.708 -31.421   1.581  1.00 40.95      A  C
ATOM   6312  CG   PHE C 181     -51.633 -30.705   0.273  1.00 40.71      A  C
ATOM   6313  CD1  PHE C 181     -51.765 -29.323   0.204  1.00 40.87      A  C
ATOM   6314  CD2  PHE C 181     -51.448 -31.410  -0.900  1.00 40.50      A  C
ATOM   6315  CE1  PHE C 181     -51.706 -28.656  -1.023  1.00 40.27      A  C
ATOM   6316  CE2  PHE C 181     -51.388 -30.748  -2.138  1.00 39.98      A  C
ATOM   6317  CZ   PHE C 181     -51.512 -29.372  -2.194  1.00 39.73      A  C
ATOM   6318  N    VAL C 182     -55.110 -30.924   0.943  1.00 39.42      A  N
ATOM   6319  CA   VAL C 182     -56.221 -31.208   0.022  1.00 38.70      A  C
ATOM   6320  C    VAL C 182     -56.124 -30.537  -1.349  1.00 37.92      A  C
ATOM   6321  O    VAL C 182     -56.834 -30.922  -2.286  1.00 37.75      A  O
ATOM   6322  CB   VAL C 182     -57.602 -30.901   0.639  1.00 38.77      A  C
ATOM   6323  CG1  VAL C 182     -58.009 -32.004   1.602  1.00 39.11      A  C
ATOM   6324  CG2  VAL C 182     -57.610 -29.528   1.309  1.00 39.13      A  C
ATOM   6325  N    GLY C 183     -55.253 -29.539  -1.464  1.00 37.20      A  N
ATOM   6326  CA   GLY C 183     -55.019 -28.871  -2.738  1.00 36.25      A  C
ATOM   6327  C    GLY C 183     -56.289 -28.476  -3.459  1.00 35.57      A  C
ATOM   6328  O    GLY C 183     -56.684 -29.107  -4.441  1.00 35.41      A  O
ATOM   6329  N    ALA C 184     -56.927 -27.427  -2.960  1.00 35.04      A  N
ATOM   6330  CA   ALA C 184     -58.182 -26.969  -3.508  1.00 34.44      A  C
ATOM   6331  C    ALA C 184     -57.991 -26.431  -4.915  1.00 33.88      A  C
ATOM   6332  O    ALA C 184     -58.729 -26.796  -5.818  1.00 33.70      A  O
ATOM   6333  CB   ALA C 184     -58.786 -25.928  -2.603  1.00 34.78      A  C
ATOM   6334  N    THR C 185     -56.987 -25.576  -5.093  1.00 33.34      A  N
ATOM   6335  CA   THR C 185     -56.659 -25.022  -6.402  1.00 32.80      A  C
ATOM   6336  C    THR C 185     -55.915 -26.052  -7.242  1.00 32.57      A  C
ATOM   6337  O    THR C 185     -55.752 -25.872  -8.447  1.00 32.59      A  O
ATOM   6338  CB   THR C 185     -55.755 -23.757  -6.307  1.00 32.73      A  C
ATOM   6339  CG2  THR C 185     -56.244 -22.796  -5.237  1.00 32.97      A  C
ATOM   6340  OG1  THR C 185     -54.404 -24.136  -6.018  1.00 32.38      A  O
ATOM   6341  N    ASP C 186     -55.474 -27.132  -6.601  1.00 32.33      A  N
ATOM   6342  CA   ASP C 186     -54.465 -28.011  -7.172  1.00 32.08      A  C
ATOM   6343  C    ASP C 186     -54.828 -29.492  -6.982  1.00 32.14      A  C
ATOM   6344  O    ASP C 186     -54.200 -30.182  -6.179  1.00 32.46      A  O
ATOM   6345  CB   ASP C 186     -53.116 -27.675  -6.516  1.00 31.97      A  C
ATOM   6346  CG   ASP C 186     -51.931 -28.298  -7.216  1.00 31.47      A  C
ATOM   6347  OD1  ASP C 186     -50.802 -28.071  -6.740  1.00 31.34      A  O
ATOM   6348  OD2  ASP C 186     -52.100 -29.007  -8.228  1.00 30.67      A  O
ATOM   6349  N    SER C 187     -55.821 -30.004  -7.714  1.00 31.90      A  N
ATOM   6350  CA   SER C 187     -56.586 -29.277  -8.723  1.00 31.61      A  C
ATOM   6351  C    SER C 187     -58.063 -29.576  -8.573  1.00 31.59      A  C
ATOM   6352  O    SER C 187     -58.757 -29.780  -9.562  1.00 31.50      A  O
ATOM   6353  CB   SER C 187     -56.134 -29.673 -10.128  1.00 31.53      A  C
ATOM   6354  OG   SER C 187     -54.879 -29.102 -10.447  1.00 31.72      A  O
ATOM   6355  N    ALA C 188     -58.541 -29.596  -7.334  1.00 31.72      A  N
ATOM   6356  CA   ALA C 188     -59.935 -29.899  -7.045  1.00 31.81      A  C
ATOM   6357  C    ALA C 188     -60.910 -28.991  -7.811  1.00 31.82      A  C
ATOM   6358  O    ALA C 188     -61.802 -29.474  -8.508  1.00 31.83      A  O
ATOM   6359  CB   ALA C 188     -60.184 -29.831  -5.561  1.00 31.99      A  C
ATOM   6360  N    VAL C 189     -60.726 -27.680  -7.696  1.00 31.74      A  N
ATOM   6361  CA   VAL C 189     -61.554 -26.717  -8.420  1.00 31.62      A  C
ATOM   6362  C    VAL C 189     -61.567 -26.987  -9.926  1.00 31.62      A  C
ATOM   6363  O    VAL C 189     -62.650 -27.105 -10.498  1.00 31.72      A  O
ATOM   6364  CB   VAL C 189     -61.150 -25.258  -8.123  1.00 31.55      A  C
ATOM   6365  CG1  VAL C 189     -61.908 -24.298  -9.013  1.00 31.34      A  C
ATOM   6366  CG2  VAL C 189     -61.408 -24.925  -6.677  1.00 31.77      A  C
ATOM   6367  N    PRO C 190     -60.376 -27.084 -10.573  1.00 31.52      A  N
ATOM   6368  CA   PRO C 190     -60.336 -27.478 -11.973  1.00 31.51      A  C
ATOM   6369  C    PRO C 190     -61.204 -28.680 -12.299  1.00 31.74      A  C
ATOM   6370  O    PRO C 190     -61.981 -28.625 -13.243  1.00 31.80      A  O
```

FIGURE 1 (cont'd)

```
ATOM   6371  CB  PRO C 190     -58.869 -27.798 -12.186  1.00 31.30      A    C
ATOM   6372  CG  PRO C 190     -58.189 -26.831 -11.348  1.00 31.28      A    C
ATOM   6373  CD  PRO C 190     -59.047 -26.610 -10.143  1.00 31.45      A    C
ATOM   6374  N   CYS C 191     -61.097 -29.744 -11.515  1.00 32.12      A    N
ATOM   6375  CA  CYS C 191     -61.918 -30.933 -11.739  1.00 32.67      A    C
ATOM   6376  C   CYS C 191     -63.408 -30.686 -11.487  1.00 32.97      A    C
ATOM   6377  O   CYS C 191     -64.257 -31.173 -12.233  1.00 33.14      A    O
ATOM   6378  CB  CYS C 191     -61.409 -32.103 -10.909  1.00 32.72      A    C
ATOM   6379  SG  CYS C 191     -59.790 -32.653 -11.428  1.00 33.24      A    S
ATOM   6380  N   ALA C 192     -63.716 -29.910 -10.453  1.00 33.20      A    N
ATOM   6381  CA  ALA C 192     -65.089 -29.562 -10.135  1.00 33.41      A    C
ATOM   6382  C   ALA C 192     -65.769 -28.841 -11.294  1.00 33.40      A    C
ATOM   6383  O   ALA C 192     -66.925 -29.112 -11.599  1.00 33.69      A    O
ATOM   6384  CB  ALA C 192     -65.131 -28.718  -8.891  1.00 33.58      A    C
ATOM   6385  N   LEU C 193     -65.044 -27.935 -11.941  1.00 32.99      A    N
ATOM   6386  CA  LEU C 193     -65.567 -27.189 -13.077  1.00 32.61      A    C
ATOM   6387  C   LEU C 193     -65.928 -28.110 -14.239  1.00 33.17      A    C
ATOM   6388  O   LEU C 193     -67.014 -28.017 -14.817  1.00 33.55      A    O
ATOM   6389  CB  LEU C 193     -64.554 -26.138 -13.532  1.00 31.29      A    C
ATOM   6390  CG  LEU C 193     -64.304 -24.959 -12.605  1.00 29.71      A    C
ATOM   6391  CD1 LEU C 193     -63.162 -24.136 -13.120  1.00 28.74      A    C
ATOM   6392  CD2 LEU C 193     -65.550 -24.120 -12.534  1.00 29.33      A    C
ATOM   6393  N   LEU C 194     -65.014 -29.009 -14.572  1.00 33.38      A    N
ATOM   6394  CA  LEU C 194     -65.250 -29.964 -15.642  1.00 33.55      A    C
ATOM   6395  C   LEU C 194     -66.565 -30.716 -15.418  1.00 34.47      A    C
ATOM   6396  O   LEU C 194     -67.310 -30.964 -16.367  1.00 34.77      A    O
ATOM   6397  CB  LEU C 194     -64.068 -30.926 -15.779  1.00 32.46      A    C
ATOM   6398  CG  LEU C 194     -62.809 -30.282 -16.351  1.00 31.24      A    C
ATOM   6399  CD1 LEU C 194     -61.994 -31.312 -17.064  1.00 30.87      A    C
ATOM   6400  N   LEU C 195     -66.851 -31.048 -14.158  1.00 35.27      A    N
ATOM   6401  CA  LEU C 195     -68.093 -31.727 -13.793  1.00 36.08      A    C
ATOM   6402  C   LEU C 195     -69.289 -30.800 -13.974  1.00 36.78      A    C
ATOM   6403  O   LEU C 195     -70.262 -31.152 -14.637  1.00 37.10      A    O
ATOM   6404  CB  LEU C 195     -68.035 -32.248 -12.353  1.00 36.01      A    C
ATOM   6405  CG  LEU C 195     -67.086 -33.401 -12.016  1.00 35.80      A    C
ATOM   6406  CD1 LEU C 195     -67.075 -33.660 -10.527  1.00 36.03      A    C
ATOM   6407  CD2 LEU C 195     -67.454 -34.669 -12.761  1.00 35.81      A    C
ATOM   6408  N   GLU C 196     -69.197 -29.609 -13.393  1.00 37.39      A    N
ATOM   6409  CA  GLU C 196     -70.272 -28.626 -13.459  1.00 38.02      A    C
ATOM   6410  C   GLU C 196     -70.623 -28.276 -14.905  1.00 38.12      A    C
ATOM   6411  O   GLU C 196     -71.797 -28.249 -15.276  1.00 38.31      A    O
ATOM   6412  CB  GLU C 196     -69.899 -27.376 -12.643  1.00 38.17      A    C
ATOM   6413  CG  GLU C 196     -70.771 -26.131 -12.872  1.00 39.28      A    C
ATOM   6414  CD  GLU C 196     -72.197 -26.263 -12.362  1.00 40.76      A    C
ATOM   6415  OE1 GLU C 196     -72.540 -27.290 -11.740  1.00 41.40      A    O
ATOM   6416  OE2 GLU C 196     -72.986 -25.326 -12.589  1.00 41.45      A    O
ATOM   6417  N   LEU C 197     -69.597 -28.023 -15.712  1.00 38.11      A    N
ATOM   6418  CA  LEU C 197     -69.775 -27.728 -17.122  1.00 38.35      A    C
ATOM   6419  C   LEU C 197     -70.534 -28.844 -17.818  1.00 38.83      A    C
ATOM   6420  O   LEU C 197     -71.463 -28.589 -18.579  1.00 39.14      A    O
ATOM   6421  CB  LEU C 197     -68.418 -27.540 -17.792  1.00 37.96      A    C
ATOM   6422  CG  LEU C 197     -67.945 -26.123 -18.087  1.00 37.73      A    C
ATOM   6423  CD1 LEU C 197     -67.360 -25.503 -16.864  1.00 37.58      A    C
ATOM   6424  CD2 LEU C 197     -66.906 -26.153 -19.190  1.00 37.65      A    C
ATOM   6425  N   ALA C 198     -70.134 -30.080 -17.542  1.00 39.29      A    N
ATOM   6426  CA  ALA C 198     -70.725 -31.248 -18.178  1.00 40.03      A    C
ATOM   6427  C   ALA C 198     -72.193 -31.419 -17.809  1.00 40.77      A    C
ATOM   6428  O   ALA C 198     -72.978 -31.987 -18.581  1.00 41.06      A    O
ATOM   6429  CB  ALA C 198     -69.941 -32.494 -17.814  1.00 39.86      A    C
ATOM   6430  N   GLN C 199     -72.543 -30.922 -16.623  1.00 41.36      A    N
ATOM   6431  CA  GLN C 199     -73.894 -31.024 -16.091  1.00 42.01      A    C
ATOM   6432  C   GLN C 199     -74.738 -29.856 -16.558  1.00 42.95      A    C
ATOM   6433  O   GLN C 199     -75.883 -30.045 -16.943  1.00 43.58      A    O
ATOM   6434  CB  GLN C 199     -73.872 -31.034 -14.569  1.00 40.93      A    C
ATOM   6435  CG  GLN C 199     -74.592 -32.196 -13.933  1.00 40.37      A    C
```

FIGURE 1 (cont'd)

```
ATOM   6436  CD   GLN C 199     -76.033 -32.307 -14.312  1.00 40.10      A    C
ATOM   6437  NE2  GLN C 199     -76.388 -33.378 -14.992  1.00 40.09      A    N
ATOM   6438  OE1  GLN C 199     -76.829 -31.457 -13.972  1.00 40.44      A    O
ATOM   6439  N    ALA C 200     -74.174 -28.651 -16.515  1.00 43.61      A    N
ATOM   6440  CA   ALA C 200     -74.892 -27.441 -16.918  1.00 44.34      A    C
ATOM   6441  C    ALA C 200     -75.252 -27.438 -18.405  1.00 44.90      A    C
ATOM   6442  O    ALA C 200     -76.352 -27.030 -18.793  1.00 45.36      A    O
ATOM   6443  CB   ALA C 200     -74.087 -26.207 -16.564  1.00 44.11      A    C
ATOM   6444  N    LEU C 201     -74.324 -27.903 -19.232  1.00 45.24      A    N
ATOM   6445  CA   LEU C 201     -74.543 -27.968 -20.670  1.00 45.78      A    C
ATOM   6446  C    LEU C 201     -75.027 -29.344 -21.111  1.00 46.51      A    C
ATOM   6447  O    LEU C 201     -75.090 -29.621 -22.303  1.00 46.77      A    O
ATOM   6448  CB   LEU C 201     -73.260 -27.609 -21.416  1.00 45.32      A    C
ATOM   6449  CG   LEU C 201     -72.728 -26.202 -21.175  1.00 45.06      A    C
ATOM   6450  CD1  LEU C 201     -71.289 -26.107 -21.598  1.00 44.76      A    C
ATOM   6451  CD2  LEU C 201     -73.571 -25.162 -21.868  1.00 45.34      A    C
ATOM   6452  N    ASP C 202     -75.373 -30.195 -20.148  1.00 47.25      A    N
ATOM   6453  CA   ASP C 202     -75.768 -31.587 -20.403  1.00 48.09      A    C
ATOM   6454  C    ASP C 202     -76.819 -31.749 -21.517  1.00 48.70      A    C
ATOM   6455  O    ASP C 202     -76.635 -32.565 -22.424  1.00 48.91      A    O
ATOM   6456  CB   ASP C 202     -76.243 -32.237 -19.088  1.00 48.23      A    C
ATOM   6457  CG   ASP C 202     -76.718 -33.677 -19.253  1.00 48.64      A    C
ATOM   6458  OD1  ASP C 202     -75.943 -34.537 -19.727  1.00 48.47      A    O
ATOM   6459  OD2  ASP C 202     -77.870 -33.944 -18.863  1.00 49.38      A    O
ATOM   6460  N    LEU C 203     -77.900 -30.971 -21.457  1.00 49.11      A    N
ATOM   6461  CA   LEU C 203     -78.998 -31.118 -22.413  1.00 49.28      A    C
ATOM   6462  C    LEU C 203     -78.631 -30.669 -23.822  1.00 49.53      A    C
ATOM   6463  O    LEU C 203     -78.907 -31.374 -24.777  1.00 49.92      A    O
ATOM   6464  CB   LEU C 203     -80.260 -30.421 -21.911  1.00 48.33      A    C
ATOM   6465  CG   LEU C 203     -81.036 -31.242 -20.892  1.00 48.04      A    C
ATOM   6466  CD1  LEU C 203     -80.732 -30.779 -19.480  1.00 47.94      A    C
ATOM   6467  N    GLU C 204     -78.001 -29.503 -23.943  1.00 49.36      A    N
ATOM   6468  CA   GLU C 204     -77.524 -29.009 -25.239  1.00 48.98      A    C
ATOM   6469  C    GLU C 204     -76.406 -29.893 -25.795  1.00 49.42      A    C
ATOM   6470  O    GLU C 204     -76.265 -30.041 -27.010  1.00 49.76      A    O
ATOM   6471  CB   GLU C 204     -77.102 -27.529 -25.185  1.00 47.47      A    C
ATOM   6472  CG   GLU C 204     -76.597 -27.043 -23.834  1.00 45.83      A    C
ATOM   6473  CD   GLU C 204     -77.716 -26.785 -22.842  1.00 45.08      A    C
ATOM   6474  OE1  GLU C 204     -78.385 -25.741 -22.974  1.00 45.24      A    O
ATOM   6475  N    LEU C 205     -75.621 -30.487 -24.903  1.00 49.61      A    N
ATOM   6476  CA   LEU C 205     -74.608 -31.470 -25.294  1.00 49.76      A    C
ATOM   6477  C    LEU C 205     -75.259 -32.759 -25.755  1.00 50.50      A    C
ATOM   6478  O    LEU C 205     -74.722 -33.460 -26.616  1.00 50.56      A    O
ATOM   6479  CB   LEU C 205     -73.682 -31.792 -24.124  1.00 49.22      A    C
ATOM   6480  CG   LEU C 205     -72.389 -31.007 -23.969  1.00 48.22      A    C
ATOM   6481  CD1  LEU C 205     -71.856 -31.214 -22.571  1.00 47.82      A    C
ATOM   6482  CD2  LEU C 205     -71.382 -31.447 -25.015  1.00 47.61      A    C
ATOM   6483  N    SER C 206     -76.412 -33.067 -25.162  1.00 51.36      A    N
ATOM   6484  CA   SER C 206     -77.125 -34.296 -25.451  1.00 52.23      A    C
ATOM   6485  C    SER C 206     -77.723 -34.261 -26.845  1.00 52.70      A    C
ATOM   6486  O    SER C 206     -77.458 -35.153 -27.644  1.00 52.76      A    O
ATOM   6487  CB   SER C 206     -78.207 -34.547 -24.408  1.00 52.47      A    C
ATOM   6488  OG   SER C 206     -78.581 -35.907 -24.398  1.00 53.15      A    O
ATOM   6489  N    ARG C 207     -78.505 -33.222 -27.142  1.00 53.23      A    N
ATOM   6490  CA   ARG C 207     -79.162 -33.112 -28.450  1.00 53.75      A    C
ATOM   6491  C    ARG C 207     -78.156 -33.187 -29.591  1.00 53.73      A    C
ATOM   6492  O    ARG C 207     -78.273 -34.041 -30.471  1.00 54.11      A    O
ATOM   6493  CB   ARG C 207     -80.106 -31.891 -28.563  1.00 54.03      A    C
ATOM   6494  CG   ARG C 207     -79.502 -30.530 -28.288  1.00 53.53      A    C
ATOM   6495  N    ALA C 208     -77.154 -32.319 -29.552  1.00 53.27      A    N
ATOM   6496  CA   ALA C 208     -76.060 -32.384 -30.508  1.00 52.88      A    C
ATOM   6497  C    ALA C 208     -75.313 -33.702 -30.318  1.00 52.65      A    C
ATOM   6498  O    ALA C 208     -74.281 -33.733 -29.648  1.00 52.44      A    O
ATOM   6499  CB   ALA C 208     -75.128 -31.197 -30.322  1.00 52.55      A    C
ATOM   6500  N    LYS C 209     -75.864 -34.784 -30.886  1.00 52.70      A    N
```

FIGURE 1 (cont'd)

```
ATOM   6501  CA   LYS C 209     -75.327 -36.155 -30.730  1.00 52.25      A  C
ATOM   6502  C    LYS C 209     -76.216 -37.338 -31.197  1.00 51.43      A  C
ATOM   6503  O    LYS C 209     -77.012 -37.800 -30.484  1.00 52.63      A  O
ATOM   6504  CB   LYS C 209     -74.970 -36.430 -29.267  1.00 52.38      A  C
ATOM   6505  CG   LYS C 209     -74.205 -37.721 -29.061  1.00 52.70      A  C
ATOM   6506  CD   LYS C 209     -74.539 -38.339 -27.724  1.00 53.56      A  C
ATOM   6507  CE   LYS C 209     -73.701 -39.576 -27.462  1.00 53.75      A  C
ATOM   6508  NZ   LYS C 209     -74.094 -40.257 -26.197  1.00 53.89      A  N
ATOM   6509  N    LYS C 210     -75.990 -38.009 -32.316  1.00 46.83      A  N
ATOM   6510  CA   LYS C 210     -75.152 -37.626 -33.380  1.00 42.37      A  C
ATOM   6511  C    LYS C 210     -75.803 -36.307 -33.662  1.00 41.15      A  C
ATOM   6512  O    LYS C 210     -75.154 -35.273 -33.540  1.00 40.97      A  O
ATOM   6513  CB   LYS C 210     -75.345 -38.614 -34.557  1.00 41.12      A  C
ATOM   6514  CG   LYS C 210     -75.075 -40.129 -34.243  1.00 36.40      A  C
ATOM   6515  CD   LYS C 210     -75.859 -41.064 -35.206  1.00 29.93      A  C
ATOM   6516  CE   LYS C 210     -74.990 -42.249 -35.706  1.00 26.45      A  C
ATOM   6517  NZ   LYS C 210     -75.672 -43.092 -36.741  1.00 23.55      A  N
ATOM   6518  N    GLN C 211     -77.119 -36.333 -33.918  1.00 39.69      A  N
ATOM   6519  CA   GLN C 211     -77.765 -35.214 -34.585  1.00 38.12      A  C
ATOM   6520  C    GLN C 211     -76.615 -34.722 -35.491  1.00 38.42      A  C
ATOM   6521  O    GLN C 211     -76.246 -33.540 -35.497  1.00 38.84      A  O
ATOM   6522  CB   GLN C 211     -78.255 -34.180 -33.558  1.00 36.91      A  C
ATOM   6523  CG   GLN C 211     -79.230 -33.131 -34.092  1.00 32.83      A  C
ATOM   6524  CD   GLN C 211     -78.704 -31.690 -33.925  1.00 28.46      A  C
ATOM   6525  NE2  GLN C 211     -79.499 -30.838 -33.267  1.00 27.54      A  N
ATOM   6526  OE1  GLN C 211     -77.604 -31.353 -34.377  1.00 27.90      A  O
ATOM   6527  N    ALA C 212     -76.043 -35.689 -36.228  1.00 37.88      A  N
ATOM   6528  CA   ALA C 212     -74.706 -35.611 -36.826  1.00 36.86      A  C
ATOM   6529  C    ALA C 212     -73.609 -35.495 -35.750  1.00 35.50      A  C
ATOM   6530  O    ALA C 212     -73.049 -36.502 -35.337  1.00 35.08      A  O
ATOM   6531  CB   ALA C 212     -74.614 -34.479 -37.894  1.00 37.40      A  C
ATOM   6532  N    ALA C 213     -73.369 -34.274 -35.267  1.00 33.83      A  N
ATOM   6533  CA   ALA C 213     -72.265 -33.929 -34.362  1.00 31.93      A  C
ATOM   6534  C    ALA C 213     -71.010 -34.596 -34.828  1.00 30.70      A  C
ATOM   6535  O    ALA C 213     -70.815 -35.787 -34.595  1.00 30.73      A  O
ATOM   6536  CB   ALA C 213     -72.566 -34.295 -32.916  1.00 31.98      A  C
ATOM   6537  N    PRO C 214     -70.173 -33.841 -35.540  1.00 30.02      A  N
ATOM   6538  CA   PRO C 214     -68.878 -34.332 -36.008  1.00 30.61      A  C
ATOM   6539  C    PRO C 214     -67.708 -33.963 -35.097  1.00 32.39      A  C
ATOM   6540  O    PRO C 214     -66.593 -34.403 -35.360  1.00 32.58      A  O
ATOM   6541  CB   PRO C 214     -68.714 -33.663 -37.384  1.00 29.85      A  C
ATOM   6542  CG   PRO C 214     -69.916 -32.711 -37.540  1.00 29.50      A  C
ATOM   6543  CD   PRO C 214     -70.547 -32.576 -36.187  1.00 29.58      A  C
ATOM   6544  N    VAL C 215     -67.962 -33.158 -34.059  1.00 35.96      A  N
ATOM   6545  CA   VAL C 215     -66.945 -32.809 -33.057  1.00 36.08      A  C
ATOM   6546  C    VAL C 215     -67.492 -32.924 -31.628  1.00 36.40      A  C
ATOM   6547  O    VAL C 215     -68.350 -32.140 -31.223  1.00 36.70      A  O
ATOM   6548  CB   VAL C 215     -66.382 -31.400 -33.280  1.00 35.40      A  C
ATOM   6549  CG1  VAL C 215     -65.061 -31.252 -32.555  1.00 34.53      A  C
ATOM   6550  N    THR C 216     -66.984 -33.896 -30.870  1.00 36.11      A  N
ATOM   6551  CA   THR C 216     -67.518 -34.212 -29.537  1.00 35.57      A  C
ATOM   6552  C    THR C 216     -66.749 -33.568 -28.394  1.00 35.08      A  C
ATOM   6553  O    THR C 216     -65.909 -32.692 -28.617  1.00 35.05      A  O
ATOM   6554  CB   THR C 216     -67.576 -35.720 -29.294  1.00 35.59      A  C
ATOM   6555  OG1  THR C 216     -68.829 -36.042 -28.682  1.00 35.48      A  O
ATOM   6556  N    LEU C 217     -67.053 -33.997 -27.170  1.00 34.45      A  N
ATOM   6557  CA   LEU C 217     -66.413 -33.454 -25.978  1.00 33.68      A  C
ATOM   6558  C    LEU C 217     -65.822 -34.573 -25.135  1.00 33.33      A  C
ATOM   6559  O    LEU C 217     -66.460 -35.612 -24.939  1.00 33.58      A  O
ATOM   6560  CB   LEU C 217     -67.412 -32.641 -25.159  1.00 33.56      A  C
ATOM   6561  CG   LEU C 217     -66.948 -32.148 -23.796  1.00 33.04      A  C
ATOM   6562  CD1  LEU C 217     -65.909 -31.067 -23.937  1.00 32.83      A  C
ATOM   6563  CD2  LEU C 217     -68.124 -31.644 -23.032  1.00 33.13      A  C
ATOM   6564  N    GLN C 218     -64.607 -34.356 -24.636  1.00 32.53      A  N
ATOM   6565  CA   GLN C 218     -63.918 -35.359 -23.841  1.00 31.87      A  C
```

FIGURE 1 (cont'd)

```
ATOM   6566  C    GLN C 218     -63.391 -34.775 -22.538  1.00 31.29      A  C
ATOM   6567  O    GLN C 218     -62.779 -33.714 -22.531  1.00 31.23      A  O
ATOM   6568  CB   GLN C 218     -62.776 -35.944 -24.649  1.00 31.92      A  C
ATOM   6569  CG   GLN C 218     -62.052 -37.084 -23.966  1.00 32.15      A  C
ATOM   6570  CD   GLN C 218     -60.784 -37.488 -24.700  1.00 32.82      A  C
ATOM   6571  NE2  GLN C 218     -59.819 -36.568 -24.804  1.00 32.85      A  N
ATOM   6572  OE1  GLN C 218     -60.679 -38.613 -25.177  1.00 33.65      A  O
ATOM   6573  N    LEU C 219     -63.628 -35.473 -21.436  1.00 30.72      A  N
ATOM   6574  CA   LEU C 219     -63.185 -34.994 -20.134  1.00 30.05      A  C
ATOM   6575  C    LEU C 219     -62.180 -35.955 -19.539  1.00 29.78      A  C
ATOM   6576  O    LEU C 219     -62.479 -37.129 -19.341  1.00 29.88      A  O
ATOM   6577  CB   LEU C 219     -64.371 -34.779 -19.188  1.00 29.90      A  C
ATOM   6578  CG   LEU C 219     -65.422 -33.766 -19.648  1.00 29.61      A  C
ATOM   6579  CD1  LEU C 219     -66.601 -33.755 -18.705  1.00 29.42      A  C
ATOM   6580  CD2  LEU C 219     -64.832 -32.381 -19.780  1.00 29.19      A  C
ATOM   6581  N    LEU C 220     -60.982 -35.447 -19.269  1.00 29.26      A  N
ATOM   6582  CA   LEU C 220     -59.913 -36.256 -18.706  1.00 28.83      A  C
ATOM   6583  C    LEU C 220     -59.613 -35.878 -17.251  1.00 28.95      A  C
ATOM   6584  O    LEU C 220     -59.341 -34.721 -16.945  1.00 28.97      A  O
ATOM   6585  CB   LEU C 220     -58.658 -36.160 -19.573  1.00 28.09      A  C
ATOM   6586  CG   LEU C 220     -58.808 -36.681 -20.998  1.00 27.39      A  C
ATOM   6587  CD1  LEU C 220     -57.478 -36.661 -21.697  1.00 26.93      A  C
ATOM   6588  N    PHE C 221     -59.687 -36.867 -16.363  1.00 29.08      A  N
ATOM   6589  CA   PHE C 221     -59.326 -36.709 -14.962  1.00 29.03      A  C
ATOM   6590  C    PHE C 221     -58.141 -37.605 -14.698  1.00 29.09      A  C
ATOM   6591  O    PHE C 221     -58.300 -38.807 -14.515  1.00 29.16      A  O
ATOM   6592  CB   PHE C 221     -60.487 -37.108 -14.062  1.00 29.09      A  C
ATOM   6593  CG   PHE C 221     -61.735 -36.307 -14.296  1.00 29.13      A  C
ATOM   6594  CD1  PHE C 221     -62.015 -35.182 -13.527  1.00 29.18      A  C
ATOM   6595  CD2  PHE C 221     -62.638 -36.681 -15.282  1.00 29.24      A  C
ATOM   6596  CE1  PHE C 221     -63.166 -34.438 -13.740  1.00 29.21      A  C
ATOM   6597  CE2  PHE C 221     -63.795 -35.941 -15.504  1.00 29.47      A  C
ATOM   6598  CZ   PHE C 221     -64.059 -34.818 -14.729  1.00 29.34      A  C
ATOM   6599  N    LEU C 222     -56.954 -37.008 -14.684  1.00 29.16      A  N
ATOM   6600  CA   LEU C 222     -55.697 -37.754 -14.655  1.00 29.41      A  C
ATOM   6601  C    LEU C 222     -55.219 -38.028 -13.239  1.00 29.75      A  C
ATOM   6602  O    LEU C 222     -55.330 -37.166 -12.371  1.00 29.75      A  O
ATOM   6603  CB   LEU C 222     -54.627 -37.003 -15.438  1.00 29.22      A  C
ATOM   6604  CG   LEU C 222     -55.025 -36.667 -16.871  1.00 29.04      A  C
ATOM   6605  CD1  LEU C 222     -54.564 -37.748 -17.825  1.00 29.10      A  C
ATOM   6606  CD2  LEU C 222     -54.474 -35.311 -17.258  1.00 28.70      A  C
ATOM   6607  N    ASP C 223     -54.703 -39.237 -13.017  1.00 30.29      A  N
ATOM   6608  CA   ASP C 223     -54.161 -39.635 -11.720  1.00 30.86      A  C
ATOM   6609  C    ASP C 223     -52.680 -39.321 -11.702  1.00 30.88      A  C
ATOM   6610  O    ASP C 223     -52.091 -39.064 -12.746  1.00 30.81      A  O
ATOM   6611  CB   ASP C 223     -54.399 -41.130 -11.466  1.00 31.29      A  C
ATOM   6612  CG   ASP C 223     -54.264 -41.521  -9.996  1.00 32.33      A  C
ATOM   6613  OD1  ASP C 223     -54.147 -40.640  -9.133  1.00 33.27      A  O
ATOM   6614  OD2  ASP C 223     -54.277 -42.725  -9.691  1.00 33.04      A  O
ATOM   6615  N    GLY C 224     -52.095 -39.318 -10.509  1.00 31.03      A  N
ATOM   6616  CA   GLY C 224     -50.646 -39.178 -10.318  1.00 31.25      A  C
ATOM   6617  C    GLY C 224     -49.941 -38.187 -11.219  1.00 31.18      A  C
ATOM   6618  O    GLY C 224     -49.118 -38.553 -12.057  1.00 31.37      A  O
ATOM   6619  N    GLU C 225     -50.284 -36.923 -11.056  1.00 31.01      A  N
ATOM   6620  CA   GLU C 225     -49.612 -35.864 -11.787  1.00 30.96      A  C
ATOM   6621  C    GLU C 225     -48.503 -35.311 -10.906  1.00 31.00      A  C
ATOM   6622  O    GLU C 225     -47.379 -35.117 -11.356  1.00 30.94      A  O
ATOM   6623  CB   GLU C 225     -50.613 -34.802 -12.216  1.00 30.78      A  C
ATOM   6624  CG   GLU C 225     -50.003 -33.662 -12.990  1.00 31.07      A  C
ATOM   6625  CD   GLU C 225     -49.476 -32.578 -12.097  1.00 31.86      A  C
ATOM   6626  OE1  GLU C 225     -50.080 -32.337 -11.036  1.00 32.64      A  O
ATOM   6627  OE2  GLU C 225     -48.454 -31.971 -12.453  1.00 32.34      A  O
ATOM   6628  N    GLU C 226     -48.839 -35.058  -9.647  1.00 31.29      A  N
ATOM   6629  CA   GLU C 226     -47.887 -34.564  -8.670  1.00 31.78      A  C
ATOM   6630  C    GLU C 226     -46.854 -35.648  -8.348  1.00 32.46      A  C
```

FIGURE 1 (cont'd)

```
ATOM   6631  O   GLU C 226     -47.203 -36.837  -8.238  1.00 32.64       A  O
ATOM   6632  CB  GLU C 226     -48.606 -34.150  -7.388  1.00 31.64       A  C
ATOM   6633  CG  GLU C 226     -49.698 -33.120  -7.571  1.00 30.91       A  C
ATOM   6634  CD  GLU C 226     -49.222 -31.697  -7.412  1.00 30.25       A  C
ATOM   6635  OE1 GLU C 226     -48.020 -31.427  -7.628  1.00 30.25       A  O
ATOM   6636  OE2 GLU C 226     -50.062 -30.838  -7.073  1.00 29.64       A  O
ATOM   6637  N   ALA C 227     -45.595 -35.222  -8.184  1.00 33.02       A  N
ATOM   6638  CA  ALA C 227     -44.467 -36.108  -7.900  1.00 33.74       A  C
ATOM   6639  C   ALA C 227     -44.593 -36.796  -6.538  1.00 34.40       A  C
ATOM   6640  O   ALA C 227     -45.394 -36.385  -5.696  1.00 34.48       A  O
ATOM   6641  CB  ALA C 227     -43.176 -35.324  -7.978  1.00 33.73       A  C
ATOM   6642  N   LEU C 228     -43.804 -37.846  -6.320  1.00 35.22       A  N
ATOM   6643  CA  LEU C 228     -43.810 -38.540  -5.035  1.00 35.89       A  C
ATOM   6644  C   LEU C 228     -42.586 -38.249  -4.154  1.00 36.64       A  C
ATOM   6645  O   LEU C 228     -42.731 -37.996  -2.968  1.00 36.91       A  O
ATOM   6646  CB  LEU C 228     -44.034 -40.045  -5.215  1.00 35.85       A  C
ATOM   6647  CG  LEU C 228     -45.451 -40.581  -5.480  1.00 35.19       A  C
ATOM   6648  CD1 LEU C 228     -45.614 -41.060  -6.885  1.00 34.76       A  C
ATOM   6649  CD2 LEU C 228     -46.551 -39.585  -5.144  1.00 34.62       A  C
ATOM   6650  N   LYS C 229     -41.385 -38.285  -4.721  1.00 37.39       A  N
ATOM   6651  CA  LYS C 229     -40.189 -37.853  -3.989  1.00 38.17       A  C
ATOM   6652  C   LYS C 229     -39.945 -36.394  -4.395  1.00 38.16       A  C
ATOM   6653  O   LYS C 229     -40.446 -35.500  -3.736  1.00 38.12       A  O
ATOM   6654  CB  LYS C 229     -38.979 -38.781  -4.259  1.00 38.70       A  C
ATOM   6655  CG  LYS C 229     -37.760 -38.614  -3.324  1.00 39.47       A  C
ATOM   6656  CD  LYS C 229     -37.824 -39.518  -2.103  1.00 40.02       A  C
ATOM   6657  N   GLU C 230     -39.213 -36.146  -5.478  1.00 38.32       A  N
ATOM   6658  CA  GLU C 230     -39.148 -34.801  -6.026  1.00 38.51       A  C
ATOM   6659  C   GLU C 230     -39.297 -34.767  -7.539  1.00 38.27       A  C
ATOM   6660  O   GLU C 230     -38.871 -35.687  -8.246  1.00 38.30       A  O
ATOM   6661  CB  GLU C 230     -37.906 -34.019  -5.557  1.00 38.96       A  C
ATOM   6662  CG  GLU C 230     -38.049 -32.444  -5.624  1.00 39.90       A  C
ATOM   6663  CD  GLU C 230     -39.320 -31.837  -4.932  1.00 40.10       A  C
ATOM   6664  OE1 GLU C 230     -40.373 -31.647  -5.596  1.00 38.78       A  O
ATOM   6665  OE2 GLU C 230     -39.237 -31.463  -3.738  1.00 39.85       A  O
ATOM   6666  N   TRP C 231     -39.916 -33.678  -8.000  1.00 37.95       A  N
ATOM   6667  CA  TRP C 231     -40.292 -33.459  -9.386  1.00 37.66       A  C
ATOM   6668  C   TRP C 231     -39.157 -33.566 -10.354  1.00 38.00       A  C
ATOM   6669  O   TRP C 231     -38.056 -33.206 -10.154  1.00 38.32       A  O
ATOM   6670  CB  TRP C 231     -40.818 -32.043  -9.560  1.00 37.32       A  C
ATOM   6671  CG  TRP C 231     -41.445 -31.816 -10.905  1.00 36.77       A  C
ATOM   6672  CD1 TRP C 231     -40.808 -31.442 -12.057  1.00 36.71       A  C
ATOM   6673  CD2 TRP C 231     -42.832 -31.954 -11.241  1.00 36.15       A  C
ATOM   6674  CE2 TRP C 231     -42.962 -31.645 -12.611  1.00 35.88       A  C
ATOM   6675  CE3 TRP C 231     -43.980 -32.303 -10.514  1.00 35.81       A  C
ATOM   6676  NE1 TRP C 231     -41.713 -31.335 -13.083  1.00 36.36       A  N
ATOM   6677  CZ2 TRP C 231     -44.192 -31.679 -13.271  1.00 35.23       A  C
ATOM   6678  CZ3 TRP C 231     -45.205 -32.337 -11.177  1.00 35.06       A  C
ATOM   6679  CH2 TRP C 231     -45.296 -32.029 -12.539  1.00 34.77       A  C
ATOM   6680  N   GLY C 232     -39.454 -34.440 -11.410  1.00 38.12       A  N
ATOM   6681  CA  GLY C 232     -38.489 -34.749 -12.444  1.00 38.50       A  C
ATOM   6682  C   GLY C 232     -39.147 -35.550 -13.551  1.00 38.70       A  C
ATOM   6683  O   GLY C 232     -40.276 -36.007 -13.392  1.00 38.43       A  O
ATOM   6684  N   PRO C 233     -38.444 -35.726 -14.682  1.00 39.12       A  N
ATOM   6685  CA  PRO C 233     -38.953 -36.496 -15.806  1.00 39.27       A  C
ATOM   6686  C   PRO C 233     -39.459 -37.889 -15.418  1.00 39.50       A  C
ATOM   6687  O   PRO C 233     -40.482 -38.323 -15.950  1.00 39.21       A  O
ATOM   6688  CB  PRO C 233     -37.741 -36.589 -16.731  1.00 39.48       A  C
ATOM   6689  CG  PRO C 233     -36.965 -35.365 -16.440  1.00 39.61       A  C
ATOM   6690  CD  PRO C 233     -37.124 -35.137 -14.976  1.00 39.41       A  C
ATOM   6691  N   LYS C 234     -38.767 -38.567 -14.499  1.00 40.07       A  N
ATOM   6692  CA  LYS C 234     -39.144 -39.928 -14.087  1.00 40.68       A  C
ATOM   6693  C   LYS C 234     -40.080 -39.981 -12.861  1.00 40.43       A  C
ATOM   6694  O   LYS C 234     -40.612 -41.038 -12.521  1.00 40.56       A  O
ATOM   6695  CB  LYS C 234     -37.895 -40.823 -13.910  1.00 41.30       A  C
```

FIGURE 1 (cont'd)

```
ATOM   6696  CG   LYS C 234     -37.372 -41.458 -15.218  1.00 42.32      A    C
ATOM   6697  CD   LYS C 234     -35.876 -41.835 -15.160  1.00 43.54      A    C
ATOM   6698  CE   LYS C 234     -35.618 -43.259 -14.620  1.00 43.78      A    C
ATOM   6699  N    ASP C 235     -40.288 -38.834 -12.221  1.00 40.05      A    N
ATOM   6700  CA   ASP C 235     -41.201 -38.719 -11.071  1.00 39.58      A    C
ATOM   6701  C    ASP C 235     -42.157 -37.529 -11.243  1.00 39.07      A    C
ATOM   6702  O    ASP C 235     -41.959 -36.466 -10.653  1.00 39.07      A    O
ATOM   6703  CB   ASP C 235     -40.411 -38.618  -9.748  1.00 39.83      A    C
ATOM   6704  CG   ASP C 235     -41.301 -38.486  -8.530  1.00 39.49      A    C
ATOM   6705  OD1  ASP C 235     -40.886 -37.798  -7.584  1.00 39.21      A    O
ATOM   6706  OD2  ASP C 235     -42.402 -39.061  -8.517  1.00 39.12      A    O
ATOM   6707  N    SER C 236     -43.179 -37.720 -12.078  1.00 38.44      A    N
ATOM   6708  CA   SER C 236     -44.235 -36.731 -12.335  1.00 37.77      A    C
ATOM   6709  C    SER C 236     -45.051 -37.134 -13.553  1.00 37.48      A    C
ATOM   6710  O    SER C 236     -44.525 -37.728 -14.488  1.00 37.55      A    O
ATOM   6711  CB   SER C 236     -43.656 -35.332 -12.558  1.00 37.65      A    C
ATOM   6712  OG   SER C 236     -42.899 -35.271 -13.745  1.00 37.61      A    O
ATOM   6713  N    LEU C 237     -46.335 -36.799 -13.546  1.00 37.17      A    N
ATOM   6714  CA   LEU C 237     -47.200 -37.004 -14.708  1.00 37.05      A    C
ATOM   6715  C    LEU C 237     -47.332 -38.477 -15.083  1.00 37.24      A    C
ATOM   6716  O    LEU C 237     -47.170 -38.837 -16.247  1.00 37.38      A    O
ATOM   6717  CB   LEU C 237     -46.682 -36.209 -15.920  1.00 36.89      A    C
ATOM   6718  CG   LEU C 237     -46.174 -34.773 -15.755  1.00 36.55      A    C
ATOM   6719  CD1  LEU C 237     -45.337 -34.380 -16.949  1.00 36.67      A    C
ATOM   6720  CD2  LEU C 237     -47.299 -33.797 -15.575  1.00 36.06      A    C
ATOM   6721  N    TYR C 238     -47.615 -39.326 -14.101  1.00 37.35      A    N
ATOM   6722  CA   TYR C 238     -47.755 -40.750 -14.363  1.00 37.45      A    C
ATOM   6723  C    TYR C 238     -49.009 -41.015 -15.163  1.00 37.12      A    C
ATOM   6724  O    TYR C 238     -48.986 -41.810 -16.085  1.00 37.23      A    O
ATOM   6725  CB   TYR C 238     -47.764 -41.569 -13.068  1.00 37.78      A    C
ATOM   6726  CG   TYR C 238     -46.494 -41.455 -12.262  1.00 38.36      A    C
ATOM   6727  CD1  TYR C 238     -45.340 -42.123 -12.644  1.00 39.32      A    C
ATOM   6728  CD2  TYR C 238     -46.445 -40.675 -11.116  1.00 38.49      A    C
ATOM   6729  CE1  TYR C 238     -44.164 -42.011 -11.902  1.00 39.70      A    C
ATOM   6730  CE2  TYR C 238     -45.279 -40.558 -10.369  1.00 38.95      A    C
ATOM   6731  CZ   TYR C 238     -44.147 -41.224 -10.765  1.00 39.35      A    C
ATOM   6732  OH   TYR C 238     -43.002 -41.096 -10.018  1.00 39.62      A    O
ATOM   6733  N    GLY C 239     -50.093 -40.334 -14.817  1.00 36.70      A    N
ATOM   6734  CA   GLY C 239     -51.373 -40.547 -15.481  1.00 36.44      A    C
ATOM   6735  C    GLY C 239     -51.374 -40.085 -16.928  1.00 36.27      A    C
ATOM   6736  O    GLY C 239     -51.843 -40.798 -17.827  1.00 36.36      A    O
ATOM   6737  N    SER C 240     -50.843 -38.889 -17.157  1.00 35.97      A    N
ATOM   6738  CA   SER C 240     -50.839 -38.309 -18.489  1.00 35.70      A    C
ATOM   6739  C    SER C 240     -49.857 -39.016 -19.418  1.00 35.71      A    C
ATOM   6740  O    SER C 240     -50.201 -39.323 -20.554  1.00 35.81      A    O
ATOM   6741  CB   SER C 240     -50.557 -36.820 -18.413  1.00 35.56      A    C
ATOM   6742  OG   SER C 240     -49.662 -36.560 -17.359  1.00 35.90      A    O
ATOM   6743  N    ARG C 241     -48.650 -39.291 -18.931  1.00 35.71      A    N
ATOM   6744  CA   ARG C 241     -47.657 -40.007 -19.723  1.00 35.92      A    C
ATOM   6745  C    ARG C 241     -48.156 -41.371 -20.176  1.00 35.98      A    C
ATOM   6746  O    ARG C 241     -47.821 -41.833 -21.262  1.00 36.19      A    O
ATOM   6747  CB   ARG C 241     -46.339 -40.147 -18.960  1.00 36.03      A    C
ATOM   6748  CG   ARG C 241     -45.405 -38.974 -19.136  1.00 36.65      A    C
ATOM   6749  CD   ARG C 241     -43.980 -39.327 -18.755  1.00 37.99      A    C
ATOM   6750  NE   ARG C 241     -43.762 -39.290 -17.308  1.00 39.20      A    N
ATOM   6751  CZ   ARG C 241     -43.597 -40.366 -16.543  1.00 40.13      A    C
ATOM   6752  NH1  ARG C 241     -43.623 -41.576 -17.075  1.00 41.09      A    N
ATOM   6753  NH2  ARG C 241     -43.399 -40.237 -15.242  1.00 40.44      A    N
ATOM   6754  N    HIS C 242     -48.965 -42.008 -19.344  1.00 35.93      A    N
ATOM   6755  CA   HIS C 242     -49.493 -43.320 -19.672  1.00 36.03      A    C
ATOM   6756  C    HIS C 242     -50.656 -43.202 -20.628  1.00 35.66      A    C
ATOM   6757  O    HIS C 242     -50.679 -43.876 -21.644  1.00 35.89      A    O
ATOM   6758  CB   HIS C 242     -49.901 -44.078 -18.411  1.00 36.32      A    C
ATOM   6759  CG   HIS C 242     -50.438 -45.447 -18.675  1.00 37.11      A    C
ATOM   6760  CD2  HIS C 242     -49.812 -46.628 -18.889  1.00 37.90      A    C
```

FIGURE 1 (cont'd)

```
ATOM   6761  ND1 HIS C 242     -51.787 -45.709 -18.748  1.00 37.30      A    N
ATOM   6762  CE1 HIS C 242     -51.971 -46.994 -18.994  1.00 37.97      A    C
ATOM   6763  NE2 HIS C 242     -50.788 -47.574 -19.088  1.00 38.39      A    N
ATOM   6764  N   LEU C 243     -51.610 -42.335 -20.313  1.00 35.06      A    N
ATOM   6765  CA  LEU C 243     -52.765 -42.159 -21.168  1.00 34.60      A    C
ATOM   6766  C   LEU C 243     -52.323 -41.784 -22.564  1.00 34.72      A    C
ATOM   6767  O   LEU C 243     -52.819 -42.348 -23.532  1.00 34.95      A    O
ATOM   6768  CB  LEU C 243     -53.726 -41.125 -20.607  1.00 34.15      A    C
ATOM   6769  CG  LEU C 243     -55.023 -40.950 -21.390  1.00 33.46      A    C
ATOM   6770  CD1 LEU C 243     -55.811 -42.225 -21.402  1.00 33.25      A    C
ATOM   6771  CD2 LEU C 243     -55.858 -39.836 -20.801  1.00 32.87      A    C
ATOM   6772  N   ALA C 244     -51.379 -40.852 -22.662  1.00 34.75      A    N
ATOM   6773  CA  ALA C 244     -50.806 -40.467 -23.949  1.00 35.02      A    C
ATOM   6774  C   ALA C 244     -50.263 -41.687 -24.700  1.00 35.49      A    C
ATOM   6775  O   ALA C 244     -50.569 -41.866 -25.873  1.00 35.66      A    O
ATOM   6776  CB  ALA C 244     -49.727 -39.405 -23.769  1.00 34.78      A    C
ATOM   6777  N   GLN C 245     -49.486 -42.530 -24.015  1.00 36.02      A    N
ATOM   6778  CA  GLN C 245     -48.935 -43.748 -24.621  1.00 36.60      A    C
ATOM   6779  C   GLN C 245     -50.060 -44.639 -25.142  1.00 36.93      A    C
ATOM   6780  O   GLN C 245     -50.002 -45.112 -26.271  1.00 37.22      A    O
ATOM   6781  CB  GLN C 245     -48.057 -44.545 -23.630  1.00 36.68      A    C
ATOM   6782  CG  GLN C 245     -46.798 -43.855 -23.078  1.00 36.19      A    C
ATOM   6783  CD  GLN C 245     -45.537 -44.028 -23.948  1.00 35.78      A    C
ATOM   6784  NE2 GLN C 245     -44.560 -43.137 -23.737  1.00 35.83      A    N
ATOM   6785  OE1 GLN C 245     -45.435 -44.946 -24.784  1.00 35.28      A    O
ATOM   6786  N   LEU C 246     -51.087 -44.836 -24.315  1.00 37.05      A    N
ATOM   6787  CA  LEU C 246     -52.192 -45.757 -24.603  1.00 37.32      A    C
ATOM   6788  C   LEU C 246     -53.125 -45.260 -25.695  1.00 37.72      A    C
ATOM   6789  O   LEU C 246     -53.717 -46.059 -26.407  1.00 38.01      A    O
ATOM   6790  CB  LEU C 246     -52.984 -46.048 -23.329  1.00 37.07      A    C
ATOM   6791  CG  LEU C 246     -54.090 -47.101 -23.312  1.00 36.47      A    C
ATOM   6792  CD1 LEU C 246     -55.401 -46.414 -23.037  1.00 35.20      A    C
ATOM   6793  N   MET C 247     -53.258 -43.944 -25.820  1.00 38.03      A    N
ATOM   6794  CA  MET C 247     -54.047 -43.340 -26.901  1.00 38.44      A    C
ATOM   6795  C   MET C 247     -53.348 -43.435 -28.252  1.00 39.22      A    C
ATOM   6796  O   MET C 247     -53.999 -43.490 -29.285  1.00 39.41      A    O
ATOM   6797  CB  MET C 247     -54.401 -41.876 -26.607  1.00 37.96      A    C
ATOM   6798  CG  MET C 247     -55.417 -41.680 -25.501  1.00 37.33      A    C
ATOM   6799  SD  MET C 247     -56.037 -39.997 -25.395  1.00 36.37      A    S
ATOM   6800  CE  MET C 247     -57.464 -40.121 -26.439  1.00 36.90      A    C
ATOM   6801  N   GLU C 248     -52.020 -43.441 -28.239  1.00 40.15      A    N
ATOM   6802  CA  GLU C 248     -51.247 -43.551 -29.471  1.00 41.15      A    C
ATOM   6803  C   GLU C 248     -51.336 -44.950 -30.033  1.00 42.19      A    C
ATOM   6804  O   GLU C 248     -51.238 -45.152 -31.241  1.00 42.72      A    O
ATOM   6805  CB  GLU C 248     -49.782 -43.194 -29.254  1.00 40.98      A    C
ATOM   6806  CG  GLU C 248     -49.121 -42.769 -30.542  1.00 39.77      A    C
ATOM   6807  CD  GLU C 248     -47.880 -41.958 -30.305  1.00 39.95      A    C
ATOM   6808  OE1 GLU C 248     -47.098 -42.327 -29.394  1.00 40.24      A    O
ATOM   6809  OE2 GLU C 248     -47.682 -40.948 -31.028  1.00 40.63      A    O
ATOM   6810  N   SER C 249     -51.520 -45.918 -29.148  1.00 43.04      A    N
ATOM   6811  CA  SER C 249     -51.589 -47.313 -29.551  1.00 44.00      A    C
ATOM   6812  C   SER C 249     -53.014 -47.743 -29.895  1.00 44.49      A    C
ATOM   6813  O   SER C 249     -53.239 -48.878 -30.329  1.00 44.92      A    O
ATOM   6814  CB  SER C 249     -51.040 -48.202 -28.440  1.00 44.14      A    C
ATOM   6815  OG  SER C 249     -51.969 -48.312 -27.371  1.00 44.11      A    O
ATOM   6816  N   ILE C 250     -53.971 -46.839 -29.706  1.00 44.78      A    N
ATOM   6817  CA  ILE C 250     -55.380 -47.159 -29.919  1.00 45.27      A    C
ATOM   6818  C   ILE C 250     -55.901 -46.524 -31.220  1.00 46.09      A    C
ATOM   6819  O   ILE C 250     -56.061 -45.310 -31.291  1.00 45.88      A    O
ATOM   6820  CB  ILE C 250     -56.220 -46.860 -28.623  1.00 44.82      A    C
ATOM   6821  CG1 ILE C 250     -57.553 -47.584 -28.631  1.00 44.78      A    C
ATOM   6822  CG2 ILE C 250     -56.386 -45.411 -28.337  1.00 45.22      A    C
ATOM   6823  CD1 ILE C 250     -58.730 -46.741 -29.059  1.00 44.42      A    C
ATOM   6824  N   PRO C 251     -56.116 -47.350 -32.270  1.00 47.21      A    N
ATOM   6825  CA  PRO C 251     -56.504 -46.885 -33.589  1.00 47.87      A    C
```

FIGURE 1 (cont'd)

```
ATOM   6826  C    PRO C 251     -57.869 -46.298 -33.560  1.00 48.31      A    C
ATOM   6827  O    PRO C 251     -58.725 -46.715 -32.783  1.00 48.35      A    O
ATOM   6828  CB   PRO C 251     -56.536 -48.156 -34.431  1.00 48.19      A    C
ATOM   6829  CG   PRO C 251     -55.663 -49.061 -33.751  1.00 48.27      A    C
ATOM   6830  CD   PRO C 251     -55.911 -48.801 -32.291  1.00 47.62      A    C
ATOM   6831  N    HIS C 252     -58.048 -45.321 -34.426  1.00 48.74      A    N
ATOM   6832  CA   HIS C 252     -59.235 -44.522 -34.475  1.00 49.08      A    C
ATOM   6833  C    HIS C 252     -59.197 -43.929 -35.850  1.00 49.68      A    C
ATOM   6834  O    HIS C 252     -58.186 -43.983 -36.538  1.00 49.95      A    O
ATOM   6835  CB   HIS C 252     -59.217 -43.456 -33.391  1.00 47.95      A    C
ATOM   6836  CG   HIS C 252     -60.459 -42.627 -33.328  1.00 47.76      A    C
ATOM   6837  CD2  HIS C 252     -60.694 -41.350 -33.712  1.00 47.59      A    C
ATOM   6838  ND1  HIS C 252     -61.641 -43.094 -32.796  1.00 48.06      A    N
ATOM   6839  CE1  HIS C 252     -62.554 -42.142 -32.864  1.00 48.05      A    C
ATOM   6840  NE2  HIS C 252     -62.005 -41.350 -33.416  1.00 47.82      A    N
ATOM   6841  N    SER C 253     -60.254 -43.219 -36.161  1.00 50.10      A    N
ATOM   6842  CA   SER C 253     -61.129 -43.633 -37.182  1.00 50.13      A    C
ATOM   6843  C    SER C 253     -61.564 -42.743 -38.296  1.00 50.23      A    C
ATOM   6844  O    SER C 253     -62.648 -42.937 -38.757  1.00 50.68      A    O
ATOM   6845  CB   SER C 253     -62.415 -43.909 -36.407  1.00 49.28      A    C
ATOM   6846  OG   SER C 253     -63.423 -42.941 -36.558  1.00 48.84      A    O
ATOM   6847  N    PRO C 254     -60.758 -41.908 -38.908  1.00 49.81      A    N
ATOM   6848  CA   PRO C 254     -59.540 -41.273 -39.342  1.00 49.42      A    C
ATOM   6849  C    PRO C 254     -59.048 -40.261 -38.373  1.00 49.05      A    C
ATOM   6850  O    PRO C 254     -59.111 -39.129 -38.748  1.00 49.23      A    O
ATOM   6851  CB   PRO C 254     -60.039 -40.430 -40.529  1.00 48.67      A    C
ATOM   6852  CG   PRO C 254     -61.524 -40.431 -40.493  1.00 48.81      A    C
ATOM   6853  CD   PRO C 254     -61.966 -41.160 -39.340  1.00 49.07      A    C
ATOM   6854  N    GLY C 255     -58.406 -40.511 -37.242  1.00 48.43      A    N
ATOM   6855  CA   GLY C 255     -57.234 -41.249 -37.013  1.00 47.56      A    C
ATOM   6856  C    GLY C 255     -56.018 -40.772 -37.746  1.00 47.07      A    C
ATOM   6857  O    GLY C 255     -56.053 -39.814 -38.497  1.00 47.38      A    O
ATOM   6858  N    PRO C 256     -54.939 -41.517 -37.647  1.00 46.57      A    N
ATOM   6859  CA   PRO C 256     -54.564 -42.886 -37.364  1.00 46.33      A    C
ATOM   6860  C    PRO C 256     -54.892 -43.399 -35.961  1.00 45.75      A    C
ATOM   6861  O    PRO C 256     -55.579 -44.414 -35.832  1.00 45.96      A    O
ATOM   6862  CB   PRO C 256     -53.049 -42.849 -37.582  1.00 46.52      A    C
ATOM   6863  CG   PRO C 256     -52.808 -41.617 -38.392  1.00 46.53      A    C
ATOM   6864  CD   PRO C 256     -53.755 -40.677 -37.868  1.00 46.28      A    C
ATOM   6865  N    THR C 257     -54.394 -42.710 -34.935  1.00 44.73      A    N
ATOM   6866  CA   THR C 257     -54.583 -43.108 -33.548  1.00 43.61      A    C
ATOM   6867  C    THR C 257     -55.548 -42.168 -32.861  1.00 42.87      A    C
ATOM   6868  O    THR C 257     -55.944 -41.171 -33.433  1.00 42.77      A    O
ATOM   6869  CB   THR C 257     -53.253 -43.125 -32.787  1.00 43.45      A    C
ATOM   6870  OG1  THR C 257     -52.571 -41.887 -32.986  1.00 43.06      A    O
ATOM   6871  N    ARG C 258     -55.933 -42.490 -31.632  1.00 42.04      A    N
ATOM   6872  CA   ARG C 258     -56.847 -41.638 -30.874  1.00 41.03      A    C
ATOM   6873  C    ARG C 258     -56.232 -40.309 -30.475  1.00 40.55      A    C
ATOM   6874  O    ARG C 258     -56.949 -39.391 -30.098  1.00 40.52      A    O
ATOM   6875  CB   ARG C 258     -57.394 -42.348 -29.639  1.00 40.13      A    C
ATOM   6876  CG   ARG C 258     -58.714 -43.069 -29.892  1.00 40.08      A    C
ATOM   6877  CD   ARG C 258     -59.558 -43.198 -28.634  1.00 40.04      A    C
ATOM   6878  NE   ARG C 258     -60.849 -43.805 -28.928  1.00 40.28      A    N
ATOM   6879  N    ILE C 259     -54.908 -40.157 -30.562  1.00 39.87      A    N
ATOM   6880  CA   ILE C 259     -54.211 -38.961 -30.268  1.00 38.89      A    C
ATOM   6881  C    ILE C 259     -54.593 -37.866 -31.246  1.00 38.82      A    C
ATOM   6882  O    ILE C 259     -54.711 -36.700 -30.876  1.00 38.83      A    O
ATOM   6883  CB   ILE C 259     -52.711 -39.150 -30.275  1.00 37.96      A    C
ATOM   6884  CG1  ILE C 259     -52.226 -39.067 -28.847  1.00 37.63      A    C
ATOM   6885  CD1  ILE C 259     -51.112 -39.961 -28.573  1.00 38.52      A    C
ATOM   6886  N    GLN C 260     -54.815 -38.246 -32.495  1.00 38.50      A    N
ATOM   6887  CA   GLN C 260     -55.180 -37.281 -33.513  1.00 37.90      A    C
ATOM   6888  C    GLN C 260     -56.656 -36.913 -33.374  1.00 37.76      A    C
ATOM   6889  O    GLN C 260     -57.154 -36.051 -34.097  1.00 38.20      A    O
ATOM   6890  CB   GLN C 260     -54.877 -37.803 -34.925  1.00 37.07      A    C
```

FIGURE 1 (cont'd)

```
ATOM   6891  CG  GLN C 260     -54.073 -39.100 -35.016  1.00 36.69      A   C
ATOM   6892  CD  GLN C 260     -52.683 -39.029 -34.426  1.00 36.30      A   C
ATOM   6893  NE2 GLN C 260     -52.280 -40.080 -33.743  1.00 36.46      A   N
ATOM   6894  OE1 GLN C 260     -51.972 -38.071 -34.610  1.00 36.67      A   O
ATOM   6895  N   ALA C 261     -57.353 -37.561 -32.443  1.00 37.15      A   N
ATOM   6896  CA  ALA C 261     -58.772 -37.273 -32.209  1.00 36.48      A   C
ATOM   6897  C   ALA C 261     -58.962 -36.025 -31.352  1.00 35.72      A   C
ATOM   6898  O   ALA C 261     -60.022 -35.402 -31.378  1.00 35.64      A   O
ATOM   6899  N   ILE C 262     -57.927 -35.670 -30.593  1.00 34.73      A   N
ATOM   6900  CA  ILE C 262     -57.925 -34.462 -29.782  1.00 33.60      A   C
ATOM   6901  C   ILE C 262     -57.740 -33.260 -30.702  1.00 33.57      A   C
ATOM   6902  O   ILE C 262     -56.634 -33.021 -31.189  1.00 33.77      A   O
ATOM   6903  CB  ILE C 262     -56.775 -34.484 -28.761  1.00 32.66      A   C
ATOM   6904  CG1 ILE C 262     -56.786 -35.775 -27.969  1.00 32.08      A   C
ATOM   6905  CG2 ILE C 262     -56.847 -33.300 -27.838  1.00 32.06      A   C
ATOM   6906  CD1 ILE C 262     -55.471 -36.062 -27.319  1.00 31.72      A   C
ATOM   6907  N   GLU C 263     -58.817 -32.520 -30.953  1.00 33.20      A   N
ATOM   6908  CA  GLU C 263     -58.734 -31.298 -31.750  1.00 32.79      A   C
ATOM   6909  C   GLU C 263     -58.077 -30.204 -30.936  1.00 32.18      A   C
ATOM   6910  O   GLU C 263     -57.334 -29.394 -31.476  1.00 32.30      A   O
ATOM   6911  CB  GLU C 263     -60.117 -30.850 -32.198  1.00 33.00      A   C
ATOM   6912  CG  GLU C 263     -60.149 -29.836 -33.319  1.00 33.00      A   C
ATOM   6913  CD  GLU C 263     -61.548 -29.691 -33.839  1.00 32.58      A   C
ATOM   6914  OE1 GLU C 263     -62.112 -28.581 -33.782  1.00 32.48      A   O
ATOM   6915  OE2 GLU C 263     -62.113 -30.732 -34.227  1.00 31.59      A   O
ATOM   6916  N   LEU C 264     -58.360 -30.190 -29.635  1.00 31.31      A   N
ATOM   6917  CA  LEU C 264     -57.742 -29.247 -28.711  1.00 30.33      A   C
ATOM   6918  C   LEU C 264     -57.672 -29.798 -27.299  1.00 29.71      A   C
ATOM   6919  O   LEU C 264     -58.692 -30.166 -26.725  1.00 29.77      A   O
ATOM   6920  CB  LEU C 264     -58.498 -27.917 -28.711  1.00 30.27      A   C
ATOM   6921  CG  LEU C 264     -57.983 -26.817 -27.783  1.00 29.84      A   C
ATOM   6922  CD1 LEU C 264     -56.556 -26.418 -28.150  1.00 29.73      A   C
ATOM   6923  CD2 LEU C 264     -58.907 -25.621 -27.814  1.00 29.58      A   C
ATOM   6924  N   PHE C 265     -56.460 -29.834 -26.755  1.00 28.86      A   N
ATOM   6925  CA  PHE C 265     -56.219 -30.255 -25.388  1.00 27.89      A   C
ATOM   6926  C   PHE C 265     -56.165 -29.020 -24.501  1.00 27.59      A   C
ATOM   6927  O   PHE C 265     -55.144 -28.344 -24.434  1.00 27.50      A   O
ATOM   6928  CB  PHE C 265     -54.905 -31.055 -25.296  1.00 27.64      A   C
ATOM   6929  CG  PHE C 265     -54.725 -31.792 -23.993  1.00 26.25      A   C
ATOM   6930  CD1 PHE C 265     -55.133 -33.107 -23.867  1.00 25.28      A   C
ATOM   6931  CD2 PHE C 265     -54.152 -31.166 -22.903  1.00 25.14      A   C
ATOM   6932  CE1 PHE C 265     -54.998 -33.772 -22.687  1.00 22.77      A   C
ATOM   6933  CE2 PHE C 265     -54.012 -31.830 -21.718  1.00 22.62      A   C
ATOM   6934  CZ  PHE C 265     -54.433 -33.140 -21.610  1.00 22.13      A   C
ATOM   6935  N   MET C 266     -57.265 -28.730 -23.821  1.00 27.27      A   N
ATOM   6936  CA  MET C 266     -57.324 -27.573 -22.947  1.00 27.13      A   C
ATOM   6937  C   MET C 266     -57.183 -28.002 -21.487  1.00 27.08      A   C
ATOM   6938  O   MET C 266     -58.136 -28.462 -20.875  1.00 27.16      A   O
ATOM   6939  CB  MET C 266     -58.625 -26.788 -23.191  1.00 27.10      A   C
ATOM   6940  CG  MET C 266     -58.788 -25.496 -22.379  1.00 26.69      A   C
ATOM   6941  SD  MET C 266     -60.417 -24.727 -22.494  1.00 22.21      A   S
ATOM   6942  CE  MET C 266     -60.049 -23.232 -23.384  1.00 20.55      A   C
ATOM   6943  N   LEU C 267     -55.982 -27.841 -20.939  1.00 26.99      A   N
ATOM   6944  CA  LEU C 267     -55.680 -28.271 -19.574  1.00 26.89      A   C
ATOM   6945  C   LEU C 267     -55.951 -27.183 -18.541  1.00 26.99      A   C
ATOM   6946  O   LEU C 267     -55.452 -26.063 -18.658  1.00 27.04      A   O
ATOM   6947  CB  LEU C 267     -54.231 -28.755 -19.478  1.00 26.81      A   C
ATOM   6948  CG  LEU C 267     -53.663 -29.142 -18.118  1.00 26.50      A   C
ATOM   6949  CD1 LEU C 267     -54.420 -30.286 -17.565  1.00 26.51      A   C
ATOM   6950  CD2 LEU C 267     -52.220 -29.520 -18.259  1.00 26.45      A   C
ATOM   6951  N   LEU C 268     -56.745 -27.533 -17.531  1.00 27.08      A   N
ATOM   6952  CA  LEU C 268     -57.142 -26.613 -16.464  1.00 27.23      A   C
ATOM   6953  C   LEU C 268     -56.369 -26.879 -15.180  1.00 27.40      A   C
ATOM   6954  O   LEU C 268     -56.403 -27.976 -14.642  1.00 27.54      A   O
ATOM   6955  CB  LEU C 268     -58.637 -26.743 -16.192  1.00 27.15      A   C
```

FIGURE 1 (cont'd)

```
ATOM   6956  CG  LEU C 268     -59.630 -25.916 -16.986  1.00 27.20      A    C
ATOM   6957  CD1 LEU C 268     -59.785 -26.436 -18.400  1.00 27.47      A    C
ATOM   6958  CD2 LEU C 268     -60.952 -25.952 -16.256  1.00 27.07      A    C
ATOM   6959  N   ASP C 269     -55.673 -25.872 -14.682  1.00 27.61      A    N
ATOM   6960  CA  ASP C 269     -54.866 -26.071 -13.501  1.00 27.94      A    C
ATOM   6961  C   ASP C 269     -54.709 -24.828 -12.658  1.00 27.92      A    C
ATOM   6962  O   ASP C 269     -54.738 -23.710 -13.178  1.00 28.11      A    O
ATOM   6963  CB  ASP C 269     -53.487 -26.567 -13.890  1.00 28.22      A    C
ATOM   6964  CG  ASP C 269     -52.945 -27.567 -12.909  1.00 29.34      A    C
ATOM   6965  OD1 ASP C 269     -53.622 -28.592 -12.694  1.00 30.28      A    O
ATOM   6966  OD2 ASP C 269     -51.847 -27.342 -12.365  1.00 30.08      A    O
ATOM   6967  N   LEU C 270     -54.524 -25.037 -11.355  1.00 27.80      A    N
ATOM   6968  CA  LEU C 270     -54.313 -23.963 -10.389  1.00 27.78      A    C
ATOM   6969  C   LEU C 270     -55.340 -22.841 -10.519  1.00 27.87      A    C
ATOM   6970  O   LEU C 270     -55.005 -21.666 -10.527  1.00 27.95      A    O
ATOM   6971  CB  LEU C 270     -52.882 -23.429 -10.491  1.00 27.73      A    C
ATOM   6972  CG  LEU C 270     -51.718 -24.431 -10.466  1.00 27.74      A    C
ATOM   6973  CD1 LEU C 270     -50.398 -23.715 -10.258  1.00 27.66      A    C
ATOM   6974  CD2 LEU C 270     -51.904 -25.484  -9.392  1.00 28.00      A    C
ATOM   6975  N   LEU C 271     -56.602 -23.220 -10.636  1.00 27.99      A    N
ATOM   6976  CA  LEU C 271     -57.685 -22.259 -10.715  1.00 28.28      A    C
ATOM   6977  C   LEU C 271     -58.455 -22.288  -9.407  1.00 28.70      A    C
ATOM   6978  O   LEU C 271     -58.646 -23.353  -8.816  1.00 28.72      A    O
ATOM   6979  CB  LEU C 271     -58.624 -22.598 -11.873  1.00 28.09      A    C
ATOM   6980  CG  LEU C 271     -58.075 -22.570 -13.296  1.00 27.69      A    C
ATOM   6981  CD1 LEU C 271     -58.465 -23.851 -13.993  1.00 27.60      A    C
ATOM   6982  N   GLY C 272     -58.896 -21.118  -8.955  1.00 29.23      A    N
ATOM   6983  CA  GLY C 272     -59.694 -21.032  -7.740  1.00 29.87      A    C
ATOM   6984  C   GLY C 272     -59.298 -19.898  -6.819  1.00 30.45      A    C
ATOM   6985  O   GLY C 272     -60.124 -19.411  -6.066  1.00 30.69      A    O
ATOM   6986  N   ALA C 273     -58.034 -19.483  -6.872  1.00 30.84      A    N
ATOM   6987  CA  ALA C 273     -57.520 -18.397  -6.030  1.00 31.23      A    C
ATOM   6988  C   ALA C 273     -58.041 -17.044  -6.532  1.00 31.56      A    C
ATOM   6989  O   ALA C 273     -58.543 -16.959  -7.661  1.00 31.57      A    O
ATOM   6990  CB  ALA C 273     -55.986 -18.419  -6.001  1.00 31.17      A    C
ATOM   6991  N   PRO C 274     -57.950 -15.992  -5.689  1.00 31.94      A    N
ATOM   6992  CA  PRO C 274     -58.274 -14.656  -6.148  1.00 32.22      A    C
ATOM   6993  C   PRO C 274     -57.243 -14.120  -7.133  1.00 32.34      A    C
ATOM   6994  O   PRO C 274     -56.087 -14.525  -7.104  1.00 32.24      A    O
ATOM   6995  CB  PRO C 274     -58.252 -13.830  -4.860  1.00 32.45      A    C
ATOM   6996  CG  PRO C 274     -57.434 -14.582  -3.936  1.00 32.41      A    C
ATOM   6997  CD  PRO C 274     -57.710 -16.004  -4.239  1.00 32.13      A    C
ATOM   6998  N   ASN C 275     -57.691 -13.225  -8.003  1.00 32.59      A    N
ATOM   6999  CA  ASN C 275     -56.835 -12.527  -8.959  1.00 32.93      A    C
ATOM   7000  C   ASN C 275     -55.843 -13.390  -9.738  1.00 32.52      A    C
ATOM   7001  O   ASN C 275     -54.645 -13.108  -9.730  1.00 32.79      A    O
ATOM   7002  CB  ASN C 275     -56.112 -11.362  -8.279  1.00 33.41      A    C
ATOM   7003  CG  ASN C 275     -57.069 -10.389  -7.627  1.00 34.79      A    C
ATOM   7004  ND2 ASN C 275     -57.128 -10.426  -6.297  1.00 35.91      A    N
ATOM   7005  OD1 ASN C 275     -57.749  -9.611  -8.303  1.00 35.81      A    O
ATOM   7006  N   PRO C 276     -56.332 -14.431 -10.432  1.00 32.02      A    N
ATOM   7007  CA  PRO C 276     -55.410 -15.165 -11.269  1.00 31.80      A    C
ATOM   7008  C   PRO C 276     -55.092 -14.367 -12.518  1.00 31.81      A    C
ATOM   7009  O   PRO C 276     -55.915 -13.551 -12.934  1.00 31.92      A    O
ATOM   7010  CB  PRO C 276     -56.202 -16.412 -11.629  1.00 31.60      A    C
ATOM   7011  CG  PRO C 276     -57.592 -15.996 -11.574  1.00 31.58      A    C
ATOM   7012  CD  PRO C 276     -57.693 -14.977 -10.511  1.00 31.86      A    C
ATOM   7013  N   THR C 277     -53.909 -14.576 -13.091  1.00 31.84      A    N
ATOM   7014  CA  THR C 277     -53.589 -14.006 -14.400  1.00 31.91      A    C
ATOM   7015  C   THR C 277     -53.199 -15.103 -15.384  1.00 31.81      A    C
ATOM   7016  O   THR C 277     -52.381 -15.957 -15.060  1.00 31.82      A    O
ATOM   7017  CB  THR C 277     -52.500 -12.912 -14.317  1.00 32.00      A    C
ATOM   7018  CG2 THR C 277     -53.094 -11.602 -13.836  1.00 32.14      A    C
ATOM   7019  OG1 THR C 277     -51.489 -13.314 -13.397  1.00 32.24      A    O
ATOM   7020  N   PHE C 278     -53.801 -15.085 -16.572  1.00 31.76      A    N
```

FIGURE 1 (cont'd)

```
ATOM   7021  CA   PHE C 278     -53.547 -16.104 -17.588  1.00 31.79      A    C
ATOM   7022  C    PHE C 278     -52.926 -15.523 -18.840  1.00 32.11      A    C
ATOM   7023  O    PHE C 278     -53.252 -14.414 -19.234  1.00 32.23      A    O
ATOM   7024  CB   PHE C 278     -54.837 -16.824 -17.959  1.00 31.56      A    C
ATOM   7025  CG   PHE C 278     -55.556 -17.421 -16.787  1.00 31.32      A    C
ATOM   7026  CD1  PHE C 278     -55.038 -18.522 -16.124  1.00 31.27      A    C
ATOM   7027  CD2  PHE C 278     -56.759 -16.890 -16.350  1.00 31.19      A    C
ATOM   7028  CE1  PHE C 278     -55.707 -19.079 -15.038  1.00 31.21      A    C
ATOM   7029  CE2  PHE C 278     -57.431 -17.440 -15.266  1.00 31.01      A    C
ATOM   7030  CZ   PHE C 278     -56.904 -18.536 -14.612  1.00 31.01      A    C
ATOM   7031  N    TYR C 279     -52.029 -16.285 -19.458  1.00 32.50      A    N
ATOM   7032  CA   TYR C 279     -51.370 -15.891 -20.712  1.00 33.07      A    C
ATOM   7033  C    TYR C 279     -51.413 -17.039 -21.714  1.00 33.69      A    C
ATOM   7034  O    TYR C 279     -51.735 -18.173 -21.351  1.00 33.68      A    O
ATOM   7035  CB   TYR C 279     -49.918 -15.464 -20.466  1.00 32.94      A    C
ATOM   7036  CG   TYR C 279     -49.804 -14.349 -19.469  1.00 32.40      A    C
ATOM   7037  CD1  TYR C 279     -49.977 -13.024 -19.857  1.00 32.30      A    C
ATOM   7038  CD2  TYR C 279     -49.542 -14.624 -18.134  1.00 29.77      A    C
ATOM   7039  CE1  TYR C 279     -49.904 -12.009 -18.933  1.00 29.93      A    C
ATOM   7040  CE2  TYR C 279     -49.462 -13.620 -17.209  1.00 28.61      A    C
ATOM   7041  CZ   TYR C 279     -49.644 -12.314 -17.611  1.00 28.59      A    C
ATOM   7042  OH   TYR C 279     -49.562 -11.305 -16.684  1.00 28.90      A    O
ATOM   7043  N    SER C 280     -51.109 -16.758 -22.975  1.00 34.59      A    N
ATOM   7044  CA   SER C 280     -51.097 -17.816 -23.976  1.00 35.42      A    C
ATOM   7045  C    SER C 280     -49.700 -18.392 -24.116  1.00 35.94      A    C
ATOM   7046  O    SER C 280     -48.802 -17.765 -24.686  1.00 36.24      A    O
ATOM   7047  CB   SER C 280     -51.613 -17.318 -25.320  1.00 35.58      A    C
ATOM   7048  OG   SER C 280     -51.758 -18.400 -26.218  1.00 35.77      A    O
ATOM   7049  N    HIS C 281     -49.522 -19.595 -23.589  1.00 36.40      A    N
ATOM   7050  CA   HIS C 281     -48.217 -20.246 -23.603  1.00 37.12      A    C
ATOM   7051  C    HIS C 281     -47.958 -21.060 -24.886  1.00 37.48      A    C
ATOM   7052  O    HIS C 281     -46.867 -21.615 -25.062  1.00 37.67      A    O
ATOM   7053  CB   HIS C 281     -48.037 -21.099 -22.341  1.00 37.18      A    C
ATOM   7054  CG   HIS C 281     -48.223 -20.333 -21.068  1.00 37.79      A    C
ATOM   7055  CD2  HIS C 281     -47.369 -19.552 -20.360  1.00 38.66      A    C
ATOM   7056  ND1  HIS C 281     -49.421 -20.305 -20.388  1.00 37.78      A    N
ATOM   7057  CE1  HIS C 281     -49.297 -19.550 -19.310  1.00 38.20      A    C
ATOM   7058  NE2  HIS C 281     -48.061 -19.083 -19.269  1.00 38.91      A    N
ATOM   7059  N    PHE C 282     -48.958 -21.129 -25.771  1.00 37.82      A    N
ATOM   7060  CA   PHE C 282     -48.796 -21.747 -27.089  1.00 38.16      A    C
ATOM   7061  C    PHE C 282     -49.416 -20.885 -28.171  1.00 38.52      A    C
ATOM   7062  O    PHE C 282     -50.643 -20.750 -28.227  1.00 38.50      A    O
ATOM   7063  CB   PHE C 282     -49.374 -23.167 -27.127  1.00 38.05      A    C
ATOM   7064  CG   PHE C 282     -48.741 -24.084 -26.144  1.00 37.99      A    C
ATOM   7065  CD1  PHE C 282     -47.441 -24.507 -26.321  1.00 38.46      A    C
ATOM   7066  CD2  PHE C 282     -49.423 -24.494 -25.016  1.00 37.86      A    C
ATOM   7067  CE1  PHE C 282     -46.831 -25.339 -25.393  1.00 38.43      A    C
ATOM   7068  CE2  PHE C 282     -48.822 -25.331 -24.089  1.00 37.94      A    C
ATOM   7069  CZ   PHE C 282     -47.522 -25.751 -24.280  1.00 38.20      A    C
ATOM   7070  N    PRO C 283     -48.570 -20.303 -29.039  1.00 38.88      A    N
ATOM   7071  CA   PRO C 283     -49.029 -19.480 -30.148  1.00 39.02      A    C
ATOM   7072  C    PRO C 283     -49.879 -20.284 -31.122  1.00 38.88      A    C
ATOM   7073  O    PRO C 283     -50.684 -19.717 -31.862  1.00 38.97      A    O
ATOM   7074  CB   PRO C 283     -47.723 -19.022 -30.807  1.00 39.28      A    C
ATOM   7075  CG   PRO C 283     -46.707 -19.156 -29.751  1.00 39.29      A    C
ATOM   7076  CD   PRO C 283     -47.104 -20.380 -29.007  1.00 39.02      A    C
ATOM   7077  N    ARG C 284     -49.712 -21.599 -31.096  1.00 38.62      A    N
ATOM   7078  CA   ARG C 284     -50.518 -22.485 -31.915  1.00 38.53      A    C
ATOM   7079  C    ARG C 284     -52.002 -22.256 -31.668  1.00 38.71      A    C
ATOM   7080  O    ARG C 284     -52.783 -22.177 -32.614  1.00 38.99      A    O
ATOM   7081  CB   ARG C 284     -50.160 -23.950 -31.657  1.00 38.26      A    C
ATOM   7082  CG   ARG C 284     -50.236 -24.876 -32.884  1.00 37.48      A    C
ATOM   7083  CD   ARG C 284     -51.625 -25.002 -33.420  1.00 35.75      A    C
ATOM   7084  NE   ARG C 284     -51.859 -26.238 -34.131  1.00 34.86      A    N
ATOM   7085  CZ   ARG C 284     -53.040 -26.532 -34.658  1.00 33.98      A    C
```

FIGURE 1 (cont'd)

```
ATOM   7086  NH1 ARG C 284     -54.062 -25.671 -34.574  1.00 33.18      A  N
ATOM   7087  NH2 ARG C 284     -53.206 -27.684 -35.277  1.00 34.67      A  N
ATOM   7088  N   THR C 285     -52.387 -22.141 -30.402  1.00 38.74      A  N
ATOM   7089  CA  THR C 285     -53.792 -21.976 -30.056  1.00 38.86      A  C
ATOM   7090  C   THR C 285     -54.124 -20.556 -29.612  1.00 39.28      A  C
ATOM   7091  O   THR C 285     -55.164 -20.335 -28.987  1.00 39.18      A  O
ATOM   7092  CB  THR C 285     -54.197 -22.944 -28.960  1.00 38.48      A  C
ATOM   7093  OG1 THR C 285     -53.205 -22.914 -27.938  1.00 38.13      A  O
ATOM   7094  N   VAL C 286     -53.261 -19.600 -29.969  1.00 39.88      A  N
ATOM   7095  CA  VAL C 286     -53.371 -18.219 -29.489  1.00 40.33      A  C
ATOM   7096  C   VAL C 286     -54.748 -17.607 -29.713  1.00 41.00      A  C
ATOM   7097  O   VAL C 286     -55.188 -16.772 -28.929  1.00 41.05      A  O
ATOM   7098  CB  VAL C 286     -52.280 -17.309 -30.084  1.00 40.27      A  C
ATOM   7099  CG1 VAL C 286     -52.616 -16.897 -31.507  1.00 39.78      A  C
ATOM   7100  CG2 VAL C 286     -52.067 -16.017 -29.191  1.00 39.64      A  C
ATOM   7101  N   ARG C 287     -55.432 -18.039 -30.768  1.00 41.87      A  N
ATOM   7102  CA  ARG C 287     -56.742 -17.492 -31.105  1.00 42.77      A  C
ATOM   7103  C   ARG C 287     -57.872 -18.018 -30.201  1.00 42.51      A  C
ATOM   7104  O   ARG C 287     -58.901 -17.368 -30.039  1.00 42.66      A  O
ATOM   7105  CB  ARG C 287     -57.050 -17.697 -32.595  1.00 43.49      A  C
ATOM   7106  CG  ARG C 287     -57.174 -19.145 -33.029  1.00 45.23      A  C
ATOM   7107  CD  ARG C 287     -57.624 -19.254 -34.477  1.00 48.24      A  C
ATOM   7108  NE  ARG C 287     -57.985 -20.633 -34.836  1.00 49.99      A  N
ATOM   7109  CZ  ARG C 287     -59.220 -21.147 -34.781  1.00 50.49      A  C
ATOM   7110  NH1 ARG C 287     -60.248 -20.400 -34.378  1.00 50.54      A  N
ATOM   7111  NH2 ARG C 287     -59.429 -22.417 -35.140  1.00 50.72      A  N
ATOM   7112  N   TRP C 288     -57.678 -19.187 -29.606  1.00 42.15      A  N
ATOM   7113  CA  TRP C 288     -58.645 -19.689 -28.654  1.00 41.85      A  C
ATOM   7114  C   TRP C 288     -58.477 -18.998 -27.322  1.00 41.63      A  C
ATOM   7115  O   TRP C 288     -59.434 -18.867 -26.562  1.00 41.69      A  O
ATOM   7116  CB  TRP C 288     -58.546 -21.202 -28.513  1.00 41.77      A  C
ATOM   7117  CG  TRP C 288     -59.139 -21.904 -29.678  1.00 42.47      A  C
ATOM   7118  CD1 TRP C 288     -58.511 -22.769 -30.517  1.00 42.99      A  C
ATOM   7119  CD2 TRP C 288     -60.479 -21.777 -30.161  1.00 43.17      A  C
ATOM   7120  CE2 TRP C 288     -60.594 -22.606 -31.293  1.00 43.56      A  C
ATOM   7121  CE3 TRP C 288     -61.594 -21.045 -29.745  1.00 43.39      A  C
ATOM   7122  NE1 TRP C 288     -59.379 -23.204 -31.488  1.00 43.40      A  N
ATOM   7123  CZ2 TRP C 288     -61.774 -22.725 -32.012  1.00 44.08      A  C
ATOM   7124  CZ3 TRP C 288     -62.762 -21.159 -30.455  1.00 43.90      A  C
ATOM   7125  CH2 TRP C 288     -62.849 -21.998 -31.576  1.00 44.30      A  C
ATOM   7126  N   PHE C 289     -57.259 -18.545 -27.048  1.00 41.46      A  N
ATOM   7127  CA  PHE C 289     -57.009 -17.718 -25.884  1.00 41.28      A  C
ATOM   7128  C   PHE C 289     -57.707 -16.369 -26.068  1.00 41.42      A  C
ATOM   7129  O   PHE C 289     -58.354 -15.883 -25.140  1.00 41.28      A  O
ATOM   7130  CB  PHE C 289     -55.512 -17.551 -25.646  1.00 41.18      A  C
ATOM   7131  CG  PHE C 289     -55.175 -16.964 -24.310  1.00 41.07      A  C
ATOM   7132  CD1 PHE C 289     -55.179 -17.756 -23.172  1.00 40.67      A  C
ATOM   7133  CD2 PHE C 289     -54.847 -15.617 -24.190  1.00 41.40      A  C
ATOM   7134  CE1 PHE C 289     -54.870 -17.218 -21.939  1.00 40.55      A  C
ATOM   7135  CE2 PHE C 289     -54.538 -15.070 -22.965  1.00 41.50      A  C
ATOM   7136  CZ  PHE C 289     -54.554 -15.872 -21.835  1.00 41.08      A  C
ATOM   7137  N   HIS C 290     -57.612 -15.783 -27.269  1.00 41.74      A  N
ATOM   7138  CA  HIS C 290     -58.323 -14.527 -27.565  1.00 42.20      A  C
ATOM   7139  C   HIS C 290     -59.815 -14.694 -27.326  1.00 42.31      A  C
ATOM   7140  O   HIS C 290     -60.469 -13.757 -26.893  1.00 42.52      A  O
ATOM   7141  CB  HIS C 290     -58.097 -13.973 -28.992  1.00 42.47      A  C
ATOM   7142  CG  HIS C 290     -56.659 -13.869 -29.391  1.00 43.15      A  C
ATOM   7143  ND1 HIS C 290     -55.980 -12.826 -30.007  1.00 44.00      A  N
ATOM   7144  CE1 HIS C 290     -56.617 -11.687 -30.159  1.00 44.48      A  C
ATOM   7145  N   ARG C 291     -60.354 -15.880 -27.600  1.00 42.37      A  N
ATOM   7146  CA  ARG C 291     -61.766 -16.138 -27.339  1.00 42.59      A  C
ATOM   7147  C   ARG C 291     -62.087 -15.959 -25.872  1.00 42.22      A  C
ATOM   7148  O   ARG C 291     -63.075 -15.311 -25.518  1.00 42.49      A  O
ATOM   7149  CB  ARG C 291     -62.173 -17.532 -27.802  1.00 42.83      A  C
ATOM   7150  CG  ARG C 291     -62.406 -17.602 -29.290  1.00 44.49      A  C
```

FIGURE 1 (cont'd)

```
ATOM   7151  CD  ARG C 291     -63.498 -16.629 -29.699  1.00 46.62      A  C
ATOM   7152  NE  ARG C 291     -64.798 -17.276 -29.675  1.00 47.69      A  N
ATOM   7153  CZ  ARG C 291     -65.388 -17.769 -30.758  1.00 48.76      A  C
ATOM   7154  NH1 ARG C 291     -64.791 -17.668 -31.945  1.00 49.28      A  N
ATOM   7155  NH2 ARG C 291     -66.575 -18.358 -30.658  1.00 49.30      A  N
ATOM   7156  N   LEU C 292     -61.232 -16.521 -25.025  1.00 41.58      A  N
ATOM   7157  CA  LEU C 292     -61.413 -16.425 -23.597  1.00 40.92      A  C
ATOM   7158  C   LEU C 292     -61.356 -14.970 -23.153  1.00 40.90      A  C
ATOM   7159  O   LEU C 292     -62.213 -14.526 -22.396  1.00 40.97      A  O
ATOM   7160  CB  LEU C 292     -60.390 -17.293 -22.873  1.00 40.54      A  C
ATOM   7161  CG  LEU C 292     -60.600 -18.791 -23.061  1.00 39.84      A  C
ATOM   7162  CD1 LEU C 292     -59.381 -19.556 -22.616  1.00 39.37      A  C
ATOM   7163  CD2 LEU C 292     -61.824 -19.259 -22.297  1.00 39.41      A  C
ATOM   7164  N   ARG C 293     -60.379 -14.219 -23.653  1.00 40.85      A  N
ATOM   7165  CA  ARG C 293     -60.316 -12.792 -23.372  1.00 40.97      A  C
ATOM   7166  C   ARG C 293     -61.623 -12.158 -23.819  1.00 41.28      A  C
ATOM   7167  O   ARG C 293     -62.241 -11.411 -23.063  1.00 41.41      A  O
ATOM   7168  CB  ARG C 293     -59.127 -12.131 -24.077  1.00 40.90      A  C
ATOM   7169  CG  ARG C 293     -58.710 -10.776 -23.500  1.00 40.66      A  C
ATOM   7170  CD  ARG C 293     -57.658 -10.080 -24.366  1.00 40.46      A  C
ATOM   7171  NE  ARG C 293     -56.393 -10.814 -24.445  1.00 39.74      A  N
ATOM   7172  N   SER C 294     -62.061 -12.492 -25.031  1.00 41.45      A  N
ATOM   7173  CA  SER C 294     -63.274 -11.905 -25.600  1.00 41.70      A  C
ATOM   7174  C   SER C 294     -64.532 -12.256 -24.828  1.00 42.09      A  C
ATOM   7175  O   SER C 294     -65.419 -11.424 -24.684  1.00 42.60      A  O
ATOM   7176  CB  SER C 294     -63.430 -12.253 -27.076  1.00 40.76      A  C
ATOM   7177  OG  SER C 294     -62.938 -11.171 -27.854  1.00 41.46      A  O
ATOM   7178  N   ILE C 295     -64.597 -13.478 -24.318  1.00 42.17      A  N
ATOM   7179  CA  ILE C 295     -65.744 -13.909 -23.534  1.00 42.24      A  C
ATOM   7180  C   ILE C 295     -65.787 -13.188 -22.184  1.00 42.51      A  C
ATOM   7181  O   ILE C 295     -66.857 -12.770 -21.739  1.00 42.71      A  O
ATOM   7182  CB  ILE C 295     -65.764 -15.438 -23.369  1.00 41.96      A  C
ATOM   7183  CG1 ILE C 295     -66.121 -16.095 -24.700  1.00 41.87      A  C
ATOM   7184  CG2 ILE C 295     -66.755 -15.862 -22.292  1.00 41.82      A  C
ATOM   7185  CD1 ILE C 295     -65.559 -17.466 -24.876  1.00 41.59      A  C
ATOM   7186  N   GLU C 296     -64.623 -13.033 -21.554  1.00 42.68      A  N
ATOM   7187  CA  GLU C 296     -64.508 -12.299 -20.293  1.00 42.99      A  C
ATOM   7188  C   GLU C 296     -64.962 -10.869 -20.525  1.00 43.52      A  C
ATOM   7189  O   GLU C 296     -65.820 -10.352 -19.812  1.00 43.79      A  O
ATOM   7190  CB  GLU C 296     -63.066 -12.330 -19.772  1.00 42.71      A  C
ATOM   7191  CG  GLU C 296     -62.875 -11.745 -18.374  1.00 42.90      A  C
ATOM   7192  CD  GLU C 296     -61.413 -11.581 -17.976  1.00 43.08      A  C
ATOM   7193  OE1 GLU C 296     -60.529 -12.187 -18.619  1.00 42.75      A  O
ATOM   7194  OE2 GLU C 296     -61.150 -10.843 -17.006  1.00 43.33      A  O
ATOM   7195  N   LYS C 297     -64.389 -10.256 -21.554  1.00 44.09      A  N
ATOM   7196  CA  LYS C 297     -64.742  -8.913 -21.978  1.00 44.82      A  C
ATOM   7197  C   LYS C 297     -66.267  -8.790 -22.096  1.00 45.47      A  C
ATOM   7198  O   LYS C 297     -66.877  -7.954 -21.430  1.00 45.76      A  O
ATOM   7199  CB  LYS C 297     -64.060  -8.615 -23.315  1.00 44.72      A  C
ATOM   7200  CG  LYS C 297     -63.262  -7.325 -23.375  1.00 44.60      A  C
ATOM   7201  CD  LYS C 297     -62.095  -7.458 -24.364  1.00 43.72      A  C
ATOM   7202  CE  LYS C 297     -61.660  -6.122 -24.974  1.00 43.77      A  C
ATOM   7203  NZ  LYS C 297     -61.930  -4.895 -24.140  1.00 45.08      A  N
ATOM   7204  N   ARG C 298     -66.871  -9.659 -22.908  1.00 45.98      A  N
ATOM   7205  CA  ARG C 298     -68.317  -9.647 -23.170  1.00 46.48      A  C
ATOM   7206  C   ARG C 298     -69.158  -9.828 -21.911  1.00 47.02      A  C
ATOM   7207  O   ARG C 298     -70.078  -9.044 -21.676  1.00 47.64      A  O
ATOM   7208  CB  ARG C 298     -68.685 -10.708 -24.219  1.00 45.50      A  C
ATOM   7209  CG  ARG C 298     -70.146 -10.715 -24.700  1.00 45.45      A  C
ATOM   7210  CD  ARG C 298     -70.361 -11.724 -25.837  1.00 45.12      A  C
ATOM   7211  NE  ARG C 298     -71.760 -11.852 -26.235  1.00 44.94      A  N
ATOM   7212  N   LEU C 299     -68.842 -10.846 -21.109  1.00 47.22      A  N
ATOM   7213  CA  LEU C 299     -69.595 -11.128 -19.881  1.00 47.46      A  C
ATOM   7214  C   LEU C 299     -69.484  -9.996 -18.862  1.00 47.88      A  C
ATOM   7215  O   LEU C 299     -70.410  -9.760 -18.073  1.00 48.12      A  O
```

FIGURE 1 (cont'd)

```
ATOM   7216  CB   LEU C 299     -69.150 -12.443 -19.250  1.00 47.13      A    C
ATOM   7217  CG   LEU C 299     -69.561 -13.734 -19.942  1.00 46.95      A    C
ATOM   7218  CD1  LEU C 299     -68.740 -14.861 -19.384  1.00 46.54      A    C
ATOM   7219  CD2  LEU C 299     -71.032 -14.017 -19.750  1.00 47.43      A    C
ATOM   7220  N    HIS C 300     -68.349  -9.300 -18.887  1.00 48.20      A    N
ATOM   7221  CA   HIS C 300     -68.162  -8.122 -18.061  1.00 48.75      A    C
ATOM   7222  C    HIS C 300     -69.102  -7.000 -18.496  1.00 49.23      A    C
ATOM   7223  O    HIS C 300     -69.799  -6.431 -17.658  1.00 49.56      A    O
ATOM   7224  CB   HIS C 300     -66.706  -7.662 -18.093  1.00 48.69      A    C
ATOM   7225  CG   HIS C 300     -66.490  -6.308 -17.492  1.00 49.37      A    C
ATOM   7226  CD2  HIS C 300     -66.113  -5.134 -18.053  1.00 50.14      A    C
ATOM   7227  ND1  HIS C 300     -66.678  -6.048 -16.151  1.00 49.66      A    N
ATOM   7228  CE1  HIS C 300     -66.423  -4.775 -15.911  1.00 50.27      A    C
ATOM   7229  NE2  HIS C 300     -66.078  -4.198 -17.048  1.00 50.72      A    N
ATOM   7230  N    ARG C 301     -69.122  -6.707 -19.800  1.00 49.67      A    N
ATOM   7231  CA   ARG C 301     -70.004  -5.695 -20.384  1.00 50.20      A    C
ATOM   7232  C    ARG C 301     -71.451  -5.955 -20.014  1.00 50.83      A    C
ATOM   7233  O    ARG C 301     -72.193  -5.030 -19.719  1.00 51.39      A    O
ATOM   7234  CB   ARG C 301     -69.893  -5.667 -21.911  1.00 50.05      A    C
ATOM   7235  CG   ARG C 301     -68.495  -5.563 -22.474  1.00 49.09      A    C
ATOM   7236  CD   ARG C 301     -67.983  -4.137 -22.563  1.00 48.43      A    C
ATOM   7237  NE   ARG C 301     -66.627  -4.098 -23.114  1.00 47.64      A    N
ATOM   7238  CZ   ARG C 301     -66.339  -4.398 -24.389  1.00 45.26      A    C
ATOM   7239  NH1  ARG C 301     -67.303  -4.762 -25.231  1.00 44.30      A    N
ATOM   7240  NH2  ARG C 301     -65.087  -4.337 -24.830  1.00 44.39      A    N
ATOM   7241  N    LEU C 302     -71.839  -7.223 -20.026  1.00 51.20      A    N
ATOM   7242  CA   LEU C 302     -73.202  -7.632 -19.705  1.00 51.83      A    C
ATOM   7243  C    LEU C 302     -73.491  -7.743 -18.205  1.00 52.19      A    C
ATOM   7244  O    LEU C 302     -74.493  -8.351 -17.824  1.00 52.48      A    O
ATOM   7245  CB   LEU C 302     -73.505  -8.975 -20.366  1.00 51.74      A    C
ATOM   7246  CG   LEU C 302     -73.582  -8.991 -21.885  1.00 52.21      A    C
ATOM   7247  CD1  LEU C 302     -73.257 -10.350 -22.437  1.00 51.82      A    C
ATOM   7248  CD2  LEU C 302     -74.956  -8.573 -22.319  1.00 53.50      A    C
ATOM   7249  N    ASN C 303     -72.624  -7.155 -17.371  1.00 52.32      A    N
ATOM   7250  CA   ASN C 303     -72.704  -7.244 -15.902  1.00 52.23      A    C
ATOM   7251  C    ASN C 303     -73.114  -8.639 -15.441  1.00 52.69      A    C
ATOM   7252  O    ASN C 303     -74.207  -8.817 -14.900  1.00 53.19      A    O
ATOM   7253  N    LEU C 304     -72.251  -9.627 -15.687  1.00 52.86      A    N
ATOM   7254  CA   LEU C 304     -72.522 -11.028 -15.300  1.00 52.75      A    C
ATOM   7255  C    LEU C 304     -71.354 -11.674 -14.552  1.00 52.43      A    C
ATOM   7256  O    LEU C 304     -71.344 -12.880 -14.306  1.00 52.15      A    O
ATOM   7257  CB   LEU C 304     -72.926 -11.882 -16.518  1.00 52.80      A    C
ATOM   7258  CG   LEU C 304     -74.372 -11.838 -17.036  1.00 53.25      A    C
ATOM   7259  CD1  LEU C 304     -74.479 -12.642 -18.301  1.00 52.93      A    C
ATOM   7260  CD2  LEU C 304     -75.387 -12.346 -16.019  1.00 53.82      A    C
ATOM   7261  N    LEU C 305     -70.376 -10.853 -14.192  1.00 52.36      A    N
ATOM   7262  CA   LEU C 305     -69.209 -11.314 -13.468  1.00 52.18      A    C
ATOM   7263  C    LEU C 305     -69.118 -10.569 -12.143  1.00 52.58      A    C
ATOM   7264  O    LEU C 305     -69.030  -9.341 -12.121  1.00 52.99      A    O
ATOM   7265  CB   LEU C 305     -67.934 -11.102 -14.299  1.00 51.74      A    C
ATOM   7266  CG   LEU C 305     -67.829 -11.685 -15.712  1.00 51.06      A    C
ATOM   7267  CD1  LEU C 305     -66.572 -11.195 -16.396  1.00 50.40      A    C
ATOM   7268  CD2  LEU C 305     -67.868 -13.197 -15.699  1.00 50.64      A    C
ATOM   7269  N    GLN C 306     -69.160 -11.320 -11.047  1.00 52.72      A    N
ATOM   7270  CA   GLN C 306     -69.004 -10.768  -9.709  1.00 53.01      A    C
ATOM   7271  C    GLN C 306     -67.602 -10.214  -9.492  1.00 52.93      A    C
ATOM   7272  O    GLN C 306     -66.648 -10.668 -10.114  1.00 52.60      A    O
ATOM   7273  CB   GLN C 306     -69.255 -11.851  -8.677  1.00 53.14      A    C
ATOM   7274  CG   GLN C 306     -70.647 -11.913  -8.126  1.00 54.02      A    C
ATOM   7275  CD   GLN C 306     -70.687 -12.782  -6.889  1.00 54.71      A    C
ATOM   7276  NE2  GLN C 306     -71.009 -12.182  -5.750  1.00 54.53      A    N
ATOM   7277  OE1  GLN C 306     -70.367 -13.967  -6.945  1.00 54.90      A    O
ATOM   7278  N    SER C 307     -67.482  -9.236  -8.598  1.00 53.27      A    N
ATOM   7279  CA   SER C 307     -66.183  -8.682  -8.206  1.00 53.50      A    C
ATOM   7280  C    SER C 307     -65.216  -8.534  -9.380  1.00 53.35      A    C
```

FIGURE 1 (cont'd)

```
ATOM   7281  O   SER C 307     -64.072  -8.983  -9.301  1.00 53.13      A   O
ATOM   7282  CB  SER C 307     -65.541  -9.553  -7.120  1.00 53.53      A   C
ATOM   7283  OG  SER C 307     -66.478  -9.908  -6.118  1.00 54.25      A   O
ATOM   7284  N   HIS C 308     -65.681  -7.900 -10.457  1.00 53.47      A   N
ATOM   7285  CA  HIS C 308     -64.919  -7.793 -11.703  1.00 53.44      A   C
ATOM   7286  C   HIS C 308     -64.850  -6.336 -12.177  1.00 53.70      A   C
ATOM   7287  O   HIS C 308     -65.514  -5.955 -13.137  1.00 53.98      A   O
ATOM   7288  CB  HIS C 308     -65.556  -8.693 -12.770  1.00 53.27      A   C
ATOM   7289  CG  HIS C 308     -64.631  -9.081 -13.886  1.00 52.96      A   C
ATOM   7290  CD2 HIS C 308     -63.608  -9.966 -13.927  1.00 52.53      A   C
ATOM   7291  ND1 HIS C 308     -64.725  -8.549 -15.154  1.00 53.23      A   N
ATOM   7292  CE1 HIS C 308     -63.797  -9.084 -15.925  1.00 52.89      A   C
ATOM   7293  NE2 HIS C 308     -63.106  -9.948 -15.205  1.00 52.35      A   N
ATOM   7294  N   PRO C 309     -64.039  -5.511 -11.504  1.00 53.89      A   N
ATOM   7295  CA  PRO C 309     -63.999  -4.086 -11.785  1.00 54.38      A   C
ATOM   7296  C   PRO C 309     -63.118  -3.671 -12.961  1.00 54.67      A   C
ATOM   7297  O   PRO C 309     -62.434  -2.649 -12.875  1.00 54.94      A   O
ATOM   7298  CB  PRO C 309     -63.441  -3.494 -10.483  1.00 54.65      A   C
ATOM   7299  CG  PRO C 309     -63.562  -4.579  -9.477  1.00 54.42      A   C
ATOM   7300  CD  PRO C 309     -63.322  -5.809 -10.264  1.00 53.82      A   C
ATOM   7301  N   GLN C 310     -63.117  -4.471 -14.029  1.00 54.73      A   N
ATOM   7302  CA  GLN C 310     -62.616  -4.072 -15.365  1.00 54.88      A   C
ATOM   7303  C   GLN C 310     -62.789  -5.161 -16.434  1.00 54.95      A   C
ATOM   7304  O   GLN C 310     -63.340  -6.225 -16.166  1.00 54.78      A   O
ATOM   7305  CB  GLN C 310     -61.192  -3.460 -15.350  1.00 54.92      A   C
ATOM   7306  CG  GLN C 310     -60.156  -4.114 -14.431  1.00 54.53      A   C
ATOM   7307  CD  GLN C 310     -59.168  -3.110 -13.849  1.00 54.54      A   C
ATOM   7308  N   GLU C 311     -62.339  -4.871 -17.648  1.00 55.36      A   N
ATOM   7309  CA  GLU C 311     -62.583  -5.726 -18.808  1.00 55.72      A   C
ATOM   7310  C   GLU C 311     -61.586  -6.875 -18.840  1.00 55.02      A   C
ATOM   7311  O   GLU C 311     -61.980  -8.034 -18.722  1.00 54.85      A   O
ATOM   7312  CB  GLU C 311     -62.511  -4.913 -20.110  1.00 56.49      A   C
ATOM   7313  CG  GLU C 311     -63.312  -3.591 -20.104  1.00 58.91      A   C
ATOM   7314  CD  GLU C 311     -62.553  -2.376 -19.505  1.00 61.45      A   C
ATOM   7315  OE1 GLU C 311     -62.898  -1.222 -19.867  1.00 62.85      A   O
ATOM   7316  OE2 GLU C 311     -61.628  -2.557 -18.672  1.00 62.02      A   O
ATOM   7317  N   VAL C 312     -60.302  -6.547 -19.003  1.00 54.45      A   N
ATOM   7318  CA  VAL C 312     -59.238  -7.533 -18.928  1.00 53.69      A   C
ATOM   7319  C   VAL C 312     -58.735  -7.624 -17.485  1.00 53.19      A   C
ATOM   7320  O   VAL C 312     -58.064  -6.718 -16.993  1.00 53.53      A   O
ATOM   7321  N   MET C 313     -59.102  -8.710 -16.807  1.00 52.15      A   N
ATOM   7322  CA  MET C 313     -58.631  -9.006 -15.455  1.00 51.18      A   C
ATOM   7323  C   MET C 313     -57.884 -10.339 -15.467  1.00 50.21      A   C
ATOM   7324  O   MET C 313     -56.725 -10.426 -15.045  1.00 50.07      A   O
ATOM   7325  CB  MET C 313     -59.810  -9.113 -14.487  1.00 51.38      A   C
ATOM   7326  CG  MET C 313     -60.634  -7.848 -14.297  1.00 52.00      A   C
ATOM   7327  SD  MET C 313     -60.593  -7.152 -12.633  1.00 52.37      A   S
ATOM   7328  CE  MET C 313     -61.248  -8.493 -11.646  1.00 52.11      A   C
ATOM   7329  N   TYR C 314     -58.562 -11.366 -15.977  1.00 49.12      A   N
ATOM   7330  CA  TYR C 314     -58.069 -12.733 -15.941  1.00 48.01      A   C
ATOM   7331  C   TYR C 314     -57.188 -13.081 -17.137  1.00 47.48      A   C
ATOM   7332  O   TYR C 314     -56.022 -13.433 -16.970  1.00 47.27      A   O
ATOM   7333  CB  TYR C 314     -59.243 -13.716 -15.838  1.00 47.82      A   C
ATOM   7334  CG  TYR C 314     -60.105 -13.545 -14.600  1.00 47.54      A   C
ATOM   7335  CD1 TYR C 314     -59.546 -13.154 -13.382  1.00 47.53      A   C
ATOM   7336  CD2 TYR C 314     -61.474 -13.800 -14.641  1.00 47.35      A   C
ATOM   7337  CE1 TYR C 314     -60.328 -13.000 -12.252  1.00 47.59      A   C
ATOM   7338  CE2 TYR C 314     -62.262 -13.652 -13.509  1.00 47.40      A   C
ATOM   7339  CZ  TYR C 314     -61.677 -13.251 -12.323  1.00 47.32      A   C
ATOM   7340  OH  TYR C 314     -62.434 -13.095 -11.200  1.00 47.30      A   O
ATOM   7341  N   PHE C 315     -57.747 -12.989 -18.337  1.00 47.02      A   N
ATOM   7342  CA  PHE C 315     -57.029 -13.403 -19.524  1.00 46.65      A   C
ATOM   7343  C   PHE C 315     -56.278 -12.239 -20.109  1.00 46.92      A   C
ATOM   7344  O   PHE C 315     -56.806 -11.485 -20.907  1.00 47.04      A   O
ATOM   7345  CB  PHE C 315     -57.984 -14.052 -20.522  1.00 46.36      A   C
```

FIGURE 1 (cont'd)

```
ATOM   7346  CG   PHE C 315     -58.640 -15.286 -19.986  1.00 45.26      A  C
ATOM   7347  CD1  PHE C 315     -58.004 -16.515 -20.059  1.00 44.51      A  C
ATOM   7348  CD2  PHE C 315     -59.868 -15.215 -19.368  1.00 44.55      A  C
ATOM   7349  CE1  PHE C 315     -58.592 -17.641 -19.549  1.00 43.97      A  C
ATOM   7350  CE2  PHE C 315     -60.458 -16.341 -18.855  1.00 43.99      A  C
ATOM   7351  CZ   PHE C 315     -59.821 -17.553 -18.948  1.00 43.75      A  C
ATOM   7352  N    GLN C 316     -55.032 -12.096 -19.686  1.00 47.19      A  N
ATOM   7353  CA   GLN C 316     -54.213 -10.959 -20.064  1.00 47.72      A  C
ATOM   7354  C    GLN C 316     -53.715 -11.052 -21.491  1.00 48.06      A  C
ATOM   7355  O    GLN C 316     -53.534 -12.142 -22.019  1.00 47.89      A  O
ATOM   7356  CB   GLN C 316     -53.026 -10.827 -19.116  1.00 47.78      A  C
ATOM   7357  CG   GLN C 316     -53.392 -10.337 -17.729  1.00 48.25      A  C
ATOM   7358  CD   GLN C 316     -53.977  -8.940 -17.738  1.00 48.98      A  C
ATOM   7359  NE2  GLN C 316     -55.212  -8.818 -17.279  1.00 49.10      A  N
ATOM   7360  OE1  GLN C 316     -53.326  -7.980 -18.146  1.00 49.79      A  O
ATOM   7361  N    PRO C 317     -53.493  -9.895 -22.125  1.00 48.65      A  N
ATOM   7362  CA   PRO C 317     -52.831  -9.878 -23.413  1.00 48.96      A  C
ATOM   7363  C    PRO C 317     -51.320 -10.095 -23.258  1.00 49.03      A  C
ATOM   7364  O    PRO C 317     -50.768  -9.933 -22.157  1.00 48.98      A  O
ATOM   7365  CB   PRO C 317     -53.104  -8.461 -23.915  1.00 49.27      A  C
ATOM   7366  CG   PRO C 317     -53.158  -7.646 -22.689  1.00 49.42      A  C
ATOM   7367  CD   PRO C 317     -53.827  -8.534 -21.668  1.00 48.95      A  C
ATOM   7368  N    GLY C 318     -50.662 -10.444 -24.361  1.00 49.07      A  N
ATOM   7369  CA   GLY C 318     -49.241 -10.755 -24.346  1.00 49.01      A  C
ATOM   7370  C    GLY C 318     -49.050 -12.243 -24.531  1.00 48.83      A  C
ATOM   7371  O    GLY C 318     -49.867 -13.048 -24.071  1.00 48.65      A  O
ATOM   7372  N    GLU C 319     -47.972 -12.605 -25.221  1.00 48.81      A  N
ATOM   7373  CA   GLU C 319     -47.613 -14.003 -25.422  1.00 48.58      A  C
ATOM   7374  C    GLU C 319     -46.207 -14.281 -24.861  1.00 48.74      A  C
ATOM   7375  O    GLU C 319     -45.236 -14.293 -25.618  1.00 49.10      A  O
ATOM   7376  CB   GLU C 319     -47.684 -14.361 -26.911  1.00 48.47      A  C
ATOM   7377  CG   GLU C 319     -49.050 -14.133 -27.565  1.00 47.85      A  C
ATOM   7378  CD   GLU C 319     -49.168 -14.738 -28.958  1.00 43.95      A  C
ATOM   7379  OE1  GLU C 319     -49.423 -13.991 -29.926  1.00 42.35      A  O
ATOM   7380  OE2  GLU C 319     -49.021 -15.967 -29.087  1.00 43.07      A  O
ATOM   7381  N    PRO C 320     -46.085 -14.481 -23.528  1.00 48.62      A  N
ATOM   7382  CA   PRO C 320     -44.770 -14.784 -22.980  1.00 48.62      A  C
ATOM   7383  C    PRO C 320     -44.340 -16.212 -23.280  1.00 48.53      A  C
ATOM   7384  O    PRO C 320     -45.179 -17.064 -23.593  1.00 48.36      A  O
ATOM   7385  CB   PRO C 320     -44.960 -14.585 -21.472  1.00 48.68      A  C
ATOM   7386  CG   PRO C 320     -46.142 -13.696 -21.350  1.00 48.69      A  C
ATOM   7387  CD   PRO C 320     -47.042 -14.186 -22.449  1.00 48.48      A  C
ATOM   7388  N    PHE C 321     -43.034 -16.450 -23.161  1.00 48.38      A  N
ATOM   7389  CA   PHE C 321     -42.371 -17.695 -23.556  1.00 47.91      A  C
ATOM   7390  C    PHE C 321     -42.915 -19.011 -22.939  1.00 48.15      A  C
ATOM   7391  O    PHE C 321     -43.338 -19.901 -23.676  1.00 48.50      A  O
ATOM   7392  N    GLY C 322     -42.918 -19.139 -21.614  1.00 48.01      A  N
ATOM   7393  CA   GLY C 322     -43.309 -20.408 -20.960  1.00 47.42      A  C
ATOM   7394  C    GLY C 322     -42.149 -21.404 -20.908  1.00 47.06      A  C
ATOM   7395  O    GLY C 322     -40.988 -21.002 -21.031  1.00 47.60      A  O
ATOM   7396  N    SER C 323     -42.420 -22.694 -20.693  1.00 46.11      A  N
ATOM   7397  CA   SER C 323     -43.733 -23.228 -20.326  1.00 45.02      A  C
ATOM   7398  C    SER C 323     -43.651 -23.756 -18.908  1.00 43.86      A  C
ATOM   7399  O    SER C 323     -42.567 -23.811 -18.328  1.00 43.99      A  O
ATOM   7400  CB   SER C 323     -44.136 -24.394 -21.235  1.00 45.23      A  C
ATOM   7401  OG   SER C 323     -44.248 -24.004 -22.588  1.00 46.07      A  O
ATOM   7402  N    VAL C 324     -44.799 -24.153 -18.367  1.00 42.28      A  N
ATOM   7403  CA   VAL C 324     -44.876 -24.771 -17.057  1.00 40.73      A  C
ATOM   7404  C    VAL C 324     -45.226 -26.228 -17.282  1.00 39.98      A  C
ATOM   7405  O    VAL C 324     -46.226 -26.525 -17.916  1.00 39.88      A  O
ATOM   7406  CB   VAL C 324     -45.933 -24.085 -16.182  1.00 40.47      A  C
ATOM   7407  CG1  VAL C 324     -45.482 -22.685 -15.843  1.00 40.39      A  C
ATOM   7408  CG2  VAL C 324     -46.195 -24.876 -14.919  1.00 40.02      A  C
ATOM   7409  N    GLU C 325     -44.391 -27.130 -16.774  1.00 39.18      A  N
ATOM   7410  CA   GLU C 325     -44.558 -28.561 -16.993  1.00 38.47      A  C
```

FIGURE 1 (cont'd)

```
ATOM   7411  C   GLU C 325     -45.788 -29.100 -16.297  1.00 37.57      A   C
ATOM   7412  O   GLU C 325     -45.911 -28.992 -15.095  1.00 37.44      A   O
ATOM   7413  CB  GLU C 325     -43.328 -29.310 -16.509  1.00 38.86      A   C
ATOM   7414  CG  GLU C 325     -42.039 -28.861 -17.169  1.00 40.44      A   C
ATOM   7415  CD  GLU C 325     -40.871 -29.764 -16.847  1.00 42.56      A   C
ATOM   7416  OE1 GLU C 325     -41.093 -30.848 -16.260  1.00 42.99      A   O
ATOM   7417  OE2 GLU C 325     -39.727 -29.389 -17.186  1.00 43.83      A   O
ATOM   7418  N   ASP C 326     -46.694 -29.692 -17.066  1.00 36.77      A   N
ATOM   7419  CA  ASP C 326     -47.972 -30.200 -16.554  1.00 36.01      A   C
ATOM   7420  C   ASP C 326     -48.440 -31.355 -17.443  1.00 35.73      A   C
ATOM   7421  O   ASP C 326     -47.700 -31.810 -18.310  1.00 35.81      A   O
ATOM   7422  CB  ASP C 326     -49.018 -29.071 -16.516  1.00 35.73      A   C
ATOM   7423  CG  ASP C 326     -50.060 -29.241 -15.413  1.00 35.09      A   C
ATOM   7424  OD1 ASP C 326     -50.278 -30.357 -14.912  1.00 34.78      A   O
ATOM   7425  OD2 ASP C 326     -50.683 -28.231 -15.053  1.00 34.56      A   O
ATOM   7426  N   ASP C 327     -49.669 -31.812 -17.222  1.00 35.30      A   N
ATOM   7427  CA  ASP C 327     -50.232 -32.984 -17.896  1.00 34.96      A   C
ATOM   7428  C   ASP C 327     -50.286 -32.892 -19.404  1.00 34.55      A   C
ATOM   7429  O   ASP C 327     -50.486 -33.895 -20.068  1.00 34.65      A   O
ATOM   7430  CB  ASP C 327     -51.644 -33.266 -17.395  1.00 35.10      A   C
ATOM   7431  CG  ASP C 327     -51.667 -33.841 -16.002  1.00 36.03      A   C
ATOM   7432  OD1 ASP C 327     -51.176 -34.969 -15.801  1.00 36.74      A   O
ATOM   7433  OD2 ASP C 327     -52.200 -33.163 -15.101  1.00 36.73      A   O
ATOM   7434  N   HIS C 328     -50.121 -31.700 -19.949  1.00 34.04      A   N
ATOM   7435  CA  HIS C 328     -50.190 -31.531 -21.381  1.00 33.68      A   C
ATOM   7436  C   HIS C 328     -48.943 -32.023 -22.086  1.00 33.62      A   C
ATOM   7437  O   HIS C 328     -49.014 -32.424 -23.236  1.00 33.83      A   O
ATOM   7438  CB  HIS C 328     -50.415 -30.077 -21.715  1.00 33.58      A   C
ATOM   7439  CG  HIS C 328     -49.235 -29.209 -21.436  1.00 33.84      A   C
ATOM   7440  CD2 HIS C 328     -48.294 -28.693 -22.259  1.00 34.43      A   C
ATOM   7441  ND1 HIS C 328     -48.918 -28.775 -20.172  1.00 34.04      A   N
ATOM   7442  CE1 HIS C 328     -47.836 -28.022 -20.226  1.00 34.30      A   C
ATOM   7443  NE2 HIS C 328     -47.435 -27.958 -21.481  1.00 34.56      A   N
ATOM   7444  N   ILE C 329     -47.808 -31.997 -21.394  1.00 33.49      A   N
ATOM   7445  CA  ILE C 329     -46.512 -32.338 -21.990  1.00 33.61      A   C
ATOM   7446  C   ILE C 329     -46.476 -33.622 -22.841  1.00 33.62      A   C
ATOM   7447  O   ILE C 329     -46.059 -33.562 -23.996  1.00 33.92      A   O
ATOM   7448  CB  ILE C 329     -45.369 -32.326 -20.947  1.00 33.68      A   C
ATOM   7449  CG1 ILE C 329     -45.146 -30.912 -20.402  1.00 33.89      A   C
ATOM   7450  CG2 ILE C 329     -44.078 -32.905 -21.539  1.00 34.18      A   C
ATOM   7451  CD1 ILE C 329     -44.708 -29.876 -21.439  1.00 34.44      A   C
ATOM   7452  N   PRO C 330     -46.913 -34.775 -22.299  1.00 33.51      A   N
ATOM   7453  CA  PRO C 330     -46.792 -35.980 -23.105  1.00 33.58      A   C
ATOM   7454  C   PRO C 330     -47.821 -36.070 -24.215  1.00 33.49      A   C
ATOM   7455  O   PRO C 330     -47.727 -36.954 -25.052  1.00 33.77      A   O
ATOM   7456  CB  PRO C 330     -47.011 -37.094 -22.100  1.00 33.68      A   C
ATOM   7457  CG  PRO C 330     -47.864 -36.507 -21.089  1.00 33.50      A   C
ATOM   7458  CD  PRO C 330     -47.485 -35.072 -20.981  1.00 33.42      A   C
ATOM   7459  N   PHE C 331     -48.795 -35.169 -24.221  1.00 33.09      A   N
ATOM   7460  CA  PHE C 331     -49.687 -35.035 -25.362  1.00 32.88      A   C
ATOM   7461  C   PHE C 331     -49.106 -34.073 -26.384  1.00 32.84      A   C
ATOM   7462  O   PHE C 331     -49.232 -34.275 -27.580  1.00 32.97      A   O
ATOM   7463  CB  PHE C 331     -51.058 -34.566 -24.913  1.00 32.67      A   C
ATOM   7464  CG  PHE C 331     -51.834 -35.605 -24.181  1.00 32.77      A   C
ATOM   7465  CD1 PHE C 331     -51.930 -35.567 -22.806  1.00 32.78      A   C
ATOM   7466  CD2 PHE C 331     -52.469 -36.625 -24.867  1.00 32.93      A   C
ATOM   7467  CE1 PHE C 331     -52.651 -36.522 -22.123  1.00 33.01      A   C
ATOM   7468  CE2 PHE C 331     -53.184 -37.586 -24.193  1.00 33.49      A   C
ATOM   7469  CZ  PHE C 331     -53.276 -37.533 -22.817  1.00 33.22      A   C
ATOM   7470  N   LEU C 332     -48.457 -33.030 -25.894  1.00 32.79      A   N
ATOM   7471  CA  LEU C 332     -47.796 -32.067 -26.742  1.00 32.94      A   C
ATOM   7472  C   LEU C 332     -46.660 -32.719 -27.507  1.00 33.39      A   C
ATOM   7473  O   LEU C 332     -46.508 -32.464 -28.691  1.00 33.67      A   O
ATOM   7474  CB  LEU C 332     -47.284 -30.893 -25.913  1.00 32.66      A   C
ATOM   7475  CG  LEU C 332     -46.498 -29.812 -26.636  1.00 32.38      A   C
```

FIGURE 1 (cont'd)

```
ATOM   7476  CD1 LEU C 332     -47.398 -28.750 -27.221  1.00 31.95          A C
ATOM   7477  CD2 LEU C 332     -45.547 -29.215 -25.655  1.00 32.39          A C
ATOM   7478  N   ARG C 333     -45.876 -33.572 -26.850  1.00 33.79          A N
ATOM   7479  CA  ARG C 333     -44.740 -34.230 -27.522  1.00 34.36          A C
ATOM   7480  C   ARG C 333     -45.202 -35.119 -28.686  1.00 34.10          A C
ATOM   7481  O   ARG C 333     -44.434 -35.424 -29.595  1.00 34.45          A O
ATOM   7482  CB  ARG C 333     -43.817 -34.963 -26.524  1.00 34.71          A C
ATOM   7483  CG  ARG C 333     -43.839 -36.492 -26.542  1.00 36.59          A C
ATOM   7484  CD  ARG C 333     -42.608 -37.128 -25.813  1.00 39.90          A C
ATOM   7485  NE  ARG C 333     -42.888 -37.535 -24.425  1.00 42.23          A N
ATOM   7486  CZ  ARG C 333     -43.084 -38.792 -24.013  1.00 42.95          A C
ATOM   7487  NH1 ARG C 333     -43.345 -39.042 -22.730  1.00 42.55          A N
ATOM   7488  NH2 ARG C 333     -43.018 -39.801 -24.873  1.00 43.81          A N
ATOM   7489  N   ARG C 334     -46.476 -35.493 -28.660  1.00 33.56          A N
ATOM   7490  CA  ARG C 334     -47.090 -36.274 -29.725  1.00 33.14          A C
ATOM   7491  C   ARG C 334     -47.825 -35.414 -30.737  1.00 32.65          A C
ATOM   7492  O   ARG C 334     -48.413 -35.923 -31.679  1.00 32.77          A O
ATOM   7493  CB  ARG C 334     -48.035 -37.308 -29.134  1.00 33.15          A C
ATOM   7494  CG  ARG C 334     -47.327 -38.551 -28.652  1.00 33.59          A C
ATOM   7495  CD  ARG C 334     -47.998 -39.094 -27.436  1.00 33.71          A C
ATOM   7496  NE  ARG C 334     -47.542 -40.440 -27.138  1.00 34.74          A N
ATOM   7497  CZ  ARG C 334     -46.739 -40.768 -26.130  1.00 35.53          A C
ATOM   7498  NH1 ARG C 334     -46.279 -39.850 -25.289  1.00 35.20          A N
ATOM   7499  NH2 ARG C 334     -46.400 -42.032 -25.957  1.00 36.56          A N
ATOM   7500  N   GLY C 335     -47.789 -34.106 -30.537  1.00 32.08          A N
ATOM   7501  CA  GLY C 335     -48.307 -33.159 -31.520  1.00 31.46          A C
ATOM   7502  C   GLY C 335     -49.713 -32.647 -31.302  1.00 30.79          A C
ATOM   7503  O   GLY C 335     -50.293 -32.057 -32.200  1.00 31.12          A O
ATOM   7504  N   VAL C 336     -50.267 -32.868 -30.117  1.00 29.92          A N
ATOM   7505  CA  VAL C 336     -51.607 -32.398 -29.801  1.00 29.06          A C
ATOM   7506  C   VAL C 336     -51.564 -30.898 -29.521  1.00 28.66          A C
ATOM   7507  O   VAL C 336     -50.723 -30.439 -28.755  1.00 28.64          A O
ATOM   7508  CB  VAL C 336     -52.183 -33.127 -28.578  1.00 28.87          A C
ATOM   7509  CG1 VAL C 336     -53.557 -32.613 -28.268  1.00 28.80          A C
ATOM   7510  CG2 VAL C 336     -52.230 -34.617 -28.816  1.00 29.00          A C
ATOM   7511  N   PRO C 337     -52.457 -30.124 -30.157  1.00 28.43          A N
ATOM   7512  CA  PRO C 337     -52.573 -28.701 -29.846  1.00 28.17          A C
ATOM   7513  C   PRO C 337     -52.980 -28.535 -28.397  1.00 27.71          A C
ATOM   7514  O   PRO C 337     -53.899 -29.208 -27.932  1.00 27.73          A O
ATOM   7515  CB  PRO C 337     -53.704 -28.232 -30.758  1.00 28.32          A C
ATOM   7516  CG  PRO C 337     -53.732 -29.216 -31.874  1.00 28.73          A C
ATOM   7517  CD  PRO C 337     -53.325 -30.523 -31.276  1.00 28.63          A C
ATOM   7518  N   VAL C 338     -52.289 -27.665 -27.681  1.00 27.24          A N
ATOM   7519  CA  VAL C 338     -52.574 -27.475 -26.263  1.00 26.70          A C
ATOM   7520  C   VAL C 338     -52.972 -26.032 -25.940  1.00 26.56          A C
ATOM   7521  O   VAL C 338     -52.412 -25.081 -26.501  1.00 26.78          A O
ATOM   7522  CB  VAL C 338     -51.372 -27.864 -25.390  1.00 26.58          A C
ATOM   7523  CG1 VAL C 338     -51.677 -27.634 -23.922  1.00 26.34          A C
ATOM   7524  CG2 VAL C 338     -50.972 -29.295 -25.637  1.00 26.57          A C
ATOM   7525  N   LEU C 339     -53.953 -25.877 -25.052  1.00 26.18          A N
ATOM   7526  CA  LEU C 339     -54.222 -24.593 -24.424  1.00 25.91          A C
ATOM   7527  C   LEU C 339     -54.085 -24.754 -22.918  1.00 25.78          A C
ATOM   7528  O   LEU C 339     -54.916 -25.394 -22.277  1.00 25.80          A O
ATOM   7529  CB  LEU C 339     -55.606 -24.057 -24.800  1.00 25.84          A C
ATOM   7530  CG  LEU C 339     -55.948 -22.691 -24.210  1.00 25.67          A C
ATOM   7531  CD1 LEU C 339     -54.896 -21.643 -24.562  1.00 26.02          A C
ATOM   7532  CD2 LEU C 339     -57.288 -22.259 -24.686  1.00 25.48          A C
ATOM   7533  N   HIS C 340     -53.032 -24.171 -22.359  1.00 25.61          A N
ATOM   7534  CA  HIS C 340     -52.681 -24.399 -20.965  1.00 25.38          A C
ATOM   7535  C   HIS C 340     -53.271 -23.314 -20.099  1.00 25.27          A C
ATOM   7536  O   HIS C 340     -52.769 -22.199 -20.057  1.00 25.31          A O
ATOM   7537  CB  HIS C 340     -51.170 -24.442 -20.826  1.00 25.46          A C
ATOM   7538  CG  HIS C 340     -50.690 -25.093 -19.575  1.00 25.60          A C
ATOM   7539  CD2 HIS C 340     -51.330 -25.855 -18.663  1.00 25.64          A C
ATOM   7540  ND1 HIS C 340     -49.387 -24.990 -19.142  1.00 26.00          A N
```

FIGURE 1 (cont'd)

```
ATOM   7541  CE1 HIS C 340     -49.245 -25.667 -18.018  1.00 25.95      A    C
ATOM   7542  NE2 HIS C 340     -50.410 -26.200 -17.704  1.00 25.87      A    N
ATOM   7543  N   LEU C 341     -54.363 -23.646 -19.423  1.00 25.15      A    N
ATOM   7544  CA  LEU C 341     -55.118 -22.679 -18.633  1.00 25.09      A    C
ATOM   7545  C   LEU C 341     -54.691 -22.743 -17.169  1.00 25.05      A    C
ATOM   7546  O   LEU C 341     -55.443 -23.165 -16.302  1.00 25.09      A    O
ATOM   7547  CB  LEU C 341     -56.617 -22.952 -18.780  1.00 25.09      A    C
ATOM   7548  CG  LEU C 341     -57.546 -21.759 -19.000  1.00 25.30      A    C
ATOM   7549  CD1 LEU C 341     -58.990 -22.218 -19.067  1.00 25.55      A    C
ATOM   7550  CD2 LEU C 341     -57.376 -20.706 -17.924  1.00 25.07      A    C
ATOM   7551  N   ILE C 342     -53.463 -22.326 -16.908  1.00 25.12      A    N
ATOM   7552  CA  ILE C 342     -52.873 -22.352 -15.572  1.00 25.17      A    C
ATOM   7553  C   ILE C 342     -52.463 -20.935 -15.209  1.00 25.49      A    C
ATOM   7554  O   ILE C 342     -51.876 -20.222 -16.024  1.00 25.74      A    O
ATOM   7555  CB  ILE C 342     -51.647 -23.303 -15.527  1.00 25.02      A    C
ATOM   7556  CG1 ILE C 342     -51.022 -23.354 -14.137  1.00 24.87      A    C
ATOM   7557  CG2 ILE C 342     -50.592 -22.922 -16.565  1.00 24.99      A    C
ATOM   7558  CD1 ILE C 342     -50.059 -24.519 -13.966  1.00 24.64      A    C
ATOM   7559  N   SER C 343     -52.779 -20.506 -14.000  1.00 25.75      A    N
ATOM   7560  CA  SER C 343     -52.443 -19.144 -13.634  1.00 26.19      A    C
ATOM   7561  C   SER C 343     -50.953 -19.003 -13.404  1.00 26.39      A    C
ATOM   7562  O   SER C 343     -50.342 -19.834 -12.742  1.00 26.33      A    O
ATOM   7563  CB  SER C 343     -53.218 -18.690 -12.407  1.00 26.32      A    C
ATOM   7564  OG  SER C 343     -52.771 -19.362 -11.251  1.00 26.95      A    O
ATOM   7565  N   THR C 344     -50.376 -17.965 -13.999  1.00 26.74      A    N
ATOM   7566  CA  THR C 344     -48.995 -17.573 -13.753  1.00 27.08      A    C
ATOM   7567  C   THR C 344     -49.034 -16.115 -13.305  1.00 27.54      A    C
ATOM   7568  O   THR C 344     -49.462 -15.251 -14.080  1.00 27.67      A    O
ATOM   7569  CB  THR C 344     -48.115 -17.729 -15.001  1.00 26.99      A    C
ATOM   7570  OG1 THR C 344     -48.934 -18.084 -16.119  1.00 26.75      A    O
ATOM   7571  N   PRO C 345     -48.599 -15.829 -12.056  1.00 27.85      A    N
ATOM   7572  CA  PRO C 345     -47.920 -16.722 -11.135  1.00 27.86      A    C
ATOM   7573  C   PRO C 345     -48.851 -17.683 -10.427  1.00 27.67      A    C
ATOM   7574  O   PRO C 345     -50.066 -17.539 -10.502  1.00 27.41      A    O
ATOM   7575  CB  PRO C 345     -47.295 -15.768 -10.114  1.00 28.15      A    C
ATOM   7576  CG  PRO C 345     -47.737 -14.386 -10.489  1.00 28.25      A    C
ATOM   7577  CD  PRO C 345     -48.877 -14.536 -11.417  1.00 28.01      A    C
ATOM   7578  N   PHE C 346     -48.260 -18.668  -9.757  1.00 27.69      A    N
ATOM   7579  CA  PHE C 346     -49.009 -19.662  -9.014  1.00 27.82      A    C
ATOM   7580  C   PHE C 346     -49.700 -18.992  -7.829  1.00 28.03      A    C
ATOM   7581  O   PHE C 346     -49.271 -17.928  -7.389  1.00 28.36      A    O
ATOM   7582  CB  PHE C 346     -48.085 -20.777  -8.530  1.00 27.83      A    C
ATOM   7583  CG  PHE C 346     -47.484 -21.601  -9.627  1.00 27.99      A    C
ATOM   7584  CD1 PHE C 346     -47.977 -21.560 -10.919  1.00 27.80      A    C
ATOM   7585  CD2 PHE C 346     -46.433 -22.456  -9.347  1.00 28.62      A    C
ATOM   7586  CE1 PHE C 346     -47.417 -22.325 -11.911  1.00 27.75      A    C
ATOM   7587  CE2 PHE C 346     -45.871 -23.237 -10.340  1.00 28.48      A    C
ATOM   7588  CZ  PHE C 346     -46.364 -23.163 -11.626  1.00 28.00      A    C
ATOM   7589  N   PRO C 347     -50.777 -19.605  -7.313  1.00 28.02      A    N
ATOM   7590  CA  PRO C 347     -51.485 -19.101  -6.140  1.00 28.38      A    C
ATOM   7591  C   PRO C 347     -50.561 -18.943  -4.950  1.00 29.00      A    C
ATOM   7592  O   PRO C 347     -49.700 -19.782  -4.748  1.00 29.17      A    O
ATOM   7593  CB  PRO C 347     -52.472 -20.219  -5.829  1.00 28.16      A    C
ATOM   7594  CG  PRO C 347     -52.682 -20.896  -7.095  1.00 27.72      A    C
ATOM   7595  CD  PRO C 347     -51.394 -20.835  -7.829  1.00 27.70      A    C
ATOM   7596  N   ALA C 348     -50.741 -17.893  -4.156  1.00 29.70      A    N
ATOM   7597  CA  ALA C 348     -49.904 -17.675  -2.960  1.00 30.34      A    C
ATOM   7598  C   ALA C 348     -49.877 -18.907  -2.065  1.00 30.59      A    C
ATOM   7599  O   ALA C 348     -48.836 -19.260  -1.506  1.00 30.71      A    O
ATOM   7600  CB  ALA C 348     -50.384 -16.464  -2.180  1.00 30.64      A    C
ATOM   7601  N   VAL C 349     -51.031 -19.563  -1.973  1.00 30.69      A    N
ATOM   7602  CA  VAL C 349     -51.221 -20.759  -1.167  1.00 30.88      A    C
ATOM   7603  C   VAL C 349     -50.765 -22.049  -1.853  1.00 30.94      A    C
ATOM   7604  O   VAL C 349     -51.216 -23.135  -1.491  1.00 31.07      A    O
ATOM   7605  CB  VAL C 349     -52.705 -20.915  -0.754  1.00 30.88      A    C
```

FIGURE 1 (cont'd)

```
ATOM   7606  CG1 VAL C 349     -53.138 -19.751   0.120  1.00 31.43      A    C
ATOM   7607  CG2 VAL C 349     -53.620 -21.033  -1.986  1.00 30.49      A    C
ATOM   7608  N   TRP C 350     -49.862 -21.938  -2.820  1.00 31.03      A    N
ATOM   7609  CA  TRP C 350     -49.482 -23.093  -3.634  1.00 31.12      A    C
ATOM   7610  C   TRP C 350     -48.568 -24.054  -2.905  1.00 31.47      A    C
ATOM   7611  O   TRP C 350     -47.615 -23.634  -2.244  1.00 31.72      A    O
ATOM   7612  CB  TRP C 350     -48.828 -22.651  -4.940  1.00 30.92      A    C
ATOM   7613  CG  TRP C 350     -48.548 -23.771  -5.882  1.00 30.49      A    C
ATOM   7614  CD1 TRP C 350     -49.465 -24.527  -6.562  1.00 30.19      A    C
ATOM   7615  CD2 TRP C 350     -47.263 -24.260  -6.263  1.00 30.16      A    C
ATOM   7616  CE2 TRP C 350     -47.472 -25.319  -7.172  1.00 29.90      A    C
ATOM   7617  CE3 TRP C 350     -45.949 -23.908  -5.923  1.00 30.18      A    C
ATOM   7618  NE1 TRP C 350     -48.826 -25.460  -7.336  1.00 29.94      A    N
ATOM   7619  CZ2 TRP C 350     -46.420 -26.032  -7.739  1.00 29.63      A    C
ATOM   7620  CZ3 TRP C 350     -44.905 -24.619  -6.491  1.00 30.00      A    C
ATOM   7621  CH2 TRP C 350     -45.150 -25.670  -7.387  1.00 29.64      A    C
ATOM   7622  N   HIS C 351     -48.871 -25.345  -3.048  1.00 31.78      A    N
ATOM   7623  CA  HIS C 351     -48.102 -26.424  -2.425  1.00 32.35      A    C
ATOM   7624  C   HIS C 351     -47.841 -26.183  -0.932  1.00 32.92      A    C
ATOM   7625  O   HIS C 351     -46.718 -26.329  -0.452  1.00 33.19      A    O
ATOM   7626  CB  HIS C 351     -46.798 -26.682  -3.188  1.00 32.34      A    C
ATOM   7627  CG  HIS C 351     -46.960 -27.547  -4.404  1.00 32.39      A    C
ATOM   7628  CD2 HIS C 351     -48.058 -27.880  -5.123  1.00 32.04      A    C
ATOM   7629  ND1 HIS C 351     -45.900 -28.193  -5.005  1.00 32.53      A    N
ATOM   7630  CE1 HIS C 351     -46.337 -28.877  -6.046  1.00 32.25      A    C
ATOM   7631  NE2 HIS C 351     -47.642 -28.702  -6.142  1.00 31.83      A    N
ATOM   7632  N   THR C 352     -48.900 -25.812  -0.214  1.00 33.36      A    N
ATOM   7633  CA  THR C 352     -48.860 -25.574   1.227  1.00 33.90      A    C
ATOM   7634  C   THR C 352     -50.217 -25.939   1.836  1.00 34.17      A    C
ATOM   7635  O   THR C 352     -51.228 -25.854   1.148  1.00 33.99      A    O
ATOM   7636  CB  THR C 352     -48.482 -24.100   1.551  1.00 34.03      A    C
ATOM   7637  CG2 THR C 352     -49.072 -23.152   0.558  1.00 33.55      A    C
ATOM   7638  OG1 THR C 352     -48.983 -23.733   2.839  1.00 34.81      A    O
ATOM   7639  N   PRO C 353     -50.246 -26.347   3.124  1.00 34.67      A    N
ATOM   7640  CA  PRO C 353     -51.463 -26.624   3.879  1.00 34.76      A    C
ATOM   7641  C   PRO C 353     -52.522 -25.544   3.726  1.00 34.58      A    C
ATOM   7642  O   PRO C 353     -53.699 -25.817   3.927  1.00 34.61      A    O
ATOM   7643  CB  PRO C 353     -50.981 -26.592   5.317  1.00 35.21      A    C
ATOM   7644  CG  PRO C 353     -49.612 -26.992   5.256  1.00 35.52      A    C
ATOM   7645  CD  PRO C 353     -49.055 -26.511   3.970  1.00 34.98      A    C
ATOM   7646  N   ALA C 354     -52.097 -24.330   3.378  1.00 34.31      A    N
ATOM   7647  CA  ALA C 354     -52.993 -23.192   3.166  1.00 34.04      A    C
ATOM   7648  C   ALA C 354     -53.983 -23.365   2.009  1.00 33.78      A    C
ATOM   7649  O   ALA C 354     -55.051 -22.758   2.020  1.00 33.74      A    O
ATOM   7650  CB  ALA C 354     -52.187 -21.930   2.980  1.00 34.06      A    C
ATOM   7651  N   ASP C 355     -53.629 -24.189   1.023  1.00 33.54      A    N
ATOM   7652  CA  ASP C 355     -54.493 -24.465  -0.121  1.00 33.30      A    C
ATOM   7653  C   ASP C 355     -55.704 -25.315   0.273  1.00 33.46      A    C
ATOM   7654  O   ASP C 355     -55.758 -26.509   0.007  1.00 33.34      A    O
ATOM   7655  CB  ASP C 355     -53.691 -25.142  -1.235  1.00 33.02      A    C
ATOM   7656  CG  ASP C 355     -54.400 -25.114  -2.577  1.00 32.53      A    C
ATOM   7657  OD1 ASP C 355     -55.571 -24.668  -2.650  1.00 32.73      A    O
ATOM   7658  OD2 ASP C 355     -53.770 -25.541  -3.569  1.00 31.66      A    O
ATOM   7659  N   THR C 356     -56.673 -24.673   0.910  1.00 33.73      A    N
ATOM   7660  CA  THR C 356     -57.907 -25.314   1.322  1.00 33.94      A    C
ATOM   7661  C   THR C 356     -59.090 -24.472   0.867  1.00 34.40      A    C
ATOM   7662  O   THR C 356     -58.903 -23.376   0.342  1.00 34.34      A    O
ATOM   7663  CB  THR C 356     -57.963 -25.492   2.850  1.00 33.37      A    C
ATOM   7664  OG1 THR C 356     -57.856 -24.219   3.503  1.00 33.32      A    O
ATOM   7665  N   GLU C 357     -60.303 -24.986   1.075  1.00 35.01      A    N
ATOM   7666  CA  GLU C 357     -61.543 -24.304   0.684  1.00 35.52      A    C
ATOM   7667  C   GLU C 357     -61.585 -22.853   1.185  1.00 35.89      A    C
ATOM   7668  O   GLU C 357     -61.955 -21.934   0.449  1.00 35.81      A    O
ATOM   7669  CB  GLU C 357     -62.753 -25.098   1.198  1.00 35.73      A    C
ATOM   7670  CG  GLU C 357     -64.129 -24.466   0.906  1.00 36.38      A    C
```

FIGURE 1 (cont'd)

```
ATOM   7671  CD   GLU C 357     -65.326 -25.352   1.286  1.00 37.42      A    C
ATOM   7672  OE1  GLU C 357     -65.135 -26.496   1.767  1.00 38.18      A    O
ATOM   7673  OE2  GLU C 357     -66.470 -24.896   1.089  1.00 37.72      A    O
ATOM   7674  N    VAL C 358     -61.176 -22.665   2.438  1.00 36.43      A    N
ATOM   7675  CA   VAL C 358     -61.206 -21.370   3.121  1.00 36.84      A    C
ATOM   7676  C    VAL C 358     -60.542 -20.239   2.335  1.00 36.65      A    C
ATOM   7677  O    VAL C 358     -60.895 -19.074   2.530  1.00 36.89      A    O
ATOM   7678  CB   VAL C 358     -60.541 -21.469   4.525  1.00 37.18      A    C
ATOM   7679  CG1  VAL C 358     -61.516 -21.047   5.606  1.00 37.97      A    C
ATOM   7680  N    ASN C 359     -59.597 -20.586   1.453  1.00 36.24      A    N
ATOM   7681  CA   ASN C 359     -58.742 -19.595   0.787  1.00 35.91      A    C
ATOM   7682  C    ASN C 359     -59.018 -19.393  -0.697  1.00 35.33      A    C
ATOM   7683  O    ASN C 359     -58.282 -18.687  -1.380  1.00 35.23      A    O
ATOM   7684  CB   ASN C 359     -57.263 -19.922   1.004  1.00 36.12      A    C
ATOM   7685  CG   ASN C 359     -56.812 -19.719   2.441  1.00 37.10      A    C
ATOM   7686  ND2  ASN C 359     -57.673 -19.149   3.276  1.00 38.07      A    N
ATOM   7687  OD1  ASN C 359     -55.688 -20.071   2.790  1.00 37.71      A    O
ATOM   7688  N    LEU C 360     -60.076 -20.019  -1.191  1.00 34.81      A    N
ATOM   7689  CA   LEU C 360     -60.546 -19.778  -2.545  1.00 34.32      A    C
ATOM   7690  C    LEU C 360     -61.368 -18.491  -2.574  1.00 34.37      A    C
ATOM   7691  O    LEU C 360     -61.888 -18.066  -1.548  1.00 34.86      A    O
ATOM   7692  CB   LEU C 360     -61.404 -20.950  -3.026  1.00 34.03      A    C
ATOM   7693  CG   LEU C 360     -60.830 -22.363  -2.925  1.00 33.48      A    C
ATOM   7694  CD1  LEU C 360     -61.865 -23.407  -3.338  1.00 32.89      A    C
ATOM   7695  CD2  LEU C 360     -59.557 -22.477  -3.750  1.00 33.10      A    C
ATOM   7696  N    HIS C 361     -61.475 -17.869  -3.744  1.00 34.07      A    N
ATOM   7697  CA   HIS C 361     -62.335 -16.710  -3.938  1.00 33.88      A    C
ATOM   7698  C    HIS C 361     -63.550 -17.180  -4.711  1.00 34.19      A    C
ATOM   7699  O    HIS C 361     -63.522 -17.195  -5.941  1.00 34.00      A    O
ATOM   7700  CB   HIS C 361     -61.602 -15.633  -4.739  1.00 33.55      A    C
ATOM   7701  CG   HIS C 361     -62.131 -14.242  -4.543  1.00 32.71      A    C
ATOM   7702  CD2  HIS C 361     -61.555 -13.144  -3.994  1.00 31.96      A    C
ATOM   7703  ND1  HIS C 361     -63.358 -13.833  -5.018  1.00 31.52      A    N
ATOM   7704  CE1  HIS C 361     -63.543 -12.563  -4.708  1.00 31.57      A    C
ATOM   7705  NE2  HIS C 361     -62.456 -12.116  -4.105  1.00 31.59      A    N
ATOM   7706  N    PRO C 362     -64.625 -17.575  -3.994  1.00 34.69      A    N
ATOM   7707  CA   PRO C 362     -65.820 -18.129  -4.637  1.00 34.87      A    C
ATOM   7708  C    PRO C 362     -66.306 -17.349  -5.861  1.00 34.85      A    C
ATOM   7709  O    PRO C 362     -66.631 -17.975  -6.867  1.00 34.76      A    O
ATOM   7710  CB   PRO C 362     -66.856 -18.119  -3.518  1.00 35.17      A    C
ATOM   7711  CG   PRO C 362     -66.041 -18.298  -2.295  1.00 35.29      A    C
ATOM   7712  CD   PRO C 362     -64.780 -17.530  -2.528  1.00 34.99      A    C
ATOM   7713  N    PRO C 363     -66.330 -16.000  -5.802  1.00 34.97      A    N
ATOM   7714  CA   PRO C 363     -66.680 -15.245  -7.000  1.00 34.98      A    C
ATOM   7715  C    PRO C 363     -65.796 -15.604  -8.182  1.00 34.63      A    C
ATOM   7716  O    PRO C 363     -66.307 -16.002  -9.225  1.00 34.57      A    O
ATOM   7717  CB   PRO C 363     -66.438 -13.802  -6.573  1.00 35.26      A    C
ATOM   7718  CG   PRO C 363     -66.754 -13.806  -5.158  1.00 35.68      A    C
ATOM   7719  CD   PRO C 363     -66.125 -15.086  -4.668  1.00 35.03      A    C
ATOM   7720  N    THR C 364     -64.484 -15.499  -8.000  1.00 34.30      A    N
ATOM   7721  CA   THR C 364     -63.538 -15.823  -9.059  1.00 33.94      A    C
ATOM   7722  C    THR C 364     -63.833 -17.192  -9.649  1.00 33.82      A    C
ATOM   7723  O    THR C 364     -63.777 -17.372 -10.854  1.00 33.67      A    O
ATOM   7724  CB   THR C 364     -62.073 -15.746  -8.571  1.00 33.85      A    C
ATOM   7725  CG2  THR C 364     -61.116 -15.999  -9.716  1.00 33.51      A    C
ATOM   7726  OG1  THR C 364     -61.805 -14.446  -8.029  1.00 34.08      A    O
ATOM   7727  N    VAL C 365     -64.170 -18.148  -8.798  1.00 33.93      A    N
ATOM   7728  CA   VAL C 365     -64.485 -19.489  -9.255  1.00 34.06      A    C
ATOM   7729  C    VAL C 365     -65.662 -19.481 -10.218  1.00 34.26      A    C
ATOM   7730  O    VAL C 365     -65.566 -20.017 -11.321  1.00 34.10      A    O
ATOM   7731  CB   VAL C 365     -64.776 -20.440  -8.085  1.00 34.12      A    C
ATOM   7732  CG1  VAL C 365     -63.502 -20.737  -7.304  1.00 34.01      A    C
ATOM   7733  CG2  VAL C 365     -65.414 -21.738  -8.584  1.00 33.97      A    C
ATOM   7734  N    HIS C 366     -66.761 -18.860  -9.804  1.00 34.67      A    N
ATOM   7735  CA   HIS C 366     -67.970 -18.848 -10.612  1.00 35.15      A    C
```

FIGURE 1 (cont'd)

```
ATOM   7736  C    HIS C 366     -67.791 -18.107 -11.923  1.00 35.35      A   C
ATOM   7737  O    HIS C 366     -68.238 -18.574 -12.972  1.00 35.50      A   O
ATOM   7738  CB   HIS C 366     -69.139 -18.304  -9.819  1.00 35.34      A   C
ATOM   7739  CG   HIS C 366     -69.462 -19.141  -8.634  1.00 35.47      A   C
ATOM   7740  CD2  HIS C 366     -69.384 -18.875  -7.313  1.00 35.29      A   C
ATOM   7741  ND1  HIS C 366     -69.885 -20.449  -8.742  1.00 35.50      A   N
ATOM   7742  CE1  HIS C 366     -70.073 -20.946  -7.534  1.00 35.53      A   C
ATOM   7743  NE2  HIS C 366     -69.781 -20.009  -6.649  1.00 36.00      A   N
ATOM   7744  N    ASN C 367     -67.118 -16.965 -11.864  1.00 35.41      A   N
ATOM   7745  CA   ASN C 367     -66.734 -16.245 -13.069  1.00 35.42      A   C
ATOM   7746  C    ASN C 367     -66.089 -17.183 -14.070  1.00 35.23      A   C
ATOM   7747  O    ASN C 367     -66.507 -17.231 -15.222  1.00 35.37      A   O
ATOM   7748  CB   ASN C 367     -65.761 -15.117 -12.738  1.00 35.50      A   C
ATOM   7749  CG   ASN C 367     -66.414 -13.976 -12.014  1.00 36.12      A   C
ATOM   7750  ND2  ASN C 367     -65.659 -12.910 -11.826  1.00 36.21      A   N
ATOM   7751  OD1  ASN C 367     -67.583 -14.044 -11.622  1.00 37.07      A   O
ATOM   7752  N    LEU C 368     -65.087 -17.941 -13.618  1.00 34.94      A   N
ATOM   7753  CA   LEU C 368     -64.340 -18.841 -14.489  1.00 34.72      A   C
ATOM   7754  C    LEU C 368     -65.250 -19.861 -15.153  1.00 34.88      A   C
ATOM   7755  O    LEU C 368     -65.033 -20.238 -16.303  1.00 35.01      A   O
ATOM   7756  CB   LEU C 368     -63.208 -19.535 -13.728  1.00 34.35      A   C
ATOM   7757  CG   LEU C 368     -61.984 -18.690 -13.354  1.00 33.74      A   C
ATOM   7758  CD1  LEU C 368     -61.074 -19.470 -12.448  1.00 33.47      A   C
ATOM   7759  CD2  LEU C 368     -61.209 -18.222 -14.568  1.00 32.87      A   C
ATOM   7760  N    ALA C 369     -66.280 -20.284 -14.428  1.00 34.16      A   N
ATOM   7761  CA   ALA C 369     -67.224 -21.271 -14.931  1.00 33.51      A   C
ATOM   7762  C    ALA C 369     -68.136 -20.676 -15.985  1.00 34.48      A   C
ATOM   7763  O    ALA C 369     -68.453 -21.321 -16.978  1.00 35.68      A   O
ATOM   7764  CB   ALA C 369     -68.033 -21.848 -13.797  1.00 24.53      A   C
ATOM   7765  N    ARG C 370     -68.558 -19.441 -15.763  1.00 35.14      A   N
ATOM   7766  CA   ARG C 370     -69.385 -18.739 -16.727  1.00 34.79      A   C
ATOM   7767  C    ARG C 370     -68.594 -18.579 -18.018  1.00 34.19      A   C
ATOM   7768  O    ARG C 370     -69.097 -18.882 -19.087  1.00 34.08      A   O
ATOM   7769  CB   ARG C 370     -69.867 -17.399 -16.154  1.00 35.11      A   C
ATOM   7770  CG   ARG C 370     -70.835 -17.546 -14.962  1.00 35.41      A   C
ATOM   7771  CD   ARG C 370     -71.313 -16.206 -14.441  1.00 35.73      A   C
ATOM   7772  NE   ARG C 370     -72.285 -16.335 -13.359  1.00 35.84      A   N
ATOM   7773  CZ   ARG C 370     -73.429 -15.661 -13.294  1.00 36.04      A   C
ATOM   7774  NH1  ARG C 370     -73.788 -14.850 -14.281  1.00 36.97      A   N
ATOM   7775  NH2  ARG C 370     -74.247 -15.849 -12.270  1.00 36.40      A   N
ATOM   7776  N    ILE C 371     -67.337 -18.156 -17.899  1.00 33.47      A   N
ATOM   7777  CA   ILE C 371     -66.450 -17.986 -19.050  1.00 32.84      A   C
ATOM   7778  C    ILE C 371     -66.248 -19.308 -19.776  1.00 32.78      A   C
ATOM   7779  O    ILE C 371     -66.367 -19.358 -20.993  1.00 32.89      A   O
ATOM   7780  CB   ILE C 371     -65.086 -17.369 -18.655  1.00 32.52      A   C
ATOM   7781  CG1  ILE C 371     -65.274 -15.922 -18.202  1.00 32.47      A   C
ATOM   7782  CG2  ILE C 371     -64.111 -17.427 -19.818  1.00 32.02      A   C
ATOM   7783  CD1  ILE C 371     -64.075 -15.308 -17.542  1.00 32.20      A   C
ATOM   7784  N    LEU C 372     -65.967 -20.377 -19.030  1.00 32.61      A   N
ATOM   7785  CA   LEU C 372     -65.764 -21.710 -19.614  1.00 32.44      A   C
ATOM   7786  C    LEU C 372     -67.012 -22.252 -20.291  1.00 32.75      A   C
ATOM   7787  O    LEU C 372     -66.932 -22.755 -21.404  1.00 32.71      A   O
ATOM   7788  CB   LEU C 372     -65.272 -22.699 -18.559  1.00 32.09      A   C
ATOM   7789  CG   LEU C 372     -63.786 -23.057 -18.460  1.00 31.33      A   C
ATOM   7790  CD1  LEU C 372     -62.858 -22.124 -19.230  1.00 30.82      A   C
ATOM   7791  CD2  LEU C 372     -63.383 -23.170 -17.008  1.00 30.86      A   C
ATOM   7792  N    ALA C 373     -68.157 -22.131 -19.622  1.00 33.16      A   N
ATOM   7793  CA   ALA C 373     -69.426 -22.621 -20.151  1.00 33.55      A   C
ATOM   7794  C    ALA C 373     -69.766 -21.974 -21.483  1.00 33.84      A   C
ATOM   7795  O    ALA C 373     -70.250 -22.637 -22.392  1.00 34.03      A   O
ATOM   7796  CB   ALA C 373     -70.538 -22.401 -19.161  1.00 33.68      A   C
ATOM   7797  N    VAL C 374     -69.506 -20.679 -21.597  1.00 34.00      A   N
ATOM   7798  CA   VAL C 374     -69.727 -19.975 -22.847  1.00 34.26      A   C
ATOM   7799  C    VAL C 374     -68.767 -20.515 -23.877  1.00 34.16      A   C
ATOM   7800  O    VAL C 374     -69.171 -20.872 -24.974  1.00 34.47      A   O
```

FIGURE 1 (cont'd)

```
ATOM   7801  CB   VAL C 374     -69.548 -18.452 -22.690  1.00 34.35      A   C
ATOM   7802  CG1  VAL C 374     -69.456 -17.762 -24.040  1.00 34.56      A   C
ATOM   7803  CG2  VAL C 374     -70.702 -17.872 -21.891  1.00 34.82      A   C
ATOM   7804  N    PHE C 375     -67.497 -20.597 -23.509  1.00 33.89      A   N
ATOM   7805  CA   PHE C 375     -66.475 -21.093 -24.415  1.00 33.75      A   C
ATOM   7806  C    PHE C 375     -66.847 -22.463 -24.941  1.00 34.06      A   C
ATOM   7807  O    PHE C 375     -66.848 -22.691 -26.144  1.00 34.17      A   O
ATOM   7808  CB   PHE C 375     -65.116 -21.154 -23.720  1.00 33.32      A   C
ATOM   7809  CG   PHE C 375     -64.014 -21.690 -24.585  1.00 32.60      A   C
ATOM   7810  CD1  PHE C 375     -63.082 -20.833 -25.157  1.00 32.45      A   C
ATOM   7811  CD2  PHE C 375     -63.900 -23.053 -24.821  1.00 32.08      A   C
ATOM   7812  CE1  PHE C 375     -62.056 -21.320 -25.947  1.00 32.37      A   C
ATOM   7813  CE2  PHE C 375     -62.886 -23.549 -25.617  1.00 32.24      A   C
ATOM   7814  CZ   PHE C 375     -61.959 -22.677 -26.183  1.00 32.33      A   C
ATOM   7815  N    LEU C 376     -67.165 -23.371 -24.031  1.00 34.41      A   N
ATOM   7816  CA   LEU C 376     -67.505 -24.728 -24.396  1.00 34.86      A   C
ATOM   7817  C    LEU C 376     -68.624 -24.694 -25.430  1.00 35.65      A   C
ATOM   7818  O    LEU C 376     -68.546 -25.357 -26.456  1.00 35.78      A   O
ATOM   7819  CB   LEU C 376     -67.915 -25.525 -23.156  1.00 34.51      A   C
ATOM   7820  CG   LEU C 376     -67.465 -26.974 -23.012  1.00 33.80      A   C
ATOM   7821  CD1  LEU C 376     -68.324 -27.628 -21.971  1.00 32.42      A   C
ATOM   7822  CD2  LEU C 376     -67.584 -27.743 -24.296  1.00 33.84      A   C
ATOM   7823  N    ALA C 377     -69.639 -23.880 -25.164  1.00 36.56      A   N
ATOM   7824  CA   ALA C 377     -70.806 -23.766 -26.030  1.00 37.43      A   C
ATOM   7825  C    ALA C 377     -70.441 -23.184 -27.380  1.00 37.89      A   C
ATOM   7826  O    ALA C 377     -70.863 -23.701 -28.400  1.00 38.22      A   O
ATOM   7827  CB   ALA C 377     -71.899 -22.936 -25.364  1.00 37.60      A   C
ATOM   7828  N    GLU C 378     -69.658 -22.112 -27.388  1.00 38.20      A   N
ATOM   7829  CA   GLU C 378     -69.229 -21.504 -28.646  1.00 38.63      A   C
ATOM   7830  C    GLU C 378     -68.364 -22.469 -29.479  1.00 38.63      A   C
ATOM   7831  O    GLU C 378     -68.636 -22.663 -30.666  1.00 38.92      A   O
ATOM   7832  CB   GLU C 378     -68.526 -20.161 -28.416  1.00 38.69      A   C
ATOM   7833  CG   GLU C 378     -69.490 -19.006 -28.115  1.00 39.89      A   C
ATOM   7834  CD   GLU C 378     -68.844 -17.604 -28.121  1.00 41.29      A   C
ATOM   7835  OE1  GLU C 378     -67.654 -17.461 -28.479  1.00 41.80      A   O
ATOM   7836  OE2  GLU C 378     -69.535 -16.624 -27.768  1.00 41.92      A   O
ATOM   7837  N    TYR C 379     -67.359 -23.092 -28.848  1.00 38.47      A   N
ATOM   7838  CA   TYR C 379     -66.442 -24.031 -29.528  1.00 38.41      A   C
ATOM   7839  C    TYR C 379     -67.183 -25.194 -30.184  1.00 38.95      A   C
ATOM   7840  O    TYR C 379     -66.912 -25.548 -31.318  1.00 39.08      A   O
ATOM   7841  CB   TYR C 379     -65.374 -24.566 -28.559  1.00 37.81      A   C
ATOM   7842  CG   TYR C 379     -64.264 -25.352 -29.229  1.00 37.03      A   C
ATOM   7843  CD1  TYR C 379     -63.018 -24.778 -29.464  1.00 36.34      A   C
ATOM   7844  CD2  TYR C 379     -64.457 -26.671 -29.630  1.00 36.81      A   C
ATOM   7845  CE1  TYR C 379     -61.986 -25.503 -30.090  1.00 36.17      A   C
ATOM   7846  CE2  TYR C 379     -63.438 -27.400 -30.260  1.00 36.53      A   C
ATOM   7847  CZ   TYR C 379     -62.204 -26.810 -30.485  1.00 36.19      A   C
ATOM   7848  OH   TYR C 379     -61.192 -27.514 -31.104  1.00 35.87      A   O
ATOM   7849  N    LEU C 380     -68.119 -25.783 -29.463  1.00 39.63      A   N
ATOM   7850  CA   LEU C 380     -68.879 -26.913 -29.975  1.00 40.42      A   C
ATOM   7851  C    LEU C 380     -70.170 -26.491 -30.668  1.00 41.20      A   C
ATOM   7852  O    LEU C 380     -70.981 -27.348 -31.025  1.00 41.78      A   O
ATOM   7853  CB   LEU C 380     -69.217 -27.871 -28.829  1.00 40.17      A   C
ATOM   7854  CG   LEU C 380     -68.432 -29.155 -28.637  1.00 39.73      A   C
ATOM   7855  CD1  LEU C 380     -66.981 -28.987 -29.034  1.00 39.38      A   C
ATOM   7856  CD2  LEU C 380     -68.565 -29.592 -27.193  1.00 39.47      A   C
ATOM   7857  N    GLY C 381     -70.369 -25.181 -30.826  1.00 39.17      A   N
ATOM   7858  CA   GLY C 381     -71.609 -24.627 -31.404  1.00 37.62      A   C
ATOM   7859  C    GLY C 381     -72.934 -25.086 -30.793  1.00 36.63      A   C
ATOM   7860  O    GLY C 381     -73.886 -25.397 -31.511  1.00 36.07      A   O
ATOM   7861  N    LEU C 382     -72.995 -25.117 -29.463  1.00 36.28      A   N
ATOM   7862  CA   LEU C 382     -74.172 -25.599 -28.735  1.00 36.08      A   C
ATOM   7863  C    LEU C 382     -75.207 -24.498 -28.555  1.00 36.15      A   C
ATOM   7864  O    LEU C 382     -76.249 -24.716 -27.937  1.00 36.24      A   O
ATOM   7865  CB   LEU C 382     -73.771 -26.181 -27.372  1.00 35.83      A   C
```

FIGURE 1 (cont'd)

```
ATOM   7866  CG   LEU C 382     -72.706 -27.283 -27.347  1.00 35.43       A  C
ATOM   7867  CD1  LEU C 382     -72.361 -27.658 -25.929  1.00 34.83       A  C
ATOM   7868  CD2  LEU C 382     -73.153 -28.510 -28.119  1.00 35.80       A  C
ATOM   7869  OXT  LEU C 382     -75.026 -23.373 -29.029  1.00 36.19       A  O
TER    7870       LEU C 382
ATOM   7871  N    SER D  75     -41.255 -80.597  -3.238  1.00 37.47       A  N
ATOM   7872  CA   SER D  75     -41.454 -81.917  -3.903  1.00 38.14       A  C
ATOM   7873  C    SER D  75     -42.940 -82.275  -3.903  1.00 39.89       A  C
ATOM   7874  O    SER D  75     -43.446 -82.782  -2.901  1.00 40.22       A  O
ATOM   7875  CB   SER D  75     -40.662 -82.999  -3.165  1.00 37.26       A  C
ATOM   7876  OG   SER D  75     -39.447 -82.492  -2.645  1.00 36.51       A  O
ATOM   7877  N    LEU D  76     -43.638 -82.007  -5.009  1.00 42.57       A  N
ATOM   7878  CA   LEU D  76     -45.105 -82.164  -5.080  1.00 45.65       A  C
ATOM   7879  C    LEU D  76     -45.535 -83.631  -5.030  1.00 49.31       A  C
ATOM   7880  O    LEU D  76     -44.891 -84.470  -5.675  1.00 49.41       A  O
ATOM   7881  CB   LEU D  76     -45.652 -81.555  -6.382  1.00 44.87       A  C
ATOM   7882  CG   LEU D  76     -46.057 -80.095  -6.623  1.00 43.08       A  C
ATOM   7883  CD1  LEU D  76     -46.279 -79.910  -8.101  1.00 41.52       A  C
ATOM   7884  CD2  LEU D  76     -47.312 -79.705  -5.866  1.00 42.27       A  C
ATOM   7885  N    PRO D  77     -46.631 -83.949  -4.292  1.00 54.16       A  N
ATOM   7886  CA   PRO D  77     -47.143 -85.330  -4.327  1.00 55.35       A  C
ATOM   7887  C    PRO D  77     -47.979 -85.626  -5.571  1.00 55.72       A  C
ATOM   7888  O    PRO D  77     -48.622 -84.729  -6.112  1.00 55.65       A  O
ATOM   7889  CB   PRO D  77     -48.008 -85.419  -3.073  1.00 56.06       A  C
ATOM   7890  CG   PRO D  77     -48.478 -84.029  -2.840  1.00 55.90       A  C
ATOM   7891  CD   PRO D  77     -47.440 -83.086  -3.408  1.00 54.79       A  C
ATOM   7892  N    GLU D  78     -47.969 -86.886  -5.999  1.00 55.90       A  N
ATOM   7893  CA   GLU D  78     -48.618 -87.318  -7.241  1.00 55.78       A  C
ATOM   7894  C    GLU D  78     -50.006 -86.726  -7.488  1.00 57.05       A  C
ATOM   7895  O    GLU D  78     -50.312 -86.278  -8.602  1.00 57.26       A  O
ATOM   7896  CB   GLU D  78     -48.687 -88.844  -7.311  1.00 53.79       A  C
ATOM   7897  CG   GLU D  78     -47.586 -89.463  -8.140  1.00 51.28       A  C
ATOM   7898  CD   GLU D  78     -48.005 -90.756  -8.776  1.00 51.38       A  C
ATOM   7899  OE1  GLU D  78     -49.009 -90.755  -9.519  1.00 51.48       A  O
ATOM   7900  OE2  GLU D  78     -47.318 -91.772  -8.552  1.00 51.32       A  O
ATOM   7901  N    ALA D  79     -50.838 -86.736  -6.449  1.00 58.29       A  N
ATOM   7902  CA   ALA D  79     -52.218 -86.255  -6.541  1.00 58.94       A  C
ATOM   7903  C    ALA D  79     -52.310 -84.807  -7.036  1.00 58.70       A  C
ATOM   7904  O    ALA D  79     -53.072 -84.510  -7.960  1.00 58.83       A  O
ATOM   7905  CB   ALA D  79     -52.921 -86.413  -5.195  1.00 59.76       A  C
ATOM   7906  N    ARG D  80     -51.525 -83.922  -6.417  1.00 57.99       A  N
ATOM   7907  CA   ARG D  80     -51.471 -82.510  -6.801  1.00 56.99       A  C
ATOM   7908  C    ARG D  80     -50.743 -82.343  -8.129  1.00 56.72       A  C
ATOM   7909  O    ARG D  80     -51.145 -81.538  -8.960  1.00 56.76       A  O
ATOM   7910  CB   ARG D  80     -50.806 -81.652  -5.710  1.00 55.30       A  C
ATOM   7911  N    LEU D  81     -49.681 -83.116  -8.328  1.00 56.41       A  N
ATOM   7912  CA   LEU D  81     -48.896 -83.035  -9.547  1.00 55.84       A  C
ATOM   7913  C    LEU D  81     -49.764 -83.316 -10.770  1.00 55.89       A  C
ATOM   7914  O    LEU D  81     -49.799 -82.523 -11.704  1.00 55.52       A  O
ATOM   7915  CB   LEU D  81     -47.714 -83.998  -9.475  1.00 55.64       A  C
ATOM   7916  CG   LEU D  81     -46.657 -83.916 -10.570  1.00 54.87       A  C
ATOM   7917  CD1  LEU D  81     -45.306 -84.252  -9.982  1.00 54.69       A  C
ATOM   7918  CD2  LEU D  81     -46.987 -84.831 -11.740  1.00 54.75       A  C
ATOM   7919  N    ARG D  82     -50.475 -84.439 -10.745  1.00 56.34       A  N
ATOM   7920  CA   ARG D  82     -51.319 -84.839 -11.864  1.00 56.77       A  C
ATOM   7921  C    ARG D  82     -52.471 -83.854 -12.062  1.00 56.69       A  C
ATOM   7922  O    ARG D  82     -52.933 -83.640 -13.184  1.00 56.67       A  O
ATOM   7923  CB   ARG D  82     -51.833 -86.273 -11.672  1.00 57.35       A  C
ATOM   7924  CG   ARG D  82     -52.398 -86.907 -12.948  1.00 58.28       A  C
ATOM   7925  CD   ARG D  82     -52.546 -88.420 -12.832  1.00 59.66       A  C
ATOM   7926  NE   ARG D  82     -51.400 -89.147 -13.382  1.00 59.76       A  N
ATOM   7927  CZ   ARG D  82     -50.360 -89.574 -12.671  1.00 59.79       A  C
ATOM   7928  NH1  ARG D  82     -50.297 -89.348 -11.365  1.00 59.97       A  N
ATOM   7929  NH2  ARG D  82     -49.379 -90.227 -13.274  1.00 59.56       A  N
ATOM   7930  N    ARG D  83     -52.918 -83.252 -10.964  1.00 56.46       A  N
```

FIGURE 1 (cont'd)

```
ATOM   7931  CA   ARG D  83     -53.961 -82.221 -10.985  1.00 55.93      A  C
ATOM   7932  C    ARG D  83     -53.449 -80.928 -11.637  1.00 55.51      A  C
ATOM   7933  O    ARG D  83     -54.176 -80.271 -12.385  1.00 55.68      A  O
ATOM   7934  CB   ARG D  83     -54.483 -81.993  -9.554  1.00 54.94      A  C
ATOM   7935  CG   ARG D  83     -55.018 -80.608  -9.205  1.00 54.46      A  C
ATOM   7936  CD   ARG D  83     -55.034 -80.470  -7.690  1.00 54.57      A  C
ATOM   7937  NE   ARG D  83     -55.346 -79.125  -7.230  1.00 54.04      A  N
ATOM   7938  N    VAL D  84     -52.189 -80.593 -11.360  1.00 54.73      A  N
ATOM   7939  CA   VAL D  84     -51.540 -79.389 -11.893  1.00 53.63      A  C
ATOM   7940  C    VAL D  84     -51.216 -79.560 -13.371  1.00 52.96      A  C
ATOM   7941  O    VAL D  84     -51.619 -78.736 -14.181  1.00 52.77      A  O
ATOM   7942  CB   VAL D  84     -50.269 -78.992 -11.066  1.00 53.50      A  C
ATOM   7943  CG1  VAL D  84     -50.667 -78.380  -9.734  1.00 53.54      A  C
ATOM   7944  CG2  VAL D  84     -49.383 -78.020 -11.831  1.00 52.78      A  C
ATOM   7945  N    VAL D  85     -50.502 -80.634 -13.711  1.00 52.17      A  N
ATOM   7946  CA   VAL D  85     -50.175 -80.951 -15.101  1.00 51.35      A  C
ATOM   7947  C    VAL D  85     -51.444 -81.027 -15.929  1.00 51.75      A  C
ATOM   7948  O    VAL D  85     -51.415 -80.785 -17.133  1.00 51.92      A  O
ATOM   7949  CB   VAL D  85     -49.412 -82.277 -15.233  1.00 49.78      A  C
ATOM   7950  N    GLY D  86     -52.554 -81.348 -15.263  1.00 52.08      A  N
ATOM   7951  CA   GLY D  86     -53.881 -81.389 -15.888  1.00 52.04      A  C
ATOM   7952  C    GLY D  86     -54.495 -80.023 -16.148  1.00 51.64      A  C
ATOM   7953  O    GLY D  86     -55.385 -79.880 -16.986  1.00 51.85      A  O
ATOM   7954  N    GLN D  87     -54.014 -79.014 -15.430  1.00 50.99      A  N
ATOM   7955  CA   GLN D  87     -54.536 -77.660 -15.565  1.00 50.20      A  C
ATOM   7956  C    GLN D  87     -54.019 -76.914 -16.793  1.00 49.56      A  C
ATOM   7957  O    GLN D  87     -54.595 -75.907 -17.193  1.00 49.51      A  O
ATOM   7958  N    LEU D  88     -52.944 -77.417 -17.392  1.00 48.72      A  N
ATOM   7959  CA   LEU D  88     -52.422 -76.862 -18.633  1.00 48.04      A  C
ATOM   7960  C    LEU D  88     -53.337 -77.298 -19.768  1.00 48.41      A  C
ATOM   7961  O    LEU D  88     -53.628 -78.488 -19.883  1.00 48.64      A  O
ATOM   7962  CB   LEU D  88     -50.992 -77.367 -18.899  1.00 47.34      A  C
ATOM   7963  CG   LEU D  88     -49.823 -76.909 -18.020  1.00 45.94      A  C
ATOM   7964  N    ASP D  89     -53.804 -76.343 -20.584  1.00 48.74      A  N
ATOM   7965  CA   ASP D  89     -54.602 -76.647 -21.797  1.00 49.13      A  C
ATOM   7966  C    ASP D  89     -53.749 -76.529 -23.060  1.00 49.19      A  C
ATOM   7967  O    ASP D  89     -53.427 -75.417 -23.478  1.00 48.98      A  O
ATOM   7968  CB   ASP D  89     -55.858 -75.763 -21.911  1.00 49.28      A  C
ATOM   7969  CG   ASP D  89     -56.694 -76.087 -23.139  1.00 49.42      A  C
ATOM   7970  N    PRO D  90     -53.379 -77.680 -23.666  1.00 49.44      A  N
ATOM   7971  CA   PRO D  90     -52.476 -77.730 -24.820  1.00 49.34      A  C
ATOM   7972  C    PRO D  90     -52.957 -76.914 -26.013  1.00 49.28      A  C
ATOM   7973  O    PRO D  90     -52.151 -76.223 -26.644  1.00 49.01      A  O
ATOM   7974  CB   PRO D  90     -52.431 -79.221 -25.167  1.00 49.47      A  C
ATOM   7975  CG   PRO D  90     -52.696 -79.904 -23.875  1.00 49.76      A  C
ATOM   7976  CD   PRO D  90     -53.730 -79.039 -23.207  1.00 49.80      A  C
ATOM   7977  N    GLN D  91     -54.251 -76.981 -26.317  1.00 49.46      A  N
ATOM   7978  CA   GLN D  91     -54.781 -76.197 -27.435  1.00 49.56      A  C
ATOM   7979  C    GLN D  91     -54.871 -74.703 -27.103  1.00 48.99      A  C
ATOM   7980  O    GLN D  91     -54.792 -73.874 -28.005  1.00 49.05      A  O
ATOM   7981  CB   GLN D  91     -56.108 -76.762 -27.983  1.00 50.16      A  C
ATOM   7982  CG   GLN D  91     -57.374 -76.335 -27.248  1.00 50.94      A  C
ATOM   7983  N    ARG D  92     -55.019 -74.372 -25.817  1.00 48.15      A  N
ATOM   7984  CA   ARG D  92     -54.964 -72.977 -25.352  1.00 47.12      A  C
ATOM   7985  C    ARG D  92     -53.567 -72.369 -25.570  1.00 46.67      A  C
ATOM   7986  O    ARG D  92     -53.436 -71.273 -26.133  1.00 46.55      A  O
ATOM   7987  CB   ARG D  92     -55.387 -72.879 -23.878  1.00 46.95      A  C
ATOM   7988  CG   ARG D  92     -55.144 -71.524 -23.218  1.00 45.16      A  C
ATOM   7989  CD   ARG D  92     -55.692 -71.459 -21.800  1.00 43.07      A  C
ATOM   7990  NE   ARG D  92     -55.184 -72.507 -20.923  1.00 41.72      A  N
ATOM   7991  CZ   ARG D  92     -54.309 -72.321 -19.945  1.00 40.62      A  C
ATOM   7992  NH1  ARG D  92     -53.791 -71.126 -19.745  1.00 40.79      A  N
ATOM   7993  NH2  ARG D  92     -53.920 -73.340 -19.187  1.00 40.23      A  N
ATOM   7994  N    LEU D  93     -52.538 -73.098 -25.128  1.00 46.08      A  N
ATOM   7995  CA   LEU D  93     -51.141 -72.716 -25.309  1.00 45.43      A  C
```

FIGURE 1 (cont'd)

```
ATOM   7996  C   LEU D  93     -50.904 -72.360 -26.761  1.00 45.50      A  C
ATOM   7997  O   LEU D  93     -50.433 -71.269 -27.073  1.00 45.40      A  O
ATOM   7998  CB  LEU D  93     -50.237 -73.882 -24.915  1.00 45.06      A  C
ATOM   7999  CG  LEU D  93     -48.838 -73.667 -24.345  1.00 43.89      A  C
ATOM   8000  CD1 LEU D  93     -48.089 -72.538 -25.010  1.00 42.75      A  C
ATOM   8001  N   TRP D  94     -51.280 -73.283 -27.642  1.00 45.70      A  N
ATOM   8002  CA  TRP D  94     -51.010 -73.179 -29.076  1.00 45.76      A  C
ATOM   8003  C   TRP D  94     -51.847 -72.124 -29.818  1.00 45.73      A  C
ATOM   8004  O   TRP D  94     -51.348 -71.447 -30.716  1.00 45.62      A  O
ATOM   8005  CB  TRP D  94     -51.183 -74.548 -29.746  1.00 45.95      A  C
ATOM   8006  CG  TRP D  94     -50.349 -74.680 -30.975  1.00 46.42      A  C
ATOM   8007  CD1 TRP D  94     -50.678 -74.280 -32.240  1.00 47.11      A  C
ATOM   8008  CD2 TRP D  94     -49.028 -75.222 -31.057  1.00 46.47      A  C
ATOM   8009  CE2 TRP D  94     -48.620 -75.129 -32.407  1.00 46.70      A  C
ATOM   8010  CE3 TRP D  94     -48.152 -75.786 -30.123  1.00 46.25      A  C
ATOM   8011  NE1 TRP D  94     -49.646 -74.552 -33.106  1.00 47.07      A  N
ATOM   8012  CZ2 TRP D  94     -47.372 -75.579 -32.847  1.00 46.60      A  C
ATOM   8013  CZ3 TRP D  94     -46.908 -76.228 -30.560  1.00 46.16      A  C
ATOM   8014  CH2 TRP D  94     -46.531 -76.121 -31.911  1.00 46.32      A  C
ATOM   8015  N   SER D  95     -53.114 -71.990 -29.437  1.00 45.77      A  N
ATOM   8016  CA  SER D  95     -54.066 -71.203 -30.213  1.00 45.75      A  C
ATOM   8017  C   SER D  95     -54.319 -69.819 -29.629  1.00 45.18      A  C
ATOM   8018  O   SER D  95     -54.307 -68.825 -30.364  1.00 45.14      A  O
ATOM   8019  CB  SER D  95     -55.384 -71.965 -30.366  1.00 46.26      A  C
ATOM   8020  OG  SER D  95     -55.871 -71.882 -31.692  1.00 47.18      A  O
ATOM   8021  N   THR D  96     -54.553 -69.756 -28.318  1.00 44.46      A  N
ATOM   8022  CA  THR D  96     -54.813 -68.477 -27.645  1.00 43.82      A  C
ATOM   8023  C   THR D  96     -53.544 -67.641 -27.434  1.00 42.92      A  C
ATOM   8024  O   THR D  96     -53.606 -66.404 -27.472  1.00 43.02      A  O
ATOM   8025  CB  THR D  96     -55.509 -68.653 -26.273  1.00 44.00      A  C
ATOM   8026  OG1 THR D  96     -56.364 -69.798 -26.308  1.00 44.73      A  O
ATOM   8027  N   TYR D  97     -52.407 -68.314 -27.223  1.00 41.63      A  N
ATOM   8028  CA  TYR D  97     -51.166 -67.633 -26.845  1.00 40.22      A  C
ATOM   8029  C   TYR D  97     -50.043 -67.665 -27.877  1.00 39.82      A  C
ATOM   8030  O   TYR D  97     -49.380 -66.650 -28.078  1.00 39.61      A  O
ATOM   8031  CB  TYR D  97     -50.673 -68.142 -25.490  1.00 39.68      A  C
ATOM   8032  CG  TYR D  97     -51.715 -67.992 -24.408  1.00 38.68      A  C
ATOM   8033  CD1 TYR D  97     -52.284 -66.754 -24.135  1.00 37.62      A  C
ATOM   8034  CD2 TYR D  97     -52.170 -69.086 -23.688  1.00 37.80      A  C
ATOM   8035  CE1 TYR D  97     -53.244 -66.600 -23.152  1.00 37.43      A  C
ATOM   8036  CE2 TYR D  97     -53.141 -68.938 -22.700  1.00 36.87      A  C
ATOM   8037  CZ  TYR D  97     -53.673 -67.689 -22.445  1.00 36.43      A  C
ATOM   8038  OH  TYR D  97     -54.633 -67.514 -21.476  1.00 36.08      A  O
ATOM   8039  N   LEU D  98     -49.824 -68.808 -28.527  1.00 39.59      A  N
ATOM   8040  CA  LEU D  98     -48.719 -68.924 -29.494  1.00 39.44      A  C
ATOM   8041  C   LEU D  98     -48.995 -68.299 -30.862  1.00 39.68      A  C
ATOM   8042  O   LEU D  98     -48.227 -67.462 -31.325  1.00 39.59      A  O
ATOM   8043  CB  LEU D  98     -48.270 -70.370 -29.675  1.00 39.24      A  C
ATOM   8044  CG  LEU D  98     -47.137 -70.543 -30.690  1.00 38.98      A  C
ATOM   8045  CD1 LEU D  98     -45.872 -69.838 -30.247  1.00 38.40      A  C
ATOM   8046  CD2 LEU D  98     -46.864 -72.009 -30.922  1.00 39.16      A  C
ATOM   8047  N   ARG D  99     -50.075 -68.729 -31.511  1.00 40.02      A  N
ATOM   8048  CA  ARG D  99     -50.425 -68.245 -32.845  1.00 40.07      A  C
ATOM   8049  C   ARG D  99     -50.587 -66.736 -32.947  1.00 40.20      A  C
ATOM   8050  O   ARG D  99     -50.096 -66.158 -33.902  1.00 40.35      A  O
ATOM   8051  CB  ARG D  99     -51.638 -68.984 -33.422  1.00 39.54      A  C
ATOM   8052  CG  ARG D  99     -51.260 -69.977 -34.522  1.00 39.42      A  C
ATOM   8053  CD  ARG D  99     -52.471 -70.631 -35.206  1.00 39.92      A  C
ATOM   8054  NE  ARG D  99     -52.614 -72.047 -34.869  1.00 39.59      A  N
ATOM   8055  N   PRO D 100     -51.256 -66.088 -31.968  1.00 40.21      A  N
ATOM   8056  CA  PRO D 100     -51.296 -64.625 -32.007  1.00 40.13      A  C
ATOM   8057  C   PRO D 100     -49.906 -63.980 -32.040  1.00 39.77      A  C
ATOM   8058  O   PRO D 100     -49.739 -62.913 -32.640  1.00 39.99      A  O
ATOM   8059  CB  PRO D 100     -52.012 -64.257 -30.703  1.00 40.24      A  C
ATOM   8060  CG  PRO D 100     -52.875 -65.412 -30.424  1.00 40.47      A  C
```

FIGURE 1 (cont'd)

```
ATOM   8061  CD  PRO D 100     -52.102 -66.613 -30.878  1.00 40.33      A  C
ATOM   8062  N   LEU D 101     -48.925 -64.633 -31.413  1.00 39.14      A  N
ATOM   8063  CA  LEU D 101     -47.553 -64.122 -31.314  1.00 38.51      A  C
ATOM   8064  C   LEU D 101     -46.730 -64.260 -32.600  1.00 38.45      A  C
ATOM   8065  O   LEU D 101     -45.722 -63.569 -32.770  1.00 38.33      A  O
ATOM   8066  CB  LEU D 101     -46.820 -64.808 -30.158  1.00 38.09      A  C
ATOM   8067  CG  LEU D 101     -46.687 -64.093 -28.812  1.00 37.77      A  C
ATOM   8068  CD1 LEU D 101     -47.924 -63.297 -28.427  1.00 38.21      A  C
ATOM   8069  CD2 LEU D 101     -46.344 -65.092 -27.726  1.00 37.49      A  C
ATOM   8070  N   LEU D 102     -47.166 -65.131 -33.504  1.00 38.51      A  N
ATOM   8071  CA  LEU D 102     -46.380 -65.472 -34.688  1.00 38.58      A  C
ATOM   8072  C   LEU D 102     -46.531 -64.490 -35.858  1.00 38.93      A  C
ATOM   8073  O   LEU D 102     -46.901 -64.886 -36.970  1.00 39.23      A  O
ATOM   8074  CB  LEU D 102     -46.701 -66.902 -35.130  1.00 38.52      A  C
ATOM   8075  CG  LEU D 102     -46.275 -68.019 -34.178  1.00 38.07      A  C
ATOM   8076  CD1 LEU D 102     -46.816 -69.353 -34.654  1.00 38.24      A  C
ATOM   8077  CD2 LEU D 102     -44.764 -68.068 -34.047  1.00 37.53      A  C
ATOM   8078  N   VAL D 103     -46.236 -63.215 -35.604  1.00 39.07      A  N
ATOM   8079  CA  VAL D 103     -46.257 -62.177 -36.646  1.00 39.39      A  C
ATOM   8080  C   VAL D 103     -44.953 -61.395 -36.641  1.00 39.11      A  C
ATOM   8081  O   VAL D 103     -44.268 -61.348 -35.617  1.00 38.84      A  O
ATOM   8082  CB  VAL D 103     -47.434 -61.174 -36.485  1.00 39.72      A  C
ATOM   8083  CG1 VAL D 103     -47.509 -60.640 -35.062  1.00 39.59      A  C
ATOM   8084  CG2 VAL D 103     -48.762 -61.807 -36.903  1.00 40.65      A  C
ATOM   8085  N   VAL D 104     -44.612 -60.786 -37.780  1.00 39.05      A  N
ATOM   8086  CA  VAL D 104     -43.438 -59.923 -37.861  1.00 38.72      A  C
ATOM   8087  C   VAL D 104     -43.598 -58.827 -36.814  1.00 38.92      A  C
ATOM   8088  O   VAL D 104     -44.646 -58.189 -36.734  1.00 39.23      A  O
ATOM   8089  CB  VAL D 104     -43.267 -59.320 -39.257  1.00 38.03      A  C
ATOM   8090  CG1 VAL D 104     -41.801 -59.060 -39.536  1.00 37.47      A  C
ATOM   8091  N   ARG D 105     -42.568 -58.639 -35.995  1.00 38.77      A  N
ATOM   8092  CA  ARG D 105     -42.681 -57.790 -34.804  1.00 38.53      A  C
ATOM   8093  C   ARG D 105     -41.370 -57.108 -34.385  1.00 38.50      A  C
ATOM   8094  O   ARG D 105     -41.119 -56.874 -33.199  1.00 38.21      A  O
ATOM   8095  CB  ARG D 105     -43.282 -58.594 -33.636  1.00 38.36      A  C
ATOM   8096  CG  ARG D 105     -42.440 -59.777 -33.161  1.00 37.71      A  C
ATOM   8097  CD  ARG D 105     -43.279 -60.796 -32.423  1.00 37.36      A  C
ATOM   8098  NE  ARG D 105     -42.434 -61.813 -31.815  1.00 36.97      A  N
ATOM   8099  CZ  ARG D 105     -42.175 -62.999 -32.350  1.00 36.78      A  C
ATOM   8100  NH1 ARG D 105     -42.700 -63.346 -33.518  1.00 36.92      A  N
ATOM   8101  NH2 ARG D 105     -41.388 -63.847 -31.706  1.00 36.41      A  N
ATOM   8102  N   THR D 106     -40.549 -56.782 -35.374  1.00 38.70      A  N
ATOM   8103  CA  THR D 106     -39.306 -56.070 -35.145  1.00 38.93      A  C
ATOM   8104  C   THR D 106     -39.575 -54.771 -34.370  1.00 38.98      A  C
ATOM   8105  O   THR D 106     -40.644 -54.195 -34.517  1.00 38.98      A  O
ATOM   8106  CB  THR D 106     -38.602 -55.778 -36.479  1.00 39.11      A  C
ATOM   8107  OG1 THR D 106     -39.439 -54.948 -37.282  1.00 39.78      A  O
ATOM   8108  N   PRO D 107     -38.610 -54.321 -33.533  1.00 39.10      A  N
ATOM   8109  CA  PRO D 107     -38.798 -53.178 -32.634  1.00 39.37      A  C
ATOM   8110  C   PRO D 107     -39.472 -51.996 -33.288  1.00 39.91      A  C
ATOM   8111  O   PRO D 107     -39.153 -51.658 -34.421  1.00 40.08      A  O
ATOM   8112  CB  PRO D 107     -37.370 -52.814 -32.235  1.00 39.28      A  C
ATOM   8113  CG  PRO D 107     -36.648 -54.118 -32.234  1.00 38.88      A  C
ATOM   8114  CD  PRO D 107     -37.284 -54.946 -33.331  1.00 38.98      A  C
ATOM   8115  N   GLY D 108     -40.420 -51.401 -32.569  1.00 40.37      A  N
ATOM   8116  CA  GLY D 108     -41.136 -50.205 -33.015  1.00 41.00      A  C
ATOM   8117  C   GLY D 108     -41.946 -50.310 -34.302  1.00 41.35      A  C
ATOM   8118  O   GLY D 108     -42.285 -49.298 -34.915  1.00 41.85      A  O
ATOM   8119  N   SER D 109     -42.252 -51.529 -34.723  1.00 41.33      A  N
ATOM   8120  CA  SER D 109     -43.130 -51.753 -35.870  1.00 41.38      A  C
ATOM   8121  C   SER D 109     -44.588 -51.872 -35.399  1.00 41.59      A  C
ATOM   8122  O   SER D 109     -44.848 -51.849 -34.182  1.00 41.38      A  O
ATOM   8123  CB  SER D 109     -42.708 -53.018 -36.623  1.00 41.24      A  C
ATOM   8124  OG  SER D 109     -42.914 -54.189 -35.846  1.00 40.64      A  O
ATOM   8125  N   PRO D 110     -45.546 -51.982 -36.349  1.00 41.94      A  N
```

FIGURE 1 (cont'd)

```
ATOM   8126  CA   PRO D 110     -46.940 -52.257 -35.986  1.00 41.87      A  C
ATOM   8127  C    PRO D 110     -47.112 -53.597 -35.275  1.00 41.31      A  C
ATOM   8128  O    PRO D 110     -47.872 -53.684 -34.305  1.00 41.13      A  O
ATOM   8129  CB   PRO D 110     -47.651 -52.279 -37.333  1.00 42.30      A  C
ATOM   8130  CG   PRO D 110     -46.841 -51.390 -38.180  1.00 42.77      A  C
ATOM   8131  CD   PRO D 110     -45.426 -51.640 -37.776  1.00 42.32      A  C
ATOM   8132  N    GLY D 111     -46.403 -54.623 -35.749  1.00 40.82      A  N
ATOM   8133  CA   GLY D 111     -46.416 -55.947 -35.111  1.00 40.15      A  C
ATOM   8134  C    GLY D 111     -45.908 -55.954 -33.675  1.00 39.59      A  C
ATOM   8135  O    GLY D 111     -46.525 -56.549 -32.786  1.00 39.39      A  O
ATOM   8136  N    ASN D 112     -44.774 -55.286 -33.460  1.00 39.18      A  N
ATOM   8137  CA   ASN D 112     -44.186 -55.115 -32.135  1.00 38.59      A  C
ATOM   8138  C    ASN D 112     -45.221 -54.533 -31.201  1.00 38.82      A  C
ATOM   8139  O    ASN D 112     -45.403 -55.039 -30.103  1.00 38.67      A  O
ATOM   8140  CB   ASN D 112     -42.928 -54.230 -32.190  1.00 38.29      A  C
ATOM   8141  CG   ASN D 112     -42.248 -54.073 -30.838  1.00 37.14      A  C
ATOM   8142  N    LEU D 113     -45.922 -53.495 -31.650  1.00 39.27      A  N
ATOM   8143  CA   LEU D 113     -46.929 -52.855 -30.817  1.00 39.74      A  C
ATOM   8144  C    LEU D 113     -48.179 -53.717 -30.679  1.00 39.78      A  C
ATOM   8145  O    LEU D 113     -48.793 -53.758 -29.613  1.00 39.74      A  O
ATOM   8146  CB   LEU D 113     -47.269 -51.466 -31.351  1.00 40.17      A  C
ATOM   8147  CG   LEU D 113     -47.916 -50.461 -30.384  1.00 40.91      A  C
ATOM   8148  CD1  LEU D 113     -47.405 -49.029 -30.634  1.00 41.47      A  C
ATOM   8149  CD2  LEU D 113     -49.443 -50.513 -30.451  1.00 41.77      A  C
ATOM   8150  N    GLN D 114     -48.545 -54.412 -31.750  1.00 39.88      A  N
ATOM   8151  CA   GLN D 114     -49.704 -55.301 -31.724  1.00 39.89      A  C
ATOM   8152  C    GLN D 114     -49.497 -56.421 -30.702  1.00 39.63      A  C
ATOM   8153  O    GLN D 114     -50.404 -56.715 -29.910  1.00 39.71      A  O
ATOM   8154  CB   GLN D 114     -49.962 -55.866 -33.118  1.00 40.04      A  C
ATOM   8155  CG   GLN D 114     -51.249 -56.626 -33.294  1.00 39.61      A  C
ATOM   8156  CD   GLN D 114     -51.349 -57.188 -34.690  1.00 39.14      A  C
ATOM   8157  NE2  GLN D 114     -51.481 -56.301 -35.673  1.00 38.53      A  N
ATOM   8158  OE1  GLN D 114     -51.276 -58.406 -34.893  1.00 39.54      A  O
ATOM   8159  N    VAL D 115     -48.301 -57.019 -30.715  1.00 39.04      A  N
ATOM   8160  CA   VAL D 115     -47.949 -58.085 -29.772  1.00 38.38      A  C
ATOM   8161  C    VAL D 115     -47.926 -57.557 -28.345  1.00 38.62      A  C
ATOM   8162  O    VAL D 115     -48.579 -58.106 -27.465  1.00 38.81      A  O
ATOM   8163  CB   VAL D 115     -46.604 -58.759 -30.112  1.00 36.87      A  C
ATOM   8164  N    ARG D 116     -47.197 -56.466 -28.137  1.00 38.85      A  N
ATOM   8165  CA   ARG D 116     -47.117 -55.779 -26.833  1.00 39.09      A  C
ATOM   8166  C    ARG D 116     -48.489 -55.557 -26.202  1.00 39.50      A  C
ATOM   8167  O    ARG D 116     -48.685 -55.796 -25.011  1.00 39.47      A  O
ATOM   8168  CB   ARG D 116     -46.393 -54.433 -26.990  1.00 38.99      A  C
ATOM   8169  CG   ARG D 116     -46.333 -53.570 -25.740  1.00 39.22      A  C
ATOM   8170  CD   ARG D 116     -45.750 -52.207 -26.057  1.00 40.25      A  C
ATOM   8171  NE   ARG D 116     -44.442 -52.314 -26.700  1.00 40.89      A  N
ATOM   8172  CZ   ARG D 116     -43.846 -51.326 -27.366  1.00 41.49      A  C
ATOM   8173  NH1  ARG D 116     -44.432 -50.143 -27.483  1.00 41.94      A  N
ATOM   8174  NH2  ARG D 116     -42.656 -51.523 -27.924  1.00 41.68      A  N
ATOM   8175  N    LYS D 117     -49.424 -55.095 -27.023  1.00 40.08      A  N
ATOM   8176  CA   LYS D 117     -50.785 -54.823 -26.598  1.00 40.55      A  C
ATOM   8177  C    LYS D 117     -51.484 -56.122 -26.195  1.00 40.18      A  C
ATOM   8178  O    LYS D 117     -52.227 -56.147 -25.215  1.00 40.27      A  O
ATOM   8179  CB   LYS D 117     -51.549 -54.102 -27.715  1.00 41.13      A  C
ATOM   8180  CG   LYS D 117     -52.763 -53.321 -27.243  1.00 42.50      A  C
ATOM   8181  CD   LYS D 117     -53.372 -52.485 -28.362  1.00 43.84      A  C
ATOM   8182  CE   LYS D 117     -52.785 -51.096 -28.394  1.00 44.08      A  C
ATOM   8183  N    PHE D 118     -51.227 -57.194 -26.942  1.00 39.56      A  N
ATOM   8184  CA   PHE D 118     -51.823 -58.500 -26.652  1.00 38.94      A  C
ATOM   8185  C    PHE D 118     -51.313 -59.076 -25.333  1.00 39.18      A  C
ATOM   8186  O    PHE D 118     -52.077 -59.690 -24.574  1.00 39.40      A  O
ATOM   8187  CB   PHE D 118     -51.585 -59.494 -27.801  1.00 37.67      A  C
ATOM   8188  CG   PHE D 118     -52.017 -60.901 -27.485  1.00 36.14      A  C
ATOM   8189  CD1  PHE D 118     -53.351 -61.186 -27.196  1.00 35.84      A  C
ATOM   8190  CD2  PHE D 118     -51.090 -61.937 -27.477  1.00 34.59      A  C
```

FIGURE 1 (cont'd)

```
ATOM   8191  CE1 PHE D 118     -53.754 -62.470 -26.899  1.00 35.47      A    C
ATOM   8192  CE2 PHE D 118     -51.481 -63.231 -27.187  1.00 33.90      A    C
ATOM   8193  CZ  PHE D 118     -52.817 -63.495 -26.893  1.00 34.75      A    C
ATOM   8194  N   LEU D 119     -50.024 -58.882 -25.069  1.00 39.19      A    N
ATOM   8195  CA  LEU D 119     -49.434 -59.332 -23.814  1.00 39.19      A    C
ATOM   8196  C   LEU D 119     -50.062 -58.581 -22.635  1.00 39.70      A    C
ATOM   8197  O   LEU D 119     -50.626 -59.212 -21.746  1.00 39.83      A    O
ATOM   8198  CB  LEU D 119     -47.906 -59.217 -23.842  1.00 38.74      A    C
ATOM   8199  CG  LEU D 119     -47.209 -60.349 -24.604  1.00 37.93      A    C
ATOM   8200  CD1 LEU D 119     -45.781 -59.968 -24.925  1.00 37.43      A    C
ATOM   8201  N   GLU D 120     -50.009 -57.246 -22.661  1.00 40.18      A    N
ATOM   8202  CA  GLU D 120     -50.646 -56.403 -21.638  1.00 40.59      A    C
ATOM   8203  C   GLU D 120     -52.051 -56.872 -21.284  1.00 41.27      A    C
ATOM   8204  O   GLU D 120     -52.371 -57.056 -20.120  1.00 41.54      A    O
ATOM   8205  CB  GLU D 120     -50.725 -54.948 -22.101  1.00 39.85      A    C
ATOM   8206  CG  GLU D 120     -49.413 -54.171 -22.083  1.00 39.53      A    C
ATOM   8207  CD  GLU D 120     -49.630 -52.688 -22.371  1.00 40.12      A    C
ATOM   8208  OE1 GLU D 120     -50.219 -51.990 -21.506  1.00 40.85      A    O
ATOM   8209  OE2 GLU D 120     -49.230 -52.227 -23.475  1.00 41.05      A    O
ATOM   8210  N   ALA D 121     -52.879 -57.064 -22.305  1.00 41.84      A    N
ATOM   8211  CA  ALA D 121     -54.269 -57.470 -22.126  1.00 42.21      A    C
ATOM   8212  C   ALA D 121     -54.406 -58.857 -21.500  1.00 42.13      A    C
ATOM   8213  O   ALA D 121     -55.124 -59.008 -20.522  1.00 42.47      A    O
ATOM   8214  CB  ALA D 121     -55.026 -57.394 -23.449  1.00 42.55      A    C
ATOM   8215  N   THR D 122     -53.716 -59.857 -22.048  1.00 41.53      A    N
ATOM   8216  CA  THR D 122     -53.788 -61.216 -21.517  1.00 40.88      A    C
ATOM   8217  C   THR D 122     -53.424 -61.252 -20.036  1.00 41.31      A    C
ATOM   8218  O   THR D 122     -54.146 -61.837 -19.232  1.00 41.69      A    O
ATOM   8219  CB  THR D 122     -52.885 -62.179 -22.294  1.00 39.44      A    C
ATOM   8220  OG1 THR D 122     -53.435 -62.400 -23.596  1.00 38.52      A    O
ATOM   8221  N   LEU D 123     -52.319 -60.596 -19.683  1.00 41.42      A    N
ATOM   8222  CA  LEU D 123     -51.816 -60.557 -18.305  1.00 41.46      A    C
ATOM   8223  C   LEU D 123     -52.813 -59.891 -17.361  1.00 42.14      A    C
ATOM   8224  O   LEU D 123     -53.043 -60.376 -16.253  1.00 42.38      A    O
ATOM   8225  CB  LEU D 123     -50.451 -59.853 -18.233  1.00 40.98      A    C
ATOM   8226  CG  LEU D 123     -49.209 -60.555 -18.784  1.00 39.80      A    C
ATOM   8227  CD1 LEU D 123     -48.631 -61.496 -17.787  1.00 39.15      A    C
ATOM   8228  CD2 LEU D 123     -49.506 -61.329 -20.040  1.00 39.73      A    C
ATOM   8229  N   ARG D 124     -53.411 -58.789 -17.810  1.00 42.76      A    N
ATOM   8230  CA  ARG D 124     -54.392 -58.056 -17.009  1.00 43.41      A    C
ATOM   8231  C   ARG D 124     -55.663 -58.866 -16.774  1.00 44.05      A    C
ATOM   8232  O   ARG D 124     -56.244 -58.812 -15.699  1.00 44.40      A    O
ATOM   8233  CB  ARG D 124     -54.713 -56.701 -17.645  1.00 43.37      A    C
ATOM   8234  CG  ARG D 124     -53.650 -55.671 -17.361  1.00 42.80      A    C
ATOM   8235  CD  ARG D 124     -54.031 -54.269 -17.819  1.00 42.39      A    C
ATOM   8236  NE  ARG D 124     -52.943 -53.298 -17.592  1.00 41.55      A    N
ATOM   8237  CZ  ARG D 124     -52.466 -52.907 -16.400  1.00 39.63      A    C
ATOM   8238  NH1 ARG D 124     -52.954 -53.386 -15.254  1.00 38.09      A    N
ATOM   8239  NH2 ARG D 124     -51.480 -52.019 -16.361  1.00 39.20      A    N
ATOM   8240  N   SER D 125     -56.057 -59.648 -17.774  1.00 44.56      A    N
ATOM   8241  CA  SER D 125     -57.308 -60.404 -17.740  1.00 45.12      A    C
ATOM   8242  C   SER D 125     -57.250 -61.653 -16.876  1.00 45.23      A    C
ATOM   8243  O   SER D 125     -58.122 -62.508 -16.980  1.00 45.57      A    O
ATOM   8244  CB  SER D 125     -57.749 -60.785 -19.163  1.00 45.29      A    C
ATOM   8245  OG  SER D 125     -56.919 -61.793 -19.719  1.00 44.94      A    O
ATOM   8246  N   LEU D 126     -56.234 -61.763 -16.030  1.00 45.11      A    N
ATOM   8247  CA  LEU D 126     -56.097 -62.934 -15.166  1.00 45.12      A    C
ATOM   8248  C   LEU D 126     -56.764 -62.736 -13.807  1.00 45.64      A    C
ATOM   8249  O   LEU D 126     -56.837 -61.619 -13.314  1.00 45.89      A    O
ATOM   8250  CB  LEU D 126     -54.627 -63.325 -14.999  1.00 44.60      A    C
ATOM   8251  CG  LEU D 126     -53.862 -63.820 -16.230  1.00 43.78      A    C
ATOM   8252  CD1 LEU D 126     -52.599 -64.566 -15.811  1.00 42.94      A    C
ATOM   8253  CD2 LEU D 126     -54.725 -64.710 -17.092  1.00 43.54      A    C
ATOM   8254  N   THR D 127     -57.239 -63.829 -13.213  1.00 46.14      A    N
ATOM   8255  CA  THR D 127     -58.031 -63.781 -11.980  1.00 46.63      A    C
```

FIGURE 1 (cont'd)

```
ATOM   8256  C    THR D 127     -57.255 -63.228 -10.794  1.00 46.68      A  C
ATOM   8257  O    THR D 127     -57.783 -62.418 -10.036  1.00 47.17      A  O
ATOM   8258  CB   THR D 127     -58.616 -65.156 -11.598  1.00 46.85      A  C
ATOM   8259  OG1  THR D 127     -58.977 -65.874 -12.784  1.00 47.07      A  O
ATOM   8260  N    ALA D 128     -56.013 -63.672 -10.622  1.00 46.31      A  N
ATOM   8261  CA   ALA D 128     -55.121 -63.043  -9.655  1.00 46.09      A  C
ATOM   8262  C    ALA D 128     -54.819 -61.635 -10.161  1.00 45.99      A  C
ATOM   8263  O    ALA D 128     -54.745 -61.415 -11.371  1.00 45.96      A  O
ATOM   8264  CB   ALA D 128     -53.860 -63.844  -9.509  1.00 45.78      A  C
ATOM   8265  N    GLY D 129     -54.666 -60.679  -9.254  1.00 45.96      A  N
ATOM   8266  CA   GLY D 129     -54.524 -59.287  -9.668  1.00 45.75      A  C
ATOM   8267  C    GLY D 129     -53.132 -58.903 -10.146  1.00 45.17      A  C
ATOM   8268  O    GLY D 129     -52.410 -58.210  -9.431  1.00 45.55      A  O
ATOM   8269  N    TRP D 130     -52.753 -59.326 -11.354  1.00 44.28      A  N
ATOM   8270  CA   TRP D 130     -51.416 -59.035 -11.884  1.00 43.26      A  C
ATOM   8271  C    TRP D 130     -51.203 -57.521 -12.058  1.00 42.98      A  C
ATOM   8272  O    TRP D 130     -52.033 -56.848 -12.663  1.00 43.18      A  O
ATOM   8273  CB   TRP D 130     -51.189 -59.767 -13.213  1.00 42.89      A  C
ATOM   8274  CG   TRP D 130     -50.820 -61.224 -13.087  1.00 42.40      A  C
ATOM   8275  CD1  TRP D 130     -51.671 -62.293 -13.099  1.00 42.62      A  C
ATOM   8276  CD2  TRP D 130     -49.498 -61.772 -12.957  1.00 41.97      A  C
ATOM   8277  CE2  TRP D 130     -49.631 -63.181 -12.886  1.00 41.84      A  C
ATOM   8278  CE3  TRP D 130     -48.216 -61.211 -12.892  1.00 41.72      A  C
ATOM   8279  NE1  TRP D 130     -50.966 -63.472 -12.971  1.00 42.23      A  N
ATOM   8280  CZ2  TRP D 130     -48.530 -64.033 -12.749  1.00 41.35      A  C
ATOM   8281  CZ3  TRP D 130     -47.123 -62.060 -12.759  1.00 41.34      A  C
ATOM   8282  CH2  TRP D 130     -47.290 -63.456 -12.688  1.00 41.12      A  C
ATOM   8283  N    HIS D 131     -50.117 -56.983 -11.500  1.00 42.56      A  N
ATOM   8284  CA   HIS D 131     -49.696 -55.596 -11.782  1.00 42.31      A  C
ATOM   8285  C    HIS D 131     -48.909 -55.522 -13.058  1.00 41.89      A  C
ATOM   8286  O    HIS D 131     -47.676 -55.554 -13.034  1.00 41.66      A  O
ATOM   8287  CB   HIS D 131     -48.739 -55.056 -10.749  1.00 42.48      A  C
ATOM   8288  CG   HIS D 131     -49.394 -54.356  -9.643  1.00 42.87      A  C
ATOM   8289  CD2  HIS D 131     -49.156 -53.201  -8.980  1.00 43.03      A  C
ATOM   8290  ND1  HIS D 131     -50.373 -55.014  -8.917  1.00 42.12      A  N
ATOM   8291  CE1  HIS D 131     -50.773 -54.254  -7.916  1.00 41.62      A  C
ATOM   8292  NE2  HIS D 131     -50.057 -53.143  -7.934  1.00 42.51      A  N
ATOM   8293  N    VAL D 132     -49.612 -55.408 -14.171  1.00 41.65      A  N
ATOM   8294  CA   VAL D 132     -48.977 -55.282 -15.461  1.00 41.28      A  C
ATOM   8295  C    VAL D 132     -48.539 -53.840 -15.679  1.00 41.33      A  C
ATOM   8296  O    VAL D 132     -49.258 -52.904 -15.332  1.00 41.61      A  O
ATOM   8297  CB   VAL D 132     -49.920 -55.711 -16.563  1.00 41.26      A  C
ATOM   8298  CG1  VAL D 132     -49.148 -56.396 -17.652  1.00 41.01      A  C
ATOM   8299  N    GLU D 133     -47.354 -53.663 -16.252  1.00 41.20      A  N
ATOM   8300  CA   GLU D 133     -46.717 -52.348 -16.310  1.00 41.40      A  C
ATOM   8301  C    GLU D 133     -45.738 -52.220 -17.467  1.00 41.12      A  C
ATOM   8302  O    GLU D 133     -44.822 -53.021 -17.595  1.00 40.98      A  O
ATOM   8303  CB   GLU D 133     -45.982 -52.083 -15.004  1.00 41.62      A  C
ATOM   8304  CG   GLU D 133     -45.294 -50.733 -14.921  1.00 42.99      A  C
ATOM   8305  CD   GLU D 133     -44.517 -50.569 -13.626  1.00 44.72      A  C
ATOM   8306  OE1  GLU D 133     -45.096 -50.867 -12.545  1.00 45.55      A  O
ATOM   8307  OE2  GLU D 133     -43.336 -50.145 -13.692  1.00 45.11      A  O
ATOM   8308  N    LEU D 134     -45.936 -51.195 -18.291  1.00 41.04      A  N
ATOM   8309  CA   LEU D 134     -45.094 -50.936 -19.453  1.00 40.72      A  C
ATOM   8310  C    LEU D 134     -43.837 -50.167 -19.069  1.00 40.50      A  C
ATOM   8311  O    LEU D 134     -43.855 -49.378 -18.127  1.00 40.68      A  O
ATOM   8312  CB   LEU D 134     -45.875 -50.137 -20.501  1.00 40.92      A  C
ATOM   8313  CG   LEU D 134     -46.348 -50.804 -21.788  1.00 41.07      A  C
ATOM   8314  CD1  LEU D 134     -47.410 -49.951 -22.461  1.00 41.93      A  C
ATOM   8315  CD2  LEU D 134     -45.139 -50.879 -22.706  1.00 40.51      A  C
ATOM   8316  N    ASP D 135     -42.750 -50.407 -19.803  1.00 40.05      A  N
ATOM   8317  CA   ASP D 135     -41.509 -49.650 -19.655  1.00 39.80      A  C
ATOM   8318  C    ASP D 135     -41.122 -49.070 -21.012  1.00 39.73      A  C
ATOM   8319  O    ASP D 135     -40.286 -49.629 -21.718  1.00 39.71      A  O
ATOM   8320  CB   ASP D 135     -40.391 -50.547 -19.114  1.00 39.61      A  C
```

FIGURE 1 (cont'd)

```
ATOM   8321  CG   ASP D 135     -39.049 -49.831 -19.022  1.00 39.83      A    C
ATOM   8322  OD1  ASP D 135     -39.041 -48.656 -18.635  1.00 40.63      A    O
ATOM   8323  OD2  ASP D 135     -37.998 -50.435 -19.331  1.00 39.52      A    O
ATOM   8324  N    PRO D 136     -41.744 -47.949 -21.396  1.00 39.74      A    N
ATOM   8325  CA   PRO D 136     -41.426 -47.356 -22.692  1.00 40.02      A    C
ATOM   8326  C    PRO D 136     -40.126 -46.576 -22.610  1.00 40.62      A    C
ATOM   8327  O    PRO D 136     -39.778 -46.091 -21.533  1.00 40.86      A    O
ATOM   8328  CB   PRO D 136     -42.594 -46.390 -22.948  1.00 39.28      A    C
ATOM   8329  CG   PRO D 136     -43.481 -46.461 -21.715  1.00 38.95      A    C
ATOM   8330  CD   PRO D 136     -42.684 -47.115 -20.635  1.00 39.55      A    C
ATOM   8331  N    PHE D 137     -39.410 -46.473 -23.731  1.00 41.11      A    N
ATOM   8332  CA   PHE D 137     -38.198 -45.652 -23.823  1.00 41.57      A    C
ATOM   8333  C    PHE D 137     -37.685 -45.575 -25.237  1.00 42.02      A    C
ATOM   8334  O    PHE D 137     -37.938 -46.459 -26.045  1.00 42.00      A    O
ATOM   8335  CB   PHE D 137     -37.083 -46.155 -22.894  1.00 41.43      A    C
ATOM   8336  CG   PHE D 137     -36.467 -47.456 -23.315  1.00 41.09      A    C
ATOM   8337  CD1  PHE D 137     -37.079 -48.673 -23.014  1.00 40.77      A    C
ATOM   8338  CD2  PHE D 137     -35.259 -47.471 -23.990  1.00 41.00      A    C
ATOM   8339  CE1  PHE D 137     -36.506 -49.882 -23.402  1.00 40.23      A    C
ATOM   8340  CE2  PHE D 137     -34.674 -48.683 -24.383  1.00 40.55      A    C
ATOM   8341  CZ   PHE D 137     -35.302 -49.887 -24.089  1.00 40.17      A    C
ATOM   8342  N    THR D 138     -36.964 -44.500 -25.526  1.00 42.75      A    N
ATOM   8343  CA   THR D 138     -36.301 -44.327 -26.818  1.00 43.37      A    C
ATOM   8344  C    THR D 138     -34.820 -44.615 -26.643  1.00 43.44      A    C
ATOM   8345  O    THR D 138     -34.256 -44.303 -25.603  1.00 43.58      A    O
ATOM   8346  CB   THR D 138     -36.481 -42.897 -27.384  1.00 43.74      A    C
ATOM   8347  OG1  THR D 138     -37.381 -42.923 -28.499  1.00 44.25      A    O
ATOM   8348  N    ALA D 139     -34.196 -45.225 -27.647  1.00 43.46      A    N
ATOM   8349  CA   ALA D 139     -32.785 -45.600 -27.556  1.00 43.54      A    C
ATOM   8350  C    ALA D 139     -32.040 -45.461 -28.870  1.00 43.92      A    C
ATOM   8351  O    ALA D 139     -32.620 -45.597 -29.956  1.00 44.01      A    O
ATOM   8352  CB   ALA D 139     -32.638 -46.998 -27.023  1.00 43.13      A    C
ATOM   8353  N    SER D 140     -30.745 -45.192 -28.747  1.00 44.34      A    N
ATOM   8354  CA   SER D 140     -29.870 -44.933 -29.878  1.00 44.75      A    C
ATOM   8355  C    SER D 140     -29.345 -46.240 -30.488  1.00 44.44      A    C
ATOM   8356  O    SER D 140     -28.593 -46.958 -29.843  1.00 44.31      A    O
ATOM   8357  CB   SER D 140     -28.728 -44.022 -29.415  1.00 45.17      A    C
ATOM   8358  OG   SER D 140     -27.635 -44.036 -30.311  1.00 46.11      A    O
ATOM   8359  N    THR D 141     -29.753 -46.542 -31.722  1.00 44.24      A    N
ATOM   8360  CA   THR D 141     -29.314 -47.754 -32.427  1.00 44.01      A    C
ATOM   8361  C    THR D 141     -28.546 -47.413 -33.717  1.00 44.32      A    C
ATOM   8362  O    THR D 141     -28.572 -46.262 -34.160  1.00 44.82      A    O
ATOM   8363  CB   THR D 141     -30.509 -48.696 -32.759  1.00 43.69      A    C
ATOM   8364  CG2  THR D 141     -31.414 -48.897 -31.553  1.00 43.37      A    C
ATOM   8365  OG1  THR D 141     -31.278 -48.153 -33.836  1.00 43.76      A    O
ATOM   8366  N    PRO D 142     -27.857 -48.403 -34.328  1.00 44.27      A    N
ATOM   8367  CA   PRO D 142     -27.217 -48.190 -35.630  1.00 44.47      A    C
ATOM   8368  C    PRO D 142     -28.194 -47.842 -36.768  1.00 44.66      A    C
ATOM   8369  O    PRO D 142     -27.764 -47.495 -37.861  1.00 45.11      A    O
ATOM   8370  CB   PRO D 142     -26.530 -49.529 -35.900  1.00 44.35      A    C
ATOM   8371  CG   PRO D 142     -26.269 -50.071 -34.568  1.00 44.09      A    C
ATOM   8372  CD   PRO D 142     -27.460 -49.696 -33.751  1.00 43.97      A    C
ATOM   8373  N    LEU D 143     -29.490 -47.943 -36.506  1.00 44.48      A    N
ATOM   8374  CA   LEU D 143     -30.518 -47.508 -37.435  1.00 44.49      A    C
ATOM   8375  C    LEU D 143     -31.098 -46.155 -36.996  1.00 44.76      A    C
ATOM   8376  O    LEU D 143     -32.127 -45.719 -37.508  1.00 45.00      A    O
ATOM   8377  CB   LEU D 143     -31.634 -48.554 -37.506  1.00 44.12      A    C
ATOM   8378  CG   LEU D 143     -31.643 -49.686 -38.529  1.00 44.06      A    C
ATOM   8379  CD1  LEU D 143     -31.864 -49.146 -39.942  1.00 45.10      A    C
ATOM   8380  CD2  LEU D 143     -30.392 -50.552 -38.465  1.00 43.71      A    C
ATOM   8381  N    GLY D 144     -30.435 -45.492 -36.050  1.00 44.86      A    N
ATOM   8382  CA   GLY D 144     -30.944 -44.249 -35.470  1.00 44.95      A    C
ATOM   8383  C    GLY D 144     -31.926 -44.501 -34.339  1.00 44.80      A    C
ATOM   8384  O    GLY D 144     -32.136 -45.648 -33.962  1.00 44.44      A    O
ATOM   8385  N    PRO D 145     -32.534 -43.431 -33.781  1.00 44.95      A    N
```

FIGURE 1 (cont'd)

```
ATOM   8386  CA   PRO D 145     -33.527 -43.523 -32.698  1.00 44.57      A    C
ATOM   8387  C    PRO D 145     -34.633 -44.543 -32.959  1.00 43.81      A    C
ATOM   8388  O    PRO D 145     -35.290 -44.497 -34.004  1.00 44.07      A    O
ATOM   8389  CB   PRO D 145     -34.126 -42.122 -32.667  1.00 44.95      A    C
ATOM   8390  CG   PRO D 145     -33.025 -41.258 -33.084  1.00 45.62      A    C
ATOM   8391  CD   PRO D 145     -32.238 -42.026 -34.110  1.00 45.48      A    C
ATOM   8392  N    VAL D 146     -34.827 -45.457 -32.014  1.00 42.48      A    N
ATOM   8393  CA   VAL D 146     -35.863 -46.481 -32.119  1.00 41.08      A    C
ATOM   8394  C    VAL D 146     -36.658 -46.537 -30.812  1.00 41.27      A    C
ATOM   8395  O    VAL D 146     -36.085 -46.469 -29.730  1.00 41.31      A    O
ATOM   8396  CB   VAL D 146     -35.258 -47.868 -32.452  1.00 39.28      A    C
ATOM   8397  CG1  VAL D 146     -36.348 -48.862 -32.804  1.00 37.83      A    C
ATOM   8398  N    ASP D 147     -37.978 -46.653 -30.920  1.00 41.34      A    N
ATOM   8399  CA   ASP D 147     -38.857 -46.683 -29.750  1.00 41.08      A    C
ATOM   8400  C    ASP D 147     -39.133 -48.092 -29.246  1.00 40.65      A    C
ATOM   8401  O    ASP D 147     -39.720 -48.918 -29.960  1.00 40.59      A    O
ATOM   8402  CB   ASP D 147     -40.176 -45.977 -30.061  1.00 41.33      A    C
ATOM   8403  CG   ASP D 147     -40.092 -44.489 -29.865  1.00 41.34      A    C
ATOM   8404  OD1  ASP D 147     -39.034 -44.001 -29.410  1.00 42.78      A    O
ATOM   8405  OD2  ASP D 147     -41.115 -43.820 -30.111  1.00 43.10      A    O
ATOM   8406  N    PHE D 148     -38.721 -48.354 -28.007  1.00 40.11      A    N
ATOM   8407  CA   PHE D 148     -38.863 -49.674 -27.391  1.00 39.51      A    C
ATOM   8408  C    PHE D 148     -39.896 -49.673 -26.286  1.00 39.31      A    C
ATOM   8409  O    PHE D 148     -40.393 -48.619 -25.895  1.00 39.50      A    O
ATOM   8410  CB   PHE D 148     -37.527 -50.138 -26.807  1.00 39.30      A    C
ATOM   8411  CG   PHE D 148     -36.436 -50.269 -27.821  1.00 39.34      A    C
ATOM   8412  CD1  PHE D 148     -36.257 -51.452 -28.520  1.00 39.10      A    C
ATOM   8413  CD2  PHE D 148     -35.589 -49.214 -28.084  1.00 39.79      A    C
ATOM   8414  CE1  PHE D 148     -35.250 -51.573 -29.467  1.00 39.24      A    C
ATOM   8415  CE2  PHE D 148     -34.580 -49.332 -29.034  1.00 39.83      A    C
ATOM   8416  CZ   PHE D 148     -34.411 -50.510 -29.723  1.00 39.54      A    C
ATOM   8417  N    GLY D 149     -40.194 -50.862 -25.770  1.00 38.96      A    N
ATOM   8418  CA   GLY D 149     -41.139 -51.014 -24.672  1.00 38.79      A    C
ATOM   8419  C    GLY D 149     -41.204 -52.410 -24.089  1.00 38.51      A    C
ATOM   8420  O    GLY D 149     -41.682 -53.348 -24.736  1.00 38.49      A    O
ATOM   8421  N    ASN D 150     -40.728 -52.535 -22.854  1.00 38.26      A    N
ATOM   8422  CA   ASN D 150     -40.798 -53.780 -22.110  1.00 37.92      A    C
ATOM   8423  C    ASN D 150     -42.173 -53.983 -21.485  1.00 38.11      A    C
ATOM   8424  O    ASN D 150     -42.885 -53.021 -21.212  1.00 38.35      A    O
ATOM   8425  CB   ASN D 150     -39.729 -53.795 -21.025  1.00 37.63      A    C
ATOM   8426  CG   ASN D 150     -38.331 -53.833 -21.585  1.00 37.25      A    C
ATOM   8427  ND2  ASN D 150     -37.511 -52.879 -21.184  1.00 37.25      A    N
ATOM   8428  OD1  ASN D 150     -37.984 -54.715 -22.358  1.00 36.75      A    O
ATOM   8429  N    VAL D 151     -42.549 -55.242 -21.274  1.00 38.15      A    N
ATOM   8430  CA   VAL D 151     -43.772 -55.576 -20.546  1.00 38.45      A    C
ATOM   8431  C    VAL D 151     -43.417 -56.307 -19.248  1.00 38.63      A    C
ATOM   8432  O    VAL D 151     -42.938 -57.444 -19.274  1.00 38.44      A    O
ATOM   8433  CB   VAL D 151     -44.751 -56.397 -21.419  1.00 38.38      A    C
ATOM   8434  CG1  VAL D 151     -45.236 -55.563 -22.597  1.00 38.73      A    C
ATOM   8435  CG2  VAL D 151     -45.944 -56.892 -20.606  1.00 38.51      A    C
ATOM   8436  N    VAL D 152     -43.643 -55.625 -18.125  1.00 39.17      A    N
ATOM   8437  CA   VAL D 152     -43.279 -56.121 -16.795  1.00 39.68      A    C
ATOM   8438  C    VAL D 152     -44.521 -56.513 -15.981  1.00 40.24      A    C
ATOM   8439  O    VAL D 152     -45.421 -55.698 -15.770  1.00 40.61      A    O
ATOM   8440  CB   VAL D 152     -42.423 -55.083 -16.024  1.00 39.63      A    C
ATOM   8441  CG1  VAL D 152     -41.015 -55.038 -16.578  1.00 39.07      A    C
ATOM   8442  CG2  VAL D 152     -42.395 -55.395 -14.532  1.00 39.99      A    C
ATOM   8443  N    ALA D 153     -44.555 -57.763 -15.526  1.00 40.64      A    N
ATOM   8444  CA   ALA D 153     -45.710 -58.300 -14.825  1.00 41.25      A    C
ATOM   8445  C    ALA D 153     -45.325 -58.899 -13.483  1.00 41.76      A    C
ATOM   8446  O    ALA D 153     -44.473 -59.780 -13.414  1.00 41.72      A    O
ATOM   8447  CB   ALA D 153     -46.405 -59.340 -15.689  1.00 41.11      A    C
ATOM   8448  N    THR D 154     -45.967 -58.421 -12.423  1.00 42.53      A    N
ATOM   8449  CA   THR D 154     -45.686 -58.889 -11.071  1.00 43.18      A    C
ATOM   8450  C    THR D 154     -46.983 -59.109 -10.282  1.00 44.00      A    C
```

FIGURE 1 (cont'd)

```
ATOM   8451  O    THR D 154     -47.757 -58.169 -10.077  1.00 44.41      A   O
ATOM   8452  CB   THR D 154     -44.790 -57.874 -10.302  1.00 43.09      A   C
ATOM   8453  CG2  THR D 154     -44.064 -58.552  -9.144  1.00 42.97      A   C
ATOM   8454  OG1  THR D 154     -43.834 -57.292 -11.195  1.00 42.60      A   O
ATOM   8455  N    LEU D 155     -47.225 -60.350  -9.854  1.00 44.68      A   N
ATOM   8456  CA   LEU D 155     -48.220 -60.624  -8.816  1.00 45.55      A   C
ATOM   8457  C    LEU D 155     -47.703 -60.063  -7.508  1.00 46.34      A   C
ATOM   8458  O    LEU D 155     -46.546 -60.289  -7.164  1.00 46.56      A   O
ATOM   8459  CB   LEU D 155     -48.419 -62.125  -8.632  1.00 45.34      A   C
ATOM   8460  CG   LEU D 155     -49.657 -62.791  -9.210  1.00 45.37      A   C
ATOM   8461  CD1  LEU D 155     -49.849 -64.122  -8.505  1.00 45.19      A   C
ATOM   8462  CD2  LEU D 155     -50.893 -61.903  -9.043  1.00 45.86      A   C
ATOM   8463  N    ASP D 156     -48.539 -59.334  -6.778  1.00 47.22      A   N
ATOM   8464  CA   ASP D 156     -48.160 -58.874  -5.438  1.00 48.05      A   C
ATOM   8465  C    ASP D 156     -46.825 -58.082  -5.437  1.00 47.90      A   C
ATOM   8466  O    ASP D 156     -45.800 -58.584  -4.974  1.00 47.68      A   O
ATOM   8467  CB   ASP D 156     -48.091 -60.086  -4.490  1.00 48.56      A   C
ATOM   8468  CG   ASP D 156     -48.098 -59.701  -3.026  1.00 50.20      A   C
ATOM   8469  OD1  ASP D 156     -48.018 -58.489  -2.708  1.00 51.17      A   O
ATOM   8470  OD2  ASP D 156     -48.180 -60.633  -2.189  1.00 51.70      A   O
ATOM   8471  N    PRO D 157     -46.836 -56.840  -5.957  1.00 48.01      A   N
ATOM   8472  CA   PRO D 157     -45.625 -56.030  -5.981  1.00 48.05      A   C
ATOM   8473  C    PRO D 157     -45.048 -55.788  -4.596  1.00 48.37      A   C
ATOM   8474  O    PRO D 157     -43.857 -55.508  -4.478  1.00 48.27      A   O
ATOM   8475  CB   PRO D 157     -46.108 -54.699  -6.560  1.00 48.03      A   C
ATOM   8476  CG   PRO D 157     -47.306 -55.027  -7.310  1.00 48.07      A   C
ATOM   8477  CD   PRO D 157     -47.973 -56.124  -6.568  1.00 48.17      A   C
ATOM   8478  N    ARG D 158     -45.884 -55.889  -3.564  1.00 48.90      A   N
ATOM   8479  CA   ARG D 158     -45.445 -55.620  -2.192  1.00 49.41      A   C
ATOM   8480  C    ARG D 158     -44.621 -56.739  -1.560  1.00 49.24      A   C
ATOM   8481  O    ARG D 158     -43.895 -56.500  -0.598  1.00 49.55      A   O
ATOM   8482  CB   ARG D 158     -46.606 -55.181  -1.275  1.00 49.93      A   C
ATOM   8483  CG   ARG D 158     -47.866 -56.039  -1.314  1.00 50.27      A   C
ATOM   8484  N    ALA D 159     -44.715 -57.949  -2.108  1.00 48.75      A   N
ATOM   8485  CA   ALA D 159     -43.906 -59.078  -1.634  1.00 48.35      A   C
ATOM   8486  C    ALA D 159     -42.418 -58.757  -1.734  1.00 48.02      A   C
ATOM   8487  O    ALA D 159     -41.984 -58.112  -2.690  1.00 47.79      A   O
ATOM   8488  CB   ALA D 159     -44.235 -60.345  -2.409  1.00 48.21      A   C
ATOM   8489  N    ALA D 160     -41.650 -59.216  -0.748  1.00 47.86      A   N
ATOM   8490  CA   ALA D 160     -40.248 -58.837  -0.605  1.00 47.60      A   C
ATOM   8491  C    ALA D 160     -39.354 -59.348  -1.725  1.00 47.10      A   C
ATOM   8492  O    ALA D 160     -38.409 -58.670  -2.129  1.00 47.03      A   O
ATOM   8493  CB   ALA D 160     -39.724 -59.298   0.727  1.00 48.02      A   C
ATOM   8494  N    ARG D 161     -39.658 -60.544  -2.218  1.00 46.51      A   N
ATOM   8495  CA   ARG D 161     -38.891 -61.172  -3.297  1.00 45.91      A   C
ATOM   8496  C    ARG D 161     -39.805 -61.904  -4.283  1.00 45.10      A   C
ATOM   8497  O    ARG D 161     -40.937 -62.249  -3.945  1.00 45.24      A   O
ATOM   8498  CB   ARG D 161     -37.874 -62.154  -2.713  1.00 46.18      A   C
ATOM   8499  CG   ARG D 161     -36.574 -61.532  -2.198  1.00 47.56      A   C
ATOM   8500  CD   ARG D 161     -36.081 -62.224  -0.920  1.00 50.39      A   C
ATOM   8501  NE   ARG D 161     -36.507 -63.622  -0.852  1.00 52.60      A   N
ATOM   8502  CZ   ARG D 161     -36.986 -64.222   0.239  1.00 53.87      A   C
ATOM   8503  NH1  ARG D 161     -37.104 -63.558   1.387  1.00 54.66      A   N
ATOM   8504  NH2  ARG D 161     -37.359 -65.497   0.181  1.00 54.17      A   N
ATOM   8505  N    HIS D 162     -39.311 -62.138  -5.497  1.00 44.03      A   N
ATOM   8506  CA   HIS D 162     -40.079 -62.851  -6.512  1.00 42.99      A   C
ATOM   8507  C    HIS D 162     -39.221 -63.717  -7.411  1.00 41.94      A   C
ATOM   8508  O    HIS D 162     -38.082 -63.369  -7.717  1.00 41.72      A   O
ATOM   8509  CB   HIS D 162     -40.892 -61.882  -7.374  1.00 43.24      A   C
ATOM   8510  CG   HIS D 162     -40.109 -60.710  -7.881  1.00 43.86      A   C
ATOM   8511  CD2  HIS D 162     -40.119 -59.407  -7.512  1.00 44.44      A   C
ATOM   8512  ND1  HIS D 162     -39.196 -60.811  -8.909  1.00 44.04      A   N
ATOM   8513  CE1  HIS D 162     -38.669 -59.623  -9.140  1.00 44.25      A   C
ATOM   8514  NE2  HIS D 162     -39.213 -58.754  -8.308  1.00 44.52      A   N
ATOM   8515  N    LEU D 163     -39.780 -64.854  -7.815  1.00 40.85      A   N
```

FIGURE 1 (cont'd)

```
ATOM   8516  CA   LEU D 163     -39.221 -65.646  -8.898  1.00 39.67      A  C
ATOM   8517  C    LEU D 163     -39.543 -64.891 -10.168  1.00 38.98      A  C
ATOM   8518  O    LEU D 163     -40.672 -64.427 -10.359  1.00 38.99      A  O
ATOM   8519  CB   LEU D 163     -39.833 -67.056  -8.948  1.00 39.56      A  C
ATOM   8520  CG   LEU D 163     -39.595 -67.889 -10.217  1.00 38.91      A  C
ATOM   8521  CD1  LEU D 163     -38.130 -68.262 -10.366  1.00 38.47      A  C
ATOM   8522  CD2  LEU D 163     -40.468 -69.125 -10.250  1.00 38.85      A  C
ATOM   8523  N    THR D 164     -38.544 -64.755 -11.029  1.00 38.03      A  N
ATOM   8524  CA   THR D 164     -38.736 -64.027 -12.274  1.00 37.06      A  C
ATOM   8525  C    THR D 164     -38.342 -64.831 -13.532  1.00 36.45      A  C
ATOM   8526  O    THR D 164     -37.188 -65.231 -13.706  1.00 36.21      A  O
ATOM   8527  CB   THR D 164     -38.132 -62.586 -12.206  1.00 36.99      A  C
ATOM   8528  CG2  THR D 164     -36.728 -62.589 -11.687  1.00 36.95      A  C
ATOM   8529  OG1  THR D 164     -38.138 -61.989 -13.503  1.00 36.67      A  O
ATOM   8530  N    LEU D 165     -39.343 -65.079 -14.373  1.00 35.83      A  N
ATOM   8531  CA   LEU D 165     -39.156 -65.719 -15.664  1.00 35.28      A  C
ATOM   8532  C    LEU D 165     -39.154 -64.663 -16.752  1.00 34.95      A  C
ATOM   8533  O    LEU D 165     -39.854 -63.662 -16.642  1.00 35.00      A  O
ATOM   8534  CB   LEU D 165     -40.265 -66.735 -15.933  1.00 35.22      A  C
ATOM   8535  CG   LEU D 165     -40.497 -67.864 -14.930  1.00 35.28      A  C
ATOM   8536  CD1  LEU D 165     -41.478 -68.860 -15.493  1.00 35.39      A  C
ATOM   8537  CD2  LEU D 165     -39.210 -68.559 -14.579  1.00 35.10      A  C
ATOM   8538  N    ALA D 166     -38.365 -64.894 -17.799  1.00 34.48      A  N
ATOM   8539  CA   ALA D 166     -38.230 -63.930 -18.884  1.00 34.06      A  C
ATOM   8540  C    ALA D 166     -38.086 -64.556 -20.255  1.00 33.78      A  C
ATOM   8541  O    ALA D 166     -37.488 -65.611 -20.414  1.00 33.61      A  O
ATOM   8542  CB   ALA D 166     -37.072 -62.993 -18.623  1.00 34.10      A  C
ATOM   8543  N    CYS D 167     -38.674 -63.875 -21.231  1.00 33.64      A  N
ATOM   8544  CA   CYS D 167     -38.518 -64.146 -22.659  1.00 33.53      A  C
ATOM   8545  C    CYS D 167     -38.405 -62.783 -23.350  1.00 33.49      A  C
ATOM   8546  O    CYS D 167     -38.676 -61.745 -22.739  1.00 33.55      A  O
ATOM   8547  CB   CYS D 167     -39.739 -64.895 -23.211  1.00 33.50      A  C
ATOM   8548  SG   CYS D 167     -41.280 -63.908 -23.259  1.00 33.71      A  S
ATOM   8549  N    HIS D 168     -38.006 -62.775 -24.613  1.00 33.44      A  N
ATOM   8550  CA   HIS D 168     -38.067 -61.543 -25.380  1.00 33.47      A  C
ATOM   8551  C    HIS D 168     -39.123 -61.660 -26.465  1.00 33.42      A  C
ATOM   8552  O    HIS D 168     -39.175 -62.658 -27.183  1.00 33.38      A  O
ATOM   8553  CB   HIS D 168     -36.702 -61.197 -25.975  1.00 33.63      A  C
ATOM   8554  CG   HIS D 168     -36.332 -62.018 -27.173  1.00 34.00      A  C
ATOM   8555  CD2  HIS D 168     -35.629 -63.169 -27.284  1.00 34.32      A  C
ATOM   8556  ND1  HIS D 168     -36.699 -61.668 -28.454  1.00 34.34      A  N
ATOM   8557  CE1  HIS D 168     -36.241 -62.571 -29.302  1.00 34.39      A  C
ATOM   8558  NE2  HIS D 168     -35.590 -63.494 -28.618  1.00 34.31      A  N
ATOM   8559  N    TYR D 169     -39.956 -60.635 -26.593  1.00 33.50      A  N
ATOM   8560  CA   TYR D 169     -41.085 -60.669 -27.532  1.00 33.66      A  C
ATOM   8561  C    TYR D 169     -40.831 -60.037 -28.920  1.00 33.74      A  C
ATOM   8562  O    TYR D 169     -41.611 -60.226 -29.847  1.00 33.76      A  O
ATOM   8563  CB   TYR D 169     -42.350 -60.104 -26.876  1.00 33.70      A  C
ATOM   8564  CG   TYR D 169     -42.424 -58.604 -26.846  1.00 33.91      A  C
ATOM   8565  CD1  TYR D 169     -41.799 -57.874 -25.841  1.00 33.84      A  C
ATOM   8566  CD2  TYR D 169     -43.131 -57.913 -27.811  1.00 34.38      A  C
ATOM   8567  CE1  TYR D 169     -41.872 -56.479 -25.807  1.00 33.94      A  C
ATOM   8568  CE2  TYR D 169     -43.207 -56.521 -27.788  1.00 34.62      A  C
ATOM   8569  CZ   TYR D 169     -42.580 -55.810 -26.785  1.00 34.20      A  C
ATOM   8570  OH   TYR D 169     -42.668 -54.439 -26.771  1.00 34.25      A  O
ATOM   8571  N    ASP D 170     -39.746 -59.288 -29.066  1.00 33.88      A  N
ATOM   8572  CA   ASP D 170     -39.367 -58.764 -30.366  1.00 34.18      A  C
ATOM   8573  C    ASP D 170     -38.934 -59.909 -31.278  1.00 34.43      A  C
ATOM   8574  O    ASP D 170     -38.595 -60.989 -30.797  1.00 34.27      A  O
ATOM   8575  CB   ASP D 170     -38.258 -57.714 -30.223  1.00 34.21      A  C
ATOM   8576  CG   ASP D 170     -36.938 -58.295 -29.735  1.00 34.15      A  C
ATOM   8577  OD1  ASP D 170     -36.901 -58.889 -28.646  1.00 33.80      A  O
ATOM   8578  OD2  ASP D 170     -35.913 -58.124 -30.424  1.00 34.56      A  O
ATOM   8579  N    SER D 171     -38.980 -59.680 -32.590  1.00 34.91      A  N
ATOM   8580  CA   SER D 171     -38.434 -60.627 -33.577  1.00 35.34      A  C
```

FIGURE 1 (cont'd)

```
ATOM   8581  C    SER D 171     -37.311 -59.950 -34.353  1.00 35.62      A  C
ATOM   8582  O    SER D 171     -37.361 -58.738 -34.555  1.00 35.93      A  O
ATOM   8583  CB   SER D 171     -39.524 -61.124 -34.534  1.00 35.39      A  C
ATOM   8584  OG   SER D 171     -39.768 -60.220 -35.589  1.00 35.80      A  O
ATOM   8585  N    LYS D 172     -36.303 -60.711 -34.785  1.00 35.79      A  N
ATOM   8586  CA   LYS D 172     -35.168 -60.108 -35.499  1.00 36.20      A  C
ATOM   8587  C    LYS D 172     -35.585 -59.413 -36.803  1.00 36.91      A  C
ATOM   8588  O    LYS D 172     -36.546 -59.816 -37.454  1.00 37.16      A  O
ATOM   8589  CB   LYS D 172     -34.040 -61.118 -35.760  1.00 35.94      A  C
ATOM   8590  CG   LYS D 172     -32.697 -60.454 -36.138  1.00 35.70      A  C
ATOM   8591  CD   LYS D 172     -31.613 -61.457 -36.479  1.00 35.08      A  C
ATOM   8592  CE   LYS D 172     -30.343 -60.771 -36.947  1.00 35.05      A  C
ATOM   8593  NZ   LYS D 172     -29.558 -60.201 -35.822  1.00 35.02      A  N
ATOM   8594  N    LEU D 173     -34.857 -58.360 -37.159  1.00 37.69      A  N
ATOM   8595  CA   LEU D 173     -35.107 -57.599 -38.369  1.00 38.55      A  C
ATOM   8596  C    LEU D 173     -34.161 -58.057 -39.472  1.00 39.07      A  C
ATOM   8597  O    LEU D 173     -32.942 -58.078 -39.301  1.00 39.17      A  O
ATOM   8598  CB   LEU D 173     -34.921 -56.108 -38.080  1.00 38.63      A  C
ATOM   8599  CG   LEU D 173     -34.923 -55.133 -39.261  1.00 39.25      A  C
ATOM   8600  CD1  LEU D 173     -36.307 -54.567 -39.505  1.00 39.59      A  C
ATOM   8601  CD2  LEU D 173     -33.903 -54.009 -39.063  1.00 39.39      A  C
ATOM   8602  N    PHE D 174     -34.726 -58.426 -40.607  1.00 39.74      A  N
ATOM   8603  CA   PHE D 174     -33.932 -58.927 -41.719  1.00 40.33      A  C
ATOM   8604  C    PHE D 174     -34.117 -58.058 -42.968  1.00 40.12      A  C
ATOM   8605  O    PHE D 174     -35.033 -57.238 -42.995  1.00 41.34      A  O
ATOM   8606  CB   PHE D 174     -34.334 -60.374 -42.029  1.00 40.59      A  C
ATOM   8607  CG   PHE D 174     -33.701 -61.396 -41.137  1.00 40.45      A  C
ATOM   8608  CD1  PHE D 174     -32.382 -61.811 -41.335  1.00 40.61      A  C
ATOM   8609  CD2  PHE D 174     -34.424 -61.966 -40.112  1.00 40.02      A  C
ATOM   8610  CE1  PHE D 174     -31.791 -62.767 -40.504  1.00 40.08      A  C
ATOM   8611  CE2  PHE D 174     -33.844 -62.918 -39.281  1.00 39.55      A  C
ATOM   8612  CZ   PHE D 174     -32.524 -63.317 -39.481  1.00 39.64      A  C
ATOM   8613  N    PRO D 175     -33.340 -58.337 -44.045  1.00 37.32      A  N
ATOM   8614  CA   PRO D 175     -33.018 -57.545 -45.227  1.00 36.13      A  C
ATOM   8615  C    PRO D 175     -34.273 -56.828 -45.802  1.00 36.11      A  C
ATOM   8616  O    PRO D 175     -34.887 -56.063 -45.063  1.00 36.06      A  O
ATOM   8617  CB   PRO D 175     -32.462 -58.603 -46.190  1.00 35.81      A  C
ATOM   8618  CG   PRO D 175     -33.262 -59.782 -45.882  1.00 35.85      A  C
ATOM   8619  CD   PRO D 175     -33.223 -59.786 -44.379  1.00 37.06      A  C
ATOM   8620  N    PRO D 176     -34.627 -57.010 -47.111  1.00 36.72      A  N
ATOM   8621  CA   PRO D 176     -35.845 -56.268 -47.452  1.00 37.64      A  C
ATOM   8622  C    PRO D 176     -36.858 -57.036 -48.331  1.00 39.47      A  C
ATOM   8623  O    PRO D 176     -36.688 -57.144 -49.549  1.00 39.51      A  O
ATOM   8624  CB   PRO D 176     -35.278 -55.085 -48.246  1.00 37.20      A  C
ATOM   8625  CG   PRO D 176     -33.996 -55.744 -49.014  1.00 36.77      A  C
ATOM   8626  CD   PRO D 176     -33.770 -57.122 -48.319  1.00 36.60      A  C
ATOM   8627  N    GLY D 177     -37.845 -57.673 -47.714  1.00 41.62      A  N
ATOM   8628  CA   GLY D 177     -37.699 -58.244 -46.393  1.00 43.91      A  C
ATOM   8629  C    GLY D 177     -37.292 -59.658 -46.766  1.00 45.39      A  C
ATOM   8630  O    GLY D 177     -37.024 -60.484 -45.870  1.00 45.37      A  O
ATOM   8631  N    SER D 178     -37.255 -59.930 -48.097  1.00 47.10      A  N
ATOM   8632  CA   SER D 178     -36.985 -61.266 -48.571  1.00 46.91      A  C
ATOM   8633  C    SER D 178     -38.052 -62.271 -48.243  1.00 46.88      A  C
ATOM   8634  O    SER D 178     -38.871 -62.553 -49.088  1.00 47.47      A  O
ATOM   8635  CB   SER D 178     -35.724 -61.719 -47.950  1.00 45.25      A  C
ATOM   8636  OG   SER D 178     -34.729 -60.888 -48.491  1.00 44.52      A  O
ATOM   8637  N    THR D 179     -38.040 -62.857 -47.055  1.00 45.43      A  N
ATOM   8638  CA   THR D 179     -39.224 -63.592 -46.660  1.00 42.94      A  C
ATOM   8639  C    THR D 179     -39.460 -63.287 -45.195  1.00 43.49      A  C
ATOM   8640  O    THR D 179     -38.500 -63.226 -44.416  1.00 44.42      A  O
ATOM   8641  CB   THR D 179     -39.180 -65.129 -47.001  1.00 37.60      A  C
ATOM   8642  CG2  THR D 179     -37.946 -65.530 -47.865  1.00 40.09      A  C
ATOM   8643  OG1  THR D 179     -39.232 -65.910 -45.805  1.00 34.52      A  O
ATOM   8644  N    PRO D 180     -40.738 -63.061 -44.819  1.00 42.30      A  N
ATOM   8645  CA   PRO D 180     -41.053 -62.613 -43.457  1.00 41.30      A  C
```

FIGURE 1 (cont'd)

```
ATOM   8646  C    PRO D 180     -40.427 -63.539 -42.405  1.00 42.05      A C
ATOM   8647  O    PRO D 180     -40.366 -64.755 -42.607  1.00 42.92      A O
ATOM   8648  CB   PRO D 180     -42.592 -62.688 -43.414  1.00 36.47      A C
ATOM   8649  CG   PRO D 180     -42.956 -63.701 -44.462  1.00 34.98      A C
ATOM   8650  CD   PRO D 180     -41.966 -63.407 -45.566  1.00 41.15      A C
ATOM   8651  N    PHE D 181     -39.940 -62.970 -41.309  1.00 41.81      A N
ATOM   8652  CA   PHE D 181     -39.346 -63.783 -40.255  1.00 40.93      A C
ATOM   8653  C    PHE D 181     -40.104 -63.642 -38.948  1.00 40.22      A C
ATOM   8654  O    PHE D 181     -40.123 -62.561 -38.358  1.00 40.04      A O
ATOM   8655  CB   PHE D 181     -37.877 -63.417 -40.059  1.00 40.99      A C
ATOM   8656  CG   PHE D 181     -37.249 -64.053 -38.847  1.00 40.74      A C
ATOM   8657  CD1  PHE D 181     -36.967 -65.412 -38.817  1.00 40.87      A C
ATOM   8658  CD2  PHE D 181     -36.936 -63.288 -37.734  1.00 40.50      A C
ATOM   8659  CE1  PHE D 181     -36.386 -65.992 -37.698  1.00 40.26      A C
ATOM   8660  CE2  PHE D 181     -36.352 -63.866 -36.611  1.00 39.97      A C
ATOM   8661  CZ   PHE D 181     -36.079 -65.217 -36.597  1.00 39.73      A C
ATOM   8662  N    VAL D 182     -40.704 -64.741 -38.491  1.00 39.43      A N
ATOM   8663  CA   VAL D 182     -41.531 -64.723 -37.270  1.00 38.70      A C
ATOM   8664  C    VAL D 182     -40.876 -65.303 -36.020  1.00 37.92      A C
ATOM   8665  O    VAL D 182     -41.409 -65.137 -34.923  1.00 37.74      A O
ATOM   8666  CB   VAL D 182     -42.908 -65.395 -37.464  1.00 38.76      A C
ATOM   8667  CG1  VAL D 182     -43.832 -64.476 -38.222  1.00 39.10      A C
ATOM   8668  CG2  VAL D 182     -42.767 -66.735 -38.173  1.00 39.13      A C
ATOM   8669  N    GLY D 183     -39.739 -65.980 -36.195  1.00 37.22      A N
ATOM   8670  CA   GLY D 183     -38.985 -66.574 -35.085  1.00 36.25      A C
ATOM   8671  C    GLY D 183     -39.841 -67.293 -34.054  1.00 35.59      A C
ATOM   8672  O    GLY D 183     -40.085 -66.776 -32.957  1.00 35.42      A O
ATOM   8673  N    ALA D 184     -40.303 -68.488 -34.406  1.00 35.04      A N
ATOM   8674  CA   ALA D 184     -41.190 -69.238 -33.530  1.00 34.48      A C
ATOM   8675  C    ALA D 184     -40.479 -69.671 -32.243  1.00 33.94      A C
ATOM   8676  O    ALA D 184     -41.010 -69.502 -31.138  1.00 33.75      A O
ATOM   8677  CB   ALA D 184     -41.757 -70.429 -34.262  1.00 34.79      A C
ATOM   8678  N    THR D 185     -39.272 -70.211 -32.394  1.00 33.38      A N
ATOM   8679  CA   THR D 185     -38.456 -70.606 -31.254  1.00 32.82      A C
ATOM   8680  C    THR D 185     -37.786 -69.386 -30.646  1.00 32.56      A C
ATOM   8681  O    THR D 185     -37.268 -69.455 -29.538  1.00 32.57      A O
ATOM   8682  CB   THR D 185     -37.331 -71.549 -31.660  1.00 32.74      A C
ATOM   8683  CG2  THR D 185     -37.852 -72.696 -32.534  1.00 32.97      A C
ATOM   8684  OG1  THR D 185     -36.325 -70.795 -32.355  1.00 32.41      A O
ATOM   8685  N    ASP D 186     -37.809 -68.271 -31.369  1.00 32.32      A N
ATOM   8686  CA   ASP D 186     -36.959 -67.141 -31.048  1.00 32.09      A C
ATOM   8687  C    ASP D 186     -37.724 -65.804 -31.049  1.00 32.14      A C
ATOM   8688  O    ASP D 186     -37.524 -64.996 -31.949  1.00 32.47      A O
ATOM   8689  CB   ASP D 186     -35.810 -67.128 -32.068  1.00 31.99      A C
ATOM   8690  CG   ASP D 186     -34.689 -66.166 -31.708  1.00 31.46      A C
ATOM   8691  OD1  ASP D 186     -33.719 -66.105 -32.495  1.00 31.32      A O
ATOM   8692  OD2  ASP D 186     -34.759 -65.479 -30.667  1.00 30.62      A O
ATOM   8693  N    SER D 187     -38.570 -65.532 -30.051  1.00 31.89      A N
ATOM   8694  CA   SER D 187     -38.793 -66.382 -28.889  1.00 31.64      A C
ATOM   8695  C    SER D 187     -40.278 -66.470 -28.580  1.00 31.62      A C
ATOM   8696  O    SER D 187     -40.688 -66.405 -27.421  1.00 31.50      A O
ATOM   8697  CB   SER D 187     -38.038 -65.836 -27.677  1.00 31.55      A C
ATOM   8698  OG   SER D 187     -36.640 -66.020 -27.818  1.00 31.70      A O
ATOM   8699  N    ALA D 188     -41.080 -66.631 -29.628  1.00 31.76      A N
ATOM   8700  CA   ALA D 188     -42.535 -66.716 -29.495  1.00 31.84      A C
ATOM   8701  C    ALA D 188     -42.974 -67.804 -28.517  1.00 31.82      A C
ATOM   8702  O    ALA D 188     -43.722 -67.526 -27.578  1.00 31.82      A O
ATOM   8703  CB   ALA D 188     -43.177 -66.923 -30.858  1.00 32.01      A C
ATOM   8704  N    VAL D 189     -42.493 -69.029 -28.737  1.00 31.73      A N
ATOM   8705  CA   VAL D 189     -42.796 -70.158 -27.862  1.00 31.64      A C
ATOM   8706  C    VAL D 189     -42.430 -69.874 -26.395  1.00 31.63      A C
ATOM   8707  O    VAL D 189     -43.276 -70.033 -25.513  1.00 31.76      A O
ATOM   8708  CB   VAL D 189     -42.139 -71.469 -28.353  1.00 31.56      A C
ATOM   8709  CG1  VAL D 189     -42.294 -72.578 -27.322  1.00 31.37      A C
ATOM   8710  CG2  VAL D 189     -42.737 -71.901 -29.664  1.00 31.77      A C
```

FIGURE 1 (cont'd)

```
ATOM   8711  N   PRO D 190    -41.181 -69.443 -26.127  1.00 31.52    A  N
ATOM   8712  CA  PRO D 190    -40.838 -69.018 -24.775  1.00 31.53    A  C
ATOM   8713  C   PRO D 190    -41.866 -68.080 -24.147  1.00 31.76    A  C
ATOM   8714  O   PRO D 190    -42.288 -68.302 -23.010  1.00 31.79    A  O
ATOM   8715  CB  PRO D 190    -39.518 -68.280 -24.982  1.00 31.34    A  C
ATOM   8716  CG  PRO D 190    -38.878 -69.008 -26.093  1.00 31.33    A  C
ATOM   8717  CD  PRO D 190    -39.983 -69.505 -26.986  1.00 31.47    A  C
ATOM   8718  N   CYS D 191    -42.269 -67.053 -24.887  1.00 32.14    A  N
ATOM   8719  CA  CYS D 191    -43.251 -66.090 -24.393  1.00 32.69    A  C
ATOM   8720  C   CYS D 191    -44.632 -66.710 -24.205  1.00 32.96    A  C
ATOM   8721  O   CYS D 191    -45.327 -66.402 -23.231  1.00 33.11    A  O
ATOM   8722  CB  CYS D 191    -43.317 -64.865 -25.311  1.00 32.76    A  C
ATOM   8723  SG  CYS D 191    -41.843 -63.823 -25.225  1.00 33.30    A  S
ATOM   8724  N   ALA D 192    -45.006 -67.591 -25.134  1.00 33.20    A  N
ATOM   8725  CA  ALA D 192    -46.275 -68.310 -25.079  1.00 33.41    A  C
ATOM   8726  C   ALA D 192    -46.400 -69.156 -23.820  1.00 33.41    A  C
ATOM   8727  O   ALA D 192    -47.471 -69.207 -23.216  1.00 33.70    A  O
ATOM   8728  CB  ALA D 192    -46.446 -69.168 -26.293  1.00 33.54    A  C
ATOM   8729  N   LEU D 193    -45.304 -69.808 -23.433  1.00 33.02    A  N
ATOM   8730  CA  LEU D 193    -45.245 -70.612 -22.206  1.00 32.63    A  C
ATOM   8731  C   LEU D 193    -45.454 -69.774 -20.938  1.00 33.18    A  C
ATOM   8732  O   LEU D 193    -46.251 -70.129 -20.066  1.00 33.55    A  O
ATOM   8733  CB  LEU D 193    -43.916 -71.366 -22.119  1.00 31.31    A  C
ATOM   8734  CG  LEU D 193    -43.664 -72.474 -23.128  1.00 29.72    A  C
ATOM   8735  CD1 LEU D 193    -42.247 -72.930 -22.985  1.00 28.75    A  C
ATOM   8736  N   LEU D 194    -44.742 -68.659 -20.844  1.00 33.38    A  N
ATOM   8737  CA  LEU D 194    -44.907 -67.755 -19.722  1.00 33.54    A  C
ATOM   8738  C   LEU D 194    -46.378 -67.359 -19.532  1.00 34.47    A  C
ATOM   8739  O   LEU D 194    -46.852 -67.269 -18.399  1.00 34.79    A  O
ATOM   8740  CB  LEU D 194    -44.020 -66.525 -19.888  1.00 32.47    A  C
ATOM   8741  CG  LEU D 194    -42.529 -66.789 -19.749  1.00 31.24    A  C
ATOM   8742  CD1 LEU D 194    -41.885 -65.542 -19.228  1.00 30.88    A  C
ATOM   8743  N   LEU D 195    -47.099 -67.140 -20.634  1.00 35.26    A  N
ATOM   8744  CA  LEU D 195    -48.529 -66.826 -20.578  1.00 36.07    A  C
ATOM   8745  C   LEU D 195    -49.354 -68.014 -20.096  1.00 36.78    A  C
ATOM   8746  O   LEU D 195    -50.152 -67.886 -19.172  1.00 37.07    A  O
ATOM   8747  CB  LEU D 195    -49.032 -66.384 -21.946  1.00 35.99    A  C
ATOM   8748  CG  LEU D 195    -48.536 -65.056 -22.489  1.00 35.80    A  C
ATOM   8749  CD1 LEU D 195    -49.049 -64.864 -23.897  1.00 36.03    A  C
ATOM   8750  CD2 LEU D 195    -48.985 -63.916 -21.603  1.00 35.82    A  C
ATOM   8751  N   GLU D 196    -49.146 -69.167 -20.731  1.00 37.41    A  N
ATOM   8752  CA  GLU D 196    -49.850 -70.405 -20.409  1.00 38.01    A  C
ATOM   8753  C   GLU D 196    -49.645 -70.820 -18.957  1.00 38.11    A  C
ATOM   8754  O   GLU D 196    -50.608 -71.175 -18.278  1.00 38.31    A  O
ATOM   8755  CB  GLU D 196    -49.415 -71.523 -21.361  1.00 38.17    A  C
ATOM   8756  CG  GLU D 196    -49.831 -72.929 -20.947  1.00 39.31    A  C
ATOM   8757  CD  GLU D 196    -51.324 -73.173 -21.048  1.00 40.78    A  C
ATOM   8758  OE1 GLU D 196    -52.050 -72.292 -21.551  1.00 41.37    A  O
ATOM   8759  OE2 GLU D 196    -51.773 -74.258 -20.625  1.00 41.51    A  O
ATOM   8760  N   LEU D 197    -48.394 -70.772 -18.497  1.00 38.10    A  N
ATOM   8761  CA  LEU D 197    -48.064 -71.029 -17.101  1.00 38.33    A  C
ATOM   8762  C   LEU D 197    -48.861 -70.123 -16.176  1.00 38.86    A  C
ATOM   8763  O   LEU D 197    -49.455 -70.600 -15.210  1.00 39.19    A  O
ATOM   8764  CB  LEU D 197    -46.576 -70.825 -16.842  1.00 37.93    A  C
ATOM   8765  CG  LEU D 197    -45.704 -72.063 -16.744  1.00 37.72    A  C
ATOM   8766  CD1 LEU D 197    -45.319 -72.547 -18.113  1.00 37.61    A  C
ATOM   8767  CD2 LEU D 197    -44.473 -71.719 -15.974  1.00 37.65    A  C
ATOM   8768  N   ALA D 198    -48.886 -68.824 -16.484  1.00 39.32    A  N
ATOM   8769  CA  ALA D 198    -49.559 -67.818 -15.648  1.00 40.04    A  C
ATOM   8770  C   ALA D 198    -51.065 -68.040 -15.558  1.00 40.76    A  C
ATOM   8771  O   ALA D 198    -51.709 -67.669 -14.573  1.00 41.05    A  O
ATOM   8772  CB  ALA D 198    -49.265 -66.425 -16.160  1.00 39.85    A  C
ATOM   8773  N   GLN D 199    -51.611 -68.655 -16.597  1.00 41.35    A  N
ATOM   8774  CA  GLN D 199    -53.031 -68.923 -16.675  1.00 42.02    A  C
ATOM   8775  C   GLN D 199    -53.355 -70.261 -16.026  1.00 42.95    A  C
```

FIGURE 1 (cont'd)

```
ATOM   8776  O   GLN D 199     -54.309 -70.360 -15.260  1.00 43.54      A  O
ATOM   8777  CB  GLN D 199     -53.472 -68.950 -18.136  1.00 40.96      A  C
ATOM   8778  CG  GLN D 199     -54.607 -67.993 -18.521  1.00 40.40      A  C
ATOM   8779  CD  GLN D 199     -55.941 -68.211 -17.817  1.00 40.12      A  C
ATOM   8780  NE2 GLN D 199     -56.511 -67.132 -17.289  1.00 39.12      A  N
ATOM   8781  OE1 GLN D 199     -56.496 -69.302 -17.833  1.00 40.47      A  O
ATOM   8782  N   ALA D 200     -52.565 -71.285 -16.342  1.00 43.61      A  N
ATOM   8783  CA  ALA D 200     -52.791 -72.625 -15.819  1.00 44.33      A  C
ATOM   8784  C   ALA D 200     -52.669 -72.677 -14.298  1.00 44.90      A  C
ATOM   8785  O   ALA D 200     -53.464 -73.342 -13.633  1.00 45.36      A  O
ATOM   8786  CB  ALA D 200     -51.848 -73.616 -16.467  1.00 44.10      A  C
ATOM   8787  N   LEU D 201     -51.684 -71.965 -13.753  1.00 45.24      A  N
ATOM   8788  CA  LEU D 201     -51.476 -71.897 -12.302  1.00 45.78      A  C
ATOM   8789  C   LEU D 201     -52.157 -70.684 -11.673  1.00 46.52      A  C
ATOM   8790  O   LEU D 201     -51.946 -70.384 -10.496  1.00 46.76      A  O
ATOM   8791  CB  LEU D 201     -49.988 -71.876 -11.969  1.00 45.30      A  C
ATOM   8792  CG  LEU D 201     -49.197 -73.106 -12.391  1.00 45.08      A  C
ATOM   8793  CD1 LEU D 201     -47.701 -72.813 -12.414  1.00 44.77      A  C
ATOM   8794  CD2 LEU D 201     -49.526 -74.299 -11.510  1.00 45.37      A  C
ATOM   8795  N   ASP D 202     -52.984 -69.999 -12.459  1.00 47.26      A  N
ATOM   8796  CA  ASP D 202     -53.605 -68.756 -12.038  1.00 48.07      A  C
ATOM   8797  C   ASP D 202     -54.263 -68.854 -10.658  1.00 48.68      A  C
ATOM   8798  O   ASP D 202     -54.014 -68.008  -9.799  1.00 48.91      A  O
ATOM   8799  CB  ASP D 202     -54.593 -68.290 -13.110  1.00 48.20      A  C
ATOM   8800  CG  ASP D 202     -55.330 -67.015 -12.730  1.00 48.65      A  C
ATOM   8801  OD1 ASP D 202     -54.679 -65.976 -12.455  1.00 48.45      A  O
ATOM   8802  OD2 ASP D 202     -56.581 -67.062 -12.736  1.00 49.43      A  O
ATOM   8803  N   LEU D 203     -55.066 -69.893 -10.434  1.00 49.09      A  N
ATOM   8804  CA  LEU D 203     -55.858 -69.989  -9.200  1.00 49.31      A  C
ATOM   8805  C   LEU D 203     -55.020 -70.275  -7.959  1.00 49.57      A  C
ATOM   8806  O   LEU D 203     -55.206 -69.634  -6.919  1.00 49.94      A  O
ATOM   8807  CB  LEU D 203     -57.003 -70.992  -9.347  1.00 48.34      A  C
ATOM   8808  CG  LEU D 203     -58.240 -70.404 -10.031  1.00 48.06      A  C
ATOM   8809  CD1 LEU D 203     -58.329 -70.813 -11.502  1.00 47.96      A  C
ATOM   8810  N   GLU D 204     -54.097 -71.228  -8.077  1.00 49.38      A  N
ATOM   8811  CA  GLU D 204     -53.147 -71.533  -6.994  1.00 49.00      A  C
ATOM   8812  C   GLU D 204     -52.189 -70.357  -6.751  1.00 49.42      A  C
ATOM   8813  O   GLU D 204     -51.744 -70.127  -5.621  1.00 49.72      A  O
ATOM   8814  CB  GLU D 204     -52.389 -72.859  -7.232  1.00 47.46      A  C
ATOM   8815  CG  GLU D 204     -52.191 -73.255  -8.698  1.00 45.83      A  C
ATOM   8816  CD  GLU D 204     -53.455 -73.808  -9.339  1.00 45.08      A  C
ATOM   8817  OE1 GLU D 204     -53.776 -74.987  -9.082  1.00 45.23      A  O
ATOM   8818  N   LEU D 205     -51.901 -69.606  -7.813  1.00 49.60      A  N
ATOM   8819  CA  LEU D 205     -51.091 -68.402  -7.706  1.00 49.75      A  C
ATOM   8820  C   LEU D 205     -51.883 -67.312  -7.029  1.00 50.48      A  C
ATOM   8821  O   LEU D 205     -51.317 -66.454  -6.349  1.00 50.55      A  O
ATOM   8822  CB  LEU D 205     -50.645 -67.910  -9.081  1.00 49.21      A  C
ATOM   8823  CG  LEU D 205     -49.278 -68.317  -9.619  1.00 48.19      A  C
ATOM   8824  CD1 LEU D 205     -49.246 -67.991 -11.077  1.00 47.82      A  C
ATOM   8825  CD2 LEU D 205     -48.162 -67.608  -8.905  1.00 47.56      A  C
ATOM   8826  N   SER D 206     -53.195 -67.345  -7.234  1.00 51.34      A  N
ATOM   8827  CA  SER D 206     -54.077 -66.325  -6.695  1.00 52.25      A  C
ATOM   8828  C   SER D 206     -54.223 -66.457  -5.182  1.00 52.73      A  C
ATOM   8829  O   SER D 206     -53.998 -65.487  -4.449  1.00 52.76      A  O
ATOM   8830  CB  SER D 206     -55.443 -66.380  -7.368  1.00 52.47      A  C
ATOM   8831  OG  SER D 206     -56.137 -65.165  -7.170  1.00 53.15      A  O
ATOM   8832  N   ARG D 207     -54.587 -67.657  -4.720  1.00 53.27      A  N
ATOM   8833  CA  ARG D 207     -54.784 -67.885  -3.285  1.00 53.76      A  C
ATOM   8834  C   ARG D 207     -53.527 -67.536  -2.501  1.00 53.76      A  C
ATOM   8835  O   ARG D 207     -53.594 -66.730  -1.584  1.00 54.16      A  O
ATOM   8836  CB  ARG D 207     -55.316 -69.296  -2.953  1.00 54.03      A  C
ATOM   8837  CG  ARG D 207     -54.490 -70.467  -3.455  1.00 53.55      A  C
ATOM   8838  N   ALA D 208     -52.384 -68.096  -2.888  1.00 53.28      A  N
ATOM   8839  CA  ALA D 208     -51.113 -67.728  -2.269  1.00 52.88      A  C
ATOM   8840  C   ALA D 208     -50.778 -66.281  -2.618  1.00 52.64      A  C
```

FIGURE 1 (cont'd)

```
ATOM   8841  O    ALA D 208     -50.036 -66.018  -3.558  1.00 52.44      A  O
ATOM   8842  CB   ALA D 208     -50.024 -68.657  -2.730  1.00 52.57      A  C
ATOM   8843  N    LYS D 209     -51.347 -65.356  -1.850  1.00 52.69      A  N
ATOM   8844  CA   LYS D 209     -51.314 -63.908  -2.099  1.00 52.25      A  C
ATOM   8845  C    LYS D 209     -52.519 -63.403  -1.350  1.00 51.43      A  C
ATOM   8846  O    LYS D 209     -52.811 -62.223  -1.280  1.00 52.68      A  O
ATOM   8847  CB   LYS D 209     -51.505 -63.574  -3.577  1.00 52.40      A  C
ATOM   8848  CG   LYS D 209     -51.206 -62.126  -3.936  1.00 52.70      A  C
ATOM   8849  CD   LYS D 209     -52.070 -61.661  -5.096  1.00 53.55      A  C
ATOM   8850  CE   LYS D 209     -51.720 -60.250  -5.505  1.00 53.75      A  C
ATOM   8851  NZ   LYS D 209     -52.622 -59.753  -6.570  1.00 53.89      A  N
ATOM   8852  N    LYS D 210     -53.324 -64.365  -0.952  1.00 46.56      A  N
ATOM   8853  CA   LYS D 210     -54.251 -64.189   0.112  1.00 41.77      A  C
ATOM   8854  C    LYS D 210     -53.586 -65.131   1.107  1.00 40.66      A  C
ATOM   8855  O    LYS D 210     -53.733 -66.361   1.051  1.00 40.46      A  O
ATOM   8856  CB   LYS D 210     -55.636 -64.615  -0.341  1.00 40.40      A  C
ATOM   8857  CG   LYS D 210     -56.438 -63.483  -0.921  1.00 35.49      A  C
ATOM   8858  CD   LYS D 210     -57.352 -62.893   0.157  1.00 29.64      A  C
ATOM   8859  CE   LYS D 210     -58.482 -62.048  -0.459  1.00 26.21      A  C
ATOM   8860  NZ   LYS D 210     -59.790 -62.302   0.207  1.00 24.16      A  N
ATOM   8861  N    GLN D 211     -52.814 -64.508   1.989  1.00 39.08      A  N
ATOM   8862  CA   GLN D 211     -51.716 -65.111   2.725  1.00 37.64      A  C
ATOM   8863  C    GLN D 211     -50.535 -64.321   2.240  1.00 38.01      A  C
ATOM   8864  O    GLN D 211     -50.328 -64.184   1.029  1.00 37.99      A  O
ATOM   8865  CB   GLN D 211     -51.517 -66.597   2.426  1.00 36.74      A  C
ATOM   8866  CG   GLN D 211     -52.346 -67.507   3.342  1.00 33.49      A  C
ATOM   8867  CD   GLN D 211     -51.981 -68.988   3.219  1.00 29.71      A  C
ATOM   8868  NE2  GLN D 211     -52.121 -69.734   4.335  1.00 28.10      A  N
ATOM   8869  OE1  GLN D 211     -51.586 -69.461   2.136  1.00 30.02      A  O
ATOM   8870  N    ALA D 212     -49.785 -63.780   3.196  1.00 38.23      A  N
ATOM   8871  CA   ALA D 212     -48.647 -62.912   2.918  1.00 38.07      A  C
ATOM   8872  C    ALA D 212     -47.549 -63.667   2.172  1.00 37.44      A  C
ATOM   8873  O    ALA D 212     -46.426 -63.797   2.676  1.00 37.75      A  O
ATOM   8874  CB   ALA D 212     -48.110 -62.300   4.230  1.00 38.34      A  C
ATOM   8875  N    ALA D 213     -47.893 -64.153   0.973  1.00 36.02      A  N
ATOM   8876  CA   ALA D 213     -47.002 -64.972   0.159  1.00 34.38      A  C
ATOM   8877  C    ALA D 213     -45.670 -64.242  -0.042  1.00 33.11      A  C
ATOM   8878  O    ALA D 213     -45.590 -63.314  -0.861  1.00 33.07      A  O
ATOM   8879  CB   ALA D 213     -47.661 -65.313  -1.165  1.00 34.49      A  C
ATOM   8880  N    PRO D 214     -44.625 -64.661   0.721  1.00 31.96      A  N
ATOM   8881  CA   PRO D 214     -43.375 -63.932   0.914  1.00 31.94      A  C
ATOM   8882  C    PRO D 214     -42.351 -64.284  -0.155  1.00 33.24      A  C
ATOM   8883  O    PRO D 214     -41.145 -64.148   0.056  1.00 33.43      A  O
ATOM   8884  CB   PRO D 214     -42.905 -64.430   2.282  1.00 31.11      A  C
ATOM   8885  CG   PRO D 214     -43.380 -65.838   2.344  1.00 30.86      A  C
ATOM   8886  CD   PRO D 214     -44.545 -65.988   1.362  1.00 31.49      A  C
ATOM   8887  N    VAL D 215     -42.848 -64.786  -1.277  1.00 36.05      A  N
ATOM   8888  CA   VAL D 215     -42.073 -64.893  -2.498  1.00 36.12      A  C
ATOM   8889  C    VAL D 215     -43.048 -64.950  -3.665  1.00 36.40      A  C
ATOM   8890  O    VAL D 215     -43.777 -65.917  -3.811  1.00 36.67      A  O
ATOM   8891  CB   VAL D 215     -41.144 -66.114  -2.503  1.00 35.41      A  C
ATOM   8892  CG1  VAL D 215     -40.086 -65.947  -3.553  1.00 34.52      A  C
ATOM   8893  N    THR D 216     -43.058 -63.900  -4.484  1.00 36.12      A  N
ATOM   8894  CA   THR D 216     -44.019 -63.762  -5.579  1.00 35.56      A  C
ATOM   8895  C    THR D 216     -43.484 -64.258  -6.915  1.00 35.06      A  C
ATOM   8896  O    THR D 216     -42.449 -64.912  -6.966  1.00 35.07      A  O
ATOM   8897  CB   THR D 216     -44.485 -62.314  -5.732  1.00 35.58      A  C
ATOM   8898  OG1  THR D 216     -45.907 -62.294  -5.894  1.00 35.48      A  O
ATOM   8899  N    LEU D 217     -44.202 -63.949  -7.991  1.00 34.46      A  N
ATOM   8900  CA   LEU D 217     -43.810 -64.350  -9.343  1.00 33.69      A  C
ATOM   8901  C    LEU D 217     -43.782 -63.146 -10.277  1.00 33.32      A  C
ATOM   8902  O    LEU D 217     -44.659 -62.279 -10.220  1.00 33.58      A  O
ATOM   8903  CB   LEU D 217     -44.754 -65.425  -9.881  1.00 33.56      A  C
ATOM   8904  CG   LEU D 217     -44.615 -65.822 -11.343  1.00 33.03      A  C
ATOM   8905  CD1  LEU D 217     -43.343 -66.591 -11.576  1.00 32.84      A  C
```

FIGURE 1 (cont'd)

```
ATOM   8906  CD2 LEU D 217     -45.811 -66.628 -11.758  1.00 33.13      A  C
ATOM   8907  N   GLN D 218     -42.774 -63.090 -11.135  1.00 32.51      A  N
ATOM   8908  CA  GLN D 218     -42.639 -61.968 -12.045  1.00 31.88      A  C
ATOM   8909  C   GLN D 218     -42.424 -62.445 -13.469  1.00 31.28      A  C
ATOM   8910  O   GLN D 218     -41.638 -63.345 -13.719  1.00 31.21      A  O
ATOM   8911  CB  GLN D 218     -41.489 -61.067 -11.594  1.00 31.95      A  C
ATOM   8912  CG  GLN D 218     -41.305 -59.778 -12.393  1.00 32.14      A  C
ATOM   8913  CD  GLN D 218     -40.032 -59.052 -12.018  1.00 32.77      A  C
ATOM   8914  NE2 GLN D 218     -38.896 -59.686 -12.237  1.00 32.82      A  N
ATOM   8915  OE1 GLN D 218     -40.073 -57.944 -11.519  1.00 33.62      A  O
ATOM   8916  N   LEU D 219     -43.127 -61.834 -14.406  1.00 30.71      A  N
ATOM   8917  CA  LEU D 219     -42.980 -62.197 -15.800  1.00 30.06      A  C
ATOM   8918  C   LEU D 219     -42.482 -61.021 -16.629  1.00 29.77      A  C
ATOM   8919  O   LEU D 219     -43.107 -59.970 -16.684  1.00 29.84      A  O
ATOM   8920  CB  LEU D 219     -44.296 -62.759 -16.348  1.00 29.94      A  C
ATOM   8921  CG  LEU D 219     -44.867 -63.996 -15.648  1.00 29.61      A  C
ATOM   8922  CD1 LEU D 219     -46.230 -64.324 -16.184  1.00 29.42      A  C
ATOM   8923  CD2 LEU D 219     -43.946 -65.183 -15.816  1.00 29.21      A  C
ATOM   8924  N   LEU D 220     -41.339 -61.217 -17.268  1.00 29.27      A  N
ATOM   8925  CA  LEU D 220     -40.713 -60.179 -18.064  1.00 28.84      A  C
ATOM   8926  C   LEU D 220     -40.743 -60.516 -19.548  1.00 28.95      A  C
ATOM   8927  O   LEU D 220     -40.229 -61.556 -19.972  1.00 28.97      A  O
ATOM   8928  CB  LEU D 220     -39.272 -59.954 -17.605  1.00 28.10      A  C
ATOM   8929  CG  LEU D 220     -39.137 -59.481 -16.163  1.00 27.40      A  C
ATOM   8930  CD1 LEU D 220     -37.695 -59.167 -15.881  1.00 26.96      A  C
ATOM   8931  N   PHE D 221     -41.359 -59.624 -20.323  1.00 29.09      A  N
ATOM   8932  CA  PHE D 221     -41.395 -59.722 -21.780  1.00 29.06      A  C
ATOM   8933  C   PHE D 221     -40.585 -58.562 -22.344  1.00 29.11      A  C
ATOM   8934  O   PHE D 221     -41.066 -57.433 -22.401  1.00 29.17      A  O
ATOM   8935  CB  PHE D 221     -42.840 -59.676 -22.302  1.00 29.10      A  C
ATOM   8936  CG  PHE D 221     -43.731 -60.757 -21.743  1.00 29.13      A  C
ATOM   8937  CD1 PHE D 221     -43.946 -61.929 -22.447  1.00 29.20      A  C
ATOM   8938  CD2 PHE D 221     -44.358 -60.600 -20.514  1.00 29.23      A  C
ATOM   8939  CE1 PHE D 221     -44.757 -62.928 -21.937  1.00 29.22      A  C
ATOM   8940  CE2 PHE D 221     -45.167 -61.594 -19.999  1.00 29.45      A  C
ATOM   8941  CZ  PHE D 221     -45.367 -62.758 -20.713  1.00 29.33      A  C
ATOM   8942  N   LEU D 222     -39.352 -58.853 -22.754  1.00 29.17      A  N
ATOM   8943  CA  LEU D 222     -38.383 -57.819 -23.115  1.00 29.41      A  C
ATOM   8944  C   LEU D 222     -38.401 -57.486 -24.593  1.00 29.73      A  C
ATOM   8945  O   LEU D 222     -38.465 -58.373 -25.426  1.00 29.72      A  O
ATOM   8946  CB  LEU D 222     -36.976 -58.242 -22.683  1.00 29.25      A  C
ATOM   8947  CG  LEU D 222     -36.840 -58.615 -21.197  1.00 29.06      A  C
ATOM   8948  CD1 LEU D 222     -36.377 -57.435 -20.353  1.00 29.11      A  C
ATOM   8949  CD2 LEU D 222     -35.903 -59.778 -21.035  1.00 28.71      A  C
ATOM   8950  N   ASP D 223     -38.350 -56.192 -24.895  1.00 30.30      A  N
ATOM   8951  CA  ASP D 223     -38.318 -55.691 -26.269  1.00 30.89      A  C
ATOM   8952  C   ASP D 223     -36.867 -55.625 -26.743  1.00 30.93      A  C
ATOM   8953  O   ASP D 223     -35.935 -55.731 -25.932  1.00 30.85      A  O
ATOM   8954  CB  ASP D 223     -38.993 -54.299 -26.362  1.00 31.30      A  C
ATOM   8955  CG  ASP D 223     -39.423 -53.924 -27.793  1.00 32.36      A  C
ATOM   8956  OD1 ASP D 223     -39.375 -54.782 -28.700  1.00 33.32      A  O
ATOM   8957  OD2 ASP D 223     -39.816 -52.761 -28.021  1.00 33.06      A  O
ATOM   8958  N   GLY D 224     -36.690 -55.482 -28.058  1.00 31.05      A  N
ATOM   8959  CA  GLY D 224     -35.386 -55.238 -28.678  1.00 31.24      A  C
ATOM   8960  C   GLY D 224     -34.239 -55.991 -28.046  1.00 31.20      A  C
ATOM   8961  O   GLY D 224     -33.355 -55.389 -27.447  1.00 31.41      A  O
ATOM   8962  N   GLU D 225     -34.270 -57.312 -28.154  1.00 31.01      A  N
ATOM   8963  CA  GLU D 225     -33.166 -58.115 -27.701  1.00 30.92      A  C
ATOM   8964  C   GLU D 225     -32.276 -58.388 -28.892  1.00 30.99      A  C
ATOM   8965  O   GLU D 225     -31.059 -58.274 -28.794  1.00 30.97      A  O
ATOM   8966  CB  GLU D 225     -33.668 -59.405 -27.072  1.00 30.79      A  C
ATOM   8967  CG  GLU D 225     -32.574 -60.329 -26.563  1.00 31.09      A  C
ATOM   8968  CD  GLU D 225     -32.061 -61.274 -27.618  1.00 31.85      A  C
ATOM   8969  OE1 GLU D 225     -32.855 -61.721 -28.459  1.00 32.64      A  O
ATOM   8970  OE2 GLU D 225     -30.860 -61.574 -27.609  1.00 32.30      A  O
```

FIGURE 1 (cont'd)

```
ATOM   8971  N   GLU D 226     -32.887 -58.735 -30.019  1.00 31.28      A   N
ATOM   8972  CA  GLU D 226     -32.144 -59.012 -31.242  1.00 31.77      A   C
ATOM   8973  C   GLU D 226     -31.562 -57.718 -31.801  1.00 32.42      A   C
ATOM   8974  O   GLU D 226     -32.213 -56.669 -31.750  1.00 32.56      A   O
ATOM   8975  CB  GLU D 226     -33.036 -59.673 -32.295  1.00 31.67      A   C
ATOM   8976  CG  GLU D 226     -33.721 -60.973 -31.863  1.00 30.97      A   C
ATOM   8977  CD  GLU D 226     -32.952 -62.242 -32.208  1.00 30.25      A   C
ATOM   8978  OE1 GLU D 226     -31.713 -62.198 -32.364  1.00 30.22      A   O
ATOM   8979  OE2 GLU D 226     -33.604 -63.303 -32.307  1.00 29.65      A   O
ATOM   8980  N   ALA D 227     -30.341 -57.813 -32.333  1.00 33.01      A   N
ATOM   8981  CA  ALA D 227     -29.606 -56.682 -32.889  1.00 33.72      A   C
ATOM   8982  C   ALA D 227     -30.283 -56.114 -34.130  1.00 34.40      A   C
ATOM   8983  O   ALA D 227     -31.143 -56.762 -34.734  1.00 34.48      A   O
ATOM   8984  CB  ALA D 227     -28.205 -57.110 -33.222  1.00 33.72      A   C
ATOM   8985  N   LEU D 228     -29.891 -54.903 -34.518  1.00 35.20      A   N
ATOM   8986  CA  LEU D 228     -30.464 -54.273 -35.709  1.00 35.90      A   C
ATOM   8987  C   LEU D 228     -29.533 -54.294 -36.923  1.00 36.65      A   C
ATOM   8988  O   LEU D 228     -29.958 -54.645 -38.022  1.00 36.90      A   O
ATOM   8989  CB  LEU D 228     -30.991 -52.860 -35.413  1.00 35.85      A   C
ATOM   8990  CG  LEU D 228     -32.383 -52.680 -34.778  1.00 35.19      A   C
ATOM   8991  CD1 LEU D 228     -32.292 -52.178 -33.366  1.00 34.77      A   C
ATOM   8992  CD2 LEU D 228     -33.249 -53.942 -34.845  1.00 34.61      A   C
ATOM   8993  N   LYS D 229     -28.275 -53.897 -36.733  1.00 37.41      A   N
ATOM   8994  CA  LYS D 229     -27.258 -54.021 -37.790  1.00 38.19      A   C
ATOM   8995  C   LYS D 229     -26.528 -55.352 -37.572  1.00 38.19      A   C
ATOM   8996  O   LYS D 229     -26.941 -56.370 -38.132  1.00 38.15      A   O
ATOM   8997  CB  LYS D 229     -26.296 -52.815 -37.822  1.00 38.68      A   C
ATOM   8998  CG  LYS D 229     -25.429 -52.698 -39.087  1.00 39.48      A   C
ATOM   8999  CD  LYS D 229     -26.100 -51.863 -40.178  1.00 40.06      A   C
ATOM   9000  N   GLU D 230     -25.470 -55.364 -36.761  1.00 38.34      A   N
ATOM   9001  CA  GLU D 230     -24.911 -56.642 -36.315  1.00 38.53      A   C
ATOM   9002  C   GLU D 230     -24.632 -56.680 -34.817  1.00 38.28      A   C
ATOM   9003  O   GLU D 230     -24.284 -55.658 -34.214  1.00 38.34      A   O
ATOM   9004  CB  GLU D 230     -23.696 -57.109 -37.146  1.00 38.95      A   C
ATOM   9005  CG  GLU D 230     -23.505 -58.659 -37.122  1.00 39.90      A   C
ATOM   9006  CD  GLU D 230     -24.810 -59.463 -37.460  1.00 40.13      A   C
ATOM   9007  OE1 GLU D 230     -25.446 -60.078 -36.556  1.00 38.79      A   O
ATOM   9008  OE2 GLU D 230     -25.226 -59.447 -38.643  1.00 41.13      A   O
ATOM   9009  N   TRP D 231     -24.810 -57.874 -34.245  1.00 37.93      A   N
ATOM   9010  CA  TRP D 231     -24.680 -58.140 -32.823  1.00 37.64      A   C
ATOM   9011  C   TRP D 231     -23.405 -57.563 -32.231  1.00 38.00      A   C
ATOM   9012  O   TRP D 231     -22.317 -57.736 -32.778  1.00 38.33      A   O
ATOM   9013  CB  TRP D 231     -24.737 -59.647 -32.573  1.00 37.30      A   C
ATOM   9014  CG  TRP D 231     -24.861 -59.976 -31.126  1.00 36.76      A   C
ATOM   9015  CD1 TRP D 231     -23.843 -60.111 -30.227  1.00 36.72      A   C
ATOM   9016  CD2 TRP D 231     -26.077 -60.188 -30.389  1.00 36.16      A   C
ATOM   9017  CE2 TRP D 231     -25.714 -60.449 -29.050  1.00 35.89      A   C
ATOM   9018  CE3 TRP D 231     -27.435 -60.184 -30.729  1.00 35.81      A   C
ATOM   9019  NE1 TRP D 231     -24.347 -60.395 -28.979  1.00 36.37      A   N
ATOM   9020  CZ2 TRP D 231     -26.658 -60.705 -28.054  1.00 35.23      A   C
ATOM   9021  CZ3 TRP D 231     -28.369 -60.437 -29.734  1.00 35.07      A   C
ATOM   9022  CH2 TRP D 231     -27.974 -60.692 -28.416  1.00 34.77      A   C
ATOM   9023  N   GLY D 232     -23.556 -56.870 -31.110  1.00 38.14      A   N
ATOM   9024  CA  GLY D 232     -22.434 -56.255 -30.418  1.00 38.51      A   C
ATOM   9025  C   GLY D 232     -22.905 -55.635 -29.127  1.00 38.68      A   C
ATOM   9026  O   GLY D 232     -24.110 -55.524 -28.907  1.00 38.40      A   O
ATOM   9027  N   PRO D 233     -21.961 -55.230 -28.264  1.00 39.09      A   N
ATOM   9028  CA  PRO D 233     -22.277 -54.608 -26.984  1.00 39.30      A   C
ATOM   9029  C   PRO D 233     -23.200 -53.406 -27.104  1.00 39.52      A   C
ATOM   9030  O   PRO D 233     -24.064 -53.223 -26.243  1.00 39.24      A   O
ATOM   9031  CB  PRO D 233     -20.912 -54.170 -26.469  1.00 39.49      A   C
ATOM   9032  CG  PRO D 233     -19.995 -55.172 -27.034  1.00 39.63      A   C
ATOM   9033  CD  PRO D 233     -20.516 -55.457 -28.407  1.00 39.38      A   C
ATOM   9034  N   LYS D 234     -23.027 -52.611 -28.161  1.00 40.09      A   N
ATOM   9035  CA  LYS D 234     -23.860 -51.428 -28.376  1.00 40.66      A   C
```

FIGURE 1 (cont'd)

```
ATOM   9036  C    LYS D 234     -25.083 -51.675 -29.286  1.00 40.46      A   C
ATOM   9037  O    LYS D 234     -25.956 -50.807 -29.407  1.00 40.62      A   O
ATOM   9038  CB   LYS D 234     -23.009 -50.244 -28.862  1.00 41.28      A   C
ATOM   9039  CG   LYS D 234     -22.311 -49.447 -27.730  1.00 42.34      A   C
ATOM   9040  CD   LYS D 234     -21.034 -48.695 -28.194  1.00 43.51      A   C
ATOM   9041  CE   LYS D 234     -21.316 -47.278 -28.698  1.00 43.73      A   C
ATOM   9042  N    ASP D 235     -25.158 -52.857 -29.900  1.00 40.08      A   N
ATOM   9043  CA   ASP D 235     -26.318 -53.237 -30.715  1.00 39.57      A   C
ATOM   9044  C    ASP D 235     -26.832 -54.617 -30.321  1.00 39.05      A   C
ATOM   9045  O    ASP D 235     -26.554 -55.601 -30.998  1.00 39.06      A   O
ATOM   9046  CB   ASP D 235     -25.974 -53.176 -32.208  1.00 39.83      A   C
ATOM   9047  CG   ASP D 235     -27.135 -53.597 -33.105  1.00 39.55      A   C
ATOM   9048  OD1  ASP D 235     -26.864 -54.194 -34.172  1.00 39.28      A   O
ATOM   9049  OD2  ASP D 235     -28.306 -53.338 -32.751  1.00 39.16      A   O
ATOM   9050  N    SER D 236     -27.562 -54.667 -29.205  1.00 38.45      A   N
ATOM   9051  CA   SER D 236     -28.225 -55.882 -28.679  1.00 37.80      A   C
ATOM   9052  C    SER D 236     -28.747 -55.650 -27.259  1.00 37.50      A   C
ATOM   9053  O    SER D 236     -28.166 -54.889 -26.491  1.00 37.54      A   O
ATOM   9054  CB   SER D 236     -27.290 -57.099 -28.680  1.00 37.67      A   C
ATOM   9055  OG   SER D 236     -26.211 -56.923 -27.777  1.00 37.62      A   O
ATOM   9056  N    LEU D 237     -29.837 -56.322 -26.910  1.00 37.17      A   N
ATOM   9057  CA   LEU D 237     -30.354 -56.316 -25.546  1.00 37.04      A   C
ATOM   9058  C    LEU D 237     -30.732 -54.926 -25.089  1.00 37.21      A   C
ATOM   9059  O    LEU D 237     -30.327 -54.508 -24.019  1.00 37.36      A   O
ATOM   9060  CB   LEU D 237     -29.322 -56.906 -24.571  1.00 36.90      A   C
ATOM   9061  CG   LEU D 237     -28.533 -58.173 -24.936  1.00 36.58      A   C
ATOM   9062  CD1  LEU D 237     -27.309 -58.292 -24.058  1.00 36.67      A   C
ATOM   9063  CD2  LEU D 237     -29.376 -59.428 -24.834  1.00 36.07      A   C
ATOM   9064  N    TYR D 238     -31.499 -54.210 -25.906  1.00 37.36      A   N
ATOM   9065  CA   TYR D 238     -31.952 -52.866 -25.557  1.00 37.46      A   C
ATOM   9066  C    TYR D 238     -32.958 -52.896 -24.428  1.00 37.12      A   C
ATOM   9067  O    TYR D 238     -32.895 -52.072 -23.533  1.00 37.26      A   O
ATOM   9068  CB   TYR D 238     -32.542 -52.132 -26.765  1.00 37.80      A   C
ATOM   9069  CG   TYR D 238     -31.566 -51.930 -27.910  1.00 38.38      A   C
ATOM   9070  CD1  TYR D 238     -30.562 -50.962 -27.842  1.00 39.32      A   C
ATOM   9071  CD2  TYR D 238     -31.653 -52.699 -29.059  1.00 38.46      A   C
ATOM   9072  CE1  TYR D 238     -29.669 -50.782 -28.891  1.00 39.70      A   C
ATOM   9073  CE2  TYR D 238     -30.771 -52.523 -30.105  1.00 38.94      A   C
ATOM   9074  CZ   TYR D 238     -29.783 -51.568 -30.020  1.00 39.35      A   C
ATOM   9075  OH   TYR D 238     -28.904 -51.406 -31.062  1.00 39.60      A   O
ATOM   9076  N    GLY D 239     -33.875 -53.852 -24.463  1.00 36.69      A   N
ATOM   9077  CA   GLY D 239     -34.898 -53.949 -23.429  1.00 36.44      A   C
ATOM   9078  C    GLY D 239     -34.346 -54.325 -22.065  1.00 36.25      A   C
ATOM   9079  O    GLY D 239     -34.662 -53.694 -21.049  1.00 36.31      A   O
ATOM   9080  N    SER D 240     -33.510 -55.359 -22.051  1.00 36.00      A   N
ATOM   9081  CA   SER D 240     -32.940 -55.877 -20.819  1.00 35.70      A   C
ATOM   9082  C    SER D 240     -31.949 -54.906 -20.196  1.00 35.71      A   C
ATOM   9083  O    SER D 240     -32.028 -54.653 -19.002  1.00 35.83      A   O
ATOM   9084  CB   SER D 240     -32.305 -57.249 -21.048  1.00 35.57      A   C
ATOM   9085  OG   SER D 240     -31.668 -57.318 -22.310  1.00 35.90      A   O
ATOM   9086  N    ARG D 241     -31.037 -54.347 -20.997  1.00 35.74      A   N
ATOM   9087  CA   ARG D 241     -30.062 -53.365 -20.500  1.00 35.91      A   C
ATOM   9088  C    ARG D 241     -30.737 -52.172 -19.870  1.00 35.98      A   C
ATOM   9089  O    ARG D 241     -30.234 -51.624 -18.899  1.00 36.21      A   O
ATOM   9090  CB   ARG D 241     -29.101 -52.906 -21.590  1.00 35.99      A   C
ATOM   9091  CG   ARG D 241     -27.889 -53.787 -21.713  1.00 36.63      A   C
ATOM   9092  CD   ARG D 241     -26.772 -53.141 -22.501  1.00 37.97      A   C
ATOM   9093  NE   ARG D 241     -27.005 -53.190 -23.940  1.00 39.19      A   N
ATOM   9094  CZ   ARG D 241     -27.375 -52.140 -24.675  1.00 40.18      A   C
ATOM   9095  NH1  ARG D 241     -27.554 -50.951 -24.100  1.00 41.13      A   N
ATOM   9096  NH2  ARG D 241     -27.567 -52.271 -25.992  1.00 40.48      A   N
ATOM   9097  N    HIS D 242     -31.888 -51.786 -20.408  1.00 35.94      A   N
ATOM   9098  CA   HIS D 242     -32.644 -50.657 -19.877  1.00 36.04      A   C
ATOM   9099  C    HIS D 242     -33.402 -51.024 -18.608  1.00 35.69      A   C
ATOM   9100  O    HIS D 242     -33.314 -50.319 -17.601  1.00 35.88      A   O
```

FIGURE 1 (cont'd)

```
ATOM   9101  CB   HIS D 242     -33.601 -50.093 -20.931  1.00 36.32      A    C
ATOM   9102  CG   HIS D 242     -34.392 -48.909 -20.463  1.00 37.13      A    C
ATOM   9103  CD2  HIS D 242     -34.079 -47.592 -20.415  1.00 37.93      A    C
ATOM   9104  ND1  HIS D 242     -35.673 -49.018 -19.966  1.00 37.27      A    N
ATOM   9105  CE1  HIS D 242     -36.115 -47.819 -19.633  1.00 37.94      A    C
ATOM   9106  NE2  HIS D 242     -35.167 -46.937 -19.895  1.00 38.39      A    N
ATOM   9107  N    LEU D 243     -34.144 -52.126 -18.656  1.00 35.10      A    N
ATOM   9108  CA   LEU D 243     -34.897 -52.578 -17.489  1.00 34.63      A    C
ATOM   9109  C    LEU D 243     -33.987 -52.799 -16.299  1.00 34.74      A    C
ATOM   9110  O    LEU D 243     -34.319 -52.389 -15.192  1.00 34.95      A    O
ATOM   9111  CB   LEU D 243     -35.679 -53.854 -17.777  1.00 34.18      A    C
ATOM   9112  CG   LEU D 243     -36.574 -54.339 -16.640  1.00 33.45      A    C
ATOM   9113  CD1  LEU D 243     -37.622 -53.313 -16.300  1.00 33.25      A    C
ATOM   9114  CD2  LEU D 243     -37.229 -55.623 -17.040  1.00 32.87      A    C
ATOM   9115  N    ALA D 244     -32.844 -53.445 -16.533  1.00 34.76      A    N
ATOM   9116  CA   ALA D 244     -31.838 -53.632 -15.503  1.00 35.00      A    C
ATOM   9117  C    ALA D 244     -31.441 -52.286 -14.895  1.00 35.49      A    C
ATOM   9118  O    ALA D 244     -31.449 -52.142 -13.675  1.00 35.66      A    O
ATOM   9119  CB   ALA D 244     -30.643 -54.350 -16.063  1.00 34.74      A    C
ATOM   9120  N    GLN D 245     -31.137 -51.296 -15.739  1.00 36.02      A    N
ATOM   9121  CA   GLN D 245     -30.779 -49.953 -15.267  1.00 36.60      A    C
ATOM   9122  C    GLN D 245     -31.890 -49.346 -14.410  1.00 36.92      A    C
ATOM   9123  O    GLN D 245     -31.635 -48.833 -13.323  1.00 37.18      A    O
ATOM   9124  CB   GLN D 245     -30.408 -49.033 -16.439  1.00 36.66      A    C
ATOM   9125  N    LEU D 246     -33.122 -49.446 -14.899  1.00 37.05      A    N
ATOM   9126  CA   LEU D 246     -34.287 -48.829 -14.261  1.00 37.32      A    C
ATOM   9127  C    LEU D 246     -34.690 -49.515 -12.966  1.00 37.72      A    C
ATOM   9128  O    LEU D 246     -35.232 -48.874 -12.073  1.00 38.01      A    O
ATOM   9129  CB   LEU D 246     -35.469 -48.789 -15.238  1.00 37.06      A    C
ATOM   9130  CG   LEU D 246     -36.770 -48.078 -14.862  1.00 36.46      A    C
ATOM   9131  CD1  LEU D 246     -37.871 -49.091 -14.712  1.00 35.18      A    C
ATOM   9132  N    MET D 247     -34.432 -50.817 -12.873  1.00 38.03      A    N
ATOM   9133  CA   MET D 247     -34.713 -51.581 -11.655  1.00 38.45      A    C
ATOM   9134  C    MET D 247     -33.709 -51.270 -10.548  1.00 39.26      A    C
ATOM   9135  O    MET D 247     -34.055 -51.299  -9.368  1.00 39.46      A    O
ATOM   9136  CB   MET D 247     -34.746 -53.088 -11.932  1.00 37.95      A    C
ATOM   9137  CG   MET D 247     -35.995 -53.562 -12.670  1.00 37.33      A    C
ATOM   9138  SD   MET D 247     -36.239 -55.360 -12.685  1.00 36.46      A    S
ATOM   9139  CE   MET D 247     -37.184 -55.607 -11.201  1.00 36.89      A    C
ATOM   9140  N    GLU D 248     -32.473 -50.964 -10.939  1.00 40.18      A    N
ATOM   9141  CA   GLU D 248     -31.416 -50.598  -9.999  1.00 41.14      A    C
ATOM   9142  C    GLU D 248     -31.709 -49.245  -9.368  1.00 42.18      A    C
ATOM   9143  O    GLU D 248     -31.342 -49.006  -8.226  1.00 42.73      A    O
ATOM   9144  CB   GLU D 248     -30.072 -50.560 -10.721  1.00 40.98      A    C
ATOM   9145  CG   GLU D 248     -28.847 -50.692  -9.852  1.00 39.63      A    C
ATOM   9146  CD   GLU D 248     -27.639 -50.110 -10.551  1.00 39.13      A    C
ATOM   9147  OE1  GLU D 248     -27.088 -49.107 -10.046  1.00 39.21      A    O
ATOM   9148  OE2  GLU D 248     -27.264 -50.624 -11.631  1.00 38.99      A    O
ATOM   9149  N    SER D 249     -32.380 -48.370 -10.112  1.00 43.04      A    N
ATOM   9150  CA   SER D 249     -32.680 -47.030  -9.629  1.00 43.97      A    C
ATOM   9151  C    SER D 249     -33.994 -46.970  -8.870  1.00 44.44      A    C
ATOM   9152  O    SER D 249     -34.343 -45.937  -8.320  1.00 44.88      A    O
ATOM   9153  CB   SER D 249     -32.706 -46.048 -10.793  1.00 44.12      A    C
ATOM   9154  OG   SER D 249     -33.877 -46.221 -11.566  1.00 44.12      A    O
ATOM   9155  N    ILE D 250     -34.712 -48.082  -8.835  1.00 44.75      A    N
ATOM   9156  CA   ILE D 250     -36.017 -48.133  -8.200  1.00 45.28      A    C
ATOM   9157  C    ILE D 250     -35.942 -48.836  -6.843  1.00 46.11      A    C
ATOM   9158  O    ILE D 250     -35.784 -50.060  -6.795  1.00 45.89      A    O
ATOM   9159  CB   ILE D 250     -37.026 -48.829  -9.117  1.00 44.83      A    C
ATOM   9160  CG1  ILE D 250     -38.444 -48.383  -8.791  1.00 44.79      A    C
ATOM   9161  CD1  ILE D 250     -39.247 -49.423  -8.053  1.00 44.42      A    C
ATOM   9162  N    PRO D 251     -36.044 -48.059  -5.736  1.00 47.22      A    N
ATOM   9163  CA   PRO D 251     -35.906 -48.569  -4.379  1.00 47.90      A    C
ATOM   9164  C    PRO D 251     -37.010 -49.510  -4.022  1.00 48.31      A    C
ATOM   9165  O    PRO D 251     -38.144 -49.377  -4.490  1.00 48.35      A    O
```

FIGURE 1 (cont'd)

```
ATOM   9166  CB   PRO D 251     -36.004 -47.312  -3.502  1.00 48.22      A  C
ATOM   9167  CG   PRO D 251     -35.605 -46.224  -4.368  1.00 48.27      A  C
ATOM   9168  CD   PRO D 251     -36.204 -46.599  -5.712  1.00 47.62      A  C
ATOM   9169  N    HIS D 252     -36.640 -50.460  -3.185  1.00 48.74      A  N
ATOM   9170  CA   HIS D 252     -37.491 -51.543  -2.829  1.00 49.10      A  C
ATOM   9171  C    HIS D 252     -36.947 -52.100  -1.554  1.00 49.69      A  C
ATOM   9172  O    HIS D 252     -35.772 -52.078  -1.283  1.00 49.95      A  O
ATOM   9173  CB   HIS D 252     -37.541 -52.597  -3.930  1.00 47.95      A  C
ATOM   9174  CG   HIS D 252     -38.511 -53.707  -3.673  1.00 47.78      A  C
ATOM   9175  CD2  HIS D 252     -38.305 -54.989  -3.283  1.00 47.60      A  C
ATOM   9176  ND1  HIS D 252     -39.875 -53.566  -3.840  1.00 48.07      A  N
ATOM   9177  CE1  HIS D 252     -40.468 -54.713  -3.552  1.00 48.09      A  C
ATOM   9178  NE2  HIS D 252     -39.536 -55.594  -3.212  1.00 47.87      A  N
ATOM   9179  N    SER D 253     -37.915 -52.119  -0.701  1.00 50.10      A  N
ATOM   9180  CA   SER D 253     -38.440 -52.995   0.231  1.00 50.11      A  C
ATOM   9181  C    SER D 253     -38.103 -53.635   1.509  1.00 50.22      A  C
ATOM   9182  O    SER D 253     -38.959 -53.611   2.335  1.00 50.66      A  O
ATOM   9183  CB   SER D 253     -39.448 -53.850  -0.453  1.00 49.26      A  C
ATOM   9184  OG   SER D 253     -40.562 -54.054   0.365  1.00 48.81      A  O
ATOM   9185  N    PRO D 254     -36.956 -54.211   1.778  1.00 49.83      A  N
ATOM   9186  CA   PRO D 254     -35.569 -54.603   1.747  1.00 49.44      A  C
ATOM   9187  C    PRO D 254     -35.159 -55.503   0.636  1.00 49.06      A  C
ATOM   9188  O    PRO D 254     -34.818 -56.605   0.969  1.00 49.19      A  O
ATOM   9189  CB   PRO D 254     -35.485 -55.531   2.987  1.00 48.70      A  C
ATOM   9190  CG   PRO D 254     -36.896 -55.855   3.414  1.00 48.84      A  C
ATOM   9191  CD   PRO D 254     -37.777 -55.292   2.394  1.00 49.11      A  C
ATOM   9192  N    GLY D 255     -34.961 -55.136  -0.620  1.00 48.44      A  N
ATOM   9193  CA   GLY D 255     -34.127 -54.132  -1.151  1.00 47.58      A  C
ATOM   9194  C    GLY D 255     -32.661 -54.236  -0.819  1.00 47.11      A  C
ATOM   9195  O    GLY D 255     -32.217 -55.134  -0.099  1.00 47.40      A  O
ATOM   9196  N    PRO D 256     -31.892 -53.230  -1.217  1.00 46.61      A  N
ATOM   9197  CA   PRO D 256     -31.995 -51.812  -1.518  1.00 46.33      A  C
ATOM   9198  C    PRO D 256     -32.833 -51.447  -2.741  1.00 45.75      A  C
ATOM   9199  O    PRO D 256     -33.782 -50.669  -2.624  1.00 45.95      A  O
ATOM   9200  CB   PRO D 256     -30.528 -51.423  -1.730  1.00 46.51      A  C
ATOM   9201  CG   PRO D 256     -29.749 -52.537  -1.116  1.00 46.55      A  C
ATOM   9202  CD   PRO D 256     -30.524 -53.708  -1.448  1.00 46.54      A  C
ATOM   9203  N    THR D 257     -32.479 -52.000  -3.896  1.00 44.73      A  N
ATOM   9204  CA   THR D 257     -33.167 -51.709  -5.138  1.00 43.60      A  C
ATOM   9205  C    THR D 257     -34.021 -52.895  -5.543  1.00 42.89      A  C
ATOM   9206  O    THR D 257     -33.957 -53.946  -4.923  1.00 42.80      A  O
ATOM   9207  CB   THR D 257     -32.173 -51.397  -6.243  1.00 43.43      A  C
ATOM   9208  OG1  THR D 257     -31.189 -52.431  -6.297  1.00 43.05      A  O
ATOM   9209  N    ARG D 258     -34.829 -52.722  -6.581  1.00 42.06      A  N
ATOM   9210  CA   ARG D 258     -35.682 -53.802  -7.080  1.00 41.06      A  C
ATOM   9211  C    ARG D 258     -34.886 -54.944  -7.707  1.00 40.54      A  C
ATOM   9212  O    ARG D 258     -35.406 -56.038  -7.903  1.00 40.51      A  O
ATOM   9213  CB   ARG D 258     -36.737 -53.277  -8.064  1.00 40.16      A  C
ATOM   9214  CG   ARG D 258     -38.062 -52.953  -7.407  1.00 40.08      A  C
ATOM   9215  CD   ARG D 258     -39.218 -53.152  -8.358  1.00 40.04      A  C
ATOM   9216  NE   ARG D 258     -40.494 -52.985  -7.673  1.00 40.32      A  N
ATOM   9217  N    ILE D 259     -33.623 -54.683  -8.011  1.00 39.83      A  N
ATOM   9218  CA   ILE D 259     -32.760 -55.703  -8.553  1.00 38.90      A  C
ATOM   9219  C    ILE D 259     -32.539 -56.843  -7.565  1.00 38.84      A  C
ATOM   9220  O    ILE D 259     -32.443 -58.007  -7.954  1.00 38.83      A  O
ATOM   9221  CB   ILE D 259     -31.445 -55.108  -8.973  1.00 37.98      A  C
ATOM   9222  CG1  ILE D 259     -31.391 -55.111 -10.486  1.00 37.66      A  C
ATOM   9223  CD1  ILE D 259     -30.625 -53.996 -11.030  1.00 38.54      A  C
ATOM   9224  N    GLN D 260     -32.490 -56.502  -6.283  1.00 38.51      A  N
ATOM   9225  CA   GLN D 260     -32.283 -57.487  -5.247  1.00 37.89      A  C
ATOM   9226  C    GLN D 260     -33.586 -58.221  -4.981  1.00 37.73      A  C
ATOM   9227  O    GLN D 260     -33.622 -59.141  -4.181  1.00 38.19      A  O
ATOM   9228  CB   GLN D 260     -31.742 -56.854  -3.954  1.00 37.06      A  C
ATOM   9229  CG   GLN D 260     -31.264 -55.410  -4.029  1.00 36.66      A  C
ATOM   9230  CD   GLN D 260     -30.226 -55.141  -5.096  1.00 36.30      A  C
```

FIGURE 1 (cont'd)

```
ATOM   9231  OE1 GLN D 260     -29.221 -55.819  -5.216  1.00 36.68      A    O
ATOM   9232  N   ALA D 261     -34.655 -57.826  -5.657  1.00 37.10      A    N
ATOM   9233  CA  ALA D 261     -35.940 -58.483  -5.469  1.00 36.45      A    C
ATOM   9234  C   ALA D 261     -36.051 -59.767  -6.284  1.00 35.71      A    C
ATOM   9235  O   ALA D 261     -36.852 -60.645  -5.970  1.00 35.66      A    O
ATOM   9236  N   ILE D 262     -35.243 -59.876  -7.332  1.00 34.73      A    N
ATOM   9237  CA  ILE D 262     -35.203 -61.078  -8.162  1.00 33.63      A    C
ATOM   9238  C   ILE D 262     -34.448 -62.160  -7.418  1.00 33.55      A    C
ATOM   9239  O   ILE D 262     -33.218 -62.106  -7.325  1.00 33.75      A    O
ATOM   9240  CB  ILE D 262     -34.478 -60.826  -9.495  1.00 32.70      A    C
ATOM   9241  CG1 ILE D 262     -34.996 -59.560 -10.172  1.00 32.09      A    C
ATOM   9242  CD1 ILE D 262     -34.025 -58.960 -11.148  1.00 31.70      A    C
ATOM   9243  N   GLU D 263     -35.178 -63.128  -6.870  1.00 33.19      A    N
ATOM   9244  CA  GLU D 263     -34.542 -64.265  -6.190  1.00 32.82      A    C
ATOM   9245  C   GLU D 263     -33.881 -65.194  -7.213  1.00 32.21      A    C
ATOM   9246  O   GLU D 263     -32.829 -65.791  -6.944  1.00 32.30      A    O
ATOM   9247  CB  GLU D 263     -35.550 -65.036  -5.328  1.00 33.01      A    C
ATOM   9248  CG  GLU D 263     -34.927 -66.027  -4.335  1.00 33.01      A    C
ATOM   9249  CD  GLU D 263     -35.929 -66.572  -3.341  1.00 32.61      A    C
ATOM   9250  OE1 GLU D 263     -36.465 -67.688  -3.545  1.00 32.69      A    O
ATOM   9251  OE2 GLU D 263     -36.164 -65.876  -2.341  1.00 32.68      A    O
ATOM   9252  N   LEU D 264     -34.507 -65.301  -8.385  1.00 31.33      A    N
ATOM   9253  CA  LEU D 264     -33.959 -66.068  -9.485  1.00 30.31      A    C
ATOM   9254  C   LEU D 264     -34.489 -65.563 -10.810  1.00 29.71      A    C
ATOM   9255  O   LEU D 264     -35.693 -65.492 -11.013  1.00 29.74      A    O
ATOM   9256  CB  LEU D 264     -34.285 -67.545  -9.323  1.00 30.25      A    C
ATOM   9257  CG  LEU D 264     -33.825 -68.487 -10.433  1.00 29.82      A    C
ATOM   9258  CD1 LEU D 264     -32.320 -68.477 -10.571  1.00 29.72      A    C
ATOM   9259  CD2 LEU D 264     -34.335 -69.898 -10.190  1.00 29.62      A    C
ATOM   9260  N   PHE D 265     -33.562 -65.224 -11.701  1.00 28.89      A    N
ATOM   9261  CA  PHE D 265     -33.853 -64.797 -13.063  1.00 27.87      A    C
ATOM   9262  C   PHE D 265     -33.708 -65.998 -13.976  1.00 27.60      A    C
ATOM   9263  O   PHE D 265     -32.599 -66.379 -14.341  1.00 27.49      A    O
ATOM   9264  CB  PHE D 265     -32.869 -63.702 -13.477  1.00 27.61      A    C
ATOM   9265  CG  PHE D 265     -33.217 -63.014 -14.764  1.00 26.25      A    C
ATOM   9266  CD1 PHE D 265     -33.972 -61.855 -14.764  1.00 25.32      A    C
ATOM   9267  CD2 PHE D 265     -32.758 -63.511 -15.980  1.00 25.14      A    C
ATOM   9268  CE1 PHE D 265     -34.286 -61.234 -15.967  1.00 23.50      A    C
ATOM   9269  CE2 PHE D 265     -33.056 -62.895 -17.179  1.00 21.89      A    C
ATOM   9270  CZ  PHE D 265     -33.816 -61.764 -17.180  1.00 22.19      A    C
ATOM   9271  N   MET D 266     -34.832 -66.607 -14.330  1.00 27.31      A    N
ATOM   9272  CA  MET D 266     -34.830 -67.788 -15.194  1.00 27.14      A    C
ATOM   9273  C   MET D 266     -35.234 -67.411 -16.616  1.00 27.07      A    C
ATOM   9274  O   MET D 266     -36.414 -67.236 -16.912  1.00 27.15      A    O
ATOM   9275  CB  MET D 266     -35.749 -68.871 -14.617  1.00 27.10      A    C
ATOM   9276  CG  MET D 266     -35.807 -70.152 -15.415  1.00 26.75      A    C
ATOM   9277  SD  MET D 266     -36.670 -71.429 -14.517  1.00 24.76      A    S
ATOM   9278  CE  MET D 266     -37.490 -72.272 -15.863  1.00 23.88      A    C
ATOM   9279  N   LEU D 267     -34.241 -67.284 -17.489  1.00 26.95      A    N
ATOM   9280  CA  LEU D 267     -34.471 -66.832 -18.859  1.00 26.89      A    C
ATOM   9281  C   LEU D 267     -34.759 -67.955 -19.850  1.00 26.98      A    C
ATOM   9282  O   LEU D 267     -33.954 -68.860 -20.032  1.00 27.03      A    O
ATOM   9283  CB  LEU D 267     -33.278 -66.027 -19.353  1.00 26.83      A    C
ATOM   9284  CG  LEU D 267     -33.301 -65.517 -20.796  1.00 26.55      A    C
ATOM   9285  CD1 LEU D 267     -34.484 -64.587 -21.038  1.00 26.53      A    C
ATOM   9286  CD2 LEU D 267     -32.001 -64.798 -21.105  1.00 26.46      A    C
ATOM   9287  N   LEU D 268     -35.905 -67.862 -20.512  1.00 27.06      A    N
ATOM   9288  CA  LEU D 268     -36.351 -68.878 -21.449  1.00 27.21      A    C
ATOM   9289  C   LEU D 268     -36.091 -68.442 -22.871  1.00 27.44      A    C
ATOM   9290  O   LEU D 268     -36.574 -67.401 -23.302  1.00 27.59      A    O
ATOM   9291  CB  LEU D 268     -37.841 -69.119 -21.274  1.00 27.15      A    C
ATOM   9292  CG  LEU D 268     -38.308 -70.172 -20.270  1.00 27.23      A    C
ATOM   9293  CD1 LEU D 268     -38.175 -69.698 -18.839  1.00 27.49      A    C
ATOM   9294  CD2 LEU D 268     -39.750 -70.529 -20.572  1.00 27.09      A    C
ATOM   9295  N   ASP D 269     -35.338 -69.246 -23.608  1.00 27.67      A    N
```

FIGURE 1 (cont'd)

```
ATOM   9296  CA  ASP D 269     -34.973 -68.890 -24.970  1.00 27.96      A    C
ATOM   9297  C   ASP D 269     -34.776 -70.084 -25.891  1.00 27.92      A    C
ATOM   9298  O   ASP D 269     -34.405 -71.167 -25.442  1.00 28.13      A    O
ATOM   9299  CB  ASP D 269     -33.704 -68.057 -24.964  1.00 28.21      A    C
ATOM   9300  CG  ASP D 269     -33.735 -66.985 -26.006  1.00 29.36      A    C
ATOM   9301  OD1 ASP D 269     -34.686 -66.172 -25.969  1.00 30.33      A    O
ATOM   9302  OD2 ASP D 269     -32.823 -66.950 -26.861  1.00 30.11      A    O
ATOM   9303  N   LEU D 270     -35.018 -69.871 -27.180  1.00 27.81      A    N
ATOM   9304  CA  LEU D 270     -34.831 -70.893 -28.214  1.00 27.80      A    C
ATOM   9305  C   LEU D 270     -35.473 -72.235 -27.866  1.00 27.90      A    C
ATOM   9306  O   LEU D 270     -34.873 -73.290 -28.069  1.00 27.97      A    O
ATOM   9307  CB  LEU D 270     -33.345 -71.060 -28.556  1.00 27.70      A    C
ATOM   9308  CG  LEU D 270     -32.544 -69.798 -28.863  1.00 27.70      A    C
ATOM   9309  CD1 LEU D 270     -31.240 -70.168 -29.507  1.00 27.65      A    C
ATOM   9310  CD2 LEU D 270     -33.298 -68.857 -29.771  1.00 28.01      A    C
ATOM   9311  N   LEU D 271     -36.692 -72.186 -27.339  1.00 27.99      A    N
ATOM   9312  CA  LEU D 271     -37.420 -73.395 -26.987  1.00 28.29      A    C
ATOM   9313  C   LEU D 271     -38.505 -73.616 -28.010  1.00 28.70      A    C
ATOM   9314  O   LEU D 271     -39.128 -72.663 -28.466  1.00 28.74      A    O
ATOM   9315  CB  LEU D 271     -38.033 -73.286 -25.590  1.00 28.08      A    C
ATOM   9316  CG  LEU D 271     -37.089 -73.129 -24.404  1.00 27.66      A    C
ATOM   9317  CD1 LEU D 271     -37.562 -71.962 -23.585  1.00 27.59      A    C
ATOM   9318  N   GLY D 272     -38.725 -74.871 -28.379  1.00 29.23      A    N
ATOM   9319  CA  GLY D 272     -39.804 -75.201 -29.306  1.00 29.90      A    C
ATOM   9320  C   GLY D 272     -39.430 -76.217 -30.366  1.00 30.47      A    C
ATOM   9321  O   GLY D 272     -40.288 -76.948 -30.864  1.00 30.67      A    O
ATOM   9322  N   ALA D 273     -38.147 -76.261 -30.716  1.00 30.86      A    N
ATOM   9323  CA  ALA D 273     -37.636 -77.221 -31.702  1.00 31.25      A    C
ATOM   9324  C   ALA D 273     -37.643 -78.661 -31.144  1.00 31.58      A    C
ATOM   9325  O   ALA D 273     -37.759 -78.857 -29.927  1.00 31.63      A    O
ATOM   9326  CB  ALA D 273     -36.224 -76.810 -32.151  1.00 31.19      A    C
ATOM   9327  N   PRO D 274     -37.542 -79.671 -32.026  1.00 31.95      A    N
ATOM   9328  CA  PRO D 274     -37.369 -81.035 -31.539  1.00 32.24      A    C
ATOM   9329  C   PRO D 274     -35.995 -81.254 -30.923  1.00 32.36      A    C
ATOM   9330  O   PRO D 274     -35.032 -80.572 -31.291  1.00 32.25      A    O
ATOM   9331  CB  PRO D 274     -37.505 -81.879 -32.806  1.00 32.49      A    C
ATOM   9332  CG  PRO D 274     -37.176 -80.946 -33.914  1.00 32.44      A    C
ATOM   9333  CD  PRO D 274     -37.735 -79.637 -33.483  1.00 32.13      A    C
ATOM   9334  N   ASN D 275     -35.930 -82.198 -29.987  1.00 32.61      A    N
ATOM   9335  CA  ASN D 275     -34.677 -82.635 -29.351  1.00 32.96      A    C
ATOM   9336  C   ASN D 275     -33.744 -81.523 -28.857  1.00 32.55      A    C
ATOM   9337  O   ASN D 275     -32.570 -81.491 -29.238  1.00 32.80      A    O
ATOM   9338  CB  ASN D 275     -33.909 -83.609 -30.269  1.00 33.44      A    C
ATOM   9339  CG  ASN D 275     -34.751 -84.810 -30.676  1.00 34.81      A    C
ATOM   9340  ND2 ASN D 275     -35.234 -84.796 -31.916  1.00 35.90      A    N
ATOM   9341  OD1 ASN D 275     -34.969 -85.739 -29.886  1.00 35.83      A    O
ATOM   9342  N   PRO D 276     -34.254 -80.610 -28.007  1.00 32.06      A    N
ATOM   9343  CA  PRO D 276     -33.348 -79.630 -27.435  1.00 31.81      A    C
ATOM   9344  C   PRO D 276     -32.506 -80.280 -26.354  1.00 31.82      A    C
ATOM   9345  O   PRO D 276     -32.924 -81.279 -25.770  1.00 31.89      A    O
ATOM   9346  CB  PRO D 276     -34.288 -78.609 -26.817  1.00 31.61      A    C
ATOM   9347  CG  PRO D 276     -35.482 -79.381 -26.465  1.00 31.60      A    C
ATOM   9348  CD  PRO D 276     -35.626 -80.442 -27.503  1.00 31.88      A    C
ATOM   9349  N   THR D 277     -31.316 -79.733 -26.127  1.00 31.87      A    N
ATOM   9350  CA  THR D 277     -30.453 -80.168 -25.031  1.00 31.92      A    C
ATOM   9351  C   THR D 277     -30.058 -78.973 -24.172  1.00 31.81      A    C
ATOM   9352  O   THR D 277     -29.586 -77.952 -24.678  1.00 31.77      A    O
ATOM   9353  CB  THR D 277     -29.200 -80.985 -25.507  1.00 32.01      A    C
ATOM   9354  CG2 THR D 277     -29.589 -82.393 -25.892  1.00 32.15      A    C
ATOM   9355  OG1 THR D 277     -28.596 -80.371 -26.650  1.00 32.30      A    O
ATOM   9356  N   PHE D 278     -30.285 -79.104 -22.871  1.00 31.78      A    N
ATOM   9357  CA  PHE D 278     -30.014 -78.036 -21.924  1.00 31.82      A    C
ATOM   9358  C   PHE D 278     -28.908 -78.400 -20.945  1.00 32.13      A    C
ATOM   9359  O   PHE D 278     -28.810 -79.543 -20.515  1.00 32.25      A    O
ATOM   9360  CB  PHE D 278     -31.286 -77.686 -21.150  1.00 31.57      A    C
```

FIGURE 1 (cont'd)

```
ATOM   9361  CG   PHE D 278     -32.444 -77.325 -22.027  1.00 31.33      A    C
ATOM   9362  CD1  PHE D 278     -32.460 -76.117 -22.727  1.00 31.29      A    C
ATOM   9363  CD2  PHE D 278     -33.521 -78.188 -22.164  1.00 31.19      A    C
ATOM   9364  CE1  PHE D 278     -33.546 -75.775 -23.560  1.00 31.22      A    C
ATOM   9365  CE2  PHE D 278     -34.603 -77.860 -22.984  1.00 31.02      A    C
ATOM   9366  CZ   PHE D 278     -34.614 -76.650 -23.683  1.00 31.02      A    C
ATOM   9367  N    TYR D 279     -28.086 -77.415 -20.597  1.00 32.51      A    N
ATOM   9368  CA   TYR D 279     -27.039 -77.577 -19.591  1.00 33.06      A    C
ATOM   9369  C    TYR D 279     -27.065 -76.436 -18.585  1.00 33.67      A    C
ATOM   9370  O    TYR D 279     -27.711 -75.414 -18.814  1.00 33.63      A    O
ATOM   9371  CB   TYR D 279     -25.667 -77.637 -20.244  1.00 32.96      A    C
ATOM   9372  CG   TYR D 279     -25.533 -78.708 -21.289  1.00 32.47      A    C
ATOM   9373  CD1  TYR D 279     -25.173 -80.018 -20.946  1.00 32.36      A    C
ATOM   9374  CD2  TYR D 279     -25.744 -78.399 -22.626  1.00 31.54      A    C
ATOM   9375  CE1  TYR D 279     -25.050 -80.977 -21.919  1.00 31.20      A    C
ATOM   9376  CE2  TYR D 279     -25.626 -79.346 -23.591  1.00 30.77      A    C
ATOM   9377  CZ   TYR D 279     -25.285 -80.621 -23.239  1.00 30.70      A    C
ATOM   9378  OH   TYR D 279     -25.188 -81.526 -24.247  1.00 31.41      A    O
ATOM   9379  N    SER D 280     -26.372 -76.610 -17.466  1.00 34.60      A    N
ATOM   9380  CA   SER D 280     -26.319 -75.559 -16.461  1.00 35.43      A    C
ATOM   9381  C    SER D 280     -25.144 -74.633 -16.713  1.00 35.94      A    C
ATOM   9382  O    SER D 280     -23.987 -74.990 -16.481  1.00 36.24      A    O
ATOM   9383  CB   SER D 280     -26.257 -76.138 -15.051  1.00 35.58      A    C
ATOM   9384  OG   SER D 280     -26.385 -75.103 -14.092  1.00 35.79      A    O
ATOM   9385  N    HIS D 281     -25.449 -73.432 -17.185  1.00 36.40      A    N
ATOM   9386  CA   HIS D 281     -24.406 -72.467 -17.521  1.00 37.14      A    C
ATOM   9387  C    HIS D 281     -24.002 -71.570 -16.343  1.00 37.45      A    C
ATOM   9388  O    HIS D 281     -23.068 -70.764 -16.453  1.00 37.62      A    O
ATOM   9389  CB   HIS D 281     -24.810 -71.639 -18.741  1.00 37.21      A    C
ATOM   9390  CG   HIS D 281     -25.172 -72.465 -19.931  1.00 37.78      A    C
ATOM   9391  CD2  HIS D 281     -24.404 -73.010 -20.901  1.00 38.65      A    C
ATOM   9392  ND1  HIS D 281     -26.471 -72.827 -20.215  1.00 37.77      A    N
ATOM   9393  CE1  HIS D 281     -26.490 -73.555 -21.315  1.00 38.22      A    C
ATOM   9394  NE2  HIS D 281     -25.248 -73.680 -21.752  1.00 38.96      A    N
ATOM   9395  N    PHE D 282     -24.704 -71.723 -15.223  1.00 37.80      A    N
ATOM   9396  CA   PHE D 282     -24.315 -71.070 -13.977  1.00 38.17      A    C
ATOM   9397  C    PHE D 282     -24.337 -72.034 -12.793  1.00 38.53      A    C
ATOM   9398  O    PHE D 282     -25.421 -72.477 -12.373  1.00 38.47      A    O
ATOM   9399  CB   PHE D 282     -25.183 -69.840 -13.701  1.00 38.06      A    C
ATOM   9400  CG   PHE D 282     -25.117 -68.818 -14.784  1.00 38.01      A    C
ATOM   9401  CD1  PHE D 282     -23.976 -68.049 -14.957  1.00 38.47      A    C
ATOM   9402  CD2  PHE D 282     -26.183 -68.641 -15.658  1.00 37.88      A    C
ATOM   9403  CE1  PHE D 282     -23.899 -67.108 -15.983  1.00 38.42      A    C
ATOM   9404  CE2  PHE D 282     -26.118 -67.705 -16.692  1.00 37.94      A    C
ATOM   9405  CZ   PHE D 282     -24.975 -66.941 -16.853  1.00 38.20      A    C
ATOM   9406  N    PRO D 283     -23.138 -72.363 -12.253  1.00 38.90      A    N
ATOM   9407  CA   PRO D 283     -23.019 -73.231 -11.095  1.00 39.02      A    C
ATOM   9408  C    PRO D 283     -23.713 -72.633  -9.872  1.00 38.91      A    C
ATOM   9409  O    PRO D 283     -24.065 -73.364  -8.954  1.00 39.03      A    O
ATOM   9410  CB   PRO D 283     -21.509 -73.311 -10.873  1.00 39.25      A    C
ATOM   9411  CG   PRO D 283     -20.918 -72.940 -12.157  1.00 39.27      A    C
ATOM   9412  CD   PRO D 283     -21.814 -71.909 -12.708  1.00 39.02      A    C
ATOM   9413  N    ARG D 284     -23.919 -71.321  -9.872  1.00 38.63      A    N
ATOM   9414  CA   ARG D 284     -24.635 -70.662  -8.798  1.00 38.50      A    C
ATOM   9415  C    ARG D 284     -26.014 -71.260  -8.621  1.00 38.69      A    C
ATOM   9416  O    ARG D 284     -26.453 -71.464  -7.499  1.00 38.97      A    O
ATOM   9417  CB   ARG D 284     -24.768 -69.173  -9.076  1.00 38.25      A    C
ATOM   9418  CG   ARG D 284     -24.713 -68.296  -7.841  1.00 37.47      A    C
ATOM   9419  CD   ARG D 284     -25.899 -68.440  -6.941  1.00 35.73      A    C
ATOM   9420  NE   ARG D 284     -26.050 -67.220  -6.184  1.00 34.83      A    N
ATOM   9421  CZ   ARG D 284     -27.090 -66.927  -5.428  1.00 33.28      A    C
ATOM   9422  NH1  ARG D 284     -28.093 -67.789  -5.296  1.00 32.65      A    N
ATOM   9423  NH2  ARG D 284     -27.116 -65.760  -4.801  1.00 33.25      A    N
ATOM   9424  N    THR D 285     -26.693 -71.540  -9.727  1.00 38.74      A    N
ATOM   9425  CA   THR D 285     -28.055 -72.052  -9.674  1.00 38.86      A    C
```

FIGURE 1 (cont'd)

```
ATOM   9426  C    THR D 285     -28.128 -73.526 -10.056  1.00 39.27      A    C
ATOM   9427  O    THR D 285     -29.207 -74.039 -10.353  1.00 39.19      A    O
ATOM   9428  CB   THR D 285     -29.010 -71.219 -10.560  1.00 38.49      A    C
ATOM   9429  OG1  THR D 285     -28.442 -71.052 -11.861  1.00 38.14      A    O
ATOM   9430  N    VAL D 286     -26.983 -74.212 -10.013  1.00 39.89      A    N
ATOM   9431  CA   VAL D 286     -26.869 -75.602 -10.497  1.00 40.39      A    C
ATOM   9432  C    VAL D 286     -27.925 -76.526  -9.921  1.00 41.02      A    C
ATOM   9433  O    VAL D 286     -28.332 -77.478 -10.585  1.00 41.06      A    O
ATOM   9434  CB   VAL D 286     -25.479 -76.216 -10.235  1.00 40.28      A    C
ATOM   9435  N    ARG D 287     -28.376 -76.233  -8.704  1.00 41.87      A    N
ATOM   9436  CA   ARG D 287     -29.341 -77.088  -8.022  1.00 42.76      A    C
ATOM   9437  C    ARG D 287     -30.769 -76.908  -8.522  1.00 42.51      A    C
ATOM   9438  O    ARG D 287     -31.581 -77.817  -8.406  1.00 42.69      A    O
ATOM   9439  CB   ARG D 287     -29.259 -76.910  -6.506  1.00 43.51      A    C
ATOM   9440  CG   ARG D 287     -29.672 -75.546  -5.991  1.00 45.23      A    C
ATOM   9441  CD   ARG D 287     -29.590 -75.482  -4.467  1.00 48.26      A    C
ATOM   9442  NE   ARG D 287     -30.161 -74.236  -3.946  1.00 49.98      A    N
ATOM   9443  CZ   ARG D 287     -31.437 -74.074  -3.583  1.00 50.48      A    C
ATOM   9444  NH1  ARG D 287     -32.308 -75.082  -3.675  1.00 50.55      A    N
ATOM   9445  NH2  ARG D 287     -31.843 -72.895  -3.122  1.00 50.70      A    N
ATOM   9446  N    TRP D 288     -31.077 -75.742  -9.079  1.00 42.18      A    N
ATOM   9447  CA   TRP D 288     -32.381 -75.534  -9.701  1.00 41.87      A    C
ATOM   9448  C    TRP D 288     -32.441 -76.206 -11.059  1.00 41.64      A    C
ATOM   9449  O    TRP D 288     -33.513 -76.596 -11.513  1.00 41.69      A    O
ATOM   9450  CB   TRP D 288     -32.731 -74.051  -9.796  1.00 41.76      A    C
ATOM   9451  CG   TRP D 288     -33.101 -73.488  -8.484  1.00 42.45      A    C
ATOM   9452  CD1  TRP D 288     -32.490 -72.463  -7.827  1.00 42.96      A    C
ATOM   9453  CD2  TRP D 288     -34.156 -73.942  -7.631  1.00 43.20      A    C
ATOM   9454  CE2  TRP D 288     -34.133 -73.133  -6.472  1.00 43.58      A    C
ATOM   9455  CE3  TRP D 288     -35.123 -74.949  -7.736  1.00 43.40      A    C
ATOM   9456  NE1  TRP D 288     -33.108 -72.236  -6.620  1.00 43.39      A    N
ATOM   9457  CZ2  TRP D 288     -35.037 -73.302  -5.424  1.00 44.05      A    C
ATOM   9458  CZ3  TRP D 288     -36.017 -75.118  -6.698  1.00 43.90      A    C
ATOM   9459  CH2  TRP D 288     -35.968 -74.296  -5.554  1.00 44.26      A    C
ATOM   9460  N    PHE D 289     -31.284 -76.346 -11.699  1.00 41.47      A    N
ATOM   9461  CA   PHE D 289     -31.184 -77.104 -12.933  1.00 41.29      A    C
ATOM   9462  C    PHE D 289     -31.447 -78.579 -12.632  1.00 41.42      A    C
ATOM   9463  O    PHE D 289     -32.165 -79.266 -13.359  1.00 41.27      A    O
ATOM   9464  CB   PHE D 289     -29.814 -76.902 -13.584  1.00 41.19      A    C
ATOM   9465  CG   PHE D 289     -29.740 -77.416 -14.982  1.00 41.06      A    C
ATOM   9466  CD1  PHE D 289     -30.292 -76.693 -16.029  1.00 40.66      A    C
ATOM   9467  CD2  PHE D 289     -29.135 -78.633 -15.252  1.00 41.40      A    C
ATOM   9468  CE1  PHE D 289     -30.242 -77.170 -17.319  1.00 40.55      A    C
ATOM   9469  CE2  PHE D 289     -29.077 -79.116 -16.541  1.00 41.52      A    C
ATOM   9470  CZ   PHE D 289     -29.640 -78.383 -17.578  1.00 41.08      A    C
ATOM   9471  N    HIS D 290     -30.877 -79.044 -11.531  1.00 41.75      A    N
ATOM   9472  CA   HIS D 290     -31.078 -80.391 -11.051  1.00 42.20      A    C
ATOM   9473  C    HIS D 290     -32.551 -80.681 -10.838  1.00 42.30      A    C
ATOM   9474  O    HIS D 290     -33.016 -81.782 -11.098  1.00 42.51      A    O
ATOM   9475  CB   HIS D 290     -30.315 -80.550  -9.749  1.00 42.49      A    C
ATOM   9476  CG   HIS D 290     -28.913 -81.031  -9.925  1.00 43.15      A    C
ATOM   9477  CD2  HIS D 290     -27.969 -80.819 -10.877  1.00 43.44      A    C
ATOM   9478  ND1  HIS D 290     -28.367 -81.930  -9.053  1.00 43.98      A    N
ATOM   9479  CE1  HIS D 290     -27.187 -82.310  -9.464  1.00 44.46      A    C
ATOM   9480  NE2  HIS D 290     -26.884 -81.600 -10.541  1.00 43.34      A    N
ATOM   9481  N    ARG D 291     -33.288 -79.681 -10.378  1.00 42.37      A    N
ATOM   9482  CA   ARG D 291     -34.725 -79.823 -10.199  1.00 42.60      A    C
ATOM   9483  C    ARG D 291     -35.399 -80.125 -11.510  1.00 42.21      A    C
ATOM   9484  O    ARG D 291     -36.242 -81.014 -11.583  1.00 42.50      A    O
ATOM   9485  CB   ARG D 291     -35.328 -78.567  -9.579  1.00 42.84      A    C
ATOM   9486  CG   ARG D 291     -35.119 -78.514  -8.090  1.00 44.49      A    C
ATOM   9487  CD   ARG D 291     -35.768 -79.716  -7.429  1.00 46.62      A    C
ATOM   9488  NE   ARG D 291     -37.138 -79.419  -7.041  1.00 47.69      A    N
ATOM   9489  CZ   ARG D 291     -37.489 -79.047  -5.816  1.00 48.73      A    C
ATOM   9490  NH1  ARG D 291     -36.573 -78.947  -4.860  1.00 49.26      A    N
```

FIGURE 1 (cont'd)

```
ATOM   9491  NH2 ARG D 291     -38.756 -78.781  -5.546  1.00 49.26      A  N
ATOM   9492  N   LEU D 292     -35.005 -79.396 -12.546  1.00 41.59      A  N
ATOM   9493  CA  LEU D 292     -35.571 -79.584 -13.865  1.00 40.94      A  C
ATOM   9494  C   LEU D 292     -35.273 -80.984 -14.382  1.00 40.90      A  C
ATOM   9495  O   LEU D 292     -36.171 -81.659 -14.883  1.00 40.96      A  O
ATOM   9496  CB  LEU D 292     -35.089 -78.495 -14.822  1.00 40.57      A  C
ATOM   9497  CG  LEU D 292     -35.600 -77.085 -14.484  1.00 39.86      A  C
ATOM   9498  CD1 LEU D 292     -34.807 -76.023 -15.219  1.00 39.39      A  C
ATOM   9499  CD2 LEU D 292     -37.065 -76.955 -14.811  1.00 39.41      A  C
ATOM   9500  N   ARG D 293     -34.032 -81.439 -14.221  1.00 40.87      A  N
ATOM   9501  CA  ARG D 293     -33.694 -82.820 -14.565  1.00 40.99      A  C
ATOM   9502  C   ARG D 293     -34.617 -83.765 -13.793  1.00 41.27      A  C
ATOM   9503  O   ARG D 293     -35.240 -84.646 -14.381  1.00 41.35      A  O
ATOM   9504  CB  ARG D 293     -32.213 -83.124 -14.288  1.00 40.89      A  C
ATOM   9505  CG  ARG D 293     -31.672 -84.355 -15.018  1.00 40.66      A  C
ATOM   9506  CD  ARG D 293     -30.265 -84.746 -14.580  1.00 40.43      A  C
ATOM   9507  NE  ARG D 293     -29.318 -83.666 -14.838  1.00 39.70      A  N
ATOM   9508  CZ  ARG D 293     -28.506 -83.140 -13.929  1.00 39.10      A  C
ATOM   9509  NH1 ARG D 293     -28.485 -83.637 -12.694  1.00 38.85      A  N
ATOM   9510  NH2 ARG D 293     -27.691 -82.139 -14.264  1.00 38.63      A  N
ATOM   9511  N   SER D 294     -34.735 -83.533 -12.486  1.00 41.45      A  N
ATOM   9512  CA  SER D 294     -35.528 -84.379 -11.597  1.00 41.70      A  C
ATOM   9513  C   SER D 294     -37.000 -84.386 -11.973  1.00 42.10      A  C
ATOM   9514  O   SER D 294     -37.652 -85.422 -11.887  1.00 42.62      A  O
ATOM   9515  CB  SER D 294     -35.357 -83.964 -10.135  1.00 40.72      A  C
ATOM   9516  N   ILE D 295     -37.519 -83.237 -12.396  1.00 42.18      A  N
ATOM   9517  CA  ILE D 295     -38.921 -83.125 -12.797  1.00 42.24      A  C
ATOM   9518  C   ILE D 295     -39.164 -83.896 -14.101  1.00 42.53      A  C
ATOM   9519  O   ILE D 295     -40.153 -84.625 -14.228  1.00 42.72      A  O
ATOM   9520  CB  ILE D 295     -39.375 -81.644 -12.885  1.00 41.94      A  C
ATOM   9521  CG1 ILE D 295     -39.511 -81.057 -11.483  1.00 41.87      A  C
ATOM   9522  CG2 ILE D 295     -40.699 -81.512 -13.610  1.00 41.82      A  C
ATOM   9523  CD1 ILE D 295     -39.317 -79.577 -11.420  1.00 41.60      A  C
ATOM   9524  N   GLU D 296     -38.242 -83.757 -15.052  1.00 42.69      A  N
ATOM   9525  CA  GLU D 296     -38.329 -84.469 -16.319  1.00 42.97      A  C
ATOM   9526  C   GLU D 296     -38.316 -85.953 -16.028  1.00 43.53      A  C
ATOM   9527  O   GLU D 296     -39.180 -86.692 -16.484  1.00 43.81      A  O
ATOM   9528  CB  GLU D 296     -37.157 -84.100 -17.219  1.00 42.69      A  C
ATOM   9529  CG  GLU D 296     -37.238 -84.685 -18.622  1.00 42.90      A  C
ATOM   9530  CD  GLU D 296     -35.957 -84.484 -19.447  1.00 43.12      A  C
ATOM   9531  OE1 GLU D 296     -35.090 -83.658 -19.066  1.00 42.80      A  O
ATOM   9532  OE2 GLU D 296     -35.820 -85.159 -20.491  1.00 43.36      A  O
ATOM   9533  N   LYS D 297     -37.331 -86.369 -15.240  1.00 44.11      A  N
ATOM   9534  CA  LYS D 297     -37.194 -87.750 -14.805  1.00 44.82      A  C
ATOM   9535  C   LYS D 297     -38.537 -88.243 -14.253  1.00 45.48      A  C
ATOM   9536  O   LYS D 297     -39.079 -89.231 -14.750  1.00 45.75      A  O
ATOM   9537  CB  LYS D 297     -36.094 -87.843 -13.746  1.00 44.72      A  C
ATOM   9538  CG  LYS D 297     -35.004 -88.889 -13.997  1.00 44.60      A  C
ATOM   9539  CD  LYS D 297     -33.679 -88.444 -13.342  1.00 43.75      A  C
ATOM   9540  CE  LYS D 297     -32.760 -89.599 -12.984  1.00 43.74      A  C
ATOM   9541  N   ARG D 298     -39.083 -87.520 -13.269  1.00 45.98      A  N
ATOM   9542  CA  ARG D 298     -40.330 -87.891 -12.583  1.00 46.48      A  C
ATOM   9543  C   ARG D 298     -41.532 -87.983 -13.523  1.00 47.01      A  C
ATOM   9544  O   ARG D 298     -42.264 -88.968 -13.496  1.00 47.63      A  O
ATOM   9545  CB  ARG D 298     -40.619 -86.917 -11.429  1.00 45.49      A  C
ATOM   9546  CG  ARG D 298     -41.825 -87.270 -10.547  1.00 45.46      A  C
ATOM   9547  CD  ARG D 298     -41.945 -86.321  -9.350  1.00 45.12      A  C
ATOM   9548  NE  ARG D 298     -43.152 -86.555  -8.557  1.00 44.96      A  N
ATOM   9549  N   LEU D 299     -41.727 -86.966 -14.352  1.00 47.21      A  N
ATOM   9550  CA  LEU D 299     -42.863 -86.934 -15.278  1.00 47.46      A  C
ATOM   9551  C   LEU D 299     -42.771 -88.024 -16.343  1.00 47.86      A  C
ATOM   9552  O   LEU D 299     -43.786 -88.502 -16.853  1.00 48.10      A  O
ATOM   9553  CB  LEU D 299     -42.975 -85.561 -15.948  1.00 47.15      A  C
ATOM   9554  CG  LEU D 299     -43.478 -84.369 -15.138  1.00 46.95      A  C
ATOM   9555  CD1 LEU D 299     -43.158 -83.091 -15.871  1.00 46.50      A  C
```

FIGURE 1 (cont'd)

```
ATOM   9556  CD2 LEU D 299     -44.965 -84.482 -14.891  1.00 47.42      A  C
ATOM   9557  N   HIS D 300     -41.541 -88.397 -16.680  1.00 48.21      A  N
ATOM   9558  CA  HIS D 300     -41.290 -89.506 -17.578  1.00 48.75      A  C
ATOM   9559  C   HIS D 300     -41.736 -90.815 -16.940  1.00 49.24      A  C
ATOM   9560  O   HIS D 300     -42.473 -91.575 -17.565  1.00 49.58      A  O
ATOM   9561  CB  HIS D 300     -39.815 -89.577 -17.956  1.00 48.68      A  C
ATOM   9562  CG  HIS D 300     -39.445 -90.842 -18.659  1.00 49.34      A  C
ATOM   9563  CD2 HIS D 300     -38.605 -91.842 -18.308  1.00 50.13      A  C
ATOM   9564  ND1 HIS D 300     -39.981 -91.200 -19.878  1.00 49.66      A  N
ATOM   9565  CE1 HIS D 300     -39.482 -92.364 -20.251  1.00 50.28      A  C
ATOM   9566  NE2 HIS D 300     -38.647 -92.777 -19.315  1.00 50.73      A  N
ATOM   9567  N   ARG D 301     -41.294 -91.061 -15.700  1.00 49.69      A  N
ATOM   9568  CA  ARG D 301     -41.688 -92.249 -14.912  1.00 50.23      A  C
ATOM   9569  C   ARG D 301     -43.208 -92.397 -14.839  1.00 50.86      A  C
ATOM   9570  O   ARG D 301     -43.738 -93.506 -14.931  1.00 51.41      A  O
ATOM   9571  CB  ARG D 301     -41.125 -92.202 -13.471  1.00 50.07      A  C
ATOM   9572  CG  ARG D 301     -39.621 -91.929 -13.316  1.00 49.11      A  C
ATOM   9573  CD  ARG D 301     -38.754 -93.184 -13.448  1.00 48.47      A  C
ATOM   9574  NE  ARG D 301     -37.330 -92.858 -13.600  1.00 47.72      A  N
ATOM   9575  N   LEU D 302     -43.895 -91.268 -14.682  1.00 51.24      A  N
ATOM   9576  CA  LEU D 302     -45.350 -91.232 -14.558  1.00 51.85      A  C
ATOM   9577  C   LEU D 302     -46.092 -91.248 -15.899  1.00 52.20      A  C
ATOM   9578  O   LEU D 302     -47.288 -90.941 -15.945  1.00 52.50      A  O
ATOM   9579  CB  LEU D 302     -45.763 -89.996 -13.763  1.00 51.75      A  C
ATOM   9580  CG  LEU D 302     -45.357 -89.984 -12.291  1.00 52.23      A  C
ATOM   9581  CD1 LEU D 302     -45.212 -88.570 -11.780  1.00 51.85      A  C
ATOM   9582  CD2 LEU D 302     -46.377 -90.730 -11.482  1.00 53.48      A  C
ATOM   9583  N   ASN D 303     -45.385 -91.622 -16.972  1.00 52.32      A  N
ATOM   9584  CA  ASN D 303     -45.913 -91.613 -18.344  1.00 52.24      A  C
ATOM   9585  C   ASN D 303     -46.772 -90.380 -18.609  1.00 52.69      A  C
ATOM   9586  O   ASN D 303     -47.977 -90.502 -18.813  1.00 53.19      A  O
ATOM   9587  N   LEU D 304     -46.148 -89.199 -18.570  1.00 52.86      A  N
ATOM   9588  CA  LEU D 304     -46.855 -87.927 -18.786  1.00 52.75      A  C
ATOM   9589  C   LEU D 304     -46.159 -87.018 -19.797  1.00 52.44      A  C
ATOM   9590  O   LEU D 304     -46.535 -85.855 -19.972  1.00 52.16      A  O
ATOM   9591  CB  LEU D 304     -47.074 -87.180 -17.464  1.00 52.80      A  C
ATOM   9592  CG  LEU D 304     -48.234 -87.593 -16.552  1.00 53.26      A  C
ATOM   9593  CD1 LEU D 304     -48.155 -86.834 -15.240  1.00 52.94      A  C
ATOM   9594  CD2 LEU D 304     -49.590 -87.362 -17.223  1.00 53.84      A  C
ATOM   9595  N   LEU D 305     -45.153 -87.568 -20.466  1.00 52.37      A  N
ATOM   9596  CA  LEU D 305     -44.420 -86.848 -21.497  1.00 52.20      A  C
ATOM   9597  C   LEU D 305     -44.528 -87.572 -22.838  1.00 52.59      A  C
ATOM   9598  O   LEU D 305     -44.130 -88.733 -22.958  1.00 53.00      A  O
ATOM   9599  CB  LEU D 305     -42.949 -86.692 -21.090  1.00 51.77      A  C
ATOM   9600  CG  LEU D 305     -42.599 -86.087 -19.730  1.00 51.07      A  C
ATOM   9601  CD1 LEU D 305     -41.117 -86.227 -19.478  1.00 50.41      A  C
ATOM   9602  CD2 LEU D 305     -43.010 -84.631 -19.661  1.00 50.65      A  C
ATOM   9603  N   GLN D 306     -45.073 -86.882 -23.836  1.00 52.73      A  N
ATOM   9604  CA  GLN D 306     -45.189 -87.425 -25.184  1.00 53.04      A  C
ATOM   9605  C   GLN D 306     -43.826 -87.601 -25.828  1.00 52.93      A  C
ATOM   9606  O   GLN D 306     -42.885 -86.894 -25.487  1.00 52.58      A  O
ATOM   9607  CB  GLN D 306     -46.024 -86.498 -26.056  1.00 53.16      A  C
ATOM   9608  CG  GLN D 306     -47.498 -86.828 -26.113  1.00 54.03      A  C
ATOM   9609  CD  GLN D 306     -48.204 -86.071 -27.220  1.00 54.72      A  C
ATOM   9610  OE1 GLN D 306     -48.092 -84.847 -27.316  1.00 54.95      A  O
ATOM   9611  N   SER D 307     -43.734 -88.548 -26.758  1.00 53.29      A  N
ATOM   9612  CA  SER D 307     -42.514 -88.783 -27.536  1.00 53.52      A  C
ATOM   9613  C   SER D 307     -41.229 -88.648 -26.700  1.00 53.37      A  C
ATOM   9614  O   SER D 307     -40.295 -87.939 -27.085  1.00 53.16      A  O
ATOM   9615  CB  SER D 307     -42.479 -87.840 -28.742  1.00 53.53      A  C
ATOM   9616  OG  SER D 307     -43.737 -87.810 -29.392  1.00 54.24      A  O
ATOM   9617  N   HIS D 308     -41.190 -89.334 -25.558  1.00 53.47      A  N
ATOM   9618  CA  HIS D 308     -40.094 -89.185 -24.609  1.00 53.43      A  C
ATOM   9619  C   HIS D 308     -39.508 -90.543 -24.240  1.00 53.72      A  C
ATOM   9620  O   HIS D 308     -39.747 -91.047 -23.143  1.00 53.98      A  O
```

FIGURE 1 (cont'd)

```
ATOM   9621  CB  HIS D 308     -40.597 -88.463 -23.364  1.00 53.27      A    C
ATOM   9622  CG  HIS D 308     -39.516 -87.815 -22.556  1.00 52.96      A    C
ATOM   9623  CD2 HIS D 308     -38.781 -86.701 -22.781  1.00 52.55      A    C
ATOM   9624  ND1 HIS D 308     -39.098 -88.307 -21.341  1.00 53.24      A    N
ATOM   9625  CE1 HIS D 308     -38.147 -87.530 -20.854  1.00 52.90      A    C
ATOM   9626  NE2 HIS D 308     -37.936 -86.548 -21.709  1.00 52.37      A    N
ATOM   9627  N   PRO D 309     -38.735 -91.146 -25.160  1.00 53.94      A    N
ATOM   9628  CA  PRO D 309     -38.266 -92.514 -24.957  1.00 54.41      A    C
ATOM   9629  C   PRO D 309     -36.997 -92.657 -24.112  1.00 54.67      A    C
ATOM   9630  O   PRO D 309     -36.147 -93.489 -24.424  1.00 54.96      A    O
ATOM   9631  CB  PRO D 309     -38.029 -93.019 -26.397  1.00 54.68      A    C
ATOM   9632  CG  PRO D 309     -38.670 -91.990 -27.304  1.00 54.43      A    C
ATOM   9633  CD  PRO D 309     -38.492 -90.713 -26.546  1.00 53.96      A    C
ATOM   9634  N   GLN D 310     -36.868 -91.839 -23.069  1.00 54.71      A    N
ATOM   9635  CA  GLN D 310     -35.917 -92.075 -21.951  1.00 54.89      A    C
ATOM   9636  C   GLN D 310     -36.024 -91.050 -20.817  1.00 54.98      A    C
ATOM   9637  O   GLN D 310     -36.857 -90.150 -20.866  1.00 54.84      A    O
ATOM   9638  CB  GLN D 310     -34.455 -92.303 -22.400  1.00 54.92      A    C
ATOM   9639  CG  GLN D 310     -33.940 -91.460 -23.575  1.00 54.54      A    C
ATOM   9640  CD  GLN D 310     -32.967 -92.235 -24.487  1.00 54.55      A    C
ATOM   9641  NE2 GLN D 310     -32.201 -91.506 -25.310  1.00 54.24      A    N
ATOM   9642  OE1 GLN D 310     -32.922 -93.470 -24.462  1.00 53.70      A    O
ATOM   9643  N   GLU D 311     -35.195 -91.199 -19.793  1.00 55.34      A    N
ATOM   9644  CA  GLU D 311     -35.315 -90.390 -18.592  1.00 55.71      A    C
ATOM   9645  C   GLU D 311     -34.692 -89.028 -18.828  1.00 55.02      A    C
ATOM   9646  O   GLU D 311     -35.392 -88.019 -18.801  1.00 54.87      A    O
ATOM   9647  CB  GLU D 311     -34.666 -91.086 -17.391  1.00 56.48      A    C
ATOM   9648  CG  GLU D 311     -35.058 -92.558 -17.206  1.00 58.90      A    C
ATOM   9649  CD  GLU D 311     -34.232 -93.545 -18.075  1.00 61.46      A    C
ATOM   9650  OE1 GLU D 311     -34.112 -94.739 -17.684  1.00 62.86      A    O
ATOM   9651  OE2 GLU D 311     -33.707 -93.139 -19.145  1.00 62.01      A    O
ATOM   9652  N   VAL D 312     -33.383 -89.002 -19.069  1.00 54.45      A    N
ATOM   9653  CA  VAL D 312     -32.691 -87.763 -19.397  1.00 53.71      A    C
ATOM   9654  C   VAL D 312     -32.658 -87.583 -20.909  1.00 53.19      A    C
ATOM   9655  O   VAL D 312     -31.965 -88.303 -21.626  1.00 53.52      A    O
ATOM   9656  N   MET D 313     -33.450 -86.632 -21.382  1.00 52.16      A    N
ATOM   9657  CA  MET D 313     -33.492 -86.277 -22.790  1.00 51.21      A    C
ATOM   9658  C   MET D 313     -33.136 -84.797 -22.909  1.00 50.21      A    C
ATOM   9659  O   MET D 313     -32.211 -84.426 -23.627  1.00 50.07      A    O
ATOM   9660  CB  MET D 313     -34.894 -86.514 -23.368  1.00 51.40      A    C
ATOM   9661  CG  MET D 313     -35.395 -87.947 -23.355  1.00 51.99      A    C
ATOM   9662  SD  MET D 313     -35.623 -88.632 -25.002  1.00 52.46      A    S
ATOM   9663  CE  MET D 313     -36.890 -87.560 -25.701  1.00 52.13      A    C
ATOM   9664  N   TYR D 314     -33.875 -83.967 -22.175  1.00 49.11      A    N
ATOM   9665  CA  TYR D 314     -33.803 -82.515 -22.307  1.00 48.02      A    C
ATOM   9666  C   TYR D 314     -32.738 -81.890 -21.422  1.00 47.48      A    C
ATOM   9667  O   TYR D 314     -31.827 -81.233 -21.915  1.00 47.26      A    O
ATOM   9668  CB  TYR D 314     -35.171 -81.884 -22.017  1.00 47.81      A    C
ATOM   9669  CG  TYR D 314     -36.279 -82.319 -22.947  1.00 47.52      A    C
ATOM   9670  CD1 TYR D 314     -36.025 -82.567 -24.294  1.00 47.54      A    C
ATOM   9671  CD2 TYR D 314     -37.584 -82.457 -22.489  1.00 47.34      A    C
ATOM   9672  CE1 TYR D 314     -37.039 -82.968 -25.163  1.00 47.63      A    C
ATOM   9673  CE2 TYR D 314     -38.610 -82.852 -23.349  1.00 47.42      A    C
ATOM   9674  CZ  TYR D 314     -38.327 -83.106 -24.689  1.00 47.36      A    C
ATOM   9675  OH  TYR D 314     -39.313 -83.494 -25.570  1.00 47.32      A    O
ATOM   9676  N   PHE D 315     -32.865 -82.082 -20.115  1.00 47.03      A    N
ATOM   9677  CA  PHE D 315     -31.946 -81.474 -19.168  1.00 46.66      A    C
ATOM   9678  C   PHE D 315     -30.788 -82.406 -18.878  1.00 46.93      A    C
ATOM   9679  O   PHE D 315     -30.851 -83.251 -17.992  1.00 47.01      A    O
ATOM   9680  CB  PHE D 315     -32.682 -81.047 -17.904  1.00 46.35      A    C
ATOM   9681  CG  PHE D 315     -33.763 -80.043 -18.161  1.00 45.27      A    C
ATOM   9682  CD1 PHE D 315     -33.474 -78.685 -18.214  1.00 44.52      A    C
ATOM   9683  CD2 PHE D 315     -35.073 -80.452 -18.386  1.00 44.57      A    C
ATOM   9684  CE1 PHE D 315     -34.478 -77.748 -18.474  1.00 43.99      A    C
ATOM   9685  CE2 PHE D 315     -36.085 -79.519 -18.639  1.00 44.02      A    C
```

FIGURE 1 (cont'd)

```
ATOM   9686  CZ  PHE D 315     -35.785 -78.166 -18.683  1.00 43.75           A  C
ATOM   9687  N   GLN D 316     -29.729 -82.242 -19.659  1.00 47.19           A  N
ATOM   9688  CA  GLN D 316     -28.578 -83.118 -19.609  1.00 47.72           A  C
ATOM   9689  C   GLN D 316     -27.709 -82.851 -18.393  1.00 48.07           A  C
ATOM   9690  O   GLN D 316     -27.661 -81.736 -17.897  1.00 47.92           A  O
ATOM   9691  CB  GLN D 316     -27.749 -82.967 -20.884  1.00 47.77           A  C
ATOM   9692  CG  GLN D 316     -28.389 -83.573 -22.127  1.00 48.22           A  C
ATOM   9693  CD  GLN D 316     -28.556 -85.081 -22.042  1.00 48.96           A  C
ATOM   9694  NE2 GLN D 316     -29.793 -85.541 -22.102  1.00 49.06           A  N
ATOM   9695  OE1 GLN D 316     -27.584 -85.819 -21.933  1.00 49.78           A  O
ATOM   9696  N   PRO D 317     -27.015 -83.885 -17.901  1.00 48.66           A  N
ATOM   9697  CA  PRO D 317     -26.042 -83.680 -16.851  1.00 48.94           A  C
ATOM   9698  C   PRO D 317     -24.781 -83.077 -17.426  1.00 49.00           A  C
ATOM   9699  O   PRO D 317     -24.586 -83.087 -18.641  1.00 48.97           A  O
ATOM   9700  CB  PRO D 317     -25.763 -85.095 -16.365  1.00 49.27           A  C
ATOM   9701  CG  PRO D 317     -25.967 -85.929 -17.550  1.00 49.42           A  C
ATOM   9702  CD  PRO D 317     -27.109 -85.302 -18.283  1.00 48.96           A  C
ATOM   9703  N   GLY D 318     -23.930 -82.559 -16.554  1.00 49.06           A  N
ATOM   9704  CA  GLY D 318     -22.721 -81.892 -16.993  1.00 49.02           A  C
ATOM   9705  C   GLY D 318     -22.885 -80.403 -16.835  1.00 48.83           A  C
ATOM   9706  O   GLY D 318     -23.981 -79.862 -17.027  1.00 48.61           A  O
ATOM   9707  N   GLU D 319     -21.784 -79.753 -16.466  1.00 48.83           A  N
ATOM   9708  CA  GLU D 319     -21.738 -78.306 -16.294  1.00 48.61           A  C
ATOM   9709  C   GLU D 319     -20.679 -77.699 -17.217  1.00 48.74           A  C
ATOM   9710  O   GLU D 319     -19.568 -77.411 -16.770  1.00 49.13           A  O
ATOM   9711  CB  GLU D 319     -21.439 -77.945 -14.832  1.00 48.49           A  C
ATOM   9712  CG  GLU D 319     -22.436 -78.489 -13.827  1.00 47.86           A  C
ATOM   9713  CD  GLU D 319     -22.266 -77.879 -12.470  1.00 44.78           A  C
ATOM   9714  OE1 GLU D 319     -22.693 -76.717 -12.291  1.00 44.24           A  O
ATOM   9715  OE2 GLU D 319     -21.719 -78.568 -11.586  1.00 43.01           A  O
ATOM   9716  N   PRO D 320     -21.003 -77.525 -18.514  1.00 48.62           A  N
ATOM   9717  CA  PRO D 320     -20.024 -76.915 -19.407  1.00 48.64           A  C
ATOM   9718  C   PRO D 320     -19.886 -75.416 -19.169  1.00 48.53           A  C
ATOM   9719  O   PRO D 320     -20.773 -74.804 -18.554  1.00 48.34           A  O
ATOM   9720  CB  PRO D 320     -20.598 -77.198 -20.803  1.00 48.70           A  C
ATOM   9721  CG  PRO D 320     -21.498 -78.360 -20.614  1.00 48.68           A  C
ATOM   9722  CD  PRO D 320     -22.118 -78.112 -19.272  1.00 48.47           A  C
ATOM   9723  N   PHE D 321     -18.787 -74.851 -19.676  1.00 48.35           A  N
ATOM   9724  CA  PHE D 321     -18.405 -73.464 -19.417  1.00 47.96           A  C
ATOM   9725  C   PHE D 321     -19.403 -72.322 -19.779  1.00 48.17           A  C
ATOM   9726  O   PHE D 321     -19.781 -71.522 -18.902  1.00 48.50           A  O
ATOM   9727  N   GLY D 322     -19.826 -72.245 -21.044  1.00 48.03           A  N
ATOM   9728  CA  GLY D 322     -20.697 -71.148 -21.516  1.00 47.44           A  C
ATOM   9729  C   GLY D 322     -19.897 -69.888 -21.850  1.00 47.08           A  C
ATOM   9730  O   GLY D 322     -18.687 -69.971 -22.077  1.00 47.62           A  O
ATOM   9731  N   SER D 323     -20.541 -68.721 -21.920  1.00 46.11           A  N
ATOM   9732  CA  SER D 323     -21.988 -68.573 -21.857  1.00 45.02           A  C
ATOM   9733  C   SER D 323     -22.475 -68.117 -23.216  1.00 43.87           A  C
ATOM   9734  O   SER D 323     -21.669 -67.858 -24.104  1.00 44.00           A  O
ATOM   9735  CB  SER D 323     -22.372 -67.526 -20.812  1.00 45.24           A  C
ATOM   9736  OG  SER D 323     -21.893 -67.896 -19.532  1.00 46.08           A  O
ATOM   9737  N   VAL D 324     -23.793 -68.020 -23.368  1.00 42.28           A  N
ATOM   9738  CA  VAL D 324     -24.400 -67.483 -24.574  1.00 40.73           A  C
ATOM   9739  C   VAL D 324     -25.026 -66.163 -24.199  1.00 39.98           A  C
ATOM   9740  O   VAL D 324     -25.852 -66.126 -23.299  1.00 39.90           A  O
ATOM   9741  CB  VAL D 324     -25.466 -68.439 -25.112  1.00 40.49           A  C
ATOM   9742  CG1 VAL D 324     -24.806 -69.703 -25.617  1.00 40.41           A  C
ATOM   9743  CG2 VAL D 324     -26.280 -67.792 -26.218  1.00 40.05           A  C
ATOM   9744  N   GLU D 325     -24.625 -65.087 -24.877  1.00 39.16           A  N
ATOM   9745  CA  GLU D 325     -25.089 -63.734 -24.546  1.00 38.49           A  C
ATOM   9746  C   GLU D 325     -26.579 -63.559 -24.812  1.00 37.60           A  C
ATOM   9747  O   GLU D 325     -27.040 -63.776 -25.920  1.00 37.48           A  O
ATOM   9748  CB  GLU D 325     -24.296 -62.687 -25.322  1.00 38.86           A  C
ATOM   9749  CG  GLU D 325     -22.800 -62.777 -25.124  1.00 40.45           A  C
ATOM   9750  CD  GLU D 325     -22.051 -61.609 -25.733  1.00 42.56           A  C
```

FIGURE 1 (cont'd)

```
ATOM   9751  OE1 GLU D 325     -22.699 -60.619 -26.134  1.00 42.98      A  O
ATOM   9752  OE2 GLU D 325     -20.805 -61.678 -25.805  1.00 43.82      A  O
ATOM   9753  N   ASP D 326     -27.329 -63.177 -23.785  1.00 36.77      A  N
ATOM   9754  CA  ASP D 326     -28.784 -63.043 -23.879  1.00 36.01      A  C
ATOM   9755  C   ASP D 326     -29.263 -62.021 -22.843  1.00 35.76      A  C
ATOM   9756  O   ASP D 326     -28.444 -61.364 -22.195  1.00 35.89      A  O
ATOM   9757  CB  ASP D 326     -29.457 -64.402 -23.665  1.00 35.72      A  C
ATOM   9758  CG  ASP D 326     -30.773 -64.543 -24.412  1.00 35.11      A  C
ATOM   9759  OD1 ASP D 326     -31.425 -63.529 -24.717  1.00 34.83      A  O
ATOM   9760  OD2 ASP D 326     -31.169 -65.691 -24.686  1.00 34.60      A  O
ATOM   9761  N   ASP D 327     -30.578 -61.889 -22.690  1.00 35.28      A  N
ATOM   9762  CA  ASP D 327     -31.182 -60.867 -21.836  1.00 34.96      A  C
ATOM   9763  C   ASP D 327     -30.770 -60.913 -20.371  1.00 34.56      A  C
ATOM   9764  O   ASP D 327     -31.025 -59.973 -19.631  1.00 34.66      A  O
ATOM   9765  CB  ASP D 327     -32.699 -60.972 -21.894  1.00 35.13      A  C
ATOM   9766  CG  ASP D 327     -33.273 -60.493 -23.206  1.00 36.04      A  C
ATOM   9767  OD1 ASP D 327     -33.139 -59.284 -23.502  1.00 36.75      A  O
ATOM   9768  OD2 ASP D 327     -33.883 -61.324 -23.926  1.00 36.70      A  O
ATOM   9769  N   HIS D 328     -30.155 -62.008 -19.947  1.00 34.06      A  N
ATOM   9770  CA  HIS D 328     -29.741 -62.156 -18.566  1.00 33.70      A  C
ATOM   9771  C   HIS D 328     -28.507 -61.320 -18.247  1.00 33.62      A  C
ATOM   9772  O   HIS D 328     -28.325 -60.895 -17.116  1.00 33.84      A  O
ATOM   9773  CB  HIS D 328     -29.490 -63.627 -18.240  1.00 33.57      A  C
ATOM   9774  CG  HIS D 328     -28.266 -64.194 -18.889  1.00 33.84      A  C
ATOM   9775  CD2 HIS D 328     -27.035 -64.458 -18.395  1.00 34.44      A  C
ATOM   9776  ND1 HIS D 328     -28.227 -64.560 -20.214  1.00 34.07      A  N
ATOM   9777  CE1 HIS D 328     -27.026 -65.025 -20.509  1.00 34.31      A  C
ATOM   9778  NE2 HIS D 328     -26.283 -64.975 -19.422  1.00 34.54      A  N
ATOM   9779  N   ILE D 329     -27.676 -61.067 -19.247  1.00 33.47      A  N
ATOM   9780  CA  ILE D 329     -26.385 -60.423 -19.027  1.00 33.61      A  C
ATOM   9781  C   ILE D 329     -26.427 -59.159 -18.168  1.00 33.61      A  C
ATOM   9782  O   ILE D 329     -25.688 -59.069 -17.199  1.00 33.90      A  O
ATOM   9783  CB  ILE D 329     -25.640 -60.165 -20.353  1.00 33.70      A  C
ATOM   9784  CG1 ILE D 329     -25.238 -61.494 -21.008  1.00 33.91      A  C
ATOM   9785  CG2 ILE D 329     -24.428 -59.253 -20.134  1.00 34.17      A  C
ATOM   9786  CD1 ILE D 329     -24.266 -62.358 -20.185  1.00 34.46      A  C
ATOM   9787  N   PRO D 330     -27.290 -58.188 -18.501  1.00 33.53      A  N
ATOM   9788  CA  PRO D 330     -27.238 -56.969 -17.709  1.00 33.60      A  C
ATOM   9789  C   PRO D 330     -27.866 -57.116 -16.322  1.00 33.49      A  C
ATOM   9790  O   PRO D 330     -27.716 -56.229 -15.489  1.00 33.75      A  O
ATOM   9791  CB  PRO D 330     -28.010 -55.968 -18.565  1.00 33.71      A  C
ATOM   9792  CG  PRO D 330     -28.963 -56.792 -19.318  1.00 33.51      A  C
ATOM   9793  CD  PRO D 330     -28.286 -58.097 -19.580  1.00 33.44      A  C
ATOM   9794  N   PHE D 331     -28.557 -58.223 -16.080  1.00 33.08      A  N
ATOM   9795  CA  PHE D 331     -29.016 -58.542 -14.738  1.00 32.87      A  C
ATOM   9796  C   PHE D 331     -27.937 -59.295 -13.987  1.00 32.84      A  C
ATOM   9797  O   PHE D 331     -27.753 -59.121 -12.793  1.00 32.97      A  O
ATOM   9798  CB  PHE D 331     -30.298 -59.360 -14.789  1.00 32.66      A  C
ATOM   9799  CG  PHE D 331     -31.484 -58.574 -15.231  1.00 32.77      A  C
ATOM   9800  CD1 PHE D 331     -31.958 -58.677 -16.522  1.00 32.76      A  C
ATOM   9801  CD2 PHE D 331     -32.117 -57.709 -14.356  1.00 33.31      A  C
ATOM   9802  CE1 PHE D 331     -33.051 -57.945 -16.928  1.00 33.00      A  C
ATOM   9803  CE2 PHE D 331     -33.207 -56.970 -14.761  1.00 33.50      A  C
ATOM   9804  CZ  PHE D 331     -33.675 -57.089 -16.048  1.00 33.20      A  C
ATOM   9805  N   LEU D 332     -27.218 -60.139 -14.703  1.00 32.81      A  N
ATOM   9806  CA  LEU D 332     -26.112 -60.873 -14.133  1.00 32.95      A  C
ATOM   9807  C   LEU D 332     -24.997 -59.928 -13.696  1.00 33.41      A  C
ATOM   9808  O   LEU D 332     -24.428 -60.111 -12.631  1.00 33.69      A  O
ATOM   9809  CB  LEU D 332     -25.594 -61.906 -15.132  1.00 32.65      A  C
ATOM   9810  CG  LEU D 332     -24.364 -62.692 -14.714  1.00 32.38      A  C
ATOM   9811  CD1 LEU D 332     -24.766 -63.903 -13.933  1.00 31.99      A  C
ATOM   9812  CD2 LEU D 332     -23.597 -63.093 -15.935  1.00 32.38      A  C
ATOM   9813  N   ARG D 333     -24.692 -58.909 -14.498  1.00 33.79      A  N
ATOM   9814  CA  ARG D 333     -23.604 -57.982 -14.156  1.00 34.35      A  C
ATOM   9815  C   ARG D 333     -23.907 -57.222 -12.845  1.00 34.10      A  C
```

FIGURE 1 (cont'd)

```
ATOM   9816  O    ARG D 333     -23.009 -56.742 -12.159  1.00 34.45      A   O
ATOM   9817  CB   ARG D 333     -23.223 -57.062 -15.351  1.00 34.72      A   C
ATOM   9818  CG   ARG D 333     -23.677 -55.591 -15.280  1.00 36.61      A   C
ATOM   9819  CD   ARG D 333     -22.943 -54.677 -16.288  1.00 39.90      A   C
ATOM   9820  NE   ARG D 333     -23.723 -54.383 -17.505  1.00 42.25      A   N
ATOM   9821  CZ   ARG D 333     -24.311 -53.213 -17.787  1.00 42.95      A   C
ATOM   9822  NH1  ARG D 333     -24.992 -53.062 -18.922  1.00 42.55      A   N
ATOM   9823  NH2  ARG D 333     -24.220 -52.189 -16.944  1.00 43.81      A   N
ATOM   9824  N    ARG D 334     -25.184 -57.161 -12.490  1.00 33.58      A   N
ATOM   9825  CA   ARG D 334     -25.635 -56.516 -11.250  1.00 33.17      A   C
ATOM   9826  C    ARG D 334     -25.794 -57.514 -10.111  1.00 32.66      A   C
ATOM   9827  O    ARG D 334     -26.202 -57.158  -9.017  1.00 32.77      A   O
ATOM   9828  CB   ARG D 334     -26.960 -55.764 -11.478  1.00 33.17      A   C
ATOM   9829  CG   ARG D 334     -26.799 -54.387 -12.089  1.00 33.60      A   C
ATOM   9830  CD   ARG D 334     -27.911 -54.087 -13.041  1.00 33.72      A   C
ATOM   9831  NE   ARG D 334     -27.929 -52.686 -13.423  1.00 34.74      A   N
ATOM   9832  CZ   ARG D 334     -27.536 -52.221 -14.604  1.00 35.53      A   C
ATOM   9833  NH1  ARG D 334     -27.085 -53.046 -15.542  1.00 35.18      A   N
ATOM   9834  NH2  ARG D 334     -27.596 -50.917 -14.849  1.00 36.59      A   N
ATOM   9835  N    GLY D 335     -25.490 -58.771 -10.384  1.00 32.07      A   N
ATOM   9836  CA   GLY D 335     -25.464 -59.784  -9.350  1.00 31.45      A   C
ATOM   9837  C    GLY D 335     -26.706 -60.639  -9.206  1.00 30.80      A   C
ATOM   9838  O    GLY D 335     -26.845 -61.352  -8.219  1.00 31.14      A   O
ATOM   9839  N    VAL D 336     -27.610 -60.588 -10.173  1.00 29.88      A   N
ATOM   9840  CA   VAL D 336     -28.812 -61.409 -10.093  1.00 29.06      A   C
ATOM   9841  C    VAL D 336     -28.456 -62.861 -10.402  1.00 28.65      A   C
ATOM   9842  O    VAL D 336     -27.749 -63.118 -11.364  1.00 28.64      A   O
ATOM   9843  CB   VAL D 336     -29.903 -60.921 -11.067  1.00 28.88      A   C
ATOM   9844  CG1  VAL D 336     -31.139 -61.777 -10.965  1.00 28.79      A   C
ATOM   9845  CG2  VAL D 336     -30.268 -59.483 -10.782  1.00 29.04      A   C
ATOM   9846  N    PRO D 337     -28.914 -63.811  -9.571  1.00 28.41      A   N
ATOM   9847  CA   PRO D 337     -28.773 -65.224  -9.895  1.00 28.16      A   C
ATOM   9848  C    PRO D 337     -29.525 -65.559 -11.177  1.00 27.72      A   C
ATOM   9849  O    PRO D 337     -30.675 -65.180 -11.327  1.00 27.73      A   O
ATOM   9850  CB   PRO D 337     -29.442 -65.916  -8.711  1.00 28.30      A   C
ATOM   9851  CG   PRO D 337     -29.341 -64.961  -7.603  1.00 28.71      A   C
ATOM   9852  CD   PRO D 337     -29.445 -63.610  -8.215  1.00 28.63      A   C
ATOM   9853  N    VAL D 338     -28.875 -66.262 -12.095  1.00 27.28      A   N
ATOM   9854  CA   VAL D 338     -29.478 -66.572 -13.383  1.00 26.71      A   C
ATOM   9855  C    VAL D 338     -29.564 -68.080 -13.607  1.00 26.55      A   C
ATOM   9856  O    VAL D 338     -28.640 -68.831 -13.271  1.00 26.73      A   O
ATOM   9857  CB   VAL D 338     -28.691 -65.920 -14.556  1.00 26.60      A   C
ATOM   9858  CG1  VAL D 338     -29.303 -66.279 -15.908  1.00 26.36      A   C
ATOM   9859  CG2  VAL D 338     -28.624 -64.408 -14.396  1.00 26.59      A   C
ATOM   9860  N    LEU D 339     -30.695 -68.508 -14.162  1.00 26.21      A   N
ATOM   9861  CA   LEU D 339     -30.807 -69.821 -14.787  1.00 25.93      A   C
ATOM   9862  C    LEU D 339     -31.169 -69.658 -16.265  1.00 25.78      A   C
ATOM   9863  O    LEU D 339     -32.274 -69.223 -16.598  1.00 25.78      A   O
ATOM   9864  CB   LEU D 339     -31.838 -70.680 -14.068  1.00 25.86      A   C
ATOM   9865  CG   LEU D 339     -31.973 -72.100 -14.606  1.00 25.68      A   C
ATOM   9866  CD1  LEU D 339     -30.623 -72.804 -14.605  1.00 26.03      A   C
ATOM   9867  CD2  LEU D 339     -32.985 -72.866 -13.784  1.00 25.48      A   C
ATOM   9868  N    HIS D 340     -30.223 -70.005 -17.137  1.00 25.62      A   N
ATOM   9869  CA   HIS D 340     -30.336 -69.723 -18.563  1.00 25.40      A   C
ATOM   9870  C    HIS D 340     -30.851 -70.937 -19.277  1.00 25.29      A   C
ATOM   9871  O    HIS D 340     -30.096 -71.871 -19.530  1.00 25.32      A   O
ATOM   9872  CB   HIS D 340     -28.984 -69.316 -19.139  1.00 25.48      A   C
ATOM   9873  CG   HIS D 340     -29.070 -68.582 -20.442  1.00 25.65      A   C
ATOM   9874  CD2  HIS D 340     -30.116 -67.994 -21.070  1.00 25.67      A   C
ATOM   9875  ND1  HIS D 340     -27.972 -68.376 -21.253  1.00 26.01      A   N
ATOM   9876  CE1  HIS D 340     -28.339 -67.671 -22.322  1.00 25.95      A   C
ATOM   9877  NE2  HIS D 340     -29.635 -67.453 -22.238  1.00 25.89      A   N
ATOM   9878  N    LEU D 341     -32.148 -70.910 -19.590  1.00 25.19      A   N
ATOM   9879  CA   LEU D 341     -32.863 -72.049 -20.176  1.00 25.14      A   C
ATOM   9880  C    LEU D 341     -32.921 -71.918 -21.693  1.00 25.07      A   C
```

FIGURE 1 (cont'd)

```
ATOM   9881  O    LEU D 341     -33.980 -71.740 -22.270  1.00 25.08      A   O
ATOM   9882  CB   LEU D 341     -34.274 -72.176 -19.579  1.00 25.08      A   C
ATOM   9883  CG   LEU D 341     -34.757 -73.562 -19.158  1.00 25.28      A   C
ATOM   9884  CD1  LEU D 341     -36.180 -73.451 -18.714  1.00 25.55      A   C
ATOM   9885  CD2  LEU D 341     -34.642 -74.599 -20.252  1.00 25.04      A   C
ATOM   9886  N    ILE D 342     -31.757 -72.014 -22.319  1.00 25.12      A   N
ATOM   9887  CA   ILE D 342     -31.602 -71.886 -23.759  1.00 25.17      A   C
ATOM   9888  C    ILE D 342     -30.969 -73.167 -24.287  1.00 25.51      A   C
ATOM   9889  O    ILE D 342     -30.044 -73.706 -23.677  1.00 25.77      A   O
ATOM   9890  CB   ILE D 342     -30.734 -70.655 -24.094  1.00 25.00      A   C
ATOM   9891  CG1  ILE D 342     -30.558 -70.486 -25.592  1.00 24.87      A   C
ATOM   9892  CG2  ILE D 342     -29.369 -70.723 -23.412  1.00 25.00      A   C
ATOM   9893  CD1  ILE D 342     -30.004 -69.117 -25.948  1.00 24.65      A   C
ATOM   9894  N    SER D 343     -31.474 -73.687 -25.394  1.00 25.77      A   N
ATOM   9895  CA   SER D 343     -30.927 -74.940 -25.895  1.00 26.22      A   C
ATOM   9896  C    SER D 343     -29.590 -74.702 -26.562  1.00 26.39      A   C
ATOM   9897  O    SER D 343     -29.420 -73.743 -27.310  1.00 26.29      A   O
ATOM   9898  CB   SER D 343     -31.891 -75.649 -26.843  1.00 26.34      A   C
ATOM   9899  OG   SER D 343     -32.042 -74.914 -28.042  1.00 27.01      A   O
ATOM   9900  N    THR D 344     -28.638 -75.567 -26.234  1.00 26.75      A   N
ATOM   9901  CA   THR D 344     -27.330 -75.594 -26.876  1.00 27.11      A   C
ATOM   9902  C    THR D 344     -27.115 -77.038 -27.343  1.00 27.54      A   C
ATOM   9903  O    THR D 344     -27.057 -77.953 -26.514  1.00 27.67      A   O
ATOM   9904  CB   THR D 344     -26.183 -75.138 -25.932  1.00 27.03      A   C
ATOM   9905  OG1  THR D 344     -26.666 -75.051 -24.585  1.00 26.77      A   O
ATOM   9906  N    PRO D 345     -26.995 -77.253 -28.672  1.00 27.87      A   N
ATOM   9907  CA   PRO D 345     -26.855 -76.225 -29.710  1.00 27.91      A   C
ATOM   9908  C    PRO D 345     -28.166 -75.513 -30.054  1.00 27.72      A   C
ATOM   9909  O    PRO D 345     -29.230 -75.926 -29.584  1.00 27.47      A   O
ATOM   9910  CB   PRO D 345     -26.337 -77.014 -30.922  1.00 28.15      A   C
ATOM   9911  CG   PRO D 345     -26.291 -78.479 -30.495  1.00 28.22      A   C
ATOM   9912  CD   PRO D 345     -27.107 -78.599 -29.264  1.00 27.99      A   C
ATOM   9913  N    PHE D 346     -28.073 -74.445 -30.850  1.00 27.71      A   N
ATOM   9914  CA   PHE D 346     -29.251 -73.716 -31.315  1.00 27.83      A   C
ATOM   9915  C    PHE D 346     -30.068 -74.571 -32.287  1.00 28.04      A   C
ATOM   9916  O    PHE D 346     -29.520 -75.471 -32.929  1.00 28.34      A   O
ATOM   9917  CB   PHE D 346     -28.853 -72.401 -31.988  1.00 27.85      A   C
ATOM   9918  CG   PHE D 346     -28.191 -71.408 -31.068  1.00 28.00      A   C
ATOM   9919  CD1  PHE D 346     -28.239 -71.542 -29.686  1.00 27.84      A   C
ATOM   9920  CD2  PHE D 346     -27.536 -70.310 -31.596  1.00 28.62      A   C
ATOM   9921  CE1  PHE D 346     -27.628 -70.606 -28.850  1.00 27.78      A   C
ATOM   9922  CE2  PHE D 346     -26.919 -69.369 -30.761  1.00 28.50      A   C
ATOM   9923  CZ   PHE D 346     -26.973 -69.523 -29.385  1.00 27.99      A   C
ATOM   9924  N    PRO D 347     -31.386 -74.302 -32.391  1.00 28.04      A   N
ATOM   9925  CA   PRO D 347     -32.255 -75.023 -33.314  1.00 28.39      A   C
ATOM   9926  C    PRO D 347     -31.699 -74.964 -34.724  1.00 29.03      A   C
ATOM   9927  O    PRO D 347     -31.126 -73.948 -35.106  1.00 29.18      A   O
ATOM   9928  CB   PRO D 347     -33.551 -74.224 -33.257  1.00 28.15      A   C
ATOM   9929  CG   PRO D 347     -33.549 -73.612 -31.948  1.00 27.70      A   C
ATOM   9930  CD   PRO D 347     -32.135 -73.291 -31.630  1.00 27.72      A   C
ATOM   9931  N    ALA D 348     -31.866 -76.038 -35.492  1.00 29.70      A   N
ATOM   9932  CA   ALA D 348     -31.376 -76.080 -36.877  1.00 30.34      A   C
ATOM   9933  C    ALA D 348     -31.912 -74.912 -37.677  1.00 30.58      A   C
ATOM   9934  O    ALA D 348     -31.198 -74.342 -38.494  1.00 30.71      A   O
ATOM   9935  CB   ALA D 348     -31.762 -77.381 -37.538  1.00 30.64      A   C
ATOM   9936  N    VAL D 349     -33.169 -74.563 -37.401  1.00 30.69      A   N
ATOM   9937  CA   VAL D 349     -33.891 -73.490 -38.073  1.00 30.87      A   C
ATOM   9938  C    VAL D 349     -33.584 -72.107 -37.506  1.00 30.96      A   C
ATOM   9939  O    VAL D 349     -34.366 -71.177 -37.684  1.00 31.11      A   O
ATOM   9940  CB   VAL D 349     -35.427 -73.717 -38.020  1.00 30.84      A   C
ATOM   9941  CG1  VAL D 349     -35.810 -74.969 -38.772  1.00 31.41      A   C
ATOM   9942  CG2  VAL D 349     -35.941 -73.776 -36.581  1.00 30.45      A   C
ATOM   9943  N    TRP D 350     -32.444 -71.955 -36.846  1.00 31.04      A   N
ATOM   9944  CA   TRP D 350     -32.166 -70.720 -36.121  1.00 31.13      A   C
ATOM   9945  C    TRP D 350     -31.806 -69.582 -37.049  1.00 31.48      A   C
```

FIGURE 1 (cont'd)

```
ATOM   9946  O    TRP D 350     -31.041 -69.776 -37.992  1.00 31.73      A  O
ATOM   9947  CB   TRP D 350     -31.056 -70.928 -35.086  1.00 30.95      A  C
ATOM   9948  CG   TRP D 350     -30.799 -69.727 -34.217  1.00 30.51      A  C
ATOM   9949  CD1  TRP D 350     -31.633 -69.206 -33.266  1.00 30.22      A  C
ATOM   9950  CD2  TRP D 350     -29.631 -68.906 -34.217  1.00 30.16      A  C
ATOM   9951  CE2  TRP D 350     -29.826 -67.906 -33.243  1.00 29.92      A  C
ATOM   9952  CE3  TRP D 350     -28.437 -68.914 -34.947  1.00 30.18      A  C
ATOM   9953  NE1  TRP D 350     -31.057 -68.111 -32.678  1.00 29.97      A  N
ATOM   9954  CZ2  TRP D 350     -28.873 -66.926 -32.981  1.00 29.65      A  C
ATOM   9955  CZ3  TRP D 350     -27.495 -67.939 -34.687  1.00 30.00      A  C
ATOM   9956  CH2  TRP D 350     -27.716 -66.959 -33.711  1.00 29.65      A  C
ATOM   9957  N    HIS D 351     -32.365 -68.404 -36.759  1.00 31.80      A  N
ATOM   9958  CA   HIS D 351     -32.115 -67.172 -37.513  1.00 32.37      A  C
ATOM   9959  C    HIS D 351     -32.267 -67.369 -39.026  1.00 32.93      A  C
ATOM   9960  O    HIS D 351     -31.427 -66.931 -39.818  1.00 33.20      A  O
ATOM   9961  CB   HIS D 351     -30.747 -66.572 -37.142  1.00 32.36      A  C
ATOM   9962  CG   HIS D 351     -30.765 -65.728 -35.902  1.00 32.40      A  C
ATOM   9963  CD2  HIS D 351     -31.644 -65.672 -34.872  1.00 32.04      A  C
ATOM   9964  ND1  HIS D 351     -29.795 -64.788 -35.627  1.00 32.53      A  N
ATOM   9965  CE1  HIS D 351     -30.070 -64.195 -34.478  1.00 32.25      A  C
ATOM   9966  NE2  HIS D 351     -31.187 -64.714 -34.000  1.00 31.83      A  N
ATOM   9967  N    THR D 352     -33.349 -68.040 -39.409  1.00 33.36      A  N
ATOM   9968  CA   THR D 352     -33.660 -68.310 -40.813  1.00 33.93      A  C
ATOM   9969  C    THR D 352     -35.170 -68.349 -40.988  1.00 34.20      A  C
ATOM   9970  O    THR D 352     -35.878 -68.700 -40.041  1.00 34.01      A  O
ATOM   9971  CB   THR D 352     -33.026 -69.648 -41.320  1.00 34.04      A  C
ATOM   9972  CG2  THR D 352     -32.999 -70.687 -40.242  1.00 33.56      A  C
ATOM   9973  OG1  THR D 352     -33.796 -70.175 -42.404  1.00 34.77      A  O
ATOM   9974  N    PRO D 353     -35.672 -67.983 -42.189  1.00 34.69      A  N
ATOM   9975  CA   PRO D 353     -37.099 -68.059 -42.545  1.00 34.80      A  C
ATOM   9976  C    PRO D 353     -37.762 -69.383 -42.152  1.00 34.60      A  C
ATOM   9977  O    PRO D 353     -38.985 -69.447 -42.002  1.00 34.61      A  O
ATOM   9978  CB   PRO D 353     -37.080 -67.960 -44.066  1.00 35.25      A  C
ATOM   9979  CG   PRO D 353     -35.869 -67.168 -44.376  1.00 35.54      A  C
ATOM   9980  CD   PRO D 353     -34.865 -67.429 -43.292  1.00 34.98      A  C
ATOM   9981  N    ALA D 354     -36.949 -70.423 -41.994  1.00 34.31      A  N
ATOM   9982  CA   ALA D 354     -37.433 -71.730 -41.605  1.00 34.05      A  C
ATOM   9983  C    ALA D 354     -38.076 -71.749 -40.211  1.00 33.78      A  C
ATOM   9984  O    ALA D 354     -38.965 -72.560 -39.960  1.00 33.73      A  O
ATOM   9985  CB   ALA D 354     -36.310 -72.741 -41.700  1.00 34.06      A  C
ATOM   9986  N    ASP D 355     -37.637 -70.855 -39.321  1.00 33.53      A  N
ATOM   9987  CA   ASP D 355     -38.140 -70.801 -37.946  1.00 33.31      A  C
ATOM   9988  C    ASP D 355     -39.590 -70.324 -37.904  1.00 33.49      A  C
ATOM   9989  O    ASP D 355     -39.874 -69.181 -37.542  1.00 33.38      A  O
ATOM   9990  CB   ASP D 355     -37.245 -69.908 -37.074  1.00 33.04      A  C
ATOM   9991  CG   ASP D 355     -37.564 -70.014 -35.575  1.00 32.55      A  C
ATOM   9992  OD1  ASP D 355     -38.535 -70.724 -35.227  1.00 32.73      A  O
ATOM   9993  OD2  ASP D 355     -36.844 -69.383 -34.752  1.00 31.64      A  O
ATOM   9994  N    THR D 356     -40.501 -71.218 -38.274  1.00 33.78      A  N
ATOM   9995  CA   THR D 356     -41.934 -70.930 -38.275  1.00 33.99      A  C
ATOM   9996  C    THR D 356     -42.694 -72.033 -37.551  1.00 34.40      A  C
ATOM   9997  O    THR D 356     -42.101 -73.031 -37.131  1.00 34.31      A  O
ATOM   9998  CB   THR D 356     -42.478 -70.788 -39.710  1.00 33.40      A  C
ATOM   9999  OG1  THR D 356     -42.211 -71.993 -40.439  1.00 33.39      A  O
ATOM  10000  N    GLU D 357     -44.003 -71.841 -37.415  1.00 35.00      A  N
ATOM  10001  CA   GLU D 357     -44.867 -72.784 -36.716  1.00 35.56      A  C
ATOM  10002  C    GLU D 357     -44.664 -74.200 -37.241  1.00 35.89      A  C
ATOM  10003  O    GLU D 357     -44.557 -75.163 -36.474  1.00 35.82      A  O
ATOM  10004  CB   GLU D 357     -46.341 -72.355 -36.842  1.00 35.75      A  C
ATOM  10005  CG   GLU D 357     -47.359 -73.317 -36.186  1.00 36.39      A  C
ATOM  10006  CD   GLU D 357     -48.788 -72.764 -36.140  1.00 37.43      A  C
ATOM  10007  OE1  GLU D 357     -49.024 -71.639 -36.626  1.00 38.18      A  O
ATOM  10008  OE2  GLU D 357     -49.684 -73.454 -35.609  1.00 37.77      A  O
ATOM  10009  N    VAL D 358     -44.582 -74.301 -38.560  1.00 36.39      A  N
ATOM  10010  CA   VAL D 358     -44.475 -75.580 -39.244  1.00 36.84      A  C
```

FIGURE 1 (cont'd)

```
ATOM  10011  C    VAL D 358     -43.339 -76.488 -38.736  1.00 36.68      A  C
ATOM  10012  O    VAL D 358     -43.398 -77.714 -38.890  1.00 36.94      A  O
ATOM  10013  CB   VAL D 358     -44.319 -75.370 -40.764  1.00 37.17      A  C
ATOM  10014  CG1  VAL D 358     -45.433 -76.088 -41.505  1.00 37.98      A  C
ATOM  10015  N    ASN D 359     -42.313 -75.894 -38.131  1.00 36.27      A  N
ATOM  10016  CA   ASN D 359     -41.095 -76.641 -37.804  1.00 35.93      A  C
ATOM  10017  C    ASN D 359     -40.885 -76.868 -36.310  1.00 35.34      A  C
ATOM  10018  O    ASN D 359     -39.847 -77.381 -35.895  1.00 35.23      A  O
ATOM  10019  CB   ASN D 359     -39.863 -75.973 -38.435  1.00 36.14      A  C
ATOM  10020  CG   ASN D 359     -39.830 -76.090 -39.962  1.00 37.12      A  C
ATOM  10021  ND2  ASN D 359     -40.735 -76.889 -40.531  1.00 38.06      A  N
ATOM  10022  OD1  ASN D 359     -38.989 -75.468 -40.616  1.00 37.71      A  O
ATOM  10023  N    LEU D 360     -41.868 -76.481 -35.507  1.00 34.81      A  N
ATOM  10024  CA   LEU D 360     -41.835 -76.775 -34.081  1.00 34.33      A  C
ATOM  10025  C    LEU D 360     -42.242 -78.233 -33.877  1.00 34.41      A  C
ATOM  10026  O    LEU D 360     -42.929 -78.798 -34.729  1.00 34.89      A  O
ATOM  10027  CB   LEU D 360     -42.790 -75.859 -33.317  1.00 34.01      A  C
ATOM  10028  CG   LEU D 360     -42.648 -74.357 -33.521  1.00 33.46      A  C
ATOM  10029  CD1  LEU D 360     -43.723 -73.635 -32.749  1.00 32.89      A  C
ATOM  10030  CD2  LEU D 360     -41.276 -73.884 -33.100  1.00 33.12      A  C
ATOM  10031  N    HIS D 361     -41.804 -78.835 -32.768  1.00 34.11      A  N
ATOM  10032  CA   HIS D 361     -42.249 -80.167 -32.366  1.00 33.90      A  C
ATOM  10033  C    HIS D 361     -43.271 -80.020 -31.239  1.00 34.19      A  C
ATOM  10034  O    HIS D 361     -42.893 -79.985 -30.069  1.00 34.00      A  O
ATOM  10035  CB   HIS D 361     -41.066 -81.028 -31.915  1.00 33.53      A  C
ATOM  10036  CG   HIS D 361     -41.307 -82.495 -32.054  1.00 32.69      A  C
ATOM  10037  ND1  HIS D 361     -42.101 -83.200 -31.179  1.00 31.52      A  N
ATOM  10038  CE1  HIS D 361     -42.134 -84.462 -31.565  1.00 31.57      A  C
ATOM  10039  N    PRO D 362     -44.572 -79.925 -31.587  1.00 34.66      A  N
ATOM  10040  CA   PRO D 362     -45.621 -79.657 -30.607  1.00 34.88      A  C
ATOM  10041  C    PRO D 362     -45.515 -80.492 -29.329  1.00 34.89      A  C
ATOM  10042  O    PRO D 362     -45.698 -79.949 -28.230  1.00 34.77      A  O
ATOM  10043  CB   PRO D 362     -46.906 -79.983 -31.375  1.00 35.19      A  C
ATOM  10044  CG   PRO D 362     -46.575 -79.660 -32.770  1.00 35.33      A  C
ATOM  10045  CD   PRO D 362     -45.137 -80.074 -32.941  1.00 35.01      A  C
ATOM  10046  N    PRO D 363     -45.209 -81.794 -29.464  1.00 34.98      A  N
ATOM  10047  CA   PRO D 363     -44.993 -82.613 -28.277  1.00 34.99      A  C
ATOM  10048  C    PRO D 363     -43.918 -82.016 -27.372  1.00 34.64      A  C
ATOM  10049  O    PRO D 363     -44.182 -81.750 -26.198  1.00 34.58      A  O
ATOM  10050  CB   PRO D 363     -44.526 -83.937 -28.860  1.00 35.28      A  C
ATOM  10051  CG   PRO D 363     -45.332 -84.102 -30.109  1.00 35.69      A  C
ATOM  10052  N    THR D 364     -42.733 -81.772 -27.926  1.00 34.30      A  N
ATOM  10053  CA   THR D 364     -41.638 -81.176 -27.159  1.00 33.95      A  C
ATOM  10054  C    THR D 364     -42.103 -79.917 -26.438  1.00 33.86      A  C
ATOM  10055  O    THR D 364     -41.757 -79.702 -25.284  1.00 33.70      A  O
ATOM  10056  CB   THR D 364     -40.417 -80.862 -28.043  1.00 33.84      A  C
ATOM  10057  CG2  THR D 364     -39.266 -80.352 -27.206  1.00 33.47      A  C
ATOM  10058  OG1  THR D 364     -40.003 -82.051 -28.721  1.00 34.10      A  O
ATOM  10059  N    VAL D 365     -42.908 -79.104 -27.120  1.00 33.99      A  N
ATOM  10060  CA   VAL D 365     -43.437 -77.870 -26.539  1.00 34.10      A  C
ATOM  10061  C    VAL D 365     -44.194 -78.162 -25.257  1.00 34.27      A  C
ATOM  10062  O    VAL D 365     -43.867 -77.624 -24.206  1.00 34.09      A  O
ATOM  10063  CB   VAL D 365     -44.335 -77.071 -27.534  1.00 34.11      A  C
ATOM  10064  CG1  VAL D 365     -43.500 -76.471 -28.641  1.00 34.01      A  C
ATOM  10065  CG2  VAL D 365     -45.101 -75.962 -26.814  1.00 33.95      A  C
ATOM  10066  N    HIS D 366     -45.188 -79.036 -25.352  1.00 34.69      A  N
ATOM  10067  CA   HIS D 366     -46.063 -79.338 -24.221  1.00 35.17      A  C
ATOM  10068  C    HIS D 366     -45.328 -79.969 -23.053  1.00 35.34      A  C
ATOM  10069  O    HIS D 366     -45.562 -79.599 -21.899  1.00 35.43      A  O
ATOM  10070  CB   HIS D 366     -47.250 -80.180 -24.680  1.00 35.39      A  C
ATOM  10071  CG   HIS D 366     -48.080 -79.481 -25.703  1.00 35.51      A  C
ATOM  10072  CD2  HIS D 366     -48.226 -79.695 -27.028  1.00 35.57      A  C
ATOM  10073  ND1  HIS D 366     -48.817 -78.351 -25.411  1.00 35.51      A  N
ATOM  10074  CE1  HIS D 366     -49.421 -77.928 -26.506  1.00 35.52      A  C
ATOM  10075  NE2  HIS D 366     -49.072 -78.720 -27.503  1.00 36.20      A  N
```

FIGURE 1 (cont'd)

```
ATOM  10076  N    ASN D 367     -44.426 -80.896 -23.367  1.00 35.41          A N
ATOM  10077  CA   ASN D 367     -43.520 -81.464 -22.380  1.00 35.42          A C
ATOM  10078  C    ASN D 367     -42.861 -80.370 -21.563  1.00 35.25          A C
ATOM  10079  O    ASN D 367     -42.910 -80.404 -20.337  1.00 35.37          A O
ATOM  10080  CB   ASN D 367     -42.443 -82.307 -23.055  1.00 35.49          A C
ATOM  10081  CG   ASN D 367     -42.972 -83.608 -23.580  1.00 36.12          A C
ATOM  10082  ND2  ASN D 367     -42.067 -84.472 -24.005  1.00 36.23          A N
ATOM  10083  OD1  ASN D 367     -44.180 -83.845 -23.606  1.00 37.06          A O
ATOM  10084  N    LEU D 368     -42.269 -79.391 -22.248  1.00 34.98          A N
ATOM  10085  CA   LEU D 368     -41.551 -78.299 -21.590  1.00 34.73          A C
ATOM  10086  C    LEU D 368     -42.457 -77.516 -20.646  1.00 34.89          A C
ATOM  10087  O    LEU D 368     -42.018 -77.061 -19.593  1.00 35.01          A O
ATOM  10088  CB   LEU D 368     -40.902 -77.366 -22.619  1.00 34.36          A C
ATOM  10089  CG   LEU D 368     -39.692 -77.886 -23.399  1.00 33.71          A C
ATOM  10090  CD1  LEU D 368     -39.337 -76.923 -24.498  1.00 33.46          A C
ATOM  10091  CD2  LEU D 368     -38.505 -78.108 -22.504  1.00 32.84          A C
ATOM  10092  N    ALA D 369     -43.725 -77.388 -21.021  1.00 34.18          A N
ATOM  10093  CA   ALA D 369     -44.686 -76.649 -20.222  1.00 33.53          A C
ATOM  10094  C    ALA D 369     -45.092 -77.444 -18.996  1.00 34.50          A C
ATOM  10095  O    ALA D 369     -45.256 -76.883 -17.912  1.00 35.70          A O
ATOM  10096  CB   ALA D 369     -45.888 -76.296 -21.045  1.00 24.57          A C
ATOM  10097  N    ARG D 370     -45.251 -78.751 -19.166  1.00 35.14          A N
ATOM  10098  CA   ARG D 370     -45.521 -79.623 -18.032  1.00 34.82          A C
ATOM  10099  C    ARG D 370     -44.369 -79.520 -17.025  1.00 34.24          A C
ATOM  10100  O    ARG D 370     -44.607 -79.299 -15.837  1.00 34.14          A O
ATOM  10101  CB   ARG D 370     -45.772 -81.067 -18.489  1.00 35.12          A C
ATOM  10102  CG   ARG D 370     -47.045 -81.235 -19.347  1.00 35.44          A C
ATOM  10103  CD   ARG D 370     -47.363 -82.702 -19.682  1.00 35.73          A C
ATOM  10104  NE   ARG D 370     -48.653 -82.846 -20.348  1.00 35.82          A N
ATOM  10105  CZ   ARG D 370     -49.401 -83.940 -20.296  1.00 36.00          A C
ATOM  10106  N    ILE D 371     -43.131 -79.627 -17.513  1.00 33.50          A N
ATOM  10107  CA   ILE D 371     -41.932 -79.518 -16.669  1.00 32.86          A C
ATOM  10108  C    ILE D 371     -41.873 -78.165 -15.961  1.00 32.79          A C
ATOM  10109  O    ILE D 371     -41.632 -78.114 -14.755  1.00 32.87          A O
ATOM  10110  CB   ILE D 371     -40.634 -79.773 -17.469  1.00 32.53          A C
ATOM  10111  CG1  ILE D 371     -40.571 -81.228 -17.912  1.00 32.48          A C
ATOM  10112  CG2  ILE D 371     -39.409 -79.443 -16.646  1.00 32.01          A C
ATOM  10113  CD1  ILE D 371     -39.494 -81.511 -18.929  1.00 32.21          A C
ATOM  10114  N    LEU D 372     -42.111 -77.083 -16.706  1.00 32.60          A N
ATOM  10115  CA   LEU D 372     -42.094 -75.730 -16.146  1.00 32.44          A C
ATOM  10116  C    LEU D 372     -43.188 -75.494 -15.102  1.00 32.76          A C
ATOM  10117  O    LEU D 372     -42.915 -74.943 -14.034  1.00 32.68          A O
ATOM  10118  CB   LEU D 372     -42.201 -74.700 -17.265  1.00 32.09          A C
ATOM  10119  CG   LEU D 372     -40.941 -73.988 -17.766  1.00 31.34          A C
ATOM  10120  CD1  LEU D 372     -39.645 -74.647 -17.353  1.00 30.79          A C
ATOM  10121  CD2  LEU D 372     -41.008 -73.785 -19.272  1.00 30.91          A C
ATOM  10122  N    ALA D 373     -44.414 -75.921 -15.415  1.00 33.16          A N
ATOM  10123  CA   ALA D 373     -45.560 -75.760 -14.523  1.00 33.55          A C
ATOM  10124  C    ALA D 373     -45.323 -76.426 -13.176  1.00 33.84          A C
ATOM  10125  O    ALA D 373     -45.649 -75.870 -12.128  1.00 34.01          A O
ATOM  10126  CB   ALA D 373     -46.810 -76.311 -15.165  1.00 33.68          A C
ATOM  10127  N    VAL D 374     -44.755 -77.624 -13.208  1.00 34.01          A N
ATOM  10128  CA   VAL D 374     -44.388 -78.320 -11.986  1.00 34.28          A C
ATOM  10129  C    VAL D 374     -43.320 -77.509 -11.247  1.00 34.21          A C
ATOM  10130  O    VAL D 374     -43.466 -77.215 -10.058  1.00 34.47          A O
ATOM  10131  CB   VAL D 374     -43.893 -79.755 -12.274  1.00 34.33          A C
ATOM  10132  CG1  VAL D 374     -43.245 -80.359 -11.050  1.00 34.57          A C
ATOM  10133  CG2  VAL D 374     -45.037 -80.620 -12.718  1.00 34.77          A C
ATOM  10134  N    PHE D 375     -42.261 -77.138 -11.965  1.00 33.93          A N
ATOM  10135  CA   PHE D 375     -41.179 -76.351 -11.395  1.00 33.76          A C
ATOM  10136  C    PHE D 375     -41.729 -75.106 -10.717  1.00 34.07          A C
ATOM  10137  O    PHE D 375     -41.432 -74.853  -9.547  1.00 34.17          A O
ATOM  10138  CB   PHE D 375     -40.152 -75.962 -12.474  1.00 33.35          A C
ATOM  10139  CG   PHE D 375     -38.996 -75.128 -11.954  1.00 32.62          A C
ATOM  10140  CD1  PHE D 375     -37.752 -75.700 -11.713  1.00 32.45          A C
```

FIGURE 1 (cont'd)

```
ATOM  10141  CD2  PHE D 375     -39.159 -73.774 -11.703  1.00 32.09       A  C
ATOM  10142  CE1  PHE D 375     -36.706 -74.941 -11.231  1.00 32.38       A  C
ATOM  10143  CE2  PHE D 375     -38.115 -73.016 -11.217  1.00 32.24       A  C
ATOM  10144  CZ   PHE D 375     -36.887 -73.598 -10.981  1.00 32.32       A  C
ATOM  10145  N    LEU D 376     -42.525 -74.337 -11.461  1.00 34.41       A  N
ATOM  10146  CA   LEU D 376     -43.084 -73.092 -10.959  1.00 34.87       A  C
ATOM  10147  C    LEU D 376     -43.830 -73.366  -9.653  1.00 35.69       A  C
ATOM  10148  O    LEU D 376     -43.651 -72.646  -8.658  1.00 35.83       A  O
ATOM  10149  CB   LEU D 376     -44.008 -72.459 -12.002  1.00 34.55       A  C
ATOM  10150  CG   LEU D 376     -44.000 -70.934 -12.111  1.00 33.84       A  C
ATOM  10151  N    ALA D 377     -44.631 -74.433  -9.652  1.00 36.58       A  N
ATOM  10152  CA   ALA D 377     -45.410 -74.828  -8.483  1.00 37.43       A  C
ATOM  10153  C    ALA D 377     -44.528 -75.248  -7.308  1.00 37.89       A  C
ATOM  10154  O    ALA D 377     -44.756 -74.826  -6.179  1.00 38.19       A  O
ATOM  10155  CB   ALA D 377     -46.381 -75.929  -8.853  1.00 37.60       A  C
ATOM  10156  N    GLU D 378     -43.521 -76.070  -7.582  1.00 38.20       A  N
ATOM  10157  CA   GLU D 378     -42.600 -76.507  -6.546  1.00 38.62       A  C
ATOM  10158  C    GLU D 378     -41.787 -75.336  -5.976  1.00 38.60       A  C
ATOM  10159  O    GLU D 378     -41.702 -75.188  -4.759  1.00 38.92       A  O
ATOM  10160  CB   GLU D 378     -41.698 -77.645  -7.044  1.00 38.71       A  C
ATOM  10161  CG   GLU D 378     -42.380 -79.021  -7.081  1.00 39.87       A  C
ATOM  10162  CD   GLU D 378     -41.423 -80.191  -7.348  1.00 41.27       A  C
ATOM  10163  OE1  GLU D 378     -40.185 -80.001  -7.379  1.00 41.79       A  O
ATOM  10164  OE2  GLU D 378     -41.914 -81.322  -7.526  1.00 41.90       A  O
ATOM  10165  N    TYR D 379     -41.225 -74.495  -6.846  1.00 38.41       A  N
ATOM  10166  CA   TYR D 379     -40.417 -73.349  -6.412  1.00 38.39       A  C
ATOM  10167  C    TYR D 379     -41.194 -72.390  -5.511  1.00 38.97       A  C
ATOM  10168  O    TYR D 379     -40.682 -71.923  -4.487  1.00 39.09       A  O
ATOM  10169  CB   TYR D 379     -39.842 -72.589  -7.613  1.00 37.80       A  C
ATOM  10170  CG   TYR D 379     -38.824 -71.518  -7.245  1.00 37.04       A  C
ATOM  10171  CD1  TYR D 379     -37.458 -71.729  -7.422  1.00 36.33       A  C
ATOM  10172  CD2  TYR D 379     -39.228 -70.287  -6.716  1.00 36.83       A  C
ATOM  10173  CE1  TYR D 379     -36.520 -70.740  -7.071  1.00 36.17       A  C
ATOM  10174  CE2  TYR D 379     -38.299 -69.297  -6.365  1.00 36.55       A  C
ATOM  10175  CZ   TYR D 379     -36.954 -69.531  -6.547  1.00 36.19       A  C
ATOM  10176  OH   TYR D 379     -36.057 -68.555  -6.201  1.00 35.88       A  O
ATOM  10177  N    LEU D 380     -42.428 -72.100  -5.899  1.00 39.62       A  N
ATOM  10178  CA   LEU D 380     -43.271 -71.188  -5.148  1.00 40.42       A  C
ATOM  10179  C    LEU D 380     -44.167 -71.892  -4.135  1.00 41.24       A  C
ATOM  10180  O    LEU D 380     -45.006 -71.245  -3.499  1.00 41.81       A  O
ATOM  10181  CB   LEU D 380     -44.131 -70.395  -6.118  1.00 40.16       A  C
ATOM  10182  CG   LEU D 380     -43.767 -68.956  -6.470  1.00 39.77       A  C
ATOM  10183  CD1  LEU D 380     -42.264 -68.689  -6.505  1.00 39.37       A  C
ATOM  10184  CD2  LEU D 380     -44.419 -68.596  -7.796  1.00 39.49       A  C
ATOM  10185  N    GLY D 381     -44.013 -73.215  -4.017  1.00 39.83       A  N
ATOM  10186  CA   GLY D 381     -44.819 -74.049  -3.112  1.00 38.13       A  C
ATOM  10187  C    GLY D 381     -46.295 -73.728  -3.200  1.00 37.21       A  C
ATOM  10188  O    GLY D 381     -46.954 -73.535  -2.191  1.00 36.87       A  O
ATOM  10189  N    LEU D 382     -46.812 -73.653  -4.416  1.00 36.76       A  N
ATOM  10190  CA   LEU D 382     -48.181 -73.224  -4.618  1.00 36.74       A  C
ATOM  10191  C    LEU D 382     -49.161 -74.367  -4.422  1.00 36.90       A  C
ATOM  10192  O    LEU D 382     -50.360 -74.193  -4.646  1.00 37.09       A  O
ATOM  10193  CB   LEU D 382     -48.352 -72.623  -6.009  1.00 36.63       A  C
ATOM  10194  CG   LEU D 382     -47.503 -71.403  -6.348  1.00 36.49       A  C
ATOM  10195  CD1  LEU D 382     -47.732 -70.974  -7.786  1.00 36.43       A  C
ATOM  10196  CD2  LEU D 382     -47.781 -70.251  -5.393  1.00 36.83       A  C
ATOM  10197  OXT  LEU D 382     -48.785 -75.478  -4.046  1.00 36.85       A  O
TER   10198       LEU D 382
ATOM  10199  N    ASN E  73     -38.527   1.212 -92.889  1.00 35.07       A  N
ATOM  10200  CA   ASN E  73     -39.914   1.728 -92.674  1.00 35.30       A  C
ATOM  10201  C    ASN E  73     -41.071   0.918 -93.277  1.00 36.69       A  C
ATOM  10202  O    ASN E  73     -40.889  -0.207 -93.743  1.00 37.25       A  O
ATOM  10203  CB   ASN E  73     -40.014   3.198 -93.074  1.00 34.13       A  C
ATOM  10204  CG   ASN E  73     -39.874   4.124 -91.887  1.00 31.70       A  C
ATOM  10205  ND2  ASN E  73     -38.853   3.888 -91.053  1.00 29.41       A  N
```

FIGURE 1 (cont'd)

```
ATOM  10206  OD1 ASN E  73     -40.683   5.038 -91.708  1.00 30.87      A  O
ATOM  10207  N   GLY E  74     -42.254   1.521 -93.272  1.00 37.67      A  N
ATOM  10208  CA  GLY E  74     -43.520   0.809 -93.393  1.00 38.48      A  C
ATOM  10209  C   GLY E  74     -44.422   1.453 -92.350  1.00 39.02      A  C
ATOM  10210  O   GLY E  74     -45.633   1.567 -92.560  1.00 39.16      A  O
ATOM  10211  N   SER E  75     -43.810   1.868 -91.223  1.00 39.15      A  N
ATOM  10212  CA  SER E  75     -44.411   2.791 -90.221  1.00 39.15      A  C
ATOM  10213  C   SER E  75     -43.427   3.315 -89.134  1.00 40.39      A  C
ATOM  10214  O   SER E  75     -42.484   2.617 -88.748  1.00 40.03      A  O
ATOM  10215  CB  SER E  75     -45.619   2.153 -89.547  1.00 38.37      A  C
ATOM  10216  OG  SER E  75     -45.180   1.100 -88.726  1.00 37.54      A  O
ATOM  10217  N   LEU E  76     -43.680   4.553 -88.678  1.00 42.75      A  N
ATOM  10218  CA  LEU E  76     -43.030   5.251 -87.525  1.00 45.37      A  C
ATOM  10219  C   LEU E  76     -41.546   5.614 -87.611  1.00 49.10      A  C
ATOM  10220  O   LEU E  76     -40.713   4.737 -87.784  1.00 49.05      A  O
ATOM  10221  CB  LEU E  76     -43.327   4.556 -86.191  1.00 44.32      A  C
ATOM  10222  CG  LEU E  76     -44.363   5.204 -85.270  1.00 42.92      A  C
ATOM  10223  CD1 LEU E  76     -43.870   6.555 -84.787  1.00 42.11      A  C
ATOM  10224  CD2 LEU E  76     -45.726   5.325 -85.950  1.00 42.47      A  C
ATOM  10225  N   PRO E  77     -41.225   6.921 -87.502  1.00 54.10      A  N
ATOM  10226  CA  PRO E  77     -39.866   7.475 -87.400  1.00 55.34      A  C
ATOM  10227  C   PRO E  77     -39.471   7.943 -85.988  1.00 55.72      A  C
ATOM  10228  O   PRO E  77     -40.336   8.335 -85.204  1.00 55.66      A  O
ATOM  10229  CB  PRO E  77     -39.905   8.660 -88.366  1.00 56.04      A  C
ATOM  10230  CG  PRO E  77     -41.331   9.096 -88.382  1.00 55.89      A  C
ATOM  10231  CD  PRO E  77     -42.193   7.941 -87.940  1.00 54.79      A  C
ATOM  10232  N   GLU E  78     -38.167   7.908 -85.692  1.00 55.90      A  N
ATOM  10233  CA  GLU E  78     -37.604   8.253 -84.366  1.00 55.77      A  C
ATOM  10234  C   GLU E  78     -38.214   9.494 -83.694  1.00 57.04      A  C
ATOM  10235  O   GLU E  78     -38.542   9.468 -82.503  1.00 57.23      A  O
ATOM  10236  CB  GLU E  78     -36.072   8.411 -84.446  1.00 53.81      A  C
ATOM  10237  CG  GLU E  78     -35.264   7.198 -84.027  1.00 51.28      A  C
ATOM  10238  N   ALA E  79     -38.349  10.573 -84.464  1.00 58.28      A  N
ATOM  10239  CA  ALA E  79     -38.874  11.845 -83.965  1.00 58.93      A  C
ATOM  10240  C   ALA E  79     -40.263  11.693 -83.331  1.00 58.71      A  C
ATOM  10241  O   ALA E  79     -40.490  12.142 -82.204  1.00 58.84      A  O
ATOM  10242  CB  ALA E  79     -38.896  12.892 -85.088  1.00 59.73      A  C
ATOM  10243  N   ARG E  80     -41.181  11.054 -84.057  1.00 57.99      A  N
ATOM  10244  CA  ARG E  80     -42.542  10.834 -83.579  1.00 56.98      A  C
ATOM  10245  C   ARG E  80     -42.535   9.779 -82.499  1.00 56.71      A  C
ATOM  10246  O   ARG E  80     -43.264   9.899 -81.525  1.00 56.76      A  O
ATOM  10247  CB  ARG E  80     -43.481  10.420 -84.720  1.00 55.29      A  C
ATOM  10248  N   LEU E  81     -41.698   8.757 -82.667  1.00 56.41      A  N
ATOM  10249  CA  LEU E  81     -41.608   7.663 -81.703  1.00 55.84      A  C
ATOM  10250  C   LEU E  81     -41.217   8.182 -80.327  1.00 55.88      A  C
ATOM  10251  O   LEU E  81     -41.897   7.910 -79.343  1.00 55.52      A  O
ATOM  10252  CB  LEU E  81     -40.624   6.590 -82.184  1.00 55.65      A  C
ATOM  10253  CG  LEU E  81     -40.536   5.265 -81.416  1.00 54.88      A  C
ATOM  10254  CD1 LEU E  81     -40.260   4.109 -82.362  1.00 54.70      A  C
ATOM  10255  CD2 LEU E  81     -39.483   5.313 -80.319  1.00 54.76      A  C
ATOM  10256  N   ARG E  82     -40.133   8.945 -80.267  1.00 56.32      A  N
ATOM  10257  CA  ARG E  82     -39.646   9.477 -79.000  1.00 56.77      A  C
ATOM  10258  C   ARG E  82     -40.632  10.490 -78.390  1.00 56.70      A  C
ATOM  10259  O   ARG E  82     -40.699  10.658 -77.168  1.00 56.67      A  O
ATOM  10260  CB  ARG E  82     -38.248  10.082 -79.177  1.00 57.35      A  C
ATOM  10261  CG  ARG E  82     -37.508  10.325 -77.864  1.00 58.27      A  C
ATOM  10262  CD  ARG E  82     -36.039  10.611 -78.090  1.00 59.65      A  C
ATOM  10263  NE  ARG E  82     -35.197   9.422 -77.951  1.00 59.76      A  N
ATOM  10264  CZ  ARG E  82     -34.809   8.641 -78.956  1.00 59.80      A  C
ATOM  10265  NH1 ARG E  82     -35.195   8.897 -80.201  1.00 59.99      A  N
ATOM  10266  NH2 ARG E  82     -34.031   7.596 -78.714  1.00 59.56      A  N
ATOM  10267  N   ARG E  83     -41.393  11.155 -79.255  1.00 56.47      A  N
ATOM  10268  CA  ARG E  83     -42.445  12.089 -78.849  1.00 55.92      A  C
ATOM  10269  C   ARG E  83     -43.654  11.347 -78.246  1.00 55.49      A  C
ATOM  10270  O   ARG E  83     -44.254  11.811 -77.272  1.00 55.64      A  O
```

FIGURE 1 (cont'd)

```
ATOM  10271  CB   ARG E  83     -42.823  12.965 -80.061  1.00 54.94    A  C
ATOM  10272  CG   ARG E  83     -44.243  13.519 -80.121  1.00 54.48    A  C
ATOM  10273  CD   ARG E  83     -44.551  13.873 -81.567  1.00 54.58    A  C
ATOM  10274  NE   ARG E  83     -45.939  14.238 -81.792  1.00 54.04    A  N
ATOM  10275  N    VAL E  84     -43.982  10.191 -78.827  1.00 54.70    A  N
ATOM  10276  CA   VAL E  84     -45.084   9.336 -78.373  1.00 53.61    A  C
ATOM  10277  C    VAL E  84     -44.750   8.614 -77.068  1.00 52.97    A  C
ATOM  10278  O    VAL E  84     -45.493   8.725 -76.093  1.00 52.78    A  O
ATOM  10279  CB   VAL E  84     -45.500   8.316 -79.458  1.00 53.48    A  C
ATOM  10280  CG1  VAL E  84     -46.261   9.018 -80.560  1.00 53.55    A  C
ATOM  10281  CG2  VAL E  84     -46.344   7.191 -78.869  1.00 52.76    A  C
ATOM  10282  N    VAL E  85     -43.635   7.880 -77.052  1.00 52.19    A  N
ATOM  10283  CA   VAL E  85     -43.126   7.242 -75.829  1.00 51.36    A  C
ATOM  10284  C    VAL E  85     -43.023   8.253 -74.682  1.00 51.77    A  C
ATOM  10285  O    VAL E  85     -43.191   7.887 -73.519  1.00 51.94    A  O
ATOM  10286  CB   VAL E  85     -41.754   6.569 -76.051  1.00 49.77    A  C
ATOM  10287  N    GLY E  86     -42.768   9.520 -75.029  1.00 52.11    A  N
ATOM  10288  CA   GLY E  86     -42.713  10.637 -74.076  1.00 52.03    A  C
ATOM  10289  C    GLY E  86     -44.071  11.083 -73.557  1.00 51.63    A  C
ATOM  10290  O    GLY E  86     -44.160  11.721 -72.510  1.00 51.85    A  O
ATOM  10291  N    GLN E  87     -45.130  10.738 -74.281  1.00 50.97    A  N
ATOM  10292  CA   GLN E  87     -46.487  11.109 -73.882  1.00 50.19    A  C
ATOM  10293  C    GLN E  87     -47.084  10.244 -72.775  1.00 49.57    A  C
ATOM  10294  O    GLN E  87     -48.066  10.637 -72.141  1.00 49.51    A  O
ATOM  10295  N    LEU E  88     -46.502   9.066 -72.557  1.00 48.75    A  N
ATOM  10296  CA   LEU E  88     -46.888   8.204 -71.448  1.00 48.03    A  C
ATOM  10297  C    LEU E  88     -46.351   8.810 -70.154  1.00 48.40    A  C
ATOM  10298  O    LEU E  88     -45.164   9.129 -70.074  1.00 48.62    A  O
ATOM  10299  CB   LEU E  88     -46.305   6.807 -71.634  1.00 47.32    A  C
ATOM  10300  CG   LEU E  88     -46.810   5.935 -72.776  1.00 45.93    A  C
ATOM  10301  N    ASP E  89     -47.219   8.982 -69.154  1.00 48.73    A  N
ATOM  10302  CA   ASP E  89     -46.792   9.443 -67.823  1.00 49.12    A  C
ATOM  10303  C    ASP E  89     -46.737   8.280 -66.822  1.00 49.19    A  C
ATOM  10304  O    ASP E  89     -47.786   7.791 -66.398  1.00 49.00    A  O
ATOM  10305  CB   ASP E  89     -47.692  10.567 -67.288  1.00 49.27    A  C
ATOM  10306  CG   ASP E  89     -47.203  11.123 -65.947  1.00 49.44    A  C
ATOM  10307  OD1  ASP E  89     -46.054  11.607 -65.886  1.00 48.67    A  O
ATOM  10308  OD2  ASP E  89     -47.956  11.100 -64.955  1.00 49.37    A  O
ATOM  10309  N    PRO E  90     -45.514   7.839 -66.442  1.00 49.43    A  N
ATOM  10310  CA   PRO E  90     -45.306   6.672 -65.588  1.00 49.33    A  C
ATOM  10311  C    PRO E  90     -45.994   6.758 -64.240  1.00 49.27    A  C
ATOM  10312  O    PRO E  90     -46.565   5.766 -63.790  1.00 49.00    A  O
ATOM  10313  CB   PRO E  90     -43.790   6.640 -65.410  1.00 49.46    A  C
ATOM  10314  CG   PRO E  90     -43.274   7.253 -66.643  1.00 49.74    A  C
ATOM  10315  CD   PRO E  90     -44.226   8.378 -66.910  1.00 49.80    A  C
ATOM  10316  N    GLN E  91     -45.959   7.926 -63.606  1.00 49.46    A  N
ATOM  10317  CA   GLN E  91     -46.622   8.062 -62.313  1.00 49.55    A  C
ATOM  10318  C    GLN E  91     -48.141   8.142 -62.465  1.00 48.97    A  C
ATOM  10319  O    GLN E  91     -48.863   7.766 -61.551  1.00 49.04    A  O
ATOM  10320  CB   GLN E  91     -46.049   9.210 -61.470  1.00 50.14    A  C
ATOM  10321  CG   GLN E  91     -46.554  10.589 -61.825  1.00 50.95    A  C
ATOM  10322  N    ARG E  92     -48.616   8.603 -63.622  1.00 48.13    A  N
ATOM  10323  CA   ARG E  92     -50.049   8.603 -63.934  1.00 47.10    A  C
ATOM  10324  C    ARG E  92     -50.549   7.168 -64.055  1.00 46.65    A  C
ATOM  10325  O    ARG E  92     -51.567   6.816 -63.472  1.00 46.59    A  O
ATOM  10326  CB   ARG E  92     -50.345   9.404 -65.210  1.00 46.93    A  C
ATOM  10327  CG   ARG E  92     -51.751   9.255 -65.776  1.00 45.14    A  C
ATOM  10328  CD   ARG E  92     -51.992  10.144 -66.993  1.00 43.09    A  C
ATOM  10329  NE   ARG E  92     -51.024   9.961 -68.075  1.00 41.81    A  N
ATOM  10330  CZ   ARG E  92     -51.234   9.250 -69.180  1.00 43.07    A  C
ATOM  10331  NH1  ARG E  92     -52.376   8.594 -69.344  1.00 43.95    A  N
ATOM  10332  NH2  ARG E  92     -50.284   9.157 -70.112  1.00 43.57    A  N
ATOM  10333  N    LEU E  93     -49.822   6.343 -64.800  1.00 46.06    A  N
ATOM  10334  CA   LEU E  93     -50.164   4.934 -64.979  1.00 45.45    A  C
ATOM  10335  C    LEU E  93     -50.373   4.297 -63.620  1.00 45.51    A  C
```

FIGURE 1 (cont'd)

```
ATOM  10336  O    LEU E  93     -51.405   3.669 -63.361  1.00 45.42       A  O
ATOM  10337  CB   LEU E  93     -49.029   4.209 -65.711  1.00 45.07       A  C
ATOM  10338  CG   LEU E  93     -49.247   2.984 -66.598  1.00 43.88       A  C
ATOM  10339  CD1  LEU E  93     -50.302   2.034 -66.091  1.00 42.71       A  C
ATOM  10340  N    TRP E  94     -49.392   4.501 -62.747  1.00 45.68       A  N
ATOM  10341  CA   TRP E  94     -49.320   3.813 -61.465  1.00 45.72       A  C
ATOM  10342  C    TRP E  94     -50.304   4.335 -60.437  1.00 45.71       A  C
ATOM  10343  O    TRP E  94     -50.870   3.555 -59.673  1.00 45.59       A  O
ATOM  10344  CB   TRP E  94     -47.903   3.906 -60.895  1.00 45.95       A  C
ATOM  10345  CG   TRP E  94     -47.596   2.788 -59.972  1.00 46.41       A  C
ATOM  10346  CD1  TRP E  94     -47.838   2.743 -58.636  1.00 47.10       A  C
ATOM  10347  CD2  TRP E  94     -47.008   1.529 -60.318  1.00 46.48       A  C
ATOM  10348  CE2  TRP E  94     -46.920   0.773 -59.134  1.00 46.70       A  C
ATOM  10349  CE3  TRP E  94     -46.541   0.968 -61.517  1.00 46.24       A  C
ATOM  10350  NE1  TRP E  94     -47.430   1.539 -58.120  1.00 47.07       A  N
ATOM  10351  CZ2  TRP E  94     -46.389  -0.514 -59.110  1.00 46.63       A  C
ATOM  10352  CZ3  TRP E  94     -46.012  -0.310 -61.493  1.00 46.14       A  C
ATOM  10353  CH2  TRP E  94     -45.942  -1.037 -60.299  1.00 46.33       A  C
ATOM  10354  N    SER E  95     -50.505   5.653 -60.433  1.00 45.76       A  N
ATOM  10355  CA   SER E  95     -51.241   6.334 -59.368  1.00 45.73       A  C
ATOM  10356  C    SER E  95     -52.695   6.668 -59.697  1.00 45.17       A  C
ATOM  10357  O    SER E  95     -53.576   6.414 -58.881  1.00 45.15       A  O
ATOM  10358  CB   SER E  95     -50.506   7.598 -58.952  1.00 46.23       A  C
ATOM  10359  OG   SER E  95     -50.471   7.687 -57.550  1.00 47.20       A  O
ATOM  10360  N    THR E  96     -52.942   7.240 -60.877  1.00 44.46       A  N
ATOM  10361  CA   THR E  96     -54.299   7.586 -61.321  1.00 43.78       A  C
ATOM  10362  C    THR E  96     -55.111   6.386 -61.812  1.00 42.87       A  C
ATOM  10363  O    THR E  96     -56.335   6.372 -61.663  1.00 42.97       A  O
ATOM  10364  CB   THR E  96     -54.284   8.638 -62.446  1.00 43.98       A  C
ATOM  10365  OG1  THR E  96     -53.175   9.526 -62.269  1.00 44.68       A  O
ATOM  10366  N    TYR E  97     -54.428   5.392 -62.388  1.00 41.59       A  N
ATOM  10367  CA   TYR E  97     -55.089   4.243 -63.014  1.00 40.24       A  C
ATOM  10368  C    TYR E  97     -54.898   2.885 -62.316  1.00 39.85       A  C
ATOM  10369  O    TYR E  97     -55.868   2.128 -62.161  1.00 39.61       A  O
ATOM  10370  CB   TYR E  97     -54.695   4.146 -64.489  1.00 39.67       A  C
ATOM  10371  CG   TYR E  97     -54.992   5.399 -65.261  1.00 38.66       A  C
ATOM  10372  CD1  TYR E  97     -56.271   5.949 -65.269  1.00 37.61       A  C
ATOM  10373  CD2  TYR E  97     -53.991   6.048 -65.968  1.00 37.13       A  C
ATOM  10374  CE1  TYR E  97     -56.556   7.110 -65.981  1.00 37.44       A  C
ATOM  10375  CE2  TYR E  97     -54.257   7.210 -66.685  1.00 36.61       A  C
ATOM  10376  CZ   TYR E  97     -55.543   7.738 -66.689  1.00 36.45       A  C
ATOM  10377  OH   TYR E  97     -55.808   8.894 -67.397  1.00 35.67       A  O
ATOM  10378  N    LEU E  98     -53.670   2.570 -61.905  1.00 39.58       A  N
ATOM  10379  CA   LEU E  98     -53.414   1.269 -61.304  1.00 39.43       A  C
ATOM  10380  C    LEU E  98     -53.889   1.148 -59.863  1.00 39.67       A  C
ATOM  10381  O    LEU E  98     -54.669   0.253 -59.546  1.00 39.60       A  O
ATOM  10382  CB   LEU E  98     -51.942   0.878 -61.400  1.00 39.26       A  C
ATOM  10383  CG   LEU E  98     -51.605  -0.489 -60.775  1.00 39.01       A  C
ATOM  10384  CD1  LEU E  98     -52.311  -1.648 -61.473  1.00 38.40       A  C
ATOM  10385  CD2  LEU E  98     -50.098  -0.728 -60.738  1.00 39.16       A  C
ATOM  10386  N    ARG E  99     -53.405   2.032 -58.993  1.00 39.98       A  N
ATOM  10387  CA   ARG E  99     -53.764   1.976 -57.571  1.00 40.08       A  C
ATOM  10388  C    ARG E  99     -55.283   1.969 -57.271  1.00 40.24       A  C
ATOM  10389  O    ARG E  99     -55.741   1.162 -56.453  1.00 40.35       A  O
ATOM  10390  CB   ARG E  99     -53.005   3.032 -56.745  1.00 39.54       A  C
ATOM  10391  CG   ARG E  99     -51.894   2.421 -55.875  1.00 39.40       A  C
ATOM  10392  CD   ARG E  99     -51.219   3.413 -54.937  1.00 39.88       A  C
ATOM  10393  NE   ARG E  99     -49.861   3.743 -55.360  1.00 39.57       A  N
ATOM  10394  N    PRO E 100     -56.071   2.838 -57.943  1.00 40.24       A  N
ATOM  10395  CA   PRO E 100     -57.517   2.777 -57.746  1.00 40.13       A  C
ATOM  10396  C    PRO E 100     -58.084   1.402 -58.030  1.00 39.77       A  C
ATOM  10397  O    PRO E 100     -59.050   1.016 -57.391  1.00 39.95       A  O
ATOM  10398  CB   PRO E 100     -58.055   3.772 -58.773  1.00 40.25       A  C
ATOM  10399  CG   PRO E 100     -56.975   4.755 -58.928  1.00 40.50       A  C
ATOM  10400  CD   PRO E 100     -55.701   3.964 -58.822  1.00 40.37       A  C
```

FIGURE 1 (cont'd)

```
ATOM  10401  N    LEU E 101     -57.479   0.676 -58.968  1.00 39.10          A  N
ATOM  10402  CA   LEU E 101     -57.954  -0.646 -59.389  1.00 38.49          A  C
ATOM  10403  C    LEU E 101     -57.631  -1.777 -58.410  1.00 38.45          A  C
ATOM  10404  O    LEU E 101     -58.230  -2.860 -58.483  1.00 38.30          A  O
ATOM  10405  CB   LEU E 101     -57.380  -0.992 -60.764  1.00 38.10          A  C
ATOM  10406  CG   LEU E 101     -58.224  -0.827 -62.027  1.00 37.77          A  C
ATOM  10407  CD1  LEU E 101     -59.106   0.398 -61.968  1.00 38.23          A  C
ATOM  10408  CD2  LEU E 101     -57.329  -0.785 -63.258  1.00 37.46          A  C
ATOM  10409  N    LEU E 102     -56.694  -1.525 -57.496  1.00 38.53          A  N
ATOM  10410  CA   LEU E 102     -56.188  -2.569 -56.606  1.00 38.60          A  C
ATOM  10411  C    LEU E 102     -57.038  -2.799 -55.346  1.00 38.93          A  C
ATOM  10412  O    LEU E 102     -56.549  -2.680 -54.219  1.00 39.20          A  O
ATOM  10413  CB   LEU E 102     -54.722  -2.294 -56.251  1.00 38.53          A  C
ATOM  10414  CG   LEU E 102     -53.696  -2.393 -57.377  1.00 38.04          A  C
ATOM  10415  CD1  LEU E 102     -52.350  -1.936 -56.873  1.00 38.23          A  C
ATOM  10416  CD2  LEU E 102     -53.608  -3.809 -57.906  1.00 37.53          A  C
ATOM  10417  N    VAL E 103     -58.311  -3.131 -55.553  1.00 39.07          A  N
ATOM  10418  CA   VAL E 103     -59.232  -3.465 -54.464  1.00 39.38          A  C
ATOM  10419  C    VAL E 103     -59.976  -4.764 -54.758  1.00 39.08          A  C
ATOM  10420  O    VAL E 103     -60.137  -5.136 -55.919  1.00 38.80          A  O
ATOM  10421  CB   VAL E 103     -60.265  -2.351 -54.203  1.00 39.71          A  C
ATOM  10422  CG1  VAL E 103     -60.961  -1.939 -55.493  1.00 39.58          A  C
ATOM  10423  CG2  VAL E 103     -59.611  -1.157 -53.526  1.00 40.63          A  C
ATOM  10424  N    VAL E 104     -60.416  -5.448 -53.702  1.00 39.02          A  N
ATOM  10425  CA   VAL E 104     -61.232  -6.646 -53.846  1.00 38.72          A  C
ATOM  10426  C    VAL E 104     -62.444  -6.278 -54.694  1.00 38.92          A  C
ATOM  10427  O    VAL E 104     -63.118  -5.288 -54.421  1.00 39.23          A  O
ATOM  10428  CB   VAL E 104     -61.665  -7.226 -52.484  1.00 38.02          A  C
ATOM  10429  CG1  VAL E 104     -61.850  -8.720 -52.588  1.00 37.45          A  C
ATOM  10430  N    ARG E 105     -62.697  -7.066 -55.737  1.00 38.79          A  N
ATOM  10431  CA   ARG E 105     -63.666  -6.694 -56.770  1.00 38.53          A  C
ATOM  10432  C    ARG E 105     -64.315  -7.890 -57.462  1.00 38.50          A  C
ATOM  10433  O    ARG E 105     -64.658  -7.824 -58.647  1.00 38.22          A  O
ATOM  10434  CB   ARG E 105     -63.014  -5.753 -57.801  1.00 38.36          A  C
ATOM  10435  CG   ARG E 105     -61.851  -6.344 -58.565  1.00 37.69          A  C
ATOM  10436  CD   ARG E 105     -60.962  -5.272 -59.141  1.00 37.34          A  C
ATOM  10437  NE   ARG E 105     -60.006  -5.865 -60.069  1.00 37.02          A  N
ATOM  10438  CZ   ARG E 105     -58.757  -6.194 -59.759  1.00 36.80          A  C
ATOM  10439  NH1  ARG E 105     -58.297  -5.964 -58.538  1.00 36.93          A  N
ATOM  10440  NH2  ARG E 105     -57.968  -6.740 -60.680  1.00 36.41          A  N
ATOM  10441  N    THR E 106     -64.489  -8.972 -56.707  1.00 38.72          A  N
ATOM  10442  CA   THR E 106     -65.221 -10.145 -57.182  1.00 38.95          A  C
ATOM  10443  C    THR E 106     -66.603  -9.743 -57.741  1.00 39.00          A  C
ATOM  10444  O    THR E 106     -67.203  -8.786 -57.253  1.00 39.00          A  O
ATOM  10445  CB   THR E 106     -65.367 -11.194 -56.065  1.00 39.10          A  C
ATOM  10446  OG1  THR E 106     -66.147 -10.650 -55.000  1.00 39.75          A  O
ATOM  10447  N    PRO E 107     -67.098 -10.461 -58.776  1.00 39.11          A  N
ATOM  10448  CA   PRO E 107     -68.351 -10.121 -59.466  1.00 39.38          A  C
ATOM  10449  C    PRO E 107     -69.502  -9.719 -58.539  1.00 39.95          A  C
ATOM  10450  O    PRO E 107     -69.747 -10.372 -57.524  1.00 40.14          A  O
ATOM  10451  CB   PRO E 107     -68.705 -11.419 -60.197  1.00 39.30          A  C
ATOM  10452  CG   PRO E 107     -67.394 -12.044 -60.503  1.00 38.90          A  C
ATOM  10453  CD   PRO E 107     -66.464 -11.658 -59.371  1.00 39.00          A  C
ATOM  10454  N    GLY E 108     -70.194  -8.640 -58.894  1.00 40.38          A  N
ATOM  10455  CA   GLY E 108     -71.368  -8.183 -58.149  1.00 41.01          A  C
ATOM  10456  C    GLY E 108     -71.144  -7.742 -56.708  1.00 41.37          A  C
ATOM  10457  O    GLY E 108     -72.095  -7.675 -55.924  1.00 41.85          A  O
ATOM  10458  N    SER E 109     -69.896  -7.444 -56.354  1.00 41.34          A  N
ATOM  10459  CA   SER E 109     -69.575  -6.903 -55.037  1.00 41.37          A  C
ATOM  10460  C    SER E 109     -69.542  -5.374 -55.118  1.00 41.58          A  C
ATOM  10461  O    SER E 109     -69.657  -4.810 -56.208  1.00 41.34          A  O
ATOM  10462  CB   SER E 109     -68.231  -7.436 -54.558  1.00 41.23          A  C
ATOM  10463  OG   SER E 109     -67.193  -6.926 -55.368  1.00 40.66          A  O
ATOM  10464  N    PRO E 110     -69.407  -4.695 -53.965  1.00 41.94          A  N
ATOM  10465  CA   PRO E 110     -69.216  -3.242 -53.968  1.00 41.87          A  C
```

FIGURE 1 (cont'd)

```
ATOM  10466  C    PRO E 110     -67.947  -2.810 -54.702  1.00 41.30      A  C
ATOM  10467  O    PRO E 110     -67.957  -1.799 -55.394  1.00 41.13      A  O
ATOM  10468  CB   PRO E 110     -69.115  -2.899 -52.480  1.00 42.32      A  C
ATOM  10469  CG   PRO E 110     -69.904  -3.959 -51.816  1.00 42.77      A  C
ATOM  10470  CD   PRO E 110     -69.629  -5.207 -52.602  1.00 42.32      A  C
ATOM  10471  N    GLY E 111     -66.869  -3.573 -54.554  1.00 40.82      A  N
ATOM  10472  CA   GLY E 111     -65.622  -3.287 -55.260  1.00 40.16      A  C
ATOM  10473  C    GLY E 111     -65.747  -3.396 -56.770  1.00 39.60      A  C
ATOM  10474  O    GLY E 111     -65.259  -2.529 -57.509  1.00 39.39      A  O
ATOM  10475  N    ASN E 112     -66.399  -4.470 -57.217  1.00 39.17      A  N
ATOM  10476  CA   ASN E 112     -66.685  -4.690 -58.632  1.00 38.59      A  C
ATOM  10477  C    ASN E 112     -67.407  -3.488 -59.227  1.00 38.84      A  C
ATOM  10478  O    ASN E 112     -67.030  -3.001 -60.292  1.00 38.66      A  O
ATOM  10479  CB   ASN E 112     -67.512  -5.961 -58.817  1.00 38.27      A  C
ATOM  10480  CG   ASN E 112     -67.845  -6.233 -60.257  1.00 37.12      A  C
ATOM  10481  ND2  ASN E 112     -69.135  -6.317 -60.566  1.00 35.44      A  N
ATOM  10482  OD1  ASN E 112     -66.960  -6.364 -61.083  1.00 34.98      A  O
ATOM  10483  N    LEU E 113     -68.426  -2.999 -58.519  1.00 39.31      A  N
ATOM  10484  CA   LEU E 113     -69.171  -1.816 -58.946  1.00 39.76      A  C
ATOM  10485  C    LEU E 113     -68.347  -0.520 -58.808  1.00 39.80      A  C
ATOM  10486  O    LEU E 113     -68.392   0.336 -59.689  1.00 39.75      A  O
ATOM  10487  CB   LEU E 113     -70.501  -1.717 -58.193  1.00 40.16      A  C
ATOM  10488  CG   LEU E 113     -71.630  -0.903 -58.838  1.00 40.90      A  C
ATOM  10489  CD1  LEU E 113     -72.986  -1.552 -58.599  1.00 41.46      A  C
ATOM  10490  CD2  LEU E 113     -71.641   0.550 -58.371  1.00 41.75      A  C
ATOM  10491  N    GLN E 114     -67.593  -0.383 -57.718  1.00 39.90      A  N
ATOM  10492  CA   GLN E 114     -66.727   0.783 -57.517  1.00 39.89      A  C
ATOM  10493  C    GLN E 114     -65.722   0.914 -58.664  1.00 39.63      A  C
ATOM  10494  O    GLN E 114     -65.555   2.004 -59.214  1.00 39.70      A  O
ATOM  10495  CB   GLN E 114     -66.007   0.720 -56.162  1.00 40.04      A  C
ATOM  10496  N    VAL E 115     -65.075  -0.198 -59.030  1.00 39.05      A  N
ATOM  10497  CA   VAL E 115     -64.115  -0.213 -60.140  1.00 38.39      A  C
ATOM  10498  C    VAL E 115     -64.811   0.098 -61.467  1.00 38.67      A  C
ATOM  10499  O    VAL E 115     -64.387   1.014 -62.183  1.00 38.85      A  O
ATOM  10500  CB   VAL E 115     -63.345  -1.546 -60.241  1.00 36.90      A  C
ATOM  10501  N    ARG E 116     -65.883  -0.646 -61.770  1.00 38.87      A  N
ATOM  10502  CA   ARG E 116     -66.703  -0.440 -62.976  1.00 39.08      A  C
ATOM  10503  C    ARG E 116     -67.015   1.038 -63.192  1.00 39.52      A  C
ATOM  10504  O    ARG E 116     -66.870   1.554 -64.304  1.00 39.49      A  O
ATOM  10505  CB   ARG E 116     -68.001  -1.242 -62.875  1.00 38.95      A  C
ATOM  10506  CG   ARG E 116     -68.968  -1.051 -64.028  1.00 39.20      A  C
ATOM  10507  CD   ARG E 116     -70.290  -1.737 -63.739  1.00 40.24      A  C
ATOM  10508  NE   ARG E 116     -70.105  -3.164 -63.495  1.00 40.90      A  N
ATOM  10509  CZ   ARG E 116     -70.999  -3.965 -62.915  1.00 41.49      A  C
ATOM  10510  NH1  ARG E 116     -72.169  -3.487 -62.502  1.00 41.93      A  N
ATOM  10511  NH2  ARG E 116     -70.719  -5.256 -62.742  1.00 41.65      A  N
ATOM  10512  N    LYS E 117     -67.426   1.704 -62.113  1.00 40.09      A  N
ATOM  10513  CA   LYS E 117     -67.784   3.123 -62.128  1.00 40.56      A  C
ATOM  10514  C    LYS E 117     -66.567   4.001 -62.449  1.00 40.17      A  C
ATOM  10515  O    LYS E 117     -66.683   4.982 -63.184  1.00 40.26      A  O
ATOM  10516  CB   LYS E 117     -68.428   3.518 -60.786  1.00 41.16      A  C
ATOM  10517  CG   LYS E 117     -69.313   4.768 -60.826  1.00 42.52      A  C
ATOM  10518  CD   LYS E 117     -70.065   4.984 -59.503  1.00 43.87      A  C
ATOM  10519  CE   LYS E 117     -71.439   4.308 -59.504  1.00 44.09      A  C
ATOM  10520  N    PHE E 118     -65.408   3.629 -61.909  1.00 39.53      A  N
ATOM  10521  CA   PHE E 118     -64.174   4.366 -62.150  1.00 38.91      A  C
ATOM  10522  C    PHE E 118     -63.735   4.253 -63.600  1.00 39.18      A  C
ATOM  10523  O    PHE E 118     -63.221   5.216 -64.177  1.00 39.38      A  O
ATOM  10524  CB   PHE E 118     -63.055   3.868 -61.237  1.00 37.67      A  C
ATOM  10525  CG   PHE E 118     -61.700   4.461 -61.547  1.00 36.16      A  C
ATOM  10526  CD1  PHE E 118     -61.507   5.849 -61.467  1.00 35.85      A  C
ATOM  10527  CD2  PHE E 118     -60.637   3.617 -61.896  1.00 34.59      A  C
ATOM  10528  CE1  PHE E 118     -60.282   6.450 -61.729  1.00 35.48      A  C
ATOM  10529  CE2  PHE E 118     -59.358   4.090 -62.179  1.00 33.87      A  C
ATOM  10530  N    LEU E 119     -63.922   3.071 -64.179  1.00 39.20      A  N
```

FIGURE 1 (cont'd)

```
ATOM  10531  CA   LEU E 119    -63.603   2.855 -65.583  1.00 39.19      A  C
ATOM  10532  C    LEU E 119    -64.500   3.734 -66.465  1.00 39.69      A  C
ATOM  10533  O    LEU E 119    -63.998   4.555 -67.234  1.00 39.82      A  O
ATOM  10534  CB   LEU E 119    -63.682   1.368 -65.950  1.00 38.73      A  C
ATOM  10535  CG   LEU E 119    -62.443   0.563 -65.553  1.00 37.91      A  C
ATOM  10536  CD1  LEU E 119    -62.756  -0.911 -65.614  1.00 37.42      A  C
ATOM  10537  N    GLU E 120    -65.818   3.594 -66.313  1.00 40.19      A  N
ATOM  10538  CA   GLU E 120    -66.796   4.436 -67.030  1.00 40.63      A  C
ATOM  10539  C    GLU E 120    -66.407   5.903 -67.035  1.00 41.29      A  C
ATOM  10540  O    GLU E 120    -66.362   6.525 -68.093  1.00 41.58      A  O
ATOM  10541  CB   GLU E 120    -68.202   4.311 -66.429  1.00 39.85      A  C
ATOM  10542  CG   GLU E 120    -68.925   3.012 -66.750  1.00 39.54      A  C
ATOM  10543  CD   GLU E 120    -70.363   3.030 -66.286  1.00 40.09      A  C
ATOM  10544  OE1  GLU E 120    -71.134   3.871 -66.799  1.00 40.85      A  O
ATOM  10545  N    ALA E 121    -66.122   6.438 -65.851  1.00 41.82      A  N
ATOM  10546  CA   ALA E 121    -65.785   7.850 -65.680  1.00 42.21      A  C
ATOM  10547  C    ALA E 121    -64.495   8.267 -66.387  1.00 42.14      A  C
ATOM  10548  O    ALA E 121    -64.488   9.270 -67.110  1.00 42.46      A  O
ATOM  10549  CB   ALA E 121    -65.715   8.202 -64.207  1.00 42.54      A  C
ATOM  10550  N    THR E 122    -63.419   7.501 -66.180  1.00 41.58      A  N
ATOM  10551  CA   THR E 122    -62.115   7.780 -66.806  1.00 40.92      A  C
ATOM  10552  C    THR E 122    -62.234   7.825 -68.327  1.00 41.32      A  C
ATOM  10553  O    THR E 122    -61.774   8.782 -68.967  1.00 41.68      A  O
ATOM  10554  CB   THR E 122    -61.031   6.747 -66.406  1.00 39.45      A  C
ATOM  10555  OG1  THR E 122    -60.670   6.936 -65.035  1.00 38.53      A  O
ATOM  10556  N    LEU E 123    -62.876   6.798 -68.886  1.00 41.40      A  N
ATOM  10557  CA   LEU E 123    -63.074   6.674 -70.329  1.00 41.48      A  C
ATOM  10558  C    LEU E 123    -63.885   7.835 -70.903  1.00 42.14      A  C
ATOM  10559  O    LEU E 123    -63.554   8.370 -71.961  1.00 42.35      A  O
ATOM  10560  CB   LEU E 123    -63.748   5.339 -70.670  1.00 41.02      A  C
ATOM  10561  CG   LEU E 123    -62.967   4.037 -70.496  1.00 39.79      A  C
ATOM  10562  CD1  LEU E 123    -62.071   3.800 -71.682  1.00 39.16      A  C
ATOM  10563  N    ARG E 124    -64.940   8.218 -70.191  1.00 42.75      A  N
ATOM  10564  CA   ARG E 124    -65.787   9.338 -70.595  1.00 43.44      A  C
ATOM  10565  C    ARG E 124    -65.062  10.678 -70.533  1.00 44.08      A  C
ATOM  10566  O    ARG E 124    -65.267  11.528 -71.403  1.00 44.45      A  O
ATOM  10567  CB   ARG E 124    -67.078   9.383 -69.769  1.00 43.40      A  C
ATOM  10568  CG   ARG E 124    -68.130   8.404 -70.257  1.00 42.79      A  C
ATOM  10569  CD   ARG E 124    -69.424   8.527 -69.491  1.00 42.36      A  C
ATOM  10570  NE   ARG E 124    -70.414   7.558 -69.949  1.00 41.58      A  N
ATOM  10571  N    SER E 125    -64.201  10.847 -69.530  1.00 44.56      A  N
ATOM  10572  CA   SER E 125    -63.484  12.109 -69.317  1.00 45.13      A  C
ATOM  10573  C    SER E 125    -62.323  12.364 -70.286  1.00 45.25      A  C
ATOM  10574  O    SER E 125    -61.492  13.238 -70.028  1.00 45.56      A  O
ATOM  10575  CB   SER E 125    -62.973  12.190 -67.880  1.00 45.28      A  C
ATOM  10576  OG   SER E 125    -61.899  11.286 -67.700  1.00 44.99      A  O
ATOM  10577  N    LEU E 126    -62.272  11.621 -71.391  1.00 45.13      A  N
ATOM  10578  CA   LEU E 126    -61.211  11.795 -72.389  1.00 45.13      A  C
ATOM  10579  C    LEU E 126    -61.581  12.782 -73.499  1.00 45.65      A  C
ATOM  10580  O    LEU E 126    -62.751  12.896 -73.859  1.00 45.88      A  O
ATOM  10581  CB   LEU E 126    -60.787  10.444 -72.973  1.00 44.62      A  C
ATOM  10582  CG   LEU E 126    -60.123   9.420 -72.041  1.00 43.78      A  C
ATOM  10583  CD1  LEU E 126    -59.403   8.371 -72.875  1.00 42.94      A  C
ATOM  10584  CD2  LEU E 126    -59.156  10.080 -71.066  1.00 43.52      A  C
ATOM  10585  N    THR E 127    -60.572  13.477 -74.035  1.00 46.15      A  N
ATOM  10586  CA   THR E 127    -60.773  14.568 -75.010  1.00 46.65      A  C
ATOM  10587  C    THR E 127    -61.433  14.124 -76.309  1.00 46.67      A  C
ATOM  10588  O    THR E 127    -62.350  14.782 -76.785  1.00 47.14      A  O
ATOM  10589  CB   THR E 127    -59.466  15.312 -75.348  1.00 46.87      A  C
ATOM  10590  OG1  THR E 127    -58.640  15.391 -74.182  1.00 47.10      A  O
ATOM  10591  N    ALA E 128    -60.957  13.024 -76.883  1.00 46.30      A  N
ATOM  10592  CA   ALA E 128    -61.681  12.357 -77.959  1.00 46.09      A  C
ATOM  10593  C    ALA E 128    -63.010  11.829 -77.401  1.00 46.00      A  C
ATOM  10594  O    ALA E 128    -63.083  11.406 -76.244  1.00 45.97      A  O
ATOM  10595  CB   ALA E 128    -60.857  11.232 -78.527  1.00 45.77      A  C
```

FIGURE 1 (cont'd)

```
ATOM  10596  N    GLY E 129     -64.064  11.869 -78.208  1.00 45.97      A  N
ATOM  10597  CA   GLY E 129     -65.400  11.556 -77.710  1.00 45.73      A  C
ATOM  10598  C    GLY E 129     -65.679  10.071 -77.620  1.00 45.16      A  C
ATOM  10599  O    GLY E 129     -66.391   9.533 -78.471  1.00 45.52      A  O
ATOM  10600  N    TRP E 130     -65.131   9.412 -76.593  1.00 44.28      A  N
ATOM  10601  CA   TRP E 130     -65.291   7.959 -76.418  1.00 43.27      A  C
ATOM  10602  C    TRP E 130     -66.740   7.588 -76.118  1.00 42.98      A  C
ATOM  10603  O    TRP E 130     -67.368   8.158 -75.228  1.00 43.15      A  O
ATOM  10604  CB   TRP E 130     -64.383   7.427 -75.305  1.00 42.93      A  C
ATOM  10605  CG   TRP E 130     -62.921   7.186 -75.692  1.00 42.43      A  C
ATOM  10606  CD1  TRP E 130     -61.874   8.064 -75.553  1.00 42.64      A  C
ATOM  10607  CD2  TRP E 130     -62.354   5.981 -76.228  1.00 41.97      A  C
ATOM  10608  CE2  TRP E 130     -60.965   6.210 -76.401  1.00 41.83      A  C
ATOM  10609  CE3  TRP E 130     -62.883   4.735 -76.587  1.00 41.72      A  C
ATOM  10610  NE1  TRP E 130     -60.699   7.487 -75.984  1.00 42.20      A  N
ATOM  10611  CZ2  TRP E 130     -60.104   5.238 -76.921  1.00 41.35      A  C
ATOM  10612  CZ3  TRP E 130     -62.021   3.766 -77.104  1.00 41.34      A  C
ATOM  10613  CH2  TRP E 130     -60.650   4.027 -77.264  1.00 41.11      A  C
ATOM  10614  N    HIS E 131     -67.264   6.635 -76.876  1.00 42.54      A  N
ATOM  10615  CA   HIS E 131     -68.638   6.162 -76.719  1.00 42.34      A  C
ATOM  10616  C    HIS E 131     -68.597   5.020 -75.714  1.00 41.92      A  C
ATOM  10617  O    HIS E 131     -68.560   3.840 -76.087  1.00 41.71      A  O
ATOM  10618  CB   HIS E 131     -69.159   5.722 -78.097  1.00 42.51      A  C
ATOM  10619  CG   HIS E 131     -70.612   5.360 -78.163  1.00 42.88      A  C
ATOM  10620  CD2  HIS E 131     -71.204   4.146 -78.293  1.00 42.09      A  C
ATOM  10621  ND1  HIS E 131     -71.629   6.289 -78.229  1.00 42.12      A  N
ATOM  10622  CE1  HIS E 131     -72.788   5.660 -78.333  1.00 42.32      A  C
ATOM  10623  NE2  HIS E 131     -72.556   4.359 -78.375  1.00 41.78      A  N
ATOM  10624  N    VAL E 132     -68.569   5.389 -74.433  1.00 41.66      A  N
ATOM  10625  CA   VAL E 132     -68.527   4.424 -73.332  1.00 41.32      A  C
ATOM  10626  C    VAL E 132     -69.916   3.836 -73.081  1.00 41.34      A  C
ATOM  10627  O    VAL E 132     -70.907   4.562 -73.086  1.00 41.62      A  O
ATOM  10628  CB   VAL E 132     -67.985   5.074 -72.049  1.00 41.28      A  C
ATOM  10629  CG1  VAL E 132     -67.197   4.066 -71.247  1.00 41.01      A  C
ATOM  10630  N    GLU E 133     -69.989   2.527 -72.860  1.00 41.20      A  N
ATOM  10631  CA   GLU E 133     -71.276   1.834 -72.837  1.00 41.41      A  C
ATOM  10632  C    GLU E 133     -71.256   0.572 -71.976  1.00 41.16      A  C
ATOM  10633  O    GLU E 133     -70.431  -0.322 -72.200  1.00 41.04      A  O
ATOM  10634  CB   GLU E 133     -71.669   1.474 -74.264  1.00 41.62      A  C
ATOM  10635  CG   GLU E 133     -73.033   0.835 -74.412  1.00 42.98      A  C
ATOM  10636  CD   GLU E 133     -73.310   0.418 -75.850  1.00 44.72      A  C
ATOM  10637  OE1  GLU E 133     -73.179   1.266 -76.766  1.00 45.52      A  O
ATOM  10638  OE2  GLU E 133     -73.652  -0.764 -76.071  1.00 45.19      A  O
ATOM  10639  N    LEU E 134     -72.170   0.499 -71.004  1.00 41.07      A  N
ATOM  10640  CA   LEU E 134     -72.277  -0.663 -70.106  1.00 40.75      A  C
ATOM  10641  C    LEU E 134     -73.030  -1.832 -70.744  1.00 40.52      A  C
ATOM  10642  O    LEU E 134     -73.938  -1.632 -71.558  1.00 40.70      A  O
ATOM  10643  CB   LEU E 134     -72.952  -0.281 -68.789  1.00 40.91      A  C
ATOM  10644  CG   LEU E 134     -72.057   0.087 -67.612  1.00 41.04      A  C
ATOM  10645  CD1  LEU E 134     -72.911   0.653 -66.504  1.00 41.92      A  C
ATOM  10646  N    ASP E 135     -72.644  -3.050 -70.372  1.00 40.05      A  N
ATOM  10647  CA   ASP E 135     -73.362  -4.246 -70.786  1.00 39.84      A  C
ATOM  10648  C    ASP E 135     -73.799  -5.018 -69.542  1.00 39.79      A  C
ATOM  10649  O    ASP E 135     -73.150  -5.998 -69.159  1.00 39.78      A  O
ATOM  10650  CB   ASP E 135     -72.496  -5.126 -71.698  1.00 39.61      A  C
ATOM  10651  CG   ASP E 135     -73.186  -6.435 -72.086  1.00 39.84      A  C
ATOM  10652  OD1  ASP E 135     -74.405  -6.415 -72.345  1.00 40.65      A  O
ATOM  10653  OD2  ASP E 135     -72.515  -7.490 -72.130  1.00 39.56      A  O
ATOM  10654  N    PRO E 136     -74.899  -4.579 -68.901  1.00 39.79      A  N
ATOM  10655  CA   PRO E 136     -75.329  -5.270 -67.687  1.00 40.03      A  C
ATOM  10656  C    PRO E 136     -76.049  -6.553 -68.045  1.00 40.61      A  C
ATOM  10657  O    PRO E 136     -76.641  -6.629 -69.118  1.00 40.86      A  O
ATOM  10658  CB   PRO E 136     -76.306  -4.280 -67.038  1.00 39.31      A  C
ATOM  10659  CG   PRO E 136     -76.363  -3.061 -67.967  1.00 38.96      A  C
ATOM  10660  CD   PRO E 136     -75.832  -3.506 -69.286  1.00 39.63      A  C
```

FIGURE 1 (cont'd)

```
ATOM  10661  N    PHE E 137     -75.973   -7.552  -67.166  1.00 41.11      A   N
ATOM  10662  CA   PHE E 137     -76.748   -8.795  -67.309  1.00 41.62      A   C
ATOM  10663  C    PHE E 137     -76.665   -9.685  -66.068  1.00 42.06      A   C
ATOM  10664  O    PHE E 137     -75.687   -9.640  -65.323  1.00 42.01      A   O
ATOM  10665  CB   PHE E 137     -76.337   -9.585  -68.563  1.00 41.44      A   C
ATOM  10666  CG   PHE E 137     -74.984  -10.219  -68.467  1.00 41.10      A   C
ATOM  10667  CD1  PHE E 137     -73.829   -9.468  -68.693  1.00 40.78      A   C
ATOM  10668  CD2  PHE E 137     -74.861  -11.574  -68.163  1.00 41.00      A   C
ATOM  10669  CE1  PHE E 137     -72.569  -10.053  -68.610  1.00 40.24      A   C
ATOM  10670  CE2  PHE E 137     -73.606  -12.173  -68.080  1.00 40.54      A   C
ATOM  10671  CZ   PHE E 137     -72.457  -11.410  -68.304  1.00 40.18      A   C
ATOM  10672  N    THR E 138     -77.706  -10.487  -65.858  1.00 42.79      A   N
ATOM  10673  CA   THR E 138     -77.709  -11.503  -64.813  1.00 43.38      A   C
ATOM  10674  C    THR E 138     -77.408  -12.873  -65.415  1.00 43.47      A   C
ATOM  10675  O    THR E 138     -77.822  -13.170  -66.545  1.00 43.58      A   O
ATOM  10676  CB   THR E 138     -79.044  -11.546  -64.066  1.00 43.76      A   C
ATOM  10677  OG1  THR E 138     -78.868  -10.955  -62.774  1.00 44.27      A   O
ATOM  10678  N    ALA E 139     -76.675  -13.697  -64.665  1.00 43.50      A   N
ATOM  10679  CA   ALA E 139     -76.252  -15.012  -65.158  1.00 43.59      A   C
ATOM  10680  C    ALA E 139     -76.209  -16.089  -64.083  1.00 43.93      A   C
ATOM  10681  O    ALA E 139     -75.941  -15.821  -62.907  1.00 43.97      A   O
ATOM  10682  CB   ALA E 139     -74.912  -14.919  -65.878  1.00 43.18      A   C
ATOM  10683  N    SER E 140     -76.474  -17.313  -64.527  1.00 44.36      A   N
ATOM  10684  CA   SER E 140     -76.572  -18.475  -63.665  1.00 44.77      A   C
ATOM  10685  C    SER E 140     -75.191  -19.074  -63.374  1.00 44.46      A   C
ATOM  10686  O    SER E 140     -74.526  -19.584  -64.275  1.00 44.33      A   O
ATOM  10687  CB   SER E 140     -77.496  -19.505  -64.325  1.00 45.21      A   C
ATOM  10688  OG   SER E 140     -77.316  -20.795  -63.774  1.00 46.15      A   O
ATOM  10689  N    THR E 141     -74.767  -19.002  -62.112  1.00 44.28      A   N
ATOM  10690  CA   THR E 141     -73.459  -19.516  -61.685  1.00 44.03      A   C
ATOM  10691  C    THR E 141     -73.629  -20.628  -60.647  1.00 44.34      A   C
ATOM  10692  O    THR E 141     -74.735  -20.809  -60.123  1.00 44.80      A   O
ATOM  10693  CB   THR E 141     -72.553  -18.386  -61.111  1.00 43.70      A   C
ATOM  10694  CG2  THR E 141     -72.555  -17.170  -62.026  1.00 43.39      A   C
ATOM  10695  OG1  THR E 141     -73.004  -17.993  -59.809  1.00 43.70      A   O
ATOM  10696  N    PRO E 142     -72.546  -21.389  -60.353  1.00 44.31      A   N
ATOM  10697  CA   PRO E 142     -72.581  -22.377  -59.264  1.00 44.49      A   C
ATOM  10698  C    PRO E 142     -72.840  -21.773  -57.881  1.00 44.67      A   C
ATOM  10699  O    PRO E 142     -73.067  -22.511  -56.925  1.00 45.09      A   O
ATOM  10700  CB   PRO E 142     -71.189  -23.011  -59.324  1.00 44.35      A   C
ATOM  10701  CG   PRO E 142     -70.789  -22.883  -60.735  1.00 44.07      A   C
ATOM  10702  CD   PRO E 142     -71.323  -21.543  -61.165  1.00 44.00      A   C
ATOM  10703  N    LEU E 143     -72.805  -20.443  -57.793  1.00 44.50      A   N
ATOM  10704  CA   LEU E 143     -73.163  -19.709  -56.579  1.00 44.53      A   C
ATOM  10705  C    LEU E 143     -74.569  -19.112  -56.689  1.00 44.79      A   C
ATOM  10706  O    LEU E 143     -74.966  -18.281  -55.859  1.00 45.02      A   O
ATOM  10707  CB   LEU E 143     -72.138  -18.596  -56.298  1.00 44.16      A   C
ATOM  10708  CG   LEU E 143     -70.901  -18.801  -55.405  1.00 44.08      A   C
ATOM  10709  CD1  LEU E 143     -71.277  -18.994  -53.930  1.00 45.10      A   C
ATOM  10710  CD2  LEU E 143     -70.015  -19.943  -55.884  1.00 43.70      A   C
ATOM  10711  N    GLY E 144     -75.316  -19.546  -57.709  1.00 44.90      A   N
ATOM  10712  CA   GLY E 144     -76.640  -18.998  -58.016  1.00 44.99      A   C
ATOM  10713  C    GLY E 144     -76.549  -17.712  -58.823  1.00 44.83      A   C
ATOM  10714  O    GLY E 144     -75.452  -17.310  -59.230  1.00 44.48      A   O
ATOM  10715  N    PRO E 145     -77.698  -17.057  -59.068  1.00 44.95      A   N
ATOM  10716  CA   PRO E 145     -77.758  -15.810  -59.832  1.00 44.61      A   C
ATOM  10717  C    PRO E 145     -76.733  -14.769  -59.377  1.00 43.84      A   C
ATOM  10718  O    PRO E 145     -76.684  -14.429  -58.188  1.00 44.04      A   O
ATOM  10719  CB   PRO E 145     -79.175  -15.306  -59.556  1.00 44.99      A   C
ATOM  10720  CG   PRO E 145     -79.957  -16.540  -59.376  1.00 45.65      A   C
ATOM  10721  CD   PRO E 145     -79.043  -17.526  -58.697  1.00 45.48      A   C
ATOM  10722  N    VAL E 146     -75.925  -14.288  -60.326  1.00 42.54      A   N
ATOM  10723  CA   VAL E 146     -74.937  -13.238  -60.081  1.00 41.09      A   C
ATOM  10724  C    VAL E 146     -75.080  -12.119  -61.127  1.00 41.29      A   C
ATOM  10725  O    VAL E 146     -75.245  -12.397  -62.319  1.00 41.33      A   O
```

FIGURE 1 (cont'd)

```
ATOM  10726  CB   VAL E 146     -73.511 -13.806 -60.092  1.00 39.26      A  C
ATOM  10727  CG1  VAL E 146     -72.540 -12.793 -59.525  1.00 37.82      A  C
ATOM  10728  N    ASP E 147     -75.031 -10.864 -60.674  1.00 41.37      A  N
ATOM  10729  CA   ASP E 147     -75.170  -9.692 -61.561  1.00 41.11      A  C
ATOM  10730  C    ASP E 147     -73.821  -9.185 -62.111  1.00 40.66      A  C
ATOM  10731  O    ASP E 147     -72.946  -8.738 -61.356  1.00 40.60      A  O
ATOM  10732  CB   ASP E 147     -75.929  -8.557 -60.854  1.00 41.32      A  C
ATOM  10733  CG   ASP E 147     -77.425  -8.805 -60.781  1.00 41.26      A  C
ATOM  10734  N    PHE E 148     -73.669  -9.250 -63.430  1.00 40.11      A  N
ATOM  10735  CA   PHE E 148     -72.429  -8.856 -64.093  1.00 39.52      A  C
ATOM  10736  C    PHE E 148     -72.588  -7.576 -64.887  1.00 39.32      A  C
ATOM  10737  O    PHE E 148     -73.699  -7.077 -65.065  1.00 39.50      A  O
ATOM  10738  CB   PHE E 148     -71.979  -9.940 -65.055  1.00 39.32      A  C
ATOM  10739  CG   PHE E 148     -71.699 -11.259 -64.407  1.00 39.37      A  C
ATOM  10740  CD1  PHE E 148     -70.434 -11.545 -63.914  1.00 39.09      A  C
ATOM  10741  CD2  PHE E 148     -72.693 -12.235 -64.328  1.00 39.82      A  C
ATOM  10742  CE1  PHE E 148     -70.166 -12.775 -63.337  1.00 39.26      A  C
ATOM  10743  CE2  PHE E 148     -72.436 -13.471 -63.747  1.00 39.84      A  C
ATOM  10744  CZ   PHE E 148     -71.172 -13.741 -63.251  1.00 39.58      A  C
ATOM  10745  N    GLY E 149     -71.468  -7.062 -65.383  1.00 38.95      A  N
ATOM  10746  CA   GLY E 149     -71.473  -5.851 -66.195  1.00 38.81      A  C
ATOM  10747  C    GLY E 149     -70.153  -5.560 -66.891  1.00 38.55      A  C
ATOM  10748  O    GLY E 149     -69.155  -5.245 -66.240  1.00 38.55      A  O
ATOM  10749  N    ASN E 150     -70.151  -5.665 -68.218  1.00 38.29      A  N
ATOM  10750  CA   ASN E 150     -68.986  -5.331 -69.026  1.00 37.94      A  C
ATOM  10751  C    ASN E 150     -68.908  -3.831 -69.282  1.00 38.11      A  C
ATOM  10752  O    ASN E 150     -69.921  -3.145 -69.260  1.00 38.35      A  O
ATOM  10753  CB   ASN E 150     -69.045  -6.089 -70.352  1.00 37.67      A  C
ATOM  10754  CG   ASN E 150     -68.913  -7.595 -70.176  1.00 37.28      A  C
ATOM  10755  ND2  ASN E 150     -69.881  -8.338 -70.697  1.00 37.28      A  N
ATOM  10756  OD1  ASN E 150     -67.950  -8.082 -69.592  1.00 36.75      A  O
ATOM  10757  N    VAL E 151     -67.703  -3.326 -69.508  1.00 38.13      A  N
ATOM  10758  CA   VAL E 151     -67.511  -1.935 -69.891  1.00 38.43      A  C
ATOM  10759  C    VAL E 151     -66.928  -1.870 -71.304  1.00 38.66      A  C
ATOM  10760  O    VAL E 151     -65.771  -2.236 -71.530  1.00 38.51      A  O
ATOM  10761  CB   VAL E 151     -66.616  -1.194 -68.886  1.00 38.34      A  C
ATOM  10762  CG1  VAL E 151     -67.313  -1.096 -67.551  1.00 38.71      A  C
ATOM  10763  CG2  VAL E 151     -66.280   0.192 -69.386  1.00 38.50      A  C
ATOM  10764  N    VAL E 152     -67.741  -1.411 -72.251  1.00 39.18      A  N
ATOM  10765  CA   VAL E 152     -67.362  -1.367 -73.662  1.00 39.66      A  C
ATOM  10766  C    VAL E 152     -67.100   0.061 -74.120  1.00 40.22      A  C
ATOM  10767  O    VAL E 152     -67.949   0.937 -73.977  1.00 40.59      A  O
ATOM  10768  CB   VAL E 152     -68.443  -2.039 -74.544  1.00 39.64      A  C
ATOM  10769  CG1  VAL E 152     -68.382  -3.546 -74.385  1.00 39.12      A  C
ATOM  10770  CG2  VAL E 152     -68.300  -1.648 -76.023  1.00 39.99      A  C
ATOM  10771  N    ALA E 153     -65.919   0.283 -74.678  1.00 40.64      A  N
ATOM  10772  CA   ALA E 153     -65.511   1.610 -75.112  1.00 41.26      A  C
ATOM  10773  C    ALA E 153     -65.050   1.614 -76.569  1.00 41.76      A  C
ATOM  10774  O    ALA E 153     -64.183   0.835 -76.968  1.00 41.69      A  O
ATOM  10775  CB   ALA E 153     -64.422   2.153 -74.194  1.00 41.12      A  C
ATOM  10776  N    THR E 154     -65.641   2.505 -77.359  1.00 42.56      A  N
ATOM  10777  CA   THR E 154     -65.322   2.624 -78.778  1.00 43.20      A  C
ATOM  10778  C    THR E 154     -65.227   4.099 -79.181  1.00 43.99      A  C
ATOM  10779  O    THR E 154     -66.195   4.840 -79.032  1.00 44.40      A  O
ATOM  10780  CB   THR E 154     -66.393   1.903 -79.651  1.00 43.08      A  C
ATOM  10781  CG2  THR E 154     -65.845   1.579 -81.028  1.00 42.98      A  C
ATOM  10782  OG1  THR E 154     -66.806   0.688 -79.012  1.00 42.60      A  O
ATOM  10783  N    LEU E 155     -64.055   4.528 -79.650  1.00 44.67      A  N
ATOM  10784  CA   LEU E 155     -63.945   5.787 -80.381  1.00 45.55      A  C
ATOM  10785  C    LEU E 155     -64.641   5.614 -81.720  1.00 46.35      A  C
ATOM  10786  O    LEU E 155     -64.432   4.597 -82.386  1.00 46.58      A  O
ATOM  10787  CB   LEU E 155     -62.482   6.121 -80.650  1.00 45.36      A  C
ATOM  10788  CG   LEU E 155     -61.785   7.204 -79.840  1.00 45.39      A  C
ATOM  10789  CD1  LEU E 155     -60.525   7.652 -80.579  1.00 45.19      A  C
ATOM  10790  CD2  LEU E 155     -62.719   8.390 -79.591  1.00 45.87      A  C
```

FIGURE 1 (cont'd)

```
ATOM  10791  N    ASP E 156     -65.463   6.581 -82.119  1.00 47.20      A  N
ATOM  10792  CA   ASP E 156     -66.060   6.556 -83.457  1.00 48.05      A  C
ATOM  10793  C    ASP E 156     -66.803   5.231 -83.745  1.00 47.90      A  C
ATOM  10794  O    ASP E 156     -66.314   4.396 -84.509  1.00 47.69      A  O
ATOM  10795  CB   ASP E 156     -64.961   6.819 -84.510  1.00 48.57      A  C
ATOM  10796  CG   ASP E 156     -65.511   7.169 -85.887  1.00 50.20      A  C
ATOM  10797  OD1  ASP E 156     -66.740   7.089 -86.111  1.00 51.17      A  O
ATOM  10798  OD2  ASP E 156     -64.689   7.529 -86.759  1.00 51.70      A  O
ATOM  10799  N    PRO E 157     -67.989   5.035 -83.137  1.00 47.99      A  N
ATOM  10800  CA   PRO E 157     -68.746   3.797 -83.355  1.00 48.06      A  C
ATOM  10801  C    PRO E 157     -69.123   3.562 -84.806  1.00 48.36      A  C
ATOM  10802  O    PRO E 157     -69.377   2.420 -85.192  1.00 48.24      A  O
ATOM  10803  CB   PRO E 157     -70.015   4.014 -82.533  1.00 48.05      A  C
ATOM  10804  CG   PRO E 157     -69.653   5.031 -81.523  1.00 48.05      A  C
ATOM  10805  CD   PRO E 157     -68.663   5.924 -82.174  1.00 48.11      A  C
ATOM  10806  N    ARG E 158     -69.159   4.643 -85.586  1.00 48.91      A  N
ATOM  10807  CA   ARG E 158     -69.551   4.585 -87.001  1.00 49.43      A  C
ATOM  10808  C    ARG E 158     -68.480   3.985 -87.941  1.00 49.26      A  C
ATOM  10809  O    ARG E 158     -68.813   3.478 -89.020  1.00 49.57      A  O
ATOM  10810  CB   ARG E 158     -70.119   5.935 -87.519  1.00 49.93      A  C
ATOM  10811  CG   ARG E 158     -69.315   7.198 -87.215  1.00 50.23      A  C
ATOM  10812  N    ALA E 159     -67.211   4.030 -87.527  1.00 48.77      A  N
ATOM  10813  CA   ALA E 159     -66.115   3.459 -88.320  1.00 48.34      A  C
ATOM  10814  C    ALA E 159     -66.377   1.992 -88.597  1.00 48.00      A  C
ATOM  10815  O    ALA E 159     -66.916   1.291 -87.756  1.00 47.79      A  O
ATOM  10816  CB   ALA E 159     -64.779   3.645 -87.618  1.00 48.21      A  C
ATOM  10817  N    ALA E 160     -66.002   1.544 -89.784  1.00 47.84      A  N
ATOM  10818  CA   ALA E 160     -66.353   0.210 -90.253  1.00 47.61      A  C
ATOM  10819  C    ALA E 160     -65.686  -0.933 -89.485  1.00 47.10      A  C
ATOM  10820  O    ALA E 160     -66.275  -2.005 -89.309  1.00 47.01      A  O
ATOM  10821  CB   ALA E 160     -66.045   0.096 -91.725  1.00 48.05      A  C
ATOM  10822  N    ARG E 161     -64.455  -0.696 -89.044  1.00 46.53      A  N
ATOM  10823  CA   ARG E 161     -63.682  -1.677 -88.276  1.00 45.91      A  C
ATOM  10824  C    ARG E 161     -62.885  -1.002 -87.158  1.00 45.11      A  C
ATOM  10825  O    ARG E 161     -62.614   0.199 -87.210  1.00 45.25      A  O
ATOM  10826  CB   ARG E 161     -62.736  -2.442 -89.199  1.00 46.17      A  C
ATOM  10827  CG   ARG E 161     -63.380  -3.574 -89.995  1.00 47.54      A  C
ATOM  10828  CD   ARG E 161     -62.833  -3.631 -91.420  1.00 50.38      A  C
ATOM  10829  NE   ARG E 161     -61.456  -3.125 -91.506  1.00 52.63      A  N
ATOM  10830  CZ   ARG E 161     -60.990  -2.333 -92.478  1.00 53.88      A  C
ATOM  10831  NH1  ARG E 161     -61.781  -1.935 -93.472  1.00 54.66      A  N
ATOM  10832  NH2  ARG E 161     -59.722  -1.925 -92.454  1.00 54.16      A  N
ATOM  10833  N    HIS E 162     -62.516  -1.779 -86.144  1.00 44.05      A  N
ATOM  10834  CA   HIS E 162     -61.713  -1.258 -85.035  1.00 43.02      A  C
ATOM  10835  C    HIS E 162     -60.709  -2.274 -84.481  1.00 41.97      A  C
ATOM  10836  O    HIS E 162     -60.978  -3.478 -84.467  1.00 41.74      A  O
ATOM  10837  CB   HIS E 162     -62.617  -0.755 -83.908  1.00 43.23      A  C
ATOM  10838  CG   HIS E 162     -63.700  -1.716 -83.530  1.00 43.87      A  C
ATOM  10839  CD2  HIS E 162     -65.038  -1.675 -83.733  1.00 44.45      A  C
ATOM  10840  ND1  HIS E 162     -63.452  -2.890 -82.850  1.00 44.08      A  N
ATOM  10841  CE1  HIS E 162     -64.590  -3.532 -82.655  1.00 44.29      A  C
ATOM  10842  NE2  HIS E 162     -65.569  -2.814 -83.178  1.00 44.55      A  N
ATOM  10843  N    LEU E 163     -59.549  -1.782 -84.044  1.00 40.85      A  N
ATOM  10844  CA   LEU E 163     -58.615  -2.583 -83.274  1.00 39.65      A  C
ATOM  10845  C    LEU E 163     -59.209  -2.672 -81.900  1.00 38.96      A  C
ATOM  10846  O    LEU E 163     -59.636  -1.659 -81.350  1.00 39.01      A  O
ATOM  10847  CB   LEU E 163     -57.249  -1.908 -83.189  1.00 39.55      A  C
ATOM  10848  CG   LEU E 163     -56.283  -2.443 -82.126  1.00 38.90      A  C
ATOM  10849  CD1  LEU E 163     -55.868  -3.878 -82.408  1.00 38.46      A  C
ATOM  10850  CD2  LEU E 163     -55.059  -1.560 -81.996  1.00 38.86      A  C
ATOM  10851  N    THR E 164     -59.248  -3.878 -81.346  1.00 38.00      A  N
ATOM  10852  CA   THR E 164     -59.842  -4.067 -80.023  1.00 37.05      A  C
ATOM  10853  C    THR E 164     -58.911  -4.720 -78.989  1.00 36.46      A  C
ATOM  10854  O    THR E 164     -58.481  -5.862 -79.145  1.00 36.23      A  O
ATOM  10855  CB   THR E 164     -61.247  -4.733 -80.095  1.00 36.99      A  C
```

FIGURE 1 (cont'd)

```
ATOM  10856  CG2 THR E 164     -61.253  -5.936 -80.992  1.00 36.93      A C
ATOM  10857  OG1 THR E 164     -61.676  -5.117 -78.786  1.00 36.63      A O
ATOM  10858  N   LEU E 165     -58.587  -3.953 -77.953  1.00 35.84      A N
ATOM  10859  CA  LEU E 165     -57.802  -4.437 -76.834  1.00 35.28      A C
ATOM  10860  C   LEU E 165     -58.732  -4.786 -75.676  1.00 35.01      A C
ATOM  10861  O   LEU E 165     -59.762  -4.122 -75.471  1.00 35.07      A O
ATOM  10862  CB  LEU E 165     -56.806  -3.378 -76.380  1.00 35.22      A C
ATOM  10863  CG  LEU E 165     -55.813  -2.816 -77.387  1.00 35.28      A C
ATOM  10864  CD1 LEU E 165     -54.800  -1.947 -76.675  1.00 35.41      A C
ATOM  10865  CD2 LEU E 165     -55.120  -3.925 -78.117  1.00 35.09      A C
ATOM  10866  N   ALA E 166     -58.366  -5.817 -74.914  1.00 34.53      A N
ATOM  10867  CA  ALA E 166     -59.210  -6.286 -73.821  1.00 34.08      A C
ATOM  10868  C   ALA E 166     -58.423  -6.730 -72.606  1.00 33.80      A C
ATOM  10869  O   ALA E 166     -57.316  -7.253 -72.734  1.00 33.66      A O
ATOM  10870  CB  ALA E 166     -60.122  -7.404 -74.301  1.00 34.08      A C
ATOM  10871  N   CYS E 167     -59.016  -6.488 -71.438  1.00 33.63      A N
ATOM  10872  CA  CYS E 167     -58.567  -7.011 -70.151  1.00 33.51      A C
ATOM  10873  C   CYS E 167     -59.824  -7.393 -69.401  1.00 33.48      A C
ATOM  10874  O   CYS E 167     -60.918  -6.999 -69.813  1.00 33.56      A O
ATOM  10875  CB  CYS E 167     -57.821  -5.934 -69.357  1.00 33.51      A C
ATOM  10876  SG  CYS E 167     -58.886  -4.587 -68.738  1.00 33.77      A S
ATOM  10877  N   HIS E 168     -59.684  -8.142 -68.308  1.00 33.46      A N
ATOM  10878  CA  HIS E 168     -60.817  -8.371 -67.403  1.00 33.49      A C
ATOM  10879  C   HIS E 168     -60.612  -7.636 -66.079  1.00 33.42      A C
ATOM  10880  O   HIS E 168     -59.515  -7.655 -65.505  1.00 33.35      A O
ATOM  10881  CB  HIS E 168     -61.073  -9.865 -67.176  1.00 33.61      A C
ATOM  10882  CG  HIS E 168     -60.124 -10.502 -66.205  1.00 34.03      A C
ATOM  10883  CD2 HIS E 168     -58.938 -11.129 -66.395  1.00 34.35      A C
ATOM  10884  ND1 HIS E 168     -60.349 -10.517 -64.844  1.00 34.38      A N
ATOM  10885  CE1 HIS E 168     -59.344 -11.127 -64.238  1.00 34.40      A C
ATOM  10886  NE2 HIS E 168     -58.474 -11.506 -65.155  1.00 34.32      A N
ATOM  10887  N   TYR E 169     -61.672  -6.992 -65.597  1.00 33.51      A N
ATOM  10888  CA  TYR E 169     -61.557  -6.111 -64.436  1.00 33.67      A C
ATOM  10889  C   TYR E 169     -62.027  -6.738 -63.137  1.00 33.73      A C
ATOM  10890  O   TYR E 169     -61.734  -6.225 -62.068  1.00 33.75      A O
ATOM  10891  CB  TYR E 169     -62.241  -4.757 -64.686  1.00 33.72      A C
ATOM  10892  CG  TYR E 169     -63.738  -4.771 -64.545  1.00 33.94      A C
ATOM  10893  CD1 TYR E 169     -64.550  -5.211 -65.582  1.00 33.83      A C
ATOM  10894  CD2 TYR E 169     -64.345  -4.328 -63.376  1.00 34.41      A C
ATOM  10895  CE1 TYR E 169     -65.930  -5.224 -65.454  1.00 33.93      A C
ATOM  10896  CE2 TYR E 169     -65.723  -4.336 -63.237  1.00 34.62      A C
ATOM  10897  CZ  TYR E 169     -66.509  -4.784 -64.280  1.00 34.21      A C
ATOM  10898  OH  TYR E 169     -67.874  -4.787 -64.141  1.00 34.29      A O
ATOM  10899  N   ASP E 170     -62.746  -7.848 -63.227  1.00 33.84      A N
ATOM  10900  CA  ASP E 170     -63.083  -8.606 -62.035  1.00 34.18      A C
ATOM  10901  C   ASP E 170     -61.813  -9.186 -61.378  1.00 34.45      A C
ATOM  10902  O   ASP E 170     -60.753  -9.274 -62.019  1.00 34.26      A O
ATOM  10903  CB  ASP E 170     -64.112  -9.700 -62.355  1.00 34.23      A C
ATOM  10904  CG  ASP E 170     -63.554 -10.820 -63.240  1.00 34.17      A C
ATOM  10905  OD1 ASP E 170     -63.061 -10.529 -64.343  1.00 33.82      A O
ATOM  10906  OD2 ASP E 170     -63.641 -12.005 -62.848  1.00 34.55      A O
ATOM  10907  N   SER E 171     -61.917  -9.534 -60.093  1.00 34.92      A N
ATOM  10908  CA  SER E 171     -60.849 -10.254 -59.379  1.00 35.35      A C
ATOM  10909  C   SER E 171     -61.398 -11.592 -58.886  1.00 35.63      A C
ATOM  10910  O   SER E 171     -62.585 -11.674 -58.562  1.00 35.96      A O
ATOM  10911  CB  SER E 171     -60.332  -9.429 -58.195  1.00 35.42      A C
ATOM  10912  OG  SER E 171     -61.162  -9.569 -57.048  1.00 35.82      A O
ATOM  10913  N   LYS E 172     -60.560 -12.629 -58.822  1.00 35.76      A N
ATOM  10914  CA  LYS E 172     -61.044 -13.945 -58.376  1.00 36.19      A C
ATOM  10915  C   LYS E 172     -61.585 -13.932 -56.945  1.00 36.92      A C
ATOM  10916  O   LYS E 172     -61.130 -13.149 -56.099  1.00 37.17      A O
ATOM  10917  CB  LYS E 172     -59.984 -15.037 -58.516  1.00 35.92      A C
ATOM  10918  CG  LYS E 172     -60.552 -16.457 -58.455  1.00 35.66      A C
ATOM  10919  CD  LYS E 172     -59.475 -17.505 -58.571  1.00 35.06      A C
ATOM  10920  CE  LYS E 172     -60.038 -18.906 -58.405  1.00 35.09      A C
```

FIGURE 1 (cont'd)

```
ATOM  10921  NZ   LYS E 172     -60.709 -19.423 -59.630  1.00 35.06      A    N
ATOM  10922  N    LEU E 173     -62.570 -14.800 -56.704  1.00 37.71      A    N
ATOM  10923  CA   LEU E 173     -63.221 -14.948 -55.404  1.00 38.58      A    C
ATOM  10924  C    LEU E 173     -62.628 -16.134 -54.653  1.00 39.10      A    C
ATOM  10925  O    LEU E 173     -62.607 -17.262 -55.148  1.00 39.21      A    O
ATOM  10926  CB   LEU E 173     -64.729 -15.149 -55.587  1.00 38.66      A    C
ATOM  10927  CG   LEU E 173     -65.569 -15.504 -54.354  1.00 39.25      A    C
ATOM  10928  CD1  LEU E 173     -66.163 -14.263 -53.709  1.00 39.57      A    C
ATOM  10929  CD2  LEU E 173     -66.657 -16.503 -54.712  1.00 39.39      A    C
ATOM  10930  N    PHE E 174     -62.155 -15.874 -53.449  1.00 39.77      A    N
ATOM  10931  CA   PHE E 174     -61.519 -16.908 -52.674  1.00 40.33      A    C
ATOM  10932  C    PHE E 174     -62.258 -17.150 -51.377  1.00 40.14      A    C
ATOM  10933  O    PHE E 174     -63.015 -16.277 -50.921  1.00 41.33      A    O
ATOM  10934  CB   PHE E 174     -60.063 -16.540 -52.406  1.00 40.61      A    C
ATOM  10935  CG   PHE E 174     -59.151 -16.822 -53.557  1.00 40.46      A    C
ATOM  10936  CD1  PHE E 174     -58.692 -18.114 -53.789  1.00 40.59      A    C
ATOM  10937  CD2  PHE E 174     -58.752 -15.801 -54.409  1.00 40.01      A    C
ATOM  10938  CE1  PHE E 174     -57.851 -18.387 -54.847  1.00 40.09      A    C
ATOM  10939  CE2  PHE E 174     -57.909 -16.059 -55.465  1.00 39.53      A    C
ATOM  10940  CZ   PHE E 174     -57.455 -17.356 -55.685  1.00 39.66      A    C
ATOM  10941  N    PRO E 175     -62.019 -18.339 -50.772  1.00 37.89      A    N
ATOM  10942  CA   PRO E 175     -62.690 -18.760 -49.561  1.00 36.72      A    C
ATOM  10943  C    PRO E 175     -62.798 -17.553 -48.648  1.00 36.62      A    C
ATOM  10944  O    PRO E 175     -61.759 -16.963 -48.275  1.00 36.24      A    O
ATOM  10945  CB   PRO E 175     -61.733 -19.809 -48.968  1.00 36.49      A    C
ATOM  10946  CG   PRO E 175     -60.408 -19.593 -49.680  1.00 36.58      A    C
ATOM  10947  CD   PRO E 175     -60.871 -19.231 -51.059  1.00 37.59      A    C
ATOM  10948  N    PRO E 176     -64.055 -17.172 -48.317  1.00 37.17      A    N
ATOM  10949  CA   PRO E 176     -64.435 -15.994 -47.515  1.00 38.13      A    C
ATOM  10950  C    PRO E 176     -63.422 -15.745 -46.411  1.00 39.86      A    C
ATOM  10951  O    PRO E 176     -63.033 -14.602 -46.141  1.00 40.01      A    O
ATOM  10952  CB   PRO E 176     -65.789 -16.407 -46.889  1.00 37.66      A    C
ATOM  10953  CG   PRO E 176     -66.050 -17.867 -47.343  1.00 37.08      A    C
ATOM  10954  CD   PRO E 176     -65.225 -18.039 -48.587  1.00 36.94      A    C
ATOM  10955  N    GLY E 177     -62.985 -16.838 -45.800  1.00 41.70      A    N
ATOM  10956  CA   GLY E 177     -62.081 -16.757 -44.700  1.00 44.02      A    C
ATOM  10957  C    GLY E 177     -60.612 -16.679 -45.048  1.00 45.66      A    C
ATOM  10958  O    GLY E 177     -59.888 -17.626 -44.651  1.00 46.31      A    O
ATOM  10959  N    SER E 178     -60.156 -15.626 -45.794  1.00 47.09      A    N
ATOM  10960  CA   SER E 178     -58.855 -15.011 -45.448  1.00 46.88      A    C
ATOM  10961  C    SER E 178     -57.470 -14.663 -45.825  1.00 46.87      A    C
ATOM  10962  O    SER E 178     -56.876 -14.375 -44.803  1.00 47.48      A    O
ATOM  10963  CB   SER E 178     -58.181 -16.426 -45.296  1.00 45.25      A    C
ATOM  10964  OG   SER E 178     -58.644 -17.385 -46.326  1.00 44.58      A    O
ATOM  10965  N    THR E 179     -56.963 -14.170 -46.938  1.00 45.45      A    N
ATOM  10966  CA   THR E 179     -56.559 -12.797 -46.981  1.00 42.94      A    C
ATOM  10967  C    THR E 179     -56.999 -12.200 -48.274  1.00 43.45      A    C
ATOM  10968  O    THR E 179     -57.109 -12.911 -49.265  1.00 44.41      A    O
ATOM  10969  CB   THR E 179     -54.963 -12.673 -46.767  1.00 37.59      A    C
ATOM  10970  CG2  THR E 179     -54.310 -13.866 -46.018  1.00 39.53      A    C
ATOM  10971  OG1  THR E 179     -54.291 -12.453 -48.009  1.00 34.54      A    O
ATOM  10972  N    PRO E 180     -57.242 -10.881 -48.275  1.00 42.24      A    N
ATOM  10973  CA   PRO E 180     -57.873 -10.238 -49.419  1.00 41.25      A    C
ATOM  10974  C    PRO E 180     -57.048 -10.473 -50.683  1.00 42.04      A    C
ATOM  10975  O    PRO E 180     -55.813 -10.473 -50.628  1.00 42.93      A    O
ATOM  10976  CB   PRO E 180     -57.860  -8.754 -49.036  1.00 36.44      A    C
ATOM  10977  CG   PRO E 180     -56.685  -8.599 -48.120  1.00 34.96      A    C
ATOM  10978  CD   PRO E 180     -56.571  -9.905 -47.387  1.00 41.09      A    C
ATOM  10979  N    PHE E 181     -57.720 -10.700 -51.803  1.00 41.79      A    N
ATOM  10980  CA   PHE E 181     -57.017 -10.958 -53.048  1.00 40.92      A    C
ATOM  10981  C    PHE E 181     -57.331  -9.907 -54.084  1.00 40.22      A    C
ATOM  10982  O    PHE E 181     -58.468  -9.813 -54.547  1.00 40.02      A    O
ATOM  10983  CB   PHE E 181     -57.363 -12.342 -53.595  1.00 41.01      A    C
ATOM  10984  CG   PHE E 181     -56.844 -12.592 -54.988  1.00 40.75      A    C
ATOM  10985  CD1  PHE E 181     -55.484 -12.781 -55.223  1.00 40.88      A    C
```

FIGURE 1 (cont'd)

```
ATOM  10986  CD2  PHE E 181     -57.715 -12.634 -56.064  1.00 40.49     A    C
ATOM  10987  CE1  PHE E 181     -55.008 -13.003 -56.516  1.00 40.28     A    C
ATOM  10988  CE2  PHE E 181     -57.242 -12.860 -57.356  1.00 39.98     A    C
ATOM  10989  CZ   PHE E 181     -55.890 -13.048 -57.579  1.00 39.74     A    C
ATOM  10990  N    VAL E 182     -56.307  -9.145 -54.464  1.00 39.44     A    N
ATOM  10991  CA   VAL E 182     -56.473  -8.029 -55.400  1.00 38.70     A    C
ATOM  10992  C    VAL E 182     -56.031  -8.320 -56.836  1.00 37.93     A    C
ATOM  10993  O    VAL E 182     -56.387  -7.576 -57.751  1.00 37.79     A    O
ATOM  10994  CB   VAL E 182     -55.815  -6.710 -54.900  1.00 38.75     A    C
ATOM  10995  CG1  VAL E 182     -56.667  -6.073 -53.832  1.00 39.11     A    C
ATOM  10996  CG2  VAL E 182     -54.403  -6.947 -54.399  1.00 39.11     A    C
ATOM  10997  N    GLY E 183     -55.270  -9.390 -57.038  1.00 37.22     A    N
ATOM  10998  CA   GLY E 183     -54.810  -9.756 -58.381  1.00 36.26     A    C
ATOM  10999  C    GLY E 183     -54.245  -8.596 -59.197  1.00 35.59     A    C
ATOM  11000  O    GLY E 183     -54.885  -8.116 -60.133  1.00 35.40     A    O
ATOM  11001  N    ALA E 184     -53.045  -8.146 -58.836  1.00 35.07     A    N
ATOM  11002  CA   ALA E 184     -52.402  -7.030 -59.512  1.00 34.46     A    C
ATOM  11003  C    ALA E 184     -52.103  -7.370 -60.963  1.00 33.91     A    C
ATOM  11004  O    ALA E 184     -52.436  -6.596 -61.853  1.00 33.74     A    O
ATOM  11005  CB   ALA E 184     -51.144  -6.625 -58.782  1.00 34.79     A    C
ATOM  11006  N    THR E 185     -51.501  -8.537 -61.196  1.00 33.37     A    N
ATOM  11007  CA   THR E 185     -51.204  -9.008 -62.552  1.00 32.81     A    C
ATOM  11008  C    THR E 185     -52.454  -9.553 -63.220  1.00 32.57     A    C
ATOM  11009  O    THR E 185     -52.482  -9.758 -64.434  1.00 32.56     A    O
ATOM  11010  CB   THR E 185     -50.168 -10.151 -62.563  1.00 32.73     A    C
ATOM  11011  CG2  THR E 185     -48.973  -9.827 -61.680  1.00 32.99     A    C
ATOM  11012  OG1  THR E 185     -50.787 -11.359 -62.110  1.00 32.36     A    O
ATOM  11013  N    ASP E 186     -53.492  -9.773 -62.423  1.00 32.33     A    N
ATOM  11014  CA   ASP E 186     -54.613 -10.593 -62.845  1.00 32.09     A    C
ATOM  11015  C    ASP E 186     -55.975  -9.963 -62.505  1.00 32.17     A    C
ATOM  11016  O    ASP E 186     -56.659 -10.459 -61.608  1.00 32.51     A    O
ATOM  11017  CB   ASP E 186     -54.464 -11.965 -62.174  1.00 31.98     A    C
ATOM  11018  CG   ASP E 186     -55.432 -12.999 -62.703  1.00 31.46     A    C
ATOM  11019  OD1  ASP E 186     -55.378 -14.144 -62.218  1.00 31.33     A    O
ATOM  11020  OD2  ASP E 186     -56.245 -12.687 -63.588  1.00 30.64     A    O
ATOM  11021  N    SER E 187     -56.400  -8.902 -63.205  1.00 31.92     A    N
ATOM  11022  CA   SER E 187     -55.679  -8.303 -64.322  1.00 31.66     A    C
ATOM  11023  C    SER E 187     -55.655  -6.781 -64.201  1.00 31.63     A    C
ATOM  11024  O    SER E 187     -55.867  -6.070 -65.185  1.00 31.54     A    O
ATOM  11025  CB   SER E 187     -56.316  -8.723 -65.650  1.00 31.55     A    C
ATOM  11026  OG   SER E 187     -56.004 -10.065 -65.960  1.00 31.68     A    O
ATOM  11027  N    ALA E 188     -55.382  -6.287 -62.998  1.00 31.73     A    N
ATOM  11028  CA   ALA E 188     -55.370  -4.854 -62.745  1.00 31.82     A    C
ATOM  11029  C    ALA E 188     -54.417  -4.096 -63.669  1.00 31.80     A    C
ATOM  11030  O    ALA E 188     -54.824  -3.154 -64.340  1.00 31.84     A    O
ATOM  11031  CB   ALA E 188     -55.047  -4.583 -61.299  1.00 32.00     A    C
ATOM  11032  N    VAL E 189     -53.159  -4.521 -63.712  1.00 31.73     A    N
ATOM  11033  CA   VAL E 189     -52.159  -3.911 -64.592  1.00 31.63     A    C
ATOM  11034  C    VAL E 189     -52.609  -3.895 -66.067  1.00 31.64     A    C
ATOM  11035  O    VAL E 189     -52.611  -2.827 -66.681  1.00 31.73     A    O
ATOM  11036  CB   VAL E 189     -50.761  -4.564 -64.430  1.00 31.56     A    C
ATOM  11037  CG1  VAL E 189     -49.788  -4.055 -65.466  1.00 31.35     A    C
ATOM  11038  CG2  VAL E 189     -50.214  -4.305 -63.054  1.00 31.77     A    C
ATOM  11039  N    PRO E 190     -53.003  -5.066 -66.640  1.00 31.54     A    N
ATOM  11040  CA   PRO E 190     -53.565  -5.055 -67.996  1.00 31.53     A    C
ATOM  11041  C    PRO E 190     -54.617  -3.965 -68.203  1.00 31.77     A    C
ATOM  11042  O    PRO E 190     -54.541  -3.228 -69.177  1.00 31.79     A    O
ATOM  11043  CB   PRO E 190     -54.193  -6.440 -68.119  1.00 31.31     A    C
ATOM  11044  CG   PRO E 190     -53.324  -7.290 -67.322  1.00 31.31     A    C
ATOM  11045  CD   PRO E 190     -52.804  -6.452 -66.174  1.00 31.47     A    C
ATOM  11046  N    CYS E 191     -55.571  -3.848 -67.284  1.00 32.15     A    N
ATOM  11047  CA   CYS E 191     -56.601  -2.823 -67.388  1.00 32.67     A    C
ATOM  11048  C    CYS E 191     -56.020  -1.423 -67.269  1.00 32.95     A    C
ATOM  11049  O    CYS E 191     -56.395  -0.530 -68.020  1.00 33.15     A    O
ATOM  11050  CB   CYS E 191     -57.713  -3.059 -66.372  1.00 32.71     A    C
```

FIGURE 1 (cont'd)

```
ATOM  11051  SG   CYS E 191     -58.629  -4.560 -66.703  1.00 33.27      A    S
ATOM  11052  N    ALA E 192     -55.079  -1.245 -66.352  1.00 33.19      A    N
ATOM  11053  CA   ALA E 192     -54.453   0.053 -66.136  1.00 33.42      A    C
ATOM  11054  C    ALA E 192     -53.775   0.561 -67.400  1.00 33.41      A    C
ATOM  11055  O    ALA E 192     -53.860   1.746 -67.716  1.00 33.68      A    O
ATOM  11056  CB   ALA E 192     -53.462  -0.019 -64.994  1.00 33.57      A    C
ATOM  11057  N    LEU E 193     -53.114  -0.341 -68.122  1.00 33.04      A    N
ATOM  11058  CA   LEU E 193     -52.411   0.017 -69.353  1.00 32.63      A    C
ATOM  11059  C    LEU E 193     -53.409   0.501 -70.399  1.00 33.20      A    C
ATOM  11060  O    LEU E 193     -53.181   1.533 -71.034  1.00 33.59      A    O
ATOM  11061  CB   LEU E 193     -51.590  -1.159 -69.894  1.00 31.32      A    C
ATOM  11062  CG   LEU E 193     -50.356  -1.612 -69.113  1.00 29.73      A    C
ATOM  11063  CD1  LEU E 193     -49.848  -2.941 -69.640  1.00 28.76      A    C
ATOM  11064  N    LEU E 194     -54.520  -0.228 -70.551  1.00 33.40      A    N
ATOM  11065  CA   LEU E 194     -55.553   0.130 -71.519  1.00 33.54      A    C
ATOM  11066  C    LEU E 194     -55.998   1.568 -71.294  1.00 34.45      A    C
ATOM  11067  O    LEU E 194     -56.213   2.314 -72.252  1.00 34.76      A    O
ATOM  11068  CB   LEU E 194     -56.731  -0.842 -71.457  1.00 32.44      A    C
ATOM  11069  CG   LEU E 194     -56.449  -2.223 -72.037  1.00 31.25      A    C
ATOM  11070  CD1  LEU E 194     -57.715  -2.811 -72.602  1.00 30.87      A    C
ATOM  11071  N    LEU E 195     -56.092   1.957 -70.026  1.00 35.24      A    N
ATOM  11072  CA   LEU E 195     -56.459   3.320 -69.660  1.00 36.08      A    C
ATOM  11073  C    LEU E 195     -55.363   4.318 -70.011  1.00 36.79      A    C
ATOM  11074  O    LEU E 195     -55.622   5.340 -70.645  1.00 37.09      A    O
ATOM  11075  CB   LEU E 195     -56.785   3.414 -68.173  1.00 36.01      A    C
ATOM  11076  CG   LEU E 195     -58.045   2.715 -67.678  1.00 35.80      A    C
ATOM  11077  CD1  LEU E 195     -58.111   2.812 -66.173  1.00 36.05      A    C
ATOM  11078  CD2  LEU E 195     -59.290   3.301 -68.304  1.00 35.81      A    C
ATOM  11079  N    GLU E 196     -54.141   4.006 -69.595  1.00 37.39      A    N
ATOM  11080  CA   GLU E 196     -52.988   4.871 -69.815  1.00 38.01      A    C
ATOM  11081  C    GLU E 196     -52.734   5.105 -71.297  1.00 38.11      A    C
ATOM  11082  O    GLU E 196     -52.467   6.233 -71.716  1.00 38.29      A    O
ATOM  11083  CB   GLU E 196     -51.749   4.270 -69.142  1.00 38.19      A    C
ATOM  11084  CG   GLU E 196     -50.404   4.865 -69.574  1.00 39.31      A    C
ATOM  11085  CD   GLU E 196     -50.189   6.280 -69.097  1.00 40.77      A    C
ATOM  11086  OE1  GLU E 196     -51.018   6.772 -68.310  1.00 41.37      A    O
ATOM  11087  OE2  GLU E 196     -49.186   6.901 -69.511  1.00 41.48      A    O
ATOM  11088  N    LEU E 197     -52.812   4.027 -72.075  1.00 38.12      A    N
ATOM  11089  CA   LEU E 197     -52.671   4.095 -73.520  1.00 38.36      A    C
ATOM  11090  C    LEU E 197     -53.698   5.051 -74.111  1.00 38.85      A    C
ATOM  11091  O    LEU E 197     -53.354   5.917 -74.919  1.00 39.13      A    O
ATOM  11092  CB   LEU E 197     -52.830   2.706 -74.142  1.00 37.96      A    C
ATOM  11093  CG   LEU E 197     -51.580   1.957 -74.583  1.00 37.71      A    C
ATOM  11094  CD1  LEU E 197     -50.928   1.259 -73.429  1.00 37.56      A    C
ATOM  11095  CD2  LEU E 197     -51.980   0.958 -75.633  1.00 37.66      A    C
ATOM  11096  N    ALA E 198     -54.951   4.894 -73.682  1.00 39.30      A    N
ATOM  11097  CA   ALA E 198     -56.060   5.677 -74.204  1.00 40.01      A    C
ATOM  11098  C    ALA E 198     -55.898   7.159 -73.899  1.00 40.77      A    C
ATOM  11099  O    ALA E 198     -56.393   8.019 -74.636  1.00 41.08      A    O
ATOM  11100  CB   ALA E 198     -57.353   5.169 -73.643  1.00 39.84      A    C
ATOM  11101  N    GLN E 199     -55.191   7.445 -72.812  1.00 41.37      A    N
ATOM  11102  CA   GLN E 199     -54.969   8.813 -72.358  1.00 42.03      A    C
ATOM  11103  C    GLN E 199     -53.720   9.408 -73.006  1.00 42.95      A    C
ATOM  11104  O    GLN E 199     -53.734  10.554 -73.451  1.00 43.53      A    O
ATOM  11105  CB   GLN E 199     -54.820   8.832 -70.836  1.00 40.96      A    C
ATOM  11106  CG   GLN E 199     -55.713   9.804 -70.078  1.00 40.39      A    C
ATOM  11107  CD   GLN E 199     -55.612  11.221 -70.559  1.00 40.12      A    C
ATOM  11108  OE1  GLN E 199     -54.614  11.891 -70.326  1.00 40.43      A    O
ATOM  11109  N    ALA E 200     -52.644   8.624 -73.050  1.00 43.63      A    N
ATOM  11110  CA   ALA E 200     -51.375   9.077 -73.619  1.00 44.36      A    C
ATOM  11111  C    ALA E 200     -51.489   9.379 -75.118  1.00 44.90      A    C
ATOM  11112  O    ALA E 200     -50.934  10.366 -75.604  1.00 45.33      A    O
ATOM  11113  CB   ALA E 200     -50.273   8.056 -73.346  1.00 44.12      A    C
ATOM  11114  N    LEU E 201     -52.225   8.533 -75.834  1.00 45.24      A    N
ATOM  11115  CA   LEU E 201     -52.442   8.707 -77.270  1.00 45.79      A    C
```

FIGURE 1 (cont'd)

```
ATOM  11116  C    LEU E 201     -53.736   9.461 -77.575  1.00 46.52      A C
ATOM  11117  O    LEU E 201     -54.158   9.538 -78.733  1.00 46.75      A O
ATOM  11118  CB   LEU E 201     -52.463   7.344 -77.970  1.00 45.33      A C
ATOM  11119  CG   LEU E 201     -51.172   6.536 -77.901  1.00 45.09      A C
ATOM  11120  CD1  LEU E 201     -51.407   5.072 -78.247  1.00 44.75      A C
ATOM  11121  CD2  LEU E 201     -50.085   7.166 -78.771  1.00 45.37      A C
ATOM  11122  N    ASP E 202     -54.354  10.016 -76.534  1.00 47.26      A N
ATOM  11123  CA   ASP E 202     -55.669  10.643 -76.638  1.00 48.09      A C
ATOM  11124  C    ASP E 202     -55.769  11.666 -77.779  1.00 48.69      A C
ATOM  11125  O    ASP E 202     -56.720  11.636 -78.563  1.00 48.90      A O
ATOM  11126  CB   ASP E 202     -56.050  11.266 -75.291  1.00 48.21      A C
ATOM  11127  CG   ASP E 202     -57.370  12.002 -75.328  1.00 48.63      A C
ATOM  11128  OD1  ASP E 202     -58.404  11.384 -75.656  1.00 48.46      A O
ATOM  11129  OD2  ASP E 202     -57.362  13.205 -75.005  1.00 49.38      A O
ATOM  11130  N    LEU E 203     -54.776  12.543 -77.888  1.00 49.08      A N
ATOM  11131  CA   LEU E 203     -54.828  13.625 -78.866  1.00 49.28      A C
ATOM  11132  C    LEU E 203     -54.644  13.151 -80.293  1.00 49.55      A C
ATOM  11133  O    LEU E 203     -55.407  13.540 -81.171  1.00 49.98      A O
ATOM  11134  CB   LEU E 203     -53.828  14.729 -78.526  1.00 48.35      A C
ATOM  11135  CG   LEU E 203     -54.338  15.732 -77.487  1.00 48.10      A C
ATOM  11136  CD1  LEU E 203     -53.780  15.432 -76.093  1.00 47.98      A C
ATOM  11137  N    GLU E 204     -53.639  12.314 -80.526  1.00 49.36      A N
ATOM  11138  CA   GLU E 204     -53.440  11.712 -81.845  1.00 48.97      A C
ATOM  11139  C    GLU E 204     -54.598  10.786 -82.228  1.00 49.43      A C
ATOM  11140  O    GLU E 204     -54.925  10.663 -83.412  1.00 49.75      A O
ATOM  11141  CB   GLU E 204     -52.094  10.993 -81.946  1.00 47.46      A C
ATOM  11142  CG   GLU E 204     -51.564  10.439 -80.633  1.00 45.82      A C
ATOM  11143  CD   GLU E 204     -50.972  11.514 -79.747  1.00 45.08      A C
ATOM  11144  OE1  GLU E 204     -49.848  11.962 -80.048  1.00 45.24      A O
ATOM  11145  N    LEU E 205     -55.217  10.149 -81.228  1.00 49.62      A N
ATOM  11146  CA   LEU E 205     -56.424   9.335 -81.436  1.00 49.76      A C
ATOM  11147  C    LEU E 205     -57.621  10.203 -81.772  1.00 50.48      A C
ATOM  11148  O    LEU E 205     -58.511   9.789 -82.522  1.00 50.54      A O
ATOM  11149  CB   LEU E 205     -56.750   8.505 -80.197  1.00 49.21      A C
ATOM  11150  CG   LEU E 205     -56.232   7.076 -80.084  1.00 48.21      A C
ATOM  11151  CD1  LEU E 205     -56.359   6.625 -78.662  1.00 47.82      A C
ATOM  11152  CD2  LEU E 205     -56.999   6.145 -80.993  1.00 47.59      A C
ATOM  11153  N    SER E 206     -57.631  11.405 -81.200  1.00 51.35      A N
ATOM  11154  CA   SER E 206     -58.719  12.352 -81.399  1.00 52.25      A C
ATOM  11155  C    SER E 206     -58.749  12.883 -82.826  1.00 52.72      A C
ATOM  11156  O    SER E 206     -59.762  12.742 -83.517  1.00 52.76      A O
ATOM  11157  CB   SER E 206     -58.631  13.504 -80.399  1.00 52.47      A C
ATOM  11158  OG   SER E 206     -59.882  14.156 -80.283  1.00 53.13      A O
ATOM  11159  N    ARG E 207     -57.636  13.468 -83.271  1.00 53.24      A N
ATOM  11160  CA   ARG E 207     -57.571  14.048 -84.611  1.00 53.75      A C
ATOM  11161  C    ARG E 207     -57.977  13.027 -85.670  1.00 53.74      A C
ATOM  11162  O    ARG E 207     -58.897  13.279 -86.448  1.00 54.12      A O
ATOM  11163  CB   ARG E 207     -56.218  14.729 -84.905  1.00 54.01      A C
ATOM  11164  CG   ARG E 207     -54.984  13.887 -84.680  1.00 53.53      A C
ATOM  11165  N    ALA E 208     -57.334  11.861 -85.658  1.00 53.28      A N
ATOM  11166  CA   ALA E 208     -57.714  10.769 -86.545  1.00 52.88      A C
ATOM  11167  C    ALA E 208     -59.087  10.301 -86.135  1.00 52.63      A C
ATOM  11168  O    ALA E 208     -59.217   9.339 -85.398  1.00 52.42      A O
ATOM  11169  CB   ALA E 208     -56.710   9.633 -86.473  1.00 52.55      A C
ATOM  11170  N    LYS E 209     -60.100  11.030 -86.591  1.00 52.69      A N
ATOM  11171  CA   LYS E 209     -61.503  10.774 -86.272  1.00 52.25      A C
ATOM  11172  C    LYS E 209     -62.382  11.881 -86.867  1.00 51.42      A C
ATOM  11173  O    LYS E 209     -63.097  12.586 -86.184  1.00 52.64      A O
ATOM  11174  CB   LYS E 209     -61.711  10.630 -84.766  1.00 52.38      A C
ATOM  11175  CG   LYS E 209     -63.050  10.045 -84.377  1.00 52.70      A C
ATOM  11176  CD   LYS E 209     -63.442  10.541 -83.002  1.00 53.56      A C
ATOM  11177  CE   LYS E 209     -64.782   9.984 -82.561  1.00 53.76      A C
ATOM  11178  NZ   LYS E 209     -65.226  10.540 -81.251  1.00 53.89      A N
ATOM  11179  N    LYS E 210     -62.450  11.873 -88.191  1.00 46.35      A N
ATOM  11180  CA   LYS E 210     -62.777  13.047 -89.005  1.00 41.45      A C
```

FIGURE 1 (cont'd)

```
ATOM  11181  C    LYS E 210     -61.617  14.013 -88.804  1.00 39.83      A   C
ATOM  11182  O    LYS E 210     -61.673  14.862 -87.914  1.00 39.52      A   O
ATOM  11183  CB   LYS E 210     -64.139  13.682 -88.677  1.00 40.20      A   C
ATOM  11184  CG   LYS E 210     -65.358  12.788 -88.919  1.00 36.21      A   C
ATOM  11185  CD   LYS E 210     -66.593  13.623 -89.295  1.00 29.96      A   C
ATOM  11186  CE   LYS E 210     -67.807  12.720 -89.533  1.00 26.68      A   C
ATOM  11187  NZ   LYS E 210     -68.926  13.441 -90.210  1.00 25.01      A   N
ATOM  11188  N    GLN E 211     -60.530  13.857 -89.572  1.00 37.92      A   N
ATOM  11189  CA   GLN E 211     -60.286  12.800 -90.595  1.00 35.97      A   C
ATOM  11190  C    GLN E 211     -60.846  11.395 -90.296  1.00 36.09      A   C
ATOM  11191  O    GLN E 211     -60.330  10.702 -89.418  1.00 36.40      A   O
ATOM  11192  CB   GLN E 211     -58.780  12.707 -90.836  1.00 34.99      A   C
ATOM  11193  CG   GLN E 211     -57.958  13.036 -89.579  1.00 30.90      A   C
ATOM  11194  CD   GLN E 211     -56.464  12.770 -89.732  1.00 26.59      A   C
ATOM  11195  NE2  GLN E 211     -55.656  13.800 -89.476  1.00 25.40      A   N
ATOM  11196  OE1  GLN E 211     -56.037  11.651 -90.058  1.00 26.01      A   O
ATOM  11197  N    ALA E 212     -61.881  10.974 -91.032  1.00 35.65      A   N
ATOM  11198  CA   ALA E 212     -62.693   9.806 -90.656  1.00 35.10      A   C
ATOM  11199  C    ALA E 212     -61.977   8.497 -90.868  1.00 34.51      A   C
ATOM  11200  O    ALA E 212     -62.378   7.690 -91.713  1.00 34.42      A   O
ATOM  11201  CB   ALA E 212     -64.002   9.805 -91.390  1.00 35.36      A   C
ATOM  11202  N    ALA E 213     -60.934   8.303 -90.058  1.00 33.62      A   N
ATOM  11203  CA   ALA E 213     -60.015   7.156 -90.111  1.00 32.42      A   C
ATOM  11204  C    ALA E 213     -60.746   5.808 -90.131  1.00 31.42      A   C
ATOM  11205  O    ALA E 213     -61.497   5.492 -89.213  1.00 31.20      A   O
ATOM  11206  CB   ALA E 213     -59.011   7.227 -88.951  1.00 32.43      A   C
ATOM  11207  N    PRO E 214     -60.509   5.003 -91.176  1.00 30.75      A   N
ATOM  11208  CA   PRO E 214     -61.428   3.935 -91.508  1.00 31.39      A   C
ATOM  11209  C    PRO E 214     -61.206   2.708 -90.634  1.00 33.12      A   C
ATOM  11210  O    PRO E 214     -61.727   1.629 -90.942  1.00 33.58      A   O
ATOM  11211  CB   PRO E 214     -61.083   3.631 -92.967  1.00 30.83      A   C
ATOM  11212  CG   PRO E 214     -59.668   4.197 -93.178  1.00 30.42      A   C
ATOM  11213  CD   PRO E 214     -59.239   4.852 -91.901  1.00 30.40      A   C
ATOM  11214  N    VAL E 215     -60.435   2.885 -89.559  1.00 36.04      A   N
ATOM  11215  CA   VAL E 215     -60.193   1.834 -88.574  1.00 36.10      A   C
ATOM  11216  C    VAL E 215     -60.033   2.439 -87.182  1.00 36.39      A   C
ATOM  11217  O    VAL E 215     -59.076   3.173 -86.932  1.00 36.68      A   O
ATOM  11218  CB   VAL E 215     -58.957   1.017 -88.929  1.00 35.40      A   C
ATOM  11219  CG1  VAL E 215     -59.022  -0.307 -88.243  1.00 34.55      A   C
ATOM  11220  N    THR E 216     -60.975   2.131 -86.288  1.00 36.10      A   N
ATOM  11221  CA   THR E 216     -61.033   2.761 -84.965  1.00 35.57      A   C
ATOM  11222  C    THR E 216     -60.383   1.925 -83.865  1.00 35.10      A   C
ATOM  11223  O    THR E 216     -59.683   0.952 -84.145  1.00 35.06      A   O
ATOM  11224  CB   THR E 216     -62.470   3.115 -84.559  1.00 35.56      A   C
ATOM  11225  OG1  THR E 216     -62.479   4.423 -83.985  1.00 35.42      A   O
ATOM  11226  N    LEU E 217     -60.604   2.323 -82.615  1.00 34.49      A   N
ATOM  11227  CA   LEU E 217     -60.047   1.624 -81.465  1.00 33.69      A   C
ATOM  11228  C    LEU E 217     -61.147   1.316 -80.461  1.00 33.31      A   C
ATOM  11229  O    LEU E 217     -62.002   2.156 -80.170  1.00 33.53      A   O
ATOM  11230  CB   LEU E 217     -58.921   2.442 -80.810  1.00 33.60      A   C
ATOM  11231  CG   LEU E 217     -58.327   1.963 -79.473  1.00 33.08      A   C
ATOM  11232  CD1  LEU E 217     -57.492   0.708 -79.644  1.00 32.85      A   C
ATOM  11233  CD2  LEU E 217     -57.498   3.049 -78.815  1.00 33.15      A   C
ATOM  11234  N    GLN E 218     -61.104   0.101 -79.929  1.00 32.56      A   N
ATOM  11235  CA   GLN E 218     -62.089  -0.361 -78.963  1.00 31.90      A   C
ATOM  11236  C    GLN E 218     -61.421  -0.942 -77.711  1.00 31.30      A   C
ATOM  11237  O    GLN E 218     -60.470  -1.717 -77.797  1.00 31.21      A   O
ATOM  11238  CB   GLN E 218     -63.001  -1.388 -79.624  1.00 31.92      A   C
ATOM  11239  CG   GLN E 218     -64.170  -1.846 -78.787  1.00 32.13      A   C
ATOM  11240  CD   GLN E 218     -64.894  -3.031 -79.406  1.00 32.80      A   C
ATOM  11241  NE2  GLN E 218     -64.207  -4.164 -79.532  1.00 32.86      A   N
ATOM  11242  OE1  GLN E 218     -66.055  -2.925 -79.778  1.00 33.65      A   O
ATOM  11243  N    LEU E 219     -61.920  -0.549 -76.546  1.00 30.74      A   N
ATOM  11244  CA   LEU E 219     -61.381  -1.026 -75.281  1.00 30.05      A   C
ATOM  11245  C    LEU E 219     -62.427  -1.815 -74.516  1.00 29.77      A   C
```

FIGURE 1 (cont'd)

```
ATOM  11246  O    LEU E 219     -63.484  -1.303 -74.164  1.00 29.89      A  O
ATOM  11247  CB   LEU E 219     -60.852   0.145 -74.444  1.00 29.91      A  C
ATOM  11248  CG   LEU E 219     -59.721   0.954 -75.077  1.00 29.61      A  C
ATOM  11249  CD1  LEU E 219     -59.366   2.117 -74.202  1.00 29.39      A  C
ATOM  11250  CD2  LEU E 219     -58.500   0.085 -75.330  1.00 29.20      A  C
ATOM  11251  N    LEU E 220     -62.127  -3.076 -74.265  1.00 29.24      A  N
ATOM  11252  CA   LEU E 220     -63.062  -3.931 -73.555  1.00 28.86      A  C
ATOM  11253  C    LEU E 220     -62.568  -4.283 -72.142  1.00 28.98      A  C
ATOM  11254  O    LEU E 220     -61.460  -4.806 -71.963  1.00 29.01      A  O
ATOM  11255  CB   LEU E 220     -63.355  -5.197 -74.367  1.00 28.13      A  C
ATOM  11256  CG   LEU E 220     -63.992  -4.972 -75.733  1.00 27.41      A  C
ATOM  11257  CD1  LEU E 220     -64.350  -6.298 -76.345  1.00 26.97      A  C
ATOM  11258  N    PHE E 221     -63.400  -3.979 -71.148  1.00 29.10      A  N
ATOM  11259  CA   PHE E 221     -63.138  -4.321 -69.756  1.00 29.06      A  C
ATOM  11260  C    PHE E 221     -64.200  -5.328 -69.356  1.00 29.09      A  C
ATOM  11261  O    PHE E 221     -65.331  -4.961 -69.060  1.00 29.20      A  O
ATOM  11262  CB   PHE E 221     -63.194  -3.069 -68.857  1.00 29.10      A  C
ATOM  11263  CG   PHE E 221     -62.216  -1.991 -69.252  1.00 29.14      A  C
ATOM  11264  CD1  PHE E 221     -60.968  -1.917 -68.656  1.00 29.19      A  C
ATOM  11265  CD2  PHE E 221     -62.539  -1.062 -70.232  1.00 29.23      A  C
ATOM  11266  CE1  PHE E 221     -60.059  -0.945 -69.025  1.00 29.20      A  C
ATOM  11267  CE2  PHE E 221     -61.631  -0.084 -70.604  1.00 29.47      A  C
ATOM  11268  CZ   PHE E 221     -60.389  -0.028 -69.996  1.00 29.33      A  C
ATOM  11269  N    LEU E 222     -63.837  -6.601 -69.370  1.00 29.14      A  N
ATOM  11270  CA   LEU E 222     -64.799  -7.677 -69.150  1.00 29.42      A  C
ATOM  11271  C    LEU E 222     -64.981  -8.034 -67.677  1.00 29.78      A  C
ATOM  11272  O    LEU E 222     -64.009  -8.089 -66.917  1.00 29.76      A  O
ATOM  11273  CB   LEU E 222     -64.395  -8.915 -69.946  1.00 29.23      A  C
ATOM  11274  CG   LEU E 222     -64.186  -8.626 -71.432  1.00 29.06      A  C
ATOM  11275  CD1  LEU E 222     -65.435  -8.936 -72.227  1.00 29.13      A  C
ATOM  11276  CD2  LEU E 222     -63.015  -9.418 -71.963  1.00 28.73      A  C
ATOM  11277  N    ASP E 223     -66.238  -8.262 -67.290  1.00 30.33      A  N
ATOM  11278  CA   ASP E 223     -66.582  -8.711 -65.944  1.00 30.90      A  C
ATOM  11279  C    ASP E 223     -66.553 -10.246 -65.879  1.00 30.93      A  C
ATOM  11280  O    ASP E 223     -66.543 -10.919 -66.916  1.00 30.82      A  O
ATOM  11281  CB   ASP E 223     -67.959  -8.170 -65.533  1.00 31.30      A  C
ATOM  11282  CG   ASP E 223     -68.184  -8.194 -64.017  1.00 32.39      A  C
ATOM  11283  OD1  ASP E 223     -67.219  -8.437 -63.245  1.00 33.33      A  O
ATOM  11284  OD2  ASP E 223     -69.341  -7.964 -63.595  1.00 33.10      A  O
ATOM  11285  N    GLY E 224     -66.506 -10.778 -64.655  1.00 31.07      A  N
ATOM  11286  CA   GLY E 224     -66.624 -12.208 -64.384  1.00 31.25      A  C
ATOM  11287  C    GLY E 224     -65.906 -13.097 -65.367  1.00 31.18      A  C
ATOM  11288  O    GLY E 224     -66.530 -13.839 -66.121  1.00 31.40      A  O
ATOM  11289  N    GLU E 225     -64.590 -13.009 -65.375  1.00 30.99      A  N
ATOM  11290  CA   GLU E 225     -63.807 -13.912 -66.189  1.00 30.95      A  C
ATOM  11291  C    GLU E 225     -63.369 -15.095 -65.340  1.00 31.01      A  C
ATOM  11292  O    GLU E 225     -63.455 -16.244 -65.770  1.00 30.93      A  O
ATOM  11293  CB   GLU E 225     -62.604 -13.184 -66.788  1.00 30.81      A  C
ATOM  11294  CG   GLU E 225     -61.703 -14.056 -67.663  1.00 31.09      A  C
ATOM  11295  CD   GLU E 225     -60.608 -14.744 -66.883  1.00 31.86      A  C
ATOM  11296  OE1  GLU E 225     -60.131 -14.160 -65.895  1.00 32.64      A  O
ATOM  11297  OE2  GLU E 225     -60.214 -15.865 -67.254  1.00 32.31      A  O
ATOM  11298  N    GLU E 226     -62.897 -14.790 -64.132  1.00 31.34      A  N
ATOM  11299  CA   GLU E 226     -62.467 -15.797 -63.164  1.00 31.79      A  C
ATOM  11300  C    GLU E 226     -63.665 -16.572 -62.630  1.00 32.43      A  C
ATOM  11301  O    GLU E 226     -64.717 -15.995 -62.329  1.00 32.59      A  O
ATOM  11302  CB   GLU E 226     -61.741 -15.135 -61.996  1.00 31.66      A  C
ATOM  11303  CG   GLU E 226     -60.541 -14.278 -62.382  1.00 30.94      A  C
ATOM  11304  CD   GLU E 226     -59.218 -15.032 -62.402  1.00 30.25      A  C
ATOM  11305  OE1  GLU E 226     -59.220 -16.267 -62.607  1.00 30.22      A  O
ATOM  11306  OE2  GLU E 226     -58.166 -14.372 -62.220  1.00 29.65      A  O
ATOM  11307  N    ALA E 227     -63.484 -17.882 -62.502  1.00 33.01      A  N
ATOM  11308  CA   ALA E 227     -64.538 -18.784 -62.055  1.00 33.75      A  C
ATOM  11309  C    ALA E 227     -64.997 -18.489 -60.628  1.00 34.41      A  C
ATOM  11310  O    ALA E 227     -64.337 -17.749 -59.889  1.00 34.47      A  O
```

FIGURE 1 (cont'd)

```
ATOM  11311  CB   ALA E 227     -64.056 -20.211 -62.158  1.00 33.76      A  C
ATOM  11312  N    LEU E 228     -66.125 -19.078 -60.239  1.00 35.22      A  N
ATOM  11313  CA   LEU E 228     -66.633 -18.896 -58.884  1.00 35.91      A  C
ATOM  11314  C    LEU E 228     -66.457 -20.114 -57.980  1.00 36.65      A  C
ATOM  11315  O    LEU E 228     -66.009 -19.981 -56.845  1.00 36.92      A  O
ATOM  11316  CB   LEU E 228     -68.078 -18.379 -58.887  1.00 35.87      A  C
ATOM  11317  CG   LEU E 228     -68.358 -16.883 -59.145  1.00 35.22      A  C
ATOM  11318  CD1  LEU E 228     -68.964 -16.647 -60.512  1.00 34.77      A  C
ATOM  11319  CD2  LEU E 228     -67.140 -15.978 -58.937  1.00 34.63      A  C
ATOM  11320  N    LYS E 229     -66.804 -21.298 -58.472  1.00 37.40      A  N
ATOM  11321  CA   LYS E 229     -66.533 -22.542 -57.728  1.00 38.20      A  C
ATOM  11322  C    LYS E 229     -65.222 -23.097 -58.270  1.00 38.17      A  C
ATOM  11323  O    LYS E 229     -64.176 -22.806 -57.712  1.00 38.13      A  O
ATOM  11324  CB   LYS E 229     -67.695 -23.564 -57.828  1.00 38.73      A  C
ATOM  11325  CG   LYS E 229     -67.654 -24.744 -56.835  1.00 39.48      A  C
ATOM  11326  CD   LYS E 229     -68.371 -24.418 -55.528  1.00 40.03      A  C
ATOM  11327  N    GLU E 230     -65.269 -23.875 -59.350  1.00 38.34      A  N
ATOM  11328  CA   GLU E 230     -64.046 -24.225 -60.066  1.00 38.53      A  C
ATOM  11329  C    GLU E 230     -64.164 -24.128 -61.581  1.00 38.26      A  C
ATOM  11330  O    GLU E 230     -65.205 -24.432 -62.165  1.00 38.29      A  O
ATOM  11331  CB   GLU E 230     -63.443 -25.576 -59.632  1.00 38.98      A  C
ATOM  11332  CG   GLU E 230     -61.890 -25.665 -59.891  1.00 39.94      A  C
ATOM  11333  CD   GLU E 230     -61.060 -24.465 -59.299  1.00 40.11      A  C
ATOM  11334  OE1  GLU E 230     -60.639 -23.526 -60.035  1.00 38.72      A  O
ATOM  11335  N    TRP E 231     -63.053 -23.709 -62.185  1.00 37.95      A  N
ATOM  11336  CA   TRP E 231     -62.944 -23.430 -63.604  1.00 37.66      A  C
ATOM  11337  C    TRP E 231     -63.549 -24.537 -64.435  1.00 38.02      A  C
ATOM  11338  O    TRP E 231     -63.294 -25.726 -64.198  1.00 38.34      A  O
ATOM  11339  CB   TRP E 231     -61.478 -23.215 -63.986  1.00 37.32      A  C
ATOM  11340  CG   TRP E 231     -61.308 -22.686 -65.370  1.00 36.74      A  C
ATOM  11341  CD1  TRP E 231     -61.233 -23.414 -66.525  1.00 36.73      A  C
ATOM  11342  CD2  TRP E 231     -61.200 -21.318 -65.752  1.00 36.14      A  C
ATOM  11343  CE2  TRP E 231     -61.066 -21.288 -67.159  1.00 35.90      A  C
ATOM  11344  CE3  TRP E 231     -61.205 -20.109 -65.045  1.00 35.81      A  C
ATOM  11345  NE1  TRP E 231     -61.090 -22.581 -67.605  1.00 36.37      A  N
ATOM  11346  CZ2  TRP E 231     -60.941 -20.100 -67.871  1.00 35.25      A  C
ATOM  11347  CZ3  TRP E 231     -61.082 -18.927 -65.752  1.00 35.09      A  C
ATOM  11348  CH2  TRP E 231     -60.951 -18.932 -67.153  1.00 34.81      A  C
ATOM  11349  N    GLY E 232     -64.362 -24.125 -65.402  1.00 38.16      A  N
ATOM  11350  CA   GLY E 232     -65.008 -25.025 -66.335  1.00 38.54      A  C
ATOM  11351  C    GLY E 232     -65.781 -24.279 -67.396  1.00 38.73      A  C
ATOM  11352  O    GLY E 232     -65.972 -23.062 -67.271  1.00 38.44      A  O
ATOM  11353  N    PRO E 233     -66.231 -24.992 -68.451  1.00 39.16      A  N
ATOM  11354  CA   PRO E 233     -67.021 -24.382 -69.522  1.00 39.31      A  C
ATOM  11355  C    PRO E 233     -68.229 -23.597 -69.016  1.00 39.50      A  C
ATOM  11356  O    PRO E 233     -68.539 -22.544 -69.561  1.00 39.21      A  O
ATOM  11357  CB   PRO E 233     -67.472 -25.589 -70.342  1.00 39.50      A  C
ATOM  11358  CG   PRO E 233     -66.365 -26.584 -70.149  1.00 39.62      A  C
ATOM  11359  CD   PRO E 233     -65.948 -26.418 -68.722  1.00 39.41      A  C
ATOM  11360  N    LYS E 234     -68.892 -24.100 -67.979  1.00 40.09      A  N
ATOM  11361  CA   LYS E 234     -70.076 -23.433 -67.425  1.00 40.68      A  C
ATOM  11362  C    LYS E 234     -69.766 -22.502 -66.240  1.00 40.45      A  C
ATOM  11363  O    LYS E 234     -70.650 -21.771 -65.777  1.00 40.58      A  O
ATOM  11364  CB   LYS E 234     -71.172 -24.454 -67.068  1.00 41.29      A  C
ATOM  11365  CG   LYS E 234     -72.049 -24.888 -68.256  1.00 42.34      A  C
ATOM  11366  CD   LYS E 234     -72.673 -26.283 -68.078  1.00 43.55      A  C
ATOM  11367  CE   LYS E 234     -74.059 -26.283 -67.393  1.00 43.78      A  C
ATOM  11368  N    ASP E 235     -68.520 -22.524 -65.763  1.00 40.05      A  N
ATOM  11369  CA   ASP E 235     -68.085 -21.605 -64.708  1.00 39.57      A  C
ATOM  11370  C    ASP E 235     -66.774 -20.900 -65.074  1.00 39.07      A  C
ATOM  11371  O    ASP E 235     -65.707 -21.274 -64.601  1.00 39.07      A  O
ATOM  11372  CB   ASP E 235     -67.975 -22.335 -63.359  1.00 39.85      A  C
ATOM  11373  CG   ASP E 235     -67.521 -21.414 -62.210  1.00 39.56      A  C
ATOM  11374  OD1  ASP E 235     -66.825 -21.914 -61.293  1.00 39.29      A  O
ATOM  11375  OD2  ASP E 235     -67.850 -20.204 -62.222  1.00 39.16      A  O
```

FIGURE 1 (cont'd)

```
ATOM  11376  N    SER E 236     -66.873 -19.890 -65.938  1.00 38.45      A  N
ATOM  11377  CA   SER E 236     -65.739 -19.060 -66.384  1.00 37.80      A  C
ATOM  11378  C    SER E 236     -66.143 -18.200 -67.576  1.00 37.51      A  C
ATOM  11379  O    SER E 236     -66.955 -18.623 -68.398  1.00 37.55      A  O
ATOM  11380  CB   SER E 236     -64.514 -19.905 -66.767  1.00 37.67      A  C
ATOM  11381  OG   SER E 236     -64.742 -20.658 -67.943  1.00 37.59      A  O
ATOM  11382  N    LEU E 237     -65.568 -16.999 -67.667  1.00 37.20      A  N
ATOM  11383  CA   LEU E 237     -65.740 -16.118 -68.826  1.00 37.06      A  C
ATOM  11384  C    LEU E 237     -67.202 -15.722 -69.029  1.00 37.23      A  C
ATOM  11385  O    LEU E 237     -67.741 -15.841 -70.121  1.00 37.38      A  O
ATOM  11386  CB   LEU E 237     -65.205 -16.802 -70.094  1.00 36.92      A  C
ATOM  11387  CG   LEU E 237     -63.906 -17.608 -70.075  1.00 36.56      A  C
ATOM  11388  CD1  LEU E 237     -63.868 -18.586 -71.232  1.00 36.66      A  C
ATOM  11389  CD2  LEU E 237     -62.722 -16.674 -70.120  1.00 36.08      A  C
ATOM  11390  N    TYR E 238     -67.852 -15.269 -67.970  1.00 37.36      A  N
ATOM  11391  CA   TYR E 238     -69.243 -14.846 -68.074  1.00 37.48      A  C
ATOM  11392  C    TYR E 238     -69.373 -13.570 -68.900  1.00 37.16      A  C
ATOM  11393  O    TYR E 238     -70.295 -13.449 -69.706  1.00 37.27      A  O
ATOM  11394  CB   TYR E 238     -69.867 -14.641 -66.690  1.00 37.80      A  C
ATOM  11395  CG   TYR E 238     -69.903 -15.889 -65.839  1.00 38.39      A  C
ATOM  11396  CD1  TYR E 238     -70.832 -16.902 -66.084  1.00 39.33      A  C
ATOM  11397  CD2  TYR E 238     -69.006 -16.000 -64.784  1.00 38.50      A  C
ATOM  11398  CE1  TYR E 238     -70.866 -18.061 -65.291  1.00 39.71      A  C
ATOM  11399  CE2  TYR E 238     -69.029 -17.213 -63.987  1.00 38.97      A  C
ATOM  11400  CZ   TYR E 238     -69.960 -18.207 -64.244  1.00 39.38      A  C
ATOM  11401  OH   TYR E 238     -69.983 -19.339 -63.460  1.00 39.59      A  O
ATOM  11402  N    GLY E 239     -68.450 -12.631 -68.699  1.00 36.72      A  N
ATOM  11403  CA   GLY E 239     -68.496 -11.351 -69.395  1.00 36.44      A  C
ATOM  11404  C    GLY E 239     -68.250 -11.490 -70.884  1.00 36.27      A  C
ATOM  11405  O    GLY E 239     -68.994 -10.932 -71.700  1.00 36.35      A  O
ATOM  11406  N    SER E 240     -67.209 -12.247 -71.231  1.00 36.00      A  N
ATOM  11407  CA   SER E 240     -66.796 -12.427 -72.621  1.00 35.72      A  C
ATOM  11408  C    SER E 240     -67.783 -13.269 -73.414  1.00 35.72      A  C
ATOM  11409  O    SER E 240     -68.153 -12.897 -74.521  1.00 35.82      A  O
ATOM  11410  CB   SER E 240     -65.388 -13.022 -72.701  1.00 35.59      A  C
ATOM  11411  OG   SER E 240     -65.160 -13.966 -71.667  1.00 35.90      A  O
ATOM  11412  N    ARG E 241     -68.213 -14.394 -72.846  1.00 35.74      A  N
ATOM  11413  CA   ARG E 241     -69.210 -15.254 -73.491  1.00 35.95      A  C
ATOM  11414  C    ARG E 241     -70.507 -14.504 -73.787  1.00 36.02      A  C
ATOM  11415  O    ARG E 241     -71.156 -14.763 -74.797  1.00 36.24      A  O
ATOM  11416  CB   ARG E 241     -69.496 -16.507 -72.658  1.00 36.04      A  C
ATOM  11417  CG   ARG E 241     -68.564 -17.669 -72.953  1.00 36.64      A  C
ATOM  11418  CD   ARG E 241     -69.107 -18.988 -72.423  1.00 37.97      A  C
ATOM  11419  NE   ARG E 241     -68.919 -19.115 -70.980  1.00 39.18      A  N
ATOM  11420  CZ   ARG E 241     -69.896 -19.033 -70.075  1.00 40.17      A  C
ATOM  11421  NH1  ARG E 241     -71.150 -18.835 -70.456  1.00 41.15      A  N
ATOM  11422  NH2  ARG E 241     -69.626 -19.152 -68.780  1.00 40.48      A  N
ATOM  11423  N    HIS E 242     -70.872 -13.570 -72.914  1.00 35.98      A  N
ATOM  11424  CA   HIS E 242     -72.081 -12.776 -73.104  1.00 36.07      A  C
ATOM  11425  C    HIS E 242     -71.880 -11.674 -74.137  1.00 35.70      A  C
ATOM  11426  O    HIS E 242     -72.692 -11.525 -75.049  1.00 35.93      A  O
ATOM  11427  CB   HIS E 242     -72.558 -12.179 -71.780  1.00 36.35      A  C
ATOM  11428  CG   HIS E 242     -73.819 -11.380 -71.899  1.00 37.15      A  C
ATOM  11429  CD2  HIS E 242     -75.121 -11.762 -71.914  1.00 37.92      A  C
ATOM  11430  ND1  HIS E 242     -73.817 -10.008 -72.038  1.00 37.29      A  N
ATOM  11431  CE1  HIS E 242     -75.063  -9.579 -72.120  1.00 37.97      A  C
ATOM  11432  NE2  HIS E 242     -75.874 -10.622 -72.049  1.00 38.40      A  N
ATOM  11433  N    LEU E 243     -70.807 -10.903 -73.990  1.00 35.10      A  N
ATOM  11434  CA   LEU E 243     -70.501  -9.852 -74.953  1.00 34.64      A  C
ATOM  11435  C    LEU E 243     -70.387 -10.414 -76.357  1.00 34.72      A  C
ATOM  11436  O    LEU E 243     -70.933  -9.849 -77.292  1.00 34.94      A  O
ATOM  11437  CB   LEU E 243     -69.226  -9.096 -74.587  1.00 34.18      A  C
ATOM  11438  CG   LEU E 243     -68.909  -7.881 -75.466  1.00 33.47      A  C
ATOM  11439  CD1  LEU E 243     -70.016  -6.844 -75.389  1.00 33.25      A  C
ATOM  11440  CD2  LEU E 243     -67.588  -7.261 -75.081  1.00 32.86      A  C
```

FIGURE 1 (cont'd)

```
ATOM  11441  N    ALA E 244     -69.693 -11.533 -76.497  1.00 34.73           A  N
ATOM  11442  CA   ALA E 244     -69.600 -12.211 -77.780  1.00 35.02           A  C
ATOM  11443  C    ALA E 244     -70.977 -12.523 -78.340  1.00 35.48           A  C
ATOM  11444  O    ALA E 244     -71.240 -12.240 -79.493  1.00 35.70           A  O
ATOM  11445  CB   ALA E 244     -68.777 -13.473 -77.665  1.00 34.79           A  C
ATOM  11446  N    GLN E 245     -71.855 -13.094 -77.522  1.00 36.03           A  N
ATOM  11447  CA   GLN E 245     -73.231 -13.390 -77.946  1.00 36.64           A  C
ATOM  11448  C    GLN E 245     -73.967 -12.116 -78.394  1.00 36.95           A  C
ATOM  11449  O    GLN E 245     -74.570 -12.082 -79.468  1.00 37.22           A  O
ATOM  11450  CB   GLN E 245     -74.014 -14.129 -76.838  1.00 36.69           A  C
ATOM  11451  N    LEU E 246     -73.883 -11.073 -77.576  1.00 37.05           A  N
ATOM  11452  CA   LEU E 246     -74.585  -9.824 -77.819  1.00 37.33           A  C
ATOM  11453  C    LEU E 246     -74.045  -9.059 -79.037  1.00 37.76           A  C
ATOM  11454  O    LEU E 246     -74.799  -8.338 -79.698  1.00 38.06           A  O
ATOM  11455  CB   LEU E 246     -74.536  -8.952 -76.560  1.00 37.06           A  C
ATOM  11456  CG   LEU E 246     -75.307  -7.631 -76.507  1.00 36.46           A  C
ATOM  11457  CD1  LEU E 246     -74.354  -6.457 -76.400  1.00 35.19           A  C
ATOM  11458  N    MET E 247     -72.752  -9.211 -79.330  1.00 38.03           A  N
ATOM  11459  CA   MET E 247     -72.145  -8.558 -80.497  1.00 38.45           A  C
ATOM  11460  C    MET E 247     -72.551  -9.246 -81.793  1.00 39.25           A  C
ATOM  11461  O    MET E 247     -72.650  -8.606 -82.839  1.00 39.47           A  O
ATOM  11462  CB   MET E 247     -70.618  -8.485 -80.385  1.00 37.94           A  C
ATOM  11463  CG   MET E 247     -70.132  -7.462 -79.392  1.00 37.32           A  C
ATOM  11464  SD   MET E 247     -68.365  -7.196 -79.484  1.00 36.49           A  S
ATOM  11465  CE   MET E 247     -68.280  -5.800 -80.597  1.00 36.92           A  C
ATOM  11466  N    GLU E 248     -72.792 -10.550 -81.713  1.00 40.15           A  N
ATOM  11467  CA   GLU E 248     -73.208 -11.340 -82.870  1.00 41.20           A  C
ATOM  11468  C    GLU E 248     -74.629 -10.990 -83.272  1.00 42.21           A  C
ATOM  11469  O    GLU E 248     -74.989 -11.084 -84.446  1.00 42.74           A  O
ATOM  11470  CB   GLU E 248     -73.129 -12.826 -82.550  1.00 41.04           A  C
ATOM  11471  CG   GLU E 248     -72.926 -13.724 -83.741  1.00 41.25           A  C
ATOM  11472  CD   GLU E 248     -72.955 -15.184 -83.349  1.00 41.97           A  C
ATOM  11473  OE1  GLU E 248     -73.721 -15.529 -82.425  1.00 42.07           A  O
ATOM  11474  OE2  GLU E 248     -72.215 -15.986 -83.956  1.00 42.16           A  O
ATOM  11475  N    SER E 249     -75.434 -10.587 -82.290  1.00 43.07           A  N
ATOM  11476  CA   SER E 249     -76.832 -10.225 -82.534  1.00 44.02           A  C
ATOM  11477  C    SER E 249     -77.008  -8.745 -82.903  1.00 44.48           A  C
ATOM  11478  O    SER E 249     -78.107  -8.309 -83.232  1.00 44.91           A  O
ATOM  11479  CB   SER E 249     -77.703 -10.584 -81.320  1.00 44.13           A  C
ATOM  11480  OG   SER E 249     -77.490  -9.685 -80.241  1.00 44.12           A  O
ATOM  11481  N    ILE E 250     -75.926  -7.980 -82.848  1.00 44.77           A  N
ATOM  11482  CA   ILE E 250     -75.992  -6.550 -83.092  1.00 45.30           A  C
ATOM  11483  C    ILE E 250     -75.441  -6.222 -84.489  1.00 46.13           A  C
ATOM  11484  O    ILE E 250     -74.225  -6.311 -84.707  1.00 45.91           A  O
ATOM  11485  CB   ILE E 250     -75.248  -5.785 -81.983  1.00 44.83           A  C
ATOM  11486  CG1  ILE E 250     -75.765  -4.358 -81.854  1.00 44.77           A  C
ATOM  11487  CD1  ILE E 250     -74.850  -3.334 -82.475  1.00 44.41           A  C
ATOM  11488  N    PRO E 251     -76.339  -5.863 -85.442  1.00 47.24           A  N
ATOM  11489  CA   PRO E 251     -75.964  -5.599 -86.834  1.00 47.90           A  C
ATOM  11490  C    PRO E 251     -75.117  -4.361 -86.971  1.00 48.32           A  C
ATOM  11491  O    PRO E 251     -75.211  -3.444 -86.156  1.00 48.35           A  O
ATOM  11492  CB   PRO E 251     -77.307  -5.376 -87.529  1.00 48.23           A  C
ATOM  11493  CG   PRO E 251     -78.293  -6.036 -86.661  1.00 48.26           A  C
ATOM  11494  CD   PRO E 251     -77.798  -5.780 -85.272  1.00 47.59           A  C
ATOM  11495  N    HIS E 252     -74.312  -4.348 -88.024  1.00 48.76           A  N
ATOM  11496  CA   HIS E 252     -73.299  -3.336 -88.271  1.00 49.12           A  C
ATOM  11497  C    HIS E 252     -72.803  -3.770 -89.636  1.00 49.72           A  C
ATOM  11498  O    HIS E 252     -73.142  -4.854 -90.044  1.00 49.98           A  O
ATOM  11499  CB   HIS E 252     -72.166  -3.545 -87.257  1.00 47.97           A  C
ATOM  11500  CG   HIS E 252     -71.075  -2.524 -87.334  1.00 47.79           A  C
ATOM  11501  CD2  HIS E 252     -69.825  -2.588 -87.855  1.00 47.60           A  C
ATOM  11502  ND1  HIS E 252     -71.212  -1.255 -86.813  1.00 48.06           A  N
ATOM  11503  CE1  HIS E 252     -70.097  -0.576 -87.017  1.00 48.04           A  C
ATOM  11504  NE2  HIS E 252     -69.241  -1.360 -87.651  1.00 47.83           A  N
ATOM  11505  N    SER E 253     -72.115  -3.005 -90.466  1.00 50.13           A  N
```

FIGURE 1 (cont'd)

```
ATOM  11506  CA   SER E 253     -72.390  -1.733 -90.983  1.00 50.14      A    C
ATOM  11507  C    SER E 253     -71.662  -1.523 -92.299  1.00 50.25      A    C
ATOM  11508  O    SER E 253     -71.739  -0.446 -92.789  1.00 50.68      A    O
ATOM  11509  CB   SER E 253     -71.901  -0.648 -90.047  1.00 49.30      A    C
ATOM  11510  OG   SER E 253     -71.232   0.410 -90.690  1.00 48.82      A    O
ATOM  11511  N    PRO E 254     -71.036  -2.484 -92.981  1.00 49.85      A    N
ATOM  11512  CA   PRO E 254     -70.661  -3.801 -93.441  1.00 49.46      A    C
ATOM  11513  C    PRO E 254     -69.862  -4.666 -92.531  1.00 49.08      A    C
ATOM  11514  O    PRO E 254     -68.702  -4.941 -92.821  1.00 49.24      A    O
ATOM  11515  CB   PRO E 254     -69.777  -3.501 -94.666  1.00 48.70      A    C
ATOM  11516  CG   PRO E 254     -69.630  -2.071 -94.752  1.00 48.83      A    C
ATOM  11517  CD   PRO E 254     -70.082  -1.486 -93.494  1.00 49.10      A    C
ATOM  11518  N    GLY E 255     -70.507  -5.081 -91.452  1.00 48.45      A    N
ATOM  11519  CA   GLY E 255     -70.231  -6.293 -90.737  1.00 47.55      A    C
ATOM  11520  C    GLY E 255     -70.481  -7.492 -91.618  1.00 47.10      A    C
ATOM  11521  O    GLY E 255     -69.738  -7.707 -92.561  1.00 47.37      A    O
ATOM  11522  N    PRO E 256     -71.560  -8.258 -91.414  1.00 46.61      A    N
ATOM  11523  CA   PRO E 256     -72.935  -8.376 -90.943  1.00 46.34      A    C
ATOM  11524  C    PRO E 256     -73.206  -7.945 -89.515  1.00 45.77      A    C
ATOM  11525  O    PRO E 256     -74.062  -7.087 -89.284  1.00 45.98      A    O
ATOM  11526  CB   PRO E 256     -73.209  -9.882 -91.093  1.00 46.53      A    C
ATOM  11527  CG   PRO E 256     -72.158 -10.383 -92.010  1.00 46.55      A    C
ATOM  11528  CD   PRO E 256     -70.992  -9.597 -91.637  1.00 46.58      A    C
ATOM  11529  N    THR E 257     -72.504  -8.558 -88.569  1.00 44.75      A    N
ATOM  11530  CA   THR E 257     -72.677  -8.258 -87.152  1.00 43.64      A    C
ATOM  11531  C    THR E 257     -71.495  -7.456 -86.644  1.00 42.92      A    C
ATOM  11532  O    THR E 257     -70.521  -7.263 -87.364  1.00 42.83      A    O
ATOM  11533  CB   THR E 257     -72.825  -9.543 -86.317  1.00 43.46      A    C
ATOM  11534  OG1  THR E 257     -71.752 -10.440 -86.614  1.00 43.06      A    O
ATOM  11535  N    ARG E 258     -71.582  -6.985 -85.403  1.00 42.07      A    N
ATOM  11536  CA   ARG E 258     -70.485  -6.232 -84.792  1.00 41.06      A    C
ATOM  11537  C    ARG E 258     -69.259  -7.095 -84.533  1.00 40.56      A    C
ATOM  11538  O    ARG E 258     -68.176  -6.567 -84.296  1.00 40.56      A    O
ATOM  11539  CB   ARG E 258     -70.923  -5.525 -83.506  1.00 40.13      A    C
ATOM  11540  CG   ARG E 258     -71.418  -4.121 -83.740  1.00 40.07      A    C
ATOM  11541  CD   ARG E 258     -71.210  -3.248 -82.529  1.00 40.04      A    C
ATOM  11542  NE   ARG E 258     -71.560  -1.855 -82.801  1.00 40.31      A    N
ATOM  11543  N    ILE E 259     -69.424  -8.415 -84.593  1.00 39.84      A    N
ATOM  11544  CA   ILE E 259     -68.311  -9.321 -84.385  1.00 38.90      A    C
ATOM  11545  C    ILE E 259     -67.292  -9.181 -85.490  1.00 38.83      A    C
ATOM  11546  O    ILE E 259     -66.088  -9.262 -85.242  1.00 38.83      A    O
ATOM  11547  CB   ILE E 259     -68.771 -10.758 -84.296  1.00 38.01      A    C
ATOM  11548  CG1  ILE E 259     -68.593 -11.230 -82.865  1.00 37.65      A    C
ATOM  11549  CD1  ILE E 259     -69.646 -12.156 -82.439  1.00 38.51      A    C
ATOM  11550  N    GLN E 260     -67.781  -8.935 -86.701  1.00 38.50      A    N
ATOM  11551  CA   GLN E 260     -66.908  -8.784 -87.858  1.00 37.92      A    C
ATOM  11552  C    GLN E 260     -66.246  -7.415 -87.844  1.00 37.76      A    C
ATOM  11553  O    GLN E 260     -65.424  -7.124 -88.705  1.00 38.22      A    O
ATOM  11554  CB   GLN E 260     -67.657  -8.992 -89.186  1.00 37.08      A    C
ATOM  11555  CG   GLN E 260     -69.072  -9.558 -89.093  1.00 36.70      A    C
ATOM  11556  CD   GLN E 260     -69.177 -10.872 -88.343  1.00 36.34      A    C
ATOM  11557  OE1  GLN E 260     -68.475 -11.835 -88.620  1.00 36.73      A    O
ATOM  11558  N    ALA E 261     -66.602  -6.581 -86.871  1.00 37.13      A    N
ATOM  11559  CA   ALA E 261     -66.017  -5.247 -86.749  1.00 36.48      A    C
ATOM  11560  C    ALA E 261     -64.658  -5.269 -86.041  1.00 35.73      A    C
ATOM  11561  O    ALA E 261     -63.860  -4.329 -86.174  1.00 35.66      A    O
ATOM  11562  N    ILE E 262     -64.403  -6.342 -85.291  1.00 34.74      A    N
ATOM  11563  CA   ILE E 262     -63.109  -6.552 -84.638  1.00 33.66      A    C
ATOM  11564  C    ILE E 262     -62.097  -7.013 -85.679  1.00 33.57      A    C
ATOM  11565  O    ILE E 262     -62.120  -8.171 -86.100  1.00 33.74      A    O
ATOM  11566  CB   ILE E 262     -63.183  -7.616 -83.529  1.00 32.70      A    C
ATOM  11567  CG1  ILE E 262     -64.378  -7.362 -82.626  1.00 32.10      A    C
ATOM  11568  CD1  ILE E 262     -64.840  -8.589 -81.937  1.00 31.72      A    C
ATOM  11569  N    GLU E 263     -61.231  -6.100 -86.111  1.00 33.22      A    N
ATOM  11570  CA   GLU E 263     -60.151  -6.440 -87.036  1.00 32.81      A    C
```

FIGURE 1 (cont'd)

```
ATOM  11571  C    GLU E 263     -59.116   -7.305  -86.313  1.00 32.21      A    C
ATOM  11572  O    GLU E 263     -58.561   -8.244  -86.898  1.00 32.31      A    O
ATOM  11573  CB   GLU E 263     -59.501   -5.173  -87.610  1.00 33.02      A    C
ATOM  11574  CG   GLU E 263     -58.707   -5.392  -88.902  1.00 33.04      A    C
ATOM  11575  CD   GLU E 263     -58.264   -4.092  -89.552  1.00 32.62      A    C
ATOM  11576  N    LEU E 264     -58.876   -6.983  -85.039  1.00 31.35      A    N
ATOM  11577  CA   LEU E 264     -57.971   -7.749  -84.177  1.00 30.35      A    C
ATOM  11578  C    LEU E 264     -58.344   -7.631  -82.705  1.00 29.73      A    C
ATOM  11579  O    LEU E 264     -58.435   -6.530  -82.150  1.00 29.75      A    O
ATOM  11580  CB   LEU E 264     -56.515   -7.305  -84.370  1.00 30.30      A    C
ATOM  11581  CG   LEU E 264     -55.431   -8.003  -83.533  1.00 29.84      A    C
ATOM  11582  CD1  LEU E 264     -55.371   -9.495  -83.844  1.00 29.71      A    C
ATOM  11583  CD2  LEU E 264     -54.077   -7.348  -83.744  1.00 29.60      A    C
ATOM  11584  N    PHE E 265     -58.531   -8.790  -82.087  1.00 28.91      A    N
ATOM  11585  CA   PHE E 265     -58.821   -8.919  -80.664  1.00 27.91      A    C
ATOM  11586  C    PHE E 265     -57.518   -9.231  -79.933  1.00 27.61      A    C
ATOM  11587  O    PHE E 265     -57.067  -10.381  -79.888  1.00 27.48      A    O
ATOM  11588  CB   PHE E 265     -59.841  -10.043  -80.467  1.00 27.63      A    C
ATOM  11589  CG   PHE E 265     -60.454  -10.102  -79.109  1.00 26.26      A    C
ATOM  11590  CD1  PHE E 265     -61.688   -9.534  -78.887  1.00 25.30      A    C
ATOM  11591  CD2  PHE E 265     -59.827  -10.780  -78.072  1.00 25.20      A    C
ATOM  11592  CE1  PHE E 265     -62.284   -9.619  -77.669  1.00 23.71      A    C
ATOM  11593  CE2  PHE E 265     -60.421  -10.860  -76.836  1.00 23.91      A    C
ATOM  11594  CZ   PHE E 265     -61.650  -10.277  -76.632  1.00 23.42      A    C
ATOM  11595  N    MET E 266     -56.908   -8.191  -79.378  1.00 27.32      A    N
ATOM  11596  CA   MET E 266     -55.647   -8.333  -78.669  1.00 27.15      A    C
ATOM  11597  C    MET E 266     -55.897   -8.348  -77.154  1.00 27.11      A    C
ATOM  11598  O    MET E 266     -56.087   -7.299  -76.537  1.00 27.21      A    O
ATOM  11599  CB   MET E 266     -54.671   -7.221  -79.083  1.00 27.10      A    C
ATOM  11600  CG   MET E 266     -53.308   -7.342  -78.451  1.00 26.83      A    C
ATOM  11601  SD   MET E 266     -52.387   -5.811  -78.321  1.00 28.51      A    S
ATOM  11602  CE   MET E 266     -51.300   -6.015  -79.713  1.00 28.31      A    C
ATOM  11603  N    LEU E 267     -55.899   -9.542  -76.564  1.00 26.99      A    N
ATOM  11604  CA   LEU E 267     -56.206   -9.716  -75.147  1.00 26.90      A    C
ATOM  11605  C    LEU E 267     -54.976   -9.628  -74.262  1.00 26.95      A    C
ATOM  11606  O    LEU E 267     -54.025  -10.373  -74.436  1.00 27.03      A    O
ATOM  11607  CB   LEU E 267     -56.917  -11.052  -74.923  1.00 26.84      A    C
ATOM  11608  CG   LEU E 267     -57.278  -11.480  -73.497  1.00 26.54      A    C
ATOM  11609  CD1  LEU E 267     -58.187  -10.486  -72.845  1.00 26.53      A    C
ATOM  11610  CD2  LEU E 267     -57.946  -12.832  -73.511  1.00 26.44      A    C
ATOM  11611  N    LEU E 268     -55.022   -8.722  -73.298  1.00 27.03      A    N
ATOM  11612  CA   LEU E 268     -53.917   -8.501  -72.378  1.00 27.22      A    C
ATOM  11613  C    LEU E 268     -54.180   -9.184  -71.054  1.00 27.43      A    C
ATOM  11614  O    LEU E 268     -55.199   -8.943  -70.417  1.00 27.61      A    O
ATOM  11615  CB   LEU E 268     -53.727   -7.008  -72.133  1.00 27.16      A    C
ATOM  11616  CG   LEU E 268     -52.815   -6.233  -73.067  1.00 27.20      A    C
ATOM  11617  CD1  LEU E 268     -53.466   -6.032  -74.406  1.00 27.49      A    C
ATOM  11618  CD2  LEU E 268     -52.512   -4.907  -72.429  1.00 27.06      A    C
ATOM  11619  N    ASP E 269     -53.259  -10.038  -70.629  1.00 27.67      A    N
ATOM  11620  CA   ASP E 269     -53.452  -10.785  -69.386  1.00 27.99      A    C
ATOM  11621  C    ASP E 269     -52.155  -11.150  -68.665  1.00 27.95      A    C
ATOM  11622  O    ASP E 269     -51.109  -11.344  -69.303  1.00 28.10      A    O
ATOM  11623  CB   ASP E 269     -54.257  -12.051  -69.650  1.00 28.22      A    C
ATOM  11624  CG   ASP E 269     -55.247  -12.340  -68.553  1.00 29.36      A    C
ATOM  11625  OD1  ASP E 269     -56.104  -11.464  -68.270  1.00 30.29      A    O
ATOM  11626  OD2  ASP E 269     -55.172  -13.448  -67.987  1.00 30.11      A    O
ATOM  11627  N    LEU E 270     -52.240  -11.238  -67.335  1.00 27.82      A    N
ATOM  11628  CA   LEU E 270     -51.114  -11.626  -66.494  1.00 27.80      A    C
ATOM  11629  C    LEU E 270     -49.841  -10.843  -66.820  1.00 27.89      A    C
ATOM  11630  O    LEU E 270     -48.757  -11.410  -66.947  1.00 27.96      A    O
ATOM  11631  CB   LEU E 270     -50.875  -13.141  -66.577  1.00 27.71      A    C
ATOM  11632  CG   LEU E 270     -52.066  -14.079  -66.397  1.00 27.69      A    C
ATOM  11633  CD1  LEU E 270     -51.569  -15.471  -66.176  1.00 27.62      A    C
ATOM  11634  CD2  LEU E 270     -52.954  -13.661  -65.246  1.00 27.99      A    C
ATOM  11635  N    LEU E 271     -49.988   -9.531  -66.962  1.00 27.99      A    N
```

FIGURE 1 (cont'd)

```
ATOM  11636  CA   LEU E 271     -48.853  -8.649 -67.214  1.00 28.29      A  C
ATOM  11637  C    LEU E 271     -48.558  -7.849 -65.965  1.00 28.69      A  C
ATOM  11638  O    LEU E 271     -49.478  -7.421 -65.274  1.00 28.72      A  O
ATOM  11639  CB   LEU E 271     -49.145  -7.691 -68.370  1.00 28.08      A  C
ATOM  11640  CG   LEU E 271     -49.398  -8.276 -69.750  1.00 27.68      A  C
ATOM  11641  CD1  LEU E 271     -50.699  -7.707 -70.242  1.00 27.61      A  C
ATOM  11642  N    GLY E 272     -47.278  -7.647 -65.675  1.00 29.22      A  N
ATOM  11643  CA   GLY E 272     -46.891  -6.851 -64.514  1.00 29.88      A  C
ATOM  11644  C    GLY E 272     -45.760  -7.434 -63.695  1.00 30.44      A  C
ATOM  11645  O    GLY E 272     -45.042  -6.695 -63.030  1.00 30.64      A  O
ATOM  11646  N    ALA E 273     -45.607  -8.758 -63.744  1.00 30.82      A  N
ATOM  11647  CA   ALA E 273     -44.544  -9.461 -63.026  1.00 31.22      A  C
ATOM  11648  C    ALA E 273     -43.182  -9.234 -63.690  1.00 31.55      A  C
ATOM  11649  O    ALA E 273     -43.124  -8.809 -64.843  1.00 31.60      A  O
ATOM  11650  CB   ALA E 273     -44.861 -10.940 -62.961  1.00 31.18      A  C
ATOM  11651  N    PRO E 274     -42.079  -9.493 -62.963  1.00 31.94      A  N
ATOM  11652  CA   PRO E 274     -40.773  -9.453 -63.609  1.00 32.22      A  C
ATOM  11653  C    PRO E 274     -40.567 -10.599 -64.593  1.00 32.36      A  C
ATOM  11654  O    PRO E 274     -41.157 -11.672 -64.435  1.00 32.24      A  O
ATOM  11655  CB   PRO E 274     -39.803  -9.601 -62.439  1.00 32.45      A  C
ATOM  11656  CG   PRO E 274     -40.596 -10.223 -61.365  1.00 32.42      A  C
ATOM  11657  CD   PRO E 274     -41.953  -9.659 -61.507  1.00 32.11      A  C
ATOM  11658  N    ASN E 275     -39.735 -10.353 -65.602  1.00 32.62      A  N
ATOM  11659  CA   ASN E 275     -39.329 -11.368 -66.585  1.00 32.95      A  C
ATOM  11660  C    ASN E 275     -40.455 -12.206 -67.200  1.00 32.54      A  C
ATOM  11661  O    ASN E 275     -40.421 -13.439 -67.131  1.00 32.78      A  O
ATOM  11662  CB   ASN E 275     -38.242 -12.274 -65.999  1.00 33.41      A  C
ATOM  11663  CG   ASN E 275     -37.047 -11.493 -65.519  1.00 34.77      A  C
ATOM  11664  ND2  ASN E 275     -36.910 -11.387 -64.205  1.00 35.89      A  N
ATOM  11665  OD1  ASN E 275     -36.259 -10.979 -66.315  1.00 35.77      A  O
ATOM  11666  N    PRO E 276     -41.454 -11.547 -67.810  1.00 32.05      A  N
ATOM  11667  CA   PRO E 276     -42.472 -12.340 -68.479  1.00 31.78      A  C
ATOM  11668  C    PRO E 276     -41.918 -12.820 -69.795  1.00 31.80      A  C
ATOM  11669  O    PRO E 276     -41.006 -12.195 -70.326  1.00 31.92      A  O
ATOM  11670  CB   PRO E 276     -43.590 -11.339 -68.711  1.00 31.60      A  C
ATOM  11671  CG   PRO E 276     -42.921 -10.016 -68.766  1.00 31.61      A  C
ATOM  11672  CD   PRO E 276     -41.710 -10.099 -67.906  1.00 31.88      A  C
ATOM  11673  N    THR E 277     -42.432 -13.936 -70.299  1.00 31.86      A  N
ATOM  11674  CA   THR E 277     -42.088 -14.406 -71.652  1.00 31.91      A  C
ATOM  11675  C    THR E 277     -43.360 -14.621 -72.469  1.00 31.82      A  C
ATOM  11676  O    THR E 277     -44.297 -15.279 -72.013  1.00 31.81      A  O
ATOM  11677  CB   THR E 277     -41.194 -15.675 -71.655  1.00 31.98      A  C
ATOM  11678  CG2  THR E 277     -39.756 -15.327 -71.281  1.00 32.11      A  C
ATOM  11679  OG1  THR E 277     -41.696 -16.620 -70.713  1.00 32.27      A  O
ATOM  11680  N    PHE E 278     -43.394 -14.040 -73.667  1.00 31.78      A  N
ATOM  11681  CA   PHE E 278     -44.568 -14.121 -74.533  1.00 31.79      A  C
ATOM  11682  C    PHE E 278     -44.289 -14.861 -75.824  1.00 32.13      A  C
ATOM  11683  O    PHE E 278     -43.202 -14.743 -76.392  1.00 32.27      A  O
ATOM  11684  CB   PHE E 278     -45.064 -12.732 -74.884  1.00 31.58      A  C
ATOM  11685  CG   PHE E 278     -45.368 -11.866 -73.690  1.00 31.35      A  C
ATOM  11686  CD1  PHE E 278     -46.479 -12.117 -72.894  1.00 31.26      A  C
ATOM  11687  CD2  PHE E 278     -44.553 -10.775 -73.378  1.00 31.21      A  C
ATOM  11688  CE1  PHE E 278     -46.761 -11.304 -71.797  1.00 31.20      A  C
ATOM  11689  CE2  PHE E 278     -44.834  -9.960 -72.287  1.00 30.99      A  C
ATOM  11690  CZ   PHE E 278     -45.937 -10.225 -71.498  1.00 31.00      A  C
ATOM  11691  N    TYR E 279     -45.283 -15.616 -76.287  1.00 32.52      A  N
ATOM  11692  CA   TYR E 279     -45.181 -16.392 -77.526  1.00 33.07      A  C
ATOM  11693  C    TYR E 279     -46.415 -16.158 -78.382  1.00 33.68      A  C
ATOM  11694  O    TYR E 279     -47.413 -15.627 -77.901  1.00 33.63      A  O
ATOM  11695  CB   TYR E 279     -45.006 -17.884 -77.219  1.00 32.94      A  C
ATOM  11696  CG   TYR E 279     -43.783 -18.171 -76.384  1.00 32.44      A  C
ATOM  11697  CD1  TYR E 279     -42.542 -18.346 -76.984  1.00 32.38      A  C
ATOM  11698  CD2  TYR E 279     -43.859 -18.237 -74.991  1.00 30.95      A  C
ATOM  11699  CE1  TYR E 279     -41.412 -18.584 -76.228  1.00 31.67      A  C
ATOM  11700  CE2  TYR E 279     -42.728 -18.467 -74.226  1.00 30.58      A  C
```

FIGURE 1 (cont'd)

```
ATOM  11701  CZ   TYR E 279     -41.507 -18.640 -74.862  1.00 30.89      A   C
ATOM  11702  OH   TYR E 279     -40.355 -18.878 -74.156  1.00 31.51      A   O
ATOM  11703  N    SER E 280     -46.346 -16.524 -79.656  1.00 34.59      A   N
ATOM  11704  CA   SER E 280     -47.507 -16.370 -80.524  1.00 35.45      A   C
ATOM  11705  C    SER E 280     -48.355 -17.639 -80.497  1.00 35.96      A   C
ATOM  11706  O    SER E 280     -47.965 -18.681 -81.027  1.00 36.25      A   O
ATOM  11707  CB   SER E 280     -47.103 -15.987 -81.956  1.00 35.59      A   C
ATOM  11708  OG   SER E 280     -48.244 -15.681 -82.749  1.00 35.75      A   O
ATOM  11709  N    HIS E 281     -49.516 -17.542 -79.865  1.00 36.40      A   N
ATOM  11710  CA   HIS E 281     -50.390 -18.690 -79.731  1.00 37.12      A   C
ATOM  11711  C    HIS E 281     -51.393 -18.799 -80.873  1.00 37.43      A   C
ATOM  11712  O    HIS E 281     -52.167 -19.752 -80.943  1.00 37.64      A   O
ATOM  11713  CB   HIS E 281     -51.088 -18.672 -78.374  1.00 37.21      A   C
ATOM  11714  CG   HIS E 281     -50.142 -18.607 -77.221  1.00 37.79      A   C
ATOM  11715  CD2  HIS E 281     -49.479 -19.581 -76.555  1.00 38.65      A   C
ATOM  11716  ND1  HIS E 281     -49.768 -17.415 -76.641  1.00 37.78      A   N
ATOM  11717  CE1  HIS E 281     -48.925 -17.658 -75.655  1.00 38.22      A   C
ATOM  11718  NE2  HIS E 281     -48.733 -18.964 -75.583  1.00 38.94      A   N
ATOM  11719  N    PHE E 282     -51.371 -17.825 -81.772  1.00 37.80      A   N
ATOM  11720  CA   PHE E 282     -52.143 -17.916 -83.016  1.00 38.19      A   C
ATOM  11721  C    PHE E 282     -51.316 -17.511 -84.235  1.00 38.51      A   C
ATOM  11722  O    PHE E 282     -50.928 -16.348 -84.360  1.00 38.44      A   O
ATOM  11723  CB   PHE E 282     -53.440 -17.107 -82.933  1.00 38.08      A   C
ATOM  11724  CG   PHE E 282     -54.329 -17.528 -81.809  1.00 38.02      A   C
ATOM  11725  CD1  PHE E 282     -55.034 -18.723 -81.880  1.00 38.46      A   C
ATOM  11726  CD2  PHE E 282     -54.450 -16.740 -80.670  1.00 37.87      A   C
ATOM  11727  CE1  PHE E 282     -55.849 -19.131 -80.832  1.00 38.44      A   C
ATOM  11728  CE2  PHE E 282     -55.262 -17.135 -79.619  1.00 37.98      A   C
ATOM  11729  CZ   PHE E 282     -55.965 -18.338 -79.697  1.00 38.24      A   C
ATOM  11730  N    PRO E 283     -51.036 -18.483 -85.131  1.00 38.89      A   N
ATOM  11731  CA   PRO E 283     -50.280 -18.231 -86.353  1.00 39.02      A   C
ATOM  11732  C    PRO E 283     -51.030 -17.278 -87.280  1.00 38.94      A   C
ATOM  11733  O    PRO E 283     -50.409 -16.636 -88.127  1.00 39.02      A   O
ATOM  11734  CB   PRO E 283     -50.168 -19.621 -86.997  1.00 39.27      A   C
ATOM  11735  CG   PRO E 283     -50.391 -20.570 -85.897  1.00 39.32      A   C
ATOM  11736  CD   PRO E 283     -51.407 -19.904 -85.021  1.00 39.06      A   C
ATOM  11737  N    ARG E 284     -52.349 -17.178 -87.113  1.00 38.69      A   N
ATOM  11738  CA   ARG E 284     -53.156 -16.233 -87.877  1.00 38.53      A   C
ATOM  11739  C    ARG E 284     -52.639 -14.805 -87.721  1.00 38.69      A   C
ATOM  11740  O    ARG E 284     -52.546 -14.076 -88.690  1.00 38.95      A   O
ATOM  11741  CB   ARG E 284     -54.613 -16.308 -87.439  1.00 38.27      A   C
ATOM  11742  CG   ARG E 284     -55.615 -16.103 -88.561  1.00 37.49      A   C
ATOM  11743  CD   ARG E 284     -55.626 -14.699 -89.133  1.00 35.77      A   C
ATOM  11744  NE   ARG E 284     -56.955 -14.368 -89.626  1.00 34.88      A   N
ATOM  11745  CZ   ARG E 284     -57.311 -13.185 -90.106  1.00 34.03      A   C
ATOM  11746  NH1  ARG E 284     -56.420 -12.205 -90.207  1.00 33.81      A   N
ATOM  11747  NH2  ARG E 284     -58.564 -12.989 -90.495  1.00 33.47      A   N
ATOM  11748  N    THR E 285     -52.296 -14.414 -86.503  1.00 38.74      A   N
ATOM  11749  CA   THR E 285     -51.811 -13.068 -86.249  1.00 38.86      A   C
ATOM  11750  C    THR E 285     -50.301 -13.024 -85.986  1.00 39.26      A   C
ATOM  11751  O    THR E 285     -49.800 -12.038 -85.442  1.00 39.15      A   O
ATOM  11752  CB   THR E 285     -52.563 -12.427 -85.076  1.00 38.49      A   C
ATOM  11753  OG1  THR E 285     -52.586 -13.337 -83.974  1.00 38.18      A   O
ATOM  11754  N    VAL E 286     -49.580 -14.074 -86.403  1.00 39.89      A   N
ATOM  11755  CA   VAL E 286     -48.146 -14.245 -86.081  1.00 40.38      A   C
ATOM  11756  C    VAL E 286     -47.308 -13.039 -86.450  1.00 41.02      A   C
ATOM  11757  O    VAL E 286     -46.269 -12.798 -85.839  1.00 41.06      A   O
ATOM  11758  CB   VAL E 286     -47.520 -15.483 -86.747  1.00 40.28      A   C
ATOM  11759  N    ARG E 287     -47.769 -12.279 -87.440  1.00 41.89      A   N
ATOM  11760  CA   ARG E 287     -47.032 -11.108 -87.922  1.00 42.78      A   C
ATOM  11761  C    ARG E 287     -47.207  -9.876 -87.041  1.00 42.52      A   C
ATOM  11762  O    ARG E 287     -46.357  -8.993 -87.044  1.00 42.68      A   O
ATOM  11763  CB   ARG E 287     -47.368 -10.790 -89.387  1.00 43.52      A   C
ATOM  11764  CG   ARG E 287     -48.802 -10.364 -89.644  1.00 45.24      A   C
ATOM  11765  CD   ARG E 287     -49.015  -9.997 -91.113  1.00 48.27      A   C
```

FIGURE 1 (cont'd)

```
ATOM  11766  NE   ARG E 287     -50.333   -9.393 -91.334  1.00 49.98      A  N
ATOM  11767  CZ   ARG E 287     -50.584   -8.084 -91.290  1.00 50.47      A  C
ATOM  11768  NH1  ARG E 287     -49.607   -7.207 -91.037  1.00 50.53      A  N
ATOM  11769  NH2  ARG E 287     -51.821   -7.655 -91.505  1.00 50.71      A  N
ATOM  11770  N    TRP E 288     -48.302   -9.818 -86.290  1.00 42.17      A  N
ATOM  11771  CA   TRP E 288     -48.481   -8.748 -85.319  1.00 41.87      A  C
ATOM  11772  C    TRP E 288     -47.674   -9.016 -84.068  1.00 41.64      A  C
ATOM  11773  O    TRP E 288     -47.283   -8.090 -83.367  1.00 41.71      A  O
ATOM  11774  CB   TRP E 288     -49.950   -8.515 -84.996  1.00 41.77      A  C
ATOM  11775  CG   TRP E 288     -50.657   -7.844 -86.115  1.00 42.47      A  C
ATOM  11776  CD1  TRP E 288     -51.722   -8.322 -86.820  1.00 42.99      A  C
ATOM  11777  CD2  TRP E 288     -50.330   -6.579 -86.694  1.00 43.18      A  C
ATOM  11778  CE2  TRP E 288     -51.252   -6.343 -87.734  1.00 43.57      A  C
ATOM  11779  CE3  TRP E 288     -49.356   -5.616 -86.426  1.00 43.39      A  C
ATOM  11780  NE1  TRP E 288     -52.093   -7.421 -87.792  1.00 43.40      A  N
ATOM  11781  CZ2  TRP E 288     -51.227   -5.188 -88.505  1.00 44.08      A  C
ATOM  11782  CZ3  TRP E 288     -49.327   -4.474 -87.196  1.00 43.90      A  C
ATOM  11783  CH2  TRP E 288     -50.260   -4.266 -88.221  1.00 44.27      A  C
ATOM  11784  N    PHE E 289     -47.409  -10.289 -83.802  1.00 41.45      A  N
ATOM  11785  CA   PHE E 289     -46.498  -10.666 -82.734  1.00 41.29      A  C
ATOM  11786  C    PHE E 289     -45.082  -10.240 -83.104  1.00 41.40      A  C
ATOM  11787  O    PHE E 289     -44.366   -9.685 -82.273  1.00 41.24      A  O
ATOM  11788  CB   PHE E 289     -46.571  -12.172 -82.463  1.00 41.20      A  C
ATOM  11789  CG   PHE E 289     -45.911  -12.591 -81.186  1.00 41.06      A  C
ATOM  11790  CD1  PHE E 289     -46.540  -12.405 -79.965  1.00 40.68      A  C
ATOM  11791  CD2  PHE E 289     -44.661  -13.169 -81.203  1.00 41.39      A  C
ATOM  11792  CE1  PHE E 289     -45.927  -12.785 -78.786  1.00 40.54      A  C
ATOM  11793  CE2  PHE E 289     -44.045  -13.550 -80.026  1.00 41.50      A  C
ATOM  11794  CZ   PHE E 289     -44.678  -13.349 -78.820  1.00 41.07      A  C
ATOM  11795  N    HIS E 290     -44.696  -10.475 -84.361  1.00 41.74      A  N
ATOM  11796  CA   HIS E 290     -43.379  -10.056 -84.851  1.00 42.20      A  C
ATOM  11797  C    HIS E 290     -43.215   -8.553 -84.681  1.00 42.31      A  C
ATOM  11798  O    HIS E 290     -42.112   -8.085 -84.441  1.00 42.51      A  O
ATOM  11799  CB   HIS E 290     -43.094  -10.435 -86.328  1.00 42.49      A  C
ATOM  11800  CG   HIS E 290     -43.350  -11.872 -86.665  1.00 43.12      A  C
ATOM  11801  ND1  HIS E 290     -42.550  -12.767 -87.358  1.00 43.98      A  N
ATOM  11802  CE1  HIS E 290     -41.327  -12.383 -87.657  1.00 44.49      A  C
ATOM  11803  N    ARG E 291     -44.303   -7.795 -84.807  1.00 42.37      A  N
ATOM  11804  CA   ARG E 291     -44.236   -6.344 -84.628  1.00 42.58      A  C
ATOM  11805  C    ARG E 291     -43.815   -6.020 -83.226  1.00 42.20      A  C
ATOM  11806  O    ARG E 291     -42.960   -5.163 -83.017  1.00 42.45      A  O
ATOM  11807  CB   ARG E 291     -45.568   -5.666 -84.940  1.00 42.82      A  C
ATOM  11808  CG   ARG E 291     -45.787   -5.475 -86.418  1.00 44.48      A  C
ATOM  11809  CD   ARG E 291     -44.694   -4.608 -87.019  1.00 46.61      A  C
ATOM  11810  NE   ARG E 291     -45.096   -3.215 -86.983  1.00 47.69      A  N
ATOM  11811  CZ   ARG E 291     -45.626   -2.577 -88.017  1.00 48.73      A  C
ATOM  11812  NH1  ARG E 291     -45.791   -3.201 -89.174  1.00 49.26      A  N
ATOM  11813  NH2  ARG E 291     -45.985   -1.312 -87.900  1.00 49.27      A  N
ATOM  11814  N    LEU E 292     -44.408   -6.737 -82.273  1.00 41.60      A  N
ATOM  11815  CA   LEU E 292     -44.121   -6.538 -80.868  1.00 40.93      A  C
ATOM  11816  C    LEU E 292     -42.672   -6.869 -80.571  1.00 40.91      A  C
ATOM  11817  O    LEU E 292     -41.995   -6.089 -79.905  1.00 40.97      A  O
ATOM  11818  CB   LEU E 292     -45.078   -7.344 -80.005  1.00 40.55      A  C
ATOM  11819  CG   LEU E 292     -46.519   -6.831 -80.042  1.00 39.84      A  C
ATOM  11820  CD1  LEU E 292     -47.451   -7.861 -79.460  1.00 39.39      A  C
ATOM  11821  CD2  LEU E 292     -46.669   -5.511 -79.305  1.00 39.38      A  C
ATOM  11822  N    ARG E 293     -42.186   -7.994 -81.099  1.00 40.88      A  N
ATOM  11823  CA   ARG E 293     -40.747   -8.315 -81.023  1.00 41.00      A  C
ATOM  11824  C    ARG E 293     -39.918   -7.161 -81.604  1.00 41.29      A  C
ATOM  11825  O    ARG E 293     -38.981   -6.677 -80.959  1.00 41.37      A  O
ATOM  11826  CB   ARG E 293     -40.418   -9.643 -81.736  1.00 40.92      A  C
ATOM  11827  CG   ARG E 293     -39.108  -10.324 -81.282  1.00 40.68      A  C
ATOM  11828  CD   ARG E 293     -38.725  -11.524 -82.165  1.00 40.45      A  C
ATOM  11829  NE   ARG E 293     -39.693  -12.620 -82.127  1.00 39.72      A  N
ATOM  11830  N    SER E 294     -40.307   -6.705 -82.800  1.00 41.48      A  N
```

FIGURE 1 (cont'd)

```
ATOM  11831  CA   SER E 294     -39.608  -5.641 -83.520  1.00 41.72      A  C
ATOM  11832  C    SER E 294     -39.617  -4.333 -82.743  1.00 42.08      A  C
ATOM  11833  O    SER E 294     -38.629  -3.616 -82.712  1.00 42.59      A  O
ATOM  11834  CB   SER E 294     -40.196  -5.448 -84.923  1.00 40.73      A  C
ATOM  11835  N    ILE E 295     -40.730  -4.029 -82.099  1.00 42.16      A  N
ATOM  11836  CA   ILE E 295     -40.831  -2.803 -81.336  1.00 42.24      A  C
ATOM  11837  C    ILE E 295     -39.932  -2.874 -80.104  1.00 42.52      A  C
ATOM  11838  O    ILE E 295     -39.236  -1.913 -79.794  1.00 42.74      A  O
ATOM  11839  CB   ILE E 295     -42.296  -2.489 -80.972  1.00 41.95      A  C
ATOM  11840  CG1  ILE E 295     -43.054  -2.036 -82.214  1.00 41.88      A  C
ATOM  11841  CG2  ILE E 295     -42.376  -1.396 -79.927  1.00 41.83      A  C
ATOM  11842  CD1  ILE E 295     -44.520  -2.319 -82.166  1.00 41.59      A  C
ATOM  11843  N    GLU E 296     -39.935  -4.018 -79.422  1.00 42.67      A  N
ATOM  11844  CA   GLU E 296     -39.094  -4.224 -78.246  1.00 42.97      A  C
ATOM  11845  C    GLU E 296     -37.648  -4.068 -78.658  1.00 43.53      A  C
ATOM  11846  O    GLU E 296     -36.895  -3.326 -78.032  1.00 43.80      A  O
ATOM  11847  CB   GLU E 296     -39.319  -5.615 -77.663  1.00 42.71      A  C
ATOM  11848  CG   GLU E 296     -38.598  -5.879 -76.342  1.00 42.91      A  C
ATOM  11849  CD   GLU E 296     -38.662  -7.338 -75.873  1.00 43.09      A  C
ATOM  11850  OE1  GLU E 296     -39.481  -8.128 -76.394  1.00 42.76      A  O
ATOM  11851  OE2  GLU E 296     -37.881  -7.690 -74.966  1.00 43.33      A  O
ATOM  11852  N    LYS E 297     -37.284  -4.768 -79.729  1.00 44.09      A  N
ATOM  11853  CA   LYS E 297     -35.953  -4.703 -80.316  1.00 44.81      A  C
ATOM  11854  C    LYS E 297     -35.566  -3.244 -80.541  1.00 45.45      A  C
ATOM  11855  O    LYS E 297     -34.547  -2.804 -80.036  1.00 45.73      A  O
ATOM  11856  CB   LYS E 297     -35.943  -5.474 -81.641  1.00 44.74      A  C
ATOM  11857  CG   LYS E 297     -34.826  -6.505 -81.831  1.00 44.61      A  C
ATOM  11858  CD   LYS E 297     -35.308  -7.628 -82.764  1.00 43.74      A  C
ATOM  11859  CE   LYS E 297     -34.166  -8.352 -83.444  1.00 43.74      A  C
ATOM  11860  N    ARG E 298     -36.409  -2.499 -81.260  1.00 45.96      A  N
ATOM  11861  CA   ARG E 298     -36.148  -1.100 -81.616  1.00 46.47      A  C
ATOM  11862  C    ARG E 298     -35.986  -0.194 -80.391  1.00 47.03      A  C
ATOM  11863  O    ARG E 298     -35.018   0.563 -80.300  1.00 47.64      A  O
ATOM  11864  CB   ARG E 298     -37.252  -0.566 -82.545  1.00 45.49      A  C
ATOM  11865  CG   ARG E 298     -37.037   0.861 -83.104  1.00 45.46      A  C
ATOM  11866  CD   ARG E 298     -38.115   1.246 -84.133  1.00 45.12      A  C
ATOM  11867  NE   ARG E 298     -38.001   2.627 -84.595  1.00 44.92      A  N
ATOM  11868  N    LEU E 299     -36.926  -0.276 -79.451  1.00 47.24      A  N
ATOM  11869  CA   LEU E 299     -36.897   0.566 -78.250  1.00 47.46      A  C
ATOM  11870  C    LEU E 299     -35.676   0.273 -77.384  1.00 47.86      A  C
ATOM  11871  O    LEU E 299     -35.145   1.163 -76.722  1.00 48.11      A  O
ATOM  11872  CB   LEU E 299     -38.180   0.396 -77.439  1.00 47.13      A  C
ATOM  11873  CG   LEU E 299     -39.454   1.025 -77.991  1.00 46.96      A  C
ATOM  11874  CD1  LEU E 299     -40.660   0.450 -77.271  1.00 46.53      A  C
ATOM  11875  CD2  LEU E 299     -39.405   2.536 -77.857  1.00 47.42      A  C
ATOM  11876  N    HIS E 300     -35.240  -0.983 -77.400  1.00 48.21      A  N
ATOM  11877  CA   HIS E 300     -34.023  -1.390 -76.721  1.00 48.75      A  C
ATOM  11878  C    HIS E 300     -32.806  -0.710 -77.339  1.00 49.22      A  C
ATOM  11879  O    HIS E 300     -32.007  -0.125 -76.621  1.00 49.55      A  O
ATOM  11880  CB   HIS E 300     -33.869  -2.916 -76.753  1.00 48.70      A  C
ATOM  11881  CG   HIS E 300     -32.523  -3.398 -76.308  1.00 49.35      A  C
ATOM  11882  CD2  HIS E 300     -31.536  -4.032 -76.983  1.00 50.13      A  C
ATOM  11883  ND1  HIS E 300     -32.063  -3.236 -75.020  1.00 49.66      A  N
ATOM  11884  CE1  HIS E 300     -30.850  -3.748 -74.921  1.00 50.27      A  C
ATOM  11885  NE2  HIS E 300     -30.507  -4.238 -76.098  1.00 50.71      A  N
ATOM  11886  N    ARG E 301     -32.682  -0.784 -78.666  1.00 49.68      A  N
ATOM  11887  CA   ARG E 301     -31.588  -0.141 -79.406  1.00 50.21      A  C
ATOM  11888  C    ARG E 301     -31.531   1.341 -79.089  1.00 50.85      A  C
ATOM  11889  O    ARG E 301     -30.452   1.907 -78.977  1.00 51.39      A  O
ATOM  11890  CB   ARG E 301     -31.745  -0.306 -80.925  1.00 50.06      A  C
ATOM  11891  CG   ARG E 301     -31.992  -1.719 -81.426  1.00 49.10      A  C
ATOM  11892  CD   ARG E 301     -30.720  -2.500 -81.683  1.00 48.44      A  C
ATOM  11893  NE   ARG E 301     -31.014  -3.905 -81.975  1.00 47.73      A  N
ATOM  11894  N    LEU E 302     -32.701   1.956 -78.935  1.00 51.22      A  N
ATOM  11895  CA   LEU E 302     -32.806   3.386 -78.670  1.00 51.84      A  C
```

FIGURE 1 (cont'd)

```
ATOM  11896  C    LEU E 302     -32.662   3.750 -77.192  1.00 52.17      A  C
ATOM  11897  O    LEU E 302     -33.001   4.857 -76.788  1.00 52.49      A  O
ATOM  11898  CB   LEU E 302     -34.134   3.913 -79.210  1.00 51.76      A  C
ATOM  11899  CG   LEU E 302     -34.300   3.943 -80.730  1.00 52.21      A  C
ATOM  11900  CD1  LEU E 302     -35.754   3.859 -81.119  1.00 51.82      A  C
ATOM  11901  CD2  LEU E 302     -33.673   5.191 -81.301  1.00 53.48      A  C
ATOM  11902  N    ASN E 303     -32.141   2.824 -76.393  1.00 52.30      A  N
ATOM  11903  CA   ASN E 303     -32.023   3.007 -74.943  1.00 52.23      A  C
ATOM  11904  C    ASN E 303     -33.254   3.686 -74.340  1.00 52.67      A  C
ATOM  11905  O    ASN E 303     -33.169   4.802 -73.855  1.00 53.16      A  O
ATOM  11906  N    LEU E 304     -34.397   3.006 -74.401  1.00 52.86      A  N
ATOM  11907  CA   LEU E 304     -35.662   3.532 -73.880  1.00 52.74      A  C
ATOM  11908  C    LEU E 304     -36.436   2.510 -73.034  1.00 52.45      A  C
ATOM  11909  O    LEU E 304     -37.602   2.732 -72.688  1.00 52.16      A  O
ATOM  11910  CB   LEU E 304     -36.549   4.037 -75.026  1.00 52.80      A  C
ATOM  11911  CG   LEU E 304     -36.292   5.418 -75.636  1.00 53.26      A  C
ATOM  11912  CD1  LEU E 304     -37.202   5.645 -76.834  1.00 52.92      A  C
ATOM  11913  CD2  LEU E 304     -36.486   6.530 -74.607  1.00 53.85      A  C
ATOM  11914  N    LEU E 305     -35.780   1.396 -72.714  1.00 52.36      A  N
ATOM  11915  CA   LEU E 305     -36.358   0.362 -71.867  1.00 52.17      A  C
ATOM  11916  C    LEU E 305     -35.496   0.159 -70.634  1.00 52.57      A  C
ATOM  11917  O    LEU E 305     -34.319  -0.173 -70.748  1.00 53.00      A  O
ATOM  11918  CB   LEU E 305     -36.482  -0.955 -72.633  1.00 51.73      A  C
ATOM  11919  CG   LEU E 305     -37.243  -0.982 -73.955  1.00 51.07      A  C
ATOM  11920  CD1  LEU E 305     -37.099  -2.321 -74.626  1.00 50.39      A  C
ATOM  11921  CD2  LEU E 305     -38.703  -0.656 -73.755  1.00 50.65      A  C
ATOM  11922  N    GLN E 306     -36.084   0.366 -69.459  1.00 52.72      A  N
ATOM  11923  CA   GLN E 306     -35.393   0.155 -68.183  1.00 53.04      A  C
ATOM  11924  C    GLN E 306     -35.095  -1.320 -67.951  1.00 52.95      A  C
ATOM  11925  O    GLN E 306     -35.817  -2.180 -68.450  1.00 52.60      A  O
ATOM  11926  CB   GLN E 306     -36.241   0.664 -67.018  1.00 53.16      A  C
ATOM  11927  CG   GLN E 306     -35.950   2.079 -66.575  1.00 54.03      A  C
ATOM  11928  CD   GLN E 306     -36.647   2.414 -65.273  1.00 54.71      A  C
ATOM  11929  OE1  GLN E 306     -37.849   2.191 -65.124  1.00 54.90      A  O
ATOM  11930  N    SER E 307     -34.035  -1.601 -67.190  1.00 53.28      A  N
ATOM  11931  CA   SER E 307     -33.675  -2.965 -66.788  1.00 53.49      A  C
ATOM  11932  C    SER E 307     -33.878  -3.972 -67.916  1.00 53.35      A  C
ATOM  11933  O    SER E 307     -34.528  -5.006 -67.729  1.00 53.11      A  O
ATOM  11934  CB   SER E 307     -34.488  -3.387 -65.564  1.00 53.53      A  C
ATOM  11935  OG   SER E 307     -34.520  -2.366 -64.584  1.00 54.27      A  O
ATOM  11936  N    HIS E 308     -33.322  -3.660 -69.085  1.00 53.47      A  N
ATOM  11937  CA   HIS E 308     -33.533  -4.464 -70.287  1.00 53.44      A  C
ATOM  11938  C    HIS E 308     -32.203  -4.838 -70.929  1.00 53.72      A  C
ATOM  11939  O    HIS E 308     -31.855  -4.288 -71.974  1.00 54.00      A  O
ATOM  11940  CB   HIS E 308     -34.398  -3.690 -71.279  1.00 53.26      A  C
ATOM  11941  CG   HIS E 308     -35.098  -4.552 -72.279  1.00 52.94      A  C
ATOM  11942  CD2  HIS E 308     -36.159  -5.383 -72.153  1.00 52.54      A  C
ATOM  11943  ND1  HIS E 308     -34.727  -4.606 -73.603  1.00 53.23      A  N
ATOM  11944  CE1  HIS E 308     -35.526  -5.437 -74.249  1.00 52.91      A  C
ATOM  11945  NE2  HIS E 308     -36.403  -5.924 -73.391  1.00 52.36      A  N
ATOM  11946  N    PRO E 309     -31.454  -5.777 -70.311  1.00 53.92      A  N
ATOM  11947  CA   PRO E 309     -30.109  -6.099 -70.772  1.00 54.38      A  C
ATOM  11948  C    PRO E 309     -30.023  -7.100 -71.940  1.00 54.67      A  C
ATOM  11949  O    PRO E 309     -29.135  -7.956 -71.951  1.00 54.96      A  O
ATOM  11950  CB   PRO E 309     -29.446  -6.674 -69.513  1.00 54.64      A  C
ATOM  11951  CG   PRO E 309     -30.378  -6.348 -68.383  1.00 54.40      A  C
ATOM  11952  CD   PRO E 309     -31.708  -6.411 -69.009  1.00 53.83      A  C
ATOM  11953  N    GLN E 310     -30.949  -7.002 -72.895  1.00 54.71      A  N
ATOM  11954  CA   GLN E 310     -30.806  -7.595 -74.245  1.00 54.88      A  C
ATOM  11955  C    GLN E 310     -31.956  -7.214 -75.196  1.00 54.98      A  C
ATOM  11956  O    GLN E 310     -32.830  -6.425 -74.840  1.00 54.84      A  O
ATOM  11957  CB   GLN E 310     -30.484  -9.108 -74.245  1.00 54.90      A  C
ATOM  11958  CG   GLN E 310     -31.158  -9.948 -73.184  1.00 54.53      A  C
ATOM  11959  CD   GLN E 310     -30.269 -11.071 -72.681  1.00 54.53      A  C
ATOM  11960  N    GLU E 311     -31.929  -7.761 -76.409  1.00 55.38      A  N
```

FIGURE 1 (cont'd)

```
ATOM  11961  CA   GLU E 311     -32.864  -7.373 -77.465  1.00 55.73      A  C
ATOM  11962  C    GLU E 311     -34.171  -8.130 -77.285  1.00 55.01      A  C
ATOM  11963  O    GLU E 311     -35.204  -7.528 -77.016  1.00 54.85      A  O
ATOM  11964  CB   GLU E 311     -32.266  -7.617 -78.867  1.00 56.50      A  C
ATOM  11965  CG   GLU E 311     -30.823  -7.107 -79.085  1.00 58.90      A  C
ATOM  11966  CD   GLU E 311     -29.727  -8.092 -78.606  1.00 61.44      A  C
ATOM  11967  OE1  GLU E 311     -28.594  -8.012 -79.131  1.00 62.85      A  O
ATOM  11968  OE2  GLU E 311     -29.978  -8.942 -77.712  1.00 62.00      A  O
ATOM  11969  N    VAL E 312     -34.120  -9.448 -77.423  1.00 54.42      A  N
ATOM  11970  CA   VAL E 312     -35.280 -10.270 -77.169  1.00 53.70      A  C
ATOM  11971  C    VAL E 312     -35.267 -10.692 -75.696  1.00 53.20      A  C
ATOM  11972  O    VAL E 312     -34.428 -11.482 -75.270  1.00 53.54      A  O
ATOM  11973  N    MET E 313     -36.183 -10.120 -74.918  1.00 52.18      A  N
ATOM  11974  CA   MET E 313     -36.398 -10.494 -73.522  1.00 51.19      A  C
ATOM  11975  C    MET E 313     -37.841 -10.966 -73.364  1.00 50.20      A  C
ATOM  11976  O    MET E 313     -38.093 -12.077 -72.911  1.00 50.06      A  O
ATOM  11977  CB   MET E 313     -36.156  -9.299 -72.593  1.00 51.39      A  C
ATOM  11978  CG   MET E 313     -34.745  -8.714 -72.607  1.00 52.00      A  C
ATOM  11979  SD   MET E 313     -33.828  -8.798 -71.048  1.00 52.37      A  S
ATOM  11980  CE   MET E 313     -34.908  -7.925 -69.930  1.00 52.13      A  C
ATOM  11981  N    TYR E 314     -38.778 -10.110 -73.766  1.00 49.11      A  N
ATOM  11982  CA   TYR E 314     -40.200 -10.323 -73.536  1.00 48.01      A  C
ATOM  11983  C    TYR E 314     -40.886 -11.136 -74.627  1.00 47.48      A  C
ATOM  11984  O    TYR E 314     -41.468 -12.183 -74.353  1.00 47.26      A  O
ATOM  11985  CB   TYR E 314     -40.916  -8.983 -73.372  1.00 47.81      A  C
ATOM  11986  CG   TYR E 314     -40.418  -8.140 -72.231  1.00 47.52      A  C
ATOM  11987  CD1  TYR E 314     -39.996  -8.724 -71.048  1.00 47.51      A  C
ATOM  11988  CD2  TYR E 314     -40.396  -6.755 -72.325  1.00 47.35      A  C
ATOM  11989  CE1  TYR E 314     -39.541  -7.952 -69.990  1.00 47.63      A  C
ATOM  11990  CE2  TYR E 314     -39.947  -5.968 -71.271  1.00 47.42      A  C
ATOM  11991  CZ   TYR E 314     -39.519  -6.573 -70.105  1.00 47.35      A  C
ATOM  11992  OH   TYR E 314     -39.069  -5.811 -69.048  1.00 47.31      A  O
ATOM  11993  N    PHE E 315     -40.837 -10.643 -75.861  1.00 47.05      A  N
ATOM  11994  CA   PHE E 315     -41.515 -11.307 -76.966  1.00 46.68      A  C
ATOM  11995  C    PHE E 315     -40.582 -12.289 -77.653  1.00 46.94      A  C
ATOM  11996  O    PHE E 315     -39.823 -11.933 -78.555  1.00 47.01      A  O
ATOM  11997  CB   PHE E 315     -42.106 -10.282 -77.930  1.00 46.36      A  C
ATOM  11998  CG   PHE E 315     -43.102  -9.378 -77.287  1.00 45.25      A  C
ATOM  11999  CD1  PHE E 315     -44.426  -9.753 -77.182  1.00 44.51      A  C
ATOM  12000  CD2  PHE E 315     -42.713  -8.166 -76.753  1.00 44.54      A  C
ATOM  12001  CE1  PHE E 315     -45.348  -8.929 -76.565  1.00 43.97      A  C
ATOM  12002  CE2  PHE E 315     -43.629  -7.339 -76.141  1.00 43.99      A  C
ATOM  12003  CZ   PHE E 315     -44.948  -7.723 -76.045  1.00 43.74      A  C
ATOM  12004  N    GLN E 316     -40.640 -13.531 -77.188  1.00 47.21      A  N
ATOM  12005  CA   GLN E 316     -39.732 -14.568 -77.633  1.00 47.73      A  C
ATOM  12006  C    GLN E 316     -40.112 -15.089 -78.999  1.00 48.08      A  C
ATOM  12007  O    GLN E 316     -41.285 -15.067 -79.370  1.00 47.89      A  O
ATOM  12008  CB   GLN E 316     -39.710 -15.724 -76.642  1.00 47.77      A  C
ATOM  12009  CG   GLN E 316     -38.990 -15.419 -75.360  1.00 48.23      A  C
ATOM  12010  CD   GLN E 316     -37.527 -15.129 -75.561  1.00 48.96      A  C
ATOM  12011  NE2  GLN E 316     -37.121 -13.930 -75.188  1.00 49.08      A  N
ATOM  12012  OE1  GLN E 316     -36.764 -15.972 -76.034  1.00 49.78      A  O
ATOM  12013  N    PRO E 317     -39.111 -15.560 -79.757  1.00 48.67      A  N
ATOM  12014  CA   PRO E 317     -39.391 -16.248 -81.006  1.00 48.97      A  C
ATOM  12015  C    PRO E 317     -39.877 -17.680 -80.744  1.00 48.99      A  C
ATOM  12016  O    PRO E 317     -39.717 -18.215 -79.647  1.00 48.94      A  O
ATOM  12017  CB   PRO E 317     -38.029 -16.258 -81.704  1.00 49.30      A  C
ATOM  12018  CG   PRO E 317     -37.044 -16.314 -80.575  1.00 49.44      A  C
ATOM  12019  CD   PRO E 317     -37.662 -15.492 -79.472  1.00 48.95      A  C
ATOM  12020  N    GLY E 318     -40.455 -18.300 -81.755  1.00 49.05      A  N
ATOM  12021  CA   GLY E 318     -41.030 -19.613 -81.568  1.00 49.02      A  C
ATOM  12022  C    GLY E 318     -42.538 -19.503 -81.565  1.00 48.85      A  C
ATOM  12023  O    GLY E 318     -43.102 -18.540 -81.041  1.00 48.67      A  O
ATOM  12024  N    GLU E 319     -43.189 -20.485 -82.182  1.00 48.86      A  N
ATOM  12025  CA   GLU E 319     -44.647 -20.557 -82.218  1.00 48.63      A  C
```

FIGURE 1 (cont'd)

```
ATOM  12026  C    GLU E 319     -45.107 -21.867 -81.557  1.00 48.78      A C
ATOM  12027  O    GLU E 319     -45.421 -22.846 -82.269  1.00 49.16      A O
ATOM  12028  CB   GLU E 319     -45.168 -20.473 -83.665  1.00 48.51      A C
ATOM  12029  CG   GLU E 319     -44.790 -19.203 -84.425  1.00 47.98      A C
ATOM  12030  CD   GLU E 319     -45.336 -19.172 -85.861  1.00 48.01      A C
ATOM  12031  OE1  GLU E 319     -45.152 -18.132 -86.537  1.00 48.49      A O
ATOM  12032  OE2  GLU E 319     -45.947 -20.171 -86.317  1.00 47.70      A O
ATOM  12033  N    PRO E 320     -45.119 -21.912 -80.198  1.00 48.66      A N
ATOM  12034  CA   PRO E 320     -45.641 -23.112 -79.530  1.00 48.68      A C
ATOM  12035  C    PRO E 320     -47.177 -23.271 -79.645  1.00 48.55      A C
ATOM  12036  O    PRO E 320     -47.891 -22.283 -79.887  1.00 48.31      A O
ATOM  12037  CB   PRO E 320     -45.192 -22.924 -78.073  1.00 48.70      A C
ATOM  12038  CG   PRO E 320     -44.043 -21.968 -78.154  1.00 48.66      A C
ATOM  12039  CD   PRO E 320     -44.441 -21.026 -79.235  1.00 48.47      A C
ATOM  12040  N    PHE E 321     -47.647 -24.513 -79.461  1.00 48.39      A N
ATOM  12041  CA   PHE E 321     -49.043 -24.925 -79.688  1.00 48.00      A C
ATOM  12042  C    PHE E 321     -50.134 -24.115 -78.947  1.00 48.18      A C
ATOM  12043  O    PHE E 321     -51.030 -23.550 -79.592  1.00 48.48      A O
ATOM  12044  N    GLY E 322     -50.066 -24.057 -77.611  1.00 48.07      A N
ATOM  12045  CA   GLY E 322     -51.139 -23.434 -76.788  1.00 47.47      A C
ATOM  12046  C    GLY E 322     -52.342 -24.371 -76.581  1.00 47.11      A C
ATOM  12047  O    GLY E 322     -52.209 -25.602 -76.714  1.00 47.64      A O
ATOM  12048  N    SER E 323     -53.512 -23.831 -76.229  1.00 46.14      A N
ATOM  12049  CA   SER E 323     -53.696 -22.426 -75.867  1.00 45.04      A C
ATOM  12050  C    SER E 323     -54.002 -22.356 -74.376  1.00 43.89      A C
ATOM  12051  O    SER E 323     -54.147 -23.391 -73.714  1.00 44.01      A O
ATOM  12052  CB   SER E 323     -54.863 -21.813 -76.666  1.00 45.26      A C
ATOM  12053  OG   SER E 323     -54.654 -21.912 -78.073  1.00 46.10      A O
ATOM  12054  N    VAL E 324     -54.105 -21.137 -73.856  1.00 42.31      A N
ATOM  12055  CA   VAL E 324     -54.559 -20.912 -72.489  1.00 40.76      A C
ATOM  12056  C    VAL E 324     -55.948 -20.283 -72.545  1.00 40.00      A C
ATOM  12057  O    VAL E 324     -56.125 -19.240 -73.168  1.00 39.89      A O
ATOM  12058  CB   VAL E 324     -53.587 -20.005 -71.751  1.00 40.50      A C
ATOM  12059  CG1  VAL E 324     -52.258 -20.714 -71.582  1.00 40.39      A C
ATOM  12060  CG2  VAL E 324     -54.163 -19.581 -70.409  1.00 40.07      A C
ATOM  12061  N    GLU E 325     -56.928 -20.926 -71.917  1.00 39.16      A N
ATOM  12062  CA   GLU E 325     -58.310 -20.467 -71.991  1.00 38.48      A C
ATOM  12063  C    GLU E 325     -58.485 -19.116 -71.300  1.00 37.61      A C
ATOM  12064  O    GLU E 325     -58.129 -18.953 -70.138  1.00 37.47      A O
ATOM  12065  CB   GLU E 325     -59.249 -21.494 -71.380  1.00 38.85      A C
ATOM  12066  CG   GLU E 325     -59.135 -22.877 -71.975  1.00 40.44      A C
ATOM  12067  CD   GLU E 325     -60.221 -23.833 -71.473  1.00 42.57      A C
ATOM  12068  OE1  GLU E 325     -61.164 -23.369 -70.783  1.00 42.98      A O
ATOM  12069  OE2  GLU E 325     -60.133 -25.053 -71.770  1.00 43.82      A O
ATOM  12070  N    ASP E 326     -59.028 -18.147 -72.029  1.00 36.78      A N
ATOM  12071  CA   ASP E 326     -59.199 -16.783 -71.528  1.00 36.02      A C
ATOM  12072  C    ASP E 326     -60.347 -16.128 -72.303  1.00 35.76      A C
ATOM  12073  O    ASP E 326     -61.033 -16.792 -73.081  1.00 35.82      A O
ATOM  12074  CB   ASP E 326     -57.886 -15.985 -71.679  1.00 35.74      A C
ATOM  12075  CG   ASP E 326     -57.706 -14.890 -70.617  1.00 35.10      A C
ATOM  12076  OD1  ASP E 326     -58.688 -14.422 -70.015  1.00 34.82      A O
ATOM  12077  OD2  ASP E 326     -56.557 -14.481 -70.394  1.00 34.56      A O
ATOM  12078  N    ASP E 327     -60.542 -14.827 -72.087  1.00 35.34      A N
ATOM  12079  CA   ASP E 327     -61.665 -14.061 -72.639  1.00 34.99      A C
ATOM  12080  C    ASP E 327     -61.784 -14.096 -74.154  1.00 34.57      A C
ATOM  12081  O    ASP E 327     -62.831 -13.773 -74.704  1.00 34.64      A O
ATOM  12082  CB   ASP E 327     -61.575 -12.606 -72.181  1.00 35.12      A C
ATOM  12083  CG   ASP E 327     -61.942 -12.428 -70.712  1.00 36.06      A C
ATOM  12084  OD1  ASP E 327     -63.102 -12.731 -70.333  1.00 36.78      A O
ATOM  12085  OD2  ASP E 327     -61.069 -11.966 -69.936  1.00 36.74      A O
ATOM  12086  N    HIS E 328     -60.710 -14.479 -74.828  1.00 34.07      A N
ATOM  12087  CA   HIS E 328     -60.699 -14.488 -76.279  1.00 33.73      A C
ATOM  12088  C    HIS E 328     -61.509 -15.659 -76.861  1.00 33.67      A C
ATOM  12089  O    HIS E 328     -62.007 -15.581 -77.985  1.00 33.85      A O
ATOM  12090  CB   HIS E 328     -59.262 -14.530 -76.786  1.00 33.56      A C
```

FIGURE 1 (cont'd)

```
ATOM  12091  CG   HIS E 328     -58.601 -15.845 -76.565  1.00 33.82      A  C
ATOM  12092  CD2  HIS E 328     -58.391 -16.890 -77.397  1.00 34.41      A  C
ATOM  12093  ND1  HIS E 328     -58.102 -16.221 -75.340  1.00 34.04      A  N
ATOM  12094  CE1  HIS E 328     -57.586 -17.433 -75.433  1.00 34.32      A  C
ATOM  12095  NE2  HIS E 328     -57.749 -17.863 -76.671  1.00 34.56      A  N
ATOM  12096  N    ILE E 329     -61.643 -16.740 -76.096  1.00 33.52      A  N
ATOM  12097  CA   ILE E 329     -62.277 -17.969 -76.593  1.00 33.63      A  C
ATOM  12098  C    ILE E 329     -63.630 -17.753 -77.274  1.00 33.61      A  C
ATOM  12099  O    ILE E 329     -63.795 -18.146 -78.418  1.00 33.87      A  O
ATOM  12100  CB   ILE E 329     -62.367 -19.071 -75.498  1.00 33.70      A  C
ATOM  12101  CG1  ILE E 329     -60.968 -19.568 -75.110  1.00 33.92      A  C
ATOM  12102  CG2  ILE E 329     -63.248 -20.227 -75.949  1.00 34.15      A  C
ATOM  12103  CD1  ILE E 329     -60.185 -20.242 -76.241  1.00 34.45      A  C
ATOM  12104  N    PRO E 330     -64.591 -17.111 -76.593  1.00 33.53      A  N
ATOM  12105  CA   PRO E 330     -65.881 -16.999 -77.244  1.00 33.60      A  C
ATOM  12106  C    PRO E 330     -65.899 -16.000 -78.406  1.00 33.51      A  C
ATOM  12107  O    PRO E 330     -66.873 -15.938 -79.140  1.00 33.77      A  O
ATOM  12108  CB   PRO E 330     -66.798 -16.537 -76.110  1.00 33.71      A  C
ATOM  12109  CG   PRO E 330     -65.929 -15.772 -75.221  1.00 33.51      A  C
ATOM  12110  CD   PRO E 330     -64.583 -16.425 -75.289  1.00 33.45      A  C
ATOM  12111  N    PHE E 331     -64.842 -15.216 -78.569  1.00 33.13      A  N
ATOM  12112  CA   PHE E 331     -64.711 -14.388 -79.761  1.00 32.89      A  C
ATOM  12113  C    PHE E 331     -64.009 -15.164 -80.846  1.00 32.86      A  C
ATOM  12114  O    PHE E 331     -64.335 -15.009 -82.019  1.00 32.97      A  O
ATOM  12115  CB   PHE E 331     -63.951 -13.113 -79.460  1.00 32.68      A  C
ATOM  12116  CG   PHE E 331     -64.719 -12.147 -78.642  1.00 32.76      A  C
ATOM  12117  CD1  PHE E 331     -64.505 -12.052 -77.287  1.00 32.78      A  C
ATOM  12118  CD2  PHE E 331     -65.672 -11.338 -79.228  1.00 33.28      A  C
ATOM  12119  CE1  PHE E 331     -65.219 -11.145 -76.529  1.00 33.05      A  C
ATOM  12120  CE2  PHE E 331     -66.398 -10.433 -78.479  1.00 33.49      A  C
ATOM  12121  CZ   PHE E 331     -66.173 -10.331 -77.129  1.00 33.23      A  C
ATOM  12122  N    LEU E 332     -63.057 -16.002 -80.439  1.00 32.81      A  N
ATOM  12123  CA   LEU E 332     -62.353 -16.899 -81.355  1.00 32.99      A  C
ATOM  12124  C    LEU E 332     -63.288 -17.933 -81.999  1.00 33.42      A  C
ATOM  12125  O    LEU E 332     -63.198 -18.192 -83.203  1.00 33.66      A  O
ATOM  12126  CB   LEU E 332     -61.190 -17.596 -80.646  1.00 32.68      A  C
ATOM  12127  CG   LEU E 332     -60.417 -18.621 -81.474  1.00 32.39      A  C
ATOM  12128  CD1  LEU E 332     -59.315 -17.963 -82.260  1.00 31.99      A  C
ATOM  12129  CD2  LEU E 332     -59.850 -19.649 -80.548  1.00 32.37      A  C
ATOM  12130  N    ARG E 333     -64.190 -18.510 -81.206  1.00 33.79      A  N
ATOM  12131  CA   ARG E 333     -65.132 -19.496 -81.744  1.00 34.36      A  C
ATOM  12132  C    ARG E 333     -66.055 -18.883 -82.827  1.00 34.14      A  C
ATOM  12133  O    ARG E 333     -66.590 -19.598 -83.675  1.00 34.51      A  O
ATOM  12134  CB   ARG E 333     -65.902 -20.238 -80.621  1.00 34.72      A  C
ATOM  12135  CG   ARG E 333     -67.389 -19.875 -80.439  1.00 36.60      A  C
ATOM  12136  CD   ARG E 333     -68.146 -20.908 -79.572  1.00 39.90      A  C
ATOM  12137  NE   ARG E 333     -68.305 -20.500 -78.167  1.00 42.22      A  N
ATOM  12138  CZ   ARG E 333     -69.432 -20.034 -77.620  1.00 42.94      A  C
ATOM  12139  NH1  ARG E 333     -69.450 -19.698 -76.332  1.00 42.53      A  N
ATOM  12140  NH2  ARG E 333     -70.539 -19.902 -78.346  1.00 43.81      A  N
ATOM  12141  N    ARG E 334     -66.198 -17.560 -82.814  1.00 33.58      A  N
ATOM  12142  CA   ARG E 334     -66.983 -16.842 -83.814  1.00 33.14      A  C
ATOM  12143  C    ARG E 334     -66.136 -16.347 -84.967  1.00 32.66      A  C
ATOM  12144  O    ARG E 334     -66.646 -15.712 -85.876  1.00 32.78      A  O
ATOM  12145  CB   ARG E 334     -67.716 -15.675 -83.167  1.00 33.16      A  C
ATOM  12146  CG   ARG E 334     -69.019 -16.084 -82.488  1.00 33.64      A  C
ATOM  12147  CD   ARG E 334     -69.288 -15.246 -81.239  1.00 33.77      A  C
ATOM  12148  NE   ARG E 334     -70.651 -15.393 -80.729  1.00 34.76      A  N
ATOM  12149  CZ   ARG E 334     -70.996 -16.135 -79.679  1.00 35.55      A  C
ATOM  12150  NH1  ARG E 334     -70.087 -16.823 -79.000  1.00 35.24      A  N
ATOM  12151  NH2  ARG E 334     -72.265 -16.192 -79.303  1.00 36.58      A  N
ATOM  12152  N    GLY E 335     -64.841 -16.633 -84.922  1.00 32.07      A  N
ATOM  12153  CA   GLY E 335     -63.934 -16.297 -86.020  1.00 31.47      A  C
ATOM  12154  C    GLY E 335     -63.124 -15.002 -85.930  1.00 30.83      A  C
ATOM  12155  O    GLY E 335     -62.534 -14.568 -86.924  1.00 31.14      A  O
```

FIGURE 1 (cont'd)

```
ATOM  12156  N    VAL E 336     -63.079 -14.381 -84.755  1.00 29.91      A   N
ATOM  12157  CA   VAL E 336     -62.332 -13.151 -84.583  1.00 29.03      A   C
ATOM  12158  C    VAL E 336     -60.863 -13.464 -84.481  1.00 28.62      A   C
ATOM  12159  O    VAL E 336     -60.481 -14.334 -83.721  1.00 28.62      A   O
ATOM  12160  CB   VAL E 336     -62.754 -12.438 -83.310  1.00 28.90      A   C
ATOM  12161  CG1  VAL E 336     -61.942 -11.160 -83.117  1.00 28.84      A   C
ATOM  12162  CG2  VAL E 336     -64.250 -12.125 -83.348  1.00 29.05      A   C
ATOM  12163  N    PRO E 337     -60.029 -12.768 -85.257  1.00 28.40      A   N
ATOM  12164  CA   PRO E 337     -58.579 -12.914 -85.139  1.00 28.19      A   C
ATOM  12165  C    PRO E 337     -58.126 -12.524 -83.745  1.00 27.76      A   C
ATOM  12166  O    PRO E 337     -58.520 -11.459 -83.265  1.00 27.76      A   O
ATOM  12167  CB   PRO E 337     -58.045 -11.898 -86.144  1.00 28.31      A   C
ATOM  12168  CG   PRO E 337     -59.119 -11.755 -87.136  1.00 28.72      A   C
ATOM  12169  CD   PRO E 337     -60.404 -11.908 -86.385  1.00 28.63      A   C
ATOM  12170  N    VAL E 338     -57.318 -13.372 -83.103  1.00 27.30      A   N
ATOM  12171  CA   VAL E 338     -56.891 -13.119 -81.722  1.00 26.72      A   C
ATOM  12172  C    VAL E 338     -55.385 -13.005 -81.588  1.00 26.54      A   C
ATOM  12173  O    VAL E 338     -54.653 -13.769 -82.197  1.00 26.75      A   O
ATOM  12174  CB   VAL E 338     -57.373 -14.219 -80.763  1.00 26.60      A   C
ATOM  12175  CG1  VAL E 338     -56.917 -13.911 -79.350  1.00 26.40      A   C
ATOM  12176  CG2  VAL E 338     -58.891 -14.351 -80.801  1.00 26.60      A   C
ATOM  12177  N    LEU E 339     -54.931 -12.037 -80.801  1.00 26.18      A   N
ATOM  12178  CA   LEU E 339     -53.554 -12.017 -80.343  1.00 25.91      A   C
ATOM  12179  C    LEU E 339     -53.568 -12.072 -78.825  1.00 25.80      A   C
ATOM  12180  O    LEU E 339     -53.988 -11.124 -78.165  1.00 25.85      A   O
ATOM  12181  CB   LEU E 339     -52.814 -10.776 -80.835  1.00 25.85      A   C
ATOM  12182  CG   LEU E 339     -51.343 -10.717 -80.430  1.00 25.68      A   C
ATOM  12183  CD1  LEU E 339     -50.590 -11.955 -80.885  1.00 25.97      A   C
ATOM  12184  CD2  LEU E 339     -50.717  -9.473 -80.994  1.00 25.52      A   C
ATOM  12185  N    HIS E 340     -53.118 -13.191 -78.273  1.00 25.63      A   N
ATOM  12186  CA   HIS E 340     -53.231 -13.439 -76.844  1.00 25.39      A   C
ATOM  12187  C    HIS E 340     -51.943 -13.041 -76.150  1.00 25.28      A   C
ATOM  12188  O    HIS E 340     -50.942 -13.748 -76.226  1.00 25.32      A   O
ATOM  12189  CB   HIS E 340     -53.546 -14.913 -76.619  1.00 25.47      A   C
ATOM  12190  CG   HIS E 340     -54.102 -15.222 -75.265  1.00 25.65      A   C
ATOM  12191  CD2  HIS E 340     -54.626 -14.418 -74.309  1.00 25.66      A   C
ATOM  12192  ND1  HIS E 340     -54.155 -16.506 -74.760  1.00 26.00      A   N
ATOM  12193  CE1  HIS E 340     -54.698 -16.478 -73.556  1.00 25.95      A   C
ATOM  12194  NE2  HIS E 340     -54.991 -15.224 -73.258  1.00 25.88      A   N
ATOM  12195  N    LEU E 341     -51.975 -11.895 -75.483  1.00 25.15      A   N
ATOM  12196  CA   LEU E 341     -50.786 -11.325 -74.862  1.00 25.10      A   C
ATOM  12197  C    LEU E 341     -50.754 -11.678 -73.385  1.00 25.06      A   C
ATOM  12198  O    LEU E 341     -50.915 -10.821 -72.521  1.00 25.07      A   O
ATOM  12199  CB   LEU E 341     -50.770  -9.810 -75.050  1.00 25.10      A   C
ATOM  12200  CG   LEU E 341     -49.470  -9.143 -75.485  1.00 25.30      A   C
ATOM  12201  CD1  LEU E 341     -49.687  -7.645 -75.557  1.00 25.55      A   C
ATOM  12202  CD2  LEU E 341     -48.311  -9.487 -74.561  1.00 25.07      A   C
ATOM  12203  N    ILE E 342     -50.549 -12.961 -73.115  1.00 25.14      A   N
ATOM  12204  CA   ILE E 342     -50.521 -13.507 -71.758  1.00 25.20      A   C
ATOM  12205  C    ILE E 342     -49.180 -14.188 -71.542  1.00 25.52      A   C
ATOM  12206  O    ILE E 342     -48.716 -14.932 -72.413  1.00 25.74      A   O
ATOM  12207  CB   ILE E 342     -51.682 -14.516 -71.537  1.00 25.03      A   C
ATOM  12208  CG1  ILE E 342     -51.681 -15.074 -70.116  1.00 24.87      A   C
ATOM  12209  CG2  ILE E 342     -51.636 -15.648 -72.558  1.00 24.98      A   C
ATOM  12210  CD1  ILE E 342     -52.964 -15.793 -69.765  1.00 24.61      A   C
ATOM  12211  N    SER E 343     -48.544 -13.926 -70.402  1.00 25.79      A   N
ATOM  12212  CA   SER E 343     -47.226 -14.512 -70.159  1.00 26.23      A   C
ATOM  12213  C    SER E 343     -47.339 -15.997 -69.875  1.00 26.40      A   C
ATOM  12214  O    SER E 343     -48.196 -16.428 -69.109  1.00 26.31      A   O
ATOM  12215  CB   SER E 343     -46.456 -13.796 -69.044  1.00 26.33      A   C
ATOM  12216  OG   SER E 343     -47.021 -14.041 -67.777  1.00 26.95      A   O
ATOM  12217  N    THR E 344     -46.490 -16.763 -70.547  1.00 26.74      A   N
ATOM  12218  CA   THR E 344     -46.344 -18.177 -70.298  1.00 27.09      A   C
ATOM  12219  C    THR E 344     -44.855 -18.395 -70.042  1.00 27.52      A   C
ATOM  12220  O    THR E 344     -44.038 -18.147 -70.933  1.00 27.64      A   O
```

FIGURE 1 (cont'd)

```
ATOM  12221  CB   THR E 344     -46.841 -19.020 -71.483  1.00 27.02      A  C
ATOM  12222  OG1  THR E 344     -47.179 -18.152 -72.571  1.00 26.76      A  O
ATOM  12223  N    PRO E 345     -44.494 -18.854 -68.822  1.00 27.85      A  N
ATOM  12224  CA   PRO E 345     -45.394 -19.338 -67.765  1.00 27.90      A  C
ATOM  12225  C    PRO E 345     -46.117 -18.226 -67.022  1.00 27.69      A  C
ATOM  12226  O    PRO E 345     -45.784 -17.047 -67.198  1.00 27.45      A  O
ATOM  12227  CB   PRO E 345     -44.450 -20.081 -66.807  1.00 28.16      A  C
ATOM  12228  CG   PRO E 345     -43.054 -19.952 -67.394  1.00 28.22      A  C
ATOM  12229  CD   PRO E 345     -43.099 -18.831 -68.360  1.00 27.98      A  C
ATOM  12230  N    PHE E 346     -47.106 -18.606 -66.215  1.00 27.65      A  N
ATOM  12231  CA   PHE E 346     -47.809 -17.652 -65.368  1.00 27.82      A  C
ATOM  12232  C    PHE E 346     -46.874 -17.065 -64.292  1.00 28.05      A  C
ATOM  12233  O    PHE E 346     -45.887 -17.710 -63.914  1.00 28.42      A  O
ATOM  12234  CB   PHE E 346     -49.010 -18.314 -64.694  1.00 27.85      A  C
ATOM  12235  CG   PHE E 346     -50.067 -18.785 -65.637  1.00 27.98      A  C
ATOM  12236  CD1  PHE E 346     -50.098 -18.358 -66.953  1.00 27.84      A  C
ATOM  12237  CD2  PHE E 346     -51.063 -19.639 -65.190  1.00 28.59      A  C
ATOM  12238  CE1  PHE E 346     -51.096 -18.788 -67.819  1.00 27.78      A  C
ATOM  12239  CE2  PHE E 346     -52.069 -20.079 -66.049  1.00 28.49      A  C
ATOM  12240  CZ   PHE E 346     -52.085 -19.649 -67.366  1.00 28.00      A  C
ATOM  12241  N    PRO E 347     -47.180 -15.849 -63.786  1.00 28.02      A  N
ATOM  12242  CA   PRO E 347     -46.400 -15.225 -62.715  1.00 28.41      A  C
ATOM  12243  C    PRO E 347     -46.237 -16.143 -61.506  1.00 29.02      A  C
ATOM  12244  O    PRO E 347     -47.177 -16.855 -61.160  1.00 29.18      A  O
ATOM  12245  CB   PRO E 347     -47.266 -14.032 -62.319  1.00 28.17      A  C
ATOM  12246  CG   PRO E 347     -48.023 -13.712 -63.516  1.00 27.71      A  C
ATOM  12247  CD   PRO E 347     -48.312 -15.001 -64.185  1.00 27.71      A  C
ATOM  12248  N    ALA E 348     -45.071 -16.128 -60.865  1.00 29.66      A  N
ATOM  12249  CA   ALA E 348     -44.864 -16.951 -59.674  1.00 30.33      A  C
ATOM  12250  C    ALA E 348     -45.978 -16.725 -58.643  1.00 30.62      A  C
ATOM  12251  O    ALA E 348     -46.472 -17.678 -58.008  1.00 30.72      A  O
ATOM  12252  CB   ALA E 348     -43.514 -16.666 -59.070  1.00 30.62      A  C
ATOM  12253  N    VAL E 349     -46.378 -15.454 -58.526  1.00 30.73      A  N
ATOM  12254  CA   VAL E 349     -47.412 -14.995 -57.595  1.00 30.90      A  C
ATOM  12255  C    VAL E 349     -48.847 -15.243 -58.077  1.00 30.96      A  C
ATOM  12256  O    VAL E 349     -49.782 -14.620 -57.573  1.00 31.10      A  O
ATOM  12257  CB   VAL E 349     -47.246 -13.481 -57.245  1.00 30.84      A  C
ATOM  12258  CG1  VAL E 349     -45.948 -13.249 -56.531  1.00 31.42      A  C
ATOM  12259  CG2  VAL E 349     -47.327 -12.603 -58.488  1.00 30.43      A  C
ATOM  12260  N    TRP E 350     -49.033 -16.167 -59.015  1.00 31.03      A  N
ATOM  12261  CA   TRP E 350     -50.337 -16.324 -59.653  1.00 31.11      A  C
ATOM  12262  C    TRP E 350     -51.355 -16.992 -58.751  1.00 31.48      A  C
ATOM  12263  O    TRP E 350     -51.033 -17.970 -58.070  1.00 31.76      A  O
ATOM  12264  CB   TRP E 350     -50.206 -17.100 -60.958  1.00 30.94      A  C
ATOM  12265  CG   TRP E 350     -51.479 -17.186 -61.743  1.00 30.51      A  C
ATOM  12266  CD1  TRP E 350     -52.121 -16.166 -62.374  1.00 30.22      A  C
ATOM  12267  CD2  TRP E 350     -52.261 -18.362 -61.987  1.00 30.16      A  C
ATOM  12268  CE2  TRP E 350     -53.360 -17.978 -62.769  1.00 29.90      A  C
ATOM  12269  CE3  TRP E 350     -52.140 -19.700 -61.612  1.00 30.19      A  C
ATOM  12270  NE1  TRP E 350     -53.255 -16.633 -62.994  1.00 29.98      A  N
ATOM  12271  CZ2  TRP E 350     -54.326 -18.877 -63.178  1.00 29.64      A  C
ATOM  12272  CZ3  TRP E 350     -53.103 -20.591 -62.023  1.00 30.00      A  C
ATOM  12273  CH2  TRP E 350     -54.180 -20.178 -62.796  1.00 29.66      A  C
ATOM  12274  N    HIS E 351     -52.576 -16.455 -58.761  1.00 31.78      A  N
ATOM  12275  CA   HIS E 351     -53.692 -16.989 -57.981  1.00 32.35      A  C
ATOM  12276  C    HIS E 351     -53.309 -17.248 -56.520  1.00 32.92      A  C
ATOM  12277  O    HIS E 351     -53.620 -18.301 -55.961  1.00 33.18      A  O
ATOM  12278  CB   HIS E 351     -54.263 -18.245 -58.651  1.00 32.35      A  C
ATOM  12279  CG   HIS E 351     -55.242 -17.954 -59.750  1.00 32.41      A  C
ATOM  12280  CD2  HIS E 351     -55.465 -16.829 -60.469  1.00 32.05      A  C
ATOM  12281  ND1  HIS E 351     -56.155 -18.885 -60.202  1.00 32.53      A  N
ATOM  12282  CE1  HIS E 351     -56.893 -18.345 -61.155  1.00 32.26      A  C
ATOM  12283  NE2  HIS E 351     -56.489 -17.101 -61.342  1.00 31.83      A  N
ATOM  12284  N    THR E 352     -52.624 -16.271 -55.921  1.00 33.37      A  N
ATOM  12285  CA   THR E 352     -52.208 -16.309 -54.514  1.00 33.93      A  C
```

FIGURE 1 (cont'd)

```
ATOM  12286  C    THR E 352     -52.224 -14.892 -53.925  1.00 34.19      A    C
ATOM  12287  O    THR E 352     -52.028 -13.938 -54.667  1.00 33.98      A    O
ATOM  12288  CB   THR E 352     -50.806 -16.976 -54.342  1.00 34.03      A    C
ATOM  12289  CG2  THR E 352     -49.909 -16.634 -55.462  1.00 33.53      A    C
ATOM  12290  OG1  THR E 352     -50.181 -16.514 -53.143  1.00 34.79      A    O
ATOM  12291  N    PRO E 353     -52.457 -14.751 -52.595  1.00 34.70      A    N
ATOM  12292  CA   PRO E 353     -52.416 -13.469 -51.882  1.00 34.79      A    C
ATOM  12293  C    PRO E 353     -51.177 -12.648 -52.210  1.00 34.58      A    C
ATOM  12294  O    PRO E 353     -51.183 -11.437 -52.036  1.00 34.61      A    O
ATOM  12295  CB   PRO E 353     -52.335 -13.891 -50.422  1.00 35.20      A    C
ATOM  12296  CG   PRO E 353     -52.998 -15.161 -50.379  1.00 35.51      A    C
ATOM  12297  CD   PRO E 353     -52.732 -15.856 -51.663  1.00 34.97      A    C
ATOM  12298  N    ALA E 354     -50.131 -13.313 -52.684  1.00 34.29      A    N
ATOM  12299  CA   ALA E 354     -48.889 -12.665 -53.054  1.00 34.03      A    C
ATOM  12300  C    ALA E 354     -49.021 -11.688 -54.234  1.00 33.78      A    C
ATOM  12301  O    ALA E 354     -48.225 -10.755 -54.353  1.00 33.73      A    O
ATOM  12302  CB   ALA E 354     -47.859 -13.711 -53.355  1.00 34.06      A    C
ATOM  12303  N    ASP E 355     -50.017 -11.904 -55.097  1.00 33.56      A    N
ATOM  12304  CA   ASP E 355     -50.263 -11.041 -56.267  1.00 33.33      A    C
ATOM  12305  C    ASP E 355     -50.804  -9.682 -55.840  1.00 33.48      A    C
ATOM  12306  O    ASP E 355     -52.005  -9.420 -55.936  1.00 33.34      A    O
ATOM  12307  CB   ASP E 355     -51.232 -11.708 -57.262  1.00 33.04      A    C
ATOM  12308  CG   ASP E 355     -51.263 -11.017 -58.629  1.00 32.51      A    C
ATOM  12309  OD1  ASP E 355     -50.593  -9.975 -58.799  1.00 32.67      A    O
ATOM  12310  OD2  ASP E 355     -51.960 -11.526 -59.537  1.00 31.61      A    O
ATOM  12311  N    THR E 356     -49.901  -8.833 -55.362  1.00 33.76      A    N
ATOM  12312  CA   THR E 356     -50.239  -7.489 -54.933  1.00 33.95      A    C
ATOM  12313  C    THR E 356     -49.262  -6.516 -55.563  1.00 34.39      A    C
ATOM  12314  O    THR E 356     -48.322  -6.930 -56.233  1.00 34.31      A    O
ATOM  12315  CB   THR E 356     -50.209  -7.363 -53.398  1.00 33.36      A    C
ATOM  12316  OG1  THR E 356     -48.913  -7.724 -52.908  1.00 33.34      A    O
ATOM  12317  N    GLU E 357     -49.502  -5.224 -55.355  1.00 35.03      A    N
ATOM  12318  CA   GLU E 357     -48.641  -4.147 -55.865  1.00 35.55      A    C
ATOM  12319  C    GLU E 357     -47.164  -4.376 -55.523  1.00 35.90      A    C
ATOM  12320  O    GLU E 357     -46.300  -4.218 -56.377  1.00 35.83      A    O
ATOM  12321  CB   GLU E 357     -49.117  -2.783 -55.330  1.00 35.75      A    C
ATOM  12322  CG   GLU E 357     -48.255  -1.579 -55.731  1.00 36.37      A    C
ATOM  12323  CD   GLU E 357     -48.834  -0.240 -55.289  1.00 37.42      A    C
ATOM  12324  OE1  GLU E 357     -49.921  -0.210 -54.661  1.00 38.18      A    O
ATOM  12325  OE2  GLU E 357     -48.196   0.793 -55.580  1.00 37.74      A    O
ATOM  12326  N    VAL E 358     -46.898  -4.767 -54.276  1.00 36.41      A    N
ATOM  12327  CA   VAL E 358     -45.546  -4.986 -53.765  1.00 36.81      A    C
ATOM  12328  C    VAL E 358     -44.662  -5.884 -54.635  1.00 36.65      A    C
ATOM  12329  O    VAL E 358     -43.435  -5.757 -54.600  1.00 36.88      A    O
ATOM  12330  CB   VAL E 358     -45.592  -5.583 -52.345  1.00 37.17      A    C
ATOM  12331  CG1  VAL E 358     -44.809  -4.709 -51.384  1.00 37.98      A    C
ATOM  12332  N    ASN E 359     -45.283  -6.776 -55.414  1.00 36.27      A    N
ATOM  12333  CA   ASN E 359     -44.553  -7.826 -56.164  1.00 35.93      A    C
ATOM  12334  C    ASN E 359     -44.488  -7.638 -57.687  1.00 35.35      A    C
ATOM  12335  O    ASN E 359     -43.987  -8.510 -58.407  1.00 35.23      A    O
ATOM  12336  CB   ASN E 359     -45.112  -9.223 -55.834  1.00 36.14      A    C
ATOM  12337  CG   ASN E 359     -44.873  -9.639 -54.386  1.00 37.12      A    C
ATOM  12338  ND2  ASN E 359     -44.059  -8.874 -53.668  1.00 38.08      A    N
ATOM  12339  OD1  ASN E 359     -45.414 -10.646 -53.926  1.00 37.71      A    O
ATOM  12340  N    LEU E 360     -45.006  -6.508 -58.168  1.00 34.83      A    N
ATOM  12341  CA   LEU E 360     -44.857  -6.116 -59.568  1.00 34.33      A    C
ATOM  12342  C    LEU E 360     -43.451  -5.562 -59.790  1.00 34.37      A    C
ATOM  12343  O    LEU E 360     -42.805  -5.100 -58.851  1.00 34.85      A    O
ATOM  12344  CB   LEU E 360     -45.903  -5.060 -59.951  1.00 34.02      A    C
ATOM  12345  CG   LEU E 360     -47.372  -5.339 -59.621  1.00 33.48      A    C
ATOM  12346  CD1  LEU E 360     -48.226  -4.134 -59.929  1.00 32.90      A    C
ATOM  12347  CD2  LEU E 360     -47.876  -6.562 -60.369  1.00 33.10      A    C
ATOM  12348  N    HIS E 361     -42.973  -5.628 -61.027  1.00 34.09      A    N
ATOM  12349  CA   HIS E 361     -41.704  -5.008 -61.397  1.00 33.89      A    C
ATOM  12350  C    HIS E 361     -42.011  -3.743 -62.176  1.00 34.18      A    C
```

FIGURE 1 (cont'd)

```
ATOM  12351  O    HIS E 361     -42.167   -3.786  -63.391  1.00 34.00      A  O
ATOM  12352  CB   HIS E 361     -40.861   -5.953  -62.239  1.00 33.54      A  C
ATOM  12353  CG   HIS E 361     -39.398   -5.675  -62.171  1.00 32.69      A  C
ATOM  12354  ND1  HIS E 361     -38.797   -4.688  -62.910  1.00 31.51      A  N
ATOM  12355  CE1  HIS E 361     -37.506   -4.693  -62.635  1.00 31.58      A  C
ATOM  12356  N    PRO E 362     -42.118   -2.605  -61.472  1.00 34.68      A  N
ATOM  12357  CA   PRO E 362     -42.527   -1.360  -62.120  1.00 34.87      A  C
ATOM  12358  C    PRO E 362     -41.815   -1.077  -63.461  1.00 34.86      A  C
ATOM  12359  O    PRO E 362     -42.488   -0.711  -64.422  1.00 34.73      A  O
ATOM  12360  CB   PRO E 362     -42.216   -0.297  -61.059  1.00 35.19      A  C
ATOM  12361  CG   PRO E 362     -42.342   -1.025  -59.767  1.00 35.30      A  C
ATOM  12362  CD   PRO E 362     -41.842   -2.411  -60.034  1.00 35.00      A  C
ATOM  12363  N    PRO E 363     -40.470   -1.244  -63.535  1.00 35.01      A  N
ATOM  12364  CA   PRO E 363     -39.830   -1.112  -64.845  1.00 34.98      A  C
ATOM  12365  C    PRO E 363     -40.514   -1.949  -65.910  1.00 34.62      A  C
ATOM  12366  O    PRO E 363     -40.956   -1.405  -66.912  1.00 34.59      A  O
ATOM  12367  CB   PRO E 363     -38.403   -1.603  -64.589  1.00 35.27      A  C
ATOM  12368  CG   PRO E 363     -38.131   -1.190  -63.183  1.00 35.68      A  C
ATOM  12369  CD   PRO E 363     -39.460   -1.258  -62.450  1.00 35.19      A  C
ATOM  12370  N    THR E 364     -40.632   -3.251  -65.678  1.00 34.29      A  N
ATOM  12371  CA   THR E 364     -41.249   -4.146  -66.652  1.00 33.94      A  C
ATOM  12372  C    THR E 364     -42.606   -3.601  -67.085  1.00 33.84      A  C
ATOM  12373  O    THR E 364     -42.942   -3.638  -68.260  1.00 33.68      A  O
ATOM  12374  CB   THR E 364     -41.372   -5.596  -66.112  1.00 33.87      A  C
ATOM  12375  CG2  THR E 364     -41.967   -6.514  -67.155  1.00 33.51      A  C
ATOM  12376  OG1  THR E 364     -40.077   -6.100  -65.743  1.00 34.08      A  O
ATOM  12377  N    VAL E 365     -43.364   -3.062  -66.137  1.00 33.96      A  N
ATOM  12378  CA   VAL E 365     -44.673   -2.491  -66.436  1.00 34.08      A  C
ATOM  12379  C    VAL E 365     -44.548   -1.388  -67.477  1.00 34.27      A  C
ATOM  12380  O    VAL E 365     -45.189   -1.436  -68.521  1.00 34.10      A  O
ATOM  12381  CB   VAL E 365     -45.379   -1.948  -65.168  1.00 34.10      A  C
ATOM  12382  CG1  VAL E 365     -45.816   -3.085  -64.273  1.00 34.03      A  C
ATOM  12383  CG2  VAL E 365     -46.581   -1.101  -65.535  1.00 33.95      A  C
ATOM  12384  N    HIS E 366     -43.699   -0.411  -67.192  1.00 34.68      A  N
ATOM  12385  CA   HIS E 366     -43.558    0.756  -68.048  1.00 35.16      A  C
ATOM  12386  C    HIS E 366     -43.012    0.406  -69.426  1.00 35.36      A  C
ATOM  12387  O    HIS E 366     -43.486    0.938  -70.442  1.00 35.51      A  O
ATOM  12388  CB   HIS E 366     -42.711    1.820  -67.358  1.00 35.37      A  C
ATOM  12389  CG   HIS E 366     -43.312    2.309  -66.078  1.00 35.47      A  C
ATOM  12390  CD2  HIS E 366     -42.892    2.205  -64.795  1.00 34.51      A  C
ATOM  12391  ND1  HIS E 366     -44.519    2.976  -66.033  1.00 35.52      A  N
ATOM  12392  CE1  HIS E 366     -44.807    3.278  -64.779  1.00 35.50      A  C
ATOM  12393  NE2  HIS E 366     -43.838    2.819  -64.007  1.00 34.85      A  N
ATOM  12394  N    ASN E 367     -42.037   -0.498  -69.458  1.00 35.39      A  N
ATOM  12395  CA   ASN E 367     -41.568   -1.065  -70.712  1.00 35.43      A  C
ATOM  12396  C    ASN E 367     -42.732   -1.549  -71.578  1.00 35.25      A  C
ATOM  12397  O    ASN E 367     -42.845   -1.180  -72.754  1.00 35.38      A  O
ATOM  12398  CB   ASN E 367     -40.606   -2.218  -70.449  1.00 35.50      A  C
ATOM  12399  CG   ASN E 367     -39.268   -1.755  -69.934  1.00 36.11      A  C
ATOM  12400  ND2  ASN E 367     -38.318   -2.674  -69.864  1.00 36.20      A  N
ATOM  12401  OD1  ASN E 367     -39.084   -0.586  -69.601  1.00 37.03      A  O
ATOM  12402  N    LEU E 368     -43.610   -2.349  -70.980  1.00 34.95      A  N
ATOM  12403  CA   LEU E 368     -44.727   -2.928  -71.707  1.00 34.73      A  C
ATOM  12404  C    LEU E 368     -45.644   -1.854  -72.296  1.00 34.89      A  C
ATOM  12405  O    LEU E 368     -46.210   -2.027  -73.382  1.00 35.02      A  O
ATOM  12406  CB   LEU E 368     -45.509   -3.895  -70.812  1.00 34.36      A  C
ATOM  12407  CG   LEU E 368     -44.874   -5.242  -70.465  1.00 33.70      A  C
ATOM  12408  CD1  LEU E 368     -45.697   -5.933  -69.421  1.00 33.47      A  C
ATOM  12409  CD2  LEU E 368     -44.738   -6.129  -71.675  1.00 32.84      A  C
ATOM  12410  N    ALA E 369     -45.770   -0.744  -71.579  1.00 34.15      A  N
ATOM  12411  CA   ALA E 369     -46.623    0.345  -72.002  1.00 33.51      A  C
ATOM  12412  C    ALA E 369     -45.993    1.109  -73.153  1.00 34.48      A  C
ATOM  12413  O    ALA E 369     -46.684    1.529  -74.082  1.00 35.65      A  O
ATOM  12414  CB   ALA E 369     -46.902    1.262  -70.843  1.00 24.55      A  C
ATOM  12415  N    ARG E 370     -44.678    1.280  -73.085  1.00 35.13      A  N
```

FIGURE 1 (cont'd)

```
ATOM  12416  CA   ARG E 370     -43.942   1.900 -74.171  1.00 34.81      A  C
ATOM  12417  C    ARG E 370     -44.099   1.063 -75.443  1.00 34.21      A  C
ATOM  12418  O    ARG E 370     -44.462   1.591 -76.489  1.00 34.11      A  O
ATOM  12419  CB   ARG E 370     -42.475   2.113 -73.782  1.00 35.11      A  C
ATOM  12420  CG   ARG E 370     -42.271   3.116 -72.623  1.00 35.41      A  C
ATOM  12421  CD   ARG E 370     -40.780   3.429 -72.369  1.00 35.75      A  C
ATOM  12422  NE   ARG E 370     -40.573   4.477 -71.366  1.00 35.86      A  N
ATOM  12423  CZ   ARG E 370     -39.520   5.290 -71.333  1.00 35.99      A  C
ATOM  12424  N    ILE E 371     -43.885  -0.247 -75.328  1.00 33.47      A  N
ATOM  12425  CA   ILE E 371     -44.076  -1.178 -76.443  1.00 32.83      A  C
ATOM  12426  C    ILE E 371     -45.494  -1.110 -76.997  1.00 32.75      A  C
ATOM  12427  O    ILE E 371     -45.688  -0.986 -78.199  1.00 32.82      A  O
ATOM  12428  CB   ILE E 371     -43.718  -2.611 -76.044  1.00 32.49      A  C
ATOM  12429  CG1  ILE E 371     -42.220  -2.699 -75.775  1.00 32.48      A  C
ATOM  12430  CG2  ILE E 371     -44.091  -3.572 -77.135  1.00 32.00      A  C
ATOM  12431  CD1  ILE E 371     -41.771  -3.974 -75.114  1.00 32.21      A  C
ATOM  12432  N    LEU E 372     -46.480  -1.168 -76.111  1.00 32.61      A  N
ATOM  12433  CA   LEU E 372     -47.887  -1.111 -76.505  1.00 32.46      A  C
ATOM  12434  C    LEU E 372     -48.267   0.190 -77.206  1.00 32.76      A  C
ATOM  12435  O    LEU E 372     -48.920   0.167 -78.254  1.00 32.68      A  O
ATOM  12436  CB   LEU E 372     -48.785  -1.359 -75.291  1.00 32.09      A  C
ATOM  12437  CG   LEU E 372     -49.368  -2.758 -75.070  1.00 31.34      A  C
ATOM  12438  CD1  LEU E 372     -48.724  -3.862 -75.887  1.00 30.79      A  C
ATOM  12439  CD2  LEU E 372     -49.365  -3.098 -73.602  1.00 30.87      A  C
ATOM  12440  N    ALA E 373     -47.844   1.315 -76.625  1.00 33.20      A  N
ATOM  12441  CA   ALA E 373     -48.167   2.653 -77.150  1.00 33.59      A  C
ATOM  12442  C    ALA E 373     -47.657   2.833 -78.569  1.00 33.86      A  C
ATOM  12443  O    ALA E 373     -48.350   3.402 -79.407  1.00 34.01      A  O
ATOM  12444  CB   ALA E 373     -47.611   3.737 -76.246  1.00 33.69      A  C
ATOM  12445  N    VAL E 374     -46.448   2.337 -78.826  1.00 34.03      A  N
ATOM  12446  CA   VAL E 374     -45.875   2.360 -80.162  1.00 34.26      A  C
ATOM  12447  C    VAL E 374     -46.698   1.475 -81.061  1.00 34.16      A  C
ATOM  12448  O    VAL E 374     -47.097   1.896 -82.132  1.00 34.43      A  O
ATOM  12449  CB   VAL E 374     -44.414   1.908 -80.169  1.00 34.34      A  C
ATOM  12450  CG1  VAL E 374     -43.937   1.638 -81.582  1.00 34.56      A  C
ATOM  12451  CG2  VAL E 374     -43.545   2.958 -79.513  1.00 34.78      A  C
ATOM  12452  N    PHE E 375     -46.972   0.258 -80.608  1.00 33.90      A  N
ATOM  12453  CA   PHE E 375     -47.785  -0.671 -81.381  1.00 33.75      A  C
ATOM  12454  C    PHE E 375     -49.125  -0.055 -81.753  1.00 34.06      A  C
ATOM  12455  O    PHE E 375     -49.524  -0.090 -82.909  1.00 34.16      A  O
ATOM  12456  CB   PHE E 375     -48.007  -1.980 -80.624  1.00 33.32      A  C
ATOM  12457  CG   PHE E 375     -48.844  -2.973 -81.368  1.00 32.58      A  C
ATOM  12458  CD1  PHE E 375     -48.263  -4.043 -82.012  1.00 32.45      A  C
ATOM  12459  CD2  PHE E 375     -50.214  -2.837 -81.425  1.00 32.08      A  C
ATOM  12460  CE1  PHE E 375     -49.039  -4.967 -82.703  1.00 32.40      A  C
ATOM  12461  CE2  PHE E 375     -50.990  -3.744 -82.114  1.00 32.24      A  C
ATOM  12462  CZ   PHE E 375     -50.402  -4.817 -82.753  1.00 32.32      A  C
ATOM  12463  N    LEU E 376     -49.815   0.505 -80.766  1.00 34.43      A  N
ATOM  12464  CA   LEU E 376     -51.142   1.071 -80.977  1.00 34.86      A  C
ATOM  12465  C    LEU E 376     -51.059   2.150 -82.036  1.00 35.65      A  C
ATOM  12466  O    LEU E 376     -51.899   2.216 -82.926  1.00 35.76      A  O
ATOM  12467  CB   LEU E 376     -51.703   1.628 -79.667  1.00 34.56      A  C
ATOM  12468  CG   LEU E 376     -53.205   1.444 -79.417  1.00 33.84      A  C
ATOM  12469  N    ALA E 377     -50.014   2.969 -81.942  1.00 36.57      A  N
ATOM  12470  CA   ALA E 377     -49.757   4.059 -82.886  1.00 37.45      A  C
ATOM  12471  C    ALA E 377     -49.438   3.564 -84.295  1.00 37.91      A  C
ATOM  12472  O    ALA E 377     -49.994   4.069 -85.270  1.00 38.21      A  O
ATOM  12473  CB   ALA E 377     -48.638   4.971 -82.368  1.00 37.59      A  C
ATOM  12474  N    GLU E 378     -48.542   2.583 -84.398  1.00 38.21      A  N
ATOM  12475  CA   GLU E 378     -48.200   1.986 -85.687  1.00 38.60      A  C
ATOM  12476  C    GLU E 378     -49.415   1.304 -86.334  1.00 38.60      A  C
ATOM  12477  O    GLU E 378     -49.715   1.575 -87.493  1.00 38.93      A  O
ATOM  12478  CB   GLU E 378     -47.002   1.035 -85.570  1.00 38.68      A  C
ATOM  12479  CG   GLU E 378     -45.653   1.753 -85.437  1.00 39.89      A  C
ATOM  12480  CD   GLU E 378     -44.422   0.834 -85.539  1.00 41.28      A  C
```

FIGURE 1 (cont'd)

```
ATOM  12481  OE1  GLU  E  378    -44.568   -0.368  -85.845  1.00  41.77    A    O
ATOM  12482  OE2  GLU  E  378    -43.289    1.317  -85.314  1.00  41.91    A    O
ATOM  12483  N    TYR  E  379    -50.132    0.461  -85.581  1.00  38.45    A    N
ATOM  12484  CA   TYR  E  379    -51.310   -0.269  -86.096  1.00  38.40    A    C
ATOM  12485  C    TYR  E  379    -52.373    0.665  -86.648  1.00  38.94    A    C
ATOM  12486  O    TYR  E  379    -52.917    0.429  -87.719  1.00  39.09    A    O
ATOM  12487  CB   TYR  E  379    -51.926   -1.185  -85.025  1.00  37.81    A    C
ATOM  12488  CG   TYR  E  379    -52.994   -2.133  -85.545  1.00  37.02    A    C
ATOM  12489  CD1  TYR  E  379    -52.721   -3.480  -85.753  1.00  36.31    A    C
ATOM  12490  CD2  TYR  E  379    -54.278   -1.680  -85.827  1.00  36.79    A    C
ATOM  12491  CE1  TYR  E  379    -53.699   -4.344  -86.232  1.00  36.14    A    C
ATOM  12492  CE2  TYR  E  379    -55.256   -2.531  -86.310  1.00  36.51    A    C
ATOM  12493  CZ   TYR  E  379    -54.963   -3.856  -86.505  1.00  36.19    A    C
ATOM  12494  OH   TYR  E  379    -55.947   -4.680  -86.978  1.00  35.90    A    O
ATOM  12495  N    LEU  E  380    -52.656    1.728  -85.911  1.00  39.62    A    N
ATOM  12496  CA   LEU  E  380    -53.686    2.685  -86.299  1.00  40.44    A    C
ATOM  12497  C    LEU  E  380    -53.176    3.832  -87.180  1.00  41.23    A    C
ATOM  12498  O    LEU  E  380    -53.858    4.847  -87.353  1.00  41.78    A    O
ATOM  12499  CB   LEU  E  380    -54.395    3.229  -85.050  1.00  40.17    A    C
ATOM  12500  CG   LEU  E  380    -55.782    2.702  -84.662  1.00  39.75    A    C
ATOM  12501  CD1  LEU  E  380    -56.003    1.226  -85.007  1.00  39.37    A    C
ATOM  12502  CD2  LEU  E  380    -56.027    2.961  -83.181  1.00  39.47    A    C
ATOM  12503  N    GLY  E  381    -52.003    3.665  -87.771  1.00  39.37    A    N
ATOM  12504  CA   GLY  E  381    -51.428    4.745  -88.548  1.00  37.93    A    C
ATOM  12505  C    GLY  E  381    -51.601    6.080  -87.843  1.00  37.10    A    C
ATOM  12506  O    GLY  E  381    -51.843    7.097  -88.481  1.00  36.96    A    O
ATOM  12507  N    LEU  E  382    -51.495    6.072  -86.518  1.00  36.74    A    N
ATOM  12508  CA   LEU  E  382    -51.483    7.307  -85.746  1.00  36.83    A    C
ATOM  12509  C    LEU  E  382    -50.285    8.163  -86.142  1.00  37.11    A    C
ATOM  12510  O    LEU  E  382    -50.229    9.343  -85.788  1.00  37.51    A    O
ATOM  12511  CB   LEU  E  382    -51.408    7.019  -84.246  1.00  36.59    A    C
ATOM  12512  CG   LEU  E  382    -52.625    6.494  -83.496  1.00  36.51    A    C
ATOM  12513  CD1  LEU  E  382    -52.318    6.513  -82.023  1.00  36.02    A    C
ATOM  12514  CD2  LEU  E  382    -53.844    7.344  -83.784  1.00  36.86    A    C
ATOM  12515  OXT  LEU  E  382    -49.347    7.698  -86.805  1.00  37.19    A    O
TER   12516       LEU  E  382
ATOM  12517  N    SER  F   75    -11.165  -49.574   19.493  1.00  47.41    A    N
ATOM  12518  CA   SER  F   75    -11.747  -48.269   19.027  1.00  47.97    A    C
ATOM  12519  C    SER  F   75    -10.767  -47.522   18.108  1.00  49.12    A    C
ATOM  12520  O    SER  F   75     -9.666  -48.020   17.863  1.00  49.21    A    O
ATOM  12521  CB   SER  F   75    -12.204  -47.403   20.222  1.00  47.43    A    C
ATOM  12522  OG   SER  F   75    -11.386  -47.584   21.379  1.00  47.05    A    O
ATOM  12523  N    LEU  F   76    -11.171  -46.357   17.588  1.00  50.88    A    N
ATOM  12524  CA   LEU  F   76    -10.327  -45.542   16.689  1.00  52.53    A    C
ATOM  12525  C    LEU  F   76    -10.933  -44.155   16.485  1.00  53.56    A    C
ATOM  12526  O    LEU  F   76    -12.050  -44.057   15.995  1.00  53.58    A    O
ATOM  12527  CB   LEU  F   76    -10.169  -46.227   15.318  1.00  52.56    A    C
ATOM  12528  CG   LEU  F   76     -8.911  -46.004   14.458  1.00  52.60    A    C
ATOM  12529  CD1  LEU  F   76     -8.847  -46.969   13.288  1.00  52.35    A    C
ATOM  12530  CD2  LEU  F   76     -8.802  -44.594   13.940  1.00  53.09    A    C
ATOM  12531  N    PRO  F   77    -10.195  -43.075   16.821  1.00  54.57    A    N
ATOM  12532  CA   PRO  F   77    -10.899  -41.791   16.749  1.00  55.47    A    C
ATOM  12533  C    PRO  F   77    -11.025  -41.217   15.328  1.00  55.75    A    C
ATOM  12534  O    PRO  F   77    -10.152  -41.439   14.487  1.00  55.66    A    O
ATOM  12535  CB   PRO  F   77    -10.053  -40.877   17.638  1.00  56.07    A    C
ATOM  12536  CG   PRO  F   77     -8.661  -41.425   17.533  1.00  55.92    A    C
ATOM  12537  CD   PRO  F   77     -8.780  -42.908   17.220  1.00  54.93    A    C
ATOM  12538  N    GLU  F   78    -12.110  -40.476   15.089  1.00  55.94    A    N
ATOM  12539  CA   GLU  F   78    -12.444  -39.890   13.769  1.00  55.80    A    C
ATOM  12540  C    GLU  F   78    -11.276  -39.282   12.996  1.00  57.06    A    C
ATOM  12541  O    GLU  F   78    -11.135  -39.511   11.790  1.00  57.26    A    O
ATOM  12542  CB   GLU  F   78    -13.567  -38.851   13.890  1.00  53.82    A    C
ATOM  12543  CG   GLU  F   78    -14.927  -39.417   13.589  1.00  51.34    A    C
ATOM  12544  CD   GLU  F   78    -15.998  -38.377   13.543  1.00  52.31    A    C
ATOM  12545  OE1  GLU  F   78    -15.929  -37.496   12.652  1.00  52.45    A    O
```

FIGURE 1 (cont'd)

```
ATOM  12546  OE2  GLU F   78    -16.919 -38.470  14.385  1.00 52.29      A    O
ATOM  12547  N    ALA F   79    -10.459 -38.497  13.696  1.00 58.30      A    N
ATOM  12548  CA   ALA F   79     -9.311 -37.823  13.098  1.00 58.95      A    C
ATOM  12549  C    ALA F   79     -8.354 -38.803  12.411  1.00 58.70      A    C
ATOM  12550  O    ALA F   79     -8.004 -38.611  11.244  1.00 58.83      A    O
ATOM  12551  CB   ALA F   79     -8.577 -36.991  14.156  1.00 59.76      A    C
ATOM  12552  N    ARG F   80     -7.948 -39.846  13.136  1.00 57.97      A    N
ATOM  12553  CA   ARG F   80     -7.051 -40.861  12.602  1.00 56.99      A    C
ATOM  12554  C    ARG F   80     -7.774 -41.727  11.573  1.00 56.72      A    C
ATOM  12555  O    ARG F   80     -7.197 -42.090  10.547  1.00 56.75      A    O
ATOM  12556  CB   ARG F   80     -6.465 -41.715  13.731  1.00 55.29      A    C
ATOM  12557  N    LEU F   81     -9.043 -42.031  11.839  1.00 56.44      A    N
ATOM  12558  CA   LEU F   81     -9.848 -42.873  10.952  1.00 55.86      A    C
ATOM  12559  C    LEU F   81     -9.954 -42.255   9.570  1.00 55.89      A    C
ATOM  12560  O    LEU F   81     -9.633 -42.903   8.583  1.00 55.54      A    O
ATOM  12561  CB   LEU F   81    -11.241 -43.130  11.547  1.00 55.67      A    C
ATOM  12562  CG   LEU F   81    -12.172 -44.152  10.889  1.00 54.88      A    C
ATOM  12563  CD1  LEU F   81    -13.015 -44.863  11.934  1.00 54.68      A    C
ATOM  12564  CD2  LEU F   81    -13.052 -43.482   9.852  1.00 54.77      A    C
ATOM  12565  N    ARG F   82    -10.386 -41.001   9.508  1.00 56.32      A    N
ATOM  12566  CA   ARG F   82    -10.540 -40.306   8.237  1.00 56.77      A    C
ATOM  12567  C    ARG F   82     -9.195 -40.140   7.512  1.00 56.69      A    C
ATOM  12568  O    ARG F   82     -9.142 -40.115   6.277  1.00 56.63      A    O
ATOM  12569  CB   ARG F   82    -11.241 -38.960   8.450  1.00 57.35      A    C
ATOM  12570  CG   ARG F   82    -11.769 -38.323   7.172  1.00 58.27      A    C
ATOM  12571  CD   ARG F   82    -12.745 -37.201   7.461  1.00 59.63      A    C
ATOM  12572  NE   ARG F   82    -14.128 -37.669   7.431  1.00 59.77      A    N
ATOM  12573  CZ   ARG F   82    -14.828 -38.037   8.502  1.00 59.83      A    C
ATOM  12574  NH1  ARG F   82    -14.281 -37.996   9.717  1.00 60.02      A    N
ATOM  12575  NH2  ARG F   82    -16.086 -38.449   8.358  1.00 59.60      A    N
ATOM  12576  N    ARG F   83     -8.121 -40.039   8.297  1.00 56.47      A    N
ATOM  12577  CA   ARG F   83     -6.743 -39.948   7.790  1.00 55.93      A    C
ATOM  12578  C    ARG F   83     -6.281 -41.283   7.188  1.00 55.52      A    C
ATOM  12579  O    ARG F   83     -5.614 -41.309   6.146  1.00 55.70      A    O
ATOM  12580  CB   ARG F   83     -5.813 -39.462   8.917  1.00 54.94      A    C
ATOM  12581  CG   ARG F   83     -4.354 -39.884   8.866  1.00 54.46      A    C
ATOM  12582  CD   ARG F   83     -3.790 -39.771  10.273  1.00 54.57      A    C
ATOM  12583  NE   ARG F   83     -2.469 -40.360  10.426  1.00 54.06      A    N
ATOM  12584  N    VAL F   84     -6.653 -42.381   7.845  1.00 54.72      A    N
ATOM  12585  CA   VAL F   84     -6.336 -43.733   7.381  1.00 53.62      A    C
ATOM  12586  C    VAL F   84     -7.143 -44.093   6.126  1.00 52.98      A    C
ATOM  12587  O    VAL F   84     -6.562 -44.429   5.098  1.00 52.76      A    O
ATOM  12588  CB   VAL F   84     -6.540 -44.778   8.515  1.00 53.49      A    C
ATOM  12589  CG1  VAL F   84     -5.420 -44.674   9.517  1.00 53.54      A    C
ATOM  12590  CG2  VAL F   84     -6.621 -46.200   7.973  1.00 52.78      A    C
ATOM  12591  N    VAL F   85     -8.474 -44.008   6.211  1.00 52.20      A    N
ATOM  12592  CA   VAL F   85     -9.358 -44.240   5.059  1.00 51.38      A    C
ATOM  12593  C    VAL F   85     -8.924 -43.394   3.862  1.00 51.77      A    C
ATOM  12594  O    VAL F   85     -9.110 -43.792   2.715  1.00 51.94      A    O
ATOM  12595  CB   VAL F   85    -10.842 -43.949   5.392  1.00 49.80      A    C
ATOM  12596  N    GLY F   86     -8.328 -42.236   4.147  1.00 52.09      A    N
ATOM  12597  CA   GLY F   86     -7.790 -41.357   3.120  1.00 52.02      A    C
ATOM  12598  C    GLY F   86     -6.497 -41.859   2.508  1.00 51.63      A    C
ATOM  12599  O    GLY F   86     -6.146 -41.471   1.401  1.00 51.85      A    O
ATOM  12600  N    GLN F   87     -5.787 -42.724   3.226  1.00 50.98      A    N
ATOM  12601  CA   GLN F   87     -4.514 -43.261   2.742  1.00 50.24      A    C
ATOM  12602  C    GLN F   87     -4.672 -44.320   1.631  1.00 49.59      A    C
ATOM  12603  O    GLN F   87     -3.713 -44.606   0.907  1.00 49.53      A    O
ATOM  12604  N    LEU F   88     -5.871 -44.897   1.504  1.00 48.76      A    N
ATOM  12605  CA   LEU F   88     -6.174 -45.849   0.429  1.00 48.05      A    C
ATOM  12606  C    LEU F   88     -6.335 -45.086  -0.874  1.00 48.40      A    C
ATOM  12607  O    LEU F   88     -7.090 -44.117  -0.928  1.00 48.63      A    O
ATOM  12608  CB   LEU F   88     -7.466 -46.628   0.712  1.00 47.31      A    C
ATOM  12609  CG   LEU F   88     -7.582 -47.645   1.847  1.00 45.94      A    C
ATOM  12610  CD1  LEU F   88     -9.037 -48.002   1.934  1.00 45.51      A    C
```

FIGURE 1 (cont'd)

```
ATOM  12611  CD2  LEU F  88      -6.756 -48.906   1.620  1.00 45.35      A    C
ATOM  12612  N    ASP F  89      -5.616 -45.507  -1.913  1.00 48.74      A    N
ATOM  12613  CA   ASP F  89      -5.781 -44.920  -3.248  1.00 49.12      A    C
ATOM  12614  C    ASP F  89      -6.608 -45.849  -4.139  1.00 49.19      A    C
ATOM  12615  O    ASP F  89      -6.128 -46.911  -4.555  1.00 48.96      A    O
ATOM  12616  CB   ASP F  89      -4.430 -44.579  -3.898  1.00 49.29      A    C
ATOM  12617  CG   ASP F  89      -4.578 -43.941  -5.292  1.00 49.43      A    C
ATOM  12618  OD1  ASP F  89      -5.625 -44.123  -5.949  1.00 49.47      A    O
ATOM  12619  OD2  ASP F  89      -3.637 -43.259  -5.748  1.00 48.49      A    O
ATOM  12620  N    PRO F  90      -7.862 -45.445  -4.429  1.00 49.44      A    N
ATOM  12621  CA   PRO F  90      -8.803 -46.270  -5.190  1.00 49.35      A    C
ATOM  12622  C    PRO F  90      -8.302 -46.674  -6.582  1.00 49.30      A    C
ATOM  12623  O    PRO F  90      -8.479 -47.834  -6.982  1.00 49.03      A    O
ATOM  12624  CB   PRO F  90     -10.053 -45.380  -5.282  1.00 49.49      A    C
ATOM  12625  CG   PRO F  90      -9.976 -44.510  -4.073  1.00 49.75      A    C
ATOM  12626  CD   PRO F  90      -8.506 -44.205  -3.944  1.00 49.80      A    C
ATOM  12627  N    GLN F  91      -7.682 -45.739  -7.308  1.00 49.50      A    N
ATOM  12628  CA   GLN F  91      -7.166 -46.050  -8.648  1.00 49.57      A    C
ATOM  12629  C    GLN F  91      -5.892 -46.896  -8.584  1.00 48.97      A    C
ATOM  12630  O    GLN F  91      -5.610 -47.638  -9.514  1.00 49.04      A    O
ATOM  12631  CB   GLN F  91      -7.004 -44.802  -9.538  1.00 50.17      A    C
ATOM  12632  CG   GLN F  91      -5.717 -44.006  -9.347  1.00 50.95      A    C
ATOM  12633  N    ARG F  92      -5.144 -46.792  -7.485  1.00 48.13      A    N
ATOM  12634  CA   ARG F  92      -3.988 -47.666  -7.247  1.00 47.12      A    C
ATOM  12635  C    ARG F  92      -4.453 -49.114  -7.062  1.00 46.66      A    C
ATOM  12636  O    ARG F  92      -3.920 -50.025  -7.704  1.00 46.55      A    O
ATOM  12637  CB   ARG F  92      -3.151 -47.176  -6.042  1.00 46.99      A    C
ATOM  12638  CG   ARG F  92      -2.062 -48.139  -5.513  1.00 45.17      A    C
ATOM  12639  CD   ARG F  92      -1.261 -47.548  -4.343  1.00 43.09      A    C
ATOM  12640  NE   ARG F  92      -2.086 -47.239  -3.180  1.00 41.74      A    N
ATOM  12641  N    LEU F  93      -5.453 -49.304  -6.198  1.00 46.08      A    N
ATOM  12642  CA   LEU F  93      -6.047 -50.619  -5.942  1.00 45.47      A    C
ATOM  12643  C    LEU F  93      -6.391 -51.273  -7.268  1.00 45.52      A    C
ATOM  12644  O    LEU F  93      -5.987 -52.405  -7.535  1.00 45.44      A    O
ATOM  12645  CB   LEU F  93      -7.320 -50.478  -5.094  1.00 45.09      A    C
ATOM  12646  CG   LEU F  93      -7.814 -51.569  -4.137  1.00 43.90      A    C
ATOM  12647  CD1  LEU F  93      -7.621 -52.977  -4.644  1.00 42.73      A    C
ATOM  12648  N    TRP F  94      -7.112 -50.527  -8.101  1.00 45.68      A    N
ATOM  12649  CA   TRP F  94      -7.692 -51.054  -9.325  1.00 45.73      A    C
ATOM  12650  C    TRP F  94      -6.676 -51.266 -10.442  1.00 45.72      A    C
ATOM  12651  O    TRP F  94      -6.775 -52.231 -11.202  1.00 45.62      A    O
ATOM  12652  CB   TRP F  94      -8.816 -50.141  -9.812  1.00 45.93      A    C
ATOM  12653  CG   TRP F  94      -9.789 -50.874 -10.647  1.00 46.40      A    C
ATOM  12654  CD1  TRP F  94      -9.700 -51.122 -11.986  1.00 47.12      A    C
ATOM  12655  CD2  TRP F  94     -10.994 -51.493 -10.204  1.00 46.47      A    C
ATOM  12656  CE2  TRP F  94     -11.597 -52.096 -11.335  1.00 46.70      A    C
ATOM  12657  CE3  TRP F  94     -11.631 -51.596  -8.962  1.00 46.26      A    C
ATOM  12658  NE1  TRP F  94     -10.786 -51.852 -12.410  1.00 47.08      A    N
ATOM  12659  CZ2  TRP F  94     -12.806 -52.794 -11.261  1.00 46.61      A    C
ATOM  12660  CZ3  TRP F  94     -12.836 -52.293  -8.885  1.00 46.17      A    C
ATOM  12661  CH2  TRP F  94     -13.410 -52.883 -10.031  1.00 46.33      A    C
ATOM  12662  N    SER F  95      -5.703 -50.363 -10.535  1.00 45.78      A    N
ATOM  12663  CA   SER F  95      -4.807 -50.314 -11.692  1.00 45.76      A    C
ATOM  12664  C    SER F  95      -3.434 -50.934 -11.425  1.00 45.18      A    C
ATOM  12665  O    SER F  95      -2.947 -51.703 -12.246  1.00 45.14      A    O
ATOM  12666  CB   SER F  95      -4.666 -48.879 -12.202  1.00 46.26      A    C
ATOM  12667  OG   SER F  95      -4.788 -48.839 -13.609  1.00 47.16      A    O
ATOM  12668  N    THR F  96      -2.821 -50.598 -10.287  1.00 44.47      A    N
ATOM  12669  CA   THR F  96      -1.497 -51.124  -9.933  1.00 43.82      A    C
ATOM  12670  C    THR F  96      -1.548 -52.554  -9.408  1.00 42.89      A    C
ATOM  12671  O    THR F  96      -0.591 -53.310  -9.590  1.00 43.01      A    O
ATOM  12672  CB   THR F  96      -0.769 -50.261  -8.874  1.00 43.99      A    C
ATOM  12673  OG1  THR F  96      -1.091 -48.882  -9.066  1.00 44.70      A    O
ATOM  12674  N    TYR F  97      -2.652 -52.919  -8.755  1.00 41.60      A    N
ATOM  12675  CA   TYR F  97      -2.756 -54.225  -8.082  1.00 40.25      A    C
```

FIGURE 1 (cont'd)

```
ATOM  12676  C    TYR F  97      -3.780 -55.204  -8.678  1.00 39.85       A  C
ATOM  12677  O    TYR F  97      -3.500 -56.398  -8.802  1.00 39.62       A  O
ATOM  12678  CB   TYR F  97      -2.982 -54.062  -6.568  1.00 39.67       A  C
ATOM  12679  CG   TYR F  97      -1.942 -53.202  -5.907  1.00 38.70       A  C
ATOM  12680  CD1  TYR F  97      -0.582 -53.501  -6.028  1.00 37.64       A  C
ATOM  12681  CD2  TYR F  97      -2.312 -52.067  -5.183  1.00 38.03       A  C
ATOM  12682  CE1  TYR F  97       0.393 -52.695  -5.424  1.00 37.48       A  C
ATOM  12683  CE2  TYR F  97      -1.351 -51.247  -4.574  1.00 37.39       A  C
ATOM  12684  CZ   TYR F  97      -0.005 -51.566  -4.701  1.00 37.02       A  C
ATOM  12685  OH   TYR F  97       0.931 -50.758  -4.106  1.00 36.51       A  O
ATOM  12686  N    LEU F  98      -4.961 -54.715  -9.039  1.00 39.61       A  N
ATOM  12687  CA   LEU F  98      -6.000 -55.612  -9.531  1.00 39.45       A  C
ATOM  12688  C    LEU F  98      -5.790 -56.032 -10.985  1.00 39.68       A  C
ATOM  12689  O    LEU F  98      -5.714 -57.227 -11.282  1.00 39.59       A  O
ATOM  12690  CB   LEU F  98      -7.402 -55.020  -9.337  1.00 39.26       A  C
ATOM  12691  CG   LEU F  98      -8.551 -55.910  -9.843  1.00 39.01       A  C
ATOM  12692  CD1  LEU F  98      -8.629 -57.232  -9.084  1.00 38.41       A  C
ATOM  12693  CD2  LEU F  98      -9.879 -55.187  -9.785  1.00 39.15       A  C
ATOM  12694  N    ARG F  99      -5.706 -55.052 -11.883  1.00 40.00       A  N
ATOM  12695  CA   ARG F  99      -5.575 -55.336 -13.315  1.00 40.09       A  C
ATOM  12696  C    ARG F  99      -4.397 -56.250 -13.677  1.00 40.21       A  C
ATOM  12697  O    ARG F  99      -4.573 -57.168 -14.462  1.00 40.37       A  O
ATOM  12698  CB   ARG F  99      -5.617 -54.064 -14.175  1.00 39.55       A  C
ATOM  12699  CG   ARG F  99      -6.937 -53.905 -14.918  1.00 39.38       A  C
ATOM  12700  CD   ARG F  99      -6.936 -52.737 -15.872  1.00 39.89       A  C
ATOM  12701  NE   ARG F  99      -7.798 -51.659 -15.400  1.00 39.62       A  N
ATOM  12702  N    PRO F 100      -3.206 -56.022 -13.093  1.00 40.21       A  N
ATOM  12703  CA   PRO F 100      -2.123 -56.961 -13.354  1.00 40.12       A  C
ATOM  12704  C    PRO F 100      -2.491 -58.402 -13.006  1.00 39.76       A  C
ATOM  12705  O    PRO F 100      -1.999 -59.324 -13.655  1.00 39.96       A  O
ATOM  12706  CB   PRO F 100      -1.004 -56.470 -12.434  1.00 40.23       A  C
ATOM  12707  CG   PRO F 100      -1.251 -55.043 -12.300  1.00 40.48       A  C
ATOM  12708  CD   PRO F 100      -2.743 -54.893 -12.271  1.00 40.35       A  C
ATOM  12709  N    LEU F 101      -3.359 -58.585 -12.007  1.00 39.12       A  N
ATOM  12710  CA   LEU F 101      -3.740 -59.917 -11.515  1.00 38.50       A  C
ATOM  12711  C    LEU F 101      -4.733 -60.650 -12.405  1.00 38.45       A  C
ATOM  12712  O    LEU F 101      -4.873 -61.875 -12.307  1.00 38.32       A  O
ATOM  12713  CB   LEU F 101      -4.303 -59.822 -10.099  1.00 38.09       A  C
ATOM  12714  CG   LEU F 101      -3.415 -60.160  -8.897  1.00 37.77       A  C
ATOM  12715  CD1  LEU F 101      -1.971 -59.713  -9.056  1.00 38.20       A  C
ATOM  12716  CD2  LEU F 101      -4.009 -59.578  -7.616  1.00 37.49       A  C
ATOM  12717  N    LEU F 102      -5.406 -59.905 -13.281  1.00 38.53       A  N
ATOM  12718  CA   LEU F 102      -6.505 -60.451 -14.087  1.00 38.61       A  C
ATOM  12719  C    LEU F 102      -6.060 -61.173 -15.363  1.00 38.93       A  C
ATOM  12720  O    LEU F 102      -6.468 -60.800 -16.468  1.00 39.20       A  O
ATOM  12721  CB   LEU F 102      -7.535 -59.357 -14.410  1.00 38.53       A  C
ATOM  12722  CG   LEU F 102      -8.327 -58.787 -13.230  1.00 38.07       A  C
ATOM  12723  CD1  LEU F 102      -9.140 -57.589 -13.660  1.00 38.23       A  C
ATOM  12724  CD2  LEU F 102      -9.224 -59.843 -12.609  1.00 37.54       A  C
ATOM  12725  N    VAL F 103      -5.230 -62.202 -15.197  1.00 39.07       A  N
ATOM  12726  CA   VAL F 103      -4.795 -63.048 -16.314  1.00 39.38       A  C
ATOM  12727  C    VAL F 103      -5.010 -64.513 -15.982  1.00 39.10       A  C
ATOM  12728  O    VAL F 103      -5.107 -64.868 -14.807  1.00 38.83       A  O
ATOM  12729  CB   VAL F 103      -3.309 -62.826 -16.694  1.00 39.72       A  C
ATOM  12730  CG1  VAL F 103      -2.416 -62.889 -15.464  1.00 39.59       A  C
ATOM  12731  CG2  VAL F 103      -3.125 -61.497 -17.427  1.00 40.65       A  C
ATOM  12732  N    VAL F 104      -5.104 -65.355 -17.013  1.00 39.03       A  N
ATOM  12733  CA   VAL F 104      -5.180 -66.799 -16.808  1.00 38.72       A  C
ATOM  12734  C    VAL F 104      -3.926 -67.232 -16.050  1.00 38.93       A  C
ATOM  12735  O    VAL F 104      -2.810 -66.875 -16.431  1.00 39.23       A  O
ATOM  12736  CB   VAL F 104      -5.301 -67.567 -18.131  1.00 38.03       A  C
ATOM  12737  CG1  VAL F 104      -6.019 -68.883 -17.914  1.00 37.45       A  C
ATOM  12738  N    ARG F 105      -4.119 -67.973 -14.963  1.00 38.77       A  N
ATOM  12739  CA   ARG F 105      -3.039 -68.247 -14.025  1.00 38.50       A  C
ATOM  12740  C    ARG F 105      -3.196 -69.569 -13.298  1.00 38.50       A  C
```

FIGURE 1 (cont'd)

```
ATOM  12741  O    ARG F 105      -2.808 -69.691 -12.137  1.00 38.26      A  O
ATOM  12742  CB   ARG F 105      -2.909 -67.099 -13.015  1.00 38.33      A  C
ATOM  12743  CG   ARG F 105      -4.132 -66.854 -12.145  1.00 37.69      A  C
ATOM  12744  CD   ARG F 105      -4.142 -65.444 -11.579  1.00 37.36      A  C
ATOM  12745  NE   ARG F 105      -5.202 -65.274 -10.588  1.00 37.01      A  N
ATOM  12746  CZ   ARG F 105      -6.403 -64.757 -10.840  1.00 36.80      A  C
ATOM  12747  NH1  ARG F 105      -6.711 -64.341 -12.061  1.00 36.92      A  N
ATOM  12748  NH2  ARG F 105      -7.299 -64.650  -9.863  1.00 36.41      A  N
ATOM  12749  N    THR F 106      -3.757 -70.559 -13.987  1.00 38.71      A  N
ATOM  12750  CA   THR F 106      -3.864 -71.922 -13.455  1.00 38.95      A  C
ATOM  12751  C    THR F 106      -2.483 -72.445 -12.993  1.00 39.02      A  C
ATOM  12752  O    THR F 106      -1.466 -72.087 -13.595  1.00 39.02      A  O
ATOM  12753  CB   THR F 106      -4.481 -72.881 -14.497  1.00 39.11      A  C
ATOM  12754  OG1  THR F 106      -3.594 -72.999 -15.613  1.00 39.78      A  O
ATOM  12755  N    PRO F 107      -2.447 -73.274 -11.919  1.00 39.10      A  N
ATOM  12756  CA   PRO F 107      -1.202 -73.761 -11.324  1.00 39.38      A  C
ATOM  12757  C    PRO F 107      -0.138 -74.175 -12.338  1.00 39.95      A  C
ATOM  12758  O    PRO F 107      -0.438 -74.860 -13.319  1.00 40.11      A  O
ATOM  12759  CB   PRO F 107      -1.660 -74.985 -10.530  1.00 39.30      A  C
ATOM  12760  CG   PRO F 107      -3.038 -74.652 -10.102  1.00 38.89      A  C
ATOM  12761  CD   PRO F 107      -3.625 -73.793 -11.191  1.00 38.98      A  C
ATOM  12762  N    GLY F 108       1.096 -73.738 -12.092  1.00 40.40      A  N
ATOM  12763  CA   GLY F 108       2.256 -74.096 -12.914  1.00 41.01      A  C
ATOM  12764  C    GLY F 108       2.244 -73.624 -14.359  1.00 41.37      A  C
ATOM  12765  O    GLY F 108       2.981 -74.154 -15.191  1.00 41.86      A  O
ATOM  12766  N    SER F 109       1.404 -72.640 -14.664  1.00 41.34      A  N
ATOM  12767  CA   SER F 109       1.362 -72.054 -15.997  1.00 41.38      A  C
ATOM  12768  C    SER F 109       2.296 -70.842 -16.028  1.00 41.57      A  C
ATOM  12769  O    SER F 109       2.874 -70.493 -15.002  1.00 41.34      A  O
ATOM  12770  CB   SER F 109      -0.074 -71.658 -16.362  1.00 41.25      A  C
ATOM  12771  OG   SER F 109      -0.555 -70.616 -15.530  1.00 40.64      A  O
ATOM  12772  N    PRO F 110       2.473 -70.216 -17.209  1.00 41.94      A  N
ATOM  12773  CA   PRO F 110       3.223 -68.955 -17.297  1.00 41.86      A  C
ATOM  12774  C    PRO F 110       2.558 -67.824 -16.535  1.00 41.27      A  C
ATOM  12775  O    PRO F 110       3.251 -67.015 -15.929  1.00 41.06      A  O
ATOM  12776  CB   PRO F 110       3.209 -68.641 -18.796  1.00 42.33      A  C
ATOM  12777  CG   PRO F 110       3.076 -69.962 -19.453  1.00 42.80      A  C
ATOM  12778  CD   PRO F 110       2.178 -70.767 -18.547  1.00 42.35      A  C
ATOM  12779  N    GLY F 111       1.228 -67.781 -16.579  1.00 40.80      A  N
ATOM  12780  CA   GLY F 111       0.444 -66.792 -15.838  1.00 40.16      A  C
ATOM  12781  C    GLY F 111       0.581 -66.921 -14.326  1.00 39.62      A  C
ATOM  12782  O    GLY F 111       0.777 -65.917 -13.621  1.00 39.44      A  O
ATOM  12783  N    ASN F 112       0.466 -68.157 -13.832  1.00 39.18      A  N
ATOM  12784  CA   ASN F 112       0.695 -68.480 -12.421  1.00 38.59      A  C
ATOM  12785  C    ASN F 112       2.042 -67.928 -11.938  1.00 38.83      A  C
ATOM  12786  O    ASN F 112       2.115 -67.289 -10.889  1.00 38.66      A  O
ATOM  12787  CB   ASN F 112       0.602 -69.999 -12.201  1.00 38.27      A  C
ATOM  12788  CG   ASN F 112       0.768 -70.404 -10.747  1.00 37.15      A  C
ATOM  12789  ND2  ASN F 112       1.433 -71.526 -10.519  1.00 36.58      A  N
ATOM  12790  OD1  ASN F 112       0.299 -69.729  -9.846  1.00 35.79      A  O
ATOM  12791  N    LEU F 113       3.093 -68.157 -12.725  1.00 39.32      A  N
ATOM  12792  CA   LEU F 113       4.436 -67.682 -12.403  1.00 39.75      A  C
ATOM  12793  C    LEU F 113       4.564 -66.161 -12.585  1.00 39.78      A  C
ATOM  12794  O    LEU F 113       5.210 -65.493 -11.777  1.00 39.70      A  O
ATOM  12795  CB   LEU F 113       5.477 -68.443 -13.232  1.00 40.17      A  C
ATOM  12796  CG   LEU F 113       6.916 -68.485 -12.711  1.00 40.91      A  C
ATOM  12797  CD1  LEU F 113       7.557 -69.840 -12.995  1.00 41.46      A  C
ATOM  12798  CD2  LEU F 113       7.772 -67.339 -13.281  1.00 41.78      A  C
ATOM  12799  N    GLN F 114       3.944 -65.624 -13.638  1.00 39.89      A  N
ATOM  12800  CA   GLN F 114       3.942 -64.175 -13.885  1.00 39.89      A  C
ATOM  12801  C    GLN F 114       3.326 -63.424 -12.713  1.00 39.63      A  C
ATOM  12802  O    GLN F 114       3.895 -62.430 -12.259  1.00 39.70      A  O
ATOM  12803  CB   GLN F 114       3.211 -63.820 -15.189  1.00 40.07      A  C
ATOM  12804  N    VAL F 115       2.175 -63.911 -12.230  1.00 39.07      A  N
ATOM  12805  CA   VAL F 115       1.473 -63.326 -11.074  1.00 38.38      A  C
```

FIGURE 1 (cont'd)

```
ATOM  12806  C    VAL F 115       2.304 -63.464  -9.803  1.00 38.65      A    C
ATOM  12807  O    VAL F 115       2.569 -62.460  -9.125  1.00 38.84      A    O
ATOM  12808  CB   VAL F 115       0.074 -63.939 -10.858  1.00 36.86      A    C
ATOM  12809  N    ARG F 116       2.734 -64.697  -9.508  1.00 38.85      A    N
ATOM  12810  CA   ARG F 116       3.633 -64.996  -8.385  1.00 39.07      A    C
ATOM  12811  C    ARG F 116       4.806 -64.012  -8.294  1.00 39.52      A    C
ATOM  12812  O    ARG F 116       5.098 -63.468  -7.219  1.00 39.51      A    O
ATOM  12813  CB   ARG F 116       4.158 -66.427  -8.495  1.00 38.96      A    C
ATOM  12814  CG   ARG F 116       5.176 -66.823  -7.431  1.00 39.21      A    C
ATOM  12815  CD   ARG F 116       5.740 -68.210  -7.701  1.00 40.26      A    C
ATOM  12816  NE   ARG F 116       4.682 -69.216  -7.820  1.00 40.89      A    N
ATOM  12817  CZ   ARG F 116       4.830 -70.403  -8.400  1.00 41.48      A    C
ATOM  12818  NH1  ARG F 116       5.995 -70.755  -8.926  1.00 41.97      A    N
ATOM  12819  NH2  ARG F 116       3.806 -71.241  -8.460  1.00 41.65      A    N
ATOM  12820  N    LYS F 117       5.461 -63.786  -9.432  1.00 40.10      A    N
ATOM  12821  CA   LYS F 117       6.590 -62.860  -9.532  1.00 40.56      A    C
ATOM  12822  C    LYS F 117       6.162 -61.428  -9.192  1.00 40.18      A    C
ATOM  12823  O    LYS F 117       6.887 -60.720  -8.498  1.00 40.29      A    O
ATOM  12824  CB   LYS F 117       7.216 -62.946 -10.936  1.00 41.15      A    C
ATOM  12825  CG   LYS F 117       8.667 -62.481 -11.040  1.00 42.51      A    C
ATOM  12826  CD   LYS F 117       9.281 -62.797 -12.411  1.00 43.83      A    C
ATOM  12827  CE   LYS F 117       9.941 -64.172 -12.454  1.00 44.08      A    C
ATOM  12828  N    PHE F 118       4.981 -61.023  -9.661  1.00 39.54      A    N
ATOM  12829  CA   PHE F 118       4.458 -59.686  -9.407  1.00 38.92      A    C
ATOM  12830  C    PHE F 118       4.168 -59.481  -7.930  1.00 39.17      A    C
ATOM  12831  O    PHE F 118       4.425 -58.406  -7.376  1.00 39.39      A    O
ATOM  12832  CB   PHE F 118       3.195 -59.413 -10.233  1.00 37.66      A    C
ATOM  12833  CG   PHE F 118       2.504 -58.101  -9.894  1.00 36.15      A    C
ATOM  12834  CD1  PHE F 118       3.173 -56.885 -10.054  1.00 35.86      A    C
ATOM  12835  CD2  PHE F 118       1.189 -58.101  -9.430  1.00 34.59      A    C
ATOM  12836  CE1  PHE F 118       2.573 -55.666  -9.755  1.00 35.46      A    C
ATOM  12837  CE2  PHE F 118       0.513 -56.928  -9.112  1.00 33.85      A    C
ATOM  12838  N    LEU F 119       3.627 -60.511  -7.296  1.00 39.17      A    N
ATOM  12839  CA   LEU F 119       3.364 -60.444  -5.870  1.00 39.20      A    C
ATOM  12840  C    LEU F 119       4.676 -60.261  -5.088  1.00 39.72      A    C
ATOM  12841  O    LEU F 119       4.822 -59.283  -4.342  1.00 39.83      A    O
ATOM  12842  CB   LEU F 119       2.569 -61.668  -5.403  1.00 38.74      A    C
ATOM  12843  CG   LEU F 119       1.079 -61.564  -5.718  1.00 37.93      A    C
ATOM  12844  CD1  LEU F 119       0.440 -62.925  -5.578  1.00 37.42      A    C
ATOM  12845  N    GLU F 120       5.632 -61.175  -5.295  1.00 40.21      A    N
ATOM  12846  CA   GLU F 120       6.961 -61.098  -4.662  1.00 40.62      A    C
ATOM  12847  C    GLU F 120       7.525 -59.688  -4.736  1.00 41.29      A    C
ATOM  12848  O    GLU F 120       7.929 -59.121  -3.723  1.00 41.57      A    O
ATOM  12849  CB   GLU F 120       7.949 -62.067  -5.320  1.00 39.86      A    C
ATOM  12850  CG   GLU F 120       7.781 -63.530  -4.935  1.00 39.54      A    C
ATOM  12851  CD   GLU F 120       8.920 -64.392  -5.454  1.00 40.10      A    C
ATOM  12852  OE1  GLU F 120      10.069 -64.205  -4.993  1.00 40.80      A    O
ATOM  12853  N    ALA F 121       7.524 -59.129  -5.942  1.00 41.82      A    N
ATOM  12854  CA   ALA F 121       8.103 -57.818  -6.200  1.00 42.23      A    C
ATOM  12855  C    ALA F 121       7.394 -56.697  -5.438  1.00 42.15      A    C
ATOM  12856  O    ALA F 121       8.040 -55.912  -4.733  1.00 42.46      A    O
ATOM  12857  CB   ALA F 121       8.127 -57.531  -7.706  1.00 42.54      A    C
ATOM  12858  N    THR F 122       6.070 -56.635  -5.573  1.00 41.57      A    N
ATOM  12859  CA   THR F 122       5.286 -55.600  -4.911  1.00 40.90      A    C
ATOM  12860  C    THR F 122       5.539 -55.620  -3.410  1.00 41.32      A    C
ATOM  12861  O    THR F 122       5.802 -54.573  -2.816  1.00 41.70      A    O
ATOM  12862  CB   THR F 122       3.791 -55.748  -5.189  1.00 39.43      A    C
ATOM  12863  OG1  THR F 122       3.535 -55.402  -6.548  1.00 38.50      A    O
ATOM  12864  N    LEU F 123       5.492 -56.815  -2.817  1.00 41.41      A    N
ATOM  12865  CA   LEU F 123       5.669 -56.988  -1.373  1.00 41.48      A    C
ATOM  12866  C    LEU F 123       7.050 -56.533  -0.924  1.00 42.15      A    C
ATOM  12867  O    LEU F 123       7.190 -55.879   0.119  1.00 42.37      A    O
ATOM  12868  CB   LEU F 123       5.418 -58.443  -0.945  1.00 41.03      A    C
ATOM  12869  CG   LEU F 123       3.994 -59.001  -0.993  1.00 39.81      A    C
ATOM  12870  CD1  LEU F 123       3.241 -58.614   0.257  1.00 39.17      A    C
```

FIGURE 1 (cont'd)

```
ATOM  12871  N    ARG F 124       8.062 -56.861  -1.725  1.00 42.75      A  N
ATOM  12872  CA   ARG F 124       9.446 -56.496  -1.411  1.00 43.43      A  C
ATOM  12873  C    ARG F 124       9.687 -54.994  -1.512  1.00 44.07      A  C
ATOM  12874  O    ARG F 124      10.444 -54.424  -0.726  1.00 44.44      A  O
ATOM  12875  CB   ARG F 124      10.441 -57.268  -2.284  1.00 43.39      A  C
ATOM  12876  CG   ARG F 124      10.760 -58.664  -1.752  1.00 42.81      A  C
ATOM  12877  CD   ARG F 124      11.769 -59.405  -2.605  1.00 42.35      A  C
ATOM  12878  NE   ARG F 124      11.976 -60.766  -2.122  1.00 41.55      A  N
ATOM  12879  N    SER F 125       9.013 -54.357  -2.462  1.00 44.57      A  N
ATOM  12880  CA   SER F 125       9.186 -52.924  -2.723  1.00 45.13      A  C
ATOM  12881  C    SER F 125       8.514 -51.992  -1.709  1.00 45.23      A  C
ATOM  12882  O    SER F 125       8.393 -50.797  -1.964  1.00 45.53      A  O
ATOM  12883  CB   SER F 125       8.692 -52.589  -4.136  1.00 45.30      A  C
ATOM  12884  OG   SER F 125       7.275 -52.672  -4.220  1.00 44.96      A  O
ATOM  12885  N    LEU F 126       8.088 -52.531  -0.568  1.00 45.11      A  N
ATOM  12886  CA   LEU F 126       7.411 -51.731   0.461  1.00 45.12      A  C
ATOM  12887  C    LEU F 126       8.380 -51.147   1.480  1.00 45.66      A  C
ATOM  12888  O    LEU F 126       9.405 -51.759   1.769  1.00 45.94      A  O
ATOM  12889  CB   LEU F 126       6.328 -52.549   1.168  1.00 44.60      A  C
ATOM  12890  CG   LEU F 126       5.091 -52.965   0.357  1.00 43.79      A  C
ATOM  12891  CD1  LEU F 126       3.958 -53.339   1.287  1.00 42.93      A  C
ATOM  12892  CD2  LEU F 126       4.630 -51.878  -0.610  1.00 43.54      A  C
ATOM  12893  N    THR F 127       8.044 -49.975   2.027  1.00 46.15      A  N
ATOM  12894  CA   THR F 127       8.953 -49.214   2.909  1.00 46.64      A  C
ATOM  12895  C    THR F 127       9.309 -49.924   4.204  1.00 46.67      A  C
ATOM  12896  O    THR F 127      10.464 -49.924   4.605  1.00 47.16      A  O
ATOM  12897  CB   THR F 127       8.416 -47.816   3.245  1.00 46.87      A  C
ATOM  12898  OG1  THR F 127       7.735 -47.278   2.107  1.00 47.08      A  O
ATOM  12899  N    ALA F 128       8.323 -50.516   4.862  1.00 46.30      A  N
ATOM  12900  CA   ALA F 128       8.602 -51.450   5.954  1.00 46.11      A  C
ATOM  12901  C    ALA F 128       9.291 -52.689   5.372  1.00 46.01      A  C
ATOM  12902  O    ALA F 128       8.984 -53.101   4.250  1.00 45.98      A  O
ATOM  12903  CB   ALA F 128       7.325 -51.835   6.650  1.00 45.80      A  C
ATOM  12904  N    GLY F 129      10.225 -53.280   6.111  1.00 45.97      A  N
ATOM  12905  CA   GLY F 129      11.050 -54.351   5.544  1.00 45.72      A  C
ATOM  12906  C    GLY F 129      10.374 -55.708   5.512  1.00 45.16      A  C
ATOM  12907  O    GLY F 129      10.694 -56.570   6.331  1.00 45.54      A  O
ATOM  12908  N    TRP F 130       9.454 -55.911   4.567  1.00 44.27      A  N
ATOM  12909  CA   TRP F 130       8.679 -57.156   4.507  1.00 43.27      A  C
ATOM  12910  C    TRP F 130       9.591 -58.339   4.199  1.00 42.98      A  C
ATOM  12911  O    TRP F 130      10.382 -58.290   3.263  1.00 43.14      A  O
ATOM  12912  CB   TRP F 130       7.546 -57.067   3.472  1.00 42.93      A  C
ATOM  12913  CG   TRP F 130       6.264 -56.367   3.937  1.00 42.43      A  C
ATOM  12914  CD1  TRP F 130       5.948 -55.041   3.785  1.00 42.63      A  C
ATOM  12915  CD2  TRP F 130       5.128 -56.972   4.590  1.00 41.99      A  C
ATOM  12916  CE2  TRP F 130       4.178 -55.945   4.811  1.00 41.85      A  C
ATOM  12917  CE3  TRP F 130       4.823 -58.278   5.016  1.00 41.74      A  C
ATOM  12918  NE1  TRP F 130       4.705 -54.781   4.314  1.00 42.21      A  N
ATOM  12919  CZ2  TRP F 130       2.949 -56.186   5.440  1.00 41.37      A  C
ATOM  12920  CZ3  TRP F 130       3.594 -58.514   5.642  1.00 41.32      A  C
ATOM  12921  CH2  TRP F 130       2.679 -57.474   5.845  1.00 41.11      A  C
ATOM  12922  N    HIS F 131       9.490 -59.388   5.009  1.00 42.55      A  N
ATOM  12923  CA   HIS F 131      10.240 -60.612   4.786  1.00 42.33      A  C
ATOM  12924  C    HIS F 131       9.427 -61.514   3.858  1.00 41.92      A  C
ATOM  12925  O    HIS F 131       8.689 -62.389   4.311  1.00 41.70      A  O
ATOM  12926  CB   HIS F 131      10.523 -61.296   6.124  1.00 42.49      A  C
ATOM  12927  CG   HIS F 131      11.491 -62.439   6.043  1.00 42.95      A  C
ATOM  12928  CD2  HIS F 131      12.810 -62.532   6.350  1.00 43.26      A  C
ATOM  12929  ND1  HIS F 131      11.111 -63.699   5.621  1.00 43.07      A  N
ATOM  12930  CE1  HIS F 131      12.153 -64.511   5.652  1.00 42.87      A  C
ATOM  12931  NE2  HIS F 131      13.194 -63.830   6.098  1.00 43.35      A  N
ATOM  12932  N    VAL F 132       9.558 -61.271   2.555  1.00 41.67      A  N
ATOM  12933  CA   VAL F 132       8.842 -62.025   1.526  1.00 41.32      A  C
ATOM  12934  C    VAL F 132       9.563 -63.330   1.248  1.00 41.31      A  C
ATOM  12935  O    VAL F 132      10.785 -63.350   1.139  1.00 41.57      A  O
```

FIGURE 1 (cont'd)

```
ATOM  12936  CB   VAL F 132      8.718  -61.208   0.223  1.00 41.28      A    C
ATOM  12937  CG1  VAL F 132      7.399  -61.497  -0.469  1.00 41.01      A    C
ATOM  12938  N    GLU F 133      8.805  -64.414   1.121  1.00 41.17      A    N
ATOM  12939  CA   GLU F 133      9.394  -65.743   1.065  1.00 41.41      A    C
ATOM  12940  C    GLU F 133      8.531  -66.728   0.284  1.00 41.13      A    C
ATOM  12941  O    GLU F 133      7.346  -66.859   0.571  1.00 40.99      A    O
ATOM  12942  CB   GLU F 133      9.606  -66.242   2.492  1.00 41.64      A    C
ATOM  12943  CG   GLU F 133     10.335  -67.570   2.631  1.00 42.99      A    C
ATOM  12944  CD   GLU F 133     10.398  -68.034   4.080  1.00 44.70      A    C
ATOM  12945  OE1  GLU F 133     10.914  -67.267   4.924  1.00 45.49      A    O
ATOM  12946  OE2  GLU F 133      9.927  -69.158   4.374  1.00 45.17      A    O
ATOM  12947  N    LEU F 134      9.136  -67.415  -0.692  1.00 41.05      A    N
ATOM  12948  CA   LEU F 134      8.445  -68.403  -1.527  1.00 40.72      A    C
ATOM  12949  C    LEU F 134      8.409  -69.767  -0.870  1.00 40.49      A    C
ATOM  12950  O    LEU F 134      9.317  -70.117  -0.125  1.00 40.64      A    O
ATOM  12951  CB   LEU F 134      9.122  -68.539  -2.886  1.00 40.92      A    C
ATOM  12952  CG   LEU F 134      8.577  -67.736  -4.063  1.00 41.07      A    C
ATOM  12953  CD1  LEU F 134      9.527  -67.867  -5.253  1.00 41.92      A    C
ATOM  12954  N    ASP F 135      7.350  -70.524  -1.154  1.00 40.04      A    N
ATOM  12955  CA   ASP F 135      7.223  -71.906  -0.705  1.00 39.83      A    C
ATOM  12956  C    ASP F 135      6.980  -72.820  -1.908  1.00 39.76      A    C
ATOM  12957  O    ASP F 135      5.850  -73.229  -2.176  1.00 39.73      A    O
ATOM  12958  CB   ASP F 135      6.103  -72.063   0.331  1.00 39.62      A    C
ATOM  12959  CG   ASP F 135      5.876  -73.529   0.732  1.00 39.86      A    C
ATOM  12960  OD1  ASP F 135      6.871  -74.264   0.908  1.00 40.62      A    O
ATOM  12961  OD2  ASP F 135      4.704  -73.954   0.860  1.00 39.58      A    O
ATOM  12962  N    PRO F 136      8.047  -73.146  -2.643  1.00 39.75      A    N
ATOM  12963  CA   PRO F 136      7.888  -73.991  -3.807  1.00 40.02      A    C
ATOM  12964  C    PRO F 136      7.709  -75.435  -3.393  1.00 40.61      A    C
ATOM  12965  O    PRO F 136      8.223  -75.829  -2.354  1.00 40.89      A    O
ATOM  12966  CB   PRO F 136      9.225  -73.828  -4.555  1.00 39.28      A    C
ATOM  12967  CG   PRO F 136     10.052  -72.887  -3.753  1.00 38.94      A    C
ATOM  12968  CD   PRO F 136      9.459  -72.847  -2.388  1.00 39.70      A    C
ATOM  12969  N    PHE F 137      6.978  -76.208  -4.190  1.00 41.09      A    N
ATOM  12970  CA   PHE F 137      6.887  -77.660  -4.006  1.00 41.60      A    C
ATOM  12971  C    PHE F 137      6.199  -78.342  -5.178  1.00 42.06      A    C
ATOM  12972  O    PHE F 137      5.411  -77.722  -5.886  1.00 42.03      A    O
ATOM  12973  CB   PHE F 137      6.171  -78.023  -2.701  1.00 41.43      A    C
ATOM  12974  CG   PHE F 137      4.703  -77.701  -2.691  1.00 41.09      A    C
ATOM  12975  CD1  PHE F 137      4.261  -76.402  -2.435  1.00 40.80      A    C
ATOM  12976  CD2  PHE F 137      3.756  -78.704  -2.906  1.00 40.98      A    C
ATOM  12977  CE1  PHE F 137      2.891  -76.109  -2.408  1.00 40.28      A    C
ATOM  12978  CE2  PHE F 137      2.387  -78.423  -2.883  1.00 40.52      A    C
ATOM  12979  CZ   PHE F 137      1.952  -77.128  -2.636  1.00 40.18      A    C
ATOM  12980  N    THR F 138      6.503  -79.619  -5.378  1.00 42.78      A    N
ATOM  12981  CA   THR F 138      5.798  -80.421  -6.370  1.00 43.37      A    C
ATOM  12982  C    THR F 138      4.772  -81.291  -5.675  1.00 43.44      A    C
ATOM  12983  O    THR F 138      5.003  -81.746  -4.555  1.00 43.61      A    O
ATOM  12984  CB   THR F 138      6.757  -81.302  -7.175  1.00 43.76      A    C
ATOM  12985  OG1  THR F 138      6.890  -80.765  -8.497  1.00 44.26      A    O
ATOM  12986  N    ALA F 139      3.637  -81.515  -6.331  1.00 43.47      A    N
ATOM  12987  CA   ALA F 139      2.559  -82.311  -5.738  1.00 43.59      A    C
ATOM  12988  C    ALA F 139      1.773  -83.176  -6.737  1.00 43.92      A    C
ATOM  12989  O    ALA F 139      1.619  -82.844  -7.914  1.00 43.96      A    O
ATOM  12990  CB   ALA F 139      1.619  -81.419  -4.918  1.00 43.19      A    C
ATOM  12991  N    SER F 140      1.285  -84.297  -6.226  1.00 44.36      A    N
ATOM  12992  CA   SER F 140      0.575  -85.294  -7.007  1.00 44.78      A    C
ATOM  12993  C    SER F 140     -0.900  -84.907  -7.189  1.00 44.47      A    C
ATOM  12994  O    SER F 140     -1.664  -84.848  -6.219  1.00 44.33      A    O
ATOM  12995  CB   SER F 140      0.723  -86.661  -6.313  1.00 45.21      A    C
ATOM  12996  OG   SER F 140     -0.226  -87.602  -6.774  1.00 46.13      A    O
ATOM  12997  N    THR F 141     -1.288  -84.636  -8.431  1.00 44.26      A    N
ATOM  12998  CA   THR F 141     -2.667  -84.258  -8.733  1.00 44.02      A    C
ATOM  12999  C    THR F 141     -3.279  -85.265  -9.702  1.00 44.34      A    C
ATOM  13000  O    THR F 141     -2.549  -86.103 -10.242  1.00 44.80      A    O
```

FIGURE 1 (cont'd)

```
ATOM  13001  CB   THR F 141      -2.754 -82.832  -9.325  1.00 43.70      A   C
ATOM  13002  CG2  THR F 141      -1.972 -81.837  -8.474  1.00 43.38      A   C
ATOM  13003  OG1  THR F 141      -2.232 -82.821 -10.659  1.00 43.74      A   O
ATOM  13004  N    PRO F 142      -4.618 -85.205  -9.913  1.00 44.31      A   N
ATOM  13005  CA   PRO F 142      -5.268 -86.054 -10.929  1.00 44.50      A   C
ATOM  13006  C    PRO F 142      -4.816 -85.766 -12.369  1.00 44.67      A   C
ATOM  13007  O    PRO F 142      -5.181 -86.496 -13.284  1.00 45.10      A   O
ATOM  13008  CB   PRO F 142      -6.759 -85.738 -10.750  1.00 44.37      A   C
ATOM  13009  CG   PRO F 142      -6.881 -85.317  -9.335  1.00 44.08      A   C
ATOM  13010  CD   PRO F 142      -5.620 -84.548  -9.049  1.00 43.98      A   C
ATOM  13011  N    LEU F 143      -4.032 -84.708 -12.550  1.00 44.48      A   N
ATOM  13012  CA   LEU F 143      -3.428 -84.381 -13.833  1.00 44.51      A   C
ATOM  13013  C    LEU F 143      -1.946 -84.756 -13.841  1.00 44.77      A   C
ATOM  13014  O    LEU F 143      -1.201 -84.381 -14.746  1.00 44.99      A   O
ATOM  13015  CB   LEU F 143      -3.594 -82.881 -14.129  1.00 44.17      A   C
ATOM  13016  CG   LEU F 143      -4.782 -82.297 -14.925  1.00 44.09      A   C
ATOM  13017  CD1  LEU F 143      -4.735 -82.692 -16.408  1.00 45.10      A   C
ATOM  13018  CD2  LEU F 143      -6.143 -82.634 -14.324  1.00 43.70      A   C
ATOM  13019  N    GLY F 144      -1.525 -85.505 -12.828  1.00 44.90      A   N
ATOM  13020  CA   GLY F 144      -0.117 -85.843 -12.651  1.00 44.99      A   C
ATOM  13021  C    GLY F 144       0.641 -84.768 -11.885  1.00 44.84      A   C
ATOM  13022  O    GLY F 144       0.041 -83.789 -11.414  1.00 44.45      A   O
ATOM  13023  N    PRO F 145       1.971 -84.946 -11.742  1.00 44.99      A   N
ATOM  13024  CA   PRO F 145       2.821 -83.986 -11.036  1.00 44.62      A   C
ATOM  13025  C    PRO F 145       2.606 -82.552 -11.515  1.00 43.82      A   C
ATOM  13026  O    PRO F 145       2.654 -82.291 -12.723  1.00 44.03      A   O
ATOM  13027  CB   PRO F 145       4.238 -84.467 -11.374  1.00 44.99      A   C
ATOM  13028  CG   PRO F 145       4.095 -85.932 -11.515  1.00 45.64      A   C
ATOM  13029  CD   PRO F 145       2.731 -86.147 -12.144  1.00 45.50      A   C
ATOM  13030  N    VAL F 146       2.346 -81.653 -10.565  1.00 42.53      A   N
ATOM  13031  CA   VAL F 146       2.167 -80.218 -10.832  1.00 41.10      A   C
ATOM  13032  C    VAL F 146       3.020 -79.380  -9.871  1.00 41.27      A   C
ATOM  13033  O    VAL F 146       3.076 -79.664  -8.672  1.00 41.31      A   O
ATOM  13034  CB   VAL F 146       0.680 -79.798 -10.726  1.00 39.28      A   C
ATOM  13035  CG1  VAL F 146       0.476 -78.405 -11.293  1.00 37.81      A   C
ATOM  13036  N    ASP F 147       3.687 -78.359 -10.406  1.00 41.34      A   N
ATOM  13037  CA   ASP F 147       4.585 -77.509  -9.622  1.00 41.09      A   C
ATOM  13038  C    ASP F 147       3.871 -76.283  -9.037  1.00 40.64      A   C
ATOM  13039  O    ASP F 147       3.370 -75.434  -9.774  1.00 40.57      A   O
ATOM  13040  CB   ASP F 147       5.805 -77.096 -10.462  1.00 41.33      A   C
ATOM  13041  CG   ASP F 147       6.855 -78.197 -10.559  1.00 41.29      A   C
ATOM  13042  N    PHE F 148       3.832 -76.203  -7.707  1.00 40.11      A   N
ATOM  13043  CA   PHE F 148       3.140 -75.128  -6.992  1.00 39.51      A   C
ATOM  13044  C    PHE F 148       4.120 -74.188  -6.313  1.00 39.32      A   C
ATOM  13045  O    PHE F 148       5.317 -74.459  -6.261  1.00 39.50      A   O
ATOM  13046  CB   PHE F 148       2.203 -75.697  -5.928  1.00 39.28      A   C
ATOM  13047  CG   PHE F 148       1.129 -76.587  -6.469  1.00 39.34      A   C
ATOM  13048  CD1  PHE F 148      -0.075 -76.060  -6.892  1.00 39.08      A   C
ATOM  13049  CD2  PHE F 148       1.313 -77.966  -6.538  1.00 39.83      A   C
ATOM  13050  CE1  PHE F 148      -1.074 -76.894  -7.391  1.00 39.26      A   C
ATOM  13051  CE2  PHE F 148       0.313 -78.811  -7.039  1.00 39.84      A   C
ATOM  13052  CZ   PHE F 148      -0.877 -78.277  -7.462  1.00 39.56      A   C
ATOM  13053  N    GLY F 149       3.595 -73.088  -5.781  1.00 38.96      A   N
ATOM  13054  CA   GLY F 149       4.400 -72.091  -5.077  1.00 38.80      A   C
ATOM  13055  C    GLY F 149       3.594 -71.036  -4.332  1.00 38.54      A   C
ATOM  13056  O    GLY F 149       2.985 -70.154  -4.942  1.00 38.51      A   O
ATOM  13057  N    ASN F 150       3.596 -71.127  -3.004  1.00 38.29      A   N
ATOM  13058  CA   ASN F 150       2.943 -70.139  -2.156  1.00 37.95      A   C
ATOM  13059  C    ASN F 150       3.798 -68.894  -2.018  1.00 38.12      A   C
ATOM  13060  O    ASN F 150       5.016 -68.967  -2.159  1.00 38.36      A   O
ATOM  13061  CB   ASN F 150       2.669 -70.734  -0.774  1.00 37.67      A   C
ATOM  13062  CG   ASN F 150       1.647 -71.850  -0.813  1.00 37.29      A   C
ATOM  13063  ND2  ASN F 150       2.011 -73.009  -0.279  1.00 37.27      A   N
ATOM  13064  OD1  ASN F 150       0.538 -71.671  -1.313  1.00 36.82      A   O
ATOM  13065  N    VAL F 151       3.158 -67.757  -1.751  1.00 38.16      A   N
```

FIGURE 1 (cont'd)

```
ATOM  13066  CA   VAL F 151     3.869  -66.513  -1.437  1.00 38.46      A    C
ATOM  13067  C    VAL F 151     3.557  -66.099   0.004  1.00 38.66      A    C
ATOM  13068  O    VAL F 151     2.428  -65.721   0.312  1.00 38.49      A    O
ATOM  13069  CB   VAL F 151     3.541  -65.384  -2.449  1.00 38.35      A    C
ATOM  13070  CG1  VAL F 151     4.074  -65.747  -3.809  1.00 38.72      A    C
ATOM  13071  CG2  VAL F 151     4.133  -64.056  -2.013  1.00 38.48      A    C
ATOM  13072  N    VAL F 152     4.566  -66.195   0.876  1.00 39.21      A    N
ATOM  13073  CA   VAL F 152     4.430  -65.904   2.313  1.00 39.69      A    C
ATOM  13074  C    VAL F 152     5.145  -64.605   2.701  1.00 40.24      A    C
ATOM  13075  O    VAL F 152     6.348  -64.455   2.466  1.00 40.61      A    O
ATOM  13076  CB   VAL F 152     4.949  -67.081   3.176  1.00 39.64      A    C
ATOM  13077  CG1  VAL F 152     3.962  -68.236   3.141  1.00 39.11      A    C
ATOM  13078  CG2  VAL F 152     5.206  -66.641   4.618  1.00 40.00      A    C
ATOM  13079  N    ALA F 153     4.396  -63.678   3.294  1.00 40.63      A    N
ATOM  13080  CA   ALA F 153     4.916  -62.358   3.633  1.00 41.27      A    C
ATOM  13081  C    ALA F 153     4.662  -62.025   5.102  1.00 41.79      A    C
ATOM  13082  O    ALA F 153     3.529  -62.095   5.583  1.00 41.74      A    O
ATOM  13083  CB   ALA F 153     4.310  -61.290   2.719  1.00 41.11      A    C
ATOM  13084  N    THR F 154     5.727  -61.662   5.811  1.00 42.55      A    N
ATOM  13085  CA   THR F 154     5.638  -61.354   7.227  1.00 43.16      A    C
ATOM  13086  C    THR F 154     6.489  -60.137   7.547  1.00 43.97      A    C
ATOM  13087  O    THR F 154     7.695  -60.147   7.326  1.00 44.39      A    O
ATOM  13088  CB   THR F 154     6.110  -62.551   8.081  1.00 43.07      A    C
ATOM  13089  CG2  THR F 154     5.607  -62.438   9.503  1.00 42.98      A    C
ATOM  13090  OG1  THR F 154     5.623  -63.772   7.511  1.00 42.59      A    O
ATOM  13091  N    LEU F 155     5.856  -59.076   8.034  1.00 44.66      A    N
ATOM  13092  CA   LEU F 155     6.587  -57.996   8.680  1.00 45.56      A    C
ATOM  13093  C    LEU F 155     7.134  -58.539   9.988  1.00 46.34      A    C
ATOM  13094  O    LEU F 155     6.407  -59.212  10.720  1.00 46.55      A    O
ATOM  13095  CB   LEU F 155     5.653  -56.826   8.991  1.00 45.36      A    C
ATOM  13096  CG   LEU F 155     5.675  -55.575   8.122  1.00 45.37      A    C
ATOM  13097  CD1  LEU F 155     5.002  -54.437   8.872  1.00 45.18      A    C
ATOM  13098  CD2  LEU F 155     7.106  -55.201   7.750  1.00 45.86      A    C
ATOM  13099  N    ASP F 156     8.403  -58.262  10.281  1.00 47.21      A    N
ATOM  13100  CA   ASP F 156     8.982  -58.597  11.587  1.00 48.05      A    C
ATOM  13101  C    ASP F 156     8.788  -60.088  11.943  1.00 47.91      A    C
ATOM  13102  O    ASP F 156     7.942  -60.427  12.780  1.00 47.72      A    O
ATOM  13103  CB   ASP F 156     8.370  -57.679  12.668  1.00 48.58      A    C
ATOM  13104  CG   ASP F 156     9.126  -57.715  13.995  1.00 50.21      A    C
ATOM  13105  OD1  ASP F 156    10.065  -58.529  14.146  1.00 51.17      A    O
ATOM  13106  OD2  ASP F 156     8.762  -56.921  14.898  1.00 51.72      A    O
ATOM  13107  N    PRO F 157     9.563  -60.986  11.303  1.00 48.01      A    N
ATOM  13108  CA   PRO F 157     9.430  -62.429  11.561  1.00 48.08      A    C
ATOM  13109  C    PRO F 157     9.702  -62.802  13.010  1.00 48.39      A    C
ATOM  13110  O    PRO F 157     9.230  -63.850  13.475  1.00 48.26      A    O
ATOM  13111  CB   PRO F 157    10.501  -63.056  10.661  1.00 48.04      A    C
ATOM  13112  CG   PRO F 157    10.743  -62.062   9.603  1.00 48.07      A    C
ATOM  13113  CD   PRO F 157    10.546  -60.711  10.240  1.00 48.14      A    C
ATOM  13114  N    ARG F 158    10.447  -61.941  13.706  1.00 48.89      A    N
ATOM  13115  CA   ARG F 158    10.839  -62.196  15.093  1.00 49.42      A    C
ATOM  13116  C    ARG F 158     9.733  -61.947  16.131  1.00 49.26      A    C
ATOM  13117  O    ARG F 158     9.811  -62.475  17.243  1.00 49.56      A    O
ATOM  13118  CB   ARG F 158    12.160  -61.488  15.472  1.00 49.92      A    C
ATOM  13119  CG   ARG F 158    12.268  -59.998  15.128  1.00 50.26      A    C
ATOM  13120  N    ALA F 159     8.711  -61.166  15.770  1.00 48.77      A    N
ATOM  13121  CA   ALA F 159     7.545  -60.954  16.642  1.00 48.35      A    C
ATOM  13122  C    ALA F 159     6.866  -62.287  16.980  1.00 48.04      A    C
ATOM  13123  O    ALA F 159     6.731  -63.160  16.116  1.00 47.83      A    O
ATOM  13124  CB   ALA F 159     6.558  -60.002  15.997  1.00 48.22      A    C
ATOM  13125  N    ALA F 160     6.448  -62.433  18.235  1.00 47.88      A    N
ATOM  13126  CA   ALA F 160     5.938  -63.705  18.760  1.00 47.61      A    C
ATOM  13127  C    ALA F 160     4.650  -64.193  18.077  1.00 47.13      A    C
ATOM  13128  O    ALA F 160     4.458  -65.399  17.887  1.00 47.03      A    O
ATOM  13129  CB   ALA F 160     5.738  -63.602  20.265  1.00 48.03      A    C
ATOM  13130  N    ARG F 161     3.783  -63.246  17.714  1.00 46.56      A    N
```

FIGURE 1 (cont'd)

```
ATOM  13131  CA   ARG F 161      2.501 -63.529  17.060  1.00 45.94       A  C
ATOM  13132  C    ARG F 161      2.172 -62.515  15.945  1.00 45.13       A  C
ATOM  13133  O    ARG F 161      2.661 -61.386  15.946  1.00 45.23       A  O
ATOM  13134  CB   ARG F 161      1.379 -63.543  18.101  1.00 46.20       A  C
ATOM  13135  CG   ARG F 161      1.256 -64.844  18.918  1.00 47.56       A  C
ATOM  13136  CD   ARG F 161      0.868 -64.536  20.365  1.00 50.41       A  C
ATOM  13137  NE   ARG F 161      0.088 -63.291  20.478  1.00 52.66       A  N
ATOM  13138  CZ   ARG F 161      0.270 -62.352  21.416  1.00 53.91       A  C
ATOM  13139  NH1  ARG F 161      1.214 -62.497  22.351  1.00 54.68       A  N
ATOM  13140  NH2  ARG F 161     -0.490 -61.253  21.419  1.00 54.18       A  N
ATOM  13141  N    HIS F 162      1.341 -62.937  14.994  1.00 44.08       A  N
ATOM  13142  CA   HIS F 162      0.925 -62.093  13.871  1.00 43.02       A  C
ATOM  13143  C    HIS F 162     -0.533 -62.331  13.456  1.00 41.97       A  C
ATOM  13144  O    HIS F 162     -1.041 -63.457  13.493  1.00 41.71       A  O
ATOM  13145  CB   HIS F 162      1.852 -62.286  12.656  1.00 43.22       A  C
ATOM  13146  CG   HIS F 162      2.086 -63.724  12.296  1.00 43.88       A  C
ATOM  13147  CD2  HIS F 162      3.176 -64.515  12.446  1.00 44.47       A  C
ATOM  13148  ND1  HIS F 162      1.118 -64.520  11.718  1.00 44.08       A  N
ATOM  13149  CE1  HIS F 162      1.600 -65.737  11.532  1.00 44.27       A  C
ATOM  13150  NE2  HIS F 162      2.848 -65.759  11.961  1.00 44.54       A  N
ATOM  13151  N    LEU F 163     -1.204 -61.249  13.076  1.00 40.89       A  N
ATOM  13152  CA   LEU F 163     -2.474 -61.337  12.368  1.00 39.70       A  C
ATOM  13153  C    LEU F 163     -2.150 -61.798  10.963  1.00 38.99       A  C
ATOM  13154  O    LEU F 163     -1.224 -61.287  10.323  1.00 39.01       A  O
ATOM  13155  CB   LEU F 163     -3.174 -59.971  12.314  1.00 39.60       A  C
ATOM  13156  CG   LEU F 163     -4.311 -59.806  11.296  1.00 38.92       A  C
ATOM  13157  CD1  LEU F 163     -5.500 -60.680  11.670  1.00 38.46       A  C
ATOM  13158  CD2  LEU F 163     -4.713 -58.333  11.164  1.00 38.89       A  C
ATOM  13159  N    THR F 164     -2.905 -62.770  10.484  1.00 38.02       A  N
ATOM  13160  CA   THR F 164     -2.636 -63.304   9.166  1.00 37.04       A  C
ATOM  13161  C    THR F 164     -3.862 -63.262   8.242  1.00 36.45       A  C
ATOM  13162  O    THR F 164     -4.894 -63.879   8.514  1.00 36.24       A  O
ATOM  13163  CB   THR F 164     -1.907 -64.673   9.235  1.00 36.98       A  C
ATOM  13164  CG2  THR F 164     -2.584 -65.633  10.184  1.00 36.92       A  C
ATOM  13165  OG1  THR F 164     -1.841 -65.251   7.935  1.00 36.65       A  O
ATOM  13166  N    LEU F 165     -3.735 -62.493   7.166  1.00 35.84       A  N
ATOM  13167  CA   LEU F 165     -4.736 -62.435   6.112  1.00 35.29       A  C
ATOM  13168  C    LEU F 165     -4.309 -63.337   4.955  1.00 35.00       A  C
ATOM  13169  O    LEU F 165     -3.114 -63.478   4.680  1.00 35.05       A  O
ATOM  13170  CB   LEU F 165     -4.919 -60.999   5.614  1.00 35.21       A  C
ATOM  13171  CG   LEU F 165     -5.284 -59.927   6.633  1.00 35.30       A  C
ATOM  13172  CD1  LEU F 165     -5.627 -58.637   5.928  1.00 35.42       A  C
ATOM  13173  CD2  LEU F 165     -6.442 -60.365   7.501  1.00 35.12       A  C
ATOM  13174  N    ALA F 166     -5.284 -63.947   4.281  1.00 34.52       A  N
ATOM  13175  CA   ALA F 166     -4.996 -64.845   3.178  1.00 34.07       A  C
ATOM  13176  C    ALA F 166     -5.991 -64.723   2.030  1.00 33.81       A  C
ATOM  13177  O    ALA F 166     -7.167 -64.456   2.244  1.00 33.65       A  O
ATOM  13178  CB   ALA F 166     -4.916 -66.273   3.673  1.00 34.06       A  C
ATOM  13179  N    CYS F 167     -5.474 -64.899   0.814  1.00 33.66       A  N
ATOM  13180  CA   CYS F 167     -6.243 -65.080  -0.414  1.00 33.51       A  C
ATOM  13181  C    CYS F 167     -5.533 -66.157  -1.220  1.00 33.47       A  C
ATOM  13182  O    CYS F 167     -4.405 -66.513  -0.901  1.00 33.57       A  O
ATOM  13183  CB   CYS F 167     -6.250 -63.791  -1.223  1.00 33.49       A  C
ATOM  13184  SG   CYS F 167     -4.636 -63.344  -1.901  1.00 33.69       A  S
ATOM  13185  N    HIS F 168     -6.176 -66.683  -2.255  1.00 33.45       A  N
ATOM  13186  CA   HIS F 168     -5.487 -67.591  -3.170  1.00 33.49       A  C
ATOM  13187  C    HIS F 168     -5.295 -66.913  -4.522  1.00 33.43       A  C
ATOM  13188  O    HIS F 168     -6.212 -66.277  -5.038  1.00 33.36       A  O
ATOM  13189  CB   HIS F 168     -6.218 -68.939  -3.298  1.00 33.61       A  C
ATOM  13190  CG   HIS F 168     -7.426 -68.896  -4.181  1.00 34.01       A  C
ATOM  13191  CD2  HIS F 168     -8.728 -68.658  -3.899  1.00 34.33       A  C
ATOM  13192  ND1  HIS F 168     -7.361 -69.102  -5.543  1.00 34.35       A  N
ATOM  13193  CE1  HIS F 168     -8.573 -68.997  -6.060  1.00 34.39       A  C
ATOM  13194  NE2  HIS F 168     -9.421 -68.727  -5.084  1.00 34.31       A  N
ATOM  13195  N    TYR F 169     -4.101 -67.043  -5.089  1.00 33.49       A  N
```

FIGURE 1 (cont'd)

```
ATOM  13196  CA   TYR F 169      -3.768 -66.307  -6.301  1.00 33.65       A    C
ATOM  13197  C    TYR F 169      -3.894 -67.118  -7.577  1.00 33.74       A    C
ATOM  13198  O    TYR F 169      -3.865 -66.553  -8.665  1.00 33.74       A    O
ATOM  13199  CB   TYR F 169      -2.386 -65.659  -6.193  1.00 33.72       A    C
ATOM  13200  CG   TYR F 169      -1.218 -66.592  -6.397  1.00 33.94       A    C
ATOM  13201  CD1  TYR F 169      -0.736 -67.384  -5.356  1.00 33.84       A    C
ATOM  13202  CD2  TYR F 169      -0.577 -66.664  -7.627  1.00 34.40       A    C
ATOM  13203  CE1  TYR F 169       0.350 -68.238  -5.543  1.00 33.94       A    C
ATOM  13204  CE2  TYR F 169       0.507 -67.508  -7.827  1.00 34.61       A    C
ATOM  13205  CZ   TYR F 169       0.966 -68.295  -6.785  1.00 34.23       A    C
ATOM  13206  OH   TYR F 169       2.044 -69.132  -6.992  1.00 34.31       A    O
ATOM  13207  N    ASP F 170      -4.030 -68.437  -7.449  1.00 33.90       A    N
ATOM  13208  CA   ASP F 170      -4.295 -69.288  -8.614  1.00 34.22       A    C
ATOM  13209  C    ASP F 170      -5.703 -69.022  -9.156  1.00 34.45       A    C
ATOM  13210  O    ASP F 170      -6.555 -68.471  -8.448  1.00 34.26       A    O
ATOM  13211  CB   ASP F 170      -4.106 -70.777  -8.286  1.00 34.24       A    C
ATOM  13212  CG   ASP F 170      -5.137 -71.298  -7.310  1.00 34.18       A    C
ATOM  13213  OD1  ASP F 170      -5.271 -70.708  -6.215  1.00 33.82       A    O
ATOM  13214  OD2  ASP F 170      -5.805 -72.307  -7.635  1.00 34.57       A    O
ATOM  13215  N    SER F 171      -5.926 -69.383 -10.418  1.00 34.91       A    N
ATOM  13216  CA   SER F 171      -7.254 -69.311 -11.025  1.00 35.33       A    C
ATOM  13217  C    SER F 171      -7.634 -70.704 -11.477  1.00 35.63       A    C
ATOM  13218  O    SER F 171      -6.767 -71.470 -11.884  1.00 35.95       A    O
ATOM  13219  CB   SER F 171      -7.257 -68.360 -12.220  1.00 35.40       A    C
ATOM  13220  OG   SER F 171      -6.766 -68.991 -13.386  1.00 35.82       A    O
ATOM  13221  N    LYS F 172      -8.918 -71.042 -11.409  1.00 35.81       A    N
ATOM  13222  CA   LYS F 172      -9.358 -72.396 -11.776  1.00 36.21       A    C
ATOM  13223  C    LYS F 172      -9.049 -72.736 -13.230  1.00 36.92       A    C
ATOM  13224  O    LYS F 172      -9.025 -71.857 -14.112  1.00 37.15       A    O
ATOM  13225  CB   LYS F 172     -10.851 -72.607 -11.492  1.00 35.96       A    C
ATOM  13226  CG   LYS F 172     -11.280 -74.074 -11.513  1.00 35.71       A    C
ATOM  13227  CD   LYS F 172     -12.776 -74.240 -11.296  1.00 35.09       A    C
ATOM  13228  CE   LYS F 172     -13.182 -75.704 -11.382  1.00 35.09       A    C
ATOM  13229  NZ   LYS F 172     -12.834 -76.464 -10.147  1.00 35.03       A    N
ATOM  13230  N    LEU F 173      -8.805 -74.022 -13.456  1.00 37.69       A    N
ATOM  13231  CA   LEU F 173      -8.501 -74.536 -14.781  1.00 38.59       A    C
ATOM  13232  C    LEU F 173      -9.758 -75.128 -15.422  1.00 39.11       A    C
ATOM  13233  O    LEU F 173     -10.416 -76.009 -14.846  1.00 39.20       A    O
ATOM  13234  CB   LEU F 173      -7.401 -75.596 -14.676  1.00 38.65       A    C
ATOM  13235  CG   LEU F 173      -7.073 -76.419 -15.923  1.00 39.26       A    C
ATOM  13236  CD1  LEU F 173      -5.894 -75.818 -16.679  1.00 39.59       A    C
ATOM  13237  CD2  LEU F 173      -6.824 -77.883 -15.567  1.00 39.40       A    C
ATOM  13238  N    PHE F 174     -10.085 -74.643 -16.613  1.00 39.77       A    N
ATOM  13239  CA   PHE F 174     -11.259 -75.125 -17.333  1.00 40.35       A    C
ATOM  13240  C    PHE F 174     -10.859 -75.777 -18.660  1.00 40.15       A    C
ATOM  13241  O    PHE F 174      -9.781 -75.481 -19.171  1.00 41.35       A    O
ATOM  13242  CB   PHE F 174     -12.222 -73.959 -17.569  1.00 40.62       A    C
ATOM  13243  CG   PHE F 174     -13.032 -73.585 -16.356  1.00 40.47       A    C
ATOM  13244  CD1  PHE F 174     -14.172 -74.314 -16.020  1.00 40.59       A    C
ATOM  13245  CD2  PHE F 174     -12.658 -72.506 -15.553  1.00 40.02       A    C
ATOM  13246  CE1  PHE F 174     -14.927 -73.981 -14.908  1.00 40.10       A    C
ATOM  13247  CE2  PHE F 174     -13.409 -72.161 -14.440  1.00 39.53       A    C
ATOM  13248  CZ   PHE F 174     -14.546 -72.900 -14.116  1.00 39.67       A    C
ATOM  13249  N    PRO F 175     -11.699 -76.690 -19.211  1.00 37.71       A    N
ATOM  13250  CA   PRO F 175     -11.430 -77.116 -20.593  1.00 36.31       A    C
ATOM  13251  C    PRO F 175     -10.825 -75.975 -21.441  1.00 35.94       A    C
ATOM  13252  O    PRO F 175     -11.497 -74.963 -21.736  1.00 35.28       A    O
ATOM  13253  CB   PRO F 175     -12.808 -77.556 -21.093  1.00 36.01       A    C
ATOM  13254  CG   PRO F 175     -13.468 -78.145 -19.832  1.00 36.21       A    C
ATOM  13255  CD   PRO F 175     -12.846 -77.438 -18.620  1.00 37.26       A    C
ATOM  13256  N    PRO F 176      -9.533 -76.131 -21.794  1.00 36.45       A    N
ATOM  13257  CA   PRO F 176      -8.720 -75.055 -22.382  1.00 37.50       A    C
ATOM  13258  C    PRO F 176      -9.098 -74.876 -23.833  1.00 39.29       A    C
ATOM  13259  O    PRO F 176      -8.331 -74.310 -24.625  1.00 39.37       A    O
ATOM  13260  CB   PRO F 176      -7.265 -75.558 -22.232  1.00 37.19       A    C
```

FIGURE 1 (cont'd)

```
ATOM  13261  CG   PRO F 176      -7.356 -76.978 -21.589  1.00 36.67      A  C
ATOM  13262  CD   PRO F 176      -8.800 -77.416 -21.757  1.00 36.28      A  C
ATOM  13263  N    GLY F 177     -10.279 -75.392 -24.162  1.00 41.26      A  N
ATOM  13264  CA   GLY F 177     -10.915 -75.122 -25.428  1.00 43.85      A  C
ATOM  13265  C    GLY F 177     -12.242 -74.430 -25.195  1.00 45.38      A  C
ATOM  13266  O    GLY F 177     -13.294 -75.010 -25.502  1.00 45.71      A  O
ATOM  13267  N    SER F 178     -12.210 -73.204 -24.642  1.00 47.08      A  N
ATOM  13268  CA   SER F 178     -13.443 -72.456 -24.411  1.00 46.91      A  C
ATOM  13269  C    SER F 178     -13.371 -70.968 -24.332  1.00 46.88      A  C
ATOM  13270  O    SER F 178     -13.285 -70.333 -25.364  1.00 47.48      A  O
ATOM  13271  CB   SER F 178     -14.093 -72.946 -23.170  1.00 45.25      A  C
ATOM  13272  OG   SER F 178     -14.634 -74.215 -23.507  1.00 44.56      A  O
ATOM  13273  N    THR F 179     -13.495 -70.388 -23.141  1.00 45.45      A  N
ATOM  13274  CA   THR F 179     -13.234 -68.960 -23.057  1.00 42.93      A  C
ATOM  13275  C    THR F 179     -12.395 -68.728 -21.812  1.00 43.45      A  C
ATOM  13276  O    THR F 179     -12.647 -69.353 -20.784  1.00 44.42      A  O
ATOM  13277  CB   THR F 179     -14.521 -68.048 -23.148  1.00 37.60      A  C
ATOM  13278  CG2  THR F 179     -15.821 -68.834 -23.530  1.00 39.47      A  C
ATOM  13279  OG1  THR F 179     -14.699 -67.313 -21.934  1.00 34.54      A  O
ATOM  13280  N    PRO F 180     -11.392 -67.836 -21.903  1.00 42.23      A  N
ATOM  13281  CA   PRO F 180     -10.397 -67.703 -20.830  1.00 41.23      A  C
ATOM  13282  C    PRO F 180     -11.081 -67.346 -19.515  1.00 42.02      A  C
ATOM  13283  O    PRO F 180     -12.035 -66.572 -19.505  1.00 42.91      A  O
ATOM  13284  CB   PRO F 180      -9.518 -66.552 -21.310  1.00 36.44      A  C
ATOM  13285  CG   PRO F 180     -10.422 -65.723 -22.190  1.00 34.98      A  C
ATOM  13286  CD   PRO F 180     -11.432 -66.649 -22.789  1.00 40.92      A  C
ATOM  13287  N    PHE F 181     -10.625 -67.926 -18.417  1.00 41.79      A  N
ATOM  13288  CA   PHE F 181     -11.238 -67.661 -17.124  1.00 40.92      A  C
ATOM  13289  C    PHE F 181     -10.270 -66.984 -16.157  1.00 40.23      A  C
ATOM  13290  O    PHE F 181      -9.262 -67.576 -15.762  1.00 40.07      A  O
ATOM  13291  CB   PHE F 181     -11.769 -68.953 -16.514  1.00 40.98      A  C
ATOM  13292  CG   PHE F 181     -12.197 -68.809 -15.082  1.00 40.75      A  C
ATOM  13293  CD1  PHE F 181     -13.348 -68.100 -14.757  1.00 40.88      A  C
ATOM  13294  CD2  PHE F 181     -11.445 -69.368 -14.055  1.00 40.51      A  C
ATOM  13295  CE1  PHE F 181     -13.747 -67.955 -13.429  1.00 40.28      A  C
ATOM  13296  CE2  PHE F 181     -11.842 -69.223 -12.719  1.00 40.01      A  C
ATOM  13297  CZ   PHE F 181     -12.995 -68.519 -12.409  1.00 39.76      A  C
ATOM  13298  N    VAL F 182     -10.589 -65.757 -15.760  1.00 39.41      A  N
ATOM  13299  CA   VAL F 182      -9.676 -64.977 -14.930  1.00 38.69      A  C
ATOM  13300  C    VAL F 182     -10.078 -64.896 -13.455  1.00 37.93      A  C
ATOM  13301  O    VAL F 182      -9.286 -64.460 -12.611  1.00 37.79      A  O
ATOM  13302  CB   VAL F 182      -9.440 -63.552 -15.490  1.00 38.76      A  C
ATOM  13303  CG1  VAL F 182      -8.457 -63.591 -16.649  1.00 39.09      A  C
ATOM  13304  CG2  VAL F 182     -10.760 -62.894 -15.886  1.00 39.11      A  C
ATOM  13305  N    GLY F 183     -11.297 -65.319 -13.144  1.00 37.21      A  N
ATOM  13306  CA   GLY F 183     -11.801 -65.274 -11.768  1.00 36.25      A  C
ATOM  13307  C    GLY F 183     -11.491 -63.994 -11.014  1.00 35.56      A  C
ATOM  13308  O    GLY F 183     -10.589 -63.968 -10.182  1.00 35.39      A  O
ATOM  13309  N    ALA F 184     -12.237 -62.936 -11.311  1.00 35.02      A  N
ATOM  13310  CA   ALA F 184     -11.990 -61.639 -10.710  1.00 34.46      A  C
ATOM  13311  C    ALA F 184     -12.320 -61.636  -9.221  1.00 33.92      A  C
ATOM  13312  O    ALA F 184     -11.541 -61.133  -8.406  1.00 33.74      A  O
ATOM  13313  CB   ALA F 184     -12.764 -60.571 -11.435  1.00 34.79      A  C
ATOM  13314  N    THR F 185     -13.469 -62.210  -8.872  1.00 33.36      A  N
ATOM  13315  CA   THR F 185     -13.872 -62.361  -7.469  1.00 32.82      A  C
ATOM  13316  C    THR F 185     -13.158 -63.555  -6.836  1.00 32.58      A  C
ATOM  13317  O    THR F 185     -13.169 -63.726  -5.617  1.00 32.56      A  O
ATOM  13318  CB   THR F 185     -15.385 -62.602  -7.310  1.00 32.71      A  C
ATOM  13319  CG2  THR F 185     -16.182 -61.654  -8.171  1.00 32.95      A  C
ATOM  13320  OG1  THR F 185     -15.696 -63.955  -7.666  1.00 32.39      A  O
ATOM  13321  N    ASP F 186     -12.526 -64.371  -7.673  1.00 32.34      A  N
ATOM  13322  CA   ASP F 186     -12.103 -65.697  -7.266  1.00 32.10      A  C
ATOM  13323  C    ASP F 186     -10.670 -66.007  -7.734  1.00 32.16      A  C
ATOM  13324  O    ASP F 186     -10.476 -66.832  -8.638  1.00 32.47      A  O
ATOM  13325  CB   ASP F 186     -13.116 -66.710  -7.829  1.00 32.00      A  C
```

FIGURE 1 (cont'd)

```
ATOM  13326  CG   ASP F 186     -12.952 -68.114  -7.265  1.00 31.49      A  C
ATOM  13327  OD1  ASP F 186     -13.741 -68.983  -7.699  1.00 31.35      A  O
ATOM  13328  OD2  ASP F 186     -12.063 -68.367  -6.411  1.00 30.66      A  O
ATOM  13329  N    SER F 187      -9.655 -65.382  -7.123  1.00 31.92      A  N
ATOM  13330  CA   SER F 187      -9.777 -64.467  -5.984  1.00 31.65      A  C
ATOM  13331  C    SER F 187      -8.880 -63.246  -6.186  1.00 31.62      A  C
ATOM  13332  O    SER F 187      -8.224 -62.774  -5.249  1.00 31.50      A  O
ATOM  13333  CB   SER F 187      -9.383 -65.182  -4.683  1.00 31.56      A  C
ATOM  13334  OG   SER F 187     -10.362 -66.124  -4.285  1.00 31.72      A  O
ATOM  13335  N    ALA F 188      -8.850 -62.745  -7.416  1.00 31.74      A  N
ATOM  13336  CA   ALA F 188      -7.995 -61.619  -7.770  1.00 31.83      A  C
ATOM  13337  C    ALA F 188      -8.227 -60.425  -6.850  1.00 31.84      A  C
ATOM  13338  O    ALA F 188      -7.272 -59.918  -6.249  1.00 31.85      A  O
ATOM  13339  CB   ALA F 188      -8.202 -61.233  -9.213  1.00 32.01      A  C
ATOM  13340  N    VAL F 189      -9.491 -60.000  -6.728  1.00 31.77      A  N
ATOM  13341  CA   VAL F 189      -9.871 -58.883  -5.845  1.00 31.66      A  C
ATOM  13342  C    VAL F 189      -9.396 -59.100  -4.395  1.00 31.65      A  C
ATOM  13343  O    VAL F 189      -8.726 -58.224  -3.833  1.00 31.77      A  O
ATOM  13344  CB   VAL F 189     -11.389 -58.570  -5.895  1.00 31.55      A  C
ATOM  13345  CG1  VAL F 189     -11.765 -57.557  -4.828  1.00 31.36      A  C
ATOM  13346  CG2  VAL F 189     -11.787 -58.068  -7.261  1.00 31.75      A  C
ATOM  13347  N    PRO F 190      -9.722 -60.267  -3.788  1.00 31.54      A  N
ATOM  13348  CA   PRO F 190      -9.174 -60.562  -2.469  1.00 31.55      A  C
ATOM  13349  C    PRO F 190      -7.681 -60.298  -2.391  1.00 31.78      A  C
ATOM  13350  O    PRO F 190      -7.238 -59.594  -1.473  1.00 31.81      A  O
ATOM  13351  CB   PRO F 190      -9.471 -62.052  -2.304  1.00 31.33      A  C
ATOM  13352  CG   PRO F 190     -10.769 -62.216  -2.984  1.00 31.34      A  C
ATOM  13353  CD   PRO F 190     -10.763 -61.247  -4.155  1.00 31.49      A  C
ATOM  13354  N    CYS F 191      -6.925 -60.822  -3.357  1.00 32.13      A  N
ATOM  13355  CA   CYS F 191      -5.471 -60.651  -3.357  1.00 32.70      A  C
ATOM  13356  C    CYS F 191      -5.055 -59.201  -3.551  1.00 32.99      A  C
ATOM  13357  O    CYS F 191      -4.119 -58.736  -2.892  1.00 33.18      A  O
ATOM  13358  CB   CYS F 191      -4.804 -61.561  -4.384  1.00 32.75      A  C
ATOM  13359  SG   CYS F 191      -4.905 -63.306  -3.928  1.00 33.34      A  S
ATOM  13360  N    ALA F 192      -5.769 -58.494  -4.427  1.00 33.20      A  N
ATOM  13361  CA   ALA F 192      -5.519 -57.081  -4.686  1.00 33.42      A  C
ATOM  13362  C    ALA F 192      -5.656 -56.240  -3.419  1.00 33.39      A  C
ATOM  13363  O    ALA F 192      -4.851 -55.345  -3.175  1.00 33.67      A  O
ATOM  13364  CB   ALA F 192      -6.445 -56.575  -5.769  1.00 33.57      A  C
ATOM  13365  N    LEU F 193      -6.668 -56.547  -2.614  1.00 33.01      A  N
ATOM  13366  CA   LEU F 193      -6.915 -55.840  -1.361  1.00 32.63      A  C
ATOM  13367  C    LEU F 193      -5.761 -56.034  -0.375  1.00 33.20      A  C
ATOM  13368  O    LEU F 193      -5.246 -55.064   0.187  1.00 33.60      A  O
ATOM  13369  CB   LEU F 193      -8.239 -56.298  -0.741  1.00 31.33      A  C
ATOM  13370  CG   LEU F 193      -9.542 -55.922  -1.458  1.00 29.74      A  C
ATOM  13371  CD1  LEU F 193     -10.719 -56.649  -0.841  1.00 28.76      A  C
ATOM  13372  N    LEU F 194      -5.350 -57.282  -0.175  1.00 33.37      A  N
ATOM  13373  CA   LEU F 194      -4.218 -57.569   0.683  1.00 33.54      A  C
ATOM  13374  C    LEU F 194      -3.007 -56.698   0.314  1.00 34.47      A  C
ATOM  13375  O    LEU F 194      -2.292 -56.218   1.198  1.00 34.78      A  O
ATOM  13376  CB   LEU F 194      -3.868 -59.047   0.610  1.00 32.45      A  C
ATOM  13377  CG   LEU F 194      -4.864 -59.950   1.317  1.00 31.27      A  C
ATOM  13378  CD1  LEU F 194      -4.175 -61.203   1.805  1.00 30.87      A  C
ATOM  13379  N    LEU F 195      -2.799 -56.482  -0.985  1.00 35.25      A  N
ATOM  13380  CA   LEU F 195      -1.701 -55.646  -1.466  1.00 36.09      A  C
ATOM  13381  C    LEU F 195      -1.939 -54.182  -1.121  1.00 36.81      A  C
ATOM  13382  O    LEU F 195      -1.062 -53.514  -0.554  1.00 37.13      A  O
ATOM  13383  CB   LEU F 195      -1.492 -55.806  -2.980  1.00 36.03      A  C
ATOM  13384  CG   LEU F 195      -0.945 -57.135  -3.520  1.00 35.83      A  C
ATOM  13385  CD1  LEU F 195      -0.931 -57.099  -5.037  1.00 36.04      A  C
ATOM  13386  CD2  LEU F 195       0.442 -57.474  -2.978  1.00 35.82      A  C
ATOM  13387  N    GLU F 196      -3.131 -53.695  -1.460  1.00 37.41      A  N
ATOM  13388  CA   GLU F 196      -3.506 -52.297  -1.232  1.00 38.03      A  C
ATOM  13389  C    GLU F 196      -3.460 -51.912   0.247  1.00 38.13      A  C
ATOM  13390  O    GLU F 196      -2.968 -50.839   0.598  1.00 38.33      A  O
```

FIGURE 1 (cont'd)

```
ATOM  13391  CB   GLU F 196     -4.890 -52.016  -1.821  1.00 38.18      A  C
ATOM  13392  CG   GLU F 196     -5.531 -50.702  -1.363  1.00 39.32      A  C
ATOM  13393  CD   GLU F 196     -4.874 -49.447  -1.945  1.00 40.80      A  C
ATOM  13394  OE1  GLU F 196     -3.958 -49.558  -2.797  1.00 41.41      A  O
ATOM  13395  OE2  GLU F 196     -5.291 -48.337  -1.546  1.00 41.50      A  O
ATOM  13396  N    LEU F 197     -3.978 -52.797   1.097  1.00 38.12      A  N
ATOM  13397  CA   LEU F 197     -3.912 -52.630   2.538  1.00 38.34      A  C
ATOM  13398  C    LEU F 197     -2.475 -52.485   3.003  1.00 38.85      A  C
ATOM  13399  O    LEU F 197     -2.156 -51.568   3.754  1.00 39.16      A  O
ATOM  13400  CB   LEU F 197     -4.551 -53.821   3.237  1.00 37.94      A  C
ATOM  13401  CG   LEU F 197     -5.964 -53.642   3.779  1.00 37.73      A  C
ATOM  13402  CD1  LEU F 197     -6.993 -53.805   2.694  1.00 37.59      A  C
ATOM  13403  CD2  LEU F 197     -6.216 -54.656   4.867  1.00 37.66      A  C
ATOM  13404  N    ALA F 198     -1.611 -53.382   2.536  1.00 39.30      A  N
ATOM  13405  CA   ALA F 198     -0.210 -53.402   2.937  1.00 40.02      A  C
ATOM  13406  C    ALA F 198      0.514 -52.132   2.531  1.00 40.77      A  C
ATOM  13407  O    ALA F 198      1.473 -51.723   3.182  1.00 41.09      A  O
ATOM  13408  CB   ALA F 198      0.478 -54.600   2.343  1.00 39.86      A  C
ATOM  13409  N    GLN F 199      0.049 -51.516   1.451  1.00 41.36      A  N
ATOM  13410  CA   GLN F 199      0.666 -50.316   0.914  1.00 42.02      A  C
ATOM  13411  C    GLN F 199      0.102 -49.086   1.596  1.00 42.95      A  C
ATOM  13412  O    GLN F 199      0.846 -48.190   1.966  1.00 43.55      A  O
ATOM  13413  CB   GLN F 199      0.412 -50.219  -0.587  1.00 40.94      A  C
ATOM  13414  CG   GLN F 199      1.657 -50.027  -1.442  1.00 40.41      A  C
ATOM  13415  CD   GLN F 199      2.509 -48.844  -1.048  1.00 40.13      A  C
ATOM  13416  OE1  GLN F 199      2.159 -47.704  -1.325  1.00 40.45      A  O
ATOM  13417  N    ALA F 200     -1.218 -49.046   1.755  1.00 43.64      A  N
ATOM  13418  CA   ALA F 200     -1.902 -47.899   2.358  1.00 44.37      A  C
ATOM  13419  C    ALA F 200     -1.515 -47.684   3.828  1.00 44.91      A  C
ATOM  13420  O    ALA F 200     -1.347 -46.542   4.281  1.00 45.33      A  O
ATOM  13421  CB   ALA F 200     -3.415 -48.046   2.209  1.00 44.11      A  C
ATOM  13422  N    LEU F 201     -1.367 -48.788   4.558  1.00 45.25      A  N
ATOM  13423  CA   LEU F 201     -0.983 -48.749   5.970  1.00 45.79      A  C
ATOM  13424  C    LEU F 201      0.507 -48.970   6.155  1.00 46.50      A  C
ATOM  13425  O    LEU F 201      0.975 -49.180   7.272  1.00 46.73      A  O
ATOM  13426  CB   LEU F 201     -1.736 -49.813   6.761  1.00 45.33      A  C
ATOM  13427  CG   LEU F 201     -3.248 -49.655   6.803  1.00 45.08      A  C
ATOM  13428  CD1  LEU F 201     -3.896 -50.949   7.241  1.00 44.77      A  C
ATOM  13429  CD2  LEU F 201     -3.661 -48.482   7.676  1.00 45.35      A  C
ATOM  13430  N    ASP F 202      1.245 -48.920   5.051  1.00 47.28      A  N
ATOM  13431  CA   ASP F 202      2.682 -49.201   5.043  1.00 48.12      A  C
ATOM  13432  C    ASP F 202      3.469 -48.432   6.112  1.00 48.71      A  C
ATOM  13433  O    ASP F 202      4.243 -49.039   6.862  1.00 48.92      A  O
ATOM  13434  CB   ASP F 202      3.262 -48.951   3.641  1.00 48.23      A  C
ATOM  13435  CG   ASP F 202      4.763 -49.151   3.575  1.00 48.66      A  C
ATOM  13436  OD1  ASP F 202      5.246 -50.265   3.899  1.00 48.48      A  O
ATOM  13437  OD2  ASP F 202      5.448 -48.180   3.182  1.00 49.41      A  O
ATOM  13438  N    LEU F 203      3.256 -47.117   6.190  1.00 49.10      A  N
ATOM  13439  CA   LEU F 203      4.022 -46.264   7.102  1.00 49.31      A  C
ATOM  13440  C    LEU F 203      3.698 -46.440   8.580  1.00 49.56      A  C
ATOM  13441  O    LEU F 203      4.603 -46.595   9.405  1.00 49.96      A  O
ATOM  13442  CB   LEU F 203      3.894 -44.794   6.712  1.00 48.35      A  C
ATOM  13443  CG   LEU F 203      4.829 -44.378   5.575  1.00 48.07      A  C
ATOM  13444  CD1  LEU F 203      4.078 -44.296   4.258  1.00 47.97      A  C
ATOM  13445  N    GLU F 204      2.414 -46.536   8.908  1.00 49.36      A  N
ATOM  13446  CA   GLU F 204      1.983 -46.876  10.267  1.00 48.99      A  C
ATOM  13447  C    GLU F 204      2.375 -48.306  10.657  1.00 49.44      A  C
ATOM  13448  O    GLU F 204      2.672 -48.581  11.827  1.00 49.74      A  O
ATOM  13449  CB   GLU F 204      0.472 -46.633  10.471  1.00 47.49      A  C
ATOM  13450  CG   GLU F 204     -0.413 -46.744   9.222  1.00 45.83      A  C
ATOM  13451  CD   GLU F 204     -0.277 -45.549   8.287  1.00 45.07      A  C
ATOM  13452  OE1  GLU F 204     -0.863 -44.488   8.579  1.00 45.21      A  O
ATOM  13453  N    LEU F 205      2.382 -49.203   9.670  1.00 49.64      A  N
ATOM  13454  CA   LEU F 205      2.862 -50.572   9.858  1.00 49.77      A  C
ATOM  13455  C    LEU F 205      4.360 -50.585  10.081  1.00 50.50      A  C
```

FIGURE 1 (cont'd)

```
ATOM  13456  O    LEU F 205       4.867 -51.436  10.815  1.00 50.57      A    O
ATOM  13457  CB   LEU F 205       2.539 -51.440   8.645  1.00 49.21      A    C
ATOM  13458  CG   LEU F 205       1.263 -52.270   8.656  1.00 48.22      A    C
ATOM  13459  CD1  LEU F 205       0.967 -52.719   7.253  1.00 47.84      A    C
ATOM  13460  CD2  LEU F 205       1.393 -53.467   9.586  1.00 47.60      A    C
ATOM  13461  N    SER F 206       5.052 -49.642   9.436  1.00 51.35      A    N
ATOM  13462  CA   SER F 206       6.512 -49.544   9.494  1.00 52.25      A    C
ATOM  13463  C    SER F 206       6.996 -49.117  10.877  1.00 52.74      A    C
ATOM  13464  O    SER F 206       7.805 -49.821  11.503  1.00 52.78      A    O
ATOM  13465  CB   SER F 206       7.042 -48.589   8.420  1.00 52.45      A    C
ATOM  13466  OG   SER F 206       8.410 -48.827   8.155  1.00 53.12      A    O
ATOM  13467  N    ARG F 207       6.492 -47.977  11.356  1.00 53.28      A    N
ATOM  13468  CA   ARG F 207       6.901 -47.452  12.665  1.00 53.77      A    C
ATOM  13469  C    ARG F 207       6.670 -48.471  13.781  1.00 53.75      A    C
ATOM  13470  O    ARG F 207       7.605 -48.800  14.514  1.00 54.12      A    O
ATOM  13471  CB   ARG F 207       6.274 -46.078  12.980  1.00 54.03      A    C
ATOM  13472  CG   ARG F 207       4.755 -46.010  12.913  1.00 53.56      A    C
ATOM  13473  N    ALA F 208       5.447 -48.996  13.878  1.00 53.28      A    N
ATOM  13474  CA   ALA F 208       5.159 -50.076  14.816  1.00 52.89      A    C
ATOM  13475  C    ALA F 208       5.940 -51.319  14.385  1.00 52.67      A    C
ATOM  13476  O    ALA F 208       5.414 -52.202  13.711  1.00 52.47      A    O
ATOM  13477  CB   ALA F 208       3.665 -50.347  14.885  1.00 52.57      A    C
ATOM  13478  N    LYS F 209       7.214 -51.347  14.769  1.00 52.72      A    N
ATOM  13479  CA   LYS F 209       8.196 -52.340  14.333  1.00 52.35      A    C
ATOM  13480  C    LYS F 209       9.577 -51.712  14.402  1.00 51.68      A    C
ATOM  13481  O    LYS F 209      10.573 -52.392  14.448  1.00 52.72      A    O
ATOM  13482  CB   LYS F 209       7.989 -52.746  12.871  1.00 52.41      A    C
ATOM  13483  CG   LYS F 209       8.792 -53.972  12.440  1.00 52.72      A    C
ATOM  13484  CD   LYS F 209       9.295 -53.822  11.007  1.00 53.58      A    C
ATOM  13485  CE   LYS F 209      10.003 -55.081  10.522  1.00 53.78      A    C
ATOM  13486  NZ   LYS F 209      10.581 -54.913   9.155  1.00 53.88      A    N
ATOM  13487  N    LYS F 210       9.669 -50.404  14.197  1.00 49.37      A    N
ATOM  13488  CA   LYS F 210      10.991 -49.779  14.292  1.00 46.81      A    C
ATOM  13489  C    LYS F 210      11.366 -49.709  15.770  1.00 47.17      A    C
ATOM  13490  O    LYS F 210      12.550 -49.644  16.136  1.00 47.59      A    O
ATOM  13491  CB   LYS F 210      11.032 -48.427  13.601  1.00 45.36      A    C
ATOM  13492  CG   LYS F 210      11.092 -48.571  12.101  1.00 39.37      A    C
ATOM  13493  CD   LYS F 210      11.255 -47.217  11.452  1.00 32.16      A    C
ATOM  13494  CE   LYS F 210      11.531 -47.355   9.968  1.00 27.65      A    C
ATOM  13495  NZ   LYS F 210      11.644 -46.079   9.366  1.00 26.72      A    N
ATOM  13496  N    GLN F 211      10.317 -49.733  16.593  1.00 46.63      A    N
ATOM  13497  CA   GLN F 211      10.362 -50.163  17.978  1.00 45.72      A    C
ATOM  13498  C    GLN F 211       8.927 -50.588  18.290  1.00 47.11      A    C
ATOM  13499  O    GLN F 211       8.088 -49.722  18.523  1.00 47.45      A    O
ATOM  13500  CB   GLN F 211      10.832 -49.034  18.914  1.00 44.43      A    C
ATOM  13501  CG   GLN F 211      12.331 -49.051  19.256  1.00 38.20      A    C
ATOM  13502  CD   GLN F 211      12.953 -47.645  19.302  1.00 32.35      A    C
ATOM  13503  NE2  GLN F 211      14.216 -47.570  19.747  1.00 30.13      A    N
ATOM  13504  OE1  GLN F 211      12.310 -46.640  18.930  1.00 31.46      A    O
ATOM  13505  N    ALA F 212       8.597 -51.883  18.246  1.00 47.83      A    N
ATOM  13506  CA   ALA F 212       9.444 -53.009  17.830  1.00 48.09      A    C
ATOM  13507  C    ALA F 212       9.308 -54.106  18.874  1.00 47.78      A    C
ATOM  13508  O    ALA F 212      10.253 -54.401  19.607  1.00 48.21      A    O
ATOM  13509  CB   ALA F 212      10.903 -52.623  17.652  1.00 48.25      A    C
ATOM  13510  N    ALA F 213       8.110 -54.680  18.954  1.00 46.29      A    N
ATOM  13511  CA   ALA F 213       7.788 -55.814  19.839  1.00 44.26      A    C
ATOM  13512  C    ALA F 213       6.333 -56.258  19.615  1.00 41.94      A    C
ATOM  13513  O    ALA F 213       5.863 -57.219  20.245  1.00 42.15      A    O
ATOM  13514  CB   ALA F 213       8.029 -55.459  21.343  1.00 44.34      A    C
ATOM  13515  N    PRO F 214       5.610 -55.571  18.709  1.00 39.52      A    N
ATOM  13516  CA   PRO F 214       4.184 -55.873  18.731  1.00 38.19      A    C
ATOM  13517  C    PRO F 214       3.817 -57.076  17.842  1.00 37.94      A    C
ATOM  13518  O    PRO F 214       4.531 -57.358  16.859  1.00 38.46      A    O
ATOM  13519  CB   PRO F 214       3.552 -54.577  18.187  1.00 37.90      A    C
ATOM  13520  CG   PRO F 214       4.746 -53.747  17.563  1.00 37.83      A    C
```

FIGURE 1 (cont'd)

```
ATOM  13521  CD   PRO F 214      5.957 -54.616  17.633  1.00 38.82      A    C
ATOM  13522  N    VAL F 215      2.755 -57.801  18.221  1.00 36.51      A    N
ATOM  13523  CA   VAL F 215      1.930 -58.601  17.298  1.00 36.25      A    C
ATOM  13524  C    VAL F 215      2.037 -58.067  15.863  1.00 36.41      A    C
ATOM  13525  O    VAL F 215      1.694 -56.908  15.596  1.00 36.67      A    O
ATOM  13526  CB   VAL F 215      0.447 -58.556  17.748  1.00 35.48      A    C
ATOM  13527  CG1  VAL F 215     -0.366 -59.659  17.078  1.00 34.59      A    C
ATOM  13528  N    THR F 216      2.527 -58.913  14.957  1.00 36.12      A    N
ATOM  13529  CA   THR F 216      2.845 -58.492  13.584  1.00 35.62      A    C
ATOM  13530  C    THR F 216      1.728 -58.776  12.571  1.00 35.13      A    C
ATOM  13531  O    THR F 216      0.602 -59.116  12.955  1.00 35.11      A    O
ATOM  13532  CB   THR F 216      4.161 -59.116  13.077  1.00 35.61      A    C
ATOM  13533  OG1  THR F 216      4.926 -58.103  12.418  1.00 35.47      A    O
ATOM  13534  N    LEU F 217      2.043 -58.620  11.282  1.00 34.51      A    N
ATOM  13535  CA   LEU F 217      1.073 -58.841  10.205  1.00 33.71      A    C
ATOM  13536  C    LEU F 217      1.640 -59.776   9.154  1.00 33.34      A    C
ATOM  13537  O    LEU F 217      2.785 -59.602   8.714  1.00 33.61      A    O
ATOM  13538  CB   LEU F 217      0.675 -57.517   9.552  1.00 33.60      A    C
ATOM  13539  CG   LEU F 217     -0.203 -57.604   8.309  1.00 33.07      A    C
ATOM  13540  CD1  LEU F 217     -1.616 -58.073   8.658  1.00 32.87      A    C
ATOM  13541  CD2  LEU F 217     -0.242 -56.265   7.626  1.00 33.14      A    C
ATOM  13542  N    GLN F 218      0.832 -60.751   8.741  1.00 32.55      A    N
ATOM  13543  CA   GLN F 218      1.266 -61.758   7.771  1.00 31.92      A    C
ATOM  13544  C    GLN F 218      0.317 -61.840   6.572  1.00 31.33      A    C
ATOM  13545  O    GLN F 218     -0.898 -61.895   6.736  1.00 31.28      A    O
ATOM  13546  CB   GLN F 218      1.401 -63.121   8.454  1.00 31.92      A    C
ATOM  13547  CG   GLN F 218      1.999 -64.195   7.588  1.00 32.12      A    C
ATOM  13548  CD   GLN F 218      1.939 -65.542   8.243  1.00 32.81      A    C
ATOM  13549  NE2  GLN F 218      0.726 -66.025   8.506  1.00 32.87      A    N
ATOM  13550  OE1  GLN F 218      2.972 -66.147   8.527  1.00 33.63      A    O
ATOM  13551  N    LEU F 219      0.869 -61.839   5.368  1.00 30.73      A    N
ATOM  13552  CA   LEU F 219      0.047 -61.932   4.177  1.00 30.05      A    C
ATOM  13553  C    LEU F 219      0.344 -63.212   3.419  1.00 29.81      A    C
ATOM  13554  O    LEU F 219      1.470 -63.433   2.984  1.00 29.95      A    O
ATOM  13555  CB   LEU F 219      0.262 -60.713   3.284  1.00 29.91      A    C
ATOM  13556  CG   LEU F 219     -0.105 -59.374   3.915  1.00 29.63      A    C
ATOM  13557  CD1  LEU F 219      0.259 -58.245   2.985  1.00 29.41      A    C
ATOM  13558  CD2  LEU F 219     -1.585 -59.324   4.266  1.00 29.21      A    C
ATOM  13559  N    LEU F 220     -0.668 -64.060   3.265  1.00 29.30      A    N
ATOM  13560  CA   LEU F 220     -0.497 -65.322   2.557  1.00 28.85      A    C
ATOM  13561  C    LEU F 220     -1.213 -65.304   1.209  1.00 28.94      A    C
ATOM  13562  O    LEU F 220     -2.397 -65.013   1.127  1.00 28.99      A    O
ATOM  13563  CB   LEU F 220     -0.966 -66.494   3.421  1.00 28.12      A    C
ATOM  13564  CG   LEU F 220     -0.216 -66.673   4.736  1.00 27.40      A    C
ATOM  13565  CD1  LEU F 220     -0.759 -67.890   5.441  1.00 26.96      A    C
ATOM  13566  N    PHE F 221     -0.461 -65.592   0.156  1.00 29.09      A    N
ATOM  13567  CA   PHE F 221     -0.999 -65.764  -1.185  1.00 29.06      A    C
ATOM  13568  C    PHE F 221     -0.783 -67.221  -1.590  1.00 29.11      A    C
ATOM  13569  O    PHE F 221      0.309 -67.614  -1.994  1.00 29.21      A    O
ATOM  13570  CB   PHE F 221     -0.299 -64.824  -2.162  1.00 29.09      A    C
ATOM  13571  CG   PHE F 221     -0.386 -63.376  -1.781  1.00 29.12      A    C
ATOM  13572  CD1  PHE F 221     -1.343 -62.555  -2.366  1.00 29.20      A    C
ATOM  13573  CD2  PHE F 221      0.490 -62.830  -0.851  1.00 29.21      A    C
ATOM  13574  CE1  PHE F 221     -1.438 -61.211  -2.033  1.00 29.24      A    C
ATOM  13575  CE2  PHE F 221      0.409 -61.496  -0.508  1.00 29.46      A    C
ATOM  13576  CZ   PHE F 221     -0.555 -60.679  -1.106  1.00 29.37      A    C
ATOM  13577  N    LEU F 222     -1.830 -68.024  -1.456  1.00 29.16      A    N
ATOM  13578  CA   LEU F 222     -1.741 -69.463  -1.657  1.00 29.39      A    C
ATOM  13579  C    LEU F 222     -1.939 -69.882  -3.113  1.00 29.77      A    C
ATOM  13580  O    LEU F 222     -2.788 -69.336  -3.822  1.00 29.80      A    O
ATOM  13581  CB   LEU F 222     -2.756 -70.162  -0.767  1.00 29.21      A    C
ATOM  13582  CG   LEU F 222     -2.636 -69.729   0.692  1.00 29.06      A    C
ATOM  13583  CD1  LEU F 222     -1.762 -70.700   1.466  1.00 29.15      A    C
ATOM  13584  CD2  LEU F 222     -4.005 -69.626   1.330  1.00 28.74      A    C
ATOM  13585  N    ASP F 223     -1.136 -70.845  -3.556  1.00 30.32      A    N
```

FIGURE 1 (cont'd)

```
ATOM  13586  CA   ASP F 223    -1.256 -71.401  -4.901  1.00 30.89      A  C
ATOM  13587  C    ASP F 223    -2.210 -72.594  -4.862  1.00 30.91      A  C
ATOM  13588  O    ASP F 223    -2.569 -73.072  -3.777  1.00 30.81      A  O
ATOM  13589  CB   ASP F 223     0.127 -71.813  -5.430  1.00 31.32      A  C
ATOM  13590  CG   ASP F 223     0.163 -71.990  -6.956  1.00 32.37      A  C
ATOM  13591  OD1  ASP F 223    -0.824 -71.643  -7.635  1.00 33.29      A  O
ATOM  13592  OD2  ASP F 223     1.190 -72.478  -7.485  1.00 33.08      A  O
ATOM  13593  N    GLY F 224    -2.640 -73.036  -6.044  1.00 31.02      A  N
ATOM  13594  CA   GLY F 224    -3.436 -74.244  -6.207  1.00 31.24      A  C
ATOM  13595  C    GLY F 224    -4.479 -74.510  -5.138  1.00 31.20      A  C
ATOM  13596  O    GLY F 224    -4.386 -75.476  -4.375  1.00 31.41      A  O
ATOM  13597  N    GLU F 225    -5.475 -73.643  -5.078  1.00 31.03      A  N
ATOM  13598  CA   GLU F 225    -6.574 -73.842  -4.157  1.00 30.96      A  C
ATOM  13599  C    GLU F 225    -7.686 -74.530  -4.916  1.00 31.01      A  C
ATOM  13600  O    GLU F 225    -8.282 -75.487  -4.427  1.00 30.97      A  O
ATOM  13601  CB   GLU F 225    -7.033 -72.506  -3.567  1.00 30.79      A  C
ATOM  13602  CG   GLU F 225    -8.178 -72.615  -2.599  1.00 31.07      A  C
ATOM  13603  CD   GLU F 225    -9.502 -72.582  -3.287  1.00 31.85      A  C
ATOM  13604  OE1  GLU F 225    -9.613 -71.864  -4.296  1.00 32.65      A  O
ATOM  13605  OE2  GLU F 225   -10.431 -73.270  -2.828  1.00 32.31      A  O
ATOM  13606  N    GLU F 226    -7.945 -74.040  -6.121  1.00 31.29      A  N
ATOM  13607  CA   GLU F 226    -8.991 -74.586  -6.964  1.00 31.79      A  C
ATOM  13608  C    GLU F 226    -8.566 -75.954  -7.466  1.00 32.41      A  C
ATOM  13609  O    GLU F 226    -7.397 -76.158  -7.790  1.00 32.57      A  O
ATOM  13610  CB   GLU F 226    -9.271 -73.653  -8.151  1.00 31.69      A  C
ATOM  13611  CG   GLU F 226    -9.678 -72.225  -7.796  1.00 30.93      A  C
ATOM  13612  CD   GLU F 226   -11.173 -72.031  -7.683  1.00 30.25      A  C
ATOM  13613  OE1  GLU F 226   -11.911 -73.005  -7.413  1.00 30.21      A  O
ATOM  13614  OE2  GLU F 226   -11.612 -70.879  -7.862  1.00 29.68      A  O
ATOM  13615  N    ALA F 227    -9.529 -76.872  -7.533  1.00 32.98      A  N
ATOM  13616  CA   ALA F 227    -9.306 -78.242  -7.983  1.00 33.75      A  C
ATOM  13617  C    ALA F 227    -8.859 -78.334  -9.448  1.00 34.41      A  C
ATOM  13618  O    ALA F 227    -8.987 -77.368 -10.211  1.00 34.47      A  O
ATOM  13619  CB   ALA F 227   -10.562 -79.060  -7.763  1.00 33.74      A  C
ATOM  13620  N    LEU F 228    -8.328 -79.496  -9.835  1.00 35.21      A  N
ATOM  13621  CA   LEU F 228    -7.914 -79.703 -11.220  1.00 35.91      A  C
ATOM  13622  C    LEU F 228    -8.842 -80.600 -12.023  1.00 36.66      A  C
ATOM  13623  O    LEU F 228    -9.177 -80.269 -13.158  1.00 36.96      A  O
ATOM  13624  CB   LEU F 228    -6.457 -80.158 -11.333  1.00 35.87      A  C
ATOM  13625  CG   LEU F 228    -5.318 -79.125 -11.218  1.00 35.21      A  C
ATOM  13626  CD1  LEU F 228    -4.569 -79.272  -9.913  1.00 34.79      A  C
ATOM  13627  CD2  LEU F 228    -5.766 -77.684 -11.398  1.00 34.61      A  C
ATOM  13628  N    LYS F 229    -9.247 -81.734 -11.459  1.00 37.36      A  N
ATOM  13629  CA   LYS F 229   -10.276 -82.555 -12.107  1.00 38.18      A  C
ATOM  13630  C    LYS F 229   -11.623 -82.182 -11.491  1.00 38.18      A  C
ATOM  13631  O    LYS F 229   -12.334 -81.330 -12.026  1.00 38.14      A  O
ATOM  13632  CB   LYS F 229    -9.973 -84.062 -12.001  1.00 38.70      A  C
ATOM  13633  CG   LYS F 229   -10.819 -84.981 -12.920  1.00 39.49      A  C
ATOM  13634  CD   LYS F 229   -10.174 -85.221 -14.292  1.00 40.04      A  C
ATOM  13635  N    GLU F 230   -11.976 -82.802 -10.370  1.00 38.35      A  N
ATOM  13636  CA   GLU F 230   -13.099 -82.301  -9.585  1.00 38.55      A  C
ATOM  13637  C    GLU F 230   -12.822 -82.251  -8.079  1.00 38.28      A  C
ATOM  13638  O    GLU F 230   -12.109 -83.092  -7.521  1.00 38.31      A  O
ATOM  13639  CB   GLU F 230   -14.433 -83.008  -9.922  1.00 38.99      A  C
ATOM  13640  CG   GLU F 230   -15.717 -82.139  -9.597  1.00 39.93      A  C
ATOM  13641  CD   GLU F 230   -15.717 -80.716 -10.231  1.00 40.09      A  C
ATOM  13642  OE1  GLU F 230   -15.474 -79.702  -9.527  1.00 38.73      A  O
ATOM  13643  N    TRP F 231   -13.402 -81.233  -7.451  1.00 37.94      A  N
ATOM  13644  CA   TRP F 231   -13.224 -80.938  -6.044  1.00 37.68      A  C
ATOM  13645  C    TRP F 231   -13.354 -82.165  -5.158  1.00 38.02      A  C
ATOM  13646  O    TRP F 231   -14.292 -82.949  -5.286  1.00 38.35      A  O
ATOM  13647  CB   TRP F 231   -14.229 -79.873  -5.614  1.00 37.33      A  C
ATOM  13648  CG   TRP F 231   -13.942 -79.321  -4.270  1.00 36.75      A  C
ATOM  13649  CD1  TRP F 231   -14.363 -79.822  -3.071  1.00 36.70      A  C
ATOM  13650  CD2  TRP F 231   -13.161 -78.161  -3.974  1.00 36.13      A  C
```

FIGURE 1 (cont'd)

```
ATOM  13651  CE2 TRP F 231     -13.149 -78.017  -2.565  1.00 35.91      A  C
ATOM  13652  CE3 TRP F 231     -12.466 -77.230  -4.759  1.00 35.79      A  C
ATOM  13653  NE1 TRP F 231     -13.890 -79.046  -2.042  1.00 36.37      A  N
ATOM  13654  CZ2 TRP F 231     -12.464 -76.975  -1.918  1.00 35.27      A  C
ATOM  13655  CZ3 TRP F 231     -11.787 -76.190  -4.120  1.00 35.09      A  C
ATOM  13656  CH2 TRP F 231     -11.791 -76.075  -2.711  1.00 34.82      A  C
ATOM  13657  N   GLY F 232     -12.393 -82.316  -4.262  1.00 38.15      A  N
ATOM  13658  CA  GLY F 232     -12.368 -83.426  -3.326  1.00 38.52      A  C
ATOM  13659  C   GLY F 232     -11.201 -83.269  -2.370  1.00 38.72      A  C
ATOM  13660  O   GLY F 232     -10.334 -82.406  -2.585  1.00 38.44      A  O
ATOM  13661  N   PRO F 233     -11.171 -84.091  -1.302  1.00 39.15      A  N
ATOM  13662  CA  PRO F 233     -10.100 -84.040  -0.306  1.00 39.32      A  C
ATOM  13663  C   PRO F 233      -8.707 -84.169  -0.928  1.00 39.53      A  C
ATOM  13664  O   PRO F 233      -7.765 -83.503  -0.479  1.00 39.24      A  O
ATOM  13665  CB  PRO F 233     -10.408 -85.240   0.592  1.00 39.50      A  C
ATOM  13666  CG  PRO F 233     -11.885 -85.371   0.513  1.00 39.64      A  C
ATOM  13667  CD  PRO F 233     -12.228 -85.044  -0.915  1.00 39.41      A  C
ATOM  13668  N   LYS F 234      -8.585 -84.998  -1.962  1.00 40.10      A  N
ATOM  13669  CA  LYS F 234      -7.288 -85.204  -2.602  1.00 40.69      A  C
ATOM  13670  C   LYS F 234      -7.034 -84.277  -3.809  1.00 40.48      A  C
ATOM  13671  O   LYS F 234      -5.910 -84.207  -4.318  1.00 40.62      A  O
ATOM  13672  CB  LYS F 234      -7.075 -86.689  -2.945  1.00 41.30      A  C
ATOM  13673  CG  LYS F 234      -6.527 -87.530  -1.754  1.00 42.35      A  C
ATOM  13674  CD  LYS F 234      -6.876 -89.045  -1.835  1.00 43.54      A  C
ATOM  13675  CE  LYS F 234      -5.843 -89.870  -2.624  1.00 43.77      A  C
ATOM  13676  N   ASP F 235      -8.069 -83.555  -4.247  1.00 40.13      A  N
ATOM  13677  CA  ASP F 235      -7.943 -82.579  -5.348  1.00 39.60      A  C
ATOM  13678  C   ASP F 235      -8.531 -81.222  -4.953  1.00 39.07      A  C
ATOM  13679  O   ASP F 235      -9.653 -80.885  -5.339  1.00 39.05      A  O
ATOM  13680  CB  ASP F 235      -8.588 -83.122  -6.638  1.00 39.83      A  C
ATOM  13681  CG  ASP F 235      -8.501 -82.146  -7.807  1.00 39.53      A  C
ATOM  13682  OD1 ASP F 235      -9.429 -82.150  -8.645  1.00 39.27      A  O
ATOM  13683  OD2 ASP F 235      -7.519 -81.375  -7.892  1.00 39.12      A  O
ATOM  13684  N   SER F 236      -7.767 -80.471  -4.159  1.00 38.45      A  N
ATOM  13685  CA  SER F 236      -8.121 -79.112  -3.716  1.00 37.81      A  C
ATOM  13686  C   SER F 236      -7.192 -78.639  -2.609  1.00 37.51      A  C
ATOM  13687  O   SER F 236      -6.743 -79.446  -1.790  1.00 37.56      A  O
ATOM  13688  CB  SER F 236      -9.563 -79.045  -3.207  1.00 37.68      A  C
ATOM  13689  OG  SER F 236      -9.719 -79.793  -2.017  1.00 37.58      A  O
ATOM  13690  N   LEU F 237      -6.927 -77.333  -2.573  1.00 37.17      A  N
ATOM  13691  CA  LEU F 237      -6.170 -76.712  -1.482  1.00 37.06      A  C
ATOM  13692  C   LEU F 237      -4.757 -77.291  -1.374  1.00 37.27      A  C
ATOM  13693  O   LEU F 237      -4.322 -77.687  -0.286  1.00 37.41      A  O
ATOM  13694  CB  LEU F 237      -6.901 -76.881  -0.134  1.00 36.92      A  C
ATOM  13695  CG  LEU F 237      -8.421 -76.718  -0.019  1.00 36.58      A  C
ATOM  13696  CD1 LEU F 237      -8.945 -77.422   1.224  1.00 36.69      A  C
ATOM  13697  CD2 LEU F 237      -8.808 -75.268  -0.002  1.00 36.06      A  C
ATOM  13698  N   TYR F 238      -4.046 -77.356  -2.498  1.00 37.38      A  N
ATOM  13699  CA  TYR F 238      -2.667 -77.852  -2.495  1.00 37.46      A  C
ATOM  13700  C   TYR F 238      -1.745 -76.905  -1.751  1.00 37.13      A  C
ATOM  13701  O   TYR F 238      -0.886 -77.344  -1.003  1.00 37.25      A  O
ATOM  13702  CB  TYR F 238      -2.151 -78.095  -3.916  1.00 37.77      A  C
ATOM  13703  CG  TYR F 238      -2.955 -79.116  -4.673  1.00 38.36      A  C
ATOM  13704  CD1 TYR F 238      -2.820 -80.476  -4.407  1.00 39.33      A  C
ATOM  13705  CD2 TYR F 238      -3.865 -78.728  -5.641  1.00 38.48      A  C
ATOM  13706  CE1 TYR F 238      -3.571 -81.432  -5.095  1.00 39.71      A  C
ATOM  13707  CE2 TYR F 238      -4.619 -79.670  -6.340  1.00 38.99      A  C
ATOM  13708  CZ  TYR F 238      -4.469 -81.022  -6.063  1.00 39.40      A  C
ATOM  13709  OH  TYR F 238      -5.219 -81.955  -6.754  1.00 39.65      A  O
ATOM  13710  N   GLY F 239      -1.942 -75.606  -1.947  1.00 36.73      A  N
ATOM  13711  CA  GLY F 239      -1.082 -74.598  -1.348  1.00 36.45      A  C
ATOM  13712  C   GLY F 239      -1.235 -74.539   0.149  1.00 36.24      A  C
ATOM  13713  O   GLY F 239      -0.247 -74.545   0.889  1.00 36.33      A  O
ATOM  13714  N   SER F 240      -2.484 -74.494   0.588  1.00 35.98      A  N
ATOM  13715  CA  SER F 240      -2.798 -74.356   2.002  1.00 35.73      A  C
```

FIGURE 1 (cont'd)

```
ATOM  13716  C    SER F 240    -2.466  -75.604   2.804  1.00 35.72      A  C
ATOM  13717  O    SER F 240    -1.856  -75.508   3.869  1.00 35.81      A  O
ATOM  13718  CB   SER F 240    -4.261  -73.959   2.188  1.00 35.61      A  C
ATOM  13719  OG   SER F 240    -5.094  -74.621   1.246  1.00 35.94      A  O
ATOM  13720  N    ARG F 241    -2.854  -76.769   2.293  1.00 35.70      A  N
ATOM  13721  CA   ARG F 241    -2.529  -78.030   2.953  1.00 35.93      A  C
ATOM  13722  C    ARG F 241    -1.021  -78.220   3.145  1.00 36.02      A  C
ATOM  13723  O    ARG F 241    -0.581  -78.809   4.131  1.00 36.20      A  O
ATOM  13724  CB   ARG F 241    -3.118  -79.218   2.194  1.00 36.05      A  C
ATOM  13725  CG   ARG F 241    -4.535  -79.579   2.610  1.00 36.67      A  C
ATOM  13726  CD   ARG F 241    -4.952  -80.978   2.129  1.00 37.98      A  C
ATOM  13727  NE   ARG F 241    -5.310  -81.004   0.710  1.00 39.18      A  N
ATOM  13728  CZ   ARG F 241    -4.554  -81.541  -0.248  1.00 40.17      A  C
ATOM  13729  NH1  ARG F 241    -3.393  -82.110   0.052  1.00 41.13      A  N
ATOM  13730  NH2  ARG F 241    -4.956  -81.520  -1.515  1.00 40.49      A  N
ATOM  13731  N    HIS F 242    -0.236  -77.707   2.203  1.00 35.99      A  N
ATOM  13732  CA   HIS F 242     1.207  -77.838   2.266  1.00 36.05      A  C
ATOM  13733  C    HIS F 242     1.800  -76.837   3.221  1.00 35.68      A  C
ATOM  13734  O    HIS F 242     2.608  -77.211   4.060  1.00 35.91      A  O
ATOM  13735  CB   HIS F 242     1.838  -77.670   0.893  1.00 36.32      A  C
ATOM  13736  CG   HIS F 242     3.325  -77.785   0.906  1.00 37.13      A  C
ATOM  13737  CD2  HIS F 242     4.132  -78.869   0.888  1.00 37.92      A  C
ATOM  13738  ND1  HIS F 242     4.155  -76.686   0.965  1.00 37.28      A  N
ATOM  13739  CE1  HIS F 242     5.412  -77.089   0.968  1.00 37.95      A  C
ATOM  13740  NE2  HIS F 242     5.425  -78.409   0.921  1.00 38.41      A  N
ATOM  13741  N    LEU F 243     1.407  -75.571   3.083  1.00 35.08      A  N
ATOM  13742  CA   LEU F 243     1.903  -74.519   3.964  1.00 34.62      A  C
ATOM  13743  C    LEU F 243     1.579  -74.844   5.406  1.00 34.74      A  C
ATOM  13744  O    LEU F 243     2.433  -74.685   6.279  1.00 34.95      A  O
ATOM  13745  CB   LEU F 243     1.339  -73.145   3.598  1.00 34.18      A  C
ATOM  13746  CG   LEU F 243     1.863  -71.975   4.434  1.00 33.47      A  C
ATOM  13747  CD1  LEU F 243     3.340  -71.796   4.235  1.00 33.25      A  C
ATOM  13748  CD2  LEU F 243     1.151  -70.705   4.089  1.00 32.88      A  C
ATOM  13749  N    ALA F 244     0.355  -75.310   5.650  1.00 34.76      A  N
ATOM  13750  CA   ALA F 244    -0.035  -75.758   6.983  1.00 35.05      A  C
ATOM  13751  C    ALA F 244     0.912  -76.851   7.515  1.00 35.51      A  C
ATOM  13752  O    ALA F 244     1.415  -76.741   8.634  1.00 35.70      A  O
ATOM  13753  CB   ALA F 244    -1.484  -76.221   6.993  1.00 34.79      A  C
ATOM  13754  N    GLN F 245     1.174  -77.880   6.709  1.00 36.02      A  N
ATOM  13755  CA   GLN F 245     2.133  -78.928   7.080  1.00 36.63      A  C
ATOM  13756  C    GLN F 245     3.516  -78.348   7.418  1.00 36.97      A  C
ATOM  13757  O    GLN F 245     4.078  -78.638   8.477  1.00 37.24      A  O
ATOM  13758  CB   GLN F 245     2.248  -79.987   5.973  1.00 36.69      A  C
ATOM  13759  N    LEU F 246     4.034  -77.509   6.524  1.00 37.09      A  N
ATOM  13760  CA   LEU F 246     5.363  -76.913   6.662  1.00 37.35      A  C
ATOM  13761  C    LEU F 246     5.480  -75.942   7.847  1.00 37.75      A  C
ATOM  13762  O    LEU F 246     6.554  -75.808   8.423  1.00 38.05      A  O
ATOM  13763  CB   LEU F 246     5.774  -76.235   5.346  1.00 37.08      A  C
ATOM  13764  CG   LEU F 246     7.178  -75.666   5.148  1.00 36.46      A  C
ATOM  13765  CD1  LEU F 246     7.084  -74.157   5.022  1.00 35.20      A  C
ATOM  13766  N    MET F 247     4.385  -75.274   8.209  1.00 38.04      A  N
ATOM  13767  CA   MET F 247     4.387  -74.356   9.357  1.00 38.47      A  C
ATOM  13768  C    MET F 247     4.371  -75.104  10.680  1.00 39.25      A  C
ATOM  13769  O    MET F 247     4.850  -74.604  11.696  1.00 39.44      A  O
ATOM  13770  CB   MET F 247     3.215  -73.379   9.296  1.00 37.95      A  C
ATOM  13771  CG   MET F 247     3.392  -72.294   8.265  1.00 37.33      A  C
ATOM  13772  SD   MET F 247     2.136  -71.029   8.437  1.00 36.57      A  S
ATOM  13773  CE   MET F 247     2.990  -69.822   9.459  1.00 36.95      A  C
ATOM  13774  N    GLU F 248     3.809  -76.305  10.656  1.00 40.16      A  N
ATOM  13775  CA   GLU F 248     3.754  -77.144  11.840  1.00 41.22      A  C
ATOM  13776  C    GLU F 248     5.132  -77.695  12.138  1.00 42.21      A  C
ATOM  13777  O    GLU F 248     5.472  -77.930  13.299  1.00 42.75      A  O
ATOM  13778  CB   GLU F 248     2.763  -78.293  11.652  1.00 41.05      A  C
ATOM  13779  CG   GLU F 248     2.784  -79.303  12.785  1.00 41.71      A  C
ATOM  13780  CD   GLU F 248     1.453  -79.974  12.999  1.00 43.23      A  C
```

FIGURE 1 (cont'd)

```
ATOM  13781  OE1  GLU F 248     0.859 -80.473  12.014  1.00 43.82      A  O
ATOM  13782  OE2  GLU F 248     1.002 -80.009  14.165  1.00 43.54      A  O
ATOM  13783  N    SER F 249     5.924 -77.898  11.089  1.00 43.05      A  N
ATOM  13784  CA   SER F 249     7.259 -78.469  11.251  1.00 44.01      A  C
ATOM  13785  C    SER F 249     8.325 -77.401  11.515  1.00 44.46      A  C
ATOM  13786  O    SER F 249     9.477 -77.714  11.754  1.00 44.92      A  O
ATOM  13787  CB   SER F 249     7.637 -79.340  10.042  1.00 44.12      A  C
ATOM  13788  OG   SER F 249     7.996 -78.546   8.925  1.00 44.13      A  O
ATOM  13789  N    ILE F 250     7.934 -76.141  11.488  1.00 44.74      A  N
ATOM  13790  CA   ILE F 250     8.886 -75.060  11.632  1.00 45.27      A  C
ATOM  13791  C    ILE F 250     8.759 -74.435  13.025  1.00 46.12      A  C
ATOM  13792  O    ILE F 250     7.796 -73.706  13.294  1.00 45.91      A  O
ATOM  13793  CB   ILE F 250     8.669 -74.012  10.519  1.00 44.84      A  C
ATOM  13794  CG1  ILE F 250     9.931 -73.192  10.270  1.00 44.80      A  C
ATOM  13795  CD1  ILE F 250     9.862 -71.779  10.819  1.00 44.43      A  C
ATOM  13796  N    PRO F 251     9.727 -74.724  13.920  1.00 47.23      A  N
ATOM  13797  CA   PRO F 251     9.705 -74.244  15.300  1.00 47.90      A  C
ATOM  13798  C    PRO F 251     9.772 -72.739  15.395  1.00 48.34      A  C
ATOM  13799  O    PRO F 251    10.369 -72.062  14.552  1.00 48.38      A  O
ATOM  13800  CB   PRO F 251    10.964 -74.856  15.908  1.00 48.22      A  C
ATOM  13801  CG   PRO F 251    11.259 -76.005  15.058  1.00 48.24      A  C
ATOM  13802  CD   PRO F 251    10.909 -75.558  13.683  1.00 47.58      A  C
ATOM  13803  N    HIS F 252     9.140 -72.233  16.435  1.00 48.76      A  N
ATOM  13804  CA   HIS F 252     8.976 -70.822  16.625  1.00 49.13      A  C
ATOM  13805  C    HIS F 252     8.657 -70.698  18.085  1.00 49.71      A  C
ATOM  13806  O    HIS F 252     8.322 -71.668  18.748  1.00 49.93      A  O
ATOM  13807  CB   HIS F 252     7.860 -70.270  15.739  1.00 47.98      A  C
ATOM  13808  CG   HIS F 252     7.684 -68.784  15.823  1.00 47.80      A  C
ATOM  13809  CD2  HIS F 252     6.717 -68.039  16.414  1.00 47.60      A  C
ATOM  13810  ND1  HIS F 252     8.556 -67.886  15.233  1.00 48.09      A  N
ATOM  13811  CE1  HIS F 252     8.136 -66.653  15.464  1.00 48.08      A  C
ATOM  13812  NE2  HIS F 252     7.024 -66.718  16.182  1.00 47.86      A  N
ATOM  13813  N    SER F 253     8.591 -69.459  18.507  1.00 50.14      A  N
ATOM  13814  CA   SER F 253     9.512 -68.926  19.438  1.00 50.16      A  C
ATOM  13815  C    SER F 253     9.114 -68.159  20.653  1.00 50.27      A  C
ATOM  13816  O    SER F 253     9.884 -67.323  21.040  1.00 50.70      A  O
ATOM  13817  CB   SER F 253    10.193 -67.836  18.610  1.00 49.30      A  C
ATOM  13818  OG   SER F 253     9.813 -66.515  18.937  1.00 48.83      A  O
ATOM  13819  N    PRO F 254     8.103 -68.477  21.427  1.00 49.87      A  N
ATOM  13820  CA   PRO F 254     7.086 -69.248  22.050  1.00 49.47      A  C
ATOM  13821  C    PRO F 254     5.968 -69.937  21.423  1.00 49.09      A  C
ATOM  13822  O    PRO F 254     4.864 -69.518  21.820  1.00 49.21      A  O
ATOM  13823  CB   PRO F 254     6.557 -68.343  23.164  1.00 48.70      A  C
ATOM  13824  CG   PRO F 254     7.523 -67.331  23.332  1.00 48.84      A  C
ATOM  13825  CD   PRO F 254     8.148 -67.128  22.024  1.00 49.13      A  C
ATOM  13826  N    GLY F 255     6.080 -70.639  20.290  1.00 48.48      A  N
ATOM  13827  CA   GLY F 255     4.867 -70.969  19.587  1.00 47.60      A  C
ATOM  13828  C    GLY F 255     4.703 -72.229  20.484  1.00 47.12      A  C
ATOM  13829  O    GLY F 255     4.201 -72.116  21.598  1.00 47.38      A  O
ATOM  13830  N    PRO F 256     4.929 -73.421  19.903  1.00 46.61      A  N
ATOM  13831  CA   PRO F 256     5.959 -74.435  19.782  1.00 46.34      A  C
ATOM  13832  C    PRO F 256     6.367 -74.330  18.297  1.00 45.78      A  C
ATOM  13833  O    PRO F 256     7.548 -74.136  17.982  1.00 45.96      A  O
ATOM  13834  CB   PRO F 256     5.208 -75.749  20.024  1.00 46.53      A  C
ATOM  13835  CG   PRO F 256     4.149 -75.395  20.925  1.00 46.53      A  C
ATOM  13836  CD   PRO F 256     3.674 -74.091  20.308  1.00 46.47      A  C
ATOM  13837  N    THR F 257     5.365 -74.423  17.408  1.00 44.78      A  N
ATOM  13838  CA   THR F 257     5.525 -74.302  15.950  1.00 43.65      A  C
ATOM  13839  C    THR F 257     4.994 -72.963  15.429  1.00 42.94      A  C
ATOM  13840  O    THR F 257     4.355 -72.209  16.174  1.00 42.83      A  O
ATOM  13841  CB   THR F 257     4.809 -75.447  15.199  1.00 43.45      A  C
ATOM  13842  OG1  THR F 257     3.427 -75.469  15.559  1.00 43.06      A  O
ATOM  13843  N    ARG F 258     5.262 -72.674  14.150  1.00 42.10      A  N
ATOM  13844  CA   ARG F 258     4.825 -71.415  13.527  1.00 41.08      A  C
ATOM  13845  C    ARG F 258     3.306 -71.334  13.394  1.00 40.57      A  C
```

FIGURE 1 (cont'd)

```
ATOM  13846  O    ARG F 258      2.747 -70.251  13.197  1.00 40.53     A    O
ATOM  13847  CB   ARG F 258      5.524 -71.166  12.181  1.00 40.13     A    C
ATOM  13848  CG   ARG F 258      6.796 -70.327  12.302  1.00 40.07     A    C
ATOM  13849  CD   ARG F 258      7.064 -69.501  11.053  1.00 40.03     A    C
ATOM  13850  NE   ARG F 258      8.208 -68.610  11.207  1.00 40.24     A    N
ATOM  13851  N    ILE F 259      2.645 -72.481  13.530  1.00 39.87     A    N
ATOM  13852  CA   ILE F 259      1.196 -72.531  13.478  1.00 38.92     A    C
ATOM  13853  C    ILE F 259      0.580 -71.766  14.626  1.00 38.84     A    C
ATOM  13854  O    ILE F 259     -0.433 -71.086  14.458  1.00 38.83     A    O
ATOM  13855  CB   ILE F 259      0.682 -73.964  13.480  1.00 38.02     A    C
ATOM  13856  CG1  ILE F 259      0.108 -74.272  12.104  1.00 37.69     A    C
ATOM  13857  CD1  ILE F 259      0.378 -75.660  11.656  1.00 38.54     A    C
ATOM  13858  N    GLN F 260      1.216 -71.851  15.787  1.00 38.52     A    N
ATOM  13859  CA   GLN F 260      0.703 -71.176  16.970  1.00 37.94     A    C
ATOM  13860  C    GLN F 260      1.003 -69.686  16.889  1.00 37.78     A    C
ATOM  13861  O    GLN F 260      0.604 -68.916  17.760  1.00 38.24     A    O
ATOM  13862  CB   GLN F 260      1.279 -71.774  18.258  1.00 37.08     A    C
ATOM  13863  CG   GLN F 260      2.038 -73.082  18.097  1.00 36.68     A    C
ATOM  13864  CD   GLN F 260      1.268 -74.186  17.406  1.00 36.30     A    C
ATOM  13865  OE1  GLN F 260      0.174 -74.557  17.796  1.00 36.69     A    O
ATOM  13866  N    ALA F 261      1.701 -69.279  15.839  1.00 37.16     A    N
ATOM  13867  CA   ALA F 261      2.032 -67.869  15.668  1.00 36.53     A    C
ATOM  13868  C    ALA F 261      0.878 -67.085  15.050  1.00 35.75     A    C
ATOM  13869  O    ALA F 261      0.815 -65.863  15.178  1.00 35.68     A    O
ATOM  13870  N    ILE F 262     -0.021 -67.793  14.372  1.00 34.75     A    N
ATOM  13871  CA   ILE F 262     -1.199 -67.169  13.787  1.00 33.67     A    C
ATOM  13872  C    ILE F 262     -2.196 -66.902  14.906  1.00 33.59     A    C
ATOM  13873  O    ILE F 262     -2.842 -67.832  15.402  1.00 33.76     A    O
ATOM  13874  CB   ILE F 262     -1.867 -68.067  12.726  1.00 32.73     A    C
ATOM  13875  CG1  ILE F 262     -0.841 -68.600  11.726  1.00 32.13     A    C
ATOM  13876  CD1  ILE F 262     -1.277 -69.900  11.065  1.00 31.71     A    C
ATOM  13877  N    GLU F 263     -2.299 -65.634  15.314  1.00 33.24     A    N
ATOM  13878  CA   GLU F 263     -3.289 -65.212  16.311  1.00 32.82     A    C
ATOM  13879  C    GLU F 263     -4.686 -65.286  15.696  1.00 32.24     A    C
ATOM  13880  O    GLU F 263     -5.640 -65.719  16.359  1.00 32.36     A    O
ATOM  13881  CB   GLU F 263     -2.993 -63.801  16.834  1.00 32.99     A    C
ATOM  13882  CG   GLU F 263     -3.651 -63.470  18.171  1.00 33.03     A    C
ATOM  13883  CD   GLU F 263     -3.142 -62.169  18.770  1.00 32.62     A    C
ATOM  13884  N    LEU F 264     -4.790 -64.891  14.422  1.00 31.38     A    N
ATOM  13885  CA   LEU F 264     -6.039 -64.978  13.668  1.00 30.35     A    C
ATOM  13886  C    LEU F 264     -5.790 -65.161  12.177  1.00 29.74     A    C
ATOM  13887  O    LEU F 264     -5.091 -64.365  11.555  1.00 29.77     A    O
ATOM  13888  CB   LEU F 264     -6.883 -63.731  13.907  1.00 30.26     A    C
ATOM  13889  CG   LEU F 264     -8.217 -63.656  13.178  1.00 29.84     A    C
ATOM  13890  CD1  LEU F 264     -9.119 -64.831  13.555  1.00 29.73     A    C
ATOM  13891  CD2  LEU F 264     -8.877 -62.315  13.482  1.00 29.63     A    C
ATOM  13892  N    PHE F 265     -6.373 -66.221  11.623  1.00 28.93     A    N
ATOM  13893  CA   PHE F 265     -6.336 -66.512  10.183  1.00 27.92     A    C
ATOM  13894  C    PHE F 265     -7.610 -65.969   9.537  1.00 27.64     A    C
ATOM  13895  O    PHE F 265     -8.672 -66.611   9.590  1.00 27.56     A    O
ATOM  13896  CB   PHE F 265     -6.226 -68.035   9.955  1.00 27.64     A    C
ATOM  13897  CG   PHE F 265     -5.897 -68.439   8.521  1.00 26.32     A    C
ATOM  13898  CD1  PHE F 265     -4.584 -68.664   8.120  1.00 25.35     A    C
ATOM  13899  CD2  PHE F 265     -6.905 -68.637   7.590  1.00 25.24     A    C
ATOM  13900  N    MET F 266     -7.516 -64.781   8.947  1.00 27.32     A    N
ATOM  13901  CA   MET F 266     -8.673 -64.156   8.310  1.00 27.15     A    C
ATOM  13902  C    MET F 266     -8.622 -64.336   6.793  1.00 27.09     A    C
ATOM  13903  O    MET F 266     -7.914 -63.620   6.105  1.00 27.19     A    O
ATOM  13904  CB   MET F 266     -8.748 -62.684   8.692  1.00 27.11     A    C
ATOM  13905  CG   MET F 266     -9.895 -61.944   8.050  1.00 26.82     A    C
ATOM  13906  SD   MET F 266     -9.890 -60.169   8.365  1.00 27.32     A    S
ATOM  13907  CE   MET F 266    -10.626 -60.163   9.991  1.00 26.63     A    C
ATOM  13908  N    LEU F 267     -9.375 -65.306   6.285  1.00 27.01     A    N
ATOM  13909  CA   LEU F 267     -9.339 -65.674   4.866  1.00 26.91     A    C
ATOM  13910  C    LEU F 267    -10.349 -64.880   4.039  1.00 26.99     A    C
```

FIGURE 1 (cont'd)

```
ATOM  13911  O    LEU F 267     -11.544 -64.873   4.323  1.00 27.06      A  O
ATOM  13912  CB   LEU F 267      -9.567 -67.185   4.690  1.00 26.83      A  C
ATOM  13913  CG   LEU F 267      -9.693 -67.777   3.282  1.00 26.53      A  C
ATOM  13914  CD1  LEU F 267      -8.436 -67.567   2.490  1.00 26.53      A  C
ATOM  13915  CD2  LEU F 267      -9.994 -69.246   3.364  1.00 26.43      A  C
ATOM  13916  N    LEU F 268      -9.850 -64.221   3.005  1.00 27.07      A  N
ATOM  13917  CA   LEU F 268     -10.668 -63.392   2.126  1.00 27.23      A  C
ATOM  13918  C    LEU F 268     -10.950 -64.115   0.807  1.00 27.46      A  C
ATOM  13919  O    LEU F 268     -10.029 -64.552   0.085  1.00 27.59      A  O
ATOM  13920  CB   LEU F 268      -9.944 -62.080   1.833  1.00 27.19      A  C
ATOM  13921  CG   LEU F 268     -10.065 -60.873   2.758  1.00 27.23      A  C
ATOM  13922  CD1  LEU F 268      -9.288 -61.060   4.043  1.00 27.50      A  C
ATOM  13923  CD2  LEU F 268      -9.562 -59.650   2.022  1.00 27.07      A  C
ATOM  13924  N    ASP F 269     -12.228 -64.235   0.479  1.00 27.68      A  N
ATOM  13925  CA   ASP F 269     -12.618 -64.981  -0.708  1.00 27.98      A  C
ATOM  13926  C    ASP F 269     -13.914 -64.492  -1.304  1.00 27.91      A  C
ATOM  13927  O    ASP F 269     -14.791 -63.996  -0.597  1.00 28.08      A  O
ATOM  13928  CB   ASP F 269     -12.755 -66.468  -0.390  1.00 28.22      A  C
ATOM  13929  CG   ASP F 269     -12.225 -67.345  -1.502  1.00 29.36      A  C
ATOM  13930  OD1  ASP F 269     -11.040 -67.163  -1.885  1.00 30.31      A  O
ATOM  13931  OD2  ASP F 269     -12.980 -68.223  -1.980  1.00 30.09      A  O
ATOM  13932  N    LEU F 270     -14.022 -64.649  -2.618  1.00 27.82      A  N
ATOM  13933  CA   LEU F 270     -15.233 -64.308  -3.362  1.00 27.83      A  C
ATOM  13934  C    LEU F 270     -15.744 -62.893  -3.048  1.00 27.93      A  C
ATOM  13935  O    LEU F 270     -16.953 -62.664  -2.871  1.00 27.95      A  O
ATOM  13936  CB   LEU F 270     -16.324 -65.364  -3.144  1.00 27.71      A  C
ATOM  13937  CG   LEU F 270     -15.959 -66.832  -3.377  1.00 27.72      A  C
ATOM  13938  CD1  LEU F 270     -17.206 -67.684  -3.491  1.00 27.64      A  C
ATOM  13939  CD2  LEU F 270     -15.105 -67.016  -4.625  1.00 28.01      A  C
ATOM  13940  N    LEU F 271     -14.804 -61.953  -2.984  1.00 28.01      A  N
ATOM  13941  CA   LEU F 271     -15.131 -60.559  -2.757  1.00 28.30      A  C
ATOM  13942  C    LEU F 271     -14.991 -59.784  -4.053  1.00 28.69      A  C
ATOM  13943  O    LEU F 271     -14.066 -60.023  -4.814  1.00 28.73      A  O
ATOM  13944  CB   LEU F 271     -14.208 -59.958  -1.697  1.00 28.10      A  C
ATOM  13945  CG   LEU F 271     -14.259 -60.561  -0.300  1.00 27.71      A  C
ATOM  13946  CD1  LEU F 271     -12.846 -60.865   0.124  1.00 27.63      A  C
ATOM  13947  N    GLY F 272     -15.910 -58.856  -4.300  1.00 29.23      A  N
ATOM  13948  CA   GLY F 272     -15.820 -57.988  -5.468  1.00 29.88      A  C
ATOM  13949  C    GLY F 272     -17.134 -57.776  -6.193  1.00 30.46      A  C
ATOM  13950  O    GLY F 272     -17.308 -56.754  -6.864  1.00 30.67      A  O
ATOM  13951  N    ALA F 273     -18.051 -58.742  -6.067  1.00 30.84      A  N
ATOM  13952  CA   ALA F 273     -19.381 -58.667  -6.691  1.00 31.22      A  C
ATOM  13953  C    ALA F 273     -20.260 -57.655  -5.947  1.00 31.58      A  C
ATOM  13954  O    ALA F 273     -19.939 -57.268  -4.813  1.00 31.63      A  O
ATOM  13955  CB   ALA F 273     -20.046 -60.048  -6.718  1.00 31.17      A  C
ATOM  13956  N    PRO F 274     -21.352 -57.199  -6.583  1.00 31.94      A  N
ATOM  13957  CA   PRO F 274     -22.309 -56.353  -5.880  1.00 32.22      A  C
ATOM  13958  C    PRO F 274     -23.101 -57.105  -4.814  1.00 32.35      A  C
ATOM  13959  O    PRO F 274     -23.306 -58.318  -4.927  1.00 32.24      A  O
ATOM  13960  CB   PRO F 274     -23.247 -55.900  -6.993  1.00 32.50      A  C
ATOM  13961  CG   PRO F 274     -23.092 -56.919  -8.058  1.00 32.46      A  C
ATOM  13962  CD   PRO F 274     -21.662 -57.293  -8.016  1.00 32.14      A  C
ATOM  13963  N    ASN F 275     -23.527 -56.373  -3.787  1.00 32.59      A  N
ATOM  13964  CA   ASN F 275     -24.370 -56.897  -2.707  1.00 32.93      A  C
ATOM  13965  C    ASN F 275     -23.944 -58.235  -2.114  1.00 32.55      A  C
ATOM  13966  O    ASN F 275     -24.728 -59.181  -2.110  1.00 32.81      A  O
ATOM  13967  CB   ASN F 275     -25.823 -56.977  -3.163  1.00 33.41      A  C
ATOM  13968  CG   ASN F 275     -26.335 -55.654  -3.661  1.00 34.80      A  C
ATOM  13969  ND2  ASN F 275     -26.478 -55.532  -4.979  1.00 35.92      A  N
ATOM  13970  OD1  ASN F 275     -26.593 -54.741  -2.876  1.00 35.80      A  O
ATOM  13971  N    PRO F 276     -22.703 -58.328  -1.609  1.00 32.06      A  N
ATOM  13972  CA   PRO F 276     -22.329 -59.558  -0.930  1.00 31.79      A  C
ATOM  13973  C    PRO F 276     -22.956 -59.595   0.446  1.00 31.78      A  C
ATOM  13974  O    PRO F 276     -23.247 -58.555   1.007  1.00 31.90      A  O
ATOM  13975  CB   PRO F 276     -20.821 -59.430  -0.804  1.00 31.62      A  C
```

FIGURE 1 (cont'd)

```
ATOM  13976  CG   PRO F 276     -20.568 -57.968  -0.763  1.00 31.61      A  C
ATOM  13977  CD   PRO F 276     -21.616 -57.334  -1.609  1.00 31.89      A  C
ATOM  13978  N    THR F 277     -23.184 -60.783   0.973  1.00 31.81      A  N
ATOM  13979  CA   THR F 277     -23.620 -60.915   2.351  1.00 31.89      A  C
ATOM  13980  C    THR F 277     -22.681 -61.851   3.118  1.00 31.84      A  C
ATOM  13981  O    THR F 277     -22.376 -62.965   2.664  1.00 31.79      A  O
ATOM  13982  CB   THR F 277     -25.085 -61.387   2.458  1.00 32.01      A  C
ATOM  13983  CG2  THR F 277     -26.035 -60.229   2.231  1.00 32.15      A  C
ATOM  13984  OG1  THR F 277     -25.341 -62.403   1.478  1.00 32.28      A  O
ATOM  13985  N    PHE F 278     -22.215 -61.379   4.278  1.00 31.83      A  N
ATOM  13986  CA   PHE F 278     -21.271 -62.121   5.115  1.00 31.81      A  C
ATOM  13987  C    PHE F 278     -21.866 -62.495   6.462  1.00 32.14      A  C
ATOM  13988  O    PHE F 278     -22.617 -61.724   7.055  1.00 32.22      A  O
ATOM  13989  CB   PHE F 278     -20.016 -61.299   5.353  1.00 31.56      A  C
ATOM  13990  CG   PHE F 278     -19.352 -60.835   4.103  1.00 31.32      A  C
ATOM  13991  CD1  PHE F 278     -18.701 -61.736   3.272  1.00 31.23      A  C
ATOM  13992  CD2  PHE F 278     -19.370 -59.486   3.759  1.00 31.19      A  C
ATOM  13993  CE1  PHE F 278     -18.084 -61.304   2.111  1.00 31.21      A  C
ATOM  13994  CE2  PHE F 278     -18.756 -59.042   2.606  1.00 31.01      A  C
ATOM  13995  CZ   PHE F 278     -18.111 -59.954   1.777  1.00 31.04      A  C
ATOM  13996  N    TYR F 279     -21.511 -63.686   6.937  1.00 32.54      A  N
ATOM  13997  CA   TYR F 279     -21.957 -64.199   8.236  1.00 33.09      A  C
ATOM  13998  C    TYR F 279     -20.758 -64.728   9.012  1.00 33.71      A  C
ATOM  13999  O    TYR F 279     -19.676 -64.908   8.443  1.00 33.68      A  O
ATOM  14000  CB   TYR F 279     -23.004 -65.304   8.051  1.00 32.96      A  C
ATOM  14001  CG   TYR F 279     -24.251 -64.840   7.322  1.00 32.45      A  C
ATOM  14002  CD1  TYR F 279     -25.294 -64.235   8.012  1.00 32.34      A  C
ATOM  14003  CD2  TYR F 279     -24.388 -65.007   5.943  1.00 30.99      A  C
ATOM  14004  CE1  TYR F 279     -26.432 -63.817   7.363  1.00 30.75      A  C
ATOM  14005  CE2  TYR F 279     -25.522 -64.575   5.286  1.00 29.83      A  C
ATOM  14006  CZ   TYR F 279     -26.532 -63.981   6.006  1.00 29.81      A  C
ATOM  14007  OH   TYR F 279     -27.661 -63.549   5.371  1.00 29.89      A  O
ATOM  14008  N    SER F 280     -20.928 -64.963  10.309  1.00 34.63      A  N
ATOM  14009  CA   SER F 280     -19.835 -65.534  11.096  1.00 35.46      A  C
ATOM  14010  C    SER F 280     -19.943 -67.051  11.119  1.00 35.96      A  C
ATOM  14011  O    SER F 280     -20.839 -67.616  11.754  1.00 36.24      A  O
ATOM  14012  CB   SER F 280     -19.794 -64.958  12.511  1.00 35.59      A  C
ATOM  14013  OG   SER F 280     -18.623 -65.369  13.194  1.00 35.77      A  O
ATOM  14014  N    HIS F 281     -19.026 -67.699  10.409  1.00 36.41      A  N
ATOM  14015  CA   HIS F 281     -19.034 -69.154  10.305  1.00 37.14      A  C
ATOM  14016  C    HIS F 281     -18.212 -69.833  11.416  1.00 37.49      A  C
ATOM  14017  O    HIS F 281     -18.162 -71.071  11.494  1.00 37.68      A  O
ATOM  14018  CB   HIS F 281     -18.577 -69.598   8.909  1.00 37.21      A  C
ATOM  14019  CG   HIS F 281     -19.365 -68.976   7.801  1.00 37.80      A  C
ATOM  14020  CD2  HIS F 281     -20.545 -69.329   7.241  1.00 38.68      A  C
ATOM  14021  ND1  HIS F 281     -18.964 -67.824   7.156  1.00 37.80      A  N
ATOM  14022  CE1  HIS F 281     -19.856 -67.502   6.236  1.00 38.21      A  C
ATOM  14023  NE2  HIS F 281     -20.827 -68.397   6.269  1.00 38.95      A  N
ATOM  14024  N    PHE F 282     -17.570 -69.024  12.264  1.00 37.84      A  N
ATOM  14025  CA   PHE F 282     -16.883 -69.535  13.453  1.00 38.19      A  C
ATOM  14026  C    PHE F 282     -17.207 -68.685  14.661  1.00 38.53      A  C
ATOM  14027  O    PHE F 282     -16.796 -67.524  14.729  1.00 38.47      A  O
ATOM  14028  CB   PHE F 282     -15.366 -69.657  13.240  1.00 38.06      A  C
ATOM  14029  CG   PHE F 282     -15.004 -70.560  12.110  1.00 38.01      A  C
ATOM  14030  CD1  PHE F 282     -15.196 -71.928  12.217  1.00 38.46      A  C
ATOM  14031  CD2  PHE F 282     -14.520 -70.040  10.915  1.00 37.86      A  C
ATOM  14032  CE1  PHE F 282     -14.894 -72.766  11.152  1.00 38.45      A  C
ATOM  14033  CE2  PHE F 282     -14.213 -70.869   9.850  1.00 37.95      A  C
ATOM  14034  CZ   PHE F 282     -14.398 -72.234   9.966  1.00 38.23      A  C
ATOM  14035  N    PRO F 283     -17.958 -69.264  15.618  1.00 38.92      A  N
ATOM  14036  CA   PRO F 283     -18.300 -68.576  16.861  1.00 39.05      A  C
ATOM  14037  C    PRO F 283     -17.050 -68.252  17.680  1.00 38.92      A  C
ATOM  14038  O    PRO F 283     -17.076 -67.327  18.501  1.00 39.01      A  O
ATOM  14039  CB   PRO F 283     -19.188 -69.591  17.602  1.00 39.30      A  C
ATOM  14040  CG   PRO F 283     -19.645 -70.547  16.558  1.00 39.33      A  C
```

FIGURE 1 (cont'd)

```
ATOM  14041  CD   PRO F 283     -18.511 -70.632  15.586  1.00 39.06      A  C
ATOM  14042  N    ARG F 284     -15.971 -69.001  17.446  1.00 38.66      A  N
ATOM  14043  CA   ARG F 284     -14.688 -68.735  18.095  1.00 38.55      A  C
ATOM  14044  C    ARG F 284     -14.242 -67.287  17.884  1.00 38.73      A  C
ATOM  14045  O    ARG F 284     -13.782 -66.630  18.818  1.00 39.00      A  O
ATOM  14046  CB   ARG F 284     -13.606 -69.692  17.590  1.00 38.26      A  C
ATOM  14047  CG   ARG F 284     -12.579 -70.125  18.651  1.00 37.48      A  C
ATOM  14048  CD   ARG F 284     -11.651 -68.996  19.105  1.00 35.81      A  C
ATOM  14049  NE   ARG F 284     -10.405 -69.495  19.690  1.00 34.94      A  N
ATOM  14050  N    THR F 285     -14.391 -66.793  16.660  1.00 38.78      A  N
ATOM  14051  CA   THR F 285     -13.982 -65.429  16.332  1.00 38.90      A  C
ATOM  14052  C    THR F 285     -15.170 -64.465  16.169  1.00 39.30      A  C
ATOM  14053  O    THR F 285     -15.012 -63.373  15.594  1.00 39.18      A  O
ATOM  14054  CB   THR F 285     -13.117 -65.414  15.057  1.00 38.52      A  C
ATOM  14055  OG1  THR F 285     -13.749 -66.207  14.044  1.00 38.17      A  O
ATOM  14056  N    VAL F 286     -16.338 -64.859  16.696  1.00 39.89      A  N
ATOM  14057  CA   VAL F 286     -17.593 -64.128  16.465  1.00 40.40      A  C
ATOM  14058  C    VAL F 286     -17.486 -62.633  16.780  1.00 41.04      A  C
ATOM  14059  O    VAL F 286     -18.158 -61.810  16.161  1.00 41.05      A  O
ATOM  14060  CB   VAL F 286     -18.771 -64.739  17.240  1.00 40.30      A  C
ATOM  14061  N    ARG F 287     -16.619 -62.288  17.723  1.00 41.90      A  N
ATOM  14062  CA   ARG F 287     -16.457 -60.894  18.135  1.00 42.79      A  C
ATOM  14063  C    ARG F 287     -15.639 -60.049  17.150  1.00 42.53      A  C
ATOM  14064  O    ARG F 287     -15.750 -58.826  17.132  1.00 42.68      A  O
ATOM  14065  CB   ARG F 287     -15.871 -60.813  19.553  1.00 43.54      A  C
ATOM  14066  CG   ARG F 287     -14.461 -61.397  19.714  1.00 45.26      A  C
ATOM  14067  CD   ARG F 287     -13.949 -61.204  21.144  1.00 48.28      A  C
ATOM  14068  NE   ARG F 287     -12.518 -61.500  21.255  1.00 50.00      A  N
ATOM  14069  CZ   ARG F 287     -11.542 -60.601  21.115  1.00 50.50      A  C
ATOM  14070  NH1  ARG F 287     -11.820 -59.316  20.858  1.00 50.54      A  N
ATOM  14071  NH2  ARG F 287     -10.277 -60.992  21.238  1.00 50.74      A  N
ATOM  14072  N    TRP F 288     -14.812 -60.697  16.343  1.00 42.17      A  N
ATOM  14073  CA   TRP F 288     -14.074 -59.978  15.325  1.00 41.87      A  C
ATOM  14074  C    TRP F 288     -14.975 -59.736  14.145  1.00 41.65      A  C
ATOM  14075  O    TRP F 288     -14.788 -58.783  13.399  1.00 41.71      A  O
ATOM  14076  CB   TRP F 288     -12.804 -60.724  14.910  1.00 41.80      A  C
ATOM  14077  CG   TRP F 288     -11.723 -60.596  15.930  1.00 42.50      A  C
ATOM  14078  CD1  TRP F 288     -11.092 -61.613  16.603  1.00 42.99      A  C
ATOM  14079  CD2  TRP F 288     -11.170 -59.374  16.434  1.00 43.21      A  C
ATOM  14080  CE2  TRP F 288     -10.199 -59.723  17.404  1.00 43.58      A  C
ATOM  14081  CE3  TRP F 288     -11.401 -58.015  16.159  1.00 43.40      A  C
ATOM  14082  NE1  TRP F 288     -10.170 -61.093  17.484  1.00 43.41      A  N
ATOM  14083  CZ2  TRP F 288      -9.457 -58.764  18.097  1.00 44.08      A  C
ATOM  14084  CZ3  TRP F 288     -10.659 -57.057  16.849  1.00 43.92      A  C
ATOM  14085  CH2  TRP F 288      -9.695 -57.438  17.804  1.00 44.29      A  C
ATOM  14086  N    PHE F 289     -15.964 -60.603  13.980  1.00 41.48      A  N
ATOM  14087  CA   PHE F 289     -16.968 -60.398  12.950  1.00 41.32      A  C
ATOM  14088  C    PHE F 289     -17.807 -59.186  13.323  1.00 41.42      A  C
ATOM  14089  O    PHE F 289     -18.143 -58.363  12.476  1.00 41.25      A  O
ATOM  14090  CB   PHE F 289     -17.839 -61.648  12.773  1.00 41.21      A  C
ATOM  14091  CG   PHE F 289     -18.732 -61.591  11.567  1.00 41.10      A  C
ATOM  14092  CD1  PHE F 289     -18.221 -61.843  10.298  1.00 40.69      A  C
ATOM  14093  CD2  PHE F 289     -20.083 -61.273  11.697  1.00 41.43      A  C
ATOM  14094  CE1  PHE F 289     -19.032 -61.780   9.181  1.00 40.54      A  C
ATOM  14095  CE2  PHE F 289     -20.905 -61.218  10.581  1.00 41.53      A  C
ATOM  14096  CZ   PHE F 289     -20.370 -61.465   9.319  1.00 41.09      A  C
ATOM  14097  N    HIS F 290     -18.109 -59.089  14.612  1.00 41.78      A  N
ATOM  14098  CA   HIS F 290     -18.827 -57.968  15.192  1.00 42.24      A  C
ATOM  14099  C    HIS F 290     -18.140 -56.631  14.960  1.00 42.33      A  C
ATOM  14100  O    HIS F 290     -18.800 -55.607  14.745  1.00 42.49      A  O
ATOM  14101  CB   HIS F 290     -19.005 -58.249  16.669  1.00 42.48      A  C
ATOM  14102  CG   HIS F 290     -20.341 -58.792  16.986  1.00 43.15      A  C
ATOM  14103  CD2  HIS F 290     -21.368 -59.155  16.178  1.00 43.93      A  C
ATOM  14104  ND1  HIS F 290     -20.839 -58.808  18.260  1.00 43.99      A  N
ATOM  14105  CE1  HIS F 290     -22.105 -59.151  18.242  1.00 44.50      A  C
```

FIGURE 1 (cont'd)

```
ATOM  14106  NE2 HIS F 290     -22.438 -59.434  16.993  1.00 44.41      A  N
ATOM  14107  N   ARG F 291     -16.811 -56.660  14.982  1.00 42.38      A  N
ATOM  14108  CA  ARG F 291     -16.008 -55.483  14.676  1.00 42.60      A  C
ATOM  14109  C   ARG F 291     -16.255 -55.003  13.264  1.00 42.21      A  C
ATOM  14110  O   ARG F 291     -16.434 -53.815  13.021  1.00 42.47      A  O
ATOM  14111  CB  ARG F 291     -14.523 -55.773  14.882  1.00 42.85      A  C
ATOM  14112  CG  ARG F 291     -14.125 -55.752  16.337  1.00 44.50      A  C
ATOM  14113  CD  ARG F 291     -14.409 -54.378  16.924  1.00 46.63      A  C
ATOM  14114  NE  ARG F 291     -13.255 -53.499  16.785  1.00 47.72      A  N
ATOM  14115  CZ  ARG F 291     -12.381 -53.271  17.763  1.00 48.75      A  C
ATOM  14116  NH1 ARG F 291     -12.535 -53.844  18.957  1.00 49.25      A  N
ATOM  14117  NH2 ARG F 291     -11.356 -52.460  17.551  1.00 49.27      A  N
ATOM  14118  N   LEU F 292     -16.287 -55.948  12.336  1.00 41.61      A  N
ATOM  14119  CA  LEU F 292     -16.524 -55.634  10.941  1.00 40.96      A  C
ATOM  14120  C   LEU F 292     -17.901 -55.005  10.749  1.00 40.91      A  C
ATOM  14121  O   LEU F 292     -18.021 -53.991  10.072  1.00 40.94      A  O
ATOM  14122  CB  LEU F 292     -16.322 -56.883  10.079  1.00 40.59      A  C
ATOM  14123  CG  LEU F 292     -14.871 -57.386  10.013  1.00 39.87      A  C
ATOM  14124  CD1 LEU F 292     -14.790 -58.819   9.488  1.00 39.40      A  C
ATOM  14125  CD2 LEU F 292     -14.018 -56.443   9.164  1.00 39.41      A  C
ATOM  14126  N   ARG F 293     -18.924 -55.593  11.374  1.00 40.91      A  N
ATOM  14127  CA  ARG F 293     -20.269 -55.021  11.371  1.00 40.99      A  C
ATOM  14128  C   ARG F 293     -20.166 -53.610  11.925  1.00 41.29      A  C
ATOM  14129  O   ARG F 293     -20.656 -52.669  11.308  1.00 41.38      A  O
ATOM  14130  CB  ARG F 293     -21.252 -55.870  12.195  1.00 40.89      A  C
ATOM  14131  CG  ARG F 293     -22.725 -55.649  11.843  1.00 40.67      A  C
ATOM  14132  CD  ARG F 293     -23.690 -56.307  12.851  1.00 40.46      A  C
ATOM  14133  NE  ARG F 293     -23.624 -57.766  12.858  1.00 39.74      A  N
ATOM  14134  N   SER F 294     -19.482 -53.465  13.061  1.00 41.46      A  N
ATOM  14135  CA  SER F 294     -19.372 -52.177  13.748  1.00 41.72      A  C
ATOM  14136  C   SER F 294     -18.639 -51.141  12.909  1.00 42.10      A  C
ATOM  14137  O   SER F 294     -18.993 -49.960  12.912  1.00 42.58      A  O
ATOM  14138  CB  SER F 294     -18.699 -52.340  15.114  1.00 40.74      A  C
ATOM  14139  N   ILE F 295     -17.625 -51.595  12.182  1.00 42.20      A  N
ATOM  14140  CA  ILE F 295     -16.843 -50.706  11.327  1.00 42.28      A  C
ATOM  14141  C   ILE F 295     -17.674 -50.218  10.130  1.00 42.55      A  C
ATOM  14142  O   ILE F 295     -17.637 -49.028   9.780  1.00 42.72      A  O
ATOM  14143  CB  ILE F 295     -15.520 -51.368  10.877  1.00 41.97      A  C
ATOM  14144  CG1 ILE F 295     -14.555 -51.465  12.061  1.00 41.89      A  C
ATOM  14145  CG2 ILE F 295     -14.883 -50.563   9.751  1.00 41.84      A  C
ATOM  14146  CD1 ILE F 295     -13.555 -52.590  11.974  1.00 41.60      A  C
ATOM  14147  N   GLU F 296     -18.420 -51.145   9.523  1.00 42.71      A  N
ATOM  14148  CA  GLU F 296     -19.321 -50.833   8.419  1.00 42.99      A  C
ATOM  14149  C   GLU F 296     -20.333 -49.819   8.904  1.00 43.54      A  C
ATOM  14150  O   GLU F 296     -20.534 -48.786   8.262  1.00 43.82      A  O
ATOM  14151  CB  GLU F 296     -20.037 -52.093   7.935  1.00 42.71      A  C
ATOM  14152  CG  GLU F 296     -20.888 -51.894   6.687  1.00 42.90      A  C
ATOM  14153  CD  GLU F 296     -21.740 -53.110   6.325  1.00 43.10      A  C
ATOM  14154  OE1 GLU F 296     -21.519 -54.221   6.867  1.00 42.78      A  O
ATOM  14155  OE2 GLU F 296     -22.641 -52.944   5.483  1.00 43.37      A  O
ATOM  14156  N   LYS F 297     -20.940 -50.120  10.053  1.00 44.10      A  N
ATOM  14157  CA  LYS F 297     -21.917 -49.252  10.698  1.00 44.82      A  C
ATOM  14158  C   LYS F 297     -21.331 -47.851  10.851  1.00 45.46      A  C
ATOM  14159  O   LYS F 297     -21.916 -46.875  10.389  1.00 45.73      A  O
ATOM  14160  CB  LYS F 297     -22.294 -49.833  12.063  1.00 44.75      A  C
ATOM  14161  CG  LYS F 297     -23.802 -49.976  12.360  1.00 44.63      A  C
ATOM  14162  CD  LYS F 297     -24.049 -51.143  13.353  1.00 43.76      A  C
ATOM  14163  CE  LYS F 297     -25.358 -50.992  14.130  1.00 43.76      A  C
ATOM  14164  N   ARG F 298     -20.150 -47.774  11.456  1.00 45.96      A  N
ATOM  14165  CA  ARG F 298     -19.479 -46.500  11.715  1.00 46.49      A  C
ATOM  14166  C   ARG F 298     -19.158 -45.705  10.442  1.00 47.03      A  C
ATOM  14167  O   ARG F 298     -19.465 -44.513  10.355  1.00 47.61      A  O
ATOM  14168  CB  ARG F 298     -18.207 -46.733  12.551  1.00 45.52      A  C
ATOM  14169  CG  ARG F 298     -17.483 -45.452  13.051  1.00 45.48      A  C
ATOM  14170  CD  ARG F 298     -16.306 -45.781  13.991  1.00 45.13      A  C
```

FIGURE 1 (cont'd)

```
ATOM  14171  NE   ARG F 298     -15.505 -44.604  14.313  1.00 44.94      A    N
ATOM  14172  N    LEU F 299     -18.541 -46.368   9.464  1.00 47.25      A    N
ATOM  14173  CA   LEU F 299     -18.148 -45.720   8.203  1.00 47.47      A    C
ATOM  14174  C    LEU F 299     -19.350 -45.241   7.415  1.00 47.87      A    C
ATOM  14175  O    LEU F 299     -19.269 -44.241   6.705  1.00 48.11      A    O
ATOM  14176  CB   LEU F 299     -17.305 -46.658   7.339  1.00 47.14      A    C
ATOM  14177  CG   LEU F 299     -15.870 -46.942   7.786  1.00 46.98      A    C
ATOM  14178  CD1  LEU F 299     -15.315 -48.138   7.046  1.00 46.52      A    C
ATOM  14179  CD2  LEU F 299     -14.985 -45.724   7.561  1.00 47.46      A    C
ATOM  14180  N    HIS F 300     -20.457 -45.972   7.548  1.00 48.21      A    N
ATOM  14181  CA   HIS F 300     -21.731 -45.580   6.968  1.00 48.76      A    C
ATOM  14182  C    HIS F 300     -22.224 -44.270   7.588  1.00 49.25      A    C
ATOM  14183  O    HIS F 300     -22.531 -43.321   6.858  1.00 49.55      A    O
ATOM  14184  CB   HIS F 300     -22.769 -46.697   7.124  1.00 48.67      A    C
ATOM  14185  CG   HIS F 300     -24.156 -46.276   6.770  1.00 49.33      A    C
ATOM  14186  CD2  HIS F 300     -25.272 -46.168   7.526  1.00 50.11      A    C
ATOM  14187  ND1  HIS F 300     -24.511 -45.874   5.500  1.00 49.66      A    N
ATOM  14188  CE1  HIS F 300     -25.788 -45.541   5.486  1.00 50.28      A    C
ATOM  14189  NE2  HIS F 300     -26.273 -45.710   6.703  1.00 50.74      A    N
ATOM  14190  N    ARG F 301     -22.276 -44.227   8.926  1.00 49.72      A    N
ATOM  14191  CA   ARG F 301     -22.683 -43.027   9.681  1.00 50.23      A    C
ATOM  14192  C    ARG F 301     -21.857 -41.818   9.242  1.00 50.87      A    C
ATOM  14193  O    ARG F 301     -22.388 -40.714   9.113  1.00 51.42      A    O
ATOM  14194  CB   ARG F 301     -22.537 -43.216  11.210  1.00 50.08      A    C
ATOM  14195  CG   ARG F 301     -23.179 -44.455  11.817  1.00 49.10      A    C
ATOM  14196  CD   ARG F 301     -24.638 -44.239  12.174  1.00 48.44      A    C
ATOM  14197  NE   ARG F 301     -25.313 -45.501  12.483  1.00 47.75      A    N
ATOM  14198  N    LEU F 302     -20.564 -42.041   8.997  1.00 51.23      A    N
ATOM  14199  CA   LEU F 302     -19.641 -40.967   8.644  1.00 51.84      A    C
ATOM  14200  C    LEU F 302     -19.664 -40.616   7.165  1.00 52.17      A    C
ATOM  14201  O    LEU F 302     -18.780 -39.916   6.686  1.00 52.48      A    O
ATOM  14202  CB   LEU F 302     -18.224 -41.340   9.066  1.00 51.75      A    C
ATOM  14203  CG   LEU F 302     -17.971 -41.367  10.570  1.00 52.23      A    C
ATOM  14204  CD1  LEU F 302     -16.851 -42.325  10.907  1.00 51.85      A    C
ATOM  14205  CD2  LEU F 302     -17.664 -39.976  11.078  1.00 53.47      A    C
ATOM  14206  N    ASN F 303     -20.683 -41.094   6.453  1.00 52.30      A    N
ATOM  14207  CA   ASN F 303     -20.803 -40.910   5.001  1.00 52.24      A    C
ATOM  14208  C    ASN F 303     -19.470 -41.117   4.290  1.00 52.69      A    C
ATOM  14209  O    ASN F 303     -18.902 -40.176   3.735  1.00 53.17      A    O
ATOM  14210  N    LEU F 304     -18.965 -42.347   4.339  1.00 52.88      A    N
ATOM  14211  CA   LEU F 304     -17.682 -42.692   3.714  1.00 52.76      A    C
ATOM  14212  C    LEU F 304     -17.775 -43.971   2.884  1.00 52.46      A    C
ATOM  14213  O    LEU F 304     -16.763 -44.486   2.412  1.00 52.19      A    O
ATOM  14214  CB   LEU F 304     -16.559 -42.806   4.763  1.00 52.81      A    C
ATOM  14215  CG   LEU F 304     -15.877 -41.539   5.292  1.00 53.24      A    C
ATOM  14216  CD1  LEU F 304     -14.927 -41.885   6.419  1.00 52.93      A    C
ATOM  14217  CD2  LEU F 304     -15.139 -40.806   4.199  1.00 53.82      A    C
ATOM  14218  N    LEU F 305     -18.993 -44.473   2.710  1.00 52.36      A    N
ATOM  14219  CA   LEU F 305     -19.225 -45.661   1.910  1.00 52.18      A    C
ATOM  14220  C    LEU F 305     -20.133 -45.313   0.737  1.00 52.61      A    C
ATOM  14221  O    LEU F 305     -21.252 -44.826   0.943  1.00 53.03      A    O
ATOM  14222  CB   LEU F 305     -19.857 -46.764   2.760  1.00 51.73      A    C
ATOM  14223  CG   LEU F 305     -19.144 -47.210   4.034  1.00 51.08      A    C
ATOM  14224  CD1  LEU F 305     -20.024 -48.163   4.809  1.00 50.42      A    C
ATOM  14225  CD2  LEU F 305     -17.805 -47.861   3.726  1.00 50.66      A    C
ATOM  14226  N    GLN F 306     -19.640 -45.548  -0.486  1.00 52.77      A    N
ATOM  14227  CA   GLN F 306     -20.410 -45.337  -1.718  1.00 53.03      A    C
ATOM  14228  C    GLN F 306     -21.552 -46.334  -1.843  1.00 52.92      A    C
ATOM  14229  O    GLN F 306     -21.465 -47.446  -1.343  1.00 52.58      A    O
ATOM  14230  CB   GLN F 306     -19.508 -45.488  -2.937  1.00 53.15      A    C
ATOM  14231  CG   GLN F 306     -18.920 -44.197  -3.463  1.00 54.03      A    C
ATOM  14232  CD   GLN F 306     -18.280 -44.370  -4.833  1.00 54.72      A    C
ATOM  14233  OE1  GLN F 306     -17.478 -45.281  -5.050  1.00 54.93      A    O
ATOM  14234  N    SER F 307     -22.620 -45.928  -2.517  1.00 53.26      A    N
ATOM  14235  CA   SER F 307     -23.747 -46.812  -2.803  1.00 53.48      A    C
```

FIGURE 1 (cont'd)

```
ATOM  14236  C    SER F 307     -24.101 -47.700  -1.621  1.00 53.33      A    C
ATOM  14237  O    SER F 307     -24.236 -48.906  -1.770  1.00 53.13      A    O
ATOM  14238  CB   SER F 307     -23.446 -47.682  -4.029  1.00 53.52      A    C
ATOM  14239  OG   SER F 307     -22.890 -46.915  -5.084  1.00 54.27      A    O
ATOM  14240  N    HIS F 308     -24.256 -47.096  -0.450  1.00 53.44      A    N
ATOM  14241  CA   HIS F 308     -24.486 -47.840   0.784  1.00 53.43      A    C
ATOM  14242  C    HIS F 308     -25.717 -47.303   1.513  1.00 53.73      A    C
ATOM  14243  O    HIS F 308     -25.590 -46.613   2.532  1.00 54.00      A    O
ATOM  14244  CB   HIS F 308     -23.253 -47.733   1.680  1.00 53.27      A    C
ATOM  14245  CG   HIS F 308     -23.140 -48.819   2.708  1.00 52.97      A    C
ATOM  14246  CD2  HIS F 308     -22.797 -50.124   2.592  1.00 52.54      A    C
ATOM  14247  ND1  HIS F 308     -23.363 -48.602   4.050  1.00 53.25      A    N
ATOM  14248  CE1  HIS F 308     -23.172 -49.728   4.714  1.00 52.90      A    C
ATOM  14249  NE2  HIS F 308     -22.829 -50.666   3.853  1.00 52.35      A    N
ATOM  14250  N    PRO F 309     -26.921 -47.612   0.991  1.00 53.95      A    N
ATOM  14251  CA   PRO F 309     -28.152 -47.031   1.536  1.00 54.41      A    C
ATOM  14252  C    PRO F 309     -28.729 -47.730   2.775  1.00 54.67      A    C
ATOM  14253  O    PRO F 309     -29.948 -47.867   2.881  1.00 54.95      A    O
ATOM  14254  CB   PRO F 309     -29.133 -47.127   0.352  1.00 54.67      A    C
ATOM  14255  CG   PRO F 309     -28.283 -47.444  -0.854  1.00 54.42      A    C
ATOM  14256  CD   PRO F 309     -27.185 -48.279  -0.294  1.00 53.93      A    C
ATOM  14257  N    GLN F 310     -27.855 -48.187   3.674  1.00 54.71      A    N
ATOM  14258  CA   GLN F 310     -28.212 -48.559   5.061  1.00 54.88      A    C
ATOM  14259  C    GLN F 310     -27.000 -48.948   5.930  1.00 54.99      A    C
ATOM  14260  O    GLN F 310     -25.856 -48.874   5.481  1.00 54.84      A    O
ATOM  14261  CB   GLN F 310     -29.379 -49.576   5.165  1.00 54.93      A    C
ATOM  14262  CG   GLN F 310     -29.438 -50.705   4.132  1.00 54.53      A    C
ATOM  14263  CD   GLN F 310     -30.869 -51.088   3.751  1.00 54.53      A    C
ATOM  14264  N    GLU F 311     -27.261 -49.330   7.179  1.00 55.38      A    N
ATOM  14265  CA   GLU F 311     -26.208 -49.567   8.166  1.00 55.74      A    C
ATOM  14266  C    GLU F 311     -25.640 -50.964   7.976  1.00 55.02      A    C
ATOM  14267  O    GLU F 311     -24.470 -51.118   7.630  1.00 54.85      A    O
ATOM  14268  CB   GLU F 311     -26.732 -49.377   9.606  1.00 56.51      A    C
ATOM  14269  CG   GLU F 311     -27.543 -48.086   9.862  1.00 58.91      A    C
ATOM  14270  CD   GLU F 311     -29.044 -48.205   9.495  1.00 61.44      A    C
ATOM  14271  OE1  GLU F 311     -29.841 -47.430  10.064  1.00 62.87      A    O
ATOM  14272  OE2  GLU F 311     -29.440 -49.055   8.654  1.00 62.00      A    O
ATOM  14273  N    VAL F 312     -26.473 -51.975   8.198  1.00 54.43      A    N
ATOM  14274  CA   VAL F 312     -26.078 -53.347   7.943  1.00 53.72      A    C
ATOM  14275  C    VAL F 312     -26.461 -53.725   6.511  1.00 53.20      A    C
ATOM  14276  O    VAL F 312     -27.639 -53.897   6.185  1.00 53.55      A    O
ATOM  14277  N    MET F 313     -25.451 -53.819   5.656  1.00 52.16      A    N
ATOM  14278  CA   MET F 313     -25.623 -54.282   4.287  1.00 51.20      A    C
ATOM  14279  C    MET F 313     -24.779 -55.541   4.103  1.00 50.21      A    C
ATOM  14280  O    MET F 313     -25.295 -56.601   3.747  1.00 50.08      A    O
ATOM  14281  CB   MET F 313     -25.170 -53.208   3.292  1.00 51.39      A    C
ATOM  14282  CG   MET F 313     -25.912 -51.882   3.354  1.00 51.98      A    C
ATOM  14283  SD   MET F 313     -26.817 -51.473   1.854  1.00 52.39      A    S
ATOM  14284  CE   MET F 313     -25.541 -51.420   0.609  1.00 52.13      A    C
ATOM  14285  N    TYR F 314     -23.484 -55.416   4.389  1.00 49.12      A    N
ATOM  14286  CA   TYR F 314     -22.495 -56.448   4.093  1.00 48.03      A    C
ATOM  14287  C    TYR F 314     -22.354 -57.493   5.185  1.00 47.49      A    C
ATOM  14288  O    TYR F 314     -22.557 -58.683   4.946  1.00 47.28      A    O
ATOM  14289  CB   TYR F 314     -21.131 -55.812   3.821  1.00 47.82      A    C
ATOM  14290  CG   TYR F 314     -21.097 -54.879   2.636  1.00 47.53      A    C
ATOM  14291  CD1  TYR F 314     -21.868 -55.129   1.502  1.00 47.53      A    C
ATOM  14292  CD2  TYR F 314     -20.273 -53.760   2.636  1.00 47.35      A    C
ATOM  14293  CE1  TYR F 314     -21.836 -54.278   0.411  1.00 47.62      A    C
ATOM  14294  CE2  TYR F 314     -20.227 -52.905   1.544  1.00 47.42      A    C
ATOM  14295  CZ   TYR F 314     -21.012 -53.171   0.435  1.00 47.36      A    C
ATOM  14296  OH   TYR F 314     -20.977 -52.336  -0.652  1.00 47.31      A    O
ATOM  14297  N    PHE F 315     -21.985 -57.043   6.379  1.00 47.05      A    N
ATOM  14298  CA   PHE F 315     -21.787 -57.948   7.499  1.00 46.71      A    C
ATOM  14299  C    PHE F 315     -23.078 -58.139   8.291  1.00 46.97      A    C
ATOM  14300  O    PHE F 315     -23.404 -57.360   9.194  1.00 47.04      A    O
```

FIGURE 1 (cont'd)

```
ATOM  14301  CB   PHE F 315     -20.628 -57.468   8.364  1.00 46.38      A    C
ATOM  14302  CG   PHE F 315     -19.348 -57.382   7.619  1.00 45.26      A    C
ATOM  14303  CD1  PHE F 315     -18.537 -58.495   7.483  1.00 44.52      A    C
ATOM  14304  CD2  PHE F 315     -18.968 -56.199   7.017  1.00 44.55      A    C
ATOM  14305  CE1  PHE F 315     -17.349 -58.423   6.770  1.00 43.99      A    C
ATOM  14306  CE2  PHE F 315     -17.783 -56.114   6.305  1.00 44.02      A    C
ATOM  14307  CZ   PHE F 315     -16.974 -57.229   6.179  1.00 43.77      A    C
ATOM  14308  N    GLN F 316     -23.813 -59.181   7.915  1.00 47.22      A    N
ATOM  14309  CA   GLN F 316     -25.125 -59.455   8.471  1.00 47.75      A    C
ATOM  14310  C    GLN F 316     -25.046 -60.069   9.866  1.00 48.10      A    C
ATOM  14311  O    GLN F 316     -24.071 -60.758  10.208  1.00 47.91      A    O
ATOM  14312  CB   GLN F 316     -25.923 -60.375   7.538  1.00 47.81      A    C
ATOM  14313  CG   GLN F 316     -26.388 -59.721   6.251  1.00 48.24      A    C
ATOM  14314  CD   GLN F 316     -27.364 -58.605   6.497  1.00 48.98      A    C
ATOM  14315  NE2  GLN F 316     -27.001 -57.402   6.073  1.00 49.08      A    N
ATOM  14316  OE1  GLN F 316     -28.435 -58.819   7.065  1.00 49.81      A    O
ATOM  14317  N    PRO F 317     -26.079 -59.814  10.683  1.00 48.68      A    N
ATOM  14318  CA   PRO F 317     -26.151 -60.479  11.963  1.00 48.97      A    C
ATOM  14319  C    PRO F 317     -26.628 -61.914  11.768  1.00 49.01      A    C
ATOM  14320  O    PRO F 317     -27.152 -62.260  10.702  1.00 48.95      A    O
ATOM  14321  CB   PRO F 317     -27.196 -59.655  12.712  1.00 49.29      A    C
ATOM  14322  CG   PRO F 317     -28.097 -59.144  11.645  1.00 49.41      A    C
ATOM  14323  CD   PRO F 317     -27.208 -58.884  10.475  1.00 48.95      A    C
ATOM  14324  N    GLY F 318     -26.454 -62.730  12.800  1.00 49.06      A    N
ATOM  14325  CA   GLY F 318     -26.825 -64.131  12.739  1.00 49.01      A    C
ATOM  14326  C    GLY F 318     -25.579 -64.971  12.629  1.00 48.84      A    C
ATOM  14327  O    GLY F 318     -24.599 -64.551  11.995  1.00 48.68      A    O
ATOM  14328  N    GLU F 319     -25.614 -66.147  13.258  1.00 48.82      A    N
ATOM  14329  CA   GLU F 319     -24.510 -67.108  13.207  1.00 48.61      A    C
ATOM  14330  C    GLU F 319     -24.991 -68.441  12.618  1.00 48.75      A    C
ATOM  14331  O    GLU F 319     -25.263 -69.372  13.367  1.00 49.12      A    O
ATOM  14332  CB   GLU F 319     -23.918 -67.328  14.608  1.00 48.50      A    C
ATOM  14333  CG   GLU F 319     -23.393 -66.069  15.301  1.00 47.96      A    C
ATOM  14334  N    PRO F 320     -25.123 -68.533  11.276  1.00 48.64      A    N
ATOM  14335  CA   PRO F 320     -25.520 -69.814  10.681  1.00 48.64      A    C
ATOM  14336  C    PRO F 320     -24.408 -70.866  10.722  1.00 48.52      A    C
ATOM  14337  O    PRO F 320     -23.236 -70.521  10.905  1.00 48.33      A    O
ATOM  14338  CB   PRO F 320     -25.866 -69.438   9.228  1.00 48.71      A    C
ATOM  14339  CG   PRO F 320     -26.144 -67.960   9.269  1.00 48.69      A    C
ATOM  14340  CD   PRO F 320     -25.143 -67.453  10.272  1.00 48.49      A    C
ATOM  14341  N    PHE F 321     -24.793 -72.128  10.532  1.00 48.35      A    N
ATOM  14342  CA   PHE F 321     -23.908 -73.284  10.713  1.00 48.00      A    C
ATOM  14343  C    PHE F 321     -22.604 -73.326   9.871  1.00 48.17      A    C
ATOM  14344  O    PHE F 321     -21.507 -73.428  10.434  1.00 48.51      A    O
ATOM  14345  N    GLY F 322     -22.708 -73.251   8.545  1.00 48.02      A    N
ATOM  14346  CA   GLY F 322     -21.529 -73.422   7.668  1.00 47.43      A    C
ATOM  14347  C    GLY F 322     -21.178 -74.896   7.455  1.00 47.07      A    C
ATOM  14348  O    GLY F 322     -22.032 -75.766   7.663  1.00 47.61      A    O
ATOM  14349  N    SER F 323     -19.958 -75.210   7.010  1.00 46.10      A    N
ATOM  14350  CA   SER F 323     -18.966 -74.244   6.542  1.00 45.03      A    C
ATOM  14351  C    SER F 323     -18.791 -74.413   5.041  1.00 43.87      A    C
ATOM  14352  O    SER F 323     -19.382 -75.306   4.441  1.00 43.99      A    O
ATOM  14353  CB   SER F 323     -17.608 -74.468   7.229  1.00 45.26      A    C
ATOM  14354  OG   SER F 323     -17.711 -74.376   8.644  1.00 46.10      A    O
ATOM  14355  N    VAL F 324     -17.977 -73.549   4.446  1.00 42.29      A    N
ATOM  14356  CA   VAL F 324     -17.622 -73.658   3.046  1.00 40.73      A    C
ATOM  14357  C    VAL F 324     -16.147 -73.991   3.011  1.00 39.99      A    C
ATOM  14358  O    VAL F 324     -15.338 -73.269   3.579  1.00 39.91      A    O
ATOM  14359  CB   VAL F 324     -17.902 -72.344   2.309  1.00 40.51      A    C
ATOM  14360  CG1  VAL F 324     -19.412 -72.094   2.227  1.00 40.39      A    C
ATOM  14361  CG2  VAL F 324     -17.262 -72.338   0.928  1.00 40.05      A    C
ATOM  14362  N    GLU F 325     -15.803 -75.098   2.364  1.00 39.18      A    N
ATOM  14363  CA   GLU F 325     -14.420 -75.582   2.334  1.00 38.50      A    C
ATOM  14364  C    GLU F 325     -13.500 -74.651   1.564  1.00 37.61      A    C
ATOM  14365  O    GLU F 325     -13.712 -74.397   0.387  1.00 37.51      A    O
```

FIGURE 1 (cont'd)

```
ATOM  14366  CB   GLU F 325     -14.356 -76.971   1.718  1.00 38.87      A  C
ATOM  14367  CG   GLU F 325     -15.260 -77.972   2.392  1.00 40.46      A  C
ATOM  14368  CD   GLU F 325     -15.028 -79.388   1.908  1.00 42.57      A  C
ATOM  14369  OE1  GLU F 325     -14.060 -79.611   1.136  1.00 42.98      A  O
ATOM  14370  OE2  GLU F 325     -15.813 -80.283   2.306  1.00 43.84      A  O
ATOM  14371  N    ASP F 326     -12.475 -74.142   2.234  1.00 36.77      A  N
ATOM  14372  CA   ASP F 326     -11.551 -73.186   1.624  1.00 36.03      A  C
ATOM  14373  C    ASP F 326     -10.162 -73.344   2.258  1.00 35.78      A  C
ATOM  14374  O    ASP F 326      -9.931 -74.278   3.034  1.00 35.89      A  O
ATOM  14375  CB   ASP F 326     -12.087 -71.751   1.788  1.00 35.74      A  C
ATOM  14376  CG   ASP F 326     -11.652 -70.805   0.655  1.00 35.13      A  C
ATOM  14377  OD1  ASP F 326     -10.610 -71.030  -0.005  1.00 34.84      A  O
ATOM  14378  OD2  ASP F 326     -12.365 -69.804   0.439  1.00 34.60      A  O
ATOM  14379  N    ASP F 327      -9.246 -72.434   1.925  1.00 35.33      A  N
ATOM  14380  CA   ASP F 327      -7.852 -72.489   2.376  1.00 35.00      A  C
ATOM  14381  C    ASP F 327      -7.662 -72.562   3.896  1.00 34.59      A  C
ATOM  14382  O    ASP F 327      -6.598 -72.930   4.374  1.00 34.68      A  O
ATOM  14383  CB   ASP F 327      -7.083 -71.284   1.828  1.00 35.12      A  C
ATOM  14384  CG   ASP F 327      -6.796 -71.395   0.340  1.00 36.05      A  C
ATOM  14385  OD1  ASP F 327      -6.037 -72.314  -0.061  1.00 36.78      A  O
ATOM  14386  OD2  ASP F 327      -7.313 -70.545  -0.429  1.00 36.70      A  O
ATOM  14387  N    HIS F 328      -8.687 -72.209   4.654  1.00 34.08      A  N
ATOM  14388  CA   HIS F 328      -8.583 -72.186   6.098  1.00 33.72      A  C
ATOM  14389  C    HIS F 328      -8.601 -73.588   6.697  1.00 33.63      A  C
ATOM  14390  O    HIS F 328      -8.056 -73.807   7.770  1.00 33.84      A  O
ATOM  14391  CB   HIS F 328      -9.723 -71.355   6.686  1.00 33.60      A  C
ATOM  14392  CG   HIS F 328     -11.072 -72.010   6.571  1.00 33.90      A  C
ATOM  14393  CD2  HIS F 328     -11.807 -72.706   7.475  1.00 34.43      A  C
ATOM  14394  ND1  HIS F 328     -11.814 -71.993   5.407  1.00 34.09      A  N
ATOM  14395  CE1  HIS F 328     -12.948 -72.646   5.601  1.00 34.33      A  C
ATOM  14396  NE2  HIS F 328     -12.968 -73.089   6.846  1.00 34.56      A  N
ATOM  14397  N    ILE F 329      -9.229 -74.531   6.007  1.00 33.47      A  N
ATOM  14398  CA   ILE F 329      -9.439 -75.869   6.553  1.00 33.62      A  C
ATOM  14399  C    ILE F 329      -8.184 -76.520   7.162  1.00 33.66      A  C
ATOM  14400  O    ILE F 329      -8.239 -76.968   8.312  1.00 33.92      A  O
ATOM  14401  CB   ILE F 329     -10.120 -76.819   5.522  1.00 33.71      A  C
ATOM  14402  CG1  ILE F 329     -11.556 -76.369   5.230  1.00 33.93      A  C
ATOM  14403  CG2  ILE F 329     -10.095 -78.272   5.995  1.00 34.17      A  C
ATOM  14404  CD1  ILE F 329     -12.495 -76.348   6.437  1.00 34.46      A  C
ATOM  14405  N    PRO F 330      -7.052 -76.571   6.416  1.00 33.59      A  N
ATOM  14406  CA   PRO F 330      -5.902 -77.278   6.987  1.00 33.63      A  C
ATOM  14407  C    PRO F 330      -5.182 -76.482   8.064  1.00 33.48      A  C
ATOM  14408  O    PRO F 330      -4.330 -77.014   8.750  1.00 33.75      A  O
ATOM  14409  CB   PRO F 330      -4.998 -77.511   5.778  1.00 33.73      A  C
ATOM  14410  CG   PRO F 330      -5.291 -76.379   4.886  1.00 33.54      A  C
ATOM  14411  CD   PRO F 330      -6.751 -76.061   5.065  1.00 33.46      A  C
ATOM  14412  N    PHE F 331      -5.532 -75.216   8.212  1.00 33.09      A  N
ATOM  14413  CA   PHE F 331      -5.088 -74.445   9.365  1.00 32.91      A  C
ATOM  14414  C    PHE F 331      -6.036 -74.626  10.541  1.00 32.86      A  C
ATOM  14415  O    PHE F 331      -5.615 -74.710  11.694  1.00 32.97      A  O
ATOM  14416  CB   PHE F 331      -4.950 -72.963   9.007  1.00 32.70      A  C
ATOM  14417  CG   PHE F 331      -3.808 -72.682   8.091  1.00 32.79      A  C
ATOM  14418  CD1  PHE F 331      -4.019 -72.516   6.734  1.00 32.81      A  C
ATOM  14419  CD2  PHE F 331      -2.511 -72.626   8.578  1.00 33.32      A  C
ATOM  14420  CE1  PHE F 331      -2.949 -72.279   5.867  1.00 33.05      A  C
ATOM  14421  CE2  PHE F 331      -1.435 -72.390   7.719  1.00 33.52      A  C
ATOM  14422  CZ   PHE F 331      -1.656 -72.215   6.360  1.00 33.22      A  C
ATOM  14423  N    LEU F 332      -7.321 -74.685  10.235  1.00 32.80      A  N
ATOM  14424  CA   LEU F 332      -8.327 -74.962  11.240  1.00 32.99      A  C
ATOM  14425  C    LEU F 332      -8.141 -76.349  11.893  1.00 33.47      A  C
ATOM  14426  O    LEU F 332      -8.257 -76.471  13.120  1.00 33.73      A  O
ATOM  14427  CB   LEU F 332      -9.730 -74.834  10.638  1.00 32.70      A  C
ATOM  14428  CG   LEU F 332     -10.912 -75.157  11.560  1.00 32.43      A  C
ATOM  14429  CD1  LEU F 332     -11.311 -73.936  12.370  1.00 32.02      A  C
ATOM  14430  CD2  LEU F 332     -12.089 -75.682  10.763  1.00 32.38      A  C
```

FIGURE 1 (cont'd)

```
ATOM  14431  N    ARG F 333      -7.849 -77.381  11.093  1.00 33.81      A   N
ATOM  14432  CA   ARG F 333      -7.687 -78.730  11.637  1.00 34.35      A   C
ATOM  14433  C    ARG F 333      -6.510 -78.792  12.621  1.00 34.14      A   C
ATOM  14434  O    ARG F 333      -6.461 -79.670  13.482  1.00 34.51      A   O
ATOM  14435  CB   ARG F 333      -7.600 -79.794  10.524  1.00 34.72      A   C
ATOM  14436  CG   ARG F 333      -6.226 -80.445  10.288  1.00 36.61      A   C
ATOM  14437  CD   ARG F 333      -6.304 -81.757   9.453  1.00 39.91      A   C
ATOM  14438  NE   ARG F 333      -6.030 -81.562   8.015  1.00 42.27      A   N
ATOM  14439  CZ   ARG F 333      -4.896 -81.900   7.385  1.00 42.97      A   C
ATOM  14440  NH1  ARG F 333      -4.761 -81.663   6.079  1.00 42.56      A   N
ATOM  14441  NH2  ARG F 333      -3.896 -82.474   8.049  1.00 43.83      A   N
ATOM  14442  N    ARG F 334      -5.590 -77.835  12.508  1.00 33.58      A   N
ATOM  14443  CA   ARG F 334      -4.466 -77.724  13.441  1.00 33.18      A   C
ATOM  14444  C    ARG F 334      -4.757 -76.779  14.620  1.00 32.72      A   C
ATOM  14445  O    ARG F 334      -3.909 -76.585  15.504  1.00 32.85      A   O
ATOM  14446  CB   ARG F 334      -3.200 -77.297  12.696  1.00 33.20      A   C
ATOM  14447  CG   ARG F 334      -2.484 -78.434  11.989  1.00 33.62      A   C
ATOM  14448  CD   ARG F 334      -1.876 -77.934  10.697  1.00 33.77      A   C
ATOM  14449  NE   ARG F 334      -0.934 -78.881  10.119  1.00 34.77      A   N
ATOM  14450  CZ   ARG F 334      -1.200 -79.676   9.088  1.00 35.55      A   C
ATOM  14451  NH1  ARG F 334      -2.395 -79.665   8.497  1.00 35.18      A   N
ATOM  14452  NH2  ARG F 334      -0.254 -80.491   8.645  1.00 36.60      A   N
ATOM  14453  N    GLY F 335      -5.952 -76.192  14.621  1.00 32.09      A   N
ATOM  14454  CA   GLY F 335      -6.413 -75.385  15.733  1.00 31.47      A   C
ATOM  14455  C    GLY F 335      -6.245 -73.891  15.588  1.00 30.83      A   C
ATOM  14456  O    GLY F 335      -6.347 -73.173  16.579  1.00 31.19      A   O
ATOM  14457  N    VAL F 336      -5.989 -73.405  14.378  1.00 29.90      A   N
ATOM  14458  CA   VAL F 336      -5.867 -71.964  14.177  1.00 29.08      A   C
ATOM  14459  C    VAL F 336      -7.263 -71.327  14.220  1.00 28.68      A   C
ATOM  14460  O    VAL F 336      -8.201 -71.852  13.616  1.00 28.61      A   O
ATOM  14461  CB   VAL F 336      -5.157 -71.623  12.852  1.00 28.91      A   C
ATOM  14462  CG1  VAL F 336      -5.042 -70.109  12.659  1.00 28.78      A   C
ATOM  14463  CG2  VAL F 336      -3.773 -72.276  12.803  1.00 29.07      A   C
ATOM  14464  N    PRO F 337      -7.414 -70.216  14.973  1.00 28.47      A   N
ATOM  14465  CA   PRO F 337      -8.648 -69.416  14.923  1.00 28.19      A   C
ATOM  14466  C    PRO F 337      -8.860 -68.858  13.524  1.00 27.77      A   C
ATOM  14467  O    PRO F 337      -7.943 -68.252  12.956  1.00 27.79      A   O
ATOM  14468  CB   PRO F 337      -8.352 -68.244  15.866  1.00 28.31      A   C
ATOM  14469  CG   PRO F 337      -7.280 -68.724  16.759  1.00 28.74      A   C
ATOM  14470  CD   PRO F 337      -6.454 -69.687  15.964  1.00 28.65      A   C
ATOM  14471  N    VAL F 338     -10.048 -69.058  12.968  1.00 27.29      A   N
ATOM  14472  CA   VAL F 338     -10.315 -68.620  11.605  1.00 26.72      A   C
ATOM  14473  C    VAL F 338     -11.435 -67.602  11.568  1.00 26.55      A   C
ATOM  14474  O    VAL F 338     -12.420 -67.736  12.290  1.00 26.78      A   O
ATOM  14475  CB   VAL F 338     -10.687 -69.807  10.682  1.00 26.61      A   C
ATOM  14476  CG1  VAL F 338     -10.982 -69.323   9.270  1.00 26.37      A   C
ATOM  14477  CG2  VAL F 338      -9.574 -70.834  10.654  1.00 26.62      A   C
ATOM  14478  N    LEU F 339     -11.270 -66.579  10.735  1.00 26.19      A   N
ATOM  14479  CA   LEU F 339     -12.389 -65.743  10.315  1.00 25.93      A   C
ATOM  14480  C    LEU F 339     -12.542 -65.824   8.799  1.00 25.80      A   C
ATOM  14481  O    LEU F 339     -11.721 -65.290   8.048  1.00 25.81      A   O
ATOM  14482  CB   LEU F 339     -12.222 -64.295  10.774  1.00 25.86      A   C
ATOM  14483  CG   LEU F 339     -13.390 -63.355  10.443  1.00 25.68      A   C
ATOM  14484  CD1  LEU F 339     -14.698 -63.873  11.006  1.00 26.01      A   C
ATOM  14485  CD2  LEU F 339     -13.131 -61.961  10.966  1.00 25.49      A   C
ATOM  14486  N    HIS F 340     -13.601 -66.496   8.360  1.00 25.64      A   N
ATOM  14487  CA   HIS F 340     -13.799 -66.800   6.949  1.00 25.42      A   C
ATOM  14488  C    HIS F 340     -14.624 -65.724   6.263  1.00 25.29      A   C
ATOM  14489  O    HIS F 340     -15.845 -65.679   6.397  1.00 25.35      A   O
ATOM  14490  CB   HIS F 340     -14.465 -68.162   6.829  1.00 25.48      A   C
ATOM  14491  CG   HIS F 340     -14.295 -68.799   5.494  1.00 25.63      A   C
ATOM  14492  CD2  HIS F 340     -13.478 -68.495   4.460  1.00 25.68      A   C
ATOM  14493  ND1  HIS F 340     -15.027 -69.897   5.099  1.00 25.99      A   N
ATOM  14494  CE1  HIS F 340     -14.662 -70.247   3.879  1.00 25.98      A   C
ATOM  14495  NE2  HIS F 340     -13.722 -69.414   3.468  1.00 25.93      A   N
```

FIGURE 1 (cont'd)

```
ATOM  14496  N    LEU F 341     -13.945 -64.845   5.544  1.00 25.14      A  N
ATOM  14497  CA   LEU F 341     -14.593 -63.681   4.953  1.00 25.13      A  C
ATOM  14498  C    LEU F 341     -14.957 -63.956   3.497  1.00 25.11      A  C
ATOM  14499  O    LEU F 341     -14.396 -63.343   2.575  1.00 25.12      A  O
ATOM  14500  CB   LEU F 341     -13.675 -62.464   5.042  1.00 25.11      A  C
ATOM  14501  CG   LEU F 341     -14.292 -61.132   5.466  1.00 25.32      A  C
ATOM  14502  CD1  LEU F 341     -13.211 -60.050   5.426  1.00 25.57      A  C
ATOM  14503  CD2  LEU F 341     -15.500 -60.735   4.610  1.00 25.09      A  C
ATOM  14504  N    ILE F 342     -15.898 -64.884   3.312  1.00 25.17      A  N
ATOM  14505  CA   ILE F 342     -16.388 -65.318   1.998  1.00 25.20      A  C
ATOM  14506  C    ILE F 342     -17.882 -65.038   1.897  1.00 25.52      A  C
ATOM  14507  O    ILE F 342     -18.634 -65.335   2.826  1.00 25.79      A  O
ATOM  14508  CB   ILE F 342     -16.119 -66.825   1.804  1.00 25.02      A  C
ATOM  14509  CG1  ILE F 342     -16.578 -67.306   0.433  1.00 24.88      A  C
ATOM  14510  CG2  ILE F 342     -16.770 -67.642   2.912  1.00 24.97      A  C
ATOM  14511  CD1  ILE F 342     -16.052 -68.687   0.088  1.00 24.63      A  C
ATOM  14512  N    SER F 343     -18.323 -64.450   0.794  1.00 25.77      A  N
ATOM  14513  CA   SER F 343     -19.737 -64.121   0.682  1.00 26.21      A  C
ATOM  14514  C    SER F 343     -20.595 -65.369   0.471  1.00 26.41      A  C
ATOM  14515  O    SER F 343     -20.263 -66.239  -0.340  1.00 26.31      A  O
ATOM  14516  CB   SER F 343     -19.980 -63.099  -0.420  1.00 26.34      A  C
ATOM  14517  OG   SER F 343     -19.710 -63.656  -1.692  1.00 27.03      A  O
ATOM  14518  N    THR F 344     -21.675 -65.455   1.243  1.00 26.75      A  N
ATOM  14519  CA   THR F 344     -22.667 -66.499   1.088  1.00 27.08      A  C
ATOM  14520  C    THR F 344     -23.980 -65.758   0.911  1.00 27.53      A  C
ATOM  14521  O    THR F 344     -24.371 -65.006   1.802  1.00 27.63      A  O
ATOM  14522  CB   THR F 344     -22.724 -67.465   2.295  1.00 27.00      A  C
ATOM  14523  OG1  THR F 344     -21.881 -66.989   3.347  1.00 26.77      A  O
ATOM  14524  N    PRO F 345     -24.656 -65.948  -0.247  1.00 27.88      A  N
ATOM  14525  CA   PRO F 345     -24.316 -66.918  -1.307  1.00 27.91      A  C
ATOM  14526  C    PRO F 345     -23.117 -66.490  -2.180  1.00 27.71      A  C
ATOM  14527  O    PRO F 345     -22.624 -65.364  -2.051  1.00 27.46      A  O
ATOM  14528  CB   PRO F 345     -25.602 -66.989  -2.144  1.00 28.14      A  C
ATOM  14529  CG   PRO F 345     -26.563 -65.984  -1.530  1.00 28.21      A  C
ATOM  14530  CD   PRO F 345     -25.771 -65.082  -0.663  1.00 27.97      A  C
ATOM  14531  N    PHE F 346     -22.647 -67.390  -3.042  1.00 27.68      A  N
ATOM  14532  CA   PHE F 346     -21.557 -67.081  -3.957  1.00 27.81      A  C
ATOM  14533  C    PHE F 346     -22.033 -66.101  -5.016  1.00 28.03      A  C
ATOM  14534  O    PHE F 346     -23.232 -66.045  -5.312  1.00 28.37      A  O
ATOM  14535  CB   PHE F 346     -21.052 -68.347  -4.650  1.00 27.86      A  C
ATOM  14536  CG   PHE F 346     -20.439 -69.359  -3.725  1.00 28.03      A  C
ATOM  14537  CD1  PHE F 346     -20.053 -69.011  -2.435  1.00 27.87      A  C
ATOM  14538  CD2  PHE F 346     -20.224 -70.665  -4.156  1.00 28.58      A  C
ATOM  14539  CE1  PHE F 346     -19.486 -69.956  -1.584  1.00 27.81      A  C
ATOM  14540  CE2  PHE F 346     -19.648 -71.611  -3.318  1.00 28.46      A  C
ATOM  14541  CZ   PHE F 346     -19.285 -71.256  -2.031  1.00 28.02      A  C
ATOM  14542  N    PRO F 347     -21.098 -65.331  -5.608  1.00 28.05      A  N
ATOM  14543  CA   PRO F 347     -21.425 -64.375  -6.677  1.00 28.42      A  C
ATOM  14544  C    PRO F 347     -22.184 -65.039  -7.823  1.00 29.02      A  C
ATOM  14545  O    PRO F 347     -21.882 -66.175  -8.171  1.00 29.18      A  O
ATOM  14546  CB   PRO F 347     -20.049 -63.933  -7.171  1.00 28.18      A  C
ATOM  14547  CG   PRO F 347     -19.149 -64.127  -6.020  1.00 27.70      A  C
ATOM  14548  CD   PRO F 347     -19.654 -65.335  -5.308  1.00 27.72      A  C
ATOM  14549  N    ALA F 348     -23.159 -64.346  -8.406  1.00 29.69      A  N
ATOM  14550  CA   ALA F 348     -23.913 -64.909  -9.535  1.00 30.35      A  C
ATOM  14551  C    ALA F 348     -22.957 -65.424 -10.626  1.00 30.60      A  C
ATOM  14552  O    ALA F 348     -23.172 -66.490 -11.227  1.00 30.69      A  O
ATOM  14553  CB   ALA F 348     -24.888 -63.875 -10.095  1.00 30.60      A  C
ATOM  14554  N    VAL F 349     -21.879 -64.668 -10.823  1.00 30.69      A  N
ATOM  14555  CA   VAL F 349     -20.890 -64.933 -11.842  1.00 30.87      A  C
ATOM  14556  C    VAL F 349     -19.865 -65.970 -11.406  1.00 30.95      A  C
ATOM  14557  O    VAL F 349     -18.778 -66.044 -11.972  1.00 31.09      A  O
ATOM  14558  CB   VAL F 349     -20.158 -63.639 -12.271  1.00 30.85      A  C
ATOM  14559  CG1  VAL F 349     -21.119 -62.684 -12.941  1.00 31.42      A  C
ATOM  14560  CG2  VAL F 349     -19.457 -62.970 -11.089  1.00 30.44      A  C
```

FIGURE 1 (cont'd)

```
ATOM  14561  N    TRP F 350     -20.212 -66.798 -10.428  1.00 31.06      A  N
ATOM  14562  CA   TRP F 350     -19.233 -67.732  -9.853  1.00 31.14      A  C
ATOM  14563  C    TRP F 350     -18.909 -68.917 -10.751  1.00 31.48      A  C
ATOM  14564  O    TRP F 350     -19.811 -69.537 -11.325  1.00 31.73      A  O
ATOM  14565  CB   TRP F 350     -19.690 -68.231  -8.488  1.00 30.94      A  C
ATOM  14566  CG   TRP F 350     -18.670 -69.053  -7.765  1.00 30.50      A  C
ATOM  14567  CD1  TRP F 350     -17.495 -68.614  -7.213  1.00 30.21      A  C
ATOM  14568  CD2  TRP F 350     -18.737 -70.461  -7.494  1.00 30.19      A  C
ATOM  14569  CE2  TRP F 350     -17.572 -70.807  -6.781  1.00 29.95      A  C
ATOM  14570  CE3  TRP F 350     -19.673 -71.469  -7.783  1.00 30.20      A  C
ATOM  14571  NE1  TRP F 350     -16.829 -69.662  -6.621  1.00 29.97      A  N
ATOM  14572  CZ2  TRP F 350     -17.319 -72.122  -6.359  1.00 29.66      A  C
ATOM  14573  CZ3  TRP F 350     -19.410 -72.775  -7.358  1.00 29.97      A  C
ATOM  14574  CH2  TRP F 350     -18.249 -73.083  -6.659  1.00 29.60      A  C
ATOM  14575  N    HIS F 351     -17.614 -69.222 -10.844  1.00 31.79      A  N
ATOM  14576  CA   HIS F 351     -17.095 -70.334 -11.655  1.00 32.37      A  C
ATOM  14577  C    HIS F 351     -17.681 -70.339 -13.063  1.00 32.92      A  C
ATOM  14578  O    HIS F 351     -18.153 -71.370 -13.551  1.00 33.17      A  O
ATOM  14579  CB   HIS F 351     -17.317 -71.687 -10.954  1.00 32.39      A  C
ATOM  14580  CG   HIS F 351     -16.286 -72.017  -9.915  1.00 32.42      A  C
ATOM  14581  CD2  HIS F 351     -15.381 -71.237  -9.272  1.00 32.07      A  C
ATOM  14582  ND1  HIS F 351     -16.097 -73.298  -9.439  1.00 32.52      A  N
ATOM  14583  CE1  HIS F 351     -15.122 -73.291  -8.546  1.00 32.29      A  C
ATOM  14584  NE2  HIS F 351     -14.673 -72.052  -8.424  1.00 31.87      A  N
ATOM  14585  N    THR F 352     -17.657 -69.162 -13.692  1.00 33.38      A  N
ATOM  14586  CA   THR F 352     -18.115 -68.958 -15.069  1.00 33.93      A  C
ATOM  14587  C    THR F 352     -17.313 -67.842 -15.754  1.00 34.18      A  C
ATOM  14588  O    THR F 352     -16.835 -66.933 -15.081  1.00 33.97      A  O
ATOM  14589  CB   THR F 352     -19.630 -68.652 -15.131  1.00 34.04      A  C
ATOM  14590  CG2  THR F 352     -20.042 -67.787 -13.992  1.00 33.55      A  C
ATOM  14591  OG1  THR F 352     -19.935 -67.956 -16.342  1.00 34.80      A  O
ATOM  14592  N    PRO F 353     -17.162 -67.911 -17.096  1.00 34.70      A  N
ATOM  14593  CA   PRO F 353     -16.464 -66.891 -17.890  1.00 34.79      A  C
ATOM  14594  C    PRO F 353     -16.891 -65.480 -17.541  1.00 34.57      A  C
ATOM  14595  O    PRO F 353     -16.158 -64.540 -17.808  1.00 34.58      A  O
ATOM  14596  CB   PRO F 353     -16.920 -67.195 -19.314  1.00 35.22      A  C
ATOM  14597  CG   PRO F 353     -17.191 -68.639 -19.315  1.00 35.52      A  C
ATOM  14598  CD   PRO F 353     -17.668 -69.004 -17.950  1.00 34.98      A  C
ATOM  14599  N    ALA F 354     -18.075 -65.354 -16.952  1.00 34.30      A  N
ATOM  14600  CA   ALA F 354     -18.647 -64.067 -16.567  1.00 34.06      A  C
ATOM  14601  C    ALA F 354     -17.865 -63.344 -15.465  1.00 33.76      A  C
ATOM  14602  O    ALA F 354     -17.930 -62.126 -15.346  1.00 33.69      A  O
ATOM  14603  CB   ALA F 354     -20.098 -64.248 -16.159  1.00 34.07      A  C
ATOM  14604  N    ASP F 355     -17.123 -64.100 -14.665  1.00 33.55      A  N
ATOM  14605  CA   ASP F 355     -16.338 -63.536 -13.564  1.00 33.32      A  C
ATOM  14606  C    ASP F 355     -15.132 -62.772 -14.087  1.00 33.47      A  C
ATOM  14607  O    ASP F 355     -13.996 -63.242 -14.014  1.00 33.37      A  O
ATOM  14608  CB   ASP F 355     -15.893 -64.643 -12.594  1.00 33.04      A  C
ATOM  14609  CG   ASP F 355     -15.321 -64.098 -11.292  1.00 32.53      A  C
ATOM  14610  OD1  ASP F 355     -15.160 -62.864 -11.182  1.00 32.71      A  O
ATOM  14611  OD2  ASP F 355     -15.031 -64.912 -10.381  1.00 31.67      A  O
ATOM  14612  N    THR F 356     -15.390 -61.590 -14.622  1.00 33.74      A  N
ATOM  14613  CA   THR F 356     -14.328 -60.750 -15.142  1.00 33.96      A  C
ATOM  14614  C    THR F 356     -14.437 -59.359 -14.533  1.00 34.40      A  C
ATOM  14615  O    THR F 356     -15.359 -59.084 -13.770  1.00 34.31      A  O
ATOM  14616  CB   THR F 356     -14.365 -60.675 -16.679  1.00 33.36      A  C
ATOM  14617  OG1  THR F 356     -15.654 -60.225 -17.111  1.00 33.33      A  O
ATOM  14618  N    GLU F 357     -13.485 -58.493 -14.868  1.00 35.01      A  N
ATOM  14619  CA   GLU F 357     -13.470 -57.116 -14.389  1.00 35.54      A  C
ATOM  14620  C    GLU F 357     -14.808 -56.420 -14.614  1.00 35.90      A  C
ATOM  14621  O    GLU F 357     -15.315 -55.748 -13.716  1.00 35.87      A  O
ATOM  14622  CB   GLU F 357     -12.339 -56.324 -15.063  1.00 35.74      A  C
ATOM  14623  CG   GLU F 357     -12.231 -54.848 -14.626  1.00 36.36      A  C
ATOM  14624  CD   GLU F 357     -10.977 -54.145 -15.148  1.00 37.43      A  C
ATOM  14625  OE1  GLU F 357     -10.186 -54.768 -15.889  1.00 38.21      A  O
```

FIGURE 1 (cont'd)

```
ATOM  14626  OE2 GLU F 357     -10.776 -52.957 -14.818  1.00 37.78      A    O
ATOM  14627  N   VAL F 358     -15.373 -56.607 -15.808  1.00 36.41      A    N
ATOM  14628  CA  VAL F 358     -16.624 -55.972 -16.232  1.00 36.82      A    C
ATOM  14629  C   VAL F 358     -17.813 -56.145 -15.274  1.00 36.64      A    C
ATOM  14630  O   VAL F 358     -18.734 -55.326 -15.275  1.00 36.90      A    O
ATOM  14631  CB  VAL F 358     -17.042 -56.472 -17.625  1.00 37.16      A    C
ATOM  14632  CG1 VAL F 358     -17.167 -55.301 -18.584  1.00 37.97      A    C
ATOM  14633  N   ASN F 359     -17.786 -57.192 -14.453  1.00 36.23      A    N
ATOM  14634  CA  ASN F 359     -18.932 -57.544 -13.611  1.00 35.89      A    C
ATOM  14635  C   ASN F 359     -18.748 -57.317 -12.104  1.00 35.33      A    C
ATOM  14636  O   ASN F 359     -19.597 -57.696 -11.299  1.00 35.20      A    O
ATOM  14637  CB  ASN F 359     -19.348 -58.992 -13.885  1.00 36.12      A    C
ATOM  14638  CG  ASN F 359     -19.928 -59.194 -15.294  1.00 37.11      A    C
ATOM  14639  ND2 ASN F 359     -20.145 -58.108 -16.020  1.00 38.06      A    N
ATOM  14640  OD1 ASN F 359     -20.180 -60.324 -15.711  1.00 37.70      A    O
ATOM  14641  N   LEU F 360     -17.633 -56.699 -11.732  1.00 34.83      A    N
ATOM  14642  CA  LEU F 360     -17.389 -56.304 -10.354  1.00 34.33      A    C
ATOM  14643  C   LEU F 360     -18.151 -55.016 -10.087  1.00 34.38      A    C
ATOM  14644  O   LEU F 360     -18.458 -54.284 -11.024  1.00 34.85      A    O
ATOM  14645  CB  LEU F 360     -15.891 -56.081 -10.124  1.00 34.02      A    C
ATOM  14646  CG  LEU F 360     -14.915 -57.186 -10.505  1.00 33.43      A    C
ATOM  14647  CD1 LEU F 360     -13.516 -56.717 -10.263  1.00 32.89      A    C
ATOM  14648  CD2 LEU F 360     -15.196 -58.416  -9.694  1.00 33.10      A    C
ATOM  14649  N   HIS F 361     -18.461 -54.747  -8.820  1.00 34.09      A    N
ATOM  14650  CA  HIS F 361     -19.050 -53.469  -8.422  1.00 33.91      A    C
ATOM  14651  C   HIS F 361     -17.968 -52.639  -7.749  1.00 34.19      A    C
ATOM  14652  O   HIS F 361     -17.754 -52.773  -6.545  1.00 33.99      A    O
ATOM  14653  CB  HIS F 361     -20.238 -53.673  -7.471  1.00 33.56      A    C
ATOM  14654  CG  HIS F 361     -21.244 -52.561  -7.506  1.00 32.71      A    C
ATOM  14655  ND1 HIS F 361     -21.071 -51.373  -6.837  1.00 31.53      A    N
ATOM  14656  CE1 HIS F 361     -22.116 -50.598  -7.061  1.00 31.55      A    C
ATOM  14657  N   PRO F 362     -17.278 -51.777  -8.527  1.00 34.67      A    N
ATOM  14658  CA  PRO F 362     -16.149 -51.015  -7.996  1.00 34.88      A    C
ATOM  14659  C   PRO F 362     -16.435 -50.344  -6.640  1.00 34.86      A    C
ATOM  14660  O   PRO F 362     -15.602 -50.441  -5.734  1.00 34.74      A    O
ATOM  14661  CB  PRO F 362     -15.861 -49.988  -9.104  1.00 35.18      A    C
ATOM  14662  CG  PRO F 362     -16.298 -50.655 -10.340  1.00 35.31      A    C
ATOM  14663  CD  PRO F 362     -17.514 -51.463  -9.950  1.00 35.01      A    C
ATOM  14664  N   PRO F 363     -17.605 -49.688  -6.482  1.00 34.97      A    N
ATOM  14665  CA  PRO F 363     -17.907 -49.136  -5.175  1.00 34.97      A    C
ATOM  14666  C   PRO F 363     -17.798 -50.188  -4.085  1.00 34.63      A    C
ATOM  14667  O   PRO F 363     -17.044 -50.004  -3.130  1.00 34.58      A    O
ATOM  14668  CB  PRO F 363     -19.350 -48.670  -5.330  1.00 35.26      A    C
ATOM  14669  CG  PRO F 363     -19.436 -48.272  -6.736  1.00 35.68      A    C
ATOM  14670  CD  PRO F 363     -18.652 -49.329  -7.457  1.00 35.05      A    C
ATOM  14671  N   THR F 364     -18.515 -51.295  -4.244  1.00 34.30      A    N
ATOM  14672  CA  THR F 364     -18.490 -52.363  -3.251  1.00 33.97      A    C
ATOM  14673  C   THR F 364     -17.045 -52.717  -2.913  1.00 33.90      A    C
ATOM  14674  O   THR F 364     -16.709 -52.907  -1.735  1.00 33.75      A    O
ATOM  14675  CB  THR F 364     -19.279 -53.619  -3.711  1.00 33.86      A    C
ATOM  14676  CG2 THR F 364     -19.304 -54.680  -2.623  1.00 33.49      A    C
ATOM  14677  OG1 THR F 364     -20.628 -53.255  -4.020  1.00 34.09      A    O
ATOM  14678  N   VAL F 365     -16.190 -52.765  -3.937  1.00 33.99      A    N
ATOM  14679  CA  VAL F 365     -14.783 -53.122  -3.748  1.00 34.09      A    C
ATOM  14680  C   VAL F 365     -14.118 -52.158  -2.788  1.00 34.27      A    C
ATOM  14681  O   VAL F 365     -13.535 -52.584  -1.790  1.00 34.12      A    O
ATOM  14682  CB  VAL F 365     -14.000 -53.183  -5.081  1.00 34.12      A    C
ATOM  14683  CG1 VAL F 365     -14.411 -54.403  -5.882  1.00 34.02      A    C
ATOM  14684  CG2 VAL F 365     -12.503 -53.219  -4.830  1.00 33.97      A    C
ATOM  14685  N   HIS F 366     -14.233 -50.868  -3.080  1.00 34.67      A    N
ATOM  14686  CA  HIS F 366     -13.562 -49.847  -2.289  1.00 35.15      A    C
ATOM  14687  C   HIS F 366     -14.100 -49.762  -0.874  1.00 35.35      A    C
ATOM  14688  O   HIS F 366     -13.327 -49.593   0.076  1.00 35.48      A    O
ATOM  14689  CB  HIS F 366     -13.642 -48.495  -2.970  1.00 35.38      A    C
ATOM  14690  CG  HIS F 366     -12.942 -48.453  -4.288  1.00 35.50      A    C
```

FIGURE 1 (cont'd)

```
ATOM  14691  CD2 HIS F 366     -13.391 -48.134  -5.525  1.00 35.25      A   C
ATOM  14692  ND1 HIS F 366     -11.601 -48.746  -4.428  1.00 35.51      A   N
ATOM  14693  CE1 HIS F 366     -11.262 -48.636  -5.700  1.00 35.54      A   C
ATOM  14694  NE2 HIS F 366     -12.327 -48.256  -6.385  1.00 35.94      A   N
ATOM  14695  N   ASN F 367     -15.416 -49.900  -0.739  1.00 35.40      A   N
ATOM  14696  CA  ASN F 367     -16.038 -50.032   0.573  1.00 35.45      A   C
ATOM  14697  C   ASN F 367     -15.355 -51.103   1.416  1.00 35.26      A   C
ATOM  14698  O   ASN F 367     -14.965 -50.849   2.560  1.00 35.40      A   O
ATOM  14699  CB  ASN F 367     -17.519 -50.362   0.436  1.00 35.51      A   C
ATOM  14700  CG  ASN F 367     -18.333 -49.194  -0.047  1.00 36.12      A   C
ATOM  14701  ND2 ASN F 367     -19.639 -49.353  -0.008  1.00 36.24      A   N
ATOM  14702  OD1 ASN F 367     -17.803 -48.161  -0.456  1.00 37.04      A   O
ATOM  14703  N   LEU F 368     -15.197 -52.293   0.841  1.00 34.95      A   N
ATOM  14704  CA  LEU F 368     -14.583 -53.404   1.552  1.00 34.73      A   C
ATOM  14705  C   LEU F 368     -13.149 -53.104   2.007  1.00 34.90      A   C
ATOM  14706  O   LEU F 368     -12.712 -53.573   3.056  1.00 35.02      A   O
ATOM  14707  CB  LEU F 368     -14.617 -54.658   0.693  1.00 34.37      A   C
ATOM  14708  CG  LEU F 368     -15.973 -55.318   0.484  1.00 33.72      A   C
ATOM  14709  CD1 LEU F 368     -15.835 -56.407  -0.553  1.00 33.49      A   C
ATOM  14710  CD2 LEU F 368     -16.495 -55.890   1.777  1.00 32.86      A   C
ATOM  14711  N   ALA F 369     -12.433 -52.312   1.216  1.00 34.17      A   N
ATOM  14712  CA  ALA F 369     -11.067 -51.938   1.530  1.00 33.51      A   C
ATOM  14713  C   ALA F 369     -11.021 -50.928   2.661  1.00 34.51      A   C
ATOM  14714  O   ALA F 369     -10.157 -51.014   3.536  1.00 35.72      A   O
ATOM  14715  CB  ALA F 369     -10.387 -51.390   0.315  1.00 24.54      A   C
ATOM  14716  N   ARG F 370     -11.945 -49.970   2.647  1.00 35.18      A   N
ATOM  14717  CA  ARG F 370     -12.071 -49.003   3.749  1.00 34.83      A   C
ATOM  14718  C   ARG F 370     -12.359 -49.743   5.053  1.00 34.22      A   C
ATOM  14719  O   ARG F 370     -11.687 -49.510   6.044  1.00 34.13      A   O
ATOM  14720  CB  ARG F 370     -13.118 -47.918   3.443  1.00 35.11      A   C
ATOM  14721  CG  ARG F 370     -12.755 -47.045   2.230  1.00 35.40      A   C
ATOM  14722  CD  ARG F 370     -13.772 -45.942   1.967  1.00 35.75      A   C
ATOM  14723  NE  ARG F 370     -13.340 -45.006   0.922  1.00 35.86      A   N
ATOM  14724  CZ  ARG F 370     -13.699 -43.723   0.866  1.00 36.00      A   C
ATOM  14725  N   ILE F 371     -13.312 -50.673   5.020  1.00 33.46      A   N
ATOM  14726  CA  ILE F 371     -13.641 -51.503   6.178  1.00 32.86      A   C
ATOM  14727  C   ILE F 371     -12.435 -52.304   6.672  1.00 32.77      A   C
ATOM  14728  O   ILE F 371     -12.132 -52.305   7.864  1.00 32.83      A   O
ATOM  14729  CB  ILE F 371     -14.846 -52.439   5.888  1.00 32.55      A   C
ATOM  14730  CG1 ILE F 371     -16.109 -51.605   5.682  1.00 32.52      A   C
ATOM  14731  CG2 ILE F 371     -15.061 -53.448   7.026  1.00 32.03      A   C
ATOM  14732  CD1 ILE F 371     -17.285 -52.389   5.149  1.00 32.24      A   C
ATOM  14733  N   LEU F 372     -11.748 -52.969   5.751  1.00 32.61      A   N
ATOM  14734  CA  LEU F 372     -10.576 -53.782   6.090  1.00 32.47      A   C
ATOM  14735  C   LEU F 372      -9.415 -52.957   6.651  1.00 32.77      A   C
ATOM  14736  O   LEU F 372      -8.816 -53.329   7.659  1.00 32.69      A   O
ATOM  14737  CB  LEU F 372     -10.115 -54.587   4.873  1.00 32.12      A   C
ATOM  14738  CG  LEU F 372     -10.517 -56.061   4.731  1.00 31.37      A   C
ATOM  14739  CD1 LEU F 372     -11.646 -56.505   5.663  1.00 30.78      A   C
ATOM  14740  CD2 LEU F 372     -10.831 -56.373   3.273  1.00 30.91      A   C
ATOM  14741  N   ALA F 373      -9.109 -51.839   5.997  1.00 33.17      A   N
ATOM  14742  CA  ALA F 373      -8.028 -50.956   6.429  1.00 33.57      A   C
ATOM  14743  C   ALA F 373      -8.225 -50.493   7.869  1.00 33.86      A   C
ATOM  14744  O   ALA F 373      -7.285 -50.473   8.657  1.00 33.97      A   O
ATOM  14745  CB  ALA F 373      -7.916 -49.760   5.496  1.00 33.69      A   C
ATOM  14746  N   VAL F 374      -9.458 -50.126   8.202  1.00 34.05      A   N
ATOM  14747  CA  VAL F 374      -9.799 -49.718   9.556  1.00 34.29      A   C
ATOM  14748  C   VAL F 374      -9.604 -50.895  10.490  1.00 34.19      A   C
ATOM  14749  O   VAL F 374      -8.940 -50.776  11.515  1.00 34.45      A   O
ATOM  14750  CB  VAL F 374     -11.249 -49.189   9.657  1.00 34.37      A   C
ATOM  14751  CG1 VAL F 374     -11.693 -49.077  11.124  1.00 34.59      A   C
ATOM  14752  CG2 VAL F 374     -11.384 -47.836   8.946  1.00 34.80      A   C
ATOM  14753  N   PHE F 375     -10.178 -52.033  10.117  1.00 33.94      A   N
ATOM  14754  CA  PHE F 375     -10.042 -53.246  10.910  1.00 33.79      A   C
ATOM  14755  C   PHE F 375      -8.573 -53.543  11.182  1.00 34.08      A   C
```

FIGURE 1 (cont'd)

```
ATOM  14756  O    PHE F 375      -8.173 -53.718  12.338  1.00 34.16      A    O
ATOM  14757  CB   PHE F 375     -10.702 -54.439  10.212  1.00 33.34      A    C
ATOM  14758  CG   PHE F 375     -10.581 -55.720  10.973  1.00 32.60      A    C
ATOM  14759  CD1  PHE F 375     -11.654 -56.214  11.698  1.00 32.44      A    C
ATOM  14760  CD2  PHE F 375      -9.386 -56.428  10.975  1.00 32.08      A    C
ATOM  14761  CE1  PHE F 375     -11.544 -57.404  12.408  1.00 32.40      A    C
ATOM  14762  CE2  PHE F 375      -9.259 -57.608  11.691  1.00 32.24      A    C
ATOM  14763  CZ   PHE F 375     -10.345 -58.103  12.410  1.00 32.33      A    C
ATOM  14764  N    LEU F 376      -7.779 -53.582  10.113  1.00 34.44      A    N
ATOM  14765  CA   LEU F 376      -6.365 -53.917  10.220  1.00 34.90      A    C
ATOM  14766  C    LEU F 376      -5.706 -52.971  11.216  1.00 35.69      A    C
ATOM  14767  O    LEU F 376      -4.973 -53.413  12.105  1.00 35.83      A    O
ATOM  14768  CB   LEU F 376      -5.677 -53.855   8.852  1.00 34.58      A    C
ATOM  14769  CG   LEU F 376      -4.598 -54.906   8.558  1.00 33.84      A    C
ATOM  14770  N    ALA F 377      -6.012 -51.860  11.085  1.00 36.59      A    N
ATOM  14771  CA   ALA F 377      -5.475 -50.644  11.979  1.00 37.48      A    C
ATOM  14772  C    ALA F 377      -5.926 -50.844  13.425  1.00 37.94      A    C
ATOM  14773  O    ALA F 377      -5.113 -50.761  14.347  1.00 38.23      A    O
ATOM  14774  CB   ALA F 377      -5.843 -49.241  11.489  1.00 37.62      A    C
ATOM  14775  N    GLU F 378      -7.215 -51.120  13.611  1.00 38.24      A    N
ATOM  14776  CA   GLU F 378      -7.755 -51.322  14.945  1.00 38.65      A    C
ATOM  14777  C    GLU F 378      -7.159 -52.572  15.582  1.00 38.61      A    C
ATOM  14778  O    GLU F 378      -6.687 -52.512  16.713  1.00 38.94      A    O
ATOM  14779  CB   GLU F 378      -9.294 -51.340  14.942  1.00 38.74      A    C
ATOM  14780  CG   GLU F 378      -9.935 -49.928  14.863  1.00 39.92      A    C
ATOM  14781  CD   GLU F 378     -11.464 -49.896  15.096  1.00 41.32      A    C
ATOM  14782  OE1  GLU F 378     -12.054 -50.933  15.498  1.00 41.81      A    O
ATOM  14783  OE2  GLU F 378     -12.079 -48.818  14.881  1.00 41.94      A    O
ATOM  14784  N    TYR F 379      -7.142 -53.681  14.846  1.00 38.43      A    N
ATOM  14785  CA   TYR F 379      -6.628 -54.953  15.381  1.00 38.43      A    C
ATOM  14786  C    TYR F 379      -5.168 -54.846  15.825  1.00 38.98      A    C
ATOM  14787  O    TYR F 379      -4.781 -55.367  16.880  1.00 39.10      A    O
ATOM  14788  CB   TYR F 379      -6.780 -56.089  14.357  1.00 37.84      A    C
ATOM  14789  CG   TYR F 379      -6.470 -57.477  14.899  1.00 37.04      A    C
ATOM  14790  CD1  TYR F 379      -7.493 -58.373  15.198  1.00 36.34      A    C
ATOM  14791  CD2  TYR F 379      -5.156 -57.898  15.100  1.00 36.80      A    C
ATOM  14792  CE1  TYR F 379      -7.215 -59.653  15.689  1.00 36.18      A    C
ATOM  14793  CE2  TYR F 379      -4.866 -59.164  15.598  1.00 36.53      A    C
ATOM  14794  CZ   TYR F 379      -5.901 -60.039  15.888  1.00 36.22      A    C
ATOM  14795  OH   TYR F 379      -5.637 -61.303  16.372  1.00 35.93      A    O
ATOM  14796  N    LEU F 380      -4.365 -54.171  15.011  1.00 39.66      A    N
ATOM  14797  CA   LEU F 380      -2.939 -54.023  15.289  1.00 40.54      A    C
ATOM  14798  C    LEU F 380      -2.590 -52.705  16.004  1.00 41.51      A    C
ATOM  14799  O    LEU F 380      -1.416 -52.415  16.228  1.00 41.91      A    O
ATOM  14800  CB   LEU F 380      -2.138 -54.129  13.982  1.00 40.18      A    C
ATOM  14801  CG   LEU F 380      -1.403 -55.405  13.564  1.00 39.75      A    C
ATOM  14802  CD1  LEU F 380      -2.096 -56.681  13.988  1.00 39.38      A    C
ATOM  14803  CD2  LEU F 380      -1.207 -55.392  12.066  1.00 39.48      A    C
ATOM  14804  N    GLY F 381      -3.589 -51.884  16.318  1.00 42.72      A    N
ATOM  14805  CA   GLY F 381      -3.344 -50.604  16.993  1.00 43.69      A    C
ATOM  14806  C    GLY F 381      -2.309 -49.736  16.294  1.00 44.43      A    C
ATOM  14807  O    GLY F 381      -1.464 -49.126  16.944  1.00 44.43      A    O
ATOM  14808  N    LEU F 382      -2.383 -49.681  14.967  1.00 45.08      A    N
ATOM  14809  CA   LEU F 382      -1.431 -48.912  14.152  1.00 45.85      A    C
ATOM  14810  C    LEU F 382      -1.775 -47.431  13.990  1.00 46.10      A    C
ATOM  14811  O    LEU F 382      -0.945 -46.643  13.520  1.00 46.25      A    O
ATOM  14812  CB   LEU F 382      -1.318 -49.517  12.756  1.00 45.91      A    C
ATOM  14813  CG   LEU F 382      -0.658 -50.885  12.634  1.00 46.27      A    C
ATOM  14814  CD1  LEU F 382      -0.831 -51.362  11.211  1.00 46.40      A    C
ATOM  14815  CD2  LEU F 382       0.813 -50.839  13.031  1.00 46.05      A    C
ATOM  14816  OXT  LEU F 382      -2.884 -46.988  14.291  1.00 46.31      A    O
TER   14817       LEU F 382
ATOM  14818  N    SER G  75     -44.097 -43.297  24.366  1.00 44.76      A    N
ATOM  14819  CA   SER G  75     -45.039 -44.165  23.621  1.00 45.22      A    C
ATOM  14820  C    SER G  75     -44.650 -45.643  23.774  1.00 46.77      A    C
```

FIGURE 1 (cont'd)

```
ATOM  14821  O    SER G  75     -44.671 -46.400  22.802  1.00 46.94      A  O
ATOM  14822  CB   SER G  75     -45.101 -43.733  22.140  1.00 44.46      A  C
ATOM  14823  OG   SER G  75     -43.801 -43.614  21.579  1.00 43.57      A  O
ATOM  14824  N    LEU G  76     -44.306 -46.045  25.001  1.00 48.95      A  N
ATOM  14825  CA   LEU G  76     -43.959 -47.448  25.318  1.00 51.08      A  C
ATOM  14826  C    LEU G  76     -45.196 -48.351  25.441  1.00 52.90      A  C
ATOM  14827  O    LEU G  76     -46.327 -47.861  25.396  1.00 53.12      A  O
ATOM  14828  CB   LEU G  76     -43.141 -47.544  26.615  1.00 50.87      A  C
ATOM  14829  CG   LEU G  76     -42.081 -46.499  26.952  1.00 50.58      A  C
ATOM  14830  CD1  LEU G  76     -41.356 -46.875  28.236  1.00 50.19      A  C
ATOM  14831  CD2  LEU G  76     -41.099 -46.318  25.805  1.00 50.79      A  C
ATOM  14832  N    PRO G  77     -44.986 -49.679  25.559  1.00 54.50      A  N
ATOM  14833  CA   PRO G  77     -46.063 -50.620  25.918  1.00 55.46      A  C
ATOM  14834  C    PRO G  77     -45.960 -51.185  27.344  1.00 55.77      A  C
ATOM  14835  O    PRO G  77     -44.851 -51.316  27.884  1.00 55.68      A  O
ATOM  14836  CB   PRO G  77     -45.902 -51.741  24.890  1.00 56.06      A  C
ATOM  14837  CG   PRO G  77     -44.449 -51.736  24.558  1.00 55.91      A  C
ATOM  14838  CD   PRO G  77     -43.881 -50.364  24.866  1.00 54.91      A  C
ATOM  14839  N    GLU G  78     -47.116 -51.527  27.924  1.00 55.91      A  N
ATOM  14840  CA   GLU G  78     -47.226 -51.994  29.320  1.00 55.79      A  C
ATOM  14841  C    GLU G  78     -46.138 -52.980  29.760  1.00 57.05      A  C
ATOM  14842  O    GLU G  78     -45.562 -52.841  30.848  1.00 57.26      A  O
ATOM  14843  CB   GLU G  78     -48.617 -52.593  29.598  1.00 53.82      A  C
ATOM  14844  CG   GLU G  78     -49.609 -51.647  30.275  1.00 51.30      A  C
ATOM  14845  N    ALA G  79     -45.869 -53.966  28.908  1.00 58.29      A  N
ATOM  14846  CA   ALA G  79     -44.889 -55.014  29.192  1.00 58.95      A  C
ATOM  14847  C    ALA G  79     -43.490 -54.465  29.486  1.00 58.70      A  C
ATOM  14848  O    ALA G  79     -42.866 -54.843  30.481  1.00 58.84      A  O
ATOM  14849  CB   ALA G  79     -44.842 -56.019  28.041  1.00 59.77      A  C
ATOM  14850  N    ARG G  80     -43.005 -53.582  28.617  1.00 57.97      A  N
ATOM  14851  CA   ARG G  80     -41.698 -52.961  28.802  1.00 57.00      A  C
ATOM  14852  C    ARG G  80     -41.747 -51.932  29.930  1.00 56.73      A  C
ATOM  14853  O    ARG G  80     -40.800 -51.808  30.706  1.00 56.75      A  O
ATOM  14854  CB   ARG G  80     -41.206 -52.316  27.500  1.00 55.30      A  C
ATOM  14855  N    LEU G  81     -42.858 -51.206  30.020  1.00 56.44      A  N
ATOM  14856  CA   LEU G  81     -43.030 -50.185  31.050  1.00 55.87      A  C
ATOM  14857  C    LEU G  81     -42.904 -50.795  32.449  1.00 55.92      A  C
ATOM  14858  O    LEU G  81     -42.081 -50.344  33.261  1.00 55.54      A  O
ATOM  14859  CB   LEU G  81     -44.372 -49.462  30.874  1.00 55.65      A  C
ATOM  14860  CG   LEU G  81     -44.650 -48.218  31.720  1.00 54.88      A  C
ATOM  14861  CD1  LEU G  81     -45.469 -47.213  30.932  1.00 54.70      A  C
ATOM  14862  CD2  LEU G  81     -45.350 -48.581  33.023  1.00 54.78      A  C
ATOM  14863  N    ARG G  82     -43.708 -51.826  32.714  1.00 56.34      A  N
ATOM  14864  CA   ARG G  82     -43.708 -52.493  34.012  1.00 56.79      A  C
ATOM  14865  C    ARG G  82     -42.348 -53.145  34.312  1.00 56.71      A  C
ATOM  14866  O    ARG G  82     -41.929 -53.224  35.472  1.00 56.69      A  O
ATOM  14867  CB   ARG G  82     -44.859 -53.506  34.110  1.00 57.35      A  C
ATOM  14868  CG   ARG G  82     -45.156 -53.973  35.543  1.00 58.28      A  C
ATOM  14869  CD   ARG G  82     -46.499 -54.665  35.664  1.00 59.64      A  C
ATOM  14870  NE   ARG G  82     -47.561 -53.739  36.060  1.00 59.78      A  N
ATOM  14871  CZ   ARG G  82     -48.382 -53.116  35.212  1.00 59.83      A  C
ATOM  14872  NH1  ARG G  82     -48.272 -53.307  33.894  1.00 60.01      A  N
ATOM  14873  NH2  ARG G  82     -49.320 -52.296  35.684  1.00 59.57      A  N
ATOM  14874  N    ARG G  83     -41.666 -53.592  33.258  1.00 56.48      A  N
ATOM  14875  CA   ARG G  83     -40.314 -54.161  33.353  1.00 55.94      A  C
ATOM  14876  C    ARG G  83     -39.275 -53.080  33.718  1.00 55.53      A  C
ATOM  14877  O    ARG G  83     -38.363 -53.331  34.520  1.00 55.67      A  O
ATOM  14878  CB   ARG G  83     -39.986 -54.900  32.041  1.00 54.95      A  C
ATOM  14879  CG   ARG G  83     -38.530 -54.990  31.622  1.00 54.47      A  C
ATOM  14880  CD   ARG G  83     -38.485 -55.262  30.125  1.00 54.57      A  C
ATOM  14881  NE   ARG G  83     -37.147 -55.165  29.564  1.00 54.07      A  N
ATOM  14882  N    VAL G  84     -39.452 -51.881  33.147  1.00 54.73      A  N
ATOM  14883  CA   VAL G  84     -38.577 -50.731  33.390  1.00 53.63      A  C
ATOM  14884  C    VAL G  84     -38.797 -50.156  34.785  1.00 52.98      A  C
ATOM  14885  O    VAL G  84     -37.848 -50.038  35.564  1.00 52.81      A  O
```

FIGURE 1 (cont'd)

```
ATOM  14886  CB   VAL G  84     -38.759 -49.634  32.308  1.00 53.50      A    C
ATOM  14887  CG1  VAL G  84     -38.121 -50.069  31.004  1.00 53.57      A    C
ATOM  14888  CG2  VAL G  84     -38.151 -48.313  32.758  1.00 52.80      A    C
ATOM  14889  N    VAL G  85     -40.047 -49.809  35.097  1.00 52.18      A    N
ATOM  14890  CA   VAL G  85     -40.407 -49.328  36.430  1.00 51.37      A    C
ATOM  14891  C    VAL G  85     -39.927 -50.316  37.488  1.00 51.76      A    C
ATOM  14892  O    VAL G  85     -39.610 -49.930  38.610  1.00 51.94      A    O
ATOM  14893  CB   VAL G  85     -41.924 -49.108  36.573  1.00 49.78      A    C
ATOM  14894  N    GLY G  86     -39.851 -51.587  37.103  1.00 52.08      A    N
ATOM  14895  CA   GLY G  86     -39.365 -52.647  37.975  1.00 52.04      A    C
ATOM  14896  C    GLY G  86     -37.863 -52.631  38.173  1.00 51.65      A    C
ATOM  14897  O    GLY G  86     -37.355 -53.178  39.156  1.00 51.91      A    O
ATOM  14898  N    GLN G  87     -37.150 -52.001  37.247  1.00 50.98      A    N
ATOM  14899  CA   GLN G  87     -35.688 -51.956  37.309  1.00 50.25      A    C
ATOM  14900  C    GLN G  87     -35.130 -50.939  38.316  1.00 49.59      A    C
ATOM  14901  O    GLN G  87     -33.969 -51.033  38.721  1.00 49.53      A    O
ATOM  14902  N    LEU G  88     -35.957 -49.982  38.724  1.00 48.74      A    N
ATOM  14903  CA   LEU G  88     -35.576 -49.055  39.781  1.00 48.04      A    C
ATOM  14904  C    LEU G  88     -35.585 -49.797  41.115  1.00 48.43      A    C
ATOM  14905  O    LEU G  88     -36.572 -50.466  41.437  1.00 48.66      A    O
ATOM  14906  CB   LEU G  88     -36.548 -47.877  39.845  1.00 47.33      A    C
ATOM  14907  CG   LEU G  88     -36.636 -46.907  38.672  1.00 45.95      A    C
ATOM  14908  N    ASP G  89     -34.491 -49.699  41.878  1.00 48.78      A    N
ATOM  14909  CA   ASP G  89     -34.442 -50.250  43.260  1.00 49.16      A    C
ATOM  14910  C    ASP G  89     -34.613 -49.129  44.306  1.00 49.22      A    C
ATOM  14911  O    ASP G  89     -33.697 -48.317  44.510  1.00 49.01      A    O
ATOM  14912  CB   ASP G  89     -33.158 -51.065  43.518  1.00 49.30      A    C
ATOM  14913  CG   ASP G  89     -33.120 -51.681  44.909  1.00 49.45      A    C
ATOM  14914  N    PRO G  90     -35.798 -49.074  44.955  1.00 49.45      A    N
ATOM  14915  CA   PRO G  90     -36.118 -48.007  45.905  1.00 49.35      A    C
ATOM  14916  C    PRO G  90     -35.111 -47.879  47.058  1.00 49.30      A    C
ATOM  14917  O    PRO G  90     -34.732 -46.760  47.408  1.00 49.03      A    O
ATOM  14918  CB   PRO G  90     -37.509 -48.403  46.420  1.00 49.48      A    C
ATOM  14919  CG   PRO G  90     -38.103 -49.199  45.300  1.00 49.74      A    C
ATOM  14920  CD   PRO G  90     -36.940 -49.994  44.772  1.00 49.80      A    C
ATOM  14921  N    GLN G  91     -34.667 -49.003  47.626  1.00 49.50      A    N
ATOM  14922  CA   GLN G  91     -33.698 -48.951  48.728  1.00 49.57      A    C
ATOM  14923  C    GLN G  91     -32.292 -48.563  48.238  1.00 48.99      A    C
ATOM  14924  O    GLN G  91     -31.513 -47.957  48.984  1.00 49.05      A    O
ATOM  14925  CB   GLN G  91     -33.711 -50.244  49.587  1.00 50.19      A    C
ATOM  14926  CG   GLN G  91     -32.931 -51.455  49.050  1.00 50.93      A    C
ATOM  14927  N    ARG G  92     -31.989 -48.892  46.982  1.00 48.15      A    N
ATOM  14928  CA   ARG G  92     -30.737 -48.465  46.346  1.00 47.13      A    C
ATOM  14929  C    ARG G  92     -30.702 -46.930  46.205  1.00 46.70      A    C
ATOM  14930  O    ARG G  92     -29.704 -46.277  46.567  1.00 46.59      A    O
ATOM  14931  CB   ARG G  92     -30.547 -49.169  44.983  1.00 46.97      A    C
ATOM  14932  CG   ARG G  92     -29.405 -48.624  44.094  1.00 45.20      A    C
ATOM  14933  CD   ARG G  92     -29.253 -49.404  42.780  1.00 43.11      A    C
ATOM  14934  NE   ARG G  92     -30.452 -49.368  41.941  1.00 41.75      A    N
ATOM  14935  N    LEU G  93     -31.799 -46.370  45.688  1.00 46.09      A    N
ATOM  14936  CA   LEU G  93     -31.957 -44.927  45.545  1.00 45.47      A    C
ATOM  14937  C    LEU G  93     -31.635 -44.242  46.871  1.00 45.53      A    C
ATOM  14938  O    LEU G  93     -30.793 -43.333  46.939  1.00 45.44      A    O
ATOM  14939  CB   LEU G  93     -33.401 -44.600  45.124  1.00 45.10      A    C
ATOM  14940  CG   LEU G  93     -33.779 -43.360  44.294  1.00 43.92      A    C
ATOM  14941  CD1  LEU G  93     -32.996 -42.096  44.636  1.00 42.75      A    C
ATOM  14942  N    TRP G  94     -32.292 -44.722  47.922  1.00 45.68      A    N
ATOM  14943  CA   TRP G  94     -32.251 -44.091  49.229  1.00 45.75      A    C
ATOM  14944  C    TRP G  94     -30.927 -44.301  49.959  1.00 45.73      A    C
ATOM  14945  O    TRP G  94     -30.422 -43.389  50.621  1.00 45.61      A    O
ATOM  14946  CB   TRP G  94     -33.415 -44.593  50.093  1.00 45.95      A    C
ATOM  14947  CG   TRP G  94     -33.803 -43.602  51.126  1.00 46.41      A    C
ATOM  14948  CD1  TRP G  94     -33.266 -43.465  52.368  1.00 47.11      A    C
ATOM  14949  CD2  TRP G  94     -34.786 -42.572  50.997  1.00 46.46      A    C
ATOM  14950  CE2  TRP G  94     -34.794 -41.851  52.211  1.00 46.70      A    C
```

FIGURE 1 (cont'd)

```
ATOM  14951  CE3  TRP G  94     -35.670 -42.190  49.974  1.00 46.26      A    C
ATOM  14952  NE1  TRP G  94     -33.857 -42.421  53.031  1.00 47.05      A    N
ATOM  14953  CZ2  TRP G  94     -35.654 -40.765  52.436  1.00 46.63      A    C
ATOM  14954  CZ3  TRP G  94     -36.526 -41.106  50.196  1.00 46.17      A    C
ATOM  14955  CH2  TRP G  94     -36.510 -40.407  51.419  1.00 46.33      A    C
ATOM  14956  N    SER G  95     -30.365 -45.497  49.819  1.00 45.76      A    N
ATOM  14957  CA   SER G  95     -29.235 -45.915  50.639  1.00 45.77      A    C
ATOM  14958  C    SER G  95     -27.869 -45.771  49.967  1.00 45.19      A    C
ATOM  14959  O    SER G  95     -26.927 -45.255  50.578  1.00 45.14      A    O
ATOM  14960  CB   SER G  95     -29.435 -47.356  51.105  1.00 46.26      A    C
ATOM  14961  OG   SER G  95     -29.095 -47.479  52.470  1.00 47.24      A    O
ATOM  14962  N    THR G  96     -27.769 -46.236  48.722  1.00 44.48      A    N
ATOM  14963  CA   THR G  96     -26.515 -46.176  47.957  1.00 43.82      A    C
ATOM  14964  C    THR G  96     -26.222 -44.791  47.389  1.00 42.90      A    C
ATOM  14965  O    THR G  96     -25.049 -44.401  47.262  1.00 42.98      A    O
ATOM  14966  CB   THR G  96     -26.498 -47.184  46.785  1.00 44.00      A    C
ATOM  14967  OG1  THR G  96     -27.212 -48.369  47.157  1.00 44.73      A    O
ATOM  14968  N    TYR G  97     -27.287 -44.058  47.052  1.00 41.62      A    N
ATOM  14969  CA   TYR G  97     -27.157 -42.776  46.352  1.00 40.26      A    C
ATOM  14970  C    TYR G  97     -27.535 -41.536  47.167  1.00 39.84      A    C
ATOM  14971  O    TYR G  97     -26.804 -40.537  47.148  1.00 39.59      A    O
ATOM  14972  CB   TYR G  97     -27.914 -42.817  45.013  1.00 39.70      A    C
ATOM  14973  CG   TYR G  97     -27.474 -43.948  44.097  1.00 38.73      A    C
ATOM  14974  CD1  TYR G  97     -26.126 -44.142  43.796  1.00 37.65      A    C
ATOM  14975  CE1  TYR G  97     -25.717 -45.170  42.972  1.00 37.48      A    C
ATOM  14976  N    LEU G  98     -28.660 -41.598  47.879  1.00 39.60      A    N
ATOM  14977  CA   LEU G  98     -29.149 -40.425  48.595  1.00 39.45      A    C
ATOM  14978  C    LEU G  98     -28.392 -40.143  49.886  1.00 39.69      A    C
ATOM  14979  O    LEU G  98     -27.854 -39.039  50.064  1.00 39.58      A    O
ATOM  14980  CB   LEU G  98     -30.659 -40.498  48.860  1.00 39.26      A    C
ATOM  14981  CG   LEU G  98     -31.227 -39.290  49.633  1.00 39.02      A    C
ATOM  14982  CD1  LEU G  98     -31.074 -37.973  48.868  1.00 38.42      A    C
ATOM  14983  CD2  LEU G  98     -32.676 -39.501  50.021  1.00 39.17      A    C
ATOM  14984  N    ARG G  99     -28.368 -41.136  50.781  1.00 40.03      A    N
ATOM  14985  CA   ARG G  99     -27.719 -40.987  52.103  1.00 40.13      A    C
ATOM  14986  C    ARG G  99     -26.245 -40.543  52.057  1.00 40.26      A    C
ATOM  14987  O    ARG G  99     -25.861 -39.641  52.817  1.00 40.40      A    O
ATOM  14988  CB   ARG G  99     -27.921 -42.219  53.008  1.00 39.54      A    C
ATOM  14989  CG   ARG G  99     -28.892 -41.951  54.150  1.00 39.41      A    C
ATOM  14990  CD   ARG G  99     -29.003 -43.118  55.112  1.00 39.91      A    C
ATOM  14991  NE   ARG G  99     -30.287 -43.807  54.985  1.00 39.63      A    N
ATOM  14992  N    PRO G 100     -25.426 -41.137  51.152  1.00 40.26      A    N
ATOM  14993  CA   PRO G 100     -24.053 -40.625  51.006  1.00 40.17      A    C
ATOM  14994  C    PRO G 100     -23.993 -39.118  50.716  1.00 39.77      A    C
ATOM  14995  O    PRO G 100     -23.062 -38.443  51.169  1.00 39.95      A    O
ATOM  14996  CB   PRO G 100     -23.496 -41.434  49.822  1.00 40.26      A    C
ATOM  14997  CG   PRO G 100     -24.256 -42.708  49.852  1.00 40.48      A    C
ATOM  14998  CD   PRO G 100     -25.649 -42.326  50.302  1.00 40.36      A    C
ATOM  14999  N    LEU G 101     -24.998 -38.611  49.996  1.00 39.16      A    N
ATOM  15000  CA   LEU G 101     -25.056 -37.210  49.561  1.00 38.53      A    C
ATOM  15001  C    LEU G 101     -25.425 -36.227  50.671  1.00 38.46      A    C
ATOM  15002  O    LEU G 101     -25.163 -35.028  50.554  1.00 38.30      A    O
ATOM  15003  CB   LEU G 101     -26.031 -37.069  48.386  1.00 38.11      A    C
ATOM  15004  CG   LEU G 101     -25.483 -37.015  46.957  1.00 37.76      A    C
ATOM  15005  CD1  LEU G 101     -24.309 -37.930  46.719  1.00 38.19      A    C
ATOM  15006  CD2  LEU G 101     -26.595 -37.312  45.969  1.00 37.49      A    C
ATOM  15007  N    LEU G 102     -26.007 -36.741  51.748  1.00 38.51      A    N
ATOM  15008  CA   LEU G 102     -26.579 -35.894  52.782  1.00 38.59      A    C
ATOM  15009  C    LEU G 102     -25.583 -35.393  53.830  1.00 38.93      A    C
ATOM  15010  O    LEU G 102     -25.772 -35.590  55.032  1.00 39.19      A    O
ATOM  15011  CB   LEU G 102     -27.765 -36.599  53.438  1.00 38.54      A    C
ATOM  15012  CG   LEU G 102     -29.011 -36.797  52.571  1.00 38.07      A    C
ATOM  15013  CD1  LEU G 102     -29.999 -37.675  53.304  1.00 38.26      A    C
ATOM  15014  CD2  LEU G 102     -29.664 -35.463  52.185  1.00 37.54      A    C
ATOM  15015  N    VAL G 103     -24.533 -34.726  53.362  1.00 39.10      A    N
```

FIGURE 1 (cont'd)

```
ATOM  15016  CA   VAL G 103     -23.522 -34.123  54.247  1.00 39.41      A  C
ATOM  15017  C    VAL G 103     -23.313 -32.659  53.894  1.00 39.11      A  C
ATOM  15018  O    VAL G 103     -23.605 -32.261  52.770  1.00 38.86      A  O
ATOM  15019  CB   VAL G 103     -22.153 -34.860  54.171  1.00 39.75      A  C
ATOM  15020  CG1  VAL G 103     -21.698 -35.036  52.718  1.00 39.59      A  C
ATOM  15021  CG2  VAL G 103     -22.212 -36.215  54.909  1.00 40.66      A  C
ATOM  15022  N    VAL G 104     -22.821 -31.862  54.845  1.00 39.03      A  N
ATOM  15023  CA   VAL G 104     -22.450 -30.468  54.564  1.00 38.73      A  C
ATOM  15024  C    VAL G 104     -21.403 -30.468  53.461  1.00 38.95      A  C
ATOM  15025  O    VAL G 104     -20.423 -31.221  53.533  1.00 39.25      A  O
ATOM  15026  CB   VAL G 104     -21.886 -29.741  55.793  1.00 38.07      A  C
ATOM  15027  CG1  VAL G 104     -22.152 -28.249  55.681  1.00 37.48      A  C
ATOM  15028  N    ARG G 105     -21.631 -29.645  52.436  1.00 38.80      A  N
ATOM  15029  CA   ARG G 105     -20.876 -29.733  51.176  1.00 38.53      A  C
ATOM  15030  C    ARG G 105     -20.790 -28.401  50.424  1.00 38.51      A  C
ATOM  15031  O    ARG G 105     -20.714 -28.375  49.190  1.00 38.25      A  O
ATOM  15032  CB   ARG G 105     -21.442 -30.843  50.271  1.00 38.33      A  C
ATOM  15033  CG   ARG G 105     -22.873 -30.616  49.819  1.00 37.69      A  C
ATOM  15034  CD   ARG G 105     -23.552 -31.906  49.406  1.00 37.37      A  C
ATOM  15035  NE   ARG G 105     -24.839 -31.626  48.766  1.00 37.04      A  N
ATOM  15036  CZ   ARG G 105     -26.023 -31.674  49.373  1.00 36.83      A  C
ATOM  15037  NH1  ARG G 105     -26.101 -32.011  50.658  1.00 36.96      A  N
ATOM  15038  NH2  ARG G 105     -27.132 -31.395  48.688  1.00 36.43      A  N
ATOM  15039  N    THR G 106     -20.783 -27.305  51.181  1.00 38.73      A  N
ATOM  15040  CA   THR G 106     -20.564 -25.970  50.630  1.00 38.94      A  C
ATOM  15041  C    THR G 106     -19.288 -25.930  49.776  1.00 39.00      A  C
ATOM  15042  O    THR G 106     -18.322 -26.622  50.085  1.00 39.00      A  O
ATOM  15043  CB   THR G 106     -20.462 -24.932  51.748  1.00 39.12      A  C
ATOM  15044  OG1  THR G 106     -19.314 -25.227  52.548  1.00 39.79      A  O
ATOM  15045  N    PRO G 107     -19.292 -25.123  48.691  1.00 39.14      A  N
ATOM  15046  CA   PRO G 107     -18.186 -25.084  47.714  1.00 39.43      A  C
ATOM  15047  C    PRO G 107     -16.788 -25.142  48.338  1.00 39.97      A  C
ATOM  15048  O    PRO G 107     -16.527 -24.465  49.350  1.00 40.13      A  O
ATOM  15049  CB   PRO G 107     -18.404 -23.740  46.996  1.00 39.32      A  C
ATOM  15050  CG   PRO G 107     -19.893 -23.535  47.036  1.00 38.90      A  C
ATOM  15051  CD   PRO G 107     -20.389 -24.199  48.310  1.00 39.01      A  C
ATOM  15052  N    GLY G 108     -15.920 -25.962  47.738  1.00 40.37      A  N
ATOM  15053  CA   GLY G 108     -14.521 -26.084  48.157  1.00 41.01      A  C
ATOM  15054  C    GLY G 108     -14.262 -26.543  49.589  1.00 41.38      A  C
ATOM  15055  O    GLY G 108     -13.190 -26.297  50.142  1.00 41.87      A  O
ATOM  15056  N    SER G 109     -15.243 -27.199  50.198  1.00 41.36      A  N
ATOM  15057  CA   SER G 109     -15.070 -27.768  51.525  1.00 41.38      A  C
ATOM  15058  C    SER G 109     -14.670 -29.224  51.362  1.00 41.59      A  C
ATOM  15059  O    SER G 109     -14.625 -29.725  50.228  1.00 41.35      A  O
ATOM  15060  CB   SER G 109     -16.366 -27.675  52.310  1.00 41.24      A  C
ATOM  15061  OG   SER G 109     -17.332 -28.531  51.742  1.00 40.63      A  O
ATOM  15062  N    PRO G 110     -14.347 -29.903  52.485  1.00 41.96      A  N
ATOM  15063  CA   PRO G 110     -14.063 -31.345  52.419  1.00 41.89      A  C
ATOM  15064  C    PRO G 110     -15.274 -32.148  51.942  1.00 41.32      A  C
ATOM  15065  O    PRO G 110     -15.113 -33.119  51.200  1.00 41.11      A  O
ATOM  15066  CB   PRO G 110     -13.704 -31.702  53.867  1.00 42.33      A  C
ATOM  15067  CG   PRO G 110     -13.173 -30.428  54.441  1.00 42.77      A  C
ATOM  15068  CD   PRO G 110     -13.983 -29.333  53.801  1.00 42.32      A  C
ATOM  15069  N    GLY G 111     -16.470 -31.728  52.359  1.00 40.86      A  N
ATOM  15070  CA   GLY G 111     -17.719 -32.394  51.967  1.00 40.19      A  C
ATOM  15071  C    GLY G 111     -18.013 -32.249  50.486  1.00 39.62      A  C
ATOM  15072  O    GLY G 111     -18.402 -33.217  49.829  1.00 39.42      A  O
ATOM  15073  N    ASN G 112     -17.824 -31.033  49.967  1.00 39.19      A  N
ATOM  15074  CA   ASN G 112     -17.955 -30.751  48.537  1.00 38.61      A  C
ATOM  15075  C    ASN G 112     -17.071 -31.685  47.718  1.00 38.84      A  C
ATOM  15076  O    ASN G 112     -17.524 -32.258  46.731  1.00 38.64      A  O
ATOM  15077  CB   ASN G 112     -17.611 -29.288  48.245  1.00 38.30      A  C
ATOM  15078  CG   ASN G 112     -17.792 -28.925  46.790  1.00 37.17      A  C
ATOM  15079  N    LEU G 113     -15.820 -31.853  48.150  1.00 39.32      A  N
ATOM  15080  CA   LEU G 113     -14.879 -32.760  47.487  1.00 39.78      A  C
```

FIGURE 1 (cont'd)

```
ATOM  15081  C    LEU G 113     -15.214 -34.242  47.722  1.00 39.82      A  C
ATOM  15082  O    LEU G 113     -15.078 -35.055  46.800  1.00 39.76      A  O
ATOM  15083  CB   LEU G 113     -13.437 -32.451  47.902  1.00 40.18      A  C
ATOM  15084  CG   LEU G 113     -12.312 -32.915  46.964  1.00 40.90      A  C
ATOM  15085  CD1  LEU G 113     -11.162 -31.902  46.961  1.00 41.48      A  C
ATOM  15086  CD2  LEU G 113     -11.794 -34.312  47.301  1.00 41.76      A  C
ATOM  15087  N    GLN G 114     -15.646 -34.587  48.941  1.00 39.92      A  N
ATOM  15088  CA   GLN G 114     -16.064 -35.965  49.266  1.00 39.92      A  C
ATOM  15089  C    GLN G 114     -17.222 -36.420  48.360  1.00 39.65      A  C
ATOM  15090  O    GLN G 114     -17.174 -37.517  47.791  1.00 39.69      A  O
ATOM  15091  CB   GLN G 114     -16.440 -36.104  50.752  1.00 40.07      A  C
ATOM  15092  N    VAL G 115     -18.240 -35.559  48.220  1.00 39.07      A  N
ATOM  15093  CA   VAL G 115     -19.404 -35.837  47.375  1.00 38.37      A  C
ATOM  15094  C    VAL G 115     -18.978 -35.935  45.914  1.00 38.65      A  C
ATOM  15095  O    VAL G 115     -19.280 -36.931  45.262  1.00 38.82      A  O
ATOM  15096  CB   VAL G 115     -20.530 -34.788  47.550  1.00 36.88      A  C
ATOM  15097  N    ARG G 116     -18.257 -34.918  45.426  1.00 38.87      A  N
ATOM  15098  CA   ARG G 116     -17.711 -34.888  44.054  1.00 39.09      A  C
ATOM  15099  C    ARG G 116     -17.023 -36.203  43.678  1.00 39.52      A  C
ATOM  15100  O    ARG G 116     -17.242 -36.760  42.591  1.00 39.46      A  O
ATOM  15101  CB   ARG G 116     -16.724 -33.718  43.896  1.00 38.98      A  C
ATOM  15102  CG   ARG G 116     -16.007 -33.632  42.539  1.00 39.19      A  C
ATOM  15103  CD   ARG G 116     -14.958 -32.538  42.550  1.00 40.24      A  C
ATOM  15104  NE   ARG G 116     -15.527 -31.246  42.952  1.00 40.89      A  N
ATOM  15105  CZ   ARG G 116     -14.819 -30.195  43.367  1.00 41.48      A  C
ATOM  15106  NH1  ARG G 116     -13.493 -30.270  43.439  1.00 41.98      A  N
ATOM  15107  NH2  ARG G 116     -15.432 -29.064  43.712  1.00 41.60      A  N
ATOM  15108  N    LYS G 117     -16.196 -36.688  44.598  1.00 40.08      A  N
ATOM  15109  CA   LYS G 117     -15.452 -37.922  44.411  1.00 40.56      A  C
ATOM  15110  C    LYS G 117     -16.405 -39.115  44.315  1.00 40.21      A  C
ATOM  15111  O    LYS G 117     -16.181 -40.028  43.509  1.00 40.28      A  O
ATOM  15112  CB   LYS G 117     -14.452 -38.106  45.564  1.00 41.17      A  C
ATOM  15113  CG   LYS G 117     -13.277 -39.059  45.265  1.00 42.55      A  C
ATOM  15114  CD   LYS G 117     -12.188 -39.020  46.361  1.00 43.87      A  C
ATOM  15115  CE   LYS G 117     -11.117 -37.946  46.097  1.00 44.08      A  C
ATOM  15116  N    PHE G 118     -17.464 -39.093  45.132  1.00 39.59      A  N
ATOM  15117  CA   PHE G 118     -18.476 -40.161  45.132  1.00 38.96      A  C
ATOM  15118  C    PHE G 118     -19.247 -40.211  43.807  1.00 39.20      A  C
ATOM  15119  O    PHE G 118     -19.540 -41.291  43.271  1.00 39.37      A  O
ATOM  15120  CB   PHE G 118     -19.446 -40.011  46.319  1.00 37.67      A  C
ATOM  15121  CG   PHE G 118     -20.602 -40.998  46.297  1.00 36.16      A  C
ATOM  15122  CD1  PHE G 118     -20.357 -42.382  46.310  1.00 35.87      A  C
ATOM  15123  CD2  PHE G 118     -21.918 -40.528  46.266  1.00 34.61      A  C
ATOM  15124  CE1  PHE G 118     -21.391 -43.328  46.290  1.00 35.49      A  C
ATOM  15125  CE2  PHE G 118     -23.031 -41.385  46.238  1.00 33.89      A  C
ATOM  15126  N    LEU G 119     -19.570 -39.032  43.289  1.00 39.20      A  N
ATOM  15127  CA   LEU G 119     -20.265 -38.934  42.031  1.00 39.18      A  C
ATOM  15128  C    LEU G 119     -19.385 -39.506  40.926  1.00 39.70      A  C
ATOM  15129  O    LEU G 119     -19.793 -40.453  40.249  1.00 39.84      A  O
ATOM  15130  CB   LEU G 119     -20.695 -37.493  41.764  1.00 38.74      A  C
ATOM  15131  CG   LEU G 119     -21.964 -37.094  42.529  1.00 37.92      A  C
ATOM  15132  CD1  LEU G 119     -22.127 -35.590  42.566  1.00 37.42      A  C
ATOM  15133  N    GLU G 120     -18.171 -38.967  40.780  1.00 40.19      A  N
ATOM  15134  CA   GLU G 120     -17.189 -39.482  39.807  1.00 40.63      A  C
ATOM  15135  C    GLU G 120     -17.141 -41.009  39.787  1.00 41.31      A  C
ATOM  15136  O    GLU G 120     -17.278 -41.625  38.731  1.00 41.57      A  O
ATOM  15137  CB   GLU G 120     -15.781 -38.943  40.104  1.00 39.87      A  C
ATOM  15138  CG   GLU G 120     -15.543 -37.488  39.702  1.00 39.56      A  C
ATOM  15139  CD   GLU G 120     -14.077 -37.077  39.809  1.00 40.11      A  C
ATOM  15140  OE1  GLU G 120     -13.243 -37.591  39.030  1.00 40.84      A  O
ATOM  15141  N    ALA G 121     -16.966 -41.597  40.969  1.00 41.83      A  N
ATOM  15142  CA   ALA G 121     -16.804 -43.029  41.122  1.00 42.21      A  C
ATOM  15143  C    ALA G 121     -18.036 -43.816  40.694  1.00 42.16      A  C
ATOM  15144  O    ALA G 121     -17.920 -44.775  39.916  1.00 42.47      A  O
ATOM  15145  CB   ALA G 121     -16.459 -43.340  42.528  1.00 42.54      A  C
```

FIGURE 1 (cont'd)

```
ATOM  15146  N    THR G 122     -19.205 -43.409  41.200  1.00 41.59      A  N
ATOM  15147  CA   THR G 122     -20.479 -44.070  40.867  1.00 40.92      A  C
ATOM  15148  C    THR G 122     -20.716 -44.095  39.360  1.00 41.33      A  C
ATOM  15149  O    THR G 122     -21.022 -45.143  38.783  1.00 41.69      A  O
ATOM  15150  CB   THR G 122     -21.675 -43.398  41.555  1.00 39.44      A  C
ATOM  15151  OG1  THR G 122     -21.635 -43.694  42.952  1.00 38.57      A  O
ATOM  15152  N    LEU G 123     -20.546 -42.934  38.732  1.00 41.45      A  N
ATOM  15153  CA   LEU G 123     -20.743 -42.775  37.292  1.00 41.50      A  C
ATOM  15154  C    LEU G 123     -19.798 -43.657  36.488  1.00 42.15      A  C
ATOM  15155  O    LEU G 123     -20.217 -44.281  35.516  1.00 42.37      A  O
ATOM  15156  CB   LEU G 123     -20.581 -41.305  36.884  1.00 41.04      A  C
ATOM  15157  CG   LEU G 123     -21.645 -40.299  37.346  1.00 39.82      A  C
ATOM  15158  CD1  LEU G 123     -22.850 -40.336  36.426  1.00 39.20      A  C
ATOM  15159  N    ARG G 124     -18.533 -43.710  36.904  1.00 42.75      A  N
ATOM  15160  CA   ARG G 124     -17.521 -44.528  36.231  1.00 43.43      A  C
ATOM  15161  C    ARG G 124     -17.783 -46.028  36.369  1.00 44.08      A  C
ATOM  15162  O    ARG G 124     -17.555 -46.794  35.432  1.00 44.43      A  O
ATOM  15163  CB   ARG G 124     -16.115 -44.181  36.727  1.00 43.40      A  C
ATOM  15164  CG   ARG G 124     -15.530 -42.949  36.066  1.00 42.81      A  C
ATOM  15165  CD   ARG G 124     -14.103 -42.684  36.508  1.00 42.38      A  C
ATOM  15166  NE   ARG G 124     -13.594 -41.444  35.927  1.00 41.59      A  N
ATOM  15167  N    SER G 125     -18.284 -46.435  37.530  1.00 44.58      A  N
ATOM  15168  CA   SER G 125     -18.531 -47.848  37.819  1.00 45.14      A  C
ATOM  15169  C    SER G 125     -19.775 -48.452  37.125  1.00 45.27      A  C
ATOM  15170  O    SER G 125     -20.235 -49.538  37.499  1.00 45.56      A  O
ATOM  15171  CB   SER G 125     -18.637 -48.039  39.334  1.00 45.30      A  C
ATOM  15172  OG   SER G 125     -19.836 -47.464  39.829  1.00 44.98      A  O
ATOM  15173  N    LEU G 126     -20.316 -47.761  36.123  1.00 45.14      A  N
ATOM  15174  CA   LEU G 126     -21.496 -48.257  35.408  1.00 45.12      A  C
ATOM  15175  C    LEU G 126     -21.120 -49.103  34.195  1.00 45.65      A  C
ATOM  15176  O    LEU G 126     -20.081 -48.870  33.578  1.00 45.92      A  O
ATOM  15177  CB   LEU G 126     -22.414 -47.102  35.006  1.00 44.60      A  C
ATOM  15178  CG   LEU G 126     -23.085 -46.287  36.119  1.00 43.78      A  C
ATOM  15179  CD1  LEU G 126     -24.264 -45.515  35.557  1.00 42.95      A  C
ATOM  15180  CD2  LEU G 126     -23.551 -47.168  37.255  1.00 43.54      A  C
ATOM  15181  N    THR G 127     -21.966 -50.076  33.860  1.00 46.13      A  N
ATOM  15182  CA   THR G 127     -21.673 -51.048  32.791  1.00 46.65      A  C
ATOM  15183  C    THR G 127     -21.488 -50.427  31.396  1.00 46.73      A  C
ATOM  15184  O    THR G 127     -20.541 -50.786  30.678  1.00 47.19      A  O
ATOM  15185  CB   THR G 127     -22.731 -52.156  32.709  1.00 46.86      A  C
ATOM  15186  OG1  THR G 127     -23.209 -52.448  34.022  1.00 47.07      A  O
ATOM  15187  N    ALA G 128     -22.390 -49.519  31.009  1.00 46.35      A  N
ATOM  15188  CA   ALA G 128     -22.175 -48.680  29.828  1.00 46.10      A  C
ATOM  15189  C    ALA G 128     -20.958 -47.779  30.098  1.00 46.01      A  C
ATOM  15190  O    ALA G 128     -20.758 -47.314  31.226  1.00 45.97      A  O
ATOM  15191  CB   ALA G 128     -23.415 -47.851  29.536  1.00 45.79      A  C
ATOM  15192  N    GLY G 129     -20.130 -47.552  29.085  1.00 45.96      A  N
ATOM  15193  CA   GLY G 129     -18.886 -46.816  29.302  1.00 45.73      A  C
ATOM  15194  C    GLY G 129     -19.049 -45.313  29.454  1.00 45.17      A  C
ATOM  15195  O    GLY G 129     -18.756 -44.571  28.519  1.00 45.56      A  O
ATOM  15196  N    TRP G 130     -19.500 -44.853  30.622  1.00 44.26      A  N
ATOM  15197  CA   TRP G 130     -19.742 -43.422  30.829  1.00 43.28      A  C
ATOM  15198  C    TRP G 130     -18.438 -42.633  30.771  1.00 42.97      A  C
ATOM  15199  O    TRP G 130     -17.475 -42.976  31.439  1.00 43.13      A  O
ATOM  15200  CB   TRP G 130     -20.469 -43.151  32.158  1.00 42.94      A  C
ATOM  15201  CG   TRP G 130     -21.969 -43.350  32.123  1.00 42.41      A  C
ATOM  15202  CD1  TRP G 130     -22.647 -44.506  32.397  1.00 42.63      A  C
ATOM  15203  CD2  TRP G 130     -22.966 -42.366  31.819  1.00 41.98      A  C
ATOM  15204  CE2  TRP G 130     -24.231 -43.009  31.917  1.00 41.87      A  C
ATOM  15205  CE3  TRP G 130     -22.921 -41.008  31.463  1.00 41.74      A  C
ATOM  15206  NE1  TRP G 130     -24.003 -44.313  32.271  1.00 42.22      A  N
ATOM  15207  CZ2  TRP G 130     -25.448 -42.333  31.670  1.00 41.38      A  C
ATOM  15208  CZ3  TRP G 130     -24.135 -40.335  31.216  1.00 41.36      A  C
ATOM  15209  CH2  TRP G 130     -25.378 -41.004  31.322  1.00 41.12      A  C
ATOM  15210  N    HIS G 131     -18.422 -41.586  29.954  1.00 42.55      A  N
```

FIGURE 1 (cont'd)

```
ATOM  15211  CA   HIS G 131     -17.283 -40.690  29.851  1.00 42.35      A  C
ATOM  15212  C    HIS G 131     -17.417 -39.597  30.916  1.00 41.92      A  C
ATOM  15213  O    HIS G 131     -17.895 -38.488  30.638  1.00 41.69      A  O
ATOM  15214  CB   HIS G 131     -17.223 -40.099  28.439  1.00 42.52      A  C
ATOM  15215  CG   HIS G 131     -15.919 -39.456  28.095  1.00 42.99      A  C
ATOM  15216  CD2  HIS G 131     -15.270 -38.404  28.652  1.00 44.49      A  C
ATOM  15217  ND1  HIS G 131     -15.136 -39.877  27.042  1.00 44.01      A  N
ATOM  15218  CE1  HIS G 131     -14.051 -39.123  26.975  1.00 45.15      A  C
ATOM  15219  NE2  HIS G 131     -14.108 -38.223  27.941  1.00 45.12      A  N
ATOM  15220  N    VAL G 132     -17.005 -39.938  32.136  1.00 41.66      A  N
ATOM  15221  CA   VAL G 132     -17.052 -39.029  33.274  1.00 41.31      A  C
ATOM  15222  C    VAL G 132     -15.872 -38.056  33.219  1.00 41.34      A  C
ATOM  15223  O    VAL G 132     -14.758 -38.457  32.895  1.00 41.63      A  O
ATOM  15224  CB   VAL G 132     -17.040 -39.816  34.597  1.00 41.28      A  C
ATOM  15225  CG1  VAL G 132     -17.897 -39.123  35.642  1.00 41.02      A  C
ATOM  15226  N    GLU G 133     -16.116 -36.785  33.537  1.00 41.20      A  N
ATOM  15227  CA   GLU G 133     -15.126 -35.734  33.311  1.00 41.41      A  C
ATOM  15228  C    GLU G 133     -15.330 -34.537  34.234  1.00 41.14      A  C
ATOM  15229  O    GLU G 133     -16.414 -33.952  34.262  1.00 41.01      A  O
ATOM  15230  CB   GLU G 133     -15.202 -35.286  31.854  1.00 41.63      A  C
ATOM  15231  CG   GLU G 133     -14.156 -34.293  31.435  1.00 42.97      A  C
ATOM  15232  CD   GLU G 133     -14.360 -33.833  30.011  1.00 44.70      A  C
ATOM  15233  OE1  GLU G 133     -14.445 -34.689  29.107  1.00 45.48      A  O
ATOM  15234  OE2  GLU G 133     -14.448 -32.609  29.792  1.00 45.20      A  O
ATOM  15235  N    LEU G 134     -14.283 -34.174  34.975  1.00 41.06      A  N
ATOM  15236  CA   LEU G 134     -14.328 -33.034  35.902  1.00 40.74      A  C
ATOM  15237  C    LEU G 134     -14.090 -31.719  35.196  1.00 40.50      A  C
ATOM  15238  O    LEU G 134     -13.366 -31.670  34.197  1.00 40.68      A  O
ATOM  15239  CB   LEU G 134     -13.277 -33.180  36.995  1.00 40.94      A  C
ATOM  15240  CG   LEU G 134     -13.684 -33.831  38.318  1.00 41.10      A  C
ATOM  15241  CD1  LEU G 134     -12.448 -34.100  39.188  1.00 41.93      A  C
ATOM  15242  N    ASP G 135     -14.698 -30.659  35.727  1.00 40.04      A  N
ATOM  15243  CA   ASP G 135     -14.485 -29.295  35.236  1.00 39.85      A  C
ATOM  15244  C    ASP G 135     -14.019 -28.405  36.389  1.00 39.79      A  C
ATOM  15245  O    ASP G 135     -14.811 -27.644  36.959  1.00 39.74      A  O
ATOM  15246  CB   ASP G 135     -15.746 -28.720  34.565  1.00 39.61      A  C
ATOM  15247  CG   ASP G 135     -15.570 -27.264  34.116  1.00 39.85      A  C
ATOM  15248  OD1  ASP G 135     -14.483 -26.924  33.604  1.00 40.62      A  O
ATOM  15249  OD2  ASP G 135     -16.514 -26.452  34.276  1.00 39.57      A  O
ATOM  15250  N    PRO G 136     -12.725 -28.500  36.744  1.00 39.80      A  N
ATOM  15251  CA   PRO G 136     -12.236 -27.694  37.855  1.00 40.04      A  C
ATOM  15252  C    PRO G 136     -12.024 -26.260  37.415  1.00 40.62      A  C
ATOM  15253  O    PRO G 136     -11.761 -26.019  36.240  1.00 40.87      A  O
ATOM  15254  CB   PRO G 136     -10.884 -28.336  38.191  1.00 39.30      A  C
ATOM  15255  CG   PRO G 136     -10.686 -29.476  37.195  1.00 38.95      A  C
ATOM  15256  CD   PRO G 136     -11.638 -29.249  36.090  1.00 39.70      A  C
ATOM  15257  N    PHE G 137     -12.149 -25.324  38.347  1.00 41.08      A  N
ATOM  15258  CA   PHE G 137     -11.813 -23.924  38.091  1.00 41.59      A  C
ATOM  15259  C    PHE G 137     -11.840 -23.094  39.361  1.00 42.05      A  C
ATOM  15260  O    PHE G 137     -12.529 -23.434  40.315  1.00 42.05      A  O
ATOM  15261  CB   PHE G 137     -12.743 -23.307  37.033  1.00 41.45      A  C
ATOM  15262  CG   PHE G 137     -14.173 -23.100  37.490  1.00 41.11      A  C
ATOM  15263  CD1  PHE G 137     -15.089 -24.151  37.461  1.00 40.78      A  C
ATOM  15264  CD2  PHE G 137     -14.614 -21.839  37.910  1.00 40.99      A  C
ATOM  15265  CE1  PHE G 137     -16.413 -23.952  37.868  1.00 40.24      A  C
ATOM  15266  CE2  PHE G 137     -15.932 -21.637  38.318  1.00 40.52      A  C
ATOM  15267  CZ   PHE G 137     -16.832 -22.694  38.295  1.00 40.15      A  C
ATOM  15268  N    THR G 138     -11.087 -22.004  39.374  1.00 42.77      A  N
ATOM  15269  CA   THR G 138     -11.166 -21.040  40.471  1.00 43.38      A  C
ATOM  15270  C    THR G 138     -11.989 -19.813  40.064  1.00 43.47      A  C
ATOM  15271  O    THR G 138     -11.956 -19.395  38.901  1.00 43.63      A  O
ATOM  15272  CB   THR G 138      -9.778 -20.599  40.923  1.00 43.77      A  C
ATOM  15273  OG1  THR G 138      -9.469 -21.246  42.159  1.00 44.27      A  O
ATOM  15274  N    ALA G 139     -12.729 -19.238  41.011  1.00 43.48      A  N
ATOM  15275  CA   ALA G 139     -13.603 -18.108  40.703  1.00 43.57      A  C
```

FIGURE 1 (cont'd)

```
ATOM  15276  C    ALA G 139     -13.706 -17.068  41.814  1.00 43.91      A  C
ATOM  15277  O    ALA G 139     -13.637 -17.377  43.000  1.00 43.96      A  O
ATOM  15278  CB   ALA G 139     -14.987 -18.601  40.298  1.00 43.19      A  C
ATOM  15279  N    SER G 140     -13.886 -15.826  41.395  1.00 44.34      A  N
ATOM  15280  CA   SER G 140     -13.958 -14.687  42.290  1.00 44.77      A  C
ATOM  15281  C    SER G 140     -15.347 -14.553  42.929  1.00 44.48      A  C
ATOM  15282  O    SER G 140     -16.333 -14.289  42.237  1.00 44.35      A  O
ATOM  15283  CB   SER G 140     -13.589 -13.419  41.506  1.00 45.21      A  C
ATOM  15284  OG   SER G 140     -14.023 -12.240  42.167  1.00 46.10      A  O
ATOM  15285  N    THR G 141     -15.421 -14.737  44.246  1.00 44.29      A  N
ATOM  15286  CA   THR G 141     -16.692 -14.614  44.988  1.00 44.05      A  C
ATOM  15287  C    THR G 141     -16.608 -13.488  46.029  1.00 44.34      A  C
ATOM  15288  O    THR G 141     -15.515 -12.992  46.308  1.00 44.82      A  O
ATOM  15289  CB   THR G 141     -17.108 -15.956  45.678  1.00 43.71      A  C
ATOM  15290  CG2  THR G 141     -16.996 -17.132  44.715  1.00 43.39      A  C
ATOM  15291  OG1  THR G 141     -16.282 -16.206  46.821  1.00 43.73      A  O
ATOM  15292  N    PRO G 142     -17.755 -13.072  46.600  1.00 44.31      A  N
ATOM  15293  CA   PRO G 142     -17.730 -12.090  47.702  1.00 44.49      A  C
ATOM  15294  C    PRO G 142     -17.013 -12.590  48.966  1.00 44.69      A  C
ATOM  15295  O    PRO G 142     -16.832 -11.826  49.909  1.00 45.11      A  O
ATOM  15296  CB   PRO G 142     -19.213 -11.849  47.993  1.00 44.40      A  C
ATOM  15297  CG   PRO G 142     -19.902 -12.168  46.702  1.00 44.13      A  C
ATOM  15298  CD   PRO G 142     -19.127 -13.318  46.117  1.00 44.00      A  C
ATOM  15299  N    LEU G 143     -16.624 -13.865  48.979  1.00 44.52      A  N
ATOM  15300  CA   LEU G 143     -15.803 -14.438  50.054  1.00 44.55      A  C
ATOM  15301  C    LEU G 143     -14.344 -14.581  49.593  1.00 44.80      A  C
ATOM  15302  O    LEU G 143     -13.527 -15.226  50.264  1.00 45.02      A  O
ATOM  15303  CB   LEU G 143     -16.359 -15.807  50.494  1.00 44.18      A  C
ATOM  15304  CG   LEU G 143     -17.367 -15.973  51.640  1.00 44.08      A  C
ATOM  15305  CD1  LEU G 143     -16.706 -15.673  52.978  1.00 45.10      A  C
ATOM  15306  CD2  LEU G 143     -18.637 -15.137  51.449  1.00 43.70      A  C
ATOM  15307  N    GLY G 144     -14.027 -13.968  48.452  1.00 44.90      A  N
ATOM  15308  CA   GLY G 144     -12.721 -14.125  47.813  1.00 44.99      A  C
ATOM  15309  C    GLY G 144     -12.635 -15.388  46.961  1.00 44.85      A  C
ATOM  15310  O    GLY G 144     -13.637 -16.091  46.762  1.00 44.49      A  O
ATOM  15311  N    PRO G 145     -11.432 -15.692  46.446  1.00 44.99      A  N
ATOM  15312  CA   PRO G 145     -11.209 -16.881  45.600  1.00 44.63      A  C
ATOM  15313  C    PRO G 145     -11.743 -18.185  46.200  1.00 43.80      A  C
ATOM  15314  O    PRO G 145     -11.412 -18.534  47.330  1.00 44.02      A  O
ATOM  15315  CB   PRO G 145      -9.681 -16.936  45.465  1.00 45.02      A  C
ATOM  15316  CG   PRO G 145      -9.256 -15.491  45.559  1.00 45.69      A  C
ATOM  15317  CD   PRO G 145     -10.228 -14.837  46.531  1.00 45.52      A  C
ATOM  15318  N    VAL G 146     -12.569 -18.878  45.426  1.00 42.51      A  N
ATOM  15319  CA   VAL G 146     -13.119 -20.169  45.807  1.00 41.09      A  C
ATOM  15320  C    VAL G 146     -12.931 -21.207  44.684  1.00 41.28      A  C
ATOM  15321  O    VAL G 146     -13.183 -20.924  43.512  1.00 41.30      A  O
ATOM  15322  CB   VAL G 146     -14.606 -20.037  46.177  1.00 39.29      A  C
ATOM  15323  CG1  VAL G 146     -15.105 -21.304  46.854  1.00 37.84      A  C
ATOM  15324  N    ASP G 147     -12.480 -22.405  45.055  1.00 41.38      A  N
ATOM  15325  CA   ASP G 147     -12.220 -23.507  44.103  1.00 41.12      A  C
ATOM  15326  C    ASP G 147     -13.448 -24.406  43.850  1.00 40.66      A  C
ATOM  15327  O    ASP G 147     -13.936 -25.105  44.751  1.00 40.58      A  O
ATOM  15328  CB   ASP G 147     -11.024 -24.364  44.562  1.00 41.33      A  C
ATOM  15329  CG   ASP G 147      -9.688 -23.694  44.310  1.00 41.28      A  C
ATOM  15330  N    PHE G 148     -13.928 -24.387  42.611  1.00 40.12      A  N
ATOM  15331  CA   PHE G 148     -15.125 -25.126  42.218  1.00 39.52      A  C
ATOM  15332  C    PHE G 148     -14.790 -26.300  41.323  1.00 39.33      A  C
ATOM  15333  O    PHE G 148     -13.649 -26.450  40.866  1.00 39.51      A  O
ATOM  15334  CB   PHE G 148     -16.090 -24.223  41.455  1.00 39.31      A  C
ATOM  15335  CG   PHE G 148     -16.570 -23.036  42.232  1.00 39.37      A  C
ATOM  15336  CD1  PHE G 148     -17.712 -23.130  43.022  1.00 39.11      A  C
ATOM  15337  CD2  PHE G 148     -15.902 -21.809  42.150  1.00 39.81      A  C
ATOM  15338  CE1  PHE G 148     -18.173 -22.023  43.737  1.00 39.27      A  C
ATOM  15339  CE2  PHE G 148     -16.357 -20.697  42.859  1.00 39.82      A  C
ATOM  15340  CZ   PHE G 148     -17.495 -20.802  43.651  1.00 39.57      A  C
```

FIGURE 1 (cont'd)

```
ATOM  15341  N    GLY G 149     -15.804 -27.112  41.044  1.00 38.97      A  N
ATOM  15342  CA   GLY G 149     -15.636 -28.271  40.178  1.00 38.82      A  C
ATOM  15343  C    GLY G 149     -16.921 -28.986  39.794  1.00 38.55      A  C
ATOM  15344  O    GLY G 149     -17.550 -29.660  40.617  1.00 38.53      A  O
ATOM  15345  N    ASN G 150     -17.301 -28.849  38.529  1.00 38.30      A  N
ATOM  15346  CA   ASN G 150     -18.460 -29.555  37.996  1.00 37.96      A  C
ATOM  15347  C    ASN G 150     -18.147 -31.026  37.695  1.00 38.15      A  C
ATOM  15348  O    ASN G 150     -16.983 -31.410  37.502  1.00 38.39      A  O
ATOM  15349  CB   ASN G 150     -18.971 -28.843  36.745  1.00 37.67      A  C
ATOM  15350  CG   ASN G 150     -19.464 -27.449  37.038  1.00 37.28      A  C
ATOM  15351  ND2  ASN G 150     -18.919 -26.461  36.337  1.00 37.31      A  N
ATOM  15352  OD1  ASN G 150     -20.329 -27.261  37.884  1.00 36.76      A  O
ATOM  15353  N    VAL G 151     -19.187 -31.847  37.670  1.00 38.16      A  N
ATOM  15354  CA   VAL G 151     -19.054 -33.235  37.249  1.00 38.47      A  C
ATOM  15355  C    VAL G 151     -19.910 -33.456  36.002  1.00 38.67      A  C
ATOM  15356  O    VAL G 151     -21.147 -33.411  36.061  1.00 38.50      A  O
ATOM  15357  CB   VAL G 151     -19.426 -34.215  38.390  1.00 38.36      A  C
ATOM  15358  CG1  VAL G 151     -18.439 -34.073  39.521  1.00 38.75      A  C
ATOM  15359  CG2  VAL G 151     -19.453 -35.658  37.902  1.00 38.48      A  C
ATOM  15360  N    VAL G 152     -19.236 -33.680  34.876  1.00 39.19      A  N
ATOM  15361  CA   VAL G 152     -19.900 -33.843  33.581  1.00 39.69      A  C
ATOM  15362  C    VAL G 152     -19.838 -35.290  33.111  1.00 40.21      A  C
ATOM  15363  O    VAL G 152     -18.760 -35.860  33.016  1.00 40.60      A  O
ATOM  15364  CB   VAL G 152     -19.287 -32.892  32.513  1.00 39.66      A  C
ATOM  15365  CG1  VAL G 152     -19.717 -31.452  32.771  1.00 39.12      A  C
ATOM  15366  CG2  VAL G 152     -19.680 -33.316  31.098  1.00 39.99      A  C
ATOM  15367  N    ALA G 153     -20.994 -35.874  32.814  1.00 40.63      A  N
ATOM  15368  CA   ALA G 153     -21.076 -37.283  32.413  1.00 41.27      A  C
ATOM  15369  C    ALA G 153     -21.823 -37.461  31.110  1.00 41.77      A  C
ATOM  15370  O    ALA G 153     -22.963 -37.012  30.980  1.00 41.73      A  O
ATOM  15371  CB   ALA G 153     -21.747 -38.111  33.502  1.00 41.14      A  C
ATOM  15372  N    THR G 154     -21.189 -38.134  30.155  1.00 42.52      A  N
ATOM  15373  CA   THR G 154     -21.797 -38.334  28.848  1.00 43.18      A  C
ATOM  15374  C    THR G 154     -21.562 -39.751  28.363  1.00 43.96      A  C
ATOM  15375  O    THR G 154     -20.424 -40.164  28.206  1.00 44.37      A  O
ATOM  15376  CB   THR G 154     -21.240 -37.327  27.799  1.00 43.10      A  C
ATOM  15377  CG2  THR G 154     -22.183 -37.197  26.612  1.00 42.99      A  C
ATOM  15378  OG1  THR G 154     -21.063 -36.036  28.398  1.00 42.60      A  O
ATOM  15379  N    LEU G 155     -22.640 -40.500  28.151  1.00 44.65      A  N
ATOM  15380  CA   LEU G 155     -22.559 -41.745  27.384  1.00 45.59      A  C
ATOM  15381  C    LEU G 155     -22.268 -41.377  25.938  1.00 46.39      A  C
ATOM  15382  O    LEU G 155     -22.907 -40.456  25.413  1.00 46.60      A  O
ATOM  15383  CB   LEU G 155     -23.883 -42.520  27.423  1.00 45.37      A  C
ATOM  15384  CG   LEU G 155     -24.004 -43.770  28.292  1.00 45.39      A  C
ATOM  15385  CD1  LEU G 155     -25.207 -44.589  27.845  1.00 45.20      A  C
ATOM  15386  CD2  LEU G 155     -22.735 -44.605  28.232  1.00 45.84      A  C
ATOM  15387  N    ASP G 156     -21.317 -42.067  25.299  1.00 47.24      A  N
ATOM  15388  CA   ASP G 156     -21.079 -41.883  23.859  1.00 48.06      A  C
ATOM  15389  C    ASP G 156     -20.854 -40.402  23.474  1.00 47.90      A  C
ATOM  15390  O    ASP G 156     -21.726 -39.781  22.853  1.00 47.70      A  O
ATOM  15391  CB   ASP G 156     -22.268 -42.477  23.077  1.00 48.58      A  C
ATOM  15392  CG   ASP G 156     -21.990 -42.644  21.598  1.00 50.20      A  C
ATOM  15393  OD1  ASP G 156     -20.938 -42.171  21.118  1.00 51.16      A  O
ATOM  15394  OD2  ASP G 156     -22.845 -43.252  20.916  1.00 51.71      A  O
ATOM  15395  N    PRO G 157     -19.688 -39.830  23.842  1.00 48.01      A  N
ATOM  15396  CA   PRO G 157     -19.403 -38.413  23.538  1.00 48.08      A  C
ATOM  15397  C    PRO G 157     -19.448 -38.099  22.043  1.00 48.41      A  C
ATOM  15398  O    PRO G 157     -19.625 -36.928  21.673  1.00 48.27      A  O
ATOM  15399  CB   PRO G 157     -17.980 -38.210  24.062  1.00 48.03      A  C
ATOM  15400  CG   PRO G 157     -17.780 -39.289  25.049  1.00 48.07      A  C
ATOM  15401  CD   PRO G 157     -18.584 -40.461  24.584  1.00 48.15      A  C
ATOM  15402  N    ARG G 158     -19.296 -39.138  21.211  1.00 48.93      A  N
ATOM  15403  CA   ARG G 158     -19.280 -38.985  19.748  1.00 49.42      A  C
ATOM  15404  C    ARG G 158     -20.669 -38.783  19.120  1.00 49.27      A  C
ATOM  15405  O    ARG G 158     -20.764 -38.267  18.000  1.00 49.59      A  O
```

FIGURE 1 (cont'd)

```
ATOM  15406  CB   ARG G 158     -18.467 -40.087  19.026  1.00 49.91       A  C
ATOM  15407  CG   ARG G 158     -18.793 -41.526  19.392  1.00 50.26       A  C
ATOM  15408  N    ALA G 159     -21.733 -39.175  19.833  1.00 48.76       A  N
ATOM  15409  CA   ALA G 159     -23.110 -38.961  19.353  1.00 48.35       A  C
ATOM  15410  C    ALA G 159     -23.366 -37.479  19.125  1.00 48.04       A  C
ATOM  15411  O    ALA G 159     -22.891 -36.640  19.900  1.00 47.82       A  O
ATOM  15412  CB   ALA G 159     -24.116 -39.525  20.325  1.00 48.20       A  C
ATOM  15413  N    ALA G 160     -24.107 -37.168  18.062  1.00 47.88       A  N
ATOM  15414  CA   ALA G 160     -24.272 -35.790  17.600  1.00 47.61       A  C
ATOM  15415  C    ALA G 160     -25.047 -34.911  18.581  1.00 47.11       A  C
ATOM  15416  O    ALA G 160     -24.744 -33.720  18.736  1.00 47.03       A  O
ATOM  15417  CB   ALA G 160     -24.922 -35.768  16.224  1.00 48.03       A  C
ATOM  15418  N    ARG G 161     -26.035 -35.509  19.244  1.00 46.53       A  N
ATOM  15419  CA   ARG G 161     -26.856 -34.808  20.234  1.00 45.93       A  C
ATOM  15420  C    ARG G 161     -27.148 -35.683  21.458  1.00 45.12       A  C
ATOM  15421  O    ARG G 161     -27.074 -36.906  21.385  1.00 45.24       A  O
ATOM  15422  CB   ARG G 161     -28.164 -34.357  19.598  1.00 46.19       A  C
ATOM  15423  CG   ARG G 161     -28.081 -33.064  18.775  1.00 47.57       A  C
ATOM  15424  CD   ARG G 161     -28.940 -33.183  17.511  1.00 50.42       A  C
ATOM  15425  NE   ARG G 161     -30.090 -34.081  17.719  1.00 52.66       A  N
ATOM  15426  CZ   ARG G 161     -30.527 -34.988  16.841  1.00 53.89       A  C
ATOM  15427  NH1  ARG G 161     -29.919 -35.141  15.664  1.00 54.67       A  N
ATOM  15428  NH2  ARG G 161     -31.580 -35.746  17.147  1.00 54.15       A  N
ATOM  15429  N    HIS G 162     -27.472 -35.046  22.580  1.00 44.07       A  N
ATOM  15430  CA   HIS G 162     -27.789 -35.759  23.814  1.00 43.01       A  C
ATOM  15431  C    HIS G 162     -28.874 -35.066  24.625  1.00 41.97       A  C
ATOM  15432  O    HIS G 162     -28.930 -33.829  24.680  1.00 41.73       A  O
ATOM  15433  CB   HIS G 162     -26.534 -35.933  24.682  1.00 43.22       A  C
ATOM  15434  CG   HIS G 162     -25.736 -34.675  24.867  1.00 43.88       A  C
ATOM  15435  CD2  HIS G 162     -24.537 -34.302  24.360  1.00 44.45       A  C
ATOM  15436  ND1  HIS G 162     -26.153 -33.629  25.667  1.00 44.06       A  N
ATOM  15437  CE1  HIS G 162     -25.251 -32.665  25.635  1.00 44.25       A  C
ATOM  15438  NE2  HIS G 162     -24.259 -33.049  24.851  1.00 44.52       A  N
ATOM  15439  N    LEU G 163     -29.737 -35.868  25.248  1.00 40.86       A  N
ATOM  15440  CA   LEU G 163     -30.616 -35.377  26.313  1.00 39.69       A  C
ATOM  15441  C    LEU G 163     -29.753 -35.075  27.523  1.00 38.98       A  C
ATOM  15442  O    LEU G 163     -28.907 -35.886  27.902  1.00 39.04       A  O
ATOM  15443  CB   LEU G 163     -31.677 -36.417  26.688  1.00 39.57       A  C
ATOM  15444  CG   LEU G 163     -32.481 -36.187  27.978  1.00 38.91       A  C
ATOM  15445  CD1  LEU G 163     -33.372 -34.955  27.892  1.00 38.47       A  C
ATOM  15446  CD2  LEU G 163     -33.315 -37.401  28.311  1.00 38.87       A  C
ATOM  15447  N    THR G 164     -29.955 -33.915  28.130  1.00 37.98       A  N
ATOM  15448  CA   THR G 164     -29.143 -33.561  29.282  1.00 37.05       A  C
ATOM  15449  C    THR G 164     -29.953 -33.195  30.545  1.00 36.48       A  C
ATOM  15450  O    THR G 164     -30.733 -32.236  30.552  1.00 36.26       A  O
ATOM  15451  CB   THR G 164     -28.039 -32.531  28.919  1.00 36.99       A  C
ATOM  15452  CG2  THR G 164     -28.598 -31.360  28.152  1.00 36.93       A  C
ATOM  15453  OG1  THR G 164     -27.402 -32.058  30.110  1.00 36.64       A  O
ATOM  15454  N    LEU G 165     -29.771 -34.001  31.595  1.00 35.86       A  N
ATOM  15455  CA   LEU G 165     -30.383 -33.773  32.897  1.00 35.28       A  C
ATOM  15456  C    LEU G 165     -29.367 -33.159  33.817  1.00 34.96       A  C
ATOM  15457  O    LEU G 165     -28.185 -33.475  33.741  1.00 35.05       A  O
ATOM  15458  CB   LEU G 165     -30.878 -35.083  33.502  1.00 35.24       A  C
ATOM  15459  CG   LEU G 165     -31.892 -35.921  32.708  1.00 35.34       A  C
ATOM  15460  CD1  LEU G 165     -32.432 -37.086  33.545  1.00 35.45       A  C
ATOM  15461  CD2  LEU G 165     -33.046 -35.072  32.189  1.00 35.13       A  C
ATOM  15462  N    ALA G 166     -29.828 -32.280  34.695  1.00 34.50       A  N
ATOM  15463  CA   ALA G 166     -28.927 -31.569  35.597  1.00 34.09       A  C
ATOM  15464  C    ALA G 166     -29.497 -31.345  36.992  1.00 33.85       A  C
ATOM  15465  O    ALA G 166     -30.707 -31.125  37.160  1.00 33.70       A  O
ATOM  15466  CB   ALA G 166     -28.501 -30.242  34.994  1.00 34.09       A  C
ATOM  15467  N    CYS G 167     -28.600 -31.429  37.979  1.00 33.68       A  N
ATOM  15468  CA   CYS G 167     -28.850 -31.051  39.368  1.00 33.53       A  C
ATOM  15469  C    CYS G 167     -27.602 -30.321  39.850  1.00 33.49       A  C
ATOM  15470  O    CYS G 167     -26.550 -30.384  39.209  1.00 33.55       A  O
```

FIGURE 1 (cont'd)

```
ATOM  15471  CB   CYS G 167     -29.083 -32.286  40.235  1.00 33.49      A  C
ATOM  15472  SG   CYS G 167     -27.604 -33.282  40.451  1.00 33.77      A  S
ATOM  15473  N    HIS G 168     -27.709 -29.633  40.976  1.00 33.46      A  N
ATOM  15474  CA   HIS G 168     -26.524 -29.075  41.608  1.00 33.51      A  C
ATOM  15475  C    HIS G 168     -26.197 -29.848  42.890  1.00 33.44      A  C
ATOM  15476  O    HIS G 168     -27.071 -30.122  43.706  1.00 33.35      A  O
ATOM  15477  CB   HIS G 168     -26.666 -27.564  41.857  1.00 33.61      A  C
ATOM  15478  CG   HIS G 168     -27.485 -27.219  43.059  1.00 34.00      A  C
ATOM  15479  CD2  HIS G 168     -28.806 -26.952  43.189  1.00 34.34      A  C
ATOM  15480  ND1  HIS G 168     -26.948 -27.128  44.326  1.00 34.34      A  N
ATOM  15481  CE1  HIS G 168     -27.903 -26.820  45.186  1.00 34.40      A  C
ATOM  15482  NE2  HIS G 168     -29.040 -26.708  44.521  1.00 34.35      A  N
ATOM  15483  N    TYR G 169     -24.930 -30.203  43.054  1.00 33.53      A  N
ATOM  15484  CA   TYR G 169     -24.509 -31.032  44.171  1.00 33.66      A  C
ATOM  15485  C    TYR G 169     -23.941 -30.249  45.355  1.00 33.75      A  C
ATOM  15486  O    TYR G 169     -23.755 -30.818  46.417  1.00 33.79      A  O
ATOM  15487  CB   TYR G 169     -23.528 -32.120  43.705  1.00 33.73      A  C
ATOM  15488  CG   TYR G 169     -22.099 -31.646  43.499  1.00 33.99      A  C
ATOM  15489  CD1  TYR G 169     -21.708 -31.003  42.311  1.00 33.88      A  C
ATOM  15490  CD2  TYR G 169     -21.129 -31.848  44.487  1.00 34.44      A  C
ATOM  15491  CE1  TYR G 169     -20.390 -30.564  42.122  1.00 33.96      A  C
ATOM  15492  CE2  TYR G 169     -19.809 -31.408  44.306  1.00 34.65      A  C
ATOM  15493  CZ   TYR G 169     -19.448 -30.770  43.122  1.00 34.24      A  C
ATOM  15494  OH   TYR G 169     -18.144 -30.349  42.949  1.00 34.31      A  O
ATOM  15495  N    ASP G 170     -23.662 -28.961  45.182  1.00 33.86      A  N
ATOM  15496  CA   ASP G 170     -23.266 -28.138  46.316  1.00 34.20      A  C
ATOM  15497  C    ASP G 170     -24.451 -27.935  47.268  1.00 34.45      A  C
ATOM  15498  O    ASP G 170     -25.607 -28.137  46.879  1.00 34.27      A  O
ATOM  15499  CB   ASP G 170     -22.711 -26.790  45.848  1.00 34.28      A  C
ATOM  15500  CG   ASP G 170     -23.765 -25.912  45.184  1.00 34.21      A  C
ATOM  15501  OD1  ASP G 170     -24.394 -26.363  44.192  1.00 33.80      A  O
ATOM  15502  OD2  ASP G 170     -23.944 -24.760  45.655  1.00 34.62      A  O
ATOM  15503  N    SER G 171     -24.151 -27.568  48.516  1.00 34.94      A  N
ATOM  15504  CA   SER G 171     -25.165 -27.181  49.512  1.00 35.37      A  C
ATOM  15505  C    SER G 171     -24.912 -25.737  49.970  1.00 35.64      A  C
ATOM  15506  O    SER G 171     -23.760 -25.298  50.043  1.00 35.95      A  O
ATOM  15507  CB   SER G 171     -25.151 -28.133  50.718  1.00 35.41      A  C
ATOM  15508  OG   SER G 171     -24.167 -27.755  51.679  1.00 35.86      A  O
ATOM  15509  N    LYS G 172     -25.972 -25.002  50.288  1.00 35.78      A  N
ATOM  15510  CA   LYS G 172     -25.800 -23.601  50.664  1.00 36.21      A  C
ATOM  15511  C    LYS G 172     -24.940 -23.452  51.916  1.00 36.93      A  C
ATOM  15512  O    LYS G 172     -24.893 -24.343  52.770  1.00 37.16      A  O
ATOM  15513  CB   LYS G 172     -27.142 -22.881  50.837  1.00 35.94      A  C
ATOM  15514  CG   LYS G 172     -27.024 -21.358  50.818  1.00 35.69      A  C
ATOM  15515  CD   LYS G 172     -28.363 -20.686  51.050  1.00 35.09      A  C
ATOM  15516  CE   LYS G 172     -28.221 -19.175  51.208  1.00 35.10      A  C
ATOM  15517  NZ   LYS G 172     -28.011 -18.487  49.908  1.00 35.08      A  N
ATOM  15518  N    LEU G 173     -24.248 -22.319  51.993  1.00 37.72      A  N
ATOM  15519  CA   LEU G 173     -23.393 -21.987  53.124  1.00 38.59      A  C
ATOM  15520  C    LEU G 173     -24.116 -21.016  54.047  1.00 39.11      A  C
ATOM  15521  O    LEU G 173     -24.563 -19.946  53.619  1.00 39.20      A  O
ATOM  15522  CB   LEU G 173     -22.078 -21.374  52.632  1.00 38.66      A  C
ATOM  15523  CG   LEU G 173     -21.119 -20.767  53.657  1.00 39.25      A  C
ATOM  15524  CD1  LEU G 173     -20.043 -21.755  54.059  1.00 39.56      A  C
ATOM  15525  CD2  LEU G 173     -20.503 -19.485  53.126  1.00 39.42      A  C
ATOM  15526  N    PHE G 174     -24.226 -21.402  55.312  1.00 39.79      A  N
ATOM  15527  CA   PHE G 174     -24.875 -20.576  56.324  1.00 40.41      A  C
ATOM  15528  C    PHE G 174     -23.858 -20.168  57.417  1.00 40.39      A  C
ATOM  15529  O    PHE G 174     -22.916 -20.912  57.695  1.00 41.41      A  O
ATOM  15530  CB   PHE G 174     -26.067 -21.334  56.907  1.00 40.63      A  C
ATOM  15531  CG   PHE G 174     -27.273 -21.368  55.999  1.00 40.49      A  C
ATOM  15532  CD1  PHE G 174     -28.130 -20.268  55.936  1.00 40.60      A  C
ATOM  15533  CD2  PHE G 174     -27.561 -22.502  55.219  1.00 40.04      A  C
ATOM  15534  CE1  PHE G 174     -29.250 -20.281  55.106  1.00 40.11      A  C
ATOM  15535  CE2  PHE G 174     -28.686 -22.529  54.386  1.00 39.55      A  C
```

FIGURE 1 (cont'd)

```
ATOM  15536  CZ   PHE G 174     -29.531 -21.417  54.330  1.00 39.67      A    C
ATOM  15537  N    PRO G 175     -23.991 -18.957  58.002  1.00 39.92      A    N
ATOM  15538  CA   PRO G 175     -22.951 -18.612  58.997  1.00 39.66      A    C
ATOM  15539  C    PRO G 175     -23.262 -19.172  60.388  1.00 39.98      A    C
ATOM  15540  O    PRO G 175     -23.520 -20.375  60.527  1.00 40.23      A    O
ATOM  15541  CB   PRO G 175     -22.938 -17.070  59.002  1.00 39.53      A    C
ATOM  15542  CG   PRO G 175     -24.168 -16.621  58.156  1.00 39.35      A    C
ATOM  15543  CD   PRO G 175     -24.962 -17.861  57.792  1.00 39.74      A    C
TER   15544       PRO G 175
ATOM  15545  N    SER G 178     -24.257 -22.421  64.034  1.00 47.22      A    N
ATOM  15546  CA   SER G 178     -25.741 -22.647  63.975  1.00 46.97      A    C
ATOM  15547  C    SER G 178     -26.128 -24.090  63.897  1.00 46.91      A    C
ATOM  15548  O    SER G 178     -25.909 -24.799  64.856  1.00 47.49      A    O
ATOM  15549  CB   SER G 178     -26.226 -21.933  62.672  1.00 45.24      A    C
ATOM  15550  OG   SER G 178     -25.872 -20.605  63.056  1.00 44.54      A    O
ATOM  15551  N    THR G 179     -26.768 -24.531  62.822  1.00 45.47      A    N
ATOM  15552  CA   THR G 179     -27.029 -25.953  62.742  1.00 43.05      A    C
ATOM  15553  C    THR G 179     -26.730 -26.385  61.329  1.00 43.54      A    C
ATOM  15554  O    THR G 179     -27.093 -25.686  60.385  1.00 44.44      A    O
ATOM  15555  CB   THR G 179     -28.456 -26.328  63.237  1.00 37.61      A    C
ATOM  15556  OG1  THR G 179     -29.197 -26.956  62.184  1.00 34.55      A    O
ATOM  15557  N    PRO G 180     -26.026 -27.519  61.184  1.00 42.46      A    N
ATOM  15558  CA   PRO G 180     -25.571 -28.005  59.885  1.00 41.29      A    C
ATOM  15559  C    PRO G 180     -26.722 -28.027  58.887  1.00 42.07      A    C
ATOM  15560  O    PRO G 180     -27.859 -28.351  59.262  1.00 42.92      A    O
ATOM  15561  CB   PRO G 180     -25.054 -29.428  60.183  1.00 36.47      A    C
ATOM  15562  CG   PRO G 180     -25.902 -29.957  61.332  1.00 34.72      A    C
ATOM  15563  N    PHE G 181     -26.436 -27.646  57.644  1.00 41.83      A    N
ATOM  15564  CA   PHE G 181     -27.454 -27.609  56.591  1.00 40.95      A    C
ATOM  15565  C    PHE G 181     -27.099 -28.548  55.438  1.00 40.24      A    C
ATOM  15566  O    PHE G 181     -26.090 -28.348  54.749  1.00 40.06      A    O
ATOM  15567  CB   PHE G 181     -27.674 -26.176  56.083  1.00 40.98      A    C
ATOM  15568  CG   PHE G 181     -28.532 -26.104  54.859  1.00 40.74      A    C
ATOM  15569  CD1  PHE G 181     -29.899 -26.347  54.940  1.00 40.89      A    C
ATOM  15570  CD2  PHE G 181     -27.977 -25.820  53.620  1.00 40.50      A    C
ATOM  15571  CE1  PHE G 181     -30.707 -26.294  53.803  1.00 40.30      A    C
ATOM  15572  CE2  PHE G 181     -28.776 -25.767  52.474  1.00 40.00      A    C
ATOM  15573  CZ   PHE G 181     -30.146 -26.002  52.568  1.00 39.77      A    C
ATOM  15574  N    VAL G 182     -27.928 -29.569  55.227  1.00 39.44      A    N
ATOM  15575  CA   VAL G 182     -27.622 -30.595  54.214  1.00 38.71      A    C
ATOM  15576  C    VAL G 182     -28.449 -30.477  52.943  1.00 37.94      A    C
ATOM  15577  O    VAL G 182     -28.122 -31.116  51.943  1.00 37.76      A    O
ATOM  15578  CB   VAL G 182     -27.734 -32.047  54.757  1.00 38.78      A    C
ATOM  15579  CG1  VAL G 182     -26.488 -32.430  55.554  1.00 39.12      A    C
ATOM  15580  CG2  VAL G 182     -29.007 -32.218  55.582  1.00 39.14      A    C
ATOM  15581  N    GLY G 183     -29.513 -29.672  52.988  1.00 37.25      A    N
ATOM  15582  CA   GLY G 183     -30.388 -29.447  51.827  1.00 36.26      A    C
ATOM  15583  C    GLY G 183     -30.749 -30.725  51.095  1.00 35.59      A    C
ATOM  15584  O    GLY G 183     -30.204 -31.008  50.023  1.00 35.42      A    O
ATOM  15585  N    ALA G 184     -31.655 -31.502  51.685  1.00 35.06      A    N
ATOM  15586  CA   ALA G 184     -32.083 -32.772  51.103  1.00 34.50      A    C
ATOM  15587  C    ALA G 184     -32.828 -32.578  49.775  1.00 33.94      A    C
ATOM  15588  O    ALA G 184     -32.538 -33.257  48.787  1.00 33.74      A    O
ATOM  15589  CB   ALA G 184     -32.935 -33.543  52.090  1.00 34.81      A    C
ATOM  15590  N    THR G 185     -33.772 -31.640  49.756  1.00 33.37      A    N
ATOM  15591  CA   THR G 185     -34.490 -31.291  48.531  1.00 32.83      A    C
ATOM  15592  C    THR G 185     -33.636 -30.409  47.626  1.00 32.58      A    C
ATOM  15593  O    THR G 185     -33.944 -30.235  46.447  1.00 32.56      A    O
ATOM  15594  CB   THR G 185     -35.789 -30.511  48.825  1.00 32.76      A    C
ATOM  15595  CG2  THR G 185     -36.581 -31.164  49.960  1.00 33.00      A    C
ATOM  15596  OG1  THR G 185     -35.475 -29.153  49.166  1.00 32.40      A    O
ATOM  15597  N    ASP G 186     -32.555 -29.871  48.189  1.00 32.38      A    N
ATOM  15598  CA   ASP G 186     -31.831 -28.751  47.593  1.00 32.13      A    C
ATOM  15599  C    ASP G 186     -30.297 -28.962  47.575  1.00 32.15      A    C
ATOM  15600  O    ASP G 186     -29.575 -28.299  48.318  1.00 32.44      A    O
```

FIGURE 1 (cont'd)

```
ATOM  15601  CB   ASP G 186     -32.219 -27.480  48.370  1.00 32.00      A  C
ATOM  15602  CG   ASP G 186     -31.799 -26.198  47.681  1.00 31.48      A  C
ATOM  15603  OD1  ASP G 186     -32.106 -25.125  48.235  1.00 31.33      A  O
ATOM  15604  OD2  ASP G 186     -31.168 -26.240  46.607  1.00 30.69      A  O
ATOM  15605  N    SER G 187     -29.790 -29.862  46.726  1.00 31.90      A  N
ATOM  15606  CA   SER G 187     -30.579 -30.647  45.766  1.00 31.64      A  C
ATOM  15607  C    SER G 187     -30.141 -32.103  45.770  1.00 31.61      A  C
ATOM  15608  O    SER G 187     -30.009 -32.730  44.714  1.00 31.48      A  O
ATOM  15609  CB   SER G 187     -30.425 -30.076  44.355  1.00 31.55      A  C
ATOM  15610  OG   SER G 187     -31.149 -28.874  44.197  1.00 31.69      A  O
ATOM  15611  N    ALA G 188     -29.910 -32.635  46.965  1.00 31.74      A  N
ATOM  15612  CA   ALA G 188     -29.425 -34.005  47.123  1.00 31.86      A  C
ATOM  15613  C    ALA G 188     -30.303 -35.032  46.381  1.00 31.85      A  C
ATOM  15614  O    ALA G 188     -29.803 -35.828  45.573  1.00 31.82      A  O
ATOM  15615  CB   ALA G 188     -29.298 -34.352  48.604  1.00 32.01      A  C
ATOM  15616  N    VAL G 189     -31.609 -34.988  46.652  1.00 31.79      A  N
ATOM  15617  CA   VAL G 189     -32.589 -35.862  45.999  1.00 31.66      A  C
ATOM  15618  C    VAL G 189     -32.529 -35.766  44.464  1.00 31.63      A  C
ATOM  15619  O    VAL G 189     -32.390 -36.789  43.802  1.00 31.72      A  O
ATOM  15620  CB   VAL G 189     -34.035 -35.618  46.521  1.00 31.57      A  C
ATOM  15621  CG1  VAL G 189     -35.041 -36.395  45.694  1.00 31.37      A  C
ATOM  15622  CG2  VAL G 189     -34.153 -35.990  47.989  1.00 31.77      A  C
ATOM  15623  N    PRO G 190     -32.635 -34.546  43.896  1.00 31.53      A  N
ATOM  15624  CA   PRO G 190     -32.444 -34.410  42.464  1.00 31.53      A  C
ATOM  15625  C    PRO G 190     -31.198 -35.148  41.970  1.00 31.79      A  C
ATOM  15626  O    PRO G 190     -31.289 -35.905  41.003  1.00 31.80      A  O
ATOM  15627  CB   PRO G 190     -32.284 -32.905  42.288  1.00 31.34      A  C
ATOM  15628  CG   PRO G 190     -33.164 -32.341  43.308  1.00 31.33      A  C
ATOM  15629  CD   PRO G 190     -33.106 -33.278  44.483  1.00 31.50      A  C
ATOM  15630  N    CYS G 191     -30.059 -34.953  42.640  1.00 32.16      A  N
ATOM  15631  CA   CYS G 191     -28.811 -35.596  42.225  1.00 32.68      A  C
ATOM  15632  C    CYS G 191     -28.858 -37.105  42.379  1.00 32.99      A  C
ATOM  15633  O    CYS G 191     -28.358 -37.836  41.510  1.00 33.15      A  O
ATOM  15634  CB   CYS G 191     -27.618 -35.013  42.973  1.00 32.73      A  C
ATOM  15635  SG   CYS G 191     -27.251 -33.323  42.478  1.00 33.35      A  S
ATOM  15636  N    ALA G 192     -29.467 -37.557  43.479  1.00 33.24      A  N
ATOM  15637  CA   ALA G 192     -29.655 -38.988  43.756  1.00 33.46      A  C
ATOM  15638  C    ALA G 192     -30.445 -39.699  42.638  1.00 33.44      A  C
ATOM  15639  O    ALA G 192     -30.108 -40.833  42.251  1.00 33.66      A  O
ATOM  15640  CB   ALA G 192     -30.332 -39.186  45.123  1.00 33.57      A  C
ATOM  15641  N    LEU G 193     -31.476 -39.014  42.124  1.00 33.05      A  N
ATOM  15642  CA   LEU G 193     -32.333 -39.535  41.054  1.00 32.65      A  C
ATOM  15643  C    LEU G 193     -31.550 -39.712  39.755  1.00 33.21      A  C
ATOM  15644  O    LEU G 193     -31.631 -40.763  39.111  1.00 33.60      A  O
ATOM  15645  CB   LEU G 193     -33.544 -38.625  40.829  1.00 31.33      A  C
ATOM  15646  CG   LEU G 193     -34.609 -38.581  41.930  1.00 29.74      A  C
ATOM  15647  CD1  LEU G 193     -35.648 -37.525  41.595  1.00 28.79      A  C
ATOM  15648  N    LEU G 194     -30.781 -38.688  39.385  1.00 33.42      A  N
ATOM  15649  CA   LEU G 194     -29.903 -38.759  38.219  1.00 33.56      A  C
ATOM  15650  C    LEU G 194     -29.007 -39.997  38.268  1.00 34.48      A  C
ATOM  15651  O    LEU G 194     -28.803 -40.648  37.246  1.00 34.80      A  O
ATOM  15652  CB   LEU G 194     -29.063 -37.488  38.090  1.00 32.47      A  C
ATOM  15653  CG   LEU G 194     -29.865 -36.258  37.672  1.00 31.27      A  C
ATOM  15654  CD1  LEU G 194     -28.991 -35.292  36.918  1.00 30.88      A  C
ATOM  15655  N    LEU G 195     -28.493 -40.326  39.454  1.00 35.27      A  N
ATOM  15656  CA   LEU G 195     -27.686 -41.531  39.648  1.00 36.09      A  C
ATOM  15657  C    LEU G 195     -28.510 -42.807  39.494  1.00 36.79      A  C
ATOM  15658  O    LEU G 195     -28.143 -43.702  38.728  1.00 37.10      A  O
ATOM  15659  CB   LEU G 195     -27.010 -41.508  41.019  1.00 36.03      A  C
ATOM  15660  CG   LEU G 195     -25.943 -40.439  41.267  1.00 35.83      A  C
ATOM  15661  CD1  LEU G 195     -25.482 -40.508  42.709  1.00 36.07      A  C
ATOM  15662  CD2  LEU G 195     -24.758 -40.604  40.327  1.00 35.85      A  C
ATOM  15663  N    GLU G 196     -29.622 -42.879  40.221  1.00 37.41      A  N
ATOM  15664  CA   GLU G 196     -30.500 -44.048  40.201  1.00 38.03      A  C
ATOM  15665  C    GLU G 196     -31.001 -44.369  38.792  1.00 38.12      A  C
```

FIGURE 1 (cont'd)

```
ATOM  15666  O    GLU G 196     -30.961 -45.527  38.362  1.00 38.30      A   O
ATOM  15667  CB   GLU G 196     -31.669 -43.853  41.175  1.00 38.17      A   C
ATOM  15668  CG   GLU G 196     -32.846 -44.844  41.005  1.00 39.31      A   C
ATOM  15669  CD   GLU G 196     -32.529 -46.278  41.427  1.00 40.78      A   C
ATOM  15670  OE1  GLU G 196     -31.422 -46.533  41.958  1.00 41.41      A   O
ATOM  15671  OE2  GLU G 196     -33.401 -47.150  41.228  1.00 41.45      A   O
ATOM  15672  N    LEU G 197     -31.465 -43.335  38.089  1.00 38.13      A   N
ATOM  15673  CA   LEU G 197     -31.905 -43.447  36.696  1.00 38.38      A   C
ATOM  15674  C    LEU G 197     -30.820 -44.054  35.812  1.00 38.86      A   C
ATOM  15675  O    LEU G 197     -31.078 -44.973  35.031  1.00 39.13      A   O
ATOM  15676  CB   LEU G 197     -32.296 -42.069  36.148  1.00 37.97      A   C
ATOM  15677  CG   LEU G 197     -33.776 -41.709  36.063  1.00 37.73      A   C
ATOM  15678  CD1  LEU G 197     -34.294 -41.240  37.388  1.00 37.58      A   C
ATOM  15679  CD2  LEU G 197     -33.967 -40.629  35.022  1.00 37.66      A   C
ATOM  15680  N    ALA G 198     -29.607 -43.530  35.962  1.00 39.32      A   N
ATOM  15681  CA   ALA G 198     -28.457 -43.959  35.183  1.00 40.05      A   C
ATOM  15682  C    ALA G 198     -28.123 -45.416  35.444  1.00 40.79      A   C
ATOM  15683  O    ALA G 198     -27.604 -46.117  34.564  1.00 41.10      A   O
ATOM  15684  CB   ALA G 198     -27.250 -43.075  35.495  1.00 39.88      A   C
ATOM  15685  N    GLN G 199     -28.428 -45.857  36.659  1.00 41.35      A   N
ATOM  15686  CA   GLN G 199     -28.130 -47.204  37.080  1.00 42.04      A   C
ATOM  15687  C    GLN G 199     -29.257 -48.145  36.682  1.00 42.97      A   C
ATOM  15688  O    GLN G 199     -29.003 -49.242  36.185  1.00 43.58      A   O
ATOM  15689  CB   GLN G 199     -27.915 -47.244  38.592  1.00 40.96      A   C
ATOM  15690  CG   GLN G 199     -26.624 -47.939  39.036  1.00 40.42      A   C
ATOM  15691  CD   GLN G 199     -26.461 -49.338  38.434  1.00 40.17      A   C
ATOM  15692  NE2  GLN G 199     -25.637 -49.453  37.398  1.00 41.08      A   N
ATOM  15693  OE1  GLN G 199     -27.096 -50.290  38.877  1.00 40.49      A   O
ATOM  15694  N    ALA G 200     -30.497 -47.714  36.901  1.00 43.63      A   N
ATOM  15695  CA   ALA G 200     -31.664 -48.541  36.591  1.00 44.37      A   C
ATOM  15696  C    ALA G 200     -31.807 -48.818  35.090  1.00 44.90      A   C
ATOM  15697  O    ALA G 200     -32.141 -49.929  34.673  1.00 45.33      A   O
ATOM  15698  CB   ALA G 200     -32.934 -47.909  37.154  1.00 44.13      A   C
ATOM  15699  N    LEU G 201     -31.536 -47.805  34.283  1.00 45.24      A   N
ATOM  15700  CA   LEU G 201     -31.657 -47.944  32.845  1.00 45.79      A   C
ATOM  15701  C    LEU G 201     -30.325 -48.298  32.205  1.00 46.52      A   C
ATOM  15702  O    LEU G 201     -30.210 -48.319  30.976  1.00 46.76      A   O
ATOM  15703  CB   LEU G 201     -32.197 -46.650  32.246  1.00 45.34      A   C
ATOM  15704  CG   LEU G 201     -33.611 -46.273  32.657  1.00 45.08      A   C
ATOM  15705  CD1  LEU G 201     -33.880 -44.813  32.332  1.00 44.77      A   C
ATOM  15706  CD2  LEU G 201     -34.635 -47.206  32.015  1.00 45.35      A   C
ATOM  15707  N    ASP G 202     -29.326 -48.582  33.043  1.00 47.28      A   N
ATOM  15708  CA   ASP G 202     -27.937 -48.792  32.599  1.00 48.11      A   C
ATOM  15709  C    ASP G 202     -27.802 -49.757  31.411  1.00 48.72      A   C
ATOM  15710  O    ASP G 202     -27.087 -49.454  30.445  1.00 48.95      A   O
ATOM  15711  CB   ASP G 202     -27.066 -49.247  33.775  1.00 48.20      A   C
ATOM  15712  CG   ASP G 202     -25.658 -49.572  33.367  1.00 48.63      A   C
ATOM  15713  OD1  ASP G 202     -24.974 -48.684  32.824  1.00 48.45      A   O
ATOM  15714  OD2  ASP G 202     -25.238 -50.720  33.602  1.00 49.41      A   O
ATOM  15715  N    LEU G 203     -28.503 -50.894  31.476  1.00 49.12      A   N
ATOM  15716  CA   LEU G 203     -28.386 -51.929  30.447  1.00 49.32      A   C
ATOM  15717  C    LEU G 203     -29.040 -51.538  29.123  1.00 49.58      A   C
ATOM  15718  O    LEU G 203     -28.430 -51.695  28.065  1.00 50.00      A   O
ATOM  15719  CB   LEU G 203     -28.896 -53.284  30.954  1.00 48.36      A   C
ATOM  15720  CG   LEU G 203     -27.856 -54.065  31.763  1.00 48.07      A   C
ATOM  15721  CD1  LEU G 203     -28.096 -53.898  33.253  1.00 47.96      A   C
ATOM  15722  N    GLU G 204     -30.266 -51.027  29.178  1.00 49.37      A   N
ATOM  15723  CA   GLU G 204     -30.932 -50.533  27.972  1.00 48.99      A   C
ATOM  15724  C    GLU G 204     -30.214 -49.315  27.379  1.00 49.43      A   C
ATOM  15725  O    GLU G 204     -30.215 -49.127  26.156  1.00 49.71      A   O
ATOM  15726  CB   GLU G 204     -32.415 -50.245  28.227  1.00 47.48      A   C
ATOM  15727  CG   GLU G 204     -32.760 -49.878  29.660  1.00 45.83      A   C
ATOM  15728  CD   GLU G 204     -32.783 -51.079  30.573  1.00 45.08      A   C
ATOM  15729  OE1  GLU G 204     -33.759 -51.848  30.484  1.00 45.24      A   O
ATOM  15730  N    LEU G 205     -29.595 -48.510  28.252  1.00 49.62      A   N
```

FIGURE 1 (cont'd)

```
ATOM   15731  CA   LEU G 205     -28.742 -47.379  27.843  1.00 49.77      A  C
ATOM   15732  C    LEU G 205     -27.444 -47.848  27.218  1.00 50.50      A  C
ATOM   15733  O    LEU G 205     -26.883 -47.173  26.354  1.00 50.57      A  O
ATOM   15734  CB   LEU G 205     -28.383 -46.484  29.030  1.00 49.23      A  C
ATOM   15735  CG   LEU G 205     -29.233 -45.256  29.356  1.00 48.24      A  C
ATOM   15736  CD1  LEU G 205     -28.870 -44.772  30.742  1.00 47.83      A  C
ATOM   15737  CD2  LEU G 205     -29.037 -44.148  28.346  1.00 47.60      A  C
ATOM   15738  N    SER G 206     -26.962 -48.996  27.681  1.00 51.36      A  N
ATOM   15739  CA   SER G 206     -25.720 -49.575  27.184  1.00 52.26      A  C
ATOM   15740  C    SER G 206     -25.857 -50.106  25.753  1.00 52.73      A  C
ATOM   15741  O    SER G 206     -25.085 -49.716  24.875  1.00 52.77      A  O
ATOM   15742  CB   SER G 206     -25.230 -50.680  28.123  1.00 52.48      A  C
ATOM   15743  OG   SER G 206     -23.849 -50.921  27.929  1.00 53.16      A  O
ATOM   15744  N    ARG G 207     -26.837 -50.985  25.524  1.00 53.27      A  N
ATOM   15745  CA   ARG G 207     -27.057 -51.575  24.199  1.00 53.77      A  C
ATOM   15746  C    ARG G 207     -27.237 -50.493  23.125  1.00 53.77      A  C
ATOM   15747  O    ARG G 207     -26.481 -50.470  22.143  1.00 54.13      A  O
ATOM   15748  CB   ARG G 207     -28.201 -52.619  24.192  1.00 54.04      A  C
ATOM   15749  CG   ARG G 207     -29.565 -52.152  24.712  1.00 53.54      A  C
ATOM   15750  N    ALA G 208     -28.205 -49.591  23.329  1.00 53.31      A  N
ATOM   15751  CA   ALA G 208     -28.378 -48.420  22.460  1.00 52.90      A  C
ATOM   15752  C    ALA G 208     -27.140 -47.512  22.579  1.00 52.68      A  C
ATOM   15753  O    ALA G 208     -27.129 -46.514  23.309  1.00 52.45      A  O
ATOM   15754  CB   ALA G 208     -29.654 -47.671  22.818  1.00 52.56      A  C
ATOM   15755  N    LYS G 209     -26.087 -47.912  21.873  1.00 52.72      A  N
ATOM   15756  CA   LYS G 209     -24.763 -47.277  21.896  1.00 52.18      A  C
ATOM   15757  C    LYS G 209     -23.934 -48.224  21.047  1.00 51.13      A  C
ATOM   15758  O    LYS G 209     -22.743 -48.479  21.265  1.00 52.51      A  O
ATOM   15759  CB   LYS G 209     -24.222 -47.099  23.309  1.00 52.39      A  C
ATOM   15760  CG   LYS G 209     -23.060 -46.132  23.411  1.00 52.72      A  C
ATOM   15761  CD   LYS G 209     -22.242 -46.447  24.647  1.00 53.58      A  C
ATOM   15762  CE   LYS G 209     -21.101 -45.474  24.827  1.00 53.75      A  C
ATOM   15763  NZ   LYS G 209     -20.235 -45.859  25.964  1.00 53.90      A  N
ATOM   15764  N    LYS G 210     -24.695 -48.701  20.051  1.00 42.83      A  N
ATOM   15765  CA   LYS G 210     -24.318 -49.491  18.897  1.00 36.00      A  C
ATOM   15766  C    LYS G 210     -25.261 -49.082  17.755  1.00 34.25      A  C
ATOM   15767  O    LYS G 210     -25.875 -48.001  17.788  1.00 32.92      A  O
ATOM   15768  CB   LYS G 210     -24.525 -50.969  19.204  1.00 34.24      A  C
ATOM   15769  CG   LYS G 210     -23.706 -51.440  20.402  1.00 30.73      A  C
ATOM   15770  CD   LYS G 210     -24.136 -52.810  20.876  1.00 27.22      A  C
ATOM   15771  CE   LYS G 210     -23.409 -53.199  22.162  1.00 25.25      A  C
ATOM   15772  NZ   LYS G 210     -24.063 -54.419  22.732  1.00 25.42      A  N
TER    15773       LYS G 210
ATOM   15774  N    PRO G 214     -26.926 -42.671  18.353  1.00 27.70      A  N
ATOM   15775  CA   PRO G 214     -27.739 -41.598  17.712  1.00 28.88      A  C
ATOM   15776  C    PRO G 214     -27.846 -40.311  18.580  1.00 31.27      A  C
ATOM   15777  O    PRO G 214     -26.984 -39.430  18.472  1.00 31.60      A  O
ATOM   15778  CB   PRO G 214     -29.111 -42.269  17.464  1.00 27.89      A  C
ATOM   15779  CG   PRO G 214     -28.975 -43.732  18.005  1.00 27.09      A  C
ATOM   15780  CD   PRO G 214     -27.498 -44.020  18.174  1.00 26.94      A  C
ATOM   15781  N    VAL G 215     -28.892 -40.225  19.413  1.00 35.88      A  N
ATOM   15782  CA   VAL G 215     -29.098 -39.212  20.472  1.00 36.11      A  C
ATOM   15783  C    VAL G 215     -28.730 -39.826  21.845  1.00 36.44      A  C
ATOM   15784  O    VAL G 215     -29.339 -40.818  22.277  1.00 36.71      A  O
ATOM   15785  CB   VAL G 215     -30.576 -38.736  20.501  1.00 35.42      A  C
ATOM   15786  CG1  VAL G 215     -30.722 -37.487  21.351  1.00 34.55      A  C
ATOM   15787  N    THR G 216     -27.740 -39.235  22.524  1.00 36.15      A  N
ATOM   15788  CA   THR G 216     -27.216 -39.796  23.780  1.00 35.61      A  C
ATOM   15789  C    THR G 216     -27.825 -39.193  25.051  1.00 35.13      A  C
ATOM   15790  O    THR G 216     -28.821 -38.457  24.988  1.00 35.11      A  O
ATOM   15791  CB   THR G 216     -25.687 -39.675  23.857  1.00 35.60      A  C
ATOM   15792  OG1  THR G 216     -25.159 -40.909  24.358  1.00 35.49      A  O
ATOM   15793  N    LEU G 217     -27.219 -39.511  26.198  1.00 34.53      A  N
ATOM   15794  CA   LEU G 217     -27.649 -38.974  27.499  1.00 33.73      A  C
ATOM   15795  C    LEU G 217     -26.491 -38.320  28.252  1.00 33.32      A  C
```

FIGURE 1 (cont'd)

```
ATOM  15796  O    LEU G 217     -25.381 -38.852  28.293  1.00 33.56      A   O
ATOM  15797  CB   LEU G 217     -28.299 -40.073  28.356  1.00 33.63      A   C
ATOM  15798  CG   LEU G 217     -28.653 -39.756  29.820  1.00 33.08      A   C
ATOM  15799  CD1  LEU G 217     -29.837 -38.812  29.921  1.00 32.85      A   C
ATOM  15800  CD2  LEU G 217     -28.928 -41.033  30.588  1.00 33.14      A   C
ATOM  15801  N    GLN G 218     -26.766 -37.172  28.851  1.00 32.50      A   N
ATOM  15802  CA   GLN G 218     -25.749 -36.436  29.567  1.00 31.89      A   C
ATOM  15803  C    GLN G 218     -26.229 -36.097  30.978  1.00 31.34      A   C
ATOM  15804  O    GLN G 218     -27.373 -35.680  31.169  1.00 31.29      A   O
ATOM  15805  CB   GLN G 218     -25.384 -35.171  28.792  1.00 31.93      A   C
ATOM  15806  CG   GLN G 218     -24.224 -34.391  29.372  1.00 32.14      A   C
ATOM  15807  CD   GLN G 218     -24.029 -33.051  28.699  1.00 32.82      A   C
ATOM  15808  NE2  GLN G 218     -25.037 -32.191  28.777  1.00 32.87      A   N
ATOM  15809  OE1  GLN G 218     -22.983 -32.791  28.111  1.00 33.65      A   O
ATOM  15810  N    LEU G 219     -25.363 -36.286  31.969  1.00 30.76      A   N
ATOM  15811  CA   LEU G 219     -25.710 -35.964  33.350  1.00 30.07      A   C
ATOM  15812  C    LEU G 219     -24.788 -34.878  33.889  1.00 29.79      A   C
ATOM  15813  O    LEU G 219     -23.573 -35.035  33.913  1.00 29.91      A   O
ATOM  15814  CB   LEU G 219     -25.674 -37.223  34.225  1.00 29.92      A   C
ATOM  15815  CG   LEU G 219     -26.642 -38.339  33.825  1.00 29.64      A   C
ATOM  15816  CD1  LEU G 219     -26.424 -39.570  34.681  1.00 29.40      A   C
ATOM  15817  CD2  LEU G 219     -28.102 -37.867  33.885  1.00 29.21      A   C
ATOM  15818  N    LEU G 220     -25.366 -33.763  34.300  1.00 29.25      A   N
ATOM  15819  CA   LEU G 220     -24.564 -32.678  34.828  1.00 28.84      A   C
ATOM  15820  C    LEU G 220     -24.801 -32.499  36.316  1.00 29.00      A   C
ATOM  15821  O    LEU G 220     -25.949 -32.339  36.753  1.00 29.05      A   O
ATOM  15822  CB   LEU G 220     -24.849 -31.377  34.087  1.00 28.11      A   C
ATOM  15823  CG   LEU G 220     -24.716 -31.435  32.570  1.00 27.42      A   C
ATOM  15824  CD1  LEU G 220     -24.785 -30.023  32.011  1.00 26.98      A   C
ATOM  15825  CD2  LEU G 220     -23.489 -32.204  32.079  1.00 27.22      A   C
ATOM  15826  N    PHE G 221     -23.712 -32.542  37.086  1.00 29.12      A   N
ATOM  15827  CA   PHE G 221     -23.736 -32.258  38.528  1.00 29.08      A   C
ATOM  15828  C    PHE G 221     -22.958 -30.972  38.784  1.00 29.12      A   C
ATOM  15829  O    PHE G 221     -21.728 -30.976  38.825  1.00 29.22      A   O
ATOM  15830  CB   PHE G 221     -23.126 -33.420  39.308  1.00 29.09      A   C
ATOM  15831  CG   PHE G 221     -23.813 -34.737  39.073  1.00 29.14      A   C
ATOM  15832  CD1  PHE G 221     -24.795 -35.195  39.960  1.00 29.23      A   C
ATOM  15833  CD2  PHE G 221     -23.483 -35.529  37.977  1.00 29.24      A   C
ATOM  15834  CE1  PHE G 221     -25.457 -36.432  39.756  1.00 29.26      A   C
ATOM  15835  CE2  PHE G 221     -24.130 -36.762  37.764  1.00 29.51      A   C
ATOM  15836  CZ   PHE G 221     -25.126 -37.211  38.659  1.00 29.37      A   C
ATOM  15837  N    LEU G 222     -23.673 -29.868  38.936  1.00 29.13      A   N
ATOM  15838  CA   LEU G 222     -23.033 -28.560  38.961  1.00 29.41      A   C
ATOM  15839  C    LEU G 222     -22.598 -28.152  40.358  1.00 29.76      A   C
ATOM  15840  O    LEU G 222     -23.303 -28.392  41.324  1.00 29.81      A   O
ATOM  15841  CB   LEU G 222     -23.965 -27.505  38.358  1.00 29.24      A   C
ATOM  15842  CG   LEU G 222     -24.447 -27.850  36.944  1.00 29.08      A   C
ATOM  15843  CD1  LEU G 222     -23.576 -27.188  35.883  1.00 29.16      A   C
ATOM  15844  CD2  LEU G 222     -25.888 -27.443  36.762  1.00 28.74      A   C
ATOM  15845  N    ASP G 223     -21.429 -27.538  40.463  1.00 30.32      A   N
ATOM  15846  CA   ASP G 223     -20.948 -27.009  41.740  1.00 30.91      A   C
ATOM  15847  C    ASP G 223     -21.407 -25.548  41.908  1.00 30.93      A   C
ATOM  15848  O    ASP G 223     -21.899 -24.925  40.959  1.00 30.83      A   O
ATOM  15849  CB   ASP G 223     -19.414 -27.101  41.800  1.00 31.33      A   C
ATOM  15850  CG   ASP G 223     -18.861 -27.051  43.223  1.00 32.39      A   C
ATOM  15851  OD1  ASP G 223     -19.648 -27.147  44.193  1.00 33.32      A   O
ATOM  15852  OD2  ASP G 223     -17.621 -26.928  43.367  1.00 33.13      A   O
ATOM  15853  N    GLY G 224     -21.257 -25.027  43.122  1.00 31.05      A   N
ATOM  15854  CA   GLY G 224     -21.497 -23.624  43.434  1.00 31.24      A   C
ATOM  15855  C    GLY G 224     -22.656 -22.978  42.717  1.00 31.20      A   C
ATOM  15856  O    GLY G 224     -22.460 -22.071  41.917  1.00 31.39      A   O
ATOM  15857  N    GLU G 225     -23.863 -23.453  42.997  1.00 31.05      A   N
ATOM  15858  CA   GLU G 225     -25.065 -22.848  42.441  1.00 30.97      A   C
ATOM  15859  C    GLU G 225     -25.625 -21.859  43.434  1.00 31.02      A   C
ATOM  15860  O    GLU G 225     -25.967 -20.740  43.064  1.00 30.96      A   O
```

FIGURE 1 (cont'd)

```
ATOM  15861  CB   GLU G 225     -26.099 -23.915  42.090  1.00 30.82      A  C
ATOM  15862  CG   GLU G 225     -27.380 -23.362  41.516  1.00 31.09      A  C
ATOM  15863  CD   GLU G 225     -28.374 -22.999  42.584  1.00 31.89      A  C
ATOM  15864  OE1  GLU G 225     -28.415 -23.698  43.628  1.00 32.65      A  O
ATOM  15865  OE2  GLU G 225     -29.110 -22.011  42.376  1.00 32.35      A  O
ATOM  15866  N    GLU G 226     -25.711 -22.288  44.690  1.00 31.30      A  N
ATOM  15867  CA   GLU G 226     -26.168 -21.440  45.783  1.00 31.79      A  C
ATOM  15868  C    GLU G 226     -25.164 -20.328  46.052  1.00 32.43      A  C
ATOM  15869  O    GLU G 226     -23.957 -20.560  46.021  1.00 32.60      A  O
ATOM  15870  CB   GLU G 226     -26.364 -22.271  47.047  1.00 31.69      A  C
ATOM  15871  CG   GLU G 226     -27.330 -23.454  46.885  1.00 30.97      A  C
ATOM  15872  CD   GLU G 226     -28.767 -23.122  47.292  1.00 30.30      A  C
ATOM  15873  OE1  GLU G 226     -29.157 -21.918  47.275  1.00 30.24      A  O
ATOM  15874  OE2  GLU G 226     -29.504 -24.081  47.635  1.00 29.68      A  O
ATOM  15875  N    ALA G 227     -25.681 -19.128  46.309  1.00 33.01      A  N
ATOM  15876  CA   ALA G 227     -24.869 -17.940  46.600  1.00 33.76      A  C
ATOM  15877  C    ALA G 227     -24.028 -18.084  47.867  1.00 34.42      A  C
ATOM  15878  O    ALA G 227     -24.255 -18.979  48.697  1.00 34.50      A  O
ATOM  15879  CB   ALA G 227     -25.759 -16.719  46.725  1.00 33.74      A  C
ATOM  15880  N    LEU G 228     -23.054 -17.193  48.019  1.00 35.23      A  N
ATOM  15881  CA   LEU G 228     -22.199 -17.222  49.207  1.00 35.96      A  C
ATOM  15882  C    LEU G 228     -22.494 -16.089  50.203  1.00 36.70      A  C
ATOM  15883  O    LEU G 228     -22.589 -16.343  51.410  1.00 36.95      A  O
ATOM  15884  CB   LEU G 228     -20.702 -17.312  48.847  1.00 35.89      A  C
ATOM  15885  CG   LEU G 228     -20.070 -18.662  48.440  1.00 35.22      A  C
ATOM  15886  CD1  LEU G 228     -19.741 -18.712  46.958  1.00 34.78      A  C
ATOM  15887  CD2  LEU G 228     -20.883 -19.887  48.844  1.00 34.59      A  C
ATOM  15888  N    LYS G 229     -22.626 -14.853  49.712  1.00 37.41      A  N
ATOM  15889  CA   LYS G 229     -23.054 -13.744  50.569  1.00 38.18      A  C
ATOM  15890  C    LYS G 229     -24.551 -13.590  50.383  1.00 38.18      A  C
ATOM  15891  O    LYS G 229     -25.311 -14.200  51.122  1.00 38.17      A  O
ATOM  15892  CB   LYS G 229     -22.295 -12.442  50.275  1.00 38.71      A  C
ATOM  15893  CG   LYS G 229     -22.478 -11.324  51.334  1.00 39.51      A  C
ATOM  15894  CD   LYS G 229     -21.410 -11.368  52.430  1.00 40.06      A  C
ATOM  15895  N    GLU G 230     -24.985 -12.798  49.404  1.00 38.37      A  N
ATOM  15896  CA   GLU G 230     -26.395 -12.843  48.994  1.00 38.58      A  C
ATOM  15897  C    GLU G 230     -26.607 -12.950  47.475  1.00 38.30      A  C
ATOM  15898  O    GLU G 230     -25.848 -12.375  46.683  1.00 38.31      A  O
ATOM  15899  CB   GLU G 230     -27.257 -11.735  49.643  1.00 38.96      A  C
ATOM  15900  CG   GLU G 230     -28.790 -12.107  49.761  1.00 39.91      A  C
ATOM  15901  CD   GLU G 230     -29.080 -13.466  50.483  1.00 40.11      A  C
ATOM  15902  OE1  GLU G 230     -29.379 -14.504  49.825  1.00 38.79      A  O
ATOM  15903  N    TRP G 231     -27.644 -13.714  47.113  1.00 37.98      A  N
ATOM  15904  CA   TRP G 231     -28.032 -14.007  45.732  1.00 37.70      A  C
ATOM  15905  C    TRP G 231     -28.034 -12.779  44.840  1.00 38.05      A  C
ATOM  15906  O    TRP G 231     -28.609 -11.732  45.185  1.00 38.36      A  O
ATOM  15907  CB   TRP G 231     -29.419 -14.653  45.689  1.00 37.36      A  C
ATOM  15908  CG   TRP G 231     -29.757 -15.211  44.357  1.00 36.75      A  C
ATOM  15909  CD1  TRP G 231     -30.329 -14.549  43.314  1.00 36.70      A  C
ATOM  15910  CD2  TRP G 231     -29.534 -16.553  43.917  1.00 36.14      A  C
ATOM  15911  CE2  TRP G 231     -30.000 -16.637  42.591  1.00 35.90      A  C
ATOM  15912  CE3  TRP G 231     -28.989 -17.699  44.519  1.00 35.80      A  C
ATOM  15913  NE1  TRP G 231     -30.475 -15.397  42.244  1.00 36.36      A  N
ATOM  15914  CZ2  TRP G 231     -29.938 -17.826  41.849  1.00 35.26      A  C
ATOM  15915  CZ3  TRP G 231     -28.928 -18.882  43.779  1.00 35.08      A  C
ATOM  15916  CH2  TRP G 231     -29.399 -18.933  42.460  1.00 34.78      A  C
ATOM  15917  N    GLY G 232     -27.392 -12.934  43.689  1.00 38.17      A  N
ATOM  15918  CA   GLY G 232     -27.266 -11.870  42.713  1.00 38.52      A  C
ATOM  15919  C    GLY G 232     -26.545 -12.378  41.483  1.00 38.71      A  C
ATOM  15920  O    GLY G 232     -25.979 -13.472  41.503  1.00 38.43      A  O
ATOM  15921  N    PRO G 233     -26.566 -11.589  40.397  1.00 39.16      A  N
ATOM  15922  CA   PRO G 233     -25.933 -11.966  39.136  1.00 39.29      A  C
ATOM  15923  C    PRO G 233     -24.462 -12.347  39.288  1.00 39.51      A  C
ATOM  15924  O    PRO G 233     -23.998 -13.255  38.599  1.00 39.21      A  O
ATOM  15925  CB   PRO G 233     -26.077 -10.703  38.289  1.00 39.50      A  C
```

FIGURE 1 (cont'd)

```
ATOM  15926  CG   PRO G 233     -27.315 -10.057  38.797  1.00 39.64      A  C
ATOM  15927  CD   PRO G 233     -27.300 -10.311  40.281  1.00 39.45      A  C
ATOM  15928  N    LYS G 234     -23.741 -11.667  40.179  1.00 40.10      A  N
ATOM  15929  CA   LYS G 234     -22.308 -11.949  40.396  1.00 40.69      A  C
ATOM  15930  C    LYS G 234     -22.029 -12.939  41.545  1.00 40.47      A  C
ATOM  15931  O    LYS G 234     -20.892 -13.389  41.718  1.00 40.58      A  O
ATOM  15932  CB   LYS G 234     -21.501 -10.647  40.566  1.00 41.29      A  C
ATOM  15933  CG   LYS G 234     -21.108  -9.976  39.239  1.00 42.33      A  C
ATOM  15934  CD   LYS G 234     -20.882  -8.453  39.373  1.00 43.54      A  C
ATOM  15935  CE   LYS G 234     -19.429  -8.081  39.737  1.00 43.76      A  C
ATOM  15936  N    ASP G 235     -23.072 -13.280  42.309  1.00 40.11      A  N
ATOM  15937  CA   ASP G 235     -22.978 -14.259  43.406  1.00 39.61      A  C
ATOM  15938  C    ASP G 235     -24.081 -15.318  43.289  1.00 39.08      A  C
ATOM  15939  O    ASP G 235     -25.085 -15.265  44.012  1.00 39.08      A  O
ATOM  15940  CB   ASP G 235     -23.008 -13.556  44.794  1.00 39.87      A  C
ATOM  15941  CG   ASP G 235     -22.901 -14.545  45.985  1.00 39.58      A  C
ATOM  15942  OD1  ASP G 235     -23.494 -14.252  47.054  1.00 39.28      A  O
ATOM  15943  OD2  ASP G 235     -22.235 -15.607  45.853  1.00 39.20      A  O
ATOM  15944  N    SER G 236     -23.888 -16.257  42.361  1.00 38.46      A  N
ATOM  15945  CA   SER G 236     -24.799 -17.396  42.139  1.00 37.82      A  C
ATOM  15946  C    SER G 236     -24.468 -18.104  40.842  1.00 37.50      A  C
ATOM  15947  O    SER G 236     -24.046 -17.467  39.876  1.00 37.53      A  O
ATOM  15948  CB   SER G 236     -26.263 -16.948  42.080  1.00 37.69      A  C
ATOM  15949  OG   SER G 236     -26.507 -16.164  40.928  1.00 37.59      A  O
ATOM  15950  N    LEU G 237     -24.684 -19.416  40.815  1.00 37.17      A  N
ATOM  15951  CA   LEU G 237     -24.552 -20.194  39.582  1.00 37.08      A  C
ATOM  15952  C    LEU G 237     -23.126 -20.134  39.014  1.00 37.27      A  C
ATOM  15953  O    LEU G 237     -22.923 -19.896  37.813  1.00 37.38      A  O
ATOM  15954  CB   LEU G 237     -25.546 -19.706  38.513  1.00 36.93      A  C
ATOM  15955  CG   LEU G 237     -26.991 -19.333  38.852  1.00 36.59      A  C
ATOM  15956  CD1  LEU G 237     -27.602 -18.435  37.776  1.00 36.65      A  C
ATOM  15957  CD2  LEU G 237     -27.814 -20.587  39.041  1.00 36.11      A  C
ATOM  15958  N    TYR G 238     -22.140 -20.350  39.879  1.00 37.40      A  N
ATOM  15959  CA   TYR G 238     -20.742 -20.385  39.447  1.00 37.50      A  C
ATOM  15960  C    TYR G 238     -20.436 -21.579  38.536  1.00 37.16      A  C
ATOM  15961  O    TYR G 238     -19.736 -21.429  37.539  1.00 37.26      A  O
ATOM  15962  CB   TYR G 238     -19.793 -20.380  40.652  1.00 37.81      A  C
ATOM  15963  CG   TYR G 238     -19.933 -19.165  41.545  1.00 38.40      A  C
ATOM  15964  CD1  TYR G 238     -19.441 -17.923  41.151  1.00 39.34      A  C
ATOM  15965  CD2  TYR G 238     -20.556 -19.255  42.785  1.00 38.51      A  C
ATOM  15966  CE1  TYR G 238     -19.575 -16.800  41.976  1.00 39.71      A  C
ATOM  15967  CE2  TYR G 238     -20.689 -18.137  43.610  1.00 38.97      A  C
ATOM  15968  CZ   TYR G 238     -20.198 -16.921  43.194  1.00 39.35      A  C
ATOM  15969  OH   TYR G 238     -20.316 -15.823  43.990  1.00 39.59      A  O
ATOM  15970  N    GLY G 239     -20.961 -22.752  38.881  1.00 36.72      A  N
ATOM  15971  CA   GLY G 239     -20.724 -23.963  38.098  1.00 36.45      A  C
ATOM  15972  C    GLY G 239     -21.375 -23.954  36.725  1.00 36.26      A  C
ATOM  15973  O    GLY G 239     -20.748 -24.315  35.726  1.00 36.32      A  O
ATOM  15974  N    SER G 240     -22.638 -23.541  36.680  1.00 36.01      A  N
ATOM  15975  CA   SER G 240     -23.396 -23.470  35.435  1.00 35.74      A  C
ATOM  15976  C    SER G 240     -22.916 -22.349  34.503  1.00 35.74      A  C
ATOM  15977  O    SER G 240     -22.741 -22.583  33.302  1.00 35.82      A  O
ATOM  15978  CB   SER G 240     -24.896 -23.341  35.726  1.00 35.61      A  C
ATOM  15979  OG   SER G 240     -25.146 -22.458  36.815  1.00 35.92      A  O
ATOM  15980  N    ARG G 241     -22.699 -21.146  35.046  1.00 35.70      A  N
ATOM  15981  CA   ARG G 241     -22.173 -20.044  34.243  1.00 35.94      A  C
ATOM  15982  C    ARG G 241     -20.827 -20.372  33.584  1.00 36.02      A  C
ATOM  15983  O    ARG G 241     -20.553 -19.955  32.457  1.00 36.23      A  O
ATOM  15984  CB   ARG G 241     -22.068 -18.764  35.061  1.00 36.04      A  C
ATOM  15985  CG   ARG G 241     -23.329 -17.923  35.016  1.00 36.66      A  C
ATOM  15986  CD   ARG G 241     -23.095 -16.494  35.518  1.00 38.00      A  C
ATOM  15987  NE   ARG G 241     -22.975 -16.408  36.980  1.00 39.21      A  N
ATOM  15988  CZ   ARG G 241     -21.831 -16.204  37.637  1.00 40.17      A  C
ATOM  15989  NH1  ARG G 241     -20.688 -16.052  36.974  1.00 41.15      A  N
ATOM  15990  NH2  ARG G 241     -21.826 -16.147  38.964  1.00 40.48      A  N
```

FIGURE 1 (cont'd)

```
ATOM  15991  N    HIS G 242     -19.996 -21.130  34.290  1.00 35.99      A  N
ATOM  15992  CA   HIS G 242     -18.689 -21.532  33.776  1.00 36.07      A  C
ATOM  15993  C    HIS G 242     -18.797 -22.646  32.738  1.00 35.71      A  C
ATOM  15994  O    HIS G 242     -18.241 -22.527  31.645  1.00 35.91      A  O
ATOM  15995  CB   HIS G 242     -17.768 -21.957  34.921  1.00 36.33      A  C
ATOM  15996  CG   HIS G 242     -16.399 -22.353  34.476  1.00 37.13      A  C
ATOM  15997  CD2  HIS G 242     -15.302 -21.608  34.196  1.00 37.92      A  C
ATOM  15998  ND1  HIS G 242     -16.041 -23.666  34.264  1.00 37.27      A  N
ATOM  15999  CE1  HIS G 242     -14.778 -23.713  33.876  1.00 37.98      A  C
ATOM  16000  NE2  HIS G 242     -14.306 -22.479  33.827  1.00 38.39      A  N
ATOM  16001  N    LEU G 243     -19.503 -23.722  33.083  1.00 35.11      A  N
ATOM  16002  CA   LEU G 243     -19.711 -24.829  32.157  1.00 34.64      A  C
ATOM  16003  C    LEU G 243     -20.322 -24.346  30.846  1.00 34.75      A  C
ATOM  16004  O    LEU G 243     -19.871 -24.748  29.775  1.00 34.93      A  O
ATOM  16005  CB   LEU G 243     -20.584 -25.925  32.774  1.00 34.20      A  C
ATOM  16006  CG   LEU G 243     -20.779 -27.174  31.907  1.00 33.49      A  C
ATOM  16007  CD1  LEU G 243     -19.447 -27.872  31.683  1.00 33.27      A  C
ATOM  16008  CD2  LEU G 243     -21.779 -28.125  32.531  1.00 32.88      A  C
ATOM  16009  N    ALA G 244     -21.340 -23.484  30.941  1.00 34.79      A  N
ATOM  16010  CA   ALA G 244     -21.949 -22.861  29.760  1.00 35.07      A  C
ATOM  16011  C    ALA G 244     -20.892 -22.155  28.900  1.00 35.54      A  C
ATOM  16012  O    ALA G 244     -20.813 -22.405  27.694  1.00 35.71      A  O
ATOM  16013  CB   ALA G 244     -23.065 -21.897  30.161  1.00 34.78      A  C
ATOM  16014  N    GLN G 245     -20.067 -21.309  29.527  1.00 36.05      A  N
ATOM  16015  CA   GLN G 245     -18.963 -20.632  28.834  1.00 36.63      A  C
ATOM  16016  C    GLN G 245     -18.022 -21.630  28.151  1.00 36.96      A  C
ATOM  16017  O    GLN G 245     -17.717 -21.478  26.965  1.00 37.22      A  O
ATOM  16018  CB   GLN G 245     -18.186 -19.715  29.791  1.00 36.70      A  C
ATOM  16019  N    LEU G 246     -17.600 -22.652  28.900  1.00 37.08      A  N
ATOM  16020  CA   LEU G 246     -16.643 -23.664  28.428  1.00 37.35      A  C
ATOM  16021  C    LEU G 246     -17.206 -24.600  27.335  1.00 37.76      A  C
ATOM  16022  O    LEU G 246     -16.453 -25.127  26.508  1.00 38.04      A  O
ATOM  16023  CB   LEU G 246     -16.100 -24.470  29.617  1.00 37.07      A  C
ATOM  16024  CG   LEU G 246     -14.989 -25.504  29.427  1.00 36.47      A  C
ATOM  16025  CD1  LEU G 246     -15.540 -26.910  29.642  1.00 35.21      A  C
ATOM  16026  N    MET G 247     -18.521 -24.806  27.333  1.00 38.05      A  N
ATOM  16027  CA   MET G 247     -19.164 -25.620  26.298  1.00 38.48      A  C
ATOM  16028  C    MET G 247     -19.319 -24.844  24.994  1.00 39.25      A  C
ATOM  16029  O    MET G 247     -19.332 -25.426  23.906  1.00 39.43      A  O
ATOM  16030  CB   MET G 247     -20.525 -26.142  26.771  1.00 37.98      A  C
ATOM  16031  CG   MET G 247     -20.434 -27.254  27.795  1.00 37.33      A  C
ATOM  16032  SD   MET G 247     -22.014 -28.052  28.109  1.00 36.58      A  S
ATOM  16033  CE   MET G 247     -21.980 -29.394  26.921  1.00 36.93      A  C
ATOM  16034  N    GLU G 248     -19.441 -23.527  25.120  1.00 40.13      A  N
ATOM  16035  CA   GLU G 248     -19.555 -22.645  23.966  1.00 41.19      A  C
ATOM  16036  C    GLU G 248     -18.224 -22.598  23.229  1.00 42.23      A  C
ATOM  16037  O    GLU G 248     -18.193 -22.475  21.997  1.00 42.80      A  O
ATOM  16038  CB   GLU G 248     -19.964 -21.226  24.402  1.00 41.04      A  C
ATOM  16039  CG   GLU G 248     -20.652 -20.338  23.335  1.00 41.05      A  C
ATOM  16040  CD   GLU G 248     -20.808 -18.860  23.760  1.00 41.29      A  C
ATOM  16041  OE1  GLU G 248     -21.659 -18.167  23.166  1.00 42.27      A  O
ATOM  16042  OE2  GLU G 248     -20.095 -18.377  24.672  1.00 40.70      A  O
ATOM  16043  N    SER G 249     -17.126 -22.702  23.978  1.00 43.07      A  N
ATOM  16044  CA   SER G 249     -15.786 -22.634  23.388  1.00 44.01      A  C
ATOM  16045  C    SER G 249     -15.279 -23.998  22.881  1.00 44.49      A  C
ATOM  16046  O    SER G 249     -14.221 -24.083  22.255  1.00 44.93      A  O
ATOM  16047  CB   SER G 249     -14.795 -22.008  24.374  1.00 44.11      A  C
ATOM  16048  OG   SER G 249     -14.432 -22.932  25.381  1.00 44.12      A  O
ATOM  16049  N    ILE G 250     -16.046 -25.053  23.133  1.00 44.77      A  N
ATOM  16050  CA   ILE G 250     -15.629 -26.398  22.781  1.00 45.29      A  C
ATOM  16051  C    ILE G 250     -16.372 -26.876  21.526  1.00 46.12      A  C
ATOM  16052  O    ILE G 250     -17.563 -27.199  21.593  1.00 45.91      A  O
ATOM  16053  CB   ILE G 250     -15.835 -27.353  23.976  1.00 44.83      A  C
ATOM  16054  CG1  ILE G 250     -14.893 -28.552  23.886  1.00 44.79      A  C
ATOM  16055  CD1  ILE G 250     -15.575 -29.847  23.467  1.00 44.42      A  C
```

FIGURE 1 (cont'd)

```
ATOM  16056  N    PRO G 251     -15.671 -26.907  20.371  1.00 47.23      A  N
ATOM  16057  CA   PRO G 251     -16.252 -27.291  19.091  1.00 47.89      A  C
ATOM  16058  C    PRO G 251     -16.732 -28.708  19.076  1.00 48.32      A  C
ATOM  16059  O    PRO G 251     -16.150 -29.597  19.703  1.00 48.39      A  O
ATOM  16060  CB   PRO G 251     -15.088 -27.149  18.115  1.00 48.23      A  C
ATOM  16061  CG   PRO G 251     -14.194 -26.178  18.752  1.00 48.26      A  C
ATOM  16062  CD   PRO G 251     -14.264 -26.515  20.204  1.00 47.61      A  C
ATOM  16063  N    HIS G 252     -17.806 -28.894  18.341  1.00 48.76      A  N
ATOM  16064  CA   HIS G 252     -18.464 -30.145  18.287  1.00 49.12      A  C
ATOM  16065  C    HIS G 252     -19.186 -30.186  16.973  1.00 49.72      A  C
ATOM  16066  O    HIS G 252     -19.465 -29.196  16.305  1.00 49.95      A  O
ATOM  16067  CB   HIS G 252     -19.401 -30.339  19.491  1.00 47.95      A  C
ATOM  16068  CG   HIS G 252     -20.072 -31.684  19.549  1.00 47.79      A  C
ATOM  16069  CD2  HIS G 252     -21.360 -32.040  19.320  1.00 47.60      A  C
ATOM  16070  ND1  HIS G 252     -19.413 -32.845  19.904  1.00 48.08      A  N
ATOM  16071  CE1  HIS G 252     -20.266 -33.857  19.880  1.00 48.06      A  C
ATOM  16072  NE2  HIS G 252     -21.452 -33.396  19.522  1.00 47.81      A  N
ATOM  16073  N    SER G 253     -19.551 -31.424  16.783  1.00 50.13      A  N
ATOM  16074  CA   SER G 253     -19.589 -32.322  15.696  1.00 50.15      A  C
ATOM  16075  C    SER G 253     -20.305 -32.185  14.405  1.00 50.26      A  C
ATOM  16076  O    SER G 253     -19.802 -32.756  13.496  1.00 50.68      A  O
ATOM  16077  CB   SER G 253     -20.139 -33.545  16.329  1.00 49.32      A  C
ATOM  16078  OG   SER G 253     -19.388 -34.677  16.170  1.00 48.83      A  O
ATOM  16079  N    PRO G 254     -21.605 -31.907  14.385  1.00 49.86      A  N
ATOM  16080  CA   PRO G 254     -22.235 -30.769  13.764  1.00 49.47      A  C
ATOM  16081  C    PRO G 254     -23.010 -30.084  14.827  1.00 49.07      A  C
ATOM  16082  O    PRO G 254     -24.231 -30.137  14.785  1.00 49.23      A  O
ATOM  16083  CB   PRO G 254     -23.271 -31.379  12.811  1.00 48.70      A  C
ATOM  16084  CG   PRO G 254     -22.911 -32.743  12.631  1.00 48.83      A  C
ATOM  16085  CD   PRO G 254     -22.189 -33.169  13.864  1.00 49.11      A  C
ATOM  16086  N    GLY G 255     -22.320 -29.513  15.804  1.00 48.42      A  N
ATOM  16087  CA   GLY G 255     -22.879 -28.440  16.589  1.00 47.56      A  C
ATOM  16088  C    GLY G 255     -22.893 -27.212  15.704  1.00 47.10      A  C
ATOM  16089  O    GLY G 255     -23.756 -27.110  14.843  1.00 47.36      A  O
ATOM  16090  N    PRO G 256     -22.153 -26.184  16.138  1.00 46.62      A  N
ATOM  16091  CA   PRO G 256     -20.840 -25.603  15.907  1.00 46.35      A  C
ATOM  16092  C    PRO G 256     -20.078 -25.901  17.211  1.00 45.76      A  C
ATOM  16093  O    PRO G 256     -19.002 -26.501  17.177  1.00 45.96      A  O
ATOM  16094  CB   PRO G 256     -21.121 -24.103  15.807  1.00 46.51      A  C
ATOM  16095  CG   PRO G 256     -22.471 -24.024  15.306  1.00 46.54      A  C
ATOM  16096  CD   PRO G 256     -23.149 -25.096  16.138  1.00 46.55      A  C
ATOM  16097  N    THR G 257     -20.675 -25.512  18.346  1.00 44.74      A  N
ATOM  16098  CA   THR G 257     -20.137 -25.767  19.688  1.00 43.66      A  C
ATOM  16099  C    THR G 257     -20.880 -26.898  20.427  1.00 42.95      A  C
ATOM  16100  O    THR G 257     -21.894 -27.406  19.947  1.00 42.86      A  O
ATOM  16101  CB   THR G 257     -20.164 -24.491  20.546  1.00 43.44      A  C
ATOM  16102  OG1  THR G 257     -21.490 -23.963  20.577  1.00 43.05      A  O
ATOM  16103  N    ARG G 258     -20.374 -27.295  21.595  1.00 42.10      A  N
ATOM  16104  CA   ARG G 258     -21.026 -28.335  22.393  1.00 41.07      A  C
ATOM  16105  C    ARG G 258     -22.364 -27.882  22.972  1.00 40.56      A  C
ATOM  16106  O    ARG G 258     -23.177 -28.715  23.371  1.00 40.54      A  O
ATOM  16107  CB   ARG G 258     -20.105 -28.862  23.498  1.00 40.14      A  C
ATOM  16108  CG   ARG G 258     -19.319 -30.088  23.078  1.00 40.08      A  C
ATOM  16109  CD   ARG G 258     -19.003 -30.995  24.257  1.00 40.03      A  C
ATOM  16110  NE   ARG G 258     -18.327 -32.221  23.844  1.00 40.30      A  N
ATOM  16111  N    ILE G 259     -22.593 -26.570  23.000  1.00 39.83      A  N
ATOM  16112  CA   ILE G 259     -23.864 -26.028  23.454  1.00 38.89      A  C
ATOM  16113  C    ILE G 259     -25.039 -26.460  22.591  1.00 38.83      A  C
ATOM  16114  O    ILE G 259     -26.133 -26.711  23.097  1.00 38.83      A  O
ATOM  16115  CB   ILE G 259     -23.829 -24.530  23.515  1.00 37.98      A  C
ATOM  16116  CG1  ILE G 259     -23.840 -24.121  24.972  1.00 37.65      A  C
ATOM  16117  CD1  ILE G 259     -23.026 -22.928  25.241  1.00 38.53      A  C
ATOM  16118  N    GLN G 260     -24.802 -26.575  21.291  1.00 38.52      A  N
ATOM  16119  CA   GLN G 260     -25.841 -27.004  20.363  1.00 37.92      A  C
ATOM  16120  C    GLN G 260     -26.037 -28.516  20.434  1.00 37.77      A  C
```

FIGURE 1 (cont'd)

```
ATOM  16121  O    GLN G 260     -26.927 -29.060  19.772  1.00 38.21      A    O
ATOM  16122  CB   GLN G 260     -25.535 -26.576  18.918  1.00 37.08      A    C
ATOM  16123  CG   GLN G 260     -24.354 -25.634  18.721  1.00 36.67      A    C
ATOM  16124  CD   GLN G 260     -24.428 -24.360  19.524  1.00 36.32      A    C
ATOM  16125  OE1  GLN G 260     -25.404 -23.632  19.483  1.00 36.74      A    O
ATOM  16126  N    ALA G 261     -25.212 -29.190  21.233  1.00 37.14      A    N
ATOM  16127  CA   ALA G 261     -25.336 -30.631  21.408  1.00 36.49      A    C
ATOM  16128  C    ALA G 261     -26.450 -31.004  22.395  1.00 35.75      A    C
ATOM  16129  O    ALA G 261     -26.964 -32.130  22.363  1.00 35.67      A    O
ATOM  16130  N    ILE G 262     -26.818 -30.055  23.260  1.00 34.75      A    N
ATOM  16131  CA   ILE G 262     -27.934 -30.226  24.196  1.00 33.67      A    C
ATOM  16132  C    ILE G 262     -29.254 -30.093  23.444  1.00 33.58      A    C
ATOM  16133  O    ILE G 262     -29.659 -28.983  23.088  1.00 33.72      A    O
ATOM  16134  CB   ILE G 262     -27.915 -29.173  25.328  1.00 32.73      A    C
ATOM  16135  CG1  ILE G 262     -26.528 -29.076  25.964  1.00 32.14      A    C
ATOM  16136  CD1  ILE G 262     -26.274 -27.761  26.672  1.00 31.72      A    C
ATOM  16137  N    GLU G 263     -29.905 -31.228  23.190  1.00 33.21      A    N
ATOM  16138  CA   GLU G 263     -31.225 -31.240  22.563  1.00 32.81      A    C
ATOM  16139  C    GLU G 263     -32.252 -30.736  23.565  1.00 32.20      A    C
ATOM  16140  O    GLU G 263     -33.178 -30.020  23.206  1.00 32.34      A    O
ATOM  16141  CB   GLU G 263     -31.603 -32.647  22.066  1.00 33.02      A    C
ATOM  16142  CG   GLU G 263     -32.719 -32.699  21.008  1.00 33.02      A    C
ATOM  16143  CD   GLU G 263     -32.864 -34.068  20.363  1.00 32.59      A    C
ATOM  16144  N    LEU G 264     -32.079 -31.107  24.827  1.00 31.34      A    N
ATOM  16145  CA   LEU G 264     -32.952 -30.641  25.896  1.00 30.35      A    C
ATOM  16146  C    LEU G 264     -32.225 -30.609  27.237  1.00 29.76      A    C
ATOM  16147  O    LEU G 264     -31.693 -31.630  27.696  1.00 29.79      A    O
ATOM  16148  CB   LEU G 264     -34.194 -31.528  26.000  1.00 30.26      A    C
ATOM  16149  CG   LEU G 264     -35.198 -31.177  27.094  1.00 29.83      A    C
ATOM  16150  CD1  LEU G 264     -35.754 -29.763  26.928  1.00 29.72      A    C
ATOM  16151  CD2  LEU G 264     -36.307 -32.196  27.096  1.00 29.61      A    C
ATOM  16152  N    PHE G 265     -32.221 -29.430  27.855  1.00 28.92      A    N
ATOM  16153  CA   PHE G 265     -31.664 -29.215  29.197  1.00 27.93      A    C
ATOM  16154  C    PHE G 265     -32.787 -29.308  30.241  1.00 27.64      A    C
ATOM  16155  O    PHE G 265     -33.515 -28.332  30.478  1.00 27.51      A    O
ATOM  16156  CB   PHE G 265     -30.995 -27.836  29.240  1.00 27.65      A    C
ATOM  16157  CG   PHE G 265     -30.132 -27.583  30.450  1.00 26.30      A    C
ATOM  16158  CD1  PHE G 265     -28.761 -27.802  30.394  1.00 25.37      A    C
ATOM  16159  CD2  PHE G 265     -30.681 -27.068  31.623  1.00 25.22      A    C
ATOM  16160  CE1  PHE G 265     -27.958 -27.535  31.493  1.00 24.90      A    C
ATOM  16161  CE2  PHE G 265     -29.885 -26.790  32.724  1.00 24.52      A    C
ATOM  16162  CZ   PHE G 265     -28.525 -27.028  32.663  1.00 24.59      A    C
ATOM  16163  N    MET G 266     -32.929 -30.483  30.851  1.00 27.32      A    N
ATOM  16164  CA   MET G 266     -33.981 -30.718  31.835  1.00 27.15      A    C
ATOM  16165  C    MET G 266     -33.412 -30.641  33.246  1.00 27.10      A    C
ATOM  16166  O    MET G 266     -32.834 -31.607  33.741  1.00 27.20      A    O
ATOM  16167  CB   MET G 266     -34.634 -32.073  31.587  1.00 27.12      A    C
ATOM  16168  CG   MET G 266     -35.783 -32.434  32.516  1.00 26.86      A    C
ATOM  16169  SD   MET G 266     -36.303 -34.133  32.152  1.00 29.06      A    S
ATOM  16170  CE   MET G 266     -37.945 -34.206  32.841  1.00 29.03      A    C
ATOM  16171  N    LEU G 267     -33.583 -29.485  33.882  1.00 27.00      A    N
ATOM  16172  CA   LEU G 267     -33.006 -29.214  35.204  1.00 26.91      A    C
ATOM  16173  C    LEU G 267     -33.904 -29.644  36.361  1.00 26.99      A    C
ATOM  16174  O    LEU G 267     -35.054 -29.207  36.471  1.00 27.06      A    O
ATOM  16175  CB   LEU G 267     -32.670 -27.731  35.335  1.00 26.83      A    C
ATOM  16176  CG   LEU G 267     -32.146 -27.213  36.671  1.00 26.55      A    C
ATOM  16177  CD1  LEU G 267     -30.839 -27.897  37.028  1.00 26.54      A    C
ATOM  16178  CD2  LEU G 267     -31.959 -25.708  36.593  1.00 26.44      A    C
ATOM  16179  N    LEU G 268     -33.357 -30.487  37.230  1.00 27.03      A    N
ATOM  16180  CA   LEU G 268     -34.103 -31.043  38.341  1.00 27.22      A    C
ATOM  16181  C    LEU G 268     -33.764 -30.299  39.612  1.00 27.45      A    C
ATOM  16182  O    LEU G 268     -32.597 -30.227  39.983  1.00 27.64      A    O
ATOM  16183  CB   LEU G 268     -33.765 -32.520  38.507  1.00 27.14      A    C
ATOM  16184  CG   LEU G 268     -34.641 -33.536  37.782  1.00 27.21      A    C
ATOM  16185  CD1  LEU G 268     -34.356 -33.552  36.294  1.00 27.51      A    C
```

FIGURE 1 (cont'd)

```
ATOM  16186  CD2  LEU  G  268   -34.403  -34.907  38.380  1.00  27.07      A    C
ATOM  16187  N    ASP  G  269   -34.769  -29.753  40.291  1.00  27.65      A    N
ATOM  16188  CA   ASP  G  269   -34.507  -28.994  41.501  1.00  27.97      A    C
ATOM  16189  C    ASP  G  269   -35.649  -29.048  42.494  1.00  27.93      A    C
ATOM  16190  O    ASP  G  269   -36.803  -29.212  42.106  1.00  28.10      A    O
ATOM  16191  CB   ASP  G  269   -34.197  -27.537  41.153  1.00  28.24      A    C
ATOM  16192  CG   ASP  G  269   -33.106  -26.942  42.039  1.00  29.37      A    C
ATOM  16193  OD1  ASP  G  269   -31.983  -27.501  42.063  1.00  30.28      A    O
ATOM  16194  OD2  ASP  G  269   -33.367  -25.907  42.699  1.00  30.10      A    O
ATOM  16195  N    LEU  G  270   -35.303  -28.901  43.775  1.00  27.86      A    N
ATOM  16196  CA   LEU  G  270   -36.257  -28.829  44.895  1.00  27.82      A    C
ATOM  16197  C    LEU  G  270   -37.271  -29.945  44.852  1.00  27.90      A    C
ATOM  16198  O    LEU  G  270   -38.462  -29.713  45.031  1.00  27.95      A    O
ATOM  16199  CB   LEU  G  270   -36.945  -27.455  44.964  1.00  27.72      A    C
ATOM  16200  CG   LEU  G  270   -36.059  -26.200  44.942  1.00  27.73      A    C
ATOM  16201  CD1  LEU  G  270   -36.850  -24.968  45.330  1.00  27.64      A    C
ATOM  16202  CD2  LEU  G  270   -34.846  -26.348  45.856  1.00  28.01      A    C
ATOM  16203  N    LEU  G  271   -36.779  -31.155  44.597  1.00  28.00      A    N
ATOM  16204  CA   LEU  G  271   -37.618  -32.343  44.547  1.00  28.31      A    C
ATOM  16205  C    LEU  G  271   -37.359  -33.182  45.778  1.00  28.69      A    C
ATOM  16206  O    LEU  G  271   -36.228  -33.302  46.221  1.00  28.70      A    O
ATOM  16207  CB   LEU  G  271   -37.348  -33.171  43.281  1.00  28.12      A    C
ATOM  16208  CG   LEU  G  271   -37.634  -32.561  41.908  1.00  27.70      A    C
ATOM  16209  CD1  LEU  G  271   -36.382  -32.694  41.087  1.00  27.62      A    C
ATOM  16210  N    GLY  G  272   -38.420  -33.754  46.330  1.00  29.25      A    N
ATOM  16211  CA   GLY  G  272   -38.300  -34.617  47.496  1.00  29.91      A    C
ATOM  16212  C    GLY  G  272   -39.354  -34.380  48.564  1.00  30.48      A    C
ATOM  16213  O    GLY  G  272   -39.703  -35.310  49.301  1.00  30.71      A    O
ATOM  16214  N    ALA  G  273   -39.854  -33.145  48.654  1.00  30.81      A    N
ATOM  16215  CA   ALA  G  273   -40.885  -32.787  49.620  1.00  31.20      A    C
ATOM  16216  C    ALA  G  273   -42.223  -33.433  49.262  1.00  31.57      A    C
ATOM  16217  O    ALA  G  273   -42.393  -33.898  48.128  1.00  31.62      A    O
ATOM  16218  CB   ALA  G  273   -41.025  -31.293  49.681  1.00  31.17      A    C
ATOM  16219  N    PRO  G  274   -43.168  -33.495  50.229  1.00  31.97      A    N
ATOM  16220  CA   PRO  G  274   -44.525  -33.936  49.893  1.00  32.26      A    C
ATOM  16221  C    PRO  G  274   -45.289  -32.898  49.059  1.00  32.37      A    C
ATOM  16222  O    PRO  G  274   -45.008  -31.688  49.143  1.00  32.20      A    O
ATOM  16223  CB   PRO  G  274   -45.187  -34.123  51.263  1.00  32.49      A    C
ATOM  16224  CG   PRO  G  274   -44.385  -33.260  52.181  1.00  32.45      A    C
ATOM  16225  CD   PRO  G  274   -42.992  -33.357  51.685  1.00  32.14      A    C
ATOM  16226  N    ASN  G  275   -46.228  -33.397  48.252  1.00  32.61      A    N
ATOM  16227  CA   ASN  G  275   -47.138  -32.578  47.450  1.00  32.94      A    C
ATOM  16228  C    ASN  G  275   -46.473  -31.457  46.666  1.00  32.53      A    C
ATOM  16229  O    ASN  G  275   -46.840  -30.294  46.810  1.00  32.76      A    O
ATOM  16230  CB   ASN  G  275   -48.270  -32.021  48.320  1.00  33.42      A    C
ATOM  16231  CG   ASN  G  275   -49.041  -33.108  49.024  1.00  34.79      A    C
ATOM  16232  ND2  ASN  G  275   -48.849  -33.214  50.342  1.00  35.88      A    N
ATOM  16233  OD1  ASN  G  275   -49.792  -33.861  48.392  1.00  35.80      A    O
ATOM  16234  N    PRO  G  276   -45.490  -31.800  45.825  1.00  32.06      A    N
ATOM  16235  CA   PRO  G  276   -44.949  -30.750  44.978  1.00  31.81      A    C
ATOM  16236  C    PRO  G  276   -45.924  -30.444  43.844  1.00  31.83      A    C
ATOM  16237  O    PRO  G  276   -46.710  -31.311  43.457  1.00  31.93      A    O
ATOM  16238  CB   PRO  G  276   -43.665  -31.378  44.435  1.00  31.62      A    C
ATOM  16239  CG   PRO  G  276   -43.925  -32.846  44.439  1.00  31.61      A    C
ATOM  16240  CD   PRO  G  276   -44.866  -33.113  45.567  1.00  31.89      A    C
ATOM  16241  N    THR  G  277   -45.899  -29.218  43.335  1.00  31.87      A    N
ATOM  16242  CA   THR  G  277   -46.661  -28.893  42.128  1.00  31.90      A    C
ATOM  16243  C    THR  G  277   -45.730  -28.322  41.067  1.00  31.83      A    C
ATOM  16244  O    THR  G  277   -44.935  -27.419  41.349  1.00  31.81      A    O
ATOM  16245  CB   THR  G  277   -47.830  -27.940  42.415  1.00  31.99      A    C
ATOM  16246  CG2  THR  G  277   -48.988  -28.702  43.021  1.00  32.14      A    C
ATOM  16247  OG1  THR  G  277   -47.411  -26.932  43.342  1.00  32.27      A    O
ATOM  16248  N    PHE  G  278   -45.813  -28.872  39.857  1.00  31.81      A    N
ATOM  16249  CA   PHE  G  278   -44.960  -28.455  38.743  1.00  31.82      A    C
ATOM  16250  C    PHE  G  278   -45.748  -27.823  37.607  1.00  32.14      A    C
```

FIGURE 1 (cont'd)

```
ATOM  16251  O    PHE G 278     -46.870 -28.231  37.309  1.00 32.24      A   O
ATOM  16252  CB   PHE G 278     -44.182 -29.644  38.203  1.00 31.57      A   C
ATOM  16253  CG   PHE G 278     -43.384 -30.355  39.235  1.00 31.31      A   C
ATOM  16254  CD1  PHE G 278     -42.238 -29.771  39.768  1.00 31.25      A   C
ATOM  16255  CD2  PHE G 278     -43.769 -31.612  39.671  1.00 31.17      A   C
ATOM  16256  CE1  PHE G 278     -41.482 -30.431  40.725  1.00 31.21      A   C
ATOM  16257  CE2  PHE G 278     -43.030 -32.282  40.621  1.00 31.02      A   C
ATOM  16258  CZ   PHE G 278     -41.877 -31.691  41.153  1.00 31.05      A   C
ATOM  16259  N    TYR G 279     -45.143 -26.829  36.969  1.00 32.54      A   N
ATOM  16260  CA   TYR G 279     -45.754 -26.150  35.830  1.00 33.09      A   C
ATOM  16261  C    TYR G 279     -44.736 -26.006  34.711  1.00 33.68      A   C
ATOM  16262  O    TYR G 279     -43.542 -26.219  34.930  1.00 33.63      A   O
ATOM  16263  CB   TYR G 279     -46.297 -24.797  36.271  1.00 32.97      A   C
ATOM  16264  CG   TYR G 279     -47.399 -24.939  37.296  1.00 32.43      A   C
ATOM  16265  CD1  TYR G 279     -48.712 -25.054  36.887  1.00 32.33      A   C
ATOM  16266  CD2  TYR G 279     -47.139 -25.018  38.657  1.00 30.94      A   C
ATOM  16267  CE1  TYR G 279     -49.746 -25.198  37.775  1.00 30.27      A   C
ATOM  16268  CE2  TYR G 279     -48.185 -25.171  39.570  1.00 29.97      A   C
ATOM  16269  CZ   TYR G 279     -49.482 -25.257  39.107  1.00 29.21      A   C
ATOM  16270  OH   TYR G 279     -50.538 -25.398  39.955  1.00 28.86      A   O
ATOM  16271  N    SER G 280     -45.201 -25.678  33.511  1.00 34.60      A   N
ATOM  16272  CA   SER G 280     -44.279 -25.501  32.392  1.00 35.45      A   C
ATOM  16273  C    SER G 280     -43.833 -24.048  32.285  1.00 35.93      A   C
ATOM  16274  O    SER G 280     -44.595 -23.187  31.870  1.00 36.24      A   O
ATOM  16275  CB   SER G 280     -44.901 -25.999  31.079  1.00 35.60      A   C
ATOM  16276  OG   SER G 280     -43.963 -25.966  30.015  1.00 35.81      A   O
ATOM  16277  N    HIS G 281     -42.591 -23.784  32.660  1.00 36.35      A   N
ATOM  16278  CA   HIS G 281     -42.097 -22.420  32.666  1.00 37.11      A   C
ATOM  16279  C    HIS G 281     -41.488 -21.994  31.337  1.00 37.48      A   C
ATOM  16280  O    HIS G 281     -41.081 -20.836  31.177  1.00 37.66      A   O
ATOM  16281  CB   HIS G 281     -41.127 -22.210  33.819  1.00 37.19      A   C
ATOM  16282  CG   HIS G 281     -41.714 -22.552  35.150  1.00 37.81      A   C
ATOM  16283  CD2  HIS G 281     -42.481 -21.829  36.001  1.00 38.66      A   C
ATOM  16284  ND1  HIS G 281     -41.559 -23.794  35.733  1.00 37.82      A   N
ATOM  16285  CE1  HIS G 281     -42.191 -23.816  36.894  1.00 38.22      A   C
ATOM  16286  NE2  HIS G 281     -42.760 -22.637  37.080  1.00 38.93      A   N
ATOM  16287  N    PHE G 282     -41.444 -22.932  30.389  1.00 37.85      A   N
ATOM  16288  CA   PHE G 282     -41.028 -22.644  29.007  1.00 38.20      A   C
ATOM  16289  C    PHE G 282     -41.959 -23.293  27.985  1.00 38.52      A   C
ATOM  16290  O    PHE G 282     -41.969 -24.526  27.842  1.00 38.44      A   O
ATOM  16291  CB   PHE G 282     -39.562 -23.041  28.759  1.00 38.09      A   C
ATOM  16292  CG   PHE G 282     -38.593 -22.355  29.680  1.00 38.01      A   C
ATOM  16293  CD1  PHE G 282     -38.292 -21.007  29.517  1.00 38.46      A   C
ATOM  16294  CD2  PHE G 282     -38.011 -23.044  30.727  1.00 37.86      A   C
ATOM  16295  CE1  PHE G 282     -37.417 -20.360  30.379  1.00 38.41      A   C
ATOM  16296  CE2  PHE G 282     -37.138 -22.403  31.590  1.00 37.97      A   C
ATOM  16297  CZ   PHE G 282     -36.840 -21.057  31.413  1.00 38.21      A   C
ATOM  16298  N    PRO G 283     -42.740 -22.457  27.271  1.00 38.91      A   N
ATOM  16299  CA   PRO G 283     -43.632 -22.918  26.211  1.00 39.03      A   C
ATOM  16300  C    PRO G 283     -42.875 -23.592  25.063  1.00 38.91      A   C
ATOM  16301  O    PRO G 283     -43.462 -24.376  24.323  1.00 38.99      A   O
ATOM  16302  CB   PRO G 283     -44.297 -21.628  25.725  1.00 39.27      A   C
ATOM  16303  CG   PRO G 283     -44.113 -20.660  26.828  1.00 39.30      A   C
ATOM  16304  CD   PRO G 283     -42.789 -20.992  27.413  1.00 39.04      A   C
ATOM  16305  N    ARG G 284     -41.585 -23.292  24.924  1.00 38.66      A   N
ATOM  16306  CA   ARG G 284     -40.733 -23.977  23.956  1.00 38.54      A   C
ATOM  16307  C    ARG G 284     -40.779 -25.500  24.139  1.00 38.73      A   C
ATOM  16308  O    ARG G 284     -40.897 -26.243  23.169  1.00 38.97      A   O
ATOM  16309  CB   ARG G 284     -39.288 -23.484  24.067  1.00 38.26      A   C
ATOM  16310  CG   ARG G 284     -38.518 -23.413  22.734  1.00 37.48      A   C
ATOM  16311  CD   ARG G 284     -38.204 -24.766  22.121  1.00 35.76      A   C
ATOM  16312  NE   ARG G 284     -37.074 -24.696  21.206  1.00 34.88      A   N
ATOM  16313  N    THR G 285     -40.697 -25.957  25.384  1.00 38.76      A   N
ATOM  16314  CA   THR G 285     -40.688 -27.380  25.665  1.00 38.86      A   C
ATOM  16315  C    THR G 285     -42.016 -27.871  26.257  1.00 39.29      A   C
```

FIGURE 1 (cont'd)

```
ATOM  16316  O    THR G 285     -42.069 -28.961  26.830  1.00 39.20      A  O
ATOM  16317  CB   THR G 285     -39.537 -27.725  26.612  1.00 38.50      A  C
ATOM  16318  OG1  THR G 285     -39.532 -26.796  27.701  1.00 38.15      A  O
ATOM  16319  N    VAL G 286     -43.086 -27.085  26.093  1.00 39.90      A  N
ATOM  16320  CA   VAL G 286     -44.390 -27.367  26.719  1.00 40.37      A  C
ATOM  16321  C    VAL G 286     -44.887 -28.768  26.465  1.00 40.99      A  C
ATOM  16322  O    VAL G 286     -45.605 -29.310  27.289  1.00 41.03      A  O
ATOM  16323  CB   VAL G 286     -45.486 -26.391  26.274  1.00 40.28      A  C
ATOM  16324  N    ARG G 287     -44.491 -29.355  25.337  1.00 41.87      A  N
ATOM  16325  CA   ARG G 287     -44.940 -30.702  24.962  1.00 42.78      A  C
ATOM  16326  C    ARG G 287     -44.215 -31.836  25.695  1.00 42.53      A  C
ATOM  16327  O    ARG G 287     -44.758 -32.937  25.827  1.00 42.70      A  O
ATOM  16328  CB   ARG G 287     -44.894 -30.910  23.441  1.00 43.50      A  C
ATOM  16329  CG   ARG G 287     -43.505 -30.890  22.836  1.00 45.24      A  C
ATOM  16330  CD   ARG G 287     -43.542 -31.205  21.340  1.00 48.25      A  C
ATOM  16331  NE   ARG G 287     -42.185 -31.384  20.815  1.00 49.98      A  N
ATOM  16332  CZ   ARG G 287     -41.543 -32.551  20.744  1.00 50.48      A  C
ATOM  16333  NH1  ARG G 287     -42.120 -33.682  21.148  1.00 50.56      A  N
ATOM  16334  NH2  ARG G 287     -40.314 -32.591  20.255  1.00 50.72      A  N
ATOM  16335  N    TRP G 288     -42.997 -31.573  26.164  1.00 42.19      A  N
ATOM  16336  CA   TRP G 288     -42.282 -32.531  27.011  1.00 41.88      A  C
ATOM  16337  C    TRP G 288     -42.809 -32.531  28.433  1.00 41.65      A  C
ATOM  16338  O    TRP G 288     -42.746 -33.503  29.141  1.00 41.68      A  O
ATOM  16339  CB   TRP G 288     -40.775 -32.290  26.982  1.00 41.78      A  C
ATOM  16340  CG   TRP G 288     -40.181 -32.730  25.702  1.00 42.47      A  C
ATOM  16341  CD1  TRP G 288     -39.495 -31.966  24.805  1.00 42.98      A  C
ATOM  16342  CD2  TRP G 288     -40.252 -34.041  25.142  1.00 43.20      A  C
ATOM  16343  CE2  TRP G 288     -39.572 -34.003  23.905  1.00 43.59      A  C
ATOM  16344  CE3  TRP G 288     -40.821 -35.252  25.568  1.00 43.41      A  C
ATOM  16345  NE1  TRP G 288     -39.118 -32.723  23.722  1.00 43.38      A  N
ATOM  16346  CZ2  TRP G 288     -39.447 -35.129  23.086  1.00 44.11      A  C
ATOM  16347  CZ3  TRP G 288     -40.696 -36.374  24.755  1.00 43.91      A  C
ATOM  16348  CH2  TRP G 288     -40.014 -36.304  23.528  1.00 44.29      A  C
ATOM  16349  N    PHE G 289     -43.334 -31.352  28.840  1.00 41.48      A  N
ATOM  16350  CA   PHE G 289     -44.052 -31.246  30.093  1.00 41.31      A  C
ATOM  16351  C    PHE G 289     -45.338 -32.080  30.017  1.00 41.43      A  C
ATOM  16352  O    PHE G 289     -45.653 -32.809  30.965  1.00 41.28      A  O
ATOM  16353  CB   PHE G 289     -44.342 -29.780  30.435  1.00 41.20      A  C
ATOM  16354  CG   PHE G 289     -44.793 -29.576  31.843  1.00 41.07      A  C
ATOM  16355  CD1  PHE G 289     -43.871 -29.589  32.882  1.00 40.68      A  C
ATOM  16356  CD2  PHE G 289     -46.139 -29.388  32.135  1.00 41.40      A  C
ATOM  16357  CE1  PHE G 289     -44.278 -29.416  34.194  1.00 40.57      A  C
ATOM  16358  CE2  PHE G 289     -46.561 -29.211  33.440  1.00 41.53      A  C
ATOM  16359  CZ   PHE G 289     -45.627 -29.233  34.476  1.00 41.11      A  C
ATOM  16360  N    HIS G 290     -46.053 -32.000  28.884  1.00 41.77      A  N
ATOM  16361  CA   HIS G 290     -47.283 -32.798  28.676  1.00 42.22      A  C
ATOM  16362  C    HIS G 290     -46.963 -34.275  28.781  1.00 42.31      A  C
ATOM  16363  O    HIS G 290     -47.792 -35.047  29.236  1.00 42.52      A  O
ATOM  16364  CB   HIS G 290     -48.037 -32.521  27.347  1.00 42.48      A  C
ATOM  16365  CG   HIS G 290     -48.327 -31.072  27.091  1.00 43.13      A  C
ATOM  16366  ND1  HIS G 290     -49.497 -30.455  26.674  1.00 43.95      A  N
ATOM  16367  CE1  HIS G 290     -50.585 -31.188  26.610  1.00 44.46      A  C
ATOM  16368  N    ARG G 291     -45.760 -34.666  28.376  1.00 42.36      A  N
ATOM  16369  CA   ARG G 291     -45.344 -36.058  28.502  1.00 42.60      A  C
ATOM  16370  C    ARG G 291     -45.312 -36.471  29.947  1.00 42.21      A  C
ATOM  16371  O    ARG G 291     -45.816 -37.530  30.309  1.00 42.48      A  O
ATOM  16372  CB   ARG G 291     -43.984 -36.303  27.858  1.00 42.84      A  C
ATOM  16373  CG   ARG G 291     -44.075 -36.442  26.360  1.00 44.49      A  C
ATOM  16374  CD   ARG G 291     -44.965 -37.608  25.991  1.00 46.61      A  C
ATOM  16375  NE   ARG G 291     -44.180 -38.822  25.844  1.00 47.70      A  N
ATOM  16376  CZ   ARG G 291     -43.797 -39.312  24.668  1.00 48.75      A  C
ATOM  16377  NH1  ARG G 291     -44.144 -38.696  23.542  1.00 49.29      A  N
ATOM  16378  NH2  ARG G 291     -43.074 -40.420  24.608  1.00 49.27      A  N
ATOM  16379  N    LEU G 292     -44.739 -35.612  30.775  1.00 41.59      A  N
ATOM  16380  CA   LEU G 292     -44.652 -35.886  32.193  1.00 40.96      A  C
```

FIGURE 1 (cont'd)

```
ATOM  16381  C    LEU G 292     -46.043 -36.019  32.802  1.00 40.91      A  C
ATOM  16382  O    LEU G 292     -46.306 -36.983  33.529  1.00 40.97      A  O
ATOM  16383  CB   LEU G 292     -43.812 -34.820  32.897  1.00 40.56      A  C
ATOM  16384  CG   LEU G 292     -42.337 -34.852  32.515  1.00 39.86      A  C
ATOM  16385  CD1  LEU G 292     -41.658 -33.573  32.961  1.00 39.38      A  C
ATOM  16386  CD2  LEU G 292     -41.647 -36.091  33.084  1.00 39.40      A  C
ATOM  16387  N    ARG G 293     -46.933 -35.078  32.481  1.00 40.86      A  N
ATOM  16388  CA   ARG G 293     -48.321 -35.171  32.919  1.00 40.99      A  C
ATOM  16389  C    ARG G 293     -48.903 -36.514  32.470  1.00 41.30      A  C
ATOM  16390  O    ARG G 293     -49.505 -37.233  33.274  1.00 41.40      A  O
ATOM  16391  CB   ARG G 293     -49.158 -34.000  32.393  1.00 40.88      A  C
ATOM  16392  CG   ARG G 293     -50.465 -33.776  33.150  1.00 40.66      A  C
ATOM  16393  CD   ARG G 293     -51.383 -32.774  32.460  1.00 40.45      A  C
ATOM  16394  NE   ARG G 293     -50.812 -31.431  32.365  1.00 39.74      A  N
ATOM  16395  N    SER G 294     -48.674 -36.861  31.203  1.00 41.47      A  N
ATOM  16396  CA   SER G 294     -49.216 -38.080  30.608  1.00 41.71      A  C
ATOM  16397  C    SER G 294     -48.641 -39.347  31.231  1.00 42.10      A  C
ATOM  16398  O    SER G 294     -49.345 -40.351  31.358  1.00 42.59      A  O
ATOM  16399  CB   SER G 294     -48.991 -38.097  29.100  1.00 40.76      A  C
ATOM  16400  OG   SER G 294     -50.077 -38.746  28.473  1.00 41.11      A  O
ATOM  16401  N    ILE G 295     -47.369 -39.296  31.620  1.00 42.18      A  N
ATOM  16402  CA   ILE G 295     -46.714 -40.430  32.272  1.00 42.26      A  C
ATOM  16403  C    ILE G 295     -47.257 -40.628  33.687  1.00 42.53      A  C
ATOM  16404  O    ILE G 295     -47.554 -41.755  34.093  1.00 42.72      A  O
ATOM  16405  CB   ILE G 295     -45.170 -40.284  32.265  1.00 41.99      A  C
ATOM  16406  CG1  ILE G 295     -44.632 -40.518  30.847  1.00 41.93      A  C
ATOM  16407  CG2  ILE G 295     -44.511 -41.275  33.224  1.00 41.83      A  C
ATOM  16408  CD1  ILE G 295     -43.319 -39.807  30.545  1.00 41.64      A  C
ATOM  16409  N    GLU G 296     -47.399 -39.528  34.421  1.00 42.68      A  N
ATOM  16410  CA   GLU G 296     -48.007 -39.562  35.739  1.00 42.99      A  C
ATOM  16411  C    GLU G 296     -49.405 -40.151  35.638  1.00 43.54      A  C
ATOM  16412  O    GLU G 296     -49.736 -41.101  36.340  1.00 43.82      A  O
ATOM  16413  CB   GLU G 296     -48.073 -38.161  36.335  1.00 42.71      A  C
ATOM  16414  CG   GLU G 296     -48.509 -38.135  37.792  1.00 42.91      A  C
ATOM  16415  CD   GLU G 296     -48.750 -36.732  38.319  1.00 43.13      A  C
ATOM  16416  OE1  GLU G 296     -48.327 -35.746  37.657  1.00 42.82      A  O
ATOM  16417  OE2  GLU G 296     -49.365 -36.622  39.408  1.00 43.39      A  O
ATOM  16418  N    LYS G 297     -50.210 -39.579  34.747  1.00 44.11      A  N
ATOM  16419  CA   LYS G 297     -51.560 -40.057  34.457  1.00 44.83      A  C
ATOM  16420  C    LYS G 297     -51.557 -41.575  34.243  1.00 45.45      A  C
ATOM  16421  O    LYS G 297     -52.259 -42.294  34.935  1.00 45.72      A  O
ATOM  16422  CB   LYS G 297     -52.100 -39.331  33.215  1.00 44.75      A  C
ATOM  16423  CG   LYS G 297     -53.446 -38.626  33.383  1.00 44.61      A  C
ATOM  16424  CD   LYS G 297     -53.562 -37.452  32.416  1.00 43.74      A  C
ATOM  16425  CE   LYS G 297     -55.010 -37.135  32.060  1.00 43.75      A  C
ATOM  16426  N    ARG G 298     -50.729 -42.042  33.311  1.00 45.98      A  N
ATOM  16427  CA   ARG G 298     -50.630 -43.465  32.951  1.00 46.51      A  C
ATOM  16428  C    ARG G 298     -50.225 -44.366  34.124  1.00 47.04      A  C
ATOM  16429  O    ARG G 298     -50.878 -45.378  34.385  1.00 47.64      A  O
ATOM  16430  CB   ARG G 298     -49.660 -43.655  31.764  1.00 45.53      A  C
ATOM  16431  CG   ARG G 298     -49.569 -45.086  31.185  1.00 45.47      A  C
ATOM  16432  CD   ARG G 298     -48.701 -45.118  29.924  1.00 45.13      A  C
ATOM  16433  NE   ARG G 298     -48.499 -46.469  29.413  1.00 44.98      A  N
ATOM  16434  N    LEU G 299     -49.149 -44.004  34.820  1.00 47.25      A  N
ATOM  16435  CA   LEU G 299     -48.651 -44.807  35.940  1.00 47.47      A  C
ATOM  16436  C    LEU G 299     -49.663 -44.885  37.078  1.00 47.87      A  C
ATOM  16437  O    LEU G 299     -49.717 -45.872  37.806  1.00 48.10      A  O
ATOM  16438  CB   LEU G 299     -47.321 -44.255  36.454  1.00 47.14      A  C
ATOM  16439  CG   LEU G 299     -46.079 -44.475  35.592  1.00 46.98      A  C
ATOM  16440  CD1  LEU G 299     -44.939 -43.582  36.065  1.00 46.54      A  C
ATOM  16441  CD2  LEU G 299     -45.656 -45.928  35.630  1.00 47.45      A  C
ATOM  16442  N    HIS G 300     -50.456 -43.827  37.220  1.00 48.22      A  N
ATOM  16443  CA   HIS G 300     -51.526 -43.781  38.201  1.00 48.76      A  C
ATOM  16444  C    HIS G 300     -52.599 -44.793  37.834  1.00 49.24      A  C
ATOM  16445  O    HIS G 300     -52.991 -45.591  38.678  1.00 49.59      A  O
```

FIGURE 1 (cont'd)

```
ATOM  16446  CB   HIS G 300     -52.116 -42.370  38.296  1.00 48.70      A  C
ATOM  16447  CG   HIS G 300     -53.402 -42.301  39.055  1.00 49.35      A  C
ATOM  16448  CD2  HIS G 300     -54.656 -41.979  38.660  1.00 50.11      A  C
ATOM  16449  ND1  HIS G 300     -53.483 -42.586  40.401  1.00 49.66      A  N
ATOM  16450  CE1  HIS G 300     -54.733 -42.444  40.801  1.00 50.28      A  C
ATOM  16451  NE2  HIS G 300     -55.464 -42.075  39.765  1.00 50.71      A  N
ATOM  16452  N    ARG G 301     -53.054 -44.763  36.576  1.00 49.72      A  N
ATOM  16453  CA   ARG G 301     -54.064 -45.708  36.045  1.00 50.24      A  C
ATOM  16454  C    ARG G 301     -53.625 -47.149  36.286  1.00 50.87      A  C
ATOM  16455  O    ARG G 301     -54.448 -48.015  36.589  1.00 51.40      A  O
ATOM  16456  CB   ARG G 301     -54.313 -45.505  34.529  1.00 50.08      A  C
ATOM  16457  CG   ARG G 301     -54.582 -44.071  34.069  1.00 49.10      A  C
ATOM  16458  CD   ARG G 301     -56.060 -43.723  34.032  1.00 48.44      A  C
ATOM  16459  NE   ARG G 301     -56.371 -42.295  34.223  1.00 47.69      A  N
ATOM  16460  CZ   ARG G 301     -55.908 -41.244  33.545  1.00 47.48      A  C
ATOM  16461  NH1  ARG G 301     -55.045 -41.378  32.538  1.00 47.20      A  N
ATOM  16462  NH2  ARG G 301     -56.332 -40.034  33.900  1.00 46.91      A  N
ATOM  16463  N    LEU G 302     -52.320 -47.389  36.156  1.00 51.23      A  N
ATOM  16464  CA   LEU G 302     -51.758 -48.726  36.276  1.00 51.85      A  C
ATOM  16465  C    LEU G 302     -51.450 -49.108  37.718  1.00 52.19      A  C
ATOM  16466  O    LEU G 302     -50.735 -50.084  37.958  1.00 52.50      A  O
ATOM  16467  CB   LEU G 302     -50.492 -48.839  35.421  1.00 51.78      A  C
ATOM  16468  CG   LEU G 302     -50.666 -48.843  33.898  1.00 52.25      A  C
ATOM  16469  CD1  LEU G 302     -49.424 -48.295  33.206  1.00 51.85      A  C
ATOM  16470  CD2  LEU G 302     -51.014 -50.241  33.392  1.00 53.47      A  C
ATOM  16471  N    ASN G 303     -51.998 -48.346  38.666  1.00 52.31      A  N
ATOM  16472  CA   ASN G 303     -51.704 -48.509  40.096  1.00 52.25      A  C
ATOM  16473  C    ASN G 303     -50.209 -48.795  40.351  1.00 52.71      A  C
ATOM  16474  O    ASN G 303     -49.837 -49.900  40.770  1.00 53.21      A  O
ATOM  16475  N    LEU G 304     -49.355 -47.810  40.061  1.00 52.87      A  N
ATOM  16476  CA   LEU G 304     -47.906 -47.959  40.257  1.00 52.75      A  C
ATOM  16477  C    LEU G 304     -47.284 -46.770  40.977  1.00 52.46      A  C
ATOM  16478  O    LEU G 304     -46.056 -46.663  41.064  1.00 52.19      A  O
ATOM  16479  CB   LEU G 304     -47.187 -48.201  38.930  1.00 52.80      A  C
ATOM  16480  CG   LEU G 304     -47.172 -49.613  38.335  1.00 53.27      A  C
ATOM  16481  CD1  LEU G 304     -46.538 -49.584  36.944  1.00 52.94      A  C
ATOM  16482  CD2  LEU G 304     -46.447 -50.602  39.241  1.00 53.83      A  C
ATOM  16483  N    LEU G 305     -48.138 -45.888  41.496  1.00 52.38      A  N
ATOM  16484  CA   LEU G 305     -47.701 -44.730  42.272  1.00 52.20      A  C
ATOM  16485  C    LEU G 305     -48.279 -44.790  43.686  1.00 52.60      A  C
ATOM  16486  O    LEU G 305     -49.502 -44.826  43.864  1.00 53.03      A  O
ATOM  16487  CB   LEU G 305     -48.128 -43.432  41.578  1.00 51.76      A  C
ATOM  16488  CG   LEU G 305     -47.740 -43.211  40.110  1.00 51.09      A  C
ATOM  16489  CD1  LEU G 305     -48.443 -41.988  39.547  1.00 50.43      A  C
ATOM  16490  CD2  LEU G 305     -46.233 -43.082  39.947  1.00 50.65      A  C
ATOM  16491  N    GLN G 306     -47.397 -44.813  44.682  1.00 52.74      A  N
ATOM  16492  CA   GLN G 306     -47.807 -44.805  46.085  1.00 53.04      A  C
ATOM  16493  C    GLN G 306     -48.453 -43.477  46.468  1.00 52.94      A  C
ATOM  16494  O    GLN G 306     -48.139 -42.445  45.878  1.00 52.61      A  O
ATOM  16495  CB   GLN G 306     -46.596 -45.031  46.981  1.00 53.18      A  C
ATOM  16496  CG   GLN G 306     -46.330 -46.473  47.361  1.00 54.03      A  C
ATOM  16497  CD   GLN G 306     -45.286 -46.585  48.457  1.00 54.72      A  C
ATOM  16498  OE1  GLN G 306     -44.202 -46.000  48.363  1.00 54.93      A  O
ATOM  16499  N    SER G 307     -49.346 -43.514  47.459  1.00 53.28      A  N
ATOM  16500  CA   SER G 307     -49.980 -42.311  48.016  1.00 53.50      A  C
ATOM  16501  C    SER G 307     -50.366 -41.292  46.933  1.00 53.36      A  C
ATOM  16502  O    SER G 307     -50.037 -40.103  47.024  1.00 53.14      A  O
ATOM  16503  CB   SER G 307     -49.062 -41.661  49.061  1.00 53.54      A  C
ATOM  16504  OG   SER G 307     -48.479 -42.622  49.924  1.00 54.26      A  O
ATOM  16505  N    HIS G 308     -51.065 -41.767  45.908  1.00 53.48      A  N
ATOM  16506  CA   HIS G 308     -51.371 -40.950  44.740  1.00 53.45      A  C
ATOM  16507  C    HIS G 308     -52.860 -41.005  44.438  1.00 53.73      A  C
ATOM  16508  O    HIS G 308     -53.284 -41.652  43.480  1.00 54.00      A  O
ATOM  16509  CB   HIS G 308     -50.563 -41.439  43.538  1.00 53.27      A  C
ATOM  16510  CG   HIS G 308     -50.397 -40.418  42.459  1.00 52.96      A  C
```

FIGURE 1 (cont'd)

```
ATOM  16511 CD2 HIS G 308     -49.622 -39.309  42.392  1.00 52.55      A  C
ATOM  16512 ND1 HIS G 308     -51.072 -40.488  41.260  1.00 53.24      A  N
ATOM  16513 CE1 HIS G 308     -50.722 -39.463  40.501  1.00 52.92      A  C
ATOM  16514 NE2 HIS G 308     -49.843 -38.733  41.165  1.00 52.38      A  N
ATOM  16515 N   PRO G 309     -53.662 -40.312  45.256  1.00 53.94      A  N
ATOM  16516 CA  PRO G 309     -55.122 -40.388  45.165  1.00 54.44      A  C
ATOM  16517 C   PRO G 309     -55.770 -39.476  44.099  1.00 54.70      A  C
ATOM  16518 O   PRO G 309     -56.834 -38.895  44.352  1.00 54.97      A  O
ATOM  16519 CB  PRO G 309     -55.586 -39.989  46.577  1.00 54.68      A  C
ATOM  16520 CG  PRO G 309     -54.367 -40.075  47.452  1.00 54.43      A  C
ATOM  16521 N   GLN G 310     -55.117 -39.335  42.943  1.00 54.71      A  N
ATOM  16522 CA  GLN G 310     -55.741 -38.812  41.709  1.00 54.89      A  C
ATOM  16523 C   GLN G 310     -54.785 -38.839  40.508  1.00 54.98      A  C
ATOM  16524 O   GLN G 310     -53.655 -39.305  40.622  1.00 54.83      A  O
ATOM  16525 CB  GLN G 310     -56.480 -37.454  41.882  1.00 54.93      A  C
ATOM  16526 CG  GLN G 310     -55.838 -36.418  42.795  1.00 54.53      A  C
ATOM  16527 CD  GLN G 310     -56.866 -35.594  43.547  1.00 54.53      A  C
ATOM  16528 N   GLU G 311     -55.256 -38.346  39.366  1.00 55.39      A  N
ATOM  16529 CA  GLU G 311     -54.523 -38.432  38.106  1.00 55.73      A  C
ATOM  16530 C   GLU G 311     -53.494 -37.316  38.037  1.00 55.01      A  C
ATOM  16531 O   GLU G 311     -52.296 -37.587  38.013  1.00 54.84      A  O
ATOM  16532 CB  GLU G 311     -55.480 -38.372  36.901  1.00 56.51      A  C
ATOM  16533 CG  GLU G 311     -56.720 -39.284  36.995  1.00 58.91      A  C
ATOM  16534 CD  GLU G 311     -57.904 -38.662  37.783  1.00 61.45      A  C
ATOM  16535 OE1 GLU G 311     -59.061 -39.083  37.536  1.00 62.87      A  O
ATOM  16536 OE2 GLU G 311     -57.697 -37.767  38.648  1.00 62.00      A  O
ATOM  16537 N   VAL G 312     -53.965 -36.072  38.013  1.00 54.43      A  N
ATOM  16538 CA  VAL G 312     -53.078 -34.921  38.039  1.00 53.72      A  C
ATOM  16539 C   VAL G 312     -52.848 -34.490  39.487  1.00 53.22      A  C
ATOM  16540 O   VAL G 312     -53.744 -33.940  40.134  1.00 53.57      A  O
ATOM  16541 N   MET G 313     -51.650 -34.774  39.993  1.00 52.17      A  N
ATOM  16542 CA  MET G 313     -51.225 -34.357  41.324  1.00 51.19      A  C
ATOM  16543 C   MET G 313     -49.983 -33.486  41.202  1.00 50.20      A  C
ATOM  16544 O   MET G 313     -49.959 -32.358  41.684  1.00 50.08      A  O
ATOM  16545 CB  MET G 313     -50.883 -35.573  42.187  1.00 51.40      A  C
ATOM  16546 CG  MET G 313     -52.023 -36.552  42.466  1.00 52.01      A  C
ATOM  16547 SD  MET G 313     -52.492 -36.704  44.210  1.00 52.44      A  S
ATOM  16548 CE  MET G 313     -50.992 -37.272  45.001  1.00 52.12      A  C
ATOM  16549 N   TYR G 314     -48.962 -34.028  40.543  1.00 49.09      A  N
ATOM  16550 CA  TYR G 314     -47.653 -33.402  40.453  1.00 48.01      A  C
ATOM  16551 C   TYR G 314     -47.514 -32.432  39.296  1.00 47.49      A  C
ATOM  16552 O   TYR G 314     -47.214 -31.258  39.507  1.00 47.29      A  O
ATOM  16553 CB  TYR G 314     -46.567 -34.463  40.350  1.00 47.80      A  C
ATOM  16554 CG  TYR G 314     -46.510 -35.397  41.529  1.00 47.54      A  C
ATOM  16555 CD1 TYR G 314     -46.771 -34.944  42.820  1.00 47.53      A  C
ATOM  16556 CD2 TYR G 314     -46.171 -36.736  41.362  1.00 47.39      A  C
ATOM  16557 CE1 TYR G 314     -46.711 -35.806  43.914  1.00 47.62      A  C
ATOM  16558 CE2 TYR G 314     -46.108 -37.609  42.452  1.00 47.44      A  C
ATOM  16559 CZ  TYR G 314     -46.378 -37.134  43.722  1.00 47.35      A  C
ATOM  16560 OH  TYR G 314     -46.318 -37.981  44.797  1.00 47.31      A  O
ATOM  16561 N   PHE G 315     -47.715 -32.925  38.079  1.00 47.03      A  N
ATOM  16562 CA  PHE G 315     -47.547 -32.095  36.898  1.00 46.69      A  C
ATOM  16563 C   PHE G 315     -48.858 -31.446  36.499  1.00 46.95      A  C
ATOM  16564 O   PHE G 315     -49.667 -32.026  35.785  1.00 47.03      A  O
ATOM  16565 CB  PHE G 315     -46.924 -32.898  35.764  1.00 46.39      A  C
ATOM  16566 CG  PHE G 315     -45.572 -33.452  36.106  1.00 45.29      A  C
ATOM  16567 CD1 PHE G 315     -44.424 -32.697  35.903  1.00 44.52      A  C
ATOM  16568 CD2 PHE G 315     -45.450 -34.719  36.653  1.00 44.56      A  C
ATOM  16569 CE1 PHE G 315     -43.181 -33.206  36.226  1.00 43.99      A  C
ATOM  16570 CE2 PHE G 315     -44.213 -35.229  36.974  1.00 44.00      A  C
ATOM  16571 CZ  PHE G 315     -43.075 -34.471  36.762  1.00 43.75      A  C
ATOM  16572 N   GLN G 316     -49.054 -30.231  36.990  1.00 47.21      A  N
ATOM  16573 CA  GLN G 316     -50.302 -29.514  36.821  1.00 47.74      A  C
ATOM  16574 C   GLN G 316     -50.424 -28.907  35.433  1.00 48.08      A  C
ATOM  16575 O   GLN G 316     -49.424 -28.557  34.808  1.00 47.90      A  O
```

FIGURE 1 (cont'd)

```
ATOM  16576  CB   GLN G 316     -50.430 -28.416  37.882  1.00 47.80      A C
ATOM  16577  CG   GLN G 316     -50.697 -28.922  39.291  1.00 48.24      A C
ATOM  16578  CD   GLN G 316     -52.030 -29.627  39.414  1.00 48.97      A C
ATOM  16579  NE2  GLN G 316     -52.001 -30.900  39.782  1.00 49.07      A N
ATOM  16580  OE1  GLN G 316     -53.073 -29.031  39.186  1.00 49.79      A O
ATOM  16581  N    PRO G 317     -51.662 -28.783  34.944  1.00 48.66      A N
ATOM  16582  CA   PRO G 317     -51.887 -28.068  33.709  1.00 48.95      A C
ATOM  16583  C    PRO G 317     -51.782 -26.565  33.952  1.00 49.00      A C
ATOM  16584  O    PRO G 317     -51.818 -26.113  35.098  1.00 48.96      A O
ATOM  16585  CB   PRO G 317     -53.318 -28.456  33.350  1.00 49.27      A C
ATOM  16586  CG   PRO G 317     -53.978 -28.668  34.663  1.00 49.42      A C
ATOM  16587  CD   PRO G 317     -52.921 -29.277  35.533  1.00 48.95      A C
ATOM  16588  N    GLY G 318     -51.662 -25.802  32.872  1.00 49.08      A N
ATOM  16589  CA   GLY G 318     -51.474 -24.359  32.970  1.00 49.04      A C
ATOM  16590  C    GLY G 318     -50.037 -23.992  32.650  1.00 48.85      A C
ATOM  16591  O    GLY G 318     -49.101 -24.737  32.986  1.00 48.67      A O
ATOM  16592  N    GLU G 319     -49.871 -22.849  31.990  1.00 48.81      A N
ATOM  16593  CA   GLU G 319     -48.562 -22.338  31.634  1.00 48.59      A C
ATOM  16594  C    GLU G 319     -48.367 -20.953  32.257  1.00 48.73      A C
ATOM  16595  O    GLU G 319     -48.516 -19.948  31.581  1.00 49.11      A O
ATOM  16596  CB   GLU G 319     -48.405 -22.270  30.106  1.00 48.49      A C
ATOM  16597  CG   GLU G 319     -48.556 -23.595  29.366  1.00 47.95      A C
ATOM  16598  N    PRO G 320     -48.053 -20.889  33.559  1.00 48.62      A N
ATOM  16599  CA   PRO G 320     -47.792 -19.571  34.152  1.00 48.64      A C
ATOM  16600  C    PRO G 320     -46.459 -18.954  33.711  1.00 48.52      A C
ATOM  16601  O    PRO G 320     -45.581 -19.661  33.226  1.00 48.34      A O
ATOM  16602  CB   PRO G 320     -47.781 -19.864  35.658  1.00 48.73      A C
ATOM  16603  CG   PRO G 320     -48.538 -21.165  35.796  1.00 48.69      A C
ATOM  16604  CD   PRO G 320     -48.140 -21.940  34.586  1.00 48.46      A C
ATOM  16605  N    PHE G 321     -46.324 -17.647  33.906  1.00 48.34      A N
ATOM  16606  CA   PHE G 321     -45.196 -16.863  33.399  1.00 47.97      A C
ATOM  16607  C    PHE G 321     -43.756 -17.298  33.830  1.00 48.18      A C
ATOM  16608  O    PHE G 321     -42.908 -17.585  32.966  1.00 48.52      A O
ATOM  16609  N    GLY G 322     -43.475 -17.351  35.135  1.00 48.03      A N
ATOM  16610  CA   GLY G 322     -42.113 -17.647  35.626  1.00 47.43      A C
ATOM  16611  C    GLY G 322     -41.237 -16.399  35.625  1.00 47.06      A C
ATOM  16612  O    GLY G 322     -41.769 -15.286  35.618  1.00 47.57      A O
ATOM  16613  N    SER G 323     -39.907 -16.542  35.666  1.00 46.13      A N
ATOM  16614  CA   SER G 323     -39.193 -17.807  35.881  1.00 45.03      A C
ATOM  16615  C    SER G 323     -38.504 -17.768  37.245  1.00 43.87      A C
ATOM  16616  O    SER G 323     -38.473 -16.735  37.913  1.00 43.99      A O
ATOM  16617  CB   SER G 323     -38.122 -18.029  34.796  1.00 45.24      A C
ATOM  16618  OG   SER G 323     -38.667 -18.014  33.485  1.00 46.08      A O
ATOM  16619  N    VAL G 324     -37.943 -18.900  37.646  1.00 42.29      A N
ATOM  16620  CA   VAL G 324     -37.160 -18.988  38.863  1.00 40.75      A C
ATOM  16621  C    VAL G 324     -35.710 -19.170  38.445  1.00 40.01      A C
ATOM  16622  O    VAL G 324     -35.377 -20.134  37.751  1.00 39.90      A O
ATOM  16623  CB   VAL G 324     -37.632 -20.173  39.730  1.00 40.50      A C
ATOM  16624  CG1  VAL G 324     -39.031 -19.914  40.246  1.00 40.41      A C
ATOM  16625  CG2  VAL G 324     -36.685 -20.426  40.885  1.00 40.05      A C
ATOM  16626  N    GLU G 325     -34.853 -18.242  38.856  1.00 39.18      A N
ATOM  16627  CA   GLU G 325     -33.452 -18.282  38.472  1.00 38.49      A C
ATOM  16628  C    GLU G 325     -32.726 -19.521  39.004  1.00 37.61      A C
ATOM  16629  O    GLU G 325     -32.672 -19.752  40.198  1.00 37.49      A O
ATOM  16630  CB   GLU G 325     -32.758 -17.025  38.955  1.00 38.86      A C
ATOM  16631  CG   GLU G 325     -33.406 -15.747  38.472  1.00 40.45      A C
ATOM  16632  CD   GLU G 325     -32.569 -14.503  38.795  1.00 42.59      A C
ATOM  16633  OE1  GLU G 325     -31.411 -14.641  39.279  1.00 42.99      A O
ATOM  16634  OE2  GLU G 325     -33.073 -13.379  38.559  1.00 43.83      A O
ATOM  16635  N    ASP G 326     -32.166 -20.320  38.107  1.00 36.78      A N
ATOM  16636  CA   ASP G 326     -31.462 -21.538  38.494  1.00 36.02      A C
ATOM  16637  C    ASP G 326     -30.378 -21.854  37.454  1.00 35.76      A C
ATOM  16638  O    ASP G 326     -30.106 -21.040  36.571  1.00 35.88      A O
ATOM  16639  CB   ASP G 326     -32.465 -22.685  38.624  1.00 35.75      A C
ATOM  16640  CG   ASP G 326     -32.027 -23.772  39.616  1.00 35.14      A C
```

FIGURE 1 (cont'd)

```
ATOM  16641  OD1 ASP G 326    -30.820 -23.933  39.899  1.00 34.83        A  O
ATOM  16642  OD2 ASP G 326    -32.915 -24.499  40.102  1.00 34.63        A  O
ATOM  16643  N   ASP G 327    -29.763 -23.028  37.560  1.00 35.29        A  N
ATOM  16644  CA  ASP G 327    -28.634 -23.413  36.713  1.00 34.98        A  C
ATOM  16645  C   ASP G 327    -28.885 -23.361  35.205  1.00 34.60        A  C
ATOM  16646  O   ASP G 327    -27.936 -23.372  34.419  1.00 34.67        A  O
ATOM  16647  CB  ASP G 327    -28.177 -24.823  37.074  1.00 35.15        A  C
ATOM  16648  CG  ASP G 327    -27.443 -24.881  38.399  1.00 36.08        A  C
ATOM  16649  OD1 ASP G 327    -26.347 -24.270  38.504  1.00 36.80        A  O
ATOM  16650  OD2 ASP G 327    -27.959 -25.559  39.327  1.00 36.74        A  O
ATOM  16651  N   HIS G 328    -30.152 -23.328  34.803  1.00 34.11        A  N
ATOM  16652  CA  HIS G 328    -30.509 -23.326  33.389  1.00 33.73        A  C
ATOM  16653  C   HIS G 328    -30.232 -21.981  32.727  1.00 33.64        A  C
ATOM  16654  O   HIS G 328    -29.985 -21.935  31.531  1.00 33.84        A  O
ATOM  16655  CB  HIS G 328    -31.977 -23.700  33.210  1.00 33.57        A  C
ATOM  16656  CG  HIS G 328    -32.928 -22.643  33.675  1.00 33.86        A  C
ATOM  16657  CD2 HIS G 328    -33.653 -21.730  32.987  1.00 34.45        A  C
ATOM  16658  ND1 HIS G 328    -33.207 -22.425  35.007  1.00 34.09        A  N
ATOM  16659  CE1 HIS G 328    -34.068 -21.428  35.119  1.00 34.34        A  C
ATOM  16660  NE2 HIS G 328    -34.359 -20.990  33.908  1.00 34.59        A  N
ATOM  16661  N   ILE G 329    -30.266 -20.900  33.504  1.00 33.47        A  N
ATOM  16662  CA  ILE G 329    -30.149 -19.544  32.961  1.00 33.62        A  C
ATOM  16663  C   ILE G 329    -28.987 -19.319  31.974  1.00 33.64        A  C
ATOM  16664  O   ILE G 329    -29.222 -18.818  30.868  1.00 33.88        A  O
ATOM  16665  CB  ILE G 329    -30.139 -18.468  34.084  1.00 33.72        A  C
ATOM  16666  CG1 ILE G 329    -31.491 -18.435  34.812  1.00 33.92        A  C
ATOM  16667  CG2 ILE G 329    -29.760 -17.075  33.537  1.00 34.17        A  C
ATOM  16668  CD1 ILE G 329    -32.687 -18.041  33.950  1.00 34.45        A  C
ATOM  16669  N   PRO G 330    -27.739 -19.684  32.356  1.00 33.59        A  N
ATOM  16670  CA  PRO G 330    -26.645 -19.403  31.422  1.00 33.64        A  C
ATOM  16671  C   PRO G 330    -26.602 -20.340  30.212  1.00 33.53        A  C
ATOM  16672  O   PRO G 330    -25.879 -20.061  29.260  1.00 33.79        A  O
ATOM  16673  CB  PRO G 330    -25.394 -19.572  32.287  1.00 33.72        A  C
ATOM  16674  CG  PRO G 330    -25.780 -20.561  33.297  1.00 33.51        A  C
ATOM  16675  CD  PRO G 330    -27.239 -20.324  33.589  1.00 33.45        A  C
ATOM  16676  N   PHE G 331    -27.362 -21.432  30.253  1.00 33.11        A  N
ATOM  16677  CA  PHE G 331    -27.576 -22.261  29.072  1.00 32.89        A  C
ATOM  16678  C   PHE G 331    -28.709 -21.708  28.211  1.00 32.86        A  C
ATOM  16679  O   PHE G 331    -28.637 -21.717  26.979  1.00 32.96        A  O
ATOM  16680  CB  PHE G 331    -27.850 -23.698  29.482  1.00 32.67        A  C
ATOM  16681  CG  PHE G 331    -26.653 -24.388  30.039  1.00 32.78        A  C
ATOM  16682  CD1 PHE G 331    -26.497 -24.536  31.402  1.00 32.81        A  C
ATOM  16683  CD2 PHE G 331    -25.662 -24.872  29.198  1.00 33.31        A  C
ATOM  16684  CE1 PHE G 331    -25.377 -25.181  31.925  1.00 33.04        A  C
ATOM  16685  CE2 PHE G 331    -24.535 -25.511  29.709  1.00 33.50        A  C
ATOM  16686  CZ  PHE G 331    -24.394 -25.668  31.074  1.00 33.22        A  C
ATOM  16687  N   LEU G 332    -29.745 -21.214  28.878  1.00 32.82        A  N
ATOM  16688  CA  LEU G 332    -30.870 -20.588  28.211  1.00 32.97        A  C
ATOM  16689  C   LEU G 332    -30.425 -19.351  27.439  1.00 33.43        A  C
ATOM  16690  O   LEU G 332    -30.827 -19.177  26.295  1.00 33.70        A  O
ATOM  16691  CB  LEU G 332    -31.971 -20.239  29.214  1.00 32.67        A  C
ATOM  16692  CG  LEU G 332    -33.202 -19.525  28.670  1.00 32.39        A  C
ATOM  16693  CD1 LEU G 332    -34.218 -20.509  28.120  1.00 31.99        A  C
ATOM  16694  CD2 LEU G 332    -33.804 -18.691  29.764  1.00 32.37        A  C
ATOM  16695  N   ARG G 333    -29.587 -18.507  28.046  1.00 33.82        A  N
ATOM  16696  CA  ARG G 333    -29.149 -17.269  27.384  1.00 34.37        A  C
ATOM  16697  C   ARG G 333    -28.364 -17.569  26.099  1.00 34.14        A  C
ATOM  16698  O   ARG G 333    -28.269 -16.713  25.208  1.00 34.49        A  O
ATOM  16699  CB  ARG G 333    -28.377 -16.341  28.351  1.00 34.76        A  C
ATOM  16700  CG  ARG G 333    -26.847 -16.226  28.157  1.00 36.62        A  C
ATOM  16701  CD  ARG G 333    -26.249 -14.996  28.888  1.00 39.89        A  C
ATOM  16702  NE  ARG G 333    -25.642 -15.333  30.190  1.00 42.26        A  N
ATOM  16703  CZ  ARG G 333    -24.326 -15.422  30.432  1.00 42.98        A  C
ATOM  16704  NH1 ARG G 333    -23.896 -15.745  31.654  1.00 42.57        A  N
ATOM  16705  NH2 ARG G 333    -23.436 -15.190  29.466  1.00 43.83        A  N
```

FIGURE 1 (cont'd)

```
ATOM  16706  N   ARG G 334     -27.835 -18.792  26.007  1.00 33.59      A  N
ATOM  16707  CA  ARG G 334     -27.150 -19.268  24.798  1.00 33.19      A  C
ATOM  16708  C   ARG G 334     -28.070 -20.029  23.835  1.00 32.69      A  C
ATOM  16709  O   ARG G 334     -27.637 -20.482  22.777  1.00 32.79      A  O
ATOM  16710  CB  ARG G 334     -25.946 -20.129  25.173  1.00 33.21      A  C
ATOM  16711  CG  ARG G 334     -24.712 -19.332  25.570  1.00 33.62      A  C
ATOM  16712  CD  ARG G 334     -23.942 -20.066  26.659  1.00 33.77      A  C
ATOM  16713  NE  ARG G 334     -22.607 -19.514  26.879  1.00 34.80      A  N
ATOM  16714  CZ  ARG G 334     -22.251 -18.744  27.910  1.00 35.57      A  C
ATOM  16715  NH1 ARG G 334     -23.128 -18.408  28.857  1.00 35.22      A  N
ATOM  16716  NH2 ARG G 334     -21.001 -18.305  27.991  1.00 36.57      A  N
ATOM  16717  N   GLY G 335     -29.331 -20.171  24.217  1.00 32.06      A  N
ATOM  16718  CA  GLY G 335     -30.339 -20.703  23.326  1.00 31.45      A  C
ATOM  16719  C   GLY G 335     -30.673 -22.164  23.512  1.00 30.81      A  C
ATOM  16720  O   GLY G 335     -31.313 -22.759  22.652  1.00 31.16      A  O
ATOM  16721  N   VAL G 336     -30.250 -22.753  24.622  1.00 29.92      A  N
ATOM  16722  CA  VAL G 336     -30.569 -24.154  24.893  1.00 29.07      A  C
ATOM  16723  C   VAL G 336     -32.035 -24.276  25.311  1.00 28.63      A  C
ATOM  16724  O   VAL G 336     -32.500 -23.525  26.144  1.00 28.60      A  O
ATOM  16725  CB  VAL G 336     -29.650 -24.749  25.984  1.00 28.88      A  C
ATOM  16726  CG1 VAL G 336     -29.966 -26.206  26.215  1.00 28.80      A  C
ATOM  16727  CG2 VAL G 336     -28.188 -24.599  25.600  1.00 29.04      A  C
ATOM  16728  N   PRO G 337     -32.780 -25.202  24.705  1.00 28.41      A  N
ATOM  16729  CA  PRO G 337     -34.126 -25.505  25.169  1.00 28.17      A  C
ATOM  16730  C   PRO G 337     -34.094 -26.010  26.608  1.00 27.76      A  C
ATOM  16731  O   PRO G 337     -33.319 -26.924  26.920  1.00 27.79      A  O
ATOM  16732  CB  PRO G 337     -34.560 -26.648  24.244  1.00 28.32      A  C
ATOM  16733  CG  PRO G 337     -33.768 -26.470  23.025  1.00 28.72      A  C
ATOM  16734  CD  PRO G 337     -32.443 -25.945  23.480  1.00 28.65      A  C
ATOM  16735  N   VAL G 338     -34.923 -25.437  27.477  1.00 27.28      A  N
ATOM  16736  CA  VAL G 338     -34.914 -25.820  28.890  1.00 26.71      A  C
ATOM  16737  C   VAL G 338     -36.251 -26.380  29.335  1.00 26.55      A  C
ATOM  16738  O   VAL G 338     -37.303 -25.888  28.933  1.00 26.75      A  O
ATOM  16739  CB  VAL G 338     -34.573 -24.637  29.801  1.00 26.57      A  C
ATOM  16740  CG1 VAL G 338     -34.592 -25.074  31.242  1.00 26.35      A  C
ATOM  16741  CG2 VAL G 338     -33.228 -24.051  29.449  1.00 26.59      A  C
ATOM  16742  N   LEU G 339     -36.198 -27.425  30.155  1.00 26.22      A  N
ATOM  16743  CA  LEU G 339     -37.357 -27.863  30.910  1.00 25.93      A  C
ATOM  16744  C   LEU G 339     -36.988 -27.781  32.369  1.00 25.78      A  C
ATOM  16745  O   LEU G 339     -36.158 -28.544  32.844  1.00 25.83      A  O
ATOM  16746  CB  LEU G 339     -37.781 -29.280  30.536  1.00 25.84      A  C
ATOM  16747  CG  LEU G 339     -39.053 -29.770  31.234  1.00 25.69      A  C
ATOM  16748  CD1 LEU G 339     -40.223 -28.796  31.051  1.00 26.01      A  C
ATOM  16749  CD2 LEU G 339     -39.440 -31.158  30.747  1.00 25.51      A  C
ATOM  16750  N   HIS G 340     -37.602 -26.841  33.070  1.00 25.62      A  N
ATOM  16751  CA  HIS G 340     -37.257 -26.550  34.454  1.00 25.42      A  C
ATOM  16752  C   HIS G 340     -38.167 -27.304  35.419  1.00 25.31      A  C
ATOM  16753  O   HIS G 340     -39.308 -26.892  35.658  1.00 25.34      A  O
ATOM  16754  CB  HIS G 340     -37.342 -25.043  34.691  1.00 25.48      A  C
ATOM  16755  CG  HIS G 340     -36.594 -24.571  35.897  1.00 25.66      A  C
ATOM  16756  CD2 HIS G 340     -35.651 -25.177  36.657  1.00 25.67      A  C
ATOM  16757  ND1 HIS G 340     -36.792 -23.323  36.450  1.00 26.02      A  N
ATOM  16758  CE1 HIS G 340     -35.997 -23.180  37.495  1.00 25.97      A  C
ATOM  16759  NE2 HIS G 340     -35.300 -24.292  37.646  1.00 25.89      A  N
ATOM  16760  N   LEU G 341     -37.647 -28.401  35.970  1.00 25.14      A  N
ATOM  16761  CA  LEU G 341     -38.426 -29.292  36.814  1.00 25.09      A  C
ATOM  16762  C   LEU G 341     -38.228 -28.947  38.285  1.00 25.07      A  C
ATOM  16763  O   LEU G 341     -37.661 -29.717  39.050  1.00 25.11      A  O
ATOM  16764  CB  LEU G 341     -38.041 -30.745  36.534  1.00 25.09      A  C
ATOM  16765  CG  LEU G 341     -39.155 -31.788  36.376  1.00 25.32      A  C
ATOM  16766  CD1 LEU G 341     -38.562 -33.181  36.194  1.00 25.55      A  C
ATOM  16767  CD2 LEU G 341     -40.125 -31.783  37.550  1.00 25.10      A  C
ATOM  16768  N   ILE G 342     -38.707 -27.772  38.667  1.00 25.13      A  N
ATOM  16769  CA  ILE G 342     -38.576 -27.260  40.020  1.00 25.18      A  C
ATOM  16770  C   ILE G 342     -39.976 -27.026  40.565  1.00 25.54      A  C
```

FIGURE 1 (cont'd)

```
ATOM  16771  O    ILE G 342     -40.815 -26.455  39.864  1.00 25.79      A  O
ATOM  16772  CB   ILE G 342     -37.760 -25.946  40.027  1.00 25.01      A  C
ATOM  16773  CG1  ILE G 342     -37.591 -25.405  41.447  1.00 24.87      A  C
ATOM  16774  CG2  ILE G 342     -38.396 -24.907  39.109  1.00 24.97      A  C
ATOM  16775  CD1  ILE G 342     -36.520 -24.356  41.575  1.00 24.62      A  C
ATOM  16776  N    SER G 343     -40.248 -27.472  41.793  1.00 25.82      A  N
ATOM  16777  CA   SER G 343     -41.580 -27.270  42.377  1.00 26.23      A  C
ATOM  16778  C    SER G 343     -41.830 -25.807  42.740  1.00 26.41      A  C
ATOM  16779  O    SER G 343     -40.969 -25.139  43.327  1.00 26.29      A  O
ATOM  16780  CB   SER G 343     -41.818 -28.173  43.586  1.00 26.33      A  C
ATOM  16781  OG   SER G 343     -41.031 -27.754  44.683  1.00 27.01      A  O
ATOM  16782  N    THR G 344     -43.004 -25.326  42.336  1.00 26.76      A  N
ATOM  16783  CA   THR G 344     -43.505 -24.011  42.694  1.00 27.08      A  C
ATOM  16784  C    THR G 344     -44.880 -24.239  43.296  1.00 27.51      A  C
ATOM  16785  O    THR G 344     -45.775 -24.705  42.603  1.00 27.63      A  O
ATOM  16786  CB   THR G 344     -43.611 -23.071  41.487  1.00 27.01      A  C
ATOM  16787  OG1  THR G 344     -43.366 -23.797  40.276  1.00 26.76      A  O
ATOM  16788  N    PRO G 345     -45.056 -23.909  44.591  1.00 27.87      A  N
ATOM  16789  CA   PRO G 345     -44.112 -23.176  45.451  1.00 27.91      A  C
ATOM  16790  C    PRO G 345     -42.958 -24.036  45.952  1.00 27.71      A  C
ATOM  16791  O    PRO G 345     -42.971 -25.263  45.765  1.00 27.45      A  O
ATOM  16792  CB   PRO G 345     -44.979 -22.714  46.634  1.00 28.16      A  C
ATOM  16793  CG   PRO G 345     -46.379 -23.273  46.380  1.00 28.24      A  C
ATOM  16794  CD   PRO G 345     -46.237 -24.348  45.351  1.00 27.99      A  C
ATOM  16795  N    PHE G 346     -41.968 -23.386  46.563  1.00 27.71      A  N
ATOM  16796  CA   PHE G 346     -40.820 -24.086  47.127  1.00 27.83      A  C
ATOM  16797  C    PHE G 346     -41.261 -24.883  48.350  1.00 28.06      A  C
ATOM  16798  O    PHE G 346     -42.259 -24.520  48.995  1.00 28.41      A  O
ATOM  16799  CB   PHE G 346     -39.733 -23.094  47.545  1.00 27.89      A  C
ATOM  16800  CG   PHE G 346     -39.120 -22.322  46.405  1.00 28.05      A  C
ATOM  16801  CD1  PHE G 346     -39.264 -22.742  45.089  1.00 27.86      A  C
ATOM  16802  CD2  PHE G 346     -38.367 -21.178  46.664  1.00 28.62      A  C
ATOM  16803  CE1  PHE G 346     -38.690 -22.031  44.059  1.00 27.81      A  C
ATOM  16804  CE2  PHE G 346     -37.791 -20.464  45.636  1.00 28.49      A  C
ATOM  16805  CZ   PHE G 346     -37.948 -20.895  44.330  1.00 28.02      A  C
ATOM  16806  N    PRO G 347     -40.521 -25.962  48.685  1.00 28.05      A  N
ATOM  16807  CA   PRO G 347     -40.798 -26.776  49.874  1.00 28.40      A  C
ATOM  16808  C    PRO G 347     -40.908 -25.919  51.132  1.00 29.03      A  C
ATOM  16809  O    PRO G 347     -40.177 -24.935  51.281  1.00 29.18      A  O
ATOM  16810  CB   PRO G 347     -39.559 -27.651  49.989  1.00 28.17      A  C
ATOM  16811  CG   PRO G 347     -39.022 -27.718  48.624  1.00 27.74      A  C
ATOM  16812  CD   PRO G 347     -39.319 -26.424  47.973  1.00 27.72      A  C
ATOM  16813  N    ALA G 348     -41.813 -26.284  52.032  1.00 29.70      A  N
ATOM  16814  CA   ALA G 348     -41.966 -25.550  53.297  1.00 30.36      A  C
ATOM  16815  C    ALA G 348     -40.630 -25.435  54.039  1.00 30.61      A  C
ATOM  16816  O    ALA G 348     -40.307 -24.391  54.602  1.00 30.75      A  O
ATOM  16817  CB   ALA G 348     -43.012 -26.224  54.178  1.00 30.62      A  C
ATOM  16818  N    VAL G 349     -39.859 -26.521  53.991  1.00 30.73      A  N
ATOM  16819  CA   VAL G 349     -38.549 -26.642  54.629  1.00 30.89      A  C
ATOM  16820  C    VAL G 349     -37.404 -26.004  53.835  1.00 30.97      A  C
ATOM  16821  O    VAL G 349     -36.233 -26.344  54.045  1.00 31.08      A  O
ATOM  16822  CB   VAL G 349     -38.189 -28.136  54.893  1.00 30.88      A  C
ATOM  16823  CG1  VAL G 349     -39.169 -28.750  55.869  1.00 31.45      A  C
ATOM  16824  CG2  VAL G 349     -38.134 -28.965  53.586  1.00 30.46      A  C
ATOM  16825  N    TRP G 350     -37.732 -25.068  52.945  1.00 31.08      A  N
ATOM  16826  CA   TRP G 350     -36.736 -24.510  52.024  1.00 31.16      A  C
ATOM  16827  C    TRP G 350     -35.773 -23.552  52.705  1.00 31.51      A  C
ATOM  16828  O    TRP G 350     -36.190 -22.679  53.485  1.00 31.75      A  O
ATOM  16829  CB   TRP G 350     -37.407 -23.822  50.829  1.00 30.96      A  C
ATOM  16830  CG   TRP G 350     -36.438 -23.374  49.777  1.00 30.51      A  C
ATOM  16831  CD1  TRP G 350     -35.694 -24.169  48.948  1.00 30.23      A  C
ATOM  16832  CD2  TRP G 350     -36.109 -22.028  49.443  1.00 30.16      A  C
ATOM  16833  CE2  TRP G 350     -35.157 -22.077  48.401  1.00 29.90      A  C
ATOM  16834  CE3  TRP G 350     -36.519 -20.784  49.928  1.00 30.19      A  C
ATOM  16835  NE1  TRP G 350     -34.924 -23.395  48.117  1.00 29.97      A  N
```

FIGURE 1 (cont'd)

```
ATOM  16836  CZ2  TRP  G  350    -34.606  -20.931  47.839  1.00  29.64    A  C
ATOM  16837  CZ3  TRP  G  350    -35.976  -19.643  49.362  1.00  30.03    A  C
ATOM  16838  CH2  TRP  G  350    -35.027  -19.725  48.328  1.00  29.67    A  C
ATOM  16839  N    HIS  G  351    -34.488  -23.723  52.390  1.00  31.81    A  N
ATOM  16840  CA   HIS  G  351    -33.425  -22.866  52.924  1.00  32.41    A  C
ATOM  16841  C    HIS  G  351    -33.555  -22.709  54.447  1.00  32.97    A  C
ATOM  16842  O    HIS  G  351    -33.535  -21.591  54.981  1.00  33.22    A  O
ATOM  16843  CB   HIS  G  351    -33.410  -21.501  52.206  1.00  32.37    A  C
ATOM  16844  CG   HIS  G  351    -32.675  -21.509  50.891  1.00  32.43    A  C
ATOM  16845  CD2  HIS  G  351    -32.325  -22.528  50.067  1.00  32.07    A  C
ATOM  16846  ND1  HIS  G  351    -32.194  -20.360  50.296  1.00  32.56    A  N
ATOM  16847  CE1  HIS  G  351    -31.589  -20.668  49.161  1.00  32.27    A  C
ATOM  16848  NE2  HIS  G  351    -31.658  -21.977  48.996  1.00  31.86    A  N
ATOM  16849  N    THR  G  352    -33.724  -23.848  55.123  1.00  33.41    A  N
ATOM  16850  CA   THR  G  352    -33.794  -23.929  56.590  1.00  33.96    A  C
ATOM  16851  C    THR  G  352    -33.248  -25.281  57.091  1.00  34.23    A  C
ATOM  16852  O    THR  G  352    -33.328  -26.282  56.358  1.00  34.01    A  O
ATOM  16853  CB   THR  G  352    -35.229  -23.702  57.130  1.00  34.04    A  C
ATOM  16854  CG2  THR  G  352    -36.238  -24.293  56.217  1.00  33.55    A  C
ATOM  16855  OG1  THR  G  352    -35.363  -24.346  58.401  1.00  34.77    A  O
ATOM  16856  N    PRO  G  353    -32.695  -25.312  58.334  1.00  34.72    A  N
ATOM  16857  CA   PRO  G  353    -32.169  -26.536  58.941  1.00  34.80    A  C
ATOM  16858  C    PRO  G  353    -33.146  -27.704  58.825  1.00  34.62    A  C
ATOM  16859  O    PRO  G  353    -32.732  -28.869  58.913  1.00  34.64    A  O
ATOM  16860  CB   PRO  G  353    -32.019  -26.152  60.408  1.00  35.22    A  C
ATOM  16861  CG   PRO  G  353    -31.794  -24.713  60.394  1.00  35.52    A  C
ATOM  16862  CD   PRO  G  353    -32.507  -24.147  59.222  1.00  34.97    A  C
ATOM  16863  N    ALA  G  354    -34.427  -27.385  58.620  1.00  34.33    A  N
ATOM  16864  CA   ALA  G  354    -35.481  -28.388  58.514  1.00  34.05    A  C
ATOM  16865  C    ALA  G  354    -35.332  -29.286  57.280  1.00  33.80    A  C
ATOM  16866  O    ALA  G  354    -35.792  -30.427  57.291  1.00  33.77    A  O
ATOM  16867  CB   ALA  G  354    -36.819  -27.728  58.532  1.00  34.04    A  C
ATOM  16868  N    ASP  G  355    -34.674  -28.782  56.232  1.00  33.57    A  N
ATOM  16869  CA   ASP  G  355    -34.457  -29.553  54.997  1.00  33.36    A  C
ATOM  16870  C    ASP  G  355    -33.467  -30.702  55.219  1.00  33.48    A  C
ATOM  16871  O    ASP  G  355    -32.302  -30.627  54.817  1.00  33.37    A  O
ATOM  16872  CB   ASP  G  355    -34.003  -28.632  53.842  1.00  33.06    A  C
ATOM  16873  CG   ASP  G  355    -34.091  -29.304  52.456  1.00  32.55    A  C
ATOM  16874  OD1  ASP  G  355    -34.479  -30.494  52.362  1.00  32.71    A  O
ATOM  16875  OD2  ASP  G  355    -33.764  -28.624  51.454  1.00  31.65    A  O
ATOM  16876  N    THR  G  356    -33.947  -31.760  55.865  1.00  33.72    A  N
ATOM  16877  CA   THR  G  356    -33.145  -32.943  56.109  1.00  33.97    A  C
ATOM  16878  C    THR  G  356    -33.914  -34.183  55.677  1.00  34.44    A  C
ATOM  16879  O    THR  G  356    -35.082  -34.080  55.276  1.00  34.37    A  O
ATOM  16880  CB   THR  G  356    -32.783  -33.066  57.585  1.00  33.38    A  C
ATOM  16881  OG1  THR  G  356    -33.986  -33.090  58.363  1.00  33.35    A  O
ATOM  16882  N    GLU  G  357    -33.255  -35.345  55.757  1.00  35.03    A  N
ATOM  16883  CA   GLU  G  357    -33.842  -36.630  55.361  1.00  35.55    A  C
ATOM  16884  C    GLU  G  357    -35.204  -36.852  56.022  1.00  35.92    A  C
ATOM  16885  O    GLU  G  357    -36.157  -37.297  55.370  1.00  35.86    A  O
ATOM  16886  CB   GLU  G  357    -32.888  -37.781  55.704  1.00  35.74    A  C
ATOM  16887  CG   GLU  G  357    -33.413  -39.183  55.350  1.00  36.38    A  C
ATOM  16888  CD   GLU  G  357    -32.381  -40.295  55.544  1.00  37.43    A  C
ATOM  16889  OE1  GLU  G  357    -31.235  -39.997  55.948  1.00  38.18    A  O
ATOM  16890  OE2  GLU  G  357    -32.720  -41.475  55.291  1.00  37.76    A  O
ATOM  16891  N    VAL  G  358    -35.283  -36.517  57.311  1.00  36.43    A  N
ATOM  16892  CA   VAL  G  358    -36.489  -36.697  58.125  1.00  36.84    A  C
ATOM  16893  C    VAL  G  358    -37.758  -36.057  57.551  1.00  36.66    A  C
ATOM  16894  O    VAL  G  358    -38.863  -36.477  57.893  1.00  36.94    A  O
ATOM  16895  CB   VAL  G  358    -36.281  -36.143  59.540  1.00  37.18    A  C
ATOM  16896  CG1  VAL  G  358    -36.518  -37.226  60.565  1.00  37.96    A  C
ATOM  16897  N    ASN  G  359    -37.608  -35.053  56.688  1.00  36.22    A  N
ATOM  16898  CA   ASN  G  359    -38.762  -34.305  56.172  1.00  35.92    A  C
ATOM  16899  C    ASN  G  359    -39.126  -34.519  54.691  1.00  35.36    A  C
ATOM  16900  O    ASN  G  359    -40.002  -33.844  54.152  1.00  35.24    A  O
```

FIGURE 1 (cont'd)

```
ATOM  16901  CB   ASN G 359     -38.584 -32.818  56.456  1.00 36.13      A  C
ATOM  16902  CG   ASN G 359     -38.621 -32.497  57.936  1.00 37.14      A  C
ATOM  16903  ND2  ASN G 359     -38.940 -33.495  58.758  1.00 38.09      A  N
ATOM  16904  OD1  ASN G 359     -38.371 -31.355  58.338  1.00 37.75      A  O
ATOM  16905  N    LEU G 360     -38.452 -35.455  54.040  1.00 34.83      A  N
ATOM  16906  CA   LEU G 360     -38.822 -35.875  52.695  1.00 34.34      A  C
ATOM  16907  C    LEU G 360     -40.005 -36.840  52.763  1.00 34.39      A  C
ATOM  16908  O    LEU G 360     -40.225 -37.485  53.787  1.00 34.87      A  O
ATOM  16909  CB   LEU G 360     -37.629 -36.566  52.014  1.00 34.08      A  C
ATOM  16910  CG   LEU G 360     -36.253 -35.864  52.047  1.00 33.50      A  C
ATOM  16911  CD1  LEU G 360     -35.178 -36.762  51.451  1.00 32.92      A  C
ATOM  16912  CD2  LEU G 360     -36.287 -34.522  51.342  1.00 33.09      A  C
ATOM  16913  N    HIS G 361     -40.769 -36.927  51.680  1.00 34.09      A  N
ATOM  16914  CA   HIS G 361     -41.849 -37.906  51.580  1.00 33.91      A  C
ATOM  16915  C    HIS G 361     -41.383 -39.037  50.666  1.00 34.22      A  C
ATOM  16916  O    HIS G 361     -41.542 -38.955  49.443  1.00 34.02      A  O
ATOM  16917  CB   HIS G 361     -43.122 -37.261  51.036  1.00 33.55      A  C
ATOM  16918  CG   HIS G 361     -44.376 -37.980  51.416  1.00 32.69      A  C
ATOM  16919  ND1  HIS G 361     -44.813 -39.110  50.766  1.00 31.52      A  N
ATOM  16920  CE1  HIS G 361     -45.943 -39.507  51.321  1.00 31.56      A  C
ATOM  16921  N    PRO G 362     -40.791 -40.097  51.255  1.00 34.70      A  N
ATOM  16922  CA   PRO G 362     -40.206 -41.179  50.458  1.00 34.89      A  C
ATOM  16923  C    PRO G 362     -41.098 -41.670  49.303  1.00 34.86      A  C
ATOM  16924  O    PRO G 362     -40.594 -41.813  48.186  1.00 34.73      A  O
ATOM  16925  CB   PRO G 362     -39.935 -42.275  51.495  1.00 35.19      A  C
ATOM  16926  CG   PRO G 362     -39.718 -41.531  52.761  1.00 35.31      A  C
ATOM  16927  CD   PRO G 362     -40.639 -40.346  52.702  1.00 35.01      A  C
ATOM  16928  N    PRO G 363     -42.405 -41.921  49.557  1.00 34.99      A  N
ATOM  16929  CA   PRO G 363     -43.270 -42.243  48.424  1.00 35.01      A  C
ATOM  16930  C    PRO G 363     -43.140 -41.241  47.272  1.00 34.67      A  C
ATOM  16931  O    PRO G 363     -42.814 -41.646  46.152  1.00 34.60      A  O
ATOM  16932  CB   PRO G 363     -44.673 -42.204  49.038  1.00 35.29      A  C
ATOM  16933  CG   PRO G 363     -44.469 -42.656  50.430  1.00 35.66      A  C
ATOM  16934  CD   PRO G 363     -43.091 -42.191  50.840  1.00 34.97      A  C
ATOM  16935  N    THR G 364     -43.363 -39.955  47.553  1.00 34.32      A  N
ATOM  16936  CA   THR G 364     -43.277 -38.917  46.527  1.00 33.97      A  C
ATOM  16937  C    THR G 364     -41.973 -39.055  45.742  1.00 33.90      A  C
ATOM  16938  O    THR G 364     -41.985 -38.953  44.507  1.00 33.72      A  O
ATOM  16939  CB   THR G 364     -43.429 -37.499  47.120  1.00 33.86      A  C
ATOM  16940  CG2  THR G 364     -43.406 -36.434  46.027  1.00 33.51      A  C
ATOM  16941  OG1  THR G 364     -44.675 -37.416  47.820  1.00 34.09      A  O
ATOM  16942  N    VAL G 365     -40.871 -39.323  46.458  1.00 34.01      A  N
ATOM  16943  CA   VAL G 365     -39.542 -39.483  45.842  1.00 34.11      A  C
ATOM  16944  C    VAL G 365     -39.541 -40.582  44.788  1.00 34.29      A  C
ATOM  16945  O    VAL G 365     -39.158 -40.344  43.634  1.00 34.10      A  O
ATOM  16946  CB   VAL G 365     -38.440 -39.765  46.889  1.00 34.12      A  C
ATOM  16947  CG1  VAL G 365     -38.154 -38.509  47.720  1.00 34.04      A  C
ATOM  16948  CG2  VAL G 365     -37.168 -40.255  46.217  1.00 33.96      A  C
ATOM  16949  N    HIS G 366     -39.986 -41.769  45.191  1.00 34.70      A  N
ATOM  16950  CA   HIS G 366     -40.002 -42.926  44.308  1.00 35.17      A  C
ATOM  16951  C    HIS G 366     -40.941 -42.739  43.112  1.00 35.38      A  C
ATOM  16952  O    HIS G 366     -40.588 -43.088  41.969  1.00 35.51      A  O
ATOM  16953  CB   HIS G 366     -40.319 -44.187  45.101  1.00 35.37      A  C
ATOM  16954  CG   HIS G 366     -39.305 -44.478  46.165  1.00 35.54      A  C
ATOM  16955  CD2  HIS G 366     -39.415 -44.553  47.514  1.00 36.48      A  C
ATOM  16956  ND1  HIS G 366     -37.976 -44.710  45.879  1.00 35.53      A  N
ATOM  16957  CE1  HIS G 366     -37.317 -44.926  47.004  1.00 35.54      A  C
ATOM  16958  NE2  HIS G 366     -38.164 -44.831  48.012  1.00 36.36      A  N
ATOM  16959  N    ASN G 367     -42.114 -42.164  43.367  1.00 35.41      A  N
ATOM  16960  CA   ASN G 367     -43.029 -41.808  42.300  1.00 35.42      A  C
ATOM  16961  C    ASN G 367     -42.301 -41.020  41.227  1.00 35.24      A  C
ATOM  16962  O    ASN G 367     -42.351 -41.378  40.052  1.00 35.37      A  O
ATOM  16963  CB   ASN G 367     -44.191 -40.991  42.855  1.00 35.52      A  C
ATOM  16964  CG   ASN G 367     -45.208 -41.840  43.608  1.00 36.14      A  C
ATOM  16965  ND2  ASN G 367     -46.324 -41.224  43.966  1.00 36.21      A  N
```

FIGURE 1 (cont'd)

```
ATOM  16966 OD1 ASN G 367     -44.996 -43.026  43.866 1.00 37.05      A  O
ATOM  16967 N   LEU G 368     -41.597 -39.970  41.648 1.00 34.97      A  N
ATOM  16968 CA  LEU G 368     -40.873 -39.086  40.729 1.00 34.76      A  C
ATOM  16969 C   LEU G 368     -39.846 -39.844  39.890 1.00 34.93      A  C
ATOM  16970 O   LEU G 368     -39.624 -39.513  38.716 1.00 35.05      A  O
ATOM  16971 CB  LEU G 368     -40.197 -37.930  41.484 1.00 34.38      A  C
ATOM  16972 CG  LEU G 368     -41.093 -36.831  42.059 1.00 33.74      A  C
ATOM  16973 CD1 LEU G 368     -40.255 -35.902  42.903 1.00 33.48      A  C
ATOM  16974 CD2 LEU G 368     -41.813 -36.059  40.973 1.00 32.87      A  C
ATOM  16975 N   ALA G 369     -39.237 -40.863  40.495 1.00 34.20      A  N
ATOM  16976 CA  ALA G 369     -38.232 -41.672  39.820 1.00 33.55      A  C
ATOM  16977 C   ALA G 369     -38.865 -42.607  38.801 1.00 34.50      A  C
ATOM  16978 O   ALA G 369     -38.323 -42.804  37.713 1.00 35.69      A  O
ATOM  16979 CB  ALA G 369     -37.410 -42.442  40.826 1.00 24.55      A  C
ATOM  16980 N   ARG G 370     -40.013 -43.169  39.157 1.00 35.12      A  N
ATOM  16981 CA  ARG G 370     -40.786 -43.959  38.219 1.00 34.82      A  C
ATOM  16982 C   ARG G 370     -41.197 -43.113  37.002 1.00 34.24      A  C
ATOM  16983 O   ARG G 370     -41.020 -43.535  35.862 1.00 34.16      A  O
ATOM  16984 CB  ARG G 370     -42.002 -44.577  38.913 1.00 35.12      A  C
ATOM  16985 CG  ARG G 370     -41.637 -45.568  40.020 1.00 35.43      A  C
ATOM  16986 CD  ARG G 370     -42.866 -46.298  40.574 1.00 35.74      A  C
ATOM  16987 NE  ARG G 370     -42.506 -47.365  41.503 1.00 35.85      A  N
ATOM  16988 CZ  ARG G 370     -43.242 -48.451  41.716 1.00 36.01      A  C
ATOM  16989 N   ILE G 371     -41.710 -41.910  37.246 1.00 33.48      A  N
ATOM  16990 CA  ILE G 371     -42.085 -40.996  36.168 1.00 32.85      A  C
ATOM  16991 C   ILE G 371     -40.885 -40.621  35.300 1.00 32.78      A  C
ATOM  16992 O   ILE G 371     -40.979 -40.644  34.072 1.00 32.89      A  O
ATOM  16993 CB  ILE G 371     -42.770 -39.733  36.709 1.00 32.54      A  C
ATOM  16994 CG1 ILE G 371     -44.117 -40.099  37.336 1.00 32.50      A  C
ATOM  16995 CG2 ILE G 371     -42.964 -38.717  35.596 1.00 32.03      A  C
ATOM  16996 CD1 ILE G 371     -44.749 -39.005  38.184 1.00 32.21      A  C
ATOM  16997 N   LEU G 372     -39.763 -40.293  35.938 1.00 32.59      A  N
ATOM  16998 CA  LEU G 372     -38.542 -39.922  35.224 1.00 32.45      A  C
ATOM  16999 C   LEU G 372     -37.952 -41.057  34.392 1.00 32.75      A  C
ATOM  17000 O   LEU G 372     -37.613 -40.870  33.228 1.00 32.68      A  O
ATOM  17001 CB  LEU G 372     -37.502 -39.392  36.207 1.00 32.11      A  C
ATOM  17002 CG  LEU G 372     -37.290 -37.881  36.376 1.00 31.37      A  C
ATOM  17003 CD1 LEU G 372     -38.405 -37.008  35.806 1.00 30.81      A  C
ATOM  17004 CD2 LEU G 372     -37.005 -37.552  37.834 1.00 30.89      A  C
ATOM  17005 N   ALA G 373     -37.835 -42.231  34.996 1.00 33.14      A  N
ATOM  17006 CA  ALA G 373     -37.308 -43.404  34.307 1.00 33.57      A  C
ATOM  17007 C   ALA G 373     -38.074 -43.741  33.024 1.00 33.85      A  C
ATOM  17008 O   ALA G 373     -37.474 -44.052  31.999 1.00 33.97      A  O
ATOM  17009 CB  ALA G 373     -37.298 -44.594  35.242 1.00 33.72      A  C
ATOM  17010 N   VAL G 374     -39.399 -43.685  33.098 1.00 34.04      A  N
ATOM  17011 CA  VAL G 374     -40.249 -43.865  31.931 1.00 34.30      A  C
ATOM  17012 C   VAL G 374     -39.958 -42.771  30.906 1.00 34.22      A  C
ATOM  17013 O   VAL G 374     -39.711 -43.069  29.734 1.00 34.47      A  O
ATOM  17014 CB  VAL G 374     -41.743 -43.851  32.313 1.00 34.37      A  C
ATOM  17015 CG1 VAL G 374     -42.627 -43.727  31.076 1.00 34.59      A  C
ATOM  17016 CG2 VAL G 374     -42.088 -45.110  33.084 1.00 34.82      A  C
ATOM  17017 N   PHE G 375     -39.977 -41.516  31.355 1.00 33.92      A  N
ATOM  17018 CA  PHE G 375     -39.676 -40.396  30.483 1.00 33.75      A  C
ATOM  17019 C   PHE G 375     -38.342 -40.588  29.786 1.00 34.07      A  C
ATOM  17020 O   PHE G 375     -38.267 -40.471  28.568 1.00 34.19      A  O
ATOM  17021 CB  PHE G 375     -39.665 -39.084  31.258 1.00 33.35      A  C
ATOM  17022 CG  PHE G 375     -39.328 -37.879  30.414 1.00 32.63      A  C
ATOM  17023 CD1 PHE G 375     -40.327 -37.015  29.993 1.00 32.48      A  C
ATOM  17024 CD2 PHE G 375     -38.011 -37.608  30.041 1.00 32.10      A  C
ATOM  17025 CE1 PHE G 375     -40.026 -35.899  29.219 1.00 32.40      A  C
ATOM  17026 CE2 PHE G 375     -37.703 -36.500  29.267 1.00 32.23      A  C
ATOM  17027 CZ  PHE G 375     -38.714 -35.642  28.858 1.00 32.33      A  C
ATOM  17028 N   LEU G 376     -37.298 -40.882  30.558 1.00 34.43      A  N
ATOM  17029 CA  LEU G 376     -35.951 -41.060  30.011 1.00 34.89      A  C
ATOM  17030 C   LEU G 376     -35.955 -42.144  28.938 1.00 35.69      A  C
```

FIGURE 1 (cont'd)

```
ATOM  17031  O    LEU G 376     -35.355 -41.978  27.871  1.00 35.80      A    O
ATOM  17032  CB   LEU G 376     -34.953 -41.411  31.117  1.00 34.57      A    C
ATOM  17033  CG   LEU G 376     -33.553 -40.802  31.002  1.00 33.84      A    C
ATOM  17034  N    ALA G 377     -36.657 -43.240  29.223  1.00 36.58      A    N
ATOM  17035  CA   ALA G 377     -36.792 -44.353  28.284  1.00 37.46      A    C
ATOM  17036  C    ALA G 377     -37.581 -43.967  27.030  1.00 37.93      A    C
ATOM  17037  O    ALA G 377     -37.174 -44.307  25.918  1.00 38.24      A    O
ATOM  17038  CB   ALA G 377     -37.422 -45.567  28.970  1.00 37.62      A    C
ATOM  17039  N    GLU G 378     -38.700 -43.262  27.209  1.00 38.22      A    N
ATOM  17040  CA   GLU G 378     -39.515 -42.827  26.078  1.00 38.62      A    C
ATOM  17041  C    GLU G 378     -38.763 -41.841  25.210  1.00 38.58      A    C
ATOM  17042  O    GLU G 378     -38.690 -42.040  24.008  1.00 38.93      A    O
ATOM  17043  CB   GLU G 378     -40.865 -42.264  26.530  1.00 38.71      A    C
ATOM  17044  CG   GLU G 378     -41.883 -43.351  26.914  1.00 39.92      A    C
ATOM  17045  CD   GLU G 378     -43.320 -42.841  27.134  1.00 41.32      A    C
ATOM  17046  OE1  GLU G 378     -43.580 -41.632  26.933  1.00 41.80      A    O
ATOM  17047  OE2  GLU G 378     -44.201 -43.660  27.506  1.00 41.95      A    O
ATOM  17048  N    TYR G 379     -38.176 -40.812  25.823  1.00 38.41      A    N
ATOM  17049  CA   TYR G 379     -37.395 -39.790  25.100  1.00 38.42      A    C
ATOM  17050  C    TYR G 379     -36.248 -40.373  24.261  1.00 38.98      A    C
ATOM  17051  O    TYR G 379     -36.058 -39.999  23.100  1.00 39.11      A    O
ATOM  17052  CB   TYR G 379     -36.843 -38.716  26.058  1.00 37.84      A    C
ATOM  17053  CG   TYR G 379     -36.249 -37.493  25.359  1.00 37.06      A    C
ATOM  17054  CD1  TYR G 379     -36.958 -36.284  25.289  1.00 36.34      A    C
ATOM  17055  CD2  TYR G 379     -34.985 -37.547  24.760  1.00 36.81      A    C
ATOM  17056  CE1  TYR G 379     -36.419 -35.163  24.636  1.00 36.18      A    C
ATOM  17057  CE2  TYR G 379     -34.439 -36.435  24.102  1.00 36.55      A    C
ATOM  17058  CZ   TYR G 379     -35.155 -35.248  24.045  1.00 36.23      A    C
ATOM  17059  OH   TYR G 379     -34.598 -34.158  23.400  1.00 35.93      A    O
ATOM  17060  N    LEU G 380     -35.489 -41.284  24.854  1.00 39.64      A    N
ATOM  17061  CA   LEU G 380     -34.364 -41.915  24.167  1.00 40.51      A    C
ATOM  17062  C    LEU G 380     -34.758 -43.183  23.392  1.00 41.45      A    C
ATOM  17063  O    LEU G 380     -33.889 -43.920  22.907  1.00 41.85      A    O
ATOM  17064  CB   LEU G 380     -33.242 -42.215  25.170  1.00 40.18      A    C
ATOM  17065  CG   LEU G 380     -32.024 -41.293  25.254  1.00 39.75      A    C
ATOM  17066  CD1  LEU G 380     -32.365 -39.833  24.952  1.00 39.40      A    C
ATOM  17067  CD2  LEU G 380     -31.369 -41.431  26.616  1.00 39.47      A    C
ATOM  17068  N    GLY G 381     -36.069 -43.414  23.279  1.00 42.06      A    N
ATOM  17069  CA   GLY G 381     -36.640 -44.621  22.668  1.00 42.79      A    C
ATOM  17070  C    GLY G 381     -36.054 -45.935  23.165  1.00 43.41      A    C
ATOM  17071  O    GLY G 381     -35.934 -46.891  22.397  1.00 43.32      A    O
ATOM  17072  N    LEU G 382     -35.698 -45.984  24.450  1.00 43.87      A    N
ATOM  17073  CA   LEU G 382     -34.973 -47.122  25.031  1.00 44.36      A    C
ATOM  17074  C    LEU G 382     -35.809 -48.394  25.186  1.00 44.57      A    C
ATOM  17075  O    LEU G 382     -35.291 -49.425  25.627  1.00 44.57      A    O
ATOM  17076  CB   LEU G 382     -34.356 -46.739  26.381  1.00 44.28      A    C
ATOM  17077  CG   LEU G 382     -33.145 -45.813  26.349  1.00 44.51      A    C
ATOM  17078  CD1  LEU G 382     -32.705 -45.493  27.769  1.00 44.39      A    C
ATOM  17079  CD2  LEU G 382     -32.005 -46.426  25.545  1.00 44.25      A    C
ATOM  17080  OXT  LEU G 382     -37.003 -48.430  24.876  1.00 44.69      A    O
TER   17081       LEU G 382
ATOM  17082  N    LEU H  76      -5.507 -79.313 -40.159  1.00 55.48      A    N
ATOM  17083  CA   LEU H  76      -4.500 -80.114 -40.917  1.00 55.55      A    C
ATOM  17084  C    LEU H  76      -3.179 -79.347 -41.143  1.00 55.29      A    C
ATOM  17085  O    LEU H  76      -3.196 -78.267 -41.738  1.00 55.09      A    O
ATOM  17086  CB   LEU H  76      -5.092 -80.591 -42.264  1.00 55.84      A    C
ATOM  17087  CG   LEU H  76      -6.001 -81.843 -42.374  1.00 56.37      A    C
ATOM  17088  CD1  LEU H  76      -6.867 -81.808 -43.636  1.00 56.22      A    C
ATOM  17089  CD2  LEU H  76      -5.235 -83.181 -42.314  1.00 56.46      A    C
ATOM  17090  N    PRO H  77      -2.035 -79.900 -40.660  1.00 54.71      A    N
ATOM  17091  CA   PRO H  77      -0.744 -79.300 -41.003  1.00 55.49      A    C
ATOM  17092  C    PRO H  77      -0.334 -79.637 -42.435  1.00 55.75      A    C
ATOM  17093  O    PRO H  77      -0.724 -80.686 -42.963  1.00 55.66      A    O
ATOM  17094  CB   PRO H  77       0.221 -79.941 -40.004  1.00 56.08      A    C
ATOM  17095  CG   PRO H  77      -0.384 -81.250 -39.672  1.00 55.91      A    C
```

FIGURE 1 (cont'd)

```
ATOM  17096  CD   PRO H  77    -1.873  -81.131  -39.859  1.00 54.97     A  C
ATOM  17097  N    GLU H  78     0.457  -78.751  -43.041  1.00 55.91     A  N
ATOM  17098  CA   GLU H  78     0.848  -78.845  -44.461  1.00 55.79     A  C
ATOM  17099  C    GLU H  78     1.233  -80.247  -44.930  1.00 57.04     A  C
ATOM  17100  O    GLU H  78     0.773  -80.718  -45.976  1.00 57.24     A  O
ATOM  17101  CB   GLU H  78     1.980  -77.855  -44.787  1.00 53.81     A  C
ATOM  17102  CG   GLU H  78     1.520  -76.558  -45.436  1.00 51.29     A  C
ATOM  17103  N    ALA H  79     2.078  -80.904  -44.145  1.00 58.30     A  N
ATOM  17104  CA   ALA H  79     2.572  -82.244  -44.467  1.00 58.96     A  C
ATOM  17105  C    ALA H  79     1.438  -83.257  -44.718  1.00 58.72     A  C
ATOM  17106  O    ALA H  79     1.423  -83.940  -45.748  1.00 58.84     A  O
ATOM  17107  CB   ALA H  79     3.532  -82.742  -43.360  1.00 59.76     A  C
ATOM  17108  N    ARG H  80     0.497  -83.336  -43.778  1.00 57.99     A  N
ATOM  17109  CA   ARG H  80    -0.638  -84.244  -43.893  1.00 57.01     A  C
ATOM  17110  C    ARG H  80    -1.591  -83.757  -44.986  1.00 56.76     A  C
ATOM  17111  O    ARG H  80    -2.117  -84.564  -45.766  1.00 56.77     A  O
ATOM  17112  CB   ARG H  80    -1.365  -84.382  -42.546  1.00 55.30     A  C
ATOM  17113  N    LEU H  81    -1.791  -82.438  -45.050  1.00 56.45     A  N
ATOM  17114  CA   LEU H  81    -2.690  -81.836  -46.035  1.00 55.87     A  C
ATOM  17115  C    LEU H  81    -2.272  -82.204  -47.465  1.00 55.92     A  C
ATOM  17116  O    LEU H  81    -3.078  -82.744  -48.236  1.00 55.54     A  O
ATOM  17117  CB   LEU H  81    -2.756  -80.314  -45.843  1.00 55.66     A  C
ATOM  17118  CG   LEU H  81    -3.807  -79.514  -46.628  1.00 54.90     A  C
ATOM  17119  CD1  LEU H  81    -4.331  -78.345  -45.804  1.00 54.71     A  C
ATOM  17120  CD2  LEU H  81    -3.261  -79.029  -47.970  1.00 54.78     A  C
ATOM  17121  N    ARG H  82    -1.011  -81.933  -47.800  1.00 56.35     A  N
ATOM  17122  CA   ARG H  82    -0.497  -82.210  -49.133  1.00 56.78     A  C
ATOM  17123  C    ARG H  82    -0.498  -83.712  -49.428  1.00 56.71     A  C
ATOM  17124  O    ARG H  82    -0.645  -84.130  -50.578  1.00 56.67     A  O
ATOM  17125  CB   ARG H  82     0.898  -81.611  -49.302  1.00 57.34     A  C
ATOM  17126  CG   ARG H  82     1.352  -81.511  -50.754  1.00 58.27     A  C
ATOM  17127  CD   ARG H  82     2.557  -80.594  -50.918  1.00 59.67     A  C
ATOM  17128  NE   ARG H  82     2.187  -79.220  -51.277  1.00 59.79     A  N
ATOM  17129  CZ   ARG H  82     2.029  -78.213  -50.414  1.00 59.81     A  C
ATOM  17130  NH1  ARG H  82     2.196  -78.397  -49.105  1.00 59.98     A  N
ATOM  17131  NH2  ARG H  82     1.698  -77.007  -50.866  1.00 59.56     A  N
ATOM  17132  N    ARG H  83    -0.351  -84.514  -48.378  1.00 56.46     A  N
ATOM  17133  CA   ARG H  83    -0.405  -85.971  -48.477  1.00 55.93     A  C
ATOM  17134  C    ARG H  83    -1.833  -86.444  -48.774  1.00 55.52     A  C
ATOM  17135  O    ARG H  83    -2.039  -87.381  -49.559  1.00 55.66     A  O
ATOM  17136  CB   ARG H  83     0.164  -86.580  -47.182  1.00 54.95     A  C
ATOM  17137  CG   ARG H  83    -0.318  -87.963  -46.776  1.00 54.50     A  C
ATOM  17138  CD   ARG H  83    -0.034  -88.148  -45.290  1.00 54.60     A  C
ATOM  17139  NE   ARG H  83    -0.681  -89.329  -44.723  1.00 54.09     A  N
ATOM  17140  N    VAL H  84    -2.804  -85.769  -48.156  1.00 54.73     A  N
ATOM  17141  CA   VAL H  84    -4.229  -86.075  -48.329  1.00 53.65     A  C
ATOM  17142  C    VAL H  84    -4.734  -85.623  -49.699  1.00 52.98     A  C
ATOM  17143  O    VAL H  84    -5.287  -86.424  -50.452  1.00 52.80     A  O
ATOM  17144  CB   VAL H  84    -5.101  -85.479  -47.174  1.00 53.53     A  C
ATOM  17145  CG1  VAL H  84    -4.902  -86.282  -45.887  1.00 53.57     A  C
ATOM  17146  CG2  VAL H  84    -6.593  -85.453  -47.543  1.00 52.79     A  C
ATOM  17147  N    VAL H  85    -4.536  -84.345  -50.016  1.00 52.17     A  N
ATOM  17148  CA   VAL H  85    -4.906  -83.808  -51.316  1.00 51.34     A  C
ATOM  17149  C    VAL H  85    -4.276  -84.641  -52.421  1.00 51.75     A  C
ATOM  17150  O    VAL H  85    -4.826  -84.743  -53.509  1.00 51.93     A  O
ATOM  17151  CB   VAL H  85    -4.467  -82.346  -51.464  1.00 49.78     A  C
ATOM  17152  N    GLY H  86    -3.126  -85.245  -52.125  1.00 52.09     A  N
ATOM  17153  CA   GLY H  86    -2.435  -86.141  -53.054  1.00 52.04     A  C
ATOM  17154  C    GLY H  86    -3.081  -87.513  -53.210  1.00 51.67     A  C
ATOM  17155  O    GLY H  86    -2.853  -88.203  -54.208  1.00 51.89     A  O
ATOM  17156  N    GLN H  87    -3.891  -87.908  -52.229  1.00 51.02     A  N
ATOM  17157  CA   GLN H  87    -4.564  -89.211  -52.243  1.00 50.27     A  C
ATOM  17158  C    GLN H  87    -5.757  -89.276  -53.201  1.00 49.58     A  C
ATOM  17159  O    GLN H  87    -6.180  -90.366  -53.581  1.00 49.52     A  O
ATOM  17160  N    LEU H  88    -6.288  -88.114  -53.584  1.00 48.75     A  N
```

FIGURE 1 (cont'd)

```
ATOM  17161  CA   LEU H  88    -7.354 -88.032 -54.581  1.00 48.05      A  C
ATOM  17162  C    LEU H  88    -6.769 -88.321 -55.955  1.00 48.42      A  C
ATOM  17163  O    LEU H  88    -5.767 -87.713 -56.328  1.00 48.62      A  O
ATOM  17164  CB   LEU H  88    -8.005 -86.644 -54.590  1.00 47.33      A  C
ATOM  17165  CG   LEU H  88    -8.828 -86.174 -53.393  1.00 45.95      A  C
ATOM  17166  N    ASP H  89    -7.381 -89.259 -56.686  1.00 48.75      A  N
ATOM  17167  CA   ASP H  89    -6.996 -89.551 -58.073  1.00 49.14      A  C
ATOM  17168  C    ASP H  89    -7.979 -88.920 -59.065  1.00 49.19      A  C
ATOM  17169  O    ASP H  89    -9.104 -89.401 -59.214  1.00 48.95      A  O
ATOM  17170  CB   ASP H  89    -6.853 -91.057 -58.322  1.00 49.29      A  C
ATOM  17171  CG   ASP H  89    -6.398 -91.374 -59.742  1.00 49.46      A  C
ATOM  17172  N    PRO H  90    -7.546 -87.835 -59.744  1.00 49.44      A  N
ATOM  17173  CA   PRO H  90    -8.412 -87.076 -60.637  1.00 49.35      A  C
ATOM  17174  C    PRO H  90    -9.022 -87.912 -61.752  1.00 49.28      A  C
ATOM  17175  O    PRO H  90   -10.215 -87.762 -62.027  1.00 49.02      A  O
ATOM  17176  CB   PRO H  90    -7.476 -85.996 -61.198  1.00 49.48      A  C
ATOM  17177  CG   PRO H  90    -6.465 -85.804 -60.130  1.00 49.74      A  C
ATOM  17178  CD   PRO H  90    -6.221 -87.196 -59.622  1.00 49.79      A  C
ATOM  17179  N    GLN H  91    -8.231 -88.783 -62.377  1.00 49.46      A  N
ATOM  17180  CA   GLN H  91    -8.763 -89.616 -63.459  1.00 49.57      A  C
ATOM  17181  C    GLN H  91    -9.676 -90.733 -62.922  1.00 48.99      A  C
ATOM  17182  O    GLN H  91   -10.574 -91.195 -63.628  1.00 49.04      A  O
ATOM  17183  CB   GLN H  91    -7.663 -90.130 -64.414  1.00 50.17      A  C
ATOM  17184  CG   GLN H  91    -6.908 -91.389 -63.963  1.00 50.97      A  C
ATOM  17185  N    ARG H  92    -9.457 -91.146 -61.673  1.00 48.13      A  N
ATOM  17186  CA   ARG H  92   -10.344 -92.106 -61.015  1.00 47.11      A  C
ATOM  17187  C    ARG H  92   -11.729 -91.476 -60.800  1.00 46.70      A  C
ATOM  17188  O    ARG H  92   -12.758 -92.078 -61.158  1.00 46.59      A  O
ATOM  17189  CB   ARG H  92    -9.738 -92.601 -59.690  1.00 46.96      A  C
ATOM  17190  CG   ARG H  92   -10.679 -93.425 -58.793  1.00 45.16      A  C
ATOM  17191  CD   ARG H  92    -9.991 -93.905 -57.522  1.00 43.10      A  C
ATOM  17192  NE   ARG H  92    -9.453 -92.793 -56.741  1.00 41.85      A  N
ATOM  17193  CZ   ARG H  92    -9.137 -92.856 -55.452  1.00 43.99      A  C
ATOM  17194  NH1  ARG H  92    -9.307 -93.985 -54.783  1.00 45.18      A  N
ATOM  17195  NH2  ARG H  92    -8.658 -91.785 -54.830  1.00 44.03      A  N
ATOM  17196  N    LEU H  93   -11.740 -90.264 -60.229  1.00 46.12      A  N
ATOM  17197  CA   LEU H  93   -12.968 -89.484 -60.024  1.00 45.48      A  C
ATOM  17198  C    LEU H  93   -13.790 -89.489 -61.309  1.00 45.53      A  C
ATOM  17199  O    LEU H  93   -14.962 -89.882 -61.315  1.00 45.43      A  O
ATOM  17200  CB   LEU H  93   -12.626 -88.036 -59.633  1.00 45.08      A  C
ATOM  17201  CG   LEU H  93   -13.538 -87.186 -58.739  1.00 43.90      A  C
ATOM  17202  CD1  LEU H  93   -15.023 -87.415 -58.932  1.00 42.72      A  C
ATOM  17203  N    TRP H  94   -13.135 -89.086 -62.397  1.00 45.70      A  N
ATOM  17204  CA   TRP H  94   -13.787 -88.848 -63.679  1.00 45.75      A  C
ATOM  17205  C    TRP H  94   -14.200 -90.118 -64.406  1.00 45.73      A  C
ATOM  17206  O    TRP H  94   -15.250 -90.151 -65.054  1.00 45.63      A  O
ATOM  17207  CB   TRP H  94   -12.883 -88.011 -64.590  1.00 45.95      A  C
ATOM  17208  CG   TRP H  94   -13.665 -87.228 -65.580  1.00 46.41      A  C
ATOM  17209  CD1  TRP H  94   -14.098 -87.654 -66.800  1.00 47.11      A  C
ATOM  17210  CD2  TRP H  94   -14.152 -85.882 -65.423  1.00 46.48      A  C
ATOM  17211  CE2  TRP H  94   -14.862 -85.559 -66.600  1.00 46.71      A  C
ATOM  17212  CE3  TRP H  94   -14.051 -84.917 -64.404  1.00 46.26      A  C
ATOM  17213  NE1  TRP H  94   -14.814 -86.656 -67.422  1.00 47.09      A  N
ATOM  17214  CZ2  TRP H  94   -15.467 -84.308 -66.791  1.00 46.62      A  C
ATOM  17215  CZ3  TRP H  94   -14.653 -83.677 -64.593  1.00 46.16      A  C
ATOM  17216  CH2  TRP H  94   -15.350 -83.384 -65.780  1.00 46.34      A  C
ATOM  17217  N    SER H  95   -13.375 -91.155 -64.294  1.00 45.76      A  N
ATOM  17218  CA   SER H  95   -13.524 -92.335 -65.137  1.00 45.76      A  C
ATOM  17219  C    SER H  95   -14.179 -93.514 -64.429  1.00 45.18      A  C
ATOM  17220  O    SER H  95   -15.071 -94.150 -64.989  1.00 45.15      A  O
ATOM  17221  CB   SER H  95   -12.174 -92.745 -65.723  1.00 46.26      A  C
ATOM  17222  OG   SER H  95   -12.298 -93.067 -67.094  1.00 47.19      A  O
ATOM  17223  N    THR H  96   -13.738 -93.804 -63.207  1.00 44.46      A  N
ATOM  17224  CA   THR H  96   -14.295 -94.918 -62.435  1.00 43.81      A  C
ATOM  17225  C    THR H  96   -15.639 -94.588 -61.788  1.00 42.90      A  C
```

FIGURE 1 (cont'd)

```
ATOM  17226  O    THR H  96     -16.486 -95.477 -61.624  1.00 42.98      A   O
ATOM  17227  CB   THR H  96     -13.343 -95.388 -61.322  1.00 44.00      A   C
ATOM  17228  OG1  THR H  96     -11.986 -95.210 -61.736  1.00 44.73      A   O
ATOM  17229  N    TYR H  97     -15.831 -93.317 -61.426  1.00 41.61      A   N
ATOM  17230  CA   TYR H  97     -17.021 -92.909 -60.678  1.00 40.24      A   C
ATOM  17231  C    TYR H  97     -18.005 -92.013 -61.431  1.00 39.85      A   C
ATOM  17232  O    TYR H  97     -19.215 -92.228 -61.335  1.00 39.62      A   O
ATOM  17233  CB   TYR H  97     -16.625 -92.264 -59.345  1.00 39.72      A   C
ATOM  17234  CG   TYR H  97     -15.770 -93.160 -58.470  1.00 38.77      A   C
ATOM  17235  CD1  TYR H  97     -16.148 -94.486 -58.211  1.00 37.65      A   C
ATOM  17236  CD2  TYR H  97     -14.589 -92.679 -57.890  1.00 39.58      A   C
ATOM  17237  CE1  TYR H  97     -15.367 -95.311 -57.410  1.00 37.52      A   C
ATOM  17238  CE2  TYR H  97     -13.800 -93.495 -57.084  1.00 39.81      A   C
ATOM  17239  CZ   TYR H  97     -14.194 -94.807 -56.851  1.00 39.18      A   C
ATOM  17240  OH   TYR H  97     -13.402 -95.606 -56.064  1.00 39.49      A   O
ATOM  17241  N    LEU H  98     -17.507 -91.019 -62.170  1.00 39.61      A   N
ATOM  17242  CA   LEU H  98     -18.405 -90.064 -62.830  1.00 39.45      A   C
ATOM  17243  C    LEU H  98     -19.050 -90.620 -64.088  1.00 39.69      A   C
ATOM  17244  O    LEU H  98     -20.277 -90.640 -64.194  1.00 39.60      A   O
ATOM  17245  CB   LEU H  98     -17.718 -88.729 -63.135  1.00 39.24      A   C
ATOM  17246  CG   LEU H  98     -18.617 -87.705 -63.848  1.00 39.00      A   C
ATOM  17247  CD1  LEU H  98     -19.811 -87.288 -62.993  1.00 38.39      A   C
ATOM  17248  CD2  LEU H  98     -17.816 -86.496 -64.278  1.00 39.16      A   C
ATOM  17249  N    ARG H  99     -18.219 -91.053 -65.038  1.00 40.03      A   N
ATOM  17250  CA   ARG H  99     -18.705 -91.547 -66.334  1.00 40.10      A   C
ATOM  17251  C    ARG H  99     -19.736 -92.666 -66.227  1.00 40.22      A   C
ATOM  17252  O    ARG H  99     -20.748 -92.613 -66.921  1.00 40.36      A   O
ATOM  17253  CB   ARG H  99     -17.557 -91.898 -67.300  1.00 39.56      A   C
ATOM  17254  CG   ARG H  99     -17.405 -90.884 -68.447  1.00 39.43      A   C
ATOM  17255  CD   ARG H  99     -16.369 -91.294 -69.502  1.00 39.89      A   C
ATOM  17256  NE   ARG H  99     -15.176 -90.454 -69.452  1.00 39.58      A   N
ATOM  17257  N    PRO H 100     -19.502 -93.666 -65.348  1.00 40.23      A   N
ATOM  17258  CA   PRO H 100     -20.522 -94.697 -65.172  1.00 40.15      A   C
ATOM  17259  C    PRO H 100     -21.882 -94.123 -64.784  1.00 39.76      A   C
ATOM  17260  O    PRO H 100     -22.917 -94.706 -65.138  1.00 39.95      A   O
ATOM  17261  CB   PRO H 100     -19.963 -95.549 -64.026  1.00 40.28      A   C
ATOM  17262  CG   PRO H 100     -18.502 -95.413 -64.142  1.00 40.50      A   C
ATOM  17263  CD   PRO H 100     -18.281 -93.986 -64.583  1.00 40.36      A   C
ATOM  17264  N    LEU H 101     -21.866 -92.988 -64.080  1.00 39.13      A   N
ATOM  17265  CA   LEU H 101     -23.085 -92.347 -63.553  1.00 38.53      A   C
ATOM  17266  C    LEU H 101     -23.884 -91.576 -64.599  1.00 38.44      A   C
ATOM  17267  O    LEU H 101     -25.061 -91.277 -64.389  1.00 38.28      A   O
ATOM  17268  CB   LEU H 101     -22.737 -91.420 -62.375  1.00 38.11      A   C
ATOM  17269  CG   LEU H 101     -22.966 -91.874 -60.926  1.00 37.77      A   C
ATOM  17270  CD1  LEU H 101     -22.671 -93.355 -60.700  1.00 38.22      A   C
ATOM  17271  CD2  LEU H 101     -22.162 -91.016 -59.962  1.00 37.45      A   C
ATOM  17272  N    LEU H 102     -23.244 -91.275 -65.723  1.00 38.50      A   N
ATOM  17273  CA   LEU H 102     -23.824 -90.392 -66.718  1.00 38.58      A   C
ATOM  17274  C    LEU H 102     -24.728 -91.106 -67.715  1.00 38.92      A   C
ATOM  17275  O    LEU H 102     -24.508 -91.047 -68.919  1.00 39.22      A   O
ATOM  17276  CB   LEU H 102     -22.722 -89.608 -67.436  1.00 38.53      A   C
ATOM  17277  CG   LEU H 102     -21.931 -88.582 -66.615  1.00 38.07      A   C
ATOM  17278  CD1  LEU H 102     -20.758 -88.044 -67.411  1.00 38.26      A   C
ATOM  17279  CD2  LEU H 102     -22.811 -87.438 -66.155  1.00 37.54      A   C
ATOM  17280  N    VAL H 103     -25.752 -91.777 -67.203  1.00 39.07      A   N
ATOM  17281  CA   VAL H 103     -26.779 -92.398 -68.043  1.00 39.38      A   C
ATOM  17282  C    VAL H 103     -28.176 -91.978 -67.597  1.00 39.11      A   C
ATOM  17283  O    VAL H 103     -28.358 -91.561 -66.451  1.00 38.85      A   O
ATOM  17284  CB   VAL H 103     -26.698 -93.926 -68.017  1.00 39.72      A   C
ATOM  17285  CG1  VAL H 103     -26.668 -94.440 -66.582  1.00 39.59      A   C
ATOM  17286  CG2  VAL H 103     -25.484 -94.396 -68.798  1.00 40.64      A   C
ATOM  17287  N    VAL H 104     -29.153 -92.077 -68.502  1.00 39.05      A   N
ATOM  17288  CA   VAL H 104     -30.552 -91.820 -68.154  1.00 38.73      A   C
ATOM  17289  C    VAL H 104     -30.946 -92.767 -67.029  1.00 38.94      A   C
ATOM  17290  O    VAL H 104     -30.699 -93.974 -67.123  1.00 39.23      A   O
```

FIGURE 1 (cont'd)

```
ATOM  17291  CB   VAL H 104     -31.497 -92.017 -69.342  1.00 38.06      A  C
ATOM  17292  CG1  VAL H 104     -32.742 -91.144 -69.172  1.00 37.50      A  C
ATOM  17293  N    ARG H 105     -31.527 -92.205 -65.964  1.00 38.81      A  N
ATOM  17294  CA   ARG H 105     -31.709 -92.918 -64.689  1.00 38.52      A  C
ATOM  17295  C    ARG H 105     -32.900 -92.438 -63.873  1.00 38.48      A  C
ATOM  17296  O    ARG H 105     -32.894 -92.510 -62.643  1.00 38.18      A  O
ATOM  17297  CB   ARG H 105     -30.427 -92.865 -63.850  1.00 38.33      A  C
ATOM  17298  CG   ARG H 105     -30.000 -91.472 -63.437  1.00 37.68      A  C
ATOM  17299  CD   ARG H 105     -28.531 -91.429 -63.105  1.00 37.37      A  C
ATOM  17300  NE   ARG H 105     -28.170 -90.169 -62.474  1.00 36.99      A  N
ATOM  17301  CZ   ARG H 105     -27.626 -89.143 -63.112  1.00 36.78      A  C
ATOM  17302  NH1  ARG H 105     -27.371 -89.225 -64.404  1.00 36.90      A  N
ATOM  17303  NH2  ARG H 105     -27.335 -88.035 -62.450  1.00 36.43      A  N
ATOM  17304  N    THR H 106     -33.923 -91.961 -64.576  1.00 38.72      A  N
ATOM  17305  CA   THR H 106     -35.205 -91.600 -63.969  1.00 38.96      A  C
ATOM  17306  C    THR H 106     -35.753 -92.740 -63.084  1.00 39.01      A  C
ATOM  17307  O    THR H 106     -35.552 -93.910 -63.405  1.00 39.01      A  O
ATOM  17308  CB   THR H 106     -36.243 -91.226 -65.052  1.00 39.14      A  C
ATOM  17309  OG1  THR H 106     -36.532 -92.377 -65.853  1.00 39.79      A  O
ATOM  17310  N    PRO H 107     -36.442 -92.398 -61.970  1.00 39.12      A  N
ATOM  17311  CA   PRO H 107     -36.897 -93.376 -60.977  1.00 39.40      A  C
ATOM  17312  C    PRO H 107     -37.497 -94.637 -61.585  1.00 39.95      A  C
ATOM  17313  O    PRO H 107     -38.280 -94.559 -62.534  1.00 40.10      A  O
ATOM  17314  CB   PRO H 107     -37.967 -92.610 -60.196  1.00 39.29      A  C
ATOM  17315  CG   PRO H 107     -37.521 -91.212 -60.250  1.00 38.90      A  C
ATOM  17316  CD   PRO H 107     -36.815 -91.025 -61.576  1.00 39.00      A  C
ATOM  17317  N    GLY H 108     -37.096 -95.787 -61.041  1.00 40.40      A  N
ATOM  17318  CA   GLY H 108     -37.635 -97.094 -61.427  1.00 41.01      A  C
ATOM  17319  C    GLY H 108     -37.396 -97.523 -62.858  1.00 41.35      A  C
ATOM  17320  O    GLY H 108     -38.101 -98.382 -63.370  1.00 41.83      A  O
ATOM  17321  N    SER H 109     -36.411 -96.920 -63.509  1.00 41.32      A  N
ATOM  17322  CA   SER H 109     -36.036 -97.320 -64.853  1.00 41.38      A  C
ATOM  17323  C    SER H 109     -34.881 -98.322 -64.765  1.00 41.59      A  C
ATOM  17324  O    SER H 109     -34.387 -98.596 -63.665  1.00 41.36      A  O
ATOM  17325  CB   SER H 109     -35.626 -96.091 -65.660  1.00 41.26      A  C
ATOM  17326  OG   SER H 109     -34.448 -95.522 -65.123  1.00 40.67      A  O
ATOM  17327  N    PRO H 110     -34.459 -98.891 -65.915  1.00 41.95      A  N
ATOM  17328  CA   PRO H 110     -33.255 -99.728 -65.939  1.00 41.88      A  C
ATOM  17329  C    PRO H 110     -31.984 -98.978 -65.529  1.00 41.30      A  C
ATOM  17330  O    PRO H 110     -31.143 -99.530 -64.820  1.00 41.11      A  O
ATOM  17331  CB   PRO H 110     -33.170-100.159 -67.400  1.00 42.31      A  C
ATOM  17332  CG   PRO H 110     -34.576-100.137 -67.864  1.00 42.76      A  C
ATOM  17333  CD   PRO H 110     -35.183 -98.955 -67.198  1.00 42.32      A  C
ATOM  17334  N    GLY H 111     -31.861 -97.730 -65.969  1.00 40.81      A  N
ATOM  17335  CA   GLY H 111     -30.727 -96.884 -65.603  1.00 40.16      A  C
ATOM  17336  C    GLY H 111     -30.651 -96.585 -64.113  1.00 39.63      A  C
ATOM  17337  O    GLY H 111     -29.573 -96.661 -63.510  1.00 39.46      A  O
ATOM  17338  N    ASN H 112     -31.798 -96.237 -63.523  1.00 39.21      A  N
ATOM  17339  CA   ASN H 112     -31.914 -96.012 -62.071  1.00 38.62      A  C
ATOM  17340  C    ASN H 112     -31.399 -97.226 -61.299  1.00 38.84      A  C
ATOM  17341  O    ASN H 112     -30.638 -97.083 -60.344  1.00 38.64      A  O
ATOM  17342  CB   ASN H 112     -33.366 -95.683 -61.676  1.00 38.31      A  C
ATOM  17343  CG   ASN H 112     -33.523 -95.382 -60.198  1.00 37.14      A  C
ATOM  17344  N    LEU H 113     -31.796 -98.415 -61.748  1.00 39.30      A  N
ATOM  17345  CA   LEU H 113     -31.371 -99.647 -61.108  1.00 39.77      A  C
ATOM  17346  C    LEU H 113     -29.901 -99.958 -61.407  1.00 39.79      A  C
ATOM  17347  O    LEU H 113     -29.170-100.417 -60.524  1.00 39.73      A  O
ATOM  17348  CB   LEU H 113     -32.292-100.809 -61.500  1.00 40.18      A  C
ATOM  17349  CG   LEU H 113     -32.334-102.028 -60.562  1.00 40.91      A  C
ATOM  17350  CD1  LEU H 113     -33.752-102.600 -60.473  1.00 41.46      A  C
ATOM  17351  CD2  LEU H 113     -31.321-103.116 -60.960  1.00 41.76      A  C
ATOM  17352  N    GLN H 114     -29.474 -99.697 -62.641  1.00 39.89      A  N
ATOM  17353  CA   GLN H 114     -28.081 -99.925 -63.044  1.00 39.91      A  C
ATOM  17354  C    GLN H 114     -27.119 -99.083 -62.193  1.00 39.65      A  C
ATOM  17355  O    GLN H 114     -26.092 -99.589 -61.717  1.00 39.71      A  O
```

FIGURE 1 (cont'd)

```
ATOM  17356  CB   GLN H 114     -27.882 -99.647 -64.542  1.00 40.06      A  C
ATOM  17357  N    VAL H 115     -27.475 -97.808 -61.990  1.00 39.09      A  N
ATOM  17358  CA   VAL H 115     -26.679 -96.873 -61.170  1.00 38.42      A  C
ATOM  17359  C    VAL H 115     -26.681 -97.310 -59.706  1.00 38.65      A  C
ATOM  17360  O    VAL H 115     -25.621 -97.468 -59.095  1.00 38.79      A  O
ATOM  17361  CB   VAL H 115     -27.164 -95.395 -61.302  1.00 36.88      A  C
ATOM  17362  N    ARG H 116     -27.882 -97.528 -59.170  1.00 38.86      A  N
ATOM  17363  CA   ARG H 116     -28.074 -98.007 -57.803  1.00 39.08      A  C
ATOM  17364  C    ARG H 116     -27.163 -99.199 -57.495  1.00 39.54      A  C
ATOM  17365  O    ARG H 116     -26.497 -99.228 -56.453  1.00 39.50      A  O
ATOM  17366  CB   ARG H 116     -29.542 -98.383 -57.584  1.00 38.96      A  C
ATOM  17367  CG   ARG H 116     -29.846 -98.999 -56.233  1.00 39.22      A  C
ATOM  17368  CD   ARG H 116     -31.276 -99.497 -56.175  1.00 40.26      A  C
ATOM  17369  NE   ARG H 116     -32.233 -98.440 -56.500  1.00 40.88      A  N
ATOM  17370  CZ   ARG H 116     -33.516 -98.638 -56.803  1.00 41.48      A  C
ATOM  17371  NH1  ARG H 116     -34.030 -99.859 -56.842  1.00 41.98      A  N
ATOM  17372  NH2  ARG H 116     -34.296 -97.605 -57.080  1.00 41.67      A  N
ATOM  17373  N    LYS H 117     -27.137-100.168 -58.414  1.00 40.10      A  N
ATOM  17374  CA   LYS H 117     -26.314-101.370 -58.285  1.00 40.55      A  C
ATOM  17375  C    LYS H 117     -24.826-101.017 -58.277  1.00 40.19      A  C
ATOM  17376  O    LYS H 117     -24.058-101.605 -57.516  1.00 40.30      A  O
ATOM  17377  CB   LYS H 117     -26.637-102.352 -59.415  1.00 41.15      A  C
ATOM  17378  CG   LYS H 117     -26.280-103.810 -59.134  1.00 42.52      A  C
ATOM  17379  CD   LYS H 117     -26.840-104.768 -60.205  1.00 43.85      A  C
ATOM  17380  CE   LYS H 117     -28.237-105.291 -59.859  1.00 44.05      A  C
ATOM  17381  N    PHE H 118     -24.435-100.044 -59.102  1.00 39.55      A  N
ATOM  17382  CA   PHE H 118     -23.041 -99.610 -59.180  1.00 38.93      A  C
ATOM  17383  C    PHE H 118     -22.592 -98.945 -57.892  1.00 39.18      A  C
ATOM  17384  O    PHE H 118     -21.459 -99.141 -57.441  1.00 39.38      A  O
ATOM  17385  CB   PHE H 118     -22.828 -98.660 -60.362  1.00 37.67      A  C
ATOM  17386  CG   PHE H 118     -21.452 -98.044 -60.416  1.00 36.14      A  C
ATOM  17387  CD1  PHE H 118     -20.312 -98.844 -60.522  1.00 35.85      A  C
ATOM  17388  CD2  PHE H 118     -21.304 -96.662 -60.384  1.00 34.58      A  C
ATOM  17389  CE1  PHE H 118     -19.043 -98.276 -60.579  1.00 35.51      A  C
ATOM  17390  CE2  PHE H 118     -20.045 -96.071 -60.441  1.00 33.92      A  C
ATOM  17391  CZ   PHE H 118     -18.911 -96.878 -60.546  1.00 35.60      A  C
ATOM  17392  N    LEU H 119     -23.486 -98.151 -57.310  1.00 39.21      A  N
ATOM  17393  CA   LEU H 119     -23.200 -97.490 -56.040  1.00 39.22      A  C
ATOM  17394  C    LEU H 119     -23.001 -98.530 -54.921  1.00 39.74      A  C
ATOM  17395  O    LEU H 119     -21.946 -98.549 -54.258  1.00 39.85      A  O
ATOM  17396  CB   LEU H 119     -24.290 -96.465 -55.702  1.00 38.75      A  C
ATOM  17397  CG   LEU H 119     -24.165 -95.136 -56.452  1.00 37.93      A  C
ATOM  17398  CD1  LEU H 119     -25.458 -94.352 -56.359  1.00 37.42      A  C
ATOM  17399  N    GLU H 120     -23.989 -99.416 -54.752  1.00 40.20      A  N
ATOM  17400  CA   GLU H 120     -23.897-100.528 -53.797  1.00 40.63      A  C
ATOM  17401  C    GLU H 120     -22.534-101.208 -53.872  1.00 41.32      A  C
ATOM  17402  O    GLU H 120     -21.827-101.310 -52.866  1.00 41.58      A  O
ATOM  17403  CB   GLU H 120     -25.002-101.562 -54.045  1.00 39.86      A  C
ATOM  17404  CG   GLU H 120     -26.393-101.143 -53.571  1.00 39.57      A  C
ATOM  17405  CD   GLU H 120     -27.390-102.291 -53.606  1.00 40.13      A  C
ATOM  17406  OE1  GLU H 120     -27.193-103.277 -52.854  1.00 40.87      A  O
ATOM  17407  N    ALA H 121     -22.170-101.641 -55.080  1.00 41.84      A  N
ATOM  17408  CA   ALA H 121     -20.944-102.390 -55.314  1.00 42.22      A  C
ATOM  17409  C    ALA H 121     -19.691-101.597 -54.953  1.00 42.16      A  C
ATOM  17410  O    ALA H 121     -18.836-102.104 -54.225  1.00 42.51      A  O
ATOM  17411  CB   ALA H 121     -20.885-102.873 -56.748  1.00 42.53      A  C
ATOM  17412  N    THR H 122     -19.592-100.362 -55.448  1.00 41.56      A  N
ATOM  17413  CA   THR H 122     -18.440 -99.504 -55.172  1.00 40.89      A  C
ATOM  17414  C    THR H 122     -18.250 -99.306 -53.678  1.00 41.32      A  C
ATOM  17415  O    THR H 122     -17.136 -99.454 -53.171  1.00 41.71      A  O
ATOM  17416  CB   THR H 122     -18.573 -98.127 -55.833  1.00 39.44      A  C
ATOM  17417  OG1  THR H 122     -18.396 -98.257 -57.244  1.00 38.53      A  O
ATOM  17418  N    LEU H 123     -19.342 -98.995 -52.980  1.00 41.41      A  N
ATOM  17419  CA   LEU H 123     -19.309 -98.743 -51.537  1.00 41.49      A  C
ATOM  17420  C    LEU H 123     -18.883 -99.972 -50.730  1.00 42.18      A  C
```

FIGURE 1 (cont'd)

```
ATOM  17421  O    LEU H 123     -18.117 -99.853 -49.758  1.00 42.41      A    O
ATOM  17422  CB   LEU H 123     -20.673 -98.253 -51.048  1.00 41.04      A    C
ATOM  17423  CG   LEU H 123     -21.139 -96.851 -51.444  1.00 39.83      A    C
ATOM  17424  CD1  LEU H 123     -20.490 -95.803 -50.545  1.00 39.20      A    C
ATOM  17425  N    ARG H 124     -19.382-101.143 -51.137  1.00 42.77      A    N
ATOM  17426  CA   ARG H 124     -19.040-102.407 -50.486  1.00 43.42      A    C
ATOM  17427  C    ARG H 124     -17.581-102.804 -50.705  1.00 44.08      A    C
ATOM  17428  O    ARG H 124     -16.943-103.327 -49.803  1.00 44.46      A    O
ATOM  17429  CB   ARG H 124     -19.970-103.526 -50.950  1.00 43.40      A    C
ATOM  17430  CG   ARG H 124     -21.299-103.547 -50.219  1.00 42.83      A    C
ATOM  17431  CD   ARG H 124     -22.193-104.701 -50.666  1.00 42.37      A    C
ATOM  17432  NE   ARG H 124     -23.489-104.646 -49.993  1.00 41.60      A    N
ATOM  17433  N    SER H 125     -17.055-102.532 -51.894  1.00 44.57      A    N
ATOM  17434  CA   SER H 125     -15.689-102.914 -52.259  1.00 45.13      A    C
ATOM  17435  C    SER H 125     -14.582-102.056 -51.608  1.00 45.25      A    C
ATOM  17436  O    SER H 125     -13.424-102.112 -52.029  1.00 45.56      A    O
ATOM  17437  CB   SER H 125     -15.539-102.906 -53.788  1.00 45.30      A    C
ATOM  17438  OG   SER H 125     -15.567-101.580 -54.308  1.00 44.99      A    O
ATOM  17439  N    LEU H 126     -14.930-101.275 -50.587  1.00 45.13      A    N
ATOM  17440  CA   LEU H 126     -13.942-100.430 -49.894  1.00 45.14      A    C
ATOM  17441  C    LEU H 126     -13.273-101.146 -48.715  1.00 45.68      A    C
ATOM  17442  O    LEU H 126     -13.890-101.994 -48.065  1.00 45.92      A    O
ATOM  17443  CB   LEU H 126     -14.559 -99.096 -49.448  1.00 44.60      A    C
ATOM  17444  CG   LEU H 126     -15.026 -98.110 -50.529  1.00 43.78      A    C
ATOM  17445  CD1  LEU H 126     -15.197 -96.724 -49.936  1.00 42.93      A    C
ATOM  17446  CD2  LEU H 126     -14.067 -98.064 -51.707  1.00 43.53      A    C
ATOM  17447  N    THR H 127     -12.012-100.796 -48.450  1.00 46.17      A    N
ATOM  17448  CA   THR H 127     -11.190-101.481 -47.436  1.00 46.65      A    C
ATOM  17449  C    THR H 127     -11.747-101.382 -46.024  1.00 46.71      A    C
ATOM  17450  O    THR H 127     -11.772-102.381 -45.309  1.00 47.20      A    O
ATOM  17451  CB   THR H 127      -9.740-100.985 -47.427  1.00 46.88      A    C
ATOM  17452  OG1  THR H 127      -9.342-100.685 -48.768  1.00 47.11      A    O
ATOM  17453  N    ALA H 128     -12.173-100.186 -45.615  1.00 46.34      A    N
ATOM  17454  CA   ALA H 128     -12.948-100.041 -44.384  1.00 46.11      A    C
ATOM  17455  C    ALA H 128     -14.292-100.743 -44.606  1.00 46.00      A    C
ATOM  17456  O    ALA H 128     -14.829-100.730 -45.721  1.00 45.94      A    O
ATOM  17457  CB   ALA H 128     -13.140 -98.576 -44.037  1.00 45.80      A    C
ATOM  17458  N    GLY H 129     -14.820-101.374 -43.560  1.00 46.00      A    N
ATOM  17459  CA   GLY H 129     -16.033-102.195 -43.697  1.00 45.77      A    C
ATOM  17460  C    GLY H 129     -17.329-101.396 -43.749  1.00 45.19      A    C
ATOM  17461  O    GLY H 129     -18.066-101.345 -42.755  1.00 45.54      A    O
ATOM  17462  N    TRP H 130     -17.615-100.779 -44.900  1.00 44.30      A    N
ATOM  17463  CA   TRP H 130     -18.799 -99.928 -45.047  1.00 43.29      A    C
ATOM  17464  C    TRP H 130     -20.059-100.768 -44.921  1.00 42.98      A    C
ATOM  17465  O    TRP H 130     -20.191-101.804 -45.582  1.00 43.16      A    O
ATOM  17466  CB   TRP H 130     -18.789 -99.167 -46.384  1.00 42.92      A    C
ATOM  17467  CG   TRP H 130     -17.961 -97.906 -46.392  1.00 42.40      A    C
ATOM  17468  CD1  TRP H 130     -16.658 -97.788 -46.774  1.00 42.63      A    C
ATOM  17469  CD2  TRP H 130     -18.385 -96.590 -46.011  1.00 41.96      A    C
ATOM  17470  CE2  TRP H 130     -17.277 -95.726 -46.186  1.00 41.85      A    C
ATOM  17471  CE3  TRP H 130     -19.596 -96.053 -45.546  1.00 41.73      A    C
ATOM  17472  NE1  TRP H 130     -16.236 -96.484 -46.652  1.00 42.23      A    N
ATOM  17473  CZ2  TRP H 130     -17.341 -94.350 -45.909  1.00 41.39      A    C
ATOM  17474  CZ3  TRP H 130     -19.662 -94.680 -45.271  1.00 41.36      A    C
ATOM  17475  CH2  TRP H 130     -18.539 -93.847 -45.454  1.00 41.15      A    C
ATOM  17476  N    HIS H 131     -20.964-100.329 -44.051  1.00 42.54      A    N
ATOM  17477  CA   HIS H 131     -22.259-100.970 -43.917  1.00 42.35      A    C
ATOM  17478  C    HIS H 131     -23.248-100.385 -44.932  1.00 41.93      A    C
ATOM  17479  O    HIS H 131     -24.028 -99.481 -44.615  1.00 41.70      A    O
ATOM  17480  CB   HIS H 131     -22.805-100.834 -42.495  1.00 42.54      A    C
ATOM  17481  CG   HIS H 131     -23.750-101.929 -42.134  1.00 43.05      A    C
ATOM  17482  CD2  HIS H 131     -23.657-102.918 -41.213  1.00 45.24      A    C
ATOM  17483  ND1  HIS H 131     -24.901-102.183 -42.854  1.00 45.17      A    N
ATOM  17484  CE1  HIS H 131     -25.505-103.248 -42.356  1.00 46.20      A    C
ATOM  17485  NE2  HIS H 131     -24.773-103.712 -41.358  1.00 46.89      A    N
```

FIGURE 1 (cont'd)

```
ATOM  17486  N    VAL H 132     -23.194-100.902 -46.156  1.00 41.69           A    N
ATOM  17487  CA   VAL H 132     -24.044-100.436 -47.244  1.00 41.32           A    C
ATOM  17488  C    VAL H 132     -25.410-101.091 -47.115  1.00 41.35           A    C
ATOM  17489  O    VAL H 132     -25.508-102.277 -46.806  1.00 41.64           A    O
ATOM  17490  CB   VAL H 132     -23.426-100.771 -48.608  1.00 41.28           A    C
ATOM  17491  CG1  VAL H 132     -23.751 -99.693 -49.602  1.00 41.01           A    C
ATOM  17492  N    GLU H 133     -26.462-100.321 -47.354  1.00 41.22           A    N
ATOM  17493  CA   GLU H 133     -27.823-100.784 -47.075  1.00 41.44           A    C
ATOM  17494  C    GLU H 133     -28.879-100.092 -47.961  1.00 41.17           A    C
ATOM  17495  O    GLU H 133     -28.945 -98.856 -48.008  1.00 41.04           A    O
ATOM  17496  CB   GLU H 133     -28.121-100.553 -45.589  1.00 41.64           A    C
ATOM  17497  CG   GLU H 133     -29.458-101.069 -45.095  1.00 42.98           A    C
ATOM  17498  CD   GLU H 133     -29.719-100.651 -43.665  1.00 44.70           A    C
ATOM  17499  OE1  GLU H 133     -28.849-100.899 -42.802  1.00 45.50           A    O
ATOM  17500  OE2  GLU H 133     -30.788-100.064 -43.401  1.00 45.18           A    O
ATOM  17501  N    LEU H 134     -29.697-100.887 -48.653  1.00 41.06           A    N
ATOM  17502  CA   LEU H 134     -30.769-100.356 -49.509  1.00 40.74           A    C
ATOM  17503  C    LEU H 134     -32.026 -99.990 -48.728  1.00 40.52           A    C
ATOM  17504  O    LEU H 134     -32.344-100.624 -47.716  1.00 40.70           A    O
ATOM  17505  CB   LEU H 134     -31.146-101.366 -50.590  1.00 40.93           A    C
ATOM  17506  CG   LEU H 134     -30.483-101.238 -51.960  1.00 41.09           A    C
ATOM  17507  CD1  LEU H 134     -30.794-102.475 -52.801  1.00 41.93           A    C
ATOM  17508  N    ASP H 135     -32.738 -98.969 -49.205  1.00 40.06           A    N
ATOM  17509  CA   ASP H 135     -34.029 -98.592 -48.640  1.00 39.83           A    C
ATOM  17510  C    ASP H 135     -35.067 -98.633 -49.741  1.00 39.77           A    C
ATOM  17511  O    ASP H 135     -35.416 -97.599 -50.306  1.00 39.76           A    O
ATOM  17512  CB   ASP H 135     -33.977 -97.194 -48.013  1.00 39.61           A    C
ATOM  17513  CG   ASP H 135     -35.345 -96.725 -47.509  1.00 39.85           A    C
ATOM  17514  OD1  ASP H 135     -36.098 -97.557 -46.951  1.00 40.64           A    O
ATOM  17515  OD2  ASP H 135     -35.674 -95.530 -47.680  1.00 39.53           A    O
ATOM  17516  N    PRO H 136     -35.556 -99.836 -50.064  1.00 39.79           A    N
ATOM  17517  CA   PRO H 136     -36.549 -99.920 -51.129  1.00 40.04           A    C
ATOM  17518  C    PRO H 136     -37.917 -99.500 -50.616  1.00 40.63           A    C
ATOM  17519  O    PRO H 136     -38.191 -99.660 -49.421  1.00 40.87           A    O
ATOM  17520  CB   PRO H 136     -36.557-101.413 -51.501  1.00 39.29           A    C
ATOM  17521  CG   PRO H 136     -35.571-102.088 -50.577  1.00 38.91           A    C
ATOM  17522  N    PHE H 137     -38.749 -98.951 -51.507  1.00 41.13           A    N
ATOM  17523  CA   PHE H 137     -40.155 -98.643 -51.200  1.00 41.62           A    C
ATOM  17524  C    PHE H 137     -40.943 -98.234 -52.439  1.00 42.05           A    C
ATOM  17525  O    PHE H 137     -40.372 -97.735 -53.412  1.00 41.99           A    O
ATOM  17526  CB   PHE H 137     -40.269 -97.553 -50.123  1.00 41.46           A    C
ATOM  17527  CG   PHE H 137     -39.850 -96.176 -50.590  1.00 41.12           A    C
ATOM  17528  CD1  PHE H 137     -38.500 -95.815 -50.657  1.00 40.79           A    C
ATOM  17529  CD2  PHE H 137     -40.811 -95.230 -50.942  1.00 41.00           A    C
ATOM  17530  CE1  PHE H 137     -38.117 -94.542 -51.078  1.00 40.23           A    C
ATOM  17531  CE2  PHE H 137     -40.437 -93.956 -51.364  1.00 40.53           A    C
ATOM  17532  CZ   PHE H 137     -39.086 -93.615 -51.433  1.00 40.16           A    C
ATOM  17533  N    THR H 138     -42.255 -98.446 -52.388  1.00 42.77           A    N
ATOM  17534  CA   THR H 138     -43.154 -97.984 -53.443  1.00 43.37           A    C
ATOM  17535  C    THR H 138     -43.873 -96.741 -52.974  1.00 43.44           A    C
ATOM  17536  O    THR H 138     -44.179 -96.616 -51.789  1.00 43.60           A    O
ATOM  17537  CB   THR H 138     -44.197 -99.048 -53.816  1.00 43.77           A    C
ATOM  17538  OG1  THR H 138     -43.869 -99.612 -55.094  1.00 44.29           A    O
ATOM  17539  N    ALA H 139     -44.141 -95.821 -53.895  1.00 43.45           A    N
ATOM  17540  CA   ALA H 139     -44.768 -94.553 -53.524  1.00 43.57           A    C
ATOM  17541  C    ALA H 139     -45.707 -94.006 -54.577  1.00 43.93           A    C
ATOM  17542  O    ALA H 139     -45.517 -94.233 -55.775  1.00 44.02           A    O
ATOM  17543  CB   ALA H 139     -43.711 -93.510 -53.174  1.00 43.20           A    C
ATOM  17544  N    SER H 140     -46.703 -93.262 -54.105  1.00 44.35           A    N
ATOM  17545  CA   SER H 140     -47.752 -92.697 -54.940  1.00 44.77           A    C
ATOM  17546  C    SER H 140     -47.322 -91.376 -55.597  1.00 44.45           A    C
ATOM  17547  O    SER H 140     -47.117 -90.378 -54.917  1.00 44.30           A    O
ATOM  17548  CB   SER H 140     -49.014 -92.510 -54.089  1.00 45.21           A    C
ATOM  17549  OG   SER H 140     -49.936 -91.633 -54.709  1.00 46.14           A    O
ATOM  17550  N    THR H 141     -47.184 -91.386 -56.919  1.00 44.24           A    N
```

FIGURE 1 (cont'd)

```
ATOM  17551  CA   THR H 141     -46.798 -90.194 -57.676  1.00 44.01      A  C
ATOM  17552  C    THR H 141     -47.901 -89.781 -58.665  1.00 44.34      A  C
ATOM  17553  O    THR H 141     -48.847 -90.542 -58.887  1.00 44.84      A  O
ATOM  17554  CB   THR H 141     -45.451 -90.401 -58.431  1.00 43.69      A  C
ATOM  17555  CG2  THR H 141     -44.416 -91.020 -57.525  1.00 43.38      A  C
ATOM  17556  OG1  THR H 141     -45.632 -91.248 -59.572  1.00 43.74      A  O
ATOM  17557  N    PRO H 142     -47.798 -88.573 -59.259  1.00 44.28      A  N
ATOM  17558  CA   PRO H 142     -48.740 -88.161 -60.312  1.00 44.49      A  C
ATOM  17559  C    PRO H 142     -48.685 -89.023 -61.576  1.00 44.68      A  C
ATOM  17560  O    PRO H 142     -49.524 -88.870 -62.463  1.00 45.10      A  O
ATOM  17561  CB   PRO H 142     -48.298 -86.731 -60.634  1.00 44.38      A  C
ATOM  17562  CG   PRO H 142     -47.680 -86.250 -59.378  1.00 44.11      A  C
ATOM  17563  CD   PRO H 142     -46.961 -87.445 -58.817  1.00 43.99      A  C
ATOM  17564  N    LEU H 143     -47.694 -89.907 -61.653  1.00 44.51      A  N
ATOM  17565  CA   LEU H 143     -47.594 -90.902 -62.723  1.00 44.54      A  C
ATOM  17566  C    LEU H 143     -48.063 -92.287 -62.249  1.00 44.78      A  C
ATOM  17567  O    LEU H 143     -47.858 -93.285 -62.944  1.00 45.02      A  O
ATOM  17568  CB   LEU H 143     -46.146 -90.985 -63.237  1.00 44.19      A  C
ATOM  17569  CG   LEU H 143     -45.617 -90.139 -64.407  1.00 44.09      A  C
ATOM  17570  CD1  LEU H 143     -46.237 -90.572 -65.744  1.00 45.10      A  C
ATOM  17571  CD2  LEU H 143     -45.795 -88.646 -64.166  1.00 43.69      A  C
ATOM  17572  N    GLY H 144     -48.694 -92.331 -61.073  1.00 44.89      A  N
ATOM  17573  CA   GLY H 144     -49.091 -93.586 -60.425  1.00 44.98      A  C
ATOM  17574  C    GLY H 144     -47.962 -94.215 -59.621  1.00 44.82      A  C
ATOM  17575  O    GLY H 144     -46.887 -93.624 -59.492  1.00 44.47      A  O
ATOM  17576  N    PRO H 145     -48.193 -95.422 -59.071  1.00 44.96      A  N
ATOM  17577  CA   PRO H 145     -47.176 -96.141 -58.290  1.00 44.59      A  C
ATOM  17578  C    PRO H 145     -45.801 -96.195 -58.967  1.00 43.79      A  C
ATOM  17579  O    PRO H 145     -45.689 -96.588 -60.128  1.00 44.03      A  O
ATOM  17580  CB   PRO H 145     -47.770 -97.544 -58.160  1.00 44.98      A  C
ATOM  17581  CG   PRO H 145     -49.241 -97.312 -58.178  1.00 45.65      A  C
ATOM  17582  CD   PRO H 145     -49.474 -96.151 -59.107  1.00 45.48      A  C
ATOM  17583  N    VAL H 146     -44.774 -95.767 -58.242  1.00 42.48      A  N
ATOM  17584  CA   VAL H 146     -43.403 -95.819 -58.729  1.00 41.09      A  C
ATOM  17585  C    VAL H 146     -42.503 -96.446 -57.662  1.00 41.28      A  C
ATOM  17586  O    VAL H 146     -42.631 -96.127 -56.477  1.00 41.31      A  O
ATOM  17587  CB   VAL H 146     -42.885 -94.423 -59.116  1.00 39.27      A  C
ATOM  17588  CG1  VAL H 146     -41.585 -94.527 -59.901  1.00 37.80      A  C
ATOM  17589  N    ASP H 147     -41.611 -97.344 -58.092  1.00 41.35      A  N
ATOM  17590  CA   ASP H 147     -40.704 -98.062 -57.191  1.00 41.09      A  C
ATOM  17591  C    ASP H 147     -39.366 -97.328 -56.998  1.00 40.66      A  C
ATOM  17592  O    ASP H 147     -38.602 -97.141 -57.950  1.00 40.60      A  O
ATOM  17593  CB   ASP H 147     -40.480 -99.501 -57.681  1.00 41.32      A  C
ATOM  17594  CG   ASP H 147     -41.634-100.432 -57.331  1.00 41.27      A  C
ATOM  17595  N    PHE H 148     -39.098 -96.914 -55.757  1.00 40.13      A  N
ATOM  17596  CA   PHE H 148     -37.882 -96.167 -55.415  1.00 39.54      A  C
ATOM  17597  C    PHE H 148     -36.905 -96.987 -54.575  1.00 39.36      A  C
ATOM  17598  O    PHE H 148     -37.230 -98.087 -54.107  1.00 39.54      A  O
ATOM  17599  CB   PHE H 148     -38.231 -94.914 -54.629  1.00 39.31      A  C
ATOM  17600  CG   PHE H 148     -39.118 -93.959 -55.359  1.00 39.36      A  C
ATOM  17601  CD1  PHE H 148     -38.578 -92.967 -56.174  1.00 39.11      A  C
ATOM  17602  CD2  PHE H 148     -40.502 -94.026 -55.212  1.00 39.82      A  C
ATOM  17603  CE1  PHE H 148     -39.409 -92.059 -56.847  1.00 39.25      A  C
ATOM  17604  CE2  PHE H 148     -41.339 -93.127 -55.881  1.00 39.84      A  C
ATOM  17605  CZ   PHE H 148     -40.789 -92.139 -56.698  1.00 39.56      A  C
ATOM  17606  N    GLY H 149     -35.714 -96.430 -54.371  1.00 38.98      A  N
ATOM  17607  CA   GLY H 149     -34.686 -97.085 -53.579  1.00 38.80      A  C
ATOM  17608  C    GLY H 149     -33.510 -96.180 -53.250  1.00 38.53      A  C
ATOM  17609  O    GLY H 149     -32.725 -95.802 -54.123  1.00 38.51      A  O
ATOM  17610  N    ASN H 150     -33.382 -95.836 -51.976  1.00 38.29      A  N
ATOM  17611  CA   ASN H 150     -32.226 -95.090 -51.489  1.00 37.96      A  C
ATOM  17612  C    ASN H 150     -31.023 -95.993 -51.233  1.00 38.14      A  C
ATOM  17613  O    ASN H 150     -31.176 -97.188 -50.964  1.00 38.38      A  O
ATOM  17614  CB   ASN H 150     -32.594 -94.361 -50.200  1.00 37.69      A  C
ATOM  17615  CG   ASN H 150     -33.637 -93.294 -50.420  1.00 37.31      A  C
```

FIGURE 1 (cont'd)

```
ATOM  17616  ND2 ASN H 150     -34.759 -93.386 -49.690  1.00 37.31      A  N
ATOM  17617  OD1 ASN H 150     -33.441 -92.392 -51.236  1.00 36.78      A  O
ATOM  17618  N   VAL H 151     -29.829 -95.421 -51.313  1.00 38.15      A  N
ATOM  17619  CA  VAL H 151     -28.619 -96.143 -50.967  1.00 38.44      A  C
ATOM  17620  C   VAL H 151     -27.976 -95.479 -49.762  1.00 38.66      A  C
ATOM  17621  O   VAL H 151     -27.470 -94.350 -49.865  1.00 38.50      A  O
ATOM  17622  CB  VAL H 151     -27.648 -96.217 -52.149  1.00 38.35      A  C
ATOM  17623  CG1 VAL H 151     -28.252 -97.061 -53.246  1.00 38.73      A  C
ATOM  17624  CG2 VAL H 151     -26.319 -96.810 -51.722  1.00 38.50      A  C
ATOM  17625  N   VAL H 152     -28.015 -96.188 -48.628  1.00 39.21      A  N
ATOM  17626  CA  VAL H 152     -27.508 -95.701 -47.333  1.00 39.70      A  C
ATOM  17627  C   VAL H 152     -26.194 -96.394 -46.926  1.00 40.25      A  C
ATOM  17628  O   VAL H 152     -26.126 -97.624 -46.827  1.00 40.57      A  O
ATOM  17629  CB  VAL H 152     -28.583 -95.835 -46.223  1.00 39.63      A  C
ATOM  17630  CG1 VAL H 152     -29.674 -94.795 -46.417  1.00 39.09      A  C
ATOM  17631  CG2 VAL H 152     -27.962 -95.703 -44.837  1.00 40.01      A  C
ATOM  17632  N   ALA H 153     -25.156 -95.586 -46.700  1.00 40.68      A  N
ATOM  17633  CA  ALA H 153     -23.822 -96.094 -46.376  1.00 41.29      A  C
ATOM  17634  C   ALA H 153     -23.291 -95.478 -45.093  1.00 41.78      A  C
ATOM  17635  O   ALA H 153     -23.246 -94.255 -44.956  1.00 41.73      A  O
ATOM  17636  CB  ALA H 153     -22.862 -95.834 -47.522  1.00 41.11      A  C
ATOM  17637  N   THR H 154     -22.890 -96.336 -44.160  1.00 42.55      A  N
ATOM  17638  CA  THR H 154     -22.377 -95.892 -42.869  1.00 43.20      A  C
ATOM  17639  C   THR H 154     -21.174 -96.733 -42.446  1.00 44.01      A  C
ATOM  17640  O   THR H 154     -21.287 -97.953 -42.301  1.00 44.43      A  O
ATOM  17641  CB  THR H 154     -23.471 -95.986 -41.770  1.00 43.11      A  C
ATOM  17642  CG2 THR H 154     -23.117 -95.097 -40.575  1.00 43.00      A  C
ATOM  17643  OG1 THR H 154     -24.747 -95.602 -42.314  1.00 42.63      A  O
ATOM  17644  N   LEU H 155     -20.020 -96.086 -42.278  1.00 44.69      A  N
ATOM  17645  CA  LEU H 155     -18.896 -96.701 -41.567  1.00 45.58      A  C
ATOM  17646  C   LEU H 155     -19.264 -96.795 -40.098  1.00 46.36      A  C
ATOM  17647  O   LEU H 155     -19.772 -95.827 -39.529  1.00 46.56      A  O
ATOM  17648  CB  LEU H 155     -17.636 -95.848 -41.682  1.00 45.38      A  C
ATOM  17649  CG  LEU H 155     -16.538 -96.252 -42.652  1.00 45.38      A  C
ATOM  17650  CD1 LEU H 155     -15.263 -95.516 -42.263  1.00 45.21      A  C
ATOM  17651  CD2 LEU H 155     -16.332 -97.756 -42.615  1.00 45.85      A  C
ATOM  17652  N   ASP H 156     -19.027 -97.950 -39.485  1.00 47.24      A  N
ATOM  17653  CA  ASP H 156     -19.236 -98.094 -38.042  1.00 48.07      A  C
ATOM  17654  C   ASP H 156     -20.654 -97.660 -37.612  1.00 47.91      A  C
ATOM  17655  O   ASP H 156     -20.825 -96.591 -37.022  1.00 47.67      A  O
ATOM  17656  CB  ASP H 156     -18.161 -97.279 -37.301  1.00 48.59      A  C
ATOM  17657  CG  ASP H 156     -18.033 -97.642 -35.830  1.00 50.20      A  C
ATOM  17658  OD1 ASP H 156     -18.859 -98.419 -35.304  1.00 51.16      A  O
ATOM  17659  OD2 ASP H 156     -17.084 -97.129 -35.197  1.00 51.70      A  O
ATOM  17660  N   PRO H 157     -21.676 -98.490 -37.909  1.00 48.01      A  N
ATOM  17661  CA  PRO H 157     -23.049 -98.169 -37.520  1.00 48.07      A  C
ATOM  17662  C   PRO H 157     -23.221 -97.996 -36.019  1.00 48.40      A  C
ATOM  17663  O   PRO H 157     -24.176 -97.341 -35.583  1.00 48.29      A  O
ATOM  17664  CB  PRO H 157     -23.840 -99.398 -37.969  1.00 48.03      A  C
ATOM  17665  CG  PRO H 157     -23.021-100.005 -39.035  1.00 48.07      A  C
ATOM  17666  CD  PRO H 157     -21.605 -99.763 -38.650  1.00 48.14      A  C
ATOM  17667  N   ARG H 158     -22.306 -98.581 -35.241  1.00 48.94      A  N
ATOM  17668  CA  ARG H 158     -22.383 -98.534 -33.768  1.00 49.45      A  C
ATOM  17669  C   ARG H 158     -21.935 -97.201 -33.140  1.00 49.27      A  C
ATOM  17670  O   ARG H 158     -22.320 -96.886 -32.004  1.00 49.57      A  O
ATOM  17671  CB  ARG H 158     -21.700 -99.759 -33.102  1.00 49.93      A  C
ATOM  17672  CG  ARG H 158     -20.281-100.080 -33.556  1.00 50.25      A  C
ATOM  17673  N   ALA H 159     -21.156 -96.412 -33.881  1.00 48.78      A  N
ATOM  17674  CA  ALA H 159     -20.768 -95.065 -33.434  1.00 48.37      A  C
ATOM  17675  C   ALA H 159     -21.997 -94.194 -33.144  1.00 48.05      A  C
ATOM  17676  O   ALA H 159     -22.989 -94.233 -33.886  1.00 47.80      A  O
ATOM  17677  CB  ALA H 159     -19.858 -94.387 -34.459  1.00 48.23      A  C
ATOM  17678  N   ALA H 160     -21.910 -93.414 -32.066  1.00 47.91      A  N
ATOM  17679  CA  ALA H 160     -23.048 -92.654 -31.537  1.00 47.63      A  C
ATOM  17680  C   ALA H 160     -23.553 -91.572 -32.488  1.00 47.12      A  C
```

FIGURE 1 (cont'd)

```
ATOM  17681  O    ALA H 160     -24.761 -91.326 -32.572  1.00 47.04      A    O
ATOM  17682  CB   ALA H 160     -22.699 -92.051 -30.181  1.00 48.03      A    C
ATOM  17683  N    ARG H 161     -22.623 -90.934 -33.198  1.00 46.56      A    N
ATOM  17684  CA   ARG H 161     -22.941 -89.871 -34.164  1.00 45.95      A    C
ATOM  17685  C    ARG H 161     -22.098 -89.982 -35.444  1.00 45.16      A    C
ATOM  17686  O    ARG H 161     -21.011 -90.571 -35.428  1.00 45.29      A    O
ATOM  17687  CB   ARG H 161     -22.728 -88.497 -33.526  1.00 46.19      A    C
ATOM  17688  CG   ARG H 161     -23.877 -88.019 -32.645  1.00 47.55      A    C
ATOM  17689  CD   ARG H 161     -23.347 -87.310 -31.417  1.00 50.38      A    C
ATOM  17690  NE   ARG H 161     -22.070 -86.649 -31.694  1.00 52.63      A    N
ATOM  17691  CZ   ARG H 161     -21.024 -86.639 -30.865  1.00 53.89      A    C
ATOM  17692  NH1  ARG H 161     -21.086 -87.259 -29.685  1.00 54.68      A    N
ATOM  17693  NH2  ARG H 161     -19.908 -86.007 -31.218  1.00 54.15      A    N
ATOM  17694  N    HIS H 162     -22.604 -89.414 -36.542  1.00 44.09      A    N
ATOM  17695  CA   HIS H 162     -21.891 -89.410 -37.828  1.00 43.03      A    C
ATOM  17696  C    HIS H 162     -22.099 -88.130 -38.642  1.00 41.98      A    C
ATOM  17697  O    HIS H 162     -23.190 -87.533 -38.647  1.00 41.72      A    O
ATOM  17698  CB   HIS H 162     -22.286 -90.621 -38.675  1.00 43.23      A    C
ATOM  17699  CG   HIS H 162     -23.765 -90.818 -38.788  1.00 43.88      A    C
ATOM  17700  CD2  HIS H 162     -24.583 -91.748 -38.239  1.00 44.47      A    C
ATOM  17701  ND1  HIS H 162     -24.572 -89.992 -39.543  1.00 44.07      A    N
ATOM  17702  CE1  HIS H 162     -25.824 -90.405 -39.454  1.00 44.30      A    C
ATOM  17703  NE2  HIS H 162     -25.858 -91.473 -38.674  1.00 44.57      A    N
ATOM  17704  N    LEU H 163     -21.033 -87.712 -39.321  1.00 40.87      A    N
ATOM  17705  CA   LEU H 163     -21.133 -86.674 -40.333  1.00 39.68      A    C
ATOM  17706  C    LEU H 163     -21.810 -87.323 -41.508  1.00 38.99      A    C
ATOM  17707  O    LEU H 163     -21.441 -88.431 -41.903  1.00 39.03      A    O
ATOM  17708  CB   LEU H 163     -19.751 -86.174 -40.755  1.00 39.57      A    C
ATOM  17709  CG   LEU H 163     -19.675 -85.366 -42.051  1.00 38.90      A    C
ATOM  17710  CD1  LEU H 163     -20.419 -84.040 -41.936  1.00 38.47      A    C
ATOM  17711  CD2  LEU H 163     -18.231 -85.141 -42.442  1.00 38.86      A    C
ATOM  17712  N    THR H 164     -22.803 -86.645 -42.064  1.00 38.03      A    N
ATOM  17713  CA   THR H 164     -23.535 -87.223 -43.185  1.00 37.07      A    C
ATOM  17714  C    THR H 164     -23.576 -86.329 -44.429  1.00 36.48      A    C
ATOM  17715  O    THR H 164     -24.102 -85.211 -44.399  1.00 36.24      A    O
ATOM  17716  CB   THR H 164     -24.937 -87.775 -42.762  1.00 37.03      A    C
ATOM  17717  CG2  THR H 164     -25.718 -86.764 -41.930  1.00 36.95      A    C
ATOM  17718  OG1  THR H 164     -25.693 -88.153 -43.922  1.00 36.66      A    O
ATOM  17719  N    LEU H 165     -22.978 -86.839 -45.506  1.00 35.88      A    N
ATOM  17720  CA   LEU H 165     -23.003 -86.197 -46.818  1.00 35.32      A    C
ATOM  17721  C    LEU H 165     -24.066 -86.846 -47.704  1.00 35.00      A    C
ATOM  17722  O    LEU H 165     -24.293 -88.061 -47.634  1.00 35.04      A    O
ATOM  17723  CB   LEU H 165     -21.629 -86.294 -47.494  1.00 35.25      A    C
ATOM  17724  CG   LEU H 165     -20.406 -85.735 -46.764  1.00 35.30      A    C
ATOM  17725  CD1  LEU H 165     -19.191 -85.742 -47.671  1.00 35.41      A    C
ATOM  17726  CD2  LEU H 165     -20.674 -84.333 -46.258  1.00 35.09      A    C
ATOM  17727  N    ALA H 166     -24.714 -86.033 -48.535  1.00 34.51      A    N
ATOM  17728  CA   ALA H 166     -25.777 -86.531 -49.395  1.00 34.09      A    C
ATOM  17729  C    ALA H 166     -25.801 -85.906 -50.786  1.00 33.82      A    C
ATOM  17730  O    ALA H 166     -25.453 -84.736 -50.975  1.00 33.66      A    O
ATOM  17731  CB   ALA H 166     -27.123 -86.371 -48.721  1.00 34.09      A    C
ATOM  17732  N    CYS H 167     -26.203 -86.730 -51.748  1.00 33.66      A    N
ATOM  17733  CA   CYS H 167     -26.492 -86.332 -53.123  1.00 33.53      A    C
ATOM  17734  C    CYS H 167     -27.713 -87.144 -53.539  1.00 33.49      A    C
ATOM  17735  O    CYS H 167     -28.098 -88.101 -52.856  1.00 33.55      A    O
ATOM  17736  CB   CYS H 167     -25.321 -86.682 -54.050  1.00 33.53      A    C
ATOM  17737  SG   CYS H 167     -25.032 -88.489 -54.276  1.00 33.77      A    S
ATOM  17738  N    HIS H 168     -28.324 -86.768 -54.654  1.00 33.46      A    N
ATOM  17739  CA   HIS H 168     -29.378 -87.595 -55.217  1.00 33.50      A    C
ATOM  17740  C    HIS H 168     -28.913 -88.201 -56.531  1.00 33.44      A    C
ATOM  17741  O    HIS H 168     -28.342 -87.509 -57.381  1.00 33.37      A    O
ATOM  17742  CB   HIS H 168     -30.675 -86.807 -55.401  1.00 33.63      A    C
ATOM  17743  CG   HIS H 168     -30.673 -85.912 -56.598  1.00 34.01      A    C
ATOM  17744  CD2  HIS H 168     -30.322 -84.613 -56.737  1.00 34.33      A    C
ATOM  17745  ND1  HIS H 168     -31.054 -86.344 -57.851  1.00 34.35      A    N
```

FIGURE 1 (cont'd)

```
ATOM  17746 CE1 HIS H 168     -30.941 -85.347 -58.709  1.00 34.39      A  C
ATOM  17747 NE2 HIS H 168     -30.498 -84.286 -58.059  1.00 34.33      A  N
ATOM  17748 N   TYR H 169     -29.171 -89.492 -56.698  1.00 33.52      A  N
ATOM  17749 CA  TYR H 169     -28.651 -90.225 -57.847  1.00 33.68      A  C
ATOM  17750 C   TYR H 169     -29.645 -90.366 -59.008  1.00 33.75      A  C
ATOM  17751 O   TYR H 169     -29.262 -90.712 -60.116  1.00 33.74      A  O
ATOM  17752 CB  TYR H 169     -28.079 -91.582 -57.406  1.00 33.74      A  C
ATOM  17753 CG  TYR H 169     -29.110 -92.660 -57.157  1.00 33.96      A  C
ATOM  17754 CD1 TYR H 169     -29.777 -92.752 -55.935  1.00 33.86      A  C
ATOM  17755 CD2 TYR H 169     -29.408 -93.598 -58.140  1.00 34.41      A  C
ATOM  17756 CE1 TYR H 169     -30.721 -93.755 -55.703  1.00 33.95      A  C
ATOM  17757 CE2 TYR H 169     -30.350 -94.599 -57.918  1.00 34.64      A  C
ATOM  17758 CZ  TYR H 169     -30.998 -94.671 -56.701  1.00 34.22      A  C
ATOM  17759 OH  TYR H 169     -31.914 -95.666 -56.499  1.00 34.30      A  O
ATOM  17760 N   ASP H 170     -30.918 -90.101 -58.754  1.00 33.89      A  N
ATOM  17761 CA  ASP H 170     -31.898 -90.092 -59.830  1.00 34.22      A  C
ATOM  17762 C   ASP H 170     -31.625 -88.925 -60.779  1.00 34.44      A  C
ATOM  17763 O   ASP H 170     -30.927 -87.977 -60.415  1.00 34.25      A  O
ATOM  17764 CB  ASP H 170     -33.325 -90.019 -59.272  1.00 34.26      A  C
ATOM  17765 CG  ASP H 170     -33.620 -88.706 -58.558  1.00 34.17      A  C
ATOM  17766 OD1 ASP H 170     -32.914 -88.355 -57.591  1.00 33.79      A  O
ATOM  17767 OD2 ASP H 170     -34.587 -88.032 -58.955  1.00 34.57      A  O
ATOM  17768 N   SER H 171     -32.152 -89.022 -61.998  1.00 34.91      A  N
ATOM  17769 CA  SER H 171     -32.089 -87.935 -62.978  1.00 35.34      A  C
ATOM  17770 C   SER H 171     -33.507 -87.549 -63.372  1.00 35.64      A  C
ATOM  17771 O   SER H 171     -34.382 -88.420 -63.425  1.00 35.96      A  O
ATOM  17772 CB  SER H 171     -31.321 -88.373 -64.224  1.00 35.42      A  C
ATOM  17773 OG  SER H 171     -32.152 -89.109 -65.110  1.00 35.85      A  O
ATOM  17774 N   LYS H 172     -33.742 -86.266 -63.665  1.00 35.78      A  N
ATOM  17775 CA  LYS H 172     -35.096 -85.818 -63.972  1.00 36.17      A  C
ATOM  17776 C   LYS H 172     -35.663 -86.498 -65.209  1.00 36.90      A  C
ATOM  17777 O   LYS H 172     -34.928 -86.883 -66.117  1.00 37.16      A  O
ATOM  17778 CB  LYS H 172     -35.168 -84.312 -64.125  1.00 35.91      A  C
ATOM  17779 CG  LYS H 172     -36.602 -83.768 -64.040  1.00 35.71      A  C
ATOM  17780 CD  LYS H 172     -36.682 -82.258 -64.279  1.00 35.09      A  C
ATOM  17781 CE  LYS H 172     -38.117 -81.776 -64.346  1.00 35.06      A  C
ATOM  17782 NZ  LYS H 172     -38.731 -81.718 -63.001  1.00 35.04      A  N
ATOM  17783 N   LEU H 173     -36.984 -86.648 -65.219  1.00 37.71      A  N
ATOM  17784 CA  LEU H 173     -37.722 -87.294 -66.307  1.00 38.60      A  C
ATOM  17785 C   LEU H 173     -38.321 -86.246 -67.229  1.00 39.11      A  C
ATOM  17786 O   LEU H 173     -39.070 -85.375 -66.784  1.00 39.20      A  O
ATOM  17787 CB  LEU H 173     -38.826 -88.133 -65.687  1.00 38.65      A  C
ATOM  17788 CG  LEU H 173     -39.823 -89.123 -66.276  1.00 39.24      A  C
ATOM  17789 CD1 LEU H 173     -39.377 -90.036 -67.390  1.00 39.58      A  C
ATOM  17790 CD2 LEU H 173     -41.277 -88.716 -66.311  1.00 39.41      A  C
ATOM  17791 N   PHE H 174     -37.985 -86.334 -68.510  1.00 39.76      A  N
ATOM  17792 CA  PHE H 174     -38.443 -85.360 -69.483  1.00 40.37      A  C
ATOM  17793 C   PHE H 174     -39.176 -86.005 -70.665  1.00 40.30      A  C
ATOM  17794 O   PHE H 174     -39.425 -87.216 -70.658  1.00 41.40      A  O
ATOM  17795 CB  PHE H 174     -37.244 -84.616 -70.071  1.00 40.61      A  C
ATOM  17796 CG  PHE H 174     -36.710 -83.517 -69.224  1.00 40.47      A  C
ATOM  17797 CD1 PHE H 174     -37.338 -82.268 -69.169  1.00 40.62      A  C
ATOM  17798 CD2 PHE H 174     -35.540 -83.710 -68.513  1.00 40.04      A  C
ATOM  17799 CE1 PHE H 174     -36.817 -81.238 -68.379  1.00 40.11      A  C
ATOM  17800 CE2 PHE H 174     -35.010 -82.693 -67.725  1.00 39.56      A  C
ATOM  17801 CZ  PHE H 174     -35.648 -81.454 -67.659  1.00 39.67      A  C
ATOM  17802 N   PRO H 175     -39.246 -85.245 -71.793  1.00 39.02      A  N
ATOM  17803 CA  PRO H 175     -40.206 -85.091 -72.886  1.00 38.33      A  C
ATOM  17804 C   PRO H 175     -41.442 -85.973 -72.777  1.00 38.53      A  C
ATOM  17805 O   PRO H 175     -42.445 -85.499 -72.251  1.00 38.66      A  O
ATOM  17806 CB  PRO H 175     -39.365 -85.395 -74.138  1.00 38.08      A  C
ATOM  17807 CG  PRO H 175     -37.931 -85.751 -73.611  1.00 37.93      A  C
ATOM  17808 CD  PRO H 175     -37.888 -85.012 -72.336  1.00 38.85      A  C
ATOM  17809 N   PRO H 176     -41.390 -87.236 -73.262  1.00 39.17      A  N
ATOM  17810 CA  PRO H 176     -40.325 -87.950 -73.961  1.00 40.36      A  C
```

FIGURE 1 (cont'd)

```
ATOM  17811  C    PRO H 176     -40.570 -87.923 -75.481  1.00 42.38      A  C
ATOM  17812  O    PRO H 176     -41.679 -87.580 -75.913  1.00 42.63      A  O
ATOM  17813  CB   PRO H 176     -40.453 -89.367 -73.406  1.00 39.98      A  C
ATOM  17814  CG   PRO H 176     -41.950 -89.511 -73.096  1.00 39.34      A  C
ATOM  17815  CD   PRO H 176     -42.558 -88.116 -73.071  1.00 38.95      A  C
ATOM  17816  N    GLY H 177     -39.557 -88.257 -76.287  1.00 44.30      A  N
ATOM  17817  CA   GLY H 177     -38.225 -88.665 -75.815  1.00 46.05      A  C
ATOM  17818  C    GLY H 177     -37.162 -87.631 -76.126  1.00 46.97      A  C
ATOM  17819  O    GLY H 177     -36.018 -87.753 -75.682  1.00 47.28      A  O
ATOM  17820  N    SER H 178     -37.567 -86.602 -76.870  1.00 47.21      A  N
ATOM  17821  CA   SER H 178     -36.704 -85.502 -77.304  1.00 46.94      A  C
ATOM  17822  C    SER H 178     -35.222 -85.700 -77.243  1.00 46.89      A  C
ATOM  17823  O    SER H 178     -34.692 -86.167 -78.213  1.00 47.48      A  O
ATOM  17824  CB   SER H 178     -37.062 -84.192 -76.674  1.00 45.28      A  C
ATOM  17825  OG   SER H 178     -38.282 -84.355 -75.938  1.00 44.54      A  O
ATOM  17826  N    THR H 179     -34.517 -85.301 -76.194  1.00 45.47      A  N
ATOM  17827  CA   THR H 179     -33.112 -85.671 -76.188  1.00 43.02      A  C
ATOM  17828  C    THR H 179     -32.771 -86.140 -74.792  1.00 43.49      A  C
ATOM  17829  O    THR H 179     -33.214 -85.522 -73.815  1.00 44.43      A  O
ATOM  17830  CB   THR H 179     -32.188 -84.558 -76.757  1.00 37.57      A  C
ATOM  17831  OG1  THR H 179     -31.212 -84.191 -75.785  1.00 34.54      A  O
ATOM  17832  N    PRO H 180     -32.015 -87.255 -74.690  1.00 42.27      A  N
ATOM  17833  CA   PRO H 180     -31.748 -87.894 -73.398  1.00 41.26      A  C
ATOM  17834  C    PRO H 180     -31.173 -86.885 -72.409  1.00 42.04      A  C
ATOM  17835  O    PRO H 180     -30.374 -86.026 -72.802  1.00 42.93      A  O
ATOM  17836  CB   PRO H 180     -30.687 -88.943 -73.744  1.00 36.48      A  C
ATOM  17837  CG   PRO H 180     -29.983 -88.387 -74.974  1.00 34.99      A  C
ATOM  17838  CD   PRO H 180     -31.144 -87.802 -75.754  1.00 41.23      A  C
ATOM  17839  N    PHE H 181     -31.590 -86.971 -71.148  1.00 41.82      A  N
ATOM  17840  CA   PHE H 181     -31.103 -86.048 -70.119  1.00 40.95      A  C
ATOM  17841  C    PHE H 181     -30.354 -86.759 -69.001  1.00 40.24      A  C
ATOM  17842  O    PHE H 181     -30.948 -87.546 -68.250  1.00 40.02      A  O
ATOM  17843  CB   PHE H 181     -32.246 -85.225 -69.540  1.00 40.99      A  C
ATOM  17844  CG   PHE H 181     -31.856 -84.425 -68.333  1.00 40.75      A  C
ATOM  17845  CD1  PHE H 181     -31.065 -83.284 -68.461  1.00 40.87      A  C
ATOM  17846  CD2  PHE H 181     -32.280 -84.812 -67.061  1.00 40.51      A  C
ATOM  17847  CE1  PHE H 181     -30.703 -82.537 -67.334  1.00 40.28      A  C
ATOM  17848  CE2  PHE H 181     -31.926 -84.051 -65.928  1.00 39.99      A  C
ATOM  17849  CZ   PHE H 181     -31.135 -82.932 -66.066  1.00 39.75      A  C
ATOM  17850  N    VAL H 182     -29.058 -86.461 -68.891  1.00 39.44      A  N
ATOM  17851  CA   VAL H 182     -28.181 -87.152 -67.930  1.00 38.72      A  C
ATOM  17852  C    VAL H 182     -27.861 -86.366 -66.647  1.00 37.94      A  C
ATOM  17853  O    VAL H 182     -27.380 -86.944 -65.664  1.00 37.77      A  O
ATOM  17854  CB   VAL H 182     -26.863 -87.680 -68.580  1.00 38.76      A  C
ATOM  17855  CG1  VAL H 182     -27.132 -88.932 -69.385  1.00 39.10      A  C
ATOM  17856  CG2  VAL H 182     -26.201 -86.613 -69.434  1.00 39.10      A  C
ATOM  17857  N    GLY H 183     -28.130 -85.062 -66.660  1.00 37.22      A  N
ATOM  17858  CA   GLY H 183     -27.912 -84.207 -65.489  1.00 36.25      A  C
ATOM  17859  C    GLY H 183     -26.568 -84.414 -64.821  1.00 35.58      A  C
ATOM  17860  O    GLY H 183     -26.479 -85.017 -63.752  1.00 35.39      A  O
ATOM  17861  N    ALA H 184     -25.521 -83.914 -65.462  1.00 35.06      A  N
ATOM  17862  CA   ALA H 184     -24.167 -84.100 -64.975  1.00 34.47      A  C
ATOM  17863  C    ALA H 184     -23.967 -83.370 -63.666  1.00 33.91      A  C
ATOM  17864  O    ALA H 184     -23.453 -83.948 -62.721  1.00 33.75      A  O
ATOM  17865  CB   ALA H 184     -23.157 -83.636 -66.011  1.00 34.80      A  C
ATOM  17866  N    THR H 185     -24.381 -82.105 -63.612  1.00 33.37      A  N
ATOM  17867  CA   THR H 185     -24.316 -81.313 -62.379  1.00 32.81      A  C
ATOM  17868  C    THR H 185     -25.437 -81.705 -61.428  1.00 32.57      A  C
ATOM  17869  O    THR H 185     -25.406 -81.349 -60.245  1.00 32.55      A  O
ATOM  17870  CB   THR H 185     -24.466 -79.803 -62.647  1.00 32.74      A  C
ATOM  17871  CG2  THR H 185     -23.581 -79.368 -63.804  1.00 33.01      A  C
ATOM  17872  OG1  THR H 185     -25.839 -79.487 -62.938  1.00 32.39      A  O
ATOM  17873  N    ASP H 186     -26.413 -82.449 -61.948  1.00 32.32      A  N
ATOM  17874  CA   ASP H 186     -27.686 -82.620 -61.279  1.00 32.08      A  C
ATOM  17875  C    ASP H 186     -28.130 -84.087 -61.271  1.00 32.14      A  C
```

FIGURE 1 (cont'd)

```
ATOM  17876  O    ASP H 186     -29.024 -84.443 -62.026  1.00 32.48       A    O
ATOM  17877  CB   ASP H 186     -28.714 -81.733 -62.003  1.00 32.00       A    C
ATOM  17878  CG   ASP H 186     -30.028 -81.568 -61.245  1.00 31.49       A    C
ATOM  17879  OD1  ASP H 186     -30.908 -80.855 -61.776  1.00 31.34       A    O
ATOM  17880  OD2  ASP H 186     -30.202 -82.132 -60.142  1.00 30.68       A    O
ATOM  17881  N    SER H 187     -27.543 -84.950 -60.433  1.00 31.91       A    N
ATOM  17882  CA   SER H 187     -26.472 -84.624 -59.487  1.00 31.66       A    C
ATOM  17883  C    SER H 187     -25.319 -85.632 -59.557  1.00 31.62       A    C
ATOM  17884  O    SER H 187     -24.727 -85.989 -58.534  1.00 31.47       A    O
ATOM  17885  CB   SER H 187     -27.023 -84.560 -58.064  1.00 31.55       A    C
ATOM  17886  OG   SER H 187     -27.789 -83.389 -57.875  1.00 31.70       A    O
ATOM  17887  N    ALA H 188     -25.000 -86.066 -60.775  1.00 31.77       A    N
ATOM  17888  CA   ALA H 188     -23.952 -87.058 -61.021  1.00 31.85       A    C
ATOM  17889  C    ALA H 188     -22.619 -86.698 -60.357  1.00 31.83       A    C
ATOM  17890  O    ALA H 188     -22.085 -87.483 -59.574  1.00 31.84       A    O
ATOM  17891  CB   ALA H 188     -23.776 -87.276 -62.520  1.00 32.02       A    C
ATOM  17892  N    VAL H 189     -22.104 -85.508 -60.662  1.00 31.76       A    N
ATOM  17893  CA   VAL H 189     -20.863 -85.012 -60.073  1.00 31.65       A    C
ATOM  17894  C    VAL H 189     -20.928 -85.045 -58.546  1.00 31.64       A    C
ATOM  17895  O    VAL H 189     -20.045 -85.623 -57.913  1.00 31.76       A    O
ATOM  17896  CB   VAL H 189     -20.492 -83.594 -60.578  1.00 31.57       A    C
ATOM  17897  CG1  VAL H 189     -19.324 -83.019 -59.801  1.00 31.34       A    C
ATOM  17898  CG2  VAL H 189     -20.155 -83.632 -62.044  1.00 31.79       A    C
ATOM  17899  N    PRO H 190     -21.969 -84.440 -57.945  1.00 31.53       A    N
ATOM  17900  CA   PRO H 190     -22.100 -84.568 -56.496  1.00 31.57       A    C
ATOM  17901  C    PRO H 190     -21.945 -86.003 -55.985  1.00 31.79       A    C
ATOM  17902  O    PRO H 190     -21.198 -86.245 -55.029  1.00 31.82       A    O
ATOM  17903  CB   PRO H 190     -23.514 -84.059 -56.245  1.00 31.38       A    C
ATOM  17904  CG   PRO H 190     -23.679 -82.986 -57.266  1.00 31.36       A    C
ATOM  17905  CD   PRO H 190     -22.902 -83.432 -58.480  1.00 31.47       A    C
ATOM  17906  N    CYS H 191     -22.627 -86.944 -56.628  1.00 32.13       A    N
ATOM  17907  CA   CYS H 191     -22.542 -88.329 -56.209  1.00 32.68       A    C
ATOM  17908  C    CYS H 191     -21.165 -88.905 -56.456  1.00 32.98       A    C
ATOM  17909  O    CYS H 191     -20.656 -89.655 -55.625  1.00 33.20       A    O
ATOM  17910  CB   CYS H 191     -23.612 -89.175 -56.883  1.00 32.75       A    C
ATOM  17911  SG   CYS H 191     -25.276 -88.796 -56.273  1.00 33.36       A    S
ATOM  17912  N    ALA H 192     -20.555 -88.540 -57.579  1.00 33.21       A    N
ATOM  17913  CA   ALA H 192     -19.201 -89.002 -57.906  1.00 33.44       A    C
ATOM  17914  C    ALA H 192     -18.172 -88.576 -56.861  1.00 33.43       A    C
ATOM  17915  O    ALA H 192     -17.268 -89.337 -56.539  1.00 33.71       A    O
ATOM  17916  CB   ALA H 192     -18.784 -88.513 -59.272  1.00 33.60       A    C
ATOM  17917  N    LEU H 193     -18.317 -87.360 -56.338  1.00 33.03       A    N
ATOM  17918  CA   LEU H 193     -17.419 -86.848 -55.317  1.00 32.64       A    C
ATOM  17919  C    LEU H 193     -17.528 -87.678 -54.041  1.00 33.19       A    C
ATOM  17920  O    LEU H 193     -16.522 -88.104 -53.473  1.00 33.57       A    O
ATOM  17921  CB   LEU H 193     -17.728 -85.382 -55.024  1.00 31.31       A    C
ATOM  17922  CG   LEU H 193     -17.363 -84.387 -56.111  1.00 29.72       A    C
ATOM  17923  CD1  LEU H 193     -17.906 -83.036 -55.732  1.00 28.77       A    C
ATOM  17924  N    LEU H 194     -18.759 -87.920 -53.606  1.00 33.40       A    N
ATOM  17925  CA   LEU H 194     -19.004 -88.725 -52.416  1.00 33.57       A    C
ATOM  17926  C    LEU H 194     -18.262 -90.068 -52.488  1.00 34.48       A    C
ATOM  17927  O    LEU H 194     -17.690 -90.531 -51.494  1.00 34.78       A    O
ATOM  17928  CB   LEU H 194     -20.510 -88.917 -52.199  1.00 32.47       A    C
ATOM  17929  CG   LEU H 194     -21.260 -87.648 -51.790  1.00 31.26       A    C
ATOM  17930  CD1  LEU H 194     -22.420 -87.992 -50.895  1.00 30.89       A    C
ATOM  17931  N    LEU H 195     -18.251 -90.670 -53.674  1.00 35.28       A    N
ATOM  17932  CA   LEU H 195     -17.542 -91.927 -53.902  1.00 36.10       A    C
ATOM  17933  C    LEU H 195     -16.031 -91.743 -53.841  1.00 36.80       A    C
ATOM  17934  O    LEU H 195     -15.346 -92.481 -53.137  1.00 37.11       A    O
ATOM  17935  CB   LEU H 195     -17.931 -92.531 -55.249  1.00 36.03       A    C
ATOM  17936  CG   LEU H 195     -19.368 -93.012 -55.423  1.00 35.80       A    C
ATOM  17937  CD1  LEU H 195     -19.590 -93.425 -56.862  1.00 36.06       A    C
ATOM  17938  CD2  LEU H 195     -19.647 -94.162 -54.488  1.00 35.82       A    C
ATOM  17939  N    GLU H 196     -15.528 -90.754 -54.579  1.00 37.42       A    N
ATOM  17940  CA   GLU H 196     -14.098 -90.443 -54.636  1.00 38.04       A    C
```

FIGURE 1 (cont'd)

```
ATOM  17941  C    GLU H 196     -13.519 -90.099 -53.262  1.00 38.14      A C
ATOM  17942  O    GLU H 196     -12.437 -90.578 -52.908  1.00 38.33      A O
ATOM  17943  CB   GLU H 196     -13.836 -89.303 -55.626  1.00 38.19      A C
ATOM  17944  CG   GLU H 196     -12.437 -88.674 -55.536  1.00 39.32      A C
ATOM  17945  CD   GLU H 196     -11.318 -89.574 -56.055  1.00 40.80      A C
ATOM  17946  OE1  GLU H 196     -11.614 -90.671 -56.591  1.00 41.42      A O
ATOM  17947  OE2  GLU H 196     -10.137 -89.167 -55.931  1.00 41.50      A O
ATOM  17948  N    LEU H 197     -14.245 -89.273 -52.508  1.00 38.12      A N
ATOM  17949  CA   LEU H 197     -13.886 -88.942 -51.138  1.00 38.36      A C
ATOM  17950  C    LEU H 197     -13.772 -90.194 -50.280  1.00 38.86      A C
ATOM  17951  O    LEU H 197     -12.799 -90.366 -49.536  1.00 39.17      A O
ATOM  17952  CB   LEU H 197     -14.926 -88.008 -50.527  1.00 37.95      A C
ATOM  17953  CG   LEU H 197     -14.584 -86.522 -50.445  1.00 37.75      A C
ATOM  17954  CD1  LEU H 197     -14.853 -85.818 -51.746  1.00 37.59      A C
ATOM  17955  CD2  LEU H 197     -15.399 -85.878 -49.344  1.00 37.67      A C
ATOM  17956  N    ALA H 198     -14.764 -91.073 -50.399  1.00 39.32      A N
ATOM  17957  CA   ALA H 198     -14.814 -92.305 -49.605  1.00 40.06      A C
ATOM  17958  C    ALA H 198     -13.655 -93.239 -49.911  1.00 40.78      A C
ATOM  17959  O    ALA H 198     -13.223 -94.007 -49.054  1.00 41.09      A O
ATOM  17960  CB   ALA H 198     -16.134 -93.020 -49.822  1.00 39.87      A C
ATOM  17961  N    GLN H 199     -13.165 -93.155 -51.141  1.00 41.36      A N
ATOM  17962  CA   GLN H 199     -12.081 -93.994 -51.615  1.00 42.04      A C
ATOM  17963  C    GLN H 199     -10.731 -93.377 -51.276  1.00 42.96      A C
ATOM  17964  O    GLN H 199      -9.840 -94.072 -50.794  1.00 43.57      A O
ATOM  17965  CB   GLN H 199     -12.193 -94.180 -53.127  1.00 40.95      A C
ATOM  17966  CG   GLN H 199     -12.176 -95.623 -53.605  1.00 40.41      A C
ATOM  17967  CD   GLN H 199     -11.010 -96.442 -53.085  1.00 40.14      A C
ATOM  17968  OE1  GLN H 199      -9.898 -96.344 -53.591  1.00 40.46      A O
ATOM  17969  N    ALA H 200     -10.583 -92.079 -51.536  1.00 43.63      A N
ATOM  17970  CA   ALA H 200      -9.323 -91.365 -51.283  1.00 44.37      A C
ATOM  17971  C    ALA H 200      -8.938 -91.339 -49.802  1.00 44.92      A C
ATOM  17972  O    ALA H 200      -7.763 -91.492 -49.457  1.00 45.36      A O
ATOM  17973  CB   ALA H 200      -9.380 -89.947 -51.842  1.00 44.13      A C
ATOM  17974  N    LEU H 201      -9.932 -91.157 -48.936  1.00 45.25      A N
ATOM  17975  CA   LEU H 201      -9.707 -91.134 -47.493  1.00 45.79      A C
ATOM  17976  C    LEU H 201      -9.970 -92.487 -46.858  1.00 46.51      A C
ATOM  17977  O    LEU H 201     -10.001 -92.602 -45.634  1.00 46.75      A O
ATOM  17978  CB   LEU H 201     -10.603 -90.092 -46.831  1.00 45.35      A C
ATOM  17979  CG   LEU H 201     -10.358 -88.644 -47.243  1.00 45.11      A C
ATOM  17980  CD1  LEU H 201     -11.552 -87.754 -46.871  1.00 44.78      A C
ATOM  17981  CD2  LEU H 201      -9.037 -88.115 -46.676  1.00 45.37      A C
ATOM  17982  N    ASP H 202     -10.149 -93.503 -47.698  1.00 47.27      A N
ATOM  17983  CA   ASP H 202     -10.518 -94.846 -47.255  1.00 48.11      A C
ATOM  17984  C    ASP H 202      -9.650 -95.377 -46.106  1.00 48.72      A C
ATOM  17985  O    ASP H 202     -10.182 -95.881 -45.107  1.00 48.93      A O
ATOM  17986  CB   ASP H 202     -10.508 -95.818 -48.448  1.00 48.22      A C
ATOM  17987  CG   ASP H 202     -10.809 -97.248 -48.047  1.00 48.66      A C
ATOM  17988  OD1  ASP H 202     -11.887 -97.504 -47.460  1.00 48.49      A O
ATOM  17989  OD2  ASP H 202      -9.956 -98.114 -48.331  1.00 49.41      A O
ATOM  17990  N    LEU H 203      -8.330 -95.246 -46.243  1.00 49.11      A N
ATOM  17991  CA   LEU H 203      -7.403 -95.813 -45.264  1.00 49.32      A C
ATOM  17992  C    LEU H 203      -7.395 -95.080 -43.922  1.00 49.58      A C
ATOM  17993  O    LEU H 203      -7.469 -95.721 -42.870  1.00 49.98      A O
ATOM  17994  CB   LEU H 203      -5.994 -95.940 -45.849  1.00 48.37      A C
ATOM  17995  CG   LEU H 203      -5.803 -97.203 -46.703  1.00 48.10      A C
ATOM  17996  CD1  LEU H 203      -5.878 -96.888 -48.199  1.00 47.97      A C
ATOM  17997  N    GLU H 204      -7.312 -93.749 -43.962  1.00 49.38      A N
ATOM  17998  CA   GLU H 204      -7.414 -92.924 -42.748  1.00 48.99      A C
ATOM  17999  C    GLU H 204      -8.803 -93.014 -42.104  1.00 49.42      A C
ATOM  18000  O    GLU H 204      -8.930 -92.901 -40.885  1.00 49.72      A O
ATOM  18001  CB   GLU H 204      -7.013 -91.467 -43.010  1.00 47.47      A C
ATOM  18002  CG   GLU H 204      -7.275 -90.976 -44.429  1.00 45.85      A C
ATOM  18003  CD   GLU H 204      -6.248 -91.490 -45.419  1.00 45.09      A C
ATOM  18004  OE1  GLU H 204      -5.108 -90.992 -45.386  1.00 45.25      A O
ATOM  18005  N    LEU H 205      -9.830 -93.231 -42.926  1.00 49.62      A N
```

FIGURE 1 (cont'd)

```
ATOM  18006  CA   LEU H 205     -11.184 -93.525 -42.440  1.00 49.78      A  C
ATOM  18007  C    LEU H 205     -11.272 -94.909 -41.800  1.00 50.51      A  C
ATOM  18008  O    LEU H 205     -12.052 -95.121 -40.864  1.00 50.58      A  O
ATOM  18009  CB   LEU H 205     -12.203 -93.458 -43.580  1.00 49.24      A  C
ATOM  18010  CG   LEU H 205     -12.955 -92.160 -43.850  1.00 48.24      A  C
ATOM  18011  CD1  LEU H 205     -13.601 -92.234 -45.220  1.00 47.84      A  C
ATOM  18012  CD2  LEU H 205     -13.993 -91.914 -42.774  1.00 47.60      A  C
ATOM  18013  N    SER H 206     -10.484 -95.847 -42.329  1.00 51.38      A  N
ATOM  18014  CA   SER H 206     -10.468 -97.230 -41.844  1.00 52.28      A  C
ATOM  18015  C    SER H 206      -9.863 -97.344 -40.438  1.00 52.75      A  C
ATOM  18016  O    SER H 206     -10.522 -97.859 -39.520  1.00 52.78      A  O
ATOM  18017  CB   SER H 206      -9.728 -98.147 -42.826  1.00 52.48      A  C
ATOM  18018  OG   SER H 206     -10.088 -99.500 -42.610  1.00 53.15      A  O
ATOM  18019  N    ARG H 207      -8.626 -96.855 -40.277  1.00 53.28      A  N
ATOM  18020  CA   ARG H 207      -7.933 -96.904 -38.982  1.00 53.78      A  C
ATOM  18021  C    ARG H 207      -8.783 -96.274 -37.867  1.00 53.77      A  C
ATOM  18022  O    ARG H 207      -9.079 -96.937 -36.864  1.00 54.15      A  O
ATOM  18023  CB   ARG H 207      -6.498 -96.333 -39.044  1.00 54.03      A  C
ATOM  18024  CG   ARG H 207      -6.363 -94.891 -39.513  1.00 53.53      A  C
ATOM  18025  N    ALA H 208      -9.203 -95.022 -38.057  1.00 53.31      A  N
ATOM  18026  CA   ALA H 208     -10.136 -94.383 -37.130  1.00 52.91      A  C
ATOM  18027  C    ALA H 208     -11.476 -95.132 -37.170  1.00 52.68      A  C
ATOM  18028  O    ALA H 208     -12.412 -94.734 -37.864  1.00 52.45      A  O
ATOM  18029  CB   ALA H 208     -10.304 -92.899 -37.457  1.00 52.58      A  C
ATOM  18030  N    LYS H 209     -11.526 -96.234 -36.425  1.00 52.73      A  N
ATOM  18031  CA   LYS H 209     -12.642 -97.171 -36.396  1.00 52.41      A  C
ATOM  18032  C    LYS H 209     -12.093 -98.418 -35.703  1.00 51.88      A  C
ATOM  18033  O    LYS H 209     -12.525 -99.538 -35.931  1.00 52.79      A  O
ATOM  18034  CB   LYS H 209     -13.142 -97.489 -37.810  1.00 52.41      A  C
ATOM  18035  CG   LYS H 209     -14.512 -98.134 -37.866  1.00 52.72      A  C
ATOM  18036  CD   LYS H 209     -14.623 -99.022 -39.092  1.00 53.59      A  C
ATOM  18037  CE   LYS H 209     -15.998 -99.670 -39.205  1.00 53.77      A  C
ATOM  18038  NZ   LYS H 209     -16.073-100.644 -40.337  1.00 53.89      A  N
TER   18039       LYS H 209
ATOM  18040  N    VAL H 215     -17.299 -90.435 -33.639  1.00 36.35      A  N
ATOM  18041  CA   VAL H 215     -18.067 -89.765 -34.697  1.00 36.21      A  C
ATOM  18042  C    VAL H 215     -17.723 -90.335 -36.078  1.00 36.46      A  C
ATOM  18043  O    VAL H 215     -16.591 -90.180 -36.562  1.00 36.74      A  O
ATOM  18044  CB   VAL H 215     -17.833 -88.238 -34.709  1.00 35.47      A  C
ATOM  18045  CG1  VAL H 215     -18.939 -87.539 -35.482  1.00 34.56      A  C
ATOM  18046  N    THR H 216     -18.704 -90.982 -36.711  1.00 36.16      A  N
ATOM  18047  CA   THR H 216     -18.492 -91.688 -37.985  1.00 35.62      A  C
ATOM  18048  C    THR H 216     -18.845 -90.863 -39.241  1.00 35.12      A  C
ATOM  18049  O    THR H 216     -19.065 -89.650 -39.172  1.00 35.06      A  O
ATOM  18050  CB   THR H 216     -19.238 -93.046 -38.006  1.00 35.60      A  C
ATOM  18051  OG1  THR H 216     -18.372 -94.056 -38.540  1.00 35.46      A  O
ATOM  18052  N    LEU H 217     -18.878 -91.540 -40.385  1.00 34.50      A  N
ATOM  18053  CA   LEU H 217     -19.220 -90.917 -41.651  1.00 33.70      A  C
ATOM  18054  C    LEU H 217     -20.339 -91.687 -42.348  1.00 33.33      A  C
ATOM  18055  O    LEU H 217     -20.336 -92.921 -42.389  1.00 33.55      A  O
ATOM  18056  CB   LEU H 217     -17.988 -90.831 -42.552  1.00 33.60      A  C
ATOM  18057  CG   LEU H 217     -18.189 -90.351 -43.995  1.00 33.10      A  C
ATOM  18058  CD1  LEU H 217     -18.507 -88.861 -44.032  1.00 32.89      A  C
ATOM  18059  CD2  LEU H 217     -16.971 -90.646 -44.852  1.00 33.15      A  C
ATOM  18060  N    GLN H 218     -21.290 -90.941 -42.900  1.00 32.57      A  N
ATOM  18061  CA   GLN H 218     -22.447 -91.520 -43.569  1.00 31.92      A  C
ATOM  18062  C    GLN H 218     -22.638 -90.917 -44.963  1.00 31.33      A  C
ATOM  18063  O    GLN H 218     -22.592 -89.700 -45.139  1.00 31.21      A  O
ATOM  18064  CB   GLN H 218     -23.696 -91.325 -42.714  1.00 31.91      A  C
ATOM  18065  CG   GLN H 218     -24.917 -92.036 -43.215  1.00 32.12      A  C
ATOM  18066  CD   GLN H 218     -26.155 -91.635 -42.443  1.00 32.82      A  C
ATOM  18067  NE2  GLN H 218     -26.509 -90.353 -42.493  1.00 32.86      A  N
ATOM  18068  OE1  GLN H 218     -26.781 -92.467 -41.794  1.00 33.66      A  O
ATOM  18069  N    LEU H 219     -22.841 -91.785 -45.951  1.00 30.77      A  N
ATOM  18070  CA   LEU H 219     -23.073 -91.354 -47.324  1.00 30.07      A  C
```

FIGURE 1 (cont'd)

```
ATOM  18071  C    LEU H 219     -24.466 -91.753 -47.792  1.00 29.80      A  C
ATOM  18072  O    LEU H 219     -24.826 -92.929 -47.807  1.00 29.85      A  O
ATOM  18073  CB   LEU H 219     -22.000 -91.910 -48.253  1.00 29.92      A  C
ATOM  18074  CG   LEU H 219     -20.567 -91.515 -47.897  1.00 29.64      A  C
ATOM  18075  CD1  LEU H 219     -19.587 -92.240 -48.801  1.00 29.43      A  C
ATOM  18076  CD2  LEU H 219     -20.366 -90.001 -47.973  1.00 29.22      A  C
ATOM  18077  N    LEU H 220     -25.253 -90.749 -48.156  1.00 29.31      A  N
ATOM  18078  CA   LEU H 220     -26.622 -90.974 -48.602  1.00 28.87      A  C
ATOM  18079  C    LEU H 220     -26.784 -90.649 -50.089  1.00 28.99      A  C
ATOM  18080  O    LEU H 220     -26.467 -89.535 -50.544  1.00 29.01      A  O
ATOM  18081  CB   LEU H 220     -27.603 -90.155 -47.766  1.00 28.13      A  C
ATOM  18082  CG   LEU H 220     -27.629 -90.481 -46.279  1.00 27.42      A  C
ATOM  18083  CD1  LEU H 220     -28.702 -89.652 -45.618  1.00 26.99      A  C
ATOM  18084  N    PHE H 221     -27.263 -91.645 -50.834  1.00 29.11      A  N
ATOM  18085  CA   PHE H 221     -27.552 -91.504 -52.258  1.00 29.08      A  C
ATOM  18086  C    PHE H 221     -29.056 -91.663 -52.402  1.00 29.10      A  C
ATOM  18087  O    PHE H 221     -29.583 -92.768 -52.354  1.00 29.19      A  O
ATOM  18088  CB   PHE H 221     -26.798 -92.507 -53.079  1.00 29.11      A  C
ATOM  18089  CG   PHE H 221     -25.293 -92.507 -52.933  1.00 29.13      A  C
ATOM  18090  CD1  PHE H 221     -24.513 -91.820 -53.854  1.00 29.19      A  C
ATOM  18091  CD2  PHE H 221     -24.657 -93.132 -51.871  1.00 29.24      A  C
ATOM  18092  CE1  PHE H 221     -23.121 -91.754 -53.722  1.00 29.22      A  C
ATOM  18093  CE2  PHE H 221     -23.263 -93.064 -51.728  1.00 29.47      A  C
ATOM  18094  CZ   PHE H 221     -22.498 -92.377 -52.657  1.00 29.33      A  C
ATOM  18095  N    LEU H 222     -29.748 -90.542 -52.548  1.00 29.17      A  N
ATOM  18096  CA   LEU H 222     -31.211 -90.536 -52.514  1.00 29.43      A  C
ATOM  18097  C    LEU H 222     -31.824 -90.716 -53.900  1.00 29.78      A  C
ATOM  18098  O    LEU H 222     -31.344 -90.160 -54.891  1.00 29.78      A  O
ATOM  18099  CB   LEU H 222     -31.734 -89.252 -51.857  1.00 29.24      A  C
ATOM  18100  CG   LEU H 222     -31.157 -88.994 -50.462  1.00 29.08      A  C
ATOM  18101  CD1  LEU H 222     -32.084 -89.494 -49.353  1.00 29.12      A  C
ATOM  18102  CD2  LEU H 222     -30.840 -87.531 -50.282  1.00 28.75      A  C
ATOM  18103  N    ASP H 223     -32.883 -91.515 -53.960  1.00 30.35      A  N
ATOM  18104  CA   ASP H 223     -33.634 -91.737 -55.198  1.00 30.91      A  C
ATOM  18105  C    ASP H 223     -34.739 -90.688 -55.304  1.00 30.91      A  C
ATOM  18106  O    ASP H 223     -35.040 -89.988 -54.333  1.00 30.84      A  O
ATOM  18107  CB   ASP H 223     -34.227 -93.168 -55.215  1.00 31.34      A  C
ATOM  18108  CG   ASP H 223     -34.643 -93.640 -56.619  1.00 32.39      A  C
ATOM  18109  OD1  ASP H 223     -34.290 -92.974 -57.621  1.00 33.36      A  O
ATOM  18110  OD2  ASP H 223     -35.329 -94.686 -56.723  1.00 33.06      A  O
ATOM  18111  N    GLY H 224     -35.319 -90.567 -56.491  1.00 31.03      A  N
ATOM  18112  CA   GLY H 224     -36.501 -89.748 -56.705  1.00 31.25      A  C
ATOM  18113  C    GLY H 224     -36.523 -88.439 -55.943  1.00 31.21      A  C
ATOM  18114  O    GLY H 224     -37.358 -88.231 -55.059  1.00 31.42      A  O
ATOM  18115  N    GLU H 225     -35.589 -87.559 -56.273  1.00 31.03      A  N
ATOM  18116  CA   GLU H 225     -35.608 -86.219 -55.717  1.00 30.97      A  C
ATOM  18117  C    GLU H 225     -36.319 -85.267 -56.685  1.00 31.04      A  C
ATOM  18118  O    GLU H 225     -37.149 -84.450 -56.271  1.00 30.98      A  O
ATOM  18119  CB   GLU H 225     -34.189 -85.754 -55.405  1.00 30.80      A  C
ATOM  18120  CG   GLU H 225     -34.103 -84.366 -54.835  1.00 31.06      A  C
ATOM  18121  CD   GLU H 225     -34.073 -83.308 -55.899  1.00 31.86      A  C
ATOM  18122  OE1  GLU H 225     -33.479 -83.538 -56.974  1.00 32.62      A  O
ATOM  18123  OE2  GLU H 225     -34.653 -82.241 -55.655  1.00 32.34      A  O
ATOM  18124  N    GLU H 226     -35.988 -85.385 -57.969  1.00 31.32      A  N
ATOM  18125  CA   GLU H 226     -36.619 -84.591 -59.018  1.00 31.78      A  C
ATOM  18126  C    GLU H 226     -38.067 -85.025 -59.205  1.00 32.46      A  C
ATOM  18127  O    GLU H 226     -38.391 -86.227 -59.147  1.00 32.60      A  O
ATOM  18128  CB   GLU H 226     -35.869 -84.743 -60.339  1.00 31.67      A  C
ATOM  18129  CG   GLU H 226     -34.390 -84.411 -60.265  1.00 30.95      A  C
ATOM  18130  CD   GLU H 226     -34.078 -82.967 -60.592  1.00 30.27      A  C
ATOM  18131  OE1  GLU H 226     -34.978 -82.099 -60.460  1.00 30.24      A  O
ATOM  18132  OE2  GLU H 226     -32.915 -82.701 -60.983  1.00 29.67      A  O
ATOM  18133  N    ALA H 227     -38.928 -84.034 -59.432  1.00 33.03      A  N
ATOM  18134  CA   ALA H 227     -40.356 -84.260 -59.617  1.00 33.78      A  C
ATOM  18135  C    ALA H 227     -40.671 -85.089 -60.878  1.00 34.42      A  C
```

FIGURE 1 (cont'd)

```
ATOM  18136  O    ALA H 227   -39.824 -85.252 -61.770  1.00 34.48    A  O
ATOM  18137  CB   ALA H 227   -41.077 -82.927 -59.657  1.00 33.75    A  C
ATOM  18138  N    LEU H 228   -41.892 -85.612 -60.945  1.00 35.21    A  N
ATOM  18139  CA   LEU H 228   -42.316 -86.354 -62.125  1.00 35.94    A  C
ATOM  18140  C    LEU H 228   -43.253 -85.562 -63.065  1.00 36.67    A  C
ATOM  18141  O    LEU H 228   -43.022 -85.525 -64.275  1.00 36.93    A  O
ATOM  18142  CB   LEU H 228   -42.885 -87.738 -61.748  1.00 35.90    A  C
ATOM  18143  CG   LEU H 228   -41.926 -88.900 -61.420  1.00 35.23    A  C
ATOM  18144  CD1  LEU H 228   -41.955 -89.223 -59.941  1.00 34.79    A  C
ATOM  18145  CD2  LEU H 228   -40.482 -88.683 -61.910  1.00 34.61    A  C
ATOM  18146  N    LYS H 229   -44.301 -84.944 -62.523  1.00 37.40    A  N
ATOM  18147  CA   LYS H 229   -45.168 -84.075 -63.323  1.00 38.18    A  C
ATOM  18148  C    LYS H 229   -44.656 -82.645 -63.172  1.00 38.16    A  C
ATOM  18149  O    LYS H 229   -43.874 -82.199 -63.993  1.00 38.16    A  O
ATOM  18150  CB   LYS H 229   -46.650 -84.225 -62.936  1.00 38.70    A  C
ATOM  18151  CG   LYS H 229   -47.654 -83.587 -63.924  1.00 39.53    A  C
ATOM  18152  CD   LYS H 229   -48.089 -84.548 -65.041  1.00 40.06    A  C
ATOM  18153  N    GLU H 230   -45.071 -81.930 -62.134  1.00 38.32    A  N
ATOM  18154  CA   GLU H 230   -44.383 -80.689 -61.793  1.00 38.53    A  C
ATOM  18155  C    GLU H 230   -44.131 -80.533 -60.298  1.00 38.27    A  C
ATOM  18156  O    GLU H 230   -44.922 -80.987 -59.465  1.00 38.33    A  O
ATOM  18157  CB   GLU H 230   -45.047 -79.438 -62.405  1.00 38.97    A  C
ATOM  18158  CG   GLU H 230   -44.076 -78.204 -62.558  1.00 39.91    A  C
ATOM  18159  CD   GLU H 230   -42.751 -78.504 -63.335  1.00 40.12    A  C
ATOM  18160  OE1  GLU H 230   -41.655 -78.671 -62.727  1.00 38.77    A  O
ATOM  18161  N    TRP H 231   -43.002 -79.892 -59.994  1.00 37.93    A  N
ATOM  18162  CA   TRP H 231   -42.508 -79.697 -58.638  1.00 37.69    A  C
ATOM  18163  C    TRP H 231   -43.580 -79.209 -57.674  1.00 38.02    A  C
ATOM  18164  O    TRP H 231   -44.310 -78.268 -57.976  1.00 38.34    A  O
ATOM  18165  CB   TRP H 231   -41.324 -78.722 -58.644  1.00 37.33    A  C
ATOM  18166  CG   TRP H 231   -40.599 -78.679 -57.334  1.00 36.75    A  C
ATOM  18167  CD1  TRP H 231   -40.918 -77.918 -56.248  1.00 36.71    A  C
ATOM  18168  CD2  TRP H 231   -39.448 -79.448 -56.962  1.00 36.15    A  C
ATOM  18169  CE2  TRP H 231   -39.124 -79.096 -55.637  1.00 35.90    A  C
ATOM  18170  CE3  TRP H 231   -38.660 -80.404 -57.621  1.00 35.82    A  C
ATOM  18171  NE1  TRP H 231   -40.038 -78.160 -55.227  1.00 36.37    A  N
ATOM  18172  CZ2  TRP H 231   -38.042 -79.661 -54.954  1.00 35.24    A  C
ATOM  18173  CZ3  TRP H 231   -37.584 -80.967 -56.940  1.00 35.08    A  C
ATOM  18174  CH2  TRP H 231   -37.288 -80.591 -55.621  1.00 34.78    A  C
ATOM  18175  N    GLY H 232   -43.655 -79.864 -56.518  1.00 38.14    A  N
ATOM  18176  CA   GLY H 232   -44.612 -79.524 -55.477  1.00 38.51    A  C
ATOM  18177  C    GLY H 232   -44.401 -80.383 -54.245  1.00 38.70    A  C
ATOM  18178  O    GLY H 232   -43.670 -81.369 -54.296  1.00 38.42    A  O
ATOM  18179  N    PRO H 233   -45.041 -80.018 -53.125  1.00 39.12    A  N
ATOM  18180  CA   PRO H 233   -44.928 -80.771 -51.883  1.00 39.29    A  C
ATOM  18181  C    PRO H 233   -45.212 -82.267 -52.044  1.00 39.50    A  C
ATOM  18182  O    PRO H 233   -44.540 -83.093 -51.440  1.00 39.20    A  O
ATOM  18183  CB   PRO H 233   -45.985 -80.117 -50.997  1.00 39.48    A  C
ATOM  18184  CG   PRO H 233   -46.034 -78.722 -51.474  1.00 39.62    A  C
ATOM  18185  CD   PRO H 233   -45.876 -78.816 -52.956  1.00 39.40    A  C
ATOM  18186  N    LYS H 234   -46.194 -82.608 -52.868  1.00 40.12    A  N
ATOM  18187  CA   LYS H 234   -46.562 -84.005 -53.081  1.00 40.68    A  C
ATOM  18188  C    LYS H 234   -45.874 -84.644 -54.302  1.00 40.46    A  C
ATOM  18189  O    LYS H 234   -45.973 -85.853 -54.502  1.00 40.61    A  O
ATOM  18190  CB   LYS H 234   -48.093 -84.164 -53.147  1.00 41.31    A  C
ATOM  18191  CG   LYS H 234   -48.797 -84.269 -51.765  1.00 42.33    A  C
ATOM  18192  CD   LYS H 234   -50.287 -83.816 -51.795  1.00 43.52    A  C
ATOM  18193  CE   LYS H 234   -51.276 -84.930 -52.163  1.00 43.74    A  C
ATOM  18194  N    ASP H 235   -45.173 -83.841 -55.102  1.00 40.07    A  N
ATOM  18195  CA   ASP H 235   -44.376 -84.366 -56.219  1.00 39.59    A  C
ATOM  18196  C    ASP H 235   -42.916 -83.853 -56.200  1.00 39.10    A  C
ATOM  18197  O    ASP H 235   -42.556 -82.951 -56.968  1.00 39.08    A  O
ATOM  18198  CB   ASP H 235   -45.068 -84.074 -57.558  1.00 39.82    A  C
ATOM  18199  CG   ASP H 235   -44.278 -84.578 -58.759  1.00 39.53    A  C
ATOM  18200  OD1  ASP H 235   -44.318 -83.902 -59.804  1.00 39.27    A  O
```

FIGURE 1 (cont'd)

```
ATOM  18201  OD2 ASP H 235     -43.618 -85.633 -58.668  1.00 39.15      A  O
ATOM  18202  N   SER H 236     -42.098 -84.433 -55.309  1.00 38.48      A  N
ATOM  18203  CA  SER H 236     -40.666 -84.116 -55.151  1.00 37.80      A  C
ATOM  18204  C   SER H 236     -40.115 -84.717 -53.866  1.00 37.48      A  C
ATOM  18205  O   SER H 236     -40.825 -84.822 -52.863  1.00 37.51      A  O
ATOM  18206  CB  SER H 236     -40.420 -82.605 -55.124  1.00 37.68      A  C
ATOM  18207  OG  SER H 236     -40.953 -82.024 -53.946  1.00 37.63      A  O
ATOM  18208  N   LEU H 237     -38.838 -85.078 -53.898  1.00 37.17      A  N
ATOM  18209  CA  LEU H 237     -38.118 -85.545 -52.714  1.00 37.07      A  C
ATOM  18210  C   LEU H 237     -38.741 -86.813 -52.133  1.00 37.28      A  C
ATOM  18211  O   LEU H 237     -39.000 -86.879 -50.927  1.00 37.43      A  O
ATOM  18212  CB  LEU H 237     -38.069 -84.451 -51.627  1.00 36.91      A  C
ATOM  18213  CG  LEU H 237     -37.794 -82.988 -51.975  1.00 36.55      A  C
ATOM  18214  CD1 LEU H 237     -38.241 -82.099 -50.846  1.00 36.64      A  C
ATOM  18215  CD2 LEU H 237     -36.349 -82.767 -52.268  1.00 36.05      A  C
ATOM  18216  N   TYR H 238     -38.994 -87.808 -52.984  1.00 37.40      A  N
ATOM  18217  CA  TYR H 238     -39.578 -89.079 -52.529  1.00 37.48      A  C
ATOM  18218  C   TYR H 238     -38.604 -89.863 -51.658  1.00 37.16      A  C
ATOM  18219  O   TYR H 238     -38.991 -90.409 -50.625  1.00 37.26      A  O
ATOM  18220  CB  TYR H 238     -40.043 -89.933 -53.710  1.00 37.79      A  C
ATOM  18221  CG  TYR H 238     -41.116 -89.275 -54.544  1.00 38.39      A  C
ATOM  18222  CD1 TYR H 238     -42.433 -89.200 -54.087  1.00 39.35      A  C
ATOM  18223  CD2 TYR H 238     -40.821 -88.728 -55.787  1.00 38.48      A  C
ATOM  18224  CE1 TYR H 238     -43.424 -88.592 -54.851  1.00 39.70      A  C
ATOM  18225  CE2 TYR H 238     -41.799 -88.123 -56.551  1.00 38.95      A  C
ATOM  18226  CZ  TYR H 238     -43.095 -88.057 -56.080  1.00 39.36      A  C
ATOM  18227  OH  TYR H 238     -44.067 -87.455 -56.840  1.00 39.64      A  O
ATOM  18228  N   GLY H 239     -37.341 -89.894 -52.068  1.00 36.73      A  N
ATOM  18229  CA  GLY H 239     -36.327 -90.635 -51.333  1.00 36.47      A  C
ATOM  18230  C   GLY H 239     -36.016 -90.042 -49.971  1.00 36.26      A  C
ATOM  18231  O   GLY H 239     -35.961 -90.761 -48.964  1.00 36.33      A  O
ATOM  18232  N   SER H 240     -35.814 -88.727 -49.943  1.00 35.99      A  N
ATOM  18233  CA  SER H 240     -35.452 -88.035 -48.715  1.00 35.73      A  C
ATOM  18234  C   SER H 240     -36.603 -87.989 -47.713  1.00 35.73      A  C
ATOM  18235  O   SER H 240     -36.394 -88.239 -46.525  1.00 35.80      A  O
ATOM  18236  CB  SER H 240     -34.943 -86.634 -49.031  1.00 35.60      A  C
ATOM  18237  OG  SER H 240     -35.663 -86.083 -50.118  1.00 35.92      A  O
ATOM  18238  N   ARG H 241     -37.810 -87.688 -48.193  1.00 35.71      A  N
ATOM  18239  CA  ARG H 241     -38.993 -87.684 -47.340  1.00 35.94      A  C
ATOM  18240  C   ARG H 241     -39.253 -89.033 -46.692  1.00 36.01      A  C
ATOM  18241  O   ARG H 241     -39.724 -89.101 -45.547  1.00 36.22      A  O
ATOM  18242  CB  ARG H 241     -40.233 -87.225 -48.105  1.00 36.04      A  C
ATOM  18243  CG  ARG H 241     -40.434 -85.721 -48.061  1.00 36.67      A  C
ATOM  18244  CD  ARG H 241     -41.836 -85.302 -48.454  1.00 37.98      A  C
ATOM  18245  NE  ARG H 241     -42.037 -85.354 -49.899  1.00 39.18      A  N
ATOM  18246  CZ  ARG H 241     -42.736 -86.300 -50.517  1.00 40.17      A  C
ATOM  18247  NH1 ARG H 241     -43.308 -87.278 -49.818  1.00 41.14      A  N
ATOM  18248  NH2 ARG H 241     -42.874 -86.265 -51.835  1.00 40.49      A  N
ATOM  18249  N   HIS H 242     -38.944 -90.101 -47.423  1.00 35.96      A  N
ATOM  18250  CA  HIS H 242     -39.115 -91.451 -46.901  1.00 36.06      A  C
ATOM  18251  C   HIS H 242     -38.001 -91.845 -45.927  1.00 35.71      A  C
ATOM  18252  O   HIS H 242     -38.276 -92.344 -44.827  1.00 35.91      A  O
ATOM  18253  CB  HIS H 242     -39.213 -92.465 -48.036  1.00 36.33      A  C
ATOM  18254  CG  HIS H 242     -39.405 -93.873 -47.569  1.00 37.13      A  C
ATOM  18255  CD2 HIS H 242     -40.520 -94.536 -47.182  1.00 37.91      A  C
ATOM  18256  ND1 HIS H 242     -38.362 -94.769 -47.450  1.00 37.28      A  N
ATOM  18257  CE1 HIS H 242     -38.831 -95.925 -47.014  1.00 37.97      A  C
ATOM  18258  NE2 HIS H 242     -40.137 -95.810 -46.846  1.00 38.41      A  N
ATOM  18259  N   LEU H 243     -36.751 -91.626 -46.333  1.00 35.10      A  N
ATOM  18260  CA  LEU H 243     -35.620 -91.946 -45.474  1.00 34.64      A  C
ATOM  18261  C   LEU H 243     -35.748 -91.228 -44.142  1.00 34.76      A  C
ATOM  18262  O   LEU H 243     -35.572 -91.846 -43.088  1.00 34.95      A  O
ATOM  18263  CB  LEU H 243     -34.290 -91.598 -46.138  1.00 34.18      A  C
ATOM  18264  CG  LEU H 243     -33.051 -92.002 -45.343  1.00 33.47      A  C
ATOM  18265  CD1 LEU H 243     -33.027 -93.510 -45.145  1.00 33.27      A  C
```

FIGURE 1 (cont'd)

```
ATOM  18266  CD2  LEU H 243    -31.808 -91.532 -46.050  1.00 32.87      A   C
ATOM  18267  N    ALA H 244    -36.068 -89.929 -44.202  1.00 34.80      A   N
ATOM  18268  CA   ALA H 244    -36.309 -89.126 -42.998  1.00 35.06      A   C
ATOM  18269  C    ALA H 244    -37.342 -89.807 -42.096  1.00 35.51      A   C
ATOM  18270  O    ALA H 244    -37.072 -90.031 -40.918  1.00 35.67      A   O
ATOM  18271  CB   ALA H 244    -36.730 -87.699 -43.356  1.00 34.78      A   C
ATOM  18272  N    GLN H 245    -38.496 -90.172 -42.662  1.00 36.05      A   N
ATOM  18273  CA   GLN H 245    -39.546 -90.877 -41.916  1.00 36.63      A   C
ATOM  18274  C    GLN H 245    -39.014 -92.164 -41.277  1.00 36.97      A   C
ATOM  18275  O    GLN H 245    -39.239 -92.413 -40.088  1.00 37.27      A   O
ATOM  18276  CB   GLN H 245    -40.761 -91.174 -42.804  1.00 36.69      A   C
ATOM  18277  N    LEU H 246    -38.284 -92.953 -42.061  1.00 37.07      A   N
ATOM  18278  CA   LEU H 246    -37.793 -94.260 -41.623  1.00 37.34      A   C
ATOM  18279  C    LEU H 246    -36.675 -94.167 -40.577  1.00 37.75      A   C
ATOM  18280  O    LEU H 246    -36.520 -95.068 -39.746  1.00 37.99      A   O
ATOM  18281  CB   LEU H 246    -37.331 -95.059 -42.844  1.00 37.09      A   C
ATOM  18282  CG   LEU H 246    -36.880 -96.509 -42.695  1.00 36.50      A   C
ATOM  18283  CD1  LEU H 246    -35.397 -96.582 -43.029  1.00 35.22      A   C
ATOM  18284  N    MET H 247    -35.901 -93.080 -40.628  1.00 38.06      A   N
ATOM  18285  CA   MET H 247    -34.838 -92.836 -39.645  1.00 38.47      A   C
ATOM  18286  C    MET H 247    -35.410 -92.370 -38.315  1.00 39.28      A   C
ATOM  18287  O    MET H 247    -34.824 -92.648 -37.263  1.00 39.51      A   O
ATOM  18288  CB   MET H 247    -33.808 -91.829 -40.155  1.00 37.94      A   C
ATOM  18289  CG   MET H 247    -32.923 -92.376 -41.250  1.00 37.33      A   C
ATOM  18290  SD   MET H 247    -31.546 -91.302 -41.676  1.00 36.55      A   S
ATOM  18291  CE   MET H 247    -30.295 -91.879 -40.507  1.00 36.97      A   C
ATOM  18292  N    GLU H 248    -36.548 -91.671 -38.365  1.00 40.15      A   N
ATOM  18293  CA   GLU H 248    -37.245 -91.220 -37.160  1.00 41.18      A   C
ATOM  18294  C    GLU H 248    -37.824 -92.396 -36.409  1.00 42.21      A   C
ATOM  18295  O    GLU H 248    -37.899 -92.364 -35.183  1.00 42.79      A   O
ATOM  18296  CB   GLU H 248    -38.364 -90.225 -37.482  1.00 41.00      A   C
ATOM  18297  N    SER H 249    -38.227 -93.435 -37.139  1.00 43.05      A   N
ATOM  18298  CA   SER H 249    -38.831 -94.620 -36.521  1.00 44.01      A   C
ATOM  18299  C    SER H 249    -37.801 -95.669 -36.090  1.00 44.48      A   C
ATOM  18300  O    SER H 249    -38.156 -96.680 -35.487  1.00 44.91      A   O
ATOM  18301  CB   SER H 249    -39.875 -95.243 -37.455  1.00 44.12      A   C
ATOM  18302  OG   SER H 249    -39.259 -95.923 -38.532  1.00 44.15      A   O
ATOM  18303  N    ILE H 250    -36.530 -95.419 -36.396  1.00 44.77      A   N
ATOM  18304  CA   ILE H 250    -35.463 -96.371 -36.110  1.00 45.31      A   C
ATOM  18305  C    ILE H 250    -34.627 -95.931 -34.894  1.00 46.14      A   C
ATOM  18306  O    ILE H 250    -33.839 -94.974 -34.996  1.00 45.88      A   O
ATOM  18307  CB   ILE H 250    -34.579 -96.585 -37.358  1.00 44.84      A   C
ATOM  18308  CG1  ILE H 250    -33.907 -97.960 -37.325  1.00 44.80      A   C
ATOM  18309  CD1  ILE H 250    -32.425 -97.917 -36.977  1.00 44.43      A   C
ATOM  18310  N    PRO H 251    -34.810 -96.626 -33.737  1.00 47.25      A   N
ATOM  18311  CA   PRO H 251    -34.132 -96.279 -32.488  1.00 47.91      A   C
ATOM  18312  C    PRO H 251    -32.634 -96.485 -32.551  1.00 48.32      A   C
ATOM  18313  O    PRO H 251    -32.135 -97.325 -33.294  1.00 48.32      A   O
ATOM  18314  CB   PRO H 251    -34.749 -97.240 -31.467  1.00 48.24      A   C
ATOM  18315  CG   PRO H 251    -36.043 -97.649 -32.058  1.00 48.25      A   C
ATOM  18316  CD   PRO H 251    -35.757 -97.736 -33.523  1.00 47.59      A   C
ATOM  18317  N    HIS H 252    -31.943 -95.710 -31.732  1.00 48.78      A   N
ATOM  18318  CA   HIS H 252    -30.494 -95.588 -31.741  1.00 49.15      A   C
ATOM  18319  C    HIS H 252    -30.236 -94.627 -30.582  1.00 49.75      A   C
ATOM  18320  O    HIS H 252    -31.182 -94.056 -30.088  1.00 50.01      A   O
ATOM  18321  CB   HIS H 252    -30.070 -94.879 -33.031  1.00 47.98      A   C
ATOM  18322  CG   HIS H 252    -28.586 -94.746 -33.200  1.00 47.79      A   C
ATOM  18323  CD2  HIS H 252    -27.748 -93.698 -33.003  1.00 47.60      A   C
ATOM  18324  ND1  HIS H 252    -27.800 -95.788 -33.642  1.00 48.08      A   N
ATOM  18325  CE1  HIS H 252    -26.542 -95.391 -33.711  1.00 48.05      A   C
ATOM  18326  NE2  HIS H 252    -26.483 -94.127 -33.328  1.00 47.83      A   N
ATOM  18327  N    SER H 253    -29.053 -94.472 -30.006  1.00 50.15      A   N
ATOM  18328  CA   SER H 253    -28.288 -95.448 -29.343  1.00 50.17      A   C
ATOM  18329  C    SER H 253    -27.483 -94.843 -28.210  1.00 50.28      A   C
ATOM  18330  O    SER H 253    -26.732 -95.567 -27.632  1.00 50.71      A   O
```

FIGURE 1 (cont'd)

```
ATOM  18331  CB   SER H 253     -27.287 -96.095 -30.286  1.00 49.33      A  C
ATOM  18332  OG   SER H 253     -25.947 -95.930 -29.891  1.00 48.85      A  O
ATOM  18333  N    PRO H 254     -27.647 -93.603 -27.749  1.00 49.86      A  N
ATOM  18334  CA   PRO H 254     -28.285 -92.343 -27.444  1.00 49.47      A  C
ATOM  18335  C    PRO H 254     -28.553 -91.371 -28.523  1.00 49.09      A  C
ATOM  18336  O    PRO H 254     -27.985 -90.295 -28.480  1.00 49.25      A  O
ATOM  18337  CB   PRO H 254     -27.273 -91.663 -26.503  1.00 48.70      A  C
ATOM  18338  CG   PRO H 254     -26.120 -92.545 -26.416  1.00 48.83      A  C
ATOM  18339  CD   PRO H 254     -26.194 -93.499 -27.508  1.00 49.10      A  C
ATOM  18340  N    GLY H 255     -29.408 -91.729 -29.467  1.00 48.46      A  N
ATOM  18341  CA   GLY H 255     -30.195 -90.760 -30.195  1.00 47.56      A  C
ATOM  18342  C    GLY H 255     -31.238 -90.280 -29.213  1.00 47.12      A  C
ATOM  18343  O    GLY H 255     -30.898 -89.546 -28.301  1.00 47.42      A  O
ATOM  18344  N    PRO H 256     -32.511 -90.447 -29.587  1.00 46.64      A  N
ATOM  18345  CA   PRO H 256     -33.577 -91.384 -29.302  1.00 46.37      A  C
ATOM  18346  C    PRO H 256     -33.694 -92.193 -30.608  1.00 45.76      A  C
ATOM  18347  O    PRO H 256     -33.644 -93.421 -30.586  1.00 45.96      A  O
ATOM  18348  CB   PRO H 256     -34.814 -90.487 -29.131  1.00 46.54      A  C
ATOM  18349  CG   PRO H 256     -34.282 -89.224 -28.641  1.00 46.56      A  C
ATOM  18350  CD   PRO H 256     -33.074 -89.080 -29.558  1.00 46.79      A  C
ATOM  18351  N    THR H 257     -33.815 -91.486 -31.735  1.00 44.76      A  N
ATOM  18352  CA   THR H 257     -33.913 -92.084 -33.070  1.00 43.64      A  C
ATOM  18353  C    THR H 257     -32.623 -91.883 -33.859  1.00 42.92      A  C
ATOM  18354  O    THR H 257     -31.727 -91.169 -33.420  1.00 42.81      A  O
ATOM  18355  CB   THR H 257     -35.097 -91.488 -33.869  1.00 43.46      A  C
ATOM  18356  OG1  THR H 257     -35.015 -90.057 -33.880  1.00 43.05      A  O
ATOM  18357  N    ARG H 258     -32.529 -92.517 -35.025  1.00 42.07      A  N
ATOM  18358  CA   ARG H 258     -31.358 -92.361 -35.898  1.00 41.06      A  C
ATOM  18359  C    ARG H 258     -31.209 -90.964 -36.488  1.00 40.56      A  C
ATOM  18360  O    ARG H 258     -30.145 -90.614 -37.001  1.00 40.51      A  O
ATOM  18361  CB   ARG H 258     -31.360 -93.400 -37.024  1.00 40.15      A  C
ATOM  18362  CG   ARG H 258     -30.597 -94.669 -36.671  1.00 40.11      A  C
ATOM  18363  CD   ARG H 258     -29.962 -95.346 -37.892  1.00 40.03      A  C
ATOM  18364  NE   ARG H 258     -29.103 -96.472 -37.519  1.00 40.27      A  N
ATOM  18365  N    ILE H 259     -32.281 -90.178 -36.420  1.00 39.88      A  N
ATOM  18366  CA   ILE H 259     -32.262 -88.799 -36.899  1.00 38.94      A  C
ATOM  18367  C    ILE H 259     -31.320 -87.920 -36.080  1.00 38.86      A  C
ATOM  18368  O    ILE H 259     -30.648 -87.034 -36.625  1.00 38.84      A  O
ATOM  18369  CB   ILE H 259     -33.658 -88.186 -36.900  1.00 38.01      A  C
ATOM  18370  CG1  ILE H 259     -34.104 -88.004 -38.335  1.00 37.65      A  C
ATOM  18371  CD1  ILE H 259     -35.543 -88.229 -38.501  1.00 38.54      A  C
ATOM  18372  N    GLN H 260     -31.262 -88.184 -34.776  1.00 38.52      A  N
ATOM  18373  CA   GLN H 260     -30.399 -87.422 -33.881  1.00 37.93      A  C
ATOM  18374  C    GLN H 260     -28.945 -87.882 -34.037  1.00 37.80      A  C
ATOM  18375  O    GLN H 260     -28.040 -87.313 -33.415  1.00 38.22      A  O
ATOM  18376  CB   GLN H 260     -30.847 -87.538 -32.415  1.00 37.09      A  C
ATOM  18377  CG   GLN H 260     -32.192 -88.219 -32.173  1.00 36.69      A  C
ATOM  18378  CD   GLN H 260     -33.372 -87.571 -32.862  1.00 36.31      A  C
ATOM  18379  OE1  GLN H 260     -33.543 -86.367 -32.845  1.00 36.70      A  O
ATOM  18380  N    ALA H 261     -28.728 -88.907 -34.867  1.00 37.19      A  N
ATOM  18381  CA   ALA H 261     -27.380 -89.432 -35.122  1.00 36.51      A  C
ATOM  18382  C    ALA H 261     -26.633 -88.602 -36.165  1.00 35.74      A  C
ATOM  18383  O    ALA H 261     -25.402 -88.642 -36.229  1.00 35.69      A  O
ATOM  18384  N    ILE H 262     -27.379 -87.862 -36.984  1.00 34.73      A  N
ATOM  18385  CA   ILE H 262     -26.780 -86.948 -37.947  1.00 33.66      A  C
ATOM  18386  C    ILE H 262     -26.290 -85.711 -37.192  1.00 33.60      A  C
ATOM  18387  O    ILE H 262     -27.099 -84.872 -36.761  1.00 33.78      A  O
ATOM  18388  CB   ILE H 262     -27.787 -86.510 -39.030  1.00 32.72      A  C
ATOM  18389  CG1  ILE H 262     -28.558 -87.705 -39.575  1.00 32.12      A  C
ATOM  18390  CD1  ILE H 262     -29.866 -87.330 -40.210  1.00 31.72      A  C
ATOM  18391  N    GLU H 263     -24.973 -85.614 -37.007  1.00 33.23      A  N
ATOM  18392  CA   GLU H 263     -24.378 -84.431 -36.379  1.00 32.82      A  C
ATOM  18393  C    GLU H 263     -24.438 -83.254 -37.363  1.00 32.22      A  C
ATOM  18394  O    GLU H 263     -24.682 -82.112 -36.965  1.00 32.31      A  O
ATOM  18395  CB   GLU H 263     -22.941 -84.713 -35.931  1.00 33.01      A  C
```

FIGURE 1 (cont'd)

```
ATOM  18396  CG   GLU H 263     -22.370 -83.721 -34.930  1.00 33.02      A C
ATOM  18397  CD   GLU H 263     -21.028 -84.162 -34.378  1.00 32.62      A C
ATOM  18398  N    LEU H 264     -24.232 -83.557 -38.648  1.00 31.37      A N
ATOM  18399  CA   LEU H 264     -24.344 -82.571 -39.723  1.00 30.36      A C
ATOM  18400  C    LEU H 264     -24.759 -83.207 -41.051  1.00 29.76      A C
ATOM  18401  O    LEU H 264     -24.112 -84.149 -41.529  1.00 29.78      A O
ATOM  18402  CB   LEU H 264     -23.032 -81.813 -39.893  1.00 30.26      A C
ATOM  18403  CG   LEU H 264     -22.995 -80.757 -40.993  1.00 29.84      A C
ATOM  18404  CD1  LEU H 264     -24.016 -79.648 -40.742  1.00 29.72      A C
ATOM  18405  CD2  LEU H 264     -21.583 -80.194 -41.108  1.00 29.63      A C
ATOM  18406  N    PHE H 265     -25.841 -82.675 -41.623  1.00 28.92      A N
ATOM  18407  CA   PHE H 265     -26.356 -83.077 -42.924  1.00 27.91      A C
ATOM  18408  C    PHE H 265     -25.843 -82.092 -43.955  1.00 27.61      A C
ATOM  18409  O    PHE H 265     -26.413 -81.026 -44.123  1.00 27.50      A O
ATOM  18410  CB   PHE H 265     -27.885 -83.060 -42.907  1.00 27.62      A C
ATOM  18411  CG   PHE H 265     -28.520 -83.751 -44.082  1.00 26.32      A C
ATOM  18412  CD1  PHE H 265     -28.915 -85.094 -43.992  1.00 25.40      A C
ATOM  18413  CD2  PHE H 265     -28.751 -83.062 -45.264  1.00 25.23      A C
ATOM  18414  CE1  PHE H 265     -29.510 -85.736 -45.061  1.00 25.18      A C
ATOM  18415  CE2  PHE H 265     -29.336 -83.693 -46.341  1.00 25.14      A C
ATOM  18416  CZ   PHE H 265     -29.721 -85.036 -46.240  1.00 25.27      A C
ATOM  18417  N    MET H 266     -24.762 -82.457 -44.634  1.00 27.32      A N
ATOM  18418  CA   MET H 266     -24.156 -81.621 -45.659  1.00 27.12      A C
ATOM  18419  C    MET H 266     -24.563 -82.103 -47.060  1.00 27.12      A C
ATOM  18420  O    MET H 266     -23.982 -83.058 -47.592  1.00 27.20      A O
ATOM  18421  CB   MET H 266     -22.641 -81.634 -45.496  1.00 27.10      A C
ATOM  18422  CG   MET H 266     -21.883 -80.722 -46.438  1.00 26.87      A C
ATOM  18423  SD   MET H 266     -20.141 -80.554 -45.952  1.00 29.16      A S
ATOM  18424  CE   MET H 266     -19.338 -81.594 -47.179  1.00 29.27      A C
ATOM  18425  N    LEU H 267     -25.559 -81.432 -47.648  1.00 27.02      A N
ATOM  18426  CA   LEU H 267     -26.126 -81.821 -48.942  1.00 26.90      A C
ATOM  18427  C    LEU H 267     -25.409 -81.186 -50.124  1.00 26.98      A C
ATOM  18428  O    LEU H 267     -25.297 -79.965 -50.215  1.00 27.05      A O
ATOM  18429  CB   LEU H 267     -27.610 -81.482 -48.990  1.00 26.82      A C
ATOM  18430  CG   LEU H 267     -28.385 -81.769 -50.279  1.00 26.56      A C
ATOM  18431  CD1  LEU H 267     -28.370 -83.226 -50.655  1.00 26.52      A C
ATOM  18432  CD2  LEU H 267     -29.817 -81.314 -50.131  1.00 26.47      A C
ATOM  18433  N    LEU H 268     -24.938 -82.029 -51.033  1.00 27.05      A N
ATOM  18434  CA   LEU H 268     -24.187 -81.586 -52.200  1.00 27.24      A C
ATOM  18435  C    LEU H 268     -25.060 -81.600 -53.441  1.00 27.45      A C
ATOM  18436  O    LEU H 268     -25.636 -82.632 -53.788  1.00 27.59      A O
ATOM  18437  CB   LEU H 268     -22.991 -82.509 -52.428  1.00 27.19      A C
ATOM  18438  CG   LEU H 268     -21.661 -82.198 -51.751  1.00 27.25      A C
ATOM  18439  CD1  LEU H 268     -21.722 -82.521 -50.253  1.00 27.50      A C
ATOM  18440  CD2  LEU H 268     -20.560 -82.994 -52.452  1.00 27.08      A C
ATOM  18441  N    ASP H 269     -25.152 -80.465 -54.123  1.00 27.65      A N
ATOM  18442  CA   ASP H 269     -26.027 -80.378 -55.275  1.00 27.95      A C
ATOM  18443  C    ASP H 269     -25.569 -79.379 -56.279  1.00 27.90      A C
ATOM  18444  O    ASP H 269     -24.957 -78.384 -55.919  1.00 28.11      A O
ATOM  18445  CB   ASP H 269     -27.423 -79.989 -54.838  1.00 28.22      A C
ATOM  18446  CG   ASP H 269     -28.472 -80.687 -55.636  1.00 29.37      A C
ATOM  18447  OD1  ASP H 269     -28.435 -81.944 -55.663  1.00 30.31      A O
ATOM  18448  OD2  ASP H 269     -29.326 -79.984 -56.227  1.00 30.11      A O
ATOM  18449  N    LEU H 270     -25.894 -79.639 -57.540  1.00 27.79      A N
ATOM  18450  CA   LEU H 270     -25.591 -78.720 -58.646  1.00 27.83      A C
ATOM  18451  C    LEU H 270     -24.127 -78.272 -58.673  1.00 27.92      A C
ATOM  18452  O    LEU H 270     -23.821 -77.088 -58.881  1.00 27.99      A O
ATOM  18453  CB   LEU H 270     -26.545 -77.507 -58.652  1.00 27.73      A C
ATOM  18454  CG   LEU H 270     -28.055 -77.761 -58.551  1.00 27.74      A C
ATOM  18455  CD1  LEU H 270     -28.811 -76.489 -58.870  1.00 27.66      A C
ATOM  18456  CD2  LEU H 270     -28.522 -78.898 -59.461  1.00 28.00      A C
ATOM  18457  N    LEU H 271     -23.233 -79.227 -58.451  1.00 28.00      A N
ATOM  18458  CA   LEU H 271     -21.809 -78.960 -58.496  1.00 28.29      A C
ATOM  18459  C    LEU H 271     -21.232 -79.537 -59.773  1.00 28.71      A C
ATOM  18460  O    LEU H 271     -21.637 -80.615 -60.205  1.00 28.76      A O
```

FIGURE 1 (cont'd)

```
ATOM  18461  CB   LEU H 271     -21.112 -79.582 -57.295  1.00 28.09      A    C
ATOM  18462  CG   LEU H 271     -21.503 -79.071 -55.915  1.00 27.73      A    C
ATOM  18463  CD1  LEU H 271     -21.822 -80.282 -55.056  1.00 27.65      A    C
ATOM  18464  N    GLY H 272     -20.292 -78.820 -60.378  1.00 29.23      A    N
ATOM  18465  CA   GLY H 272     -19.625 -79.311 -61.574  1.00 29.89      A    C
ATOM  18466  C    GLY H 272     -19.436 -78.262 -62.647  1.00 30.47      A    C
ATOM  18467  O    GLY H 272     -18.495 -78.356 -63.434  1.00 30.68      A    O
ATOM  18468  N    ALA H 273     -20.326 -77.268 -62.681  1.00 30.83      A    N
ATOM  18469  CA   ALA H 273     -20.251 -76.174 -63.656  1.00 31.23      A    C
ATOM  18470  C    ALA H 273     -19.082 -75.221 -63.356  1.00 31.56      A    C
ATOM  18471  O    ALA H 273     -18.544 -75.237 -62.245  1.00 31.59      A    O
ATOM  18472  CB   ALA H 273     -21.572 -75.414 -63.690  1.00 31.19      A    C
ATOM  18473  N    PRO H 274     -18.666 -74.408 -64.347  1.00 31.94      A    N
ATOM  18474  CA   PRO H 274     -17.660 -73.389 -64.067  1.00 32.24      A    C
ATOM  18475  C    PRO H 274     -18.212 -72.271 -63.190  1.00 32.38      A    C
ATOM  18476  O    PRO H 274     -19.423 -72.024 -63.203  1.00 32.28      A    O
ATOM  18477  CB   PRO H 274     -17.319 -72.839 -65.455  1.00 32.48      A    C
ATOM  18478  CG   PRO H 274     -18.479 -73.179 -66.295  1.00 32.44      A    C
ATOM  18479  CD   PRO H 274     -18.954 -74.492 -65.788  1.00 32.13      A    C
ATOM  18480  N    ASN H 275     -17.321 -71.622 -62.432  1.00 32.65      A    N
ATOM  18481  CA   ASN H 275     -17.641 -70.446 -61.590  1.00 32.96      A    C
ATOM  18482  C    ASN H 275     -18.889 -70.577 -60.718  1.00 32.55      A    C
ATOM  18483  O    ASN H 275     -19.809 -69.760 -60.829  1.00 32.81      A    O
ATOM  18484  CB   ASN H 275     -17.723 -69.166 -62.441  1.00 33.39      A    C
ATOM  18485  CG   ASN H 275     -16.461 -68.915 -63.222  1.00 34.78      A    C
ATOM  18486  ND2  ASN H 275     -16.522 -69.160 -64.520  1.00 35.89      A    N
ATOM  18487  OD1  ASN H 275     -15.431 -68.523 -62.665  1.00 35.83      A    O
ATOM  18488  N    PRO H 276     -18.939 -71.608 -59.858  1.00 32.04      A    N
ATOM  18489  CA   PRO H 276     -20.081 -71.666 -58.962  1.00 31.82      A    C
ATOM  18490  C    PRO H 276     -19.885 -70.666 -57.840  1.00 31.83      A    C
ATOM  18491  O    PRO H 276     -18.746 -70.321 -57.534  1.00 31.91      A    O
ATOM  18492  CB   PRO H 276     -20.031 -73.094 -58.420  1.00 31.62      A    C
ATOM  18493  CG   PRO H 276     -18.621 -73.478 -58.510  1.00 31.61      A    C
ATOM  18494  CD   PRO H 276     -18.029 -72.748 -59.673  1.00 31.87      A    C
ATOM  18495  N    THR H 277     -20.981 -70.181 -57.263  1.00 31.86      A    N
ATOM  18496  CA   THR H 277     -20.908 -69.356 -56.068  1.00 31.90      A    C
ATOM  18497  C    THR H 277     -21.785 -69.953 -54.981  1.00 31.82      A    C
ATOM  18498  O    THR H 277     -22.954 -70.288 -55.214  1.00 31.78      A    O
ATOM  18499  CB   THR H 277     -21.270 -67.884 -56.333  1.00 32.00      A    C
ATOM  18500  CG2  THR H 277     -20.114 -67.163 -57.010  1.00 32.13      A    C
ATOM  18501  OG1  THR H 277     -22.417 -67.820 -57.181  1.00 32.28      A    O
ATOM  18502  N    PHE H 278     -21.187 -70.110 -53.801  1.00 31.81      A    N
ATOM  18503  CA   PHE H 278     -21.849 -70.707 -52.640  1.00 31.84      A    C
ATOM  18504  C    PHE H 278     -22.022 -69.717 -51.483  1.00 32.16      A    C
ATOM  18505  O    PHE H 278     -21.154 -68.866 -51.239  1.00 32.28      A    O
ATOM  18506  CB   PHE H 278     -21.068 -71.923 -52.151  1.00 31.57      A    C
ATOM  18507  CG   PHE H 278     -20.836 -72.953 -53.199  1.00 31.30      A    C
ATOM  18508  CD1  PHE H 278     -21.878 -73.755 -53.652  1.00 31.26      A    C
ATOM  18509  CD2  PHE H 278     -19.572 -73.134 -53.728  1.00 31.18      A    C
ATOM  18510  CE1  PHE H 278     -21.659 -74.724 -54.632  1.00 31.23      A    C
ATOM  18511  CE2  PHE H 278     -19.335 -74.089 -54.706  1.00 31.02      A    C
ATOM  18512  CZ   PHE H 278     -20.381 -74.889 -55.160  1.00 31.05      A    C
ATOM  18513  N    TYR H 279     -23.150 -69.838 -50.782  1.00 32.53      A    N
ATOM  18514  CA   TYR H 279     -23.447 -69.009 -49.625  1.00 33.08      A    C
ATOM  18515  C    TYR H 279     -23.933 -69.877 -48.481  1.00 33.67      A    C
ATOM  18516  O    TYR H 279     -24.280 -71.030 -48.687  1.00 33.63      A    O
ATOM  18517  CB   TYR H 279     -24.508 -67.975 -49.969  1.00 32.95      A    C
ATOM  18518  CG   TYR H 279     -24.126 -67.027 -51.069  1.00 32.44      A    C
ATOM  18519  CD1  TYR H 279     -23.300 -65.932 -50.821  1.00 32.37      A    C
ATOM  18520  CD2  TYR H 279     -24.638 -67.196 -52.343  1.00 31.30      A    C
ATOM  18521  CE1  TYR H 279     -22.982 -65.052 -51.819  1.00 31.76      A    C
ATOM  18522  CE2  TYR H 279     -24.316 -66.322 -53.353  1.00 31.48      A    C
ATOM  18523  CZ   TYR H 279     -23.489 -65.252 -53.081  1.00 31.36      A    C
ATOM  18524  OH   TYR H 279     -23.161 -64.374 -54.074  1.00 31.50      A    O
ATOM  18525  N    SER H 280     -23.949 -69.334 -47.269  1.00 34.62      A    N
```

FIGURE 1 (cont'd)

```
ATOM  18526  CA   SER H 280     -24.469 -70.090 -46.127  1.00 35.46      A    C
ATOM  18527  C    SER H 280     -25.978 -69.857 -45.932  1.00 35.99      A    C
ATOM  18528  O    SER H 280     -26.413 -68.769 -45.516  1.00 36.29      A    O
ATOM  18529  CB   SER H 280     -23.689 -69.771 -44.851  1.00 35.58      A    C
ATOM  18530  OG   SER H 280     -24.086 -70.647 -43.810  1.00 35.76      A    O
ATOM  18531  N    HIS H 281     -26.777 -70.878 -46.240  1.00 36.42      A    N
ATOM  18532  CA   HIS H 281     -28.228 -70.726 -46.189  1.00 37.12      A    C
ATOM  18533  C    HIS H 281     -28.790 -71.120 -44.840  1.00 37.44      A    C
ATOM  18534  O    HIS H 281     -29.986 -71.005 -44.610  1.00 37.63      A    O
ATOM  18535  CB   HIS H 281     -28.895 -71.502 -47.320  1.00 37.19      A    C
ATOM  18536  CG   HIS H 281     -28.401 -71.116 -48.678  1.00 37.80      A    C
ATOM  18537  CD2  HIS H 281     -28.778 -70.118 -49.512  1.00 38.67      A    C
ATOM  18538  ND1  HIS H 281     -27.371 -71.780 -49.309  1.00 37.80      A    N
ATOM  18539  CE1  HIS H 281     -27.139 -71.213 -50.479  1.00 38.23      A    C
ATOM  18540  NE2  HIS H 281     -27.980 -70.203 -50.627  1.00 38.95      A    N
ATOM  18541  N    PHE H 282     -27.916 -71.582 -43.952  1.00 37.82      A    N
ATOM  18542  CA   PHE H 282     -28.277 -71.816 -42.550  1.00 38.19      A    C
ATOM  18543  C    PHE H 282     -27.226 -71.279 -41.583  1.00 38.54      A    C
ATOM  18544  O    PHE H 282     -26.108 -71.816 -41.516  1.00 38.46      A    O
ATOM  18545  CB   PHE H 282     -28.533 -73.290 -42.277  1.00 38.05      A    C
ATOM  18546  CG   PHE H 282     -29.593 -73.860 -43.128  1.00 38.00      A    C
ATOM  18547  CD1  PHE H 282     -30.919 -73.538 -42.899  1.00 38.44      A    C
ATOM  18548  CD2  PHE H 282     -29.270 -74.697 -44.186  1.00 37.89      A    C
ATOM  18549  CE1  PHE H 282     -31.923 -74.057 -43.702  1.00 38.44      A    C
ATOM  18550  CE2  PHE H 282     -30.265 -75.231 -45.003  1.00 38.00      A    C
ATOM  18551  CZ   PHE H 282     -31.599 -74.908 -44.761  1.00 38.26      A    C
ATOM  18552  N    PRO H 283     -27.589 -70.212 -40.826  1.00 38.94      A    N
ATOM  18553  CA   PRO H 283     -26.723 -69.594 -39.816  1.00 39.03      A    C
ATOM  18554  C    PRO H 283     -26.369 -70.574 -38.709  1.00 38.90      A    C
ATOM  18555  O    PRO H 283     -25.372 -70.385 -38.024  1.00 38.99      A    O
ATOM  18556  CB   PRO H 283     -27.583 -68.457 -39.256  1.00 39.27      A    C
ATOM  18557  CG   PRO H 283     -28.589 -68.183 -40.308  1.00 39.30      A    C
ATOM  18558  CD   PRO H 283     -28.891 -69.520 -40.906  1.00 39.08      A    C
ATOM  18559  N    ARG H 284     -27.179 -71.617 -38.552  1.00 38.66      A    N
ATOM  18560  CA   ARG H 284     -26.899 -72.686 -37.599  1.00 38.55      A    C
ATOM  18561  C    ARG H 284     -25.546 -73.322 -37.853  1.00 38.72      A    C
ATOM  18562  O    ARG H 284     -24.817 -73.612 -36.912  1.00 38.99      A    O
ATOM  18563  CB   ARG H 284     -27.972 -73.777 -37.669  1.00 38.29      A    C
ATOM  18564  CG   ARG H 284     -28.290 -74.452 -36.329  1.00 37.52      A    C
ATOM  18565  CD   ARG H 284     -27.143 -75.255 -35.748  1.00 35.78      A    C
ATOM  18566  NE   ARG H 284     -27.639 -76.316 -34.887  1.00 34.97      A    N
ATOM  18567  CZ   ARG H 284     -26.884 -77.310 -34.443  1.00 36.72      A    C
ATOM  18568  NH1  ARG H 284     -25.592 -77.350 -34.758  1.00 37.07      A    N
ATOM  18569  NH2  ARG H 284     -27.418 -78.258 -33.683  1.00 37.23      A    N
ATOM  18570  N    THR H 285     -25.219 -73.550 -39.121  1.00 38.75      A    N
ATOM  18571  CA   THR H 285     -23.951 -74.175 -39.467  1.00 38.88      A    C
ATOM  18572  C    THR H 285     -22.967 -73.187 -40.096  1.00 39.27      A    C
ATOM  18573  O    THR H 285     -21.994 -73.597 -40.724  1.00 39.17      A    O
ATOM  18574  CB   THR H 285     -24.163 -75.357 -40.406  1.00 38.50      A    C
ATOM  18575  OG1  THR H 285     -25.022 -74.946 -41.469  1.00 38.18      A    O
ATOM  18576  N    VAL H 286     -23.201 -71.890 -39.887  1.00 39.89      A    N
ATOM  18577  CA   VAL H 286     -22.426 -70.826 -40.547  1.00 40.40      A    C
ATOM  18578  C    VAL H 286     -20.924 -70.997 -40.401  1.00 41.01      A    C
ATOM  18579  O    VAL H 286     -20.154 -70.596 -41.271  1.00 41.01      A    O
ATOM  18580  CB   VAL H 286     -22.819 -69.422 -40.044  1.00 40.30      A    C
ATOM  18581  N    ARG H 287     -20.514 -71.607 -39.298  1.00 41.89      A    N
ATOM  18582  CA   ARG H 287     -19.093 -71.765 -39.008  1.00 42.79      A    C
ATOM  18583  C    ARG H 287     -18.439 -72.901 -39.786  1.00 42.53      A    C
ATOM  18584  O    ARG H 287     -17.228 -72.895 -39.985  1.00 42.69      A    O
ATOM  18585  CB   ARG H 287     -18.847 -71.918 -37.500  1.00 43.52      A    C
ATOM  18586  CG   ARG H 287     -19.437 -73.166 -36.866  1.00 45.25      A    C
ATOM  18587  CD   ARG H 287     -19.030 -73.273 -35.391  1.00 48.26      A    C
ATOM  18588  NE   ARG H 287     -19.426 -74.569 -34.833  1.00 50.01      A    N
ATOM  18589  CZ   ARG H 287     -18.639 -75.646 -34.787  1.00 50.50      A    C
ATOM  18590  NH1  ARG H 287     -17.385 -75.585 -35.251  1.00 50.55      A    N
```

FIGURE 1 (cont'd)

```
ATOM  18591  NH2  ARG H 287   -19.106  -76.786  -34.270  1.00  50.72      A  N
ATOM  18592  N    TRP H 288   -19.234  -73.876  -40.213  1.00  42.18      A  N
ATOM  18593  CA   TRP H 288   -18.717  -74.929  -41.079  1.00  41.89      A  C
ATOM  18594  C    TRP H 288   -18.596  -74.436  -42.506  1.00  41.66      A  C
ATOM  18595  O    TRP H 288   -17.781  -74.939  -43.281  1.00  41.70      A  O
ATOM  18596  CB   TRP H 288   -19.573  -76.188  -41.006  1.00  41.80      A  C
ATOM  18597  CG   TRP H 288   -19.362  -76.925  -39.727  1.00  42.50      A  C
ATOM  18598  CD1  TRP H 288   -20.303  -77.226  -38.778  1.00  42.99      A  C
ATOM  18599  CD2  TRP H 288   -18.118  -77.430  -39.231  1.00  43.22      A  C
ATOM  18600  CE2  TRP H 288   -18.383  -78.042  -37.979  1.00  43.59      A  C
ATOM  18601  CE3  TRP H 288   -16.805  -77.436  -39.725  1.00  43.42      A  C
ATOM  18602  NE1  TRP H 288   -19.723  -77.904  -37.728  1.00  43.38      A  N
ATOM  18603  CZ2  TRP H 288   -17.380  -78.652  -37.213  1.00  44.08      A  C
ATOM  18604  CZ3  TRP H 288   -15.808  -78.044  -38.961  1.00  43.93      A  C
ATOM  18605  CH2  TRP H 288   -16.104  -78.645  -37.719  1.00  44.27      A  C
ATOM  18606  N    PHE H 289   -19.408  -73.440  -42.844  1.00  41.49      A  N
ATOM  18607  CA   PHE H 289   -19.267  -72.755  -44.118  1.00  41.32      A  C
ATOM  18608  C    PHE H 289   -17.956  -71.961  -44.113  1.00  41.46      A  C
ATOM  18609  O    PHE H 289   -17.205  -72.009  -45.095  1.00  41.31      A  O
ATOM  18610  CB   PHE H 289   -20.477  -71.855  -44.408  1.00  41.21      A  C
ATOM  18611  CG   PHE H 289   -20.539  -71.364  -45.827  1.00  41.08      A  C
ATOM  18612  CD1  PHE H 289   -20.982  -72.197  -46.847  1.00  40.68      A  C
ATOM  18613  CD2  PHE H 289   -20.149  -70.066  -46.142  1.00  41.41      A  C
ATOM  18614  CE1  PHE H 289   -21.034  -71.745  -48.153  1.00  40.56      A  C
ATOM  18615  CE2  PHE H 289   -20.199  -69.606  -47.446  1.00  41.51      A  C
ATOM  18616  CZ   PHE H 289   -20.638  -70.450  -48.453  1.00  41.09      A  C
ATOM  18617  N    HIS H 290   -17.668  -71.268  -43.001  1.00  41.78      A  N
ATOM  18618  CA   HIS H 290   -16.409  -70.514  -42.870  1.00  42.22      A  C
ATOM  18619  C    HIS H 290   -15.194  -71.426  -43.043  1.00  42.32      A  C
ATOM  18620  O    HIS H 290   -14.173  -70.996  -43.565  1.00  42.48      A  O
ATOM  18621  CB   HIS H 290   -16.297  -69.747  -41.537  1.00  42.50      A  C
ATOM  18622  CG   HIS H 290   -17.476  -68.876  -41.228  1.00  43.13      A  C
ATOM  18623  ND1  HIS H 290   -17.509  -67.557  -40.797  1.00  43.99      A  N
ATOM  18624  CE1  HIS H 290   -16.372  -66.894  -40.759  1.00  44.50      A  C
ATOM  18625  N    ARG H 291   -15.312  -72.679  -42.605  1.00  42.39      A  N
ATOM  18626  CA   ARG H 291   -14.252  -73.665  -42.795  1.00  42.59      A  C
ATOM  18627  C    ARG H 291   -13.984  -73.875  -44.265  1.00  42.23      A  C
ATOM  18628  O    ARG H 291   -12.825  -73.873  -44.677  1.00  42.50      A  O
ATOM  18629  CB   ARG H 291   -14.594  -74.996  -42.130  1.00  42.83      A  C
ATOM  18630  CG   ARG H 291   -14.393  -74.959  -40.644  1.00  44.46      A  C
ATOM  18631  CD   ARG H 291   -12.939  -74.661  -40.331  1.00  46.61      A  C
ATOM  18632  NE   ARG H 291   -12.178  -75.904  -40.234  1.00  47.74      A  N
ATOM  18633  CZ   ARG H 291   -11.856  -76.500  -39.084  1.00  48.77      A  C
ATOM  18634  NH1  ARG H 291   -12.209  -75.950  -37.924  1.00  49.26      A  N
ATOM  18635  NH2  ARG H 291   -11.173  -77.647  -39.087  1.00  49.28      A  N
ATOM  18636  N    LEU H 292   -15.054  -74.032  -45.051  1.00  41.60      A  N
ATOM  18637  CA   LEU H 292   -14.937  -74.215  -46.495  1.00  40.93      A  C
ATOM  18638  C    LEU H 292   -14.274  -73.013  -47.153  1.00  40.91      A  C
ATOM  18639  O    LEU H 292   -13.366  -73.178  -47.955  1.00  40.97      A  O
ATOM  18640  CB   LEU H 292   -16.288  -74.531  -47.119  1.00  40.53      A  C
ATOM  18641  CG   LEU H 292   -16.847  -75.879  -46.677  1.00  39.84      A  C
ATOM  18642  CD1  LEU H 292   -18.313  -75.974  -47.020  1.00  39.41      A  C
ATOM  18643  CD2  LEU H 292   -16.080  -77.019  -47.307  1.00  39.39      A  C
ATOM  18644  N    ARG H 293   -14.696  -71.806  -46.783  1.00  40.88      A  N
ATOM  18645  CA   ARG H 293   -14.025  -70.587  -47.239  1.00  40.99      A  C
ATOM  18646  C    ARG H 293   -12.549  -70.647  -46.849  1.00  41.28      A  C
ATOM  18647  O    ARG H 293   -11.674  -70.422  -47.684  1.00  41.36      A  O
ATOM  18648  CB   ARG H 293   -14.693  -69.330  -46.661  1.00  40.90      A  C
ATOM  18649  CG   ARG H 293   -14.427  -68.049  -47.456  1.00  40.66      A  C
ATOM  18650  CD   ARG H 293   -14.880  -66.784  -46.718  1.00  40.45      A  C
ATOM  18651  NE   ARG H 293   -16.323  -66.715  -46.508  1.00  39.74      A  N
ATOM  18652  N    SER H 294   -12.289  -70.991  -45.588  1.00  41.47      A  N
ATOM  18653  CA   SER H 294   -10.927  -71.068  -45.051  1.00  41.74      A  C
ATOM  18654  C    SER H 294   -10.072  -72.112  -45.762  1.00  42.12      A  C
ATOM  18655  O    SER H 294    -8.882  -71.878  -45.993  1.00  42.63      A  O
```

FIGURE 1 (cont'd)

```
ATOM  18656  CB   SER H 294     -10.929 -71.333 -43.539  1.00 40.75      A    C
ATOM  18657  N    ILE H 295     -10.672 -73.251 -46.107  1.00 42.18      A    N
ATOM  18658  CA   ILE H 295      -9.945 -74.320 -46.798  1.00 42.25      A    C
ATOM  18659  C    ILE H 295      -9.599 -73.886 -48.224  1.00 42.54      A    C
ATOM  18660  O    ILE H 295      -8.473 -74.108 -48.684  1.00 42.73      A    O
ATOM  18661  CB   ILE H 295     -10.713 -75.674 -46.769  1.00 41.98      A    C
ATOM  18662  CG1  ILE H 295     -10.691 -76.268 -45.358  1.00 41.91      A    C
ATOM  18663  CG2  ILE H 295     -10.107 -76.679 -47.747  1.00 41.81      A    C
ATOM  18664  CD1  ILE H 295     -11.887 -77.155 -45.010  1.00 41.59      A    C
ATOM  18665  N    GLU H 296     -10.559 -73.251 -48.902  1.00 42.69      A    N
ATOM  18666  CA   GLU H 296     -10.352 -72.737 -50.252  1.00 42.99      A    C
ATOM  18667  C    GLU H 296      -9.213 -71.716 -50.224  1.00 43.54      A    C
ATOM  18668  O    GLU H 296      -8.250 -71.809 -50.994  1.00 43.79      A    O
ATOM  18669  CB   GLU H 296     -11.642 -72.108 -50.790  1.00 42.72      A    C
ATOM  18670  CG   GLU H 296     -11.584 -71.714 -52.269  1.00 42.93      A    C
ATOM  18671  CD   GLU H 296     -12.749 -70.844 -52.712  1.00 43.11      A    C
ATOM  18672  OE1  GLU H 296     -13.774 -70.788 -51.992  1.00 42.80      A    O
ATOM  18673  OE2  GLU H 296     -12.632 -70.219 -53.789  1.00 43.38      A    O
ATOM  18674  N    LYS H 297      -9.329 -70.763 -49.307  1.00 44.11      A    N
ATOM  18675  CA   LYS H 297      -8.308 -69.748 -49.076  1.00 44.84      A    C
ATOM  18676  C    LYS H 297      -6.925 -70.402 -48.923  1.00 45.47      A    C
ATOM  18677  O    LYS H 297      -5.994 -70.067 -49.652  1.00 45.73      A    O
ATOM  18678  CB   LYS H 297      -8.674 -68.951 -47.817  1.00 44.76      A    C
ATOM  18679  CG   LYS H 297      -8.696 -67.416 -47.953  1.00 44.62      A    C
ATOM  18680  CD   LYS H 297      -9.685 -66.798 -46.942  1.00 43.74      A    C
ATOM  18681  CE   LYS H 297      -9.347 -65.361 -46.579  1.00 43.71      A    C
ATOM  18682  N    ARG H 298      -6.821 -71.355 -47.997  1.00 45.98      A    N
ATOM  18683  CA   ARG H 298      -5.571 -72.062 -47.711  1.00 46.50      A    C
ATOM  18684  C    ARG H 298      -5.023 -72.809 -48.929  1.00 47.03      A    C
ATOM  18685  O    ARG H 298      -3.854 -72.648 -49.273  1.00 47.63      A    O
ATOM  18686  CB   ARG H 298      -5.755 -73.019 -46.522  1.00 45.52      A    C
ATOM  18687  CG   ARG H 298      -4.480 -73.710 -45.996  1.00 45.47      A    C
ATOM  18688  CD   ARG H 298      -4.772 -74.543 -44.736  1.00 45.13      A    C
ATOM  18689  NE   ARG H 298      -3.621 -75.326 -44.300  1.00 44.98      A    N
ATOM  18690  N    LEU H 299      -5.861 -73.610 -49.581  1.00 47.22      A    N
ATOM  18691  CA   LEU H 299      -5.428 -74.404 -50.738  1.00 47.47      A    C
ATOM  18692  C    LEU H 299      -4.992 -73.522 -51.899  1.00 47.88      A    C
ATOM  18693  O    LEU H 299      -4.130 -73.903 -52.702  1.00 48.13      A    O
ATOM  18694  CB   LEU H 299      -6.525 -75.376 -51.195  1.00 47.14      A    C
ATOM  18695  CG   LEU H 299      -6.818 -76.606 -50.325  1.00 46.97      A    C
ATOM  18696  CD1  LEU H 299      -8.125 -77.230 -50.709  1.00 46.51      A    C
ATOM  18697  CD2  LEU H 299      -5.710 -77.633 -50.430  1.00 47.46      A    C
ATOM  18698  N    HIS H 300      -5.599 -72.343 -51.979  1.00 48.21      A    N
ATOM  18699  CA   HIS H 300      -5.217 -71.346 -52.968  1.00 48.77      A    C
ATOM  18700  C    HIS H 300      -3.813 -70.823 -52.685  1.00 49.24      A    C
ATOM  18701  O    HIS H 300      -2.967 -70.825 -53.586  1.00 49.56      A    O
ATOM  18702  CB   HIS H 300      -6.234 -70.201 -53.006  1.00 48.71      A    C
ATOM  18703  CG   HIS H 300      -5.779 -69.013 -53.794  1.00 49.35      A    C
ATOM  18704  CD2  HIS H 300      -5.506 -67.743 -53.414  1.00 50.12      A    C
ATOM  18705  ND1  HIS H 300      -5.551 -69.062 -55.152  1.00 49.66      A    N
ATOM  18706  CE1  HIS H 300      -5.156 -67.876 -55.575  1.00 50.29      A    C
ATOM  18707  NE2  HIS H 300      -5.121 -67.057 -54.540  1.00 50.72      A    N
ATOM  18708  N    ARG H 301      -3.579 -70.396 -51.438  1.00 49.69      A    N
ATOM  18709  CA   ARG H 301      -2.266 -69.919 -50.980  1.00 50.23      A    C
ATOM  18710  C    ARG H 301      -1.159 -70.943 -51.269  1.00 50.89      A    C
ATOM  18711  O    ARG H 301      -0.043 -70.570 -51.642  1.00 51.42      A    O
ATOM  18712  CB   ARG H 301      -2.274 -69.616 -49.477  1.00 50.08      A    C
ATOM  18713  CG   ARG H 301      -3.397 -68.729 -48.974  1.00 49.11      A    C
ATOM  18714  CD   ARG H 301      -3.054 -67.248 -49.080  1.00 48.46      A    C
ATOM  18715  NE   ARG H 301      -4.205 -66.400 -48.767  1.00 47.71      A    N
ATOM  18716  N    LEU H 302      -1.481 -72.226 -51.097  1.00 51.25      A    N
ATOM  18717  CA   LEU H 302      -0.534 -73.316 -51.318  1.00 51.85      A    C
ATOM  18718  C    LEU H 302      -0.434 -73.761 -52.778  1.00 52.19      A    C
ATOM  18719  O    LEU H 302       0.087 -74.843 -53.048  1.00 52.50      A    O
ATOM  18720  CB   LEU H 302      -0.915 -74.513 -50.453  1.00 51.76      A    C
```

FIGURE 1 (cont'd)

```
ATOM  18721  CG   LEU H 302    -0.758 -74.329 -48.949  1.00 52.23      A    C
ATOM  18722  CD1  LEU H 302    -1.726 -75.244 -48.213  1.00 51.86      A    C
ATOM  18723  CD2  LEU H 302     0.680 -74.589 -48.529  1.00 53.47      A    C
ATOM  18724  N    ASN H 303    -0.918 -72.924 -53.703  1.00 52.30      A    N
ATOM  18725  CA   ASN H 303    -0.963 -73.237 -55.139  1.00 52.24      A    C
ATOM  18726  C    ASN H 303    -1.356 -74.694 -55.396  1.00 52.69      A    C
ATOM  18727  O    ASN H 303    -0.558 -75.485 -55.901  1.00 53.17      A    O
ATOM  18728  N    LEU H 304    -2.583 -75.045 -55.017  1.00 52.86      A    N
ATOM  18729  CA   LEU H 304    -3.093 -76.412 -55.201  1.00 52.76      A    C
ATOM  18730  C    LEU H 304    -4.478 -76.462 -55.850  1.00 52.47      A    C
ATOM  18731  O    LEU H 304    -5.107 -77.529 -55.903  1.00 52.18      A    O
ATOM  18732  CB   LEU H 304    -3.111 -77.180 -53.872  1.00 52.82      A    C
ATOM  18733  CG   LEU H 304    -1.810 -77.797 -53.342  1.00 53.27      A    C
ATOM  18734  CD1  LEU H 304    -2.048 -78.347 -51.956  1.00 52.95      A    C
ATOM  18735  CD2  LEU H 304    -1.264 -78.894 -54.258  1.00 53.84      A    C
ATOM  18736  N    LEU H 305    -4.938 -75.304 -56.335  1.00 52.40      A    N
ATOM  18737  CA   LEU H 305    -6.213 -75.179 -57.058  1.00 52.20      A    C
ATOM  18738  C    LEU H 305    -5.987 -74.661 -58.476  1.00 52.60      A    C
ATOM  18739  O    LEU H 305    -5.471 -73.556 -58.675  1.00 52.99      A    O
ATOM  18740  CB   LEU H 305    -7.180 -74.245 -56.326  1.00 51.74      A    C
ATOM  18741  CG   LEU H 305    -7.476 -74.514 -54.853  1.00 51.10      A    C
ATOM  18742  CD1  LEU H 305    -8.250 -73.355 -54.267  1.00 50.44      A    C
ATOM  18743  CD2  LEU H 305    -8.235 -75.816 -54.667  1.00 50.66      A    C
ATOM  18744  N    GLN H 306    -6.375 -75.475 -59.454  1.00 52.75      A    N
ATOM  18745  CA   GLN H 306    -6.285 -75.105 -60.860  1.00 53.03      A    C
ATOM  18746  C    GLN H 306    -7.213 -73.951 -61.170  1.00 52.94      A    C
ATOM  18747  O    GLN H 306    -8.227 -73.774 -60.500  1.00 52.61      A    O
ATOM  18748  CB   GLN H 306    -6.668 -76.290 -61.740  1.00 53.16      A    C
ATOM  18749  CG   GLN H 306    -5.504 -77.146 -62.195  1.00 54.04      A    C
ATOM  18750  CD   GLN H 306    -5.913 -78.122 -63.282  1.00 54.73      A    C
ATOM  18751  OE1  GLN H 306    -6.909 -78.841 -63.147  1.00 54.95      A    O
ATOM  18752  N    SER H 307    -6.863 -73.168 -62.187  1.00 53.29      A    N
ATOM  18753  CA   SER H 307    -7.734 -72.091 -62.694  1.00 53.53      A    C
ATOM  18754  C    SER H 307    -8.432 -71.312 -61.572  1.00 53.36      A    C
ATOM  18755  O    SER H 307    -9.651 -71.107 -61.610  1.00 53.11      A    O
ATOM  18756  CB   SER H 307    -8.787 -72.652 -63.673  1.00 53.55      A    C
ATOM  18757  OG   SER H 307    -8.220 -73.578 -64.589  1.00 54.27      A    O
ATOM  18758  N    HIS H 308    -7.648 -70.886 -60.582  1.00 53.49      A    N
ATOM  18759  CA   HIS H 308    -8.184 -70.253 -59.376  1.00 53.46      A    C
ATOM  18760  C    HIS H 308    -7.484 -68.907 -59.114  1.00 53.73      A    C
ATOM  18761  O    HIS H 308    -6.655 -68.798 -58.205  1.00 53.99      A    O
ATOM  18762  CB   HIS H 308    -8.031 -71.210 -58.184  1.00 53.29      A    C
ATOM  18763  CG   HIS H 308    -8.961 -70.928 -57.045  1.00 52.97      A    C
ATOM  18764  CD2  HIS H 308   -10.285 -71.159 -56.899  1.00 52.54      A    C
ATOM  18765  ND1  HIS H 308    -8.544 -70.348 -55.866  1.00 53.25      A    N
ATOM  18766  CE1  HIS H 308    -9.571 -70.231 -55.045  1.00 52.90      A    C
ATOM  18767  NE2  HIS H 308   -10.639 -70.718 -55.647  1.00 52.37      A    N
ATOM  18768  N    PRO H 309    -7.816 -67.872 -59.917  1.00 53.96      A    N
ATOM  18769  CA   PRO H 309    -7.085 -66.604 -59.834  1.00 54.42      A    C
ATOM  18770  C    PRO H 309    -7.546 -65.637 -58.741  1.00 54.68      A    C
ATOM  18771  O    PRO H 309    -7.599 -64.428 -58.980  1.00 54.94      A    O
ATOM  18772  CB   PRO H 309    -7.309 -65.981 -61.229  1.00 54.68      A    C
ATOM  18773  CG   PRO H 309    -7.884 -67.097 -62.081  1.00 54.43      A    C
ATOM  18774  CD   PRO H 309    -8.694 -67.880 -61.100  1.00 53.91      A    C
ATOM  18775  N    GLN H 310    -7.898 -66.177 -57.572  1.00 54.73      A    N
ATOM  18776  CA   GLN H 310    -8.032 -65.408 -56.313  1.00 54.89      A    C
ATOM  18777  C    GLN H 310    -8.379 -66.277 -55.094  1.00 54.99      A    C
ATOM  18778  O    GLN H 310    -8.450 -67.504 -55.194  1.00 54.83      A    O
ATOM  18779  CB   GLN H 310    -8.937 -64.154 -56.433  1.00 54.91      A    C
ATOM  18780  CG   GLN H 310   -10.216 -64.293 -57.267  1.00 54.52      A    C
ATOM  18781  CD   GLN H 310   -10.563 -63.034 -58.058  1.00 54.51      A    C
ATOM  18782  NE2  GLN H 310    -9.745 -61.998 -57.919  1.00 53.53      A    N
ATOM  18783  OE1  GLN H 310   -11.550 -63.006 -58.797  1.00 52.36      A    O
ATOM  18784  N    GLU H 311    -8.564 -65.639 -53.943  1.00 55.37      A    N
ATOM  18785  CA   GLU H 311    -8.731 -66.349 -52.679  1.00 55.74      A    C
```

FIGURE 1 (cont'd)

```
ATOM  18786  C    GLU H 311     -10.180 -66.817 -52.526  1.00 55.04      A  C
ATOM  18787  O    GLU H 311     -10.448 -68.022 -52.495  1.00 54.85      A  O
ATOM  18788  CB   GLU H 311      -8.302 -65.465 -51.491  1.00 56.50      A  C
ATOM  18789  CG   GLU H 311      -6.944 -64.743 -51.640  1.00 58.90      A  C
ATOM  18790  CD   GLU H 311      -7.016 -63.411 -52.425  1.00 61.43      A  C
ATOM  18791  OE1  GLU H 311      -6.136 -62.548 -52.212  1.00 62.84      A  O
ATOM  18792  OE2  GLU H 311      -7.933 -63.216 -53.257  1.00 62.00      A  O
ATOM  18793  N    VAL H 312     -11.104 -65.862 -52.439  1.00 54.45      A  N
ATOM  18794  CA   VAL H 312     -12.519 -66.174 -52.391  1.00 53.71      A  C
ATOM  18795  C    VAL H 312     -13.073 -66.170 -53.812  1.00 53.20      A  C
ATOM  18796  O    VAL H 312     -13.200 -65.122 -54.442  1.00 53.52      A  O
ATOM  18797  N    MET H 313     -13.364 -67.362 -54.318  1.00 52.16      A  N
ATOM  18798  CA   MET H 313     -13.986 -67.538 -55.623  1.00 51.19      A  C
ATOM  18799  C    MET H 313     -15.298 -68.283 -55.427  1.00 50.20      A  C
ATOM  18800  O    MET H 313     -16.357 -67.806 -55.823  1.00 50.07      A  O
ATOM  18801  CB   MET H 313     -13.084 -68.361 -56.546  1.00 51.40      A  C
ATOM  18802  CG   MET H 313     -11.721 -67.754 -56.875  1.00 52.00      A  C
ATOM  18803  SD   MET H 313     -11.470 -67.350 -58.612  1.00 52.40      A  S
ATOM  18804  CE   MET H 313     -11.679 -68.940 -59.413  1.00 52.15      A  C
ATOM  18805  N    TYR H 314     -15.210 -69.444 -54.785  1.00 49.11      A  N
ATOM  18806  CA   TYR H 314     -16.331 -70.364 -54.635  1.00 48.02      A  C
ATOM  18807  C    TYR H 314     -17.214 -70.085 -53.419  1.00 47.47      A  C
ATOM  18808  O    TYR H 314     -18.403 -69.834 -53.556  1.00 47.28      A  O
ATOM  18809  CB   TYR H 314     -15.816 -71.804 -54.574  1.00 47.83      A  C
ATOM  18810  CG   TYR H 314     -15.060 -72.270 -55.800  1.00 47.55      A  C
ATOM  18811  CD1  TYR H 314     -15.422 -71.832 -57.073  1.00 47.55      A  C
ATOM  18812  CD2  TYR H 314     -14.006 -73.180 -55.689  1.00 47.38      A  C
ATOM  18813  CE1  TYR H 314     -14.741 -72.268 -58.206  1.00 47.63      A  C
ATOM  18814  CE2  TYR H 314     -13.322 -73.624 -56.819  1.00 47.43      A  C
ATOM  18815  CZ   TYR H 314     -13.699 -73.161 -58.073  1.00 47.35      A  C
ATOM  18816  OH   TYR H 314     -13.046 -73.578 -59.205  1.00 47.31      A  O
ATOM  18817  N    PHE H 315     -16.635 -70.149 -52.230  1.00 47.02      A  N
ATOM  18818  CA   PHE H 315     -17.399 -69.950 -51.013  1.00 46.67      A  C
ATOM  18819  C    PHE H 315     -17.395 -68.484 -50.616  1.00 46.95      A  C
ATOM  18820  O    PHE H 315     -16.491 -67.999 -49.932  1.00 47.02      A  O
ATOM  18821  CB   PHE H 315     -16.874 -70.855 -49.904  1.00 46.38      A  C
ATOM  18822  CG   PHE H 315     -16.955 -72.315 -50.238  1.00 45.28      A  C
ATOM  18823  CD1  PHE H 315     -18.122 -73.029 -50.004  1.00 44.53      A  C
ATOM  18824  CD2  PHE H 315     -15.871 -72.975 -50.804  1.00 44.57      A  C
ATOM  18825  CE1  PHE H 315     -18.208 -74.381 -50.324  1.00 43.99      A  C
ATOM  18826  CE2  PHE H 315     -15.948 -74.327 -51.124  1.00 44.01      A  C
ATOM  18827  CZ   PHE H 315     -17.120 -75.028 -50.884  1.00 43.75      A  C
ATOM  18828  N    GLN H 316     -18.424 -67.786 -51.076  1.00 47.20      A  N
ATOM  18829  CA   GLN H 316     -18.529 -66.351 -50.913  1.00 47.73      A  C
ATOM  18830  C    GLN H 316     -18.967 -65.974 -49.513  1.00 48.10      A  C
ATOM  18831  O    GLN H 316     -19.708 -66.729 -48.878  1.00 47.92      A  O
ATOM  18832  CB   GLN H 316     -19.529 -65.783 -51.915  1.00 47.79      A  C
ATOM  18833  CG   GLN H 316     -19.039 -65.738 -53.357  1.00 48.23      A  C
ATOM  18834  CD   GLN H 316     -17.850 -64.823 -53.560  1.00 48.97      A  C
ATOM  18835  NE2  GLN H 316     -16.733 -65.401 -53.984  1.00 49.09      A  N
ATOM  18836  OE1  GLN H 316     -17.934 -63.610 -53.350  1.00 49.79      A  O
ATOM  18837  N    PRO H 317     -18.515 -64.795 -49.027  1.00 48.69      A  N
ATOM  18838  CA   PRO H 317     -18.988 -64.294 -47.749  1.00 48.96      A  C
ATOM  18839  C    PRO H 317     -20.388 -63.736 -47.920  1.00 49.01      A  C
ATOM  18840  O    PRO H 317     -20.838 -63.499 -49.045  1.00 48.94      A  O
ATOM  18841  CB   PRO H 317     -18.000 -63.176 -47.427  1.00 49.28      A  C
ATOM  18842  CG   PRO H 317     -17.601 -62.654 -48.761  1.00 49.44      A  C
ATOM  18843  CD   PRO H 317     -17.540 -63.873 -49.643  1.00 48.97      A  C
ATOM  18844  N    GLY H 318     -21.065 -63.526 -46.802  1.00 49.09      A  N
ATOM  18845  CA   GLY H 318     -22.449 -63.096 -46.835  1.00 49.04      A  C
ATOM  18846  C    GLY H 318     -23.365 -64.245 -46.472  1.00 48.87      A  C
ATOM  18847  O    GLY H 318     -23.113 -65.409 -46.841  1.00 48.65      A  O
ATOM  18848  N    GLU H 319     -24.421 -63.903 -45.731  1.00 48.88      A  N
ATOM  18849  CA   GLU H 319     -25.445 -64.852 -45.294  1.00 48.64      A  C
ATOM  18850  C    GLU H 319     -26.818 -64.428 -45.849  1.00 48.78      A  C
```

FIGURE 1 (cont'd)

```
ATOM  18851  O    GLU H 319     -27.633 -63.858 -45.102  1.00 49.12      A    O
ATOM  18852  CB   GLU H 319     -25.483 -64.918 -43.762  1.00 48.49      A    C
ATOM  18853  CG   GLU H 319     -24.211 -65.425 -43.122  1.00 47.99      A    C
ATOM  18854  CD   GLU H 319     -24.306 -66.896 -42.795  1.00 49.13      A    C
ATOM  18855  OE1  GLU H 319     -23.250 -67.543 -42.658  1.00 49.97      A    O
ATOM  18856  OE2  GLU H 319     -25.442 -67.413 -42.671  1.00 49.82      A    O
ATOM  18857  N    PRO H 320     -27.071 -64.678 -47.163  1.00 48.66      A    N
ATOM  18858  CA   PRO H 320     -28.401 -64.385 -47.701  1.00 48.66      A    C
ATOM  18859  C    PRO H 320     -29.490 -65.363 -47.213  1.00 48.56      A    C
ATOM  18860  O    PRO H 320     -29.184 -66.497 -46.789  1.00 48.32      A    O
ATOM  18861  CB   PRO H 320     -28.197 -64.488 -49.218  1.00 48.69      A    C
ATOM  18862  CG   PRO H 320     -26.735 -64.303 -49.416  1.00 48.66      A    C
ATOM  18863  CD   PRO H 320     -26.133 -65.013 -48.249  1.00 48.48      A    C
ATOM  18864  N    PHE H 321     -30.745 -64.902 -47.297  1.00 48.41      A    N
ATOM  18865  CA   PHE H 321     -31.923 -65.570 -46.712  1.00 48.02      A    C
ATOM  18866  C    PHE H 321     -32.165 -67.036 -47.129  1.00 48.17      A    C
ATOM  18867  O    PHE H 321     -32.224 -67.913 -46.260  1.00 48.48      A    O
ATOM  18868  N    GLY H 322     -32.289 -67.299 -48.437  1.00 48.04      A    N
ATOM  18869  CA   GLY H 322     -32.686 -68.629 -48.956  1.00 47.45      A    C
ATOM  18870  C    GLY H 322     -34.201 -68.889 -48.861  1.00 47.10      A    C
ATOM  18871  O    GLY H 322     -35.006 -67.944 -48.771  1.00 47.59      A    O
ATOM  18872  N    SER H 323     -34.621 -70.157 -48.894  1.00 46.16      A    N
ATOM  18873  CA   SER H 323     -33.762 -71.324 -49.154  1.00 45.07      A    C
ATOM  18874  C    SER H 323     -34.123 -71.908 -50.526  1.00 43.98      A    C
ATOM  18875  O    SER H 323     -35.059 -71.442 -51.182  1.00 44.04      A    O
ATOM  18876  CB   SER H 323     -33.956 -72.400 -48.055  1.00 45.26      A    C
ATOM  18877  OG   SER H 323     -33.662 -71.898 -46.754  1.00 46.06      A    O
ATOM  18878  N    VAL H 324     -33.388 -72.930 -50.949  1.00 42.30      A    N
ATOM  18879  CA   VAL H 324     -33.729 -73.674 -52.149  1.00 40.75      A    C
ATOM  18880  C    VAL H 324     -34.163 -75.068 -51.733  1.00 39.99      A    C
ATOM  18881  O    VAL H 324     -33.396 -75.786 -51.100  1.00 39.88      A    O
ATOM  18882  CB   VAL H 324     -32.522 -73.748 -53.085  1.00 40.52      A    C
ATOM  18883  CG1  VAL H 324     -32.199 -72.357 -53.612  1.00 40.42      A    C
ATOM  18884  CG2  VAL H 324     -32.766 -74.732 -54.228  1.00 40.06      A    C
ATOM  18885  N    GLU H 325     -35.392 -75.440 -52.079  1.00 39.17      A    N
ATOM  18886  CA   GLU H 325     -35.957 -76.720 -51.655  1.00 38.48      A    C
ATOM  18887  C    GLU H 325     -35.188 -77.901 -52.228  1.00 37.60      A    C
ATOM  18888  O    GLU H 325     -35.048 -78.024 -53.426  1.00 37.48      A    O
ATOM  18889  CB   GLU H 325     -37.421 -76.809 -52.052  1.00 38.86      A    C
ATOM  18890  CG   GLU H 325     -38.267 -75.664 -51.534  1.00 40.45      A    C
ATOM  18891  CD   GLU H 325     -39.762 -75.866 -51.762  1.00 42.56      A    C
ATOM  18892  OE1  GLU H 325     -40.180 -76.960 -52.203  1.00 42.99      A    O
ATOM  18893  OE2  GLU H 325     -40.532 -74.923 -51.492  1.00 43.79      A    O
ATOM  18894  N    ASP H 326     -34.682 -78.770 -51.364  1.00 36.76      A    N
ATOM  18895  CA   ASP H 326     -33.874 -79.908 -51.801  1.00 36.01      A    C
ATOM  18896  C    ASP H 326     -34.001 -81.006 -50.747  1.00 35.74      A    C
ATOM  18897  O    ASP H 326     -34.799 -80.886 -49.821  1.00 35.83      A    O
ATOM  18898  CB   ASP H 326     -32.410 -79.471 -51.998  1.00 35.75      A    C
ATOM  18899  CG   ASP H 326     -31.654 -80.301 -53.043  1.00 35.11      A    C
ATOM  18900  OD1  ASP H 326     -32.040 -81.449 -53.337  1.00 34.81      A    O
ATOM  18901  OD2  ASP H 326     -30.637 -79.791 -53.557  1.00 34.56      A    O
ATOM  18902  N    ASP H 327     -33.204 -82.064 -50.890  1.00 35.32      A    N
ATOM  18903  CA   ASP H 327     -33.304 -83.274 -50.063  1.00 34.99      A    C
ATOM  18904  C    ASP H 327     -33.172 -83.036 -48.572  1.00 34.57      A    C
ATOM  18905  O    ASP H 327     -33.542 -83.888 -47.780  1.00 34.65      A    O
ATOM  18906  CB   ASP H 327     -32.263 -84.311 -50.495  1.00 35.12      A    C
ATOM  18907  CG   ASP H 327     -32.618 -85.002 -51.817  1.00 36.06      A    C
ATOM  18908  OD1  ASP H 327     -33.618 -85.766 -51.879  1.00 36.73      A    O
ATOM  18909  OD2  ASP H 327     -31.863 -84.792 -52.799  1.00 36.75      A    O
ATOM  18910  N    HIS H 328     -32.647 -81.879 -48.191  1.00 34.08      A    N
ATOM  18911  CA   HIS H 328     -32.410 -81.579 -46.791  1.00 33.72      A    C
ATOM  18912  C    HIS H 328     -33.704 -81.271 -46.067  1.00 33.64      A    C
ATOM  18913  O    HIS H 328     -33.798 -81.488 -44.869  1.00 33.86      A    O
ATOM  18914  CB   HIS H 328     -31.435 -80.414 -46.648  1.00 33.57      A    C
ATOM  18915  CG   HIS H 328     -32.000 -79.097 -47.078  1.00 33.86      A    C
```

FIGURE 1 (cont'd)

```
ATOM  18916  CD2 HIS H 328    -32.488 -78.060 -46.359  1.00 34.44     A    C
ATOM  18917  ND1 HIS H 328    -32.113 -78.730 -48.401  1.00 34.08     A    N
ATOM  18918  CE1 HIS H 328    -32.643 -77.523 -48.479  1.00 34.33     A    C
ATOM  18919  NE2 HIS H 328    -32.880 -77.092 -47.254  1.00 34.58     A    N
ATOM  18920  N   ILE H 329    -34.701 -80.780 -46.793  1.00 33.49     A    N
ATOM  18921  CA  ILE H 329    -35.936 -80.299 -46.172  1.00 33.63     A    C
ATOM  18922  C   ILE H 329    -36.550 -81.257 -45.149  1.00 33.61     A    C
ATOM  18923  O   ILE H 329    -36.780 -80.864 -44.008  1.00 33.88     A    O
ATOM  18924  CB  ILE H 329    -36.981 -79.823 -47.224  1.00 33.71     A    C
ATOM  18925  CG1 ILE H 329    -36.476 -78.571 -47.951  1.00 33.91     A    C
ATOM  18926  CG2 ILE H 329    -38.357 -79.581 -46.593  1.00 34.15     A    C
ATOM  18927  CD1 ILE H 329    -36.270 -77.351 -47.060  1.00 34.44     A    C
ATOM  18928  N   PRO H 330    -36.790 -82.518 -45.532  1.00 33.54     A    N
ATOM  18929  CA  PRO H 330    -37.477 -83.375 -44.566  1.00 33.65     A    C
ATOM  18930  C   PRO H 330    -36.579 -83.825 -43.404  1.00 33.52     A    C
ATOM  18931  O   PRO H 330    -37.060 -84.412 -42.430  1.00 33.77     A    O
ATOM  18932  CB  PRO H 330    -37.942 -84.561 -45.416  1.00 33.72     A    C
ATOM  18933  CG  PRO H 330    -36.945 -84.641 -46.498  1.00 33.53     A    C
ATOM  18934  CD  PRO H 330    -36.502 -83.232 -46.785  1.00 33.44     A    C
ATOM  18935  N   PHE H 331    -35.289 -83.546 -43.511  1.00 33.10     A    N
ATOM  18936  CA  PHE H 331    -34.385 -83.747 -42.388  1.00 32.92     A    C
ATOM  18937  C   PHE H 331    -34.346 -82.494 -41.532  1.00 32.87     A    C
ATOM  18938  O   PHE H 331    -34.291 -82.562 -40.310  1.00 32.99     A    O
ATOM  18939  CB  PHE H 331    -32.981 -84.136 -42.869  1.00 32.70     A    C
ATOM  18940  CG  PHE H 331    -32.909 -85.519 -43.431  1.00 32.78     A    C
ATOM  18941  CD1 PHE H 331    -32.914 -85.718 -44.799  1.00 32.79     A    C
ATOM  18942  CD2 PHE H 331    -32.873 -86.622 -42.591  1.00 33.30     A    C
ATOM  18943  CE1 PHE H 331    -32.861 -86.992 -45.332  1.00 33.03     A    C
ATOM  18944  CE2 PHE H 331    -32.823 -87.898 -43.109  1.00 33.51     A    C
ATOM  18945  CZ  PHE H 331    -32.817 -88.087 -44.489  1.00 33.24     A    C
ATOM  18946  N   LEU H 332    -34.388 -81.347 -42.187  1.00 32.80     A    N
ATOM  18947  CA  LEU H 332    -34.441 -80.083 -41.493  1.00 32.96     A    C
ATOM  18948  C   LEU H 332    -35.719 -79.947 -40.660  1.00 33.44     A    C
ATOM  18949  O   LEU H 332    -35.658 -79.508 -39.511  1.00 33.70     A    O
ATOM  18950  CB  LEU H 332    -34.333 -78.935 -42.488  1.00 32.68     A    C
ATOM  18951  CG  LEU H 332    -34.442 -77.522 -41.928  1.00 32.41     A    C
ATOM  18952  CD1 LEU H 332    -33.083 -77.031 -41.439  1.00 32.01     A    C
ATOM  18953  CD2 LEU H 332    -35.000 -76.603 -42.990  1.00 32.37     A    C
ATOM  18954  N   ARG H 333    -36.867 -80.334 -41.215  1.00 33.80     A    N
ATOM  18955  CA  ARG H 333    -38.125 -80.212 -40.470  1.00 34.35     A    C
ATOM  18956  C   ARG H 333    -38.102 -81.053 -39.179  1.00 34.12     A    C
ATOM  18957  O   ARG H 333    -38.848 -80.785 -38.242  1.00 34.48     A    O
ATOM  18958  CB  ARG H 333    -39.360 -80.485 -41.363  1.00 34.73     A    C
ATOM  18959  CG  ARG H 333    -40.081 -81.837 -41.165  1.00 36.61     A    C
ATOM  18960  CD  ARG H 333    -41.486 -81.870 -41.821  1.00 39.92     A    C
ATOM  18961  NE  ARG H 333    -41.521 -82.555 -43.131  1.00 42.26     A    N
ATOM  18962  CZ  ARG H 333    -42.049 -83.769 -43.363  1.00 42.98     A    C
ATOM  18963  NH1 ARG H 333    -42.018 -84.281 -44.593  1.00 42.56     A    N
ATOM  18964  NH2 ARG H 333    -42.611 -84.476 -42.380  1.00 43.83     A    N
ATOM  18965  N   ARG H 334    -37.217 -82.045 -39.132  1.00 33.57     A    N
ATOM  18966  CA  ARG H 334    -37.052 -82.887 -37.957  1.00 33.16     A    C
ATOM  18967  C   ARG H 334    -35.924 -82.397 -37.052  1.00 32.68     A    C
ATOM  18968  O   ARG H 334    -35.616 -83.012 -36.037  1.00 32.81     A    O
ATOM  18969  CB  ARG H 334    -36.804 -84.332 -38.389  1.00 33.19     A    C
ATOM  18970  CG  ARG H 334    -38.067 -85.112 -38.714  1.00 33.62     A    C
ATOM  18971  CD  ARG H 334    -37.807 -86.120 -39.803  1.00 33.74     A    C
ATOM  18972  NE  ARG H 334    -38.897 -87.079 -39.936  1.00 34.78     A    N
ATOM  18973  CZ  ARG H 334    -39.811 -87.059 -40.906  1.00 35.56     A    C
ATOM  18974  NH1 ARG H 334    -39.778 -86.118 -41.848  1.00 35.22     A    N
ATOM  18975  NH2 ARG H 334    -40.759 -87.990 -40.936  1.00 36.56     A    N
ATOM  18976  N   GLY H 335    -35.299 -81.292 -37.430  1.00 32.07     A    N
ATOM  18977  CA  GLY H 335    -34.301 -80.655 -36.578  1.00 31.48     A    C
ATOM  18978  C   GLY H 335    -32.842 -80.982 -36.838  1.00 30.80     A    C
ATOM  18979  O   GLY H 335    -31.982 -80.655 -36.028  1.00 31.09     A    O
ATOM  18980  N   VAL H 336    -32.550 -81.618 -37.964  1.00 29.91     A    N
```

FIGURE 1 (cont'd)

```
ATOM  18981  CA   VAL H 336     -31.175 -81.942 -38.304  1.00 29.07      A  C
ATOM  18982  C    VAL H 336     -30.470 -80.682 -38.788  1.00 28.65      A  C
ATOM  18983  O    VAL H 336     -31.007 -79.972 -39.621  1.00 28.63      A  O
ATOM  18984  CB   VAL H 336     -31.107 -83.025 -39.400  1.00 28.91      A  C
ATOM  18985  CG1  VAL H 336     -29.663 -83.334 -39.766  1.00 28.83      A  C
ATOM  18986  CG2  VAL H 336     -31.815 -84.301 -38.949  1.00 29.04      A  C
ATOM  18987  N    PRO H 337     -29.274 -80.387 -38.251  1.00 28.43      A  N
ATOM  18988  CA   PRO H 337     -28.451 -79.282 -38.755  1.00 28.16      A  C
ATOM  18989  C    PRO H 337     -28.104 -79.516 -40.216  1.00 27.75      A  C
ATOM  18990  O    PRO H 337     -27.690 -80.623 -40.574  1.00 27.79      A  O
ATOM  18991  CB   PRO H 337     -27.183 -79.375 -37.911  1.00 28.30      A  C
ATOM  18992  CG   PRO H 337     -27.598 -80.078 -36.672  1.00 28.74      A  C
ATOM  18993  CD   PRO H 337     -28.670 -81.036 -37.074  1.00 28.66      A  C
ATOM  18994  N    VAL H 338     -28.289 -78.502 -41.060  1.00 27.27      A  N
ATOM  18995  CA   VAL H 338     -28.037 -78.662 -42.495  1.00 26.71      A  C
ATOM  18996  C    VAL H 338     -26.988 -77.694 -43.004  1.00 26.52      A  C
ATOM  18997  O    VAL H 338     -26.969 -76.544 -42.616  1.00 26.72      A  O
ATOM  18998  CB   VAL H 338     -29.306 -78.469 -43.333  1.00 26.58      A  C
ATOM  18999  CG1  VAL H 338     -28.995 -78.646 -44.800  1.00 26.37      A  C
ATOM  19000  CG2  VAL H 338     -30.371 -79.450 -42.928  1.00 26.62      A  C
ATOM  19001  N    LEU H 339     -26.106 -78.183 -43.862  1.00 26.19      A  N
ATOM  19002  CA   LEU H 339     -25.259 -77.323 -44.668  1.00 25.92      A  C
ATOM  19003  C    LEU H 339     -25.557 -77.625 -46.132  1.00 25.80      A  C
ATOM  19004  O    LEU H 339     -25.236 -78.697 -46.654  1.00 25.84      A  O
ATOM  19005  CB   LEU H 339     -23.772 -77.516 -44.347  1.00 25.86      A  C
ATOM  19006  CG   LEU H 339     -22.796 -76.614 -45.109  1.00 25.67      A  C
ATOM  19007  CD1  LEU H 339     -23.129 -75.153 -44.895  1.00 25.99      A  C
ATOM  19008  CD2  LEU H 339     -21.372 -76.891 -44.698  1.00 25.49      A  C
ATOM  19009  N    HIS H 340     -26.192 -76.667 -46.787  1.00 25.65      A  N
ATOM  19010  CA   HIS H 340     -26.662 -76.839 -48.159  1.00 25.45      A  C
ATOM  19011  C    HIS H 340     -25.635 -76.342 -49.176  1.00 25.33      A  C
ATOM  19012  O    HIS H 340     -25.544 -75.136 -49.458  1.00 25.33      A  O
ATOM  19013  CB   HIS H 340     -27.988 -76.107 -48.336  1.00 25.49      A  C
ATOM  19014  CG   HIS H 340     -28.808 -76.606 -49.479  1.00 25.66      A  C
ATOM  19015  CD2  HIS H 340     -28.696 -77.717 -50.247  1.00 25.69      A  C
ATOM  19016  ND1  HIS H 340     -29.912 -75.927 -49.943  1.00 26.04      A  N
ATOM  19017  CE1  HIS H 340     -30.450 -76.601 -50.947  1.00 25.99      A  C
ATOM  19018  NE2  HIS H 340     -29.728 -77.688 -51.155  1.00 25.91      A  N
ATOM  19019  N    LEU H 341     -24.867 -77.288 -49.716  1.00 25.18      A  N
ATOM  19020  CA   LEU H 341     -23.782 -76.982 -50.629  1.00 25.13      A  C
ATOM  19021  C    LEU H 341     -24.282 -77.038 -52.077  1.00 25.13      A  C
ATOM  19022  O    LEU H 341     -23.894 -77.925 -52.850  1.00 25.12      A  O
ATOM  19023  CB   LEU H 341     -22.628 -77.957 -50.414  1.00 25.10      A  C
ATOM  19024  CG   LEU H 341     -21.211 -77.371 -50.362  1.00 25.33      A  C
ATOM  19025  CD1  LEU H 341     -20.218 -78.507 -50.207  1.00 25.56      A  C
ATOM  19026  CD2  LEU H 341     -20.846 -76.508 -51.578  1.00 25.07      A  C
ATOM  19027  N    ILE H 342     -25.148 -76.078 -52.416  1.00 25.21      A  N
ATOM  19028  CA   ILE H 342     -25.751 -75.933 -53.748  1.00 25.23      A  C
ATOM  19029  C    ILE H 342     -25.372 -74.555 -54.326  1.00 25.54      A  C
ATOM  19030  O    ILE H 342     -25.433 -73.535 -53.614  1.00 25.77      A  O
ATOM  19031  CB   ILE H 342     -27.294 -76.118 -53.662  1.00 25.02      A  C
ATOM  19032  CG1  ILE H 342     -27.950 -76.019 -55.038  1.00 24.90      A  C
ATOM  19033  CG2  ILE H 342     -27.908 -75.123 -52.690  1.00 24.96      A  C
ATOM  19034  CD1  ILE H 342     -29.385 -76.550 -55.074  1.00 24.64      A  C
ATOM  19035  N    SER H 343     -24.954 -74.517 -55.588  1.00 25.77      A  N
ATOM  19036  CA   SER H 343     -24.573 -73.240 -56.165  1.00 26.21      A  C
ATOM  19037  C    SER H 343     -25.795 -72.376 -56.444  1.00 26.41      A  C
ATOM  19038  O    SER H 343     -26.809 -72.850 -56.974  1.00 26.30      A  O
ATOM  19039  CB   SER H 343     -23.719 -73.419 -57.411  1.00 26.31      A  C
ATOM  19040  OG   SER H 343     -24.470 -73.980 -58.457  1.00 26.97      A  O
ATOM  19041  N    THR H 344     -25.694 -71.116 -56.032  1.00 26.77      A  N
ATOM  19042  CA   THR H 344     -26.692 -70.105 -56.344  1.00 27.11      A  C
ATOM  19043  C    THR H 344     -25.931 -68.948 -56.975  1.00 27.53      A  C
ATOM  19044  O    THR H 344     -25.079 -68.346 -56.316  1.00 27.65      A  O
ATOM  19045  CB   THR H 344     -27.447 -69.641 -55.096  1.00 27.03      A  C
```

FIGURE 1 (cont'd)

```
ATOM  19046  OG1 THR H 344    -26.807 -70.185 -53.937  1.00 26.77      A    O
ATOM  19047  N   PRO H 345    -26.228 -68.636 -58.253  1.00 27.84      A    N
ATOM  19048  CA  PRO H 345    -27.334 -69.167 -59.048  1.00 27.88      A    C
ATOM  19049  C   PRO H 345    -27.085 -70.570 -59.589  1.00 27.68      A    C
ATOM  19050  O   PRO H 345    -25.973 -71.076 -59.499  1.00 27.41      A    O
ATOM  19051  CB  PRO H 345    -27.452 -68.164 -60.204  1.00 28.15      A    C
ATOM  19052  CG  PRO H 345    -26.345 -67.150 -60.005  1.00 28.24      A    C
ATOM  19053  CD  PRO H 345    -25.371 -67.763 -59.065  1.00 28.00      A    C
ATOM  19054  N   PHE H 346    -28.132 -71.187 -60.132  1.00 27.69      A    N
ATOM  19055  CA  PHE H 346    -28.034 -72.511 -60.731  1.00 27.83      A    C
ATOM  19056  C   PHE H 346    -27.189 -72.454 -61.998  1.00 28.07      A    C
ATOM  19057  O   PHE H 346    -27.108 -71.397 -62.636  1.00 28.42      A    O
ATOM  19058  CB  PHE H 346    -29.418 -73.049 -61.086  1.00 27.85      A    C
ATOM  19059  CG  PHE H 346    -30.307 -73.287 -59.904  1.00 28.02      A    C
ATOM  19060  CD1 PHE H 346    -29.795 -73.332 -58.613  1.00 27.86      A    C
ATOM  19061  CD2 PHE H 346    -31.672 -73.495 -60.085  1.00 28.61      A    C
ATOM  19062  CE1 PHE H 346    -30.638 -73.562 -57.524  1.00 27.82      A    C
ATOM  19063  CE2 PHE H 346    -32.519 -73.733 -59.000  1.00 28.48      A    C
ATOM  19064  CZ  PHE H 346    -32.003 -73.764 -57.719  1.00 28.01      A    C
ATOM  19065  N   PRO H 347    -26.565 -73.589 -62.381  1.00 28.05      A    N
ATOM  19066  CA  PRO H 347    -25.762 -73.681 -63.602  1.00 28.41      A    C
ATOM  19067  C   PRO H 347    -26.541 -73.209 -64.812  1.00 29.02      A    C
ATOM  19068  O   PRO H 347    -27.736 -73.470 -64.896  1.00 29.16      A    O
ATOM  19069  CB  PRO H 347    -25.514 -75.180 -63.737  1.00 28.18      A    C
ATOM  19070  CG  PRO H 347    -25.572 -75.696 -62.363  1.00 27.72      A    C
ATOM  19071  CD  PRO H 347    -26.590 -74.870 -61.653  1.00 27.73      A    C
ATOM  19072  N   ALA H 348    -25.876 -72.521 -65.737  1.00 29.70      A    N
ATOM  19073  CA  ALA H 348    -26.539 -72.064 -66.964  1.00 30.35      A    C
ATOM  19074  C   ALA H 348    -27.256 -73.225 -67.669  1.00 30.62      A    C
ATOM  19075  O   ALA H 348    -28.385 -73.080 -68.176  1.00 30.73      A    O
ATOM  19076  CB  ALA H 348    -25.540 -71.408 -67.891  1.00 30.62      A    C
ATOM  19077  N   VAL H 349    -26.594 -74.381 -67.652  1.00 30.71      A    N
ATOM  19078  CA  VAL H 349    -27.074 -75.594 -68.299  1.00 30.89      A    C
ATOM  19079  C   VAL H 349    -28.127 -76.343 -67.468  1.00 30.96      A    C
ATOM  19080  O   VAL H 349    -28.367 -77.530 -67.688  1.00 31.10      A    O
ATOM  19081  CB  VAL H 349    -25.885 -76.550 -68.652  1.00 30.86      A    C
ATOM  19082  CG1 VAL H 349    -24.974 -75.916 -69.673  1.00 31.42      A    C
ATOM  19083  CG2 VAL H 349    -25.077 -76.946 -67.412  1.00 30.45      A    C
ATOM  19084  N   TRP H 350    -28.774 -75.658 -66.533  1.00 31.04      A    N
ATOM  19085  CA  TRP H 350    -29.636 -76.354 -65.576  1.00 31.14      A    C
ATOM  19086  C   TRP H 350    -30.938 -76.813 -66.193  1.00 31.49      A    C
ATOM  19087  O   TRP H 350    -31.569 -76.062 -66.940  1.00 31.76      A    O
ATOM  19088  CB  TRP H 350    -29.915 -75.476 -64.353  1.00 30.97      A    C
ATOM  19089  CG  TRP H 350    -30.679 -76.173 -63.260  1.00 30.50      A    C
ATOM  19090  CD1 TRP H 350    -30.236 -77.196 -62.461  1.00 30.20      A    C
ATOM  19091  CD2 TRP H 350    -32.014 -75.892 -62.848  1.00 30.16      A    C
ATOM  19092  CE2 TRP H 350    -32.321 -76.779 -61.793  1.00 29.91      A    C
ATOM  19093  CE3 TRP H 350    -32.989 -74.982 -63.276  1.00 30.19      A    C
ATOM  19094  NE1 TRP H 350    -31.217 -77.562 -61.578  1.00 29.95      A    N
ATOM  19095  CZ2 TRP H 350    -33.562 -76.781 -61.155  1.00 29.64      A    C
ATOM  19096  CZ3 TRP H 350    -34.223 -74.987 -62.644  1.00 30.03      A    C
ATOM  19097  CH2 TRP H 350    -34.498 -75.883 -61.594  1.00 29.66      A    C
ATOM  19098  N   HIS H 351    -31.333 -78.042 -65.858  1.00 31.78      A    N
ATOM  19099  CA  HIS H 351    -32.587 -78.639 -66.334  1.00 32.38      A    C
ATOM  19100  C   HIS H 351    -32.768 -78.047 -67.846  1.00 32.93      A    C
ATOM  19101  O   HIS H 351    -33.840 -78.102 -68.330  1.00 33.18      A    O
ATOM  19102  CB  HIS H 351    -33.803 -78.096 -65.562  1.00 32.37      A    C
ATOM  19103  CG  HIS H 351    -34.041 -78.775 -64.245  1.00 32.41      A    C
ATOM  19104  CD2 HIS H 351    -33.225 -79.524 -63.464  1.00 32.04      A    C
ATOM  19105  ND1 HIS H 351    -35.255 -78.726 -63.591  1.00 32.56      A    N
ATOM  19106  CE1 HIS H 351    -35.173 -79.409 -62.462  1.00 32.27      A    C
ATOM  19107  NE2 HIS H 351    -33.951 -79.901 -62.360  1.00 31.83      A    N
ATOM  19108  N   THR H 352    -31.695 -78.796 -68.573  1.00 33.37      A    N
ATOM  19109  CA  THR H 352    -31.675 -78.774 -70.036  1.00 33.94      A    C
ATOM  19110  C   THR H 352    -30.741 -79.877 -70.561  1.00 34.20      A    C
```

FIGURE 1 (cont'd)

```
ATOM  19111  O    THR H 352     -29.801 -80.254 -69.864  1.00 33.98      A  O
ATOM  19112  CB   THR H 352     -31.282 -77.363 -70.606  1.00 34.06      A  C
ATOM  19113  CG2  THR H 352     -30.248 -76.687 -69.747  1.00 33.57      A  C
ATOM  19114  OG1  THR H 352     -30.740 -77.492 -71.928  1.00 34.79      A  O
ATOM  19115  N    PRO H 353     -31.010 -80.409 -71.779  1.00 34.72      A  N
ATOM  19116  CA   PRO H 353     -30.147 -81.380 -72.458  1.00 34.79      A  C
ATOM  19117  C    PRO H 353     -28.676 -80.985 -72.442  1.00 34.61      A  C
ATOM  19118  O    PRO H 353     -27.817 -81.852 -72.601  1.00 34.61      A  O
ATOM  19119  CB   PRO H 353     -30.638 -81.324 -73.901  1.00 35.24      A  C
ATOM  19120  CG   PRO H 353     -32.062 -80.961 -73.801  1.00 35.54      A  C
ATOM  19121  CD   PRO H 353     -32.212 -80.104 -72.582  1.00 35.02      A  C
ATOM  19122  N    ALA H 354     -28.402 -79.688 -72.266  1.00 34.34      A  N
ATOM  19123  CA   ALA H 354     -27.033 -79.152 -72.226  1.00 34.06      A  C
ATOM  19124  C    ALA H 354     -26.207 -79.661 -71.042  1.00 33.79      A  C
ATOM  19125  O    ALA H 354     -24.981 -79.703 -71.122  1.00 33.74      A  O
ATOM  19126  CB   ALA H 354     -27.061 -77.639 -72.235  1.00 34.07      A  C
ATOM  19127  N    ASP H 355     -26.880 -80.045 -69.956  1.00 33.56      A  N
ATOM  19128  CA   ASP H 355     -26.215 -80.546 -68.748  1.00 33.33      A  C
ATOM  19129  C    ASP H 355     -25.627 -81.937 -68.984  1.00 33.50      A  C
ATOM  19130  O    ASP H 355     -26.175 -82.948 -68.526  1.00 33.39      A  O
ATOM  19131  CB   ASP H 355     -27.182 -80.564 -67.553  1.00 33.04      A  C
ATOM  19132  CG   ASP H 355     -26.479 -80.803 -66.221  1.00 32.52      A  C
ATOM  19133  OD1  ASP H 355     -25.246 -81.014 -66.211  1.00 32.67      A  O
ATOM  19134  OD2  ASP H 355     -27.171 -80.774 -65.179  1.00 31.67      A  O
ATOM  19135  N    THR H 356     -24.510 -81.977 -69.704  1.00 33.77      A  N
ATOM  19136  CA   THR H 356     -23.807 -83.224 -69.977  1.00 33.97      A  C
ATOM  19137  C    THR H 356     -22.347 -83.051 -69.614  1.00 34.42      A  C
ATOM  19138  O    THR H 356     -21.927 -81.951 -69.227  1.00 34.35      A  O
ATOM  19139  CB   THR H 356     -23.920 -83.621 -71.453  1.00 33.39      A  C
ATOM  19140  OG1  THR H 356     -23.408 -82.560 -72.269  1.00 33.39      A  O
ATOM  19141  N    GLU H 357     -21.583 -84.137 -69.744  1.00 35.03      A  N
ATOM  19142  CA   GLU H 357     -20.145 -84.145 -69.446  1.00 35.57      A  C
ATOM  19143  C    GLU H 357     -19.392 -82.998 -70.142  1.00 35.92      A  C
ATOM  19144  O    GLU H 357     -18.552 -82.316 -69.527  1.00 35.83      A  O
ATOM  19145  CB   GLU H 357     -19.532 -85.502 -69.826  1.00 35.75      A  C
ATOM  19146  CG   GLU H 357     -18.020 -85.618 -69.594  1.00 36.36      A  C
ATOM  19147  CD   GLU H 357     -17.493 -87.018 -69.792  1.00 37.39      A  C
ATOM  19148  OE1  GLU H 357     -18.280 -87.931 -70.122  1.00 38.14      A  O
ATOM  19149  OE2  GLU H 357     -16.281 -87.206 -69.610  1.00 37.73      A  O
ATOM  19150  N    VAL H 358     -19.730 -82.786 -71.417  1.00 36.42      A  N
ATOM  19151  CA   VAL H 358     -19.099 -81.770 -72.266  1.00 36.84      A  C
ATOM  19152  C    VAL H 358     -19.067 -80.362 -71.670  1.00 36.65      A  C
ATOM  19153  O    VAL H 358     -18.211 -79.556 -72.037  1.00 36.89      A  O
ATOM  19154  CB   VAL H 358     -19.790 -81.695 -73.650  1.00 37.19      A  C
ATOM  19155  CG1  VAL H 358     -18.793 -81.995 -74.764  1.00 37.98      A  C
ATOM  19156  N    ASN H 359     -19.992 -80.074 -70.756  1.00 36.25      A  N
ATOM  19157  CA   ASN H 359     -20.168 -78.710 -70.238  1.00 35.94      A  C
ATOM  19158  C    ASN H 359     -19.711 -78.468 -68.790  1.00 35.35      A  C
ATOM  19159  O    ASN H 359     -19.854 -77.362 -68.251  1.00 35.21      A  O
ATOM  19160  CB   ASN H 359     -21.618 -78.250 -70.441  1.00 36.14      A  C
ATOM  19161  CG   ASN H 359     -21.981 -78.057 -71.910  1.00 37.12      A  C
ATOM  19162  ND2  ASN H 359     -20.990 -78.145 -72.803  1.00 38.08      A  N
ATOM  19163  OD1  ASN H 359     -23.147 -77.823 -72.234  1.00 37.72      A  O
ATOM  19164  N    LEU H 360     -19.156 -79.507 -68.176  1.00 34.82      A  N
ATOM  19165  CA   LEU H 360     -18.530 -79.383 -66.871  1.00 34.35      A  C
ATOM  19166  C    LEU H 360     -17.166 -78.698 -66.997  1.00 34.41      A  C
ATOM  19167  O    LEU H 360     -16.552 -78.744 -68.057  1.00 34.90      A  O
ATOM  19168  CB   LEU H 360     -18.356 -80.763 -66.246  1.00 34.03      A  C
ATOM  19169  CG   LEU H 360     -19.597 -81.649 -66.176  1.00 33.48      A  C
ATOM  19170  CD1  LEU H 360     -19.213 -82.988 -65.597  1.00 32.93      A  C
ATOM  19171  CD2  LEU H 360     -20.701 -81.006 -65.351  1.00 33.10      A  C
ATOM  19172  N    HIS H 361     -16.706 -78.054 -65.925  1.00 34.11      A  N
ATOM  19173  CA   HIS H 361     -15.359 -77.491 -65.870  1.00 33.91      A  C
ATOM  19174  C    HIS H 361     -14.509 -78.423 -65.011  1.00 34.22      A  C
ATOM  19175  O    HIS H 361     -14.469 -78.280 -63.788  1.00 34.04      A  O
```

FIGURE 1 (cont'd)

```
ATOM  19176  CB   HIS H 361     -15.379 -76.084 -65.273  1.00 33.53       A  C
ATOM  19177  CG   HIS H 361     -14.231 -75.234 -65.698  1.00 32.70       A  C
ATOM  19178  CD2  HIS H 361     -14.153 -74.236 -66.609  1.00 32.71       A  C
ATOM  19179  ND1  HIS H 361     -12.971 -75.365 -65.159  1.00 31.56       A  N
ATOM  19180  CE1  HIS H 361     -12.161 -74.488 -65.727  1.00 31.63       A  C
ATOM  19181  NE2  HIS H 361     -12.855 -73.785 -66.604  1.00 32.88       A  N
ATOM  19182  N    PRO H 362     -13.837 -79.401 -65.646  1.00 34.70       A  N
ATOM  19183  CA   PRO H 362     -13.070 -80.398 -64.902  1.00 34.91       A  C
ATOM  19184  C    PRO H 362     -12.190 -79.816 -63.786  1.00 34.89       A  C
ATOM  19185  O    PRO H 362     -12.223 -80.355 -62.674  1.00 34.76       A  O
ATOM  19186  CB   PRO H 362     -12.227 -81.073 -65.989  1.00 35.21       A  C
ATOM  19187  CG   PRO H 362     -13.069 -80.961 -67.202  1.00 35.33       A  C
ATOM  19188  CD   PRO H 362     -13.732 -79.617 -67.100  1.00 35.01       A  C
ATOM  19189  N    PRO H 363     -11.426 -78.723 -64.063  1.00 34.99       A  N
ATOM  19190  CA   PRO H 363     -10.690 -78.085 -62.966  1.00 35.02       A  C
ATOM  19191  C    PRO H 363     -11.586 -77.787 -61.747  1.00 34.68       A  C
ATOM  19192  O    PRO H 363     -11.314 -78.270 -60.632  1.00 34.59       A  O
ATOM  19193  CB   PRO H 363     -10.177 -76.790 -63.605  1.00 35.27       A  C
ATOM  19194  CG   PRO H 363      -9.965 -77.154 -65.006  1.00 35.68       A  C
ATOM  19195  CD   PRO H 363     -11.090 -78.095 -65.355  1.00 34.92       A  C
ATOM  19196  N    THR H 364     -12.663 -77.033 -61.973  1.00 34.35       A  N
ATOM  19197  CA   THR H 364     -13.591 -76.672 -60.902  1.00 33.98       A  C
ATOM  19198  C    THR H 364     -13.995 -77.917 -60.121  1.00 33.86       A  C
ATOM  19199  O    THR H 364     -14.060 -77.885 -58.897  1.00 33.69       A  O
ATOM  19200  CB   THR H 364     -14.848 -75.913 -61.435  1.00 33.87       A  C
ATOM  19201  CG2  THR H 364     -15.735 -75.479 -60.283  1.00 33.50       A  C
ATOM  19202  OG1  THR H 364     -14.453 -74.753 -62.189  1.00 34.08       A  O
ATOM  19203  N    VAL H 365     -14.231 -79.015 -60.837  1.00 33.99       A  N
ATOM  19204  CA   VAL H 365     -14.619 -80.280 -60.204  1.00 34.14       A  C
ATOM  19205  C    VAL H 365     -13.566 -80.738 -59.189  1.00 34.31       A  C
ATOM  19206  O    VAL H 365     -13.873 -80.987 -58.013  1.00 34.10       A  O
ATOM  19207  CB   VAL H 365     -14.892 -81.406 -61.249  1.00 34.14       A  C
ATOM  19208  CG1  VAL H 365     -16.138 -81.092 -62.065  1.00 34.03       A  C
ATOM  19209  CG2  VAL H 365     -15.029 -82.777 -60.553  1.00 33.96       A  C
ATOM  19210  N    HIS H 366     -12.326 -80.818 -59.654  1.00 34.70       A  N
ATOM  19211  CA   HIS H 366     -11.255 -81.349 -58.844  1.00 35.16       A  C
ATOM  19212  C    HIS H 366     -10.964 -80.455 -57.668  1.00 35.35       A  C
ATOM  19213  O    HIS H 366     -10.787 -80.948 -56.553  1.00 35.47       A  O
ATOM  19214  CB   HIS H 366     -10.033 -81.624 -59.706  1.00 35.40       A  C
ATOM  19215  CG   HIS H 366     -10.300 -82.651 -60.761  1.00 35.52       A  C
ATOM  19216  CD2  HIS H 366     -10.477 -82.535 -62.098  1.00 35.95       A  C
ATOM  19217  ND1  HIS H 366     -10.518 -83.980 -60.461  1.00 35.52       A  N
ATOM  19218  CE1  HIS H 366     -10.761 -84.646 -61.575  1.00 35.54       A  C
ATOM  19219  NE2  HIS H 366     -10.755 -83.791 -62.582  1.00 36.27       A  N
ATOM  19220  N    ASN H 367     -10.965 -79.146 -57.909  1.00 35.39       A  N
ATOM  19221  CA   ASN H 367     -10.861 -78.173 -56.823  1.00 35.45       A  C
ATOM  19222  C    ASN H 367     -11.828 -78.497 -55.689  1.00 35.26       A  C
ATOM  19223  O    ASN H 367     -11.428 -78.578 -54.519  1.00 35.36       A  O
ATOM  19224  CB   ASN H 367     -11.120 -76.759 -57.331  1.00 35.51       A  C
ATOM  19225  CG   ASN H 367      -9.976 -76.219 -58.136  1.00 36.15       A  C
ATOM  19226  ND2  ASN H 367     -10.049 -74.938 -58.469  1.00 36.26       A  N
ATOM  19227  OD1  ASN H 367      -9.029 -76.940 -58.461  1.00 37.08       A  O
ATOM  19228  N    LEU H 368     -13.093 -78.711 -56.054  1.00 34.97       A  N
ATOM  19229  CA   LEU H 368     -14.148 -78.961 -55.078  1.00 34.75       A  C
ATOM  19230  C    LEU H 368     -13.848 -80.204 -54.256  1.00 34.93       A  C
ATOM  19231  O    LEU H 368     -14.172 -80.277 -53.058  1.00 35.01       A  O
ATOM  19232  CB   LEU H 368     -15.513 -79.085 -55.759  1.00 34.37       A  C
ATOM  19233  CG   LEU H 368     -16.133 -77.794 -56.281  1.00 33.76       A  C
ATOM  19234  CD1  LEU H 368     -17.354 -78.147 -57.091  1.00 33.50       A  C
ATOM  19235  CD2  LEU H 368     -16.474 -76.811 -55.157  1.00 32.87       A  C
ATOM  19236  N    ALA H 369     -13.210 -81.172 -54.909  1.00 34.21       A  N
ATOM  19237  CA   ALA H 369     -12.881 -82.433 -54.265  1.00 33.58       A  C
ATOM  19238  C    ALA H 369     -11.719 -82.247 -53.293  1.00 34.52       A  C
ATOM  19239  O    ALA H 369     -11.708 -82.813 -52.200  1.00 35.71       A  O
ATOM  19240  CB   ALA H 369     -12.568 -83.502 -55.309  1.00 24.56       A  C
```

FIGURE 1 (cont'd)

```
ATOM  19241  N    ARG H 370   -10.749 -81.436 -53.691  1.00 35.16      A  N
ATOM  19242  CA   ARG H 370    -9.636 -81.127 -52.815  1.00 34.83      A  C
ATOM  19243  C    ARG H 370   -10.175 -80.439 -51.574  1.00 34.22      A  C
ATOM  19244  O    ARG H 370    -9.844 -80.834 -50.455  1.00 34.12      A  O
ATOM  19245  CB   ARG H 370    -8.575 -80.294 -53.544  1.00 35.10      A  C
ATOM  19246  CG   ARG H 370    -7.881 -81.075 -54.675  1.00 35.41      A  C
ATOM  19247  CD   ARG H 370    -6.729 -80.313 -55.316  1.00 35.75      A  C
ATOM  19248  NE   ARG H 370    -6.022 -81.116 -56.322  1.00 35.86      A  N
ATOM  19249  CZ   ARG H 370    -4.754 -80.916 -56.672  1.00 36.01      A  C
ATOM  19250  N    ILE H 371   -11.055 -79.460 -51.781  1.00 33.47      A  N
ATOM  19251  CA   ILE H 371   -11.663 -78.720 -50.677  1.00 32.86      A  C
ATOM  19252  C    ILE H 371   -12.478 -79.624 -49.776  1.00 32.77      A  C
ATOM  19253  O    ILE H 371   -12.355 -79.545 -48.560  1.00 32.87      A  O
ATOM  19254  CB   ILE H 371   -12.530 -77.555 -51.164  1.00 32.53      A  C
ATOM  19255  CG1  ILE H 371   -11.655 -76.481 -51.811  1.00 32.50      A  C
ATOM  19256  CG2  ILE H 371   -13.299 -76.959 -50.007  1.00 32.04      A  C
ATOM  19257  CD1  ILE H 371   -12.422 -75.415 -52.574  1.00 32.23      A  C
ATOM  19258  N    LEU H 372   -13.290 -80.490 -50.375  1.00 32.58      A  N
ATOM  19259  CA   LEU H 372   -14.098 -81.454 -49.614  1.00 32.47      A  C
ATOM  19260  C    LEU H 372   -13.279 -82.481 -48.814  1.00 32.78      A  C
ATOM  19261  O    LEU H 372   -13.564 -82.743 -47.639  1.00 32.69      A  O
ATOM  19262  CB   LEU H 372   -15.071 -82.178 -50.543  1.00 32.11      A  C
ATOM  19263  CG   LEU H 372   -16.530 -81.720 -50.603  1.00 31.38      A  C
ATOM  19264  CD1  LEU H 372   -16.801 -80.338 -49.975  1.00 30.82      A  C
ATOM  19265  CD2  LEU H 372   -17.019 -81.798 -52.042  1.00 30.92      A  C
ATOM  19266  N    ALA H 373   -12.264 -83.055 -49.463  1.00 33.21      A  N
ATOM  19267  CA   ALA H 373   -11.393 -84.061 -48.847  1.00 33.59      A  C
ATOM  19268  C    ALA H 373   -10.702 -83.515 -47.605  1.00 33.88      A  C
ATOM  19269  O    ALA H 373   -10.616 -84.205 -46.585  1.00 34.03      A  O
ATOM  19270  CB   ALA H 373   -10.366 -84.559 -49.848  1.00 33.70      A  C
ATOM  19271  N    VAL H 374   -10.220 -82.278 -47.697  1.00 34.01      A  N
ATOM  19272  CA   VAL H 374    -9.624 -81.615 -46.558  1.00 34.26      A  C
ATOM  19273  C    VAL H 374   -10.668 -81.437 -45.476  1.00 34.19      A  C
ATOM  19274  O    VAL H 374   -10.431 -81.812 -44.334  1.00 34.47      A  O
ATOM  19275  CB   VAL H 374    -9.031 -80.262 -46.940  1.00 34.36      A  C
ATOM  19276  CG1  VAL H 374    -8.693 -79.439 -45.701  1.00 34.60      A  C
ATOM  19277  CG2  VAL H 374    -7.795 -80.467 -47.773  1.00 34.83      A  C
ATOM  19278  N    PHE H 375   -11.821 -80.879 -45.842  1.00 33.93      A  N
ATOM  19279  CA   PHE H 375   -12.923 -80.673 -44.902  1.00 33.77      A  C
ATOM  19280  C    PHE H 375   -13.311 -81.972 -44.207  1.00 34.08      A  C
ATOM  19281  O    PHE H 375   -13.421 -82.013 -42.984  1.00 34.19      A  O
ATOM  19282  CB   PHE H 375   -14.149 -80.084 -45.606  1.00 33.36      A  C
ATOM  19283  CG   PHE H 375   -15.342 -79.882 -44.702  1.00 32.64      A  C
ATOM  19284  CD1  PHE H 375   -15.680 -78.605 -44.264  1.00 32.47      A  C
ATOM  19285  CD2  PHE H 375   -16.130 -80.963 -44.296  1.00 32.09      A  C
ATOM  19286  CE1  PHE H 375   -16.777 -78.399 -43.432  1.00 32.38      A  C
ATOM  19287  CE2  PHE H 375   -17.218 -80.765 -43.465  1.00 32.25      A  C
ATOM  19288  CZ   PHE H 375   -17.545 -79.472 -43.032  1.00 32.33      A  C
ATOM  19289  N    LEU H 376   -13.522 -83.028 -44.985  1.00 34.42      A  N
ATOM  19290  CA   LEU H 376   -13.912 -84.315 -44.426  1.00 34.89      A  C
ATOM  19291  C    LEU H 376   -12.884 -84.767 -43.388  1.00 35.69      A  C
ATOM  19292  O    LEU H 376   -13.250 -85.215 -42.291  1.00 35.79      A  O
ATOM  19293  CB   LEU H 376   -14.058 -85.359 -45.537  1.00 34.58      A  C
ATOM  19294  CG   LEU H 376   -15.201 -86.376 -45.403  1.00 33.85      A  C
ATOM  19295  N    ALA H 377   -11.604 -84.614 -43.740  1.00 36.60      A  N
ATOM  19296  CA   ALA H 377   -10.479 -84.971 -42.863  1.00 37.46      A  C
ATOM  19297  C    ALA H 377   -10.410 -84.119 -41.599  1.00 37.90      A  C
ATOM  19298  O    ALA H 377   -10.227 -84.645 -40.512  1.00 38.19      A  O
ATOM  19299  CB   ALA H 377    -9.161 -84.900 -43.627  1.00 37.62      A  C
ATOM  19300  N    GLU H 378   -10.554 -82.806 -41.750  1.00 38.20      A  N
ATOM  19301  CA   GLU H 378   -10.553 -81.904 -40.604  1.00 38.63      A  C
ATOM  19302  C    GLU H 378   -11.741 -82.162 -39.683  1.00 38.60      A  C
ATOM  19303  O    GLU H 378   -11.555 -82.295 -38.477  1.00 38.93      A  O
ATOM  19304  CB   GLU H 378   -10.476 -80.426 -41.031  1.00 38.72      A  C
ATOM  19305  CG   GLU H 378    -9.070 -79.988 -41.492  1.00 39.90      A  C
```

FIGURE 1 (cont'd)

```
ATOM  19306  CD   GLU H 378      -8.921  -78.490  -41.738  1.00 41.29      A  C
ATOM  19307  OE1  GLU H 378      -9.862  -77.727  -41.425  1.00 41.81      A  O
ATOM  19308  OE2  GLU H 378      -7.853  -78.073  -42.248  1.00 41.92      A  O
ATOM  19309  N    TYR H 379     -12.945  -82.271  -40.250  1.00 38.44      A  N
ATOM  19310  CA   TYR H 379     -14.171  -82.496  -39.460  1.00 38.43      A  C
ATOM  19311  C    TYR H 379     -14.093  -83.779  -38.628  1.00 38.97      A  C
ATOM  19312  O    TYR H 379     -14.446  -83.801  -37.450  1.00 39.09      A  O
ATOM  19313  CB   TYR H 379     -15.429  -82.504  -40.354  1.00 37.84      A  C
ATOM  19314  CG   TYR H 379     -16.748  -82.521  -39.586  1.00 37.05      A  C
ATOM  19315  CD1  TYR H 379     -17.515  -81.364  -39.449  1.00 36.33      A  C
ATOM  19316  CD2  TYR H 379     -17.230  -83.701  -38.997  1.00 36.83      A  C
ATOM  19317  CE1  TYR H 379     -18.731  -81.378  -38.740  1.00 36.17      A  C
ATOM  19318  CE2  TYR H 379     -18.438  -83.725  -38.280  1.00 36.56      A  C
ATOM  19319  CZ   TYR H 379     -19.185  -82.562  -38.157  1.00 36.22      A  C
ATOM  19320  OH   TYR H 379     -20.374  -82.588  -37.456  1.00 35.89      A  O
ATOM  19321  N    LEU H 380     -13.622  -84.844  -39.251  1.00 39.64      A  N
ATOM  19322  CA   LEU H 380     -13.529  -86.120  -38.580  1.00 40.53      A  C
ATOM  19323  C    LEU H 380     -12.177  -86.341  -37.881  1.00 41.58      A  C
ATOM  19324  O    LEU H 380     -11.873  -87.466  -37.457  1.00 41.91      A  O
ATOM  19325  CB   LEU H 380     -13.816  -87.239  -39.585  1.00 40.19      A  C
ATOM  19326  CG   LEU H 380     -15.180  -87.943  -39.590  1.00 39.77      A  C
ATOM  19327  CD1  LEU H 380     -16.338  -87.028  -39.209  1.00 39.38      A  C
ATOM  19328  CD2  LEU H 380     -15.418  -88.590  -40.945  1.00 39.50      A  C
ATOM  19329  N    GLY H 381     -11.390  -85.270  -37.729  1.00 43.42      A  N
ATOM  19330  CA   GLY H 381      -9.983  -85.375  -37.297  1.00 45.38      A  C
ATOM  19331  C    GLY H 381      -9.322  -86.645  -37.836  1.00 46.70      A  C
ATOM  19332  O    GLY H 381      -9.091  -87.588  -37.070  1.00 47.13      A  O
ATOM  19333  N    LEU H 382      -9.038  -86.687  -39.147  1.00 47.47      A  N
ATOM  19334  CA   LEU H 382      -8.592  -87.930  -39.816  1.00 48.04      A  C
ATOM  19335  C    LEU H 382      -7.133  -87.946  -40.276  1.00 48.25      A  C
ATOM  19336  O    LEU H 382      -6.642  -88.984  -40.746  1.00 48.28      A  O
ATOM  19337  CB   LEU H 382      -9.492  -88.267  -41.009  1.00 48.07      A  C
ATOM  19338  CG   LEU H 382     -10.883  -88.884  -40.810  1.00 48.61      A  C
ATOM  19339  CD1  LEU H 382     -11.347  -89.503  -42.130  1.00 48.79      A  C
ATOM  19340  CD2  LEU H 382     -10.957  -89.918  -39.676  1.00 48.64      A  C
ATOM  19341  OXT  LEU H 382      -6.425  -86.936  -40.199  1.00 48.44      A  O
TER   19342       LEU H 382
ATOM  19343  N    SER I  75      -2.363  -33.678  -44.079  1.00 55.86      A  N
ATOM  19344  CA   SER I  75      -3.118  -34.851  -44.626  1.00 56.24      A  C
ATOM  19345  C    SER I  75      -2.555  -36.214  -44.156  1.00 57.54      A  C
ATOM  19346  O    SER I  75      -1.473  -36.647  -44.576  1.00 57.78      A  O
ATOM  19347  CB   SER I  75      -3.286  -34.758  -46.173  1.00 55.42      A  C
ATOM  19348  OG   SER I  75      -2.137  -34.236  -46.850  1.00 54.21      A  O
ATOM  19349  N    LEU I  76      -3.313  -36.873  -43.280  1.00 58.77      A  N
ATOM  19350  CA   LEU I  76      -2.943  -38.161  -42.678  1.00 59.49      A  C
ATOM  19351  C    LEU I  76      -4.197  -38.706  -41.965  1.00 58.13      A  C
ATOM  19352  O    LEU I  76      -4.651  -38.096  -40.988  1.00 58.53      A  O
ATOM  19353  CB   LEU I  76      -1.788  -37.934  -41.692  1.00 60.22      A  C
ATOM  19354  CG   LEU I  76      -0.938  -39.033  -41.052  1.00 61.62      A  C
ATOM  19355  CD1  LEU I  76       0.532  -38.694  -41.153  1.00 61.37      A  C
ATOM  19356  CD2  LEU I  76      -1.309  -39.206  -39.603  1.00 62.16      A  C
ATOM  19357  N    PRO I  77      -4.766  -39.850  -42.437  1.00 55.05      A  N
ATOM  19358  CA   PRO I  77      -6.134  -40.160  -41.974  1.00 55.61      A  C
ATOM  19359  C    PRO I  77      -6.241  -40.627  -40.507  1.00 55.78      A  C
ATOM  19360  O    PRO I  77      -5.315  -41.254  -39.984  1.00 55.65      A  O
ATOM  19361  CB   PRO I  77      -6.587  -41.262  -42.939  1.00 56.11      A  C
ATOM  19362  CG   PRO I  77      -5.318  -41.970  -43.313  1.00 55.93      A  C
ATOM  19363  CD   PRO I  77      -4.189  -40.963  -43.226  1.00 55.04      A  C
ATOM  19364  N    GLU I  78      -7.380  -40.326  -39.878  1.00 55.93      A  N
ATOM  19365  CA   GLU I  78      -7.619  -40.583  -38.449  1.00 55.80      A  C
ATOM  19366  C    GLU I  78      -7.131  -41.937  -37.946  1.00 57.05      A  C
ATOM  19367  O    GLU I  78      -6.495  -42.019  -36.892  1.00 57.28      A  O
ATOM  19368  CB   GLU I  78      -9.104  -40.399  -38.099  1.00 53.83      A  C
ATOM  19369  CG   GLU I  78      -9.447  -39.047  -37.473  1.00 51.32      A  C
ATOM  19370  N    ALA I  79      -7.434  -42.988  -38.702  1.00 58.30      A  N
```

FIGURE 1 (cont'd)

```
ATOM  19371  CA   ALA I  79     -7.061 -44.355 -38.341  1.00 58.95      A  C
ATOM  19372  C    ALA I  79     -5.551 -44.522 -38.129  1.00 58.71      A  C
ATOM  19373  O    ALA I  79     -5.124 -45.047 -37.102  1.00 58.85      A  O
ATOM  19374  CB   ALA I  79     -7.573 -45.341 -39.393  1.00 59.75      A  C
ATOM  19375  N    ARG I  80     -4.749 -44.071 -39.092  1.00 57.97      A  N
ATOM  19376  CA   ARG I  80     -3.296 -44.159 -38.974  1.00 57.00      A  C
ATOM  19377  C    ARG I  80     -2.767 -43.157 -37.939  1.00 56.76      A  C
ATOM  19378  O    ARG I  80     -1.837 -43.468 -37.195  1.00 56.77      A  O
ATOM  19379  CB   ARG I  80     -2.616 -43.960 -40.334  1.00 55.29      A  C
ATOM  19380  N    LEU I  81     -3.372 -41.968 -37.887  1.00 56.46      A  N
ATOM  19381  CA   LEU I  81     -2.960 -40.914 -36.956  1.00 55.85      A  C
ATOM  19382  C    LEU I  81     -3.056 -41.394 -35.526  1.00 55.88      A  C
ATOM  19383  O    LEU I  81     -2.084 -41.314 -34.785  1.00 55.53      A  O
ATOM  19384  CB   LEU I  81     -3.802 -39.649 -37.158  1.00 55.68      A  C
ATOM  19385  CG   LEU I  81     -3.426 -38.352 -36.434  1.00 54.91      A  C
ATOM  19386  CD1  LEU I  81     -3.724 -37.131 -37.308  1.00 54.70      A  C
ATOM  19387  CD2  LEU I  81     -4.149 -38.242 -35.101  1.00 54.78      A  C
ATOM  19388  N    ARG I  82     -4.226 -41.906 -35.153  1.00 56.33      A  N
ATOM  19389  CA   ARG I  82     -4.468 -42.402 -33.795  1.00 56.81      A  C
ATOM  19390  C    ARG I  82     -3.596 -43.627 -33.464  1.00 56.72      A  C
ATOM  19391  O    ARG I  82     -3.220 -43.854 -32.304  1.00 56.67      A  O
ATOM  19392  CB   ARG I  82     -5.962 -42.699 -33.579  1.00 57.37      A  C
ATOM  19393  CG   ARG I  82     -6.372 -42.870 -32.110  1.00 58.29      A  C
ATOM  19394  CD   ARG I  82     -7.881 -42.813 -31.916  1.00 59.64      A  C
ATOM  19395  NE   ARG I  82     -8.348 -41.468 -31.585  1.00 59.76      A  N
ATOM  19396  CZ   ARG I  82     -8.780 -40.570 -32.471  1.00 59.81      A  C
ATOM  19397  NH1  ARG I  82     -8.809 -40.856 -33.767  1.00 59.98      A  N
ATOM  19398  NH2  ARG I  82     -9.185 -39.374 -32.056  1.00 59.58      A  N
ATOM  19399  N    ARG I  83     -3.273 -44.398 -34.498  1.00 56.48      A  N
ATOM  19400  CA   ARG I  83     -2.360 -45.540 -34.390  1.00 55.94      A  C
ATOM  19401  C    ARG I  83     -0.907 -45.083 -34.140  1.00 55.54      A  C
ATOM  19402  O    ARG I  83     -0.185 -45.682 -33.333  1.00 55.67      A  O
ATOM  19403  CB   ARG I  83     -2.497 -46.398 -35.659  1.00 54.95      A  C
ATOM  19404  CG   ARG I  83     -1.297 -47.220 -36.090  1.00 54.48      A  C
ATOM  19405  CD   ARG I  83     -1.487 -47.605 -37.551  1.00 54.58      A  C
ATOM  19406  NE   ARG I  83     -0.323 -48.256 -38.138  1.00 54.05      A  N
ATOM  19407  N    VAL I  84     -0.510 -44.010 -34.832  1.00 54.76      A  N
ATOM  19408  CA   VAL I  84      0.823 -43.411 -34.713  1.00 53.65      A  C
ATOM  19409  C    VAL I  84      0.991 -42.706 -33.369  1.00 52.99      A  C
ATOM  19410  O    VAL I  84      1.922 -43.025 -32.626  1.00 52.80      A  O
ATOM  19411  CB   VAL I  84      1.126 -42.444 -35.902  1.00 53.52      A  C
ATOM  19412  CG1  VAL I  84      1.403 -43.238 -37.165  1.00 53.54      A  C
ATOM  19413  CG2  VAL I  84      2.301 -41.509 -35.589  1.00 52.80      A  C
ATOM  19414  N    VAL I  85      0.094 -41.762 -33.066  1.00 52.18      A  N
ATOM  19415  CA   VAL I  85      0.092 -41.077 -31.771  1.00 51.39      A  C
ATOM  19416  C    VAL I  85      0.105 -42.103 -30.624  1.00 51.80      A  C
ATOM  19417  O    VAL I  85      0.661 -41.848 -29.542  1.00 51.96      A  O
ATOM  19418  CB   VAL I  85     -1.113 -40.117 -31.620  1.00 49.80      A  C
ATOM  19419  N    GLY I  86     -0.486 -43.269 -30.887  1.00 52.10      A  N
ATOM  19420  CA   GLY I  86     -0.507 -44.370 -29.929  1.00 52.05      A  C
ATOM  19421  C    GLY I  86      0.827 -45.075 -29.765  1.00 51.66      A  C
ATOM  19422  O    GLY I  86      1.067 -45.716 -28.740  1.00 51.87      A  O
ATOM  19423  N    GLN I  87      1.691 -44.958 -30.777  1.00 51.02      A  N
ATOM  19424  CA   GLN I  87      3.012 -45.615 -30.777  1.00 50.27      A  C
ATOM  19425  C    GLN I  87      4.050 -44.934 -29.859  1.00 49.63      A  C
ATOM  19426  O    GLN I  87      5.051 -45.564 -29.482  1.00 49.55      A  O
ATOM  19427  N    LEU I  88      3.811 -43.659 -29.512  1.00 48.79      A  N
ATOM  19428  CA   LEU I  88      4.639 -42.927 -28.539  1.00 48.06      A  C
ATOM  19429  C    LEU I  88      4.382 -43.462 -27.133  1.00 48.43      A  C
ATOM  19430  O    LEU I  88      3.233 -43.493 -26.693  1.00 48.68      A  O
ATOM  19431  CB   LEU I  88      4.321 -41.428 -28.567  1.00 47.33      A  C
ATOM  19432  CG   LEU I  88      4.666 -40.597 -29.804  1.00 45.97      A  C
ATOM  19433  N    ASP I  89      5.433 -43.896 -26.436  1.00 48.76      A  N
ATOM  19434  CA   ASP I  89      5.298 -44.296 -25.029  1.00 49.15      A  C
ATOM  19435  C    ASP I  89      5.756 -43.171 -24.088  1.00 49.23      A  C
```

FIGURE 1 (cont'd)

```
ATOM  19436  O    ASP I  89      6.960 -42.894 -23.982  1.00 49.00      A    O
ATOM  19437  CB   ASP I  89      6.042 -45.602 -24.722  1.00 49.30      A    C
ATOM  19438  CG   ASP I  89      5.873 -46.036 -23.271  1.00 49.45      A    C
ATOM  19439  OD1  ASP I  89      4.844 -45.666 -22.660  1.00 49.11      A    O
ATOM  19440  OD2  ASP I  89      6.762 -46.729 -22.736  1.00 49.02      A    O
ATOM  19441  N    PRO I  90      4.790 -42.516 -23.407  1.00 49.47      A    N
ATOM  19442  CA   PRO I  90      5.081 -41.362 -22.546  1.00 49.38      A    C
ATOM  19443  C    PRO I  90      6.103 -41.636 -21.436  1.00 49.31      A    C
ATOM  19444  O    PRO I  90      6.990 -40.802 -21.218  1.00 49.01      A    O
ATOM  19445  CB   PRO I  90      3.702 -41.012 -21.956  1.00 49.52      A    C
ATOM  19446  CG   PRO I  90      2.726 -41.495 -22.996  1.00 49.76      A    C
ATOM  19447  CD   PRO I  90      3.338 -42.784 -23.477  1.00 49.81      A    C
ATOM  19448  N    GLN I  91      5.982 -42.785 -20.759  1.00 49.50      A    N
ATOM  19449  CA   GLN I  91      6.934 -43.154 -19.694  1.00 49.59      A    C
ATOM  19450  C    GLN I  91      8.323 -43.559 -20.249  1.00 49.01      A    C
ATOM  19451  O    GLN I  91      9.341 -43.389 -19.571  1.00 49.05      A    O
ATOM  19452  CB   GLN I  91      6.345 -44.195 -18.707  1.00 50.17      A    C
ATOM  19453  CG   GLN I  91      6.453 -45.661 -19.117  1.00 50.93      A    C
ATOM  19454  N    ARG I  92      8.355 -44.070 -21.483  1.00 48.17      A    N
ATOM  19455  CA   ARG I  92      9.613 -44.348 -22.184  1.00 47.13      A    C
ATOM  19456  C    ARG I  92     10.357 -43.044 -22.478  1.00 46.69      A    C
ATOM  19457  O    ARG I  92     11.548 -42.933 -22.179  1.00 46.58      A    O
ATOM  19458  CB   ARG I  92      9.357 -45.137 -23.475  1.00 46.96      A    C
ATOM  19459  CG   ARG I  92     10.554 -45.279 -24.404  1.00 45.18      A    C
ATOM  19460  CD   ARG I  92     10.224 -46.126 -25.635  1.00 43.13      A    C
ATOM  19461  NE   ARG I  92      9.131 -45.570 -26.435  1.00 41.79      A    N
ATOM  19462  N    LEU I  93      9.643 -42.066 -23.048  1.00 46.10      A    N
ATOM  19463  CA   LEU I  93     10.180 -40.722 -23.309  1.00 45.49      A    C
ATOM  19464  C    LEU I  93     10.863 -40.177 -22.059  1.00 45.55      A    C
ATOM  19465  O    LEU I  93     12.028 -39.768 -22.104  1.00 45.46      A    O
ATOM  19466  CB   LEU I  93      9.049 -39.760 -23.719  1.00 45.11      A    C
ATOM  19467  CG   LEU I  93      9.267 -38.544 -24.639  1.00 43.92      A    C
ATOM  19468  CD1  LEU I  93     10.597 -37.835 -24.479  1.00 42.74      A    C
ATOM  19469  N    TRP I  94     10.122 -40.201 -20.950  1.00 45.72      A    N
ATOM  19470  CA   TRP I  94     10.540 -39.596 -19.691  1.00 45.76      A    C
ATOM  19471  C    TRP I  94     11.633 -40.378 -18.961  1.00 45.76      A    C
ATOM  19472  O    TRP I  94     12.552 -39.779 -18.386  1.00 45.69      A    O
ATOM  19473  CB   TRP I  94      9.333 -39.418 -18.762  1.00 45.95      A    C
ATOM  19474  CG   TRP I  94      9.539 -38.303 -17.816  1.00 46.43      A    C
ATOM  19475  CD1  TRP I  94     10.161 -38.365 -16.596  1.00 47.13      A    C
ATOM  19476  CD2  TRP I  94      9.169 -36.930 -18.014  1.00 46.49      A    C
ATOM  19477  CE2  TRP I  94      9.586 -36.217 -16.864  1.00 46.74      A    C
ATOM  19478  CE3  TRP I  94      8.516 -36.233 -19.046  1.00 46.25      A    C
ATOM  19479  NE1  TRP I  94     10.188 -37.117 -16.017  1.00 47.11      A    N
ATOM  19480  CZ2  TRP I  94      9.371 -34.832 -16.716  1.00 46.65      A    C
ATOM  19481  CZ3  TRP I  94      8.306 -34.862 -18.903  1.00 46.16      A    C
ATOM  19482  CH2  TRP I  94      8.732 -34.177 -17.744  1.00 46.35      A    C
ATOM  19483  N    SER I  95     11.547 -41.707 -19.001  1.00 45.77      A    N
ATOM  19484  CA   SER I  95     12.402 -42.549 -18.170  1.00 45.77      A    C
ATOM  19485  C    SER I  95     13.612 -43.149 -18.899  1.00 45.21      A    C
ATOM  19486  O    SER I  95     14.726 -43.113 -18.374  1.00 45.18      A    O
ATOM  19487  CB   SER I  95     11.572 -43.649 -17.520  1.00 46.29      A    C
ATOM  19488  OG   SER I  95     11.911 -43.785 -16.152  1.00 47.23      A    O
ATOM  19489  N    THR I  96     13.398 -43.693 -20.098  1.00 44.49      A    N
ATOM  19490  CA   THR I  96     14.490 -44.292 -20.884  1.00 43.82      A    C
ATOM  19491  C    THR I  96     15.374 -43.261 -21.605  1.00 42.92      A    C
ATOM  19492  O    THR I  96     16.574 -43.497 -21.794  1.00 43.03      A    O
ATOM  19493  CB   THR I  96     13.969 -45.289 -21.931  1.00 44.00      A    C
ATOM  19494  OG1  THR I  96     12.785 -45.924 -21.438  1.00 44.73      A    O
ATOM  19495  N    TYR I  97     14.786 -42.128 -22.002  1.00 41.62      A    N
ATOM  19496  CA   TYR I  97     15.490 -41.109 -22.811  1.00 40.26      A    C
ATOM  19497  C    TYR I  97     15.803 -39.787 -22.106  1.00 39.87      A    C
ATOM  19498  O    TYR I  97     16.911 -39.274 -22.249  1.00 39.64      A    O
ATOM  19499  CB   TYR I  97     14.747 -40.855 -24.136  1.00 39.73      A    C
ATOM  19500  CG   TYR I  97     14.511 -42.145 -24.902  1.00 38.89      A    C
```

FIGURE 1 (cont'd)

```
ATOM  19501  CD1 TYR I  97    15.586 -42.996 -25.208  1.00 37.76      A  C
ATOM  19502  CD2 TYR I  97    13.217 -42.550 -25.279  1.00 42.81      A  C
ATOM  19503  CE1 TYR I  97    15.393 -44.196 -25.894  1.00 37.68      A  C
ATOM  19504  CE2 TYR I  97    13.015 -43.760 -25.964  1.00 44.12      A  C
ATOM  19505  CZ  TYR I  97    14.111 -44.576 -26.253  1.00 43.52      A  C
ATOM  19506  OH  TYR I  97    13.946 -45.770 -26.906  1.00 45.40      A  O
ATOM  19507  N   LEU I  98    14.843 -39.239 -21.354  1.00 39.65      A  N
ATOM  19508  CA  LEU I  98    15.017 -37.930 -20.716  1.00 39.47      A  C
ATOM  19509  C   LEU I  98    15.876 -37.967 -19.456  1.00 39.70      A  C
ATOM  19510  O   LEU I  98    16.884 -37.265 -19.381  1.00 39.62      A  O
ATOM  19511  CB  LEU I  98    13.674 -37.264 -20.410  1.00 39.26      A  C
ATOM  19512  CG  LEU I  98    13.819 -35.880 -19.763  1.00 39.06      A  C
ATOM  19513  CD1 LEU I  98    14.546 -34.874 -20.690  1.00 38.41      A  C
ATOM  19514  CD2 LEU I  98    12.456 -35.340 -19.309  1.00 39.20      A  C
ATOM  19515  N   ARG I  99    15.467 -38.767 -18.472  1.00 40.02      A  N
ATOM  19516  CA  ARG I  99    16.194 -38.866 -17.195  1.00 40.12      A  C
ATOM  19517  C   ARG I  99    17.693 -39.207 -17.318  1.00 40.26      A  C
ATOM  19518  O   ARG I  99    18.520 -38.574 -16.642  1.00 40.41      A  O
ATOM  19519  CB  ARG I  99    15.477 -39.785 -16.187  1.00 39.56      A  C
ATOM  19520  CG  ARG I  99    14.785 -39.006 -15.075  1.00 39.42      A  C
ATOM  19521  CD  ARG I  99    14.196 -39.903 -14.007  1.00 39.90      A  C
ATOM  19522  NE  ARG I  99    12.738 -39.892 -14.043  1.00 39.60      A  N
ATOM  19523  N   PRO I 100    18.056 -40.179 -18.186  1.00 40.28      A  N
ATOM  19524  CA  PRO I 100    19.491 -40.420 -18.403  1.00 40.19      A  C
ATOM  19525  C   PRO I 100    20.250 -39.171 -18.873  1.00 39.78      A  C
ATOM  19526  O   PRO I 100    21.413 -39.001 -18.527  1.00 39.98      A  O
ATOM  19527  CB  PRO I 100    19.503 -41.484 -19.509  1.00 40.31      A  C
ATOM  19528  CG  PRO I 100    18.211 -42.209 -19.344  1.00 40.51      A  C
ATOM  19529  CD  PRO I 100    17.227 -41.148 -18.935  1.00 40.36      A  C
ATOM  19530  N   LEU I 101    19.584 -38.312 -19.637  1.00 39.10      A  N
ATOM  19531  CA  LEU I 101    20.191 -37.093 -20.162  1.00 38.53      A  C
ATOM  19532  C   LEU I 101    20.404 -35.963 -19.127  1.00 38.50      A  C
ATOM  19533  O   LEU I 101    21.188 -35.017 -19.361  1.00 38.34      A  O
ATOM  19534  CB  LEU I 101    19.341 -36.567 -21.325  1.00 38.14      A  C
ATOM  19535  CG  LEU I 101    19.763 -36.866 -22.765  1.00 37.78      A  C
ATOM  19536  CD1 LEU I 101    20.330 -38.269 -22.907  1.00 38.23      A  C
ATOM  19537  CD2 LEU I 101    18.603 -36.631 -23.735  1.00 37.48      A  C
ATOM  19538  N   LEU I 102    19.713 -36.058 -17.992  1.00 38.55      A  N
ATOM  19539  CA  LEU I 102    19.690 -34.965 -17.024  1.00 38.63      A  C
ATOM  19540  C   LEU I 102    20.877 -34.974 -16.041  1.00 38.99      A  C
ATOM  19541  O   LEU I 102    20.694 -35.042 -14.813  1.00 39.25      A  O
ATOM  19542  CB  LEU I 102    18.343 -34.934 -16.287  1.00 38.56      A  C
ATOM  19543  CG  LEU I 102    17.101 -34.550 -17.104  1.00 38.08      A  C
ATOM  19544  CD1 LEU I 102    15.851 -34.754 -16.277  1.00 38.26      A  C
ATOM  19545  CD2 LEU I 102    17.169 -33.114 -17.601  1.00 37.53      A  C
ATOM  19546  N   VAL I 103    22.090 -34.904 -16.597  1.00 39.14      A  N
ATOM  19547  CA  VAL I 103    23.330 -34.810 -15.800  1.00 39.43      A  C
ATOM  19548  C   VAL I 103    24.197 -33.671 -16.312  1.00 39.15      A  C
ATOM  19549  O   VAL I 103    24.073 -33.269 -17.487  1.00 38.83      A  O
ATOM  19550  CB  VAL I 103    24.169 -36.120 -15.813  1.00 39.73      A  C
ATOM  19551  CG1 VAL I 103    24.408 -36.603 -17.246  1.00 39.60      A  C
ATOM  19552  CG2 VAL I 103    23.501 -37.200 -14.966  1.00 40.65      A  C
ATOM  19553  N   VAL I 104    25.062 -33.155 -15.429  1.00 39.09      A  N
ATOM  19554  CA  VAL I 104    26.049 -32.150 -15.824  1.00 38.77      A  C
ATOM  19555  C   VAL I 104    26.884 -32.734 -16.971  1.00 38.97      A  C
ATOM  19556  O   VAL I 104    27.395 -33.864 -16.875  1.00 39.24      A  O
ATOM  19557  CB  VAL I 104    26.944 -31.715 -14.651  1.00 38.06      A  C
ATOM  19558  CG1 VAL I 104    27.425 -30.293 -14.871  1.00 37.47      A  C
ATOM  19559  N   ARG I 105    26.983 -31.973 -18.062  1.00 38.82      A  N
ATOM  19560  CA  ARG I 105    27.533 -32.492 -19.319  1.00 38.56      A  C
ATOM  19561  C   ARG I 105    28.186 -31.410 -20.188  1.00 38.54      A  C
ATOM  19562  O   ARG I 105    28.150 -31.474 -21.425  1.00 38.26      A  O
ATOM  19563  CB  ARG I 105    26.447 -33.239 -20.107  1.00 38.36      A  C
ATOM  19564  CG  ARG I 105    25.292 -32.359 -20.543  1.00 37.71      A  C
ATOM  19565  CD  ARG I 105    24.052 -33.172 -20.829  1.00 37.41      A  C
```

FIGURE 1 (cont'd)

```
ATOM  19566  NE   ARG I 105      23.017 -32.333 -21.438  1.00 37.05       A  N
ATOM  19567  CZ   ARG I 105      21.982 -31.803 -20.786  1.00 36.84       A  C
ATOM  19568  NH1  ARG I 105      21.813 -32.034 -19.483  1.00 36.93       A  N
ATOM  19569  NH2  ARG I 105      21.104 -31.050 -21.450  1.00 36.44       A  N
ATOM  19570  N    THR I 106      28.785 -30.423 -19.530  1.00 38.74       A  N
ATOM  19571  CA   THR I 106      29.591 -29.418 -20.209  1.00 38.97       A  C
ATOM  19572  C    THR I 106      30.670 -30.072 -21.106  1.00 39.01       A  C
ATOM  19573  O    THR I 106      31.177 -31.155 -20.785  1.00 38.97       A  O
ATOM  19574  CB   THR I 106      30.238 -28.467 -19.187  1.00 39.15       A  C
ATOM  19575  OG1  THR I 106      31.092 -29.222 -18.317  1.00 39.83       A  O
ATOM  19576  N    PRO I 107      31.008 -29.418 -22.238  1.00 39.12       A  N
ATOM  19577  CA   PRO I 107      31.927 -29.974 -23.236  1.00 39.42       A  C
ATOM  19578  C    PRO I 107      33.171 -30.647 -22.654  1.00 39.96       A  C
ATOM  19579  O    PRO I 107      33.802 -30.110 -21.748  1.00 40.12       A  O
ATOM  19580  CB   PRO I 107      32.329 -28.744 -24.057  1.00 39.32       A  C
ATOM  19581  CG   PRO I 107      31.131 -27.862 -24.002  1.00 38.91       A  C
ATOM  19582  CD   PRO I 107      30.481 -28.101 -22.658  1.00 38.99       A  C
ATOM  19583  N    GLY I 108      33.504 -31.822 -23.182  1.00 40.39       A  N
ATOM  19584  CA   GLY I 108      34.712 -32.545 -22.792  1.00 41.01       A  C
ATOM  19585  C    GLY I 108      34.778 -33.006 -21.347  1.00 41.37       A  C
ATOM  19586  O    GLY I 108      35.857 -33.317 -20.843  1.00 41.86       A  O
ATOM  19587  N    SER I 109      33.634 -33.046 -20.671  1.00 41.35       A  N
ATOM  19588  CA   SER I 109      33.578 -33.564 -19.306  1.00 41.42       A  C
ATOM  19589  C    SER I 109      33.250 -35.065 -19.331  1.00 41.60       A  C
ATOM  19590  O    SER I 109      33.006 -35.627 -20.407  1.00 41.32       A  O
ATOM  19591  CB   SER I 109      32.546 -32.789 -18.474  1.00 41.28       A  C
ATOM  19592  OG   SER I 109      31.231 -33.011 -18.958  1.00 40.68       A  O
ATOM  19593  N    PRO I 110      33.271 -35.721 -18.151  1.00 41.96       A  N
ATOM  19594  CA   PRO I 110      32.799 -37.105 -18.079  1.00 41.92       A  C
ATOM  19595  C    PRO I 110      31.306 -37.230 -18.429  1.00 41.36       A  C
ATOM  19596  O    PRO I 110      30.913 -38.208 -19.088  1.00 41.17       A  O
ATOM  19597  CB   PRO I 110      33.037 -37.485 -16.608  1.00 42.35       A  C
ATOM  19598  CG   PRO I 110      34.135 -36.589 -16.165  1.00 42.79       A  C
ATOM  19599  CD   PRO I 110      33.900 -35.295 -16.884  1.00 42.34       A  C
ATOM  19600  N    GLY I 111      30.498 -36.257 -17.989  1.00 40.85       A  N
ATOM  19601  CA   GLY I 111      29.063 -36.214 -18.307  1.00 40.18       A  C
ATOM  19602  C    GLY I 111      28.789 -36.067 -19.802  1.00 39.66       A  C
ATOM  19603  O    GLY I 111      27.940 -36.782 -20.362  1.00 39.49       A  O
ATOM  19604  N    ASN I 112      29.511 -35.143 -20.446  1.00 39.21       A  N
ATOM  19605  CA   ASN I 112      29.455 -34.960 -21.899  1.00 38.62       A  C
ATOM  19606  C    ASN I 112      29.715 -36.268 -22.651  1.00 38.86       A  C
ATOM  19607  O    ASN I 112      28.987 -36.611 -23.591  1.00 38.69       A  O
ATOM  19608  CB   ASN I 112      30.441 -33.874 -22.347  1.00 38.32       A  C
ATOM  19609  CG   ASN I 112      30.408 -33.628 -23.856  1.00 37.23       A  C
ATOM  19610  ND2  ASN I 112      30.776 -34.645 -24.632  1.00 37.86       A  N
ATOM  19611  OD1  ASN I 112      30.061 -32.540 -24.314  1.00 38.15       A  O
ATOM  19612  N    LEU I 113      30.746 -36.994 -22.225  1.00 39.31       A  N
ATOM  19613  CA   LEU I 113      31.076 -38.290 -22.824  1.00 39.81       A  C
ATOM  19614  C    LEU I 113      30.079 -39.407 -22.444  1.00 39.82       A  C
ATOM  19615  O    LEU I 113      29.731 -40.246 -23.286  1.00 39.75       A  O
ATOM  19616  CB   LEU I 113      32.523 -38.694 -22.480  1.00 40.24       A  C
ATOM  19617  CG   LEU I 113      33.241 -39.722 -23.378  1.00 40.94       A  C
ATOM  19618  CD1  LEU I 113      34.723 -39.374 -23.525  1.00 41.48       A  C
ATOM  19619  CD2  LEU I 113      33.057 -41.161 -22.878  1.00 41.75       A  C
ATOM  19620  N    GLN I 114      29.633 -39.419 -21.188  1.00 39.89       A  N
ATOM  19621  CA   GLN I 114      28.633 -40.388 -20.737  1.00 39.91       A  C
ATOM  19622  C    GLN I 114      27.338 -40.269 -21.554  1.00 39.67       A  C
ATOM  19623  O    GLN I 114      26.797 -41.289 -22.007  1.00 39.73       A  O
ATOM  19624  CB   GLN I 114      28.344 -40.229 -19.244  1.00 40.06       A  C
ATOM  19625  N    VAL I 115      26.868 -39.027 -21.752  1.00 39.09       A  N
ATOM  19626  CA   VAL I 115      25.681 -38.724 -22.584  1.00 38.43       A  C
ATOM  19627  C    VAL I 115      25.888 -39.104 -24.068  1.00 38.71       A  C
ATOM  19628  O    VAL I 115      25.090 -39.882 -24.638  1.00 38.88       A  O
ATOM  19629  CB   VAL I 115      25.241 -37.234 -22.481  1.00 36.91       A  C
ATOM  19630  N    ARG I 116      26.949 -38.563 -24.680  1.00 38.89       A  N
```

FIGURE 1 (cont'd)

```
ATOM  19631  CA   ARG I 116     27.361 -38.940 -26.043  1.00 39.12      A  C
ATOM  19632  C    ARG I 116     27.329 -40.472 -26.289  1.00 39.55      A  C
ATOM  19633  O    ARG I 116     26.819 -40.941 -27.317  1.00 39.48      A  O
ATOM  19634  CB   ARG I 116     28.758 -38.392 -26.327  1.00 38.99      A  C
ATOM  19635  CG   ARG I 116     29.360 -38.823 -27.665  1.00 39.24      A  C
ATOM  19636  CD   ARG I 116     30.828 -38.397 -27.768  1.00 40.29      A  C
ATOM  19637  NE   ARG I 116     30.999 -36.951 -27.551  1.00 40.97      A  N
ATOM  19638  CZ   ARG I 116     32.155 -36.350 -27.252  1.00 41.53      A  C
ATOM  19639  NH1  ARG I 116     33.274 -37.062 -27.123  1.00 41.98      A  N
ATOM  19640  NH2  ARG I 116     32.189 -35.030 -27.078  1.00 41.66      A  N
ATOM  19641  N    LYS I 117     27.871 -41.227 -25.332  1.00 40.08      A  N
ATOM  19642  CA   LYS I 117     27.897 -42.681 -25.398  1.00 40.57      A  C
ATOM  19643  C    LYS I 117     26.483 -43.273 -25.361  1.00 40.22      A  C
ATOM  19644  O    LYS I 117     26.181 -44.224 -26.099  1.00 40.33      A  O
ATOM  19645  CB   LYS I 117     28.758 -43.251 -24.258  1.00 41.18      A  C
ATOM  19646  CG   LYS I 117     29.301 -44.677 -24.504  1.00 42.55      A  C
ATOM  19647  CD   LYS I 117     30.351 -45.105 -23.464  1.00 43.87      A  C
ATOM  19648  CE   LYS I 117     31.773 -44.722 -23.889  1.00 44.07      A  C
ATOM  19649  N    PHE I 118     25.626 -42.711 -24.510  1.00 39.58      A  N
ATOM  19650  CA   PHE I 118     24.230 -43.153 -24.418  1.00 38.97      A  C
ATOM  19651  C    PHE I 118     23.452 -42.886 -25.711  1.00 39.20      A  C
ATOM  19652  O    PHE I 118     22.639 -43.713 -26.140  1.00 39.40      A  O
ATOM  19653  CB   PHE I 118     23.521 -42.490 -23.229  1.00 37.70      A  C
ATOM  19654  CG   PHE I 118     22.031 -42.776 -23.158  1.00 36.19      A  C
ATOM  19655  CD1  PHE I 118     21.577 -44.092 -22.978  1.00 35.87      A  C
ATOM  19656  CD2  PHE I 118     21.106 -41.718 -23.258  1.00 34.61      A  C
ATOM  19657  CE1  PHE I 118     20.222 -44.404 -22.901  1.00 35.49      A  C
ATOM  19658  CE2  PHE I 118     19.721 -41.914 -23.188  1.00 33.87      A  C
ATOM  19659  N    LEU I 119     23.701 -41.733 -26.321  1.00 39.18      A  N
ATOM  19660  CA   LEU I 119     23.060 -41.416 -27.585  1.00 39.24      A  C
ATOM  19661  C    LEU I 119     23.459 -42.431 -28.675  1.00 39.74      A  C
ATOM  19662  O    LEU I 119     22.584 -43.080 -29.284  1.00 39.83      A  O
ATOM  19663  CB   LEU I 119     23.349 -39.965 -28.002  1.00 38.77      A  C
ATOM  19664  CG   LEU I 119     22.475 -38.936 -27.285  1.00 37.95      A  C
ATOM  19665  CD1  LEU I 119     23.074 -37.557 -27.417  1.00 37.44      A  C
ATOM  19666  N    GLU I 120     24.771 -42.576 -28.893  1.00 40.23      A  N
ATOM  19667  CA   GLU I 120     25.314 -43.539 -29.864  1.00 40.66      A  C
ATOM  19668  C    GLU I 120     24.627 -44.900 -29.739  1.00 41.34      A  C
ATOM  19669  O    GLU I 120     24.123 -45.436 -30.738  1.00 41.57      A  O
ATOM  19670  CB   GLU I 120     26.827 -43.723 -29.670  1.00 39.90      A  C
ATOM  19671  CG   GLU I 120     27.704 -42.586 -30.183  1.00 39.57      A  C
ATOM  19672  CD   GLU I 120     29.185 -42.938 -30.125  1.00 40.12      A  C
ATOM  19673  OE1  GLU I 120     29.604 -43.885 -30.832  1.00 40.87      A  O
ATOM  19674  N    ALA I 121     24.604 -45.427 -28.506  1.00 41.87      A  N
ATOM  19675  CA   ALA I 121     24.050 -46.755 -28.197  1.00 42.26      A  C
ATOM  19676  C    ALA I 121     22.546 -46.872 -28.499  1.00 42.19      A  C
ATOM  19677  O    ALA I 121     22.117 -47.806 -29.192  1.00 42.49      A  O
ATOM  19678  CB   ALA I 121     24.342 -47.135 -26.745  1.00 42.55      A  C
ATOM  19679  N    THR I 122     21.757 -45.927 -27.982  1.00 41.61      A  N
ATOM  19680  CA   THR I 122     20.315 -45.883 -28.251  1.00 40.96      A  C
ATOM  19681  C    THR I 122     20.009 -45.871 -29.758  1.00 41.39      A  C
ATOM  19682  O    THR I 122     19.204 -46.691 -30.234  1.00 41.74      A  O
ATOM  19683  CB   THR I 122     19.640 -44.670 -27.575  1.00 39.49      A  C
ATOM  19684  OG1  THR I 122     19.652 -44.863 -26.156  1.00 38.57      A  O
ATOM  19685  N    LEU I 123     20.665 -44.962 -30.492  1.00 41.45      A  N
ATOM  19686  CA   LEU I 123     20.482 -44.835 -31.942  1.00 41.52      A  C
ATOM  19687  C    LEU I 123     20.832 -46.121 -32.708  1.00 42.19      A  C
ATOM  19688  O    LEU I 123     20.112 -46.519 -33.645  1.00 42.38      A  O
ATOM  19689  CB   LEU I 123     21.301 -43.659 -32.485  1.00 41.06      A  C
ATOM  19690  CG   LEU I 123     20.879 -42.227 -32.121  1.00 39.86      A  C
ATOM  19691  CD1  LEU I 123     19.780 -41.719 -33.059  1.00 39.20      A  C
ATOM  19692  N    ARG I 124     21.933 -46.761 -32.300  1.00 42.79      A  N
ATOM  19693  CA   ARG I 124     22.383 -48.019 -32.915  1.00 43.47      A  C
ATOM  19694  C    ARG I 124     21.444 -49.196 -32.643  1.00 44.11      A  C
ATOM  19695  O    ARG I 124     21.235 -50.042 -33.522  1.00 44.46      A  O
```

FIGURE 1 (cont'd)

```
ATOM  19696  CB   ARG I 124      23.819 -48.366 -32.494  1.00 43.43       A    C
ATOM  19697  CG   ARG I 124      24.872 -47.601 -33.290  1.00 42.84       A    C
ATOM  19698  CD   ARG I 124      26.288 -48.007 -32.917  1.00 42.42       A    C
ATOM  19699  NE   ARG I 124      27.275 -47.206 -33.644  1.00 41.62       A    N
ATOM  19700  N    SER I 125      20.871 -49.228 -31.437  1.00 44.60       A    N
ATOM  19701  CA   SER I 125      19.987 -50.320 -31.002  1.00 45.15       A    C
ATOM  19702  C    SER I 125      18.568 -50.286 -31.619  1.00 45.27       A    C
ATOM  19703  O    SER I 125      17.671 -50.992 -31.158  1.00 45.57       A    O
ATOM  19704  CB   SER I 125      19.901 -50.342 -29.473  1.00 45.29       A    C
ATOM  19705  OG   SER I 125      19.184 -49.214 -28.993  1.00 44.98       A    O
ATOM  19706  N    LEU I 126      18.372 -49.478 -32.659  1.00 45.15       A    N
ATOM  19707  CA   LEU I 126      17.073 -49.394 -33.333  1.00 45.15       A    C
ATOM  19708  C    LEU I 126      16.933 -50.423 -34.467  1.00 45.70       A    C
ATOM  19709  O    LEU I 126      17.926 -50.810 -35.100  1.00 45.93       A    O
ATOM  19710  CB   LEU I 126      16.800 -47.967 -33.835  1.00 44.62       A    C
ATOM  19711  CG   LEU I 126      16.627 -46.858 -32.782  1.00 43.82       A    C
ATOM  19712  CD1  LEU I 126      15.957 -45.627 -33.394  1.00 42.94       A    C
ATOM  19713  CD2  LEU I 126      15.845 -47.347 -31.548  1.00 43.56       A    C
ATOM  19714  N    THR I 127      15.693 -50.859 -34.707  1.00 46.20       A    N
ATOM  19715  CA   THR I 127      15.383 -51.923 -35.682  1.00 46.67       A    C
ATOM  19716  C    THR I 127      15.743 -51.554 -37.120  1.00 46.69       A    C
ATOM  19717  O    THR I 127      16.337 -52.360 -37.832  1.00 47.16       A    O
ATOM  19718  CB   THR I 127      13.898 -52.368 -35.624  1.00 46.89       A    C
ATOM  19719  OG1  THR I 127      13.433 -52.360 -34.266  1.00 47.09       A    O
ATOM  19720  N    ALA I 128      15.374 -50.349 -37.546  1.00 46.32       A    N
ATOM  19721  CA   ALA I 128      15.897 -49.802 -38.795  1.00 46.13       A    C
ATOM  19722  C    ALA I 128      17.397 -49.576 -38.619  1.00 46.04       A    C
ATOM  19723  O    ALA I 128      17.838 -49.167 -37.535  1.00 45.99       A    O
ATOM  19724  CB   ALA I 128      15.204 -48.498 -39.146  1.00 45.82       A    C
ATOM  19725  N    GLY I 129      18.177 -49.851 -39.668  1.00 46.03       A    N
ATOM  19726  CA   GLY I 129      19.647 -49.806 -39.579  1.00 45.77       A    C
ATOM  19727  C    GLY I 129      20.229 -48.399 -39.595  1.00 45.19       A    C
ATOM  19728  O    GLY I 129      20.782 -47.972 -40.615  1.00 45.54       A    O
ATOM  19729  N    TRP I 130      20.110 -47.680 -38.472  1.00 44.30       A    N
ATOM  19730  CA   TRP I 130      20.621 -46.302 -38.359  1.00 43.32       A    C
ATOM  19731  C    TRP I 130      22.149 -46.248 -38.503  1.00 43.04       A    C
ATOM  19732  O    TRP I 130      22.881 -46.951 -37.790  1.00 43.20       A    O
ATOM  19733  CB   TRP I 130      20.204 -45.655 -37.028  1.00 42.94       A    C
ATOM  19734  CG   TRP I 130      18.796 -45.100 -36.996  1.00 42.44       A    C
ATOM  19735  CD1  TRP I 130      17.673 -45.741 -36.544  1.00 42.65       A    C
ATOM  19736  CD2  TRP I 130      18.367 -43.790 -37.413  1.00 41.99       A    C
ATOM  19737  CE2  TRP I 130      16.965 -43.715 -37.185  1.00 41.86       A    C
ATOM  19738  CE3  TRP I 130      19.026 -42.674 -37.959  1.00 41.74       A    C
ATOM  19739  NE1  TRP I 130      16.572 -44.915 -36.653  1.00 42.25       A    N
ATOM  19740  CZ2  TRP I 130      16.206 -42.566 -37.491  1.00 41.37       A    C
ATOM  19741  CZ3  TRP I 130      18.266 -41.520 -38.261  1.00 41.37       A    C
ATOM  19742  CH2  TRP I 130      16.870 -41.486 -38.025  1.00 41.14       A    C
ATOM  19743  N    HIS I 131      22.622 -45.420 -39.431  1.00 42.60       A    N
ATOM  19744  CA   HIS I 131      24.055 -45.222 -39.629  1.00 42.37       A    C
ATOM  19745  C    HIS I 131      24.521 -44.137 -38.656  1.00 41.95       A    C
ATOM  19746  O    HIS I 131      24.596 -42.946 -38.996  1.00 41.71       A    O
ATOM  19747  CB   HIS I 131      24.333 -44.833 -41.084  1.00 42.55       A    C
ATOM  19748  CG   HIS I 131      25.750 -45.041 -41.516  1.00 42.93       A    C
ATOM  19749  N    VAL I 132      24.793 -44.566 -37.427  1.00 41.70       A    N
ATOM  19750  CA   VAL I 132      25.254 -43.674 -36.364  1.00 41.37       A    C
ATOM  19751  C    VAL I 132      26.764 -43.389 -36.507  1.00 41.40       A    C
ATOM  19752  O    VAL I 132      27.562 -44.301 -36.750  1.00 41.64       A    O
ATOM  19753  CB   VAL I 132      24.940 -44.266 -34.968  1.00 41.31       A    C
ATOM  19754  CG1  VAL I 132      24.620 -43.153 -33.987  1.00 41.05       A    C
ATOM  19755  N    GLU I 133      27.151 -42.125 -36.346  1.00 41.28       A    N
ATOM  19756  CA   GLU I 133      28.507 -41.694 -36.686  1.00 41.48       A    C
ATOM  19757  C    GLU I 133      28.961 -40.473 -35.865  1.00 41.20       A    C
ATOM  19758  O    GLU I 133      28.299 -39.425 -35.882  1.00 41.03       A    O
ATOM  19759  CB   GLU I 133      28.573 -41.380 -38.184  1.00 41.66       A    C
ATOM  19760  CG   GLU I 133      29.947 -41.024 -38.701  1.00 42.99       A    C
```

FIGURE 1 (cont'd)

```
ATOM  19761  CD   GLU I 133      29.894 -40.599 -40.147  1.00 44.74      A   C
ATOM  19762  OE1  GLU I 133      29.375 -41.389 -40.974  1.00 45.56      A   O
ATOM  19763  OE2  GLU I 133      30.362 -39.479 -40.458  1.00 45.19      A   O
ATOM  19764  N    LEU I 134      30.093 -40.625 -35.164  1.00 41.11      A   N
ATOM  19765  CA   LEU I 134      30.698 -39.551 -34.365  1.00 40.76      A   C
ATOM  19766  C    LEU I 134      31.490 -38.572 -35.221  1.00 40.52      A   C
ATOM  19767  O    LEU I 134      32.044 -38.939 -36.254  1.00 40.69      A   O
ATOM  19768  CB   LEU I 134      31.615 -40.125 -33.290  1.00 40.93      A   C
ATOM  19769  CG   LEU I 134      31.016 -40.398 -31.910  1.00 41.08      A   C
ATOM  19770  CD1  LEU I 134      32.024 -41.173 -31.044  1.00 41.93      A   C
ATOM  19771  N    ASP I 135      31.525 -37.320 -34.782  1.00 40.07      A   N
ATOM  19772  CA   ASP I 135      32.338 -36.291 -35.418  1.00 39.85      A   C
ATOM  19773  C    ASP I 135      33.230 -35.676 -34.353  1.00 39.82      A   C
ATOM  19774  O    ASP I 135      32.940 -34.583 -33.844  1.00 39.80      A   O
ATOM  19775  CB   ASP I 135      31.462 -35.210 -36.075  1.00 39.64      A   C
ATOM  19776  CG   ASP I 135      32.285 -34.035 -36.642  1.00 39.88      A   C
ATOM  19777  OD1  ASP I 135      33.390 -34.285 -37.178  1.00 40.65      A   O
ATOM  19778  OD2  ASP I 135      31.833 -32.860 -36.546  1.00 39.58      A   O
ATOM  19779  N    PRO I 136      34.311 -36.389 -33.990  1.00 39.85      A   N
ATOM  19780  CA   PRO I 136      35.227 -35.842 -32.980  1.00 40.09      A   C
ATOM  19781  C    PRO I 136      36.061 -34.687 -33.561  1.00 40.67      A   C
ATOM  19782  O    PRO I 136      36.310 -34.656 -34.777  1.00 40.90      A   O
ATOM  19783  CB   PRO I 136      36.117 -37.049 -32.594  1.00 39.29      A   C
ATOM  19784  CG   PRO I 136      35.658 -38.215 -33.445  1.00 38.90      A   C
ATOM  19785  N    PHE I 137      36.443 -33.733 -32.709  1.00 41.14      A   N
ATOM  19786  CA   PHE I 137      37.396 -32.682 -33.092  1.00 41.64      A   C
ATOM  19787  C    PHE I 137      37.824 -31.857 -31.894  1.00 42.10      A   C
ATOM  19788  O    PHE I 137      37.081 -31.750 -30.911  1.00 42.03      A   O
ATOM  19789  CB   PHE I 137      36.836 -31.764 -34.189  1.00 41.45      A   C
ATOM  19790  CG   PHE I 137      35.726 -30.869 -33.730  1.00 41.11      A   C
ATOM  19791  CD1  PHE I 137      34.422 -31.362 -33.588  1.00 40.81      A   C
ATOM  19792  CD2  PHE I 137      35.970 -29.520 -33.462  1.00 41.01      A   C
ATOM  19793  CE1  PHE I 137      33.368 -30.521 -33.171  1.00 40.28      A   C
ATOM  19794  CE2  PHE I 137      34.926 -28.662 -33.046  1.00 40.56      A   C
ATOM  19795  CZ   PHE I 137      33.624 -29.167 -32.896  1.00 40.20      A   C
ATOM  19796  N    THR I 138      39.028 -31.286 -31.990  1.00 42.83      A   N
ATOM  19797  CA   THR I 138      39.537 -30.341 -30.990  1.00 43.42      A   C
ATOM  19798  C    THR I 138      39.369 -28.914 -31.503  1.00 43.48      A   C
ATOM  19799  O    THR I 138      39.509 -28.657 -32.709  1.00 43.59      A   O
ATOM  19800  CB   THR I 138      41.015 -30.610 -30.632  1.00 43.78      A   C
ATOM  19801  OG1  THR I 138      41.082 -31.230 -29.341  1.00 44.26      A   O
ATOM  19802  N    ALA I 139      39.047 -27.995 -30.595  1.00 43.49      A   N
ATOM  19803  CA   ALA I 139      38.828 -26.603 -30.994  1.00 43.61      A   C
ATOM  19804  C    ALA I 139      39.309 -25.587 -29.965  1.00 43.99      A   C
ATOM  19805  O    ALA I 139      39.332 -25.857 -28.743  1.00 44.03      A   O
ATOM  19806  CB   ALA I 139      37.360 -26.352 -31.352  1.00 43.22      A   C
ATOM  19807  N    SER I 140      39.682 -24.418 -30.495  1.00 44.42      A   N
ATOM  19808  CA   SER I 140      40.231 -23.307 -29.722  1.00 44.82      A   C
ATOM  19809  C    SER I 140      39.117 -22.465 -29.066  1.00 44.49      A   C
ATOM  19810  O    SER I 140      38.328 -21.815 -29.765  1.00 44.31      A   O
ATOM  19811  CB   SER I 140      41.128 -22.450 -30.633  1.00 45.22      A   C
ATOM  19812  OG   SER I 140      41.428 -21.186 -30.056  1.00 46.15      A   O
ATOM  19813  N    THR I 141      39.059 -22.502 -27.729  1.00 44.30      A   N
ATOM  19814  CA   THR I 141      38.062 -21.753 -26.951  1.00 44.06      A   C
ATOM  19815  C    THR I 141      38.749 -20.739 -26.021  1.00 44.36      A   C
ATOM  19816  O    THR I 141      39.968 -20.821 -25.817  1.00 44.84      A   O
ATOM  19817  CB   THR I 141      37.127 -22.707 -26.130  1.00 43.72      A   C
ATOM  19818  CG2  THR I 141      36.622 -23.862 -26.994  1.00 43.37      A   C
ATOM  19819  OG1  THR I 141      37.828 -23.245 -25.002  1.00 43.75      A   O
ATOM  19820  N    PRO I 142      37.983 -19.775 -25.461  1.00 44.33      A   N
ATOM  19821  CA   PRO I 142      38.532 -18.872 -24.430  1.00 44.52      A   C
ATOM  19822  C    PRO I 142      39.010 -19.588 -23.146  1.00 44.71      A   C
ATOM  19823  O    PRO I 142      39.628 -18.964 -22.288  1.00 45.14      A   O
ATOM  19824  CB   PRO I 142      37.358 -17.929 -24.126  1.00 44.39      A   C
ATOM  19825  CG   PRO I 142      36.551 -17.931 -25.372  1.00 44.09      A   C
```

FIGURE 1 (cont'd)

```
ATOM  19826  CD   PRO I 142      36.643 -19.341 -25.897  1.00 44.00      A  C
ATOM  19827  N    LEU I 143      38.719 -20.881 -23.028  1.00 44.50      A  N
ATOM  19828  CA   LEU I 143      39.244 -21.705 -21.950  1.00 44.52      A  C
ATOM  19829  C    LEU I 143      40.399 -22.572 -22.445  1.00 44.79      A  C
ATOM  19830  O    LEU I 143      40.836 -23.494 -21.755  1.00 45.03      A  O
ATOM  19831  CB   LEU I 143      38.137 -22.602 -21.394  1.00 44.18      A  C
ATOM  19832  CG   LEU I 143      37.253 -22.164 -20.218  1.00 44.11      A  C
ATOM  19833  CD1  LEU I 143      38.045 -22.130 -18.902  1.00 45.12      A  C
ATOM  19834  CD2  LEU I 143      36.530 -20.831 -20.474  1.00 43.71      A  C
ATOM  19835  N    GLY I 144      40.891 -22.270 -23.642  1.00 44.90      A  N
ATOM  19836  CA   GLY I 144      41.933 -23.070 -24.280  1.00 45.01      A  C
ATOM  19837  C    GLY I 144      41.361 -24.253 -25.039  1.00 44.84      A  C
ATOM  19838  O    GLY I 144      40.136 -24.376 -25.147  1.00 44.45      A  O
ATOM  19839  N    PRO I 145      42.245 -25.130 -25.575  1.00 45.01      A  N
ATOM  19840  CA   PRO I 145      41.844 -26.349 -26.301  1.00 44.63      A  C
ATOM  19841  C    PRO I 145      40.792 -27.181 -25.569  1.00 43.84      A  C
ATOM  19842  O    PRO I 145      40.994 -27.559 -24.407  1.00 44.06      A  O
ATOM  19843  CB   PRO I 145      43.154 -27.147 -26.394  1.00 45.02      A  C
ATOM  19844  CG   PRO I 145      44.215 -26.096 -26.458  1.00 45.68      A  C
ATOM  19845  CD   PRO I 145      43.717 -24.967 -25.568  1.00 45.52      A  C
ATOM  19846  N    VAL I 146      39.681 -27.448 -26.255  1.00 42.54      A  N
ATOM  19847  CA   VAL I 146      38.603 -28.275 -25.713  1.00 41.12      A  C
ATOM  19848  C    VAL I 146      38.188 -29.343 -26.734  1.00 41.31      A  C
ATOM  19849  O    VAL I 146      38.052 -29.056 -27.940  1.00 41.31      A  O
ATOM  19850  CB   VAL I 146      37.386 -27.413 -25.300  1.00 39.31      A  C
ATOM  19851  CG1  VAL I 146      36.405 -28.236 -24.469  1.00 37.86      A  C
ATOM  19852  N    ASP I 147      38.000 -30.570 -26.238  1.00 41.38      A  N
ATOM  19853  CA   ASP I 147      37.639 -31.717 -27.081  1.00 41.14      A  C
ATOM  19854  C    ASP I 147      36.119 -31.899 -27.227  1.00 40.69      A  C
ATOM  19855  O    ASP I 147      35.409 -32.155 -26.244  1.00 40.61      A  O
ATOM  19856  CB   ASP I 147      38.309 -33.006 -26.575  1.00 41.35      A  C
ATOM  19857  CG   ASP I 147      39.784 -33.079 -26.941  1.00 41.29      A  C
ATOM  19858  N    PHE I 148      35.641 -31.765 -28.465  1.00 40.18      A  N
ATOM  19859  CA   PHE I 148      34.212 -31.867 -28.785  1.00 39.58      A  C
ATOM  19860  C    PHE I 148      33.891 -33.153 -29.541  1.00 39.38      A  C
ATOM  19861  O    PHE I 148      34.799 -33.851 -30.014  1.00 39.53      A  O
ATOM  19862  CB   PHE I 148      33.759 -30.669 -29.630  1.00 39.34      A  C
ATOM  19863  CG   PHE I 148      33.940 -29.339 -28.956  1.00 39.39      A  C
ATOM  19864  CD1  PHE I 148      32.942 -28.817 -28.133  1.00 39.11      A  C
ATOM  19865  CD2  PHE I 148      35.107 -28.596 -29.159  1.00 39.83      A  C
ATOM  19866  CE1  PHE I 148      33.103 -27.574 -27.517  1.00 39.26      A  C
ATOM  19867  CE2  PHE I 148      35.279 -27.348 -28.548  1.00 39.86      A  C
ATOM  19868  CZ   PHE I 148      34.272 -26.834 -27.728  1.00 39.58      A  C
ATOM  19869  N    GLY I 149      32.593 -33.444 -29.655  1.00 39.03      A  N
ATOM  19870  CA   GLY I 149      32.093 -34.590 -30.427  1.00 38.85      A  C
ATOM  19871  C    GLY I 149      30.601 -34.536 -30.756  1.00 38.56      A  C
ATOM  19872  O    GLY I 149      29.763 -34.707 -29.867  1.00 38.50      A  O
ATOM  19873  N    ASN I 150      30.277 -34.295 -32.031  1.00 38.30      A  N
ATOM  19874  CA   ASN I 150      28.903 -34.370 -32.524  1.00 37.98      A  C
ATOM  19875  C    ASN I 150      28.436 -35.813 -32.727  1.00 38.16      A  C
ATOM  19876  O    ASN I 150      29.249 -36.711 -32.968  1.00 38.40      A  O
ATOM  19877  CB   ASN I 150      28.775 -33.608 -33.839  1.00 37.69      A  C
ATOM  19878  CG   ASN I 150      29.009 -32.120 -33.674  1.00 37.32      A  C
ATOM  19879  ND2  ASN I 150      29.940 -31.575 -34.454  1.00 37.31      A  N
ATOM  19880  OD1  ASN I 150      28.353 -31.464 -32.867  1.00 36.81      A  O
ATOM  19881  N    VAL I 151      27.128 -36.032 -32.618  1.00 38.17      A  N
ATOM  19882  CA   VAL I 151      26.535 -37.336 -32.898  1.00 38.47      A  C
ATOM  19883  C    VAL I 151      25.595 -37.183 -34.096  1.00 38.68      A  C
ATOM  19884  O    VAL I 151      24.547 -36.522 -34.020  1.00 38.45      A  O
ATOM  19885  CB   VAL I 151      25.835 -37.959 -31.651  1.00 38.37      A  C
ATOM  19886  CG1  VAL I 151      26.856 -38.279 -30.578  1.00 38.74      A  C
ATOM  19887  CG2  VAL I 151      25.102 -39.238 -32.007  1.00 38.52      A  C
ATOM  19888  N    VAL I 152      26.012 -37.790 -35.210  1.00 39.27      A  N
ATOM  19889  CA   VAL I 152      25.294 -37.728 -36.495  1.00 39.75      A  C
ATOM  19890  C    VAL I 152      24.637 -39.078 -36.843  1.00 40.29      A  C
```

FIGURE 1 (cont'd)

```
ATOM  19891  O    VAL I 152      25.310  -40.121  -36.930  1.00 40.59      A    O
ATOM  19892  CB   VAL I 152      26.224  -37.244  -37.648  1.00 39.68      A    C
ATOM  19893  CG1  VAL I 152      26.482  -35.735  -37.529  1.00 39.11      A    C
ATOM  19894  CG2  VAL I 152      25.628  -37.588  -39.013  1.00 40.03      A    C
ATOM  19895  N    ALA I 153      23.317  -39.033  -37.036  1.00 40.72      A    N
ATOM  19896  CA   ALA I 153      22.515  -40.233  -37.289  1.00 41.34      A    C
ATOM  19897  C    ALA I 153      21.670  -40.076  -38.561  1.00 41.83      A    C
ATOM  19898  O    ALA I 153      20.906  -39.106  -38.710  1.00 41.71      A    O
ATOM  19899  CB   ALA I 153      21.632  -40.569  -36.064  1.00 41.14      A    C
ATOM  19900  N    THR I 154      21.826  -41.039  -39.473  1.00 42.59      A    N
ATOM  19901  CA   THR I 154      21.117  -41.013  -40.746  1.00 43.23      A    C
ATOM  19902  C    THR I 154      20.636  -42.419  -41.076  1.00 44.02      A    C
ATOM  19903  O    THR I 154      21.443  -43.349  -41.147  1.00 44.40      A    O
ATOM  19904  CB   THR I 154      22.020  -40.454  -41.899  1.00 43.13      A    C
ATOM  19905  CG2  THR I 154      21.183  -39.967  -43.079  1.00 42.97      A    C
ATOM  19906  OG1  THR I 154      22.818  -39.361  -41.409  1.00 42.65      A    O
ATOM  19907  N    LEU I 155      19.316  -42.572  -41.227  1.00 44.73      A    N
ATOM  19908  CA   LEU I 155      18.725  -43.747  -41.893  1.00 45.60      A    C
ATOM  19909  C    LEU I 155      19.026  -43.668  -43.382  1.00 46.37      A    C
ATOM  19910  O    LEU I 155      18.839  -42.607  -43.986  1.00 46.56      A    O
ATOM  19911  CB   LEU I 155      17.205  -43.779  -41.724  1.00 45.38      A    C
ATOM  19912  CG   LEU I 155      16.587  -44.758  -40.724  1.00 45.40      A    C
ATOM  19913  CD1  LEU I 155      15.109  -44.915  -41.041  1.00 45.22      A    C
ATOM  19914  CD2  LEU I 155      17.281  -46.124  -40.737  1.00 45.83      A    C
ATOM  19915  N    ASP I 156      19.503  -44.768  -43.969  1.00 47.25      A    N
ATOM  19916  CA   ASP I 156      19.736  -44.827  -45.417  1.00 48.08      A    C
ATOM  19917  C    ASP I 156      20.619  -43.649  -45.918  1.00 47.94      A    C
ATOM  19918  O    ASP I 156      20.109  -42.674  -46.521  1.00 47.67      A    O
ATOM  19919  CB   ASP I 156      18.371  -44.851  -46.131  1.00 48.63      A    C
ATOM  19920  CG   ASP I 156      18.454  -45.261  -47.615  1.00 50.25      A    C
ATOM  19921  OD1  ASP I 156      19.572  -45.383  -48.178  1.00 51.17      A    O
ATOM  19922  OD2  ASP I 156      17.362  -45.449  -48.219  1.00 51.74      A    O
ATOM  19923  N    PRO I 157      21.948  -43.737  -45.667  1.00 48.06      A    N
ATOM  19924  CA   PRO I 157      22.875  -42.662  -46.091  1.00 48.13      A    C
ATOM  19925  C    PRO I 157      22.867  -42.434  -47.602  1.00 48.44      A    C
ATOM  19926  O    PRO I 157      23.220  -41.330  -48.066  1.00 48.27      A    O
ATOM  19927  CB   PRO I 157      24.257  -43.188  -45.662  1.00 48.08      A    C
ATOM  19928  CG   PRO I 157      23.973  -44.193  -44.588  1.00 48.10      A    C
ATOM  19929  CD   PRO I 157      22.655  -44.826  -44.955  1.00 48.15      A    C
ATOM  19930  N    ARG I 158      22.466  -43.482  -48.341  1.00 48.99      A    N
ATOM  19931  CA   ARG I 158      22.449  -43.470  -49.813  1.00 49.47      A    C
ATOM  19932  C    ARG I 158      21.281  -42.664  -50.421  1.00 49.28      A    C
ATOM  19933  O    ARG I 158      21.378  -42.215  -51.568  1.00 49.56      A    O
ATOM  19934  CB   ARG I 158      22.584  -44.888  -50.421  1.00 49.93      A    C
ATOM  19935  CG   ARG I 158      21.627  -45.945  -49.892  1.00 50.25      A    C
ATOM  19936  N    ALA I 159      20.208  -42.466  -49.653  1.00 48.76      A    N
ATOM  19937  CA   ALA I 159      19.104  -41.612  -50.093  1.00 48.37      A    C
ATOM  19938  C    ALA I 159      19.597  -40.201  -50.453  1.00 48.06      A    C
ATOM  19939  O    ALA I 159      20.451  -39.640  -49.757  1.00 47.81      A    O
ATOM  19940  CB   ALA I 159      18.013  -41.552  -49.036  1.00 48.23      A    C
ATOM  19941  N    ALA I 160      19.053  -39.649  -51.542  1.00 47.91      A    N
ATOM  19942  CA   ALA I 160      19.523  -38.379  -52.131  1.00 47.66      A    C
ATOM  19943  C    ALA I 160      19.337  -37.158  -51.221  1.00 47.14      A    C
ATOM  19944  O    ALA I 160      20.168  -36.241  -51.218  1.00 47.04      A    O
ATOM  19945  CB   ALA I 160      18.853  -38.143  -53.496  1.00 48.04      A    C
ATOM  19946  N    ARG I 161      18.241  -37.166  -50.463  1.00 46.56      A    N
ATOM  19947  CA   ARG I 161      17.892  -36.094  -49.530  1.00 45.96      A    C
ATOM  19948  C    ARG I 161      17.308  -36.648  -48.215  1.00 45.17      A    C
ATOM  19949  O    ARG I 161      16.826  -37.786  -48.161  1.00 45.26      A    O
ATOM  19950  CB   ARG I 161      16.911  -35.116  -50.182  1.00 46.19      A    C
ATOM  19951  CG   ARG I 161      17.556  -34.088  -51.113  1.00 47.56      A    C
ATOM  19952  CD   ARG I 161      16.662  -33.863  -52.324  1.00 50.43      A    C
ATOM  19953  NE   ARG I 161      15.238  -34.058  -52.004  1.00 52.65      A    N
ATOM  19954  CZ   ARG I 161      14.355  -34.671  -52.797  1.00 53.88      A    C
ATOM  19955  NH1  ARG I 161      14.728  -35.168  -53.974  1.00 54.68      A    N
```

FIGURE 1 (cont'd)

```
ATOM  19956  NH2  ARG I 161      13.094 -34.795 -52.406  1.00 54.15      A    N
ATOM  19957  N    HIS I 162      17.379 -35.836 -47.155  1.00 44.14      A    N
ATOM  19958  CA   HIS I 162      16.850 -36.202 -45.829  1.00 43.08      A    C
ATOM  19959  C    HIS I 162      16.282 -34.996 -45.071  1.00 42.02      A    C
ATOM  19960  O    HIS I 162      16.787 -33.847 -45.185  1.00 41.72      A    O
ATOM  19961  CB   HIS I 162      17.908 -36.929 -44.963  1.00 43.25      A    C
ATOM  19962  CG   HIS I 162      19.234 -36.228 -44.915  1.00 43.91      A    C
ATOM  19963  CD2  HIS I 162      20.433 -36.548 -45.462  1.00 44.47      A    C
ATOM  19964  ND1  HIS I 162      19.422 -35.029 -44.254  1.00 44.11      A    N
ATOM  19965  CE1  HIS I 162      20.679 -34.643 -44.395  1.00 44.31      A    C
ATOM  19966  NE2  HIS I 162      21.314 -35.550 -45.118  1.00 44.58      A    N
ATOM  19967  N    LEU I 163      15.209 -35.273 -44.326  1.00 40.91      A    N
ATOM  19968  CA   LEU I 163      14.715 -34.353 -43.309  1.00 39.74      A    C
ATOM  19969  C    LEU I 163      15.674 -34.470 -42.146  1.00 39.05      A    C
ATOM  19970  O    LEU I 163      16.025 -35.590 -41.730  1.00 39.04      A    O
ATOM  19971  CB   LEU I 163      13.305 -34.731 -42.835  1.00 39.63      A    C
ATOM  19972  CG   LEU I 163      12.789 -34.047 -41.555  1.00 38.95      A    C
ATOM  19973  CD1  LEU I 163      12.599 -32.533 -41.762  1.00 38.48      A    C
ATOM  19974  CD2  LEU I 163      11.495 -34.706 -41.067  1.00 38.91      A    C
ATOM  19975  N    THR I 164      16.096 -33.315 -41.631  1.00 38.06      A    N
ATOM  19976  CA   THR I 164      17.053 -33.298 -40.542  1.00 37.07      A    C
ATOM  19977  C    THR I 164      16.593 -32.483 -39.327  1.00 36.48      A    C
ATOM  19978  O    THR I 164      16.364 -31.267 -39.395  1.00 36.22      A    O
ATOM  19979  CB   THR I 164      18.492 -32.962 -41.023  1.00 37.03      A    C
ATOM  19980  CG2  THR I 164      18.528 -31.690 -41.888  1.00 36.95      A    C
ATOM  19981  OG1  THR I 164      19.358 -32.823 -39.889  1.00 36.71      A    O
ATOM  19982  N    LEU I 165      16.435 -33.206 -38.221  1.00 35.91      A    N
ATOM  19983  CA   LEU I 165      16.102 -32.631 -36.916  1.00 35.35      A    C
ATOM  19984  C    LEU I 165      17.365 -32.525 -36.068  1.00 35.04      A    C
ATOM  19985  O    LEU I 165      18.248 -33.400 -36.130  1.00 35.09      A    O
ATOM  19986  CB   LEU I 165      15.064 -33.494 -36.176  1.00 35.27      A    C
ATOM  19987  CG   LEU I 165      13.718 -33.765 -36.857  1.00 35.35      A    C
ATOM  19988  CD1  LEU I 165      12.794 -34.493 -35.904  1.00 35.42      A    C
ATOM  19989  CD2  LEU I 165      13.062 -32.468 -37.384  1.00 35.11      A    C
ATOM  19990  N    ALA I 166      17.439 -31.461 -35.271  1.00 34.57      A    N
ATOM  19991  CA   ALA I 166      18.619 -31.202 -34.456  1.00 34.13      A    C
ATOM  19992  C    ALA I 166      18.289 -30.659 -33.068  1.00 33.85      A    C
ATOM  19993  O    ALA I 166      17.324 -29.907 -32.889  1.00 33.69      A    O
ATOM  19994  CB   ALA I 166      19.577 -30.256 -35.195  1.00 34.10      A    C
ATOM  19995  N    CYS I 167      19.093 -31.082 -32.097  1.00 33.67      A    N
ATOM  19996  CA   CYS I 167      19.123 -30.524 -30.747  1.00 33.53      A    C
ATOM  19997  C    CYS I 167      20.592 -30.439 -30.378  1.00 33.51      A    C
ATOM  19998  O    CYS I 167      21.430 -31.034 -31.064  1.00 33.63      A    O
ATOM  19999  CB   CYS I 167      18.426 -31.465 -29.770  1.00 33.50      A    C
ATOM  20000  SG   CYS I 167      19.312 -33.071 -29.555  1.00 33.78      A    S
ATOM  20001  N    HIS I 168      20.921 -29.730 -29.301  1.00 33.48      A    N
ATOM  20002  CA   HIS I 168      22.294 -29.792 -28.769  1.00 33.54      A    C
ATOM  20003  C    HIS I 168      22.328 -30.524 -27.425  1.00 33.44      A    C
ATOM  20004  O    HIS I 168      21.511 -30.262 -26.539  1.00 33.36      A    O
ATOM  20005  CB   HIS I 168      22.932 -28.400 -28.664  1.00 33.64      A    C
ATOM  20006  CG   HIS I 168      22.462 -27.623 -27.480  1.00 34.03      A    C
ATOM  20007  CD2  HIS I 168      21.443 -26.744 -27.343  1.00 34.36      A    C
ATOM  20008  ND1  HIS I 168      23.031 -27.753 -26.231  1.00 34.36      A    N
ATOM  20009  CE1  HIS I 168      22.396 -26.969 -25.378  1.00 34.41      A    C
ATOM  20010  NE2  HIS I 168      21.427 -26.349 -26.027  1.00 34.37      A    N
ATOM  20011  N    TYR I 169      23.279 -31.437 -27.280  1.00 33.51      A    N
ATOM  20012  CA   TYR I 169      23.312 -32.302 -26.103  1.00 33.71      A    C
ATOM  20013  C    TYR I 169      24.259 -31.823 -24.983  1.00 33.81      A    C
ATOM  20014  O    TYR I 169      24.207 -32.338 -23.854  1.00 33.80      A    O
ATOM  20015  CB   TYR I 169      23.608 -33.764 -26.504  1.00 33.77      A    C
ATOM  20016  CG   TYR I 169      25.080 -34.074 -26.772  1.00 34.02      A    C
ATOM  20017  CD1  TYR I 169      25.670 -33.750 -28.013  1.00 33.86      A    C
ATOM  20018  CD2  TYR I 169      25.881 -34.700 -25.788  1.00 34.44      A    C
ATOM  20019  CE1  TYR I 169      27.016 -34.028 -28.266  1.00 33.96      A    C
ATOM  20020  CE2  TYR I 169      27.233 -34.983 -26.035  1.00 34.65      A    C
```

FIGURE 1 (cont'd)

```
ATOM  20021  CZ   TYR I 169      27.793 -34.642 -27.274  1.00 34.26      A    C
ATOM  20022  OH   TYR I 169      29.122 -34.916 -27.517  1.00 34.30      A    O
ATOM  20023  N    ASP I 170      25.127 -30.857 -25.291  1.00 33.91      A    N
ATOM  20024  CA   ASP I 170      25.957 -30.253 -24.253  1.00 34.25      A    C
ATOM  20025  C    ASP I 170      25.073 -29.431 -23.285  1.00 34.50      A    C
ATOM  20026  O    ASP I 170      23.928 -29.063 -23.629  1.00 34.31      A    O
ATOM  20027  CB   ASP I 170      27.060 -29.389 -24.874  1.00 34.26      A    C
ATOM  20028  CG   ASP I 170      26.512 -28.160 -25.595  1.00 34.20      A    C
ATOM  20029  OD1  ASP I 170      25.685 -28.326 -26.521  1.00 33.80      A    O
ATOM  20030  OD2  ASP I 170      26.918 -27.028 -25.236  1.00 34.61      A    O
ATOM  20031  N    SER I 171      25.592 -29.185 -22.076  1.00 34.96      A    N
ATOM  20032  CA   SER I 171      24.945 -28.296 -21.101  1.00 35.38      A    C
ATOM  20033  C    SER I 171      25.881 -27.131 -20.809  1.00 35.66      A    C
ATOM  20034  O    SER I 171      27.104 -27.316 -20.813  1.00 35.98      A    O
ATOM  20035  CB   SER I 171      24.602 -29.047 -19.804  1.00 35.43      A    C
ATOM  20036  OG   SER I 171      25.729 -29.175 -18.944  1.00 35.84      A    O
ATOM  20037  N    LYS I 172      25.326 -25.943 -20.552  1.00 35.84      A    N
ATOM  20038  CA   LYS I 172      26.162 -24.759 -20.275  1.00 36.25      A    C
ATOM  20039  C    LYS I 172      27.074 -24.952 -19.057  1.00 36.94      A    C
ATOM  20040  O    LYS I 172      26.726 -25.668 -18.110  1.00 37.19      A    O
ATOM  20041  CB   LYS I 172      25.333 -23.475 -20.131  1.00 35.93      A    C
ATOM  20042  CG   LYS I 172      26.178 -22.209 -20.285  1.00 35.71      A    C
ATOM  20043  CD   LYS I 172      25.368 -20.928 -20.092  1.00 35.13      A    C
ATOM  20044  CE   LYS I 172      26.242 -19.661 -20.083  1.00 35.09      A    C
ATOM  20045  NZ   LYS I 172      26.710 -19.262 -21.434  1.00 35.03      A    N
ATOM  20046  N    LEU I 173      28.249 -24.330 -19.118  1.00 37.70      A    N
ATOM  20047  CA   LEU I 173      29.217 -24.367 -18.034  1.00 38.60      A    C
ATOM  20048  C    LEU I 173      29.106 -23.109 -17.161  1.00 39.14      A    C
ATOM  20049  O    LEU I 173      29.194 -21.978 -17.661  1.00 39.20      A    O
ATOM  20050  CB   LEU I 173      30.625 -24.474 -18.612  1.00 38.68      A    C
ATOM  20051  CG   LEU I 173      31.810 -24.337 -17.645  1.00 39.29      A    C
ATOM  20052  CD1  LEU I 173      32.319 -25.705 -17.144  1.00 39.58      A    C
ATOM  20053  CD2  LEU I 173      32.930 -23.518 -18.292  1.00 39.43      A    C
ATOM  20054  N    PHE I 174      28.926 -23.320 -15.855  1.00 39.84      A    N
ATOM  20055  CA   PHE I 174      28.782 -22.219 -14.894  1.00 40.45      A    C
ATOM  20056  C    PHE I 174      29.890 -22.190 -13.830  1.00 40.45      A    C
ATOM  20057  O    PHE I 174      30.530 -23.205 -13.547  1.00 41.47      A    O
ATOM  20058  CB   PHE I 174      27.406 -22.277 -14.226  1.00 40.62      A    C
ATOM  20059  CG   PHE I 174      26.288 -21.768 -15.094  1.00 40.48      A    C
ATOM  20060  CD1  PHE I 174      26.056 -20.396 -15.209  1.00 40.60      A    C
ATOM  20061  CD2  PHE I 174      25.464 -22.656 -15.791  1.00 40.03      A    C
ATOM  20062  CE1  PHE I 174      25.027 -19.912 -16.005  1.00 40.12      A    C
ATOM  20063  CE2  PHE I 174      24.428 -22.188 -16.591  1.00 39.56      A    C
ATOM  20064  CZ   PHE I 174      24.206 -20.809 -16.697  1.00 39.70      A    C
TER   20065       PHE I 174
ATOM  20066  N    SER I 178      28.928 -23.749  -7.546  1.00 47.25      A    N
ATOM  20067  CA   SER I 178      27.649 -23.183  -7.163  1.00 46.95      A    C
ATOM  20068  C    SER I 178      26.488 -24.123  -7.024  1.00 46.91      A    C
ATOM  20069  O    SER I 178      26.296 -24.654  -5.950  1.00 47.49      A    O
ATOM  20070  CB   SER I 178      27.283 -22.112  -8.125  1.00 45.27      A    C
ATOM  20071  OG   SER I 178      28.261 -21.122  -7.980  1.00 44.55      A    O
ATOM  20072  N    THR I 179      25.672 -24.303  -8.052  1.00 45.48      A    N
ATOM  20073  CA   THR I 179      24.730 -25.408  -7.989  1.00 43.05      A    C
ATOM  20074  C    THR I 179      24.691 -26.031  -9.367  1.00 43.54      A    C
ATOM  20075  O    THR I 179      24.664 -25.319 -10.375  1.00 44.43      A    O
ATOM  20076  CB   THR I 179      23.349 -24.993  -7.395  1.00 37.60      A    C
ATOM  20077  OG1  THR I 179      22.294 -25.366  -8.281  1.00 34.55      A    O
ATOM  20078  N    PRO I 180      24.756 -27.366  -9.414  1.00 42.46      A    N
ATOM  20079  CA   PRO I 180      24.862 -28.092 -10.671  1.00 41.29      A    C
ATOM  20080  C    PRO I 180      23.783 -27.648 -11.663  1.00 42.07      A    C
ATOM  20081  O    PRO I 180      22.642 -27.411 -11.259  1.00 42.95      A    O
ATOM  20082  CB   PRO I 180      24.656 -29.552 -10.247  1.00 36.47      A    C
ATOM  20083  CG   PRO I 180      23.755 -29.504  -9.029  1.00 34.71      A    C
ATOM  20084  N    PHE I 181      24.147 -27.510 -12.936  1.00 41.83      A    N
ATOM  20085  CA   PHE I 181      23.194 -27.082 -13.964  1.00 40.96      A    C
```

FIGURE 1 (cont'd)

```
ATOM  20086  C    PHE I 181      22.976 -28.146 -15.033  1.00 40.24      A  C
ATOM  20087  O    PHE I 181      23.897 -28.486 -15.774  1.00 40.07      A  O
ATOM  20088  CB   PHE I 181      23.641 -25.766 -14.602  1.00 41.01      A  C
ATOM  20089  CG   PHE I 181      22.828 -25.370 -15.803  1.00 40.76      A  C
ATOM  20090  CD1  PHE I 181      21.524 -24.896 -15.659  1.00 40.89      A  C
ATOM  20091  CD2  PHE I 181      23.367 -25.466 -17.080  1.00 40.51      A  C
ATOM  20092  CE1  PHE I 181      20.768 -24.516 -16.777  1.00 40.30      A  C
ATOM  20093  CE2  PHE I 181      22.621 -25.093 -18.201  1.00 40.02      A  C
ATOM  20094  CZ   PHE I 181      21.318 -24.614 -18.049  1.00 39.77      A  C
ATOM  20095  N    VAL I 182      21.752 -28.656 -15.115  1.00 39.43      A  N
ATOM  20096  CA   VAL I 182      21.442 -29.752 -16.033  1.00 38.72      A  C
ATOM  20097  C    VAL I 182      20.695 -29.314 -17.299  1.00 37.95      A  C
ATOM  20098  O    VAL I 182      20.586 -30.097 -18.250  1.00 37.81      A  O
ATOM  20099  CB   VAL I 182      20.692 -30.942 -15.342  1.00 38.76      A  C
ATOM  20100  CG1  VAL I 182      21.647 -31.779 -14.537  1.00 39.07      A  C
ATOM  20101  CG2  VAL I 182      19.546 -30.452 -14.474  1.00 39.13      A  C
ATOM  20102  N    GLY I 183      20.191 -28.081 -17.311  1.00 37.23      A  N
ATOM  20103  CA   GLY I 183      19.430 -27.557 -18.456  1.00 36.27      A  C
ATOM  20104  C    GLY I 183      18.444 -28.544 -19.065  1.00 35.62      A  C
ATOM  20105  O    GLY I 183      18.702 -29.121 -20.136  1.00 35.46      A  O
ATOM  20106  N    ALA I 184      17.321 -28.753 -18.379  1.00 35.09      A  N
ATOM  20107  CA   ALA I 184      16.298 -29.688 -18.852  1.00 34.52      A  C
ATOM  20108  C    ALA I 184      15.677 -29.229 -20.183  1.00 33.95      A  C
ATOM  20109  O    ALA I 184      15.583 -30.015 -21.128  1.00 33.76      A  O
ATOM  20110  CB   ALA I 184      15.228 -29.896 -17.782  1.00 34.83      A  C
ATOM  20111  N    THR I 185      15.292 -27.954 -20.258  1.00 33.37      A  N
ATOM  20112  CA   THR I 185      14.745 -27.387 -21.486  1.00 32.84      A  C
ATOM  20113  C    THR I 185      15.855 -27.090 -22.467  1.00 32.59      A  C
ATOM  20114  O    THR I 185      15.600 -26.833 -23.641  1.00 32.61      A  O
ATOM  20115  CB   THR I 185      13.996 -26.048 -21.253  1.00 32.77      A  C
ATOM  20116  CG2  THR I 185      13.070 -26.136 -20.039  1.00 33.02      A  C
ATOM  20117  OG1  THR I 185      14.937 -24.976 -21.090  1.00 32.39      A  O
ATOM  20118  N    ASP I 186      17.087 -27.133 -21.979  1.00 32.34      A  N
ATOM  20119  CA   ASP I 186      18.202 -26.544 -22.694  1.00 32.12      A  C
ATOM  20120  C    ASP I 186      19.442 -27.460 -22.732  1.00 32.17      A  C
ATOM  20121  O    ASP I 186      20.449 -27.156 -22.093  1.00 32.45      A  O
ATOM  20122  CB   ASP I 186      18.521 -25.201 -22.023  1.00 32.03      A  C
ATOM  20123  CG   ASP I 186      19.501 -24.351 -22.807  1.00 31.52      A  C
ATOM  20124  OD1  ASP I 186      19.836 -23.248 -22.306  1.00 31.36      A  O
ATOM  20125  OD2  ASP I 186      19.936 -24.768 -23.902  1.00 30.72      A  O
ATOM  20126  N    SER I 187      19.396 -28.557 -23.495  1.00 31.94      A  N
ATOM  20127  CA   SER I 187      18.280 -28.916 -24.377  1.00 31.67      A  C
ATOM  20128  C    SER I 187      17.944 -30.394 -24.241  1.00 31.64      A  C
ATOM  20129  O    SER I 187      17.675 -31.078 -25.238  1.00 31.51      A  O
ATOM  20130  CB   SER I 187      18.643 -28.598 -25.835  1.00 31.58      A  C
ATOM  20131  OG   SER I 187      18.583 -27.205 -26.104  1.00 31.70      A  O
ATOM  20132  N    ALA I 188      17.970 -30.885 -23.003  1.00 31.76      A  N
ATOM  20133  CA   ALA I 188      17.755 -32.310 -22.727  1.00 31.88      A  C
ATOM  20134  C    ALA I 188      16.454 -32.828 -23.363  1.00 31.90      A  C
ATOM  20135  O    ALA I 188      16.479 -33.805 -24.125  1.00 31.88      A  O
ATOM  20136  CB   ALA I 188      17.779 -32.579 -21.226  1.00 32.01      A  C
ATOM  20137  N    VAL I 189      15.338 -32.146 -23.070  1.00 31.84      A  N
ATOM  20138  CA   VAL I 189      14.010 -32.472 -23.637  1.00 31.70      A  C
ATOM  20139  C    VAL I 189      14.038 -32.519 -25.172  1.00 31.65      A  C
ATOM  20140  O    VAL I 189      13.649 -33.534 -25.754  1.00 31.74      A  O
ATOM  20141  CB   VAL I 189      12.879 -31.525 -23.109  1.00 31.59      A  C
ATOM  20142  CG1  VAL I 189      11.573 -31.739 -23.868  1.00 31.36      A  C
ATOM  20143  CG2  VAL I 189      12.666 -31.730 -21.615  1.00 31.78      A  C
ATOM  20144  N    PRO I 190      14.513 -31.440 -25.828  1.00 31.55      A  N
ATOM  20145  CA   PRO I 190      14.659 -31.520 -27.285  1.00 31.59      A  C
ATOM  20146  C    PRO I 190      15.346 -32.800 -27.746  1.00 31.79      A  C
ATOM  20147  O    PRO I 190      14.840 -33.478 -28.643  1.00 31.81      A  O
ATOM  20148  CB   PRO I 190      15.504 -30.290 -27.617  1.00 31.37      A  C
ATOM  20149  CG   PRO I 190      15.038 -29.283 -26.617  1.00 31.35      A  C
ATOM  20150  CD   PRO I 190      14.731 -30.062 -25.345  1.00 31.50      A  C
```

FIGURE 1 (cont'd)

```
ATOM  20151  N    CYS I 191      16.460 -33.145 -27.114  1.00 32.14      A  N
ATOM  20152  CA   CYS I 191      17.192 -34.351 -27.498  1.00 32.73      A  C
ATOM  20153  C    CYS I 191      16.404 -35.627 -27.213  1.00 33.00      A  C
ATOM  20154  O    CYS I 191      16.413 -36.571 -28.008  1.00 33.16      A  O
ATOM  20155  CB   CYS I 191      18.579 -34.390 -26.839  1.00 32.79      A  C
ATOM  20156  SG   CYS I 191      19.759 -33.172 -27.542  1.00 33.46      A  S
ATOM  20157  N    ALA I 192      15.709 -35.636 -26.083  1.00 33.24      A  N
ATOM  20158  CA   ALA I 192      14.920 -36.788 -25.668  1.00 33.47      A  C
ATOM  20159  C    ALA I 192      13.838 -37.091 -26.694  1.00 33.43      A  C
ATOM  20160  O    ALA I 192      13.576 -38.258 -27.000  1.00 33.69      A  O
ATOM  20161  CB   ALA I 192      14.310 -36.550 -24.275  1.00 33.60      A  C
ATOM  20162  N    LEU I 193      13.231 -36.030 -27.226  1.00 33.04      A  N
ATOM  20163  CA   LEU I 193      12.162 -36.147 -28.222  1.00 32.68      A  C
ATOM  20164  C    LEU I 193      12.669 -36.792 -29.506  1.00 33.22      A  C
ATOM  20165  O    LEU I 193      12.058 -37.740 -30.016  1.00 33.57      A  O
ATOM  20166  CB   LEU I 193      11.535 -34.775 -28.527  1.00 31.37      A  C
ATOM  20167  CG   LEU I 193      10.664 -34.122 -27.442  1.00 29.78      A  C
ATOM  20168  CD1  LEU I 193      10.301 -32.710 -27.880  1.00 28.78      A  C
ATOM  20169  N    LEU I 194      13.793 -36.282 -30.012  1.00 33.44      A  N
ATOM  20170  CA   LEU I 194      14.444 -36.853 -31.195  1.00 33.60      A  C
ATOM  20171  C    LEU I 194      14.647 -38.368 -31.059  1.00 34.48      A  C
ATOM  20172  O    LEU I 194      14.450 -39.105 -32.020  1.00 34.76      A  O
ATOM  20173  CB   LEU I 194      15.770 -36.145 -31.482  1.00 32.48      A  C
ATOM  20174  CG   LEU I 194      15.614 -34.709 -31.996  1.00 31.30      A  C
ATOM  20175  CD1  LEU I 194      16.794 -34.310 -32.876  1.00 30.91      A  C
ATOM  20176  N    LEU I 195      15.010 -38.815 -29.856  1.00 35.28      A  N
ATOM  20177  CA   LEU I 195      15.161 -40.238 -29.553  1.00 36.12      A  C
ATOM  20178  C    LEU I 195      13.830 -40.970 -29.555  1.00 36.84      A  C
ATOM  20179  O    LEU I 195      13.691 -42.020 -30.196  1.00 37.15      A  O
ATOM  20180  CB   LEU I 195      15.835 -40.448 -28.191  1.00 36.05      A  C
ATOM  20181  CG   LEU I 195      17.307 -40.036 -28.054  1.00 35.87      A  C
ATOM  20182  CD1  LEU I 195      17.750 -40.185 -26.608  1.00 36.09      A  C
ATOM  20183  CD2  LEU I 195      18.231 -40.837 -28.991  1.00 35.88      A  C
ATOM  20184  N    GLU I 196      12.862 -40.416 -28.823  1.00 37.45      A  N
ATOM  20185  CA   GLU I 196      11.514 -40.995 -28.720  1.00 38.08      A  C
ATOM  20186  C    GLU I 196      10.815 -41.125 -30.082  1.00 38.16      A  C
ATOM  20187  O    GLU I 196      10.246 -42.181 -30.396  1.00 38.32      A  O
ATOM  20188  CB   GLU I 196      10.653 -40.176 -27.744  1.00 38.21      A  C
ATOM  20189  CG   GLU I 196       9.148 -40.500 -27.772  1.00 39.31      A  C
ATOM  20190  CD   GLU I 196       8.790 -41.893 -27.238  1.00 40.80      A  C
ATOM  20191  OE1  GLU I 196       9.682 -42.617 -26.717  1.00 41.41      A  O
ATOM  20192  OE2  GLU I 196       7.594 -42.254 -27.340  1.00 41.51      A  O
ATOM  20193  N    LEU I 197      10.862 -40.044 -30.867  1.00 38.15      A  N
ATOM  20194  CA   LEU I 197      10.351 -40.035 -32.235  1.00 38.38      A  C
ATOM  20195  C    LEU I 197      10.959 -41.155 -33.062  1.00 38.89      A  C
ATOM  20196  O    LEU I 197      10.234 -41.900 -33.719  1.00 39.18      A  O
ATOM  20197  CB   LEU I 197      10.655 -38.703 -32.915  1.00 37.97      A  C
ATOM  20198  CG   LEU I 197       9.521 -37.684 -32.991  1.00 37.76      A  C
ATOM  20199  CD1  LEU I 197       9.355 -36.913 -31.687  1.00 37.62      A  C
ATOM  20200  CD2  LEU I 197       9.772 -36.719 -34.134  1.00 37.67      A  C
ATOM  20201  N    ALA I 198      12.287 -41.273 -33.018  1.00 39.35      A  N
ATOM  20202  CA   ALA I 198      13.016 -42.276 -33.801  1.00 40.07      A  C
ATOM  20203  C    ALA I 198      12.646 -43.704 -33.421  1.00 40.81      A  C
ATOM  20204  O    ALA I 198      12.731 -44.614 -34.255  1.00 41.11      A  O
ATOM  20205  CB   ALA I 198      14.509 -42.076 -33.653  1.00 39.92      A  C
ATOM  20206  N    GLN I 199      12.243 -43.882 -32.163  1.00 41.38      A  N
ATOM  20207  CA   GLN I 199      11.881 -45.180 -31.625  1.00 42.05      A  C
ATOM  20208  C    GLN I 199      10.407 -45.495 -31.904  1.00 42.98      A  C
ATOM  20209  O    GLN I 199      10.070 -46.600 -32.340  1.00 43.55      A  O
ATOM  20210  CB   GLN I 199      12.144 -45.193 -30.123  1.00 40.95      A  C
ATOM  20211  CG   GLN I 199      12.988 -46.351 -29.645  1.00 40.41      A  C
ATOM  20212  CD   GLN I 199      12.454 -47.712 -30.049  1.00 40.17      A  C
ATOM  20213  OE1  GLN I 199      11.444 -48.177 -29.520  1.00 40.50      A  O
ATOM  20214  N    ALA I 200       9.537 -44.515 -31.650  1.00 43.69      A  N
ATOM  20215  CA   ALA I 200       8.085 -44.668 -31.860  1.00 44.41      A  C
```

FIGURE 1 (cont'd)

```
ATOM  20216  C   ALA I 200      7.726 -44.926 -33.334  1.00 44.94      A    C
ATOM  20217  O   ALA I 200      6.862 -45.764 -33.635  1.00 45.36      A    O
ATOM  20218  CB  ALA I 200      7.320 -43.444 -31.310  1.00 44.13      A    C
ATOM  20219  N   LEU I 201      8.403 -44.210 -34.235  1.00 45.27      A    N
ATOM  20220  CA  LEU I 201      8.186 -44.348 -35.678  1.00 45.82      A    C
ATOM  20221  C   LEU I 201      9.172 -45.319 -36.300  1.00 46.55      A    C
ATOM  20222  O   LEU I 201      9.259 -45.407 -37.534  1.00 46.79      A    O
ATOM  20223  CB  LEU I 201      8.307 -42.994 -36.390  1.00 45.34      A    C
ATOM  20224  CG  LEU I 201      7.280 -41.936 -36.003  1.00 45.11      A    C
ATOM  20225  CD1 LEU I 201      7.726 -40.548 -36.461  1.00 44.78      A    C
ATOM  20226  CD2 LEU I 201      5.880 -42.294 -36.514  1.00 45.38      A    C
ATOM  20227  N   ASP I 202      9.904 -46.041 -35.447  1.00 47.28      A    N
ATOM  20228  CA  ASP I 202     10.980 -46.917 -35.885  1.00 48.10      A    C
ATOM  20229  C   ASP I 202     10.553 -47.883 -36.999  1.00 48.74      A    C
ATOM  20230  O   ASP I 202     11.254 -47.990 -38.021  1.00 48.96      A    O
ATOM  20231  CB  ASP I 202     11.554 -47.675 -34.687  1.00 48.22      A    C
ATOM  20232  CG  ASP I 202     12.621 -48.679 -35.081  1.00 48.68      A    C
ATOM  20233  OD1 ASP I 202     13.637 -48.285 -35.714  1.00 48.51      A    O
ATOM  20234  OD2 ASP I 202     12.428 -49.870 -34.741  1.00 49.43      A    O
ATOM  20235  N   LEU I 203      9.406 -48.554 -36.813  1.00 49.15      A    N
ATOM  20236  CA  LEU I 203      8.938 -49.584 -37.764  1.00 49.34      A    C
ATOM  20237  C   LEU I 203      8.453 -49.037 -39.101  1.00 49.56      A    C
ATOM  20238  O   LEU I 203      8.827 -49.556 -40.147  1.00 49.96      A    O
ATOM  20239  CB  LEU I 203      7.890 -50.496 -37.131  1.00 48.36      A    C
ATOM  20240  CG  LEU I 203      8.498 -51.600 -36.262  1.00 48.08      A    C
ATOM  20241  CD1 LEU I 203      8.429 -51.223 -34.790  1.00 47.97      A    C
ATOM  20242  N   GLU I 204      7.629 -47.995 -39.061  1.00 49.36      A    N
ATOM  20243  CA  GLU I 204      7.226 -47.285 -40.284  1.00 49.01      A    C
ATOM  20244  C   GLU I 204      8.414 -46.607 -40.990  1.00 49.47      A    C
ATOM  20245  O   GLU I 204      8.420 -46.477 -42.223  1.00 49.76      A    O
ATOM  20246  CB  GLU I 204      6.088 -46.280 -40.024  1.00 47.48      A    C
ATOM  20247  CG  GLU I 204      6.062 -45.692 -38.628  1.00 45.82      A    C
ATOM  20248  CD  GLU I 204      5.560 -46.679 -37.601  1.00 45.07      A    C
ATOM  20249  OE1 GLU I 204      4.338 -46.899 -37.575  1.00 45.26      A    O
ATOM  20250  N   LEU I 205      9.407 -46.178 -40.205  1.00 49.65      A    N
ATOM  20251  CA  LEU I 205     10.665 -45.633 -40.737  1.00 49.80      A    C
ATOM  20252  C   LEU I 205     11.515 -46.718 -41.380  1.00 50.51      A    C
ATOM  20253  O   LEU I 205     12.231 -46.472 -42.356  1.00 50.58      A    O
ATOM  20254  CB  LEU I 205     11.481 -44.958 -39.631  1.00 49.24      A    C
ATOM  20255  CG  LEU I 205     11.328 -43.453 -39.403  1.00 48.26      A    C
ATOM  20256  CD1 LEU I 205     11.933 -43.107 -38.058  1.00 47.84      A    C
ATOM  20257  CD2 LEU I 205     11.973 -42.627 -40.540  1.00 47.63      A    C
ATOM  20258  N   SER I 206     11.432 -47.916 -40.811  1.00 51.37      A    N
ATOM  20259  CA  SER I 206     12.205 -49.062 -41.278  1.00 52.27      A    C
ATOM  20260  C   SER I 206     11.743 -49.537 -42.660  1.00 52.76      A    C
ATOM  20261  O   SER I 206     12.548 -49.574 -43.598  1.00 52.79      A    O
ATOM  20262  CB  SER I 206     12.139 -50.204 -40.257  1.00 52.47      A    C
ATOM  20263  OG  SER I 206     13.197 -51.115 -40.456  1.00 53.14      A    O
ATOM  20264  N   ARG I 207     10.453 -49.888 -42.778  1.00 53.31      A    N
ATOM  20265  CA  ARG I 207      9.883 -50.367 -44.050  1.00 53.79      A    C
ATOM  20266  C   ARG I 207     10.178 -49.389 -45.201  1.00 53.79      A    C
ATOM  20267  O   ARG I 207     10.778 -49.791 -46.208  1.00 54.16      A    O
ATOM  20268  CB  ARG I 207      8.383 -50.753 -43.942  1.00 54.03      A    C
ATOM  20269  CG  ARG I 207      7.420 -49.666 -43.478  1.00 53.55      A    C
ATOM  20270  N   ALA I 208      9.806 -48.115 -45.030  1.00 53.32      A    N
ATOM  20271  CA  ALA I 208     10.152 -47.074 -45.993  1.00 52.91      A    C
ATOM  20272  C   ALA I 208     11.663 -46.908 -45.983  1.00 52.67      A    C
ATOM  20273  O   ALA I 208     12.197 -46.011 -45.335  1.00 52.45      A    O
ATOM  20274  CB  ALA I 208      9.446 -45.760 -45.669  1.00 52.58      A    C
ATOM  20275  N   LYS I 209     12.327 -47.814 -46.700  1.00 52.74      A    N
ATOM  20276  CA  LYS I 209     13.780 -47.913 -46.800  1.00 52.43      A    C
ATOM  20277  C   LYS I 209     14.055 -49.257 -47.479  1.00 51.90      A    C
ATOM  20278  O   LYS I 209     15.073 -49.902 -47.265  1.00 52.82      A    O
ATOM  20279  CB  LYS I 209     14.434 -47.843 -45.416  1.00 52.44      A    C
ATOM  20280  CG  LYS I 209     15.930 -47.592 -45.429  1.00 52.73      A    C
```

FIGURE 1 (cont'd)

```
ATOM  20281  CD   LYS I 209      16.565 -48.196 -44.185  1.00 53.59      A    C
ATOM  20282  CE   LYS I 209      18.062 -47.935 -44.142  1.00 53.78      A    C
ATOM  20283  NZ   LYS I 209      18.699 -48.596 -42.975  1.00 53.91      A    N
TER   20284       LYS I 209
ATOM  20285  N    VAL I 215      13.546 -39.803 -49.818  1.00 36.38      A    N
ATOM  20286  CA   VAL I 215      13.801 -38.785 -48.787  1.00 36.25      A    C
ATOM  20287  C    VAL I 215      13.905 -39.406 -47.381  1.00 36.46      A    C
ATOM  20288  O    VAL I 215      12.907 -39.900 -46.834  1.00 36.73      A    O
ATOM  20289  CB   VAL I 215      12.729 -37.663 -48.802  1.00 35.46      A    C
ATOM  20290  CG1  VAL I 215      13.254 -36.421 -48.114  1.00 34.55      A    C
ATOM  20291  N    THR I 216      15.113 -39.372 -46.810  1.00 36.15      A    N
ATOM  20292  CA   THR I 216      15.395 -40.031 -45.528  1.00 35.63      A    C
ATOM  20293  C    THR I 216      15.256 -39.120 -44.291  1.00 35.16      A    C
ATOM  20294  O    THR I 216      14.747 -37.981 -44.380  1.00 35.12      A    O
ATOM  20295  CB   THR I 216      16.787 -40.699 -45.532  1.00 35.62      A    C
ATOM  20296  OG1  THR I 216      16.692 -41.973 -44.878  1.00 35.49      A    O
ATOM  20297  N    LEU I 217      15.697 -39.633 -43.139  1.00 34.53      A    N
ATOM  20298  CA   LEU I 217      15.656 -38.871 -41.891  1.00 33.76      A    C
ATOM  20299  C    LEU I 217      17.024 -38.810 -41.211  1.00 33.38      A    C
ATOM  20300  O    LEU I 217      17.736 -39.823 -41.101  1.00 33.59      A    O
ATOM  20301  CB   LEU I 217      14.616 -39.463 -40.933  1.00 33.67      A    C
ATOM  20302  CG   LEU I 217      14.540 -38.881 -39.514  1.00 33.11      A    C
ATOM  20303  CD1  LEU I 217      13.957 -37.459 -39.523  1.00 32.86      A    C
ATOM  20304  CD2  LEU I 217      13.737 -39.817 -38.620  1.00 33.17      A    C
ATOM  20305  N    GLN I 218      17.371 -37.616 -40.741  1.00 32.60      A    N
ATOM  20306  CA   GLN I 218      18.655 -37.391 -40.100  1.00 31.95      A    C
ATOM  20307  C    GLN I 218      18.483 -36.759 -38.719  1.00 31.37      A    C
ATOM  20308  O    GLN I 218      17.732 -35.784 -38.553  1.00 31.24      A    O
ATOM  20309  CB   GLN I 218      19.528 -36.513 -40.989  1.00 31.94      A    C
ATOM  20310  CG   GLN I 218      20.965 -36.400 -40.538  1.00 32.16      A    C
ATOM  20311  CD   GLN I 218      21.734 -35.401 -41.379  1.00 32.85      A    C
ATOM  20312  NE2  GLN I 218      21.299 -34.132 -41.352  1.00 32.89      A    N
ATOM  20313  OE1  GLN I 218      22.697 -35.764 -42.069  1.00 33.66      A    O
ATOM  20314  N    LEU I 219      19.178 -37.329 -37.731  1.00 30.81      A    N
ATOM  20315  CA   LEU I 219      19.160 -36.790 -36.358  1.00 30.12      A    C
ATOM  20316  C    LEU I 219      20.536 -36.272 -35.925  1.00 29.88      A    C
ATOM  20317  O    LEU I 219      21.536 -37.015 -35.911  1.00 29.97      A    O
ATOM  20318  CB   LEU I 219      18.643 -37.831 -35.369  1.00 29.95      A    C
ATOM  20319  CG   LEU I 219      17.232 -38.339 -35.664  1.00 29.68      A    C
ATOM  20320  CD1  LEU I 219      16.878 -39.490 -34.733  1.00 29.44      A    C
ATOM  20321  CD2  LEU I 219      16.196 -37.196 -35.594  1.00 29.24      A    C
ATOM  20322  N    LEU I 220      20.585 -34.987 -35.590  1.00 29.34      A    N
ATOM  20323  CA   LEU I 220      21.840 -34.369 -35.211  1.00 28.89      A    C
ATOM  20324  C    LEU I 220      21.800 -34.013 -33.729  1.00 28.98      A    C
ATOM  20325  O    LEU I 220      20.881 -33.340 -33.251  1.00 29.01      A    O
ATOM  20326  CB   LEU I 220      22.130 -33.146 -36.094  1.00 28.15      A    C
ATOM  20327  CG   LEU I 220      22.280 -33.424 -37.590  1.00 27.43      A    C
ATOM  20328  CD1  LEU I 220      22.651 -32.133 -38.301  1.00 27.00      A    C
ATOM  20329  N    PHE I 221      22.786 -34.520 -33.006  1.00 29.11      A    N
ATOM  20330  CA   PHE I 221      23.012 -34.143 -31.616  1.00 29.10      A    C
ATOM  20331  C    PHE I 221      24.349 -33.380 -31.525  1.00 29.17      A    C
ATOM  20332  O    PHE I 221      25.438 -33.974 -31.508  1.00 29.26      A    O
ATOM  20333  CB   PHE I 221      23.022 -35.381 -30.728  1.00 29.10      A    C
ATOM  20334  CG   PHE I 221      21.777 -36.206 -30.831  1.00 29.17      A    C
ATOM  20335  CD1  PHE I 221      20.758 -36.071 -29.877  1.00 29.24      A    C
ATOM  20336  CD2  PHE I 221      21.612 -37.139 -31.875  1.00 29.30      A    C
ATOM  20337  CE1  PHE I 221      19.575 -36.861 -29.947  1.00 29.28      A    C
ATOM  20338  CE2  PHE I 221      20.435 -37.947 -31.968  1.00 29.52      A    C
ATOM  20339  CZ   PHE I 221      19.413 -37.802 -30.999  1.00 29.40      A    C
ATOM  20340  N    LEU I 222      24.260 -32.059 -31.483  1.00 29.17      A    N
ATOM  20341  CA   LEU I 222      25.441 -31.209 -31.533  1.00 29.44      A    C
ATOM  20342  C    LEU I 222      26.082 -30.987 -30.159  1.00 29.81      A    C
ATOM  20343  O    LEU I 222      25.392 -30.772 -29.156  1.00 29.80      A    O
ATOM  20344  CB   LEU I 222      25.093 -29.868 -32.191  1.00 29.26      A    C
ATOM  20345  CG   LEU I 222      24.439 -30.041 -33.570  1.00 29.10      A    C
```

FIGURE 1 (cont'd)

```
ATOM  20346  CD1 LEU I 222      25.465 -29.978 -34.713  1.00 29.16      A  C
ATOM  20347  CD2 LEU I 222      23.365 -29.000 -33.764  1.00 28.74      A  C
ATOM  20348  N   ASP I 223      27.411 -31.057 -30.124  1.00 30.38      A  N
ATOM  20349  CA  ASP I 223      28.183 -30.736 -28.925  1.00 30.94      A  C
ATOM  20350  C   ASP I 223      28.490 -29.226 -28.898  1.00 30.95      A  C
ATOM  20351  O   ASP I 223      28.329 -28.520 -29.911  1.00 30.84      A  O
ATOM  20352  CB  ASP I 223      29.483 -31.570 -28.888  1.00 31.35      A  C
ATOM  20353  CG  ASP I 223      30.094 -31.682 -27.476  1.00 32.40      A  C
ATOM  20354  OD1 ASP I 223      29.423 -31.284 -26.493  1.00 33.31      A  O
ATOM  20355  OD2 ASP I 223      31.247 -32.172 -27.351  1.00 33.07      A  O
ATOM  20356  N   GLY I 224      28.904 -28.746 -27.726  1.00 31.06      A  N
ATOM  20357  CA  GLY I 224      29.399 -27.386 -27.556  1.00 31.27      A  C
ATOM  20358  C   GLY I 224      28.645 -26.325 -28.330  1.00 31.23      A  C
ATOM  20359  O   GLY I 224      29.185 -25.704 -29.255  1.00 31.41      A  O
ATOM  20360  N   GLU I 225      27.388 -26.127 -27.958  1.00 31.04      A  N
ATOM  20361  CA  GLU I 225      26.606 -25.052 -28.534  1.00 30.99      A  C
ATOM  20362  C   GLU I 225      26.683 -23.831 -27.612  1.00 31.06      A  C
ATOM  20363  O   GLU I 225      26.889 -22.691 -28.068  1.00 30.98      A  O
ATOM  20364  CB  GLU I 225      25.162 -25.513 -28.746  1.00 30.82      A  C
ATOM  20365  CG  GLU I 225      24.251 -24.452 -29.342  1.00 31.13      A  C
ATOM  20366  CD  GLU I 225      23.604 -23.568 -28.288  1.00 31.91      A  C
ATOM  20367  OE1 GLU I 225      23.269 -24.103 -27.203  1.00 32.62      A  O
ATOM  20368  OE2 GLU I 225      23.432 -22.344 -28.549  1.00 32.37      A  O
ATOM  20369  N   GLU I 226      26.518 -24.091 -26.315  1.00 31.35      A  N
ATOM  20370  CA  GLU I 226      26.583 -23.060 -25.281  1.00 31.82      A  C
ATOM  20371  C   GLU I 226      28.013 -22.553 -25.141  1.00 32.45      A  C
ATOM  20372  O   GLU I 226      28.964 -23.344 -25.136  1.00 32.61      A  O
ATOM  20373  CB  GLU I 226      26.099 -23.613 -23.927  1.00 31.71      A  C
ATOM  20374  CG  GLU I 226      24.677 -24.209 -23.916  1.00 30.97      A  C
ATOM  20375  CD  GLU I 226      23.583 -23.201 -23.561  1.00 30.30      A  C
ATOM  20376  OE1 GLU I 226      23.764 -21.969 -23.791  1.00 30.26      A  O
ATOM  20377  OE2 GLU I 226      22.533 -23.664 -23.049  1.00 29.67      A  O
ATOM  20378  N   ALA I 227      28.146 -21.235 -25.016  1.00 33.04      A  N
ATOM  20379  CA  ALA I 227      29.443 -20.570 -24.871  1.00 33.78      A  C
ATOM  20380  C   ALA I 227      30.210 -21.039 -23.629  1.00 34.42      A  C
ATOM  20381  O   ALA I 227      29.639 -21.692 -22.747  1.00 34.50      A  O
ATOM  20382  CB  ALA I 227      29.244 -19.057 -24.842  1.00 33.74      A  C
ATOM  20383  N   LEU I 228      31.500 -20.710 -23.564  1.00 35.22      A  N
ATOM  20384  CA  LEU I 228      32.305 -21.057 -22.385  1.00 35.97      A  C
ATOM  20385  C   LEU I 228      32.682 -19.877 -21.480  1.00 36.68      A  C
ATOM  20386  O   LEU I 228      32.615 -19.985 -20.246  1.00 36.89      A  O
ATOM  20387  CB  LEU I 228      33.544 -21.881 -22.765  1.00 35.92      A  C
ATOM  20388  CG  LEU I 228      33.412 -23.390 -23.036  1.00 35.24      A  C
ATOM  20389  CD1 LEU I 228      33.583 -23.670 -24.515  1.00 34.81      A  C
ATOM  20390  CD2 LEU I 228      32.120 -24.008 -22.497  1.00 34.59      A  C
ATOM  20391  N   LYS I 229      33.099 -18.769 -22.092  1.00 37.38      A  N
ATOM  20392  CA  LYS I 229      33.316 -17.535 -21.342  1.00 38.20      A  C
ATOM  20393  C   LYS I 229      32.051 -16.702 -21.518  1.00 38.21      A  C
ATOM  20394  O   LYS I 229      31.120 -16.846 -20.723  1.00 38.21      A  O
ATOM  20395  CB  LYS I 229      34.592 -16.782 -21.778  1.00 38.72      A  C
ATOM  20396  CG  LYS I 229      35.064 -15.644 -20.824  1.00 39.50      A  C
ATOM  20397  CD  LYS I 229      36.049 -16.141 -19.760  1.00 40.05      A  C
ATOM  20398  N   GLU I 230      31.992 -15.846 -22.538  1.00 38.37      A  N
ATOM  20399  CA  GLU I 230      30.712 -15.222 -22.890  1.00 38.57      A  C
ATOM  20400  C   GLU I 230      30.372 -15.301 -24.388  1.00 38.32      A  C
ATOM  20401  O   GLU I 230      31.260 -15.209 -25.252  1.00 38.33      A  O
ATOM  20402  CB  GLU I 230      30.538 -13.803 -22.308  1.00 38.95      A  C
ATOM  20403  CG  GLU I 230      29.033 -13.395 -22.124  1.00 39.91      A  C
ATOM  20404  CD  GLU I 230      28.174 -14.425 -21.310  1.00 40.11      A  C
ATOM  20405  OE1 GLU I 230      27.376 -15.224 -21.882  1.00 38.75      A  O
ATOM  20406  N   TRP I 231      29.075 -15.493 -24.652  1.00 37.98      A  N
ATOM  20407  CA  TRP I 231      28.519 -15.671 -25.980  1.00 37.69      A  C
ATOM  20408  C   TRP I 231      29.064 -14.656 -26.972  1.00 38.05      A  C
ATOM  20409  O   TRP I 231      29.071 -13.445 -26.710  1.00 38.36      A  O
ATOM  20410  CB  TRP I 231      26.997 -15.567 -25.923  1.00 37.35      A  C
```

FIGURE 1 (cont'd)

```
ATOM  20411  CG   TRP I 231      26.345 -15.997 -27.192  1.00 36.78      A  C
ATOM  20412  CD1  TRP I 231      26.105 -15.222 -28.293  1.00 36.72      A  C
ATOM  20413  CD2  TRP I 231      25.864 -17.314 -27.511  1.00 36.17      A  C
ATOM  20414  CE2  TRP I 231      25.342 -17.259 -28.821  1.00 35.92      A  C
ATOM  20415  CE3  TRP I 231      25.824 -18.535 -26.817  1.00 35.81      A  C
ATOM  20416  NE1  TRP I 231      25.502 -15.972 -29.276  1.00 36.39      A  N
ATOM  20417  CZ2  TRP I 231      24.782 -18.378 -29.450  1.00 35.27      A  C
ATOM  20418  CZ3  TRP I 231      25.267 -19.649 -27.449  1.00 35.06      A  C
ATOM  20419  CH2  TRP I 231      24.752 -19.558 -28.746  1.00 34.78      A  C
ATOM  20420  N    GLY I 232      29.522 -15.174 -28.109  1.00 38.19      A  N
ATOM  20421  CA   GLY I 232      30.065 -14.367 -29.191  1.00 38.52      A  C
ATOM  20422  C    GLY I 232      30.353 -15.245 -30.389  1.00 38.70      A  C
ATOM  20423  O    GLY I 232      30.321 -16.468 -30.286  1.00 38.40      A  O
ATOM  20424  N    PRO I 233      30.632 -14.622 -31.544  1.00 39.17      A  N
ATOM  20425  CA   PRO I 233      30.934 -15.351 -32.785  1.00 39.34      A  C
ATOM  20426  C    PRO I 233      32.028 -16.415 -32.611  1.00 39.54      A  C
ATOM  20427  O    PRO I 233      31.936 -17.513 -33.184  1.00 39.22      A  O
ATOM  20428  CB   PRO I 233      31.399 -14.239 -33.735  1.00 39.52      A  C
ATOM  20429  CG   PRO I 233      30.657 -13.022 -33.257  1.00 39.66      A  C
ATOM  20430  CD   PRO I 233      30.594 -13.159 -31.755  1.00 39.44      A  C
ATOM  20431  N    LYS I 234      33.044 -16.096 -31.813  1.00 40.12      A  N
ATOM  20432  CA   LYS I 234      34.173 -17.018 -31.602  1.00 40.72      A  C
ATOM  20433  C    LYS I 234      33.984 -17.960 -30.386  1.00 40.48      A  C
ATOM  20434  O    LYS I 234      34.729 -18.939 -30.211  1.00 40.57      A  O
ATOM  20435  CB   LYS I 234      35.520 -16.248 -31.562  1.00 41.31      A  C
ATOM  20436  CG   LYS I 234      36.113 -15.934 -32.966  1.00 42.36      A  C
ATOM  20437  CD   LYS I 234      37.041 -14.688 -32.996  1.00 43.54      A  C
ATOM  20438  CE   LYS I 234      38.515 -15.009 -32.684  1.00 43.77      A  C
ATOM  20439  N    ASP I 235      32.972 -17.667 -29.567  1.00 40.12      A  N
ATOM  20440  CA   ASP I 235      32.643 -18.489 -28.389  1.00 39.63      A  C
ATOM  20441  C    ASP I 235      31.151 -18.887 -28.381  1.00 39.11      A  C
ATOM  20442  O    ASP I 235      30.335 -18.304 -27.638  1.00 39.08      A  O
ATOM  20443  CB   ASP I 235      33.059 -17.777 -27.067  1.00 39.87      A  C
ATOM  20444  CG   ASP I 235      32.772 -18.625 -25.786  1.00 39.58      A  C
ATOM  20445  OD1  ASP I 235      32.472 -18.024 -24.724  1.00 39.26      A  O
ATOM  20446  OD2  ASP I 235      32.851 -19.883 -25.828  1.00 39.20      A  O
ATOM  20447  N    SER I 236      30.810 -19.870 -29.222  1.00 38.47      A  N
ATOM  20448  CA   SER I 236      29.455 -20.435 -29.311  1.00 37.81      A  C
ATOM  20449  C    SER I 236      29.329 -21.290 -30.556  1.00 37.54      A  C
ATOM  20450  O    SER I 236      29.954 -20.990 -31.581  1.00 37.57      A  O
ATOM  20451  CB   SER I 236      28.377 -19.339 -29.357  1.00 37.68      A  C
ATOM  20452  OG   SER I 236      28.416 -18.608 -30.573  1.00 37.61      A  O
ATOM  20453  N    LEU I 237      28.502 -22.335 -30.471  1.00 37.20      A  N
ATOM  20454  CA   LEU I 237      28.165 -23.162 -31.631  1.00 37.08      A  C
ATOM  20455  C    LEU I 237      29.406 -23.854 -32.219  1.00 37.29      A  C
ATOM  20456  O    LEU I 237      29.650 -23.817 -33.441  1.00 37.42      A  O
ATOM  20457  CB   LEU I 237      27.491 -22.306 -32.719  1.00 36.93      A  C
ATOM  20458  CG   LEU I 237      26.434 -21.262 -32.364  1.00 36.59      A  C
ATOM  20459  CD1  LEU I 237      26.275 -20.255 -33.492  1.00 36.66      A  C
ATOM  20460  CD2  LEU I 237      25.105 -21.937 -32.035  1.00 36.10      A  C
ATOM  20461  N    TYR I 238      30.204 -24.472 -31.355  1.00 37.41      A  N
ATOM  20462  CA   TYR I 238      31.384 -25.208 -31.821  1.00 37.55      A  C
ATOM  20463  C    TYR I 238      31.005 -26.458 -32.647  1.00 37.23      A  C
ATOM  20464  O    TYR I 238      31.602 -26.711 -33.708  1.00 37.33      A  O
ATOM  20465  CB   TYR I 238      32.313 -25.585 -30.650  1.00 37.84      A  C
ATOM  20466  CG   TYR I 238      32.840 -24.394 -29.883  1.00 38.41      A  C
ATOM  20467  CD1  TYR I 238      33.846 -23.575 -30.418  1.00 39.35      A  C
ATOM  20468  CD2  TYR I 238      32.328 -24.077 -28.628  1.00 38.50      A  C
ATOM  20469  CE1  TYR I 238      34.331 -22.458 -29.708  1.00 39.74      A  C
ATOM  20470  CE2  TYR I 238      32.804 -22.971 -27.908  1.00 39.00      A  C
ATOM  20471  CZ   TYR I 238      33.807 -22.163 -28.453  1.00 39.41      A  C
ATOM  20472  OH   TYR I 238      34.290 -21.077 -27.755  1.00 39.59      A  O
ATOM  20473  N    GLY I 239      30.019 -27.223 -32.164  1.00 36.77      A  N
ATOM  20474  CA   GLY I 239      29.578 -28.444 -32.846  1.00 36.47      A  C
ATOM  20475  C    GLY I 239      28.964 -28.195 -34.213  1.00 36.26      A  C
```

FIGURE 1 (cont'd)

```
ATOM  20476  O    GLY I 239      29.299 -28.873 -35.191  1.00 36.30      A    O
ATOM  20477  N    SER I 240      28.072 -27.207 -34.269  1.00 36.03      A    N
ATOM  20478  CA   SER I 240      27.356 -26.850 -35.499  1.00 35.78      A    C
ATOM  20479  C    SER I 240      28.246 -26.172 -36.532  1.00 35.75      A    C
ATOM  20480  O    SER I 240      28.210 -26.545 -37.707  1.00 35.86      A    O
ATOM  20481  CB   SER I 240      26.120 -25.992 -35.205  1.00 35.62      A    C
ATOM  20482  OG   SER I 240      26.410 -25.009 -34.230  1.00 35.94      A    O
ATOM  20483  N    ARG I 241      29.039 -25.191 -36.106  1.00 35.73      A    N
ATOM  20484  CA   ARG I 241      29.993 -24.543 -37.017  1.00 35.99      A    C
ATOM  20485  C    ARG I 241      30.981 -25.529 -37.672  1.00 36.05      A    C
ATOM  20486  O    ARG I 241      31.367 -25.367 -38.840  1.00 36.23      A    O
ATOM  20487  CB   ARG I 241      30.753 -23.410 -36.319  1.00 36.07      A    C
ATOM  20488  CG   ARG I 241      30.057 -22.064 -36.427  1.00 36.66      A    C
ATOM  20489  CD   ARG I 241      30.982 -20.903 -36.086  1.00 37.98      A    C
ATOM  20490  NE   ARG I 241      31.204 -20.771 -34.641  1.00 39.24      A    N
ATOM  20491  CZ   ARG I 241      32.320 -21.146 -34.007  1.00 40.21      A    C
ATOM  20492  NH1  ARG I 241      33.329 -21.680 -34.695  1.00 41.18      A    N
ATOM  20493  NH2  ARG I 241      32.435 -20.984 -32.683  1.00 40.51      A    N
ATOM  20494  N    HIS I 242      31.375 -26.548 -36.913  1.00 36.00      A    N
ATOM  20495  CA   HIS I 242      32.296 -27.561 -37.408  1.00 36.09      A    C
ATOM  20496  C    HIS I 242      31.603 -28.555 -38.349  1.00 35.77      A    C
ATOM  20497  O    HIS I 242      32.125 -28.841 -39.450  1.00 35.95      A    O
ATOM  20498  CB   HIS I 242      32.961 -28.307 -36.248  1.00 36.34      A    C
ATOM  20499  CG   HIS I 242      33.918 -29.363 -36.696  1.00 37.17      A    C
ATOM  20500  CD2  HIS I 242      35.211 -29.276 -37.095  1.00 37.97      A    C
ATOM  20501  ND1  HIS I 242      33.564 -30.694 -36.813  1.00 37.31      A    N
ATOM  20502  CE1  HIS I 242      34.607 -31.385 -37.244  1.00 38.00      A    C
ATOM  20503  NE2  HIS I 242      35.619 -30.549 -37.422  1.00 38.48      A    N
ATOM  20504  N    LEU I 243      30.451 -29.088 -37.910  1.00 35.17      A    N
ATOM  20505  CA   LEU I 243      29.663 -30.027 -38.734  1.00 34.70      A    C
ATOM  20506  C    LEU I 243      29.281 -29.415 -40.080  1.00 34.76      A    C
ATOM  20507  O    LEU I 243      29.447 -30.054 -41.116  1.00 34.92      A    O
ATOM  20508  CB   LEU I 243      28.408 -30.538 -38.004  1.00 34.25      A    C
ATOM  20509  CG   LEU I 243      27.615 -31.646 -38.725  1.00 33.52      A    C
ATOM  20510  CD1  LEU I 243      28.451 -32.918 -38.926  1.00 33.26      A    C
ATOM  20511  CD2  LEU I 243      26.336 -31.968 -37.978  1.00 32.89      A    C
ATOM  20512  N    ALA I 244      28.791 -28.176 -40.048  1.00 34.76      A    N
ATOM  20513  CA   ALA I 244      28.517 -27.419 -41.266  1.00 35.05      A    C
ATOM  20514  C    ALA I 244      29.731 -27.377 -42.198  1.00 35.52      A    C
ATOM  20515  O    ALA I 244      29.611 -27.661 -43.386  1.00 35.67      A    O
ATOM  20516  CB   ALA I 244      28.051 -26.014 -40.931  1.00 34.79      A    C
ATOM  20517  N    GLN I 245      30.897 -27.035 -41.650  1.00 36.07      A    N
ATOM  20518  CA   GLN I 245      32.144 -27.017 -42.421  1.00 36.66      A    C
ATOM  20519  C    GLN I 245      32.447 -28.384 -43.016  1.00 36.97      A    C
ATOM  20520  O    GLN I 245      32.746 -28.475 -44.206  1.00 37.26      A    O
ATOM  20521  CB   GLN I 245      33.327 -26.533 -41.568  1.00 36.72      A    C
ATOM  20522  N    LEU I 246      32.345 -29.429 -42.188  1.00 37.07      A    N
ATOM  20523  CA   LEU I 246      32.689 -30.805 -42.577  1.00 37.36      A    C
ATOM  20524  C    LEU I 246      31.709 -31.419 -43.590  1.00 37.80      A    C
ATOM  20525  O    LEU I 246      32.095 -32.281 -44.408  1.00 38.05      A    O
ATOM  20526  CB   LEU I 246      32.810 -31.701 -41.333  1.00 37.10      A    C
ATOM  20527  CG   LEU I 246      33.314 -33.147 -41.474  1.00 36.49      A    C
ATOM  20528  CD1  LEU I 246      32.197 -34.115 -41.129  1.00 35.20      A    C
ATOM  20529  N    MET I 247      30.448 -30.980 -43.527  1.00 38.11      A    N
ATOM  20530  CA   MET I 247      29.416 -31.431 -44.495  1.00 38.53      A    C
ATOM  20531  C    MET I 247      29.581 -30.734 -45.864  1.00 39.30      A    C
ATOM  20532  O    MET I 247      29.241 -31.331 -46.894  1.00 39.51      A    O
ATOM  20533  CB   MET I 247      27.991 -31.191 -43.958  1.00 37.98      A    C
ATOM  20534  CG   MET I 247      27.602 -32.147 -42.852  1.00 37.34      A    C
ATOM  20535  SD   MET I 247      25.849 -31.999 -42.494  1.00 36.65      A    S
ATOM  20536  CE   MET I 247      25.156 -33.284 -43.545  1.00 36.95      A    C
ATOM  20537  N    GLU I 248      30.093 -29.496 -45.864  1.00 40.16      A    N
ATOM  20538  CA   GLU I 248      30.374 -28.760 -47.101  1.00 41.20      A    C
ATOM  20539  C    GLU I 248      31.521 -29.401 -47.875  1.00 42.24      A    C
ATOM  20540  O    GLU I 248      31.539 -29.375 -49.106  1.00 42.79      A    O
```

FIGURE 1 (cont'd)

```
ATOM  20541  CB   GLU I 248      30.702 -27.294 -46.813  1.00 41.01           A    C
ATOM  20542  N    SER I 249      32.474 -29.984 -47.150  1.00 43.10           A    N
ATOM  20543  CA   SER I 249      33.640 -30.627 -47.763  1.00 44.03           A    C
ATOM  20544  C    SER I 249      33.385 -32.101 -48.121  1.00 44.52           A    C
ATOM  20545  O    SER I 249      34.240 -32.745 -48.739  1.00 44.97           A    O
ATOM  20546  CB   SER I 249      34.866 -30.506 -46.845  1.00 44.13           A    C
ATOM  20547  OG   SER I 249      34.794 -31.422 -45.758  1.00 44.14           A    O
ATOM  20548  N    ILE I 250      32.223 -32.627 -47.733  1.00 44.79           A    N
ATOM  20549  CA   ILE I 250      31.889 -34.027 -47.986  1.00 45.35           A    C
ATOM  20550  C    ILE I 250      30.924 -34.174 -49.204  1.00 46.19           A    C
ATOM  20551  O    ILE I 250      29.722 -33.830 -49.101  1.00 45.92           A    O
ATOM  20552  CB   ILE I 250      31.354 -34.704 -46.695  1.00 44.86           A    C
ATOM  20553  CG1  ILE I 250      31.627 -36.213 -46.704  1.00 44.81           A    C
ATOM  20554  CD1  ILE I 250      30.396 -37.052 -47.027  1.00 44.44           A    C
ATOM  20555  N    PRO I 251      31.460 -34.669 -50.364  1.00 47.32           A    N
ATOM  20556  CA   PRO I 251      30.672 -34.813 -51.602  1.00 47.97           A    C
ATOM  20557  C    PRO I 251      29.588 -35.869 -51.486  1.00 48.38           A    C
ATOM  20558  O    PRO I 251      29.735 -36.862 -50.747  1.00 48.38           A    O
ATOM  20559  CB   PRO I 251      31.710 -35.265 -52.646  1.00 48.28           A    C
ATOM  20560  CG   PRO I 251      33.033 -34.882 -52.077  1.00 48.28           A    C
ATOM  20561  CD   PRO I 251      32.861 -35.089 -50.590  1.00 47.63           A    C
ATOM  20562  N    HIS I 252      28.525 -35.646 -52.249  1.00 48.82           A    N
ATOM  20563  CA   HIS I 252      27.292 -36.418 -52.180  1.00 49.21           A    C
ATOM  20564  C    HIS I 252      26.480 -35.848 -53.319  1.00 49.80           A    C
ATOM  20565  O    HIS I 252      26.863 -34.811 -53.827  1.00 50.03           A    O
ATOM  20566  CB   HIS I 252      26.555 -36.046 -50.883  1.00 48.03           A    C
ATOM  20567  CG   HIS I 252      25.296 -36.825 -50.656  1.00 47.85           A    C
ATOM  20568  CD2  HIS I 252      23.990 -36.500 -50.849  1.00 47.66           A    C
ATOM  20569  ND1  HIS I 252      25.308 -38.125 -50.182  1.00 48.11           A    N
ATOM  20570  CE1  HIS I 252      24.063 -38.564 -50.085  1.00 48.10           A    C
ATOM  20571  NE2  HIS I 252      23.245 -37.600 -50.488  1.00 47.90           A    N
ATOM  20572  N    SER I 253      25.437 -36.475 -53.851  1.00 50.20           A    N
ATOM  20573  CA   SER I 253      25.411 -37.728 -54.514  1.00 50.20           A    C
ATOM  20574  C    SER I 253      24.327 -37.668 -55.601  1.00 50.33           A    C
ATOM  20575  O    SER I 253      24.013 -38.694 -56.150  1.00 50.74           A    O
ATOM  20576  CB   SER I 253      25.045 -38.838 -53.559  1.00 49.33           A    C
ATOM  20577  OG   SER I 253      23.770 -39.386 -53.793  1.00 48.86           A    O
ATOM  20578  N    PRO I 254      23.675 -36.491 -55.831  1.00 49.94           A    N
ATOM  20579  CA   PRO I 254      23.518 -35.203 -56.509  1.00 49.53           A    C
ATOM  20580  C    PRO I 254      23.183 -34.176 -55.481  1.00 49.14           A    C
ATOM  20581  O    PRO I 254      22.090 -33.617 -55.551  1.00 49.28           A    O
ATOM  20582  CB   PRO I 254      22.236 -35.345 -57.353  1.00 48.74           A    C
ATOM  20583  CG   PRO I 254      21.980 -36.714 -57.463  1.00 48.85           A    C
ATOM  20584  CD   PRO I 254      22.542 -37.367 -56.249  1.00 49.16           A    C
ATOM  20585  N    GLY I 255      24.065 -33.985 -54.505  1.00 48.49           A    N
ATOM  20586  CA   GLY I 255      24.145 -32.728 -53.804  1.00 47.60           A    C
ATOM  20587  C    GLY I 255      24.714 -31.717 -54.781  1.00 47.16           A    C
ATOM  20588  O    GLY I 255      24.006 -31.223 -55.671  1.00 47.42           A    O
ATOM  20589  N    PRO I 256      25.935 -31.294 -54.443  1.00 46.66           A    N
ATOM  20590  CA   PRO I 256      27.341 -31.285 -54.799  1.00 46.36           A    C
ATOM  20591  C    PRO I 256      27.926 -31.848 -53.487  1.00 45.79           A    C
ATOM  20592  O    PRO I 256      28.579 -32.897 -53.480  1.00 45.96           A    O
ATOM  20593  CB   PRO I 256      27.707 -29.801 -54.937  1.00 46.52           A    C
ATOM  20594  CG   PRO I 256      26.586 -29.132 -55.615  1.00 46.54           A    C
ATOM  20595  N    THR I 257      27.626 -31.164 -52.375  1.00 44.81           A    N
ATOM  20596  CA   THR I 257      28.073 -31.546 -51.023  1.00 43.68           A    C
ATOM  20597  C    THR I 257      26.913 -32.072 -50.177  1.00 42.97           A    C
ATOM  20598  O    THR I 257      25.741 -31.967 -50.575  1.00 42.85           A    O
ATOM  20599  CB   THR I 257      28.692 -30.347 -50.286  1.00 43.48           A    C
ATOM  20600  OG1  THR I 257      27.765 -29.248 -50.290  1.00 43.08           A    O
ATOM  20601  N    ARG I 258      27.241 -32.629 -49.010  1.00 42.09           A    N
ATOM  20602  CA   ARG I 258      26.224 -33.170 -48.097  1.00 41.09           A    C
ATOM  20603  C    ARG I 258      25.313 -32.102 -47.500  1.00 40.59           A    C
ATOM  20604  O    ARG I 258      24.256 -32.431 -46.936  1.00 40.53           A    O
ATOM  20605  CB   ARG I 258      26.855 -34.008 -46.984  1.00 40.16           A    C
```

FIGURE 1 (cont'd)

```
ATOM  20606  CG   ARG I 258      26.920 -35.480 -47.311  1.00 40.08       A  C
ATOM  20607  CD   ARG I 258      26.862 -36.336 -46.053  1.00 40.03       A  C
ATOM  20608  NE   ARG I 258      26.794 -37.763 -46.359  1.00 40.28       A  N
ATOM  20609  N    ILE I 259      25.727 -30.836 -47.632  1.00 39.89       A  N
ATOM  20610  CA   ILE I 259      24.917 -29.695 -47.190  1.00 38.95       A  C
ATOM  20611  C    ILE I 259      23.615 -29.557 -47.977  1.00 38.91       A  C
ATOM  20612  O    ILE I 259      22.557 -29.219 -47.410  1.00 38.87       A  O
ATOM  20613  CB   ILE I 259      25.680 -28.385 -47.266  1.00 38.02       A  C
ATOM  20614  CG1  ILE I 259      25.984 -27.945 -45.843  1.00 37.70       A  C
ATOM  20615  CD1  ILE I 259      27.293 -27.243 -45.719  1.00 38.58       A  C
ATOM  20616  N    GLN I 260      23.692 -29.849 -49.278  1.00 38.59       A  N
ATOM  20617  CA   GLN I 260      22.516 -29.795 -50.157  1.00 37.97       A  C
ATOM  20618  C    GLN I 260      21.609 -31.016 -49.929  1.00 37.81       A  C
ATOM  20619  O    GLN I 260      20.520 -31.111 -50.510  1.00 38.22       A  O
ATOM  20620  CB   GLN I 260      22.927 -29.695 -51.636  1.00 37.11       A  C
ATOM  20621  CG   GLN I 260      24.427 -29.441 -51.915  1.00 36.72       A  C
ATOM  20622  CD   GLN I 260      25.013 -28.205 -51.213  1.00 36.37       A  C
ATOM  20623  OE1  GLN I 260      24.474 -27.095 -51.244  1.00 36.76       A  O
ATOM  20624  N    ALA I 261      22.065 -31.945 -49.084  1.00 37.19       A  N
ATOM  20625  CA   ALA I 261      21.286 -33.134 -48.740  1.00 36.54       A  C
ATOM  20626  C    ALA I 261      20.207 -32.844 -47.672  1.00 35.78       A  C
ATOM  20627  O    ALA I 261      19.205 -33.564 -47.555  1.00 35.69       A  O
ATOM  20628  N    ILE I 262      20.408 -31.782 -46.899  1.00 34.76       A  N
ATOM  20629  CA   ILE I 262      19.398 -31.360 -45.934  1.00 33.71       A  C
ATOM  20630  C    ILE I 262      18.253 -30.656 -46.670  1.00 33.63       A  C
ATOM  20631  O    ILE I 262      18.402 -29.502 -47.129  1.00 33.78       A  O
ATOM  20632  CB   ILE I 262      19.981 -30.397 -44.882  1.00 32.78       A  C
ATOM  20633  CG1  ILE I 262      21.302 -30.928 -44.330  1.00 32.16       A  C
ATOM  20634  CD1  ILE I 262      22.192 -29.821 -43.790  1.00 31.76       A  C
ATOM  20635  N    GLU I 263      17.122 -31.353 -46.797  1.00 33.24       A  N
ATOM  20636  CA   GLU I 263      15.940 -30.754 -47.421  1.00 32.85       A  C
ATOM  20637  C    GLU I 263      15.344 -29.715 -46.481  1.00 32.25       A  C
ATOM  20638  O    GLU I 263      14.873 -28.657 -46.921  1.00 32.33       A  O
ATOM  20639  CB   GLU I 263      14.901 -31.822 -47.768  1.00 33.04       A  C
ATOM  20640  CG   GLU I 263      13.829 -31.375 -48.775  1.00 33.07       A  C
ATOM  20641  CD   GLU I 263      12.987 -32.542 -49.289  1.00 32.66       A  C
ATOM  20642  N    LEU I 264      15.383 -30.039 -45.185  1.00 31.41       A  N
ATOM  20643  CA   LEU I 264      14.935 -29.140 -44.122  1.00 30.40       A  C
ATOM  20644  C    LEU I 264      15.683 -29.398 -42.809  1.00 29.81       A  C
ATOM  20645  O    LEU I 264      15.693 -30.532 -42.290  1.00 29.81       A  O
ATOM  20646  CB   LEU I 264      13.427 -29.287 -43.887  1.00 30.31       A  C
ATOM  20647  CG   LEU I 264      12.791 -28.401 -42.811  1.00 29.87       A  C
ATOM  20648  CD1  LEU I 264      12.960 -26.890 -43.160  1.00 29.75       A  C
ATOM  20649  CD2  LEU I 264      11.319 -28.790 -42.596  1.00 29.63       A  C
ATOM  20650  N    PHE I 265      16.293 -28.323 -42.292  1.00 29.01       A  N
ATOM  20651  CA   PHE I 265      16.947 -28.285 -40.974  1.00 27.96       A  C
ATOM  20652  C    PHE I 265      15.964 -27.730 -39.926  1.00 27.64       A  C
ATOM  20653  O    PHE I 265      15.771 -26.511 -39.792  1.00 27.47       A  O
ATOM  20654  CB   PHE I 265      18.213 -27.419 -41.057  1.00 27.69       A  C
ATOM  20655  CG   PHE I 265      19.150 -27.577 -39.881  1.00 26.38       A  C
ATOM  20656  CD1  PHE I 265      20.196 -28.502 -39.916  1.00 25.39       A  C
ATOM  20657  CD2  PHE I 265      19.001 -26.776 -38.747  1.00 25.28       A  C
ATOM  20658  N    MET I 266      15.323 -28.644 -39.210  1.00 27.35       A  N
ATOM  20659  CA   MET I 266      14.352 -28.271 -38.190  1.00 27.20       A  C
ATOM  20660  C    MET I 266      15.015 -28.391 -36.813  1.00 27.17       A  C
ATOM  20661  O    MET I 266      15.175 -29.510 -36.268  1.00 27.21       A  O
ATOM  20662  CB   MET I 266      13.089 -29.151 -38.293  1.00 27.18       A  C
ATOM  20663  CG   MET I 266      11.952 -28.840 -37.299  1.00 26.84       A  C
ATOM  20664  N    LEU I 267      15.399 -27.230 -36.270  1.00 27.06       A  N
ATOM  20665  CA   LEU I 267      16.122 -27.158 -34.994  1.00 26.98       A  C
ATOM  20666  C    LEU I 267      15.194 -27.045 -33.782  1.00 27.02       A  C
ATOM  20667  O    LEU I 267      14.385 -26.119 -33.690  1.00 27.04       A  O
ATOM  20668  CB   LEU I 267      17.122 -25.994 -35.012  1.00 26.88       A  C
ATOM  20669  CG   LEU I 267      17.977 -25.775 -33.755  1.00 26.61       A  C
ATOM  20670  CD1  LEU I 267      18.830 -27.019 -33.380  1.00 26.55       A  C
```

FIGURE 1 (cont'd)

```
ATOM  20671  CD2 LEU I 267    18.856 -24.545 -33.957  1.00 26.47      A  C
ATOM  20672  N   LEU I 268    15.346 -27.992 -32.861  1.00 27.06      A  N
ATOM  20673  CA  LEU I 268    14.522 -28.068 -31.664  1.00 27.28      A  C
ATOM  20674  C   LEU I 268    15.260 -27.527 -30.453  1.00 27.52      A  C
ATOM  20675  O   LEU I 268    16.311 -28.069 -30.068  1.00 27.67      A  O
ATOM  20676  CB  LEU I 268    14.134 -29.522 -31.381  1.00 27.23      A  C
ATOM  20677  CG  LEU I 268    12.833 -30.042 -31.993  1.00 27.27      A  C
ATOM  20678  CD1 LEU I 268    12.973 -30.302 -33.499  1.00 27.52      A  C
ATOM  20679  CD2 LEU I 268    12.431 -31.310 -31.246  1.00 27.10      A  C
ATOM  20680  N   ASP I 269    14.698 -26.484 -29.836  1.00 27.76      A  N
ATOM  20681  CA  ASP I 269    15.355 -25.822 -28.700  1.00 28.06      A  C
ATOM  20682  C   ASP I 269    14.404 -25.247 -27.656  1.00 27.98      A  C
ATOM  20683  O   ASP I 269    13.303 -24.783 -27.991  1.00 28.14      A  O
ATOM  20684  CB  ASP I 269    16.312 -24.726 -29.189  1.00 28.25      A  C
ATOM  20685  CG  ASP I 269    17.614 -24.701 -28.392  1.00 29.39      A  C
ATOM  20686  OD1 ASP I 269    18.328 -25.745 -28.345  1.00 30.28      A  O
ATOM  20687  OD2 ASP I 269    17.916 -23.630 -27.811  1.00 30.14      A  O
ATOM  20688  N   LEU I 270    14.853 -25.275 -26.397  1.00 27.86      A  N
ATOM  20689  CA  LEU I 270    14.127 -24.668 -25.275  1.00 27.86      A  C
ATOM  20690  C   LEU I 270    12.677 -25.153 -25.246  1.00 27.94      A  C
ATOM  20691  O   LEU I 270    11.720 -24.370 -25.128  1.00 28.00      A  O
ATOM  20692  CB  LEU I 270    14.211 -23.127 -25.323  1.00 27.76      A  C
ATOM  20693  CG  LEU I 270    15.584 -22.468 -25.480  1.00 27.73      A  C
ATOM  20694  CD1 LEU I 270    15.481 -20.979 -25.187  1.00 27.64      A  C
ATOM  20695  CD2 LEU I 270    16.622 -23.142 -24.584  1.00 27.99      A  C
ATOM  20696  N   LEU I 271    12.522 -26.457 -25.388  1.00 27.99      A  N
ATOM  20697  CA  LEU I 271    11.210 -27.048 -25.304  1.00 28.32      A  C
ATOM  20698  C   LEU I 271    11.122 -27.806 -23.990  1.00 28.75      A  C
ATOM  20699  O   LEU I 271    12.102 -28.439 -23.567  1.00 28.76      A  O
ATOM  20700  CB  LEU I 271    10.963 -27.992 -26.485  1.00 28.13      A  C
ATOM  20701  CG  LEU I 271    10.969 -27.394 -27.897  1.00 27.74      A  C
ATOM  20702  CD1 LEU I 271    11.939 -28.181 -28.767  1.00 27.64      A  C
ATOM  20703  N   GLY I 272     9.953 -27.732 -23.343  1.00 29.29      A  N
ATOM  20704  CA  GLY I 272     9.680 -28.515 -22.117  1.00 29.95      A  C
ATOM  20705  C   GLY I 272     8.964 -27.743 -21.016  1.00 30.48      A  C
ATOM  20706  O   GLY I 272     8.287 -28.327 -20.155  1.00 30.64      A  O
ATOM  20707  N   ALA I 273     9.125 -26.420 -21.044  1.00 30.87      A  N
ATOM  20708  CA  ALA I 273     8.458 -25.531 -20.092  1.00 31.28      A  C
ATOM  20709  C   ALA I 273     6.940 -25.469 -20.364  1.00 31.62      A  C
ATOM  20710  O   ALA I 273     6.474 -25.883 -21.440  1.00 31.66      A  O
ATOM  20711  CB  ALA I 273     9.082 -24.125 -20.132  1.00 31.19      A  C
ATOM  20712  N   PRO I 274     6.157 -24.988 -19.377  1.00 32.02      A  N
ATOM  20713  CA  PRO I 274     4.742 -24.751 -19.641  1.00 32.27      A  C
ATOM  20714  C   PRO I 274     4.546 -23.554 -20.561  1.00 32.37      A  C
ATOM  20715  O   PRO I 274     5.407 -22.668 -20.618  1.00 32.25      A  O
ATOM  20716  CB  PRO I 274     4.168 -24.446 -18.247  1.00 32.52      A  C
ATOM  20717  CG  PRO I 274     5.348 -24.015 -17.419  1.00 32.45      A  C
ATOM  20718  CD  PRO I 274     6.482 -24.835 -17.943  1.00 32.18      A  C
ATOM  20719  N   ASN I 275     3.424 -23.558 -21.275  1.00 32.61      A  N
ATOM  20720  CA  ASN I 275     2.998 -22.444 -22.126  1.00 32.96      A  C
ATOM  20721  C   ASN I 275     4.076 -21.850 -23.047  1.00 32.56      A  C
ATOM  20722  O   ASN I 275     4.333 -20.641 -23.010  1.00 32.78      A  O
ATOM  20723  CB  ASN I 275     2.331 -21.350 -21.281  1.00 33.42      A  C
ATOM  20724  CG  ASN I 275     1.170 -21.879 -20.475  1.00 34.80      A  C
ATOM  20725  ND2 ASN I 275     1.371 -21.992 -19.164  1.00 35.90      A  N
ATOM  20726  OD1 ASN I 275     0.102 -22.200 -21.022  1.00 35.83      A  O
ATOM  20727  N   PRO I 276     4.707 -22.691 -23.885  1.00 32.08      A  N
ATOM  20728  CA  PRO I 276     5.627 -22.092 -24.840  1.00 31.82      A  C
ATOM  20729  C   PRO I 276     4.848 -21.424 -25.962  1.00 31.82      A  C
ATOM  20730  O   PRO I 276     3.713 -21.802 -26.240  1.00 31.92      A  O
ATOM  20731  CB  PRO I 276     6.405 -23.294 -25.372  1.00 31.64      A  C
ATOM  20732  CG  PRO I 276     5.463 -24.462 -25.219  1.00 31.62      A  C
ATOM  20733  CD  PRO I 276     4.593 -24.158 -24.044  1.00 31.89      A  C
ATOM  20734  N   THR I 277     5.440 -20.422 -26.585  1.00 31.86      A  N
ATOM  20735  CA  THR I 277     4.849 -19.845 -27.784  1.00 31.93      A  C
```

FIGURE 1 (cont'd)

```
ATOM  20736  C    THR I 277     5.869 -19.855 -28.920  1.00 31.86      A  C
ATOM  20737  O    THR I 277     7.016 -19.432 -28.736  1.00 31.83      A  O
ATOM  20738  CB   THR I 277     4.295 -18.427 -27.540  1.00 32.03      A  C
ATOM  20739  CG2  THR I 277     2.957 -18.493 -26.806  1.00 32.17      A  C
ATOM  20740  OG1  THR I 277     5.214 -17.684 -26.738  1.00 32.27      A  O
ATOM  20741  N    PHE I 278     5.449 -20.366 -30.080  1.00 31.84      A  N
ATOM  20742  CA   PHE I 278     6.323 -20.496 -31.248  1.00 31.84      A  C
ATOM  20743  C    PHE I 278     5.850 -19.621 -32.395  1.00 32.15      A  C
ATOM  20744  O    PHE I 278     4.651 -19.451 -32.604  1.00 32.25      A  O
ATOM  20745  CB   PHE I 278     6.410 -21.952 -31.707  1.00 31.58      A  C
ATOM  20746  CG   PHE I 278     6.823 -22.894 -30.629  1.00 31.33      A  C
ATOM  20747  CD1  PHE I 278     8.124 -22.887 -30.154  1.00 31.25      A  C
ATOM  20748  CD2  PHE I 278     5.905 -23.794 -30.079  1.00 31.22      A  C
ATOM  20749  CE1  PHE I 278     8.511 -23.768 -29.141  1.00 31.25      A  C
ATOM  20750  CE2  PHE I 278     6.278 -24.684 -29.066  1.00 31.03      A  C
ATOM  20751  CZ   PHE I 278     7.581 -24.673 -28.595  1.00 31.05      A  C
ATOM  20752  N    TYR I 279     6.813 -19.067 -33.125  1.00 32.54      A  N
ATOM  20753  CA   TYR I 279     6.551 -18.272 -34.322  1.00 33.11      A  C
ATOM  20754  C    TYR I 279     7.414 -18.755 -35.508  1.00 33.74      A  C
ATOM  20755  O    TYR I 279     8.375 -19.526 -35.331  1.00 33.68      A  O
ATOM  20756  CB   TYR I 279     6.780 -16.785 -34.026  1.00 32.96      A  C
ATOM  20757  CG   TYR I 279     5.939 -16.268 -32.872  1.00 32.49      A  C
ATOM  20758  CD1  TYR I 279     4.632 -15.823 -33.070  1.00 32.40      A  C
ATOM  20759  N    SER I 280     7.062 -18.334 -36.720  1.00 34.65      A  N
ATOM  20760  CA   SER I 280     7.878 -18.677 -37.879  1.00 35.48      A  C
ATOM  20761  C    SER I 280     8.952 -17.601 -38.098  1.00 35.99      A  C
ATOM  20762  O    SER I 280     8.653 -16.471 -38.508  1.00 36.26      A  O
ATOM  20763  CB   SER I 280     7.005 -18.879 -39.125  1.00 35.59      A  C
ATOM  20764  OG   SER I 280     7.773 -19.374 -40.208  1.00 35.80      A  O
ATOM  20765  N    HIS I 281    10.200 -17.960 -37.809  1.00 36.43      A  N
ATOM  20766  CA   HIS I 281    11.316 -17.016 -37.935  1.00 37.16      A  C
ATOM  20767  C    HIS I 281    11.969 -17.045 -39.324  1.00 37.47      A  C
ATOM  20768  O    HIS I 281    12.851 -16.232 -39.625  1.00 37.64      A  O
ATOM  20769  CB   HIS I 281    12.349 -17.247 -36.813  1.00 37.26      A  C
ATOM  20770  CG   HIS I 281    11.763 -17.189 -35.430  1.00 37.85      A  C
ATOM  20771  CD2  HIS I 281    11.491 -16.136 -34.621  1.00 38.69      A  C
ATOM  20772  ND1  HIS I 281    11.371 -18.318 -34.737  1.00 37.83      A  N
ATOM  20773  CE1  HIS I 281    10.884 -17.961 -33.560  1.00 38.24      A  C
ATOM  20774  NE2  HIS I 281    10.946 -16.643 -33.466  1.00 38.96      A  N
ATOM  20775  N    PHE I 282    11.526 -17.991 -40.156  1.00 37.85      A  N
ATOM  20776  CA   PHE I 282    11.925 -18.058 -41.569  1.00 38.23      A  C
ATOM  20777  C    PHE I 282    10.727 -18.224 -42.510  1.00 38.56      A  C
ATOM  20778  O    PHE I 282    10.109 -19.304 -42.539  1.00 38.45      A  O
ATOM  20779  CB   PHE I 282    12.979 -19.146 -41.811  1.00 38.09      A  C
ATOM  20780  CG   PHE I 282    14.211 -18.949 -41.005  1.00 38.03      A  C
ATOM  20781  CD1  PHE I 282    15.076 -17.878 -41.274  1.00 38.48      A  C
ATOM  20782  CD2  PHE I 282    14.486 -19.795 -39.942  1.00 37.89      A  C
ATOM  20783  CE1  PHE I 282    16.222 -17.671 -40.502  1.00 38.45      A  C
ATOM  20784  CE2  PHE I 282    15.627 -19.601 -39.157  1.00 38.00      A  C
ATOM  20785  CZ   PHE I 282    16.500 -18.538 -39.436  1.00 38.25      A  C
ATOM  20786  N    PRO I 283    10.407 -17.149 -43.282  1.00 38.96      A  N
ATOM  20787  CA   PRO I 283     9.317 -17.181 -44.262  1.00 39.06      A  C
ATOM  20788  C    PRO I 283     9.575 -18.224 -45.341  1.00 38.93      A  C
ATOM  20789  O    PRO I 283     8.628 -18.691 -45.977  1.00 39.02      A  O
ATOM  20790  CB   PRO I 283     9.337 -15.769 -44.868  1.00 39.30      A  C
ATOM  20791  CG   PRO I 283    10.056 -14.922 -43.868  1.00 39.32      A  C
ATOM  20792  CD   PRO I 283    11.087 -15.834 -43.279  1.00 39.07      A  C
ATOM  20793  N    ARG I 284    10.842 -18.593 -45.531  1.00 38.67      A  N
ATOM  20794  CA   ARG I 284    11.196 -19.648 -46.470  1.00 38.57      A  C
ATOM  20795  C    ARG I 284    10.461 -20.948 -46.158  1.00 38.76      A  C
ATOM  20796  O    ARG I 284     9.982 -21.620 -47.077  1.00 39.02      A  O
ATOM  20797  CB   ARG I 284    12.701 -19.908 -46.468  1.00 38.31      A  C
ATOM  20798  CG   ARG I 284    13.275 -20.329 -47.840  1.00 37.53      A  C
ATOM  20799  CD   ARG I 284    12.858 -21.738 -48.284  1.00 35.78      A  C
ATOM  20800  NE   ARG I 284    13.805 -22.315 -49.235  1.00 34.96      A  N
```

FIGURE 1 (cont'd)

```
ATOM   20801  N    THR I 285      10.375 -21.296 -44.871  1.00 38.79           A  N
ATOM   20802  CA   THR I 285       9.719 -22.546 -44.444  1.00 38.93           A  C
ATOM   20803  C    THR I 285       8.320 -22.315 -43.807  1.00 39.32           A  C
ATOM   20804  O    THR I 285       7.745 -23.229 -43.178  1.00 39.17           A  O
ATOM   20805  CB   THR I 285      10.644 -23.364 -43.489  1.00 38.55           A  C
ATOM   20806  OG1  THR I 285      11.180 -22.491 -42.476  1.00 38.20           A  O
ATOM   20807  N    VAL I 286       7.772 -21.107 -44.010  1.00 39.92           A  N
ATOM   20808  CA   VAL I 286       6.541 -20.656 -43.342  1.00 40.40           A  C
ATOM   20809  C    VAL I 286       5.412 -21.664 -43.434  1.00 41.02           A  C
ATOM   20810  O    VAL I 286       4.579 -21.753 -42.538  1.00 41.04           A  O
ATOM   20811  CB   VAL I 286       6.051 -19.287 -43.870  1.00 40.31           A  C
ATOM   20812  N    ARG I 287       5.405 -22.433 -44.514  1.00 41.91           A  N
ATOM   20813  CA   ARG I 287       4.352 -23.425 -44.753  1.00 42.83           A  C
ATOM   20814  C    ARG I 287       4.510 -24.711 -43.926  1.00 42.56           A  C
ATOM   20815  O    ARG I 287       3.522 -25.406 -43.654  1.00 42.71           A  O
ATOM   20816  CB   ARG I 287       4.202 -23.741 -46.257  1.00 43.55           A  C
ATOM   20817  CG   ARG I 287       5.389 -24.451 -46.896  1.00 45.24           A  C
ATOM   20818  CD   ARG I 287       5.107 -24.769 -48.354  1.00 48.24           A  C
ATOM   20819  NE   ARG I 287       6.153 -25.626 -48.912  1.00 50.00           A  N
ATOM   20820  CZ   ARG I 287       6.132 -26.963 -48.897  1.00 50.51           A  C
ATOM   20821  NH1  ARG I 287       5.106 -27.620 -48.353  1.00 50.58           A  N
ATOM   20822  NH2  ARG I 287       7.141 -27.652 -49.431  1.00 50.72           A  N
ATOM   20823  N    TRP I 288       5.738 -25.027 -43.529  1.00 42.17           A  N
ATOM   20824  CA   TRP I 288       5.944 -26.149 -42.619  1.00 41.91           A  C
ATOM   20825  C    TRP I 288       5.599 -25.781 -41.179  1.00 41.71           A  C
ATOM   20826  O    TRP I 288       5.246 -26.644 -40.357  1.00 41.72           A  O
ATOM   20827  CB   TRP I 288       7.366 -26.676 -42.712  1.00 41.81           A  C
ATOM   20828  CG   TRP I 288       7.582 -27.435 -43.967  1.00 42.53           A  C
ATOM   20829  CD1  TRP I 288       8.496 -27.160 -44.961  1.00 43.03           A  C
ATOM   20830  CD2  TRP I 288       6.854 -28.588 -44.401  1.00 43.24           A  C
ATOM   20831  CE2  TRP I 288       7.389 -28.973 -45.660  1.00 43.63           A  C
ATOM   20832  CE3  TRP I 288       5.805 -29.341 -43.848  1.00 43.42           A  C
ATOM   20833  NE1  TRP I 288       8.390 -28.088 -45.975  1.00 43.41           A  N
ATOM   20834  CZ2  TRP I 288       6.904 -30.080 -46.375  1.00 44.13           A  C
ATOM   20835  CZ3  TRP I 288       5.325 -30.445 -44.560  1.00 43.93           A  C
ATOM   20836  CH2  TRP I 288       5.876 -30.801 -45.810  1.00 44.31           A  C
ATOM   20837  N    PHE I 289       5.711 -24.492 -40.876  1.00 41.51           A  N
ATOM   20838  CA   PHE I 289       5.223 -23.985 -39.616  1.00 41.33           A  C
ATOM   20839  C    PHE I 289       3.688 -24.107 -39.586  1.00 41.47           A  C
ATOM   20840  O    PHE I 289       3.136 -24.571 -38.578  1.00 41.30           A  O
ATOM   20841  CB   PHE I 289       5.688 -22.540 -39.397  1.00 41.23           A  C
ATOM   20842  CG   PHE I 289       5.474 -22.049 -37.994  1.00 41.14           A  C
ATOM   20843  CD1  PHE I 289       6.323 -22.463 -36.965  1.00 40.71           A  C
ATOM   20844  CD2  PHE I 289       4.408 -21.191 -37.691  1.00 41.44           A  C
ATOM   20845  CE1  PHE I 289       6.122 -22.027 -35.666  1.00 40.57           A  C
ATOM   20846  CE2  PHE I 289       4.201 -20.753 -36.389  1.00 41.53           A  C
ATOM   20847  CZ   PHE I 289       5.056 -21.178 -35.376  1.00 41.09           A  C
ATOM   20848  N    HIS I 290       3.017 -23.726 -40.694  1.00 41.81           A  N
ATOM   20849  CA   HIS I 290       1.541 -23.839 -40.807  1.00 42.26           A  C
ATOM   20850  C    HIS I 290       1.092 -25.274 -40.582  1.00 42.34           A  C
ATOM   20851  O    HIS I 290       0.016 -25.506 -40.030  1.00 42.51           A  O
ATOM   20852  CB   HIS I 290       0.963 -23.334 -42.147  1.00 42.50           A  C
ATOM   20853  CG   HIS I 290       1.382 -21.946 -42.514  1.00 43.13           A  C
ATOM   20854  ND1  HIS I 290       0.610 -20.886 -42.963  1.00 43.98           A  N
ATOM   20855  CE1  HIS I 290      -0.696 -21.031 -42.953  1.00 44.46           A  C
ATOM   20856  N    ARG I 291       1.919 -26.229 -41.005  1.00 42.38           A  N
ATOM   20857  CA   ARG I 291       1.634 -27.638 -40.763  1.00 42.62           A  C
ATOM   20858  C    ARG I 291       1.555 -27.933 -39.285  1.00 42.23           A  C
ATOM   20859  O    ARG I 291       0.634 -28.617 -38.833  1.00 42.48           A  O
ATOM   20860  CB   ARG I 291       2.673 -28.540 -41.426  1.00 42.86           A  C
ATOM   20861  CG   ARG I 291       2.432 -28.707 -42.907  1.00 44.49           A  C
ATOM   20862  CD   ARG I 291       1.055 -29.327 -43.154  1.00 46.63           A  C
ATOM   20863  NE   ARG I 291       1.133 -30.786 -43.189  1.00 47.73           A  N
ATOM   20864  CZ   ARG I 291       1.176 -31.495 -44.313  1.00 48.76           A  C
ATOM   20865  NH1  ARG I 291       1.132 -30.878 -45.492  1.00 49.28           A  N
```

FIGURE 1 (cont'd)

```
ATOM  20866  NH2 ARG I 291      1.262 -32.820 -44.263  1.00 49.26      A    N
ATOM  20867  N   LEU I 292      2.516 -27.393 -38.540  1.00 41.61      A    N
ATOM  20868  CA  LEU I 292      2.560 -27.582 -37.097  1.00 40.99      A    C
ATOM  20869  C   LEU I 292      1.328 -26.969 -36.414  1.00 40.96      A    C
ATOM  20870  O   LEU I 292      0.695 -27.617 -35.559  1.00 40.99      A    O
ATOM  20871  CB  LEU I 292      3.876 -27.048 -36.526  1.00 40.59      A    C
ATOM  20872  CG  LEU I 292      5.110 -27.858 -36.949  1.00 39.90      A    C
ATOM  20873  CD1 LEU I 292      6.375 -27.047 -36.707  1.00 39.44      A    C
ATOM  20874  CD2 LEU I 292      5.172 -29.224 -36.240  1.00 39.39      A    C
ATOM  20875  N   ARG I 293      0.971 -25.747 -36.819  1.00 40.90      A    N
ATOM  20876  CA  ARG I 293     -0.253 -25.120 -36.348  1.00 40.99      A    C
ATOM  20877  C   ARG I 293     -1.419 -26.050 -36.660  1.00 41.29      A    C
ATOM  20878  O   ARG I 293     -2.199 -26.389 -35.770  1.00 41.38      A    O
ATOM  20879  CB  ARG I 293     -0.452 -23.746 -36.992  1.00 40.89      A    C
ATOM  20880  CG  ARG I 293     -1.413 -22.839 -36.220  1.00 40.70      A    C
ATOM  20881  CD  ARG I 293     -1.772 -21.557 -36.975  1.00 40.46      A    C
ATOM  20882  NE  ARG I 293     -0.626 -20.679 -37.191  1.00 39.73      A    N
ATOM  20883  N   SER I 294     -1.492 -26.496 -37.916  1.00 41.47      A    N
ATOM  20884  CA  SER I 294     -2.566 -27.378 -38.381  1.00 41.75      A    C
ATOM  20885  C   SER I 294     -2.625 -28.713 -37.624  1.00 42.14      A    C
ATOM  20886  O   SER I 294     -3.717 -29.219 -37.344  1.00 42.64      A    O
ATOM  20887  CB  SER I 294     -2.470 -27.622 -39.894  1.00 40.76      A    C
ATOM  20888  N   ILE I 295     -1.462 -29.274 -37.293  1.00 42.20      A    N
ATOM  20889  CA  ILE I 295     -1.405 -30.542 -36.568  1.00 42.27      A    C
ATOM  20890  C   ILE I 295     -1.894 -30.352 -35.135  1.00 42.55      A    C
ATOM  20891  O   ILE I 295     -2.668 -31.173 -34.619  1.00 42.73      A    O
ATOM  20892  CB  ILE I 295      0.005 -31.176 -36.608  1.00 41.98      A    C
ATOM  20893  CG1 ILE I 295      0.300 -31.711 -38.015  1.00 41.93      A    C
ATOM  20894  CG2 ILE I 295      0.115 -32.311 -35.601  1.00 41.81      A    C
ATOM  20895  CD1 ILE I 295      1.782 -31.756 -38.392  1.00 41.61      A    C
ATOM  20896  N   GLU I 296     -1.458 -29.257 -34.510  1.00 42.70      A    N
ATOM  20897  CA  GLU I 296     -1.903 -28.913 -33.161  1.00 43.03      A    C
ATOM  20898  C   GLU I 296     -3.422 -28.749 -33.154  1.00 43.58      A    C
ATOM  20899  O   GLU I 296     -4.120 -29.375 -32.346  1.00 43.83      A    O
ATOM  20900  CB  GLU I 296     -1.221 -27.633 -32.681  1.00 42.74      A    C
ATOM  20901  CG  GLU I 296     -1.483 -27.285 -31.220  1.00 42.92      A    C
ATOM  20902  CD  GLU I 296     -1.013 -25.873 -30.845  1.00 43.14      A    C
ATOM  20903  OE1 GLU I 296     -0.218 -25.266 -31.603  1.00 42.81      A    O
ATOM  20904  OE2 GLU I 296     -1.441 -25.366 -29.780  1.00 43.40      A    O
ATOM  20905  N   LYS I 297     -3.912 -27.920 -34.081  1.00 44.14      A    N
ATOM  20906  CA  LYS I 297     -5.344 -27.696 -34.302  1.00 44.85      A    C
ATOM  20907  C   LYS I 297     -6.091 -29.028 -34.371  1.00 45.48      A    C
ATOM  20908  O   LYS I 297     -7.025 -29.259 -33.602  1.00 45.73      A    O
ATOM  20909  CB  LYS I 297     -5.544 -26.912 -35.603  1.00 44.73      A    C
ATOM  20910  CG  LYS I 297     -6.408 -25.665 -35.487  1.00 44.62      A    C
ATOM  20911  CD  LYS I 297     -5.971 -24.608 -36.518  1.00 43.77      A    C
ATOM  20912  CE  LYS I 297     -7.086 -23.615 -36.852  1.00 43.77      A    C
ATOM  20913  N   ARG I 298     -5.633 -29.903 -35.272  1.00 46.00      A    N
ATOM  20914  CA  ARG I 298     -6.245 -31.214 -35.520  1.00 46.53      A    C
ATOM  20915  C   ARG I 298     -6.247 -32.117 -34.287  1.00 47.05      A    C
ATOM  20916  O   ARG I 298     -7.295 -32.682 -33.941  1.00 47.65      A    O
ATOM  20917  CB  ARG I 298     -5.562 -31.921 -36.713  1.00 45.54      A    C
ATOM  20918  CG  ARG I 298     -6.222 -33.241 -37.186  1.00 45.48      A    C
ATOM  20919  CD  ARG I 298     -5.556 -33.778 -38.464  1.00 45.14      A    C
ATOM  20920  NE  ARG I 298     -6.029 -35.111 -38.825  1.00 45.01      A    N
ATOM  20921  N   LEU I 299     -5.090 -32.248 -33.634  1.00 47.23      A    N
ATOM  20922  CA  LEU I 299     -4.959 -33.131 -32.466  1.00 47.49      A    C
ATOM  20923  C   LEU I 299     -5.803 -32.647 -31.293  1.00 47.90      A    C
ATOM  20924  O   LEU I 299     -6.284 -33.449 -30.469  1.00 48.11      A    O
ATOM  20925  CB  LEU I 299     -3.495 -33.263 -32.043  1.00 47.17      A    C
ATOM  20926  CG  LEU I 299     -2.569 -34.131 -32.906  1.00 47.02      A    C
ATOM  20927  CD1 LEU I 299     -1.106 -33.861 -32.561  1.00 46.55      A    C
ATOM  20928  CD2 LEU I 299     -2.893 -35.620 -32.758  1.00 47.46      A    C
ATOM  20929  N   HIS I 300     -5.972 -31.324 -31.237  1.00 48.25      A    N
ATOM  20930  CA  HIS I 300     -6.851 -30.681 -30.267  1.00 48.80      A    C
```

FIGURE 1 (cont'd)

```
ATOM  20931  C    HIS I 300      -8.307 -31.090 -30.503  1.00 49.27          A C
ATOM  20932  O    HIS I 300      -8.966 -31.581 -29.577  1.00 49.59          A O
ATOM  20933  CB   HIS I 300      -6.696 -29.150 -30.303  1.00 48.72          A C
ATOM  20934  CG   HIS I 300      -7.728 -28.424 -29.499  1.00 49.37          A C
ATOM  20935  CD2  HIS I 300      -8.716 -27.580 -29.877  1.00 50.13          A C
ATOM  20936  ND1  HIS I 300      -7.835 -28.552 -28.127  1.00 49.69          A N
ATOM  20937  CE1  HIS I 300      -8.842 -27.813 -27.696  1.00 50.29          A C
ATOM  20938  NE2  HIS I 300      -9.392 -27.212 -28.737  1.00 50.74          A N
ATOM  20939  N    ARG I 301      -8.784 -30.894 -31.741  1.00 49.73          A N
ATOM  20940  CA   ARG I 301     -10.130 -31.306 -32.172  1.00 50.23          A C
ATOM  20941  C    ARG I 301     -10.407 -32.761 -31.806  1.00 50.87          A C
ATOM  20942  O    ARG I 301     -11.491 -33.090 -31.344  1.00 51.42          A O
ATOM  20943  CB   ARG I 301     -10.315 -31.128 -33.685  1.00 50.06          A C
ATOM  20944  CG   ARG I 301      -9.931 -29.769 -34.245  1.00 49.10          A C
ATOM  20945  CD   ARG I 301     -11.042 -28.743 -34.099  1.00 48.46          A C
ATOM  20946  NE   ARG I 301     -10.593 -27.395 -34.452  1.00 47.73          A N
ATOM  20947  N    LEU I 302      -9.411 -33.621 -31.994  1.00 51.24          A N
ATOM  20948  CA   LEU I 302      -9.544 -35.050 -31.716  1.00 51.86          A C
ATOM  20949  C    LEU I 302      -9.361 -35.416 -30.247  1.00 52.21          A C
ATOM  20950  O    LEU I 302      -9.207 -36.594 -29.931  1.00 52.51          A O
ATOM  20951  CB   LEU I 302      -8.544 -35.846 -32.559  1.00 51.78          A C
ATOM  20952  CG   LEU I 302      -8.777 -35.873 -34.066  1.00 52.25          A C
ATOM  20953  CD1  LEU I 302      -7.464 -36.073 -34.808  1.00 51.85          A C
ATOM  20954  CD2  LEU I 302      -9.781 -36.956 -34.424  1.00 53.48          A C
ATOM  20955  N    ASN I 303      -9.388 -34.414 -29.365  1.00 52.33          A N
ATOM  20956  CA   ASN I 303      -9.155 -34.604 -27.929  1.00 52.27          A C
ATOM  20957  C    ASN I 303      -7.986 -35.558 -27.669  1.00 52.72          A C
ATOM  20958  O    ASN I 303      -8.174 -36.657 -27.127  1.00 53.22          A O
ATOM  20959  N    LEU I 304      -6.788 -35.147 -28.084  1.00 52.88          A N
ATOM  20960  CA   LEU I 304      -5.579 -35.963 -27.890  1.00 52.77          A C
ATOM  20961  C    LEU I 304      -4.409 -35.185 -27.271  1.00 52.48          A C
ATOM  20962  O    LEU I 304      -3.290 -35.701 -27.182  1.00 52.20          A O
ATOM  20963  CB   LEU I 304      -5.152 -36.622 -29.211  1.00 52.83          A C
ATOM  20964  CG   LEU I 304      -5.838 -37.916 -29.678  1.00 53.27          A C
ATOM  20965  CD1  LEU I 304      -5.362 -38.287 -31.071  1.00 52.95          A C
ATOM  20966  CD2  LEU I 304      -5.605 -39.082 -28.717  1.00 53.83          A C
ATOM  20967  N    LEU I 305      -4.682 -33.949 -26.846  1.00 52.41          A N
ATOM  20968  CA   LEU I 305      -3.692 -33.081 -26.205  1.00 52.20          A C
ATOM  20969  C    LEU I 305      -4.118 -32.764 -24.780  1.00 52.62          A C
ATOM  20970  O    LEU I 305      -5.194 -32.184 -24.570  1.00 53.05          A O
ATOM  20971  CB   LEU I 305      -3.529 -31.781 -26.992  1.00 51.72          A C
ATOM  20972  CG   LEU I 305      -3.189 -31.887 -28.472  1.00 51.06          A C
ATOM  20973  CD1  LEU I 305      -3.213 -30.519 -29.084  1.00 50.40          A C
ATOM  20974  CD2  LEU I 305      -1.836 -32.546 -28.693  1.00 50.66          A C
ATOM  20975  N    GLN I 306      -3.284 -33.154 -23.811  1.00 52.76          A N
ATOM  20976  CA   GLN I 306      -3.528 -32.860 -22.394  1.00 53.06          A C
ATOM  20977  C    GLN I 306      -3.454 -31.363 -22.107  1.00 52.96          A C
ATOM  20978  O    GLN I 306      -2.731 -30.641 -22.797  1.00 52.60          A O
ATOM  20979  CB   GLN I 306      -2.509 -33.581 -21.519  1.00 53.16          A C
ATOM  20980  CG   GLN I 306      -2.973 -34.914 -20.981  1.00 54.04          A C
ATOM  20981  CD   GLN I 306      -2.053 -35.433 -19.901  1.00 54.71          A C
ATOM  20982  OE1  GLN I 306      -0.836 -35.428 -20.072  1.00 54.92          A O
ATOM  20983  N    SER I 307      -4.208 -30.912 -21.098  1.00 53.29          A N
ATOM  20984  CA   SER I 307      -4.169 -29.521 -20.628  1.00 53.52          A C
ATOM  20985  C    SER I 307      -4.079 -28.517 -21.784  1.00 53.39          A C
ATOM  20986  O    SER I 307      -3.201 -27.640 -21.800  1.00 53.16          A O
ATOM  20987  CB   SER I 307      -2.990 -29.323 -19.669  1.00 53.56          A C
ATOM  20988  OG   SER I 307      -2.894 -30.390 -18.743  1.00 54.27          A O
ATOM  20989  N    HIS I 308      -4.988 -28.653 -22.748  1.00 53.50          A N
ATOM  20990  CA   HIS I 308      -4.929 -27.874 -23.985  1.00 53.47          A C
ATOM  20991  C    HIS I 308      -6.272 -27.216 -24.265  1.00 53.74          A C
ATOM  20992  O    HIS I 308      -7.010 -27.651 -25.150  1.00 53.99          A O
ATOM  20993  CB   HIS I 308      -4.527 -28.778 -25.152  1.00 53.30          A C
ATOM  20994  CG   HIS I 308      -3.972 -28.040 -26.326  1.00 52.99          A C
ATOM  20995  CD2  HIS I 308      -2.766 -27.455 -26.519  1.00 52.57          A C
```

FIGURE 1 (cont'd)

```
ATOM  20996  ND1  HIS I 308     -4.687 -27.842 -27.488  1.00 53.25      A    N
ATOM  20997  CE1  HIS I 308     -3.944 -27.168 -28.349  1.00 52.93      A    C
ATOM  20998  NE2  HIS I 308     -2.775 -26.918 -27.784  1.00 52.43      A    N
ATOM  20999  N    PRO I 309     -6.588 -26.153 -23.509  1.00 53.95      A    N
ATOM  21000  CA   PRO I 309     -7.910 -25.517 -23.547  1.00 54.44      A    C
ATOM  21001  C    PRO I 309     -8.103 -24.481 -24.668  1.00 54.69      A    C
ATOM  21002  O    PRO I 309     -8.742 -23.450 -24.447  1.00 54.96      A    O
ATOM  21003  CB   PRO I 309     -8.038 -24.854 -22.163  1.00 54.68      A    C
ATOM  21004  CG   PRO I 309     -6.959 -25.461 -21.292  1.00 54.46      A    C
ATOM  21005  N    GLN I 310     -7.529 -24.751 -25.841  1.00 54.73      A    N
ATOM  21006  CA   GLN I 310     -7.908 -24.103 -27.114  1.00 54.90      A    C
ATOM  21007  C    GLN I 310     -7.152 -24.666 -28.332  1.00 55.00      A    C
ATOM  21008  O    GLN I 310     -6.377 -25.619 -28.217  1.00 54.83      A    O
ATOM  21009  CB   GLN I 310     -7.891 -22.560 -27.070  1.00 54.92      A    C
ATOM  21010  CG   GLN I 310     -6.777 -21.895 -26.291  1.00 54.53      A    C
ATOM  21011  CD   GLN I 310     -7.311 -20.771 -25.430  1.00 54.59      A    C
ATOM  21012  NE2  GLN I 310     -8.502 -20.278 -25.768  1.00 54.58      A    N
ATOM  21013  OE1  GLN I 310     -6.707 -20.414 -24.422  1.00 55.23      A    O
ATOM  21014  N    GLU I 311     -7.400 -24.074 -29.496  1.00 55.38      A    N
ATOM  21015  CA   GLU I 311     -6.895 -24.591 -30.753  1.00 55.72      A    C
ATOM  21016  C    GLU I 311     -5.466 -24.138 -30.945  1.00 55.03      A    C
ATOM  21017  O    GLU I 311     -4.549 -24.968 -30.962  1.00 54.86      A    O
ATOM  21018  CB   GLU I 311     -7.767 -24.117 -31.917  1.00 56.50      A    C
ATOM  21019  CG   GLU I 311     -9.282 -24.333 -31.724  1.00 58.92      A    C
ATOM  21020  CD   GLU I 311     -9.993 -23.194 -30.956  1.00 61.45      A    C
ATOM  21021  OE1  GLU I 311    -11.226 -23.040 -31.146  1.00 62.84      A    O
ATOM  21022  OE2  GLU I 311     -9.336 -22.458 -30.170  1.00 62.01      A    O
ATOM  21023  N    VAL I 312     -5.282 -22.825 -31.088  1.00 54.46      A    N
ATOM  21024  CA   VAL I 312     -3.944 -22.243 -31.175  1.00 53.76      A    C
ATOM  21025  C    VAL I 312     -3.438 -21.879 -29.772  1.00 53.24      A    C
ATOM  21026  O    VAL I 312     -3.919 -20.924 -29.149  1.00 53.57      A    O
ATOM  21027  N    MET I 313     -2.491 -22.672 -29.276  1.00 52.21      A    N
ATOM  21028  CA   MET I 313     -1.836 -22.420 -27.994  1.00 51.22      A    C
ATOM  21029  C    MET I 313     -0.336 -22.258 -28.241  1.00 50.23      A    C
ATOM  21030  O    MET I 313      0.262 -21.230 -27.912  1.00 50.08      A    O
ATOM  21031  CB   MET I 313     -2.072 -23.591 -27.036  1.00 51.40      A    C
ATOM  21032  CG   MET I 313     -3.523 -23.840 -26.640  1.00 52.01      A    C
ATOM  21033  SD   MET I 313     -3.890 -23.566 -24.886  1.00 52.48      A    S
ATOM  21034  CE   MET I 313     -2.842 -24.787 -24.076  1.00 52.14      A    C
ATOM  21035  N    TYR I 314      0.248 -23.284 -28.855  1.00 49.14      A    N
ATOM  21036  CA   TYR I 314      1.688 -23.389 -29.037  1.00 48.04      A    C
ATOM  21037  C    TYR I 314      2.199 -22.661 -30.275  1.00 47.52      A    C
ATOM  21038  O    TYR I 314      2.989 -21.724 -30.161  1.00 47.30      A    O
ATOM  21039  CB   TYR I 314      2.103 -24.862 -29.080  1.00 47.82      A    C
ATOM  21040  CG   TYR I 314      1.791 -25.639 -27.815  1.00 47.55      A    C
ATOM  21041  CD1  TYR I 314      1.873 -25.036 -26.561  1.00 47.54      A    C
ATOM  21042  CD2  TYR I 314      1.452 -26.990 -27.870  1.00 47.39      A    C
ATOM  21043  CE1  TYR I 314      1.602 -25.753 -25.401  1.00 47.63      A    C
ATOM  21044  CE2  TYR I 314      1.178 -27.717 -26.714  1.00 47.42      A    C
ATOM  21045  CZ   TYR I 314      1.256 -27.092 -25.488  1.00 47.36      A    C
ATOM  21046  OH   TYR I 314      0.989 -27.804 -24.347  1.00 47.33      A    O
ATOM  21047  N    PHE I 315      1.748 -23.092 -31.451  1.00 47.09      A    N
ATOM  21048  CA   PHE I 315      2.220 -22.519 -32.708  1.00 46.70      A    C
ATOM  21049  C    PHE I 315      1.350 -21.355 -33.117  1.00 46.95      A    C
ATOM  21050  O    PHE I 315      0.313 -21.513 -33.751  1.00 47.02      A    O
ATOM  21051  CB   PHE I 315      2.299 -23.588 -33.786  1.00 46.39      A    C
ATOM  21052  CG   PHE I 315      3.213 -24.719 -33.425  1.00 45.31      A    C
ATOM  21053  CD1  PHE I 315      4.575 -24.634 -33.699  1.00 44.55      A    C
ATOM  21054  CD2  PHE I 315      2.721 -25.863 -32.787  1.00 44.59      A    C
ATOM  21055  CE1  PHE I 315      5.438 -25.678 -33.354  1.00 44.01      A    C
ATOM  21056  CE2  PHE I 315      3.576 -26.914 -32.445  1.00 44.04      A    C
ATOM  21057  CZ   PHE I 315      4.937 -26.819 -32.728  1.00 43.78      A    C
ATOM  21058  N    GLN I 316      1.790 -20.177 -32.706  1.00 47.21      A    N
ATOM  21059  CA   GLN I 316      1.048 -18.950 -32.916  1.00 47.76      A    C
ATOM  21060  C    GLN I 316      1.116 -18.449 -34.359  1.00 48.12      A    C
```

FIGURE 1 (cont'd)

```
ATOM  21061  O    GLN I 316      2.108 -18.673 -35.061  1.00 47.94      A    O
ATOM  21062  CB   GLN I 316      1.549 -17.863 -31.959  1.00 47.81      A    C
ATOM  21063  CG   GLN I 316      1.149 -18.081 -30.501  1.00 48.26      A    C
ATOM  21064  CD   GLN I 316     -0.363 -18.053 -30.289  1.00 49.01      A    C
ATOM  21065  NE2  GLN I 316     -0.910 -19.169 -29.805  1.00 49.10      A    N
ATOM  21066  OE1  GLN I 316     -1.030 -17.043 -30.555  1.00 49.82      A    O
ATOM  21067  N    PRO I 317      0.052 -17.764 -34.811  1.00 48.70      A    N
ATOM  21068  CA   PRO I 317      0.122 -17.125 -36.115  1.00 48.99      A    C
ATOM  21069  C    PRO I 317      0.961 -15.851 -36.018  1.00 49.05      A    C
ATOM  21070  O    PRO I 317      1.240 -15.370 -34.909  1.00 49.00      A    O
ATOM  21071  CB   PRO I 317     -1.340 -16.782 -36.406  1.00 49.30      A    C
ATOM  21072  CG   PRO I 317     -1.937 -16.547 -35.045  1.00 49.43      A    C
ATOM  21073  CD   PRO I 317     -1.241 -17.520 -34.137  1.00 48.96      A    C
ATOM  21074  N    GLY I 318      1.346 -15.308 -37.167  1.00 49.09      A    N
ATOM  21075  CA   GLY I 318      2.214 -14.146 -37.202  1.00 49.02      A    C
ATOM  21076  C    GLY I 318      3.611 -14.574 -37.597  1.00 48.86      A    C
ATOM  21077  O    GLY I 318      4.073 -15.673 -37.238  1.00 48.66      A    O
ATOM  21078  N    GLU I 319      4.270 -13.702 -38.358  1.00 48.87      A    N
ATOM  21079  CA   GLU I 319      5.656 -13.900 -38.792  1.00 48.66      A    C
ATOM  21080  C    GLU I 319      6.519 -12.714 -38.316  1.00 48.78      A    C
ATOM  21081  O    GLU I 319      6.814 -11.803 -39.107  1.00 49.11      A    O
ATOM  21082  CB   GLU I 319      5.742 -14.068 -40.321  1.00 48.53      A    C
ATOM  21083  CG   GLU I 319      4.934 -15.248 -40.891  1.00 47.97      A    C
ATOM  21084  N    PRO I 320      6.901 -12.705 -37.012  1.00 48.68      A    N
ATOM  21085  CA   PRO I 320      7.823 -11.660 -36.541  1.00 48.68      A    C
ATOM  21086  C    PRO I 320      9.264 -11.838 -37.070  1.00 48.55      A    C
ATOM  21087  O    PRO I 320      9.651 -12.936 -37.503  1.00 48.37      A    O
ATOM  21088  CB   PRO I 320      7.766 -11.802 -35.008  1.00 48.72      A    C
ATOM  21089  CG   PRO I 320      6.486 -12.574 -34.739  1.00 48.68      A    C
ATOM  21090  CD   PRO I 320      6.401 -13.526 -35.889  1.00 48.49      A    C
ATOM  21091  N    PHE I 321     10.039 -10.756 -37.012  1.00 48.38      A    N
ATOM  21092  CA   PHE I 321     11.376 -10.675 -37.631  1.00 48.02      A    C
ATOM  21093  C    PHE I 321     12.434 -11.731 -37.205  1.00 48.20      A    C
ATOM  21094  O    PHE I 321     12.987 -12.432 -38.070  1.00 48.51      A    O
ATOM  21095  N    GLY I 322     12.714 -11.851 -35.899  1.00 48.07      A    N
ATOM  21096  CA   GLY I 322     13.820 -12.710 -35.402  1.00 47.46      A    C
ATOM  21097  C    GLY I 322     15.198 -12.045 -35.532  1.00 47.09      A    C
ATOM  21098  O    GLY I 322     15.295 -10.817 -35.617  1.00 47.63      A    O
ATOM  21099  N    SER I 323     16.281 -12.818 -35.510  1.00 46.15      A    N
ATOM  21100  CA   SER I 323     16.271 -14.239 -35.180  1.00 45.06      A    C
ATOM  21101  C    SER I 323     16.971 -14.443 -33.838  1.00 43.89      A    C
ATOM  21102  O    SER I 323     17.529 -13.511 -33.248  1.00 44.00      A    O
ATOM  21103  CB   SER I 323     17.001 -15.057 -36.263  1.00 45.27      A    C
ATOM  21104  OG   SER I 323     16.443 -14.831 -37.549  1.00 46.11      A    O
ATOM  21105  N    VAL I 324     16.940 -15.680 -33.373  1.00 42.30      A    N
ATOM  21106  CA   VAL I 324     17.659 -16.063 -32.188  1.00 40.77      A    C
ATOM  21107  C    VAL I 324     18.824 -16.957 -32.620  1.00 40.04      A    C
ATOM  21108  O    VAL I 324     18.605 -18.001 -33.241  1.00 39.95      A    O
ATOM  21109  CB   VAL I 324     16.713 -16.792 -31.215  1.00 40.54      A    C
ATOM  21110  CG1  VAL I 324     15.677 -15.812 -30.661  1.00 40.42      A    C
ATOM  21111  CG2  VAL I 324     17.484 -17.466 -30.086  1.00 40.09      A    C
ATOM  21112  N    GLU I 325     20.051 -16.538 -32.305  1.00 39.22      A    N
ATOM  21113  CA   GLU I 325     21.256 -17.276 -32.682  1.00 38.53      A    C
ATOM  21114  C    GLU I 325     21.334 -18.671 -32.058  1.00 37.62      A    C
ATOM  21115  O    GLU I 325     21.312 -18.829 -30.850  1.00 37.48      A    O
ATOM  21116  CB   GLU I 325     22.496 -16.465 -32.322  1.00 38.89      A    C
ATOM  21117  CG   GLU I 325     22.512 -15.066 -32.918  1.00 40.46      A    C
ATOM  21118  CD   GLU I 325     23.868 -14.383 -32.778  1.00 42.59      A    C
ATOM  21119  OE1  GLU I 325     24.851 -15.043 -32.355  1.00 42.99      A    O
ATOM  21120  OE2  GLU I 325     23.952 -13.174 -33.094  1.00 43.87      A    O
ATOM  21121  N    ASP I 326     21.425 -19.685 -32.898  1.00 36.79      A    N
ATOM  21122  CA   ASP I 326     21.453 -21.057 -32.422  1.00 36.04      A    C
ATOM  21123  C    ASP I 326     22.177 -21.922 -33.466  1.00 35.81      A    C
ATOM  21124  O    ASP I 326     22.725 -21.389 -34.447  1.00 35.91      A    O
ATOM  21125  CB   ASP I 326     20.020 -21.542 -32.180  1.00 35.75      A    C
```

FIGURE 1 (cont'd)

```
ATOM  21126  CG   ASP I 326      19.927 -22.637 -31.125  1.00 35.14      A  C
ATOM  21127  OD1  ASP I 326      20.917 -23.357 -30.862  1.00 34.83      A  O
ATOM  21128  OD2  ASP I 326      18.828 -22.792 -30.563  1.00 34.64      A  O
ATOM  21129  N    ASP I 327      22.173 -23.241 -33.259  1.00 35.33      A  N
ATOM  21130  CA   ASP I 327      22.899 -24.196 -34.104  1.00 34.99      A  C
ATOM  21131  C    ASP I 327      22.595 -24.132 -35.601  1.00 34.61      A  C
ATOM  21132  O    ASP I 327      23.357 -24.674 -36.408  1.00 34.69      A  O
ATOM  21133  CB   ASP I 327      22.633 -25.623 -33.630  1.00 35.15      A  C
ATOM  21134  CG   ASP I 327      23.334 -25.957 -32.313  1.00 36.11      A  C
ATOM  21135  OD1  ASP I 327      24.596 -25.994 -32.295  1.00 36.81      A  O
ATOM  21136  OD2  ASP I 327      22.615 -26.221 -31.302  1.00 36.77      A  O
ATOM  21137  N    HIS I 328      21.485 -23.493 -35.970  1.00 34.10      A  N
ATOM  21138  CA   HIS I 328      21.068 -23.426 -37.369  1.00 33.77      A  C
ATOM  21139  C    HIS I 328      21.914 -22.440 -38.172  1.00 33.69      A  C
ATOM  21140  O    HIS I 328      22.089 -22.625 -39.389  1.00 33.88      A  O
ATOM  21141  CB   HIS I 328      19.594 -23.043 -37.476  1.00 33.61      A  C
ATOM  21142  CG   HIS I 328      19.320 -21.618 -37.107  1.00 33.89      A  C
ATOM  21143  CD2  HIS I 328      19.097 -20.522 -37.871  1.00 34.44      A  C
ATOM  21144  ND1  HIS I 328      19.284 -21.187 -35.798  1.00 34.12      A  N
ATOM  21145  CE1  HIS I 328      19.032 -19.889 -35.771  1.00 34.36      A  C
ATOM  21146  NE2  HIS I 328      18.913 -19.460 -37.015  1.00 34.59      A  N
ATOM  21147  N    ILE I 329      22.434 -21.410 -37.494  1.00 33.52      A  N
ATOM  21148  CA   ILE I 329      23.179 -20.322 -38.156  1.00 33.67      A  C
ATOM  21149  C    ILE I 329      24.255 -20.753 -39.182  1.00 33.70      A  C
ATOM  21150  O    ILE I 329      24.224 -20.273 -40.334  1.00 33.93      A  O
ATOM  21151  CB   ILE I 329      23.778 -19.327 -37.140  1.00 33.72      A  C
ATOM  21152  CG1  ILE I 329      22.652 -18.608 -36.395  1.00 33.93      A  C
ATOM  21153  CG2  ILE I 329      24.718 -18.329 -37.846  1.00 34.17      A  C
ATOM  21154  CD1  ILE I 329      21.770 -17.730 -37.292  1.00 34.48      A  C
ATOM  21155  N    PRO I 330      25.198 -21.652 -38.784  1.00 33.63      A  N
ATOM  21156  CA   PRO I 330      26.219 -22.017 -39.777  1.00 33.69      A  C
ATOM  21157  C    PRO I 330      25.686 -22.946 -40.893  1.00 33.58      A  C
ATOM  21158  O    PRO I 330      26.373 -23.140 -41.905  1.00 33.85      A  O
ATOM  21159  CB   PRO I 330      27.300 -22.713 -38.933  1.00 33.75      A  C
ATOM  21160  CG   PRO I 330      26.538 -23.333 -37.793  1.00 33.54      A  C
ATOM  21161  CD   PRO I 330      25.385 -22.388 -37.510  1.00 33.48      A  C
ATOM  21162  N    PHE I 331      24.490 -23.509 -40.715  1.00 33.11      A  N
ATOM  21163  CA   PHE I 331      23.847 -24.209 -41.803  1.00 32.89      A  C
ATOM  21164  C    PHE I 331      23.090 -23.236 -42.678  1.00 32.88      A  C
ATOM  21165  O    PHE I 331      23.086 -23.365 -43.903  1.00 32.99      A  O
ATOM  21166  CB   PHE I 331      22.942 -25.288 -41.264  1.00 32.67      A  C
ATOM  21167  CG   PHE I 331      23.689 -26.434 -40.689  1.00 32.81      A  C
ATOM  21168  CD1  PHE I 331      23.840 -26.557 -39.317  1.00 32.84      A  C
ATOM  21169  CD2  PHE I 331      24.283 -27.391 -41.518  1.00 33.34      A  C
ATOM  21170  CE1  PHE I 331      24.557 -27.647 -38.765  1.00 33.07      A  C
ATOM  21171  CE2  PHE I 331      25.000 -28.482 -40.975  1.00 33.52      A  C
ATOM  21172  CZ   PHE I 331      25.136 -28.607 -39.598  1.00 33.21      A  C
ATOM  21173  N    LEU I 332      22.467 -22.253 -42.041  1.00 32.82      A  N
ATOM  21174  CA   LEU I 332      21.741 -21.210 -42.751  1.00 33.01      A  C
ATOM  21175  C    LEU I 332      22.655 -20.362 -43.647  1.00 33.46      A  C
ATOM  21176  O    LEU I 332      22.281 -20.024 -44.780  1.00 33.69      A  O
ATOM  21177  CB   LEU I 332      20.985 -20.312 -41.767  1.00 32.70      A  C
ATOM  21178  CG   LEU I 332      20.241 -19.110 -42.370  1.00 32.45      A  C
ATOM  21179  CD1  LEU I 332      18.841 -19.492 -42.837  1.00 32.02      A  C
ATOM  21180  CD2  LEU I 332      20.178 -17.977 -41.362  1.00 32.41      A  C
ATOM  21181  N    ARG I 333      23.844 -20.024 -43.142  1.00 33.84      A  N
ATOM  21182  CA   ARG I 333      24.804 -19.226 -43.922  1.00 34.41      A  C
ATOM  21183  C    ARG I 333      25.247 -19.960 -45.230  1.00 34.19      A  C
ATOM  21184  O    ARG I 333      25.648 -19.332 -46.235  1.00 34.49      A  O
ATOM  21185  CB   ARG I 333      25.982 -18.735 -43.038  1.00 34.75      A  C
ATOM  21186  CG   ARG I 333      27.342 -19.412 -43.269  1.00 36.62      A  C
ATOM  21187  CD   ARG I 333      28.499 -18.581 -42.683  1.00 39.93      A  C
ATOM  21188  NE   ARG I 333      28.960 -19.085 -41.378  1.00 42.25      A  N
ATOM  21189  CZ   ARG I 333      30.101 -19.760 -41.170  1.00 42.98      A  C
ATOM  21190  NH1  ARG I 333      30.420 -20.182 -39.943  1.00 42.60      A  N
```

FIGURE 1 (cont'd)

```
ATOM  21191  NH2 ARG I 333     30.932 -20.024 -42.179  1.00 43.84      A  N
ATOM  21192  N   ARG I 334     25.131 -21.290 -45.203  1.00 33.64      A  N
ATOM  21193  CA  ARG I 334     25.405 -22.138 -46.365  1.00 33.21      A  C
ATOM  21194  C   ARG I 334     24.158 -22.410 -47.222  1.00 32.74      A  C
ATOM  21195  O   ARG I 334     24.224 -23.161 -48.199  1.00 32.86      A  O
ATOM  21196  CB  ARG I 334     26.043 -23.458 -45.919  1.00 33.19      A  C
ATOM  21197  CG  ARG I 334     27.525 -23.340 -45.626  1.00 33.64      A  C
ATOM  21198  CD  ARG I 334     27.926 -24.286 -44.512  1.00 33.77      A  C
ATOM  21199  NE  ARG I 334     29.376 -24.436 -44.406  1.00 34.80      A  N
ATOM  21200  CZ  ARG I 334     30.138 -23.821 -43.503  1.00 35.58      A  C
ATOM  21201  NH1 ARG I 334     29.600 -23.003 -42.596  1.00 35.27      A  N
ATOM  21202  NH2 ARG I 334     31.451 -24.028 -43.503  1.00 36.58      A  N
ATOM  21203  N   GLY I 335     23.027 -21.812 -46.843  1.00 32.14      A  N
ATOM  21204  CA  GLY I 335     21.794 -21.876 -47.638  1.00 31.52      A  C
ATOM  21205  C   GLY I 335     20.817 -23.006 -47.331  1.00 30.87      A  C
ATOM  21206  O   GLY I 335     19.906 -23.272 -48.130  1.00 31.16      A  O
ATOM  21207  N   VAL I 336     20.997 -23.674 -46.190  1.00 29.95      A  N
ATOM  21208  CA  VAL I 336     20.071 -24.729 -45.781  1.00 29.10      A  C
ATOM  21209  C   VAL I 336     18.779 -24.077 -45.303  1.00 28.69      A  C
ATOM  21210  O   VAL I 336     18.823 -23.112 -44.533  1.00 28.62      A  O
ATOM  21211  CB  VAL I 336     20.650 -25.637 -44.669  1.00 28.91      A  C
ATOM  21212  CG1 VAL I 336     19.658 -26.721 -44.271  1.00 28.78      A  C
ATOM  21213  CG2 VAL I 336     21.953 -26.267 -45.116  1.00 29.05      A  C
ATOM  21214  N   PRO I 337     17.623 -24.573 -45.802  1.00 28.52      A  N
ATOM  21215  CA  PRO I 337     16.314 -24.169 -45.262  1.00 28.25      A  C
ATOM  21216  C   PRO I 337     16.214 -24.547 -43.782  1.00 27.81      A  C
ATOM  21217  O   PRO I 337     16.526 -25.692 -43.400  1.00 27.76      A  O
ATOM  21218  CB  PRO I 337     15.306 -24.985 -46.094  1.00 28.35      A  C
ATOM  21219  CG  PRO I 337     16.018 -25.289 -47.377  1.00 28.76      A  C
ATOM  21220  CD  PRO I 337     17.482 -25.455 -46.981  1.00 28.71      A  C
ATOM  21221  N   VAL I 338     15.807 -23.577 -42.962  1.00 27.37      A  N
ATOM  21222  CA  VAL I 338     15.722 -23.785 -41.520  1.00 26.78      A  C
ATOM  21223  C   VAL I 338     14.308 -23.572 -40.987  1.00 26.59      A  C
ATOM  21224  O   VAL I 338     13.613 -22.601 -41.355  1.00 26.77      A  O
ATOM  21225  CB  VAL I 338     16.694 -22.854 -40.747  1.00 26.66      A  C
ATOM  21226  CG1 VAL I 338     16.568 -23.073 -39.230  1.00 26.40      A  C
ATOM  21227  CG2 VAL I 338     18.146 -23.072 -41.205  1.00 26.63      A  C
ATOM  21228  N   LEU I 339     13.898 -24.493 -40.121  1.00 26.22      A  N
ATOM  21229  CA  LEU I 339     12.741 -24.262 -39.265  1.00 25.99      A  C
ATOM  21230  C   LEU I 339     13.183 -24.251 -37.806  1.00 25.86      A  C
ATOM  21231  O   LEU I 339     13.562 -25.308 -37.244  1.00 25.84      A  O
ATOM  21232  CB  LEU I 339     11.647 -25.313 -39.488  1.00 25.91      A  C
ATOM  21233  CG  LEU I 339     10.336 -25.069 -38.728  1.00 25.73      A  C
ATOM  21234  CD1 LEU I 339      9.749 -23.639 -38.977  1.00 26.01      A  C
ATOM  21235  CD2 LEU I 339      9.341 -26.174 -39.081  1.00 25.52      A  C
ATOM  21236  N   HIS I 340     13.132 -23.055 -37.207  1.00 25.68      A  N
ATOM  21237  CA  HIS I 340     13.648 -22.841 -35.850  1.00 25.49      A  C
ATOM  21238  C   HIS I 340     12.567 -23.019 -34.796  1.00 25.33      A  C
ATOM  21239  O   HIS I 340     11.790 -22.096 -34.529  1.00 25.35      A  O
ATOM  21240  CB  HIS I 340     14.284 -21.453 -35.730  1.00 25.52      A  C
ATOM  21241  CG  HIS I 340     15.285 -21.339 -34.616  1.00 25.71      A  C
ATOM  21242  CD2 HIS I 340     15.909 -22.288 -33.872  1.00 25.70      A  C
ATOM  21243  ND1 HIS I 340     15.756 -20.120 -34.162  1.00 26.04      A  N
ATOM  21244  CE1 HIS I 340     16.629 -20.325 -33.190  1.00 25.98      A  C
ATOM  21245  NE2 HIS I 340     16.739 -21.629 -32.994  1.00 25.94      A  N
ATOM  21246  N   LEU I 341     12.534 -24.209 -34.203  1.00 25.17      A  N
ATOM  21247  CA  LEU I 341     11.493 -24.561 -33.244  1.00 25.16      A  C
ATOM  21248  C   LEU I 341     11.930 -24.280 -31.793  1.00 25.16      A  C
ATOM  21249  O   LEU I 341     12.096 -25.209 -30.969  1.00 25.11      A  O
ATOM  21250  CB  LEU I 341     11.095 -26.031 -33.409  1.00 25.16      A  C
ATOM  21251  CG  LEU I 341      9.595 -26.381 -33.424  1.00 25.35      A  C
ATOM  21252  CD1 LEU I 341      9.435 -27.901 -33.511  1.00 25.58      A  C
ATOM  21253  CD2 LEU I 341      8.816 -25.827 -32.226  1.00 25.09      A  C
ATOM  21254  N   ILE I 342     12.099 -22.987 -31.504  1.00 25.21      A  N
ATOM  21255  CA  ILE I 342     12.542 -22.489 -30.204  1.00 25.23      A  C
```

FIGURE 1 (cont'd)

```
ATOM  21256  C    ILE I 342      11.458 -21.551 -29.661  1.00 25.55      A    C
ATOM  21257  O    ILE I 342      10.941 -20.691 -30.401  1.00 25.76      A    O
ATOM  21258  CB   ILE I 342      13.899 -21.749 -30.343  1.00 25.05      A    C
ATOM  21259  CG1  ILE I 342      14.428 -21.290 -28.981  1.00 24.92      A    C
ATOM  21260  CG2  ILE I 342      13.786 -20.570 -31.347  1.00 25.00      A    C
ATOM  21261  CD1  ILE I 342      15.883 -20.821 -29.001  1.00 24.65      A    C
ATOM  21262  N    SER I 343      11.094 -21.723 -28.388  1.00 25.83      A    N
ATOM  21263  CA   SER I 343      10.051 -20.870 -27.794  1.00 26.26      A    C
ATOM  21264  C    SER I 343      10.559 -19.458 -27.555  1.00 26.42      A    C
ATOM  21265  O    SER I 343      11.671 -19.257 -27.052  1.00 26.34      A    O
ATOM  21266  CB   SER I 343       9.478 -21.459 -26.504  1.00 26.35      A    C
ATOM  21267  OG   SER I 343      10.441 -21.464 -25.472  1.00 27.00      A    O
ATOM  21268  N    THR I 344       9.747 -18.492 -27.971  1.00 26.78      A    N
ATOM  21269  CA   THR I 344      10.003 -17.071 -27.740  1.00 27.12      A    C
ATOM  21270  C    THR I 344       8.737 -16.530 -27.101  1.00 27.57      A    C
ATOM  21271  O    THR I 344       7.673 -16.564 -27.731  1.00 27.70      A    O
ATOM  21272  CB   THR I 344      10.310 -16.283 -29.038  1.00 27.04      A    C
ATOM  21273  OG1  THR I 344      10.066 -17.112 -30.185  1.00 26.80      A    O
ATOM  21274  N    PRO I 345       8.836 -16.045 -25.845  1.00 27.91      A    N
ATOM  21275  CA   PRO I 345      10.065 -15.840 -25.078  1.00 27.93      A    C
ATOM  21276  C    PRO I 345      10.664 -17.132 -24.512  1.00 27.72      A    C
ATOM  21277  O    PRO I 345      10.025 -18.201 -24.563  1.00 27.44      A    O
ATOM  21278  CB   PRO I 345       9.613 -14.924 -23.930  1.00 28.16      A    C
ATOM  21279  CG   PRO I 345       8.114 -14.766 -24.078  1.00 28.27      A    C
ATOM  21280  CD   PRO I 345       7.654 -15.841 -24.995  1.00 28.04      A    C
ATOM  21281  N    PHE I 346      11.890 -17.016 -23.996  1.00 27.70      A    N
ATOM  21282  CA   PHE I 346      12.592 -18.136 -23.382  1.00 27.84      A    C
ATOM  21283  C    PHE I 346      11.899 -18.550 -22.087  1.00 28.07      A    C
ATOM  21284  O    PHE I 346      11.223 -17.724 -21.459  1.00 28.43      A    O
ATOM  21285  CB   PHE I 346      14.053 -17.778 -23.085  1.00 27.88      A    C
ATOM  21286  CG   PHE I 346      14.877 -17.464 -24.307  1.00 28.03      A    C
ATOM  21287  CD1  PHE I 346      14.460 -17.852 -25.579  1.00 27.86      A    C
ATOM  21288  CD2  PHE I 346      16.094 -16.795 -24.176  1.00 28.61      A    C
ATOM  21289  CE1  PHE I 346      15.230 -17.566 -26.694  1.00 27.81      A    C
ATOM  21290  CE2  PHE I 346      16.878 -16.503 -25.287  1.00 28.49      A    C
ATOM  21291  CZ   PHE I 346      16.445 -16.888 -26.548  1.00 28.04      A    C
ATOM  21292  N    PRO I 347      12.068 -19.823 -21.673  1.00 28.04      A    N
ATOM  21293  CA   PRO I 347      11.506 -20.316 -20.422  1.00 28.42      A    C
ATOM  21294  C    PRO I 347      11.882 -19.422 -19.239  1.00 29.04      A    C
ATOM  21295  O    PRO I 347      12.996 -18.900 -19.198  1.00 29.20      A    O
ATOM  21296  CB   PRO I 347      12.180 -21.682 -20.259  1.00 28.19      A    C
ATOM  21297  CG   PRO I 347      12.506 -22.107 -21.609  1.00 27.72      A    C
ATOM  21298  CD   PRO I 347      12.856 -20.863 -22.353  1.00 27.73      A    C
ATOM  21299  N    ALA I 348      10.967 -19.247 -18.287  1.00 29.71      A    N
ATOM  21300  CA   ALA I 348      11.264 -18.464 -17.078  1.00 30.38      A    C
ATOM  21301  C    ALA I 348      12.537 -18.965 -16.389  1.00 30.62      A    C
ATOM  21302  O    ALA I 348      13.369 -18.175 -15.913  1.00 30.73      A    O
ATOM  21303  CB   ALA I 348      10.075 -18.488 -16.101  1.00 30.65      A    C
ATOM  21304  N    VAL I 349      12.675 -20.289 -16.376  1.00 30.71      A    N
ATOM  21305  CA   VAL I 349      13.800 -20.975 -15.751  1.00 30.91      A    C
ATOM  21306  C    VAL I 349      15.045 -21.028 -16.639  1.00 31.01      A    C
ATOM  21307  O    VAL I 349      15.898 -21.915 -16.454  1.00 31.13      A    O
ATOM  21308  CB   VAL I 349      13.436 -22.423 -15.339  1.00 30.86      A    C
ATOM  21309  CG1  VAL I 349      12.352 -22.416 -14.282  1.00 31.44      A    C
ATOM  21310  CG2  VAL I 349      13.009 -23.252 -16.555  1.00 30.46      A    C
ATOM  21311  N    TRP I 350      15.171 -20.077 -17.572  1.00 31.09      A    N
ATOM  21312  CA   TRP I 350      16.259 -20.125 -18.557  1.00 31.17      A    C
ATOM  21313  C    TRP I 350      17.598 -19.681 -17.997  1.00 31.51      A    C
ATOM  21314  O    TRP I 350      17.692 -18.649 -17.308  1.00 31.70      A    O
ATOM  21315  CB   TRP I 350      15.930 -19.320 -19.805  1.00 30.96      A    C
ATOM  21316  CG   TRP I 350      16.934 -19.488 -20.894  1.00 30.51      A    C
ATOM  21317  CD1  TRP I 350      17.161 -20.608 -21.639  1.00 30.21      A    C
ATOM  21318  CD2  TRP I 350      17.855 -18.498 -21.363  1.00 30.18      A    C
ATOM  21319  CE2  TRP I 350      18.602 -19.081 -22.406  1.00 29.93      A    C
ATOM  21320  CE3  TRP I 350      18.118 -17.169 -21.007  1.00 30.22      A    C
```

FIGURE 1 (cont'd)

```
ATOM  21321  NE1 TRP I 350     18.162 -20.371 -22.551  1.00 29.99      A    N
ATOM  21322  CZ2 TRP I 350     19.598 -18.382 -23.096  1.00 29.65      A    C
ATOM  21323  CZ3 TRP I 350     19.114 -16.472 -21.699  1.00 30.03      A    C
ATOM  21324  CH2 TRP I 350     19.840 -17.084 -22.726  1.00 29.66      A    C
ATOM  21325  N   HIS I 351     18.619 -20.483 -18.319  1.00 31.87      A    N
ATOM  21326  CA  HIS I 351     20.011 -20.264 -17.891  1.00 32.43      A    C
ATOM  21327  C   HIS I 351     20.110 -20.017 -16.386  1.00 32.96      A    C
ATOM  21328  O   HIS I 351     20.740 -19.053 -15.941  1.00 33.21      A    O
ATOM  21329  CB  HIS I 351     20.675 -19.134 -18.710  1.00 32.39      A    C
ATOM  21330  CG  HIS I 351     21.215 -19.579 -20.042  1.00 32.45      A    C
ATOM  21331  CD2 HIS I 351     20.950 -20.680 -20.796  1.00 32.10      A    C
ATOM  21332  ND1 HIS I 351     22.166 -18.858 -20.739  1.00 32.57      A    N
ATOM  21333  CE1 HIS I 351     22.450 -19.486 -21.870  1.00 32.30      A    C
ATOM  21334  NE2 HIS I 351     21.725 -20.593 -21.930  1.00 31.89      A    N
ATOM  21335  N   THR I 352     19.463 -20.897 -15.622  1.00 33.39      A    N
ATOM  21336  CA  THR I 352     19.454 -20.830 -14.161  1.00 33.96      A    C
ATOM  21337  C   THR I 352     19.302 -22.230 -13.581  1.00 34.22      A    C
ATOM  21338  O   THR I 352     18.697 -23.087 -14.227  1.00 33.99      A    O
ATOM  21339  CB  THR I 352     18.333 -19.895 -13.603  1.00 34.08      A    C
ATOM  21340  CG2 THR I 352     17.083 -19.960 -14.439  1.00 33.58      A    C
ATOM  21341  OG1 THR I 352     17.999 -20.294 -12.264  1.00 34.84      A    O
ATOM  21342  N   PRO I 353     19.849 -22.463 -12.363  1.00 34.73      A    N
ATOM  21343  CA  PRO I 353     19.742 -23.734 -11.631  1.00 34.80      A    C
ATOM  21344  C   PRO I 353     18.329 -24.275 -11.601  1.00 34.61      A    C
ATOM  21345  O   PRO I 353     18.142 -25.471 -11.404  1.00 34.61      A    O
ATOM  21346  CB  PRO I 353     20.113 -23.342 -10.212  1.00 35.24      A    C
ATOM  21347  CG  PRO I 353     21.034 -22.194 -10.380  1.00 35.55      A    C
ATOM  21348  CD  PRO I 353     20.627 -21.462 -11.605  1.00 34.98      A    C
ATOM  21349  N   ALA I 354     17.354 -23.383 -11.788  1.00 34.34      A    N
ATOM  21350  CA  ALA I 354     15.933 -23.724 -11.803  1.00 34.09      A    C
ATOM  21351  C   ALA I 354     15.527 -24.673 -12.941  1.00 33.79      A    C
ATOM  21352  O   ALA I 354     14.577 -25.444 -12.800  1.00 33.72      A    O
ATOM  21353  CB  ALA I 354     15.094 -22.445 -11.839  1.00 34.09      A    C
ATOM  21354  N   ASP I 355     16.252 -24.611 -14.057  1.00 33.58      A    N
ATOM  21355  CA  ASP I 355     15.996 -25.470 -15.225  1.00 33.35      A    C
ATOM  21356  C   ASP I 355     16.322 -26.948 -14.965  1.00 33.48      A    C
ATOM  21357  O   ASP I 355     17.318 -27.485 -15.453  1.00 33.32      A    O
ATOM  21358  CB  ASP I 355     16.763 -24.953 -16.454  1.00 33.06      A    C
ATOM  21359  CG  ASP I 355     16.316 -25.618 -17.754  1.00 32.56      A    C
ATOM  21360  OD1 ASP I 355     15.432 -26.509 -17.698  1.00 32.73      A    O
ATOM  21361  OD2 ASP I 355     16.850 -25.247 -18.831  1.00 31.68      A    O
ATOM  21362  N   THR I 356     15.457 -27.593 -14.193  1.00 33.79      A    N
ATOM  21363  CA  THR I 356     15.597 -29.005 -13.861  1.00 33.99      A    C
ATOM  21364  C   THR I 356     14.301 -29.735 -14.194  1.00 34.44      A    C
ATOM  21365  O   THR I 356     13.318 -29.110 -14.640  1.00 34.33      A    O
ATOM  21366  CB  THR I 356     15.962 -29.219 -12.366  1.00 33.38      A    C
ATOM  21367  OG1 THR I 356     14.972 -28.604 -11.532  1.00 33.34      A    O
ATOM  21368  N   GLU I 357     14.315 -31.056 -13.990  1.00 35.06      A    N
ATOM  21369  CA  GLU I 357     13.150 -31.920 -14.230  1.00 35.58      A    C
ATOM  21370  C   GLU I 357     11.883 -31.415 -13.517  1.00 35.95      A    C
ATOM  21371  O   GLU I 357     10.801 -31.357 -14.123  1.00 35.89      A    O
ATOM  21372  CB  GLU I 357     13.455 -33.355 -13.807  1.00 35.73      A    C
ATOM  21373  CG  GLU I 357     12.283 -34.330 -13.982  1.00 36.38      A    C
ATOM  21374  CD  GLU I 357     12.663 -35.807 -13.725  1.00 37.47      A    C
ATOM  21375  OE1 GLU I 357     13.842 -36.098 -13.386  1.00 38.23      A    O
ATOM  21376  OE2 GLU I 357     11.780 -36.692 -13.864  1.00 37.78      A    O
ATOM  21377  N   VAL I 358     12.041 -31.036 -12.245  1.00 36.43      A    N
ATOM  21378  CA  VAL I 358     10.958 -30.528 -11.400  1.00 36.82      A    C
ATOM  21379  C   VAL I 358     10.122 -29.395 -12.015  1.00 36.66      A    C
ATOM  21380  O   VAL I 358      8.967 -29.223 -11.638  1.00 36.93      A    O
ATOM  21381  CB  VAL I 358     11.503 -30.039 -10.048  1.00 37.19      A    C
ATOM  21382  CG1 VAL I 358     10.885 -30.825  -8.910  1.00 37.96      A    C
ATOM  21383  N   ASN I 359     10.688 -28.635 -12.954  1.00 36.25      A    N
ATOM  21384  CA  ASN I 359     10.011 -27.443 -13.492  1.00 35.93      A    C
ATOM  21385  C   ASN I 359      9.498 -27.552 -14.928  1.00 35.36      A    C
```

FIGURE 1 (cont'd)

```
ATOM  21386  O    ASN I 359      9.016 -26.569 -15.502  1.00 35.24      A    O
ATOM  21387  CB   ASN I 359     10.916 -26.216 -13.357  1.00 36.15      A    C
ATOM  21388  CG   ASN I 359     11.147 -25.806 -11.912  1.00 37.14      A    C
ATOM  21389  ND2  ASN I 359     10.455 -26.455 -10.980  1.00 38.09      A    N
ATOM  21390  OD1  ASN I 359     11.938 -24.904 -11.641  1.00 37.74      A    O
ATOM  21391  N    LEU I 360      9.615 -28.741 -15.509  1.00 34.85      A    N
ATOM  21392  CA   LEU I 360      9.025 -29.018 -16.817  1.00 34.36      A    C
ATOM  21393  C    LEU I 360      7.524 -29.254 -16.655  1.00 34.44      A    C
ATOM  21394  O    LEU I 360      7.078 -29.650 -15.564  1.00 34.93      A    O
ATOM  21395  CB   LEU I 360      9.672 -30.264 -17.415  1.00 34.05      A    C
ATOM  21396  CG   LEU I 360     11.199 -30.294 -17.484  1.00 33.49      A    C
ATOM  21397  CD1  LEU I 360     11.647 -31.648 -18.008  1.00 32.93      A    C
ATOM  21398  CD2  LEU I 360     11.730 -29.160 -18.356  1.00 33.10      A    C
ATOM  21399  N    HIS I 361      6.748 -28.998 -17.715  1.00 34.12      A    N
ATOM  21400  CA   HIS I 361      5.315 -29.347 -17.726  1.00 33.95      A    C
ATOM  21401  C    HIS I 361      5.102 -30.649 -18.518  1.00 34.22      A    C
ATOM  21402  O    HIS I 361      4.915 -30.606 -19.739  1.00 34.02      A    O
ATOM  21403  CB   HIS I 361      4.469 -28.202 -18.312  1.00 33.57      A    C
ATOM  21404  CG   HIS I 361      3.047 -28.187 -17.829  1.00 32.74      A    C
ATOM  21405  ND1  HIS I 361      2.074 -29.030 -18.325  1.00 31.58      A    N
ATOM  21406  CE1  HIS I 361      0.932 -28.788 -17.707  1.00 31.59      A    C
ATOM  21407  N    PRO I 362      5.140 -31.811 -17.831  1.00 34.69      A    N
ATOM  21408  CA   PRO I 362      5.095 -33.102 -18.534  1.00 34.93      A    C
ATOM  21409  C    PRO I 362      4.020 -33.193 -19.630  1.00 34.91      A    C
ATOM  21410  O    PRO I 362      4.308 -33.688 -20.738  1.00 34.77      A    O
ATOM  21411  CB   PRO I 362      4.835 -34.110 -17.402  1.00 35.24      A    C
ATOM  21412  CG   PRO I 362      5.485 -33.482 -16.211  1.00 35.34      A    C
ATOM  21413  CD   PRO I 362      5.227 -31.997 -16.368  1.00 35.01      A    C
ATOM  21414  N    PRO I 363      2.797 -32.716 -19.330  1.00 35.00      A    N
ATOM  21415  CA   PRO I 363      1.776 -32.656 -20.372  1.00 35.05      A    C
ATOM  21416  C    PRO I 363      2.291 -31.924 -21.628  1.00 34.69      A    C
ATOM  21417  O    PRO I 363      2.303 -32.514 -22.722  1.00 34.64      A    O
ATOM  21418  CB   PRO I 363      0.637 -31.875 -19.704  1.00 35.31      A    C
ATOM  21419  CG   PRO I 363      0.666 -32.307 -18.286  1.00 35.69      A    C
ATOM  21420  N    THR I 364      2.733 -30.676 -21.464  1.00 34.32      A    N
ATOM  21421  CA   THR I 364      3.254 -29.895 -22.581  1.00 33.98      A    C
ATOM  21422  C    THR I 364      4.297 -30.706 -23.362  1.00 33.90      A    C
ATOM  21423  O    THR I 364      4.314 -30.678 -24.596  1.00 33.75      A    O
ATOM  21424  CB   THR I 364      3.846 -28.540 -22.115  1.00 33.87      A    C
ATOM  21425  CG2  THR I 364      4.291 -27.698 -23.313  1.00 33.51      A    C
ATOM  21426  OG1  THR I 364      2.862 -27.815 -21.368  1.00 34.07      A    O
ATOM  21427  N    VAL I 365      5.142 -31.446 -22.642  1.00 34.00      A    N
ATOM  21428  CA   VAL I 365      6.180 -32.270 -23.275  1.00 34.14      A    C
ATOM  21429  C    VAL I 365      5.569 -33.286 -24.233  1.00 34.32      A    C
ATOM  21430  O    VAL I 365      5.906 -33.310 -25.431  1.00 34.14      A    O
ATOM  21431  CB   VAL I 365      7.080 -32.993 -22.230  1.00 34.15      A    C
ATOM  21432  CG1  VAL I 365      8.025 -31.992 -21.552  1.00 34.02      A    C
ATOM  21433  CG2  VAL I 365      7.874 -34.128 -22.884  1.00 33.99      A    C
ATOM  21434  N    HIS I 366      4.661 -34.102 -23.700  1.00 34.71      A    N
ATOM  21435  CA   HIS I 366      4.016 -35.159 -24.475  1.00 35.20      A    C
ATOM  21436  C    HIS I 366      3.219 -34.637 -25.683  1.00 35.38      A    C
ATOM  21437  O    HIS I 366      3.322 -35.199 -26.784  1.00 35.46      A    O
ATOM  21438  CB   HIS I 366      3.162 -36.031 -23.555  1.00 35.38      A    C
ATOM  21439  CG   HIS I 366      3.954 -36.702 -22.478  1.00 35.49      A    C
ATOM  21440  ND1  HIS I 366      5.003 -37.553 -22.757  1.00 35.55      A    N
ATOM  21441  CE1  HIS I 366      5.525 -37.998 -21.627  1.00 35.54      A    C
ATOM  21442  N    ASN I 367      2.454 -33.564 -25.467  1.00 35.40      A    N
ATOM  21443  CA   ASN I 367      1.795 -32.845 -26.544  1.00 35.44      A    C
ATOM  21444  C    ASN I 367      2.745 -32.567 -27.702  1.00 35.28      A    C
ATOM  21445  O    ASN I 367      2.438 -32.891 -28.856  1.00 35.41      A    O
ATOM  21446  CB   ASN I 367      1.228 -31.526 -26.031  1.00 35.51      A    C
ATOM  21447  CG   ASN I 367      0.020 -31.716 -25.152  1.00 36.15      A    C
ATOM  21448  ND2  ASN I 367     -0.667 -30.611 -24.855  1.00 36.25      A    N
ATOM  21449  OD1  ASN I 367     -0.307 -32.842 -24.744  1.00 37.05      A    O
ATOM  21450  N    LEU I 368      3.904 -31.990 -27.384  1.00 34.98      A    N
```

FIGURE 1 (cont'd)

```
ATOM  21451  CA   LEU I 368      4.891 -31.620 -28.395  1.00 34.77      A  C
ATOM  21452  C    LEU I 368      5.355 -32.827 -29.197  1.00 34.93      A  C
ATOM  21453  O    LEU I 368      5.596 -32.728 -30.407  1.00 35.01      A  O
ATOM  21454  CB   LEU I 368      6.088 -30.914 -27.751  1.00 34.39      A  C
ATOM  21455  CG   LEU I 368      5.881 -29.470 -27.281  1.00 33.78      A  C
ATOM  21456  CD1  LEU I 368      7.108 -28.996 -26.513  1.00 33.49      A  C
ATOM  21457  CD2  LEU I 368      5.557 -28.517 -28.447  1.00 32.90      A  C
ATOM  21458  N    ALA I 369      5.454 -33.963 -28.509  1.00 34.23      A  N
ATOM  21459  CA   ALA I 369      5.896 -35.213 -29.119  1.00 33.60      A  C
ATOM  21460  C    ALA I 369      4.832 -35.776 -30.059  1.00 34.58      A  C
ATOM  21461  O    ALA I 369      5.157 -36.301 -31.138  1.00 35.76      A  O
ATOM  21462  CB   ALA I 369      6.267 -36.231 -28.046  1.00 24.57      A  C
ATOM  21463  N    ARG I 370      3.569 -35.663 -29.641  1.00 35.20      A  N
ATOM  21464  CA   ARG I 370      2.439 -36.067 -30.478  1.00 34.86      A  C
ATOM  21465  C    ARG I 370      2.423 -35.222 -31.752  1.00 34.26      A  C
ATOM  21466  O    ARG I 370      2.318 -35.760 -32.862  1.00 34.16      A  O
ATOM  21467  CB   ARG I 370      1.114 -35.981 -29.705  1.00 35.13      A  C
ATOM  21468  CG   ARG I 370      1.034 -36.975 -28.523  1.00 35.45      A  C
ATOM  21469  CD   ARG I 370     -0.333 -36.968 -27.834  1.00 35.76      A  C
ATOM  21470  NE   ARG I 370     -0.462 -38.016 -26.820  1.00 35.87      A  N
ATOM  21471  CZ   ARG I 370     -1.616 -38.581 -26.475  1.00 36.02      A  C
ATOM  21472  N    ILE I 371      2.589 -33.912 -31.590  1.00 33.49      A  N
ATOM  21473  CA   ILE I 371      2.652 -33.001 -32.730  1.00 32.89      A  C
ATOM  21474  C    ILE I 371      3.825 -33.338 -33.653  1.00 32.79      A  C
ATOM  21475  O    ILE I 371      3.670 -33.428 -34.875  1.00 32.88      A  O
ATOM  21476  CB   ILE I 371      2.703 -31.527 -32.277  1.00 32.57      A  C
ATOM  21477  CG1  ILE I 371      1.381 -31.152 -31.585  1.00 32.54      A  C
ATOM  21478  CG2  ILE I 371      2.969 -30.601 -33.467  1.00 32.05      A  C
ATOM  21479  CD1  ILE I 371      1.396 -29.818 -30.841  1.00 32.24      A  C
ATOM  21480  N    LEU I 372      4.993 -33.546 -33.064  1.00 32.62      A  N
ATOM  21481  CA   LEU I 372      6.186 -33.878 -33.851  1.00 32.51      A  C
ATOM  21482  C    LEU I 372      6.057 -35.195 -34.600  1.00 32.80      A  C
ATOM  21483  O    LEU I 372      6.347 -35.257 -35.798  1.00 32.73      A  O
ATOM  21484  CB   LEU I 372      7.450 -33.885 -32.973  1.00 32.14      A  C
ATOM  21485  CG   LEU I 372      8.348 -32.631 -32.949  1.00 31.40      A  C
ATOM  21486  CD1  LEU I 372      7.729 -31.344 -33.578  1.00 30.83      A  C
ATOM  21487  CD2  LEU I 372      8.835 -32.373 -31.521  1.00 30.95      A  C
ATOM  21488  N    ALA I 373      5.615 -36.234 -33.888  1.00 33.20      A  N
ATOM  21489  CA   ALA I 373      5.466 -37.583 -34.453  1.00 33.60      A  C
ATOM  21490  C    ALA I 373      4.573 -37.574 -35.686  1.00 33.89      A  C
ATOM  21491  O    ALA I 373      4.874 -38.232 -36.689  1.00 34.02      A  O
ATOM  21492  CB   ALA I 373      4.924 -38.559 -33.404  1.00 33.69      A  C
ATOM  21493  N    VAL I 374      3.481 -36.815 -35.598  1.00 34.06      A  N
ATOM  21494  CA   VAL I 374      2.562 -36.655 -36.717  1.00 34.33      A  C
ATOM  21495  C    VAL I 374      3.276 -35.934 -37.853  1.00 34.24      A  C
ATOM  21496  O    VAL I 374      3.278 -36.418 -38.994  1.00 34.51      A  O
ATOM  21497  CB   VAL I 374      1.267 -35.895 -36.314  1.00 34.39      A  C
ATOM  21498  CG1  VAL I 374      0.485 -35.445 -37.554  1.00 34.59      A  C
ATOM  21499  CG2  VAL I 374      0.392 -36.771 -35.415  1.00 34.81      A  C
ATOM  21500  N    PHE I 375      3.891 -34.798 -37.532  1.00 33.94      A  N
ATOM  21501  CA   PHE I 375      4.631 -34.035 -38.523  1.00 33.79      A  C
ATOM  21502  C    PHE I 375      5.671 -34.891 -39.249  1.00 34.10      A  C
ATOM  21503  O    PHE I 375      5.732 -34.890 -40.485  1.00 34.15      A  O
ATOM  21504  CB   PHE I 375      5.322 -32.847 -37.872  1.00 33.38      A  C
ATOM  21505  CG   PHE I 375      6.140 -32.023 -38.833  1.00 32.66      A  C
ATOM  21506  CD1  PHE I 375      5.650 -30.796 -39.299  1.00 32.49      A  C
ATOM  21507  CD2  PHE I 375      7.404 -32.466 -39.269  1.00 32.09      A  C
ATOM  21508  CE1  PHE I 375      6.408 -30.008 -40.181  1.00 32.41      A  C
ATOM  21509  CE2  PHE I 375      8.162 -31.706 -40.150  1.00 32.23      A  C
ATOM  21510  CZ   PHE I 375      7.663 -30.466 -40.612  1.00 32.36      A  C
ATOM  21511  N    LEU I 376      6.487 -35.607 -38.469  1.00 34.47      A  N
ATOM  21512  CA   LEU I 376      7.550 -36.461 -39.007  1.00 34.92      A  C
ATOM  21513  C    LEU I 376      6.955 -37.463 -40.002  1.00 35.72      A  C
ATOM  21514  O    LEU I 376      7.461 -37.622 -41.127  1.00 35.82      A  O
ATOM  21515  CB   LEU I 376      8.291 -37.185 -37.873  1.00 34.58      A  C
```

FIGURE 1 (cont'd)

```
ATOM  21516  CG  LEU I 376      9.810 -37.320 -38.033  1.00 33.87      A    C
ATOM  21517  N   ALA I 377      5.860 -38.103 -39.582  1.00 36.63      A    N
ATOM  21518  CA  ALA I 377      5.118 -39.063 -40.405  1.00 37.49      A    C
ATOM  21519  C   ALA I 377      4.536 -38.426 -41.676  1.00 37.96      A    C
ATOM  21520  O   ALA I 377      4.697 -38.982 -42.769  1.00 38.25      A    O
ATOM  21521  CB  ALA I 377      4.016 -39.735 -39.578  1.00 37.62      A    C
ATOM  21522  N   GLU I 378      3.870 -37.274 -41.534  1.00 38.23      A    N
ATOM  21523  CA  GLU I 378      3.312 -36.564 -42.689  1.00 38.65      A    C
ATOM  21524  C   GLU I 378      4.404 -36.121 -43.672  1.00 38.65      A    C
ATOM  21525  O   GLU I 378      4.292 -36.398 -44.878  1.00 38.95      A    O
ATOM  21526  CB  GLU I 378      2.422 -35.384 -42.264  1.00 38.72      A    C
ATOM  21527  CG  GLU I 378      1.035 -35.808 -41.751  1.00 39.93      A    C
ATOM  21528  CD  GLU I 378      0.026 -34.646 -41.567  1.00 41.33      A    C
ATOM  21529  OE1 GLU I 378      0.363 -33.490 -41.932  1.00 41.82      A    O
ATOM  21530  OE2 GLU I 378     -1.112 -34.892 -41.063  1.00 41.94      A    O
ATOM  21531  N   TYR I 379      5.457 -35.464 -43.155  1.00 38.48      A    N
ATOM  21532  CA  TYR I 379      6.579 -34.968 -43.987  1.00 38.47      A    C
ATOM  21533  C   TYR I 379      7.248 -36.094 -44.813  1.00 39.03      A    C
ATOM  21534  O   TYR I 379      7.501 -35.949 -46.026  1.00 39.09      A    O
ATOM  21535  CB  TYR I 379      7.631 -34.228 -43.130  1.00 37.87      A    C
ATOM  21536  CG  TYR I 379      8.691 -33.493 -43.953  1.00 37.09      A    C
ATOM  21537  CD1 TYR I 379      8.628 -32.099 -44.136  1.00 36.33      A    C
ATOM  21538  CD2 TYR I 379      9.752 -34.196 -44.560  1.00 36.84      A    C
ATOM  21539  CE1 TYR I 379      9.591 -31.419 -44.901  1.00 36.15      A    C
ATOM  21540  CE2 TYR I 379     10.717 -33.528 -45.332  1.00 36.58      A    C
ATOM  21541  CZ  TYR I 379     10.630 -32.134 -45.499  1.00 36.24      A    C
ATOM  21542  OH  TYR I 379     11.576 -31.463 -46.257  1.00 35.91      A    O
ATOM  21543  N   LEU I 380      7.527 -37.207 -44.138  1.00 39.71      A    N
ATOM  21544  CA  LEU I 380      8.151 -38.359 -44.771  1.00 40.66      A    C
ATOM  21545  C   LEU I 380      7.121 -39.322 -45.355  1.00 41.89      A    C
ATOM  21546  O   LEU I 380      7.488 -40.421 -45.806  1.00 42.06      A    O
ATOM  21547  CB  LEU I 380      9.052 -39.091 -43.766  1.00 40.22      A    C
ATOM  21548  CG  LEU I 380     10.569 -38.865 -43.800  1.00 39.78      A    C
ATOM  21549  CD1 LEU I 380     10.977 -37.439 -44.225  1.00 39.39      A    C
ATOM  21550  CD2 LEU I 380     11.153 -39.230 -42.436  1.00 39.49      A    C
ATOM  21551  N   GLY I 381      5.845 -38.912 -45.334  1.00 46.80      A    N
ATOM  21552  CA  GLY I 381      4.722 -39.768 -45.732  1.00 51.73      A    C
ATOM  21553  C   GLY I 381      4.950 -41.239 -45.392  1.00 54.68      A    C
ATOM  21554  O   GLY I 381      4.969 -42.092 -46.288  1.00 55.33      A    O
ATOM  21555  N   LEU I 382      5.156 -41.539 -44.109  1.00 56.62      A    N
ATOM  21556  CA  LEU I 382      5.371 -42.926 -43.683  1.00 57.99      A    C
ATOM  21557  C   LEU I 382      4.065 -43.720 -43.719  1.00 58.46      A    C
ATOM  21558  O   LEU I 382      4.099 -44.955 -43.678  1.00 58.88      A    O
ATOM  21559  CB  LEU I 382      6.001 -43.000 -42.283  1.00 58.25      A    C
ATOM  21560  CG  LEU I 382      7.457 -42.556 -42.102  1.00 58.58      A    C
ATOM  21561  CD1 LEU I 382      7.801 -42.500 -40.612  1.00 58.82      A    C
ATOM  21562  CD2 LEU I 382      8.429 -43.461 -42.868  1.00 58.40      A    C
ATOM  21563  OXT LEU I 382      2.960 -43.154 -43.793  1.00 58.59      A    O
TER   21564      LEU I 382
ATOM  21565  N   LEU J  76    -16.313  -3.957-100.841  1.00 64.07      A    N
ATOM  21566  CA  LEU J  76    -17.651  -3.281-100.941  1.00 63.37      A    C
ATOM  21567  C   LEU J  76    -17.688  -1.922-100.161  1.00 60.52      A    C
ATOM  21568  O   LEU J  76    -16.900  -1.729 -99.220  1.00 60.94      A    O
ATOM  21569  CB  LEU J  76    -18.796  -4.264-100.570  1.00 64.65      A    C
ATOM  21570  CG  LEU J  76    -19.065  -5.480-101.500  1.00 66.01      A    C
ATOM  21571  CD1 LEU J  76    -19.894  -6.596-100.831  1.00 66.30      A    C
ATOM  21572  CD2 LEU J  76    -19.694  -5.076-102.840  1.00 66.16      A    C
ATOM  21573  N   PRO J  77    -18.615  -0.999-100.550  1.00 55.29      A    N
ATOM  21574  CA  PRO J  77    -18.655   0.486-100.414  1.00 55.67      A    C
ATOM  21575  C   PRO J  77    -18.887   1.027 -99.002  1.00 55.80      A    C
ATOM  21576  O   PRO J  77    -19.537   0.361 -98.190  1.00 55.70      A    O
ATOM  21577  CB  PRO J  77    -19.839   0.877-101.306  1.00 56.12      A    C
ATOM  21578  CG  PRO J  77    -20.763  -0.307-101.235  1.00 55.95      A    C
ATOM  21579  CD  PRO J  77    -19.932  -1.532-100.957  1.00 55.13      A    C
ATOM  21580  N   GLU J  78    -18.382   2.236 -98.739  1.00 55.94      A    N
```

FIGURE 1 (cont'd)

```
ATOM   21581  CA   GLU J  78     -18.447   2.874 -97.405  1.00 55.83       A    C
ATOM   21582  C    GLU J  78     -19.782   2.717 -96.647  1.00 57.08       A    C
ATOM   21583  O    GLU J  78     -19.788   2.402 -95.444  1.00 57.27       A    O
ATOM   21584  CB   GLU J  78     -18.057   4.361 -97.486  1.00 53.84       A    C
ATOM   21585  CG   GLU J  78     -16.605   4.660 -97.135  1.00 51.31       A    C
ATOM   21586  N    ALA J  79     -20.892   2.928 -97.358  1.00 58.30       A    N
ATOM   21587  CA   ALA J  79     -22.239   2.846 -96.779  1.00 58.96       A    C
ATOM   21588  C    ALA J  79     -22.533   1.490 -96.138  1.00 58.74       A    C
ATOM   21589  O    ALA J  79     -22.976   1.430 -94.985  1.00 58.88       A    O
ATOM   21590  CB   ALA J  79     -23.290   3.164 -97.831  1.00 59.76       A    C
ATOM   21591  N    ARG J  80     -22.288   0.414 -96.890  1.00 58.02       A    N
ATOM   21592  CA   ARG J  80     -22.468  -0.952 -96.389  1.00 57.02       A    C
ATOM   21593  C    ARG J  80     -21.396  -1.321 -95.354  1.00 56.76       A    C
ATOM   21594  O    ARG J  80     -21.703  -1.978 -94.358  1.00 56.76       A    O
ATOM   21595  CB   ARG J  80     -22.466  -1.957 -97.545  1.00 55.31       A    C
ATOM   21596  N    LEU J  81     -20.156  -0.882 -95.593  1.00 56.45       A    N
ATOM   21597  CA   LEU J  81     -19.032  -1.150 -94.697  1.00 55.86       A    C
ATOM   21598  C    LEU J  81     -19.301  -0.618 -93.290  1.00 55.92       A    C
ATOM   21599  O    LEU J  81     -19.206  -1.359 -92.302  1.00 55.54       A    O
ATOM   21600  CB   LEU J  81     -17.747  -0.549 -95.263  1.00 55.65       A    C
ATOM   21601  CG   LEU J  81     -16.434  -0.914 -94.577  1.00 54.89       A    C
ATOM   21602  CD1  LEU J  81     -15.334  -0.994 -95.614  1.00 54.72       A    C
ATOM   21603  CD2  LEU J  81     -16.073   0.076 -93.471  1.00 54.79       A    C
ATOM   21604  N    ARG J  82     -19.645   0.664 -93.207  1.00 56.37       A    N
ATOM   21605  CA   ARG J  82     -19.934   1.300 -91.922  1.00 56.83       A    C
ATOM   21606  C    ARG J  82     -21.178   0.681 -91.241  1.00 56.74       A    C
ATOM   21607  O    ARG J  82     -21.259   0.614 -90.004  1.00 56.69       A    O
ATOM   21608  CB   ARG J  82     -20.072   2.823 -92.095  1.00 57.38       A    C
ATOM   21609  CG   ARG J  82     -19.970   3.613 -90.780  1.00 58.31       A    C
ATOM   21610  CD   ARG J  82     -19.759   5.113 -91.000  1.00 59.67       A    C
ATOM   21611  NE   ARG J  82     -18.340   5.487 -90.939  1.00 59.81       A    N
ATOM   21612  CZ   ARG J  82     -17.516   5.558 -91.988  1.00 59.84       A    C
ATOM   21613  NH1  ARG J  82     -17.946   5.281 -93.220  1.00 60.02       A    N
ATOM   21614  NH2  ARG J  82     -16.248   5.913 -91.803  1.00 59.58       A    N
ATOM   21615  N    ARG J  83     -22.123   0.221 -92.059  1.00 56.47       A    N
ATOM   21616  CA   ARG J  83     -23.321  -0.493 -91.595  1.00 55.95       A    C
ATOM   21617  C    ARG J  83     -23.000  -1.891 -91.018  1.00 55.55       A    C
ATOM   21618  O    ARG J  83     -23.600  -2.334 -90.020  1.00 55.67       A    O
ATOM   21619  CB   ARG J  83     -24.317  -0.578 -92.761  1.00 54.96       A    C
ATOM   21620  CG   ARG J  83     -25.312  -1.723 -92.763  1.00 54.47       A    C
ATOM   21621  CD   ARG J  83     -25.849  -1.851 -94.177  1.00 54.56       A    C
ATOM   21622  NE   ARG J  83     -26.705  -3.009 -94.370  1.00 54.06       A    N
ATOM   21623  N    VAL J  84     -22.050  -2.569 -91.661  1.00 54.75       A    N
ATOM   21624  CA   VAL J  84     -21.582  -3.886 -91.231  1.00 53.66       A    C
ATOM   21625  C    VAL J  84     -20.704  -3.788 -89.974  1.00 53.01       A    C
ATOM   21626  O    VAL J  84     -20.991  -4.458 -88.977  1.00 52.81       A    O
ATOM   21627  CB   VAL J  84     -20.838  -4.629 -92.386  1.00 53.54       A    C
ATOM   21628  CG1  VAL J  84     -21.834  -5.117 -93.435  1.00 53.56       A    C
ATOM   21629  CG2  VAL J  84     -19.983  -5.802 -91.861  1.00 52.81       A    C
ATOM   21630  N    VAL J  85     -19.649  -2.961 -90.023  1.00 52.20       A    N
ATOM   21631  CA   VAL J  85     -18.787  -2.717 -88.856  1.00 51.40       A    C
ATOM   21632  C    VAL J  85     -19.613  -2.274 -87.640  1.00 51.80       A    C
ATOM   21633  O    VAL J  85     -19.224  -2.528 -86.488  1.00 51.95       A    O
ATOM   21634  CB   VAL J  85     -17.713  -1.655 -89.152  1.00 49.83       A    C
ATOM   21635  N    GLY J  86     -20.747  -1.618 -87.919  1.00 52.12       A    N
ATOM   21636  CA   GLY J  86     -21.733  -1.221 -86.910  1.00 52.05       A    C
ATOM   21637  C    GLY J  86     -22.567  -2.372 -86.348  1.00 51.68       A    C
ATOM   21638  O    GLY J  86     -23.105  -2.260 -85.244  1.00 51.91       A    O
ATOM   21639  N    GLN J  87     -22.675  -3.476 -87.095  1.00 51.03       A    N
ATOM   21640  CA   GLN J  87     -23.445  -4.655 -86.657  1.00 50.27       A    C
ATOM   21641  C    GLN J  87     -22.744  -5.497 -85.568  1.00 49.60       A    C
ATOM   21642  O    GLN J  87     -23.404  -6.269 -84.869  1.00 49.54       A    O
ATOM   21643  N    LEU J  88     -21.422  -5.348 -85.435  1.00 48.76       A    N
ATOM   21644  CA   LEU J  88     -20.664  -5.990 -84.355  1.00 48.06       A    C
ATOM   21645  C    LEU J  88     -20.961  -5.297 -83.032  1.00 48.44       A    C
```

FIGURE 1 (cont'd)

```
ATOM  21646  O    LEU J  88    -20.807  -4.074 -82.938  1.00 48.66    A  O
ATOM  21647  CB   LEU J  88    -19.157  -5.912 -84.613  1.00 47.35    A  C
ATOM  21648  CG   LEU J  88    -18.555  -6.679 -85.789  1.00 45.99    A  C
ATOM  21649  N    ASP J  89    -21.389  -6.068 -82.024  1.00 48.77    A  N
ATOM  21650  CA   ASP J  89    -21.591  -5.536 -80.659  1.00 49.17    A  C
ATOM  21651  C    ASP J  89    -20.402  -5.864 -79.737  1.00 49.23    A  C
ATOM  21652  O    ASP J  89    -20.251  -7.015 -79.312  1.00 49.01    A  O
ATOM  21653  CB   ASP J  89    -22.916  -6.018 -80.047  1.00 49.30    A  C
ATOM  21654  CG   ASP J  89    -23.162  -5.439 -78.659  1.00 49.45    A  C
ATOM  21655  N    PRO J  90    -19.554  -4.853 -79.436  1.00 49.46    A  N
ATOM  21656  CA   PRO J  90    -18.326  -5.059 -78.659  1.00 49.37    A  C
ATOM  21657  C    PRO J  90    -18.554  -5.680 -77.279  1.00 49.31    A  C
ATOM  21658  O    PRO J  90    -17.767  -6.535 -76.862  1.00 49.03    A  O
ATOM  21659  CB   PRO J  90    -17.750  -3.643 -78.527  1.00 49.50    A  C
ATOM  21660  CG   PRO J  90    -18.282  -2.917 -79.715  1.00 49.75    A  C
ATOM  21661  CD   PRO J  90    -19.676  -3.451 -79.881  1.00 49.80    A  C
ATOM  21662  N    GLN J  91    -19.613  -5.264 -76.581  1.00 49.51    A  N
ATOM  21663  CA   GLN J  91    -19.909  -5.845 -75.266  1.00 49.60    A  C
ATOM  21664  C    GLN J  91    -20.475  -7.263 -75.400  1.00 49.02    A  C
ATOM  21665  O    GLN J  91    -20.244  -8.094 -74.519  1.00 49.11    A  O
ATOM  21666  CB   GLN J  91    -20.783  -4.924 -74.373  1.00 50.19    A  C
ATOM  21667  CG   GLN J  91    -22.307  -4.994 -74.580  1.00 50.92    A  C
ATOM  21668  N    ARG J  92    -21.176  -7.547 -76.503  1.00 48.16    A  N
ATOM  21669  CA   ARG J  92    -21.652  -8.915 -76.793  1.00 47.14    A  C
ATOM  21670  C    ARG J  92    -20.487  -9.894 -77.001  1.00 46.68    A  C
ATOM  21671  O    ARG J  92    -20.469 -10.976 -76.406  1.00 46.58    A  O
ATOM  21672  CB   ARG J  92    -22.596  -8.921 -78.008  1.00 47.00    A  C
ATOM  21673  CG   ARG J  92    -22.990 -10.312 -78.570  1.00 45.21    A  C
ATOM  21674  CD   ARG J  92    -23.956 -10.208 -79.791  1.00 43.12    A  C
ATOM  21675  NE   ARG J  92    -23.405  -9.443 -80.916  1.00 41.76    A  N
ATOM  21676  N    LEU J  93    -19.530  -9.500 -77.844  1.00 46.09    A  N
ATOM  21677  CA   LEU J  93    -18.295 -10.259 -78.072  1.00 45.48    A  C
ATOM  21678  C    LEU J  93    -17.654 -10.663 -76.733  1.00 45.55    A  C
ATOM  21679  O    LEU J  93    -17.371 -11.847 -76.490  1.00 45.42    A  O
ATOM  21680  CB   LEU J  93    -17.307  -9.403 -78.888  1.00 45.11    A  C
ATOM  21681  CG   LEU J  93    -16.258  -9.984 -79.843  1.00 43.91    A  C
ATOM  21682  CD1  LEU J  93    -15.637 -11.283 -79.365  1.00 42.76    A  C
ATOM  21683  N    TRP J  94    -17.465  -9.661 -75.867  1.00 45.73    A  N
ATOM  21684  CA   TRP J  94    -16.724  -9.804 -74.617  1.00 45.77    A  C
ATOM  21685  C    TRP J  94    -17.496 -10.582 -73.553  1.00 45.75    A  C
ATOM  21686  O    TRP J  94    -16.915 -11.384 -72.820  1.00 45.64    A  O
ATOM  21687  CB   TRP J  94    -16.305  -8.425 -74.079  1.00 45.94    A  C
ATOM  21688  CG   TRP J  94    -15.107  -8.517 -73.228  1.00 46.38    A  C
ATOM  21689  CD1  TRP J  94    -15.074  -8.795 -71.900  1.00 47.09    A  C
ATOM  21690  CD2  TRP J  94    -13.749  -8.375 -73.646  1.00 46.44    A  C
ATOM  21691  CE2  TRP J  94    -12.938  -8.571 -72.503  1.00 46.70    A  C
ATOM  21692  CE3  TRP J  94    -13.136  -8.100 -74.871  1.00 46.25    A  C
ATOM  21693  NE1  TRP J  94    -13.778  -8.824 -71.452  1.00 47.08    A  N
ATOM  21694  CZ2  TRP J  94    -11.533  -8.504 -72.546  1.00 46.61    A  C
ATOM  21695  CZ3  TRP J  94    -11.735  -8.032 -74.919  1.00 46.18    A  C
ATOM  21696  CH2  TRP J  94    -10.951  -8.237 -73.758  1.00 46.34    A  C
ATOM  21697  N    SER J  95    -18.807 -10.359 -73.490  1.00 45.78    A  N
ATOM  21698  CA   SER J  95    -19.610 -10.839 -72.366  1.00 45.78    A  C
ATOM  21699  C    SER J  95    -20.409 -12.091 -72.677  1.00 45.19    A  C
ATOM  21700  O    SER J  95    -20.399 -13.031 -71.892  1.00 45.17    A  O
ATOM  21701  CB   SER J  95    -20.542  -9.736 -71.854  1.00 46.28    A  C
ATOM  21702  OG   SER J  95    -20.501  -9.660 -70.440  1.00 47.21    A  O
ATOM  21703  N    THR J  96    -21.105 -12.099 -73.809  1.00 44.47    A  N
ATOM  21704  CA   THR J  96    -21.910 -13.262 -74.205  1.00 43.83    A  C
ATOM  21705  C    THR J  96    -21.079 -14.426 -74.747  1.00 42.91    A  C
ATOM  21706  O    THR J  96    -21.479 -15.587 -74.599  1.00 43.00    A  O
ATOM  21707  CB   THR J  96    -22.970 -12.902 -75.271  1.00 44.03    A  C
ATOM  21708  OG1  THR J  96    -23.394 -11.545 -75.090  1.00 44.74    A  O
ATOM  21709  N    TYR J  97    -19.934 -14.111 -75.363  1.00 41.63    A  N
ATOM  21710  CA   TYR J  97    -19.126 -15.109 -76.071  1.00 40.25    A  C
```

FIGURE 1 (cont'd)

```
ATOM  21711  C    TYR J  97     -17.755 -15.383 -75.456  1.00 39.84      A  C
ATOM  21712  O    TYR J  97     -17.356 -16.541 -75.351  1.00 39.60      A  O
ATOM  21713  CB   TYR J  97     -18.994 -14.747 -77.557  1.00 39.70      A  C
ATOM  21714  CG   TYR J  97     -20.327 -14.589 -78.272  1.00 38.72      A  C
ATOM  21715  CD1  TYR J  97     -21.304 -15.578 -78.186  1.00 37.64      A  C
ATOM  21716  CE1  TYR J  97     -22.520 -15.451 -78.833  1.00 37.47      A  C
ATOM  21717  N    LEU J  98     -17.041 -14.335 -75.046  1.00 39.61      A  N
ATOM  21718  CA   LEU J  98     -15.673 -14.524 -74.544  1.00 39.48      A  C
ATOM  21719  C    LEU J  98     -15.601 -15.042 -73.107  1.00 39.72      A  C
ATOM  21720  O    LEU J  98     -14.954 -16.065 -72.834  1.00 39.60      A  O
ATOM  21721  CB   LEU J  98     -14.821 -13.251 -74.683  1.00 39.27      A  C
ATOM  21722  CG   LEU J  98     -13.378 -13.397 -74.158  1.00 39.03      A  C
ATOM  21723  CD1  LEU J  98     -12.581 -14.455 -74.928  1.00 38.44      A  C
ATOM  21724  CD2  LEU J  98     -12.640 -12.079 -74.196  1.00 39.17      A  C
ATOM  21725  N    ARG J  99     -16.243 -14.314 -72.195  1.00 40.05      A  N
ATOM  21726  CA   ARG J  99     -16.207 -14.662 -70.767  1.00 40.13      A  C
ATOM  21727  C    ARG J  99     -16.697 -16.085 -70.470  1.00 40.26      A  C
ATOM  21728  O    ARG J  99     -16.038 -16.798 -69.713  1.00 40.40      A  O
ATOM  21729  CB   ARG J  99     -16.907 -13.600 -69.881  1.00 39.58      A  C
ATOM  21730  CG   ARG J  99     -15.931 -12.779 -69.028  1.00 39.42      A  C
ATOM  21731  CD   ARG J  99     -16.636 -11.799 -68.105  1.00 39.90      A  C
ATOM  21732  NE   ARG J  99     -16.508 -10.416 -68.563  1.00 39.61      A  N
ATOM  21733  N    PRO J 100     -17.823 -16.523 -71.084  1.00 40.25      A  N
ATOM  21734  CA   PRO J 100     -18.227 -17.908 -70.862  1.00 40.15      A  C
ATOM  21735  C    PRO J 100     -17.108 -18.896 -71.200  1.00 39.77      A  C
ATOM  21736  O    PRO J 100     -16.982 -19.931 -70.543  1.00 39.96      A  O
ATOM  21737  CB   PRO J 100     -19.406 -18.082 -71.823  1.00 40.26      A  C
ATOM  21738  CG   PRO J 100     -19.989 -16.735 -71.927  1.00 40.49      A  C
ATOM  21739  CD   PRO J 100     -18.805 -15.810 -71.923  1.00 40.36      A  C
ATOM  21740  N    LEU J 101     -16.291 -18.552 -72.194  1.00 39.12      A  N
ATOM  21741  CA   LEU J 101     -15.230 -19.431 -72.682  1.00 38.52      A  C
ATOM  21742  C    LEU J 101     -14.016 -19.536 -71.766  1.00 38.47      A  C
ATOM  21743  O    LEU J 101     -13.208 -20.463 -71.902  1.00 38.31      A  O
ATOM  21744  CB   LEU J 101     -14.780 -18.981 -74.076  1.00 38.12      A  C
ATOM  21745  CG   LEU J 101     -15.313 -19.717 -75.312  1.00 37.80      A  C
ATOM  21746  CD1  LEU J 101     -16.786 -20.159 -75.197  1.00 38.22      A  C
ATOM  21747  CD2  LEU J 101     -15.086 -18.856 -76.558  1.00 37.52      A  C
ATOM  21748  N    LEU J 102     -13.889 -18.594 -70.837  1.00 38.54      A  N
ATOM  21749  CA   LEU J 102     -12.662 -18.463 -70.055  1.00 38.61      A  C
ATOM  21750  C    LEU J 102     -12.658 -19.337 -68.807  1.00 38.94      A  C
ATOM  21751  O    LEU J 102     -12.536 -18.849 -67.686  1.00 39.25      A  O
ATOM  21752  CB   LEU J 102     -12.395 -16.991 -69.709  1.00 38.55      A  C
ATOM  21753  CG   LEU J 102     -12.072 -16.041 -70.868  1.00 38.09      A  C
ATOM  21754  CD1  LEU J 102     -12.088 -14.583 -70.416  1.00 38.27      A  C
ATOM  21755  CD2  LEU J 102     -10.724 -16.395 -71.472  1.00 37.56      A  C
ATOM  21756  N    VAL J 103     -12.784 -20.639 -69.017  1.00 39.09      A  N
ATOM  21757  CA   VAL J 103     -12.709 -21.617 -67.930  1.00 39.41      A  C
ATOM  21758  C    VAL J 103     -11.724 -22.733 -68.262  1.00 39.11      A  C
ATOM  21759  O    VAL J 103     -11.444 -22.980 -69.429  1.00 38.86      A  O
ATOM  21760  CB   VAL J 103     -14.098 -22.230 -67.609  1.00 39.76      A  C
ATOM  21761  CG1  VAL J 103     -14.759 -22.789 -68.860  1.00 39.60      A  C
ATOM  21762  CG2  VAL J 103     -15.004 -21.188 -66.956  1.00 40.65      A  C
ATOM  21763  N    VAL J 104     -11.192 -23.400 -67.242  1.00 39.04      A  N
ATOM  21764  CA   VAL J 104     -10.333 -24.557 -67.473  1.00 38.73      A  C
ATOM  21765  C    VAL J 104     -11.139 -25.573 -68.280  1.00 38.94      A  C
ATOM  21766  O    VAL J 104     -12.284 -25.887 -67.926  1.00 39.25      A  O
ATOM  21767  CB   VAL J 104      -9.847 -25.176 -66.151  1.00 38.07      A  C
ATOM  21768  CG1  VAL J 104      -8.497 -25.848 -66.339  1.00 37.49      A  C
ATOM  21769  N    ARG J 105     -10.551 -26.056 -69.375  1.00 38.79      A  N
ATOM  21770  CA   ARG J 105     -11.287 -26.858 -70.373  1.00 38.54      A  C
ATOM  21771  C    ARG J 105     -10.425 -27.883 -71.130  1.00 38.50      A  C
ATOM  21772  O    ARG J 105     -10.688 -28.207 -72.293  1.00 38.21      A  O
ATOM  21773  CB   ARG J 105     -12.030 -25.937 -71.357  1.00 38.35      A  C
ATOM  21774  CG   ARG J 105     -11.128 -25.044 -72.187  1.00 37.69      A  C
ATOM  21775  CD   ARG J 105     -11.868 -23.844 -72.710  1.00 37.35      A  C
```

FIGURE 1 (cont'd)

```
ATOM  21776  NE   ARG J 105     -11.034 -23.107 -73.656  1.00 37.02      A  N
ATOM  21777  CZ   ARG J 105     -10.304 -22.028 -73.367  1.00 36.81      A  C
ATOM  21778  NH1  ARG J 105     -10.285 -21.519 -72.139  1.00 36.94      A  N
ATOM  21779  NH2  ARG J 105      -9.589 -21.452 -74.324  1.00 36.43      A  N
ATOM  21780  N    THR J 106      -9.401 -28.391 -70.450  1.00 38.73      A  N
ATOM  21781  CA   THR J 106      -8.554 -29.451 -70.980  1.00 38.94      A  C
ATOM  21782  C    THR J 106      -9.411 -30.626 -71.480  1.00 39.00      A  C
ATOM  21783  O    THR J 106     -10.462 -30.893 -70.911  1.00 39.01      A  O
ATOM  21784  CB   THR J 106      -7.555 -29.933 -69.909  1.00 39.12      A  C
ATOM  21785  OG1  THR J 106      -8.273 -30.510 -68.812  1.00 39.79      A  O
ATOM  21786  N    PRO J 107      -8.965 -31.321 -72.548  1.00 39.10      A  N
ATOM  21787  CA   PRO J 107      -9.729 -32.396 -73.178  1.00 39.39      A  C
ATOM  21788  C    PRO J 107     -10.427 -33.356 -72.205  1.00 39.95      A  C
ATOM  21789  O    PRO J 107      -9.826 -33.804 -71.220  1.00 40.09      A  O
ATOM  21790  CB   PRO J 107      -8.663 -33.142 -73.977  1.00 39.29      A  C
ATOM  21791  CG   PRO J 107      -7.685 -32.103 -74.353  1.00 38.89      A  C
ATOM  21792  CD   PRO J 107      -7.675 -31.105 -73.235  1.00 38.98      A  C
ATOM  21793  N    GLY J 108     -11.697 -33.647 -72.492  1.00 40.39      A  N
ATOM  21794  CA   GLY J 108     -12.491 -34.604 -71.715  1.00 41.02      A  C
ATOM  21795  C    GLY J 108     -12.756 -34.264 -70.256  1.00 41.37      A  C
ATOM  21796  O    GLY J 108     -13.081 -35.142 -69.453  1.00 41.86      A  O
ATOM  21797  N    SER J 109     -12.612 -32.991 -69.906  1.00 41.35      A  N
ATOM  21798  CA   SER J 109     -12.912 -32.523 -68.560  1.00 41.38      A  C
ATOM  21799  C    SER J 109     -14.334 -31.986 -68.539  1.00 41.58      A  C
ATOM  21800  O    SER J 109     -14.974 -31.903 -69.591  1.00 41.38      A  O
ATOM  21801  CB   SER J 109     -11.936 -31.422 -68.162  1.00 41.25      A  C
ATOM  21802  OG   SER J 109     -12.153 -30.257 -68.942  1.00 40.66      A  O
ATOM  21803  N    PRO J 110     -14.843 -31.628 -67.348  1.00 41.92      A  N
ATOM  21804  CA   PRO J 110     -16.148 -30.977 -67.269  1.00 41.86      A  C
ATOM  21805  C    PRO J 110     -16.195 -29.652 -68.025  1.00 41.29      A  C
ATOM  21806  O    PRO J 110     -17.192 -29.352 -68.676  1.00 41.11      A  O
ATOM  21807  CB   PRO J 110     -16.324 -30.747 -65.768  1.00 42.33      A  C
ATOM  21808  CG   PRO J 110     -15.531 -31.837 -65.142  1.00 42.76      A  C
ATOM  21809  CD   PRO J 110     -14.337 -31.995 -66.013  1.00 42.29      A  C
ATOM  21810  N    GLY J 111     -15.115 -28.879 -67.941  1.00 40.83      A  N
ATOM  21811  CA   GLY J 111     -15.011 -27.592 -68.631  1.00 40.17      A  C
ATOM  21812  C    GLY J 111     -15.040 -27.733 -70.144  1.00 39.62      A  C
ATOM  21813  O    GLY J 111     -15.748 -26.983 -70.838  1.00 39.45      A  O
ATOM  21814  N    ASN J 112     -14.271 -28.698 -70.652  1.00 39.18      A  N
ATOM  21815  CA   ASN J 112     -14.260 -29.026 -72.080  1.00 38.60      A  C
ATOM  21816  C    ASN J 112     -15.670 -29.307 -72.579  1.00 38.84      A  C
ATOM  21817  O    ASN J 112     -16.066 -28.797 -73.623  1.00 38.66      A  O
ATOM  21818  CB   ASN J 112     -13.345 -30.223 -72.362  1.00 38.31      A  C
ATOM  21819  CG   ASN J 112     -13.260 -30.562 -73.836  1.00 37.17      A  C
ATOM  21820  N    LEU J 113     -16.427 -30.094 -71.815  1.00 39.30      A  N
ATOM  21821  CA   LEU J 113     -17.795 -30.428 -72.177  1.00 39.74      A  C
ATOM  21822  C    LEU J 113     -18.731 -29.233 -71.973  1.00 39.78      A  C
ATOM  21823  O    LEU J 113     -19.639 -29.017 -72.774  1.00 39.74      A  O
ATOM  21824  CB   LEU J 113     -18.266 -31.667 -71.412  1.00 40.15      A  C
ATOM  21825  CG   LEU J 113     -19.431 -32.469 -71.991  1.00 40.89      A  C
ATOM  21826  CD1  LEU J 113     -19.239 -33.947 -71.710  1.00 41.44      A  C
ATOM  21827  CD2  LEU J 113     -20.797 -31.977 -71.471  1.00 41.79      A  C
ATOM  21828  N    GLN J 114     -18.499 -28.453 -70.917  1.00 39.86      A  N
ATOM  21829  CA   GLN J 114     -19.325 -27.277 -70.637  1.00 39.88      A  C
ATOM  21830  C    GLN J 114     -19.216 -26.283 -71.787  1.00 39.64      A  C
ATOM  21831  O    GLN J 114     -20.241 -25.776 -72.270  1.00 39.71      A  O
ATOM  21832  CB   GLN J 114     -18.953 -26.619 -69.297  1.00 40.05      A  C
ATOM  21833  N    VAL J 115     -17.979 -26.031 -72.232  1.00 39.06      A  N
ATOM  21834  CA   VAL J 115     -17.712 -25.116 -73.351  1.00 38.39      A  C
ATOM  21835  C    VAL J 115     -18.312 -25.664 -74.654  1.00 38.65      A  C
ATOM  21836  O    VAL J 115     -19.070 -24.965 -75.335  1.00 38.82      A  O
ATOM  21837  CB   VAL J 115     -16.206 -24.806 -73.517  1.00 36.87      A  C
ATOM  21838  N    ARG J 116     -18.001 -26.924 -74.967  1.00 38.85      A  N
ATOM  21839  CA   ARG J 116     -18.554 -27.621 -76.139  1.00 39.09      A  C
ATOM  21840  C    ARG J 116     -20.068 -27.425 -76.260  1.00 39.53      A  C
```

FIGURE 1 (cont'd)

```
ATOM  21841  O    ARG J 116     -20.582 -27.101 -77.344  1.00 39.51      A  O
ATOM  21842  CB   ARG J 116     -18.210 -29.118 -76.087  1.00 38.96      A  C
ATOM  21843  CG   ARG J 116     -18.808 -29.969 -77.192  1.00 39.17      A  C
ATOM  21844  CD   ARG J 116     -18.539 -31.427 -76.944  1.00 40.20      A  C
ATOM  21845  NE   ARG J 116     -17.112 -31.689 -76.776  1.00 40.87      A  N
ATOM  21846  CZ   ARG J 116     -16.593 -32.790 -76.226  1.00 41.48      A  C
ATOM  21847  NH1  ARG J 116     -17.379 -33.757 -75.777  1.00 41.95      A  N
ATOM  21848  NH2  ARG J 116     -15.276 -32.928 -76.121  1.00 41.64      A  N
ATOM  21849  N    LYS J 117     -20.760 -27.616 -75.136  1.00 40.08      A  N
ATOM  21850  CA   LYS J 117     -22.209 -27.496 -75.062  1.00 40.54      A  C
ATOM  21851  C    LYS J 117     -22.650 -26.060 -75.347  1.00 40.19      A  C
ATOM  21852  O    LYS J 117     -23.666 -25.848 -76.025  1.00 40.28      A  O
ATOM  21853  CB   LYS J 117     -22.701 -27.966 -73.689  1.00 41.15      A  C
ATOM  21854  CG   LYS J 117     -24.177 -28.377 -73.631  1.00 42.54      A  C
ATOM  21855  CD   LYS J 117     -24.557 -29.036 -72.281  1.00 43.88      A  C
ATOM  21856  CE   LYS J 117     -24.346 -30.557 -72.275  1.00 44.06      A  C
ATOM  21857  N    PHE J 118     -21.877 -25.087 -74.847  1.00 39.56      A  N
ATOM  21858  CA   PHE J 118     -22.168 -23.660 -75.072  1.00 38.94      A  C
ATOM  21859  C    PHE J 118     -22.027 -23.276 -76.544  1.00 39.20      A  C
ATOM  21860  O    PHE J 118     -22.836 -22.500 -77.084  1.00 39.40      A  O
ATOM  21861  CB   PHE J 118     -21.281 -22.758 -74.203  1.00 37.67      A  C
ATOM  21862  CG   PHE J 118     -21.409 -21.284 -74.514  1.00 36.13      A  C
ATOM  21863  CD1  PHE J 118     -22.643 -20.644 -74.398  1.00 35.84      A  C
ATOM  21864  CD2  PHE J 118     -20.292 -20.560 -74.902  1.00 34.57      A  C
ATOM  21865  CE1  PHE J 118     -22.805 -19.299 -74.666  1.00 35.46      A  C
ATOM  21866  CE2  PHE J 118     -20.358 -19.215 -75.184  1.00 33.87      A  C
ATOM  21867  N    LEU J 119     -20.998 -23.825 -77.185  1.00 39.20      A  N
ATOM  21868  CA   LEU J 119     -20.780 -23.583 -78.600  1.00 39.20      A  C
ATOM  21869  C    LEU J 119     -21.956 -24.133 -79.407  1.00 39.70      A  C
ATOM  21870  O    LEU J 119     -22.632 -23.375 -80.106  1.00 39.82      A  O
ATOM  21871  CB   LEU J 119     -19.429 -24.144 -79.056  1.00 38.75      A  C
ATOM  21872  CG   LEU J 119     -18.233 -23.240 -78.723  1.00 37.95      A  C
ATOM  21873  CD1  LEU J 119     -16.920 -24.013 -78.839  1.00 37.44      A  C
ATOM  21874  N    GLU J 120     -22.223 -25.434 -79.267  1.00 40.19      A  N
ATOM  21875  CA   GLU J 120     -23.377 -26.070 -79.911  1.00 40.63      A  C
ATOM  21876  C    GLU J 120     -24.630 -25.188 -79.831  1.00 41.33      A  C
ATOM  21877  O    GLU J 120     -25.282 -24.913 -80.851  1.00 41.59      A  O
ATOM  21878  CB   GLU J 120     -23.677 -27.432 -79.279  1.00 39.84      A  C
ATOM  21879  CG   GLU J 120     -22.725 -28.539 -79.657  1.00 39.52      A  C
ATOM  21880  CD   GLU J 120     -23.202 -29.894 -79.173  1.00 40.09      A  C
ATOM  21881  OE1  GLU J 120     -24.257 -30.360 -79.655  1.00 40.86      A  O
ATOM  21882  N    ALA J 121     -24.941 -24.739 -78.617  1.00 41.84      A  N
ATOM  21883  CA   ALA J 121     -26.159 -23.994 -78.357  1.00 42.22      A  C
ATOM  21884  C    ALA J 121     -26.161 -22.650 -79.069  1.00 42.14      A  C
ATOM  21885  O    ALA J 121     -27.122 -22.320 -79.771  1.00 42.47      A  O
ATOM  21886  CB   ALA J 121     -26.357 -23.818 -76.860  1.00 42.56      A  C
ATOM  21887  N    THR J 122     -25.083 -21.889 -78.895  1.00 41.54      A  N
ATOM  21888  CA   THR J 122     -24.978 -20.567 -79.507  1.00 40.90      A  C
ATOM  21889  C    THR J 122     -25.157 -20.645 -81.024  1.00 41.36      A  C
ATOM  21890  O    THR J 122     -25.933 -19.873 -81.610  1.00 41.73      A  O
ATOM  21891  CB   THR J 122     -23.638 -19.893 -79.185  1.00 39.45      A  C
ATOM  21892  OG1  THR J 122     -23.605 -19.549 -77.797  1.00 38.54      A  O
ATOM  21893  N    LEU J 123     -24.451 -21.595 -81.644  1.00 41.46      A  N
ATOM  21894  CA   LEU J 123     -24.501 -21.812 -83.095  1.00 41.51      A  C
ATOM  21895  C    LEU J 123     -25.906 -22.185 -83.583  1.00 42.17      A  C
ATOM  21896  O    LEU J 123     -26.375 -21.675 -84.607  1.00 42.39      A  O
ATOM  21897  CB   LEU J 123     -23.483 -22.881 -83.520  1.00 41.04      A  C
ATOM  21898  CG   LEU J 123     -21.993 -22.526 -83.420  1.00 39.84      A  C
ATOM  21899  CD1  LEU J 123     -21.531 -21.738 -84.640  1.00 39.19      A  C
ATOM  21900  N    ARG J 124     -26.574 -23.062 -82.840  1.00 42.74      A  N
ATOM  21901  CA   ARG J 124     -27.922 -23.482 -83.194  1.00 43.43      A  C
ATOM  21902  C    ARG J 124     -28.946 -22.362 -83.062  1.00 44.06      A  C
ATOM  21903  O    ARG J 124     -29.858 -22.268 -83.874  1.00 44.43      A  O
ATOM  21904  CB   ARG J 124     -28.343 -24.689 -82.362  1.00 43.43      A  C
ATOM  21905  CG   ARG J 124     -27.800 -26.018 -82.883  1.00 42.84      A  C
```

FIGURE 1 (cont'd)

```
ATOM  21906  CD   ARG J 124     -28.324 -27.213 -82.090  1.00 42.38      A  C
ATOM  21907  NE   ARG J 124     -27.776 -28.468 -82.588  1.00 41.59      A  N
ATOM  21908  N    SER J 125     -28.776 -21.511 -82.055  1.00 44.56      A  N
ATOM  21909  CA   SER J 125     -29.712 -20.417 -81.779  1.00 45.13      A  C
ATOM  21910  C    SER J 125     -29.631 -19.218 -82.761  1.00 45.29      A  C
ATOM  21911  O    SER J 125     -30.180 -18.137 -82.481  1.00 45.58      A  O
ATOM  21912  CB   SER J 125     -29.530 -19.931 -80.338  1.00 45.27      A  C
ATOM  21913  OG   SER J 125     -28.307 -19.227 -80.195  1.00 44.96      A  O
ATOM  21914  N    LEU J 126     -28.961 -19.404 -83.902  1.00 45.16      A  N
ATOM  21915  CA   LEU J 126     -28.830 -18.330 -84.892  1.00 45.14      A  C
ATOM  21916  C    LEU J 126     -29.955 -18.357 -85.919  1.00 45.68      A  C
ATOM  21917  O    LEU J 126     -30.497 -19.428 -86.219  1.00 45.89      A  O
ATOM  21918  CB   LEU J 126     -27.466 -18.368 -85.576  1.00 44.59      A  C
ATOM  21919  CG   LEU J 126     -26.233 -18.087 -84.707  1.00 43.80      A  C
ATOM  21920  CD1  LEU J 126     -25.024 -17.762 -85.589  1.00 42.97      A  C
ATOM  21921  CD2  LEU J 126     -26.481 -16.957 -83.708  1.00 43.56      A  C
ATOM  21922  N    THR J 127     -30.291 -17.172 -86.447  1.00 46.20      A  N
ATOM  21923  CA   THR J 127     -31.452 -16.978 -87.346  1.00 46.67      A  C
ATOM  21924  C    THR J 127     -31.335 -17.740 -88.656  1.00 46.71      A  C
ATOM  21925  O    THR J 127     -32.305 -18.374 -89.094  1.00 47.17      A  O
ATOM  21926  CB   THR J 127     -31.722 -15.497 -87.649  1.00 46.88      A  C
ATOM  21927  OG1  THR J 127     -31.428 -14.715 -86.484  1.00 47.08      A  O
ATOM  21928  N    ALA J 128     -30.155 -17.665 -89.276  1.00 46.33      A  N
ATOM  21929  CA   ALA J 128     -29.828 -18.549 -90.391  1.00 46.13      A  C
ATOM  21930  C    ALA J 128     -29.741 -19.983 -89.856  1.00 46.01      A  C
ATOM  21931  O    ALA J 128     -29.257 -20.194 -88.737  1.00 45.95      A  O
ATOM  21932  CB   ALA J 128     -28.525 -18.125 -91.037  1.00 45.80      A  C
ATOM  21933  N    GLY J 129     -30.221 -20.954 -90.634  1.00 45.97      A  N
ATOM  21934  CA   GLY J 129     -30.321 -22.334 -90.153  1.00 45.74      A  C
ATOM  21935  C    GLY J 129     -29.009 -23.096 -90.134  1.00 45.17      A  C
ATOM  21936  O    GLY J 129     -28.798 -23.956 -90.988  1.00 45.53      A  O
ATOM  21937  N    TRP J 130     -28.135 -22.793 -89.164  1.00 44.29      A  N
ATOM  21938  CA   TRP J 130     -26.803 -23.418 -89.078  1.00 43.28      A  C
ATOM  21939  C    TRP J 130     -26.889 -24.912 -88.793  1.00 42.98      A  C
ATOM  21940  O    TRP J 130     -27.549 -25.325 -87.848  1.00 43.18      A  O
ATOM  21941  CB   TRP J 130     -25.943 -22.744 -88.009  1.00 42.93      A  C
ATOM  21942  CG   TRP J 130     -25.273 -21.459 -88.447  1.00 42.42      A  C
ATOM  21943  CD1  TRP J 130     -25.763 -20.195 -88.308  1.00 42.63      A  C
ATOM  21944  CD2  TRP J 130     -23.981 -21.319 -89.066  1.00 41.98      A  C
ATOM  21945  CE2  TRP J 130     -23.764 -19.936 -89.273  1.00 41.86      A  C
ATOM  21946  CE3  TRP J 130     -22.985 -22.227 -89.466  1.00 41.74      A  C
ATOM  21947  NE1  TRP J 130     -24.868 -19.276 -88.803  1.00 42.24      A  N
ATOM  21948  CZ2  TRP J 130     -22.592 -19.435 -89.865  1.00 41.39      A  C
ATOM  21949  CZ3  TRP J 130     -21.818 -21.729 -90.059  1.00 41.35      A  C
ATOM  21950  CH2  TRP J 130     -21.635 -20.345 -90.251  1.00 41.14      A  C
ATOM  21951  N    HIS J 131     -26.230 -25.715 -89.622  1.00 42.55      A  N
ATOM  21952  CA   HIS J 131     -26.213 -27.167 -89.451  1.00 42.35      A  C
ATOM  21953  C    HIS J 131     -25.069 -27.513 -88.510  1.00 41.93      A  C
ATOM  21954  O    HIS J 131     -23.968 -27.858 -88.950  1.00 41.72      A  O
ATOM  21955  CB   HIS J 131     -26.045 -27.868 -90.806  1.00 42.50      A  C
ATOM  21956  CG   HIS J 131     -26.418 -29.315 -90.799  1.00 42.87      A  C
ATOM  21957  N    VAL J 132     -25.333 -27.388 -87.211  1.00 41.67      A  N
ATOM  21958  CA   VAL J 132     -24.340 -27.671 -86.183  1.00 41.32      A  C
ATOM  21959  C    VAL J 132     -24.246 -29.117 -85.970  1.00 41.34      A  C
ATOM  21960  O    VAL J 132     -25.261 -29.874 -85.976  1.00 41.60      A  O
ATOM  21961  CB   VAL J 132     -24.683 -26.963 -84.868  1.00 41.29      A  C
ATOM  21962  CG1  VAL J 132     -23.417 -26.519 -84.162  1.00 41.01      A  C
ATOM  21963  N    GLU J 133     -23.026 -29.672 -85.788  1.00 41.21      A  N
ATOM  21964  CA   GLU J 133     -22.785 -31.114 -85.773  1.00 41.43      A  C
ATOM  21965  C    GLU J 133     -21.528 -31.484 -84.986  1.00 41.15      A  C
ATOM  21966  O    GLU J 133     -20.448 -30.943 -85.248  1.00 41.01      A  O
ATOM  21967  CB   GLU J 133     -22.672 -31.615 -87.212  1.00 41.65      A  C
ATOM  21968  CG   GLU J 133     -22.546 -33.126 -87.386  1.00 42.99      A  C
ATOM  21969  CD   GLU J 133     -22.319 -33.514 -88.848  1.00 44.72      A  C
ATOM  21970  OE1  GLU J 133     -23.139 -33.114 -89.714  1.00 45.50      A  O
```

FIGURE 1 (cont'd)

```
ATOM  21971  OE2  GLU J 133    -21.313 -34.210 -89.131  1.00 45.20      A  O
ATOM  21972  N    LEU J 134    -21.680 -32.403 -84.029  1.00 41.06      A  N
ATOM  21973  CA   LEU J 134    -20.566 -32.881 -83.198  1.00 40.74      A  C
ATOM  21974  C    LEU J 134    -19.776 -33.990 -83.878  1.00 40.50      A  C
ATOM  21975  O    LEU J 134    -20.326 -34.751 -84.669  1.00 40.67      A  O
ATOM  21976  CB   LEU J 134    -21.080 -33.409 -81.861  1.00 40.95      A  C
ATOM  21977  CG   LEU J 134    -21.093 -32.467 -80.660  1.00 41.09      A  C
ATOM  21978  CD1  LEU J 134    -21.829 -33.139 -79.487  1.00 41.93      A  C
ATOM  21979  N    ASP J 135    -18.486 -34.073 -83.558  1.00 40.04      A  N
ATOM  21980  CA   ASP J 135    -17.617 -35.142 -84.049  1.00 39.83      A  C
ATOM  21981  C    ASP J 135    -16.965 -35.823 -82.867  1.00 39.76      A  C
ATOM  21982  O    ASP J 135    -15.794 -35.579 -82.564  1.00 39.75      A  O
ATOM  21983  CB   ASP J 135    -16.543 -34.600 -85.018  1.00 39.63      A  C
ATOM  21984  CG   ASP J 135    -15.552 -35.685 -85.491  1.00 39.84      A  C
ATOM  21985  OD1  ASP J 135    -15.969 -36.841 -85.713  1.00 40.62      A  O
ATOM  21986  OD2  ASP J 135    -14.351 -35.379 -85.643  1.00 39.53      A  O
ATOM  21987  N    PRO J 136    -17.727 -36.677 -82.184  1.00 39.76      A  N
ATOM  21988  CA   PRO J 136    -17.142 -37.324 -81.023  1.00 40.03      A  C
ATOM  21989  C    PRO J 136    -16.182 -38.429 -81.434  1.00 40.61      A  C
ATOM  21990  O    PRO J 136    -16.363 -39.013 -82.492  1.00 40.88      A  O
ATOM  21991  CB   PRO J 136    -18.357 -37.924 -80.318  1.00 39.29      A  C
ATOM  21992  CG   PRO J 136    -19.545 -37.557 -81.173  1.00 38.88      A  C
ATOM  21993  N    PHE J 137    -15.167 -38.697 -80.615  1.00 41.11      A  N
ATOM  21994  CA   PHE J 137    -14.266 -39.842 -80.820  1.00 41.61      A  C
ATOM  21995  C    PHE J 137    -13.328 -40.088 -79.636  1.00 42.06      A  C
ATOM  21996  O    PHE J 137    -13.006 -39.165 -78.881  1.00 42.02      A  O
ATOM  21997  CB   PHE J 137    -13.450 -39.692 -82.114  1.00 41.45      A  C
ATOM  21998  CG   PHE J 137    -12.396 -38.603 -82.073  1.00 41.10      A  C
ATOM  21999  CD1  PHE J 137    -12.735 -37.265 -82.291  1.00 40.75      A  C
ATOM  22000  CD2  PHE J 137    -11.056 -38.929 -81.856  1.00 40.99      A  C
ATOM  22001  CE1  PHE J 137    -11.761 -36.274 -82.275  1.00 40.21      A  C
ATOM  22002  CE2  PHE J 137    -10.077 -37.940 -81.833  1.00 40.52      A  C
ATOM  22003  CZ   PHE J 137    -10.430 -36.612 -82.042  1.00 40.15      A  C
ATOM  22004  N    THR J 138    -12.888 -41.333 -79.484  1.00 42.76      A  N
ATOM  22005  CA   THR J 138    -11.855 -41.662 -78.504  1.00 43.38      A  C
ATOM  22006  C    THR J 138    -10.497 -41.810 -79.182  1.00 43.46      A  C
ATOM  22007  O    THR J 138    -10.418 -42.288 -80.321  1.00 43.59      A  O
ATOM  22008  CB   THR J 138    -12.183 -42.943 -77.738  1.00 43.75      A  C
ATOM  22009  OG1  THR J 138    -12.569 -42.589 -76.407  1.00 44.29      A  O
ATOM  22010  N    ALA J 139     -9.436 -41.392 -78.490  1.00 43.46      A  N
ATOM  22011  CA   ALA J 139     -8.092 -41.428 -79.063  1.00 43.56      A  C
ATOM  22012  C    ALA J 139     -7.004 -41.748 -78.055  1.00 43.92      A  C
ATOM  22013  O    ALA J 139     -7.104 -41.407 -76.873  1.00 43.97      A  O
ATOM  22014  CB   ALA J 139     -7.776 -40.136 -79.789  1.00 43.18      A  C
ATOM  22015  N    SER J 140     -5.961 -42.404 -78.558  1.00 44.36      A  N
ATOM  22016  CA   SER J 140     -4.839 -42.877 -77.755  1.00 44.77      A  C
ATOM  22017  C    SER J 140     -3.810 -41.762 -77.513  1.00 44.46      A  C
ATOM  22018  O    SER J 140     -3.160 -41.287 -78.448  1.00 44.34      A  O
ATOM  22019  CB   SER J 140     -4.195 -44.081 -78.450  1.00 45.20      A  C
ATOM  22020  OG   SER J 140     -2.899 -44.343 -77.941  1.00 46.11      A  O
ATOM  22021  N    THR J 141     -3.676 -41.342 -76.256  1.00 44.28      A  N
ATOM  22022  CA   THR J 141     -2.718 -40.289 -75.880  1.00 44.04      A  C
ATOM  22023  C    THR J 141     -1.660 -40.818 -74.897  1.00 44.35      A  C
ATOM  22024  O    THR J 141     -1.806 -41.930 -74.367  1.00 44.82      A  O
ATOM  22025  CB   THR J 141     -3.420 -39.042 -75.278  1.00 43.69      A  C
ATOM  22026  CG2  THR J 141     -4.612 -38.629 -76.124  1.00 43.37      A  C
ATOM  22027  OG1  THR J 141     -3.851 -39.320 -73.942  1.00 43.73      A  O
ATOM  22028  N    PRO J 142     -0.581 -40.036 -74.659  1.00 44.30      A  N
ATOM  22029  CA   PRO J 142      0.415 -40.430 -73.653  1.00 44.49      A  C
ATOM  22030  C    PRO J 142     -0.147 -40.476 -72.238  1.00 44.68      A  C
ATOM  22031  O    PRO J 142      0.542 -40.914 -71.319  1.00 45.10      A  O
ATOM  22032  CB   PRO J 142      1.474 -39.330 -73.764  1.00 44.37      A  C
ATOM  22033  CG   PRO J 142      1.368 -38.853 -75.171  1.00 44.09      A  C
ATOM  22034  CD   PRO J 142     -0.105 -38.896 -75.471  1.00 43.98      A  C
ATOM  22035  N    LEU J 143     -1.385 -40.014 -72.078  1.00 44.50      A  N
```

FIGURE 1 (cont'd)

```
ATOM  22036  CA   LEU J 143      -2.118 -40.123 -70.819  1.00 44.54       A  C
ATOM  22037  C    LEU J 143      -3.145 -41.269 -70.870  1.00 44.78       A  C
ATOM  22038  O    LEU J 143      -3.993 -41.407 -69.983  1.00 45.02       A  O
ATOM  22039  CB   LEU J 143      -2.808 -38.785 -70.487  1.00 44.18       A  C
ATOM  22040  CG   LEU J 143      -2.129 -37.693 -69.636  1.00 44.09       A  C
ATOM  22041  CD1  LEU J 143      -1.994 -38.122 -68.169  1.00 45.10       A  C
ATOM  22042  CD2  LEU J 143      -0.781 -37.241 -70.200  1.00 43.68       A  C
ATOM  22043  N    GLY J 144      -3.054 -42.092 -71.911  1.00 44.89       A  N
ATOM  22044  CA   GLY J 144      -4.032 -43.147 -72.150  1.00 44.99       A  C
ATOM  22045  C    GLY J 144      -5.252 -42.629 -72.890  1.00 44.82       A  C
ATOM  22046  O    GLY J 144      -5.298 -41.463 -73.294  1.00 44.45       A  O
ATOM  22047  N    PRO J 145      -6.253 -43.497 -73.082  1.00 44.97       A  N
ATOM  22048  CA   PRO J 145      -7.490 -43.121 -73.765  1.00 44.61       A  C
ATOM  22049  C    PRO J 145      -8.096 -41.799 -73.262  1.00 43.80       A  C
ATOM  22050  O    PRO J 145      -8.295 -41.618 -72.061  1.00 44.01       A  O
ATOM  22051  CB   PRO J 145      -8.422 -44.308 -73.469  1.00 45.00       A  C
ATOM  22052  CG   PRO J 145      -7.498 -45.473 -73.372  1.00 45.65       A  C
ATOM  22053  CD   PRO J 145      -6.224 -44.934 -72.746  1.00 45.50       A  C
ATOM  22054  N    VAL J 146      -8.368 -40.891 -74.193  1.00 42.50       A  N
ATOM  22055  CA   VAL J 146      -9.023 -39.627 -73.891  1.00 41.07       A  C
ATOM  22056  C    VAL J 146     -10.181 -39.350 -74.862  1.00 41.26       A  C
ATOM  22057  O    VAL J 146     -10.047 -39.553 -76.062  1.00 41.32       A  O
ATOM  22058  CB   VAL J 146      -8.019 -38.484 -73.952  1.00 39.28       A  C
ATOM  22059  CG1  VAL J 146      -8.611 -37.236 -73.363  1.00 37.84       A  C
ATOM  22060  N    ASP J 147     -11.313 -38.892 -74.335  1.00 41.33       A  N
ATOM  22061  CA   ASP J 147     -12.508 -38.638 -75.139  1.00 41.08       A  C
ATOM  22062  C    ASP J 147     -12.571 -37.198 -75.677  1.00 40.64       A  C
ATOM  22063  O    ASP J 147     -12.641 -36.233 -74.917  1.00 40.54       A  O
ATOM  22064  CB   ASP J 147     -13.776 -38.989 -74.351  1.00 41.30       A  C
ATOM  22065  CG   ASP J 147     -14.034 -40.485 -74.291  1.00 41.26       A  C
ATOM  22066  N    PHE J 148     -12.557 -37.072 -77.002  1.00 40.12       A  N
ATOM  22067  CA   PHE J 148     -12.563 -35.774 -77.675  1.00 39.51       A  C
ATOM  22068  C    PHE J 148     -13.880 -35.501 -78.381  1.00 39.31       A  C
ATOM  22069  O    PHE J 148     -14.717 -36.387 -78.524  1.00 39.47       A  O
ATOM  22070  CB   PHE J 148     -11.447 -35.706 -78.723  1.00 39.31       A  C
ATOM  22071  CG   PHE J 148     -10.064 -35.879 -78.168  1.00 39.35       A  C
ATOM  22072  CD1  PHE J 148      -9.333 -34.783 -77.742  1.00 39.09       A  C
ATOM  22073  CD2  PHE J 148      -9.481 -37.139 -78.094  1.00 39.81       A  C
ATOM  22074  CE1  PHE J 148      -8.051 -34.943 -77.233  1.00 39.25       A  C
ATOM  22075  CE2  PHE J 148      -8.202 -37.306 -77.586  1.00 39.82       A  C
ATOM  22076  CZ   PHE J 148      -7.488 -36.211 -77.157  1.00 39.56       A  C
ATOM  22077  N    GLY J 149     -14.043 -34.269 -78.848  1.00 38.95       A  N
ATOM  22078  CA   GLY J 149     -15.227 -33.887 -79.604  1.00 38.78       A  C
ATOM  22079  C    GLY J 149     -15.108 -32.546 -80.296  1.00 38.50       A  C
ATOM  22080  O    GLY J 149     -15.059 -31.512 -79.644  1.00 38.50       A  O
ATOM  22081  N    ASN J 150     -15.063 -32.569 -81.625  1.00 38.27       A  N
ATOM  22082  CA   ASN J 150     -15.046 -31.348 -82.430  1.00 37.95       A  C
ATOM  22083  C    ASN J 150     -16.445 -30.761 -82.581  1.00 38.13       A  C
ATOM  22084  O    ASN J 150     -17.446 -31.478 -82.466  1.00 38.36       A  O
ATOM  22085  CB   ASN J 150     -14.439 -31.623 -83.810  1.00 37.67       A  C
ATOM  22086  CG   ASN J 150     -12.970 -32.009 -83.740  1.00 37.28       A  C
ATOM  22087  ND2  ASN J 150     -12.630 -33.173 -84.278  1.00 37.29       A  N
ATOM  22088  OD1  ASN J 150     -12.154 -31.266 -83.217  1.00 36.77       A  O
ATOM  22089  N    VAL J 151     -16.512 -29.455 -82.823  1.00 38.15       A  N
ATOM  22090  CA   VAL J 151     -17.783 -28.796 -83.120  1.00 38.46       A  C
ATOM  22091  C    VAL J 151     -17.738 -28.216 -84.538  1.00 38.68       A  C
ATOM  22092  O    VAL J 151     -17.005 -27.249 -84.799  1.00 38.48       A  O
ATOM  22093  CB   VAL J 151     -18.133 -27.716 -82.070  1.00 38.36       A  C
ATOM  22094  CG1  VAL J 151     -18.389 -28.364 -80.729  1.00 38.72       A  C
ATOM  22095  CG2  VAL J 151     -19.352 -26.905 -82.489  1.00 38.49       A  C
ATOM  22096  N    VAL J 152     -18.519 -28.826 -85.442  1.00 39.21       A  N
ATOM  22097  CA   VAL J 152     -18.536 -28.473 -86.869  1.00 39.69       A  C
ATOM  22098  C    VAL J 152     -19.828 -27.753 -87.252  1.00 40.23       A  C
ATOM  22099  O    VAL J 152     -20.923 -28.271 -87.043  1.00 40.59       A  O
ATOM  22100  CB   VAL J 152     -18.333 -29.728 -87.756  1.00 39.64       A  C
```

FIGURE 1 (cont'd)

```
ATOM  22101  CG1 VAL J 152     -16.887 -30.195 -87.694  1.00 39.11      A    C
ATOM  22102  CG2 VAL J 152     -18.749 -29.456 -89.205  1.00 40.01      A    C
ATOM  22103  N   ALA J 153     -19.687 -26.558 -87.811  1.00 40.63      A    N
ATOM  22104  CA  ALA J 153     -20.838 -25.733 -88.143  1.00 41.26      A    C
ATOM  22105  C   ALA J 153     -20.793 -25.265 -89.591  1.00 41.78      A    C
ATOM  22106  O   ALA J 153     -19.810 -24.664 -90.036  1.00 41.74      A    O
ATOM  22107  CB  ALA J 153     -20.910 -24.542 -87.205  1.00 41.12      A    C
ATOM  22108  N   THR J 154     -21.867 -25.532 -90.325  1.00 42.54      A    N
ATOM  22109  CA  THR J 154     -21.943 -25.170 -91.743  1.00 43.20      A    C
ATOM  22110  C   THR J 154     -23.329 -24.622 -92.096  1.00 44.02      A    C
ATOM  22111  O   THR J 154     -24.339 -25.323 -91.957  1.00 44.41      A    O
ATOM  22112  CB  THR J 154     -21.656 -26.399 -92.656  1.00 43.11      A    C
ATOM  22113  CG2 THR J 154     -21.221 -25.966 -94.044  1.00 42.98      A    C
ATOM  22114  OG1 THR J 154     -20.632 -27.212 -92.073  1.00 42.65      A    O
ATOM  22115  N   LEU J 155     -23.378 -23.365 -92.534  1.00 44.69      A    N
ATOM  22116  CA  LEU J 155     -24.571 -22.840 -93.179  1.00 45.55      A    C
ATOM  22117  C   LEU J 155     -24.697 -23.534 -94.514  1.00 46.37      A    C
ATOM  22118  O   LEU J 155     -23.703 -23.658 -95.235  1.00 46.59      A    O
ATOM  22119  CB  LEU J 155     -24.420 -21.353 -93.446  1.00 45.37      A    C
ATOM  22120  CG  LEU J 155     -25.151 -20.361 -92.560  1.00 45.40      A    C
ATOM  22121  CD1 LEU J 155     -25.220 -19.005 -93.276  1.00 45.22      A    C
ATOM  22122  CD2 LEU J 155     -26.536 -20.888 -92.254  1.00 45.86      A    C
ATOM  22123  N   ASP J 156     -25.899 -23.997 -94.850  1.00 47.26      A    N
ATOM  22124  CA  ASP J 156     -26.155 -24.567 -96.184  1.00 48.08      A    C
ATOM  22125  C   ASP J 156     -25.166 -25.701 -96.551  1.00 47.92      A    C
ATOM  22126  O   ASP J 156     -24.256 -25.501 -97.375  1.00 47.70      A    O
ATOM  22127  CB  ASP J 156     -26.115 -23.439 -97.236  1.00 48.58      A    C
ATOM  22128  CG  ASP J 156     -26.748 -23.836 -98.566  1.00 50.23      A    C
ATOM  22129  OD1 ASP J 156     -27.087 -25.032 -98.765  1.00 51.18      A    O
ATOM  22130  OD2 ASP J 156     -26.904 -22.931 -99.421  1.00 51.72      A    O
ATOM  22131  N   PRO J 157     -25.335 -26.892 -95.937  1.00 48.03      A    N
ATOM  22132  CA  PRO J 157     -24.439 -28.027 -96.220  1.00 48.10      A    C
ATOM  22133  C   PRO J 157     -24.448 -28.447 -97.691  1.00 48.41      A    C
ATOM  22134  O   PRO J 157     -23.480 -29.052 -98.172  1.00 48.27      A    O
ATOM  22135  CB  PRO J 157     -25.018 -29.161 -95.365  1.00 48.07      A    C
ATOM  22136  CG  PRO J 157     -25.788 -28.478 -94.298  1.00 48.10      A    C
ATOM  22137  CD  PRO J 157     -26.346 -27.238 -94.921  1.00 48.15      A    C
ATOM  22138  N   ARG J 158     -25.534 -28.123 -98.390  1.00 48.93      A    N
ATOM  22139  CA  ARG J 158     -25.678 -28.495 -99.798  1.00 49.44      A    C
ATOM  22140  C   ARG J 158     -24.846 -27.645-100.773  1.00 49.27      A    C
ATOM  22141  O   ARG J 158     -24.587 -28.090-101.898  1.00 49.59      A    O
ATOM  22142  CB  ARG J 158     -27.160 -28.607-100.235  1.00 49.94      A    C
ATOM  22143  CG  ARG J 158     -28.058 -27.419 -99.880  1.00 50.27      A    C
ATOM  22144  N   ALA J 159     -24.421 -26.449-100.348  1.00 48.75      A    N
ATOM  22145  CA  ALA J 159     -23.554 -25.594-101.178  1.00 48.36      A    C
ATOM  22146  C   ALA J 159     -22.264 -26.331-101.546  1.00 48.05      A    C
ATOM  22147  O   ALA J 159     -21.691 -27.043-100.711  1.00 47.83      A    O
ATOM  22148  CB  ALA J 159     -23.242 -24.284-100.473  1.00 48.20      A    C
ATOM  22149  N   ALA J 160     -21.822 -26.165-102.792  1.00 47.87      A    N
ATOM  22150  CA  ALA J 160     -20.701 -26.934-103.327  1.00 47.62      A    C
ATOM  22151  C   ALA J 160     -19.359 -26.666-102.623  1.00 47.12      A    C
ATOM  22152  O   ALA J 160     -18.532 -27.577-102.488  1.00 47.04      A    O
ATOM  22153  CB  ALA J 160     -20.577 -26.706-104.826  1.00 48.04      A    C
ATOM  22154  N   ARG J 161     -19.154 -25.424-102.185  1.00 46.53      A    N
ATOM  22155  CA  ARG J 161     -17.925 -25.009-101.509  1.00 45.91      A    C
ATOM  22156  C   ARG J 161     -18.240 -24.049-100.371  1.00 45.13      A    C
ATOM  22157  O   ARG J 161     -19.302 -23.425-100.361  1.00 45.26      A    O
ATOM  22158  CB  ARG J 161     -16.969 -24.334-102.496  1.00 46.18      A    C
ATOM  22159  CG  ARG J 161     -16.109 -25.291-103.329  1.00 47.57      A    C
ATOM  22160  CD  ARG J 161     -15.943 -24.791-104.771  1.00 50.41      A    C
ATOM  22161  NE  ARG J 161     -15.978 -23.328-104.857  1.00 52.64      A    N
ATOM  22162  CZ  ARG J 161     -16.635 -22.633-105.789  1.00 53.87      A    C
ATOM  22163  NH1 ARG J 161     -17.323 -23.250-106.743  1.00 54.66      A    N
ATOM  22164  NH2 ARG J 161     -16.612 -21.306-105.765  1.00 54.15      A    N
ATOM  22165  N   HIS J 162     -17.316 -23.937 -99.416  1.00 44.07      A    N
```

FIGURE 1 (cont'd)

```
ATOM  22166  CA   HIS J 162     -17.461 -23.018 -98.280  1.00 43.02      A    C
ATOM  22167  C    HIS J 162     -16.141 -22.394 -97.825  1.00 41.97      A    C
ATOM  22168  O    HIS J 162     -15.088 -23.041 -97.866  1.00 41.74      A    O
ATOM  22169  CB   HIS J 162     -18.144 -23.718 -97.095  1.00 43.23      A    C
ATOM  22170  CG   HIS J 162     -17.569 -25.063 -96.765  1.00 43.87      A    C
ATOM  22171  CD2  HIS J 162     -18.050 -26.313 -96.969  1.00 44.45      A    C
ATOM  22172  ND1  HIS J 162     -16.352 -25.221 -96.134  1.00 44.07      A    N
ATOM  22173  CE1  HIS J 162     -16.104 -26.509 -95.976  1.00 44.27      A    C
ATOM  22174  NE2  HIS J 162     -17.121 -27.193 -96.469  1.00 44.54      A    N
ATOM  22175  N    LEU J 163     -16.203 -21.132 -97.406  1.00 40.85      A    N
ATOM  22176  CA   LEU J 163     -15.116 -20.535 -96.642  1.00 39.68      A    C
ATOM  22177  C    LEU J 163     -15.136 -21.153 -95.255  1.00 39.01      A    C
ATOM  22178  O    LEU J 163     -16.195 -21.240 -94.624  1.00 39.05      A    O
ATOM  22179  CB   LEU J 163     -15.288 -19.026 -96.519  1.00 39.56      A    C
ATOM  22180  CG   LEU J 163     -14.381 -18.326 -95.499  1.00 38.91      A    C
ATOM  22181  CD1  LEU J 163     -12.898 -18.398 -95.888  1.00 38.46      A    C
ATOM  22182  CD2  LEU J 163     -14.816 -16.884 -95.313  1.00 38.90      A    C
ATOM  22183  N    THR J 164     -13.973 -21.578 -94.774  1.00 38.03      A    N
ATOM  22184  CA   THR J 164     -13.920 -22.208 -93.462  1.00 37.06      A    C
ATOM  22185  C    THR J 164     -12.921 -21.562 -92.485  1.00 36.47      A    C
ATOM  22186  O    THR J 164     -11.708 -21.528 -92.724  1.00 36.23      A    O
ATOM  22187  CB   THR J 164     -13.777 -23.750 -93.570  1.00 36.99      A    C
ATOM  22188  CG2  THR J 164     -12.639 -24.144 -94.506  1.00 36.93      A    C
ATOM  22189  OG1  THR J 164     -13.561 -24.311 -92.271  1.00 36.66      A    O
ATOM  22190  N    LEU J 165     -13.473 -21.010 -91.406  1.00 35.83      A    N
ATOM  22191  CA   LEU J 165     -12.690 -20.437 -90.330  1.00 35.28      A    C
ATOM  22192  C    LEU J 165     -12.568 -21.446 -89.202  1.00 35.00      A    C
ATOM  22193  O    LEU J 165     -13.495 -22.227 -88.958  1.00 35.09      A    O
ATOM  22194  CB   LEU J 165     -13.353 -19.165 -89.810  1.00 35.23      A    C
ATOM  22195  CG   LEU J 165     -13.596 -18.029 -90.804  1.00 35.32      A    C
ATOM  22196  CD1  LEU J 165     -14.076 -16.801 -90.074  1.00 35.43      A    C
ATOM  22197  CD2  LEU J 165     -12.333 -17.692 -91.605  1.00 35.14      A    C
ATOM  22198  N    ALA J 166     -11.432 -21.428 -88.508  1.00 34.53      A    N
ATOM  22199  CA   ALA J 166     -11.206 -22.372 -87.413  1.00 34.10      A    C
ATOM  22200  C    ALA J 166     -10.417 -21.799 -86.240  1.00 33.83      A    C
ATOM  22201  O    ALA J 166      -9.527 -20.958 -86.420  1.00 33.65      A    O
ATOM  22202  CB   ALA J 166     -10.544 -23.642 -87.927  1.00 34.11      A    C
ATOM  22203  N    CYS J 167     -10.788 -22.269 -85.046  1.00 33.67      A    N
ATOM  22204  CA   CYS J 167     -10.077 -22.045 -83.788  1.00 33.53      A    C
ATOM  22205  C    CYS J 167     -10.093 -23.372 -83.042  1.00 33.49      A    C
ATOM  22206  O    CYS J 167     -10.863 -24.273 -83.391  1.00 33.57      A    O
ATOM  22207  CB   CYS J 167     -10.807 -21.003 -82.945  1.00 33.51      A    C
ATOM  22208  SG   CYS J 167     -12.416 -21.573 -82.270  1.00 33.81      A    S
ATOM  22209  N    HIS J 168      -9.269 -23.493 -82.010  1.00 33.45      A    N
ATOM  22210  CA   HIS J 168      -9.388 -24.643 -81.122  1.00 33.50      A    C
ATOM  22211  C    HIS J 168      -9.934 -24.209 -79.757  1.00 33.46      A    C
ATOM  22212  O    HIS J 168      -9.511 -23.179 -79.210  1.00 33.36      A    O
ATOM  22213  CB   HIS J 168      -8.063 -25.382 -80.986  1.00 33.61      A    C
ATOM  22214  CG   HIS J 168      -7.095 -24.705 -80.075  1.00 34.00      A    C
ATOM  22215  CD2  HIS J 168      -6.136 -23.781 -80.320  1.00 34.33      A    C
ATOM  22216  ND1  HIS J 168      -7.066 -24.941 -78.719  1.00 34.36      A    N
ATOM  22217  CE1  HIS J 168      -6.122 -24.200 -78.166  1.00 34.42      A    C
ATOM  22218  NE2  HIS J 168      -5.545 -23.484 -79.116  1.00 34.34      A    N
ATOM  22219  N    TYR J 169     -10.874 -24.995 -79.221  1.00 33.54      A    N
ATOM  22220  CA   TYR J 169     -11.600 -24.622 -77.997  1.00 33.67      A    C
ATOM  22221  C    TYR J 169     -11.075 -25.285 -76.733  1.00 33.72      A    C
ATOM  22222  O    TYR J 169     -11.419 -24.879 -75.635  1.00 33.74      A    O
ATOM  22223  CB   TYR J 169     -13.121 -24.825 -78.148  1.00 33.73      A    C
ATOM  22224  CG   TYR J 169     -13.584 -26.247 -77.985  1.00 33.95      A    C
ATOM  22225  CD1  TYR J 169     -13.553 -27.139 -79.053  1.00 33.86      A    C
ATOM  22226  CD2  TYR J 169     -14.060 -26.700 -76.766  1.00 34.41      A    C
ATOM  22227  CE1  TYR J 169     -13.976 -28.449 -78.906  1.00 33.93      A    C
ATOM  22228  CE2  TYR J 169     -14.480 -28.010 -76.606  1.00 34.62      A    C
ATOM  22229  CZ   TYR J 169     -14.436 -28.876 -77.678  1.00 34.21      A    C
ATOM  22230  OH   TYR J 169     -14.861 -30.167 -77.510  1.00 34.31      A    O
```

FIGURE 1 (cont'd)

```
ATOM  22231  N    ASP J 170     -10.244 -26.304 -76.884  1.00 33.85      A  N
ATOM  22232  CA   ASP J 170      -9.574 -26.891 -75.733  1.00 34.21      A  C
ATOM  22233  C    ASP J 170      -8.557 -25.914 -75.145  1.00 34.45      A  C
ATOM  22234  O    ASP J 170      -8.145 -24.972 -75.817  1.00 34.28      A  O
ATOM  22235  CB   ASP J 170      -8.898 -28.208 -76.111  1.00 34.25      A  C
ATOM  22236  CG   ASP J 170      -7.727 -28.022 -77.071  1.00 34.19      A  C
ATOM  22237  OD1  ASP J 170      -7.921 -27.486 -78.186  1.00 33.82      A  O
ATOM  22238  OD2  ASP J 170      -6.605 -28.442 -76.716  1.00 34.60      A  O
ATOM  22239  N    SER J 171      -8.182 -26.124 -73.884  1.00 34.91      A  N
ATOM  22240  CA   SER J 171      -7.131 -25.331 -73.238  1.00 35.35      A  C
ATOM  22241  C    SER J 171      -6.044 -26.289 -72.790  1.00 35.64      A  C
ATOM  22242  O    SER J 171      -6.358 -27.429 -72.429  1.00 35.97      A  O
ATOM  22243  CB   SER J 171      -7.683 -24.546 -72.036  1.00 35.42      A  C
ATOM  22244  OG   SER J 171      -7.773 -25.340 -70.859  1.00 35.87      A  O
ATOM  22245  N    LYS J 172      -4.783 -25.845 -72.797  1.00 35.79      A  N
ATOM  22246  CA   LYS J 172      -3.677 -26.744 -72.435  1.00 36.21      A  C
ATOM  22247  C    LYS J 172      -3.776 -27.284 -70.998  1.00 36.92      A  C
ATOM  22248  O    LYS J 172      -4.322 -26.622 -70.110  1.00 37.17      A  O
ATOM  22249  CB   LYS J 172      -2.316 -26.098 -72.682  1.00 35.92      A  C
ATOM  22250  CG   LYS J 172      -1.171 -27.112 -72.720  1.00 35.70      A  C
ATOM  22251  CD   LYS J 172       0.190 -26.452 -72.869  1.00 35.11      A  C
ATOM  22252  CE   LYS J 172       1.322 -27.469 -72.731  1.00 35.09      A  C
ATOM  22253  NZ   LYS J 172       1.453 -28.322 -73.945  1.00 35.07      A  N
ATOM  22254  N    LEU J 173      -3.264 -28.498 -70.797  1.00 37.69      A  N
ATOM  22255  CA   LEU J 173      -3.262 -29.155 -69.498  1.00 38.57      A  C
ATOM  22256  C    LEU J 173      -1.909 -28.989 -68.839  1.00 39.08      A  C
ATOM  22257  O    LEU J 173      -0.886 -29.350 -69.411  1.00 39.19      A  O
ATOM  22258  CB   LEU J 173      -3.562 -30.641 -69.666  1.00 38.65      A  C
ATOM  22259  CG   LEU J 173      -3.413 -31.547 -68.443  1.00 39.25      A  C
ATOM  22260  CD1  LEU J 173      -4.734 -31.703 -67.694  1.00 39.59      A  C
ATOM  22261  CD2  LEU J 173      -2.857 -32.901 -68.856  1.00 39.39      A  C
ATOM  22262  N    PHE J 174      -1.910 -28.451 -67.630  1.00 39.76      A  N
ATOM  22263  CA   PHE J 174      -0.677 -28.239 -66.876  1.00 40.38      A  C
ATOM  22264  C    PHE J 174      -0.706 -29.082 -65.579  1.00 40.28      A  C
ATOM  22265  O    PHE J 174      -1.794 -29.351 -65.072  1.00 41.42      A  O
ATOM  22266  CB   PHE J 174      -0.515 -26.740 -66.586  1.00 40.62      A  C
ATOM  22267  CG   PHE J 174      -0.020 -25.937 -67.773  1.00 40.49      A  C
ATOM  22268  CD1  PHE J 174       1.336 -25.935 -68.111  1.00 40.61      A  C
ATOM  22269  CD2  PHE J 174      -0.903 -25.180 -68.550  1.00 40.05      A  C
ATOM  22270  CE1  PHE J 174       1.804 -25.204 -69.199  1.00 40.09      A  C
ATOM  22271  CE2  PHE J 174      -0.440 -24.438 -69.639  1.00 39.54      A  C
ATOM  22272  CZ   PHE J 174       0.915 -24.452 -69.961  1.00 39.66      A  C
ATOM  22273  N    PRO J 175       0.463 -29.549 -65.050  1.00 38.70      A  N
ATOM  22274  CA   PRO J 175       0.418 -30.308 -63.771  1.00 37.94      A  C
ATOM  22275  C    PRO J 175      -0.583 -29.722 -62.750  1.00 38.29      A  C
ATOM  22276  O    PRO J 175      -0.637 -28.497 -62.572  1.00 38.13      A  O
ATOM  22277  CB   PRO J 175       1.854 -30.203 -63.239  1.00 37.51      A  C
ATOM  22278  CG   PRO J 175       2.548 -29.193 -64.128  1.00 37.50      A  C
ATOM  22279  CD   PRO J 175       1.863 -29.315 -65.465  1.00 38.27      A  C
ATOM  22280  N    PRO J 176      -1.356 -30.596 -62.067  1.00 38.95      A  N
ATOM  22281  CA   PRO J 176      -2.639 -30.197 -61.472  1.00 40.07      A  C
ATOM  22282  C    PRO J 176      -2.537 -29.410 -60.167  1.00 42.05      A  C
ATOM  22283  O    PRO J 176      -3.569 -29.093 -59.563  1.00 42.33      A  O
ATOM  22284  CB   PRO J 176      -3.322 -31.541 -61.211  1.00 39.43      A  C
ATOM  22285  CG   PRO J 176      -2.191 -32.456 -60.870  1.00 38.90      A  C
ATOM  22286  CD   PRO J 176      -0.962 -31.951 -61.627  1.00 38.84      A  C
ATOM  22287  N    GLY J 177      -1.320 -29.091 -59.736  1.00 43.87      A  N
ATOM  22288  CA   GLY J 177      -1.151 -28.397 -58.471  1.00 45.94      A  C
ATOM  22289  C    GLY J 177      -1.375 -26.896 -58.532  1.00 46.94      A  C
ATOM  22290  O    GLY J 177      -1.977 -26.293 -57.649  1.00 47.54      A  O
ATOM  22291  N    SER J 178      -0.951 -26.314 -59.633  1.00 47.25      A  N
ATOM  22292  CA   SER J 178      -0.431 -24.968 -59.660  1.00 46.96      A  C
ATOM  22293  C    SER J 178      -1.348 -23.794 -59.747  1.00 46.90      A  C
ATOM  22294  O    SER J 178      -1.798 -23.324 -58.726  1.00 47.47      A  O
ATOM  22295  CB   SER J 178       0.532 -24.905 -60.787  1.00 45.27      A  C
```

FIGURE 1 (cont'd)

```
ATOM  22296  OG   SER J 178      1.385 -25.992 -60.632  1.00 44.54      A  O
ATOM  22297  N    THR J 179     -1.549 -23.238 -60.930  1.00 45.46      A  N
ATOM  22298  CA   THR J 179     -2.517 -22.168 -61.026  1.00 42.96      A  C
ATOM  22299  C    THR J 179     -3.336 -22.417 -62.282  1.00 43.47      A  C
ATOM  22300  O    THR J 179     -2.773 -22.744 -63.328  1.00 44.41      A  O
ATOM  22301  CB   THR J 179     -1.881 -20.715 -60.873  1.00 37.60      A  C
ATOM  22302  CG2  THR J 179     -0.325 -20.747 -60.769  1.00 39.31      A  C
ATOM  22303  OG1  THR J 179     -2.259 -19.887 -61.979  1.00 34.58      A  O
ATOM  22304  N    PRO J 180     -4.671 -22.299 -62.172  1.00 42.24      A  N
ATOM  22305  CA   PRO J 180     -5.542 -22.630 -63.293  1.00 41.26      A  C
ATOM  22306  C    PRO J 180     -5.113 -21.896 -64.573  1.00 42.06      A  C
ATOM  22307  O    PRO J 180     -4.697 -20.726 -64.521  1.00 42.92      A  O
ATOM  22308  CB   PRO J 180     -6.909 -22.126 -62.818  1.00 36.47      A  C
ATOM  22309  CG   PRO J 180     -6.578 -21.005 -61.867  1.00 34.98      A  C
ATOM  22310  CD   PRO J 180     -5.407 -21.584 -61.114  1.00 40.93      A  C
ATOM  22311  N    PHE J 181     -5.201 -22.581 -65.707  1.00 41.82      A  N
ATOM  22312  CA   PHE J 181     -4.818 -21.980 -66.977  1.00 40.94      A  C
ATOM  22313  C    PHE J 181     -5.980 -21.909 -67.950  1.00 40.20      A  C
ATOM  22314  O    PHE J 181     -6.489 -22.939 -68.394  1.00 40.03      A  O
ATOM  22315  CB   PHE J 181     -3.659 -22.753 -67.595  1.00 41.01      A  C
ATOM  22316  CG   PHE J 181     -3.356 -22.355 -69.004  1.00 40.75      A  C
ATOM  22317  CD1  PHE J 181     -2.750 -21.126 -69.274  1.00 40.91      A  C
ATOM  22318  CD2  PHE J 181     -3.678 -23.201 -70.063  1.00 40.48      A  C
ATOM  22319  CE1  PHE J 181     -2.463 -20.740 -70.582  1.00 40.31      A  C
ATOM  22320  CE2  PHE J 181     -3.401 -22.833 -71.374  1.00 40.00      A  C
ATOM  22321  CZ   PHE J 181     -2.788 -21.595 -71.637  1.00 39.79      A  C
ATOM  22322  N    VAL J 182     -6.380 -20.692 -68.295  1.00 39.41      A  N
ATOM  22323  CA   VAL J 182     -7.552 -20.495 -69.168  1.00 38.72      A  C
ATOM  22324  C    VAL J 182     -7.239 -20.147 -70.623  1.00 37.95      A  C
ATOM  22325  O    VAL J 182     -8.140 -20.191 -71.469  1.00 37.78      A  O
ATOM  22326  CB   VAL J 182     -8.573 -19.459 -68.616  1.00 38.78      A  C
ATOM  22327  CG1  VAL J 182     -9.402 -20.070 -67.509  1.00 39.13      A  C
ATOM  22328  CG2  VAL J 182     -7.868 -18.193 -68.149  1.00 39.13      A  C
ATOM  22329  N    GLY J 183     -5.983 -19.794 -70.904  1.00 37.21      A  N
ATOM  22330  CA   GLY J 183     -5.548 -19.476 -72.263  1.00 36.23      A  C
ATOM  22331  C    GLY J 183     -6.507 -18.572 -73.014  1.00 35.57      A  C
ATOM  22332  O    GLY J 183     -7.243 -19.017 -73.884  1.00 35.41      A  O
ATOM  22333  N    ALA J 184     -6.501 -17.294 -72.670  1.00 35.06      A  N
ATOM  22334  CA   ALA J 184     -7.399 -16.326 -73.287  1.00 34.49      A  C
ATOM  22335  C    ALA J 184     -7.081 -16.118 -74.763  1.00 33.93      A  C
ATOM  22336  O    ALA J 184     -7.975 -16.130 -75.601  1.00 33.74      A  O
ATOM  22337  CB   ALA J 184     -7.335 -15.014 -72.537  1.00 34.82      A  C
ATOM  22338  N    THR J 185     -5.802 -15.935 -75.073  1.00 33.38      A  N
ATOM  22339  CA   THR J 185     -5.356 -15.803 -76.453  1.00 32.83      A  C
ATOM  22340  C    THR J 185     -5.305 -17.166 -77.126  1.00 32.59      A  C
ATOM  22341  O    THR J 185     -5.231 -17.254 -78.353  1.00 32.59      A  O
ATOM  22342  CB   THR J 185     -3.934 -15.204 -76.554  1.00 32.76      A  C
ATOM  22343  CG2  THR J 185     -3.794 -13.962 -75.674  1.00 33.00      A  C
ATOM  22344  OG1  THR J 185     -2.961 -16.195 -76.184  1.00 32.40      A  O
ATOM  22345  N    ASP J 186     -5.355 -18.221 -76.316  1.00 32.36      A  N
ATOM  22346  CA   ASP J 186     -4.975 -19.560 -76.757  1.00 32.12      A  C
ATOM  22347  C    ASP J 186     -6.005 -20.639 -76.358  1.00 32.16      A  C
ATOM  22348  O    ASP J 186     -5.717 -21.474 -75.488  1.00 32.46      A  O
ATOM  22349  CB   ASP J 186     -3.590 -19.873 -76.170  1.00 31.99      A  C
ATOM  22350  CG   ASP J 186     -2.959 -21.110 -76.753  1.00 31.46      A  C
ATOM  22351  OD1  ASP J 186     -1.844 -21.430 -76.310  1.00 31.31      A  O
ATOM  22352  OD2  ASP J 186     -3.547 -21.760 -77.637  1.00 30.63      A  O
ATOM  22353  N    SER J 187     -7.188 -20.655 -76.987  1.00 31.90      A  N
ATOM  22354  CA   SER J 187     -7.568 -19.776 -78.094  1.00 31.65      A  C
ATOM  22355  C    SER J 187     -8.990 -19.251 -77.915  1.00 31.63      A  C
ATOM  22356  O    SER J 187     -9.778 -19.214 -78.866  1.00 31.52      A  O
ATOM  22357  CB   SER J 187     -7.463 -20.535 -79.422  1.00 31.57      A  C
ATOM  22358  OG   SER J 187     -6.110 -20.722 -79.804  1.00 31.71      A  O
ATOM  22359  N    ALA J 188     -9.314 -18.845 -76.692  1.00 31.77      A  N
ATOM  22360  CA   ALA J 188    -10.671 -18.401 -76.346  1.00 31.87      A  C
```

FIGURE 1 (cont'd)

```
ATOM  22361  C    ALA J 188     -11.147 -17.232 -77.221  1.00 31.86      A  C
ATOM  22362  O    ALA J 188     -12.242 -17.284 -77.793  1.00 31.83      A  O
ATOM  22363  CB   ALA J 188     -10.754 -18.043 -74.862  1.00 32.02      A  C
ATOM  22364  N    VAL J 189     -10.310 -16.195 -77.320  1.00 31.79      A  N
ATOM  22365  CA   VAL J 189     -10.585 -15.020 -78.158  1.00 31.69      A  C
ATOM  22366  C    VAL J 189     -10.831 -15.415 -79.626  1.00 31.67      A  C
ATOM  22367  O    VAL J 189     -11.872 -15.042 -80.188  1.00 31.76      A  O
ATOM  22368  CB   VAL J 189      -9.458 -13.944 -78.054  1.00 31.59      A  C
ATOM  22369  CG1  VAL J 189      -9.669 -12.830 -79.078  1.00 31.37      A  C
ATOM  22370  CG2  VAL J 189      -9.382 -13.379 -76.648  1.00 31.78      A  C
ATOM  22371  N    PRO J 190      -9.886 -16.163 -80.246  1.00 31.53      A  N
ATOM  22372  CA   PRO J 190     -10.165 -16.688 -81.574  1.00 31.55      A  C
ATOM  22373  C    PRO J 190     -11.565 -17.311 -81.710  1.00 31.79      A  C
ATOM  22374  O    PRO J 190     -12.295 -16.989 -82.655  1.00 31.81      A  O
ATOM  22375  CB   PRO J 190      -9.079 -17.750 -81.743  1.00 31.37      A  C
ATOM  22376  CG   PRO J 190      -7.904 -17.169 -81.023  1.00 31.34      A  C
ATOM  22377  CD   PRO J 190      -8.480 -16.410 -79.856  1.00 31.48      A  C
ATOM  22378  N    CYS J 191     -11.937 -18.176 -80.770  1.00 32.16      A  N
ATOM  22379  CA   CYS J 191     -13.234 -18.841 -80.823  1.00 32.69      A  C
ATOM  22380  C    CYS J 191     -14.370 -17.859 -80.611  1.00 32.98      A  C
ATOM  22381  O    CYS J 191     -15.403 -17.942 -81.271  1.00 33.18      A  O
ATOM  22382  CB   CYS J 191     -13.299 -19.988 -79.817  1.00 32.75      A  C
ATOM  22383  SG   CYS J 191     -12.205 -21.370 -80.241  1.00 33.33      A  S
ATOM  22384  N    ALA J 192     -14.163 -16.915 -79.704  1.00 33.22      A  N
ATOM  22385  CA   ALA J 192     -15.151 -15.882 -79.431  1.00 33.46      A  C
ATOM  22386  C    ALA J 192     -15.487 -15.072 -80.691  1.00 33.43      A  C
ATOM  22387  O    ALA J 192     -16.657 -14.790 -80.978  1.00 33.66      A  O
ATOM  22388  CB   ALA J 192     -14.646 -14.975 -78.316  1.00 33.61      A  C
ATOM  22389  N    LEU J 193     -14.449 -14.716 -81.443  1.00 33.04      A  N
ATOM  22390  CA   LEU J 193     -14.613 -13.962 -82.682  1.00 32.67      A  C
ATOM  22391  C    LEU J 193     -15.481 -14.719 -83.693  1.00 33.22      A  C
ATOM  22392  O    LEU J 193     -16.445 -14.164 -84.234  1.00 33.59      A  O
ATOM  22393  CB   LEU J 193     -13.249 -13.619 -83.293  1.00 31.34      A  C
ATOM  22394  CG   LEU J 193     -12.366 -12.638 -82.525  1.00 29.74      A  C
ATOM  22395  CD1  LEU J 193     -10.994 -12.580 -83.162  1.00 28.78      A  C
ATOM  22396  N    LEU J 194     -15.140 -15.984 -83.931  1.00 33.41      A  N
ATOM  22397  CA   LEU J 194     -15.912 -16.829 -84.834  1.00 33.58      A  C
ATOM  22398  C    LEU J 194     -17.405 -16.789 -84.484  1.00 34.50      A  C
ATOM  22399  O    LEU J 194     -18.258 -16.779 -85.381  1.00 34.80      A  O
ATOM  22400  CB   LEU J 194     -15.393 -18.265 -84.809  1.00 32.49      A  C
ATOM  22401  CG   LEU J 194     -14.022 -18.458 -85.441  1.00 31.29      A  C
ATOM  22402  CD1  LEU J 194     -13.942 -19.854 -86.016  1.00 30.92      A  C
ATOM  22403  N    LEU J 195     -17.711 -16.744 -83.186  1.00 35.28      A  N
ATOM  22404  CA   LEU J 195     -19.095 -16.679 -82.733  1.00 36.10      A  C
ATOM  22405  C    LEU J 195     -19.688 -15.319 -83.036  1.00 36.82      A  C
ATOM  22406  O    LEU J 195     -20.782 -15.236 -83.613  1.00 37.14      A  O
ATOM  22407  CB   LEU J 195     -19.203 -16.979 -81.241  1.00 36.03      A  C
ATOM  22408  CG   LEU J 195     -18.929 -18.410 -80.769  1.00 35.82      A  C
ATOM  22409  CD1  LEU J 195     -18.921 -18.444 -79.264  1.00 36.06      A  C
ATOM  22410  CD2  LEU J 195     -19.946 -19.408 -81.312  1.00 35.82      A  C
ATOM  22411  N    GLU J 196     -18.950 -14.266 -82.663  1.00 37.43      A  N
ATOM  22412  CA   GLU J 196     -19.385 -12.873 -82.847  1.00 38.06      A  C
ATOM  22413  C    GLU J 196     -19.645 -12.528 -84.314  1.00 38.15      A  C
ATOM  22414  O    GLU J 196     -20.661 -11.896 -84.644  1.00 38.30      A  O
ATOM  22415  CB   GLU J 196     -18.363 -11.907 -82.231  1.00 38.17      A  C
ATOM  22416  CG   GLU J 196     -18.545 -10.434 -82.619  1.00 39.31      A  C
ATOM  22417  CD   GLU J 196     -19.826  -9.777 -82.071  1.00 40.81      A  C
ATOM  22418  OE1  GLU J 196     -20.554 -10.397 -81.267  1.00 41.44      A  O
ATOM  22419  OE2  GLU J 196     -20.104  -8.614 -82.447  1.00 41.54      A  O
ATOM  22420  N    LEU J 197     -18.712 -12.954 -85.170  1.00 38.15      A  N
ATOM  22421  CA   LEU J 197     -18.826 -12.817 -86.616  1.00 38.37      A  C
ATOM  22422  C    LEU J 197     -20.084 -13.482 -87.141  1.00 38.85      A  C
ATOM  22423  O    LEU J 197     -20.827 -12.884 -87.914  1.00 39.15      A  O
ATOM  22424  CB   LEU J 197     -17.608 -13.427 -87.303  1.00 37.96      A  C
ATOM  22425  CG   LEU J 197     -16.505 -12.481 -87.778  1.00 37.75      A  C
```

FIGURE 1 (cont'd)

```
ATOM  22426  CD1 LEU J 197     -15.576 -12.073 -86.650  1.00 37.59    A    C
ATOM  22427  CD2 LEU J 197     -15.704 -13.134 -88.897  1.00 37.67    A    C
ATOM  22428  N   ALA J 198     -20.320 -14.715 -86.708  1.00 39.29    A    N
ATOM  22429  CA  ALA J 198     -21.473 -15.487 -87.154  1.00 40.04    A    C
ATOM  22430  C   ALA J 198     -22.789 -14.823 -86.764  1.00 40.79    A    C
ATOM  22431  O   ALA J 198     -23.804 -14.959 -87.463  1.00 41.08    A    O
ATOM  22432  CB  ALA J 198     -21.408 -16.895 -86.594  1.00 39.87    A    C
ATOM  22433  N   GLN J 199     -22.756 -14.105 -85.645  1.00 41.38    A    N
ATOM  22434  CA  GLN J 199     -23.933 -13.437 -85.099  1.00 42.06    A    C
ATOM  22435  C   GLN J 199     -24.137 -12.063 -85.763  1.00 43.01    A    C
ATOM  22436  O   GLN J 199     -25.252 -11.736 -86.205  1.00 43.58    A    O
ATOM  22437  CB  GLN J 199     -23.791 -13.281 -83.574  1.00 40.97    A    C
ATOM  22438  CG  GLN J 199     -24.950 -13.843 -82.736  1.00 40.40    A    C
ATOM  22439  CD  GLN J 199     -26.316 -13.341 -83.162  1.00 40.14    A    C
ATOM  22440  OE1 GLN J 199     -26.649 -12.184 -82.932  1.00 40.51    A    O
ATOM  22441  N   ALA J 200     -23.058 -11.272 -85.828  1.00 43.69    A    N
ATOM  22442  CA  ALA J 200     -23.088  -9.922 -86.420  1.00 44.39    A    C
ATOM  22443  C   ALA J 200     -23.515  -9.925 -87.902  1.00 44.94    A    C
ATOM  22444  O   ALA J 200     -24.302  -9.069 -88.341  1.00 45.35    A    O
ATOM  22445  CB  ALA J 200     -21.730  -9.227 -86.240  1.00 44.12    A    C
ATOM  22446  N   LEU J 201     -22.999 -10.899 -88.653  1.00 45.27    A    N
ATOM  22447  CA  LEU J 201     -23.318 -11.057 -90.073  1.00 45.82    A    C
ATOM  22448  C   LEU J 201     -24.453 -12.048 -90.306  1.00 46.53    A    C
ATOM  22449  O   LEU J 201     -24.727 -12.421 -91.453  1.00 46.74    A    O
ATOM  22450  CB  LEU J 201     -22.078 -11.510 -90.852  1.00 45.36    A    C
ATOM  22451  CG  LEU J 201     -20.887 -10.545 -90.849  1.00 45.12    A    C
ATOM  22452  CD1 LEU J 201     -19.600 -11.243 -91.297  1.00 44.79    A    C
ATOM  22453  CD2 LEU J 201     -21.170  -9.288 -91.682  1.00 45.39    A    C
ATOM  22454  N   ASP J 202     -25.105 -12.459 -89.220  1.00 47.26    A    N
ATOM  22455  CA  ASP J 202     -26.147 -13.477 -89.265  1.00 48.11    A    C
ATOM  22456  C   ASP J 202     -27.219 -13.227 -90.349  1.00 48.74    A    C
ATOM  22457  O   ASP J 202     -27.540 -14.139 -91.127  1.00 48.95    A    O
ATOM  22458  CB  ASP J 202     -26.783 -13.633 -87.876  1.00 48.23    A    C
ATOM  22459  CG  ASP J 202     -27.948 -14.629 -87.854  1.00 48.68    A    C
ATOM  22460  OD1 ASP J 202     -27.760 -15.819 -88.223  1.00 48.50    A    O
ATOM  22461  OD2 ASP J 202     -29.054 -14.207 -87.447  1.00 49.41    A    O
ATOM  22462  N   LEU J 203     -27.757 -12.004 -90.407  1.00 49.15    A    N
ATOM  22463  CA  LEU J 203     -28.859 -11.683 -91.341  1.00 49.35    A    C
ATOM  22464  C   LEU J 203     -28.438 -11.655 -92.819  1.00 49.60    A    C
ATOM  22465  O   LEU J 203     -29.090 -12.271 -93.667  1.00 49.98    A    O
ATOM  22466  CB  LEU J 203     -29.580 -10.390 -90.931  1.00 48.38    A    C
ATOM  22467  CG  LEU J 203     -30.604 -10.587 -89.804  1.00 48.09    A    C
ATOM  22468  CD1 LEU J 203     -30.024 -10.170 -88.441  1.00 47.97    A    C
ATOM  22469  N   GLU J 204     -27.352 -10.948 -93.120  1.00 49.38    A    N
ATOM  22470  CA  GLU J 204     -26.780 -10.961 -94.467  1.00 49.01    A    C
ATOM  22471  C   GLU J 204     -26.318 -12.373 -94.888  1.00 49.46    A    C
ATOM  22472  O   GLU J 204     -26.431 -12.753 -96.063  1.00 49.74    A    O
ATOM  22473  CB  GLU J 204     -25.649  -9.929 -94.602  1.00 47.50    A    C
ATOM  22474  CG  GLU J 204     -24.866  -9.637 -93.320  1.00 45.84    A    C
ATOM  22475  CD  GLU J 204     -25.618  -8.720 -92.373  1.00 45.11    A    C
ATOM  22476  OE1 GLU J 204     -25.714  -7.513 -92.678  1.00 45.27    A    O
ATOM  22477  OE2 GLU J 204     -26.094  -9.206 -91.320  1.00 45.65    A    O
ATOM  22478  N   LEU J 205     -25.815 -13.142 -93.920  1.00 49.65    A    N
ATOM  22479  CA  LEU J 205     -25.479 -14.550 -94.140  1.00 49.80    A    C
ATOM  22480  C   LEU J 205     -26.728 -15.369 -94.419  1.00 50.52    A    C
ATOM  22481  O   LEU J 205     -26.684 -16.343 -95.181  1.00 50.60    A    O
ATOM  22482  CB  LEU J 205     -24.753 -15.146 -92.927  1.00 49.24    A    C
ATOM  22483  CG  LEU J 205     -23.225 -15.139 -92.913  1.00 48.26    A    C
ATOM  22484  CD1 LEU J 205     -22.742 -15.412 -91.500  1.00 47.86    A    C
ATOM  22485  CD2 LEU J 205     -22.661 -16.168 -93.896  1.00 47.62    A    C
ATOM  22486  N   SER J 206     -27.831 -14.965 -93.790  1.00 51.37    A    N
ATOM  22487  CA  SER J 206     -29.083 -15.702 -93.874  1.00 52.28    A    C
ATOM  22488  C   SER J 206     -29.704 -15.561 -95.265  1.00 52.76    A    C
ATOM  22489  O   SER J 206     -30.016 -16.567 -95.923  1.00 52.79    A    O
ATOM  22490  CB  SER J 206     -30.060 -15.248 -92.779  1.00 52.48    A    C
```

FIGURE 1 (cont'd)

```
ATOM  22491  OG   SER J 206     -31.087 -16.209 -92.583  1.00 53.16      A    O
ATOM  22492  N    ARG J 207     -29.867 -14.318 -95.716  1.00 53.27      A    N
ATOM  22493  CA   ARG J 207     -30.520 -14.074 -97.003  1.00 53.78      A    C
ATOM  22494  C    ARG J 207     -29.756 -14.789 -98.116  1.00 53.78      A    C
ATOM  22495  O    ARG J 207     -30.355 -15.567 -98.878  1.00 54.13      A    O
ATOM  22496  CB   ARG J 207     -30.721 -12.573 -97.288  1.00 54.05      A    C
ATOM  22497  CG   ARG J 207     -29.476 -11.697 -97.130  1.00 53.56      A    C
ATOM  22498  N    ALA J 208     -28.438 -14.556 -98.170  1.00 53.32      A    N
ATOM  22499  CA   ALA J 208     -27.558 -15.265 -99.101  1.00 52.93      A    C
ATOM  22500  C    ALA J 208     -27.536 -16.744 -98.723  1.00 52.68      A    C
ATOM  22501  O    ALA J 208     -26.630 -17.209 -98.029  1.00 52.42      A    O
ATOM  22502  CB   ALA J 208     -26.148 -14.666 -99.090  1.00 52.59      A    C
ATOM  22503  N    LYS J 209     -28.570 -17.452 -99.177  1.00 52.73      A    N
ATOM  22504  CA   LYS J 209     -28.830 -18.842 -98.847  1.00 52.40      A    C
ATOM  22505  C    LYS J 209     -30.283 -19.053 -99.240  1.00 51.87      A    C
ATOM  22506  O    LYS J 209     -30.964 -19.945 -98.765  1.00 52.81      A    O
ATOM  22507  CB   LYS J 209     -28.618 -19.103 -97.356  1.00 52.41      A    C
ATOM  22508  CG   LYS J 209     -28.520 -20.572 -96.976  1.00 52.73      A    C
ATOM  22509  CD   LYS J 209     -29.026 -20.790 -95.540  1.00 53.62      A    C
ATOM  22510  CE   LYS J 209     -28.930 -22.260 -95.095  1.00 53.79      A    C
ATOM  22511  NZ   LYS J 209     -29.523 -22.498 -93.743  1.00 53.90      A    N
TER   22512       LYS J 209
ATOM  22513  N    VAL J 215     -21.241 -20.436-102.608  1.00 36.34      A    N
ATOM  22514  CA   VAL J 215     -20.130 -20.555-101.665  1.00 36.21      A    C
ATOM  22515  C    VAL J 215     -20.566 -20.211-100.223  1.00 36.47      A    C
ATOM  22516  O    VAL J 215     -20.904 -19.054 -99.919  1.00 36.76      A    O
ATOM  22517  CB   VAL J 215     -18.935 -19.671-102.084  1.00 35.44      A    C
ATOM  22518  CG1  VAL J 215     -17.664 -20.134-101.397  1.00 34.56      A    C
ATOM  22519  N    THR J 216     -20.548 -21.214 -99.338  1.00 36.17      A    N
ATOM  22520  CA   THR J 216     -21.055 -21.059 -97.963  1.00 35.62      A    C
ATOM  22521  C    THR J 216     -19.984 -20.693 -96.930  1.00 35.11      A    C
ATOM  22522  O    THR J 216     -18.854 -20.329 -97.285  1.00 35.08      A    O
ATOM  22523  CB   THR J 216     -21.818 -22.316 -97.503  1.00 35.59      A    C
ATOM  22524  OG1  THR J 216     -23.042 -21.914 -96.879  1.00 35.47      A    O
ATOM  22525  N    LEU J 217     -20.362 -20.776 -95.655  1.00 34.49      A    N
ATOM  22526  CA   LEU J 217     -19.445 -20.501 -94.547  1.00 33.72      A    C
ATOM  22527  C    LEU J 217     -19.430 -21.638 -93.531  1.00 33.34      A    C
ATOM  22528  O    LEU J 217     -20.482 -22.176 -93.158  1.00 33.58      A    O
ATOM  22529  CB   LEU J 217     -19.806 -19.183 -93.864  1.00 33.62      A    C
ATOM  22530  CG   LEU J 217     -19.054 -18.826 -92.583  1.00 33.09      A    C
ATOM  22531  CD1  LEU J 217     -17.615 -18.437 -92.883  1.00 32.88      A    C
ATOM  22532  CD2  LEU J 217     -19.772 -17.702 -91.869  1.00 33.16      A    C
ATOM  22533  N    GLN J 218     -18.230 -21.998 -93.087  1.00 32.55      A    N
ATOM  22534  CA   GLN J 218     -18.066 -23.112 -92.165  1.00 31.93      A    C
ATOM  22535  C    GLN J 218     -17.236 -22.675 -90.964  1.00 31.34      A    C
ATOM  22536  O    GLN J 218     -16.213 -21.995 -91.119  1.00 31.24      A    O
ATOM  22537  CB   GLN J 218     -17.423 -24.302 -92.879  1.00 31.94      A    C
ATOM  22538  CG   GLN J 218     -17.331 -25.565 -92.049  1.00 32.14      A    C
ATOM  22539  CD   GLN J 218     -16.497 -26.636 -92.720  1.00 32.80      A    C
ATOM  22540  NE2  GLN J 218     -15.229 -26.339 -92.948  1.00 32.86      A    N
ATOM  22541  OE1  GLN J 218     -16.990 -27.714 -93.044  1.00 33.62      A    O
ATOM  22542  N    LEU J 219     -17.692 -23.049 -89.770  1.00 30.74      A    N
ATOM  22543  CA   LEU J 219     -16.982 -22.715 -88.546  1.00 30.06      A    C
ATOM  22544  C    LEU J 219     -16.548 -23.980 -87.820  1.00 29.81      A    C
ATOM  22545  O    LEU J 219     -17.376 -24.842 -87.483  1.00 29.91      A    O
ATOM  22546  CB   LEU J 219     -17.836 -21.818 -87.652  1.00 29.93      A    C
ATOM  22547  CG   LEU J 219     -18.240 -20.467 -88.241  1.00 29.64      A    C
ATOM  22548  CD1  LEU J 219     -19.225 -19.755 -87.334  1.00 29.43      A    C
ATOM  22549  CD2  LEU J 219     -17.007 -19.604 -88.497  1.00 29.21      A    C
ATOM  22550  N    LEU J 220     -15.242 -24.094 -87.603  1.00 29.28      A    N
ATOM  22551  CA   LEU J 220     -14.681 -25.270 -86.955  1.00 28.87      A    C
ATOM  22552  C    LEU J 220     -14.106 -24.918 -85.585  1.00 29.00      A    C
ATOM  22553  O    LEU J 220     -13.239 -24.047 -85.472  1.00 29.02      A    O
ATOM  22554  CB   LEU J 220     -13.619 -25.932 -87.836  1.00 28.12      A    C
ATOM  22555  CG   LEU J 220     -14.124 -26.442 -89.182  1.00 27.42      A    C
```

FIGURE 1 (cont'd)

```
ATOM  22556  CD1 LEU J 220     -13.012 -27.158 -89.900  1.00 26.96      A    C
ATOM  22557  N   PHE J 221     -14.618 -25.592 -84.552  1.00 29.15      A    N
ATOM  22558  CA  PHE J 221     -14.108 -25.485 -83.184  1.00 29.08      A    C
ATOM  22559  C   PHE J 221     -13.513 -26.841 -82.830  1.00 29.12      A    C
ATOM  22560  O   PHE J 221     -14.235 -27.807 -82.543  1.00 29.19      A    O
ATOM  22561  CB  PHE J 221     -15.231 -25.118 -82.208  1.00 29.12      A    C
ATOM  22562  CG  PHE J 221     -15.947 -23.839 -82.553  1.00 29.16      A    C
ATOM  22563  CD1 PHE J 221     -15.571 -22.635 -81.960  1.00 29.20      A    C
ATOM  22564  CD2 PHE J 221     -17.005 -23.835 -83.464  1.00 29.26      A    C
ATOM  22565  CE1 PHE J 221     -16.226 -21.446 -82.272  1.00 29.23      A    C
ATOM  22566  CE2 PHE J 221     -17.668 -22.645 -83.781  1.00 29.49      A    C
ATOM  22567  CZ  PHE J 221     -17.275 -21.450 -83.183  1.00 29.36      A    C
ATOM  22568  N   LEU J 222     -12.190 -26.905 -82.879  1.00 29.16      A    N
ATOM  22569  CA  LEU J 222     -11.469 -28.166 -82.736  1.00 29.43      A    C
ATOM  22570  C   LEU J 222     -11.084 -28.473 -81.287  1.00 29.76      A    C
ATOM  22571  O   LEU J 222     -10.667 -27.590 -80.543  1.00 29.75      A    O
ATOM  22572  CB  LEU J 222     -10.231 -28.172 -83.642  1.00 29.24      A    C
ATOM  22573  CG  LEU J 222     -10.532 -27.853 -85.108  1.00 29.05      A    C
ATOM  22574  CD1 LEU J 222     -10.727 -29.122 -85.917  1.00 29.14      A    C
ATOM  22575  CD2 LEU J 222      -9.416 -27.032 -85.679  1.00 28.73      A    C
ATOM  22576  N   ASP J 223     -11.239 -29.733 -80.899  1.00 30.30      A    N
ATOM  22577  CA  ASP J 223     -10.869 -30.187 -79.570  1.00 30.89      A    C
ATOM  22578  C   ASP J 223      -9.431 -30.654 -79.617  1.00 30.89      A    C
ATOM  22579  O   ASP J 223      -8.857 -30.811 -80.694  1.00 30.79      A    O
ATOM  22580  CB  ASP J 223     -11.799 -31.328 -79.103  1.00 31.34      A    C
ATOM  22581  CG  ASP J 223     -11.788 -31.544 -77.570  1.00 32.40      A    C
ATOM  22582  OD1 ASP J 223     -11.192 -30.725 -76.827  1.00 33.32      A    O
ATOM  22583  OD2 ASP J 223     -12.392 -32.546 -77.106  1.00 33.11      A    O
ATOM  22584  N   GLY J 224      -8.858 -30.855 -78.436  1.00 31.04      A    N
ATOM  22585  CA  GLY J 224      -7.533 -31.446 -78.276  1.00 31.27      A    C
ATOM  22586  C   GLY J 224      -6.508 -31.039 -79.321  1.00 31.24      A    C
ATOM  22587  O   GLY J 224      -6.037 -31.879 -80.106  1.00 31.42      A    O
ATOM  22588  N   GLU J 225      -6.174 -29.750 -79.343  1.00 31.04      A    N
ATOM  22589  CA  GLU J 225      -5.100 -29.274 -80.190  1.00 30.96      A    C
ATOM  22590  C   GLU J 225      -3.795 -29.257 -79.409  1.00 31.00      A    C
ATOM  22591  O   GLU J 225      -2.773 -29.731 -79.897  1.00 30.94      A    O
ATOM  22592  CB  GLU J 225      -5.439 -27.905 -80.760  1.00 30.78      A    C
ATOM  22593  CG  GLU J 225      -4.385 -27.372 -81.696  1.00 31.09      A    C
ATOM  22594  CD  GLU J 225      -3.323 -26.605 -80.960  1.00 31.88      A    C
ATOM  22595  OE1 GLU J 225      -3.664 -25.985 -79.936  1.00 32.67      A    O
ATOM  22596  OE2 GLU J 225      -2.151 -26.620 -81.393  1.00 32.37      A    O
ATOM  22597  N   GLU J 226      -3.851 -28.721 -78.194  1.00 31.29      A    N
ATOM  22598  CA  GLU J 226      -2.704 -28.682 -77.294  1.00 31.78      A    C
ATOM  22599  C   GLU J 226      -2.322 -30.083 -76.818  1.00 32.42      A    C
ATOM  22600  O   GLU J 226      -3.195 -30.901 -76.521  1.00 32.58      A    O
ATOM  22601  CB  GLU J 226      -3.005 -27.795 -76.088  1.00 31.67      A    C
ATOM  22602  CG  GLU J 226      -3.443 -26.372 -76.423  1.00 30.94      A    C
ATOM  22603  CD  GLU J 226      -2.296 -25.368 -76.465  1.00 30.26      A    C
ATOM  22604  OE1 GLU J 226      -1.126 -25.760 -76.680  1.00 30.22      A    O
ATOM  22605  OE2 GLU J 226      -2.576 -24.162 -76.288  1.00 29.67      A    O
ATOM  22606  N   ALA J 227      -1.014 -30.335 -76.743  1.00 33.01      A    N
ATOM  22607  CA  ALA J 227      -0.457 -31.635 -76.365  1.00 33.75      A    C
ATOM  22608  C   ALA J 227      -0.807 -31.989 -74.931  1.00 34.41      A    C
ATOM  22609  O   ALA J 227      -1.241 -31.131 -74.164  1.00 34.53      A    O
ATOM  22610  CB  ALA J 227       1.041 -31.622 -76.534  1.00 33.73      A    C
ATOM  22611  N   LEU J 228      -0.615 -33.250 -74.562  1.00 35.20      A    N
ATOM  22612  CA  LEU J 228      -0.883 -33.670 -73.189  1.00 35.92      A    C
ATOM  22613  C   LEU J 228       0.376 -33.931 -72.353  1.00 36.68      A    C
ATOM  22614  O   LEU J 228       0.456 -33.470 -71.211  1.00 36.96      A    O
ATOM  22615  CB  LEU J 228      -1.848 -34.859 -73.133  1.00 35.89      A    C
ATOM  22616  CG  LEU J 228      -3.359 -34.620 -73.291  1.00 35.23      A    C
ATOM  22617  CD1 LEU J 228      -3.859 -35.152 -74.618  1.00 34.78      A    C
ATOM  22618  CD2 LEU J 228      -3.784 -33.156 -73.077  1.00 34.61      A    C
ATOM  22619  N   LYS J 229       1.345 -34.666 -72.902  1.00 37.40      A    N
ATOM  22620  CA  LYS J 229       2.653 -34.818 -72.241  1.00 38.19      A    C
```

FIGURE 1 (cont'd)

```
ATOM  22621  C    LYS J 229       3.596 -33.752 -72.808  1.00 38.19      A  C
ATOM  22622  O    LYS J 229       3.694 -32.660 -72.242  1.00 38.15      A  O
ATOM  22623  CB   LYS J 229       3.210 -36.250 -72.374  1.00 38.69      A  C
ATOM  22624  CG   LYS J 229       4.398 -36.598 -71.445  1.00 39.49      A  C
ATOM  22625  CD   LYS J 229       3.970 -37.192 -70.097  1.00 40.02      A  C
ATOM  22626  N    GLU J 230       4.272 -34.048 -73.920  1.00 38.36      A  N
ATOM  22627  CA   GLU J 230       4.947 -32.987 -74.674  1.00 38.57      A  C
ATOM  22628  C    GLU J 230       4.706 -33.055 -76.188  1.00 38.30      A  C
ATOM  22629  O    GLU J 230       4.594 -34.151 -76.773  1.00 38.31      A  O
ATOM  22630  CB   GLU J 230       6.446 -32.855 -74.324  1.00 38.97      A  C
ATOM  22631  CG   GLU J 230       7.034 -31.436 -74.607  1.00 39.88      A  C
ATOM  22632  CD   GLU J 230       6.233 -30.279 -73.953  1.00 40.10      A  C
ATOM  22633  OE1  GLU J 230       5.426 -29.586 -74.626  1.00 38.76      A  O
ATOM  22634  N    TRP J 231       4.625 -31.858 -76.784  1.00 37.96      A  N
ATOM  22635  CA   TRP J 231       4.324 -31.650 -78.196  1.00 37.67      A  C
ATOM  22636  C    TRP J 231       5.124 -32.555 -79.110  1.00 38.03      A  C
ATOM  22637  O    TRP J 231       6.337 -32.693 -78.957  1.00 38.38      A  O
ATOM  22638  CB   TRP J 231       4.581 -30.203 -78.577  1.00 37.31      A  C
ATOM  22639  CG   TRP J 231       4.053 -29.873 -79.925  1.00 36.77      A  C
ATOM  22640  CD1  TRP J 231       4.681 -30.071 -81.124  1.00 36.73      A  C
ATOM  22641  CD2  TRP J 231       2.775 -29.288 -80.233  1.00 36.18      A  C
ATOM  22642  CE2  TRP J 231       2.703 -29.154 -81.641  1.00 35.93      A  C
ATOM  22643  CE3  TRP J 231       1.686 -28.859 -79.457  1.00 35.81      A  C
ATOM  22644  NE1  TRP J 231       3.876 -29.642 -82.159  1.00 36.40      A  N
ATOM  22645  CZ2  TRP J 231       1.586 -28.611 -82.287  1.00 35.25      A  C
ATOM  22646  CZ3  TRP J 231       0.578 -28.320 -80.105  1.00 35.07      A  C
ATOM  22647  CH2  TRP J 231       0.539 -28.204 -81.503  1.00 34.79      A  C
ATOM  22648  N    GLY J 232       4.427 -33.163 -80.063  1.00 38.18      A  N
ATOM  22649  CA   GLY J 232       5.026 -34.096 -81.006  1.00 38.52      A  C
ATOM  22650  C    GLY J 232       3.987 -34.580 -81.992  1.00 38.70      A  C
ATOM  22651  O    GLY J 232       2.792 -34.354 -81.805  1.00 38.44      A  O
ATOM  22652  N    PRO J 233       4.434 -35.246 -83.060  1.00 39.15      A  N
ATOM  22653  CA   PRO J 233       3.529 -35.777 -84.082  1.00 39.33      A  C
ATOM  22654  C    PRO J 233       2.418 -36.665 -83.517  1.00 39.53      A  C
ATOM  22655  O    PRO J 233       1.281 -36.608 -84.000  1.00 39.24      A  O
ATOM  22656  CB   PRO J 233       4.465 -36.593 -84.978  1.00 39.52      A  C
ATOM  22657  CG   PRO J 233       5.779 -35.878 -84.865  1.00 39.65      A  C
ATOM  22658  CD   PRO J 233       5.851 -35.429 -83.428  1.00 39.42      A  C
ATOM  22659  N    LYS J 234       2.744 -37.467 -82.505  1.00 40.09      A  N
ATOM  22660  CA   LYS J 234       1.756 -38.360 -81.902  1.00 40.68      A  C
ATOM  22661  C    LYS J 234       1.034 -37.767 -80.678  1.00 40.46      A  C
ATOM  22662  O    LYS J 234       0.073 -38.352 -80.179  1.00 40.60      A  O
ATOM  22663  CB   LYS J 234       2.369 -39.735 -81.594  1.00 41.29      A  C
ATOM  22664  CG   LYS J 234       2.374 -40.707 -82.804  1.00 42.35      A  C
ATOM  22665  CD   LYS J 234       3.484 -41.798 -82.722  1.00 43.55      A  C
ATOM  22666  CE   LYS J 234       3.049 -43.072 -81.984  1.00 43.74      A  C
ATOM  22667  N    ASP J 235       1.480 -36.598 -80.220  1.00 40.08      A  N
ATOM  22668  CA   ASP J 235       0.830 -35.892 -79.101  1.00 39.60      A  C
ATOM  22669  C    ASP J 235       0.556 -34.410 -79.428  1.00 39.07      A  C
ATOM  22670  O    ASP J 235       1.254 -33.506 -78.958  1.00 39.06      A  O
ATOM  22671  CB   ASP J 235       1.650 -36.053 -77.801  1.00 39.85      A  C
ATOM  22672  CG   ASP J 235       1.033 -35.320 -76.607  1.00 39.56      A  C
ATOM  22673  OD1  ASP J 235       1.802 -34.799 -75.768  1.00 39.27      A  O
ATOM  22674  OD2  ASP J 235      -0.212 -35.255 -76.508  1.00 39.20      A  O
ATOM  22675  N    SER J 236      -0.462 -34.182 -80.252  1.00 38.44      A  N
ATOM  22676  CA   SER J 236      -0.898 -32.840 -80.646  1.00 37.81      A  C
ATOM  22677  C    SER J 236      -1.893 -32.939 -81.796  1.00 37.52      A  C
ATOM  22678  O    SER J 236      -1.799 -33.845 -82.634  1.00 37.52      A  O
ATOM  22679  CB   SER J 236       0.281 -31.961 -81.079  1.00 37.66      A  C
ATOM  22680  OG   SER J 236       0.847 -32.433 -82.288  1.00 37.61      A  O
ATOM  22681  N    LEU J 237      -2.834 -31.995 -81.832  1.00 37.21      A  N
ATOM  22682  CA   LEU J 237      -3.789 -31.862 -82.938  1.00 37.09      A  C
ATOM  22683  C    LEU J 237      -4.640 -33.120 -83.101  1.00 37.27      A  C
ATOM  22684  O    LEU J 237      -4.742 -33.670 -84.207  1.00 37.37      A  O
ATOM  22685  CB   LEU J 237      -3.060 -31.554 -84.257  1.00 36.93      A  C
```

FIGURE 1 (cont'd)

```
ATOM  22686  CG   LEU J 237      -1.892 -30.562 -84.305  1.00 36.59      A  C
ATOM  22687  CD1  LEU J 237      -1.028 -30.831 -85.540  1.00 36.69      A  C
ATOM  22688  CD2  LEU J 237      -2.379 -29.121 -84.266  1.00 36.05      A  C
ATOM  22689  N    TYR J 238      -5.233 -33.579 -81.999  1.00 37.37      A  N
ATOM  22690  CA   TYR J 238      -6.126 -34.736 -82.039  1.00 37.48      A  C
ATOM  22691  C    TYR J 238      -7.428 -34.430 -82.780  1.00 37.15      A  C
ATOM  22692  O    TYR J 238      -7.918 -35.264 -83.537  1.00 37.25      A  O
ATOM  22693  CB   TYR J 238      -6.433 -35.257 -80.635  1.00 37.79      A  C
ATOM  22694  CG   TYR J 238      -5.222 -35.710 -79.863  1.00 38.38      A  C
ATOM  22695  CD1  TYR J 238      -4.608 -36.938 -80.137  1.00 39.33      A  C
ATOM  22696  CD2  TYR J 238      -4.690 -34.919 -78.851  1.00 38.49      A  C
ATOM  22697  CE1  TYR J 238      -3.485 -37.361 -79.422  1.00 39.70      A  C
ATOM  22698  CE2  TYR J 238      -3.568 -35.333 -78.131  1.00 38.98      A  C
ATOM  22699  CZ   TYR J 238      -2.971 -36.552 -78.422  1.00 39.37      A  C
ATOM  22700  OH   TYR J 238      -1.864 -36.959 -77.712  1.00 39.62      A  O
ATOM  22701  N    GLY J 239      -7.974 -33.235 -82.564  1.00 36.71      A  N
ATOM  22702  CA   GLY J 239      -9.236 -32.853 -83.172  1.00 36.43      A  C
ATOM  22703  C    GLY J 239      -9.116 -32.651 -84.665  1.00 36.25      A  C
ATOM  22704  O    GLY J 239      -9.941 -33.143 -85.440  1.00 36.35      A  O
ATOM  22705  N    SER J 240      -8.078 -31.927 -85.066  1.00 36.00      A  N
ATOM  22706  CA   SER J 240      -7.859 -31.593 -86.473  1.00 35.73      A  C
ATOM  22707  C    SER J 240      -7.430 -32.800 -87.294  1.00 35.71      A  C
ATOM  22708  O    SER J 240      -7.953 -33.011 -88.381  1.00 35.81      A  O
ATOM  22709  CB   SER J 240      -6.850 -30.448 -86.612  1.00 35.60      A  C
ATOM  22710  OG   SER J 240      -5.825 -30.542 -85.633  1.00 35.93      A  O
ATOM  22711  N    ARG J 241      -6.492 -33.589 -86.770  1.00 35.70      A  N
ATOM  22712  CA   ARG J 241      -6.047 -34.806 -87.441  1.00 35.93      A  C
ATOM  22713  C    ARG J 241      -7.187 -35.790 -87.699  1.00 36.00      A  C
ATOM  22714  O    ARG J 241      -7.208 -36.485 -88.719  1.00 36.19      A  O
ATOM  22715  CB   ARG J 241      -4.928 -35.479 -86.654  1.00 36.02      A  C
ATOM  22716  CG   ARG J 241      -3.552 -34.998 -87.050  1.00 36.66      A  C
ATOM  22717  CD   ARG J 241      -2.448 -35.950 -86.602  1.00 37.99      A  C
ATOM  22718  NE   ARG J 241      -2.152 -35.828 -85.171  1.00 39.22      A  N
ATOM  22719  CZ   ARG J 241      -2.501 -36.717 -84.240  1.00 40.16      A  C
ATOM  22720  NH1  ARG J 241      -3.163 -37.815 -84.569  1.00 41.13      A  N
ATOM  22721  NH2  ARG J 241      -2.182 -36.516 -82.971  1.00 40.46      A  N
ATOM  22722  N    HIS J 242      -8.135 -35.836 -86.772  1.00 35.97      A  N
ATOM  22723  CA   HIS J 242      -9.293 -36.700 -86.908  1.00 36.05      A  C
ATOM  22724  C    HIS J 242     -10.346 -36.140 -87.861  1.00 35.71      A  C
ATOM  22725  O    HIS J 242     -10.829 -36.864 -88.730  1.00 35.94      A  O
ATOM  22726  CB   HIS J 242      -9.923 -36.979 -85.556  1.00 36.32      A  C
ATOM  22727  CG   HIS J 242     -11.100 -37.893 -85.630  1.00 37.13      A  C
ATOM  22728  CD2  HIS J 242     -11.177 -39.244 -85.661  1.00 37.90      A  C
ATOM  22729  ND1  HIS J 242     -12.395 -37.429 -85.707  1.00 37.31      A  N
ATOM  22730  CE1  HIS J 242     -13.221 -38.458 -85.767  1.00 37.98      A  C
ATOM  22731  NE2  HIS J 242     -12.507 -39.570 -85.741  1.00 38.39      A  N
ATOM  22732  N    LEU J 243     -10.711 -34.870 -87.693  1.00 35.08      A  N
ATOM  22733  CA   LEU J 243     -11.663 -34.239 -88.591  1.00 34.60      A  C
ATOM  22734  C    LEU J 243     -11.192 -34.313 -90.033  1.00 34.70      A  C
ATOM  22735  O    LEU J 243     -11.966 -34.660 -90.912  1.00 34.92      A  O
ATOM  22736  CB   LEU J 243     -11.934 -32.793 -88.195  1.00 34.18      A  C
ATOM  22737  CG   LEU J 243     -13.014 -32.071 -89.008  1.00 33.47      A  C
ATOM  22738  CD1  LEU J 243     -14.361 -32.744 -88.868  1.00 33.25      A  C
ATOM  22739  CD2  LEU J 243     -13.112 -30.635 -88.575  1.00 32.86      A  C
ATOM  22740  N    ALA J 244      -9.921 -34.001 -90.267  1.00 34.75      A  N
ATOM  22741  CA   ALA J 244      -9.319 -34.128 -91.595  1.00 35.02      A  C
ATOM  22742  C    ALA J 244      -9.505 -35.531 -92.164  1.00 35.49      A  C
ATOM  22743  O    ALA J 244      -9.961 -35.679 -93.287  1.00 35.66      A  O
ATOM  22744  CB   ALA J 244      -7.848 -33.755 -91.562  1.00 34.77      A  C
ATOM  22745  N    GLN J 245      -9.169 -36.557 -91.384  1.00 36.03      A  N
ATOM  22746  CA   GLN J 245      -9.384 -37.952 -91.794  1.00 36.63      A  C
ATOM  22747  C    GLN J 245     -10.854 -38.230 -92.146  1.00 36.98      A  C
ATOM  22748  O    GLN J 245     -11.139 -38.851 -93.177  1.00 37.25      A  O
ATOM  22749  CB   GLN J 245      -8.900 -38.930 -90.710  1.00 36.69      A  C
ATOM  22750  N    LEU J 246     -11.771 -37.753 -91.295  1.00 37.09      A  N
```

FIGURE 1 (cont'd)

```
ATOM  22751  CA   LEU J 246     -13.208 -38.016 -91.429  1.00 37.34      A  C
ATOM  22752  C    LEU J 246     -13.849 -37.245 -92.578  1.00 37.75      A  C
ATOM  22753  O    LEU J 246     -14.828 -37.711 -93.167  1.00 38.05      A  O
ATOM  22754  CB   LEU J 246     -13.937 -37.724 -90.113  1.00 37.08      A  C
ATOM  22755  CG   LEU J 246     -15.432 -38.045 -89.959  1.00 36.48      A  C
ATOM  22756  CD1  LEU J 246     -16.225 -36.756 -89.826  1.00 35.21      A  C
ATOM  22757  N    MET J 247     -13.304 -36.074 -92.894  1.00 38.04      A  N
ATOM  22758  CA   MET J 247     -13.777 -35.296 -94.046  1.00 38.46      A  C
ATOM  22759  C    MET J 247     -13.321 -35.899 -95.371  1.00 39.26      A  C
ATOM  22760  O    MET J 247     -14.008 -35.773 -96.382  1.00 39.45      A  O
ATOM  22761  CB   MET J 247     -13.340 -33.834 -93.960  1.00 37.95      A  C
ATOM  22762  CG   MET J 247     -14.063 -33.047 -92.889  1.00 37.34      A  C
ATOM  22763  SD   MET J 247     -13.763 -31.267 -92.961  1.00 36.55      A  S
ATOM  22764  CE   MET J 247     -15.055 -30.731 -94.073  1.00 36.93      A  C
ATOM  22765  N    GLU J 248     -12.162 -36.550 -95.360  1.00 40.14      A  N
ATOM  22766  CA   GLU J 248     -11.649 -37.180 -96.552  1.00 41.15      A  C
ATOM  22767  C    GLU J 248     -12.481 -38.402 -96.894  1.00 42.21      A  C
ATOM  22768  O    GLU J 248     -12.605 -38.759 -98.066  1.00 42.79      A  O
ATOM  22769  CB   GLU J 248     -10.187 -37.565 -96.385  1.00 40.99      A  C
ATOM  22770  CG   GLU J 248      -9.453 -37.519 -97.698  1.00 40.60      A  C
ATOM  22771  CD   GLU J 248      -7.957 -37.622 -97.546  1.00 40.92      A  C
ATOM  22772  OE1  GLU J 248      -7.254 -37.639 -98.582  1.00 41.59      A  O
ATOM  22773  OE2  GLU J 248      -7.476 -37.689 -96.397  1.00 40.88      A  O
ATOM  22774  N    SER J 249     -13.059 -39.039 -95.880  1.00 43.03      A  N
ATOM  22775  CA   SER J 249     -13.838 -40.253 -96.101  1.00 43.99      A  C
ATOM  22776  C    SER J 249     -15.301 -39.943 -96.391  1.00 44.48      A  C
ATOM  22777  O    SER J 249     -16.090 -40.844 -96.678  1.00 44.93      A  O
ATOM  22778  CB   SER J 249     -13.713 -41.210 -94.909  1.00 44.14      A  C
ATOM  22779  OG   SER J 249     -14.400 -40.720 -93.768  1.00 44.14      A  O
ATOM  22780  N    ILE J 250     -15.656 -38.666 -96.325  1.00 44.76      A  N
ATOM  22781  CA   ILE J 250     -17.041 -38.252 -96.480  1.00 45.29      A  C
ATOM  22782  C    ILE J 250     -17.265 -37.629 -97.862  1.00 46.12      A  C
ATOM  22783  O    ILE J 250     -16.839 -36.502 -98.095  1.00 45.90      A  O
ATOM  22784  CB   ILE J 250     -17.443 -37.273 -95.348  1.00 44.84      A  C
ATOM  22785  CG1  ILE J 250     -18.951 -37.290 -95.113  1.00 44.80      A  C
ATOM  22786  CD1  ILE J 250     -19.674 -36.082 -95.674  1.00 44.42      A  C
ATOM  22787  N    PRO J 251     -17.930 -38.367 -98.782  1.00 47.23      A  N
ATOM  22788  CA   PRO J 251     -18.173 -37.912-100.154  1.00 47.89      A  C
ATOM  22789  C    PRO J 251     -19.066 -36.701-100.222  1.00 48.30      A  C
ATOM  22790  O    PRO J 251     -19.930 -36.507 -99.374  1.00 48.35      A  O
ATOM  22791  CB   PRO J 251     -18.900 -39.095-100.797  1.00 48.24      A  C
ATOM  22792  CG   PRO J 251     -18.530 -40.259 -99.967  1.00 48.26      A  C
ATOM  22793  CD   PRO J 251     -18.466 -39.723 -98.577  1.00 47.59      A  C
ATOM  22794  N    HIS J 252     -18.858 -35.917-101.266  1.00 48.74      A  N
ATOM  22795  CA   HIS J 252     -19.492 -34.624-101.458  1.00 49.12      A  C
ATOM  22796  C    HIS J 252     -19.008 -34.267-102.842  1.00 49.72      A  C
ATOM  22797  O    HIS J 252     -18.143 -34.952-103.333  1.00 49.96      A  O
ATOM  22798  CB   HIS J 252     -18.863 -33.629-100.478  1.00 47.97      A  C
ATOM  22799  CG   HIS J 252     -19.456 -32.256-100.531  1.00 47.78      A  C
ATOM  22800  CD2  HIS J 252     -19.015 -31.109-101.103  1.00 47.59      A  C
ATOM  22801  ND1  HIS J 252     -20.655 -31.949 -99.925  1.00 48.09      A  N
ATOM  22802  CE1  HIS J 252     -20.932 -30.672-100.127  1.00 48.06      A  C
ATOM  22803  NE2  HIS J 252     -19.954 -30.141-100.842  1.00 47.83      A  N
ATOM  22804  N    SER J 253     -19.553 -33.323-103.590  1.00 50.14      A  N
ATOM  22805  CA   SER J 253     -20.872 -33.234-104.062  1.00 50.15      A  C
ATOM  22806  C    SER J 253     -20.900 -32.519-105.407  1.00 50.27      A  C
ATOM  22807  O    SER J 253     -21.972 -32.300-105.884  1.00 50.72      A  O
ATOM  22808  CB   SER J 253     -21.731 -32.426-103.108  1.00 49.30      A  C
ATOM  22809  OG   SER J 253     -22.407 -31.359-103.722  1.00 48.85      A  O
ATOM  22810  N    PRO J 254     -19.809 -32.214-106.121  1.00 49.86      A  N
ATOM  22811  CA   PRO J 254     -18.442 -32.311-106.614  1.00 49.45      A  C
ATOM  22812  C    PRO J 254     -17.420 -31.535-105.854  1.00 49.07      A  C
ATOM  22813  O    PRO J 254     -16.952 -30.605-106.436  1.00 49.22      A  O
ATOM  22814  CB   PRO J 254     -18.542 -31.503-107.930  1.00 48.69      A  C
ATOM  22815  CG   PRO J 254     -19.885 -30.800-107.936  1.00 48.83      A  C
```

FIGURE 1 (cont'd)

```
ATOM  22816  CD   PRO J 254     -20.441 -30.966-106.601  1.00 49.10      A  C
ATOM  22817  N    GLY J 255     -16.865 -31.865-104.704  1.00 48.46      A  N
ATOM  22818  CA   GLY J 255     -16.128 -32.988-104.309  1.00 47.58      A  C
ATOM  22819  C    GLY J 255     -14.996 -33.478-105.163  1.00 47.10      A  C
ATOM  22820  O    GLY J 255     -14.470 -32.800-106.045  1.00 47.36      A  O
ATOM  22821  N    PRO J 256     -14.830 -34.785-105.030  1.00 46.61      A  N
ATOM  22822  CA   PRO J 256     -14.728 -36.120-104.451  1.00 46.37      A  C
ATOM  22823  C    PRO J 256     -15.187 -36.138-102.994  1.00 45.78      A  C
ATOM  22824  O    PRO J 256     -16.294 -36.618-102.701  1.00 45.96      A  O
ATOM  22825  CB   PRO J 256     -13.256 -36.517-104.601  1.00 46.53      A  C
ATOM  22826  CG   PRO J 256     -12.712 -35.757-105.697  1.00 46.54      A  C
ATOM  22827  N    THR J 257     -14.341 -35.616-102.104  1.00 44.76      A  N
ATOM  22828  CA   THR J 257     -14.581 -35.654-100.666  1.00 43.65      A  C
ATOM  22829  C    THR J 257     -14.897 -34.268-100.113  1.00 42.91      A  C
ATOM  22830  O    THR J 257     -14.792 -33.277-100.818  1.00 42.78      A  O
ATOM  22831  CB   THR J 257     -13.374 -36.237 -99.923  1.00 43.46      A  C
ATOM  22832  OG1  THR J 257     -12.200 -35.506-100.283  1.00 43.06      A  O
ATOM  22833  N    ARG J 258     -15.293 -34.210 -98.845  1.00 42.07      A  N
ATOM  22834  CA   ARG J 258     -15.627 -32.944 -98.201  1.00 41.06      A  C
ATOM  22835  C    ARG J 258     -14.399 -32.070 -97.996  1.00 40.56      A  C
ATOM  22836  O    ARG J 258     -14.525 -30.878 -97.725  1.00 40.53      A  O
ATOM  22837  CB   ARG J 258     -16.372 -33.158 -96.874  1.00 40.15      A  C
ATOM  22838  CG   ARG J 258     -17.901 -33.152 -97.021  1.00 40.09      A  C
ATOM  22839  CD   ARG J 258     -18.606 -32.667 -95.765  1.00 40.04      A  C
ATOM  22840  NE   ARG J 258     -20.046 -32.549 -95.966  1.00 40.27      A  N
ATOM  22841  N    ILE J 259     -13.215 -32.659 -98.133  1.00 39.86      A  N
ATOM  22842  CA   ILE J 259     -11.974 -31.904 -98.023  1.00 38.91      A  C
ATOM  22843  C    ILE J 259     -11.820 -30.890 -99.148  1.00 38.85      A  C
ATOM  22844  O    ILE J 259     -11.314 -29.783 -98.935  1.00 38.82      A  O
ATOM  22845  CB   ILE J 259     -10.773 -32.815 -98.005  1.00 37.99      A  C
ATOM  22846  CG1  ILE J 259     -10.178 -32.788 -96.614  1.00 37.64      A  C
ATOM  22847  CD1  ILE J 259      -9.635 -34.089 -96.213  1.00 38.55      A  C
ATOM  22848  N    GLN J 260     -12.280 -31.263-100.339  1.00 38.53      A  N
ATOM  22849  CA   GLN J 260     -12.222 -30.374-101.497  1.00 37.92      A  C
ATOM  22850  C    GLN J 260     -13.320 -29.301-101.418  1.00 37.79      A  C
ATOM  22851  O    GLN J 260     -13.405 -28.423-102.273  1.00 38.22      A  O
ATOM  22852  CB   GLN J 260     -12.326 -31.148-102.816  1.00 37.07      A  C
ATOM  22853  CG   GLN J 260     -12.274 -32.675-102.720  1.00 36.70      A  C
ATOM  22854  CD   GLN J 260     -11.046 -33.218-102.024  1.00 36.30      A  C
ATOM  22855  OE1  GLN J 260      -9.924 -32.872-102.343  1.00 36.68      A  O
ATOM  22856  N    ALA J 261     -14.157 -29.373-100.388  1.00 37.18      A  N
ATOM  22857  CA   ALA J 261     -15.206 -28.380-100.194  1.00 36.50      A  C
ATOM  22858  C    ALA J 261     -14.669 -27.118 -99.515  1.00 35.73      A  C
ATOM  22859  O    ALA J 261     -15.277 -26.057 -99.603  1.00 35.68      A  O
ATOM  22860  N    ILE J 262     -13.534 -27.237 -98.835  1.00 34.72      A  N
ATOM  22861  CA   ILE J 262     -12.921 -26.091 -98.180  1.00 33.66      A  C
ATOM  22862  C    ILE J 262     -12.217 -25.281 -99.240  1.00 33.58      A  C
ATOM  22863  O    ILE J 262     -11.170 -25.695 -99.738  1.00 33.81      A  O
ATOM  22864  CB   ILE J 262     -11.883 -26.512 -97.120  1.00 32.74      A  C
ATOM  22865  CG1  ILE J 262     -12.475 -27.548 -96.159  1.00 32.13      A  C
ATOM  22866  CD1  ILE J 262     -11.434 -28.368 -95.444  1.00 31.74      A  C
ATOM  22867  N    GLU J 263     -12.799 -24.142 -99.605  1.00 33.23      A  N
ATOM  22868  CA   GLU J 263     -12.185 -23.243-100.593  1.00 32.83      A  C
ATOM  22869  C    GLU J 263     -10.983 -22.560 -99.954  1.00 32.21      A  C
ATOM  22870  O    GLU J 263      -9.957 -22.351-100.609  1.00 32.31      A  O
ATOM  22871  CB   GLU J 263     -13.200 -22.208-101.115  1.00 33.02      A  C
ATOM  22872  CG   GLU J 263     -12.801 -21.495-102.409  1.00 33.05      A  C
ATOM  22873  CD   GLU J 263     -13.930 -20.661-102.998  1.00 32.62      A  C
ATOM  22874  N    LEU J 264     -11.123 -22.245 -98.665  1.00 31.36      A  N
ATOM  22875  CA   LEU J 264     -10.066 -21.624 -97.876  1.00 30.36      A  C
ATOM  22876  C    LEU J 264     -10.192 -21.964 -96.389  1.00 29.77      A  C
ATOM  22877  O    LEU J 264     -11.227 -21.695 -95.766  1.00 29.82      A  O
ATOM  22878  CB   LEU J 264     -10.082 -20.107 -98.062  1.00 30.25      A  C
ATOM  22879  CG   LEU J 264      -9.002 -19.332 -97.310  1.00 29.87      A  C
ATOM  22880  CD1  LEU J 264      -7.574 -19.767 -97.699  1.00 29.74      A  C
```

FIGURE 1 (cont'd)

```
ATOM  22881  CD2 LEU J 264      -9.200 -17.836 -97.527  1.00 29.66      A  C
ATOM  22882  N   PHE J 265      -9.126 -22.550 -95.840  1.00 28.94      A  N
ATOM  22883  CA  PHE J 265      -8.995 -22.855 -94.406  1.00 27.94      A  C
ATOM  22884  C   PHE J 265      -8.232 -21.692 -93.740  1.00 27.64      A  C
ATOM  22885  O   PHE J 265      -6.991 -21.629 -93.784  1.00 27.49      A  O
ATOM  22886  CB  PHE J 265      -8.249 -24.199 -94.213  1.00 27.66      A  C
ATOM  22887  CG  PHE J 265      -8.332 -24.781 -92.806  1.00 26.32      A  C
ATOM  22888  CD1 PHE J 265      -9.295 -25.716 -92.486  1.00 25.38      A  C
ATOM  22889  CD2 PHE J 265      -7.424 -24.421 -91.820  1.00 25.21      A  C
ATOM  22890  N   MET J 266      -8.984 -20.771 -93.140  1.00 27.34      A  N
ATOM  22891  CA  MET J 266      -8.405 -19.623 -92.431  1.00 27.17      A  C
ATOM  22892  C   MET J 266      -8.369 -19.853 -90.901  1.00 27.13      A  C
ATOM  22893  O   MET J 266      -9.366 -19.632 -90.201  1.00 27.22      A  O
ATOM  22894  CB  MET J 266      -9.178 -18.345 -92.787  1.00 27.11      A  C
ATOM  22895  CG  MET J 266      -8.658 -17.067 -92.139  1.00 26.82      A  C
ATOM  22896  N   LEU J 267      -7.220 -20.296 -90.390  1.00 27.02      A  N
ATOM  22897  CA  LEU J 267      -7.096 -20.697 -88.985  1.00 26.91      A  C
ATOM  22898  C   LEU J 267      -6.718 -19.510 -88.122  1.00 27.01      A  C
ATOM  22899  O   LEU J 267      -5.715 -18.837 -88.384  1.00 27.08      A  O
ATOM  22900  CB  LEU J 267      -6.053 -21.795 -88.826  1.00 26.84      A  C
ATOM  22901  CG  LEU J 267      -5.669 -22.247 -87.422  1.00 26.53      A  C
ATOM  22902  CD1 LEU J 267      -6.887 -22.775 -86.716  1.00 26.53      A  C
ATOM  22903  CD2 LEU J 267      -4.581 -23.311 -87.478  1.00 26.44      A  C
ATOM  22904  N   LEU J 268      -7.518 -19.278 -87.084  1.00 27.09      A  N
ATOM  22905  CA  LEU J 268      -7.316 -18.155 -86.150  1.00 27.26      A  C
ATOM  22906  C   LEU J 268      -6.684 -18.618 -84.839  1.00 27.47      A  C
ATOM  22907  O   LEU J 268      -7.219 -19.494 -84.159  1.00 27.61      A  O
ATOM  22908  CB  LEU J 268      -8.650 -17.478 -85.844  1.00 27.17      A  C
ATOM  22909  CG  LEU J 268      -9.155 -16.368 -86.751  1.00 27.23      A  C
ATOM  22910  CD1 LEU J 268      -9.653 -16.912 -88.093  1.00 27.50      A  C
ATOM  22911  CD2 LEU J 268     -10.254 -15.630 -86.015  1.00 27.07      A  C
ATOM  22912  N   ASP J 269      -5.554 -18.027 -84.474  1.00 27.66      A  N
ATOM  22913  CA  ASP J 269      -4.845 -18.480 -83.290  1.00 27.98      A  C
ATOM  22914  C   ASP J 269      -4.022 -17.399 -82.636  1.00 27.95      A  C
ATOM  22915  O   ASP J 269      -3.507 -16.503 -83.313  1.00 28.14      A  O
ATOM  22916  CB  ASP J 269      -3.922 -19.642 -83.638  1.00 28.23      A  C
ATOM  22917  CG  ASP J 269      -3.878 -20.682 -82.545  1.00 29.38      A  C
ATOM  22918  OD1 ASP J 269      -4.957 -21.244 -82.218  1.00 30.29      A  O
ATOM  22919  OD2 ASP J 269      -2.768 -20.942 -82.020  1.00 30.12      A  O
ATOM  22920  N   LEU J 270      -3.885 -17.504 -81.315  1.00 27.86      A  N
ATOM  22921  CA  LEU J 270      -3.070 -16.576 -80.509  1.00 27.84      A  C
ATOM  22922  C   LEU J 270      -3.406 -15.113 -80.777  1.00 27.93      A  C
ATOM  22923  O   LEU J 270      -2.516 -14.266 -80.890  1.00 27.97      A  O
ATOM  22924  CB  LEU J 270      -1.573 -16.840 -80.701  1.00 27.73      A  C
ATOM  22925  CG  LEU J 270      -1.069 -18.279 -80.553  1.00 27.75      A  C
ATOM  22926  CD1 LEU J 270       0.447 -18.280 -80.423  1.00 27.66      A  C
ATOM  22927  CD2 LEU J 270      -1.705 -19.005 -79.368  1.00 28.00      A  C
ATOM  22928  N   LEU J 271      -4.703 -14.834 -80.893  1.00 28.04      A  N
ATOM  22929  CA  LEU J 271      -5.184 -13.476 -81.103  1.00 28.33      A  C
ATOM  22930  C   LEU J 271      -5.767 -12.940 -79.800  1.00 28.75      A  C
ATOM  22931  O   LEU J 271      -6.454 -13.670 -79.071  1.00 28.78      A  O
ATOM  22932  CB  LEU J 271      -6.249 -13.446 -82.196  1.00 28.11      A  C
ATOM  22933  CG  LEU J 271      -5.829 -13.878 -83.593  1.00 27.70      A  C
ATOM  22934  CD1 LEU J 271      -6.855 -14.864 -84.071  1.00 27.63      A  C
ATOM  22935  N   GLY J 272      -5.490 -11.671 -79.506  1.00 29.26      A  N
ATOM  22936  CA  GLY J 272      -6.039 -11.029 -78.307  1.00 29.93      A  C
ATOM  22937  C   GLY J 272      -5.056 -10.134 -77.557  1.00 30.51      A  C
ATOM  22938  O   GLY J 272      -5.466  -9.151 -76.908  1.00 30.70      A  O
ATOM  22939  N   ALA J 273      -3.762 -10.471 -77.639  1.00 30.87      A  N
ATOM  22940  CA  ALA J 273      -2.706  -9.682 -77.002  1.00 31.24      A  C
ATOM  22941  C   ALA J 273      -2.545  -8.320 -77.707  1.00 31.60      A  C
ATOM  22942  O   ALA J 273      -3.007  -8.132 -78.839  1.00 31.62      A  O
ATOM  22943  CB  ALA J 273      -1.389 -10.455 -76.995  1.00 31.16      A  C
ATOM  22944  N   PRO J 274      -1.912  -7.348 -77.032  1.00 32.04      A  N
ATOM  22945  CA  PRO J 274      -1.602  -6.074 -77.695  1.00 32.28      A  C
```

FIGURE 1 (cont'd)

```
ATOM  22946  C    PRO  J 274    -0.500   -6.259  -78.732  1.00 32.41      A    C
ATOM  22947  O    PRO  J 274     0.331   -7.191  -78.606  1.00 32.31      A    O
ATOM  22948  CB   PRO  J 274    -1.088   -5.199  -76.546  1.00 32.53      A    C
ATOM  22949  CG   PRO  J 274    -0.599   -6.186  -75.517  1.00 32.48      A    C
ATOM  22950  CD   PRO  J 274    -1.542   -7.333  -75.602  1.00 32.22      A    C
ATOM  22951  N    ASN  J 275    -0.503   -5.383  -79.740  1.00 32.63      A    N
ATOM  22952  CA   ASN  J 275     0.558   -5.351  -80.779  1.00 33.00      A    C
ATOM  22953  C    ASN  J 275     0.948   -6.707  -81.407  1.00 32.60      A    C
ATOM  22954  O    ASN  J 275     2.144   -7.092  -81.402  1.00 32.78      A    O
ATOM  22955  CB   ASN  J 275     1.815   -4.628  -80.263  1.00 33.46      A    C
ATOM  22956  CG   ASN  J 275     1.499   -3.253  -79.732  1.00 34.82      A    C
ATOM  22957  ND2  ASN  J 275     1.482   -3.134  -78.408  1.00 35.89      A    N
ATOM  22958  OD1  ASN  J 275     1.249   -2.306  -80.498  1.00 35.85      A    O
ATOM  22959  N    PRO  J 276    -0.055   -7.433  -81.951  1.00 32.13      A    N
ATOM  22960  CA   PRO  J 276     0.300   -8.632  -82.697  1.00 31.87      A    C
ATOM  22961  C    PRO  J 276     0.849   -8.265  -84.084  1.00 31.87      A    C
ATOM  22962  O    PRO  J 276     0.441   -7.253  -84.685  1.00 31.92      A    O
ATOM  22963  CB   PRO  J 276    -1.041   -9.358  -82.840  1.00 31.67      A    C
ATOM  22964  CG   PRO  J 276    -2.062   -8.249  -82.884  1.00 31.64      A    C
ATOM  22965  CD   PRO  J 276    -1.513   -7.165  -81.982  1.00 31.93      A    C
ATOM  22966  N    THR  J 277     1.774   -9.082  -84.574  1.00 31.91      A    N
ATOM  22967  CA   THR  J 277     2.248   -8.944  -85.944  1.00 31.96      A    C
ATOM  22968  C    THR  J 277     1.982  -10.219  -86.759  1.00 31.87      A    C
ATOM  22969  O    THR  J 277     2.339  -11.335  -86.353  1.00 31.81      A    O
ATOM  22970  CB   THR  J 277     3.736   -8.536  -85.994  1.00 32.03      A    C
ATOM  22971  CG2  THR  J 277     3.882   -7.047  -85.720  1.00 32.14      A    C
ATOM  22972  OG1  THR  J 277     4.472   -9.281  -85.013  1.00 32.24      A    O
ATOM  22973  N    PHE  J 278     1.342  -10.037  -87.907  1.00 31.84      A    N
ATOM  22974  CA   PHE  J 278     0.979  -11.149  -88.775  1.00 31.87      A    C
ATOM  22975  C    PHE  J 278     1.736  -11.118  -90.106  1.00 32.20      A    C
ATOM  22976  O    PHE  J 278     1.992  -10.037  -90.669  1.00 32.29      A    O
ATOM  22977  CB   PHE  J 278    -0.533  -11.135  -89.039  1.00 31.62      A    C
ATOM  22978  CG   PHE  J 278    -1.365  -11.142  -87.795  1.00 31.35      A    C
ATOM  22979  CD1  PHE  J 278    -1.431  -12.283  -86.991  1.00 31.28      A    C
ATOM  22980  CD2  PHE  J 278    -2.095  -10.016  -87.432  1.00 31.21      A    C
ATOM  22981  CE1  PHE  J 278    -2.208  -12.299  -85.832  1.00 31.24      A    C
ATOM  22982  CE2  PHE  J 278    -2.877  -10.016  -86.282  1.00 31.05      A    C
ATOM  22983  CZ   PHE  J 278    -2.931  -11.161  -85.477  1.00 31.08      A    C
ATOM  22984  N    TYR  J 279     2.077  -12.312  -90.599  1.00 32.57      A    N
ATOM  22985  CA   TYR  J 279     2.722  -12.487  -91.903  1.00 33.11      A    C
ATOM  22986  C    TYR  J 279     2.011  -13.565  -92.708  1.00 33.71      A    C
ATOM  22987  O    TYR  J 279     1.197  -14.326  -92.169  1.00 33.63      A    O
ATOM  22988  CB   TYR  J 279     4.203  -12.814  -91.727  1.00 32.97      A    C
ATOM  22989  CG   TYR  J 279     4.890  -11.755  -90.925  1.00 32.63      A    C
ATOM  22990  CD1  TYR  J 279     5.477  -10.657  -91.548  1.00 32.57      A    C
ATOM  22991  CD2  TYR  J 279     4.885  -11.809  -89.534  1.00 36.72      A    C
ATOM  22992  CE1  TYR  J 279     6.087   -9.665  -90.813  1.00 38.18      A    C
ATOM  22993  CE2  TYR  J 279     5.484  -10.819  -88.788  1.00 40.12      A    C
ATOM  22994  CZ   TYR  J 279     6.083   -9.751  -89.435  1.00 40.77      A    C
ATOM  22995  OH   TYR  J 279     6.688   -8.769  -88.702  1.00 42.89      A    O
ATOM  22996  N    SER  J 280     2.290  -13.608  -94.009  1.00 34.67      A    N
ATOM  22997  CA   SER  J 280     1.712  -14.649  -94.860  1.00 35.48      A    C
ATOM  22998  C    SER  J 280     2.641  -15.853  -94.897  1.00 35.98      A    C
ATOM  22999  O    SER  J 280     3.706  -15.843  -95.516  1.00 36.27      A    O
ATOM  23000  CB   SER  J 280     1.424  -14.133  -96.275  1.00 35.60      A    C
ATOM  23001  OG   SER  J 280     0.725  -15.107  -97.036  1.00 35.76      A    O
ATOM  23002  N    HIS  J 281     2.232  -16.919  -94.218  1.00 36.41      A    N
ATOM  23003  CA   HIS  J 281     3.046  -18.125  -94.147  1.00 37.14      A    C
ATOM  23004  C    HIS  J 281     2.734  -19.107  -95.283  1.00 37.49      A    C
ATOM  23005  O    HIS  J 281     3.376  -20.157  -95.394  1.00 37.68      A    O
ATOM  23006  CB   HIS  J 281     2.906  -18.790  -92.780  1.00 37.21      A    C
ATOM  23007  CG   HIS  J 281     3.200  -17.870  -91.631  1.00 37.84      A    C
ATOM  23008  CD2  HIS  J 281     4.369  -17.538  -91.034  1.00 38.69      A    C
ATOM  23009  ND1  HIS  J 281     2.216  -17.162  -90.966  1.00 37.83      A    N
ATOM  23010  CE1  HIS  J 281     2.769  -16.438  -90.008  1.00 38.22      A    C
```

FIGURE 1 (cont'd)

```
ATOM  23011  NE2  HIS J 281      4.073 -16.648 -90.027  1.00 38.93      A  N
ATOM  23012  N    PHE J 282      1.759 -18.757 -96.127  1.00 37.84      A  N
ATOM  23013  CA   PHE J 282      1.501 -19.501 -97.364  1.00 38.19      A  C
ATOM  23014  C    PHE J 282      1.329 -18.574 -98.562  1.00 38.54      A  C
ATOM  23015  O    PHE J 282      0.331 -17.832 -98.645  1.00 38.48      A  O
ATOM  23016  CB   PHE J 282      0.300 -20.444 -97.214  1.00 38.08      A  C
ATOM  23017  CG   PHE J 282      0.470 -21.446 -96.118  1.00 38.03      A  C
ATOM  23018  CD1  PHE J 282      1.380 -22.498 -96.249  1.00 38.47      A  C
ATOM  23019  CD2  PHE J 282     -0.245 -21.319 -94.936  1.00 37.89      A  C
ATOM  23020  CE1  PHE J 282      1.563 -23.415 -95.222  1.00 38.42      A  C
ATOM  23021  CE2  PHE J 282     -0.069 -22.241 -93.900  1.00 37.99      A  C
ATOM  23022  CZ   PHE J 282      0.838 -23.286 -94.045  1.00 38.22      A  C
ATOM  23023  N    PRO J 283      2.302 -18.618 -99.499  1.00 38.92      A  N
ATOM  23024  CA   PRO J 283      2.230 -17.832-100.734  1.00 39.05      A  C
ATOM  23025  C    PRO J 283      1.009 -18.218-101.580  1.00 38.92      A  C
ATOM  23026  O    PRO J 283      0.528 -17.408-102.367  1.00 39.03      A  O
ATOM  23027  CB   PRO J 283      3.534 -18.194-101.465  1.00 39.29      A  C
ATOM  23028  CG   PRO J 283      4.433 -18.761-100.414  1.00 39.32      A  C
ATOM  23029  CD   PRO J 283      3.517 -19.456 -99.456  1.00 39.05      A  C
ATOM  23030  N    ARG J 284      0.511 -19.439-101.404  1.00 38.67      A  N
ATOM  23031  CA   ARG J 284     -0.687 -19.892-102.098  1.00 38.54      A  C
ATOM  23032  C    ARG J 284     -1.828 -18.907-101.885  1.00 38.73      A  C
ATOM  23033  O    ARG J 284     -2.552 -18.565-102.831  1.00 38.99      A  O
ATOM  23034  CB   ARG J 284     -1.100 -21.290-101.616  1.00 38.27      A  C
ATOM  23035  CG   ARG J 284     -1.714 -22.201-102.693  1.00 37.49      A  C
ATOM  23036  CD   ARG J 284     -3.105 -21.750-103.161  1.00 35.80      A  C
ATOM  23037  NE   ARG J 284     -3.843 -22.829-103.816  1.00 34.92      A  N
ATOM  23038  N    THR J 285     -1.974 -18.441-100.644  1.00 38.79      A  N
ATOM  23039  CA   THR J 285     -3.085 -17.552-100.279  1.00 38.94      A  C
ATOM  23040  C    THR J 285     -2.647 -16.111-100.063  1.00 39.30      A  C
ATOM  23041  O    THR J 285     -3.412 -15.315 -99.508  1.00 39.18      A  O
ATOM  23042  CB   THR J 285     -3.824 -18.055 -99.008  1.00 38.55      A  C
ATOM  23043  OG1  THR J 285     -2.859 -18.411 -98.008  1.00 38.16      A  O
ATOM  23044  N    VAL J 286     -1.432 -15.785-100.521  1.00 39.90      A  N
ATOM  23045  CA   VAL J 286     -0.795 -14.487-100.257  1.00 40.39      A  C
ATOM  23046  C    VAL J 286     -1.683 -13.285-100.572  1.00 41.04      A  C
ATOM  23047  O    VAL J 286     -1.564 -12.239 -99.930  1.00 41.02      A  O
ATOM  23048  CB   VAL J 286      0.532 -14.335-101.011  1.00 40.29      A  C
ATOM  23049  N    ARG J 287     -2.583 -13.447-101.544  1.00 41.92      A  N
ATOM  23050  CA   ARG J 287     -3.484 -12.363-101.955  1.00 42.80      A  C
ATOM  23051  C    ARG J 287     -4.661 -12.124-100.993  1.00 42.55      A  C
ATOM  23052  O    ARG J 287     -5.196 -11.010-100.931  1.00 42.69      A  O
ATOM  23053  CB   ARG J 287     -3.983 -12.579-103.392  1.00 43.52      A  C
ATOM  23054  CG   ARG J 287     -4.852 -13.825-103.601  1.00 45.26      A  C
ATOM  23055  CD   ARG J 287     -5.400 -13.877-105.037  1.00 48.27      A  C
ATOM  23056  NE   ARG J 287     -6.424 -14.916-105.191  1.00 49.99      A  N
ATOM  23057  CZ   ARG J 287     -7.738 -14.718-105.082  1.00 50.49      A  C
ATOM  23058  NH1  ARG J 287     -8.226 -13.506-104.825  1.00 50.55      A  N
ATOM  23059  NH2  ARG J 287     -8.574 -15.740-105.237  1.00 50.73      A  N
ATOM  23060  N    TRP J 288     -5.068 -13.167-100.261  1.00 42.22      A  N
ATOM  23061  CA   TRP J 288     -6.070 -13.008 -99.201  1.00 41.91      A  C
ATOM  23062  C    TRP J 288     -5.481 -12.337 -97.968  1.00 41.68      A  C
ATOM  23063  O    TRP J 288     -6.189 -11.660 -97.227  1.00 41.69      A  O
ATOM  23064  CB   TRP J 288     -6.728 -14.337 -98.845  1.00 41.79      A  C
ATOM  23065  CG   TRP J 288     -7.672 -14.771 -99.904  1.00 42.49      A  C
ATOM  23066  CD1  TRP J 288     -7.617 -15.926-100.630  1.00 43.02      A  C
ATOM  23067  CD2  TRP J 288     -8.804 -14.046-100.391  1.00 43.20      A  C
ATOM  23068  CE2  TRP J 288     -9.401 -14.833-101.405  1.00 43.59      A  C
ATOM  23069  CE3  TRP J 288     -9.380 -12.808-100.067  1.00 43.42      A  C
ATOM  23070  NE1  TRP J 288     -8.659 -15.977-101.529  1.00 43.40      A  N
ATOM  23071  CZ2  TRP J 288    -10.547 -14.421-102.102  1.00 44.11      A  C
ATOM  23072  CZ3  TRP J 288    -10.527 -12.394-100.761  1.00 43.93      A  C
ATOM  23073  CH2  TRP J 288    -11.096 -13.200-101.765  1.00 44.30      A  C
ATOM  23074  N    PHE J 289     -4.178 -12.524 -97.768  1.00 41.51      A  N
ATOM  23075  CA   PHE J 289     -3.450 -11.800 -96.743  1.00 41.33      A  C
```

FIGURE 1 (cont'd)

```
ATOM  23076  C    PHE J 289      -3.408 -10.314 -97.109  1.00 41.45      A  C
ATOM  23077  O    PHE J 289      -3.623  -9.449 -96.244  1.00 41.26      A  O
ATOM  23078  CB   PHE J 289      -2.040 -12.376 -96.559  1.00 41.21      A  C
ATOM  23079  CG   PHE J 289      -1.352 -11.885 -95.320  1.00 41.10      A  C
ATOM  23080  CD1  PHE J 289      -1.687 -12.405 -94.070  1.00 40.70      A  C
ATOM  23081  CD2  PHE J 289      -0.383 -10.892 -95.397  1.00 41.42      A  C
ATOM  23082  CE1  PHE J 289      -1.061 -11.948 -92.920  1.00 40.58      A  C
ATOM  23083  CE2  PHE J 289       0.251 -10.429 -94.251  1.00 41.53      A  C
ATOM  23084  CZ   PHE J 289      -0.095 -10.952 -93.010  1.00 41.09      A  C
ATOM  23085  N    HIS J 290      -3.159 -10.028 -98.395  1.00 41.80      A  N
ATOM  23086  CA   HIS J 290      -3.137  -8.636 -98.881  1.00 42.27      A  C
ATOM  23087  C    HIS J 290      -4.489  -7.986 -98.620  1.00 42.36      A  C
ATOM  23088  O    HIS J 290      -4.546  -6.797 -98.326  1.00 42.55      A  O
ATOM  23089  CB   HIS J 290      -2.758  -8.474-100.381  1.00 42.53      A  C
ATOM  23090  CG   HIS J 290      -1.482  -9.156-100.776  1.00 43.17      A  C
ATOM  23091  ND1  HIS J 290      -0.411  -8.674-101.513  1.00 44.00      A  N
ATOM  23092  CE1  HIS J 290      -0.409  -7.395-101.819  1.00 44.49      A  C
ATOM  23093  N    ARG J 291      -5.568  -8.757 -98.721  1.00 42.39      A  N
ATOM  23094  CA   ARG J 291      -6.891  -8.222 -98.423  1.00 42.62      A  C
ATOM  23095  C    ARG J 291      -6.973  -7.731 -96.989  1.00 42.25      A  C
ATOM  23096  O    ARG J 291      -7.522  -6.657 -96.719  1.00 42.52      A  O
ATOM  23097  CB   ARG J 291      -7.974  -9.258 -98.686  1.00 42.85      A  C
ATOM  23098  CG   ARG J 291      -8.289  -9.372-100.141  1.00 44.49      A  C
ATOM  23099  CD   ARG J 291      -8.792  -8.031-100.659  1.00 46.64      A  C
ATOM  23100  NE   ARG J 291     -10.245  -7.945-100.542  1.00 47.74      A  N
ATOM  23101  CZ   ARG J 291     -11.088  -8.201-101.543  1.00 48.77      A  C
ATOM  23102  NH1  ARG J 291     -10.625  -8.538-102.747  1.00 49.29      A  N
ATOM  23103  NH2  ARG J 291     -12.397  -8.113-101.345  1.00 49.28      A  N
ATOM  23104  N    LEU J 292      -6.409  -8.516 -96.077  1.00 41.61      A  N
ATOM  23105  CA   LEU J 292      -6.439  -8.177 -94.671  1.00 40.97      A  C
ATOM  23106  C    LEU J 292      -5.638  -6.920 -94.429  1.00 40.93      A  C
ATOM  23107  O    LEU J 292      -6.120  -6.021 -93.750  1.00 41.01      A  O
ATOM  23108  CB   LEU J 292      -5.940  -9.340 -93.812  1.00 40.60      A  C
ATOM  23109  CG   LEU J 292      -6.893 -10.544 -93.779  1.00 39.89      A  C
ATOM  23110  CD1  LEU J 292      -6.181 -11.780 -93.220  1.00 39.40      A  C
ATOM  23111  CD2  LEU J 292      -8.181 -10.228 -93.012  1.00 39.41      A  C
ATOM  23112  N    ARG J 293      -4.443  -6.838 -95.012  1.00 40.90      A  N
ATOM  23113  CA   ARG J 293      -3.652  -5.598 -94.964  1.00 41.03      A  C
ATOM  23114  C    ARG J 293      -4.477  -4.420 -95.513  1.00 41.31      A  C
ATOM  23115  O    ARG J 293      -4.573  -3.372 -94.872  1.00 41.39      A  O
ATOM  23116  CB   ARG J 293      -2.334  -5.747 -95.738  1.00 40.93      A  C
ATOM  23117  CG   ARG J 293      -1.253  -4.752 -95.331  1.00 40.69      A  C
ATOM  23118  CD   ARG J 293      -0.064  -4.774 -96.300  1.00 40.50      A  C
ATOM  23119  NE   ARG J 293       0.676  -6.037 -96.283  1.00 39.78      A  N
ATOM  23120  N    SER J 294      -5.093  -4.619 -96.681  1.00 41.50      A  N
ATOM  23121  CA   SER J 294      -5.929  -3.598 -97.335  1.00 41.76      A  C
ATOM  23122  C    SER J 294      -7.140  -3.181 -96.489  1.00 42.14      A  C
ATOM  23123  O    SER J 294      -7.503  -2.006 -96.469  1.00 42.62      A  O
ATOM  23124  CB   SER J 294      -6.392  -4.057 -98.729  1.00 40.75      A  C
ATOM  23125  N    ILE J 295      -7.755  -4.138 -95.799  1.00 42.20      A  N
ATOM  23126  CA   ILE J 295      -8.902  -3.843 -94.952  1.00 42.28      A  C
ATOM  23127  C    ILE J 295      -8.475  -3.027 -93.721  1.00 42.56      A  C
ATOM  23128  O    ILE J 295      -9.132  -2.043 -93.352  1.00 42.74      A  O
ATOM  23129  CB   ILE J 295      -9.661  -5.128 -94.563  1.00 41.99      A  C
ATOM  23130  CG1  ILE J 295     -10.397  -5.681 -95.786  1.00 41.93      A  C
ATOM  23131  CG2  ILE J 295     -10.667  -4.851 -93.440  1.00 41.85      A  C
ATOM  23132  CD1  ILE J 295     -10.618  -7.179 -95.740  1.00 41.65      A  C
ATOM  23133  N    GLU J 296      -7.367  -3.426 -93.102  1.00 42.72      A  N
ATOM  23134  CA   GLU J 296      -6.812  -2.691 -91.964  1.00 43.03      A  C
ATOM  23135  C    GLU J 296      -6.516  -1.261 -92.402  1.00 43.58      A  C
ATOM  23136  O    GLU J 296      -6.982  -0.301 -91.776  1.00 43.83      A  O
ATOM  23137  CB   GLU J 296      -5.541  -3.369 -91.449  1.00 42.72      A  C
ATOM  23138  CG   GLU J 296      -4.986  -2.782 -90.173  1.00 42.89      A  C
ATOM  23139  CD   GLU J 296      -3.619  -3.345 -89.812  1.00 43.13      A  C
ATOM  23140  OE1  GLU J 296      -3.212  -4.379 -90.393  1.00 42.82      A  O
```

FIGURE 1 (cont'd)

```
ATOM  23141 OE2 GLU J 296      -2.945  -2.751 -88.937  1.00 43.42      A  O
ATOM  23142 N   LYS J 297      -5.762  -1.149 -93.498  1.00 44.15      A  N
ATOM  23143 CA  LYS J 297      -5.422   0.128 -94.129  1.00 44.87      A  C
ATOM  23144 C   LYS J 297      -6.687   0.995 -94.248  1.00 45.52      A  C
ATOM  23145 O   LYS J 297      -6.730   2.107 -93.710  1.00 45.76      A  O
ATOM  23146 CB  LYS J 297      -4.796  -0.129 -95.514  1.00 44.75      A  C
ATOM  23147 CG  LYS J 297      -3.459   0.564 -95.793  1.00 44.63      A  C
ATOM  23148 CD  LYS J 297      -2.598  -0.270 -96.771  1.00 43.74      A  C
ATOM  23149 CE  LYS J 297      -1.555   0.560 -97.507  1.00 43.74      A  C
ATOM  23150 N   ARG J 298      -7.716   0.451 -94.914  1.00 46.04      A  N
ATOM  23151 CA  ARG J 298      -8.977   1.162 -95.198  1.00 46.53      A  C
ATOM  23152 C   ARG J 298      -9.717   1.581 -93.926  1.00 47.05      A  C
ATOM  23153 O   ARG J 298     -10.152   2.733 -93.822  1.00 47.64      A  O
ATOM  23154 CB  ARG J 298      -9.885   0.318 -96.118  1.00 45.53      A  C
ATOM  23155 CG  ARG J 298     -11.166   1.009 -96.602  1.00 45.47      A  C
ATOM  23156 CD  ARG J 298     -11.945   0.095 -97.549  1.00 45.15      A  C
ATOM  23157 NE  ARG J 298     -13.268   0.626 -97.878  1.00 45.01      A  N
ATOM  23158 N   LEU J 299      -9.845   0.655 -92.970  1.00 47.24      A  N
ATOM  23159 CA  LEU J 299     -10.562   0.925 -91.716  1.00 47.51      A  C
ATOM  23160 C   LEU J 299      -9.839   1.955 -90.858  1.00 47.94      A  C
ATOM  23161 O   LEU J 299     -10.469   2.707 -90.090  1.00 48.17      A  O
ATOM  23162 CB  LEU J 299     -10.777  -0.354 -90.909  1.00 47.17      A  C
ATOM  23163 CG  LEU J 299     -11.863  -1.320 -91.402  1.00 47.02      A  C
ATOM  23164 CD1 LEU J 299     -11.696  -2.687 -90.740  1.00 46.56      A  C
ATOM  23165 CD2 LEU J 299     -13.276  -0.768 -91.167  1.00 47.45      A  C
ATOM  23166 N   HIS J 300      -8.514   1.982 -90.997  1.00 48.26      A  N
ATOM  23167 CA  HIS J 300      -7.685   3.006 -90.360  1.00 48.81      A  C
ATOM  23168 C   HIS J 300      -7.948   4.408 -90.937  1.00 49.27      A  C
ATOM  23169 O   HIS J 300      -8.169   5.361 -90.182  1.00 49.55      A  O
ATOM  23170 CB  HIS J 300      -6.207   2.641 -90.490  1.00 48.73      A  C
ATOM  23171 CG  HIS J 300      -5.290   3.746 -90.102  1.00 49.36      A  C
ATOM  23172 CD2 HIS J 300      -4.418   4.477 -90.832  1.00 50.13      A  C
ATOM  23173 ND1 HIS J 300      -5.223   4.228 -88.814  1.00 49.65      A  N
ATOM  23174 CE1 HIS J 300      -4.333   5.202 -88.764  1.00 50.31      A  C
ATOM  23175 NE2 HIS J 300      -3.832   5.374 -89.975  1.00 50.74      A  N
ATOM  23176 N   ARG J 301      -7.922   4.505 -92.273  1.00 49.75      A  N
ATOM  23177 CA  ARG J 301      -8.246   5.737 -93.020  1.00 50.28      A  C
ATOM  23178 C   ARG J 301      -9.613   6.281 -92.624  1.00 50.90      A  C
ATOM  23179 O   ARG J 301      -9.786   7.491 -92.507  1.00 51.45      A  O
ATOM  23180 CB  ARG J 301      -8.240   5.509 -94.550  1.00 50.11      A  C
ATOM  23181 CG  ARG J 301      -6.998   4.813 -95.141  1.00 49.14      A  C
ATOM  23182 CD  ARG J 301      -5.834   5.763 -95.429  1.00 48.48      A  C
ATOM  23183 NE  ARG J 301      -4.607   5.045 -95.783  1.00 47.70      A  N
ATOM  23184 N   LEU J 302     -10.571   5.380 -92.421  1.00 51.24      A  N
ATOM  23185 CA  LEU J 302     -11.929   5.754 -92.053  1.00 51.88      A  C
ATOM  23186 C   LEU J 302     -12.128   6.006 -90.553  1.00 52.23      A  C
ATOM  23187 O   LEU J 302     -13.276   6.097 -90.085  1.00 52.51      A  O
ATOM  23188 CB  LEU J 302     -12.898   4.673 -92.521  1.00 51.80      A  C
ATOM  23189 CG  LEU J 302     -13.097   4.545 -94.029  1.00 52.28      A  C
ATOM  23190 CD1 LEU J 302     -13.498   3.118 -94.387  1.00 51.88      A  C
ATOM  23191 CD2 LEU J 302     -14.133   5.556 -94.531  1.00 53.49      A  C
ATOM  23192 N   ASN J 303     -11.015   6.135 -89.821  1.00 52.35      A  N
ATOM  23193 CA  ASN J 303     -11.019   6.313 -88.362  1.00 52.31      A  C
ATOM  23194 C   ASN J 303     -12.037   5.379 -87.700  1.00 52.77      A  C
ATOM  23195 O   ASN J 303     -13.053   5.840 -87.154  1.00 53.27      A  O
ATOM  23196 N   LEU J 304     -11.785   4.068 -87.792  1.00 52.91      A  N
ATOM  23197 CA  LEU J 304     -12.693   3.049 -87.217  1.00 52.80      A  C
ATOM  23198 C   LEU J 304     -11.940   1.994 -86.405  1.00 52.49      A  C
ATOM  23199 O   LEU J 304     -12.513   0.975 -85.988  1.00 52.22      A  O
ATOM  23200 CB  LEU J 304     -13.576   2.385 -88.299  1.00 52.84      A  C
ATOM  23201 CG  LEU J 304     -14.851   3.097 -88.807  1.00 53.29      A  C
ATOM  23202 CD1 LEU J 304     -15.461   2.337 -89.986  1.00 52.97      A  C
ATOM  23203 CD2 LEU J 304     -15.905   3.309 -87.713  1.00 53.83      A  C
ATOM  23204 N   LEU J 305     -10.656   2.256 -86.178  1.00 52.40      A  N
ATOM  23205 CA  LEU J 305      -9.813   1.378 -85.378  1.00 52.22      A  C
```

FIGURE 1 (cont'd)

```
ATOM  23206  C    LEU J 305      -9.250   2.132 -84.173  1.00 52.63      A   C
ATOM  23207  O    LEU J 305      -8.517   3.120 -84.336  1.00 53.02      A   O
ATOM  23208  CB   LEU J 305      -8.665   0.815 -86.227  1.00 51.78      A   C
ATOM  23209  CG   LEU J 305      -8.987   0.088 -87.541  1.00 51.12      A   C
ATOM  23210  CD1  LEU J 305      -7.705  -0.229 -88.299  1.00 50.42      A   C
ATOM  23211  CD2  LEU J 305      -9.804  -1.186 -87.299  1.00 50.68      A   C
ATOM  23212  N    GLN J 306      -9.607   1.665 -82.973  1.00 52.78      A   N
ATOM  23213  CA   GLN J 306      -9.095   2.229 -81.717  1.00 53.06      A   C
ATOM  23214  C    GLN J 306      -7.601   1.996 -81.583  1.00 52.96      A   C
ATOM  23215  O    GLN J 306      -7.066   1.025 -82.122  1.00 52.62      A   O
ATOM  23216  CB   GLN J 306      -9.782   1.585 -80.512  1.00 53.19      A   C
ATOM  23217  CG   GLN J 306     -11.000   2.317 -79.971  1.00 54.05      A   C
ATOM  23218  CD   GLN J 306     -11.485   1.733 -78.639  1.00 54.73      A   C
ATOM  23219  OE1  GLN J 306     -11.652   0.512 -78.478  1.00 54.93      A   O
ATOM  23220  N    SER J 307      -6.937   2.885 -80.850  1.00 53.30      A   N
ATOM  23221  CA   SER J 307      -5.510   2.740 -80.528  1.00 53.53      A   C
ATOM  23222  C    SER J 307      -4.686   2.232 -81.715  1.00 53.41      A   C
ATOM  23223  O    SER J 307      -3.891   1.290 -81.567  1.00 53.17      A   O
ATOM  23224  CB   SER J 307      -5.311   1.798 -79.330  1.00 53.55      A   C
ATOM  23225  OG   SER J 307      -6.230   2.070 -78.286  1.00 54.28      A   O
ATOM  23226  N    HIS J 308      -4.879   2.861 -82.879  1.00 53.54      A   N
ATOM  23227  CA   HIS J 308      -4.272   2.410 -84.136  1.00 53.48      A   C
ATOM  23228  C    HIS J 308      -3.522   3.565 -84.814  1.00 53.76      A   C
ATOM  23229  O    HIS J 308      -4.001   4.147 -85.796  1.00 54.04      A   O
ATOM  23230  CB   HIS J 308      -5.361   1.833 -85.053  1.00 53.30      A   C
ATOM  23231  CG   HIS J 308      -4.842   0.899 -86.100  1.00 52.99      A   C
ATOM  23232  CD2  HIS J 308      -4.380  -0.369 -86.010  1.00 52.57      A   C
ATOM  23233  ND1  HIS J 308      -4.762   1.242 -87.433  1.00 53.28      A   N
ATOM  23234  CE1  HIS J 308      -4.270   0.226 -88.118  1.00 52.93      A   C
ATOM  23235  NE2  HIS J 308      -4.029  -0.763 -87.278  1.00 52.40      A   N
ATOM  23236  N    PRO J 309      -2.335   3.904 -84.287  1.00 53.96      A   N
ATOM  23237  CA   PRO J 309      -1.618   5.100 -84.758  1.00 54.48      A   C
ATOM  23238  C    PRO J 309      -0.724   4.882 -86.000  1.00 54.74      A   C
ATOM  23239  O    PRO J 309       0.381   5.441 -86.068  1.00 55.00      A   O
ATOM  23240  CB   PRO J 309      -0.769   5.522 -83.539  1.00 54.71      A   C
ATOM  23241  CG   PRO J 309      -1.344   4.798 -82.359  1.00 54.47      A   C
ATOM  23242  N    GLN J 310      -1.191   4.060 -86.946  1.00 54.75      A   N
ATOM  23243  CA   GLN J 310      -0.655   3.996 -88.324  1.00 54.92      A   C
ATOM  23244  C    GLN J 310      -1.444   3.036 -89.208  1.00 55.01      A   C
ATOM  23245  O    GLN J 310      -2.434   2.448 -88.770  1.00 54.84      A   O
ATOM  23246  CB   GLN J 310       0.884   3.779 -88.421  1.00 54.93      A   C
ATOM  23247  CG   GLN J 310       1.526   2.807 -87.431  1.00 54.54      A   C
ATOM  23248  CD   GLN J 310       2.907   3.262 -86.984  1.00 54.55      A   C
ATOM  23249  N    GLU J 311      -1.004   2.897 -90.456  1.00 55.42      A   N
ATOM  23250  CA   GLU J 311      -1.736   2.143 -91.479  1.00 55.77      A   C
ATOM  23251  C    GLU J 311      -1.465   0.642 -91.333  1.00 55.07      A   C
ATOM  23252  O    GLU J 311      -2.389  -0.141 -91.058  1.00 54.87      A   O
ATOM  23253  CB   GLU J 311      -1.360   2.633 -92.893  1.00 56.52      A   C
ATOM  23254  CG   GLU J 311      -1.375   4.164 -93.100  1.00 58.93      A   C
ATOM  23255  CD   GLU J 311      -0.063   4.883 -92.687  1.00 61.45      A   C
ATOM  23256  OE1  GLU J 311       0.181   5.992 -93.224  1.00 62.85      A   O
ATOM  23257  OE2  GLU J 311       0.713   4.366 -91.835  1.00 62.00      A   O
ATOM  23258  N    VAL J 312      -0.199   0.258 -91.525  1.00 54.49      A   N
ATOM  23259  CA   VAL J 312       0.250  -1.116 -91.311  1.00 53.77      A   C
ATOM  23260  C    VAL J 312       0.749  -1.261 -89.873  1.00 53.24      A   C
ATOM  23261  O    VAL J 312       1.817  -0.749 -89.511  1.00 53.55      A   O
ATOM  23262  N    MET J 313      -0.065  -1.932 -89.061  1.00 52.19      A   N
ATOM  23263  CA   MET J 313       0.263  -2.246 -87.677  1.00 51.23      A   C
ATOM  23264  C    MET J 313       0.251  -3.759 -87.515  1.00 50.24      A   C
ATOM  23265  O    MET J 313       1.246  -4.362 -87.087  1.00 50.11      A   O
ATOM  23266  CB   MET J 313      -0.768  -1.637 -86.720  1.00 51.41      A   C
ATOM  23267  CG   MET J 313      -0.833  -0.103 -86.699  1.00 52.04      A   C
ATOM  23268  SD   MET J 313      -0.281   0.675 -85.141  1.00 52.57      A   S
ATOM  23269  CE   MET J 313      -1.463  -0.003 -83.972  1.00 52.16      A   C
ATOM  23270  N    TYR J 314      -0.882  -4.358 -87.884  1.00 49.15      A   N
```

FIGURE 1 (cont'd)

| | | | | | | | | | | | |
|---|---|---|---|---|---|---|---|---|---|---|---|
| ATOM | 23271 | CA | TYR | J | 314 | -1.152 | -5.786 | -87.648 | 1.00 | 48.09 | A C |
| ATOM | 23272 | C | TYR | J | 314 | -0.662 | -6.734 | -88.756 | 1.00 | 47.53 | A C |
| ATOM | 23273 | O | TYR | J | 314 | 0.146 | -7.642 | -88.514 | 1.00 | 47.30 | A O |
| ATOM | 23274 | CB | TYR | J | 314 | -2.655 | -6.004 | -87.401 | 1.00 | 47.85 | A C |
| ATOM | 23275 | CG | TYR | J | 314 | -3.208 | -5.261 | -86.203 | 1.00 | 47.57 | A C |
| ATOM | 23276 | CD1 | TYR | J | 314 | -2.430 | -5.068 | -85.043 | 1.00 | 47.57 | A C |
| ATOM | 23277 | CD2 | TYR | J | 314 | -4.516 | -4.776 | -86.213 | 1.00 | 47.38 | A C |
| ATOM | 23278 | CE1 | TYR | J | 314 | -2.939 | -4.384 | -83.938 | 1.00 | 47.64 | A C |
| ATOM | 23279 | CE2 | TYR | J | 314 | -5.042 | -4.098 | -85.112 | 1.00 | 47.44 | A C |
| ATOM | 23280 | CZ | TYR | J | 314 | -4.249 | -3.904 | -83.983 | 1.00 | 47.38 | A C |
| ATOM | 23281 | OH | TYR | J | 314 | -4.776 | -3.233 | -82.907 | 1.00 | 47.33 | A O |
| ATOM | 23282 | N | PHE | J | 315 | -1.171 | -6.522 | -89.963 | 1.00 | 47.08 | A N |
| ATOM | 23283 | CA | PHE | J | 315 | -0.823 | -7.361 | -91.095 | 1.00 | 46.72 | A C |
| ATOM | 23284 | C | PHE | J | 315 | 0.364 | -6.774 | -91.846 | 1.00 | 46.97 | A C |
| ATOM | 23285 | O | PHE | J | 315 | 0.231 | -5.915 | -92.732 | 1.00 | 47.03 | A O |
| ATOM | 23286 | CB | PHE | J | 315 | -2.046 | -7.554 | -91.987 | 1.00 | 46.43 | A C |
| ATOM | 23287 | CG | PHE | J | 315 | -3.196 | -8.199 | -91.277 | 1.00 | 45.31 | A C |
| ATOM | 23288 | CD1 | PHE | J | 315 | -3.265 | -9.582 | -91.167 | 1.00 | 44.55 | A C |
| ATOM | 23289 | CD2 | PHE | J | 315 | -4.197 | -7.426 | -90.698 | 1.00 | 44.59 | A C |
| ATOM | 23290 | CE1 | PHE | J | 315 | -4.328 | -10.188 | -90.504 | 1.00 | 44.04 | A C |
| ATOM | 23291 | CE2 | PHE | J | 315 | -5.265 | -8.022 | -90.031 | 1.00 | 44.04 | A C |
| ATOM | 23292 | CZ | PHE | J | 315 | -5.331 | -9.406 | -89.932 | 1.00 | 43.80 | A C |
| ATOM | 23293 | N | GLN | J | 316 | 1.535 | -7.247 | -91.450 | 1.00 | 47.20 | A N |
| ATOM | 23294 | CA | GLN | J | 316 | 2.783 | -6.727 | -91.959 | 1.00 | 47.77 | A C |
| ATOM | 23295 | C | GLN | J | 316 | 3.068 | -7.238 | -93.366 | 1.00 | 48.13 | A C |
| ATOM | 23296 | O | GLN | J | 316 | 2.644 | -8.344 | -93.723 | 1.00 | 47.96 | A O |
| ATOM | 23297 | CB | GLN | J | 316 | 3.937 | -7.100 | -91.021 | 1.00 | 47.81 | A C |
| ATOM | 23298 | CG | GLN | J | 316 | 3.985 | -6.303 | -89.711 | 1.00 | 48.26 | A C |
| ATOM | 23299 | CD | GLN | J | 316 | 4.194 | -4.798 | -89.924 | 1.00 | 49.01 | A C |
| ATOM | 23300 | NE2 | GLN | J | 316 | 3.200 | -4.006 | -89.536 | 1.00 | 49.11 | A N |
| ATOM | 23301 | OE1 | GLN | J | 316 | 5.234 | -4.358 | -90.425 | 1.00 | 49.81 | A O |
| ATOM | 23302 | N | PRO | J | 317 | 3.786 | -6.431 | -94.174 | 1.00 | 48.71 | A N |
| ATOM | 23303 | CA | PRO | J | 317 | 4.258 | -6.915 | -95.463 | 1.00 | 49.00 | A C |
| ATOM | 23304 | C | PRO | J | 317 | 5.463 | -7.839 | -95.269 | 1.00 | 49.03 | A C |
| ATOM | 23305 | O | PRO | J | 317 | 6.087 | -7.847 | -94.196 | 1.00 | 48.96 | A O |
| ATOM | 23306 | CB | PRO | J | 317 | 4.675 | -5.629 | -96.180 | 1.00 | 49.30 | A C |
| ATOM | 23307 | CG | PRO | J | 317 | 5.138 | -4.744 | -95.078 | 1.00 | 49.45 | A C |
| ATOM | 23308 | CD | PRO | J | 317 | 4.208 | -5.038 | -93.929 | 1.00 | 48.98 | A C |
| ATOM | 23309 | N | GLY | J | 318 | 5.784 | -8.599 | -96.309 | 1.00 | 49.07 | A N |
| ATOM | 23310 | CA | GLY | J | 318 | 6.837 | -9.595 | -96.228 | 1.00 | 49.03 | A C |
| ATOM | 23311 | C | GLY | J | 318 | 6.236 | -10.989 | -96.201 | 1.00 | 48.86 | A C |
| ATOM | 23312 | O | GLY | J | 318 | 5.151 | -11.207 | -95.635 | 1.00 | 48.68 | A O |
| ATOM | 23313 | N | GLU | J | 319 | 6.935 | -11.931 | -96.829 | 1.00 | 48.83 | A N |
| ATOM | 23314 | CA | GLU | J | 319 | 6.520 | -13.319 | -96.838 | 1.00 | 48.59 | A C |
| ATOM | 23315 | C | GLU | J | 319 | 7.647 | -14.171 | -96.270 | 1.00 | 48.75 | A C |
| ATOM | 23316 | O | GLU | J | 319 | 8.410 | -14.758 | -97.038 | 1.00 | 49.13 | A O |
| ATOM | 23317 | CB | GLU | J | 319 | 6.189 | -13.769 | -98.262 | 1.00 | 48.50 | A C |
| ATOM | 23318 | CG | GLU | J | 319 | 5.068 | -12.982 | -98.939 | 1.00 | 47.97 | A C |
| ATOM | 23319 | N | PRO | J | 320 | 7.781 | -14.223 | -94.924 | 1.00 | 48.65 | A N |
| ATOM | 23320 | CA | PRO | J | 320 | 8.790 | -15.115 | -94.315 | 1.00 | 48.66 | A C |
| ATOM | 23321 | C | PRO | J | 320 | 8.451 | -16.612 | -94.412 | 1.00 | 48.52 | A C |
| ATOM | 23322 | O | PRO | J | 320 | 7.291 | -16.976 | -94.609 | 1.00 | 48.33 | A O |
| ATOM | 23323 | CB | PRO | J | 320 | 8.823 | -14.660 | -92.844 | 1.00 | 48.71 | A C |
| ATOM | 23324 | CG | PRO | J | 320 | 8.246 | -13.266 | -92.852 | 1.00 | 48.69 | A C |
| ATOM | 23325 | CD | PRO | J | 320 | 7.181 | -13.330 | -93.913 | 1.00 | 48.48 | A C |
| ATOM | 23326 | N | PHE | J | 321 | 9.469 | -17.454 | -94.245 | 1.00 | 48.35 | A N |
| ATOM | 23327 | CA | PHE | J | 321 | 9.376 | -18.895 | -94.488 | 1.00 | 48.00 | A C |
| ATOM | 23328 | C | PHE | J | 321 | 8.312 | -19.667 | -93.684 | 1.00 | 48.18 | A C |
| ATOM | 23329 | O | PHE | J | 321 | 7.481 | -20.347 | -94.280 | 1.00 | 48.54 | A O |
| ATOM | 23330 | N | GLY | J | 322 | 8.327 | -19.581 | -92.355 | 1.00 | 48.03 | A N |
| ATOM | 23331 | CA | GLY | J | 322 | 7.415 | -20.398 | -91.515 | 1.00 | 47.45 | A C |
| ATOM | 23332 | C | GLY | J | 322 | 7.911 | -21.842 | -91.361 | 1.00 | 47.09 | A C |
| ATOM | 23333 | O | GLY | J | 322 | 9.095 | -22.105 | -91.591 | 1.00 | 47.61 | A O |
| ATOM | 23334 | N | SER | J | 323 | 7.055 | -22.787 | -90.951 | 1.00 | 46.14 | A N |
| ATOM | 23335 | CA | SER | J | 323 | 5.692 | -22.537 | -90.489 | 1.00 | 45.03 | A C |

FIGURE 1 (cont'd)

```
ATOM  23336  C    SER J 323      5.611 -22.824 -89.003  1.00 43.89      A  C
ATOM  23337  O    SER J 323      6.568 -23.330 -88.405  1.00 44.00      A  O
ATOM  23338  CB   SER J 323      4.701 -23.460 -91.205  1.00 45.23      A  C
ATOM  23339  OG   SER J 323      4.763 -23.290 -92.603  1.00 46.10      A  O
ATOM  23340  N    VAL J 324      4.453 -22.511 -88.424  1.00 42.32      A  N
ATOM  23341  CA   VAL J 324      4.147 -22.840 -87.036  1.00 40.78      A  C
ATOM  23342  C    VAL J 324      3.103 -23.944 -87.027  1.00 40.01      A  C
ATOM  23343  O    VAL J 324      2.016 -23.751 -87.565  1.00 39.90      A  O
ATOM  23344  CB   VAL J 324      3.624 -21.599 -86.272  1.00 40.53      A  C
ATOM  23345  CG1  VAL J 324      4.732 -20.559 -86.145  1.00 40.42      A  C
ATOM  23346  CG2  VAL J 324      3.107 -21.987 -84.891  1.00 40.09      A  C
ATOM  23347  N    GLU J 325      3.436 -25.085 -86.425  1.00 39.17      A  N
ATOM  23348  CA   GLU J 325      2.545 -26.242 -86.428  1.00 38.50      A  C
ATOM  23349  C    GLU J 325      1.257 -25.973 -85.659  1.00 37.61      A  C
ATOM  23350  O    GLU J 325      1.280 -25.613 -84.493  1.00 37.47      A  O
ATOM  23351  CB   GLU J 325      3.248 -27.467 -85.864  1.00 38.88      A  C
ATOM  23352  CG   GLU J 325      4.547 -27.814 -86.566  1.00 40.46      A  C
ATOM  23353  CD   GLU J 325      5.128 -29.142 -86.100  1.00 42.57      A  C
ATOM  23354  OE1  GLU J 325      4.433 -29.882 -85.368  1.00 42.98      A  O
ATOM  23355  OE2  GLU J 325      6.282 -29.447 -86.470  1.00 43.81      A  O
ATOM  23356  N    ASP J 326      0.132 -26.143 -86.333  1.00 36.78      A  N
ATOM  23357  CA   ASP J 326     -1.172 -25.861 -85.747  1.00 36.04      A  C
ATOM  23358  C    ASP J 326     -2.227 -26.721 -86.453  1.00 35.80      A  C
ATOM  23359  O    ASP J 326     -1.877 -27.592 -87.263  1.00 35.87      A  O
ATOM  23360  CB   ASP J 326     -1.499 -24.367 -85.872  1.00 35.74      A  C
ATOM  23361  CG   ASP J 326     -2.445 -23.862 -84.781  1.00 35.14      A  C
ATOM  23362  OD1  ASP J 326     -3.201 -24.650 -84.170  1.00 34.84      A  O
ATOM  23363  OD2  ASP J 326     -2.444 -22.642 -84.542  1.00 34.65      A  O
ATOM  23364  N    ASP J 327     -3.505 -26.468 -86.148  1.00 35.34      A  N
ATOM  23365  CA   ASP J 327     -4.637 -27.263 -86.650  1.00 35.02      A  C
ATOM  23366  C    ASP J 327     -4.742 -27.397 -88.178  1.00 34.62      A  C
ATOM  23367  O    ASP J 327     -5.426 -28.298 -88.684  1.00 34.68      A  O
ATOM  23368  CB   ASP J 327     -5.954 -26.706 -86.106  1.00 35.13      A  C
ATOM  23369  CG   ASP J 327     -6.161 -27.019 -84.631  1.00 36.08      A  C
ATOM  23370  OD1  ASP J 327     -6.271 -28.221 -84.261  1.00 36.79      A  O
ATOM  23371  OD2  ASP J 327     -6.236 -26.047 -83.843  1.00 36.75      A  O
ATOM  23372  N    HIS J 328     -4.071 -26.504 -88.906  1.00 34.11      A  N
ATOM  23373  CA   HIS J 328     -4.145 -26.498 -90.352  1.00 33.71      A  C
ATOM  23374  C    HIS J 328     -3.351 -27.641 -90.966  1.00 33.65      A  C
ATOM  23375  O    HIS J 328     -3.707 -28.128 -92.031  1.00 33.85      A  O
ATOM  23376  CB   HIS J 328     -3.643 -25.179 -90.890  1.00 33.56      A  C
ATOM  23377  CG   HIS J 328     -2.173 -24.989 -90.732  1.00 33.85      A  C
ATOM  23378  CD2  HIS J 328     -1.164 -25.084 -91.627  1.00 34.44      A  C
ATOM  23379  ND1  HIS J 328     -1.591 -24.661 -89.529  1.00 34.07      A  N
ATOM  23380  CE1  HIS J 328     -0.285 -24.550 -89.692  1.00 34.35      A  C
ATOM  23381  NE2  HIS J 328      0.001 -24.804 -90.955  1.00 34.60      A  N
ATOM  23382  N    ILE J 329     -2.293 -28.082 -90.289  1.00 33.52      A  N
ATOM  23383  CA   ILE J 329     -1.390 -29.103 -90.836  1.00 33.62      A  C
ATOM  23384  C    ILE J 329     -2.077 -30.315 -91.472  1.00 33.63      A  C
ATOM  23385  O    ILE J 329     -1.793 -30.635 -92.621  1.00 33.91      A  O
ATOM  23386  CB   ILE J 329     -0.321 -29.552 -89.813  1.00 33.71      A  C
ATOM  23387  CG1  ILE J 329      0.613 -28.381 -89.466  1.00 33.93      A  C
ATOM  23388  CG2  ILE J 329      0.466 -30.772 -90.326  1.00 34.16      A  C
ATOM  23389  CD1  ILE J 329      1.429 -27.834 -90.639  1.00 34.45      A  C
ATOM  23390  N    PRO J 330     -2.987 -30.988 -90.748  1.00 33.56      A  N
ATOM  23391  CA   PRO J 330     -3.542 -32.186 -91.384  1.00 33.64      A  C
ATOM  23392  C    PRO J 330     -4.544 -31.868 -92.495  1.00 33.52      A  C
ATOM  23393  O    PRO J 330     -4.949 -32.762 -93.237  1.00 33.79      A  O
ATOM  23394  CB   PRO J 330     -4.218 -32.919 -90.224  1.00 33.73      A  C
ATOM  23395  CG   PRO J 330     -4.609 -31.821 -89.285  1.00 33.54      A  C
ATOM  23396  CD   PRO J 330     -3.541 -30.770 -89.398  1.00 33.44      A  C
ATOM  23397  N    PHE J 331     -4.942 -30.611 -92.610  1.00 33.06      A  N
ATOM  23398  CA   PHE J 331     -5.748 -30.219 -93.739  1.00 32.88      A  C
ATOM  23399  C    PHE J 331     -4.853 -29.832 -94.891  1.00 32.87      A  C
ATOM  23400  O    PHE J 331     -5.159 -30.108 -96.048  1.00 32.99      A  O
```

FIGURE 1 (cont'd)

```
ATOM  23401  CB   PHE J 331      -6.668 -29.075 -93.363  1.00 32.70      A    C
ATOM  23402  CG   PHE J 331      -7.802 -29.486 -92.477  1.00 32.81      A    C
ATOM  23403  CD1  PHE J 331      -7.758 -29.234 -91.117  1.00 32.80      A    C
ATOM  23404  CD2  PHE J 331      -8.919 -30.133 -93.006  1.00 33.32      A    C
ATOM  23405  CE1  PHE J 331      -8.813 -29.613 -90.301  1.00 33.03      A    C
ATOM  23406  CE2  PHE J 331      -9.970 -30.514 -92.195  1.00 33.49      A    C
ATOM  23407  CZ   PHE J 331      -9.918 -30.255 -90.842  1.00 33.21      A    C
ATOM  23408  N    LEU J 332      -3.739 -29.189 -94.561  1.00 32.84      A    N
ATOM  23409  CA   LEU J 332      -2.742 -28.809 -95.552  1.00 32.99      A    C
ATOM  23410  C    LEU J 332      -2.135 -30.047 -96.228  1.00 33.44      A    C
ATOM  23411  O    LEU J 332      -1.989 -30.061 -97.450  1.00 33.69      A    O
ATOM  23412  CB   LEU J 332      -1.656 -27.937 -94.918  1.00 32.68      A    C
ATOM  23413  CG   LEU J 332      -0.475 -27.546 -95.802  1.00 32.41      A    C
ATOM  23414  CD1  LEU J 332      -0.764 -26.276 -96.572  1.00 32.01      A    C
ATOM  23415  CD2  LEU J 332       0.752 -27.379 -94.941  1.00 32.39      A    C
ATOM  23416  N    ARG J 333      -1.813 -31.087 -95.450  1.00 33.80      A    N
ATOM  23417  CA   ARG J 333      -1.205 -32.298 -96.013  1.00 34.35      A    C
ATOM  23418  C    ARG J 333      -2.140 -32.954 -97.040  1.00 34.13      A    C
ATOM  23419  O    ARG J 333      -1.694 -33.717 -97.901  1.00 34.49      A    O
ATOM  23420  CB   ARG J 333      -0.716 -33.269 -94.912  1.00 34.71      A    C
ATOM  23421  CG   ARG J 333      -1.485 -34.589 -94.751  1.00 36.60      A    C
ATOM  23422  CD   ARG J 333      -0.719 -35.647 -93.903  1.00 39.89      A    C
ATOM  23423  NE   ARG J 333      -1.091 -35.660 -92.470  1.00 42.26      A    N
ATOM  23424  CZ   ARG J 333      -1.864 -36.577 -91.869  1.00 42.96      A    C
ATOM  23425  NH1  ARG J 333      -2.140 -36.481 -90.567  1.00 42.53      A    N
ATOM  23426  NH2  ARG J 333      -2.363 -37.592 -92.561  1.00 43.84      A    N
ATOM  23427  N    ARG J 334      -3.427 -32.616 -96.957  1.00 33.58      A    N
ATOM  23428  CA   ARG J 334      -4.443 -33.109 -97.895  1.00 33.18      A    C
ATOM  23429  C    ARG J 334      -4.726 -32.126 -99.027  1.00 32.69      A    C
ATOM  23430  O    ARG J 334      -5.600 -32.357 -99.860  1.00 32.80      A    O
ATOM  23431  CB   ARG J 334      -5.744 -33.446 -97.153  1.00 33.18      A    C
ATOM  23432  CG   ARG J 334      -5.746 -34.813 -96.495  1.00 33.62      A    C
ATOM  23433  CD   ARG J 334      -6.518 -34.783 -95.203  1.00 33.74      A    C
ATOM  23434  NE   ARG J 334      -6.780 -36.127 -94.700  1.00 34.79      A    N
ATOM  23435  CZ   ARG J 334      -6.138 -36.704 -93.683  1.00 35.58      A    C
ATOM  23436  NH1  ARG J 334      -5.171 -36.059 -93.022  1.00 35.22      A    N
ATOM  23437  NH2  ARG J 334      -6.477 -37.941 -93.318  1.00 36.59      A    N
ATOM  23438  N    GLY J 335      -3.991 -31.024 -99.043  1.00 32.08      A    N
ATOM  23439  CA   GLY J 335      -4.080 -30.068-100.140  1.00 31.48      A    C
ATOM  23440  C    GLY J 335      -5.037 -28.897 -99.973  1.00 30.83      A    C
ATOM  23441  O    GLY J 335      -5.333 -28.197-100.937  1.00 31.12      A    O
ATOM  23442  N    VAL J 336      -5.518 -28.667 -98.758  1.00 29.93      A    N
ATOM  23443  CA   VAL J 336      -6.411 -27.547 -98.511  1.00 29.07      A    C
ATOM  23444  C    VAL J 336      -5.598 -26.264 -98.478  1.00 28.65      A    C
ATOM  23445  O    VAL J 336      -4.568 -26.209 -97.818  1.00 28.62      A    O
ATOM  23446  CB   VAL J 336      -7.184 -27.713 -97.186  1.00 28.89      A    C
ATOM  23447  CG1  VAL J 336      -8.124 -26.544 -96.971  1.00 28.82      A    C
ATOM  23448  CG2  VAL J 336      -7.972 -29.014 -97.178  1.00 29.03      A    C
ATOM  23449  N    PRO J 337      -6.046 -25.234 -99.207  1.00 28.43      A    N
ATOM  23450  CA   PRO J 337      -5.444 -23.909 -99.096  1.00 28.19      A    C
ATOM  23451  C    PRO J 337      -5.594 -23.365 -97.683  1.00 27.73      A    C
ATOM  23452  O    PRO J 337      -6.686 -23.391 -97.124  1.00 27.73      A    O
ATOM  23453  CB   PRO J 337      -6.280 -23.063-100.058  1.00 28.33      A    C
ATOM  23454  CG   PRO J 337      -6.871 -24.022-101.010  1.00 28.73      A    C
ATOM  23455  CD   PRO J 337      -7.094 -25.279-100.241  1.00 28.65      A    C
ATOM  23456  N    VAL J 338      -4.505 -22.876 -97.109  1.00 27.28      A    N
ATOM  23457  CA   VAL J 338      -4.533 -22.402 -95.729  1.00 26.74      A    C
ATOM  23458  C    VAL J 338      -4.136 -20.937 -95.613  1.00 26.56      A    C
ATOM  23459  O    VAL J 338      -3.189 -20.481 -96.263  1.00 26.77      A    O
ATOM  23460  CB   VAL J 338      -3.588 -23.232 -94.815  1.00 26.65      A    C
ATOM  23461  CG1  VAL J 338      -3.607 -22.690 -93.387  1.00 26.38      A    C
ATOM  23462  CG2  VAL J 338      -3.951 -24.729 -94.845  1.00 26.62      A    C
ATOM  23463  N    LEU J 339      -4.869 -20.207 -94.783  1.00 26.19      A    N
ATOM  23464  CA   LEU J 339      -4.408 -18.908 -94.329  1.00 25.95      A    C
ATOM  23465  C    LEU J 339      -4.265 -18.947 -92.808  1.00 25.85      A    C
```

FIGURE 1 (cont'd)

```
ATOM  23466  O    LEU J 339      -5.265 -19.044 -92.078  1.00 25.85           A  O
ATOM  23467  CB   LEU J 339      -5.350 -17.787 -94.769  1.00 25.86           A  C
ATOM  23468  CG   LEU J 339      -4.897 -16.373 -94.378  1.00 25.70           A  C
ATOM  23469  CD1  LEU J 339      -3.485 -16.059 -94.881  1.00 26.01           A  C
ATOM  23470  CD2  LEU J 339      -5.888 -15.352 -94.899  1.00 25.53           A  C
ATOM  23471  N    HIS J 340      -3.016 -18.878 -92.340  1.00 25.70           A  N
ATOM  23472  CA   HIS J 340      -2.687 -19.090 -90.924  1.00 25.44           A  C
ATOM  23473  C    HIS J 340      -2.581 -17.759 -90.202  1.00 25.29           A  C
ATOM  23474  O    HIS J 340      -1.565 -17.074 -90.269  1.00 25.33           A  O
ATOM  23475  CB   HIS J 340      -1.390 -19.900 -90.810  1.00 25.49           A  C
ATOM  23476  CG   HIS J 340      -1.202 -20.567 -89.489  1.00 25.66           A  C
ATOM  23477  CD2  HIS J 340      -2.075 -20.821 -88.486  1.00 25.70           A  C
ATOM  23478  ND1  HIS J 340       0.020 -21.049 -89.068  1.00 26.02           A  N
ATOM  23479  CE1  HIS J 340      -0.107 -21.570 -87.860  1.00 25.96           A  C
ATOM  23480  NE2  HIS J 340      -1.369 -21.445 -87.485  1.00 25.93           A  N
ATOM  23481  N    LEU J 341      -3.655 -17.400 -89.521  1.00 25.15           A  N
ATOM  23482  CA   LEU J 341      -3.759 -16.101 -88.886  1.00 25.14           A  C
ATOM  23483  C    LEU J 341      -3.309 -16.200 -87.427  1.00 25.11           A  C
ATOM  23484  O    LEU J 341      -4.109 -16.055 -86.501  1.00 25.14           A  O
ATOM  23485  CB   LEU J 341      -5.204 -15.583 -88.990  1.00 25.14           A  C
ATOM  23486  CG   LEU J 341      -5.451 -14.114 -89.356  1.00 25.33           A  C
ATOM  23487  CD1  LEU J 341      -6.943 -13.811 -89.316  1.00 25.54           A  C
ATOM  23488  CD2  LEU J 341      -4.683 -13.149 -88.451  1.00 25.08           A  C
ATOM  23489  N    ILE J 342      -2.021 -16.452 -87.240  1.00 25.13           A  N
ATOM  23490  CA   ILE J 342      -1.429 -16.605 -85.919  1.00 25.20           A  C
ATOM  23491  C    ILE J 342      -0.338 -15.558 -85.755  1.00 25.52           A  C
ATOM  23492  O    ILE J 342       0.484 -15.383 -86.652  1.00 25.76           A  O
ATOM  23493  CB   ILE J 342      -0.849 -18.036 -85.744  1.00 25.06           A  C
ATOM  23494  CG1  ILE J 342      -0.244 -18.237 -84.349  1.00 24.92           A  C
ATOM  23495  CG2  ILE J 342       0.179 -18.357 -86.835  1.00 25.00           A  C
ATOM  23496  CD1  ILE J 342       0.074 -19.687 -84.037  1.00 24.62           A  C
ATOM  23497  N    SER J 343      -0.322 -14.855 -84.628  1.00 25.80           A  N
ATOM  23498  CA   SER J 343       0.701 -13.824 -84.435  1.00 26.24           A  C
ATOM  23499  C    SER J 343       2.091 -14.424 -84.204  1.00 26.43           A  C
ATOM  23500  O    SER J 343       2.269 -15.359 -83.406  1.00 26.33           A  O
ATOM  23501  CB   SER J 343       0.332 -12.856 -83.313  1.00 26.33           A  C
ATOM  23502  OG   SER J 343       0.501 -13.470 -82.049  1.00 27.04           A  O
ATOM  23503  N    THR J 344       3.057 -13.887 -84.945  1.00 26.78           A  N
ATOM  23504  CA   THR J 344       4.469 -14.213 -84.783  1.00 27.12           A  C
ATOM  23505  C    THR J 344       5.175 -12.874 -84.558  1.00 27.57           A  C
ATOM  23506  O    THR J 344       5.144 -11.996 -85.431  1.00 27.68           A  O
ATOM  23507  CB   THR J 344       5.061 -14.958 -86.009  1.00 27.03           A  C
ATOM  23508  OG1  THR J 344       4.108 -14.979 -87.085  1.00 26.78           A  O
ATOM  23509  N    PRO J 345       5.803 -12.702 -83.376  1.00 27.92           A  N
ATOM  23510  CA   PRO J 345       6.015 -13.735 -82.345  1.00 27.96           A  C
ATOM  23511  C    PRO J 345       4.751 -14.029 -81.515  1.00 27.76           A  C
ATOM  23512  O    PRO J 345       3.729 -13.323 -81.636  1.00 27.48           A  O
ATOM  23513  CB   PRO J 345       7.132 -13.135 -81.454  1.00 28.18           A  C
ATOM  23514  CG   PRO J 345       7.380 -11.719 -81.984  1.00 28.28           A  C
ATOM  23515  CD   PRO J 345       6.220 -11.375 -82.889  1.00 28.03           A  C
ATOM  23516  N    PHE J 346       4.829 -15.073 -80.692  1.00 27.72           A  N
ATOM  23517  CA   PHE J 346       3.726 -15.440 -79.821  1.00 27.85           A  C
ATOM  23518  C    PHE J 346       3.555 -14.386 -78.738  1.00 28.08           A  C
ATOM  23519  O    PHE J 346       4.519 -13.684 -78.425  1.00 28.44           A  O
ATOM  23520  CB   PHE J 346       4.010 -16.790 -79.167  1.00 27.91           A  C
ATOM  23521  CG   PHE J 346       4.079 -17.941 -80.138  1.00 28.06           A  C
ATOM  23522  CD1  PHE J 346       3.533 -17.831 -81.417  1.00 27.87           A  C
ATOM  23523  CD2  PHE J 346       4.671 -19.151 -79.758  1.00 28.60           A  C
ATOM  23524  CE1  PHE J 346       3.602 -18.896 -82.300  1.00 27.82           A  C
ATOM  23525  CE2  PHE J 346       4.744 -20.222 -80.631  1.00 28.45           A  C
ATOM  23526  CZ   PHE J 346       4.213 -20.099 -81.903  1.00 28.03           A  C
ATOM  23527  N    PRO J 347       2.340 -14.274 -78.154  1.00 28.08           A  N
ATOM  23528  CA   PRO J 347       2.074 -13.356 -77.030  1.00 28.45           A  C
ATOM  23529  C    PRO J 347       3.075 -13.520 -75.875  1.00 29.06           A  C
ATOM  23530  O    PRO J 347       3.470 -14.641 -75.565  1.00 29.17           A  O
```

FIGURE 1 (cont'd)

```
ATOM  23531  CB   PRO J 347       0.688 -13.783 -76.556  1.00 28.19      A    C
ATOM  23532  CG   PRO J 347       0.063 -14.377 -77.743  1.00 27.74      A    C
ATOM  23533  CD   PRO J 347       1.143 -15.055 -78.504  1.00 27.73      A    C
ATOM  23534  N    ALA J 348       3.485 -12.413 -75.256  1.00 29.72      A    N
ATOM  23535  CA   ALA J 348       4.396 -12.467 -74.123  1.00 30.37      A    C
ATOM  23536  C    ALA J 348       3.882 -13.469 -73.074  1.00 30.64      A    C
ATOM  23537  O    ALA J 348       4.658 -14.268 -72.493  1.00 30.73      A    O
ATOM  23538  CB   ALA J 348       4.545 -11.084 -73.527  1.00 30.64      A    C
ATOM  23539  N    VAL J 349       2.558 -13.426 -72.882  1.00 30.75      A    N
ATOM  23540  CA   VAL J 349       1.832 -14.248 -71.902  1.00 30.94      A    C
ATOM  23541  C    VAL J 349       1.556 -15.689 -72.360  1.00 31.00      A    C
ATOM  23542  O    VAL J 349       0.684 -16.368 -71.807  1.00 31.11      A    O
ATOM  23543  CB   VAL J 349       0.480 -13.575 -71.483  1.00 30.89      A    C
ATOM  23544  CG1  VAL J 349       0.731 -12.251 -70.804  1.00 31.45      A    C
ATOM  23545  CG2  VAL J 349      -0.446 -13.373 -72.677  1.00 30.44      A    C
ATOM  23546  N    TRP J 350       2.310 -16.162 -73.347  1.00 31.10      A    N
ATOM  23547  CA   TRP J 350       2.012 -17.447 -73.982  1.00 31.16      A    C
ATOM  23548  C    TRP J 350       2.390 -18.632 -73.114  1.00 31.50      A    C
ATOM  23549  O    TRP J 350       3.479 -18.659 -72.530  1.00 31.72      A    O
ATOM  23550  CB   TRP J 350       2.705 -17.558 -75.342  1.00 30.96      A    C
ATOM  23551  CG   TRP J 350       2.329 -18.783 -76.098  1.00 30.52      A    C
ATOM  23552  CD1  TRP J 350       1.113 -19.053 -76.665  1.00 30.24      A    C
ATOM  23553  CD2  TRP J 350       3.165 -19.914 -76.377  1.00 30.17      A    C
ATOM  23554  CE2  TRP J 350       2.388 -20.834 -77.124  1.00 29.93      A    C
ATOM  23555  CE3  TRP J 350       4.496 -20.239 -76.077  1.00 30.20      A    C
ATOM  23556  NE1  TRP J 350       1.141 -20.286 -77.284  1.00 29.99      A    N
ATOM  23557  CZ2  TRP J 350       2.897 -22.060 -77.571  1.00 29.66      A    C
ATOM  23558  CZ3  TRP J 350       5.007 -21.470 -76.525  1.00 30.02      A    C
ATOM  23559  CH2  TRP J 350       4.203 -22.361 -77.261  1.00 29.67      A    C
ATOM  23560  N    HIS J 351       1.474 -19.604 -73.056  1.00 31.82      A    N
ATOM  23561  CA   HIS J 351       1.651 -20.858 -72.299  1.00 32.41      A    C
ATOM  23562  C    HIS J 351       2.108 -20.600 -70.858  1.00 32.97      A    C
ATOM  23563  O    HIS J 351       3.067 -21.219 -70.360  1.00 33.20      A    O
ATOM  23564  CB   HIS J 351       2.602 -21.832 -73.031  1.00 32.38      A    C
ATOM  23565  CG   HIS J 351       1.939 -22.650 -74.104  1.00 32.42      A    C
ATOM  23566  CD2  HIS J 351       0.778 -22.466 -74.779  1.00 32.07      A    C
ATOM  23567  ND1  HIS J 351       2.476 -23.828 -74.583  1.00 32.52      A    N
ATOM  23568  CE1  HIS J 351       1.680 -24.326 -75.512  1.00 32.25      A    C
ATOM  23569  NE2  HIS J 351       0.643 -23.520 -75.650  1.00 31.85      A    N
ATOM  23570  N    THR J 352       1.411 -19.662 -70.212  1.00 33.41      A    N
ATOM  23571  CA   THR J 352       1.680 -19.273 -68.829  1.00 33.95      A    C
ATOM  23572  C    THR J 352       0.388 -18.804 -68.161  1.00 34.22      A    C
ATOM  23573  O    THR J 352      -0.528 -18.323 -68.853  1.00 33.98      A    O
ATOM  23574  CB   THR J 352       2.788 -18.171 -68.712  1.00 34.06      A    C
ATOM  23575  CG2  THR J 352       2.694 -17.161 -69.831  1.00 33.56      A    C
ATOM  23576  OG1  THR J 352       2.646 -17.471 -67.468  1.00 34.82      A    O
ATOM  23577  N    PRO J 353       0.312 -18.947 -66.812  1.00 34.75      A    N
ATOM  23578  CA   PRO J 353      -0.819 -18.469 -66.003  1.00 34.84      A    C
ATOM  23579  C    PRO J 353      -1.239 -17.047 -66.331  1.00 34.62      A    C
ATOM  23580  O    PRO J 353      -2.395 -16.671 -66.106  1.00 34.65      A    O
ATOM  23581  CB   PRO J 353      -0.262 -18.507 -64.583  1.00 35.24      A    C
ATOM  23582  CG   PRO J 353       0.714 -19.638 -64.602  1.00 35.53      A    C
ATOM  23583  CD   PRO J 353       1.304 -19.669 -65.980  1.00 35.00      A    C
ATOM  23584  N    ALA J 354      -0.300 -16.276 -66.869  1.00 34.33      A    N
ATOM  23585  CA   ALA J 354      -0.530 -14.882 -67.236  1.00 34.08      A    C
ATOM  23586  C    ALA J 354      -1.587 -14.693 -68.323  1.00 33.80      A    C
ATOM  23587  O    ALA J 354      -2.255 -13.655 -68.362  1.00 33.73      A    O
ATOM  23588  CB   ALA J 354       0.766 -14.245 -67.652  1.00 34.07      A    C
ATOM  23589  N    ASP J 355      -1.734 -15.696 -69.193  1.00 33.59      A    N
ATOM  23590  CA   ASP J 355      -2.710 -15.647 -70.292  1.00 33.37      A    C
ATOM  23591  C    ASP J 355      -4.149 -15.701 -69.767  1.00 33.51      A    C
ATOM  23592  O    ASP J 355      -4.817 -16.737 -69.841  1.00 33.40      A    O
ATOM  23593  CB   ASP J 355      -2.453 -16.771 -71.317  1.00 33.06      A    C
ATOM  23594  CG   ASP J 355      -3.214 -16.562 -72.639  1.00 32.54      A    C
ATOM  23595  OD1  ASP J 355      -4.002 -15.589 -72.737  1.00 32.71      A    O
```

FIGURE 1 (cont'd)

```
ATOM  23596  OD2 ASP J 355      -3.025 -17.376 -73.579  1.00 31.66      A  O
ATOM  23597  N   THR J 356      -4.605 -14.576 -69.228  1.00 33.78      A  N
ATOM  23598  CA  THR J 356      -5.970 -14.450 -68.727  1.00 34.01      A  C
ATOM  23599  C   THR J 356      -6.620 -13.185 -69.300  1.00 34.46      A  C
ATOM  23600  O   THR J 356      -5.966 -12.416 -70.024  1.00 34.36      A  O
ATOM  23601  CB  THR J 356      -6.013 -14.425 -67.180  1.00 33.38      A  C
ATOM  23602  OG1 THR J 356      -5.209 -13.344 -66.698  1.00 33.38      A  O
ATOM  23603  N   GLU J 357      -7.902 -12.986 -68.975  1.00 35.04      A  N
ATOM  23604  CA  GLU J 357      -8.677 -11.853 -69.454  1.00 35.55      A  C
ATOM  23605  C   GLU J 357      -7.942 -10.544 -69.182  1.00 35.94      A  C
ATOM  23606  O   GLU J 357      -7.836  -9.679 -70.076  1.00 35.90      A  O
ATOM  23607  CB  GLU J 357     -10.060 -11.844 -68.800  1.00 35.73      A  C
ATOM  23608  CG  GLU J 357     -10.947 -10.663 -69.205  1.00 36.39      A  C
ATOM  23609  CD  GLU J 357     -12.392 -10.780 -68.710  1.00 37.46      A  C
ATOM  23610  OE1 GLU J 357     -12.745 -11.803 -68.064  1.00 38.20      A  O
ATOM  23611  OE2 GLU J 357     -13.185  -9.840 -68.971  1.00 37.79      A  O
ATOM  23612  N   VAL J 358      -7.416 -10.422 -67.960  1.00 36.44      A  N
ATOM  23613  CA  VAL J 358      -6.703  -9.218 -67.494  1.00 36.87      A  C
ATOM  23614  C   VAL J 358      -5.601  -8.679 -68.437  1.00 36.69      A  C
ATOM  23615  O   VAL J 358      -5.292  -7.477 -68.428  1.00 36.92      A  O
ATOM  23616  CB  VAL J 358      -6.085  -9.456 -66.099  1.00 37.19      A  C
ATOM  23617  CG1 VAL J 358      -6.664  -8.464 -65.097  1.00 37.99      A  C
ATOM  23618  N   ASN J 359      -5.025  -9.567 -69.249  1.00 36.28      A  N
ATOM  23619  CA  ASN J 359      -3.851  -9.233 -70.073  1.00 35.97      A  C
ATOM  23620  C   ASN J 359      -4.108  -9.083 -71.588  1.00 35.41      A  C
ATOM  23621  O   ASN J 359      -3.160  -8.924 -72.387  1.00 35.25      A  O
ATOM  23622  CB  ASN J 359      -2.717 -10.238 -69.808  1.00 36.15      A  C
ATOM  23623  CG  ASN J 359      -2.149 -10.131 -68.388  1.00 37.14      A  C
ATOM  23624  ND2 ASN J 359      -2.611  -9.136 -67.627  1.00 38.07      A  N
ATOM  23625  OD1 ASN J 359      -1.298 -10.935 -67.986  1.00 37.72      A  O
ATOM  23626  N   LEU J 360      -5.387  -9.144 -71.967  1.00 34.88      A  N
ATOM  23627  CA  LEU J 360      -5.805  -8.877 -73.339  1.00 34.38      A  C
ATOM  23628  C   LEU J 360      -5.866  -7.364 -73.557  1.00 34.44      A  C
ATOM  23629  O   LEU J 360      -6.066  -6.601 -72.600  1.00 34.88      A  O
ATOM  23630  CB  LEU J 360      -7.179  -9.505 -73.616  1.00 34.07      A  C
ATOM  23631  CG  LEU J 360      -7.363 -10.997 -73.313  1.00 33.51      A  C
ATOM  23632  CD1 LEU J 360      -8.821 -11.378 -73.566  1.00 32.93      A  C
ATOM  23633  CD2 LEU J 360      -6.381 -11.895 -74.110  1.00 33.10      A  C
ATOM  23634  N   HIS J 361      -5.673  -6.938 -74.807  1.00 34.14      A  N
ATOM  23635  CA  HIS J 361      -5.878  -5.547 -75.188  1.00 33.94      A  C
ATOM  23636  C   HIS J 361      -7.231  -5.405 -75.888  1.00 34.22      A  C
ATOM  23637  O   HIS J 361      -7.315  -5.552 -77.112  1.00 34.01      A  O
ATOM  23638  CB  HIS J 361      -4.749  -5.054 -76.094  1.00 33.58      A  C
ATOM  23639  CG  HIS J 361      -4.564  -3.573 -76.035  1.00 32.85      A  C
ATOM  23640  CD2 HIS J 361      -3.688  -2.813 -75.331  1.00 35.41      A  C
ATOM  23641  ND1 HIS J 361      -5.394  -2.690 -76.698  1.00 31.63      A  N
ATOM  23642  CE1 HIS J 361      -5.015  -1.449 -76.432  1.00 31.72      A  C
ATOM  23643  NE2 HIS J 361      -3.991  -1.495 -75.595  1.00 35.56      A  N
ATOM  23644  N   PRO J 362      -8.302  -5.135 -75.113  1.00 34.70      A  N
ATOM  23645  CA  PRO J 362      -9.671  -5.095 -75.670  1.00 34.94      A  C
ATOM  23646  C   PRO J 362      -9.814  -4.308 -76.987  1.00 34.94      A  C
ATOM  23647  O   PRO J 362     -10.502  -4.784 -77.899  1.00 34.75      A  O
ATOM  23648  CB  PRO J 362     -10.501  -4.451 -74.544  1.00 35.22      A  C
ATOM  23649  CG  PRO J 362      -9.774  -4.843 -73.296  1.00 35.34      A  C
ATOM  23650  CD  PRO J 362      -8.296  -4.848 -73.665  1.00 35.02      A  C
ATOM  23651  N   PRO J 363      -9.171  -3.114 -77.091  1.00 35.11      A  N
ATOM  23652  CA  PRO J 363      -9.179  -2.447 -78.402  1.00 35.08      A  C
ATOM  23653  C   PRO J 363      -8.678  -3.376 -79.525  1.00 34.69      A  C
ATOM  23654  O   PRO J 363      -9.406  -3.603 -80.500  1.00 34.58      A  O
ATOM  23655  CB  PRO J 363      -8.218  -1.252 -78.192  1.00 35.34      A  C
ATOM  23656  CG  PRO J 363      -8.354  -0.918 -76.740  1.00 35.72      A  C
ATOM  23657  CD  PRO J 363      -8.490  -2.278 -76.066  1.00 35.52      A  C
ATOM  23658  N   THR J 364      -7.466  -3.921 -79.361  1.00 34.33      A  N
ATOM  23659  CA  THR J 364      -6.871  -4.796 -80.364  1.00 33.99      A  C
ATOM  23660  C   THR J 364      -7.865  -5.882 -80.773  1.00 33.90      A  C
```

FIGURE 1 (cont'd)

```
ATOM  23661  O    THR J 364      -8.016  -6.183 -81.962  1.00 33.70       A  O
ATOM  23662  CB   THR J 364      -5.536  -5.437 -79.878  1.00 33.88       A  C
ATOM  23663  CG2  THR J 364      -4.896  -6.270 -80.998  1.00 33.51       A  C
ATOM  23664  OG1  THR J 364      -4.618  -4.416 -79.455  1.00 34.10       A  O
ATOM  23665  N    VAL J 365      -8.550  -6.445 -79.779  1.00 34.01       A  N
ATOM  23666  CA   VAL J 365      -9.561  -7.483 -80.022  1.00 34.15       A  C
ATOM  23667  C    VAL J 365     -10.654  -7.016 -81.007  1.00 34.35       A  C
ATOM  23668  O    VAL J 365     -10.889  -7.659 -82.046  1.00 34.14       A  O
ATOM  23669  CB   VAL J 365     -10.216  -7.987 -78.696  1.00 34.16       A  C
ATOM  23670  CG1  VAL J 365      -9.199  -8.759 -77.857  1.00 34.03       A  C
ATOM  23671  CG2  VAL J 365     -11.468  -8.848 -78.992  1.00 33.97       A  C
ATOM  23672  N    HIS J 366     -11.302  -5.897 -80.674  1.00 34.74       A  N
ATOM  23673  CA   HIS J 366     -12.407  -5.367 -81.466  1.00 35.18       A  C
ATOM  23674  C    HIS J 366     -11.956  -4.980 -82.880  1.00 35.39       A  C
ATOM  23675  O    HIS J 366     -12.652  -5.269 -83.870  1.00 35.46       A  O
ATOM  23676  CB   HIS J 366     -13.053  -4.182 -80.751  1.00 35.40       A  C
ATOM  23677  CG   HIS J 366     -13.696  -4.538 -79.442  1.00 35.58       A  C
ATOM  23678  CD2  HIS J 366     -13.579  -3.984 -78.209  1.00 37.09       A  C
ATOM  23679  ND1  HIS J 366     -14.634  -5.544 -79.321  1.00 35.60       A  N
ATOM  23680  CE1  HIS J 366     -15.031  -5.624 -78.061  1.00 35.60       A  C
ATOM  23681  NE2  HIS J 366     -14.426  -4.673 -77.371  1.00 37.19       A  N
ATOM  23682  N    ASN J 367     -10.783  -4.347 -82.965  1.00 35.46       A  N
ATOM  23683  CA   ASN J 367     -10.141  -4.059 -84.254  1.00 35.50       A  C
ATOM  23684  C    ASN J 367     -10.142  -5.303 -85.139  1.00 35.29       A  C
ATOM  23685  O    ASN J 367     -10.642  -5.277 -86.278  1.00 35.38       A  O
ATOM  23686  CB   ASN J 367      -8.696  -3.558 -84.048  1.00 35.55       A  C
ATOM  23687  CG   ASN J 367      -8.633  -2.130 -83.524  1.00 36.16       A  C
ATOM  23688  ND2  ASN J 367      -7.420  -1.577 -83.488  1.00 36.20       A  N
ATOM  23689  OD1  ASN J 367      -9.664  -1.525 -83.163  1.00 37.09       A  O
ATOM  23690  N    LEU J 368      -9.604  -6.390 -84.583  1.00 35.00       A  N
ATOM  23691  CA   LEU J 368      -9.480  -7.648 -85.302  1.00 34.78       A  C
ATOM  23692  C    LEU J 368     -10.830  -8.132 -85.791  1.00 34.93       A  C
ATOM  23693  O    LEU J 368     -10.927  -8.705 -86.880  1.00 35.06       A  O
ATOM  23694  CB   LEU J 368      -8.795  -8.721 -84.445  1.00 34.39       A  C
ATOM  23695  CG   LEU J 368      -7.285  -8.562 -84.194  1.00 33.78       A  C
ATOM  23696  CD1  LEU J 368      -6.814  -9.558 -83.155  1.00 33.49       A  C
ATOM  23697  CD2  LEU J 368      -6.449  -8.693 -85.472  1.00 32.90       A  C
ATOM  23698  N    ALA J 369     -11.869  -7.884 -84.998  1.00 34.20       A  N
ATOM  23699  CA   ALA J 369     -13.215  -8.325 -85.361  1.00 33.60       A  C
ATOM  23700  C    ALA J 369     -13.805  -7.469 -86.483  1.00 34.58       A  C
ATOM  23701  O    ALA J 369     -14.517  -7.978 -87.377  1.00 35.73       A  O
ATOM  23702  CB   ALA J 369     -14.127  -8.328 -84.149  1.00 24.60       A  C
ATOM  23703  N    ARG J 370     -13.503  -6.175 -86.436  1.00 35.18       A  N
ATOM  23704  CA   ARG J 370     -13.931  -5.278 -87.499  1.00 34.87       A  C
ATOM  23705  C    ARG J 370     -13.273  -5.695 -88.812  1.00 34.25       A  C
ATOM  23706  O    ARG J 370     -13.961  -5.835 -89.829  1.00 34.14       A  O
ATOM  23707  CB   ARG J 370     -13.625  -3.822 -87.136  1.00 35.17       A  C
ATOM  23708  CG   ARG J 370     -14.439  -3.308 -85.938  1.00 35.48       A  C
ATOM  23709  CD   ARG J 370     -14.222  -1.811 -85.709  1.00 35.80       A  C
ATOM  23710  NE   ARG J 370     -15.067  -1.278 -84.637  1.00 35.94       A  N
ATOM  23711  CZ   ARG J 370     -15.536  -0.034 -84.611  1.00 36.11       A  C
ATOM  23712  NH1  ARG J 370     -15.280   0.803 -85.619  1.00 36.87       A  N
ATOM  23713  NH2  ARG J 370     -16.286   0.363 -83.594  1.00 38.20       A  N
ATOM  23714  N    ILE J 371     -11.961  -5.934 -88.764  1.00 33.46       A  N
ATOM  23715  CA   ILE J 371     -11.216  -6.407 -89.927  1.00 32.87       A  C
ATOM  23716  C    ILE J 371     -11.770  -7.739 -90.473  1.00 32.82       A  C
ATOM  23717  O    ILE J 371     -11.996  -7.885 -91.690  1.00 32.89       A  O
ATOM  23718  CB   ILE J 371      -9.712  -6.523 -89.619  1.00 32.55       A  C
ATOM  23719  CG1  ILE J 371      -9.131  -5.134 -89.361  1.00 32.51       A  C
ATOM  23720  CG2  ILE J 371      -8.965  -7.206 -90.769  1.00 32.05       A  C
ATOM  23721  CD1  ILE J 371      -7.721  -5.145 -88.787  1.00 32.25       A  C
ATOM  23722  N    LEU J 372     -12.000  -8.697 -89.573  1.00 32.63       A  N
ATOM  23723  CA   LEU J 372     -12.530 -10.015 -89.946  1.00 32.48       A  C
ATOM  23724  C    LEU J 372     -13.925  -9.943 -90.551  1.00 32.80       A  C
ATOM  23725  O    LEU J 372     -14.181 -10.573 -91.585  1.00 32.71       A  O
```

FIGURE 1 (cont'd)

```
ATOM  23726  CB   LEU J 372     -12.531 -10.959 -88.739  1.00 32.11      A    C
ATOM  23727  CG   LEU J 372     -11.398 -11.984 -88.586  1.00 31.37      A    C
ATOM  23728  CD1  LEU J 372     -10.168 -11.708 -89.458  1.00 30.84      A    C
ATOM  23729  CD2  LEU J 372     -11.002 -12.142 -87.138  1.00 30.89      A    C
ATOM  23730  N    ALA J 373     -14.808  -9.175 -89.901  1.00 33.21      A    N
ATOM  23731  CA   ALA J 373     -16.203  -9.026 -90.332  1.00 33.61      A    C
ATOM  23732  C    ALA J 373     -16.284  -8.481 -91.758  1.00 33.91      A    C
ATOM  23733  O    ALA J 373     -17.104  -8.952 -92.567  1.00 34.02      A    O
ATOM  23734  CB   ALA J 373     -16.976  -8.128 -89.361  1.00 33.71      A    C
ATOM  23735  N    VAL J 374     -15.426  -7.497 -92.053  1.00 34.05      A    N
ATOM  23736  CA   VAL J 374     -15.343  -6.920 -93.387  1.00 34.31      A    C
ATOM  23737  C    VAL J 374     -14.857  -7.988 -94.351  1.00 34.24      A    C
ATOM  23738  O    VAL J 374     -15.492  -8.232 -95.387  1.00 34.50      A    O
ATOM  23739  CB   VAL J 374     -14.413  -5.693 -93.430  1.00 34.39      A    C
ATOM  23740  CG1  VAL J 374     -14.068  -5.314 -94.879  1.00 34.60      A    C
ATOM  23741  CG2  VAL J 374     -15.066  -4.522 -92.710  1.00 34.82      A    C
ATOM  23742  N    PHE J 375     -13.750  -8.638 -93.990  1.00 33.96      A    N
ATOM  23743  CA   PHE J 375     -13.194  -9.713 -94.810  1.00 33.80      A    C
ATOM  23744  C    PHE J 375     -14.234 -10.774 -95.137  1.00 34.07      A    C
ATOM  23745  O    PHE J 375     -14.423 -11.123 -96.298  1.00 34.13      A    O
ATOM  23746  CB   PHE J 375     -12.002 -10.361 -94.115  1.00 33.36      A    C
ATOM  23747  CG   PHE J 375     -11.394 -11.483 -94.895  1.00 32.62      A    C
ATOM  23748  CD1  PHE J 375     -10.201 -11.300 -95.569  1.00 32.48      A    C
ATOM  23749  CD2  PHE J 375     -12.011 -12.725 -94.951  1.00 32.09      A    C
ATOM  23750  CE1  PHE J 375      -9.623 -12.341 -96.288  1.00 32.42      A    C
ATOM  23751  CE2  PHE J 375     -11.447 -13.769 -95.662  1.00 32.25      A    C
ATOM  23752  CZ   PHE J 375     -10.248 -13.580 -96.334  1.00 32.36      A    C
ATOM  23753  N    LEU J 376     -14.901 -11.270 -94.099  1.00 34.44      A    N
ATOM  23754  CA   LEU J 376     -15.908 -12.309 -94.245  1.00 34.91      A    C
ATOM  23755  C    LEU J 376     -16.977 -11.853 -95.235  1.00 35.71      A    C
ATOM  23756  O    LEU J 376     -17.385 -12.629 -96.108  1.00 35.83      A    O
ATOM  23757  CB   LEU J 376     -16.532 -12.667 -92.887  1.00 34.59      A    C
ATOM  23758  CG   LEU J 376     -16.866 -14.145 -92.635  1.00 33.85      A    C
ATOM  23759  N    ALA J 377     -17.402 -10.592 -95.103  1.00 36.60      A    N
ATOM  23760  CA   ALA J 377     -18.424  -9.996 -95.983  1.00 37.49      A    C
ATOM  23761  C    ALA J 377     -17.930  -9.831 -97.422  1.00 37.96      A    C
ATOM  23762  O    ALA J 377     -18.658 -10.123 -98.380  1.00 38.24      A    O
ATOM  23763  CB   ALA J 377     -18.902  -8.657 -95.431  1.00 37.63      A    C
ATOM  23764  N    GLU J 378     -16.695  -9.361 -97.570  1.00 38.24      A    N
ATOM  23765  CA   GLU J 378     -16.117  -9.207 -98.894  1.00 38.66      A    C
ATOM  23766  C    GLU J 378     -15.942 -10.569 -99.560  1.00 38.62      A    C
ATOM  23767  O    GLU J 378     -16.427 -10.763-100.674  1.00 38.94      A    O
ATOM  23768  CB   GLU J 378     -14.809  -8.398 -98.856  1.00 38.73      A    C
ATOM  23769  CG   GLU J 378     -15.036  -6.877 -98.764  1.00 39.93      A    C
ATOM  23770  CD   GLU J 378     -13.753  -6.022 -98.922  1.00 41.35      A    C
ATOM  23771  OE1  GLU J 378     -12.676  -6.579 -99.264  1.00 41.82      A    O
ATOM  23772  OE2  GLU J 378     -13.827  -4.777 -98.704  1.00 41.98      A    O
ATOM  23773  N    TYR J 379     -15.302 -11.513 -98.866  1.00 38.42      A    N
ATOM  23774  CA   TYR J 379     -15.030 -12.847 -99.430  1.00 38.43      A    C
ATOM  23775  C    TYR J 379     -16.303 -13.565 -99.901  1.00 39.00      A    C
ATOM  23776  O    TYR J 379     -16.327 -14.169-100.976  1.00 39.13      A    O
ATOM  23777  CB   TYR J 379     -14.270 -13.729 -98.428  1.00 37.87      A    C
ATOM  23778  CG   TYR J 379     -13.774 -15.050 -98.992  1.00 37.05      A    C
ATOM  23779  CD1  TYR J 379     -12.421 -15.241 -99.270  1.00 36.34      A    C
ATOM  23780  CD2  TYR J 379     -14.655 -16.112 -99.234  1.00 36.80      A    C
ATOM  23781  CE1  TYR J 379     -11.953 -16.458 -99.785  1.00 36.20      A    C
ATOM  23782  CE2  TYR J 379     -14.205 -17.323 -99.754  1.00 36.55      A    C
ATOM  23783  CZ   TYR J 379     -12.852 -17.495-100.028  1.00 36.24      A    C
ATOM  23784  OH   TYR J 379     -12.404 -18.700-100.539  1.00 35.93      A    O
ATOM  23785  N    LEU J 380     -17.351 -13.500 -99.088  1.00 39.68      A    N
ATOM  23786  CA   LEU J 380     -18.622 -14.140 -99.415  1.00 40.60      A    C
ATOM  23787  C    LEU J 380     -19.565 -13.209-100.173  1.00 41.73      A    C
ATOM  23788  O    LEU J 380     -20.748 -13.535-100.360  1.00 41.96      A    O
ATOM  23789  CB   LEU J 380     -19.297 -14.654 -98.137  1.00 40.21      A    C
ATOM  23790  CG   LEU J 380     -19.225 -16.146 -97.770  1.00 39.80      A    C
```

FIGURE 1 (cont'd)

```
ATOM  23791  CD1  LEU J 380   -17.913 -16.813 -98.207  1.00 39.42      A    C
ATOM  23792  CD2  LEU J 380   -19.457 -16.341 -96.271  1.00 39.51      A    C
ATOM  23793  N    GLY J 381   -19.028 -12.060-100.600  1.00 45.25      A    N
ATOM  23794  CA   GLY J 381   -19.796 -11.009-101.272  1.00 48.83      A    C
ATOM  23795  C    GLY J 381   -21.113 -10.732-100.571  1.00 51.17      A    C
ATOM  23796  O    GLY J 381   -22.110 -10.404-101.219  1.00 51.46      A    O
ATOM  23797  N    LEU J 382   -21.105 -10.875 -99.243  1.00 52.92      A    N
ATOM  23798  CA   LEU J 382   -22.316 -10.800 -98.413  1.00 54.31      A    C
ATOM  23799  C    LEU J 382   -23.107  -9.519 -98.644  1.00 54.84      A    C
ATOM  23800  O    LEU J 382   -24.322  -9.490 -98.421  1.00 55.02      A    O
ATOM  23801  CB   LEU J 382   -21.981 -10.953 -96.913  1.00 54.50      A    C
ATOM  23802  CG   LEU J 382   -21.680 -12.353 -96.336  1.00 54.77      A    C
ATOM  23803  CD1  LEU J 382   -21.285 -12.266 -94.848  1.00 54.60      A    C
ATOM  23804  CD2  LEU J 382   -22.831 -13.385 -96.556  1.00 55.39      A    C
ATOM  23805  OXT  LEU J 382   -22.540  -8.503 -99.064  1.00 55.22      A    O
TER   23806       LEU J 382
ATOM  23807  N    PRO K  77    32.944 -14.295 -80.524  1.00 54.69      A    N
ATOM  23808  CA   PRO K  77    34.147 -15.136 -80.560  1.00 55.53      A    C
ATOM  23809  C    PRO K  77    35.023 -14.957 -79.321  1.00 55.78      A    C
ATOM  23810  O    PRO K  77    35.023 -13.870 -78.724  1.00 55.67      A    O
ATOM  23811  CB   PRO K  77    34.880 -14.650 -81.814  1.00 56.07      A    C
ATOM  23812  CG   PRO K  77    34.455 -13.223 -81.971  1.00 55.93      A    C
ATOM  23813  CD   PRO K  77    33.091 -13.066 -81.326  1.00 54.98      A    C
ATOM  23814  N    GLU K  78    35.762 -16.018 -78.965  1.00 55.92      A    N
ATOM  23815  CA   GLU K  78    36.614 -16.067 -77.754  1.00 55.82      A    C
ATOM  23816  C    GLU K  78    37.436 -14.793 -77.446  1.00 57.11      A    C
ATOM  23817  O    GLU K  78    37.516 -14.352 -76.276  1.00 57.27      A    O
ATOM  23818  CB   GLU K  78    37.554 -17.281 -77.804  1.00 53.81      A    C
ATOM  23819  CG   GLU K  78    37.116 -18.455 -76.965  1.00 51.29      A    C
ATOM  23820  N    ALA K  79    38.045 -14.226 -78.498  1.00 58.35      A    N
ATOM  23821  CA   ALA K  79    38.893 -13.027 -78.396  1.00 58.97      A    C
ATOM  23822  C    ALA K  79    38.130 -11.818 -77.837  1.00 58.73      A    C
ATOM  23823  O    ALA K  79    38.607 -11.163 -76.895  1.00 58.86      A    O
ATOM  23824  CB   ALA K  79    39.525 -12.697 -79.755  1.00 59.75      A    C
ATOM  23825  N    ARG K  80    36.950 -11.540 -78.409  1.00 58.00      A    N
ATOM  23826  CA   ARG K  80    36.102 -10.429 -77.960  1.00 57.03      A    C
ATOM  23827  C    ARG K  80    35.460 -10.749 -76.611  1.00 56.76      A    C
ATOM  23828  O    ARG K  80    35.363  -9.881 -75.740  1.00 56.75      A    O
ATOM  23829  CB   ARG K  80    35.032 -10.085 -79.007  1.00 55.30      A    C
ATOM  23830  N    LEU K  81    35.040 -12.003 -76.448  1.00 56.46      A    N
ATOM  23831  CA   LEU K  81    34.415 -12.466 -75.206  1.00 55.90      A    C
ATOM  23832  C    LEU K  81    35.343 -12.251 -73.991  1.00 55.94      A    C
ATOM  23833  O    LEU K  81    34.942 -11.618 -72.998  1.00 55.54      A    O
ATOM  23834  CB   LEU K  81    33.975 -13.944 -75.337  1.00 55.71      A    C
ATOM  23835  CG   LEU K  81    33.128 -14.605 -74.230  1.00 54.92      A    C
ATOM  23836  CD1  LEU K  81    32.163 -15.622 -74.811  1.00 54.70      A    C
ATOM  23837  CD2  LEU K  81    33.994 -15.253 -73.139  1.00 54.80      A    C
ATOM  23838  N    ARG K  82    36.572 -12.770 -74.086  1.00 56.38      A    N
ATOM  23839  CA   ARG K  82    37.541 -12.664 -72.998  1.00 56.82      A    C
ATOM  23840  C    ARG K  82    37.944 -11.206 -72.735  1.00 56.73      A    C
ATOM  23841  O    ARG K  82    38.264 -10.838 -71.594  1.00 56.67      A    O
ATOM  23842  CB   ARG K  82    38.764 -13.540 -73.275  1.00 57.37      A    C
ATOM  23843  CG   ARG K  82    39.626 -13.763 -72.038  1.00 58.30      A    C
ATOM  23844  CD   ARG K  82    40.623 -14.882 -72.244  1.00 59.67      A    C
ATOM  23845  NE   ARG K  82    40.127 -16.173 -71.763  1.00 59.80      A    N
ATOM  23846  CZ   ARG K  82    39.478 -17.071 -72.506  1.00 59.83      A    C
ATOM  23847  NH1  ARG K  82    39.207 -16.842 -73.795  1.00 60.01      A    N
ATOM  23848  NH2  ARG K  82    39.097 -18.212 -71.951  1.00 59.58      A    N
ATOM  23849  N    ARG K  83    37.908 -10.395 -73.798  1.00 56.50      A    N
ATOM  23850  CA   ARG K  83    38.132  -8.938 -73.737  1.00 55.96      A    C
ATOM  23851  C    ARG K  83    36.979  -8.196 -73.016  1.00 55.54      A    C
ATOM  23852  O    ARG K  83    37.213  -7.262 -72.233  1.00 55.68      A    O
ATOM  23853  CB   ARG K  83    38.374  -8.398 -75.158  1.00 54.94      A    C
ATOM  23854  CG   ARG K  83    38.032  -6.935 -75.417  1.00 54.48      A    C
ATOM  23855  CD   ARG K  83    37.857  -6.753 -76.916  1.00 54.60      A    C
```

FIGURE 1 (cont'd)

```
ATOM  23856  NE   ARG K  83      37.365  -5.437 -77.297  1.00 54.07      A  N
ATOM  23857  N    VAL K  84      35.747  -8.637 -73.277  1.00 54.76      A  N
ATOM  23858  CA   VAL K  84      34.538  -8.082 -72.647  1.00 53.67      A  C
ATOM  23859  C    VAL K  84      34.395  -8.496 -71.177  1.00 53.00      A  C
ATOM  23860  O    VAL K  84      34.238  -7.633 -70.308  1.00 52.80      A  O
ATOM  23861  CB   VAL K  84      33.247  -8.462 -73.442  1.00 53.55      A  C
ATOM  23862  CG1  VAL K  84      33.161  -7.655 -74.746  1.00 53.57      A  C
ATOM  23863  CG2  VAL K  84      31.975  -8.271 -72.583  1.00 52.80      A  C
ATOM  23864  N    VAL K  85      34.438  -9.807 -70.916  1.00 52.19      A  N
ATOM  23865  CA   VAL K  85      34.464 -10.335 -69.550  1.00 51.38      A  C
ATOM  23866  C    VAL K  85      35.579  -9.677 -68.719  1.00 51.81      A  C
ATOM  23867  O    VAL K  85      35.445  -9.508 -67.500  1.00 51.98      A  O
ATOM  23868  CB   VAL K  85      34.658 -11.860 -69.535  1.00 49.82      A  C
ATOM  23869  N    GLY K  86      36.670  -9.303 -69.394  1.00 52.14      A  N
ATOM  23870  CA   GLY K  86      37.770  -8.544 -68.787  1.00 52.06      A  C
ATOM  23871  C    GLY K  86      37.461  -7.090 -68.448  1.00 51.67      A  C
ATOM  23872  O    GLY K  86      38.103  -6.507 -67.575  1.00 51.89      A  O
ATOM  23873  N    GLN K  87      36.480  -6.507 -69.138  1.00 51.02      A  N
ATOM  23874  CA   GLN K  87      36.076  -5.109 -68.926  1.00 50.38      A  C
ATOM  23875  C    GLN K  87      35.282  -4.872 -67.633  1.00 49.63      A  C
ATOM  23876  O    GLN K  87      35.195  -3.736 -67.155  1.00 49.56      A  O
ATOM  23877  N    LEU K  88      34.689  -5.929 -67.083  1.00 48.76      A  N
ATOM  23878  CA   LEU K  88      34.028  -5.830 -65.789  1.00 48.07      A  C
ATOM  23879  C    LEU K  88      35.068  -5.723 -64.676  1.00 48.46      A  C
ATOM  23880  O    LEU K  88      35.991  -6.549 -64.612  1.00 48.68      A  O
ATOM  23881  CB   LEU K  88      33.143  -7.047 -65.533  1.00 47.38      A  C
ATOM  23882  CG   LEU K  88      31.889  -7.267 -66.389  1.00 46.08      A  C
ATOM  23883  CD1  LEU K  88      31.402  -8.690 -66.185  1.00 48.18      A  C
ATOM  23884  CD2  LEU K  88      30.745  -6.252 -66.097  1.00 47.07      A  C
ATOM  23885  N    ASP K  89      34.927  -4.705 -63.817  1.00 48.77      A  N
ATOM  23886  CA   ASP K  89      35.788  -4.560 -62.635  1.00 49.16      A  C
ATOM  23887  C    ASP K  89      35.071  -5.036 -61.362  1.00 49.23      A  C
ATOM  23888  O    ASP K  89      34.172  -4.336 -60.875  1.00 49.00      A  O
ATOM  23889  CB   ASP K  89      36.280  -3.114 -62.475  1.00 49.34      A  C
ATOM  23890  CG   ASP K  89      37.282  -2.958 -61.318  1.00 49.63      A  C
ATOM  23891  OD1  ASP K  89      36.859  -2.615 -60.187  1.00 52.19      A  O
ATOM  23892  OD2  ASP K  89      38.502  -3.183 -61.545  1.00 52.25      A  O
ATOM  23893  N    PRO K  90      35.473  -6.222 -60.824  1.00 49.46      A  N
ATOM  23894  CA   PRO K  90      34.826  -6.847 -59.660  1.00 49.38      A  C
ATOM  23895  C    PRO K  90      34.776  -5.970 -58.407  1.00 49.32      A  C
ATOM  23896  O    PRO K  90      33.740  -5.938 -57.723  1.00 49.04      A  O
ATOM  23897  CB   PRO K  90      35.691  -8.094 -59.401  1.00 49.49      A  C
ATOM  23898  CG   PRO K  90      36.256  -8.428 -60.727  1.00 49.76      A  C
ATOM  23899  CD   PRO K  90      36.559  -7.081 -61.341  1.00 49.81      A  C
ATOM  23900  N    GLN K  91      35.875  -5.272 -58.108  1.00 49.51      A  N
ATOM  23901  CA   GLN K  91      35.903  -4.361 -56.955  1.00 49.60      A  C
ATOM  23902  C    GLN K  91      35.091  -3.065 -57.187  1.00 49.03      A  C
ATOM  23903  O    GLN K  91      34.601  -2.467 -56.211  1.00 49.09      A  O
ATOM  23904  CB   GLN K  91      37.341  -4.088 -56.454  1.00 50.20      A  C
ATOM  23905  CG   GLN K  91      38.127  -2.978 -57.178  1.00 50.94      A  C
ATOM  23906  N    ARG K  92      34.941  -2.655 -58.461  1.00 48.16      A  N
ATOM  23907  CA   ARG K  92      34.074  -1.520 -58.855  1.00 47.13      A  C
ATOM  23908  C    ARG K  92      32.597  -1.834 -58.639  1.00 46.67      A  C
ATOM  23909  O    ARG K  92      31.853  -1.047 -58.058  1.00 46.55      A  O
ATOM  23910  CB   ARG K  92      34.304  -1.132 -60.316  1.00 46.96      A  C
ATOM  23911  CG   ARG K  92      33.310  -0.114 -60.885  1.00 45.18      A  C
ATOM  23912  CD   ARG K  92      33.650   0.258 -62.348  1.00 43.17      A  C
ATOM  23913  NE   ARG K  92      33.690  -0.922 -63.231  1.00 41.98      A  N
ATOM  23914  CZ   ARG K  92      33.489  -0.922 -64.553  1.00 46.99      A  C
ATOM  23915  NH1  ARG K  92      33.236   0.201 -65.204  1.00 47.57      A  N
ATOM  23916  NH2  ARG K  92      33.545  -2.064 -65.230  1.00 48.11      A  N
ATOM  23917  N    LEU K  93      32.183  -2.995 -59.125  1.00 46.10      A  N
ATOM  23918  CA   LEU K  93      30.846  -3.515 -58.868  1.00 45.51      A  C
ATOM  23919  C    LEU K  93      30.515  -3.429 -57.369  1.00 45.57      A  C
ATOM  23920  O    LEU K  93      29.510  -2.824 -56.979  1.00 45.46      A  O
```

FIGURE 1 (cont'd)

```
ATOM  23921  CB   LEU K  93      30.750  -4.985 -59.342  1.00 45.16      A    C
ATOM  23922  CG   LEU K  93      29.456  -5.509 -59.996  1.00 43.98      A    C
ATOM  23923  CD1  LEU K  93      28.158  -5.304 -59.150  1.00 42.77      A    C
ATOM  23924  CD2  LEU K  93      29.643  -6.928 -60.525  1.00 45.17      A    C
ATOM  23925  N    TRP K  94      31.383  -4.025 -56.547  1.00 45.71      A    N
ATOM  23926  CA   TRP K  94      31.140  -4.193 -55.124  1.00 45.76      A    C
ATOM  23927  C    TRP K  94      31.227  -2.891 -54.339  1.00 45.76      A    C
ATOM  23928  O    TRP K  94      30.438  -2.671 -53.411  1.00 45.65      A    O
ATOM  23929  CB   TRP K  94      32.119  -5.212 -54.539  1.00 45.96      A    C
ATOM  23930  CG   TRP K  94      31.566  -5.849 -53.333  1.00 46.42      A    C
ATOM  23931  CD1  TRP K  94      31.640  -5.384 -52.055  1.00 47.12      A    C
ATOM  23932  CD2  TRP K  94      30.802  -7.059 -53.282  1.00 46.51      A    C
ATOM  23933  CE2  TRP K  94      30.455  -7.277 -51.923  1.00 46.74      A    C
ATOM  23934  CE3  TRP K  94      30.382  -7.990 -54.250  1.00 46.31      A    C
ATOM  23935  NE1  TRP K  94      30.979  -6.236 -51.201  1.00 47.12      A    N
ATOM  23936  CZ2  TRP K  94      29.701  -8.400 -51.497  1.00 46.64      A    C
ATOM  23937  CZ3  TRP K  94      29.627  -9.112 -53.828  1.00 46.21      A    C
ATOM  23938  CH2  TRP K  94      29.297  -9.300 -52.459  1.00 46.36      A    C
ATOM  23939  N    SER K  95      32.175  -2.034 -54.723  1.00 45.79      A    N
ATOM  23940  CA   SER K  95      32.545  -0.872 -53.921  1.00 45.78      A    C
ATOM  23941  C    SER K  95      31.919   0.443 -54.381  1.00 45.20      A    C
ATOM  23942  O    SER K  95      31.348   1.167 -53.564  1.00 45.16      A    O
ATOM  23943  CB   SER K  95      34.065  -0.752 -53.849  1.00 46.27      A    C
ATOM  23944  OG   SER K  95      34.462  -0.526 -52.514  1.00 47.26      A    O
ATOM  23945  N    THR K  96      32.028   0.742 -55.678  1.00 44.51      A    N
ATOM  23946  CA   THR K  96      31.451   1.979 -56.274  1.00 43.86      A    C
ATOM  23947  C    THR K  96      29.924   1.940 -56.468  1.00 42.93      A    C
ATOM  23948  O    THR K  96      29.260   2.988 -56.420  1.00 43.00      A    O
ATOM  23949  CB   THR K  96      32.074   2.333 -57.660  1.00 44.03      A    C
ATOM  23950  OG1  THR K  96      33.439   1.899 -57.717  1.00 44.77      A    O
ATOM  23951  N    TYR K  97      29.385   0.735 -56.690  1.00 41.67      A    N
ATOM  23952  CA   TYR K  97      27.968   0.546 -57.047  1.00 40.30      A    C
ATOM  23953  C    TYR K  97      27.091  -0.160 -55.984  1.00 39.88      A    C
ATOM  23954  O    TYR K  97      25.983   0.310 -55.681  1.00 39.61      A    O
ATOM  23955  CB   TYR K  97      27.871  -0.170 -58.404  1.00 39.74      A    C
ATOM  23956  CG   TYR K  97      28.331   0.658 -59.600  1.00 38.91      A    C
ATOM  23957  CD1  TYR K  97      28.295   2.063 -59.573  1.00 37.74      A    C
ATOM  23958  CD2  TYR K  97      28.692   0.045 -60.807  1.00 43.81      A    C
ATOM  23959  CE1  TYR K  97      28.698   2.835 -60.666  1.00 37.75      A    C
ATOM  23960  CE2  TYR K  97      29.065   0.830 -61.938  1.00 46.33      A    C
ATOM  23961  CZ   TYR K  97      29.042   2.232 -61.850  1.00 45.46      A    C
ATOM  23962  OH   TYR K  97      29.398   3.052 -62.909  1.00 47.77      A    O
ATOM  23963  N    LEU K  98      27.589  -1.270 -55.426  1.00 39.64      A    N
ATOM  23964  CA   LEU K  98      26.813  -2.070 -54.477  1.00 39.47      A    C
ATOM  23965  C    LEU K  98      26.738  -1.488 -53.066  1.00 39.75      A    C
ATOM  23966  O    LEU K  98      25.634  -1.307 -52.529  1.00 39.65      A    O
ATOM  23967  CB   LEU K  98      27.326  -3.509 -54.393  1.00 39.28      A    C
ATOM  23968  CG   LEU K  98      26.549  -4.362 -53.375  1.00 39.06      A    C
ATOM  23969  CD1  LEU K  98      25.062  -4.527 -53.778  1.00 38.42      A    C
ATOM  23970  CD2  LEU K  98      27.228  -5.715 -53.158  1.00 39.18      A    C
ATOM  23971  N    ARG K  99      27.903  -1.235 -52.457  1.00 40.08      A    N
ATOM  23972  CA   ARG K  99      27.963  -0.697 -51.090  1.00 40.14      A    C
ATOM  23973  C    ARG K  99      27.234   0.641 -50.876  1.00 40.28      A    C
ATOM  23974  O    ARG K  99      26.557   0.783 -49.845  1.00 40.41      A    O
ATOM  23975  CB   ARG K  99      29.397  -0.657 -50.550  1.00 39.59      A    C
ATOM  23976  CG   ARG K  99      29.652  -1.728 -49.492  1.00 39.42      A    C
ATOM  23977  CD   ARG K  99      31.024  -1.581 -48.848  1.00 39.93      A    C
ATOM  23978  NE   ARG K  99      31.942  -2.631 -49.285  1.00 39.64      A    N
ATOM  23979  N    PRO K 100      27.346   1.609 -51.838  1.00 40.26      A    N
ATOM  23980  CA   PRO K 100      26.508   2.831 -51.746  1.00 40.19      A    C
ATOM  23981  C    PRO K 100      24.983   2.564 -51.664  1.00 39.82      A    C
ATOM  23982  O    PRO K 100      24.236   3.318 -51.006  1.00 40.00      A    O
ATOM  23983  CB   PRO K 100      26.831   3.582 -53.047  1.00 40.28      A    C
ATOM  23984  CG   PRO K 100      28.189   3.139 -53.395  1.00 40.50      A    C
ATOM  23985  CD   PRO K 100      28.275   1.695 -52.984  1.00 40.33      A    C
```

FIGURE 1 (cont'd)

```
ATOM  23986  N    LEU K 101     24.542   1.493 -52.328  1.00 39.20      A  N
ATOM  23987  CA   LEU K 101     23.125   1.093 -52.366  1.00 38.56      A  C
ATOM  23988  C    LEU K 101     22.602   0.446 -51.074  1.00 38.50      A  C
ATOM  23989  O    LEU K 101     21.386   0.430 -50.852  1.00 38.36      A  O
ATOM  23990  CB   LEU K 101     22.877   0.152 -53.556  1.00 38.13      A  C
ATOM  23991  CG   LEU K 101     22.330   0.715 -54.879  1.00 37.81      A  C
ATOM  23992  CD1  LEU K 101     22.843   2.112 -55.225  1.00 38.25      A  C
ATOM  23993  CD2  LEU K 101     22.610  -0.240 -56.034  1.00 37.50      A  C
ATOM  23994  N    LEU K 102     23.511  -0.065 -50.234  1.00 38.55      A  N
ATOM  23995  CA   LEU K 102     23.150  -0.851 -49.046  1.00 38.64      A  C
ATOM  23996  C    LEU K 102     22.757  -0.026 -47.795  1.00 38.98      A  C
ATOM  23997  O    LEU K 102     23.326  -0.190 -46.702  1.00 39.23      A  O
ATOM  23998  CB   LEU K 102     24.257  -1.872 -48.730  1.00 38.58      A  C
ATOM  23999  CG   LEU K 102     24.508  -2.981 -49.758  1.00 38.07      A  C
ATOM  24000  CD1  LEU K 102     25.744  -3.760 -49.372  1.00 38.25      A  C
ATOM  24001  CD2  LEU K 102     23.304  -3.901 -49.857  1.00 37.53      A  C
ATOM  24002  N    VAL K 103     21.765   0.848 -47.977  1.00 39.14      A  N
ATOM  24003  CA   VAL K 103     21.184   1.654 -46.893  1.00 39.44      A  C
ATOM  24004  C    VAL K 103     19.654   1.499 -46.849  1.00 39.14      A  C
ATOM  24005  O    VAL K 103     19.017   1.205 -47.876  1.00 38.86      A  O
ATOM  24006  CB   VAL K 103     21.556   3.165 -47.030  1.00 39.76      A  C
ATOM  24007  CG1  VAL K 103     21.212   3.708 -48.443  1.00 39.59      A  C
ATOM  24008  CG2  VAL K 103     23.031   3.399 -46.680  1.00 40.64      A  C
ATOM  24009  N    VAL K 104     19.069   1.689 -45.667  1.00 39.05      A  N
ATOM  24010  CA   VAL K 104     17.614   1.753 -45.552  1.00 38.76      A  C
ATOM  24011  C    VAL K 104     17.072   2.813 -46.523  1.00 39.00      A  C
ATOM  24012  O    VAL K 104     17.537   3.978 -46.532  1.00 39.31      A  O
ATOM  24013  CB   VAL K 104     17.158   2.089 -44.119  1.00 38.10      A  C
ATOM  24014  CG1  VAL K 104     15.784   1.459 -43.841  1.00 37.53      A  C
ATOM  24015  N    ARG K 105     16.098   2.404 -47.341  1.00 38.85      A  N
ATOM  24016  CA   ARG K 105     15.657   3.220 -48.486  1.00 38.58      A  C
ATOM  24017  C    ARG K 105     14.181   2.990 -48.872  1.00 38.56      A  C
ATOM  24018  O    ARG K 105     13.799   3.069 -50.063  1.00 38.25      A  O
ATOM  24019  CB   ARG K 105     16.590   2.986 -49.688  1.00 38.36      A  C
ATOM  24020  CG   ARG K 105     16.601   1.534 -50.165  1.00 37.73      A  C
ATOM  24021  CD   ARG K 105     17.833   1.196 -50.988  1.00 37.41      A  C
ATOM  24022  NE   ARG K 105     17.686  -0.098 -51.662  1.00 37.04      A  N
ATOM  24023  CZ   ARG K 105     18.160  -1.252 -51.203  1.00 36.80      A  C
ATOM  24024  NH1  ARG K 105     18.837  -1.291 -50.062  1.00 36.91      A  N
ATOM  24025  NH2  ARG K 105     17.963  -2.368 -51.898  1.00 36.41      A  N
ATOM  24026  N    THR K 106     13.364   2.705 -47.858  1.00 38.75      A  N
ATOM  24027  CA   THR K 106     11.921   2.603 -48.027  1.00 38.96      A  C
ATOM  24028  C    THR K 106     11.354   3.866 -48.705  1.00 39.02      A  C
ATOM  24029  O    THR K 106     11.863   4.971 -48.481  1.00 39.01      A  O
ATOM  24030  CB   THR K 106     11.249   2.410 -46.668  1.00 39.18      A  C
ATOM  24031  OG1  THR K 106     11.493   3.570 -45.854  1.00 39.86      A  O
ATOM  24032  N    PRO K 107     10.302   3.702 -49.535  1.00 39.14      A  N
ATOM  24033  CA   PRO K 107      9.731   4.800 -50.344  1.00 39.46      A  C
ATOM  24034  C    PRO K 107      9.584   6.158 -49.627  1.00 40.00      A  C
ATOM  24035  O    PRO K 107      9.134   6.207 -48.470  1.00 40.14      A  O
ATOM  24036  CB   PRO K 107      8.346   4.255 -50.740  1.00 39.36      A  C
ATOM  24037  CG   PRO K 107      8.536   2.772 -50.829  1.00 38.93      A  C
ATOM  24038  CD   PRO K 107      9.594   2.424 -49.777  1.00 39.02      A  C
ATOM  24039  N    GLY K 108      9.965   7.238 -50.321  1.00 40.42      A  N
ATOM  24040  CA   GLY K 108      9.843   8.608 -49.791  1.00 41.04      A  C
ATOM  24041  C    GLY K 108     10.647   8.935 -48.528  1.00 41.41      A  C
ATOM  24042  O    GLY K 108     10.361   9.930 -47.855  1.00 41.84      A  O
ATOM  24043  N    SER K 109     11.639   8.096 -48.202  1.00 41.38      A  N
ATOM  24044  CA   SER K 109     12.543   8.336 -47.075  1.00 41.42      A  C
ATOM  24045  C    SER K 109     13.768   9.135 -47.558  1.00 41.63      A  C
ATOM  24046  O    SER K 109     13.914   9.373 -48.769  1.00 41.39      A  O
ATOM  24047  CB   SER K 109     12.961   7.004 -46.408  1.00 41.27      A  C
ATOM  24048  OG   SER K 109     13.817   6.231 -47.239  1.00 40.65      A  O
ATOM  24049  N    PRO K 110     14.643   9.564 -46.618  1.00 42.00      A  N
ATOM  24050  CA   PRO K 110     15.942  10.156 -47.014  1.00 41.92      A  C
```

FIGURE 1 (cont'd)

```
ATOM  24051  C    PRO K 110      16.856   9.179 -47.773  1.00 41.33      A    C
ATOM  24052  O    PRO K 110      17.523   9.587 -48.726  1.00 41.10      A    O
ATOM  24053  CB   PRO K 110      16.575  10.533 -45.674  1.00 42.37      A    C
ATOM  24054  CG   PRO K 110      15.386  10.728 -44.757  1.00 42.82      A    C
ATOM  24055  CD   PRO K 110      14.402   9.687 -45.163  1.00 42.34      A    C
ATOM  24056  N    GLY K 111      16.874   7.912 -47.345  1.00 40.85      A    N
ATOM  24057  CA   GLY K 111      17.626   6.857 -48.032  1.00 40.19      A    C
ATOM  24058  C    GLY K 111      17.156   6.594 -49.460  1.00 39.65      A    C
ATOM  24059  O    GLY K 111      17.981   6.438 -50.375  1.00 39.47      A    O
ATOM  24060  N    ASN K 112      15.831   6.536 -49.642  1.00 39.20      A    N
ATOM  24061  CA   ASN K 112      15.205   6.412 -50.967  1.00 38.64      A    C
ATOM  24062  C    ASN K 112      15.662   7.518 -51.927  1.00 38.88      A    C
ATOM  24063  O    ASN K 112      16.039   7.250 -53.083  1.00 38.67      A    O
ATOM  24064  CB   ASN K 112      13.673   6.425 -50.843  1.00 38.32      A    C
ATOM  24065  CG   ASN K 112      12.968   6.231 -52.184  1.00 37.21      A    C
ATOM  24066  N    LEU K 113      15.631   8.756 -51.434  1.00 39.33      A    N
ATOM  24067  CA   LEU K 113      16.083   9.909 -52.209  1.00 39.80      A    C
ATOM  24068  C    LEU K 113      17.622   9.955 -52.381  1.00 39.85      A    C
ATOM  24069  O    LEU K 113      18.119  10.343 -53.458  1.00 39.78      A    O
ATOM  24070  CB   LEU K 113      15.555  11.205 -51.582  1.00 40.21      A    C
ATOM  24071  CG   LEU K 113      15.481  12.453 -52.475  1.00 40.93      A    C
ATOM  24072  CD1  LEU K 113      14.265  13.306 -52.129  1.00 41.45      A    C
ATOM  24073  CD2  LEU K 113      16.766  13.285 -52.394  1.00 41.80      A    C
ATOM  24074  N    GLN K 114      18.364   9.573 -51.330  1.00 39.93      A    N
ATOM  24075  CA   GLN K 114      19.836   9.493 -51.397  1.00 39.95      A    C
ATOM  24076  C    GLN K 114      20.292   8.510 -52.489  1.00 39.68      A    C
ATOM  24077  O    GLN K 114      21.177   8.857 -53.294  1.00 39.72      A    O
ATOM  24078  CB   GLN K 114      20.447   9.119 -50.034  1.00 40.10      A    C
ATOM  24079  N    VAL K 115      19.667   7.313 -52.512  1.00 39.10      A    N
ATOM  24080  CA   VAL K 115      19.931   6.263 -53.521  1.00 38.43      A    C
ATOM  24081  C    VAL K 115      19.525   6.720 -54.925  1.00 38.67      A    C
ATOM  24082  O    VAL K 115      20.340   6.650 -55.859  1.00 38.83      A    O
ATOM  24083  CB   VAL K 115      19.251   4.917 -53.174  1.00 36.89      A    C
ATOM  24084  N    ARG K 116      18.284   7.201 -55.053  1.00 38.84      A    N
ATOM  24085  CA   ARG K 116      17.776   7.797 -56.293  1.00 39.09      A    C
ATOM  24086  C    ARG K 116      18.736   8.810 -56.934  1.00 39.55      A    C
ATOM  24087  O    ARG K 116      18.979   8.774 -58.158  1.00 39.51      A    O
ATOM  24088  CB   ARG K 116      16.436   8.485 -56.030  1.00 38.99      A    C
ATOM  24089  CG   ARG K 116      15.853   9.241 -57.248  1.00 39.25      A    C
ATOM  24090  CD   ARG K 116      14.568  10.002 -56.884  1.00 40.28      A    C
ATOM  24091  NE   ARG K 116      13.572   9.120 -56.255  1.00 40.97      A    N
ATOM  24092  CZ   ARG K 116      12.517   9.526 -55.539  1.00 41.54      A    C
ATOM  24093  NH1  ARG K 116      12.293  10.829 -55.345  1.00 41.99      A    N
ATOM  24094  NH2  ARG K 116      11.682   8.620 -55.008  1.00 41.67      A    N
ATOM  24095  N    LYS K 117      19.252   9.715 -56.095  1.00 40.11      A    N
ATOM  24096  CA   LYS K 117      20.232  10.737 -56.490  1.00 40.59      A    C
ATOM  24097  C    LYS K 117      21.559  10.121 -56.993  1.00 40.24      A    C
ATOM  24098  O    LYS K 117      22.126  10.598 -57.990  1.00 40.28      A    O
ATOM  24099  CB   LYS K 117      20.486  11.702 -55.318  1.00 41.17      A    C
ATOM  24100  CG   LYS K 117      21.087  13.049 -55.724  1.00 42.55      A    C
ATOM  24101  CD   LYS K 117      21.069  14.052 -54.569  1.00 43.89      A    C
ATOM  24102  CE   LYS K 117      19.783  14.904 -54.543  1.00 44.13      A    C
ATOM  24103  NZ   LYS K 117      19.920  16.102 -55.441  1.00 45.15      A    N
ATOM  24104  N    PHE K 118      22.028   9.066 -56.304  1.00 39.62      A    N
ATOM  24105  CA   PHE K 118      23.244   8.321 -56.682  1.00 38.95      A    C
ATOM  24106  C    PHE K 118      23.110   7.615 -58.031  1.00 39.20      A    C
ATOM  24107  O    PHE K 118      24.051   7.591 -58.843  1.00 39.38      A    O
ATOM  24108  CB   PHE K 118      23.624   7.296 -55.612  1.00 37.66      A    C
ATOM  24109  CG   PHE K 118      24.787   6.416 -56.003  1.00 36.18      A    C
ATOM  24110  CD1  PHE K 118      26.030   6.989 -56.330  1.00 35.90      A    C
ATOM  24111  CD2  PHE K 118      24.634   5.032 -56.044  1.00 34.63      A    C
ATOM  24112  CE1  PHE K 118      27.142   6.222 -56.702  1.00 35.49      A    C
ATOM  24113  CE2  PHE K 118      25.681   4.171 -56.404  1.00 33.90      A    C
ATOM  24114  N    LEU K 119      21.938   7.026 -58.250  1.00 39.23      A    N
ATOM  24115  CA   LEU K 119      21.620   6.417 -59.534  1.00 39.24      A    C
```

FIGURE 1 (cont'd)

```
ATOM  24116  C    LEU K 119      21.666   7.463 -60.654  1.00 39.74           A  C
ATOM  24117  O    LEU K 119      22.458   7.315 -61.594  1.00 39.88           A  O
ATOM  24118  CB   LEU K 119      20.278   5.666 -59.479  1.00 38.75           A  C
ATOM  24119  CG   LEU K 119      20.401   4.304 -58.778  1.00 37.98           A  C
ATOM  24120  CD1  LEU K 119      19.032   3.723 -58.444  1.00 37.46           A  C
ATOM  24121  N    GLU K 120      20.861   8.524 -60.532  1.00 40.19           A  N
ATOM  24122  CA   GLU K 120      20.850   9.622 -61.515  1.00 40.65           A  C
ATOM  24123  C    GLU K 120      22.259  10.072 -61.924  1.00 41.35           A  C
ATOM  24124  O    GLU K 120      22.576  10.182 -63.124  1.00 41.60           A  O
ATOM  24125  CB   GLU K 120      20.098  10.831 -60.966  1.00 39.87           A  C
ATOM  24126  CG   GLU K 120      18.585  10.693 -60.939  1.00 39.57           A  C
ATOM  24127  CD   GLU K 120      17.892  12.009 -60.583  1.00 40.13           A  C
ATOM  24128  OE1  GLU K 120      18.011  13.000 -61.351  1.00 40.87           A  O
ATOM  24129  N    ALA K 121      23.093  10.319 -60.913  1.00 41.87           A  N
ATOM  24130  CA   ALA K 121      24.450  10.819 -61.114  1.00 42.24           A  C
ATOM  24131  C    ALA K 121      25.350   9.818 -61.827  1.00 42.17           A  C
ATOM  24132  O    ALA K 121      26.001  10.184 -62.813  1.00 42.49           A  O
ATOM  24133  CB   ALA K 121      25.064  11.225 -59.790  1.00 42.57           A  C
ATOM  24134  N    THR K 122      25.385   8.575 -61.328  1.00 41.58           A  N
ATOM  24135  CA   THR K 122      26.185   7.503 -61.943  1.00 40.94           A  C
ATOM  24136  C    THR K 122      25.849   7.318 -63.434  1.00 41.37           A  C
ATOM  24137  O    THR K 122      26.764   7.256 -64.280  1.00 41.72           A  O
ATOM  24138  CB   THR K 122      26.023   6.152 -61.207  1.00 39.47           A  C
ATOM  24139  OG1  THR K 122      26.612   6.242 -59.906  1.00 38.55           A  O
ATOM  24140  N    LEU K 123      24.541   7.256 -63.737  1.00 41.47           A  N
ATOM  24141  CA   LEU K 123      24.015   7.083 -65.114  1.00 41.54           A  C
ATOM  24142  C    LEU K 123      24.400   8.236 -66.045  1.00 42.22           A  C
ATOM  24143  O    LEU K 123      24.789   8.007 -67.214  1.00 42.44           A  O
ATOM  24144  CB   LEU K 123      22.485   6.900 -65.124  1.00 41.03           A  C
ATOM  24145  CG   LEU K 123      21.894   5.598 -64.573  1.00 39.84           A  C
ATOM  24146  CD1  LEU K 123      21.953   4.465 -65.598  1.00 39.20           A  C
ATOM  24147  N    ARG K 124      24.292   9.460 -65.516  1.00 42.78           A  N
ATOM  24148  CA   ARG K 124      24.665  10.665 -66.256  1.00 43.47           A  C
ATOM  24149  C    ARG K 124      26.173  10.766 -66.534  1.00 44.11           A  C
ATOM  24150  O    ARG K 124      26.582  11.183 -67.626  1.00 44.46           A  O
ATOM  24151  CB   ARG K 124      24.161  11.914 -65.532  1.00 43.44           A  C
ATOM  24152  CG   ARG K 124      22.693  12.192 -65.781  1.00 42.84           A  C
ATOM  24153  CD   ARG K 124      22.249  13.498 -65.144  1.00 42.39           A  C
ATOM  24154  NE   ARG K 124      20.826  13.736 -65.376  1.00 41.64           A  N
ATOM  24155  N    SER K 125      26.984  10.363 -65.553  1.00 44.60           A  N
ATOM  24156  CA   SER K 125      28.450  10.435 -65.646  1.00 45.17           A  C
ATOM  24157  C    SER K 125      29.095   9.389 -66.601  1.00 45.31           A  C
ATOM  24158  O    SER K 125      30.320   9.179 -66.565  1.00 45.62           A  O
ATOM  24159  CB   SER K 125      29.081  10.359 -64.239  1.00 45.29           A  C
ATOM  24160  OG   SER K 125      29.013   9.045 -63.698  1.00 44.97           A  O
ATOM  24161  N    LEU K 126      28.285   8.746 -67.450  1.00 45.16           A  N
ATOM  24162  CA   LEU K 126      28.807   7.752 -68.401  1.00 45.18           A  C
ATOM  24163  C    LEU K 126      29.200   8.375 -69.749  1.00 45.71           A  C
ATOM  24164  O    LEU K 126      28.580   9.361 -70.181  1.00 45.94           A  O
ATOM  24165  CB   LEU K 126      27.811   6.598 -68.595  1.00 44.64           A  C
ATOM  24166  CG   LEU K 126      27.557   5.668 -67.400  1.00 43.82           A  C
ATOM  24167  CD1  LEU K 126      26.922   4.359 -67.877  1.00 42.94           A  C
ATOM  24168  CD2  LEU K 126      28.846   5.390 -66.598  1.00 43.57           A  C
ATOM  24169  N    THR K 127      30.224   7.795 -70.395  1.00 46.20           A  N
ATOM  24170  CA   THR K 127      30.805   8.339 -71.647  1.00 46.69           A  C
ATOM  24171  C    THR K 127      29.799   8.439 -72.806  1.00 46.74           A  C
ATOM  24172  O    THR K 127      29.729   9.473 -73.500  1.00 47.18           A  O
ATOM  24173  CB   THR K 127      32.060   7.553 -72.117  1.00 46.89           A  C
ATOM  24174  OG1  THR K 127      32.802   7.102 -70.977  1.00 47.11           A  O
ATOM  24175  N    ALA K 128      29.036   7.362 -73.013  1.00 46.38           A  N
ATOM  24176  CA   ALA K 128      27.892   7.400 -73.927  1.00 46.16           A  C
ATOM  24177  C    ALA K 128      26.862   8.342 -73.309  1.00 46.04           A  C
ATOM  24178  O    ALA K 128      26.697   8.357 -72.076  1.00 45.97           A  O
ATOM  24179  CB   ALA K 128      27.311   5.997 -74.130  1.00 45.83           A  C
ATOM  24180  N    GLY K 129      26.197   9.143 -74.148  1.00 46.03           A  N
```

FIGURE 1 (cont'd)

```
ATOM  24181  CA   GLY K 129      25.261  10.172 -73.653  1.00 45.78      A   C
ATOM  24182  C    GLY K 129      23.912   9.646 -73.161  1.00 45.21      A   C
ATOM  24183  O    GLY K 129      22.898   9.823 -73.860  1.00 45.54      A   O
ATOM  24184  N    TRP K 130      23.899   9.013 -71.969  1.00 44.33      A   N
ATOM  24185  CA   TRP K 130      22.674   8.412 -71.379  1.00 43.32      A   C
ATOM  24186  C    TRP K 130      21.617   9.476 -71.083  1.00 43.03      A   C
ATOM  24187  O    TRP K 130      21.901  10.469 -70.401  1.00 43.17      A   O
ATOM  24188  CB   TRP K 130      22.974   7.599 -70.104  1.00 42.93      A   C
ATOM  24189  CG   TRP K 130      23.494   6.187 -70.356  1.00 42.46      A   C
ATOM  24190  CD1  TRP K 130      24.813   5.794 -70.434  1.00 42.67      A   C
ATOM  24191  CD2  TRP K 130      22.711   4.986 -70.549  1.00 42.01      A   C
ATOM  24192  CE2  TRP K 130      23.628   3.913 -70.740  1.00 41.89      A   C
ATOM  24193  CE3  TRP K 130      21.327   4.711 -70.574  1.00 41.72      A   C
ATOM  24194  NE1  TRP K 130      24.898   4.431 -70.666  1.00 42.27      A   N
ATOM  24195  CZ2  TRP K 130      23.203   2.591 -70.959  1.00 41.41      A   C
ATOM  24196  CZ3  TRP K 130      20.906   3.395 -70.787  1.00 41.33      A   C
ATOM  24197  CH2  TRP K 130      21.843   2.353 -70.978  1.00 41.14      A   C
ATOM  24198  N    HIS K 131      20.416   9.272 -71.626  1.00 42.60      A   N
ATOM  24199  CA   HIS K 131      19.286  10.169 -71.402  1.00 42.37      A   C
ATOM  24200  C    HIS K 131      18.587   9.729 -70.117  1.00 41.94      A   C
ATOM  24201  O    HIS K 131      17.576   9.019 -70.144  1.00 41.73      A   O
ATOM  24202  CB   HIS K 131      18.329  10.149 -72.605  1.00 42.53      A   C
ATOM  24203  CG   HIS K 131      17.390  11.311 -72.660  1.00 42.90      A   C
ATOM  24204  N    VAL K 132      19.163  10.136 -68.989  1.00 41.71      A   N
ATOM  24205  CA   VAL K 132      18.625   9.811 -67.670  1.00 41.37      A   C
ATOM  24206  C    VAL K 132      17.432  10.717 -67.378  1.00 41.38      A   C
ATOM  24207  O    VAL K 132      17.472  11.912 -67.680  1.00 41.62      A   O
ATOM  24208  CB   VAL K 132      19.706   9.945 -66.560  1.00 41.34      A   C
ATOM  24209  CG1  VAL K 132      19.503   8.876 -65.473  1.00 41.03      A   C
ATOM  24210  N    GLU K 133      16.379  10.143 -66.798  1.00 41.23      A   N
ATOM  24211  CA   GLU K 133      15.119  10.856 -66.642  1.00 41.45      A   C
ATOM  24212  C    GLU K 133      14.312  10.344 -65.448  1.00 41.19      A   C
ATOM  24213  O    GLU K 133      14.039   9.136 -65.347  1.00 41.04      A   O
ATOM  24214  CB   GLU K 133      14.309  10.720 -67.930  1.00 41.64      A   C
ATOM  24215  CG   GLU K 133      13.028  11.532 -67.968  1.00 42.98      A   C
ATOM  24216  CD   GLU K 133      12.229  11.272 -69.227  1.00 44.70      A   C
ATOM  24217  OE1  GLU K 133      12.795  11.413 -70.334  1.00 45.52      A   O
ATOM  24218  OE2  GLU K 133      11.036  10.925 -69.113  1.00 45.15      A   O
ATOM  24219  N    LEU K 134      13.929  11.267 -64.558  1.00 41.10      A   N
ATOM  24220  CA   LEU K 134      13.097  10.936 -63.380  1.00 40.80      A   C
ATOM  24221  C    LEU K 134      11.604  10.851 -63.704  1.00 40.55      A   C
ATOM  24222  O    LEU K 134      11.101  11.580 -64.575  1.00 40.71      A   O
ATOM  24223  CB   LEU K 134      13.298  11.958 -62.251  1.00 40.97      A   C
ATOM  24224  CG   LEU K 134      14.306  11.652 -61.140  1.00 41.11      A   C
ATOM  24225  CD1  LEU K 134      14.529  12.909 -60.297  1.00 41.94      A   C
ATOM  24226  N    ASP K 135      10.909   9.966 -62.990  1.00 40.08      A   N
ATOM  24227  CA   ASP K 135       9.461   9.863 -63.096  1.00 39.87      A   C
ATOM  24228  C    ASP K 135       8.852  10.055 -61.714  1.00 39.82      A   C
ATOM  24229  O    ASP K 135       8.498   9.075 -61.034  1.00 39.80      A   O
ATOM  24230  CB   ASP K 135       9.039   8.515 -63.702  1.00 39.66      A   C
ATOM  24231  CG   ASP K 135       7.519   8.328 -63.715  1.00 39.90      A   C
ATOM  24232  OD1  ASP K 135       6.805   9.334 -63.983  1.00 40.67      A   O
ATOM  24233  OD2  ASP K 135       7.047   7.186 -63.440  1.00 39.62      A   O
ATOM  24234  N    PRO K 136       8.746  11.322 -61.284  1.00 39.84      A   N
ATOM  24235  CA   PRO K 136       8.159  11.576 -59.962  1.00 40.10      A   C
ATOM  24236  C    PRO K 136       6.633  11.451 -59.996  1.00 40.67      A   C
ATOM  24237  O    PRO K 136       6.012  11.708 -61.042  1.00 40.90      A   O
ATOM  24238  CB   PRO K 136       8.574  13.026 -59.655  1.00 39.31      A   C
ATOM  24239  CG   PRO K 136       9.332  13.511 -60.893  1.00 38.92      A   C
ATOM  24240  N    PHE K 137       6.045  11.039 -58.871  1.00 41.17      A   N
ATOM  24241  CA   PHE K 137       4.578  10.998 -58.713  1.00 41.67      A   C
ATOM  24242  C    PHE K 137       4.153  10.719 -57.271  1.00 42.10      A   C
ATOM  24243  O    PHE K 137       4.895  10.082 -56.501  1.00 42.06      A   O
ATOM  24244  CB   PHE K 137       3.925   9.977 -59.675  1.00 41.47      A   C
ATOM  24245  CG   PHE K 137       4.192   8.534 -59.325  1.00 41.10      A   C
```

FIGURE 1 (cont'd)

```
ATOM  24246  CD1 PHE K 137       5.389   7.915 -59.707  1.00 40.78       A  C
ATOM  24247  CD2 PHE K 137       3.238   7.791 -58.634  1.00 40.98       A  C
ATOM  24248  CE1 PHE K 137       5.640   6.573 -59.394  1.00 40.26       A  C
ATOM  24249  CE2 PHE K 137       3.472   6.455 -58.312  1.00 40.55       A  C
ATOM  24250  CZ  PHE K 137       4.677   5.842 -58.694  1.00 40.19       A  C
ATOM  24251  N   THR K 138       2.963  11.201 -56.917  1.00 42.79       A  N
ATOM  24252  CA  THR K 138       2.356  10.873 -55.630  1.00 43.41       A  C
ATOM  24253  C   THR K 138       1.299   9.783 -55.810  1.00 43.48       A  C
ATOM  24254  O   THR K 138       0.600   9.748 -56.826  1.00 43.57       A  O
ATOM  24255  CB  THR K 138       1.735  12.110 -54.952  1.00 43.78       A  C
ATOM  24256  OG1 THR K 138       2.541  12.496 -53.831  1.00 44.27       A  O
ATOM  24257  N   ALA K 139       1.198   8.893 -54.825  1.00 43.51       A  N
ATOM  24258  CA  ALA K 139       0.278   7.758 -54.918  1.00 43.62       A  C
ATOM  24259  C   ALA K 139      -0.360   7.365 -53.581  1.00 43.98       A  C
ATOM  24260  O   ALA K 139       0.265   7.459 -52.511  1.00 44.04       A  O
ATOM  24261  CB  ALA K 139       0.971   6.549 -55.566  1.00 43.21       A  C
ATOM  24262  N   SER K 140      -1.609   6.908 -53.677  1.00 44.40       A  N
ATOM  24263  CA  SER K 140      -2.422   6.523 -52.531  1.00 44.80       A  C
ATOM  24264  C   SER K 140      -2.039   5.113 -52.017  1.00 44.50       A  C
ATOM  24265  O   SER K 140      -2.218   4.111 -52.726  1.00 44.36       A  O
ATOM  24266  CB  SER K 140      -3.905   6.615 -52.939  1.00 45.22       A  C
ATOM  24267  OG  SER K 140      -4.757   5.909 -52.050  1.00 46.16       A  O
ATOM  24268  N   THR K 141      -1.496   5.050 -50.799  1.00 44.28       A  N
ATOM  24269  CA  THR K 141      -1.104   3.768 -50.187  1.00 44.08       A  C
ATOM  24270  C   THR K 141      -1.894   3.523 -48.890  1.00 44.36       A  C
ATOM  24271  O   THR K 141      -2.552   4.448 -48.402  1.00 44.79       A  O
ATOM  24272  CB  THR K 141       0.446   3.662 -49.932  1.00 43.72       A  C
ATOM  24273  CG2 THR K 141       1.241   4.113 -51.150  1.00 43.34       A  C
ATOM  24274  OG1 THR K 141       0.818   4.453 -48.798  1.00 43.77       A  O
ATOM  24275  N   PRO K 142      -1.851   2.277 -48.343  1.00 44.33       A  N
ATOM  24276  CA  PRO K 142      -2.465   2.000 -47.034  1.00 44.52       A  C
ATOM  24277  C   PRO K 142      -1.828   2.783 -45.878  1.00 44.72       A  C
ATOM  24278  O   PRO K 142      -2.352   2.762 -44.754  1.00 45.13       A  O
ATOM  24279  CB  PRO K 142      -2.234   0.494 -46.848  1.00 44.40       A  C
ATOM  24280  CG  PRO K 142      -2.167  -0.042 -48.229  1.00 44.12       A  C
ATOM  24281  CD  PRO K 142      -1.437   1.022 -49.009  1.00 44.01       A  C
ATOM  24282  N   LEU K 143      -0.711   3.457 -46.161  1.00 44.53       A  N
ATOM  24283  CA  LEU K 143      -0.071   4.375 -45.212  1.00 44.56       A  C
ATOM  24284  C   LEU K 143      -0.396   5.840 -45.538  1.00 44.81       A  C
ATOM  24285  O   LEU K 143       0.212   6.760 -44.975  1.00 45.04       A  O
ATOM  24286  CB  LEU K 143       1.453   4.164 -45.195  1.00 44.18       A  C
ATOM  24287  CG  LEU K 143       2.132   3.182 -44.228  1.00 44.09       A  C
ATOM  24288  CD1 LEU K 143       2.057   3.702 -42.788  1.00 45.10       A  C
ATOM  24289  CD2 LEU K 143       1.603   1.743 -44.345  1.00 43.68       A  C
ATOM  24290  N   GLY K 144      -1.362   6.046 -46.437  1.00 44.92       A  N
ATOM  24291  CA  GLY K 144      -1.701   7.383 -46.931  1.00 45.02       A  C
ATOM  24292  C   GLY K 144      -0.798   7.808 -48.083  1.00 44.86       A  C
ATOM  24293  O   GLY K 144       0.023   7.004 -48.560  1.00 44.49       A  O
ATOM  24294  N   PRO K 145      -0.942   9.072 -48.546  1.00 45.00       A  N
ATOM  24295  CA  PRO K 145      -0.125   9.612 -49.644  1.00 44.64       A  C
ATOM  24296  C   PRO K 145       1.379   9.393 -49.443  1.00 43.85       A  C
ATOM  24297  O   PRO K 145       1.920   9.746 -48.391  1.00 44.06       A  O
ATOM  24298  CB  PRO K 145      -0.462  11.105 -49.625  1.00 45.00       A  C
ATOM  24299  CG  PRO K 145      -1.868  11.138 -49.149  1.00 45.66       A  C
ATOM  24300  CD  PRO K 145      -1.986  10.027 -48.128  1.00 45.50       A  C
ATOM  24301  N   VAL K 146       2.025   8.794 -50.445  1.00 42.55       A  N
ATOM  24302  CA  VAL K 146       3.470   8.565 -50.443  1.00 41.13       A  C
ATOM  24303  C   VAL K 146       4.081   9.040 -51.771  1.00 41.32       A  C
ATOM  24304  O   VAL K 146       3.537   8.776 -52.854  1.00 41.33       A  O
ATOM  24305  CB  VAL K 146       3.815   7.072 -50.183  1.00 39.33       A  C
ATOM  24306  CG1 VAL K 146       5.321   6.894 -49.930  1.00 37.84       A  C
ATOM  24307  N   ASP K 147       5.208   9.745 -51.668  1.00 41.39       A  N
ATOM  24308  CA  ASP K 147       5.914  10.289 -52.835  1.00 41.13       A  C
ATOM  24309  C   ASP K 147       6.948   9.304 -53.420  1.00 40.68       A  C
ATOM  24310  O   ASP K 147       7.915   8.906 -52.747  1.00 40.61       A  O
```

FIGURE 1 (cont'd)

```
ATOM  24311  CB   ASP K 147       6.564  11.643 -52.490  1.00 41.35      A  C
ATOM  24312  CG   ASP K 147       5.555  12.775 -52.402  1.00 41.29      A  C
ATOM  24313  N    PHE K 148       6.725   8.923 -54.678  1.00 40.13      A  N
ATOM  24314  CA   PHE K 148       7.584   7.970 -55.385  1.00 39.56      A  C
ATOM  24315  C    PHE K 148       8.376   8.623 -56.513  1.00 39.37      A  C
ATOM  24316  O    PHE K 148       8.100   9.763 -56.902  1.00 39.52      A  O
ATOM  24317  CB   PHE K 148       6.746   6.841 -55.979  1.00 39.33      A  C
ATOM  24318  CG   PHE K 148       5.969   6.063 -54.961  1.00 39.41      A  C
ATOM  24319  CD1  PHE K 148       6.547   4.940 -54.335  1.00 39.15      A  C
ATOM  24320  CD2  PHE K 148       4.653   6.435 -54.629  1.00 39.81      A  C
ATOM  24321  CE1  PHE K 148       5.825   4.200 -53.385  1.00 39.28      A  C
ATOM  24322  CE2  PHE K 148       3.920   5.710 -53.687  1.00 39.83      A  C
ATOM  24323  CZ   PHE K 148       4.503   4.590 -53.060  1.00 39.59      A  C
ATOM  24324  N    GLY K 149       9.347   7.889 -57.052  1.00 39.00      A  N
ATOM  24325  CA   GLY K 149      10.148   8.392 -58.162  1.00 38.81      A  C
ATOM  24326  C    GLY K 149      10.965   7.315 -58.840  1.00 38.56      A  C
ATOM  24327  O    GLY K 149      11.916   6.785 -58.247  1.00 38.54      A  O
ATOM  24328  N    ASN K 150      10.589   6.991 -60.083  1.00 38.33      A  N
ATOM  24329  CA   ASN K 150      11.332   6.026 -60.910  1.00 38.00      A  C
ATOM  24330  C    ASN K 150      12.540   6.671 -61.570  1.00 38.16      A  C
ATOM  24331  O    ASN K 150      12.552   7.887 -61.815  1.00 38.36      A  O
ATOM  24332  CB   ASN K 150      10.426   5.400 -61.971  1.00 37.69      A  C
ATOM  24333  CG   ASN K 150       9.329   4.547 -61.366  1.00 37.32      A  C
ATOM  24334  ND2  ASN K 150       8.068   4.904 -61.660  1.00 37.28      A  N
ATOM  24335  OD1  ASN K 150       9.606   3.578 -60.637  1.00 36.79      A  O
ATOM  24336  N    VAL K 151      13.559   5.855 -61.831  1.00 38.20      A  N
ATOM  24337  CA   VAL K 151      14.740   6.308 -62.574  1.00 38.53      A  C
ATOM  24338  C    VAL K 151      14.832   5.576 -63.932  1.00 38.71      A  C
ATOM  24339  O    VAL K 151      15.141   4.369 -64.002  1.00 38.50      A  O
ATOM  24340  CB   VAL K 151      16.054   6.179 -61.740  1.00 38.41      A  C
ATOM  24341  CG1  VAL K 151      16.007   7.103 -60.530  1.00 38.74      A  C
ATOM  24342  CG2  VAL K 151      17.268   6.518 -62.597  1.00 38.55      A  C
ATOM  24343  N    VAL K 152      14.546   6.325 -65.000  1.00 39.25      A  N
ATOM  24344  CA   VAL K 152      14.498   5.790 -66.370  1.00 39.74      A  C
ATOM  24345  C    VAL K 152      15.713   6.244 -67.203  1.00 40.30      A  C
ATOM  24346  O    VAL K 152      15.960   7.458 -67.380  1.00 40.64      A  O
ATOM  24347  CB   VAL K 152      13.169   6.193 -67.083  1.00 39.68      A  C
ATOM  24348  CG1  VAL K 152      12.007   5.394 -66.523  1.00 39.12      A  C
ATOM  24349  CG2  VAL K 152      13.275   6.008 -68.602  1.00 40.02      A  C
ATOM  24350  N    ALA K 153      16.455   5.260 -67.712  1.00 40.70      A  N
ATOM  24351  CA   ALA K 153      17.692   5.519 -68.462  1.00 41.33      A  C
ATOM  24352  C    ALA K 153      17.671   4.848 -69.840  1.00 41.83      A  C
ATOM  24353  O    ALA K 153      17.448   3.635 -69.964  1.00 41.74      A  O
ATOM  24354  CB   ALA K 153      18.928   5.068 -67.654  1.00 41.16      A  C
ATOM  24355  N    THR K 154      17.909   5.655 -70.871  1.00 42.61      A  N
ATOM  24356  CA   THR K 154      17.873   5.183 -72.255  1.00 43.24      A  C
ATOM  24357  C    THR K 154      19.028   5.813 -73.068  1.00 44.04      A  C
ATOM  24358  O    THR K 154      19.102   7.043 -73.239  1.00 44.41      A  O
ATOM  24359  CB   THR K 154      16.484   5.493 -72.948  1.00 43.14      A  C
ATOM  24360  CG2  THR K 154      16.265   4.588 -74.161  1.00 43.00      A  C
ATOM  24361  OG1  THR K 154      15.396   5.331 -72.016  1.00 42.61      A  O
ATOM  24362  N    LEU K 155      19.941   4.968 -73.546  1.00 44.72      A  N
ATOM  24363  CA   LEU K 155      20.867   5.379 -74.601  1.00 45.60      A  C
ATOM  24364  C    LEU K 155      20.045   5.603 -75.854  1.00 46.38      A  C
ATOM  24365  O    LEU K 155      19.177   4.781 -76.169  1.00 46.59      A  O
ATOM  24366  CB   LEU K 155      21.894   4.282 -74.890  1.00 45.38      A  C
ATOM  24367  CG   LEU K 155      23.305   4.418 -74.332  1.00 45.40      A  C
ATOM  24368  CD1  LEU K 155      24.227   3.464 -75.078  1.00 45.21      A  C
ATOM  24369  CD2  LEU K 155      23.786   5.856 -74.465  1.00 45.85      A  C
ATOM  24370  N    ASP K 156      20.291   6.712 -76.552  1.00 47.24      A  N
ATOM  24371  CA   ASP K 156      19.676   6.945 -77.863  1.00 48.07      A  C
ATOM  24372  C    ASP K 156      18.139   6.800 -77.805  1.00 47.92      A  C
ATOM  24373  O    ASP K 156      17.593   5.798 -78.288  1.00 47.69      A  O
ATOM  24374  CB   ASP K 156      20.288   5.964 -78.884  1.00 48.58      A  C
ATOM  24375  CG   ASP K 156      20.002   6.335 -80.325  1.00 50.20      A  C
```

FIGURE 1 (cont'd)

```
ATOM  24376  OD1 ASP K 156      19.220   7.273 -80.579  1.00 51.16      A    O
ATOM  24377  OD2 ASP K 156      20.576   5.668 -81.211  1.00 51.69      A    O
ATOM  24378  N   PRO K 157      17.435   7.796 -77.204  1.00 48.06      A    N
ATOM  24379  CA  PRO K 157      15.956   7.772 -77.127  1.00 48.12      A    C
ATOM  24380  C   PRO K 157      15.273   7.720 -78.498  1.00 48.44      A    C
ATOM  24381  O   PRO K 157      14.113   7.285 -78.583  1.00 48.32      A    O
ATOM  24382  CB  PRO K 157      15.599   9.103 -76.443  1.00 48.04      A    C
ATOM  24383  CG  PRO K 157      16.818   9.511 -75.731  1.00 48.08      A    C
ATOM  24384  CD  PRO K 157      17.982   9.004 -76.551  1.00 48.19      A    C
ATOM  24385  N   ARG K 158      15.979   8.164 -79.547  1.00 48.96      A    N
ATOM  24386  CA  ARG K 158      15.440   8.173 -80.923  1.00 49.45      A    C
ATOM  24387  C   ARG K 158      15.402   6.789 -81.619  1.00 49.28      A    C
ATOM  24388  O   ARG K 158      14.622   6.603 -82.566  1.00 49.55      A    O
ATOM  24389  CB  ARG K 158      16.104   9.258 -81.810  1.00 49.93      A    C
ATOM  24390  CG  ARG K 158      17.633   9.298 -81.822  1.00 50.25      A    C
ATOM  24391  N   ALA K 159      16.219   5.833 -81.142  1.00 48.80      A    N
ATOM  24392  CA  ALA K 159      16.190   4.436 -81.636  1.00 48.40      A    C
ATOM  24393  C   ALA K 159      14.772   3.834 -81.522  1.00 48.09      A    C
ATOM  24394  O   ALA K 159      14.089   4.029 -80.501  1.00 47.85      A    O
ATOM  24395  CB  ALA K 159      17.239   3.557 -80.907  1.00 48.21      A    C
ATOM  24396  N   ALA K 160      14.334   3.130 -82.575  1.00 47.94      A    N
ATOM  24397  CA  ALA K 160      12.955   2.621 -82.674  1.00 47.64      A    C
ATOM  24398  C   ALA K 160      12.604   1.585 -81.589  1.00 47.15      A    C
ATOM  24399  O   ALA K 160      11.457   1.532 -81.132  1.00 47.06      A    O
ATOM  24400  CB  ALA K 160      12.692   2.057 -84.061  1.00 48.02      A    C
ATOM  24401  N   ARG K 161      13.591   0.777 -81.184  1.00 46.55      A    N
ATOM  24402  CA  ARG K 161      13.408  -0.241 -80.145  1.00 45.96      A    C
ATOM  24403  C   ARG K 161      14.624  -0.349 -79.215  1.00 45.17      A    C
ATOM  24404  O   ARG K 161      15.737   0.039 -79.592  1.00 45.26      A    O
ATOM  24405  CB  ARG K 161      13.117  -1.607 -80.780  1.00 46.22      A    C
ATOM  24406  CG  ARG K 161      11.660  -1.832 -81.211  1.00 47.57      A    C
ATOM  24407  CD  ARG K 161      11.599  -2.657 -82.495  1.00 50.41      A    C
ATOM  24408  NE  ARG K 161      12.775  -3.529 -82.662  1.00 52.65      A    N
ATOM  24409  CZ  ARG K 161      13.501  -3.649 -83.784  1.00 53.92      A    C
ATOM  24410  NH1 ARG K 161      13.182  -2.978 -84.899  1.00 54.69      A    N
ATOM  24411  NH2 ARG K 161      14.552  -4.468 -83.799  1.00 54.18      A    N
ATOM  24412  N   HIS K 162      14.396  -0.882 -78.008  1.00 44.10      A    N
ATOM  24413  CA  HIS K 162      15.453  -1.057 -77.005  1.00 43.05      A    C
ATOM  24414  C   HIS K 162      15.278  -2.309 -76.156  1.00 42.00      A    C
ATOM  24415  O   HIS K 162      14.148  -2.682 -75.807  1.00 41.73      A    O
ATOM  24416  CB  HIS K 162      15.581   0.182 -76.080  1.00 43.28      A    C
ATOM  24417  CG  HIS K 162      14.280   0.662 -75.495  1.00 43.91      A    C
ATOM  24418  CD2 HIS K 162      13.529   1.760 -75.771  1.00 44.48      A    C
ATOM  24419  ND1 HIS K 162      13.619  -0.010 -74.487  1.00 44.09      A    N
ATOM  24420  CE1 HIS K 162      12.507   0.643 -74.182  1.00 44.30      A    C
ATOM  24421  NE2 HIS K 162      12.433   1.724 -74.940  1.00 44.55      A    N
ATOM  24422  N   LEU K 163      16.408  -2.951 -75.842  1.00 40.91      A    N
ATOM  24423  CA  LEU K 163      16.460  -3.968 -74.792  1.00 39.72      A    C
ATOM  24424  C   LEU K 163      16.318  -3.234 -73.483  1.00 39.02      A    C
ATOM  24425  O   LEU K 163      16.982  -2.222 -73.259  1.00 39.05      A    O
ATOM  24426  CB  LEU K 163      17.792  -4.723 -74.791  1.00 39.57      A    C
ATOM  24427  CG  LEU K 163      18.094  -5.582 -73.551  1.00 38.91      A    C
ATOM  24428  CD1 LEU K 163      17.111  -6.758 -73.397  1.00 38.49      A    C
ATOM  24429  CD2 LEU K 163      19.515  -6.094 -73.597  1.00 38.89      A    C
ATOM  24430  N   THR K 164      15.451  -3.745 -72.622  1.00 38.05      A    N
ATOM  24431  CA  THR K 164      15.238  -3.104 -71.336  1.00 37.09      A    C
ATOM  24432  C   THR K 164      15.443  -4.020 -70.115  1.00 36.50      A    C
ATOM  24433  O   THR K 164      14.723  -5.012 -69.919  1.00 36.27      A    O
ATOM  24434  CB  THR K 164      13.899  -2.289 -71.300  1.00 37.04      A    C
ATOM  24435  CG2 THR K 164      12.691  -3.117 -71.768  1.00 36.93      A    C
ATOM  24436  OG1 THR K 164      13.668  -1.788 -69.975  1.00 36.72      A    O
ATOM  24437  N   LEU K 165      16.460  -3.692 -69.322  1.00 35.88      A    N
ATOM  24438  CA  LEU K 165      16.685  -4.361 -68.046  1.00 35.32      A    C
ATOM  24439  C   LEU K 165      16.089  -3.546 -66.901  1.00 35.04      A    C
ATOM  24440  O   LEU K 165      16.026  -2.301 -66.956  1.00 35.09      A    O
```

FIGURE 1 (cont'd)

```
ATOM  24441  CB   LEU K 165      18.172  -4.595 -67.799  1.00 35.26           A    C
ATOM  24442  CG   LEU K 165      18.956  -5.327 -68.893  1.00 35.37           A    C
ATOM  24443  CD1  LEU K 165      20.384  -5.607 -68.399  1.00 35.48           A    C
ATOM  24444  CD2  LEU K 165      18.281  -6.625 -69.326  1.00 35.12           A    C
ATOM  24445  N    ALA K 166      15.647  -4.251 -65.863  1.00 34.57           A    N
ATOM  24446  CA   ALA K 166      15.030  -3.598 -64.716  1.00 34.14           A    C
ATOM  24447  C    ALA K 166      15.341  -4.271 -63.377  1.00 33.85           A    C
ATOM  24448  O    ALA K 166      15.520  -5.497 -63.281  1.00 33.63           A    O
ATOM  24449  CB   ALA K 166      13.513  -3.444 -64.921  1.00 34.13           A    C
ATOM  24450  N    CYS K 167      15.432  -3.414 -62.364  1.00 33.70           A    N
ATOM  24451  CA   CYS K 167      15.512  -3.782 -60.951  1.00 33.58           A    C
ATOM  24452  C    CYS K 167      14.648  -2.756 -60.185  1.00 33.54           A    C
ATOM  24453  O    CYS K 167      14.255  -1.711 -60.728  1.00 33.58           A    O
ATOM  24454  CB   CYS K 167      16.963  -3.686 -60.457  1.00 33.55           A    C
ATOM  24455  SG   CYS K 167      17.578  -1.920 -60.408  1.00 33.85           A    S
ATOM  24456  N    HIS K 168      14.356  -3.047 -58.922  1.00 33.51           A    N
ATOM  24457  CA   HIS K 168      13.708  -2.051 -58.078  1.00 33.52           A    C
ATOM  24458  C    HIS K 168      14.686  -1.602 -57.013  1.00 33.46           A    C
ATOM  24459  O    HIS K 168      15.384  -2.427 -56.381  1.00 33.37           A    O
ATOM  24460  CB   HIS K 168      12.409  -2.582 -57.454  1.00 33.66           A    C
ATOM  24461  CG   HIS K 168      12.622  -3.524 -56.299  1.00 34.07           A    C
ATOM  24462  CD2  HIS K 168      12.741  -4.875 -56.256  1.00 34.37           A    C
ATOM  24463  ND1  HIS K 168      12.742  -3.088 -54.993  1.00 34.40           A    N
ATOM  24464  CE1  HIS K 168      12.931  -4.127 -54.198  1.00 34.43           A    C
ATOM  24465  NE2  HIS K 168      12.937  -5.224 -54.939  1.00 34.37           A    N
ATOM  24466  N    TYR K 169      14.736  -0.289 -56.818  1.00 33.55           A    N
ATOM  24467  CA   TYR K 169      15.753   0.290 -55.934  1.00 33.74           A    C
ATOM  24468  C    TYR K 169      15.257   0.574 -54.515  1.00 33.81           A    C
ATOM  24469  O    TYR K 169      16.076   0.804 -53.613  1.00 33.80           A    O
ATOM  24470  CB   TYR K 169      16.425   1.531 -56.572  1.00 33.78           A    C
ATOM  24471  CG   TYR K 169      15.609   2.797 -56.497  1.00 33.97           A    C
ATOM  24472  CD1  TYR K 169      14.630   3.070 -57.445  1.00 33.86           A    C
ATOM  24473  CD2  TYR K 169      15.819   3.723 -55.474  1.00 34.44           A    C
ATOM  24474  CE1  TYR K 169      13.880   4.236 -57.380  1.00 33.96           A    C
ATOM  24475  CE2  TYR K 169      15.064   4.887 -55.391  1.00 34.65           A    C
ATOM  24476  CZ   TYR K 169      14.100   5.135 -56.348  1.00 34.24           A    C
ATOM  24477  OH   TYR K 169      13.361   6.284 -56.270  1.00 34.30           A    O
ATOM  24478  N    ASP K 170      13.934   0.562 -54.326  1.00 33.94           A    N
ATOM  24479  CA   ASP K 170      13.357   0.668 -52.978  1.00 34.27           A    C
ATOM  24480  C    ASP K 170      13.703  -0.577 -52.118  1.00 34.48           A    C
ATOM  24481  O    ASP K 170      14.068  -1.650 -52.642  1.00 34.26           A    O
ATOM  24482  CB   ASP K 170      11.839   0.910 -53.050  1.00 34.29           A    C
ATOM  24483  CG   ASP K 170      11.069  -0.291 -53.626  1.00 34.21           A    C
ATOM  24484  OD1  ASP K 170      11.343  -0.720 -54.775  1.00 33.77           A    O
ATOM  24485  OD2  ASP K 170      10.165  -0.795 -52.921  1.00 34.63           A    O
ATOM  24486  N    SER K 171      13.628  -0.401 -50.799  1.00 34.96           A    N
ATOM  24487  CA   SER K 171      13.797  -1.505 -49.833  1.00 35.41           A    C
ATOM  24488  C    SER K 171      12.504  -1.627 -49.024  1.00 35.68           A    C
ATOM  24489  O    SER K 171      11.838  -0.604 -48.751  1.00 35.97           A    O
ATOM  24490  CB   SER K 171      15.014  -1.277 -48.895  1.00 35.45           A    C
ATOM  24491  OG   SER K 171      14.727  -0.418 -47.781  1.00 35.83           A    O
ATOM  24492  N    LYS K 172      12.146  -2.857 -48.642  1.00 35.84           A    N
ATOM  24493  CA   LYS K 172      10.898  -3.066 -47.899  1.00 36.25           A    C
ATOM  24494  C    LYS K 172      10.892  -2.340 -46.550  1.00 36.97           A    C
ATOM  24495  O    LYS K 172      11.941  -2.168 -45.911  1.00 37.22           A    O
ATOM  24496  CB   LYS K 172      10.581  -4.547 -47.704  1.00 35.98           A    C
ATOM  24497  CG   LYS K 172       9.115  -4.796 -47.308  1.00 35.74           A    C
ATOM  24498  CD   LYS K 172       8.834  -6.282 -47.042  1.00 35.14           A    C
ATOM  24499  CE   LYS K 172       7.406  -6.506 -46.548  1.00 35.12           A    C
ATOM  24500  NZ   LYS K 172       6.387  -6.294 -47.637  1.00 35.05           A    N
ATOM  24501  N    LEU K 173       9.701  -1.898 -46.150  1.00 37.75           A    N
ATOM  24502  CA   LEU K 173       9.504  -1.185 -44.892  1.00 38.62           A    C
ATOM  24503  C    LEU K 173       9.039  -2.176 -43.816  1.00 39.15           A    C
ATOM  24504  O    LEU K 173       8.039  -2.895 -43.996  1.00 39.24           A    O
ATOM  24505  CB   LEU K 173       8.489  -0.047 -45.083  1.00 38.67           A    C
```

FIGURE 1 (cont'd)

```
ATOM  24506  CG   LEU K 173       7.992   0.707 -43.841  1.00 39.28      A    C
ATOM  24507  CD1  LEU K 173       8.777   1.991 -43.585  1.00 39.56      A    C
ATOM  24508  CD2  LEU K 173       6.492   0.989 -43.952  1.00 39.44      A    C
ATOM  24509  N    PHE K 174       9.773  -2.215 -42.706  1.00 39.82      A    N
ATOM  24510  CA   PHE K 174       9.439  -3.107 -41.598  1.00 40.46      A    C
ATOM  24511  C    PHE K 174       9.086  -2.334 -40.329  1.00 40.47      A    C
ATOM  24512  O    PHE K 174       9.462  -1.169 -40.180  1.00 41.49      A    O
ATOM  24513  CB   PHE K 174      10.589  -4.079 -41.340  1.00 40.62      A    C
ATOM  24514  CG   PHE K 174      10.650  -5.204 -42.318  1.00 40.46      A    C
ATOM  24515  CD1  PHE K 174       9.830  -6.315 -42.153  1.00 40.60      A    C
ATOM  24516  CD2  PHE K 174      11.520  -5.153 -43.408  1.00 40.03      A    C
ATOM  24517  CE1  PHE K 174       9.873  -7.373 -43.052  1.00 40.14      A    C
ATOM  24518  CE2  PHE K 174      11.581  -6.205 -44.322  1.00 39.57      A    C
ATOM  24519  CZ   PHE K 174      10.754  -7.323 -44.145  1.00 39.71      A    C
TER   24520       PHE K 174
ATOM  24521  N    SER K 178      13.014  -2.259 -34.849  1.00 47.26      A    N
ATOM  24522  CA   SER K 178      13.571  -3.605 -34.844  1.00 46.96      A    C
ATOM  24523  C    SER K 178      15.003  -3.730 -35.255  1.00 46.91      A    C
ATOM  24524  O    SER K 178      15.862  -3.495 -34.447  1.00 47.47      A    O
ATOM  24525  CB   SER K 178      12.758  -4.463 -35.747  1.00 45.26      A    C
ATOM  24526  OG   SER K 178      11.501  -4.549 -35.153  1.00 44.56      A    O
ATOM  24527  N    THR K 179      15.280  -4.157 -36.479  1.00 45.51      A    N
ATOM  24528  CA   THR K 179      16.650  -4.076 -36.964  1.00 43.07      A    C
ATOM  24529  C    THR K 179      16.591  -3.628 -38.415  1.00 43.58      A    C
ATOM  24530  O    THR K 179      15.759  -4.130 -39.193  1.00 44.46      A    O
ATOM  24531  CB   THR K 179      17.463  -5.393 -36.716  1.00 37.60      A    C
ATOM  24532  OG1  THR K 179      18.023  -5.877 -37.941  1.00 34.52      A    O
ATOM  24533  N    PRO K 180      17.438  -2.644 -38.772  1.00 42.50      A    N
ATOM  24534  CA   PRO K 180      17.443  -2.042 -40.111  1.00 41.33      A    C
ATOM  24535  C    PRO K 180      17.482  -3.115 -41.215  1.00 42.11      A    C
ATOM  24536  O    PRO K 180      18.189  -4.141 -41.085  1.00 42.94      A    O
ATOM  24537  CB   PRO K 180      18.711  -1.175 -40.113  1.00 36.48      A    C
ATOM  24538  CG   PRO K 180      19.699  -1.902 -39.197  1.00 34.75      A    C
ATOM  24539  N    PHE K 181      16.690  -2.898 -42.265  1.00 41.87      A    N
ATOM  24540  CA   PHE K 181      16.617  -3.854 -43.371  1.00 40.99      A    C
ATOM  24541  C    PHE K 181      17.097  -3.224 -44.685  1.00 40.29      A    C
ATOM  24542  O    PHE K 181      16.470  -2.281 -45.203  1.00 40.11      A    O
ATOM  24543  CB   PHE K 181      15.197  -4.421 -43.516  1.00 41.02      A    C
ATOM  24544  CG   PHE K 181      14.997  -5.224 -44.769  1.00 40.77      A    C
ATOM  24545  CD1  PHE K 181      15.558  -6.497 -44.881  1.00 40.91      A    C
ATOM  24546  CD2  PHE K 181      14.259  -4.701 -45.848  1.00 40.50      A    C
ATOM  24547  CE1  PHE K 181      15.382  -7.251 -46.050  1.00 40.32      A    C
ATOM  24548  CE2  PHE K 181      14.075  -5.432 -47.017  1.00 39.99      A    C
ATOM  24549  CZ   PHE K 181      14.633  -6.713 -47.122  1.00 39.81      A    C
ATOM  24550  N    VAL K 182      18.205  -3.748 -45.216  1.00 39.50      A    N
ATOM  24551  CA   VAL K 182      18.837  -3.181 -46.428  1.00 38.75      A    C
ATOM  24552  C    VAL K 182      18.574  -3.960 -47.729  1.00 37.97      A    C
ATOM  24553  O    VAL K 182      18.879  -3.456 -48.826  1.00 37.79      A    O
ATOM  24554  CB   VAL K 182      20.373  -2.940 -46.247  1.00 38.79      A    C
ATOM  24555  CG1  VAL K 182      20.622  -1.685 -45.424  1.00 39.11      A    C
ATOM  24556  CG2  VAL K 182      21.064  -4.169 -45.619  1.00 39.14      A    C
ATOM  24557  N    GLY K 183      18.022  -5.175 -47.595  1.00 37.28      A    N
ATOM  24558  CA   GLY K 183      17.730  -6.060 -48.734  1.00 36.29      A    C
ATOM  24559  C    GLY K 183      18.826  -6.081 -49.792  1.00 35.63      A    C
ATOM  24560  O    GLY K 183      18.716  -5.417 -50.841  1.00 35.41      A    O
ATOM  24561  N    ALA K 184      19.894  -6.829 -49.509  1.00 35.12      A    N
ATOM  24562  CA   ALA K 184      21.034  -6.908 -50.427  1.00 34.55      A    C
ATOM  24563  C    ALA K 184      20.650  -7.611 -51.735  1.00 33.97      A    C
ATOM  24564  O    ALA K 184      20.951  -7.131 -52.837  1.00 33.73      A    O
ATOM  24565  CB   ALA K 184      22.205  -7.610 -49.754  1.00 34.82      A    C
ATOM  24566  N    THR K 185      19.966  -8.744 -51.594  1.00 33.40      A    N
ATOM  24567  CA   THR K 185      19.502  -9.494 -52.747  1.00 32.86      A    C
ATOM  24568  C    THR K 185      18.272  -8.816 -53.312  1.00 32.61      A    C
ATOM  24569  O    THR K 185      17.886  -9.075 -54.448  1.00 32.63      A    O
ATOM  24570  CB   THR K 185      19.132 -10.975 -52.398  1.00 32.78      A    C
```

FIGURE 1 (cont'd)

```
ATOM  24571  CG2  THR K 185      20.243  -11.671  -51.571  1.00 32.99      A    C
ATOM  24572  OG1  THR K 185      17.885  -11.004  -51.688  1.00 32.41      A    O
ATOM  24573  N    ASP K 186      17.675   -7.930  -52.520  1.00 32.36      A    N
ATOM  24574  CA   ASP K 186      16.296   -7.500  -52.746  1.00 32.15      A    C
ATOM  24575  C    ASP K 186      16.089   -5.943  -52.701  1.00 32.21      A    C
ATOM  24576  O    ASP K 186      15.495   -5.414  -51.745  1.00 32.52      A    O
ATOM  24577  CB   ASP K 186      15.418   -8.245  -51.710  1.00 32.02      A    C
ATOM  24578  CG   ASP K 186      13.929   -8.118  -51.976  1.00 31.53      A    C
ATOM  24579  OD1  ASP K 186      13.169   -8.694  -51.150  1.00 31.38      A    O
ATOM  24580  OD2  ASP K 186      13.521   -7.460  -52.982  1.00 30.71      A    O
ATOM  24581  N    SER K 187      16.549   -5.196  -53.712  1.00 31.94      A    N
ATOM  24582  CA   SER K 187      17.208   -5.713  -54.902  1.00 31.67      A    C
ATOM  24583  C    SER K 187      18.472   -4.916  -55.218  1.00 31.67      A    C
ATOM  24584  O    SER K 187      18.740   -4.593  -56.381  1.00 31.56      A    O
ATOM  24585  CB   SER K 187      16.253   -5.649  -56.087  1.00 31.55      A    C
ATOM  24586  OG   SER K 187      15.260   -6.635  -55.958  1.00 31.68      A    O
ATOM  24587  N    ALA K 188      19.247   -4.608  -54.181  1.00 31.81      A    N
ATOM  24588  CA   ALA K 188      20.495   -3.845  -54.328  1.00 31.90      A    C
ATOM  24589  C    ALA K 188      21.443   -4.442  -55.395  1.00 31.88      A    C
ATOM  24590  O    ALA K 188      21.824   -3.748  -56.354  1.00 31.83      A    O
ATOM  24591  CB   ALA K 188      21.207   -3.713  -52.957  1.00 32.06      A    C
ATOM  24592  N    VAL K 189      21.797   -5.727  -55.224  1.00 31.83      A    N
ATOM  24593  CA   VAL K 189      22.678   -6.453  -56.167  1.00 31.72      A    C
ATOM  24594  C    VAL K 189      22.161   -6.355  -57.622  1.00 31.68      A    C
ATOM  24595  O    VAL K 189      22.926   -5.949  -58.510  1.00 31.71      A    O
ATOM  24596  CB   VAL K 189      22.938   -7.945  -55.738  1.00 31.60      A    C
ATOM  24597  CG1  VAL K 189      23.663   -8.708  -56.844  1.00 31.36      A    C
ATOM  24598  CG2  VAL K 189      23.714   -8.016  -54.428  1.00 31.75      A    C
ATOM  24599  N    PRO K 190      20.870   -6.721  -57.859  1.00 31.57      A    N
ATOM  24600  CA   PRO K 190      20.264   -6.494  -59.173  1.00 31.59      A    C
ATOM  24601  C    PRO K 190      20.528   -5.110  -59.724  1.00 31.83      A    C
ATOM  24602  O    PRO K 190      20.947   -4.997  -60.885  1.00 31.86      A    O
ATOM  24603  CB   PRO K 190      18.774   -6.667  -58.904  1.00 31.35      A    C
ATOM  24604  CG   PRO K 190      18.751   -7.750  -57.885  1.00 31.36      A    C
ATOM  24605  CD   PRO K 190      19.983   -7.549  -57.014  1.00 31.50      A    C
ATOM  24606  N    CYS K 191      20.313   -4.077  -58.907  1.00 32.15      A    N
ATOM  24607  CA   CYS K 191      20.527   -2.697  -59.357  1.00 32.71      A    C
ATOM  24608  C    CYS K 191      21.987   -2.375  -59.586  1.00 33.00      A    C
ATOM  24609  O    CYS K 191      22.319   -1.646  -60.539  1.00 33.15      A    O
ATOM  24610  CB   CYS K 191      19.914   -1.687  -58.391  1.00 32.79      A    C
ATOM  24611  SG   CYS K 191      18.084   -1.619  -58.434  1.00 33.46      A    S
ATOM  24612  N    ALA K 192      22.842   -2.928  -58.718  1.00 33.24      A    N
ATOM  24613  CA   ALA K 192      24.302   -2.773  -58.825  1.00 33.49      A    C
ATOM  24614  C    ALA K 192      24.849   -3.316  -60.154  1.00 33.47      A    C
ATOM  24615  O    ALA K 192      25.700   -2.675  -60.799  1.00 33.70      A    O
ATOM  24616  CB   ALA K 192      25.008   -3.447  -57.637  1.00 33.62      A    C
ATOM  24617  N    LEU K 193      24.353   -4.496  -60.544  1.00 33.09      A    N
ATOM  24618  CA   LEU K 193      24.726   -5.135  -61.812  1.00 32.70      A    C
ATOM  24619  C    LEU K 193      24.369   -4.268  -63.024  1.00 33.24      A    C
ATOM  24620  O    LEU K 193      25.212   -4.077  -63.910  1.00 33.59      A    O
ATOM  24621  CB   LEU K 193      24.072   -6.506  -61.937  1.00 31.34      A    C
ATOM  24622  CG   LEU K 193      24.571   -7.556  -60.943  1.00 29.78      A    C
ATOM  24623  CD1  LEU K 193      23.683   -8.799  -61.052  1.00 28.83      A    C
ATOM  24624  N    LEU K 194      23.135   -3.742  -63.044  1.00 33.45      A    N
ATOM  24625  CA   LEU K 194      22.664   -2.838  -64.120  1.00 33.62      A    C
ATOM  24626  C    LEU K 194      23.603   -1.651  -64.322  1.00 34.53      A    C
ATOM  24627  O    LEU K 194      23.850   -1.246  -65.472  1.00 34.81      A    O
ATOM  24628  CB   LEU K 194      21.231   -2.342  -63.871  1.00 32.50      A    C
ATOM  24629  CG   LEU K 194      20.141   -3.400  -64.037  1.00 31.30      A    C
ATOM  24630  CD1  LEU K 194      18.850   -2.744  -64.421  1.00 30.90      A    C
ATOM  24631  N    LEU K 195      24.127   -1.116  -63.208  1.00 35.31      A    N
ATOM  24632  CA   LEU K 195      25.138   -0.039  -63.245  1.00 36.15      A    C
ATOM  24633  C    LEU K 195      26.493   -0.523  -63.795  1.00 36.85      A    C
ATOM  24634  O    LEU K 195      27.044    0.084  -64.729  1.00 37.11      A    O
ATOM  24635  CB   LEU K 195      25.332    0.597  -61.860  1.00 36.06      A    C
```

FIGURE 1 (cont'd)

```
ATOM  24636  CG   LEU K 195     24.180   1.391 -61.236  1.00 35.87      A   C
ATOM  24637  CD1  LEU K 195     24.529   1.791 -59.789  1.00 36.10      A   C
ATOM  24638  CD2  LEU K 195     23.823   2.619 -62.066  1.00 35.83      A   C
ATOM  24639  N    GLU K 196     27.008  -1.615 -63.211  1.00 37.45      A   N
ATOM  24640  CA   GLU K 196     28.293  -2.213 -63.589  1.00 38.05      A   C
ATOM  24641  C    GLU K 196     28.351  -2.577 -65.074  1.00 38.16      A   C
ATOM  24642  O    GLU K 196     29.342  -2.288 -65.756  1.00 38.31      A   O
ATOM  24643  CB   GLU K 196     28.580  -3.441 -62.711  1.00 38.18      A   C
ATOM  24644  CG   GLU K 196     29.726  -4.334 -63.214  1.00 39.34      A   C
ATOM  24645  CD   GLU K 196     31.099  -3.645 -63.200  1.00 40.84      A   C
ATOM  24646  OE1  GLU K 196     31.214  -2.506 -62.667  1.00 41.47      A   O
ATOM  24647  OE2  GLU K 196     32.066  -4.260 -63.715  1.00 41.54      A   O
ATOM  24648  N    LEU K 197     27.282  -3.225 -65.545  1.00 38.19      A   N
ATOM  24649  CA   LEU K 197     27.097  -3.553 -66.959  1.00 38.42      A   C
ATOM  24650  C    LEU K 197     27.165  -2.306 -67.833  1.00 38.89      A   C
ATOM  24651  O    LEU K 197     27.889  -2.292 -68.825  1.00 39.20      A   O
ATOM  24652  CB   LEU K 197     25.753  -4.271 -67.191  1.00 38.01      A   C
ATOM  24653  CG   LEU K 197     25.748  -5.801 -67.342  1.00 37.79      A   C
ATOM  24654  CD1  LEU K 197     25.822  -6.521 -65.979  1.00 37.63      A   C
ATOM  24655  CD2  LEU K 197     24.514  -6.252 -68.137  1.00 37.69      A   C
ATOM  24656  N    ALA K 198     26.418  -1.267 -67.456  1.00 39.33      A   N
ATOM  24657  CA   ALA K 198     26.339  -0.031 -68.240  1.00 40.07      A   C
ATOM  24658  C    ALA K 198     27.689   0.669 -68.345  1.00 40.81      A   C
ATOM  24659  O    ALA K 198     27.954   1.393 -69.314  1.00 41.08      A   O
ATOM  24660  CB   ALA K 198     25.318   0.903 -67.634  1.00 39.89      A   C
ATOM  24661  N    GLN K 199     28.523   0.445 -67.330  1.00 41.41      A   N
ATOM  24662  CA   GLN K 199     29.850   1.038 -67.237  1.00 42.08      A   C
ATOM  24663  C    GLN K 199     30.893   0.176 -67.992  1.00 43.00      A   C
ATOM  24664  O    GLN K 199     31.687   0.697 -68.788  1.00 43.55      A   O
ATOM  24665  CB   GLN K 199     30.236   1.198 -65.756  1.00 40.96      A   C
ATOM  24666  CG   GLN K 199     30.661   2.596 -65.345  1.00 40.39      A   C
ATOM  24667  CD   GLN K 199     31.766   3.189 -66.208  1.00 40.18      A   C
ATOM  24668  OE1  GLN K 199     32.932   2.794 -66.112  1.00 40.52      A   O
ATOM  24669  N    ALA K 200     30.880  -1.138 -67.736  1.00 43.71      A   N
ATOM  24670  CA   ALA K 200     31.835  -2.089 -68.354  1.00 44.43      A   C
ATOM  24671  C    ALA K 200     31.734  -2.130 -69.890  1.00 44.96      A   C
ATOM  24672  O    ALA K 200     32.752  -2.205 -70.590  1.00 45.36      A   O
ATOM  24673  CB   ALA K 200     31.669  -3.509 -67.755  1.00 44.14      A   C
ATOM  24674  N    LEU K 201     30.499  -2.076 -70.391  1.00 45.29      A   N
ATOM  24675  CA   LEU K 201     30.205  -2.091 -71.821  1.00 45.80      A   C
ATOM  24676  C    LEU K 201     30.018  -0.693 -72.381  1.00 46.53      A   C
ATOM  24677  O    LEU K 201     29.593  -0.547 -73.530  1.00 46.71      A   O
ATOM  24678  CB   LEU K 201     28.911  -2.846 -72.071  1.00 45.34      A   C
ATOM  24679  CG   LEU K 201     28.797  -4.359 -72.258  1.00 45.12      A   C
ATOM  24680  CD1  LEU K 201     27.665  -5.059 -71.510  1.00 44.79      A   C
ATOM  24681  CD2  LEU K 201     30.061  -5.185 -72.480  1.00 45.39      A   C
ATOM  24682  N    ASP K 202     30.322   0.317 -71.559  1.00 47.31      A   N
ATOM  24683  CA   ASP K 202     30.095   1.740 -71.888  1.00 48.15      A   C
ATOM  24684  C    ASP K 202     30.639   2.178 -73.265  1.00 48.75      A   C
ATOM  24685  O    ASP K 202     29.937   2.853 -74.033  1.00 48.93      A   O
ATOM  24686  CB   ASP K 202     30.653   2.650 -70.771  1.00 48.26      A   C
ATOM  24687  CG   ASP K 202     30.542   4.142 -71.099  1.00 48.68      A   C
ATOM  24688  OD1  ASP K 202     29.408   4.643 -71.316  1.00 48.48      A   O
ATOM  24689  OD2  ASP K 202     31.607   4.801 -71.123  1.00 49.43      A   O
ATOM  24690  N    LEU K 203     31.879   1.789 -73.567  1.00 49.15      A   N
ATOM  24691  CA   LEU K 203     32.525   2.197 -74.813  1.00 49.34      A   C
ATOM  24692  C    LEU K 203     31.971   1.508 -76.069  1.00 49.59      A   C
ATOM  24693  O    LEU K 203     31.690   2.174 -77.074  1.00 49.96      A   O
ATOM  24694  CB   LEU K 203     34.038   2.031 -74.702  1.00 48.39      A   C
ATOM  24695  CG   LEU K 203     34.720   3.196 -73.974  1.00 48.10      A   C
ATOM  24696  CD1  LEU K 203     35.072   2.808 -72.537  1.00 47.99      A   C
ATOM  24697  N    GLU K 204     31.815   0.185 -76.007  1.00 49.39      A   N
ATOM  24698  CA   GLU K 204     31.142  -0.571 -77.079  1.00 49.03      A   C
ATOM  24699  C    GLU K 204     29.667  -0.152 -77.276  1.00 49.48      A   C
ATOM  24700  O    GLU K 204     29.164  -0.134 -78.413  1.00 49.75      A   O
```

FIGURE 1 (cont'd)

```
ATOM  24701  CB   GLU K 204      31.280  -2.093 -76.878  1.00 47.50       A  C
ATOM  24702  CG   GLU K 204      31.406  -2.541 -75.427  1.00 45.82       A  C
ATOM  24703  CD   GLU K 204      32.783  -2.261 -74.852  1.00 45.08       A  C
ATOM  24704  OE1  GLU K 204      33.719  -3.016 -75.189  1.00 45.27       A  O
ATOM  24705  OE2  GLU K 204      32.926  -1.290 -74.068  1.00 44.48       A  O
ATOM  24706  N    LEU K 205      28.992   0.178 -76.169  1.00 49.66       A  N
ATOM  24707  CA   LEU K 205      27.639   0.751 -76.202  1.00 49.80       A  C
ATOM  24708  C    LEU K 205      27.634   2.151 -76.813  1.00 50.54       A  C
ATOM  24709  O    LEU K 205      26.646   2.565 -77.439  1.00 50.60       A  O
ATOM  24710  CB   LEU K 205      27.050   0.846 -74.791  1.00 49.26       A  C
ATOM  24711  CG   LEU K 205      26.182  -0.279 -74.246  1.00 48.28       A  C
ATOM  24712  CD1  LEU K 205      26.059  -0.114 -72.728  1.00 47.86       A  C
ATOM  24713  CD2  LEU K 205      24.805  -0.291 -74.932  1.00 47.61       A  C
ATOM  24714  N    SER K 206      28.732   2.880 -76.600  1.00 51.39       A  N
ATOM  24715  CA   SER K 206      28.870   4.253 -77.076  1.00 52.30       A  C
ATOM  24716  C    SER K 206      28.992   4.287 -78.601  1.00 52.76       A  C
ATOM  24717  O    SER K 206      28.192   4.958 -79.274  1.00 52.77       A  O
ATOM  24718  CB   SER K 206      30.073   4.955 -76.409  1.00 52.50       A  C
ATOM  24719  OG   SER K 206      29.983   6.371 -76.523  1.00 53.16       A  O
ATOM  24720  N    ARG K 207      29.978   3.559 -79.134  1.00 53.27       A  N
ATOM  24721  CA   ARG K 207      30.220   3.557 -80.578  1.00 53.79       A  C
ATOM  24722  C    ARG K 207      28.953   3.168 -81.349  1.00 53.78       A  C
ATOM  24723  O    ARG K 207      28.513   3.914 -82.240  1.00 54.13       A  O
ATOM  24724  CB   ARG K 207      31.451   2.713 -80.977  1.00 54.05       A  C
ATOM  24725  CG   ARG K 207      31.451   1.265 -80.512  1.00 53.54       A  C
ATOM  24726  N    ALA K 208      28.361   2.025 -80.979  1.00 53.33       A  N
ATOM  24727  CA   ALA K 208      27.079   1.579 -81.550  1.00 52.93       A  C
ATOM  24728  C    ALA K 208      25.975   2.544 -81.120  1.00 52.70       A  C
ATOM  24729  O    ALA K 208      25.239   2.284 -80.156  1.00 52.44       A  O
ATOM  24730  CB   ALA K 208      26.754   0.146 -81.130  1.00 52.58       A  C
ATOM  24731  N    LYS K 209      25.895   3.661 -81.849  1.00 52.76       A  N
ATOM  24732  CA   LYS K 209      25.034   4.804 -81.542  1.00 52.43       A  C
ATOM  24733  C    LYS K 209      25.578   5.948 -82.396  1.00 51.88       A  C
ATOM  24734  O    LYS K 209      25.406   7.122 -82.103  1.00 52.81       A  O
ATOM  24735  CB   LYS K 209      25.083   5.157 -80.043  1.00 52.45       A  C
ATOM  24736  CG   LYS K 209      23.970   6.078 -79.565  1.00 52.75       A  C
ATOM  24737  CD   LYS K 209      24.439   6.915 -78.379  1.00 53.61       A  C
ATOM  24738  CE   LYS K 209      23.343   7.861 -77.895  1.00 53.79       A  C
ATOM  24739  NZ   LYS K 209      23.813   8.769 -76.807  1.00 53.92       A  N
TER   24740       LYS K 209
ATOM  24741  N    VAL K 215      18.610  -0.763 -82.448  1.00 36.36       A  N
ATOM  24742  CA   VAL K 215      18.082  -1.334 -81.211  1.00 36.24       A  C
ATOM  24743  C    VAL K 215      18.940  -0.902 -80.016  1.00 36.47       A  C
ATOM  24744  O    VAL K 215      20.110  -1.301 -79.894  1.00 36.75       A  O
ATOM  24745  CB   VAL K 215      17.990  -2.886 -81.276  1.00 35.48       A  C
ATOM  24746  CG1  VAL K 215      17.069  -3.411 -80.172  1.00 34.61       A  C
ATOM  24747  N    THR K 216      18.347  -0.094 -79.137  1.00 36.16       A  N
ATOM  24748  CA   THR K 216      19.085   0.512 -78.021  1.00 35.66       A  C
ATOM  24749  C    THR K 216      19.024  -0.294 -76.698  1.00 35.16       A  C
ATOM  24750  O    THR K 216      18.579  -1.459 -76.677  1.00 35.10       A  O
ATOM  24751  CB   THR K 216      18.643   1.985 -77.792  1.00 35.63       A  C
ATOM  24752  OG1  THR K 216      19.805   2.796 -77.581  1.00 35.53       A  O
ATOM  24753  N    LEU K 217      19.490   0.333 -75.613  1.00 34.54       A  N
ATOM  24754  CA   LEU K 217      19.461  -0.269 -74.280  1.00 33.74       A  C
ATOM  24755  C    LEU K 217      18.771   0.675 -73.296  1.00 33.39       A  C
ATOM  24756  O    LEU K 217      19.010   1.902 -73.313  1.00 33.66       A  O
ATOM  24757  CB   LEU K 217      20.885  -0.616 -73.799  1.00 33.65       A  C
ATOM  24758  CG   LEU K 217      21.061  -1.073 -72.343  1.00 33.10       A  C
ATOM  24759  CD1  LEU K 217      20.459  -2.462 -72.124  1.00 32.91       A  C
ATOM  24760  CD2  LEU K 217      22.519  -1.067 -71.971  1.00 33.15       A  C
ATOM  24761  N    GLN K 218      17.916   0.098 -72.448  1.00 32.61       A  N
ATOM  24762  CA   GLN K 218      17.167   0.862 -71.448  1.00 31.96       A  C
ATOM  24763  C    GLN K 218      17.342   0.263 -70.042  1.00 31.36       A  C
ATOM  24764  O    GLN K 218      17.246  -0.955 -69.848  1.00 31.24       A  O
ATOM  24765  CB   GLN K 218      15.693   0.949 -71.853  1.00 31.94       A  C
```

FIGURE 1 (cont'd)

```
ATOM  24766  CG   GLN K 218     14.853   1.878 -70.994  1.00 32.18      A    C
ATOM  24767  CD   GLN K 218     13.349   1.774 -71.295  1.00 32.85      A    C
ATOM  24768  NE2  GLN K 218     12.758   0.609 -71.022  1.00 32.87      A    N
ATOM  24769  OE1  GLN K 218     12.732   2.734 -71.770  1.00 33.66      A    O
ATOM  24770  N    LEU K 219     17.631   1.123 -69.072  1.00 30.78      A    N
ATOM  24771  CA   LEU K 219     17.782   0.675 -67.693  1.00 30.11      A    C
ATOM  24772  C    LEU K 219     16.701   1.292 -66.807  1.00 29.87      A    C
ATOM  24773  O    LEU K 219     16.572   2.536 -66.716  1.00 29.98      A    O
ATOM  24774  CB   LEU K 219     19.189   0.980 -67.170  1.00 29.97      A    C
ATOM  24775  CG   LEU K 219     20.329   0.312 -67.951  1.00 29.68      A    C
ATOM  24776  CD1  LEU K 219     21.664   0.800 -67.421  1.00 29.47      A    C
ATOM  24777  CD2  LEU K 219     20.254  -1.214 -67.896  1.00 29.21      A    C
ATOM  24778  N    LEU K 220     15.907   0.420 -66.180  1.00 29.33      A    N
ATOM  24779  CA   LEU K 220     14.813   0.876 -65.312  1.00 28.91      A    C
ATOM  24780  C    LEU K 220     15.097   0.565 -63.842  1.00 29.03      A    C
ATOM  24781  O    LEU K 220     15.333  -0.603 -63.487  1.00 29.05      A    O
ATOM  24782  CB   LEU K 220     13.466   0.284 -65.754  1.00 28.17      A    C
ATOM  24783  CG   LEU K 220     13.009   0.699 -67.163  1.00 27.47      A    C
ATOM  24784  CD1  LEU K 220     11.611   0.175 -67.453  1.00 26.98      A    C
ATOM  24785  N    PHE K 221     15.111   1.628 -63.019  1.00 29.16      A    N
ATOM  24786  CA   PHE K 221     15.250   1.548 -61.547  1.00 29.13      A    C
ATOM  24787  C    PHE K 221     13.927   1.991 -60.912  1.00 29.16      A    C
ATOM  24788  O    PHE K 221     13.646   3.196 -60.777  1.00 29.20      A    O
ATOM  24789  CB   PHE K 221     16.422   2.413 -61.045  1.00 29.12      A    C
ATOM  24790  CG   PHE K 221     17.732   2.059 -61.667  1.00 29.14      A    C
ATOM  24791  CD1  PHE K 221     18.597   1.156 -61.036  1.00 29.22      A    C
ATOM  24792  CD2  PHE K 221     18.094   2.601 -62.897  1.00 29.23      A    C
ATOM  24793  CE1  PHE K 221     19.827   0.795 -61.613  1.00 29.25      A    C
ATOM  24794  CE2  PHE K 221     19.306   2.254 -63.496  1.00 29.51      A    C
ATOM  24795  CZ   PHE K 221     20.182   1.346 -62.847  1.00 29.41      A    C
ATOM  24796  N    LEU K 222     13.110   1.007 -60.544  1.00 29.21      A    N
ATOM  24797  CA   LEU K 222     11.732   1.278 -60.131  1.00 29.47      A    C
ATOM  24798  C    LEU K 222     11.638   1.529 -58.638  1.00 29.83      A    C
ATOM  24799  O    LEU K 222     12.294   0.831 -57.826  1.00 29.83      A    O
ATOM  24800  CB   LEU K 222     10.798   0.126 -60.543  1.00 29.29      A    C
ATOM  24801  CG   LEU K 222     10.836  -0.196 -62.046  1.00 29.13      A    C
ATOM  24802  CD1  LEU K 222      9.726   0.537 -62.831  1.00 29.16      A    C
ATOM  24803  CD2  LEU K 222     10.777  -1.694 -62.270  1.00 28.77      A    C
ATOM  24804  N    ASP K 223     10.830   2.532 -58.287  1.00 30.32      A    N
ATOM  24805  CA   ASP K 223     10.551   2.838 -56.881  1.00 30.95      A    C
ATOM  24806  C    ASP K 223      9.349   2.002 -56.391  1.00 30.99      A    C
ATOM  24807  O    ASP K 223      8.618   1.408 -57.218  1.00 30.87      A    O
ATOM  24808  CB   ASP K 223     10.299   4.356 -56.686  1.00 31.36      A    C
ATOM  24809  CG   ASP K 223     10.514   4.836 -55.214  1.00 32.43      A    C
ATOM  24810  OD1  ASP K 223     11.023   4.044 -54.362  1.00 33.36      A    O
ATOM  24811  OD2  ASP K 223     10.178   6.018 -54.919  1.00 33.07      A    O
ATOM  24812  N    GLY K 224      9.167   1.956 -55.060  1.00 31.10      A    N
ATOM  24813  CA   GLY K 224      7.986   1.362 -54.420  1.00 31.29      A    C
ATOM  24814  C    GLY K 224      7.451   0.094 -55.080  1.00 31.26      A    C
ATOM  24815  O    GLY K 224      6.332   0.078 -55.601  1.00 31.43      A    O
ATOM  24816  N    GLU K 225      8.260  -0.961 -55.076  1.00 31.06      A    N
ATOM  24817  CA   GLU K 225      7.816  -2.248 -55.580  1.00 30.98      A    C
ATOM  24818  C    GLU K 225      7.274  -3.068 -54.419  1.00 31.06      A    C
ATOM  24819  O    GLU K 225      6.176  -3.646 -54.518  1.00 30.98      A    O
ATOM  24820  CB   GLU K 225      8.972  -2.972 -56.266  1.00 30.84      A    C
ATOM  24821  CG   GLU K 225      8.624  -4.348 -56.809  1.00 31.12      A    C
ATOM  24822  CD   GLU K 225      8.808  -5.452 -55.781  1.00 31.89      A    C
ATOM  24823  OE1  GLU K 225      9.714  -5.329 -54.923  1.00 32.62      A    O
ATOM  24824  OE2  GLU K 225      8.037  -6.439 -55.833  1.00 32.35      A    O
ATOM  24825  N    GLU K 226      8.062  -3.119 -53.336  1.00 31.36      A    N
ATOM  24826  CA   GLU K 226      7.673  -3.781 -52.079  1.00 31.84      A    C
ATOM  24827  C    GLU K 226      6.474  -3.078 -51.419  1.00 32.50      A    C
ATOM  24828  O    GLU K 226      6.396  -1.819 -51.390  1.00 32.63      A    O
ATOM  24829  CB   GLU K 226      8.843  -3.814 -51.089  1.00 31.70      A    C
ATOM  24830  CG   GLU K 226     10.115  -4.442 -51.630  1.00 30.95      A    C
```

FIGURE 1 (cont'd)

```
ATOM  24831  CD   GLU K 226     10.227  -5.914 -51.305  1.00 30.27      A    C
ATOM  24832  OE1  GLU K 226      9.186  -6.573 -51.109  1.00 30.26      A    O
ATOM  24833  OE2  GLU K 226     11.365  -6.416 -51.239  1.00 29.67      A    O
ATOM  24834  N    ALA K 227      5.559  -3.903 -50.891  1.00 33.08      A    N
ATOM  24835  CA   ALA K 227      4.323  -3.430 -50.260  1.00 33.82      A    C
ATOM  24836  C    ALA K 227      4.596  -2.600 -48.997  1.00 34.46      A    C
ATOM  24837  O    ALA K 227      5.707  -2.630 -48.429  1.00 34.51      A    O
ATOM  24838  CB   ALA K 227      3.410  -4.610 -49.937  1.00 33.76      A    C
ATOM  24839  N    LEU K 228      3.579  -1.859 -48.561  1.00 35.24      A    N
ATOM  24840  CA   LEU K 228      3.708  -1.080 -47.337  1.00 35.98      A    C
ATOM  24841  C    LEU K 228      2.982  -1.690 -46.128  1.00 36.72      A    C
ATOM  24842  O    LEU K 228      3.576  -1.797 -45.043  1.00 36.99      A    O
ATOM  24843  CB   LEU K 228      3.312   0.393 -47.556  1.00 35.94      A    C
ATOM  24844  CG   LEU K 228      4.338   1.333 -48.216  1.00 35.26      A    C
ATOM  24845  CD1  LEU K 228      3.874   1.740 -49.611  1.00 34.81      A    C
ATOM  24846  CD2  LEU K 228      5.794   0.783 -48.217  1.00 34.61      A    C
ATOM  24847  N    LYS K 229      1.716  -2.078 -46.299  1.00 37.42      A    N
ATOM  24848  CA   LYS K 229      1.017  -2.818 -45.243  1.00 38.22      A    C
ATOM  24849  C    LYS K 229      1.221  -4.313 -45.527  1.00 38.21      A    C
ATOM  24850  O    LYS K 229      2.188  -4.909 -45.041  1.00 38.13      A    O
ATOM  24851  CB   LYS K 229     -0.474  -2.409 -45.130  1.00 38.73      A    C
ATOM  24852  CG   LYS K 229     -1.226  -2.895 -43.845  1.00 39.51      A    C
ATOM  24853  CD   LYS K 229     -1.139  -1.900 -42.674  1.00 40.06      A    C
ATOM  24854  N    GLU K 230      0.334  -4.912 -46.321  1.00 38.40      A    N
ATOM  24855  CA   GLU K 230      0.598  -6.252 -46.845  1.00 38.57      A    C
ATOM  24856  C    GLU K 230      0.317  -6.378 -48.336  1.00 38.31      A    C
ATOM  24857  O    GLU K 230     -0.620  -5.756 -48.875  1.00 38.33      A    O
ATOM  24858  CB   GLU K 230     -0.096  -7.370 -46.036  1.00 38.98      A    C
ATOM  24859  CG   GLU K 230      0.602  -8.762 -46.176  1.00 39.90      A    C
ATOM  24860  CD   GLU K 230      2.126  -8.727 -45.900  1.00 40.11      A    C
ATOM  24861  OE1  GLU K 230      2.950  -8.687 -46.852  1.00 38.78      A    O
ATOM  24862  N    TRP K 231      1.160  -7.199 -48.972  1.00 37.98      A    N
ATOM  24863  CA   TRP K 231      1.143  -7.458 -50.411  1.00 37.73      A    C
ATOM  24864  C    TRP K 231     -0.261  -7.696 -50.975  1.00 38.07      A    C
ATOM  24865  O    TRP K 231     -1.023  -8.519 -50.446  1.00 38.38      A    O
ATOM  24866  CB   TRP K 231      2.060  -8.641 -50.748  1.00 37.32      A    C
ATOM  24867  CG   TRP K 231      2.293  -8.755 -52.209  1.00 36.77      A    C
ATOM  24868  CD1  TRP K 231      1.490  -9.393 -53.116  1.00 36.75      A    C
ATOM  24869  CD2  TRP K 231      3.384  -8.189 -52.962  1.00 36.18      A    C
ATOM  24870  CE2  TRP K 231      3.179  -8.535 -54.323  1.00 35.95      A    C
ATOM  24871  CE3  TRP K 231      4.513  -7.427 -52.620  1.00 35.83      A    C
ATOM  24872  NE1  TRP K 231      2.018  -9.267 -54.388  1.00 36.45      A    N
ATOM  24873  CZ2  TRP K 231      4.070  -8.148 -55.347  1.00 35.26      A    C
ATOM  24874  CZ3  TRP K 231      5.393  -7.039 -53.636  1.00 35.11      A    C
ATOM  24875  CH2  TRP K 231      5.164  -7.406 -54.984  1.00 34.83      A    C
ATOM  24876  N    GLY K 232     -0.583  -6.972 -52.047  1.00 38.19      A    N
ATOM  24877  CA   GLY K 232     -1.875  -7.084 -52.711  1.00 38.54      A    C
ATOM  24878  C    GLY K 232     -1.878  -6.256 -53.976  1.00 38.73      A    C
ATOM  24879  O    GLY K 232     -0.967  -5.450 -54.192  1.00 38.42      A    O
ATOM  24880  N    PRO K 233     -2.901  -6.454 -54.827  1.00 39.17      A    N
ATOM  24881  CA   PRO K 233     -3.061  -5.678 -56.067  1.00 39.35      A    C
ATOM  24882  C    PRO K 233     -2.992  -4.151 -55.859  1.00 39.56      A    C
ATOM  24883  O    PRO K 233     -2.389  -3.437 -56.679  1.00 39.22      A    O
ATOM  24884  CB   PRO K 233     -4.450  -6.098 -56.561  1.00 39.52      A    C
ATOM  24885  CG   PRO K 233     -4.596  -7.495 -56.046  1.00 39.64      A    C
ATOM  24886  CD   PRO K 233     -3.941  -7.493 -54.690  1.00 39.41      A    C
ATOM  24887  N    LYS K 234     -3.587  -3.668 -54.767  1.00 40.14      A    N
ATOM  24888  CA   LYS K 234     -3.586  -2.235 -54.463  1.00 40.73      A    C
ATOM  24889  C    LYS K 234     -2.396  -1.769 -53.574  1.00 40.51      A    C
ATOM  24890  O    LYS K 234     -2.180  -0.557 -53.389  1.00 40.64      A    O
ATOM  24891  CB   LYS K 234     -4.955  -1.803 -53.896  1.00 41.32      A    C
ATOM  24892  CG   LYS K 234     -6.037  -1.529 -54.976  1.00 42.35      A    C
ATOM  24893  CD   LYS K 234     -7.495  -1.681 -54.445  1.00 43.53      A    C
ATOM  24894  CE   LYS K 234     -8.079  -0.379 -53.873  1.00 43.74      A    C
ATOM  24895  N    ASP K 235     -1.625  -2.727 -53.047  1.00 40.12      A    N
```

FIGURE 1 (cont'd)

```
ATOM  24896  CA   ASP K 235      -0.434  -2.416 -52.241  1.00 39.62      A    C
ATOM  24897  C    ASP K 235       0.786  -3.209 -52.717  1.00 39.09      A    C
ATOM  24898  O    ASP K 235       1.172  -4.219 -52.111  1.00 39.05      A    O
ATOM  24899  CB   ASP K 235      -0.706  -2.632 -50.730  1.00 39.88      A    C
ATOM  24900  CG   ASP K 235       0.523  -2.316 -49.833  1.00 39.58      A    C
ATOM  24901  OD1  ASP K 235       0.686  -2.996 -48.788  1.00 39.27      A    O
ATOM  24902  OD2  ASP K 235       1.320  -1.399 -50.166  1.00 39.20      A    O
ATOM  24903  N    SER K 236       1.378  -2.739 -53.815  1.00 38.49      A    N
ATOM  24904  CA   SER K 236       2.600  -3.332 -54.411  1.00 37.86      A    C
ATOM  24905  C    SER K 236       2.831  -2.777 -55.818  1.00 37.54      A    C
ATOM  24906  O    SER K 236       1.875  -2.447 -56.535  1.00 37.54      A    O
ATOM  24907  CB   SER K 236       2.544  -4.878 -54.464  1.00 37.70      A    C
ATOM  24908  OG   SER K 236       1.548  -5.354 -55.371  1.00 37.66      A    O
ATOM  24909  N    LEU K 237       4.100  -2.688 -56.209  1.00 37.20      A    N
ATOM  24910  CA   LEU K 237       4.462  -2.310 -57.578  1.00 37.10      A    C
ATOM  24911  C    LEU K 237       3.912  -0.933 -57.964  1.00 37.30      A    C
ATOM  24912  O    LEU K 237       3.308  -0.774 -59.034  1.00 37.42      A    O
ATOM  24913  CB   LEU K 237       3.939  -3.354 -58.581  1.00 36.95      A    C
ATOM  24914  CG   LEU K 237       4.004  -4.858 -58.272  1.00 36.62      A    C
ATOM  24915  CD1  LEU K 237       3.007  -5.629 -59.149  1.00 36.70      A    C
ATOM  24916  CD2  LEU K 237       5.423  -5.404 -58.435  1.00 36.10      A    C
ATOM  24917  N    TYR K 238       4.111   0.056 -57.093  1.00 37.44      A    N
ATOM  24918  CA   TYR K 238       3.704   1.440 -57.387  1.00 37.53      A    C
ATOM  24919  C    TYR K 238       4.498   2.064 -58.549  1.00 37.20      A    C
ATOM  24920  O    TYR K 238       3.924   2.731 -59.419  1.00 37.26      A    O
ATOM  24921  CB   TYR K 238       3.821   2.313 -56.141  1.00 37.80      A    C
ATOM  24922  CG   TYR K 238       2.972   1.836 -55.000  1.00 38.39      A    C
ATOM  24923  CD1  TYR K 238       1.588   2.055 -54.998  1.00 39.35      A    C
ATOM  24924  CD2  TYR K 238       3.546   1.164 -53.914  1.00 38.49      A    C
ATOM  24925  CE1  TYR K 238       0.787   1.613 -53.930  1.00 39.75      A    C
ATOM  24926  CE2  TYR K 238       2.760   0.716 -52.840  1.00 38.99      A    C
ATOM  24927  CZ   TYR K 238       1.381   0.944 -52.852  1.00 39.42      A    C
ATOM  24928  OH   TYR K 238       0.604   0.511 -51.793  1.00 39.65      A    O
ATOM  24929  N    GLY K 239       5.812   1.837 -58.556  1.00 36.76      A    N
ATOM  24930  CA   GLY K 239       6.669   2.387 -59.596  1.00 36.49      A    C
ATOM  24931  C    GLY K 239       6.381   1.804 -60.971  1.00 36.30      A    C
ATOM  24932  O    GLY K 239       6.243   2.543 -61.964  1.00 36.35      A    O
ATOM  24933  N    SER K 240       6.290   0.475 -61.022  1.00 36.05      A    N
ATOM  24934  CA   SER K 240       6.099  -0.244 -62.278  1.00 35.77      A    C
ATOM  24935  C    SER K 240       4.716   0.005 -62.855  1.00 35.73      A    C
ATOM  24936  O    SER K 240       4.592   0.306 -64.044  1.00 35.81      A    O
ATOM  24937  CB   SER K 240       6.380  -1.741 -62.105  1.00 35.60      A    C
ATOM  24938  OG   SER K 240       5.899  -2.212 -60.860  1.00 35.88      A    O
ATOM  24939  N    ARG K 241       3.688  -0.101 -62.013  1.00 35.73      A    N
ATOM  24940  CA   ARG K 241       2.302   0.158 -62.447  1.00 35.99      A    C
ATOM  24941  C    ARG K 241       2.103   1.558 -63.035  1.00 36.06      A    C
ATOM  24942  O    ARG K 241       1.326   1.745 -63.981  1.00 36.23      A    O
ATOM  24943  CB   ARG K 241       1.292  -0.087 -61.315  1.00 36.06      A    C
ATOM  24944  CG   ARG K 241       0.789  -1.525 -61.253  1.00 36.67      A    C
ATOM  24945  CD   ARG K 241      -0.467  -1.667 -60.417  1.00 37.99      A    C
ATOM  24946  NE   ARG K 241      -0.190  -1.625 -58.978  1.00 39.24      A    N
ATOM  24947  CZ   ARG K 241      -0.455  -0.585 -58.179  1.00 40.20      A    C
ATOM  24948  NH1  ARG K 241      -1.015   0.516 -58.675  1.00 41.14      A    N
ATOM  24949  NH2  ARG K 241      -0.167  -0.645 -56.874  1.00 40.51      A    N
ATOM  24950  N    HIS K 242       2.812   2.532 -62.466  1.00 36.05      A    N
ATOM  24951  CA   HIS K 242       2.749   3.915 -62.937  1.00 36.10      A    C
ATOM  24952  C    HIS K 242       3.560   4.129 -64.220  1.00 35.75      A    C
ATOM  24953  O    HIS K 242       3.044   4.722 -65.178  1.00 35.93      A    O
ATOM  24954  CB   HIS K 242       3.222   4.880 -61.850  1.00 36.36      A    C
ATOM  24955  CG   HIS K 242       3.169   6.317 -62.265  1.00 37.18      A    C
ATOM  24956  CD2  HIS K 242       2.146   7.207 -62.261  1.00 37.95      A    C
ATOM  24957  ND1  HIS K 242       4.264   6.990 -62.773  1.00 37.34      A    N
ATOM  24958  CE1  HIS K 242       3.918   8.235 -63.053  1.00 37.99      A    C
ATOM  24959  NE2  HIS K 242       2.640   8.392 -62.752  1.00 38.42      A    N
ATOM  24960  N    LEU K 243       4.818   3.662 -64.227  1.00 35.14      A    N
```

FIGURE 1 (cont'd)

```
ATOM  24961  CA   LEU K 243       5.670   3.763 -65.414  1.00 34.69      A  C
ATOM  24962  C    LEU K 243       4.998   3.112 -66.631  1.00 34.78      A  C
ATOM  24963  O    LEU K 243       4.951   3.706 -67.724  1.00 34.92      A  O
ATOM  24964  CB   LEU K 243       7.059   3.154 -65.173  1.00 34.21      A  C
ATOM  24965  CG   LEU K 243       8.049   3.344 -66.332  1.00 33.50      A  C
ATOM  24966  CD1  LEU K 243       8.285   4.828 -66.614  1.00 33.27      A  C
ATOM  24967  CD2  LEU K 243       9.354   2.631 -66.040  1.00 32.88      A  C
ATOM  24968  N    ALA K 244       4.479   1.899 -66.425  1.00 34.80      A  N
ATOM  24969  CA   ALA K 244       3.706   1.214 -67.453  1.00 35.08      A  C
ATOM  24970  C    ALA K 244       2.579   2.117 -67.976  1.00 35.56      A  C
ATOM  24971  O    ALA K 244       2.462   2.291 -69.192  1.00 35.76      A  O
ATOM  24972  CB   ALA K 244       3.157  -0.129 -66.945  1.00 34.80      A  C
ATOM  24973  N    GLN K 245       1.784   2.705 -67.070  1.00 36.06      A  N
ATOM  24974  CA   GLN K 245       0.691   3.617 -67.453  1.00 36.64      A  C
ATOM  24975  C    GLN K 245       1.204   4.809 -68.272  1.00 37.00      A  C
ATOM  24976  O    GLN K 245       0.640   5.149 -69.326  1.00 37.27      A  O
ATOM  24977  CB   GLN K 245      -0.082   4.112 -66.221  1.00 36.69      A  C
ATOM  24978  N    LEU K 246       2.286   5.421 -67.791  1.00 37.12      A  N
ATOM  24979  CA   LEU K 246       2.867   6.623 -68.408  1.00 37.40      A  C
ATOM  24980  C    LEU K 246       3.573   6.351 -69.772  1.00 37.80      A  C
ATOM  24981  O    LEU K 246       3.602   7.224 -70.660  1.00 38.02      A  O
ATOM  24982  CB   LEU K 246       3.806   7.312 -67.395  1.00 37.12      A  C
ATOM  24983  CG   LEU K 246       4.456   8.663 -67.724  1.00 36.51      A  C
ATOM  24984  CD1  LEU K 246       5.956   8.453 -67.913  1.00 35.24      A  C
ATOM  24985  N    MET K 247       4.136   5.150 -69.929  1.00 38.07      A  N
ATOM  24986  CA   MET K 247       4.740   4.746 -71.202  1.00 38.50      A  C
ATOM  24987  C    MET K 247       3.694   4.447 -72.284  1.00 39.29      A  C
ATOM  24988  O    MET K 247       3.957   4.655 -73.469  1.00 39.47      A  O
ATOM  24989  CB   MET K 247       5.664   3.543 -71.009  1.00 38.00      A  C
ATOM  24990  CG   MET K 247       6.939   3.882 -70.248  1.00 37.35      A  C
ATOM  24991  SD   MET K 247       8.212   2.597 -70.251  1.00 36.57      A  S
ATOM  24992  CE   MET K 247       9.031   2.905 -71.828  1.00 36.94      A  C
ATOM  24993  N    GLU K 248       2.522   3.953 -71.866  1.00 40.20      A  N
ATOM  24994  CA   GLU K 248       1.387   3.688 -72.768  1.00 41.23      A  C
ATOM  24995  C    GLU K 248       0.795   4.985 -73.313  1.00 42.24      A  C
ATOM  24996  O    GLU K 248       0.300   5.019 -74.443  1.00 42.75      A  O
ATOM  24997  CB   GLU K 248       0.283   2.885 -72.061  1.00 41.05      A  C
ATOM  24998  N    SER K 249       0.844   6.044 -72.503  1.00 43.08      A  N
ATOM  24999  CA   SER K 249       0.312   7.353 -72.898  1.00 44.04      A  C
ATOM  25000  C    SER K 249       1.335   8.216 -73.663  1.00 44.52      A  C
ATOM  25001  O    SER K 249       0.992   9.307 -74.156  1.00 44.91      A  O
ATOM  25002  CB   SER K 249      -0.212   8.106 -71.666  1.00 44.16      A  C
ATOM  25003  OG   SER K 249       0.855   8.580 -70.853  1.00 44.16      A  O
ATOM  25004  N    ILE K 250       2.576   7.717 -73.758  1.00 44.82      A  N
ATOM  25005  CA   ILE K 250       3.679   8.432 -74.419  1.00 45.36      A  C
ATOM  25006  C    ILE K 250       3.953   7.898 -75.847  1.00 46.17      A  C
ATOM  25007  O    ILE K 250       4.534   6.804 -76.000  1.00 45.91      A  O
ATOM  25008  CB   ILE K 250       4.964   8.415 -73.537  1.00 44.88      A  C
ATOM  25009  CG1  ILE K 250       5.844   9.635 -73.831  1.00 44.80      A  C
ATOM  25010  CD1  ILE K 250       7.056   9.318 -74.667  1.00 44.41      A  C
ATOM  25011  N    PRO K 251       3.521   8.668 -76.889  1.00 47.28      A  N
ATOM  25012  CA   PRO K 251       3.663   8.234 -78.277  1.00 47.96      A  C
ATOM  25013  C    PRO K 251       5.115   8.089 -78.663  1.00 48.38      A  C
ATOM  25014  O    PRO K 251       6.002   8.838 -78.213  1.00 48.38      A  O
ATOM  25015  CB   PRO K 251       2.993   9.356 -79.088  1.00 48.25      A  C
ATOM  25016  CG   PRO K 251       2.079   9.995 -78.135  1.00 48.27      A  C
ATOM  25017  CD   PRO K 251       2.828   9.968 -76.828  1.00 47.60      A  C
ATOM  25018  N    HIS K 252       5.336   7.069 -79.466  1.00 48.83      A  N
ATOM  25019  CA   HIS K 252       6.653   6.740 -79.873  1.00 49.19      A  C
ATOM  25020  C    HIS K 252       6.579   6.502 -81.326  1.00 49.79      A  C
ATOM  25021  O    HIS K 252       5.509   5.994 -81.775  1.00 50.03      A  O
ATOM  25022  CB   HIS K 252       7.363   5.758 -78.973  1.00 48.02      A  C
ATOM  25023  CG   HIS K 252       8.802   5.527 -79.314  1.00 47.83      A  C
ATOM  25024  CD2  HIS K 252       9.411   4.416 -79.789  1.00 47.65      A  C
ATOM  25025  ND1  HIS K 252       9.801   6.467 -79.132  1.00 48.09      A  N
```

FIGURE 1 (cont'd)

```
ATOM  25026  CE1 HIS K 252    10.960   5.944 -79.498  1.00 48.07    A    C
ATOM  25027  NE2 HIS K 252    10.750   4.702 -79.901  1.00 47.87    A    N
ATOM  25028  N   SER K 253     7.733   6.512 -81.976  1.00 50.19    A    N
ATOM  25029  CA  SER K 253     7.880   6.345 -83.367  1.00 50.22    A    C
ATOM  25030  C   SER K 253     8.340   5.306 -84.234  1.00 50.34    A    C
ATOM  25031  O   SER K 253     9.330   5.601 -84.826  1.00 50.76    A    O
ATOM  25032  CB  SER K 253     9.128   7.177 -83.620  1.00 49.34    A    C
ATOM  25033  OG  SER K 253    10.301   6.797 -82.816  1.00 48.84    A    O
ATOM  25034  N   PRO K 254     7.445   4.525 -84.785  1.00 49.97    A    N
ATOM  25035  CA  PRO K 254     6.704   3.306 -84.951  1.00 49.54    A    C
ATOM  25036  C   PRO K 254     6.681   2.407 -83.747  1.00 49.14    A    C
ATOM  25037  O   PRO K 254     7.029   1.248 -83.896  1.00 49.28    A    O
ATOM  25038  CB  PRO K 254     7.363   2.568 -86.126  1.00 48.73    A    C
ATOM  25039  CG  PRO K 254     8.409   3.326 -86.600  1.00 48.84    A    C
ATOM  25040  CD  PRO K 254     8.635   4.477 -85.695  1.00 49.18    A    C
ATOM  25041  N   GLY K 255     6.286   2.918 -82.582  1.00 48.49    A    N
ATOM  25042  CA  GLY K 255     5.638   2.088 -81.586  1.00 47.58    A    C
ATOM  25043  C   GLY K 255     4.237   1.857 -82.114  1.00 47.14    A    C
ATOM  25044  O   GLY K 255     4.021   1.033 -83.005  1.00 47.42    A    O
ATOM  25045  N   PRO K 256     3.304   2.517 -81.430  1.00 46.66    A    N
ATOM  25046  CA  PRO K 256     2.220   3.490 -81.372  1.00 46.39    A    C
ATOM  25047  C   PRO K 256     2.690   4.252 -80.122  1.00 45.81    A    C
ATOM  25048  O   PRO K 256     2.964   5.451 -80.190  1.00 46.00    A    O
ATOM  25049  CB  PRO K 256     0.951   2.691 -81.024  1.00 46.57    A    C
ATOM  25050  CG  PRO K 256     0.932   1.485 -81.860  1.00 46.57    A    C
ATOM  25051  N   THR K 257     2.828   3.516 -79.009  1.00 44.80    A    N
ATOM  25052  CA  THR K 257     3.311   4.033 -77.722  1.00 43.69    A    C
ATOM  25053  C   THR K 257     4.743   3.543 -77.397  1.00 42.97    A    C
ATOM  25054  O   THR K 257     5.316   2.692 -78.106  1.00 42.82    A    O
ATOM  25055  CB  THR K 257     2.331   3.660 -76.557  1.00 43.50    A    C
ATOM  25056  OG1 THR K 257     2.117   2.237 -76.519  1.00 43.10    A    O
ATOM  25057  N   ARG K 258     5.314   4.092 -76.323  1.00 42.12    A    N
ATOM  25058  CA  ARG K 258     6.658   3.704 -75.868  1.00 41.11    A    C
ATOM  25059  C   ARG K 258     6.724   2.282 -75.316  1.00 40.60    A    C
ATOM  25060  O   ARG K 258     7.818   1.704 -75.192  1.00 40.54    A    O
ATOM  25061  CB  ARG K 258     7.205   4.707 -74.837  1.00 40.19    A    C
ATOM  25062  CG  ARG K 258     8.012   5.843 -75.469  1.00 40.11    A    C
ATOM  25063  CD  ARG K 258     9.096   6.356 -74.538  1.00 40.04    A    C
ATOM  25064  NE  ARG K 258     9.984   7.283 -75.232  1.00 40.31    A    N
ATOM  25065  N   ILE K 259     5.553   1.733 -74.983  1.00 39.92    A    N
ATOM  25066  CA  ILE K 259     5.444   0.352 -74.505  1.00 38.99    A    C
ATOM  25067  C   ILE K 259     5.880  -0.658 -75.571  1.00 38.89    A    C
ATOM  25068  O   ILE K 259     6.529  -1.671 -75.260  1.00 38.84    A    O
ATOM  25069  CB  ILE K 259     4.021   0.037 -74.026  1.00 38.07    A    C
ATOM  25070  CG1 ILE K 259     4.027  -0.063 -72.504  1.00 37.70    A    C
ATOM  25071  CD1 ILE K 259     2.754   0.385 -71.890  1.00 38.52    A    C
ATOM  25072  N   GLN K 260     5.546  -0.351 -76.824  1.00 38.53    A    N
ATOM  25073  CA  GLN K 260     5.919  -1.202 -77.938  1.00 37.95    A    C
ATOM  25074  C   GLN K 260     7.406  -1.019 -78.247  1.00 37.83    A    C
ATOM  25075  O   GLN K 260     7.968  -1.726 -79.097  1.00 38.27    A    O
ATOM  25076  CB  GLN K 260     5.075  -0.911 -79.194  1.00 37.11    A    C
ATOM  25077  CG  GLN K 260     3.847  -0.001 -79.023  1.00 36.71    A    C
ATOM  25078  CD  GLN K 260     2.903  -0.388 -77.878  1.00 36.34    A    C
ATOM  25079  OE1 GLN K 260     2.407  -1.501 -77.766  1.00 36.76    A    O
ATOM  25080  N   ALA K 261     8.047  -0.076 -77.559  1.00 37.20    A    N
ATOM  25081  CA  ALA K 261     9.479   0.149 -77.753  1.00 36.56    A    C
ATOM  25082  C   ALA K 261    10.340  -0.907 -77.028  1.00 35.76    A    C
ATOM  25083  O   ALA K 261    11.487  -1.184 -77.416  1.00 35.67    A    O
ATOM  25084  N   ILE K 262     9.770  -1.496 -75.983  1.00 34.74    A    N
ATOM  25085  CA  ILE K 262    10.452  -2.546 -75.243  1.00 33.69    A    C
ATOM  25086  C   ILE K 262    10.441  -3.834 -76.056  1.00 33.61    A    C
ATOM  25087  O   ILE K 262     9.420  -4.520 -76.133  1.00 33.78    A    O
ATOM  25088  CB  ILE K 262     9.783  -2.804 -73.877  1.00 32.77    A    C
ATOM  25089  CG1 ILE K 262     9.472  -1.478 -73.172  1.00 32.14    A    C
ATOM  25090  CD1 ILE K 262     8.351  -1.572 -72.166  1.00 31.72    A    C
```

FIGURE 1 (cont'd)

```
ATOM  25091  N    GLU K 263     11.573  -4.151 -76.679  1.00 33.28      A  N
ATOM  25092  CA   GLU K 263     11.712  -5.418 -77.424  1.00 32.88      A  C
ATOM  25093  C    GLU K 263     11.748  -6.597 -76.447  1.00 32.25      A  C
ATOM  25094  O    GLU K 263     11.175  -7.655 -76.720  1.00 32.35      A  O
ATOM  25095  CB   GLU K 263     12.973  -5.408 -78.314  1.00 33.07      A  C
ATOM  25096  CG   GLU K 263     12.985  -6.452 -79.432  1.00 33.06      A  C
ATOM  25097  CD   GLU K 263     14.120  -6.233 -80.418  1.00 32.64      A  C
ATOM  25098  N    LEU K 264     12.425  -6.391 -75.315  1.00 31.39      A  N
ATOM  25099  CA   LEU K 264     12.496  -7.379 -74.243  1.00 30.41      A  C
ATOM  25100  C    LEU K 264     12.658  -6.717 -72.866  1.00 29.82      A  C
ATOM  25101  O    LEU K 264     13.628  -5.982 -72.642  1.00 29.84      A  O
ATOM  25102  CB   LEU K 264     13.650  -8.364 -74.483  1.00 30.28      A  C
ATOM  25103  CG   LEU K 264     13.829  -9.453 -73.416  1.00 29.87      A  C
ATOM  25104  CD1  LEU K 264     12.560 -10.351 -73.278  1.00 29.77      A  C
ATOM  25105  CD2  LEU K 264     15.057 -10.281 -73.720  1.00 29.62      A  C
ATOM  25106  N    PHE K 265     11.705  -6.997 -71.967  1.00 28.99      A  N
ATOM  25107  CA   PHE K 265     11.731  -6.570 -70.559  1.00 27.95      A  C
ATOM  25108  C    PHE K 265     12.348  -7.701 -69.721  1.00 27.66      A  C
ATOM  25109  O    PHE K 265     11.661  -8.653 -69.320  1.00 27.54      A  O
ATOM  25110  CB   PHE K 265     10.297  -6.276 -70.101  1.00 27.68      A  C
ATOM  25111  CG   PHE K 265     10.183  -5.543 -68.782  1.00 26.40      A  C
ATOM  25112  CD1  PHE K 265     10.027  -4.152 -68.757  1.00 25.54      A  C
ATOM  25113  CD2  PHE K 265     10.167  -6.235 -67.570  1.00 25.40      A  C
ATOM  25114  CE1  PHE K 265      9.877  -3.445 -67.541  1.00 28.99      A  C
ATOM  25115  CE2  PHE K 265     10.024  -5.537 -66.351  1.00 29.98      A  C
ATOM  25116  CZ   PHE K 265      9.879  -4.137 -66.344  1.00 30.39      A  C
ATOM  25117  N    MET K 266     13.651  -7.602 -69.481  1.00 27.36      A  N
ATOM  25118  CA   MET K 266     14.348  -8.601 -68.681  1.00 27.19      A  C
ATOM  25119  C    MET K 266     14.492  -8.122 -67.227  1.00 27.19      A  C
ATOM  25120  O    MET K 266     15.405  -7.334 -66.919  1.00 27.33      A  O
ATOM  25121  CB   MET K 266     15.709  -8.913 -69.300  1.00 27.13      A  C
ATOM  25122  CG   MET K 266     16.534  -9.917 -68.513  1.00 26.81      A  C
ATOM  25123  N    LEU K 267     13.597  -8.588 -66.347  1.00 27.04      A  N
ATOM  25124  CA   LEU K 267     13.595  -8.167 -64.937  1.00 26.95      A  C
ATOM  25125  C    LEU K 267     14.563  -8.969 -64.022  1.00 27.04      A  C
ATOM  25126  O    LEU K 267     14.489 -10.203 -63.927  1.00 27.04      A  O
ATOM  25127  CB   LEU K 267     12.163  -8.177 -64.383  1.00 26.87      A  C
ATOM  25128  CG   LEU K 267     11.889  -7.817 -62.906  1.00 26.61      A  C
ATOM  25129  CD1  LEU K 267     12.355  -6.396 -62.567  1.00 26.58      A  C
ATOM  25130  CD2  LEU K 267     10.405  -7.985 -62.561  1.00 26.44      A  C
ATOM  25131  N    LEU K 268     15.459  -8.242 -63.350  1.00 27.11      A  N
ATOM  25132  CA   LEU K 268     16.451  -8.839 -62.456  1.00 27.29      A  C
ATOM  25133  C    LEU K 268     16.021  -8.724 -60.998  1.00 27.52      A  C
ATOM  25134  O    LEU K 268     15.767  -7.610 -60.507  1.00 27.70      A  O
ATOM  25135  CB   LEU K 268     17.797  -8.136 -62.629  1.00 27.21      A  C
ATOM  25136  CG   LEU K 268     18.752  -8.670 -63.694  1.00 27.29      A  C
ATOM  25137  CD1  LEU K 268     18.300  -8.283 -65.130  1.00 27.53      A  C
ATOM  25138  CD2  LEU K 268     20.161  -8.155 -63.385  1.00 27.10      A  C
ATOM  25139  N    ASP K 269     15.959  -9.854 -60.297  1.00 27.71      A  N
ATOM  25140  CA   ASP K 269     15.487  -9.839 -58.918  1.00 28.00      A  C
ATOM  25141  C    ASP K 269     16.054 -10.966 -58.079  1.00 27.93      A  C
ATOM  25142  O    ASP K 269     16.381 -12.038 -58.591  1.00 28.08      A  O
ATOM  25143  CB   ASP K 269     13.954  -9.894 -58.879  1.00 28.27      A  C
ATOM  25144  CG   ASP K 269     13.372  -9.025 -57.777  1.00 29.40      A  C
ATOM  25145  OD1  ASP K 269     13.660  -7.794 -57.797  1.00 30.31      A  O
ATOM  25146  OD2  ASP K 269     12.625  -9.569 -56.915  1.00 30.10      A  O
ATOM  25147  N    LEU K 270     16.144 -10.712 -56.779  1.00 27.83      A  N
ATOM  25148  CA   LEU K 270     16.619 -11.697 -55.796  1.00 27.84      A  C
ATOM  25149  C    LEU K 270     17.886 -12.426 -56.231  1.00 27.97      A  C
ATOM  25150  O    LEU K 270     17.996 -13.657 -56.088  1.00 28.00      A  O
ATOM  25151  CB   LEU K 270     15.525 -12.698 -55.453  1.00 27.74      A  C
ATOM  25152  CG   LEU K 270     14.161 -12.114 -55.075  1.00 27.77      A  C
ATOM  25153  CD1  LEU K 270     13.297 -13.205 -54.450  1.00 27.71      A  C
ATOM  25154  CD2  LEU K 270     14.277 -10.937 -54.124  1.00 28.00      A  C
ATOM  25155  N    LEU K 271     18.833 -11.648 -56.770  1.00 28.11      A  N
```

FIGURE 1 (cont'd)

```
ATOM  25156  CA   LEU K 271     20.145 -12.154 -57.197  1.00 28.36      A  C
ATOM  25157  C    LEU K 271     21.207 -11.716 -56.193  1.00 28.76      A  C
ATOM  25158  O    LEU K 271     21.192 -10.567 -55.717  1.00 28.75      A  O
ATOM  25159  CB   LEU K 271     20.507 -11.642 -58.599  1.00 28.13      A  C
ATOM  25160  CG   LEU K 271     19.566 -11.979 -59.766  1.00 27.74      A  C
ATOM  25161  CD1  LEU K 271     19.183 -10.720 -60.539  1.00 27.61      A  C
ATOM  25162  N    GLY K 272     22.116 -12.634 -55.869  1.00 29.28      A  N
ATOM  25163  CA   GLY K 272     23.229 -12.312 -54.983  1.00 29.91      A  C
ATOM  25164  C    GLY K 272     23.554 -13.443 -54.037  1.00 30.49      A  C
ATOM  25165  O    GLY K 272     24.706 -13.593 -53.630  1.00 30.70      A  O
ATOM  25166  N    ALA K 273     22.539 -14.239 -53.690  1.00 30.87      A  N
ATOM  25167  CA   ALA K 273     22.698 -15.364 -52.755  1.00 31.27      A  C
ATOM  25168  C    ALA K 273     23.516 -16.491 -53.379  1.00 31.58      A  C
ATOM  25169  O    ALA K 273     23.678 -16.519 -54.596  1.00 31.60      A  O
ATOM  25170  CB   ALA K 273     21.321 -15.885 -52.306  1.00 31.22      A  C
ATOM  25171  N    PRO K 274     24.049 -17.409 -52.550  1.00 31.98      A  N
ATOM  25172  CA   PRO K 274     24.677 -18.603 -53.102  1.00 32.26      A  C
ATOM  25173  C    PRO K 274     23.663 -19.553 -53.714  1.00 32.39      A  C
ATOM  25174  O    PRO K 274     22.499 -19.560 -53.289  1.00 32.27      A  O
ATOM  25175  CB   PRO K 274     25.306 -19.264 -51.878  1.00 32.50      A  C
ATOM  25176  CG   PRO K 274     24.535 -18.743 -50.724  1.00 32.46      A  C
ATOM  25177  CD   PRO K 274     24.250 -17.328 -51.093  1.00 32.16      A  C
ATOM  25178  N    ASN K 275     24.120 -20.331 -54.706  1.00 32.66      A  N
ATOM  25179  CA   ASN K 275     23.337 -21.397 -55.384  1.00 32.97      A  C
ATOM  25180  C    ASN K 275     21.918 -21.024 -55.817  1.00 32.56      A  C
ATOM  25181  O    ASN K 275     20.967 -21.717 -55.462  1.00 32.77      A  O
ATOM  25182  CB   ASN K 275     23.293 -22.670 -54.529  1.00 33.42      A  C
ATOM  25183  CG   ASN K 275     24.668 -23.169 -54.168  1.00 34.79      A  C
ATOM  25184  ND2  ASN K 275     25.062 -22.965 -52.916  1.00 35.89      A  N
ATOM  25185  OD1  ASN K 275     25.372 -23.738 -55.001  1.00 35.83      A  O
ATOM  25186  N    PRO K 276     21.766 -19.925 -56.584  1.00 32.14      A  N
ATOM  25187  CA   PRO K 276     20.419 -19.628 -57.099  1.00 31.87      A  C
ATOM  25188  C    PRO K 276     20.064 -20.599 -58.226  1.00 31.91      A  C
ATOM  25189  O    PRO K 276     20.958 -21.105 -58.938  1.00 31.98      A  O
ATOM  25190  CB   PRO K 276     20.553 -18.205 -57.667  1.00 31.66      A  C
ATOM  25191  CG   PRO K 276     22.002 -18.104 -58.096  1.00 31.67      A  C
ATOM  25192  CD   PRO K 276     22.786 -18.986 -57.110  1.00 31.95      A  C
ATOM  25193  N    THR K 277     18.774 -20.870 -58.378  1.00 31.94      A  N
ATOM  25194  CA   THR K 277     18.317 -21.662 -59.514  1.00 31.97      A  C
ATOM  25195  C    THR K 277     17.283 -20.858 -60.293  1.00 31.87      A  C
ATOM  25196  O    THR K 277     16.323 -20.317 -59.711  1.00 31.83      A  O
ATOM  25197  CB   THR K 277     17.776 -23.056 -59.091  1.00 32.02      A  C
ATOM  25198  CG2  THR K 277     18.921 -24.021 -58.807  1.00 32.11      A  C
ATOM  25199  OG1  THR K 277     16.982 -22.921 -57.909  1.00 32.27      A  O
ATOM  25200  N    PHE K 278     17.514 -20.764 -61.603  1.00 31.83      A  N
ATOM  25201  CA   PHE K 278     16.627 -20.025 -62.513  1.00 31.88      A  C
ATOM  25202  C    PHE K 278     15.898 -20.928 -63.534  1.00 32.20      A  C
ATOM  25203  O    PHE K 278     16.458 -21.910 -64.045  1.00 32.27      A  O
ATOM  25204  CB   PHE K 278     17.397 -18.918 -63.254  1.00 31.64      A  C
ATOM  25205  CG   PHE K 278     18.163 -17.988 -62.348  1.00 31.39      A  C
ATOM  25206  CD1  PHE K 278     17.494 -17.019 -61.591  1.00 31.27      A  C
ATOM  25207  CD2  PHE K 278     19.562 -18.076 -62.268  1.00 31.25      A  C
ATOM  25208  CE1  PHE K 278     18.204 -16.162 -60.755  1.00 31.23      A  C
ATOM  25209  CE2  PHE K 278     20.282 -17.224 -61.438  1.00 31.07      A  C
ATOM  25210  CZ   PHE K 278     19.602 -16.261 -60.676  1.00 31.07      A  C
ATOM  25211  N    TYR K 279     14.645 -20.573 -63.822  1.00 32.59      A  N
ATOM  25212  CA   TYR K 279     13.830 -21.279 -64.805  1.00 33.11      A  C
ATOM  25213  C    TYR K 279     13.157 -20.279 -65.747  1.00 33.73      A  C
ATOM  25214  O    TYR K 279     13.116 -19.071 -65.462  1.00 33.68      A  O
ATOM  25215  CB   TYR K 279     12.793 -22.139 -64.091  1.00 32.99      A  C
ATOM  25216  CG   TYR K 279     13.408 -23.139 -63.125  1.00 32.50      A  C
ATOM  25217  CD1  TYR K 279     13.871 -24.371 -63.567  1.00 32.37      A  C
ATOM  25218  N    SER K 280     12.657 -20.765 -66.883  1.00 34.65      A  N
ATOM  25219  CA   SER K 280     11.969 -19.872 -67.817  1.00 35.48      A  C
ATOM  25220  C    SER K 280     10.482 -19.793 -67.504  1.00 35.97      A  C
```

FIGURE 1 (cont'd)

```
ATOM  25221  O    SER K 280      9.735 -20.752 -67.729  1.00 36.26      A   O
ATOM  25222  CB   SER K 280     12.194 -20.285 -69.273  1.00 35.61      A   C
ATOM  25223  OG   SER K 280     11.626 -19.313 -70.148  1.00 35.80      A   O
ATOM  25224  N    HIS K 281     10.063 -18.645 -66.982  1.00 36.42      A   N
ATOM  25225  CA   HIS K 281      8.675 -18.469 -66.552  1.00 37.17      A   C
ATOM  25226  C    HIS K 281      7.809 -17.904 -67.658  1.00 37.49      A   C
ATOM  25227  O    HIS K 281      6.595 -17.752 -67.488  1.00 37.67      A   O
ATOM  25228  CB   HIS K 281      8.580 -17.628 -65.271  1.00 37.22      A   C
ATOM  25229  CG   HIS K 281      9.397 -18.180 -64.142  1.00 37.83      A   C
ATOM  25230  CD2  HIS K 281      9.132 -19.153 -63.238  1.00 38.68      A   C
ATOM  25231  ND1  HIS K 281     10.683 -17.755 -63.879  1.00 37.85      A   N
ATOM  25232  CE1  HIS K 281     11.170 -18.428 -62.852  1.00 38.23      A   C
ATOM  25233  NE2  HIS K 281     10.249 -19.284 -62.446  1.00 38.95      A   N
ATOM  25234  N    PHE K 282      8.441 -17.606 -68.791  1.00 37.83      A   N
ATOM  25235  CA   PHE K 282      7.701 -17.263 -70.004  1.00 38.23      A   C
ATOM  25236  C    PHE K 282      8.249 -17.997 -71.228  1.00 38.58      A   C
ATOM  25237  O    PHE K 282      9.384 -17.724 -71.659  1.00 38.51      A   O
ATOM  25238  CB   PHE K 282      7.640 -15.747 -70.224  1.00 38.09      A   C
ATOM  25239  CG   PHE K 282      7.027 -15.010 -69.072  1.00 38.04      A   C
ATOM  25240  CD1  PHE K 282      5.649 -15.037 -68.861  1.00 38.49      A   C
ATOM  25241  CD2  PHE K 282      7.825 -14.320 -68.171  1.00 37.90      A   C
ATOM  25242  CE1  PHE K 282      5.069 -14.368 -67.781  1.00 38.43      A   C
ATOM  25243  CE2  PHE K 282      7.251 -13.645 -67.096  1.00 38.00      A   C
ATOM  25244  CZ   PHE K 282      5.867 -13.671 -66.904  1.00 38.23      A   C
ATOM  25245  N    PRO K 283      7.445 -18.940 -71.782  1.00 38.95      A   N
ATOM  25246  CA   PRO K 283      7.814 -19.653 -73.001  1.00 39.06      A   C
ATOM  25247  C    PRO K 283      7.971 -18.687 -74.191  1.00 38.94      A   C
ATOM  25248  O    PRO K 283      8.677 -19.007 -75.142  1.00 39.04      A   O
ATOM  25249  CB   PRO K 283      6.635 -20.608 -73.218  1.00 39.32      A   C
ATOM  25250  CG   PRO K 283      5.955 -20.702 -71.889  1.00 39.33      A   C
ATOM  25251  CD   PRO K 283      6.113 -19.353 -71.296  1.00 39.07      A   C
ATOM  25252  N    ARG K 284      7.339 -17.514 -74.121  1.00 38.69      A   N
ATOM  25253  CA   ARG K 284      7.495 -16.494 -75.156  1.00 38.56      A   C
ATOM  25254  C    ARG K 284      8.968 -16.173 -75.381  1.00 38.73      A   C
ATOM  25255  O    ARG K 284      9.417 -16.031 -76.512  1.00 38.98      A   O
ATOM  25256  CB   ARG K 284      6.738 -15.214 -74.781  1.00 38.29      A   C
ATOM  25257  CG   ARG K 284      6.161 -14.448 -75.964  1.00 37.47      A   C
ATOM  25258  CD   ARG K 284      7.207 -13.789 -76.839  1.00 35.78      A   C
ATOM  25259  NE   ARG K 284      6.643 -12.696 -77.619  1.00 34.96      A   N
ATOM  25260  N    THR K 285      9.719 -16.067 -74.295  1.00 38.78      A   N
ATOM  25261  CA   THR K 285     11.125 -15.687 -74.384  1.00 38.93      A   C
ATOM  25262  C    THR K 285     12.054 -16.863 -74.077  1.00 39.30      A   C
ATOM  25263  O    THR K 285     13.247 -16.671 -73.799  1.00 39.18      A   O
ATOM  25264  CB   THR K 285     11.440 -14.490 -73.442  1.00 38.56      A   C
ATOM  25265  OG1  THR K 285     10.911 -14.758 -72.132  1.00 38.21      A   O
ATOM  25266  N    VAL K 286     11.506 -18.075 -74.147  1.00 39.88      A   N
ATOM  25267  CA   VAL K 286     12.231 -19.284 -73.735  1.00 40.42      A   C
ATOM  25268  C    VAL K 286     13.625 -19.424 -74.363  1.00 41.05      A   C
ATOM  25269  O    VAL K 286     14.535 -20.011 -73.765  1.00 41.02      A   O
ATOM  25270  CB   VAL K 286     11.413 -20.562 -74.027  1.00 40.33      A   C
ATOM  25271  N    ARG K 287     13.780 -18.877 -75.567  1.00 41.93      A   N
ATOM  25272  CA   ARG K 287     15.036 -18.986 -76.320  1.00 42.82      A   C
ATOM  25273  C    ARG K 287     16.121 -18.031 -75.809  1.00 42.57      A   C
ATOM  25274  O    ARG K 287     17.318 -18.290 -75.976  1.00 42.70      A   O
ATOM  25275  CB   ARG K 287     14.797 -18.800 -77.835  1.00 43.56      A   C
ATOM  25276  CG   ARG K 287     14.252 -17.422 -78.272  1.00 45.26      A   C
ATOM  25277  CD   ARG K 287     14.142 -17.328 -79.798  1.00 48.26      A   C
ATOM  25278  NE   ARG K 287     13.873 -15.956 -80.241  1.00 49.99      A   N
ATOM  25279  CZ   ARG K 287     14.809 -15.064 -80.582  1.00 50.50      A   C
ATOM  25280  NH1  ARG K 287     16.101 -15.387 -80.546  1.00 50.56      A   N
ATOM  25281  NH2  ARG K 287     14.453 -13.840 -80.964  1.00 50.72      A   N
ATOM  25282  N    TRP K 288     15.701 -16.924 -75.198  1.00 42.24      A   N
ATOM  25283  CA   TRP K 288     16.653 -16.015 -74.574  1.00 41.93      A   C
ATOM  25284  C    TRP K 288     17.136 -16.596 -73.259  1.00 41.70      A   C
ATOM  25285  O    TRP K 288     18.277 -16.343 -72.848  1.00 41.74      A   O
```

FIGURE 1 (cont'd)

```
ATOM  25286  CB   TRP K 288      16.057 -14.619 -74.387  1.00 41.83      A    C
ATOM  25287  CG   TRP K 288      15.991 -13.889 -75.674  1.00 42.52      A    C
ATOM  25288  CD1  TRP K 288      14.867 -13.388 -76.290  1.00 43.00      A    C
ATOM  25289  CD2  TRP K 288      17.093 -13.601 -76.539  1.00 43.22      A    C
ATOM  25290  CE2  TRP K 288      16.568 -12.902 -77.661  1.00 43.62      A    C
ATOM  25291  CE3  TRP K 288      18.476 -13.850 -76.471  1.00 43.39      A    C
ATOM  25292  NE1  TRP K 288      15.211 -12.786 -77.481  1.00 43.41      A    N
ATOM  25293  CZ2  TRP K 288      17.381 -12.453 -78.713  1.00 44.12      A    C
ATOM  25294  CZ3  TRP K 288      19.285 -13.406 -77.513  1.00 43.92      A    C
ATOM  25295  CH2  TRP K 288      18.735 -12.712 -78.622  1.00 44.31      A    C
ATOM  25296  N    PHE K 289      16.272 -17.382 -72.612  1.00 41.50      A    N
ATOM  25297  CA   PHE K 289      16.674 -18.121 -71.422  1.00 41.35      A    C
ATOM  25298  C    PHE K 289      17.742 -19.153 -71.801  1.00 41.47      A    C
ATOM  25299  O    PHE K 289      18.742 -19.357 -71.095  1.00 41.29      A    O
ATOM  25300  CB   PHE K 289      15.469 -18.796 -70.758  1.00 41.22      A    C
ATOM  25301  CG   PHE K 289      15.771 -19.332 -69.392  1.00 41.09      A    C
ATOM  25302  CD1  PHE K 289      15.831 -18.473 -68.296  1.00 40.70      A    C
ATOM  25303  CD2  PHE K 289      16.031 -20.688 -69.202  1.00 41.41      A    C
ATOM  25304  CE1  PHE K 289      16.134 -18.961 -67.025  1.00 40.58      A    C
ATOM  25305  CE2  PHE K 289      16.333 -21.188 -67.931  1.00 41.53      A    C
ATOM  25306  CZ   PHE K 289      16.392 -20.324 -66.843  1.00 41.09      A    C
ATOM  25307  N    HIS K 290      17.514 -19.783 -72.942  1.00 41.81      A    N
ATOM  25308  CA   HIS K 290      18.429 -20.742 -73.494  1.00 42.26      A    C
ATOM  25309  C    HIS K 290      19.805 -20.138 -73.728  1.00 42.35      A    C
ATOM  25310  O    HIS K 290      20.839 -20.784 -73.499  1.00 42.53      A    O
ATOM  25311  CB   HIS K 290      17.820 -21.267 -74.780  1.00 42.53      A    C
ATOM  25312  CG   HIS K 290      17.511 -22.712 -74.717  1.00 43.24      A    C
ATOM  25313  CD2  HIS K 290      18.183 -23.701 -74.066  1.00 45.23      A    C
ATOM  25314  ND1  HIS K 290      16.559 -23.342 -75.483  1.00 44.06      A    N
ATOM  25315  CE1  HIS K 290      16.633 -24.645 -75.281  1.00 44.53      A    C
ATOM  25316  NE2  HIS K 290      17.588 -24.889 -74.402  1.00 45.87      A    N
ATOM  25317  N    ARG K 291      19.803 -18.881 -74.156  1.00 42.39      A    N
ATOM  25318  CA   ARG K 291      21.042 -18.145 -74.343  1.00 42.65      A    C
ATOM  25319  C    ARG K 291      21.839 -18.093 -73.049  1.00 42.26      A    C
ATOM  25320  O    ARG K 291      23.040 -18.391 -73.043  1.00 42.47      A    O
ATOM  25321  CB   ARG K 291      20.759 -16.735 -74.881  1.00 42.88      A    C
ATOM  25322  CG   ARG K 291      20.501 -16.725 -76.374  1.00 44.50      A    C
ATOM  25323  CD   ARG K 291      21.707 -17.306 -77.115  1.00 46.63      A    C
ATOM  25324  NE   ARG K 291      22.640 -16.252 -77.486  1.00 47.71      A    N
ATOM  25325  CZ   ARG K 291      22.684 -15.701 -78.693  1.00 48.75      A    C
ATOM  25326  NH1  ARG K 291      21.860 -16.123 -79.644  1.00 49.28      A    N
ATOM  25327  NH2  ARG K 291      23.550 -14.732 -78.955  1.00 49.27      A    N
ATOM  25328  N    LEU K 292      21.146 -17.740 -71.964  1.00 41.64      A    N
ATOM  25329  CA   LEU K 292      21.751 -17.638 -70.635  1.00 41.00      A    C
ATOM  25330  C    LEU K 292      22.319 -18.975 -70.173  1.00 40.95      A    C
ATOM  25331  O    LEU K 292      23.434 -19.026 -69.650  1.00 41.00      A    O
ATOM  25332  CB   LEU K 292      20.755 -17.067 -69.618  1.00 40.60      A    C
ATOM  25333  CG   LEU K 292      20.336 -15.608 -69.910  1.00 39.92      A    C
ATOM  25334  CD1  LEU K 292      19.079 -15.210 -69.118  1.00 39.42      A    C
ATOM  25335  CD2  LEU K 292      21.490 -14.630 -69.655  1.00 39.44      A    C
ATOM  25336  N    ARG K 293      21.571 -20.054 -70.396  1.00 40.90      A    N
ATOM  25337  CA   ARG K 293      22.094 -21.380 -70.131  1.00 41.01      A    C
ATOM  25338  C    ARG K 293      23.348 -21.590 -70.975  1.00 41.32      A    C
ATOM  25339  O    ARG K 293      24.377 -22.040 -70.454  1.00 41.43      A    O
ATOM  25340  CB   ARG K 293      21.051 -22.459 -70.423  1.00 40.92      A    C
ATOM  25341  CG   ARG K 293      21.347 -23.805 -69.727  1.00 40.69      A    C
ATOM  25342  CD   ARG K 293      20.443 -24.959 -70.224  1.00 40.49      A    C
ATOM  25343  NE   ARG K 293      19.017 -24.756 -69.949  1.00 39.78      A    N
ATOM  25344  N    SER K 294      23.262 -21.228 -72.261  1.00 41.47      A    N
ATOM  25345  CA   SER K 294      24.360 -21.427 -73.213  1.00 41.75      A    C
ATOM  25346  C    SER K 294      25.609 -20.624 -72.849  1.00 42.14      A    C
ATOM  25347  O    SER K 294      26.735 -21.117 -72.999  1.00 42.62      A    O
ATOM  25348  CB   SER K 294      23.914 -21.097 -74.642  1.00 40.76      A    C
ATOM  25349  N    ILE K 295      25.399 -19.395 -72.366  1.00 42.24      A    N
ATOM  25350  CA   ILE K 295      26.499 -18.500 -71.934  1.00 42.30      A    C
```

FIGURE 1 (cont'd)

```
ATOM  25351  C    ILE K 295      27.209 -19.019 -70.676  1.00 42.54      A    C
ATOM  25352  O    ILE K 295      28.441 -19.023 -70.610  1.00 42.68      A    O
ATOM  25353  CB   ILE K 295      26.008 -17.026 -71.743  1.00 42.01      A    C
ATOM  25354  CG1  ILE K 295      25.685 -16.395 -73.105  1.00 41.94      A    C
ATOM  25355  CG2  ILE K 295      27.050 -16.181 -71.012  1.00 41.83      A    C
ATOM  25356  CD1  ILE K 295      24.654 -15.284 -73.030  1.00 41.63      A    C
ATOM  25357  N    GLU K 296      26.419 -19.458 -69.696  1.00 42.71      A    N
ATOM  25358  CA   GLU K 296      26.938 -20.106 -68.491  1.00 43.04      A    C
ATOM  25359  C    GLU K 296      27.780 -21.336 -68.856  1.00 43.57      A    C
ATOM  25360  O    GLU K 296      28.935 -21.461 -68.441  1.00 43.80      A    O
ATOM  25361  CB   GLU K 296      25.784 -20.519 -67.571  1.00 42.76      A    C
ATOM  25362  CG   GLU K 296      26.233 -21.022 -66.189  1.00 42.95      A    C
ATOM  25363  CD   GLU K 296      25.107 -21.681 -65.376  1.00 43.15      A    C
ATOM  25364  OE1  GLU K 296      23.897 -21.486 -65.685  1.00 42.82      A    O
ATOM  25365  OE2  GLU K 296      25.448 -22.404 -64.415  1.00 43.38      A    O
ATOM  25366  N    LYS K 297      27.173 -22.226 -69.639  1.00 44.14      A    N
ATOM  25367  CA   LYS K 297      27.831 -23.394 -70.201  1.00 44.85      A    C
ATOM  25368  C    LYS K 297      29.194 -23.017 -70.780  1.00 45.50      A    C
ATOM  25369  O    LYS K 297      30.225 -23.542 -70.348  1.00 45.75      A    O
ATOM  25370  CB   LYS K 297      26.941 -23.987 -71.298  1.00 44.74      A    C
ATOM  25371  CG   LYS K 297      26.677 -25.476 -71.162  1.00 44.66      A    C
ATOM  25372  CD   LYS K 297      25.300 -25.850 -71.774  1.00 43.81      A    C
ATOM  25373  CE   LYS K 297      25.194 -27.360 -72.138  1.00 43.80      A    C
ATOM  25374  N    ARG K 298      29.179 -22.083 -71.737  1.00 46.04      A    N
ATOM  25375  CA   ARG K 298      30.389 -21.605 -72.449  1.00 46.57      A    C
ATOM  25376  C    ARG K 298      31.463 -21.036 -71.499  1.00 47.09      A    C
ATOM  25377  O    ARG K 298      32.634 -21.441 -71.579  1.00 47.62      A    O
ATOM  25378  CB   ARG K 298      30.008 -20.572 -73.545  1.00 45.54      A    C
ATOM  25379  CG   ARG K 298      31.153 -20.096 -74.457  1.00 45.49      A    C
ATOM  25380  CD   ARG K 298      30.630 -19.156 -75.562  1.00 45.15      A    C
ATOM  25381  NE   ARG K 298      31.704 -18.606 -76.394  1.00 45.02      A    N
ATOM  25382  N    LEU K 299      31.051 -20.114 -70.612  1.00 47.30      A    N
ATOM  25383  CA   LEU K 299      31.973 -19.439 -69.682  1.00 47.51      A    C
ATOM  25384  C    LEU K 299      32.575 -20.425 -68.689  1.00 47.90      A    C
ATOM  25385  O    LEU K 299      33.711 -20.256 -68.236  1.00 48.12      A    O
ATOM  25386  CB   LEU K 299      31.280 -18.278 -68.951  1.00 47.18      A    C
ATOM  25387  CG   LEU K 299      30.982 -16.972 -69.723  1.00 47.01      A    C
ATOM  25388  CD1  LEU K 299      29.995 -16.083 -68.964  1.00 46.56      A    C
ATOM  25389  CD2  LEU K 299      32.249 -16.183 -70.025  1.00 47.45      A    C
ATOM  25390  N    HIS K 300      31.801 -21.457 -68.373  1.00 48.23      A    N
ATOM  25391  CA   HIS K 300      32.278 -22.548 -67.548  1.00 48.79      A    C
ATOM  25392  C    HIS K 300      33.382 -23.324 -68.251  1.00 49.26      A    C
ATOM  25393  O    HIS K 300      34.453 -23.538 -67.666  1.00 49.56      A    O
ATOM  25394  CB   HIS K 300      31.136 -23.492 -67.179  1.00 48.72      A    C
ATOM  25395  CG   HIS K 300      31.603 -24.768 -66.555  1.00 49.37      A    C
ATOM  25396  CD2  HIS K 300      31.522 -26.050 -66.982  1.00 50.14      A    C
ATOM  25397  ND1  HIS K 300      32.268 -24.807 -65.345  1.00 49.69      A    N
ATOM  25398  CE1  HIS K 300      32.567 -26.061 -65.048  1.00 50.31      A    C
ATOM  25399  NE2  HIS K 300      32.127 -26.836 -66.025  1.00 50.75      A    N
ATOM  25400  N    ARG K 301      33.107 -23.743 -69.493  1.00 49.73      A    N
ATOM  25401  CA   ARG K 301      34.087 -24.446 -70.349  1.00 50.28      A    C
ATOM  25402  C    ARG K 301      35.421 -23.672 -70.438  1.00 50.92      A    C
ATOM  25403  O    ARG K 301      36.510 -24.266 -70.394  1.00 51.43      A    O
ATOM  25404  CB   ARG K 301      33.532 -24.667 -71.772  1.00 50.11      A    C
ATOM  25405  CG   ARG K 301      32.156 -25.317 -71.867  1.00 49.13      A    C
ATOM  25406  CD   ARG K 301      32.220 -26.840 -71.813  1.00 48.46      A    C
ATOM  25407  NE   ARG K 301      30.885 -27.429 -71.712  1.00 47.72      A    N
ATOM  25408  N    LEU K 302      35.314 -22.345 -70.546  1.00 51.29      A    N
ATOM  25409  CA   LEU K 302      36.466 -21.453 -70.670  1.00 51.88      A    C
ATOM  25410  C    LEU K 302      37.129 -21.120 -69.325  1.00 52.23      A    C
ATOM  25411  O    LEU K 302      37.920 -20.176 -69.247  1.00 52.54      A    O
ATOM  25412  CB   LEU K 302      36.044 -20.159 -71.386  1.00 51.77      A    C
ATOM  25413  CG   LEU K 302      35.683 -20.265 -72.873  1.00 52.26      A    C
ATOM  25414  CD1  LEU K 302      34.713 -19.168 -73.283  1.00 51.86      A    C
ATOM  25415  CD2  LEU K 302      36.933 -20.252 -73.763  1.00 53.50      A    C
```

FIGURE 1 (cont'd)

```
ATOM  25416  N   ASN K 303      36.819 -21.894 -68.279  1.00 52.36      A   N
ATOM  25417  CA  ASN K 303      37.294 -21.621 -66.910  1.00 52.30      A   C
ATOM  25418  C   ASN K 303      37.306 -20.112 -66.590  1.00 52.74      A   C
ATOM  25419  O   ASN K 303      38.368 -19.509 -66.413  1.00 53.21      A   O
ATOM  25420  N   LEU K 304      36.119 -19.507 -66.560  1.00 52.91      A   N
ATOM  25421  CA  LEU K 304      35.971 -18.071 -66.256  1.00 52.80      A   C
ATOM  25422  C   LEU K 304      34.911 -17.803 -65.174  1.00 52.50      A   C
ATOM  25423  O   LEU K 304      34.543 -16.649 -64.913  1.00 52.24      A   O
ATOM  25424  CB  LEU K 304      35.654 -17.262 -67.528  1.00 52.84      A   C
ATOM  25425  CG  LEU K 304      36.787 -16.826 -68.460  1.00 53.29      A   C
ATOM  25426  CD1 LEU K 304      36.219 -16.161 -69.722  1.00 52.96      A   C
ATOM  25427  CD2 LEU K 304      37.769 -15.889 -67.758  1.00 53.84      A   C
ATOM  25428  N   LEU K 305      34.429 -18.878 -64.553  1.00 52.41      A   N
ATOM  25429  CA  LEU K 305      33.432 -18.783 -63.497  1.00 52.24      A   C
ATOM  25430  C   LEU K 305      34.000 -19.376 -62.209  1.00 52.64      A   C
ATOM  25431  O   LEU K 305      34.357 -20.567 -62.171  1.00 53.04      A   O
ATOM  25432  CB  LEU K 305      32.127 -19.509 -63.904  1.00 51.80      A   C
ATOM  25433  CG  LEU K 305      31.399 -19.127 -65.207  1.00 51.11      A   C
ATOM  25434  CD1 LEU K 305      30.254 -20.089 -65.479  1.00 50.40      A   C
ATOM  25435  CD2 LEU K 305      30.892 -17.667 -65.188  1.00 50.68      A   C
ATOM  25436  N   GLN K 306      34.092 -18.537 -61.172  1.00 52.79      A   N
ATOM  25437  CA  GLN K 306      34.524 -18.968 -59.838  1.00 53.07      A   C
ATOM  25438  C   GLN K 306      33.528 -19.936 -59.206  1.00 52.97      A   C
ATOM  25439  O   GLN K 306      32.318 -19.869 -59.482  1.00 52.60      A   O
ATOM  25440  CB  GLN K 306      34.696 -17.763 -58.912  1.00 53.19      A   C
ATOM  25441  CG  GLN K 306      36.102 -17.175 -58.868  1.00 54.06      A   C
ATOM  25442  CD  GLN K 306      36.250 -16.158 -57.752  1.00 54.73      A   C
ATOM  25443  OE1 GLN K 306      35.408 -15.266 -57.595  1.00 54.93      A   O
ATOM  25444  N   SER K 307      34.052 -20.829 -58.362  1.00 53.31      A   N
ATOM  25445  CA  SER K 307      33.235 -21.756 -57.565  1.00 53.54      A   C
ATOM  25446  C   SER K 307      32.084 -22.335 -58.391  1.00 53.39      A   C
ATOM  25447  O   SER K 307      30.924 -22.296 -57.973  1.00 53.17      A   O
ATOM  25448  CB  SER K 307      32.674 -21.048 -56.309  1.00 53.58      A   C
ATOM  25449  OG  SER K 307      33.654 -20.281 -55.619  1.00 54.29      A   O
ATOM  25450  N   HIS K 308      32.407 -22.856 -59.571  1.00 53.52      A   N
ATOM  25451  CA  HIS K 308      31.388 -23.306 -60.530  1.00 53.50      A   C
ATOM  25452  C   HIS K 308      31.644 -24.743 -60.988  1.00 53.75      A   C
ATOM  25453  O   HIS K 308      32.046 -24.970 -62.133  1.00 53.99      A   O
ATOM  25454  CB  HIS K 308      31.338 -22.349 -61.734  1.00 53.30      A   C
ATOM  25455  CG  HIS K 308      30.050 -22.405 -62.502  1.00 53.03      A   C
ATOM  25456  CD2 HIS K 308      28.809 -21.942 -62.203  1.00 52.60      A   C
ATOM  25457  ND1 HIS K 308      29.945 -22.999 -63.742  1.00 53.31      A   N
ATOM  25458  CE1 HIS K 308      28.698 -22.897 -64.177  1.00 52.95      A   C
ATOM  25459  NE2 HIS K 308      27.988 -22.261 -63.262  1.00 52.42      A   N
ATOM  25460  N   PRO K 309      31.405 -25.714 -60.090  1.00 53.94      A   N
ATOM  25461  CA  PRO K 309      31.831 -27.094 -60.337  1.00 54.45      A   C
ATOM  25462  C   PRO K 309      30.862 -27.920 -61.194  1.00 54.72      A   C
ATOM  25463  O   PRO K 309      30.688 -29.120 -60.930  1.00 54.99      A   O
ATOM  25464  CB  PRO K 309      31.970 -27.695 -58.924  1.00 54.68      A   C
ATOM  25465  CG  PRO K 309      32.047 -26.528 -57.989  1.00 54.44      A   C
ATOM  25466  N   GLN K 310      30.230 -27.281 -62.187  1.00 54.75      A   N
ATOM  25467  CA  GLN K 310      29.570 -27.981 -63.329  1.00 54.93      A   C
ATOM  25468  C   GLN K 310      29.006 -27.005 -64.361  1.00 55.02      A   C
ATOM  25469  O   GLN K 310      29.143 -25.787 -64.201  1.00 54.85      A   O
ATOM  25470  CB  GLN K 310      28.522 -29.043 -62.915  1.00 54.94      A   C
ATOM  25471  CG  GLN K 310      27.600 -28.663 -61.753  1.00 54.58      A   C
ATOM  25472  CD  GLN K 310      27.231 -29.848 -60.862  1.00 54.66      A   C
ATOM  25473  NE2 GLN K 310      26.431 -29.566 -59.827  1.00 55.61      A   N
ATOM  25474  OE1 GLN K 310      27.638 -30.997 -61.101  1.00 55.60      A   O
ATOM  25475  N   GLU K 311      28.390 -27.549 -65.413  1.00 55.40      A   N
ATOM  25476  CA  GLU K 311      27.963 -26.760 -66.582  1.00 55.77      A   C
ATOM  25477  C   GLU K 311      26.660 -26.000 -66.286  1.00 55.08      A   C
ATOM  25478  O   GLU K 311      26.634 -24.750 -66.285  1.00 54.87      A   O
ATOM  25479  CB  GLU K 311      27.806 -27.665 -67.823  1.00 56.52      A   C
ATOM  25480  CG  GLU K 311      28.974 -28.643 -68.085  1.00 58.92      A   C
```

FIGURE 1 (cont'd)

```
ATOM  25481  CD   GLU K 311     28.919 -29.951 -67.263  1.00 61.43      A  C
ATOM  25482  OE1  GLU K 311     29.496 -30.948 -67.749  1.00 62.84      A  O
ATOM  25483  OE2  GLU K 311     28.321 -29.997 -66.152  1.00 61.98      A  O
ATOM  25484  N    VAL K 312     25.594 -26.771 -66.033  1.00 54.50      A  N
ATOM  25485  CA   VAL K 312     24.306 -26.227 -65.614  1.00 53.77      A  C
ATOM  25486  C    VAL K 312     24.241 -26.171 -64.080  1.00 53.26      A  C
ATOM  25487  O    VAL K 312     24.108 -27.203 -63.397  1.00 53.58      A  O
ATOM  25488  N    MET K 313     24.372 -24.955 -63.552  1.00 52.22      A  N
ATOM  25489  CA   MET K 313     24.248 -24.707 -62.121  1.00 51.24      A  C
ATOM  25490  C    MET K 313     23.094 -23.736 -61.922  1.00 50.23      A  C
ATOM  25491  O    MET K 313     22.137 -24.035 -61.214  1.00 50.07      A  O
ATOM  25492  CB   MET K 313     25.547 -24.095 -61.559  1.00 51.44      A  C
ATOM  25493  CG   MET K 313     26.818 -24.954 -61.704  1.00 52.04      A  C
ATOM  25494  SD   MET K 313     27.565 -25.461 -60.137  1.00 52.55      A  S
ATOM  25495  CE   MET K 313     27.859 -23.870 -59.329  1.00 52.13      A  C
ATOM  25496  N    TYR K 314     23.193 -22.586 -62.590  1.00 49.15      A  N
ATOM  25497  CA   TYR K 314     22.297 -21.446 -62.373  1.00 48.09      A  C
ATOM  25498  C    TYR K 314     21.031 -21.510 -63.216  1.00 47.56      A  C
ATOM  25499  O    TYR K 314     19.919 -21.531 -62.669  1.00 47.32      A  O
ATOM  25500  CB   TYR K 314     23.022 -20.112 -62.633  1.00 47.86      A  C
ATOM  25501  CG   TYR K 314     24.202 -19.850 -61.718  1.00 47.58      A  C
ATOM  25502  CD1  TYR K 314     24.195 -20.280 -60.384  1.00 47.55      A  C
ATOM  25503  CD2  TYR K 314     25.321 -19.150 -62.180  1.00 47.41      A  C
ATOM  25504  CE1  TYR K 314     25.278 -20.039 -59.542  1.00 47.64      A  C
ATOM  25505  CE2  TYR K 314     26.410 -18.890 -61.339  1.00 47.46      A  C
ATOM  25506  CZ   TYR K 314     26.379 -19.339 -60.023  1.00 47.39      A  C
ATOM  25507  OH   TYR K 314     27.448 -19.092 -59.188  1.00 47.36      A  O
ATOM  25508  N    PHE K 315     21.205 -21.521 -64.537  1.00 47.08      A  N
ATOM  25509  CA   PHE K 315     20.069 -21.518 -65.445  1.00 46.72      A  C
ATOM  25510  C    PHE K 315     19.689 -22.947 -65.776  1.00 46.99      A  C
ATOM  25511  O    PHE K 315     20.252 -23.575 -66.680  1.00 47.06      A  O
ATOM  25512  CB   PHE K 315     20.367 -20.686 -66.689  1.00 46.43      A  C
ATOM  25513  CG   PHE K 315     20.688 -19.258 -66.381  1.00 45.31      A  C
ATOM  25514  CD1  PHE K 315     19.667 -18.324 -66.255  1.00 44.55      A  C
ATOM  25515  CD2  PHE K 315     22.005 -18.852 -66.188  1.00 44.60      A  C
ATOM  25516  CE1  PHE K 315     19.948 -17.001 -65.955  1.00 44.01      A  C
ATOM  25517  CE2  PHE K 315     22.299 -17.539 -65.892  1.00 44.06      A  C
ATOM  25518  CZ   PHE K 315     21.265 -16.606 -65.773  1.00 43.81      A  C
ATOM  25519  N    GLN K 316     18.739 -23.456 -65.000  1.00 47.24      A  N
ATOM  25520  CA   GLN K 316     18.299 -24.836 -65.107  1.00 47.78      A  C
ATOM  25521  C    GLN K 316     17.399 -25.063 -66.325  1.00 48.14      A  C
ATOM  25522  O    GLN K 316     16.692 -24.132 -66.768  1.00 47.93      A  O
ATOM  25523  CB   GLN K 316     17.570 -25.271 -63.827  1.00 47.82      A  C
ATOM  25524  CG   GLN K 316     18.484 -25.469 -62.631  1.00 48.26      A  C
ATOM  25525  CD   GLN K 316     19.489 -26.574 -62.846  1.00 49.00      A  C
ATOM  25526  NE2  GLN K 316     20.780 -26.227 -62.799  1.00 49.11      A  N
ATOM  25527  OE1  GLN K 316     19.114 -27.730 -63.051  1.00 49.79      A  O
ATOM  25528  N    PRO K 317     17.422 -26.308 -66.869  1.00 48.73      A  N
ATOM  25529  CA   PRO K 317     16.473 -26.682 -67.917  1.00 49.00      A  C
ATOM  25530  C    PRO K 317     15.096 -26.973 -67.315  1.00 49.04      A  C
ATOM  25531  O    PRO K 317     14.981 -27.211 -66.107  1.00 49.01      A  O
ATOM  25532  CB   PRO K 317     17.076 -27.973 -68.477  1.00 49.30      A  C
ATOM  25533  CG   PRO K 317     17.754 -28.600 -67.310  1.00 49.41      A  C
ATOM  25534  CD   PRO K 317     18.309 -27.440 -66.511  1.00 48.96      A  C
ATOM  25535  N    GLY K 318     14.068 -26.969 -68.156  1.00 49.08      A  N
ATOM  25536  CA   GLY K 318     12.706 -27.164 -67.696  1.00 49.01      A  C
ATOM  25537  C    GLY K 318     11.966 -25.854 -67.778  1.00 48.85      A  C
ATOM  25538  O    GLY K 318     12.553 -24.768 -67.577  1.00 48.68      A  O
ATOM  25539  N    GLU K 319     10.676 -25.957 -68.084  1.00 48.82      A  N
ATOM  25540  CA   GLU K 319      9.811 -24.783 -68.142  1.00 48.64      A  C
ATOM  25541  C    GLU K 319      8.632 -24.945 -67.167  1.00 48.76      A  C
ATOM  25542  O    GLU K 319      7.540 -25.318 -67.587  1.00 49.13      A  O
ATOM  25543  CB   GLU K 319      9.315 -24.538 -69.586  1.00 48.55      A  C
ATOM  25544  CG   GLU K 319     10.407 -24.320 -70.656  1.00 47.96      A  C
ATOM  25545  N    PRO K 320      8.853 -24.696 -65.857  1.00 48.65      A  N
```

FIGURE 1 (cont'd)

```
ATOM  25546  CA   PRO K 320     7.728 -24.782 -64.926  1.00 48.67      A    C
ATOM  25547  C    PRO K 320     6.729 -23.616 -65.073  1.00 48.56      A    C
ATOM  25548  O    PRO K 320     7.076 -22.569 -65.647  1.00 48.36      A    O
ATOM  25549  CB   PRO K 320     8.417 -24.761 -63.553  1.00 48.71      A    C
ATOM  25550  CG   PRO K 320     9.819 -25.190 -63.818  1.00 48.65      A    C
ATOM  25551  CD   PRO K 320    10.127 -24.560 -65.129  1.00 48.48      A    C
ATOM  25552  N    PHE K 321     5.515 -23.816 -64.544  1.00 48.37      A    N
ATOM  25553  CA   PHE K 321     4.374 -22.896 -64.716  1.00 48.02      A    C
ATOM  25554  C    PHE K 321     4.558 -21.411 -64.278  1.00 48.20      A    C
ATOM  25555  O    PHE K 321     4.333 -20.497 -65.092  1.00 48.52      A    O
ATOM  25556  N    GLY K 322     4.958 -21.170 -63.022  1.00 48.05      A    N
ATOM  25557  CA   GLY K 322     5.037 -19.797 -62.467  1.00 47.45      A    C
ATOM  25558  C    GLY K 322     3.654 -19.247 -62.091  1.00 47.11      A    C
ATOM  25559  O    GLY K 322     2.706 -20.031 -61.889  1.00 47.65      A    O
ATOM  25560  N    SER K 323     3.505 -17.923 -61.961  1.00 46.14      A    N
ATOM  25561  CA   SER K 323     4.588 -16.947 -61.999  1.00 45.03      A    C
ATOM  25562  C    SER K 323     4.783 -16.373 -60.603  1.00 43.90      A    C
ATOM  25563  O    SER K 323     4.021 -16.679 -59.686  1.00 44.05      A    O
ATOM  25564  CB   SER K 323     4.242 -15.814 -62.965  1.00 45.23      A    C
ATOM  25565  OG   SER K 323     3.999 -16.315 -64.265  1.00 46.08      A    O
ATOM  25566  N    VAL K 324     5.812 -15.549 -60.442  1.00 42.32      A    N
ATOM  25567  CA   VAL K 324     6.033 -14.810 -59.203  1.00 40.78      A    C
ATOM  25568  C    VAL K 324     5.737 -13.344 -59.499  1.00 40.05      A    C
ATOM  25569  O    VAL K 324     6.325 -12.766 -60.421  1.00 39.96      A    O
ATOM  25570  CB   VAL K 324     7.479 -14.984 -58.714  1.00 40.51      A    C
ATOM  25571  CG1  VAL K 324     7.707 -16.428 -58.276  1.00 40.40      A    C
ATOM  25572  CG2  VAL K 324     7.804 -13.993 -57.597  1.00 40.04      A    C
ATOM  25573  N    GLU K 325     4.812 -12.752 -58.748  1.00 39.21      A    N
ATOM  25574  CA   GLU K 325     4.408 -11.368 -59.013  1.00 38.55      A    C
ATOM  25575  C    GLU K 325     5.550 -10.367 -58.747  1.00 37.67      A    C
ATOM  25576  O    GLU K 325     6.111 -10.327 -57.649  1.00 37.54      A    O
ATOM  25577  CB   GLU K 325     3.172 -11.003 -58.195  1.00 38.92      A    C
ATOM  25578  CG   GLU K 325     1.991 -11.924 -58.411  1.00 40.47      A    C
ATOM  25579  CD   GLU K 325     0.728 -11.420 -57.723  1.00 42.59      A    C
ATOM  25580  OE1  GLU K 325     0.722 -10.268 -57.217  1.00 42.97      A    O
ATOM  25581  OE2  GLU K 325    -0.266 -12.183 -57.696  1.00 43.87      A    O
ATOM  25582  N    ASP K 326     5.893  -9.575 -59.762  1.00 36.83      A    N
ATOM  25583  CA   ASP K 326     7.002  -8.627 -59.678  1.00 36.05      A    C
ATOM  25584  C    ASP K 326     6.763  -7.480 -60.663  1.00 35.79      A    C
ATOM  25585  O    ASP K 326     5.690  -7.385 -61.278  1.00 35.89      A    O
ATOM  25586  CB   ASP K 326     8.326  -9.340 -59.983  1.00 35.74      A    C
ATOM  25587  CG   ASP K 326     9.514  -8.732 -59.257  1.00 35.14      A    C
ATOM  25588  OD1  ASP K 326     9.487  -7.533 -58.907  1.00 34.90      A    O
ATOM  25589  OD2  ASP K 326    10.497  -9.467 -59.046  1.00 34.62      A    O
ATOM  25590  N    ASP K 327     7.770  -6.624 -60.818  1.00 35.34      A    N
ATOM  25591  CA   ASP K 327     7.643  -5.384 -61.578  1.00 35.03      A    C
ATOM  25592  C    ASP K 327     7.222  -5.590 -63.034  1.00 34.63      A    C
ATOM  25593  O    ASP K 327     6.765  -4.647 -63.703  1.00 34.70      A    O
ATOM  25594  CB   ASP K 327     8.959  -4.603 -61.522  1.00 35.17      A    C
ATOM  25595  CG   ASP K 327     9.183  -3.908 -60.183  1.00 36.07      A    C
ATOM  25596  OD1  ASP K 327     8.391  -2.991 -59.837  1.00 36.79      A    O
ATOM  25597  OD2  ASP K 327    10.172  -4.271 -59.496  1.00 36.69      A    O
ATOM  25598  N    HIS K 328     7.368  -6.818 -63.521  1.00 34.10      A    N
ATOM  25599  CA   HIS K 328     7.073  -7.103 -64.915  1.00 33.76      A    C
ATOM  25600  C    HIS K 328     5.578  -7.120 -65.193  1.00 33.65      A    C
ATOM  25601  O    HIS K 328     5.157  -6.837 -66.308  1.00 33.82      A    O
ATOM  25602  CB   HIS K 328     7.718  -8.418 -65.328  1.00 33.60      A    C
ATOM  25603  CG   HIS K 328     7.092  -9.614 -64.692  1.00 33.89      A    C
ATOM  25604  CD2  HIS K 328     6.188 -10.502 -65.168  1.00 34.49      A    C
ATOM  25605  ND1  HIS K 328     7.361  -9.998 -63.395  1.00 34.09      A    N
ATOM  25606  CE1  HIS K 328     6.655 -11.078 -63.102  1.00 34.32      A    C
ATOM  25607  NE2  HIS K 328     5.938 -11.407 -64.161  1.00 34.61      A    N
ATOM  25608  N    ILE K 329     4.794  -7.440 -64.172  1.00 33.46      A    N
ATOM  25609  CA   ILE K 329     3.360  -7.641 -64.338  1.00 33.66      A    C
ATOM  25610  C    ILE K 329     2.624  -6.546 -65.137  1.00 33.70      A    C
```

FIGURE 1 (cont'd)

```
ATOM  25611  O    ILE K 329      1.928  -6.876 -66.128  1.00 33.92      A  O
ATOM  25612  CB   ILE K 329      2.646  -7.929 -62.980  1.00 33.75      A  C
ATOM  25613  CG1  ILE K 329      3.092  -9.292 -62.422  1.00 33.96      A  C
ATOM  25614  CG2  ILE K 329      1.093  -7.860 -63.113  1.00 34.20      A  C
ATOM  25615  CD1  ILE K 329      2.730 -10.519 -63.295  1.00 34.45      A  C
ATOM  25616  N    PRO K 330      2.763  -5.254 -64.727  1.00 33.63      A  N
ATOM  25617  CA   PRO K 330      1.995  -4.217 -65.445  1.00 33.69      A  C
ATOM  25618  C    PRO K 330      2.559  -3.887 -66.840  1.00 33.54      A  C
ATOM  25619  O    PRO K 330      1.917  -3.175 -67.622  1.00 33.77      A  O
ATOM  25620  CB   PRO K 330      2.079  -3.011 -64.513  1.00 33.73      A  C
ATOM  25621  CG   PRO K 330      3.373  -3.189 -63.814  1.00 33.54      A  C
ATOM  25622  CD   PRO K 330      3.557  -4.670 -63.627  1.00 33.47      A  C
ATOM  25623  N    PHE K 331      3.747  -4.405 -67.140  1.00 33.13      A  N
ATOM  25624  CA   PHE K 331      4.265  -4.382 -68.512  1.00 32.96      A  C
ATOM  25625  C    PHE K 331      3.783  -5.595 -69.335  1.00 32.96      A  C
ATOM  25626  O    PHE K 331      3.454  -5.482 -70.537  1.00 33.02      A  O
ATOM  25627  CB   PHE K 331      5.792  -4.300 -68.501  1.00 32.71      A  C
ATOM  25628  CG   PHE K 331      6.300  -2.984 -68.015  1.00 32.83      A  C
ATOM  25629  CD1  PHE K 331      6.775  -2.841 -66.714  1.00 32.83      A  C
ATOM  25630  CD2  PHE K 331      6.260  -1.862 -68.840  1.00 33.34      A  C
ATOM  25631  CE1  PHE K 331      7.249  -1.598 -66.249  1.00 33.03      A  C
ATOM  25632  CE2  PHE K 331      6.722  -0.616 -68.379  1.00 33.53      A  C
ATOM  25633  CZ   PHE K 331      7.217  -0.489 -67.080  1.00 33.22      A  C
ATOM  25634  N    LEU K 332      3.748  -6.749 -68.671  1.00 32.88      A  N
ATOM  25635  CA   LEU K 332      3.226  -7.952 -69.263  1.00 32.98      A  C
ATOM  25636  C    LEU K 332      1.750  -7.782 -69.630  1.00 33.45      A  C
ATOM  25637  O    LEU K 332      1.366  -8.153 -70.744  1.00 33.71      A  O
ATOM  25638  CB   LEU K 332      3.427  -9.124 -68.311  1.00 32.70      A  C
ATOM  25639  CG   LEU K 332      2.903 -10.485 -68.771  1.00 32.45      A  C
ATOM  25640  CD1  LEU K 332      3.926 -11.220 -69.621  1.00 31.99      A  C
ATOM  25641  CD2  LEU K 332      2.505 -11.322 -67.570  1.00 32.42      A  C
ATOM  25642  N    ARG K 333      0.935  -7.215 -68.726  1.00 33.81      A  N
ATOM  25643  CA   ARG K 333     -0.508  -7.034 -69.007  1.00 34.39      A  C
ATOM  25644  C    ARG K 333     -0.778  -6.169 -70.263  1.00 34.16      A  C
ATOM  25645  O    ARG K 333     -1.834  -6.276 -70.900  1.00 34.50      A  O
ATOM  25646  CB   ARG K 333     -1.292  -6.561 -67.760  1.00 34.74      A  C
ATOM  25647  CG   ARG K 333     -1.829  -5.129 -67.789  1.00 36.62      A  C
ATOM  25648  CD   ARG K 333     -2.890  -4.875 -66.688  1.00 39.92      A  C
ATOM  25649  NE   ARG K 333     -2.354  -4.225 -65.472  1.00 42.26      A  N
ATOM  25650  CZ   ARG K 333     -2.530  -2.936 -65.128  1.00 42.98      A  C
ATOM  25651  NH1  ARG K 333     -1.992  -2.470 -63.997  1.00 42.57      A  N
ATOM  25652  NH2  ARG K 333     -3.243  -2.103 -65.897  1.00 43.85      A  N
ATOM  25653  N    ARG K 334      0.206  -5.342 -70.616  1.00 33.62      A  N
ATOM  25654  CA   ARG K 334      0.164  -4.518 -71.829  1.00 33.21      A  C
ATOM  25655  C    ARG K 334      0.834  -5.193 -73.033  1.00 32.74      A  C
ATOM  25656  O    ARG K 334      0.911  -4.606 -74.114  1.00 32.85      A  O
ATOM  25657  CB   ARG K 334      0.815  -3.156 -71.564  1.00 33.21      A  C
ATOM  25658  CG   ARG K 334     -0.090  -2.173 -70.857  1.00 33.63      A  C
ATOM  25659  CD   ARG K 334      0.715  -1.288 -69.935  1.00 33.76      A  C
ATOM  25660  NE   ARG K 334     -0.079  -0.152 -69.485  1.00 34.79      A  N
ATOM  25661  CZ   ARG K 334     -0.630  -0.040 -68.277  1.00 35.57      A  C
ATOM  25662  NH1  ARG K 334     -0.473  -0.996 -67.359  1.00 35.25      A  N
ATOM  25663  NH2  ARG K 334     -1.337   1.044 -67.982  1.00 36.57      A  N
ATOM  25664  N    GLY K 335      1.332  -6.413 -72.839  1.00 32.13      A  N
ATOM  25665  CA   GLY K 335      1.867  -7.213 -73.941  1.00 31.52      A  C
ATOM  25666  C    GLY K 335      3.372  -7.180 -74.150  1.00 30.87      A  C
ATOM  25667  O    GLY K 335      3.868  -7.621 -75.193  1.00 31.20      A  O
ATOM  25668  N    VAL K 336      4.113  -6.675 -73.168  1.00 29.96      A  N
ATOM  25669  CA   VAL K 336      5.564  -6.634 -73.298  1.00 29.12      A  C
ATOM  25670  C    VAL K 336      6.141  -8.016 -73.050  1.00 28.66      A  C
ATOM  25671  O    VAL K 336      5.801  -8.641 -72.062  1.00 28.61      A  O
ATOM  25672  CB   VAL K 336      6.202  -5.623 -72.318  1.00 28.95      A  C
ATOM  25673  CG1  VAL K 336      7.730  -5.601 -72.474  1.00 28.82      A  C
ATOM  25674  CG2  VAL K 336      5.605  -4.207 -72.524  1.00 29.07      A  C
ATOM  25675  N    PRO K 337      6.996  -8.502 -73.964  1.00 28.45      A  N
```

FIGURE 1 (cont'd)

```
ATOM  25676  CA   PRO K 337       7.745  -9.741 -73.732  1.00 28.23      A    C
ATOM  25677  C    PRO K 337       8.594  -9.628 -72.487  1.00 27.76      A    C
ATOM  25678  O    PRO K 337       9.331  -8.663 -72.334  1.00 27.77      A    O
ATOM  25679  CB   PRO K 337       8.663  -9.845 -74.956  1.00 28.35      A    C
ATOM  25680  CG   PRO K 337       7.946  -9.073 -76.028  1.00 28.78      A    C
ATOM  25681  CD   PRO K 337       7.234  -7.952 -75.314  1.00 28.68      A    C
ATOM  25682  N    VAL K 338       8.492 -10.609 -71.607  1.00 27.29      A    N
ATOM  25683  CA   VAL K 338       9.219 -10.553 -70.353  1.00 26.75      A    C
ATOM  25684  C    VAL K 338      10.193 -11.720 -70.213  1.00 26.58      A    C
ATOM  25685  O    VAL K 338       9.884 -12.856 -70.570  1.00 26.81      A    O
ATOM  25686  CB   VAL K 338       8.245 -10.527 -69.123  1.00 26.67      A    C
ATOM  25687  CG1  VAL K 338       9.026 -10.516 -67.787  1.00 26.41      A    C
ATOM  25688  CG2  VAL K 338       7.278  -9.324 -69.189  1.00 26.66      A    C
ATOM  25689  N    LEU K 339      11.376 -11.429 -69.696  1.00 26.21      A    N
ATOM  25690  CA   LEU K 339      12.218 -12.475 -69.153  1.00 25.97      A    C
ATOM  25691  C    LEU K 339      12.443 -12.199 -67.665  1.00 25.84      A    C
ATOM  25692  O    LEU K 339      13.092 -11.213 -67.289  1.00 25.85      A    O
ATOM  25693  CB   LEU K 339      13.538 -12.573 -69.915  1.00 25.89      A    C
ATOM  25694  CG   LEU K 339      14.473 -13.702 -69.455  1.00 25.73      A    C
ATOM  25695  CD1  LEU K 339      13.790 -15.073 -69.490  1.00 26.01      A    C
ATOM  25696  CD2  LEU K 339      15.730 -13.707 -70.317  1.00 25.55      A    C
ATOM  25697  N    HIS K 340      11.890 -13.073 -66.830  1.00 25.66      A    N
ATOM  25698  CA   HIS K 340      11.919 -12.895 -65.386  1.00 25.46      A    C
ATOM  25699  C    HIS K 340      13.101 -13.645 -64.749  1.00 25.34      A    C
ATOM  25700  O    HIS K 340      13.057 -14.870 -64.525  1.00 25.31      A    O
ATOM  25701  CB   HIS K 340      10.575 -13.321 -64.795  1.00 25.51      A    C
ATOM  25702  CG   HIS K 340      10.286 -12.738 -63.449  1.00 25.68      A    C
ATOM  25703  CD2  HIS K 340      10.828 -11.682 -62.795  1.00 25.70      A    C
ATOM  25704  ND1  HIS K 340       9.336 -13.270 -62.604  1.00 26.05      A    N
ATOM  25705  CE1  HIS K 340       9.301 -12.562 -61.488  1.00 26.02      A    C
ATOM  25706  NE2  HIS K 340      10.200 -11.596 -61.577  1.00 25.97      A    N
ATOM  25707  N    LEU K 341      14.156 -12.878 -64.465  1.00 25.22      A    N
ATOM  25708  CA   LEU K 341      15.409 -13.413 -63.941  1.00 25.17      A    C
ATOM  25709  C    LEU K 341      15.436 -13.332 -62.421  1.00 25.14      A    C
ATOM  25710  O    LEU K 341      16.226 -12.562 -61.841  1.00 25.14      A    O
ATOM  25711  CB   LEU K 341      16.589 -12.635 -64.520  1.00 25.13      A    C
ATOM  25712  CG   LEU K 341      17.760 -13.490 -65.026  1.00 25.37      A    C
ATOM  25713  CD1  LEU K 341      18.881 -12.558 -65.542  1.00 25.58      A    C
ATOM  25714  CD2  LEU K 341      18.284 -14.522 -63.986  1.00 25.08      A    C
ATOM  25715  N    ILE K 342      14.561 -14.132 -61.801  1.00 25.22      A    N
ATOM  25716  CA   ILE K 342      14.366 -14.186 -60.338  1.00 25.27      A    C
ATOM  25717  C    ILE K 342      14.612 -15.625 -59.858  1.00 25.56      A    C
ATOM  25718  O    ILE K 342      14.079 -16.570 -60.441  1.00 25.79      A    O
ATOM  25719  CB   ILE K 342      12.932 -13.685 -59.928  1.00 25.06      A    C
ATOM  25720  CG1  ILE K 342      12.758 -13.692 -58.407  1.00 24.91      A    C
ATOM  25721  CG2  ILE K 342      11.839 -14.515 -60.614  1.00 24.98      A    C
ATOM  25722  CD1  ILE K 342      11.569 -12.877 -57.938  1.00 24.65      A    C
ATOM  25723  N    SER K 343      15.435 -15.799 -58.828  1.00 25.81      A    N
ATOM  25724  CA   SER K 343      15.733 -17.150 -58.380  1.00 26.23      A    C
ATOM  25725  C    SER K 343      14.507 -17.734 -57.709  1.00 26.44      A    C
ATOM  25726  O    SER K 343      13.806 -17.041 -56.951  1.00 26.35      A    O
ATOM  25727  CB   SER K 343      16.956 -17.208 -57.453  1.00 26.36      A    C
ATOM  25728  OG   SER K 343      16.711 -16.586 -56.192  1.00 27.04      A    O
ATOM  25729  N    THR K 344      14.244 -18.998 -58.045  1.00 26.81      A    N
ATOM  25730  CA   THR K 344      13.213 -19.828 -57.409  1.00 27.12      A    C
ATOM  25731  C    THR K 344      13.894 -21.143 -57.040  1.00 27.55      A    C
ATOM  25732  O    THR K 344      14.359 -21.857 -57.931  1.00 27.67      A    O
ATOM  25733  CB   THR K 344      11.991 -20.099 -58.332  1.00 27.05      A    C
ATOM  25734  OG1  THR K 344      12.265 -19.641 -59.668  1.00 26.83      A    O
ATOM  25735  N    PRO K 345      13.979 -21.461 -55.726  1.00 27.93      A    N
ATOM  25736  CA   PRO K 345      13.337 -20.738 -54.604  1.00 27.99      A    C
ATOM  25737  C    PRO K 345      13.983 -19.399 -54.238  1.00 27.74      A    C
ATOM  25738  O    PRO K 345      15.097 -19.082 -54.704  1.00 27.44      A    O
ATOM  25739  CB   PRO K 345      13.463 -21.727 -53.410  1.00 28.19      A    C
ATOM  25740  CG   PRO K 345      14.215 -22.930 -53.933  1.00 28.24      A    C
```

FIGURE 1 (cont'd)

```
ATOM  25741  CD   PRO K 345      14.872 -22.520 -55.220  1.00 28.03      A    C
ATOM  25742  N    PHE K 346      13.270 -18.635 -53.409  1.00 27.71      A    N
ATOM  25743  CA   PHE K 346      13.790 -17.384 -52.890  1.00 27.91      A    C
ATOM  25744  C    PHE K 346      14.995 -17.638 -51.962  1.00 28.15      A    C
ATOM  25745  O    PHE K 346      15.075 -18.728 -51.341  1.00 28.45      A    O
ATOM  25746  CB   PHE K 346      12.700 -16.632 -52.119  1.00 27.93      A    C
ATOM  25747  CG   PHE K 346      11.555 -16.166 -52.969  1.00 28.05      A    C
ATOM  25748  CD1  PHE K 346      11.644 -16.149 -54.363  1.00 27.88      A    C
ATOM  25749  CD2  PHE K 346      10.396 -15.699 -52.366  1.00 28.61      A    C
ATOM  25750  CE1  PHE K 346      10.576 -15.692 -55.143  1.00 27.84      A    C
ATOM  25751  CE2  PHE K 346       9.325 -15.239 -53.133  1.00 28.50      A    C
ATOM  25752  CZ   PHE K 346       9.415 -15.237 -54.523  1.00 28.05      A    C
ATOM  25753  N    PRO K 347      15.920 -16.636 -51.854  1.00 28.14      A    N
ATOM  25754  CA   PRO K 347      17.070 -16.752 -50.935  1.00 28.46      A    C
ATOM  25755  C    PRO K 347      16.614 -17.139 -49.518  1.00 29.06      A    C
ATOM  25756  O    PRO K 347      15.553 -16.677 -49.056  1.00 29.16      A    O
ATOM  25757  CB   PRO K 347      17.664 -15.331 -50.929  1.00 28.22      A    C
ATOM  25758  CG   PRO K 347      17.229 -14.722 -52.241  1.00 27.78      A    C
ATOM  25759  CD   PRO K 347      15.887 -15.324 -52.549  1.00 27.75      A    C
ATOM  25760  N    ALA K 348      17.394 -17.988 -48.845  1.00 29.75      A    N
ATOM  25761  CA   ALA K 348      17.127 -18.344 -47.432  1.00 30.40      A    C
ATOM  25762  C    ALA K 348      16.919 -17.095 -46.562  1.00 30.63      A    C
ATOM  25763  O    ALA K 348      16.009 -17.041 -45.726  1.00 30.72      A    O
ATOM  25764  CB   ALA K 348      18.263 -19.201 -46.869  1.00 30.65      A    C
ATOM  25765  N    VAL K 349      17.766 -16.096 -46.811  1.00 30.74      A    N
ATOM  25766  CA   VAL K 349      17.741 -14.796 -46.127  1.00 30.97      A    C
ATOM  25767  C    VAL K 349      16.656 -13.817 -46.632  1.00 31.02      A    C
ATOM  25768  O    VAL K 349      16.782 -12.592 -46.455  1.00 31.13      A    O
ATOM  25769  CB   VAL K 349      19.144 -14.081 -46.205  1.00 30.93      A    C
ATOM  25770  CG1  VAL K 349      20.222 -14.913 -45.489  1.00 31.46      A    C
ATOM  25771  CG2  VAL K 349      19.545 -13.746 -47.676  1.00 30.48      A    C
ATOM  25772  N    TRP K 350      15.594 -14.343 -47.238  1.00 31.09      A    N
ATOM  25773  CA   TRP K 350      14.623 -13.469 -47.888  1.00 31.18      A    C
ATOM  25774  C    TRP K 350      13.674 -12.823 -46.895  1.00 31.51      A    C
ATOM  25775  O    TRP K 350      13.193 -13.474 -45.947  1.00 31.71      A    O
ATOM  25776  CB   TRP K 350      13.843 -14.207 -48.976  1.00 31.00      A    C
ATOM  25777  CG   TRP K 350      12.911 -13.320 -49.748  1.00 30.53      A    C
ATOM  25778  CD1  TRP K 350      13.253 -12.344 -50.645  1.00 30.20      A    C
ATOM  25779  CD2  TRP K 350      11.485 -13.333 -49.685  1.00 30.19      A    C
ATOM  25780  CE2  TRP K 350      11.025 -12.343 -50.581  1.00 29.94      A    C
ATOM  25781  CE3  TRP K 350      10.544 -14.095 -48.961  1.00 30.20      A    C
ATOM  25782  NE1  TRP K 350      12.128 -11.756 -51.150  1.00 29.95      A    N
ATOM  25783  CZ2  TRP K 350       9.656 -12.085 -50.778  1.00 29.69      A    C
ATOM  25784  CZ3  TRP K 350       9.183 -13.838 -49.149  1.00 30.04      A    C
ATOM  25785  CH2  TRP K 350       8.752 -12.834 -50.052  1.00 29.70      A    C
ATOM  25786  N    HIS K 351      13.421 -11.537 -47.134  1.00 31.84      A    N
ATOM  25787  CA   HIS K 351      12.540 -10.724 -46.285  1.00 32.45      A    C
ATOM  25788  C    HIS K 351      12.845 -10.872 -44.772  1.00 32.99      A    C
ATOM  25789  O    HIS K 351      11.945 -11.089 -43.944  1.00 33.23      A    O
ATOM  25790  CB   HIS K 351      11.060 -11.001 -46.628  1.00 32.40      A    C
ATOM  25791  CG   HIS K 351      10.554 -10.225 -47.816  1.00 32.47      A    C
ATOM  25792  CD2  HIS K 351      11.211  -9.631 -48.844  1.00 32.10      A    C
ATOM  25793  ND1  HIS K 351       9.211  -9.971 -48.025  1.00 32.59      A    N
ATOM  25794  CE1  HIS K 351       9.062  -9.269 -49.136  1.00 32.27      A    C
ATOM  25795  NE2  HIS K 351      10.261  -9.044 -49.650  1.00 31.89      A    N
ATOM  25796  N    THR K 352      14.133 -10.758 -44.443  1.00 33.43      A    N
ATOM  25797  CA   THR K 352      14.645 -10.877 -43.071  1.00 33.97      A    C
ATOM  25798  C    THR K 352      15.890  -9.984 -42.905  1.00 34.24      A    C
ATOM  25799  O    THR K 352      16.613  -9.735 -43.891  1.00 34.01      A    O
ATOM  25800  CB   THR K 352      14.932 -12.393 -42.643  1.00 34.09      A    C
ATOM  25801  CG2  THR K 352      15.456 -13.223 -43.781  1.00 33.54      A    C
ATOM  25802  OG1  THR K 352      15.892 -12.458 -41.572  1.00 34.82      A    O
ATOM  25803  N    PRO K 353      16.136  -9.488 -41.663  1.00 34.76      A    N
ATOM  25804  CA   PRO K 353      17.360  -8.739 -41.316  1.00 34.85      A    C
ATOM  25805  C    PRO K 353      18.656  -9.406 -41.811  1.00 34.64      A    C
```

FIGURE 1 (cont'd)

```
ATOM  25806  O    PRO K 353      19.657  -8.719 -42.036  1.00 34.65      A   O
ATOM  25807  CB   PRO K 353      17.344  -8.747 -39.784  1.00 35.27      A   C
ATOM  25808  CG   PRO K 353      15.903  -8.821 -39.415  1.00 35.54      A   C
ATOM  25809  CD   PRO K 353      15.217  -9.602 -40.504  1.00 35.01      A   C
ATOM  25810  N    ALA K 354      18.623 -10.732 -41.966  1.00 34.37      A   N
ATOM  25811  CA   ALA K 354      19.751 -11.509 -42.499  1.00 34.12      A   C
ATOM  25812  C    ALA K 354      20.216 -11.091 -43.926  1.00 33.84      A   C
ATOM  25813  O    ALA K 354      21.392 -11.279 -44.279  1.00 33.77      A   O
ATOM  25814  CB   ALA K 354      19.438 -13.022 -42.438  1.00 34.08      A   C
ATOM  25815  N    ASP K 355      19.305 -10.530 -44.732  1.00 33.60      A   N
ATOM  25816  CA   ASP K 355      19.636 -10.093 -46.102  1.00 33.39      A   C
ATOM  25817  C    ASP K 355      20.514  -8.833 -46.085  1.00 33.53      A   C
ATOM  25818  O    ASP K 355      20.072  -7.711 -46.364  1.00 33.35      A   O
ATOM  25819  CB   ASP K 355      18.374  -9.883 -46.965  1.00 33.10      A   C
ATOM  25820  CG   ASP K 355      18.696  -9.711 -48.474  1.00 32.58      A   C
ATOM  25821  OD1  ASP K 355      19.898  -9.743 -48.854  1.00 32.66      A   O
ATOM  25822  OD2  ASP K 355      17.736  -9.542 -49.281  1.00 31.72      A   O
ATOM  25823  N    THR K 356      21.774  -9.052 -45.745  1.00 33.82      A   N
ATOM  25824  CA   THR K 356      22.767  -7.997 -45.742  1.00 34.03      A   C
ATOM  25825  C    THR K 356      23.992  -8.451 -46.561  1.00 34.48      A   C
ATOM  25826  O    THR K 356      24.056  -9.621 -47.009  1.00 34.36      A   O
ATOM  25827  CB   THR K 356      23.175  -7.635 -44.301  1.00 33.39      A   C
ATOM  25828  OG1  THR K 356      23.666  -8.809 -43.638  1.00 33.40      A   O
ATOM  25829  N    GLU K 357      24.944  -7.523 -46.750  1.00 35.08      A   N
ATOM  25830  CA   GLU K 357      26.201  -7.774 -47.483  1.00 35.61      A   C
ATOM  25831  C    GLU K 357      26.927  -9.072 -47.039  1.00 35.97      A   C
ATOM  25832  O    GLU K 357      27.396  -9.859 -47.882  1.00 35.88      A   O
ATOM  25833  CB   GLU K 357      27.140  -6.555 -47.367  1.00 35.79      A   C
ATOM  25834  CG   GLU K 357      28.515  -6.710 -48.097  1.00 36.42      A   C
ATOM  25835  CD   GLU K 357      29.367  -5.413 -48.123  1.00 37.45      A   C
ATOM  25836  OE1  GLU K 357      28.930  -4.365 -47.580  1.00 38.21      A   O
ATOM  25837  OE2  GLU K 357      30.482  -5.443 -48.692  1.00 37.73      A   O
ATOM  25838  N    VAL K 358      26.996  -9.277 -45.719  1.00 36.47      A   N
ATOM  25839  CA   VAL K 358      27.644 -10.437 -45.097  1.00 36.86      A   C
ATOM  25840  C    VAL K 358      27.194 -11.804 -45.649  1.00 36.67      A   C
ATOM  25841  O    VAL K 358      27.959 -12.777 -45.607  1.00 36.88      A   O
ATOM  25842  CB   VAL K 358      27.426 -10.415 -43.563  1.00 37.20      A   C
ATOM  25843  CG1  VAL K 358      28.766 -10.366 -42.839  1.00 37.98      A   C
ATOM  25844  N    ASN K 359      25.967 -11.863 -46.170  1.00 36.25      A   N
ATOM  25845  CA   ASN K 359      25.355 -13.129 -46.588  1.00 35.96      A   C
ATOM  25846  C    ASN K 359      25.267 -13.404 -48.102  1.00 35.40      A   C
ATOM  25847  O    ASN K 359      24.715 -14.432 -48.527  1.00 35.27      A   O
ATOM  25848  CB   ASN K 359      23.977 -13.269 -45.942  1.00 36.13      A   C
ATOM  25849  CG   ASN K 359      24.059 -13.447 -44.441  1.00 37.16      A   C
ATOM  25850  ND2  ASN K 359      25.289 -13.577 -43.904  1.00 38.12      A   N
ATOM  25851  OD1  ASN K 359      23.025 -13.482 -43.764  1.00 37.76      A   O
ATOM  25852  N    LEU K 360      25.804 -12.486 -48.903  1.00 34.87      A   N
ATOM  25853  CA   LEU K 360      25.923 -12.683 -50.341  1.00 34.35      A   C
ATOM  25854  C    LEU K 360      27.098 -13.612 -50.609  1.00 34.43      A   C
ATOM  25855  O    LEU K 360      28.018 -13.708 -49.786  1.00 34.90      A   O
ATOM  25856  CB   LEU K 360      26.156 -11.352 -51.057  1.00 34.04      A   C
ATOM  25857  CG   LEU K 360      25.166 -10.222 -50.779  1.00 33.52      A   C
ATOM  25858  CD1  LEU K 360      25.602  -8.946 -51.502  1.00 32.94      A   C
ATOM  25859  CD2  LEU K 360      23.733 -10.618 -51.145  1.00 33.12      A   C
ATOM  25860  N    HIS K 361      27.053 -14.310 -51.746  1.00 34.17      A   N
ATOM  25861  CA   HIS K 361      28.194 -15.104 -52.230  1.00 33.98      A   C
ATOM  25862  C    HIS K 361      28.894 -14.321 -53.355  1.00 34.27      A   C
ATOM  25863  O    HIS K 361      28.493 -14.442 -54.535  1.00 34.03      A   O
ATOM  25864  CB   HIS K 361      27.739 -16.486 -52.723  1.00 33.59      A   C
ATOM  25865  CG   HIS K 361      28.807 -17.537 -52.656  1.00 32.72      A   C
ATOM  25866  ND1  HIS K 361      29.835 -17.620 -53.568  1.00 31.57      A   N
ATOM  25867  CE1  HIS K 361      30.602 -18.645 -53.244  1.00 31.60      A   C
ATOM  25868  N    PRO K 362      29.927 -13.504 -52.992  1.00 34.76      A   N
ATOM  25869  CA   PRO K 362      30.600 -12.616 -53.966  1.00 34.95      A   C
ATOM  25870  C    PRO K 362      30.959 -13.288 -55.307  1.00 34.92      A   C
```

FIGURE 1 (cont'd)

```
ATOM  25871  O    PRO K 362      30.734 -12.681 -56.367  1.00 34.75      A    O
ATOM  25872  CB   PRO K 362      31.860 -12.151 -53.211  1.00 35.24      A    C
ATOM  25873  CG   PRO K 362      31.445 -12.166 -51.759  1.00 35.34      A    C
ATOM  25874  CD   PRO K 362      30.532 -13.381 -51.641  1.00 35.03      A    C
ATOM  25875  N    PRO K 363      31.493 -14.531 -55.262  1.00 35.02      A    N
ATOM  25876  CA   PRO K 363      31.725 -15.299 -56.497  1.00 35.06      A    C
ATOM  25877  C    PRO K 363      30.456 -15.394 -57.371  1.00 34.70      A    C
ATOM  25878  O    PRO K 363      30.464 -14.967 -58.546  1.00 34.60      A    O
ATOM  25879  CB   PRO K 363      32.135 -16.686 -55.980  1.00 35.31      A    C
ATOM  25880  CG   PRO K 363      32.893 -16.415 -54.718  1.00 35.70      A    C
ATOM  25881  N    THR K 364      29.378 -15.920 -56.786  1.00 34.34      A    N
ATOM  25882  CA   THR K 364      28.113 -16.044 -57.498  1.00 34.01      A    C
ATOM  25883  C    THR K 364      27.715 -14.721 -58.158  1.00 33.91      A    C
ATOM  25884  O    THR K 364      27.286 -14.709 -59.320  1.00 33.72      A    O
ATOM  25885  CB   THR K 364      26.995 -16.567 -56.580  1.00 33.90      A    C
ATOM  25886  CG2  THR K 364      25.696 -16.760 -57.376  1.00 33.54      A    C
ATOM  25887  OG1  THR K 364      27.399 -17.826 -56.016  1.00 34.11      A    O
ATOM  25888  N    VAL K 365      27.892 -13.621 -57.421  1.00 34.02      A    N
ATOM  25889  CA   VAL K 365      27.579 -12.271 -57.923  1.00 34.16      A    C
ATOM  25890  C    VAL K 365      28.328 -11.978 -59.217  1.00 34.34      A    C
ATOM  25891  O    VAL K 365      27.710 -11.591 -60.218  1.00 34.15      A    O
ATOM  25892  CB   VAL K 365      27.878 -11.135 -56.873  1.00 34.17      A    C
ATOM  25893  CG1  VAL K 365      26.887 -11.198 -55.704  1.00 34.07      A    C
ATOM  25894  CG2  VAL K 365      27.844  -9.735 -57.528  1.00 33.97      A    C
ATOM  25895  N    HIS K 366      29.648 -12.171 -59.180  1.00 34.74      A    N
ATOM  25896  CA   HIS K 366      30.512 -11.833 -60.308  1.00 35.21      A    C
ATOM  25897  C    HIS K 366      30.243 -12.749 -61.509  1.00 35.39      A    C
ATOM  25898  O    HIS K 366      30.211 -12.278 -62.656  1.00 35.49      A    O
ATOM  25899  CB   HIS K 366      31.997 -11.832 -59.888  1.00 35.43      A    C
ATOM  25900  CG   HIS K 366      32.324 -10.817 -58.828  1.00 35.54      A    C
ATOM  25901  ND1  HIS K 366      32.154  -9.456 -59.007  1.00 35.56      A    N
ATOM  25902  CE1  HIS K 366      32.509  -8.813 -57.907  1.00 35.54      A    C
ATOM  25903  N    ASN K 367      30.029 -14.038 -61.235  1.00 35.41      A    N
ATOM  25904  CA   ASN K 367      29.594 -14.975 -62.257  1.00 35.45      A    C
ATOM  25905  C    ASN K 367      28.397 -14.446 -63.030  1.00 35.27      A    C
ATOM  25906  O    ASN K 367      28.430 -14.368 -64.264  1.00 35.41      A    O
ATOM  25907  CB   ASN K 367      29.243 -16.313 -61.628  1.00 35.52      A    C
ATOM  25908  CG   ASN K 367      30.463 -17.076 -61.186  1.00 36.13      A    C
ATOM  25909  ND2  ASN K 367      30.274 -18.339 -60.825  1.00 36.19      A    N
ATOM  25910  OD1  ASN K 367      31.569 -16.540 -61.170  1.00 37.05      A    O
ATOM  25911  N    LEU K 368      27.353 -14.061 -62.300  1.00 34.96      A    N
ATOM  25912  CA   LEU K 368      26.129 -13.523 -62.914  1.00 34.77      A    C
ATOM  25913  C    LEU K 368      26.351 -12.315 -63.826  1.00 34.95      A    C
ATOM  25914  O    LEU K 368      25.658 -12.166 -64.835  1.00 35.03      A    O
ATOM  25915  CB   LEU K 368      25.101 -13.159 -61.842  1.00 34.43      A    C
ATOM  25916  CG   LEU K 368      24.460 -14.327 -61.080  1.00 33.82      A    C
ATOM  25917  CD1  LEU K 368      23.639 -13.807 -59.880  1.00 33.54      A    C
ATOM  25918  CD2  LEU K 368      23.600 -15.182 -62.008  1.00 32.90      A    C
ATOM  25919  N    ALA K 369      27.311 -11.462 -63.450  1.00 34.29      A    N
ATOM  25920  CA   ALA K 369      27.657 -10.247 -64.209  1.00 33.62      A    C
ATOM  25921  C    ALA K 369      28.404 -10.602 -65.488  1.00 34.59      A    C
ATOM  25922  O    ALA K 369      28.164  -9.986 -66.533  1.00 35.74      A    O
ATOM  25923  CB   ALA K 369      28.488  -9.274 -63.353  1.00 24.62      A    C
ATOM  25924  N    ARG K 370      29.305 -11.589 -65.398  1.00 35.21      A    N
ATOM  25925  CA   ARG K 370      30.027 -12.095 -66.565  1.00 34.86      A    C
ATOM  25926  C    ARG K 370      29.011 -12.648 -67.555  1.00 34.26      A    C
ATOM  25927  O    ARG K 370      29.050 -12.309 -68.746  1.00 34.12      A    O
ATOM  25928  CB   ARG K 370      31.071 -13.147 -66.154  1.00 35.15      A    C
ATOM  25929  CG   ARG K 370      32.211 -12.572 -65.287  1.00 35.44      A    C
ATOM  25930  CD   ARG K 370      33.310 -13.586 -64.986  1.00 35.76      A    C
ATOM  25931  NE   ARG K 370      34.480 -12.954 -64.364  1.00 35.88      A    N
ATOM  25932  CZ   ARG K 370      35.734 -13.380 -64.515  1.00 36.03      A    C
ATOM  25933  N    ILE K 371      28.077 -13.449 -67.034  1.00 33.50      A    N
ATOM  25934  CA   ILE K 371      26.986 -14.005 -67.839  1.00 32.92      A    C
ATOM  25935  C    ILE K 371      26.132 -12.904 -68.495  1.00 32.84      A    C
```

FIGURE 1 (cont'd)

```
ATOM  25936  O    ILE K 371     25.883 -12.928 -69.724  1.00 32.90      A   O
ATOM  25937  CB   ILE K 371     26.116 -15.013 -67.035  1.00 32.57      A   C
ATOM  25938  CG1  ILE K 371     26.952 -16.263 -66.701  1.00 32.51      A   C
ATOM  25939  CG2  ILE K 371     24.861 -15.415 -67.831  1.00 32.05      A   C
ATOM  25940  CD1  ILE K 371     26.306 -17.230 -65.722  1.00 32.22      A   C
ATOM  25941  N    LEU K 372     25.712 -11.940 -67.674  1.00 32.65      A   N
ATOM  25942  CA   LEU K 372     24.908 -10.791 -68.146  1.00 32.53      A   C
ATOM  25943  C    LEU K 372     25.619  -9.917 -69.192  1.00 32.83      A   C
ATOM  25944  O    LEU K 372     25.033  -9.558 -70.230  1.00 32.72      A   O
ATOM  25945  CB   LEU K 372     24.438  -9.925 -66.956  1.00 32.15      A   C
ATOM  25946  CG   LEU K 372     23.011 -10.094 -66.396  1.00 31.40      A   C
ATOM  25947  CD1  LEU K 372     22.283 -11.387 -66.845  1.00 30.86      A   C
ATOM  25948  CD2  LEU K 372     23.045  -9.984 -64.879  1.00 30.94      A   C
ATOM  25949  N    ALA K 373     26.878  -9.580 -68.905  1.00 33.22      A   N
ATOM  25950  CA   ALA K 373     27.671  -8.732 -69.796  1.00 33.64      A   C
ATOM  25951  C    ALA K 373     27.781  -9.352 -71.191  1.00 33.94      A   C
ATOM  25952  O    ALA K 373     27.626  -8.641 -72.204  1.00 34.04      A   O
ATOM  25953  CB   ALA K 373     29.066  -8.468 -69.203  1.00 33.74      A   C
ATOM  25954  N    VAL K 374     28.038 -10.669 -71.225  1.00 34.10      A   N
ATOM  25955  CA   VAL K 374     28.113 -11.420 -72.476  1.00 34.33      A   C
ATOM  25956  C    VAL K 374     26.758 -11.374 -73.175  1.00 34.23      A   C
ATOM  25957  O    VAL K 374     26.671 -11.018 -74.361  1.00 34.47      A   O
ATOM  25958  CB   VAL K 374     28.529 -12.887 -72.239  1.00 34.39      A   C
ATOM  25959  CG1  VAL K 374     28.319 -13.710 -73.515  1.00 34.62      A   C
ATOM  25960  CG2  VAL K 374     29.977 -12.964 -71.784  1.00 34.81      A   C
ATOM  25961  N    PHE K 375     25.713 -11.726 -72.423  1.00 33.95      A   N
ATOM  25962  CA   PHE K 375     24.351 -11.665 -72.929  1.00 33.81      A   C
ATOM  25963  C    PHE K 375     24.038 -10.291 -73.550  1.00 34.14      A   C
ATOM  25964  O    PHE K 375     23.579 -10.212 -74.709  1.00 34.22      A   O
ATOM  25965  CB   PHE K 375     23.328 -12.004 -71.830  1.00 33.35      A   C
ATOM  25966  CG   PHE K 375     21.902 -11.955 -72.308  1.00 32.64      A   C
ATOM  25967  CD1  PHE K 375     21.206 -13.135 -72.571  1.00 32.50      A   C
ATOM  25968  CD2  PHE K 375     21.262 -10.723 -72.537  1.00 32.11      A   C
ATOM  25969  CE1  PHE K 375     19.878 -13.096 -73.040  1.00 32.46      A   C
ATOM  25970  CE2  PHE K 375     19.942 -10.660 -73.005  1.00 32.28      A   C
ATOM  25971  CZ   PHE K 375     19.241 -11.851 -73.256  1.00 32.39      A   C
ATOM  25972  N    LEU K 376     24.291  -9.226 -72.775  1.00 34.49      A   N
ATOM  25973  CA   LEU K 376     23.983  -7.853 -73.193  1.00 34.94      A   C
ATOM  25974  C    LEU K 376     24.693  -7.540 -74.517  1.00 35.73      A   C
ATOM  25975  O    LEU K 376     24.088  -6.960 -75.441  1.00 35.80      A   O
ATOM  25976  CB   LEU K 376     24.385  -6.857 -72.094  1.00 34.61      A   C
ATOM  25977  CG   LEU K 376     23.479  -5.629 -71.906  1.00 33.90      A   C
ATOM  25978  N    ALA K 377     25.963  -7.963 -74.594  1.00 36.61      A   N
ATOM  25979  CA   ALA K 377     26.796  -7.787 -75.787  1.00 37.49      A   C
ATOM  25980  C    ALA K 377     26.256  -8.597 -76.973  1.00 37.98      A   C
ATOM  25981  O    ALA K 377     26.141  -8.066 -78.092  1.00 38.26      A   O
ATOM  25982  CB   ALA K 377     28.266  -8.141 -75.495  1.00 37.61      A   C
ATOM  25983  N    GLU K 378     25.915  -9.868 -76.723  1.00 38.26      A   N
ATOM  25984  CA   GLU K 378     25.389 -10.733 -77.774  1.00 38.66      A   C
ATOM  25985  C    GLU K 378     24.050 -10.203 -78.286  1.00 38.62      A   C
ATOM  25986  O    GLU K 378     23.871 -10.048 -79.494  1.00 38.95      A   O
ATOM  25987  CB   GLU K 378     25.309 -12.192 -77.316  1.00 38.70      A   C
ATOM  25988  CG   GLU K 378     26.671 -12.902 -77.327  1.00 39.90      A   C
ATOM  25989  CD   GLU K 378     26.589 -14.431 -77.116  1.00 41.34      A   C
ATOM  25990  OE1  GLU K 378     25.467 -14.988 -77.120  1.00 41.85      A   O
ATOM  25991  OE2  GLU K 378     27.651 -15.092 -76.947  1.00 41.97      A   O
ATOM  25992  N    TYR K 379     23.139  -9.884 -77.369  1.00 38.44      A   N
ATOM  25993  CA   TYR K 379     21.798  -9.407 -77.742  1.00 38.46      A   C
ATOM  25994  C    TYR K 379     21.841  -8.128 -78.603  1.00 39.02      A   C
ATOM  25995  O    TYR K 379     21.127  -8.009 -79.614  1.00 39.12      A   O
ATOM  25996  CB   TYR K 379     20.917  -9.204 -76.495  1.00 37.85      A   C
ATOM  25997  CG   TYR K 379     19.457  -8.906 -76.805  1.00 37.07      A   C
ATOM  25998  CD1  TYR K 379     18.474  -9.878 -76.630  1.00 36.33      A   C
ATOM  25999  CD2  TYR K 379     19.057  -7.641 -77.279  1.00 36.84      A   C
ATOM  26000  CE1  TYR K 379     17.118  -9.601 -76.923  1.00 36.19      A   C
```

FIGURE 1 (cont'd)

```
ATOM  26001  CE2 TYR K 379      17.709  -7.350 -77.578  1.00 36.57      A    C
ATOM  26002  CZ  TYR K 379      16.742  -8.333 -77.396  1.00 36.25      A    C
ATOM  26003  OH  TYR K 379      15.415  -8.035 -77.672  1.00 35.92      A    O
ATOM  26004  N   LEU K 380      22.686  -7.184 -78.195  1.00 39.71      A    N
ATOM  26005  CA  LEU K 380      22.820  -5.903 -78.898  1.00 40.69      A    C
ATOM  26006  C   LEU K 380      23.898  -5.943 -79.993  1.00 41.94      A    C
ATOM  26007  O   LEU K 380      24.232  -4.900 -80.577  1.00 42.04      A    O
ATOM  26008  CB  LEU K 380      23.092  -4.764 -77.892  1.00 40.25      A    C
ATOM  26009  CG  LEU K 380      21.981  -3.795 -77.440  1.00 39.80      A    C
ATOM  26010  CD1 LEU K 380      20.594  -4.449 -77.424  1.00 39.41      A    C
ATOM  26011  CD2 LEU K 380      22.322  -3.164 -76.069  1.00 39.48      A    C
ATOM  26012  N   GLY K 381      24.433  -7.146 -80.247  1.00 47.38      A    N
ATOM  26013  CA  GLY K 381      25.412  -7.412 -81.316  1.00 52.84      A    C
ATOM  26014  C   GLY K 381      26.577  -6.438 -81.424  1.00 56.55      A    C
ATOM  26015  O   GLY K 381      27.136  -6.248 -82.515  1.00 57.01      A    O
ATOM  26016  N   LEU K 382      26.951  -5.852 -80.281  1.00 59.02      A    N
ATOM  26017  CA  LEU K 382      27.888  -4.716 -80.196  1.00 60.99      A    C
ATOM  26018  C   LEU K 382      29.324  -4.995 -80.700  1.00 61.68      A    C
ATOM  26019  O   LEU K 382      30.159  -4.082 -80.813  1.00 62.06      A    O
ATOM  26020  CB  LEU K 382      27.921  -4.165 -78.754  1.00 61.35      A    C
ATOM  26021  CG  LEU K 382      26.628  -3.663 -78.074  1.00 61.92      A    C
ATOM  26022  CD1 LEU K 382      26.923  -3.206 -76.637  1.00 62.28      A    C
ATOM  26023  CD2 LEU K 382      25.909  -2.551 -78.862  1.00 62.28      A    C
ATOM  26024  OXT LEU K 382      29.699  -6.131 -81.014  1.00 62.09      A    O
END
```

FIGURE 1 (cont'd)

(REMARKS)

```
HEADER    ----                                       XX-XXX-9-   xxxx
COMPND    ---
REMARK   3
REMARK   3 REFINEMENT.
REMARK   3   PROGRAM     : REFMAC 5.5.0110
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   3.42
REMARK   3   RESOLUTION RANGE LOW  (ANGSTROMS) :  34.72
REMARK   3   DATA CUTOFF            (SIGMA(F)) :  NONE
REMARK   3   COMPLETENESS FOR RANGE        (%) : 100.00
REMARK   3   NUMBER OF REFLECTIONS             :  53920
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.27090
REMARK   3   R VALUE            (WORKING SET) : 0.26846
REMARK   3   FREE R VALUE                     : 0.31780
REMARK   3   FREE R VALUE TEST SET SIZE   (%) : 5.0
REMARK   3   FREE R VALUE TEST SET COUNT      : 2838
REMARK   3
REMARK   3  FIT IN THE HIGHEST RESOLUTION BIN.
REMARK   3   TOTAL NUMBER OF BINS USED           :      20
REMARK   3   BIN RESOLUTION RANGE HIGH           :   3.420
REMARK   3   BIN RESOLUTION RANGE LOW            :   3.508
REMARK   3   REFLECTION IN BIN     (WORKING SET) :    3937
REMARK   3   BIN COMPLETENESS (WORKING+TEST) (%) :  100.00
REMARK   3   BIN R VALUE           (WORKING SET) :   0.327
REMARK   3   BIN FREE R VALUE SET COUNT          :     207
REMARK   3   BIN FREE R VALUE                    :   0.381
REMARK   3
REMARK   3  NUMBER OF NON-HYDROGEN ATOMS USED IN REFINEMENT.
REMARK   3   ALL ATOMS          :     25844
REMARK   3
REMARK   3  B VALUES.
REMARK   3   FROM WILSON PLOT           (A**2) : NULL
REMARK   3   MEAN B VALUE      (OVERALL, A**2) : 39.962
REMARK   3   OVERALL ANISOTROPIC B VALUE.
REMARK   3    B11 (A**2) :   -1.04
REMARK   3    B22 (A**2) :    4.61
REMARK   3    B33 (A**2) :   -4.17
REMARK   3    B12 (A**2) :    0.00
REMARK   3    B13 (A**2) :   -1.16
REMARK   3    B23 (A**2) :    0.00
REMARK   3
REMARK   3  ESTIMATED OVERALL COORDINATE ERROR.
REMARK   3   ESU BASED ON R VALUE                   (A): NULL
REMARK   3   ESU BASED ON FREE R VALUE              (A):  0.765
REMARK   3   ESU BASED ON MAXIMUM LIKELIHOOD        (A):  0.639
REMARK   3   ESU FOR B VALUES BASED ON MAXIMUM LIKELIHOOD (A**2): 92.126
REMARK   3
REMARK   3 CORRELATION COEFFICIENTS.
REMARK   3   CORRELATION COEFFICIENT FO-FC      :  0.833
REMARK   3   CORRELATION COEFFICIENT FO-FC FREE :  0.762
REMARK   3
REMARK   3  RMS DEVIATIONS FROM IDEAL VALUES        COUNT    RMS    WEIGHT
REMARK   3   BOND LENGTHS REFINED ATOMS        (A): 26270 ; 0.011 ; 0.021
REMARK   3   BOND ANGLES REFINED ATOMS   (DEGREES): 35738 ; 1.748 ; 1.989
```

FIGURE 1 (cont'd)

```
REMARK   3    TORSION ANGLES, PERIOD 1    (DEGREES):  3334 ; 6.547 ; 5.000
REMARK   3    TORSION ANGLES, PERIOD 2    (DEGREES):   928 ;33.216 ;22.543
REMARK   3    TORSION ANGLES, PERIOD 3    (DEGREES):  3688 ;20.000 ;15.000
REMARK   3    TORSION ANGLES, PERIOD 4    (DEGREES):   139 ;19.811 ;15.000
REMARK   3    CHIRAL-CENTER RESTRAINTS        (A**3):  3915 ; 0.094 ; 0.200
REMARK   3    GENERAL PLANES REFINED ATOMS      (A): 19873 ; 0.008 ; 0.022
REMARK   3
REMARK   3  ISOTROPIC THERMAL FACTOR RESTRAINTS.     COUNT    RMS    WEIGHT
REMARK   3    MAIN-CHAIN BOND REFINED ATOMS  (A**2): 16905 ; 1.066 ; 1.500
REMARK   3    MAIN-CHAIN ANGLE REFINED ATOMS (A**2): 27039 ; 1.713 ; 2.000
REMARK   3    SIDE-CHAIN BOND REFINED ATOMS  (A**2):  9365 ; 1.993 ; 3.000
REMARK   3    SIDE-CHAIN ANGLE REFINED ATOMS (A**2):  8629 ; 3.280 ; 4.500
REMARK   3
REMARK   3 ANISOTROPIC THERMAL FACTOR RESTRAINTS.    COUNT    RMS    WEIGHT
REMARK   3    RIGID-BOND RESTRAINTS          (A**2): 26270 ; 1.408 ; 3.000
REMARK   3    SPHERICITY; FREE ATOMS         (A**2):   338 ;28.003 ; 3.000
REMARK   3    SPHERICITY; BONDED ATOMS       (A**2): 25506 ; 8.525 ; 3.000
REMARK   3
REMARK   3  NCS RESTRAINTS STATISTICS
REMARK   3    NUMBER OF DIFFERENT NCS GROUPS :     2
REMARK   3
REMARK   3    NCS GROUP NUMBER                  :     1
REMARK   3       CHAIN NAMES                    : A  B  C  D  E  F  G  H  I  J  K
REMARK   3       NUMBER OF COMPONENTS NCS GROUP :    1
REMARK   3          COMPONENT  C  SSSEQI   TO   C   SSSEQI   CODE
REMARK   3              1      A    77          A    380      2
REMARK   3              1      B    77          B    380      2
REMARK   3              1      C    77          C    380      2
REMARK   3              1      D    77          D    380      2
REMARK   3              1      E    77          E    380      2
REMARK   3              1      F    77          F    380      2
REMARK   3              1      G    77          G    380      2
REMARK   3              1      H    77          H    380      2
REMARK   3              1      I    77          I    380      2
REMARK   3              1      J    77          J    380      2
REMARK   3              1      K    77          K    380      2
REMARK   3                     GROUP CHAIN       COUNT    RMS    WEIGHT
REMARK   3    TIGHT POSITIONAL    1     1   (A):  1160 ;  0.05 ;  0.05
REMARK   3    TIGHT POSITIONAL    1     2   (A):  1160 ;  0.07 ;  0.05
REMARK   3    TIGHT POSITIONAL    1     3   (A):  1160 ;  0.06 ;  0.05
REMARK   3    TIGHT POSITIONAL    1     4   (A):  1160 ;  0.05 ;  0.05
REMARK   3    TIGHT POSITIONAL    1     5   (A):  1160 ;  0.05 ;  0.05
REMARK   3    TIGHT POSITIONAL    1     6   (A):  1160 ;  0.05 ;  0.05
REMARK   3    TIGHT POSITIONAL    1     7   (A):  1160 ;  0.04 ;  0.05
REMARK   3    TIGHT POSITIONAL    1     8   (A):  1160 ;  0.04 ;  0.05
REMARK   3    TIGHT POSITIONAL    1     9   (A):  1160 ;  0.05 ;  0.05
REMARK   3    TIGHT POSITIONAL    1     0   (A):  1160 ;  0.05 ;  0.05
REMARK   3    TIGHT POSITIONAL    1     1   (A):  1160 ;  0.06 ;  0.05
REMARK   3    MEDIUM POSITIONAL   1     1   (A):   988 ;  0.11 ;  0.50
REMARK   3    MEDIUM POSITIONAL   1     2   (A):   988 ;  0.16 ;  0.50
REMARK   3    MEDIUM POSITIONAL   1     3   (A):   988 ;  0.08 ;  0.50
REMARK   3    MEDIUM POSITIONAL   1     4   (A):   988 ;  0.08 ;  0.50
REMARK   3    MEDIUM POSITIONAL   1     5   (A):   988 ;  0.06 ;  0.50
REMARK   3    MEDIUM POSITIONAL   1     6   (A):   988 ;  0.06 ;  0.50
REMARK   3    MEDIUM POSITIONAL   1     7   (A):   988 ;  0.06 ;  0.50
REMARK   3    MEDIUM POSITIONAL   1     8   (A):   988 ;  0.06 ;  0.50
REMARK   3    MEDIUM POSITIONAL   1     9   (A):   988 ;  0.06 ;  0.50
REMARK   3    MEDIUM POSITIONAL   1     0   (A):   988 ;  0.06 ;  0.50
REMARK   3    MEDIUM POSITIONAL   1     1   (A):   988 ;  0.08 ;  0.50
REMARK   3    TIGHT THERMAL       1     1 (A**2):  1160 ;  3.17 ;  0.50
REMARK   3    TIGHT THERMAL       1     2 (A**2):  1160 ;  2.16 ;  0.50
REMARK   3    TIGHT THERMAL       1     3 (A**2):  1160 ;  2.82 ;  0.50
REMARK   3    TIGHT THERMAL       1     4 (A**2):  1160 ;  2.47 ;  0.50
REMARK   3    TIGHT THERMAL       1     5 (A**2):  1160 ;  2.38 ;  0.50
REMARK   3    TIGHT THERMAL       1     6 (A**2):  1160 ;  2.10 ;  0.50
```

FIGURE 1 (cont'd)

```
REMARK   3    TIGHT THERMAL      1   7   (A**2):    1160 ;   2.17 ;   0.50
REMARK   3    TIGHT THERMAL      1   8   (A**2):    1160 ;   1.72 ;   0.50
REMARK   3    TIGHT THERMAL      1   9   (A**2):    1160 ;   6.01 ;   0.50
REMARK   3    TIGHT THERMAL      1   0   (A**2):    1160 ;   4.37 ;   0.50
REMARK   3    TIGHT THERMAL      1   1   (A**2):    1160 ;   6.19 ;   0.50
REMARK   3    MEDIUM THERMAL     1   1   (A**2):     988 ;   2.61 ;   2.00
REMARK   3    MEDIUM THERMAL     1   2   (A**2):     988 ;   2.57 ;   2.00
REMARK   3    MEDIUM THERMAL     1   3   (A**2):     988 ;   2.42 ;   2.00
REMARK   3    MEDIUM THERMAL     1   4   (A**2):     988 ;   2.00 ;   2.00
REMARK   3    MEDIUM THERMAL     1   5   (A**2):     988 ;   1.94 ;   2.00
REMARK   3    MEDIUM THERMAL     1   6   (A**2):     988 ;   1.71 ;   2.00
REMARK   3    MEDIUM THERMAL     1   7   (A**2):     988 ;   1.75 ;   2.00
REMARK   3    MEDIUM THERMAL     1   8   (A**2):     988 ;   1.43 ;   2.00
REMARK   3    MEDIUM THERMAL     1   9   (A**2):     988 ;   4.97 ;   2.00
REMARK   3    MEDIUM THERMAL     1   0   (A**2):     988 ;   3.83 ;   2.00
REMARK   3    MEDIUM THERMAL     1   1   (A**2):     988 ;   5.15 ;   2.00
REMARK   3
REMARK   3   NCS GROUP NUMBER                 :    2
REMARK   3      CHAIN NAMES                   : X W Y Z a b c d e f
REMARK   3      NUMBER OF COMPONENTS NCS GROUP :    1
REMARK   3         COMPONENT  C  SSSEQI   TO   C  SSSEQI    CODE
REMARK   3              1     X      1         X      1        1
REMARK   3              1     W      1         W      1        1
REMARK   3              1     Y      1         Y      1        1
REMARK   3              1     Z      1         Z      1        1
REMARK   3              1     a      1         a      1        1
REMARK   3              1     b      1         b      1        1
REMARK   3              1     c      1         c      1        1
REMARK   3              1     d      1         d      1        1
REMARK   3              1     e      1         e      1        1
REMARK   3              1     f      1         f      1        1
REMARK   3                     GROUP CHAIN         COUNT    RMS      WEIGHT
REMARK   3    TIGHT POSITIONAL    2    1    (A):     22 ;   0.46 ;   0.05
REMARK   3    TIGHT POSITIONAL    2    2    (A):     22 ;   0.35 ;   0.05
REMARK   3    TIGHT POSITIONAL    2    3    (A):     22 ;   0.42 ;   0.05
REMARK   3    TIGHT POSITIONAL    2    4    (A):     22 ;   0.63 ;   0.05
REMARK   3    TIGHT POSITIONAL    2    5    (A):     22 ;   0.64 ;   0.05
REMARK   3    TIGHT POSITIONAL    2    6    (A):     22 ;   0.60 ;   0.05
REMARK   3    TIGHT POSITIONAL    2    7    (A):     22 ;   0.53 ;   0.05
REMARK   3    TIGHT POSITIONAL    2    8    (A):     22 ;   0.65 ;   0.05
REMARK   3    TIGHT POSITIONAL    2    9    (A):     22 ;   0.34 ;   0.05
REMARK   3    TIGHT POSITIONAL    2    0    (A):     22 ;   0.53 ;   0.05
REMARK   3    TIGHT THERMAL       2    1  (A**2):    22 ;  11.09 ;   0.50
REMARK   3    TIGHT THERMAL       2    2  (A**2):    22 ;  11.84 ;   0.50
REMARK   3    TIGHT THERMAL       2    3  (A**2):    22 ;  12.29 ;   0.50
REMARK   3    TIGHT THERMAL       2    4  (A**2):    22 ;  23.49 ;   0.50
REMARK   3    TIGHT THERMAL       2    5  (A**2):    22 ;  10.67 ;   0.50
REMARK   3    TIGHT THERMAL       2    6  (A**2):    22 ;  43.50 ;   0.50
REMARK   3    TIGHT THERMAL       2    7  (A**2):    22 ;  14.70 ;   0.50
REMARK   3    TIGHT THERMAL       2    8  (A**2):    22 ;  10.31 ;   0.50
REMARK   3    TIGHT THERMAL       2    9  (A**2):    22 ;   6.25 ;   0.50
REMARK   3    TIGHT THERMAL       2    0  (A**2):    22 ;   8.45 ;   0.50
REMARK   3
REMARK   3   TWIN DETAILS
REMARK   3    NUMBER OF TWIN DOMAINS  : NULL
REMARK   3
REMARK   3
REMARK   3   TLS DETAILS
REMARK   3    NUMBER OF TLS GROUPS  : NULL
REMARK   3
REMARK   3
REMARK   3   BULK SOLVENT MODELLING.
REMARK   3    METHOD USED : MASK
REMARK   3    PARAMETERS FOR MASK CALCULATION
REMARK   3    VDW PROBE RADIUS    :   1.40
```

FIGURE 1 (cont'd)

```
REMARK   3   ION PROBE RADIUS   :   0.80
REMARK   3   SHRINKAGE RADIUS   :   0.80
REMARK   3
REMARK   3   OTHER REFINEMENT REMARKS:
REMARK   3   HYDROGENS HAVE BEEN ADDED IN THE RIDING POSITIONS
REMARK   3   U VALUES       : REFINED INDIVIDUALLY
REMARK   3
```

FIGURE 2

```
ChainB    ----------------------GSLPEARLRRVVGQLDPQRLWSTYLRPLLVVRTPGSPG  38
ChainJ    -----------------------LPEARLRRVVGQLDPQRLWSTYLRPLLVVRTPGSPG  36
ChainH    -----------------------LPEARLRRVVGQLDPQRLWSTYLRPLLVVRTPGSPG  36
hisoQC    EFHHHHHHEELPLGRELRVPLNGSLPEARLRRVVGQLDPQRLWSTYLRPLLVVRTPGSPG  60
ChainK    ------------------------PEARLRRVVGQLDPQRLWSTYLRPLLVVRTPGSPG  35
ChainE    --------------------NGSLPEARLRRVVGQLDPQRLWSTYLRPLLVVRTPGSPG  39
ChainC    ----------------------GSLPEARLRRVVGQLDPQRLWSTYLRPLLVVRTPGSPG  38
ChainA    ----------------------GSLPEARLRRVVGQLDPQRLWSTYLRPLLVVRTPGSPG  38
ChainG    -----------------------SLPEARLRRVVGQLDPQRLWSTYLRPLLVVRTPGSPG  37
ChainI    -----------------------SLPEARLRRVVGQLDPQRLWSTYLRPLLVVRTPGSPG  37
ChainD    -----------------------SLPEARLRRVVGQLDPQRLWSTYLRPLLVVRTPGSPG  37
ChainF    -----------------------SLPEARLRRVVGQLDPQRLWSTYLRPLLVVRTPGSPG  37
                                 ************************************

ChainB    NLQVRKFLEATLRSLTAGWHVELDPFTASTPLGPVDFGNVVATLDPRAARHLTLACHYDS  98
ChainJ    NLQVRKFLEATLRSLTAGWHVELDPFTASTPLGPVDFGNVVATLDPRAARHLTLACHYDS  96
ChainH    NLQVRKFLEATLRSLTAGWHVELDPFTASTPLGPVDFGNVVATLDPRAARHLTLACHYDS  96
hisoQC    NLQVRKFLEATLRSLTAGWHVELDPFTASTPLGPVDFGNVVATLDPRAARHLTLACHYDS 120
ChainK    NLQVRKFLEATLRSLTAGWHVELDPFTASTPLGPVDFGNVVATLDPRAARHLTLACHYDS  95
ChainE    NLQVRKFLEATLRSLTAGWHVELDPFTASTPLGPVDFGNVVATLDPRAARHLTLACHYDS  99
ChainC    NLQVRKFLEATLRSLTAGWHVELDPFTASTPLGPVDFGNVVATLDPRAARHLTLACHYDS  98
ChainA    NLQVRKFLEATLRSLTAGWHVELDPFTASTPLGPVDFGNVVATLDPRAARHLTLACHYDS  98
ChainG    NLQVRKFLEATLRSLTAGWHVELDPFTASTPLGPVDFGNVVATLDPRAARHLTLACHYDS  97
ChainI    NLQVRKFLEATLRSLTAGWHVELDPFTASTPLGPVDFGNVVATLDPRAARHLTLACHYDS  97
ChainD    NLQVRKFLEATLRSLTAGWHVELDPFTASTPLGPVDFGNVVATLDPRAARHLTLACHYDS  97
ChainF    NLQVRKFLEATLRSLTAGWHVELDPFTASTPLGPVDFGNVVATLDPRAARHLTLACHYDS  97
          ************************************************************

ChainB    KLFPPGSTPFVGATDSAVPCALLLELAQALDLELSRAKKQA--VTLQLLFLDGEEALKEW 156
ChainJ    KLFPPGSTPFVGATDSAVPCALLLELAQALDLELSRAK-----VTLQLLFLDGEEALKEW 151
ChainH    KLFPPGSTPFVGATDSAVPCALLLELAQALDLELSRAK-----VTLQLLFLDGEEALKEW 151
hisoQC    KLFPPGSTPFVGATDSAVPCALLLELAQALDLELSRAKKQAAPVTLQLLFLDGEEALKEW 180
ChainK    KLF---STPFVGATDSAVPCALLLELAQALDLELSRAK-----VTLQLLFLDGEEALKEW 147
ChainE    KLFPPGSTPFVGATDSAVPCALLLELAQALDLELSRAKKQAAPVTLQLLFLDGEEALKEW 159
ChainC    KLFPPGSTPFVGATDSAVPCALLLELAQALDLELSRAKKQAAPVTLQLLFLDGEEALKEW 158
ChainA    KLFPPGSTPFVGATDSAVPCALLLELAQALDLELSRAKKQAAPVTLQLLFLDGEEALKEW 158
ChainG    KLFP--STPFVGATDSAVPCALLLELAQALDLELSRAKK---PVTLQLLFLDGEEALKEW 152
ChainI    KLF---STPFVGATDSAVPCALLLELAQALDLELSRAK-----VTLQLLFLDGEEALKEW 149
ChainD    KLFPPGSTPFVGATDSAVPCALLLELAQALDLELSRAKKQAAPVTLQLLFLDGEEALKEW 157
ChainF    KLFPPGSTPFVGATDSAVPCALLLELAQALDLELSRAKKQAAPVTLQLLFLDGEEALKEW 157
          ***   *****************************        *****************

ChainB    GPKDSLYGSRHLAQLMESIPHSPGPTRIQAIELFMLLDLLGAPNPTFYSHFPRTVRWFHR 216
ChainJ    GPKDSLYGSRHLAQLMESIPHSPGPTRIQAIELFMLLDLLGAPNPTFYSHFPRTVRWFHR 211
ChainH    GPKDSLYGSRHLAQLMESIPHSPGPTRIQAIELFMLLDLLGAPNPTFYSHFPRTVRWFHR 211
hisoQC    GPKDSLYGSRHLAQLMESIPHSPGPTRIQAIELFMLLDLLGAPNPTFYSHFPRTVRWFHR 240
ChainK    GPKDSLYGSRHLAQLMESIPHSPGPTRIQAIELFMLLDLLGAPNPTFYSHFPRTVRWFHR 207
ChainE    GPKDSLYGSRHLAQLMESIPHSPGPTRIQAIELFMLLDLLGAPNPTFYSHFPRTVRWFHR 219
ChainC    GPKDSLYGSRHLAQLMESIPHSPGPTRIQAIELFMLLDLLGAPNPTFYSHFPRTVRWFHR 218
ChainA    GPKDSLYGSRHLAQLMESIPHSPGPTRIQAIELFMLLDLLGAPNPTFYSHFPRTVRWFHR 218
ChainG    GPKDSLYGSRHLAQLMESIPHSPGPTRIQAIELFMLLDLLGAPNPTFYSHFPRTVRWFHR 212
ChainI    GPKDSLYGSRHLAQLMESIPHSPGPTRIQAIELFMLLDLLGAPNPTFYSHFPRTVRWFHR 209
ChainD    GPKDSLYGSRHLAQLMESIPHSPGPTRIQAIELFMLLDLLGAPNPTFYSHFPRTVRWFHR 217
ChainF    GPKDSLYGSRHLAQLMESIPHSPGPTRIQAIELFMLLDLLGAPNPTFYSHFPRTVRWFHR 217
          ************************************************************

ChainB    LRSIEKRLHRLNLLQSHPQEVMYFQPGEPFGSVEDDHIPFLRRGVPVLHLISTPFPAVWH 276
ChainJ    LRSIEKRLHRLNLLQSHPQEVMYFQPGEPFGSVEDDHIPFLRRGVPVLHLISTPFPAVWH 271
ChainH    LRSIEKRLHRLNLLQSHPQEVMYFQPGEPFGSVEDDHIPFLRRGVPVLHLISTPFPAVWH 271
hisoQC    LRSIEKRLHRLNLLQSHPQEVMYFQPGEPFGSVEDDHIPFLRRGVPVLHLISTPFPAVWH 300
ChainK    LRSIEKRLHRLNLLQSHPQEVMYFQPGEPFGSVEDDHIPFLRRGVPVLHLISTPFPAVWH 267
ChainE    LRSIEKRLHRLNLLQSHPQEVMYFQPGEPFGSVEDDHIPFLRRGVPVLHLISTPFPAVWH 279
ChainC    LRSIEKRLHRLNLLQSHPQEVMYFQPGEPFGSVEDDHIPFLRRGVPVLHLISTPFPAVWH 278
ChainA    LRSIEKRLHRLNLLQSHPQEVMYFQPGEPFGSVEDDHIPFLRRGVPVLHLISTPFPAVWH 278
```

FIGURE 2 (cont'd)

```
ChainG   LRSIEKRLHRLNLLQSHPQEVMYFQPGEPFGSVEDDHIPFLRRGVPVLHLISTPFPAVWH 272
ChainI   LRSIEKRLHRLNLLQSHPQEVMYFQPGEPFGSVEDDHIPFLRRGVPVLHLISTPFPAVWH 269
ChainD   LRSIEKRLHRLNLLQSHPQEVMYFQPGEPFGSVEDDHIPFLRRGVPVLHLISTPFPAVWH 277
ChainF   LRSIEKRLHRLNLLQSHPQEVMYFQPGEPFGSVEDDHIPFLRRGVPVLHLISTPFPAVWH 277
         ************************************************************

ChainB   TPADTEVNLHPPTVHNLARILAVFLAEYLGL- 307
ChainJ   TPADTEVNLHPPTVHNLARILAVFLAEYLGL- 302
ChainH   TPADTEVNLHPPTVHNLARILAVFLAEYLGL- 302
hisoQC   TPADTEVNLHPPTVHNLARILAVFLAEYLGL- 331
ChainK   TPADTEVNLHPPTVHNLARILAVFLAEYLGL- 298
ChainE   TPADTEVNLHPPTVHNLARILAVFLAEYLGL- 310
ChainC   TPADTEVNLHPPTVHNLARILAVFLAEYLGL- 309
ChainA   TPADTEVNLHPPTVHNLARILAVFLAEYLGL- 309
ChainG   TPADTEVNLHPPTVHNLARILAVFLAEYLGL- 303
ChainI   TPADTEVNLHPPTVHNLARILAVFLAEYLGL- 300
ChainD   TPADTEVNLHPPTVHNLARILAVFLAEYLGL- 308
ChainF   TPADTEVNLHPPTVHNLARILAVFLAEYLGL- 308
         *******************************
```

FIGURE 6
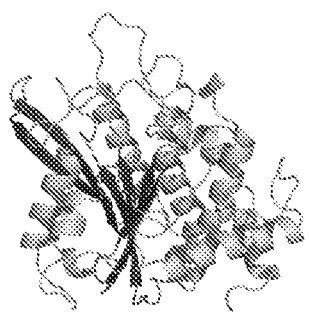
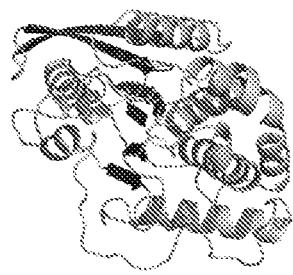

SEQUENCE LISTING

```
<160> NUMBER OF SEQ ID NOS: 19

<210> SEQ ID NO 1
<211> LENGTH: 382
<212> TYPE: PRT
<213> ORGANISM: Human

<400> SEQUENCE: 1

Met Arg Ser Gly Gly Arg Gly Arg Pro Arg Leu Arg Leu Gly Glu Arg
1               5                   10                  15

Gly Leu Met Glu Pro Leu Leu Pro Pro Lys Arg Arg Leu Leu Pro Arg
            20                  25                  30

Val Arg Leu Leu Pro Leu Leu Leu Ala Leu Ala Val Gly Ser Ala Phe
        35                  40                  45

Tyr Thr Ile Trp Ser Gly Trp His Arg Arg Thr Glu Glu Leu Pro Leu
    50                  55                  60

Gly Arg Glu Leu Arg Val Pro Leu Ile Gly Ser Leu Pro Glu Ala Arg
65                  70                  75                  80

Leu Arg Arg Val Val Gly Gln Leu Asp Pro Gln Arg Leu Trp Ser Thr
                85                  90                  95

Tyr Leu Arg Pro Leu Leu Val Val Arg Thr Pro Gly Ser Pro Gly Asn
            100                 105                 110

Leu Gln Val Arg Lys Phe Leu Glu Ala Thr Leu Arg Ser Leu Thr Ala
        115                 120                 125

Gly Trp His Val Glu Leu Asp Pro Phe Thr Ala Ser Thr Pro Leu Gly
    130                 135                 140

Pro Val Asp Phe Gly Asn Val Val Ala Thr Leu Asp Pro Arg Ala Ala
145                 150                 155                 160
```

-continued

```
Arg His Leu Thr Leu Ala Cys His Tyr Asp Ser Lys Leu Phe Pro Pro
            165                 170                 175
Gly Ser Thr Pro Phe Val Gly Ala Thr Asp Ser Ala Val Pro Cys Ala
        180                 185                 190
Leu Leu Leu Glu Leu Ala Gln Ala Leu Asp Leu Glu Leu Ser Arg Ala
        195                 200                 205
Lys Lys Gln Ala Ala Pro Val Thr Leu Gln Leu Leu Phe Leu Asp Gly
        210                 215                 220
Glu Glu Ala Leu Lys Glu Trp Gly Pro Lys Asp Ser Leu Tyr Gly Ser
225                 230                 235                 240
Arg His Leu Ala Gln Leu Met Glu Ser Ile Pro His Ser Pro Gly Pro
            245                 250                 255
Thr Arg Ile Gln Ala Ile Glu Leu Phe Met Leu Leu Asp Leu Leu Gly
            260                 265                 270
Ala Pro Asn Pro Thr Phe Tyr Ser His Phe Pro Arg Thr Val Arg Trp
        275                 280                 285
Phe His Arg Leu Arg Ser Ile Glu Lys Arg Leu His Arg Leu Asn Leu
        290                 295                 300
Leu Gln Ser His Pro Gln Glu Val Met Tyr Phe Gln Pro Gly Glu Pro
305                 310                 315                 320
Phe Gly Ser Val Glu Asp His Ile Pro Phe Leu Arg Arg Gly Val
            325                 330                 335
Pro Val Leu His Leu Ile Ser Thr Pro Phe Pro Ala Val Trp His Thr
            340                 345                 350
Pro Ala Asp Thr Glu Val Asn Leu His Pro Pro Thr Val His Asn Leu
        355                 360                 365
Cys Arg Ile Leu Ala Val Phe Leu Ala Glu Tyr Leu Gly Leu
        370                 375                 380

<210> SEQ ID NO 2
<211> LENGTH: 309
<212> TYPE: PRT
<213> ORGANISM: Human

<400> SEQUENCE: 2

Gly Ser Leu Pro Glu Ala Arg Leu Arg Arg Val Val Gly Gln Leu Asp
1               5                   10                  15
Pro Gln Arg Leu Trp Ser Thr Tyr Leu Arg Pro Leu Leu Val Val Arg
            20                  25                  30
Thr Pro Gly Ser Pro Gly Asn Leu Gln Val Arg Lys Phe Leu Glu Ala
        35                  40                  45
Thr Leu Arg Ser Leu Thr Ala Gly Trp His Val Glu Leu Asp Pro Phe
    50                  55                  60
Thr Ala Ser Thr Pro Leu Gly Pro Val Asp Phe Gly Asn Val Val Ala
65                  70                  75                  80
Thr Leu Asp Pro Arg Ala Ala Arg His Leu Thr Leu Ala Cys His Tyr
            85                  90                  95
Asp Ser Lys Leu Phe Pro Pro Gly Ser Thr Pro Phe Val Gly Ala Thr
            100                 105                 110
Asp Ser Ala Val Pro Cys Ala Leu Leu Leu Glu Leu Ala Gln Ala Leu
        115                 120                 125
Asp Leu Glu Leu Ser Arg Ala Lys Lys Gln Ala Ala Pro Val Thr Leu
    130                 135                 140
Gln Leu Leu Phe Leu Asp Gly Glu Glu Ala Leu Lys Glu Trp Gly Pro
145                 150                 155                 160
```

```
Lys Asp Ser Leu Tyr Gly Ser Arg His Leu Ala Gln Leu Met Glu Ser
                165                 170                 175

Ile Pro His Ser Pro Gly Pro Thr Arg Ile Gln Ala Ile Glu Leu Phe
                180                 185                 190

Met Leu Leu Asp Leu Leu Gly Ala Pro Asn Pro Thr Phe Tyr Ser His
                195                 200                 205

Phe Pro Arg Thr Val Arg Trp Phe His Arg Leu Arg Ser Ile Glu Lys
                210                 215                 220

Arg Leu His Arg Leu Asn Leu Leu Gln Ser His Pro Gln Glu Val Met
225                 230                 235                 240

Tyr Phe Gln Pro Gly Glu Pro Phe Gly Ser Val Glu Asp Asp His Ile
                245                 250                 255

Pro Phe Leu Arg Arg Gly Val Pro Val Leu His Leu Ile Ser Thr Pro
                260                 265                 270

Phe Pro Ala Val Trp His Thr Pro Ala Asp Thr Glu Val Asn Leu His
                275                 280                 285

Pro Pro Thr Val His Asn Leu Ala Arg Ile Leu Ala Val Phe Leu Ala
                290                 295                 300

Glu Tyr Leu Gly Leu
305

<210> SEQ ID NO 3
<211> LENGTH: 307
<212> TYPE: PRT
<213> ORGANISM: Human

<400> SEQUENCE: 3

Gly Ser Leu Pro Glu Ala Arg Leu Arg Arg Val Val Gly Gln Leu Asp
1               5                   10                  15

Pro Gln Arg Leu Trp Ser Thr Tyr Leu Arg Pro Leu Leu Val Val Arg
                20                  25                  30

Thr Pro Gly Ser Pro Gly Asn Leu Gln Val Arg Lys Phe Leu Glu Ala
                35                  40                  45

Thr Leu Arg Ser Leu Thr Ala Gly Trp His Val Glu Leu Asp Pro Phe
                50                  55                  60

Thr Ala Ser Thr Pro Leu Gly Pro Val Asp Phe Gly Asn Val Val Ala
65                  70                  75                  80

Thr Leu Asp Pro Arg Ala Ala Arg His Leu Thr Leu Ala Cys His Tyr
                85                  90                  95

Asp Ser Lys Leu Phe Pro Pro Gly Ser Thr Pro Phe Val Gly Ala Thr
                100                 105                 110

Asp Ser Ala Val Pro Cys Ala Leu Leu Leu Glu Leu Ala Gln Ala Leu
                115                 120                 125

Asp Leu Glu Leu Ser Arg Ala Lys Lys Gln Ala Val Thr Leu Gln Leu
                130                 135                 140

Leu Phe Leu Asp Gly Glu Glu Ala Leu Lys Glu Trp Gly Pro Lys Asp
145                 150                 155                 160

Ser Leu Tyr Gly Ser Arg His Leu Ala Gln Leu Met Glu Ser Ile Pro
                165                 170                 175

His Ser Pro Gly Pro Thr Arg Ile Gln Ala Ile Glu Leu Phe Met Leu
                180                 185                 190

Leu Asp Leu Leu Gly Ala Pro Asn Pro Thr Phe Tyr Ser His Phe Pro
                195                 200                 205

Arg Thr Val Arg Trp Phe His Arg Leu Arg Ser Ile Glu Lys Arg Leu
                210                 215                 220
```

His Arg Leu Asn Leu Leu Gln Ser His Pro Gln Glu Val Met Tyr Phe
225                 230                 235                 240

Gln Pro Gly Glu Pro Phe Gly Ser Val Glu Asp Asp His Ile Pro Phe
                245                 250                 255

Leu Arg Arg Gly Val Pro Val Leu His Leu Ile Ser Thr Pro Phe Pro
            260                 265                 270

Ala Val Trp His Thr Pro Ala Asp Thr Glu Val Asn Leu His Pro Pro
        275                 280                 285

Thr Val His Asn Leu Ala Arg Ile Leu Ala Val Phe Leu Ala Glu Tyr
    290                 295                 300

Leu Gly Leu
305

<210> SEQ ID NO 4
<211> LENGTH: 309
<212> TYPE: PRT
<213> ORGANISM: Human

<400> SEQUENCE: 4

Gly Ser Leu Pro Glu Ala Arg Leu Arg Arg Val Val Gly Gln Leu Asp
1               5                   10                  15

Pro Gln Arg Leu Trp Ser Thr Tyr Leu Arg Pro Leu Leu Val Val Arg
                20                  25                  30

Thr Pro Gly Ser Pro Gly Asn Leu Gln Val Arg Lys Phe Leu Glu Ala
            35                  40                  45

Thr Leu Arg Ser Leu Thr Ala Gly Trp His Val Glu Leu Asp Pro Phe
    50                  55                  60

Thr Ala Ser Thr Pro Leu Gly Pro Val Asp Phe Gly Asn Val Val Ala
65                  70                  75                  80

Thr Leu Asp Pro Arg Ala Ala Arg His Leu Thr Leu Ala Cys His Tyr
                85                  90                  95

Asp Ser Lys Leu Phe Pro Pro Gly Ser Thr Pro Phe Val Gly Ala Thr
            100                 105                 110

Asp Ser Ala Val Pro Cys Ala Leu Leu Leu Glu Leu Ala Gln Ala Leu
        115                 120                 125

Asp Leu Glu Leu Ser Arg Ala Lys Lys Gln Ala Ala Pro Val Thr Leu
    130                 135                 140

Gln Leu Leu Phe Leu Asp Gly Glu Glu Ala Leu Lys Glu Trp Gly Pro
145                 150                 155                 160

Lys Asp Ser Leu Tyr Gly Ser Arg His Leu Ala Gln Leu Met Glu Ser
                165                 170                 175

Ile Pro His Ser Pro Gly Pro Thr Arg Ile Gln Ala Ile Glu Leu Phe
            180                 185                 190

Met Leu Leu Asp Leu Leu Gly Ala Pro Asn Pro Thr Phe Tyr Ser His
        195                 200                 205

Phe Pro Arg Thr Val Arg Trp Phe His Arg Leu Arg Ser Ile Glu Lys
    210                 215                 220

Arg Leu His Arg Leu Asn Leu Leu Gln Ser His Pro Gln Glu Val Met
225                 230                 235                 240

Tyr Phe Gln Pro Gly Glu Pro Phe Gly Ser Val Glu Asp Asp His Ile
                245                 250                 255

Pro Phe Leu Arg Arg Gly Val Pro Val Leu His Leu Ile Ser Thr Pro
            260                 265                 270

Phe Pro Ala Val Trp His Thr Pro Ala Asp Thr Glu Val Asn Leu His
        275                 280                 285

```
Pro Pro Thr Val His Asn Leu Ala Arg Ile Leu Ala Val Phe Leu Ala
    290                 295                 300

Glu Tyr Leu Gly Leu
305

<210> SEQ ID NO 5
<211> LENGTH: 308
<212> TYPE: PRT
<213> ORGANISM: Human

<400> SEQUENCE: 5

Ser Leu Pro Glu Ala Arg Leu Arg Arg Val Val Gly Gln Leu Asp Pro
1               5                   10                  15

Gln Arg Leu Trp Ser Thr Tyr Leu Arg Pro Leu Val Val Arg Thr
                20                  25                  30

Pro Gly Ser Pro Gly Asn Leu Gln Val Arg Lys Phe Leu Glu Ala Thr
            35                  40                  45

Leu Arg Ser Leu Thr Ala Gly Trp His Val Glu Leu Asp Pro Phe Thr
    50                  55                  60

Ala Ser Thr Pro Leu Gly Pro Val Asp Phe Gly Asn Val Val Ala Thr
65                  70                  75                  80

Leu Asp Pro Arg Ala Ala Arg His Leu Thr Leu Ala Cys His Tyr Asp
                85                  90                  95

Ser Lys Leu Phe Pro Pro Gly Ser Thr Pro Phe Val Gly Ala Thr Asp
            100                 105                 110

Ser Ala Val Pro Cys Ala Leu Leu Leu Glu Leu Ala Gln Ala Leu Asp
        115                 120                 125

Leu Glu Leu Ser Arg Ala Lys Lys Gln Ala Ala Pro Val Thr Leu Gln
    130                 135                 140

Leu Leu Phe Leu Asp Gly Glu Glu Ala Leu Lys Glu Trp Gly Pro Lys
145                 150                 155                 160

Asp Ser Leu Tyr Gly Ser Arg His Leu Ala Gln Leu Met Glu Ser Ile
                165                 170                 175

Pro His Ser Pro Gly Pro Thr Arg Ile Gln Ala Ile Glu Leu Phe Met
            180                 185                 190

Leu Leu Asp Leu Leu Gly Ala Pro Asn Pro Thr Phe Tyr Ser His Phe
        195                 200                 205

Pro Arg Thr Val Arg Trp Phe His Arg Leu Arg Ser Ile Glu Lys Arg
    210                 215                 220

Leu His Arg Leu Asn Leu Leu Gln Ser His Pro Gln Glu Val Met Tyr
225                 230                 235                 240

Phe Gln Pro Gly Glu Pro Phe Gly Ser Val Glu Asp Asp His Ile Pro
                245                 250                 255

Phe Leu Arg Arg Gly Val Pro Val Leu His Leu Ile Ser Thr Pro Phe
            260                 265                 270

Pro Ala Val Trp His Thr Pro Ala Asp Thr Glu Val Asn Leu His Pro
        275                 280                 285

Pro Thr Val His Asn Leu Ala Arg Ile Leu Ala Val Phe Leu Ala Glu
    290                 295                 300

Tyr Leu Gly Leu
305

<210> SEQ ID NO 6
<211> LENGTH: 310
<212> TYPE: PRT
<213> ORGANISM: Human
```

<400> SEQUENCE: 6

```
Asn Gly Ser Leu Pro Glu Ala Arg Leu Arg Arg Val Val Gly Gln Leu
1               5                   10                  15

Asp Pro Gln Arg Leu Trp Ser Thr Tyr Leu Arg Pro Leu Leu Val Val
            20                  25                  30

Arg Thr Pro Gly Ser Pro Gly Asn Leu Gln Val Arg Lys Phe Leu Glu
        35                  40                  45

Ala Thr Leu Arg Ser Leu Thr Ala Gly Trp His Val Glu Leu Asp Pro
50                  55                  60

Phe Thr Ala Ser Thr Pro Leu Gly Pro Val Asp Phe Gly Asn Val Val
65                  70                  75                  80

Ala Thr Leu Asp Pro Arg Ala Ala Arg His Leu Thr Leu Ala Cys His
                85                  90                  95

Tyr Asp Ser Lys Leu Phe Pro Pro Gly Ser Thr Pro Phe Val Gly Ala
            100                 105                 110

Thr Asp Ser Ala Val Pro Cys Ala Leu Leu Glu Leu Ala Gln Ala
        115                 120                 125

Leu Asp Leu Glu Leu Ser Arg Ala Lys Lys Gln Ala Ala Pro Val Thr
130                 135                 140

Leu Gln Leu Leu Phe Leu Asp Gly Glu Glu Ala Leu Lys Glu Trp Gly
145                 150                 155                 160

Pro Lys Asp Ser Leu Tyr Gly Ser Arg His Leu Ala Gln Leu Met Glu
                165                 170                 175

Ser Ile Pro His Ser Pro Gly Pro Thr Arg Ile Gln Ala Ile Glu Leu
            180                 185                 190

Phe Met Leu Leu Asp Leu Leu Gly Ala Pro Asn Pro Thr Phe Tyr Ser
        195                 200                 205

His Phe Pro Arg Thr Val Arg Trp Phe His Arg Leu Arg Ser Ile Glu
210                 215                 220

Lys Arg Leu His Arg Leu Asn Leu Leu Gln Ser His Pro Gln Glu Val
225                 230                 235                 240

Met Tyr Phe Gln Pro Gly Glu Pro Phe Gly Ser Val Glu Asp Asp His
                245                 250                 255

Ile Pro Phe Leu Arg Arg Gly Val Pro Val Leu His Leu Ile Ser Thr
            260                 265                 270

Pro Phe Pro Ala Val Trp His Thr Pro Ala Asp Thr Glu Val Asn Leu
        275                 280                 285

His Pro Pro Thr Val His Asn Leu Ala Arg Ile Leu Ala Val Phe Leu
290                 295                 300

Ala Glu Tyr Leu Gly Leu
305             310
```

<210> SEQ ID NO 7
<211> LENGTH: 308
<212> TYPE: PRT
<213> ORGANISM: Human

<400> SEQUENCE: 7

```
Ser Leu Pro Glu Ala Arg Leu Arg Arg Val Val Gly Gln Leu Asp Pro
1               5                   10                  15

Gln Arg Leu Trp Ser Thr Tyr Leu Arg Pro Leu Leu Val Val Arg Thr
            20                  25                  30

Pro Gly Ser Pro Gly Asn Leu Gln Val Arg Lys Phe Leu Glu Ala Thr
        35                  40                  45

Leu Arg Ser Leu Thr Ala Gly Trp His Val Glu Leu Asp Pro Phe Thr
```

```
                 50                  55                  60

Ala Ser Thr Pro Leu Gly Pro Val Asp Phe Gly Asn Val Val Ala Thr
 65                  70                  75                  80

Leu Asp Pro Arg Ala Arg His Leu Thr Leu Ala Cys His Tyr Asp
                 85                  90                  95

Ser Lys Leu Phe Pro Gly Ser Thr Pro Phe Val Gly Ala Thr Asp
                100                 105                 110

Ser Ala Val Pro Cys Ala Leu Leu Glu Leu Ala Gln Ala Leu Asp
                115                 120                 125

Leu Glu Leu Ser Arg Ala Lys Lys Gln Ala Pro Val Thr Leu Gln
            130                 135                 140

Leu Leu Phe Leu Asp Gly Glu Glu Ala Leu Lys Glu Trp Gly Pro Lys
145                 150                 155                 160

Asp Ser Leu Tyr Gly Ser Arg His Leu Ala Gln Leu Met Glu Ser Ile
                165                 170                 175

Pro His Ser Pro Gly Pro Thr Arg Ile Gln Ala Ile Glu Leu Phe Met
                180                 185                 190

Leu Leu Asp Leu Leu Gly Ala Pro Asn Pro Thr Phe Tyr Ser His Phe
                195                 200                 205

Pro Arg Thr Val Arg Trp Phe His Arg Leu Arg Ser Ile Glu Lys Arg
                210                 215                 220

Leu His Arg Leu Asn Leu Gln Ser His Pro Gln Glu Val Met Tyr
225                 230                 235                 240

Phe Gln Pro Gly Glu Pro Phe Gly Ser Val Glu Asp Asp His Ile Pro
                245                 250                 255

Phe Leu Arg Arg Gly Val Pro Val Leu His Leu Ile Ser Thr Pro Phe
                260                 265                 270

Pro Ala Val Trp His Thr Pro Ala Asp Thr Glu Val Asn Leu His Pro
                275                 280                 285

Pro Thr Val His Asn Leu Ala Arg Ile Leu Ala Val Phe Leu Ala Glu
                290                 295                 300

Tyr Leu Gly Leu
305

<210> SEQ ID NO 8
<211> LENGTH: 303
<212> TYPE: PRT
<213> ORGANISM: Human

<400> SEQUENCE: 8

Ser Leu Pro Glu Ala Arg Leu Arg Arg Val Val Gly Gln Leu Asp Pro
 1                5                  10                  15

Gln Arg Leu Trp Ser Thr Tyr Leu Arg Pro Leu Leu Val Val Arg Thr
                 20                  25                  30

Pro Gly Ser Pro Gly Asn Leu Gln Val Arg Lys Phe Leu Glu Ala Thr
                 35                  40                  45

Leu Arg Ser Leu Thr Ala Gly Trp His Val Glu Leu Asp Pro Phe Thr
             50                  55                  60

Ala Ser Thr Pro Leu Gly Pro Val Asp Phe Gly Asn Val Val Ala Thr
 65                  70                  75                  80

Leu Asp Pro Arg Ala Ala Arg His Leu Thr Leu Ala Cys His Tyr Asp
                 85                  90                  95

Ser Lys Leu Phe Pro Ser Thr Pro Phe Val Gly Ala Thr Asp Ser Ala
                100                 105                 110

Val Pro Cys Ala Leu Leu Leu Glu Leu Ala Gln Ala Leu Asp Leu Glu
```

-continued

```
                115                 120                 125
Leu Ser Arg Ala Lys Lys Pro Val Thr Leu Gln Leu Leu Phe Leu Asp
    130                 135                 140
Gly Glu Glu Ala Leu Lys Glu Trp Gly Pro Lys Asp Ser Leu Tyr Gly
145                 150                 155                 160
Ser Arg His Leu Ala Gln Leu Met Glu Ser Ile Pro His Ser Pro Gly
                165                 170                 175
Pro Thr Arg Ile Gln Ala Ile Glu Leu Phe Met Leu Leu Asp Leu Leu
            180                 185                 190
Gly Ala Pro Asn Pro Thr Phe Tyr Ser His Phe Pro Arg Thr Val Arg
        195                 200                 205
Trp Phe His Arg Leu Arg Ser Ile Glu Lys Arg Leu His Arg Leu Asn
    210                 215                 220
Leu Leu Gln Ser His Pro Gln Glu Val Met Tyr Phe Gln Pro Gly Glu
225                 230                 235                 240
Pro Phe Gly Ser Val Glu Asp Asp His Ile Pro Phe Leu Arg Arg Gly
                245                 250                 255
Val Pro Val Leu His Leu Ile Ser Thr Pro Phe Pro Ala Val Trp His
            260                 265                 270
Thr Pro Ala Asp Thr Glu Val Asn Leu His Pro Pro Thr Val His Asn
        275                 280                 285
Leu Ala Arg Ile Leu Ala Val Phe Leu Ala Glu Tyr Leu Gly Leu
    290                 295                 300

<210> SEQ ID NO 9
<211> LENGTH: 302
<212> TYPE: PRT
<213> ORGANISM: Human

<400> SEQUENCE: 9

Leu Pro Glu Ala Arg Leu Arg Arg Val Val Gly Gln Leu Asp Pro Gln
1               5                   10                  15
Arg Leu Trp Ser Thr Tyr Leu Arg Pro Leu Leu Val Arg Thr Pro
            20                  25                  30
Gly Ser Pro Gly Asn Leu Gln Val Arg Lys Phe Leu Glu Ala Thr Leu
        35                  40                  45
Arg Ser Leu Thr Ala Gly Trp His Val Glu Leu Asp Pro Phe Thr Ala
    50                  55                  60
Ser Thr Pro Leu Gly Pro Val Asp Phe Gly Asn Val Val Ala Thr Leu
65                  70                  75                  80
Asp Pro Arg Ala Ala Arg His Leu Thr Leu Ala Cys His Tyr Asp Ser
                85                  90                  95
Lys Leu Phe Pro Pro Gly Ser Thr Pro Phe Val Gly Ala Thr Asp Ser
            100                 105                 110
Ala Val Pro Cys Ala Leu Leu Leu Glu Leu Ala Gln Ala Leu Asp Leu
        115                 120                 125
Glu Leu Ser Arg Ala Lys Val Thr Leu Gln Leu Leu Phe Leu Asp Gly
    130                 135                 140
Glu Glu Ala Leu Lys Glu Trp Gly Pro Lys Asp Ser Leu Tyr Gly Ser
145                 150                 155                 160
Arg His Leu Ala Gln Leu Met Glu Ser Ile Pro His Ser Pro Gly Pro
                165                 170                 175
Thr Arg Ile Gln Ala Ile Glu Leu Phe Met Leu Leu Asp Leu Leu Gly
            180                 185                 190
Ala Pro Asn Pro Thr Phe Tyr Ser His Phe Pro Arg Thr Val Arg Trp
```

```
            195                 200                 205
Phe His Arg Leu Arg Ser Ile Glu Lys Arg Leu His Arg Leu Asn Leu
    210                 215                 220

Leu Gln Ser His Pro Gln Glu Val Met Tyr Phe Gln Pro Gly Glu Pro
225                 230                 235                 240

Phe Gly Ser Val Glu Asp Asp His Ile Pro Phe Leu Arg Arg Gly Val
                245                 250                 255

Pro Val Leu His Leu Ile Ser Thr Pro Phe Pro Ala Val Trp His Thr
            260                 265                 270

Pro Ala Asp Thr Glu Val Asn Leu His Pro Pro Thr Val His Asn Leu
        275                 280                 285

Ala Arg Ile Leu Ala Val Phe Leu Ala Glu Tyr Leu Gly Leu
    290                 295                 300

<210> SEQ ID NO 10
<211> LENGTH: 300
<212> TYPE: PRT
<213> ORGANISM: Human

<400> SEQUENCE: 10

Ser Leu Pro Glu Ala Arg Leu Arg Arg Val Val Gly Gln Leu Asp Pro
1               5                   10                  15

Gln Arg Leu Trp Ser Thr Tyr Leu Arg Pro Leu Leu Val Val Arg Thr
            20                  25                  30

Pro Gly Ser Pro Gly Asn Leu Gln Val Arg Lys Phe Leu Glu Ala Thr
        35                  40                  45

Leu Arg Ser Leu Thr Ala Gly Trp His Val Glu Leu Asp Pro Phe Thr
    50                  55                  60

Ala Ser Thr Pro Leu Gly Pro Val Asp Phe Gly Asn Val Val Ala Thr
65                  70                  75                  80

Leu Asp Pro Arg Ala Ala Arg His Leu Thr Leu Ala Cys His Tyr Asp
                85                  90                  95

Ser Lys Leu Phe Ser Thr Pro Phe Val Gly Ala Thr Asp Ser Ala Val
            100                 105                 110

Pro Cys Ala Leu Leu Leu Glu Leu Ala Gln Ala Leu Asp Leu Glu Leu
        115                 120                 125

Ser Arg Ala Lys Val Thr Leu Gln Leu Leu Phe Leu Asp Gly Glu Glu
    130                 135                 140

Ala Leu Lys Glu Trp Gly Pro Lys Asp Ser Leu Tyr Gly Ser Arg His
145                 150                 155                 160

Leu Ala Gln Leu Met Glu Ser Ile Pro His Ser Pro Gly Pro Thr Arg
                165                 170                 175

Ile Gln Ala Ile Glu Leu Phe Met Leu Leu Asp Leu Leu Gly Ala Pro
            180                 185                 190

Asn Pro Thr Phe Tyr Ser His Phe Pro Arg Thr Val Arg Trp Phe His
        195                 200                 205

Arg Leu Arg Ser Ile Glu Lys Arg Leu His Arg Leu Asn Leu Leu Gln
    210                 215                 220

Ser His Pro Gln Glu Val Met Tyr Phe Gln Pro Gly Glu Pro Phe Gly
225                 230                 235                 240

Ser Val Glu Asp Asp His Ile Pro Phe Leu Arg Arg Gly Val Pro Val
                245                 250                 255

Leu His Leu Ile Ser Thr Pro Phe Pro Ala Val Trp His Thr Pro Ala
            260                 265                 270

Asp Thr Glu Val Asn Leu His Pro Pro Thr Val His Asn Leu Ala Arg
```

```
                275                 280                 285
Ile Leu Ala Val Phe Leu Ala Glu Tyr Leu Gly Leu
    290                 295                 300

<210> SEQ ID NO 11
<211> LENGTH: 302
<212> TYPE: PRT
<213> ORGANISM: Human

<400> SEQUENCE: 11

Leu Pro Glu Ala Arg Leu Arg Arg Val Val Gly Gln Leu Asp Pro Gln
1               5                   10                  15

Arg Leu Trp Ser Thr Tyr Leu Arg Pro Leu Leu Val Val Arg Thr Pro
            20                  25                  30

Gly Ser Pro Gly Asn Leu Gln Val Arg Lys Phe Leu Glu Ala Thr Leu
        35                  40                  45

Arg Ser Leu Thr Ala Gly Trp His Val Glu Leu Asp Pro Phe Thr Ala
    50                  55                  60

Ser Thr Pro Leu Gly Pro Val Asp Phe Gly Asn Val Val Ala Thr Leu
65                  70                  75                  80

Asp Pro Arg Ala Ala Arg His Leu Thr Leu Ala Cys His Tyr Asp Ser
                85                  90                  95

Lys Leu Phe Pro Pro Gly Ser Thr Pro Phe Val Gly Ala Thr Asp Ser
            100                 105                 110

Ala Val Pro Cys Ala Leu Leu Leu Glu Leu Ala Gln Ala Leu Asp Leu
        115                 120                 125

Glu Leu Ser Arg Ala Lys Val Thr Leu Gln Leu Phe Leu Asp Gly
    130                 135                 140

Glu Glu Ala Leu Lys Glu Trp Gly Pro Lys Asp Ser Leu Tyr Gly Ser
145                 150                 155                 160

Arg His Leu Ala Gln Leu Met Glu Ser Ile Pro His Ser Pro Gly Pro
                165                 170                 175

Thr Arg Ile Gln Ala Ile Glu Leu Phe Met Leu Leu Asp Leu Leu Gly
            180                 185                 190

Ala Pro Asn Pro Thr Phe Tyr Ser His Phe Pro Arg Thr Val Arg Trp
        195                 200                 205

Phe His Arg Leu Arg Ser Ile Glu Lys Arg Leu His Arg Leu Asn Leu
    210                 215                 220

Leu Gln Ser His Pro Gln Glu Val Met Tyr Phe Gln Pro Gly Glu Pro
225                 230                 235                 240

Phe Gly Ser Val Glu Asp Asp His Ile Pro Phe Leu Arg Arg Gly Val
                245                 250                 255

Pro Val Leu His Leu Ile Ser Thr Pro Phe Pro Ala Val Trp His Thr
            260                 265                 270

Pro Ala Asp Thr Glu Val Asn Leu His Pro Pro Thr Val His Asn Leu
        275                 280                 285

Ala Arg Ile Leu Ala Val Phe Leu Ala Glu Tyr Leu Gly Leu
    290                 295                 300

<210> SEQ ID NO 12
<211> LENGTH: 298
<212> TYPE: PRT
<213> ORGANISM: Human

<400> SEQUENCE: 12

Pro Glu Ala Arg Leu Arg Arg Val Val Gly Gln Leu Asp Pro Gln Arg
1               5                   10                  15
```

Leu Trp Ser Thr Tyr Leu Arg Pro Leu Leu Val Val Arg Thr Pro Gly
            20                  25                  30

Ser Pro Gly Asn Leu Gln Val Arg Lys Phe Leu Glu Ala Thr Leu Arg
        35                  40                  45

Ser Leu Thr Ala Gly Trp His Val Glu Leu Asp Pro Phe Thr Ala Ser
    50                  55                  60

Thr Pro Leu Gly Pro Val Asp Phe Gly Asn Val Val Ala Thr Leu Asp
65                  70                  75                  80

Pro Arg Ala Ala Arg His Leu Thr Leu Ala Cys His Tyr Asp Ser Lys
                85                  90                  95

Leu Phe Ser Thr Pro Phe Val Gly Ala Thr Asp Ser Ala Val Pro Cys
            100                 105                 110

Ala Leu Leu Leu Glu Leu Ala Gln Ala Leu Asp Leu Glu Leu Ser Arg
        115                 120                 125

Ala Lys Val Thr Leu Gln Leu Leu Phe Leu Asp Gly Glu Glu Ala Leu
    130                 135                 140

Lys Glu Trp Gly Pro Lys Asp Ser Leu Tyr Gly Ser Arg His Leu Ala
145                 150                 155                 160

Gln Leu Met Glu Ser Ile Pro His Ser Pro Gly Pro Thr Arg Ile Gln
                165                 170                 175

Ala Ile Glu Leu Phe Met Leu Leu Asp Leu Leu Gly Ala Pro Asn Pro
            180                 185                 190

Thr Phe Tyr Ser His Phe Pro Arg Thr Val Arg Trp Phe His Arg Leu
        195                 200                 205

Arg Ser Ile Glu Lys Arg Leu His Arg Leu Asn Leu Leu Gln Ser His
    210                 215                 220

Pro Gln Glu Val Met Tyr Phe Gln Pro Gly Pro Phe Gly Ser Val
225                 230                 235                 240

Glu Asp Asp His Ile Pro Phe Leu Arg Arg Gly Val Pro Val Leu His
                245                 250                 255

Leu Ile Ser Thr Pro Phe Pro Ala Val Trp His Thr Pro Ala Asp Thr
            260                 265                 270

Glu Val Asn Leu His Pro Pro Thr Val His Asn Leu Ala Arg Ile Leu
        275                 280                 285

Ala Val Phe Leu Ala Glu Tyr Leu Gly Leu
    290                 295

<210> SEQ ID NO 13
<211> LENGTH: 48
<212> TYPE: DNA
<213> ORGANISM: Artificial
<220> FEATURE:
<223> OTHER INFORMATION: Synthetic Primer

<400> SEQUENCE: 13
tatgaattcc atcaccatca ccatcacgag gagctgccgc tgggccgg                48

<210> SEQ ID NO 14
<211> LENGTH: 35
<212> TYPE: DNA
<213> ORGANISM: Artificial
<220> FEATURE:
<223> OTHER INFORMATION: Synthetic Primer

<400> SEQUENCE: 14
atatatgcgg ccgcctagag ccccaggtat tcagc                              35

<210> SEQ ID NO 15
<211> LENGTH: 33
<212> TYPE: DNA
<213> ORGANISM: Artificial
<220> FEATURE:
<223> OTHER INFORMATION: Synthetic Primer

<400> SEQUENCE: 15
ctgcgggtcc cattgaacgg aagcctcccc gaa                33

<210> SEQ ID NO 16
<211> LENGTH: 33
<212> TYPE: DNA
<213> ORGANISM: Artificial
<220> FEATURE:
<223> OTHER INFORMATION: Synthetic Primer

<400> SEQUENCE: 16
ttcggggagg cttccgttca atgggacccg cag                33

<210> SEQ ID NO 17
<211> LENGTH: 33
<212> TYPE: DNA
<213> ORGANISM: Artificial
<220> FEATURE:
<223> OTHER INFORMATION: Synthetic Primer

<400> SEQUENCE: 17
acggtacaca acttggcccg cattctcgct gtg                33

<210> SEQ ID NO 18
<211> LENGTH: 33
<212> TYPE: DNA
<213> ORGANISM: Artificial
<220> FEATURE:
<223> OTHER INFORMATION: Synthetic Primer

<400> SEQUENCE: 18
cacagcgaga atgcgggcca agttgtgtac cgt                33

<210> SEQ ID NO 19
<211> LENGTH: 331
<212> TYPE: PRT
<213> ORGANISM: Human

<400> SEQUENCE: 19

Glu Phe His His His His His His Glu Glu Leu Pro Leu Gly Arg Glu
1               5                   10                  15

Leu Arg Val Pro Leu Asn Gly Ser Leu Pro Glu Ala Arg Leu Arg Arg
            20                  25                  30

Val Val Gly Gln Leu Asp Pro Gln Arg Leu Trp Ser Thr Tyr Leu Arg
        35                  40                  45

Pro Leu Leu Val Val Arg Thr Pro Gly Ser Pro Gly Asn Leu Gln Val
    50                  55                  60

Arg Lys Phe Leu Glu Ala Thr Leu Arg Ser Leu Thr Ala Gly Trp His
65                  70                  75                  80

Val Glu Leu Asp Pro Phe Thr Ala Ser Thr Pro Leu Gly Pro Val Asp
                85                  90                  95

Phe Gly Asn Val Val Ala Thr Leu Asp Pro Arg Ala Ala Arg His Leu
            100                 105                 110

Thr Leu Ala Cys His Tyr Asp Ser Lys Leu Phe Pro Pro Gly Ser Thr
        115                 120                 125

Pro Phe Val Gly Ala Thr Asp Ser Ala Val Pro Cys Ala Leu Leu Leu

-continued

```
            130                 135                 140
Glu Leu Ala Gln Ala Leu Asp Leu Glu Leu Ser Arg Ala Lys Lys Gln
145                 150                 155                 160

Ala Ala Pro Val Thr Leu Gln Leu Leu Phe Leu Asp Gly Glu Glu Ala
                165                 170                 175

Leu Lys Glu Trp Gly Pro Lys Asp Ser Leu Tyr Gly Ser Arg His Leu
                180                 185                 190

Ala Gln Leu Met Glu Ser Ile Pro His Ser Pro Gly Pro Thr Arg Ile
                195                 200                 205

Gln Ala Ile Glu Leu Phe Met Leu Leu Asp Leu Leu Gly Ala Pro Asn
    210                 215                 220

Pro Thr Phe Tyr Ser His Phe Pro Arg Thr Val Arg Trp Phe His Arg
225                 230                 235                 240

Leu Arg Ser Ile Glu Lys Arg Leu His Arg Leu Asn Leu Leu Gln Ser
                245                 250                 255

His Pro Gln Glu Val Met Tyr Phe Gln Pro Gly Glu Pro Phe Gly Ser
                260                 265                 270

Val Glu Asp Asp His Ile Pro Phe Leu Arg Arg Gly Val Pro Val Leu
                275                 280                 285

His Leu Ile Ser Thr Pro Phe Pro Ala Val Trp His Thr Pro Ala Asp
    290                 295                 300

Thr Glu Val Asn Leu His Pro Pro Thr Val His Asn Leu Ala Arg Ile
305                 310                 315                 320

Leu Ala Val Phe Leu Ala Glu Tyr Leu Gly Leu
                325                 330
```

CRYSTAL STRUCTURE OF ISOGLUTAMINYL CYCLASE

CROSS REFERENCE TO RELATED APPLICATIONS

This application is a Nonprovisional of U.S. Provisional Application No. 61/409,200, filed Nov. 2, 2010. U.S. Provisional Application No. 61/409,200 is incorporated herein by reference in its entirety for all purposes.

MATERIAL INCORPORATED BY REFERENCE

The Sequence Listing, which is a part of the present disclosure, includes a computer readable form comprising sequences of the present invention. The subject matter of the Sequence Listing is incorporated herein by reference in its entirety.

FIELD OF THE INVENTION

The invention relates to the novel crystal structure of isoglutaminyl cyclase (isoQC). QC catalyzes the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

BACKGROUND OF THE INVENTION

Glutaminyl cyclase (QC, EC 2.3.2.5; Qpct; glutaminyl peptide cyclotransferase) catalyzes the intramolecular cyclization of N-terminal glutamine residues into pyroglutamic acid (5-oxo-proline, pGlu*) under liberation of ammonia and the intramolecular cyclization of N-terminal glutamate residues into pyroglutamic acid under liberation of water.

A QC was first isolated by Messer from the Latex of the tropical plant *Carica papaya* in 1963 (Messer, M. 1963 Nature 4874, 1299). 24 years later, a corresponding enzymatic activity was discovered in animal pituitary (Busby, W. H. J. et al. 1987 J Biol Chem 262, 8532-8536; Fischer, W. H. and Spiess, J. 1987 Proc Natl Acad Sci USA 84, 3628-3632). For the mammalian QC, the conversion of Gln into pGlu by QC could be shown for the precursors of TRH and GnRH (Busby, W. H. J. et al. 1987 J Biol Chem 262, 8532-8536; Fischer, W. H. and Spiess, J. 1987 Proc Natl Acad Sci USA 84, 3628-3632). In addition, initial localization experiments of QC revealed a co-localization with its putative products of catalysis in bovine pituitary, further improving the suggested function in peptide hormone synthesis (Bockers, T. M. et al. 1995 J Neuroendocrinol 7, 445-453). In contrast, the physiological function of the plant QC is less clear. In the case of the enzyme from *C. papaya*, a role in the plant defense against pathogenic microorganisms was suggested (El Moussaoui, A. et al. 2001 Cell Mol Life Sci 58, 556-570). Putative QCs from other plants were identified by sequence comparisons recently (Dahl, S. W. et al. 2000 Protein Expr Purif 20, 27-36). The physiological function of these enzymes, however, is still ambiguous.

The QCs known from plants and animals show a strict specificity for L-glutamine in the N-terminal position of the substrates and their kinetic behavior was found to obey the Michaelis-Menten equation (Pohl, T. et al. 1991 Proc Natl Acad Sci USA 88, 10059-10063; Consalvo, A. P. et al. 1988 Anal Biochem 175, 131-138; Gololobov, M. Y. et al. 1996 Biol Chem Hoppe Seyler 377, 395-398). A comparison of the primary structures of the QCs from *C. papaya* and that of the highly conserved QC from mammals, however, did not reveal any sequence homology (Dahl, S. W. et al. 2000 Protein Expr Purif 20, 27-36). Whereas the plant QCs appear to belong to a new enzyme family (Dahl, S. W. et al. 2000 Protein Expr Purif 20, 27-36), the mammalian QCs were found to have a pronounced sequence homology to bacterial aminopeptidases (Bateman, R. C. et al. 2001 Biochemistry 40, 11246-11250), leading to the conclusion that the QCs from plants and animals have different evolutionary origins.

Recently, it was shown that recombinant human QC as well as QC-activity from brain extracts catalyze both, the N-terminal glutaminyl as well as glutamate cyclization. Most striking is the finding, that cyclase-catalyzed $Glu_1$-conversion is favored around pH 6.0 while $Gln_1$-conversion to pGlu-derivatives occurs with a pH-optimum of around 8.0. Since the formation of pGlu-Aβ-related peptides can be suppressed by inhibition of recombinant human QC and QC-activity from pig pituitary extracts, the enzyme QC is a target in drug development for treatment of Alzheimer's disease.

Isoenzymes of QC (i.e. isoglutaminyl peptide cyclotransferase; isoQC; QPCTL) have been described in WO 2008/034891, WO 2008/087197 and WO 2010/026209 (each in the name of Probiodrug AG).

U.S. Pat. No. 7,572,614 (Wang et al) and Huang et al (2005) PNAS 102(37), 13117-13122 both describe one example of the crystal structure of soluble glutaminyl cyclase. The crystal structure disclosed in Wang et al and Huang et al was generated using a protein expressed in *E. coli*, which results in a lack of glycosylation. It is well known that all mammalian QC contain at least one glycosylation site (Pohl, T. et al. (1991) Proc Natl Acad Sci USA 88, 10059-10063; Song, I. et al. (1994) J Mol Endocrinol 13, 77-86), which is glycosylated in the isoQC crystallized according to the invention by virtue of being expressed in eukaryotic hosts, which can be observed in the crystal structures presented herein. In addition, all mammalian QCs contain two conserved cysteine residues close to the active site, which form a disulfide bond. In the crystal structure of Wang et al and Huang et al, the disulfide bond is lacking. The expression of mammalian secretory proteins in bacteria frequently results in the absence of disulfide formation (Hannig, G. and Makrides, S. C. (1998) Trends Biotechnol 16, 54-60). The disulfide bond is clearly present in the human isoQC crystal structure presented herein. Notably, mutational analyses conducted by the inventors with human QC have suggested an important stabilizing function of the disulfide bond upon the overall structure. Furthermore, in the structure of Wang et al and Huang et al, a segment of residues (L205-H206-W207) close to the active site appears in two different conformations. Due to the orientations, the binding mode of substrates is affected and reliable mechanistic conclusions could not be drawn (Huang et al., 2005).

BRIEF SUMMARY OF THE INVENTION

The expression of human isoQC in an eukaryotic host, as described in the present disclosure, allows the crystallization and structural refinement of a native mammalian isoQC and, importantly, unambiguous determination of the binding modes of inhibitors.

According to a first aspect of the invention there is provided a crystal comprising human isoglutaminyl cyclase having a characterised space group of P1211 and unit cell dimensions of +/−5% of a=126.51 Å, b=109.68 Å, c=159.53 Å, α=90.0°, β=104.9° and γ=90.0°.

According to a second aspect of the invention there is provided a method of preparing the crystal of human isoglutaminyl cyclase as described herein, which comprises the steps of:
(a) providing a solution of human isoglutaminyl cyclase, optionally in the presence of a known isoglutaminyl cyclase inhibitor, in a suitable buffer such as 25 mM Bis-Tris pH6.8/100 mM NaCl buffer;
(b) mixing the solution with a crystallization solution comprising 0.1 M sodium citrate, 0.1 M ammonium sulfate and 13% (w/v) 35000 PEG; and
(c) incubating the mixture under conditions to promote hanging drop vapor diffusion for a time sufficient to produce the crystal of human isoglutaminyl cyclase.

According to a third aspect there is provided a crystal comprising human isoglutaminyl cyclase obtainable by the crystallisation method as defined herein.

According to a fourth aspect of the invention there is provided a method of identifying an inhibitor of human isoglutaminyl cyclase which comprises the following steps:
(a) generating a 3-dimensional model of human isoglutaminyl cyclase using the structural coordinates described in FIG. 1;
(b) analysing the binding pocket provided by residues E226, D186 and H351 of SEQ ID NO: 1 according to the coordinates of FIG. 1;
(c) performing computer modeling analysis to identify an inhibitor compound which may associate with the binding pocket of human isoglutaminyl cyclase.

Other objects and features will be in part apparent and in part pointed out hereinafter.

BRIEF DESCRIPTION OF THE FIGURES

Those of skill in the art will understand that the drawings, described below, are for illustrative purposes only. The drawings are not intended to limit the scope of the present teachings in any way.

FIG. 1 describes the X-ray coordinates of human isoQC crystallized with 1 mM Inhibitor A. The crystal structure contains 11 molecules in the AU (designated chain A to chain K). The sequences of these different chains are as follows:
chain A (SEQ ID NO: 2): A74-A383
chain B (SEQ ID NO: 3): G74-L382
chain C (SEQ ID NO: 4): G74-L382
chain D (SEQ ID NO: 5): A75-L382
chain E (SEQ ID NO: 6): A73-L382
chain F (SEQ ID NO: 7): A75-L382
chain G (SEQ ID NO: 8): A75-L382
chain H (SEQ ID NO: 9): L76-L382
chain I (SEQ ID NO: 10): A75-L382
chain J (SEQ ID NO: 11): L76-L382
chain K (SEQ ID NO: 12): P77-L382

FIG. 2 shows the sequence alignment of chains A-K (SEQ ID NOS: 2-12) in comparison with the expressed human isoQC as described herein (SEQ ID NO: 19).

FIG. 6 describes a cartoon representation of the obtained three dimensional structure of the human isoQC of (chain A) described by the coordinates shown in FIG. 1. The structure is shown in two orthogonal views. The structure clearly comprises β-sheet structures, α-helices and random coiled loops.

DETAILED DESCRIPTION OF THE INVENTION

Figure 3:
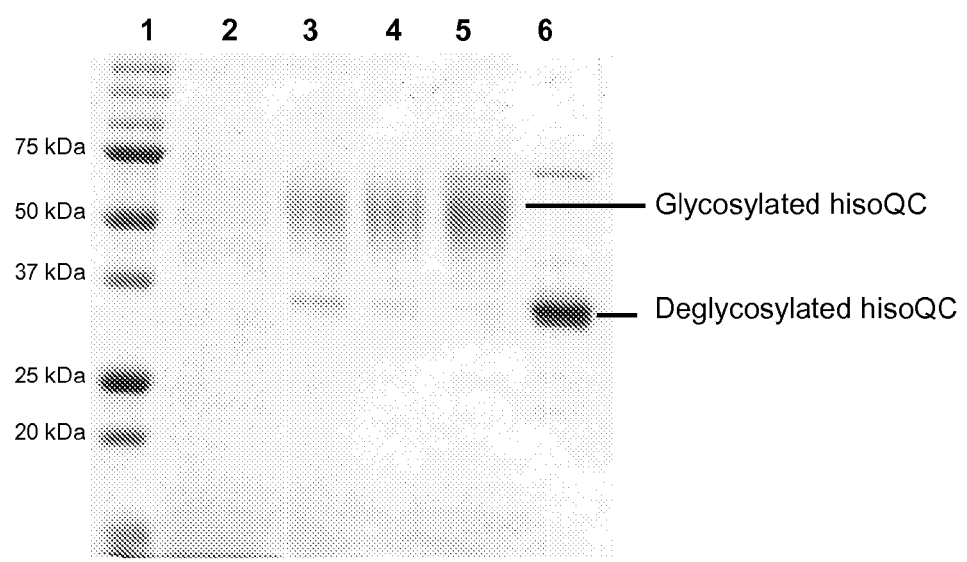
FIG. 3 shows the purification of human isoQC (SEQ ID NO: 19), based on construct YSShisoQCE42I55NC351A N-His, from the medium of a transgenic *P. pastoris* strain. The isoQC (SEQ ID NO: 19) was purified by a combination of IMAC (immobilized metal affinity chromatography, lane 3), HIC (hydrophobic interaction chromatography, lane 4) and desalting (lane 5). The glycosylation of the enzyme was evidenced by enzymatic deglycosalytion, which resulted in a shift in migration of the protein (lane 6). Lane 1, protein standard: Lane 2, medium prior to purification.

The present invention relates to crystals of human isoglutaminyl cyclase, where the crystals are of sufficient quality and size to allow for the determination of the three-dimensional X-ray diffraction structure of isoglutaminyl cyclase to a resolution of about 3.4 angstrom in a P1211 space group. The invention also relates to methods for preparing and crystallizing human isoglutaminyl cyclase. The crystal structure of human isoglutaminyl cyclase, as well as information derived from the crystal structure, can be used to analyze and modify isoglutaminyl cyclase as well as to identify compounds that interact with isoglutaminyl cyclase.

According to a first aspect of the invention there is provided a crystal comprising human isoglutaminyl cyclase having a characterised space group of P1211 and unit cell dimensions of +/−5% of a=126.51 Å, b=109.68 Å, c=159.53 Å, α=90.0°, β=104.9° and γ=90.0°.

In one embodiment of the first aspect of the invention, the crystal has unit cell dimensions of a=126.51 Å, b=109.68 Å and c=159.53 Å.

In one embodiment of the first aspect of the invention, the crystal has unit cell dimensions of α=90.0°, β=104.9° and γ=90.0°.

In one embodiment of the first aspect of the invention, the crystal diffracts x-rays for determination of atomic co-ordinates of the crystal to a resolution of between 3.42 Å and 34.72 Å.

In one embodiment of the first aspect of the invention, the crystal has unit cell dimensions of a=126.51 Å, b=109.68 Å and c=159.53 Å, α=90.0°, β=104.9° and γ=90.0°. This embodiment of the first aspect of the invention relates to the crystal structure of human isoglutaminyl cyclase complexed with an glutaminyl cyclase inhibitor referred to herein as Inhibitor A which has the structure as follows:

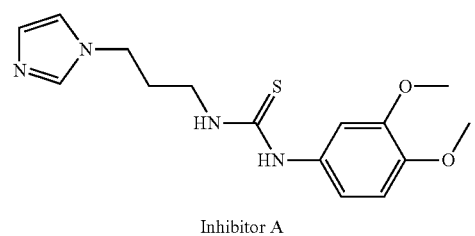 [SMILES: COc1ccc(NC(=S)NCCCn2ccnc2)cc1OC]

Inhibitor A

Inhibitor A inhibits both human and mouse QC in vitro and moreover, Inhibitor A is soluble in water and therefore useful for crystallization.

It will be appreciated that the crystals within the scope of the invention include both apo crystals and co-crystals. The apo crystals generally comprise substantially pure isoglutaminyl cyclase. The co-crystals generally comprise substantially pure isoglutaminyl cyclase with a binding ligand, such as an isoglutaminyl cyclase inhibitor, bound to isoglutaminyl cyclase. Thus, according to a further aspect of the invention there is provided a co-crystal comprising the crystal as defined herein bound to a binding ligand, such as an isoglutaminyl cyclase inhibitor.

In one embodiment of the first aspect of the invention, the human isoglutaminyl cyclase consists of amino acid residues I73 to L382 of the native human isoQC sequence of SEQ ID NO:1. In an alternative embodiment, the human isoglutaminyl cyclase consists of amino acid residues A74 to A383 of SEQ ID NO: 2. In an alternative embodiment, the human isoglutaminyl cyclase consists of amino acid residues G74 to L382 (SEQ ID NO: 3). In an alternative embodiment, the human isoglutaminyl cyclase consists of amino acid residues G74 to L382 (SEQ ID NO: 4). In an alternative embodiment, the human isoglutaminyl cyclase consists of amino acid A75 to L382 (SEQ ID NO: 5). In an alternative embodiment, the human isoglutaminyl cyclase consists of amino acid residues A73 to L382 (SEQ ID NO: 6). In an alternative embodiment, the human isoglutaminyl cyclase consists of amino acid residues A75 to L382 (SEQ ID NO: 7). In an alternative embodiment, the human isoglutaminyl cyclase consists of amino acid residues A75 to L382 (SEQ ID NO: 8). In an alternative embodiment, the human isoglutaminyl cyclase consists of amino acid residues L76 to L382 (SEQ ID NO: 9). In an alternative embodiment, the human isoglutaminyl cyclase consists of amino acid residues A75 to L382 (SEQ ID NO: 10). In an alternative embodiment, the human isoglutaminyl cyclase consists of amino acid residues L76 to L382 (SEQ ID NO: 11). In an alternative embodiment, the human isoglutaminyl cyclase consists of amino acid residues P77 to L382 (SEQ ID NO: 12).

It will be appreciated that the crystals comprising isoglutaminyl cyclase are not limited to those obtainable from naturally occurring or native isoglutaminyl cyclase. The crystals include mutants that have one or more amino acid insertions, deletions, or substitutions in native isoglutaminyl cyclase. Therefore, mutants of native isoglutaminyl cyclase are obtained by replacing at least one (such as up to 10, e.g. up to 25) amino acid residue in a native isoglutaminyl cyclase with a different amino acid residue, or by adding or deleting amino acid residues within the native protein or at the N- or C-terminus of the native protein, and have substantially the same three-dimensional structure as native isoglutaminyl cyclase from which the mutant is derived.

By having substantially the same three-dimensional structure is meant as having a set of atomic structure coordinates from an apo- or co-crystal that have a root mean square deviation of less than or equal to about 2 Å when superimposed with the atomic structure coordinates of native isoglutaminyl cyclase from which the mutant is derived when at least about 50% to about 100% of the alpha carbon atoms of native isoglutaminyl cyclase are included in the superposition.

In some instances, it may be particularly advantageous or convenient to substitute, delete, and/or add amino acid residues to native isoglutaminyl cyclase in order to provide convenient cloning sites in the cDNA encoding the protein, to aid in protein purification, and the like. Such substitutions, deletions, and/or additions, which do not substantially alter the three dimensional structure of native isoglutaminyl cyclase will be apparent to those skilled in the art.

It should be noted that the mutant polypeptides contemplated herein need not exhibit isoglutaminyl cyclase activity. Indeed, amino acid substitutions, additions, or deletions that interfere with the activity of isoglutaminyl cyclase but which do not significantly alter the three-dimensional structure of isoglutaminyl cyclase are also included. Such polypeptide crystals, or the atomic structure coordinates obtained therefrom, can be used to identify compounds that bind to native isoglutaminyl cyclase and which may affect the activity of the native isoglutaminyl cyclase.

The derivative crystals of the invention generally comprise isoglutaminyl cyclase crystals in non-covalent/covalent association with one or more metal atoms. The polypeptide may correspond to native or mutated isoglutaminyl cyclase. One such example of a suitable metal atom is zinc.

The co-crystals of isoglutaminyl cyclase generally comprise crystals comprising isoglutaminyl cyclase in association with one or more compounds bound to isoglutaminyl cyclase. The association may be covalent or non-covalent. In one embodiment, the compounds bound to isoglutaminyl cyclase comprise isoglutaminyl cyclase inhibitors. Examples of such isoglutaminyl cyclase inhibitors include those described in WO 2008/034891, WO 2008/087197 and WO 2010/026209.

The native and mutated isoglutaminyl cyclase described herein may be isolated from natural sources or produced by methods well known to those skilled in the art of molecular biology. Detailed experimental for the preparation of human isoglutaminyl cyclase is described in Example 1 herein.

The apo, derivative and co-crystals of isoglutaminyl cyclase can be obtained by techniques well-known in the art of protein crystallography, including batch, liquid bridge, dialysis, vapor diffusion, such as hanging drop vapor diffusion, and the like (See for example, McPherson, 1982, Preparation and Analysis of Protein Crystals, John Wiley, NY; McPherson, 1990, Eur. J. Biochem. 189:1-23; Webber, 1991, Adv. Protein Chem. 41:1-36; Crystallization of Nucleic Acids and Proteins, Edited by Ducruix and Giege, Oxford University Press; Protein Crystallization Techniques, Strategies, and Tips, Edited by Bergfors, International University Line, 1999).

In one embodiment, isoglutaminyl cyclase crystals, apo or co-crystals are grown by vapor diffusion, such as hanging drop vapor diffusion.

According to a second aspect of the invention there is provided a method of preparing the crystal of human isoglutaminyl cyclase as described herein, which comprises the steps of:
(a) providing a solution of human isoglutaminyl cyclase, optionally in the presence of a known isoglutaminyl cyclase inhibitor, in a suitable buffer such as 25 mM Bis-Tris pH6.8/100 mM NaCl buffer;
(b) mixing the solution with a crystallization solution comprising 0.1 M sodium citrate, 0.1 M ammonium sulfate and 13% (w/v) 35000 PEG; and
(c) incubating the mixture under conditions to promote hanging drop vapor diffusion for a time sufficient to produce the crystal of human isoglutaminyl cyclase.

According to a further aspect of the invention, there is provided a method of preparing the co-crystal of human isoglutaminyl cyclase bound to a binding ligand, such as a isoglutaminyl cyclase inhibitor, which comprises the steps of:
(a) providing a solution of human isoglutaminyl cyclase in the presence of a binding ligand, such as a isoglutaminyl cyclase inhibitor, in a suitable buffer such as 25 mM Bis-Tris pH6.8/100 mM NaCl buffer;

(b) mixing the solution with a crystallization solution comprising 0.1 M sodium citrate, 0.1 M ammonium sulfate and 13% (w/v) 35000 PEG; and (c) incubating the mixture under conditions to promote hanging drop vapor diffusion for a time sufficient to produce the co-crystal of human isoglutaminyl cyclase bound to a binding ligand, such as a isoglutaminyl cyclase inhibitor.

According to a further aspect there is provided a crystal or co-crystal comprising human isoglutaminyl cyclase obtainable by the crystallisation method as defined herein.

Figure 4:
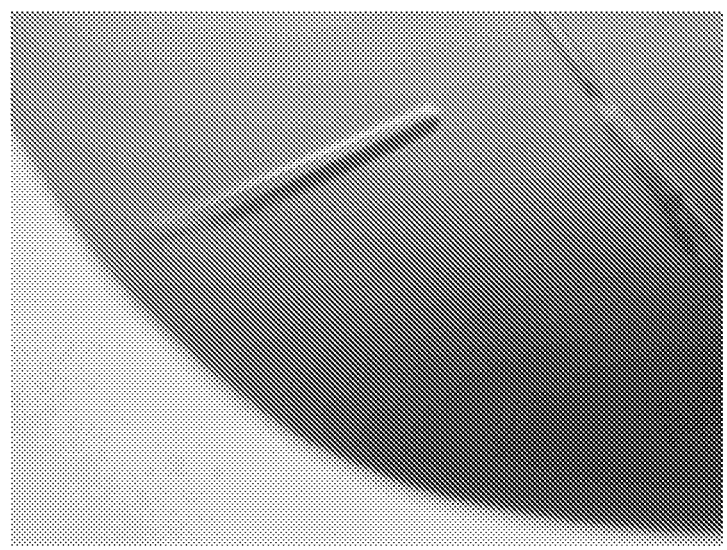
FIG. 4 shows crystals of human isoglutaminyl cyclase grown in buffer consisting of 0.1M sodium citrate 0.1M ammonium sulfate pH 6.5 and 13% (w/v) 35 k PEG.

Crystallization of human isoglutaminyl cyclase to produce co-crystals can be carried out as described below and in Example 1. As described, purified human isoglutaminyl cyclase is concentrated to 10 mg/mL in the presence of a suitable buffer, such as 25 mM Bis-Tris pH6.8/100 mM NaCl buffer and 1 mM of Inhibitor A. Macroscopic rod crystal forms are grown by hanging drop vapor diffusion at 21° C. by mixing an equal volume of protein solution with a crystallization solution comprising 0.1 M sodium citrate, 0.1 M ammonium sulfate and 13% (w/v) 35000 PEG. Crystals typically appeared 10-15 days after the experiment was initiated and examples of such crystals obtained following this protocol are shown in FIG. 4. It will be appreciated that to produce apo-crystals, the ligand is omitted in the above protocol.

In one embodiment, human isoglutaminyl cyclase is deglycosylated prior to crystallisation. Glycosylation is known to result in a significant loss in solubility. As described herein, the best results for deglycosylation were obtained using endoglycosidase $H_f$.

In one embodiment, a solubility enhancing moiety is added prior to crystallisation of human isoglutaminyl cyclase. As described herein, the best results for enhanced solubility were obtained using an acyl-N-glucamid based non-ionic detergent MEGA-8.

The human isoglutaminyl cyclase crystals may be frozen prior to data collection. The crystals can be cryo-protected with for example, either (a) 20-30% saturated glucose present in the crystallization setup, (b) ethanol added to 15-20%, (c) ethylene glycol added to 10-20% and PEG10,000 brought up to 25%, or (d) glycerol added to 15%. In one embodiment of the third aspect of the invention, the crystals are cryo-protected with the addition of glycerol added to 15% (v/v). The crystals can be either briefly immersed in the cryo-protectant or soaked in the cryo-protectant for periods as long as a day. Freezing can be accomplished by immersing the crystal in a bath of liquid nitrogen or by placing the crystal in a stream of nitrogen gas at −180° C.

As described in Example 1, the crystal structure of human isoglutaminyl cyclase in complex with Inhibitor A was obtained. A summary of the crystal's attributes for human isoglutaminyl cyclase bound to Inhibitor A are listed in Table 2 and the three dimensional structure coordinates for space groups P1211 for human isoglutaminyl cyclase bound to Inhibitor A are shown in FIG. 1.

References herein to "coordinates" include references to Cartesian coordinates derived from the mathematical equations related to the patterns obtained on diffraction of a monochromatic beam of X-ray by the atoms of a protein or protein complex in crystal form. The diffraction data are used to calculate an electron density map of the repeating units of the crystal, The electron density maps are then used to establish the positions of the individual atoms of the molecule or molecular complex.

Figure 5:
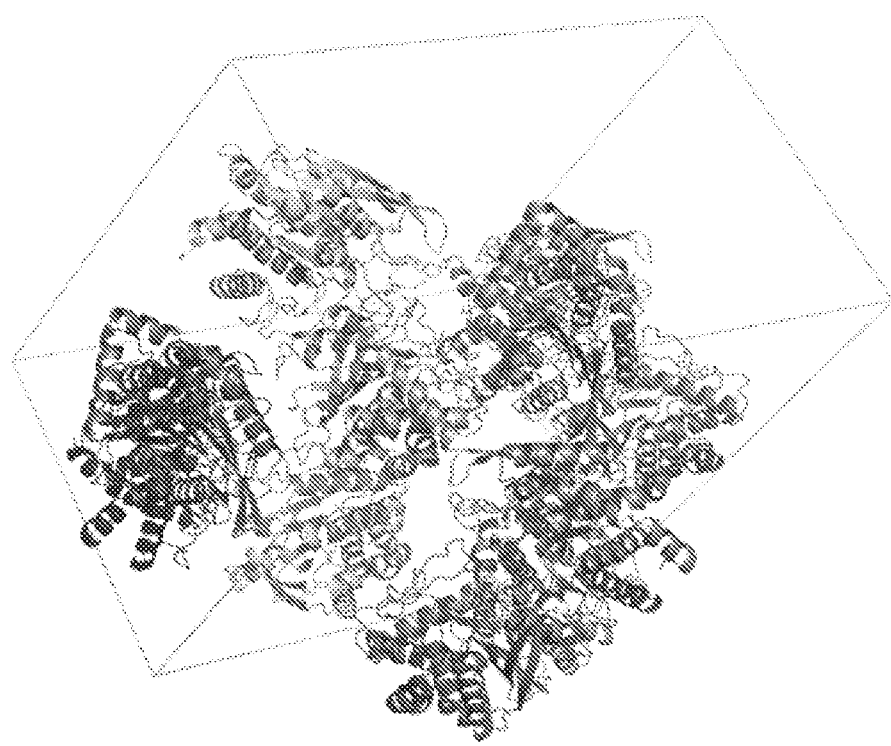
FIG. 5 describes a representation of the arrangement of the eleven human isoglutaminyl cyclase molecules contained in the AU with the unit cell as background shown with axes.

Ribbon and overlay diagrams of human isoglutaminyl cyclase bound to Inhibitor A based upon the coordinates for space groups P1211 are shown in FIG. 5. In particular, it was found that the protein comprised a globular α/β hydrolase fold. A central β-sheet was formed with six β-strands all in parallel fashion but not the second. This β-sheet was observed to be surrounded by α-helices in a sandwich manner with two helices in one side and six more α-helices in the opposite face. The protein's structure was completed with a rather large amount of random coiled loops which are believed to build the active site of the enzyme.

References herein to "active site" include references to a specific region (or atom) in a molecular entity that is capable of entering into a stabilising interaction with another molecular entity. In certain embodiments, the term also refers to the reactive parts of a macromolecule that directly participate in its specific combination with another molecule. In an alternative embodiment, a binding site may be comprised or defined by the three dimensional arrangement of one or more amino acid residues within a folded polypeptide. References to "binding pocket" shall be interpreted in an analogous manner to "active site" and it will be appreciated that these terms may be used interchangeably.

This active site of human isoglutaminyl cyclase was found to accommodate a zinc ion which is coordinated by three protein residues, E226, D186 and H351. Thus, in one embodiment of the first aspect of the invention, the crystal comprises a binding pocket provided by residues E226, D186 and H351 of SEQ ID NO: 1 according to the coordinates of FIG. 1.

Moreover, the protein shows the presence of a disulfide bridge between residues $C^{167}$ and $C^{191}$. Thus, in one embodiment of the first aspect of the invention, the crystal comprises a disulfide bridge between residues C167 and C191 of SEQ ID NO: 1. The presence of such a disulfide bridge has not previously been reported during crystallisation studies with QC (Wang et al, Huang et al).

Finally two segments of the polypeptide chain are not visible in the electron density. The gaps include residues between $K^{182}$ and $D^{190}$ and between $F^{146}$ and $N^{150}$.

The present invention is also directed to machine-readable data storage media having data storage material encoded with machine-readable data that comprises structure coordinates for isoglutaminyl cyclase. The present invention is also directed to a machine readable data storage media having data storage material encoded with machine readable data, which, when read by an appropriate machine, can display a three dimensional representation of a structure of isoglutaminyl cyclase.

All or a portion of isoglutaminyl cyclase coordinate data shown in FIG. 1, when used in conjunction with a computer programmed with software to translate those coordinates into the three-dimensional structure of isoglutaminyl cyclase may be used for a variety of purposes, especially for purposes relating to drug discovery. Software for generating three-dimensional graphical representations are known and commercially available. The ready use of the coordinate data requires that it be stored in a computer-readable format. Thus, in accordance with the present invention, data capable of being displayed as the three-dimensional structure of isoglutaminyl cyclase and/or portions thereof and/or their structurally similar variants may be stored in a machine-readable storage medium, which is capable of displaying a graphical three-dimensional representation of the structure.

Another embodiment of this invention provides a machine-readable data storage medium, comprising a data storage material encoded with machine readable data which, when used by a machine programmed with instructions for using said data, displays a graphical three-dimensional representation comprising isoglutaminyl cyclase or variant thereof.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

The three-dimensional crystal structure of the present invention may be used to identify isoglutaminyl cyclase binding sites, be used as a molecular replacement model to solve the structure of unknown crystallized proteins, to design mutants having desirable binding properties, and ultimately, to design, characterize, identify entities capable of binding and inhibiting isoglutaminyl cyclase and other structurally similar proteins as well as other uses that would be recognized by one of ordinary skill in the art. Such entities may be chemical entities or proteins. The term "chemical entity", as used herein, refers to chemical compounds, complexes of at least two chemical compounds, and fragments of such compounds.

The isoglutaminyl cyclase structural coordinates provided herein are useful for screening and identifying drugs that inhibit isoglutaminyl cyclase and other structurally similar proteins. For example, the structure encoded by the data may be computationally evaluated for its ability to associate with putative substrates or ligands. Such compounds that associate with isoglutaminyl cyclase may inhibit isoglutaminyl cyclase activity, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to a fourth aspect of the invention there is provided a method of identifying an inhibitor of human isoglutaminyl cyclase which comprises the following steps:
 (a) generating a 3-dimensional model of human isoglutaminyl cyclase using the structural coordinates described in FIG. 1;
 (b) analysing the binding pocket provided by residues E226, D186 and H351 of SEQ ID NO: 1 according to the coordinates of FIG. 1;
 (c) performing computer modeling analysis to identify an inhibitor compound which may associate with the binding pocket of human isoglutaminyl cyclase.

A method is also provided for evaluating the potential of an entity to associate with isoglutaminyl cyclase or variant thereof by using all or a portion of the structure coordinates provided in FIG. 1 or functional equivalents thereof. A method is also provided for evaluating the potential of an entity to associate with isoglutaminyl cyclase or variant thereof by using structure coordinates similar to all or a portion of the structure coordinates provided in FIG. 1 or functional equivalents thereof.

In one embodiment of the fourth aspect of the invention, the method additionally comprises the step of synthesizing the inhibitor compound and contacting the compound with the binding pocket of isoglutaminyl cyclase to determine the ability of the compound to inhibit isoglutaminyl cyclase.

In one embodiment of the fourth aspect of the invention, the step of performing computer modeling analysis to identify said inhibitor compound comprises identifying said compound from a library of compounds.

In one embodiment of the fourth aspect of the invention, the step of performing computer modeling analysis to identify said inhibitor compound comprises identifying said compound in a database.

In one embodiment of the fourth aspect of the invention, the step of performing computer modeling analysis to identify said inhibitor compound comprises designing the compound from a known isoglutaminyl cyclase inhibitor.

With the structures provided herein, the present invention permits the use of molecular design techniques to identify, select or design potential inhibitors of isoglutaminyl cyclase based on the structure of isoglutaminyl cyclase. Such a predictive model is valuable in light of the high costs associated with the preparation and testing of the many diverse compounds that may possibly bind to isoglutaminyl cyclase.

According to the invention, a potential isoglutaminyl cyclase inhibitor may be evaluated for its ability to bind isoglutaminyl cyclase prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of isoglutaminyl cyclase may be computationally evaluated using a series of steps in which chemical entities or fragments are screened and selected for their ability to associate with isoglutaminyl cyclase.

One skilled in the art may use one of several methods to screen entities (whether chemical or protein) for their ability to associate with isoglutaminyl cyclase. This process may begin by visual inspection of, for example, isoglutaminyl cyclase on a computer screen based on the isoglutaminyl cyclase structure coordinates in FIG. 1 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (Goodford, "A Computational Procedure for Determining Energetically Favorable Binding Sites on Biologically Important Macromolecules", J. Med. Chem., 28, pp. 849-857 (1985)). GRID is available from Oxford University, Oxford, UK; MCSS (Miranker et al., "Functionality. Maps of Binding Sites: A Multiple Copy Simultaneous Search Method." Proteins: Structure, Function and Genetics, 11, pp. 29-34 (1991)). MCSS is available from Molecular Simulations, San Diego, Calif.; AUTODOCK (Goodsell et al., "Automated Docking of Substrates to Proteins by Simulated Annealing", Proteins: Structure, Function, and Genetics, 8, pp. 195-202 (1990)). AUTODOCK is available from Scripps Research Institute, La Jolla, Calif.; & DOCK (Kuntz et al., "A Geometric Approach to Macromolecule-Ligand Interactions", J. Mol. Biol., 161, pp. 269-288 (1982)). DOCK is available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of isoglutaminyl cyclase. This may then be followed by manual model building using software such as MOE, QUANTA or Sybyl (Tripos Associates, St. Louis, Mo.).

Useful programs to aid one of skill in the art in connecting the individual chemical entities or fragments include: CAVEAT (Bartlett et al., "CAVEAT: A Program to Facilitate the Structure-Derived Design of Biologically Active Molecules", in "Molecular Recognition in Chemical and Biological Problems", Special Pub., Royal Chem. Soc., 78, pp. 182-196 (1989); Lauri and Bartlett, "CAVEAT: a Program to Facilitate the Design of Organic Molecules", J. Comput. Aided Mol. Des., 8, pp. 51-66 (1994)). CAVEAT is available from the University of California, Berkeley, Calif.; 3D Database systems such as ISIS (MDL Information Systems, San Leandro, Calif.). This area is reviewed in Martin, "3D. Database Searching in Drug Design", J. Med. Chem., 35, pp. 2.145-2154 (1992); HOOK (Eisen et al., "HOOK: A Program for Finding Novel Molecular Architectures that Satisfy the Chemical and Steric Requirements of a Macromolecule Binding Site", Proteins: Struct., Funct., Genet., 19, pp. 199-221 (1994). HOOK is available from Molecular Simulations, San Diego, Calif.

Instead of proceeding to build an inhibitor of isoglutaminyl cyclase in a step-wise fashion one fragment or entity at a time as described above, inhibitory or other isoglutaminyl cyclase binding compounds may be designed as a whole or "de novo" using either an empty binding site or optionally including some portion(s) of a known inhibitor(s). There are many de novo ligand design methods including: LUDI (Bohm, "The Computer Program LUDI: A New Method for the De Novo Design of Enzyme Inhibitors", J. Comp. Aid. Molec. Design, 6, pp. 61-78 (1992)). LUDI is available from Molecular Simulations Incorporated, San Diego, Calif.; LEGEND (Nishibata et al., Tetrahedron, 47, p. 8985 (1991)). LEGEND is available from Molecular Simulations Incorporated, San Diego, Calif.; LEAPFROG (available from Tripos Associates, St. Louis, Mo.); & SPROUT (Gillet et al., "SPROUT: A Program for Structure Generation)", J. Comput. Aided Mol. Design, 7, pp. 127-153 (1993)). SPROUT is available from the University of Leeds, UK.

Other molecular modeling techniques may also be employed in accordance with this invention (See, for example, Cohen et al., "Molecular Modeling Software and Methods for Medicinal Chemistry, J. Med. Chem., 33, pp. 883-894 (1990); See also, Navia and Murcko, "The Use of Structural Information in Drug Design", Current Opinions in Structural Biology, 2, pp. 202-210 (1992); Balbes et al., "A Perspective of Modern Methods in Computer-Aided Drug Design", in Reviews in Computational Chemistry, Vol. 5, Lipkowitz and Boyd, Eds., VCH, New York, pp. 337-380 (1994); See also, Guida, "Software For Structure-Based Drug Design", Curr. Opin. Struct. Biology, 4, pp. 777-781 (1994)).

Once an entity has been designed or selected, for example, by the above methods, the efficiency with which that entity may bind to isoglutaminyl cyclase may be tested and optimized by computational evaluation. For example, an effective isoglutaminyl cyclase inhibitor preferably demonstrates a relatively small difference in energy between its bound and free states (i.e., a small deformation energy of binding). Thus, the most efficient isoglutaminyl cyclase inhibitors should preferably be designed with deformation energy of binding of not greater than about 10 kcal/mole, more preferably, not greater than 7 kcal/mole. Isoglutaminyl cyclase inhibitors may interact with the protein in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to isoglutaminyl cyclase may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (Frisch, Gaussian, Inc., Pittsburgh, Pa. 1995); AMBER, version 4.1 (Kollman, University of California at San Francisco, 1995); QUANTA/CHARMM (Molecular Simulations, Inc., San Diego, Calif. 1995); Insight II/Discover (Molecular Simulations, Inc., San Diego, Calif. 1995); DelPhi (Molecular Simulations, Inc., San Diego, Calif. 1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by the invention, is the computational screening of small molecule databases for chemical entities or compounds that can bind in whole, or in part, to isoglutaminyl cyclase. In this screening, the quality of fit of such entities to the binding site may be judged either by shape complementarities or by estimated interaction energy (Meng et al., J. Comp. Chem., 13, 505-524 (1992)).

According to a further aspect of the invention there is provided a compound that associates with isoglutaminyl cyclase produced or identified by various methods as described hereinbefore.

The structure coordinates set forth in FIG. 1 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIG. 1 as a molecular replacement model.

By using molecular replacement, all or part of the structure coordinates of isoglutaminyl cyclase provided by the invention (and set forth in FIG. 1) can be used to determine the structure of another crystallized molecule or molecular complex more quickly and efficiently than attempting an ab initio structure determination. One particular use includes use with other structurally similar proteins. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of isoglutaminyl cyclase according to FIG. 1 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (Lattman, "Use of the Rotation and Translation Functions", in Meth. Enzymol., 115, pp. 55-77 (1985); Rossmann, ed., "The Molecular Replacement Method", Int. Sci. Rev. Ser., No. 13, Gordon & Breach, New York (1972)).

The structure of any portion of any crystallized molecule or molecular complex that is sufficiently homologous to any portion of isoglutaminyl cyclase can be resolved by this method.

In one embodiment, the method of molecular replacement is utilized to obtain structural information about the present invention and any other isoglutaminyl cyclase-like molecule.

The structure coordinates of isoglutaminyl cyclase as provided by the invention are useful in solving the structure of isoglutaminyl cyclase variants that have amino acid substitutions, additions and/or deletions (referred to collectively as "isoglutaminyl cyclase mutants", as compared to naturally occurring isoglutaminyl cyclase). These isoglutaminyl cyclase mutants may optionally be crystallized in co-complex with a ligand, such as an inhibitor or substrate analogue. The crystal structures of a series of such complexes may then be solved by molecular replacement and compared with that of isoglutaminyl cyclase. Potential sites for modification within the various binding sites of the enzyme may thus be identified. This information provides an additional tool for determining the most efficient binding interactions such as, for example, increased hydrophobic interactions, between isoglutaminyl cyclase and a ligand. It is noted that the ligand may be the protein's natural ligand or may be a potential agonist or antagonist of a protein.

According to a further aspect of the invention there is provided a method of designing, selecting and/or optimising a chemical entity that binds to all or part of the binding pocket of human isoglutaminyl cyclase according to FIG. 1 comprising the steps of:
(a) providing the structural coordinates of said binding pocket of human isoglutaminyl cyclase on a computer comprising the means for generating 3-dimensional structural information from said structural coordinates; and
(b) designing selecting and/or optimising said chemical entity by performing a fitting operation between said chemical entity and said 3-dimensional structural information of all or part of said binding pocket of human isoglutaminyl cyclase.

According to a further aspect of the invention there is provided a method for evaluating the ability of a chemical entity to associate with all or part of the binding pocket of human isoglutaminyl cyclase according to FIG. 1 comprising the steps of:
(a) providing the structural coordinates of said binding pocket of human isoglutaminyl cyclase on a computer comprising the means for generating 3-dimensional structural information from said structural coordinates;
(b) employing computational means to perform a fitting operation between the chemical entity and all or part of the binding pocket of human isoglutaminyl cyclase; and
(c) analyzing the results of said fitting operation to quantitate the association between the chemical entity and all or part of the binding pocket of human isoglutaminyl cyclase.

In one embodiment, the method further comprises generating a 3-dimensional graphical representation of all or part of the binding pocket of human isoglutaminyl cyclase prior to step (b).

According to a further aspect of the invention there is provided a method of using a computer for evaluating the ability of a chemical entity to associate with all or part of the binding pocket of human isoglutaminyl cyclase according to FIG. 1, wherein said computer comprises a machine-readable data storage medium comprising a data storage material encoded with said structural coordinates defining said binding pocket of human isoglutaminyl cyclase and means for generating a three-dimensional graphical representation of the binding pocket of human isoglutaminyl cyclase, and wherein said method comprises the steps of:
(a) positioning a first chemical entity within all or part of said binding pocket of human isoglutaminyl cyclase using a graphical 3-dimensional representation of the structure of the chemical entity and the binding pocket of human isoglutaminyl cyclase;
(b) performing a fitting operation between said chemical entity and said binding pocket of human isoglutaminyl cyclase by employing computational means; and
(c) analyzing the results of said fitting operation to quantitate the association between said chemical entity and all or part of the binding pocket of human isoglutaminyl cyclase.

In one embodiment, the method further comprises the steps of:
(d) repeating steps (a) through (c) with a second chemical entity; and
(e) selecting at least one of said first or second chemical entity that associates with said all or part of said binding pocket of human isoglutaminyl cyclase based on said quantitated association of said first or second chemical entity.

According to a further aspect of the invention there is provided a method for identifying an agonist or antagonist of human isoglutaminyl cyclase according to FIG. 1, comprising the steps of:
(a) using a 3-dimensional structure of the binding pocket of human isoglutaminyl cyclase to design or select a chemical entity;
(b) contacting the chemical entity with human isoglutaminyl cyclase;
(c) monitoring the catalytic activity of human isoglutaminyl cyclase; and
(d) classifying the chemical entity as an agonist or antagonist based on the effect of the chemical entity on the catalytic activity of human isoglutaminyl cyclase.

According to a further aspect of the invention there is provided a method of designing a compound or complex that associates with all or part of the binding pocket of human isoglutaminyl cyclase according to FIG. 1, comprising the steps of:
(a) providing the structural coordinates of said binding pocket of human isoglutaminyl cyclase on a computer comprising the means for generating 3-dimensional structural information from said structural coordinates; and (b) using the computer to perform a fitting operation to associate a first chemical entity with all or part of the binding pocket;
(c) performing a fitting operation to associate at least a second chemical entity with all or part of the binding pocket;
(d) quantifying the association between the first and second chemical entity and all or part of the binding pocket;
(e) optionally repeating steps (b) to (d) with another first and second chemical entity, selecting a first and a second chemical entity based on said quantified association of all of said first and second chemical entity;
(f) optionally, visually inspecting the relationship of the first and second chemical entity to each other in relation to the binding pocket on a computer screen using the 3-dimensional graphical representation of the binding pocket and said first and second chemical entity; and
(g) assembling the first and second chemical entity into a compound or complex that associates with all or part of said binding pocket by model building.

All of the complexes referred to above may be studied using well-known X-ray diffraction techniques and may be refined versus 1.5-3.5 Å resolution X-ray data to an R value of about 0.22 or less using computer software, such as X-PLOR (Brunger et al., X-PLOR, Version 3.1, A system for X-ray crystallography and NMR, Yale University, (1992)), CNS (Brunger et al., Crystallography & NMR System (CNS), A new software suite for macromolecular structure determination, Acta Cryst. D54: 905-921 (1998)), TNT (Tronrud et al., An efficient general-Purpose least-squares refinement program for macromolecular structures, Acta Cryst. A43, 489-501 (1987)), Buster (Bricogne, The Bayesian Statistical Viewpoint on Structure Determination: Basic Concepts and Examples", in Methods in Enzymology, 276A, 361-423. Carter & Sweet, eds. (1997)) and Refmac (Murshudov et al., Refinement of macromolecular structures by the maximum-likelihood method, Acta Cryst D53:240-255 (1997)) (See, e.g., Blundell & Johnson, supra; Meth. Enzymol., Vol. 114 & 115, Wyckoff et al., eds., Academic Press (1985)). This information may thus be used to optimize known isoglutaminyl cyclase inhibitors, and more importantly, to design new isoglutaminyl cyclase inhibitors.

The structure coordinates described herein may also be used to derive the dihedral angles, phi and psi, that define the conformation of the amino acids in the protein backbone. As will be understood by those skilled in the art, the phi angle refers to the rotation around the bond between the alpha-carbon and the nitrogen, and the psi angle refers to the rotation around the bond between the carbonyl carbon and the alpha-carbon. The subscript "n" identifies the amino acid whose conformation is being described (for a general reference, See Blundell and Johnson, Protein Crystallography, Academic Press, London, 1976).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Preparation of 1-(3-(1H-Imidazol-1-yl)propyl)-3-(3, 4-dimethoxyphenyl)thiourea (Inhibitor A)

4.0 mmol of 3,4-dimethoxyphenyl isothiocyanate and 4.0 mmol of 3-(1H-imidazol-1-yl)alkyl-1-amine were dissolved in 10 mL of absolute ethanol. After stirring for 2 h under reflux, the solvent was evaporated and the resulting solid was recrystallized from ethanol.
Yield: 0.66 g (51.3%); mp: 160.0-161.0° C.
$^1$H NMR δ 1.8-2.0 (m, 2H), 3.4-3.5 (m, 2H), 3.75 (s, 6H), 3.9-4.0 (m, 2H), 6.7-6.8 (m, 1H), 6.9 (br m, 2H), 6.95 (s, 1H), 7.15 (s, 1H), 7.55 (br s, 1H), 7.6 (s, 1H), 9.3 (s, 1H); MS m/z 321.2 (M+H), 253.3 (M-$C_3H_3N_2$.)

Example 1

Expression, Purification and Crystallisation of Human Isoglutaminyl Cyclase (A) Expression and Purification of Human Isoglutaminyl Cyclase in *P. pastoris*
Host Strains and Media
*Escherichia coli* strain DH5α was used for propagation of plasmids and *P. pastoris* strain X-33 was used for the expression of human isoQC in yeast. *E. coli* and *P. pastoris* strains were grown, transformed and analyzed according to the manufacturer's instructions (Qiagen (DH5α), Invitrogen (X-33)). The media required for *E. coli*, i.e. Luria-Bertani (LB) medium, was prepared according to the manufacturers recommendations. The media required for *Pichia pastoris*, i.e. BMMY, BMGY, YPD, YPDS and the concentration of the antibiotics, i.e. Zeocin, were prepared as described in the *Pichia* manual (Invitrogen, catalog. No. K1740-01). The manual also includes all relevant descriptions for the handling of yeast.
Molecular Cloning of Plasmid Vectors Encoding the Human isoQC
All cloning procedures were done applying standard molecular biology techniques. For expression in *Pichia pastoris* X-33, the pPiCZαA (Invitrogen) was used. The cDNA of the mature human isoQC starting with codon 42 (counting from methionine II) was fused in frame with the plasmid encoded α-factor, directing the protein into the secretory pathway. After amplification utilizing the primers 5'-ATA TGA ATT CCA TCA CCA TCA CCA TCA CGA GGA GCT GCC GCT GGG CCG G-3' (SEQ ID NO: 13) (sense) and 5'-ATA TAT GCG GCC GCC TAG AGC CCC AGG TAT TCA GC-3' (SEQ ID NO: 14) (antisense), the fragment was inserted into the expression vector employing the restriction sites of NotI and EcoR I. Mutations were introduced in codons 55 using the primer 5'-CTG CGG GTC CCA TTG AAC GGA AGC CTC CCC GAA-3' (SEQ ID NO: 15) (sense) and 5'-TTC GGG GAG GCT TCC GTT CAA TGG GAC CCG CAG-3' (SEQ ID NO: 16) (antisense) as well as in codon 351 (Cys) using the primer 5'-ACG GTA CAC AAC TTG GCC CGC ATT CTC GCT GTG-3' (SEQ ID NO: 17) (sense) and 5'-CAC AGC GAG AAT GCG GGC CAA GTT GTG TAC CGT-3' (SEQ ID NO: 18) (antisense). The mutagenesis was performed according to standard PCR techniques followed by digestion of the parent DNA using DpnI (quik-change II site-directed mutagenesis kit, Stratagene, Catalog No. 200524).
Transformation of *P. pastoris* and Mini-Scale Expression
1-2 μg of plasmid DNA were applied for transformation of competent *P. pastoris* cells by electroporation according to the manufacturer's instructions (BioRad). Selection was done on plates containing 100 μg/ml Zeocin. In order to test the recombinant yeast clones upon isoQC expression, recombinants were grown for 24 h in 10 ml conical tubes containing 2 ml BMGY. Afterwards, the yeast was centrifuged and resuspended in 2 ml BMMY containing 0.5% methanol. This concentration was maintained by addition of methanol every 24 h for about 72 h. Subsequently, QC activity in the supernatant was determined. Clones that displayed the highest activity were chosen for further experiments and large scale expression.
Expression and Purification of hisoQC in *P. pastoris*
For large scale expression of isoQC in *Pichia pastoris*, the conditions were kept as described in the mini-scale expression, however, the total volume was 8 L. The expression was performed in shake flasks. After expression, cells were separated from the medium by centrifugation (1500×g, 20 min), and the pellet discarded. The pH-value of the supernatant was adjusted to neutrality, centrifuged again and applied for the first purification step. The expressed hisoQC protein was purified utilizing a 3-step protocol (Table 1) and identified as having an amino acid sequence of SEQ ID NO: 19 (see hisoQC, FIG. 2). The purification is illustrated by SDS-PAGE analysis in FIG. 3. The yield of purification was 60%. The apparent protein was inhomogeneous glycosylated as evidenced by the migration of hisoQC between 50 and 75 kDa (FIG. 3). After purification the protein was concentrated to 12 mg/ml using U-Tube™ Concentrators (Novagen) with a molecular weight cut off of 10 kDa and stored at −80° C. The hisoQC of SEQ ID NO. 19 is an N-terminal shortened fragment, representing the amino acids E60-L382 of the wild type hisoQC of SEQ ID NO: 1. Specifically, SEQ ID NO: 19 contains a his-tag (amino acid positions 1-8). The hisoQC sequence of SEQ ID NO: 19 starts at position 9 with E9 corresponding to E60 in the wildtype hisoQC of SEQ ID NO: 1. There are two mutations in SEQ ID NO. 19, the first of which is I22N, which corresponds to I73N in the wt peptide of SEQ ID NO: 1; and the second of which is C319A, which corresponds to C369A in the wt peptide of SEQ ID NO: 1. SEQ ID NO. 19 ends with L331, which corresponds to L382 of the wt peptide of SEQ ID NO: 1.

TABLE 1

Purification of hisoQC (YSShisoQCE$_{42}$I55NC351A N-His) following Expression in *P. pastoris*.

| | Purification Step | | |
|---|---|---|---|
| | 1 | 2 | 3 |
| Method | Ni$^{2+}$-IMAC | HIC | GF (Desalting) |
| Column type | Chelating | Butyl Sepharose | Sephadex G-25 |

TABLE 1-continued

Purification of hisoQC (YSShisoQCE$_{42}$I55NC351A N-His) following Expression in *P. pastoris*.

| | Purification Step | | |
|---|---|---|---|
| | 1 | 2 | 3 |
| (Amersham Biosciences AB, Sweden) | Sepharose Fast Flow | 4Fast Flow | Fine |
| Column size | d = 2.5 cm<br>l = 42 cm<br>CV = 206 cm$^3$ | d = 1.6 cm<br>l = 15.5 cm<br>CV = 23 cm$^3$ | d = 2.6 cm<br>l = 10 cm<br>CV = 53 cm$^3$ |
| Equilibration | | | |
| Buffer | 50 mM NaH$_2$PO$_4$ | 30 mM NaH$_2$PO$_4$<br>1M (NH$_4$)$_2$SO$_4$ | 50 mM Bis-Tris<br>100 mM NaCl |
| pH | 7.0 | 7.0 | 6.8 |
| Volume | 10 CV | 10 CV | 10 CV |
| Intermediate (Wash) | | | |
| Buffer | 50 mM NaH$_2$PO$_4$<br>0.5 mM Histidin | 30 mM NaH$_2$PO$_4$<br>1M (NH$_4$)$_2$SO$_4$ | — |
| pH | 7.0 | 7.0 | |
| Volume | 10 CV | 6 CV | |
| Elution | | | |
| Buffer | 50 mM NaH$_2$PO$_4$<br>100 mM Histidin | 30 mM NaH$_2$PO$_4$ | 50 mM Bis-Tris<br>100 mM NaCl |
| pH | 7.0 | 7.0 | 6.8 |
| Volume | 1.5 CV | 5 CV | 1 CV |

(B) Crystallization of Human Isoglutaminyl Cyclase

Crystal Growth

Crystals were grown using the hanging drop vapor diffusion technique at room temperature (21° C.) in Easyxtal 24-well plates plates (Qiagen). The mother liquor buffer consisted of 0.1 M sodium citrate, 0.1 M ammonium sulfate and 13% (w/v) 35000 PEG. Protein solution concentrated up to a 10 mg/ml was recombinant human isoglutaminyl cyclase (hisoQC) in the presence of 25 mM Bis-Tris pH6.8/100 mM NaCl Buffer. Before crystallization hisoQC was deglycosylated using endoglycosidase H$_f$ (New England Biolabs). The removal of the sugar chains resulted in a tremendous decrease of the solubility of hisoQC. To keep the protein soluble hisoQC was treated with detergent MEGA-8 (Fluka) (final concentration 100 mM). Afterwards the endoglycosidase H$_f$ was added (final activity 4.8*10$^3$ units/ml). The reaction was performed over night at room temperature. After deglycosylation Inhibitor A was added (final concentration 1 mM).

The crystallization of hisoQC requires homogenous protein. Therefore it was necessary to remove the glycosylation. As mentioned above deglycosylation results in a tremendous loss of solubility. To avoid protein aggregation different agents and detergents were tested on their influence on protein solubility and stability. The acyl-N-glucamid based nonionic detergent MEGA-8 turned out to be a suitable additive. Besides the mediation of solubility of hisoQC it had no detectable influence on endoglycosidase H$_f$ activity.

A mixture of 1 μl mother liquor buffer and 1 μl deglycosylated protein solution as described above was set. Crystals appeared usually ten to fifteen days after experiment was initiated and they displayed a macroscopic rod shape (FIG. 4). The crystal structure was determined to contain eleven molecules (designated as chains A-K). The sequences of these different chains were as follows:

chain A (SEQ ID NO: 2): A74-A383,
chain B (SEQ ID NO: 3): G74-L382,
chain C (SEQ ID NO: 4): G74-L382,
chain D (SEQ ID NO: 5): A75-L382,
chain E (SEQ ID NO: 6): A73-L382,
chain F (SEQ ID NO: 7): A75-L382,
chain G (SEQ ID NO: 8): A75-L382,
chain H (SEQ ID NO: 9): L76-L382,
chain I (SEQ ID NO: 10): A75-L382,
chain J (SEQ ID NO: 11): L76-L382, and
chain K (SEQ ID NO: 12): P77-L382.

Cryosolution

Before x-ray measurements, crystals were rapidly soaked into a new cryo-buffer solution where mother liquor buffer solution was saturated with 15% (vol/vol) glycerol. Immediately crystals were collected from the cryo-buffer solution using a pin nylon loop and they were mounted onto the goniometer and flash frozen at −180° C. under a nitrogen stream.

Data Collection

Data collection from a single crystal was undertaken by means of Cu Kα radiation (λ=1.5418 Å) by using a rotating-anode source (RA Micro 007; Rigaku/MSC, Tokyo, Japan) and CCD detector device (CCD Saturn 944+, Rigaku) with Varimax™ Optics (Rigaku) and an AFC-11 goniometer.

Finally, the crystal was demounted and stored in liquid nitrogen for an additional measurement in the beam line Bessx-MX BL14.1 of the synchrotron in Berlin (Bessy). Resolution cut-off was set to an I/sig(I) of 1.9 with a Rmerge of 13.7 achieving finally a 3.42 Angstrom of resolution.

Data Processing

The image reflection intensities were indexed and integrated using the program XDS. Further data processing was carried out using the programs included in the crystallographic suite CCP4. The integrated intensities were scaled and merged using the program Scala. The initial mtz file was analysed by calculating Mathews coefficient. Mathews coefficient showed the highest probability for an asymmetric unit (AU) containing either 11 or 12 molecules with a water content of about 50%.

Moreover, initial phases were subsequently obtained with a molecular replacement approach using Phaser. The crystal structure of human glutaminyl cyclase (hQC) (structure not yet published) was taken as a searching model. Previous to phasing the PDB file of the hQC file was modified with Chainsaw program to replace the original sequence of hQC for the one of hisoQC. This model gave a solution that showed rotational (RFZ) and translational (TFZ)I scores of 4.7 and 29.1 respectively and a LLG score of 4846 indicating the likeliness of a useful solution. The Phaser solution succeeded with an initial model containing 11 molecules in the AU (FIG. 5) showing additional well defined positive electron density maps localized on the area of active site related residues Thus, initial electron densities were obtained. Subsequent manual building of the missing fragments and maximum-likelihood refinement cycles were performed by using the programs COOT and REFMAC5 as well from the CCP4 suite. Initially, model building was eased using an averaged FoFc density map that was used to more accurately model the chain A. Furthermore an Non-crystallographic symmetry (NCS) refinement was performed using chain A as template and applying tight NCS restrains to main chain and side chain residues of chains B, C, D, E, F, G, H, I, J and K in the residue range from 77 to 380. Thus the model was improved achieving $R_{work}$ and $R_{free}$ of 26.84 and 31.7 respectively Results Table 2 summarizes the statistics of the data set obtained in Berlin synchrotron Bessy with a crystal of the human isoglutaminyl cyclase and their corresponding statistics for the data processing and model building. Programs used were for data processing XDS and SCALA, for molecular replacement PHASER, for refinement REFMAC5 and for Model Building: Coot (all of them included in the CCP4 suite). Numbers between brackets belong to the outer shell resolution limit.

TABLE 2

Summary of Statistics for Human Isoglutaminyl Cyclase Crystal

Data collection

| | |
|---|---|
| Data set collected at | BESSY |
| Space group | P1 21 1 |
| Cell dimensions | |
| a, b, c (Å) | 126.51 109.68 159.53 |
| α, β, γ (°) | 90.0 104.9 90.0 |
| Resolution (Å) | 34.72-3.42 |
| Rmerge | 13.7 (46.3) |
| I/Signal | 6.7 (1.9) |
| Completeness (%) | 83.7 (86.2) |
| Redundancy | 1.8 (1.7) |
| Refinement | |
| Resolution (Å) | 3.42 |
| No. reflections (work/test) | 53920/2838 |
| $R_{work}/R_{free}$ | 26.8/31.31 |
| No. atoms | |
| Protein | 26523 |
| Water | 203 |
| B-factors (Mean value) | 42.37 |

TABLE 2-continued

Summary of Statistics for Human Isoglutaminyl Cyclase Crystal

Data collection

R.m.s deviations

| | |
|---|---|
| Bond lengths (Å) | 0.011 |
| Bond angles (°) | 1.748 |

Figure 7:
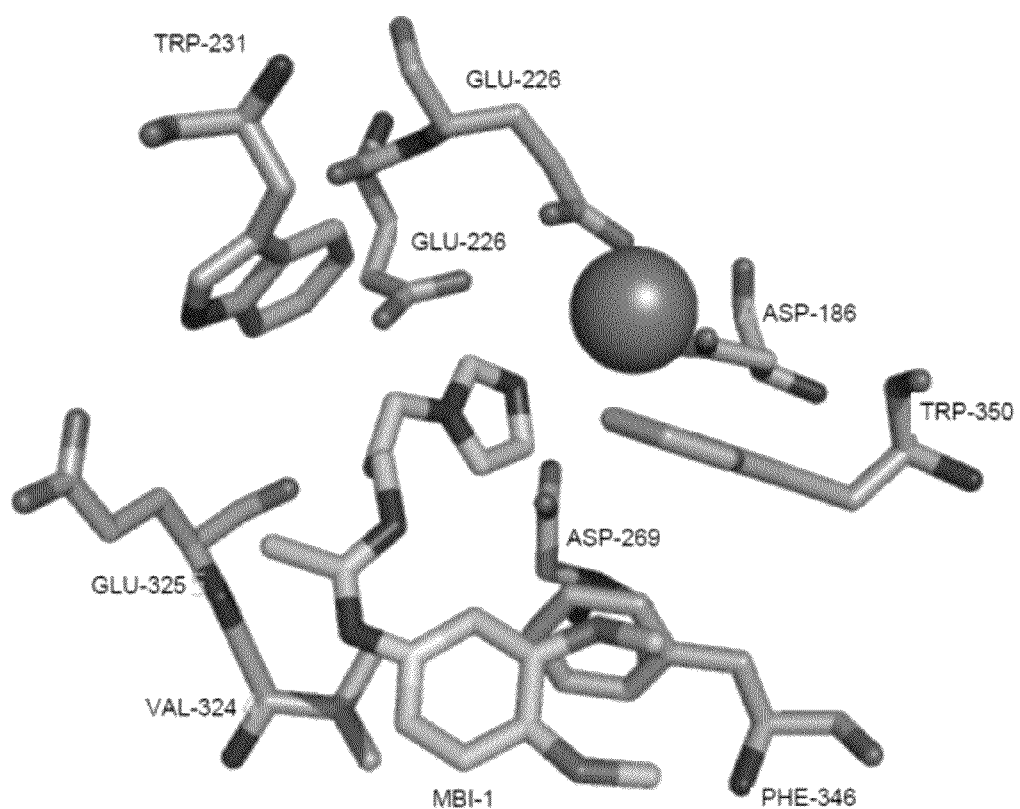
FIG. 7 describes a detailed representation of the modeled active site of chain A in complex with an inhibitory molecule. Stick representation of the active site related residues of human isoQC forming complex with Inhibitor A with the catalytic zinc ion shown with a sphere.

Overall three dimensional structure. For the sake of simplicity the chain A of the asymmetric unit will be described. The model built from the obtained experimental electron density includes 11 molecules of the hisoQC and expands the polypeptide chain from residue 75 to 383. The model includes a zinc ion that is achieving a complex with the Inhibitor A molecule (FIG. 7). The protein shows a globular α/β hydrolase fold (FIG. 6). A central β-sheet is formed with six β-strands all in parallel fashion but not the second. This β-sheet is surrounded by α-helices in a sandwich manner with two helices in one side and six more α-helices in the opposite face. The protein's structure is completed with a rather large amount of random coiled loops which are building the active site of the enzyme. This active site is accommodating a zinc ion which is coordinated by three protein residues, $E^{226}$, $D^{186}$ and $H^{351}$ and a molecule of Inhibitor A (FIG. 7). Moreover the protein shows the presence of a disulfide bridge between residues $C^{167}$ and $C^{191}$. Finally two segments of the polypeptide chain are not visible in the electron density. The gaps include residues between $K^{182}$ and $D^{190}$ and between $F^{146}$ and $N^{150}$.

What is claimed is:

1. A crystal comprising:
human isoglutaminyl cyclase comprising SEQ ID NOS: 19 wherein said crystal is characterized as having space group P1211 and unit cell dimensions of +/−5% of a=126.51 Å, b=109.68 Å, c=159.53 Å, α=90.0°, β=104.9° and γ=90.0°.

2. A crystal as defined in claim 1, which diffracts x-rays for determination of atomic co-ordinates of the crystal to a resolution of between 3.42 Å and 34.72 Å.

3. A crystal as defined in claim 1, wherein the human isoglutaminyl cyclase consists of amino acid residues N22 to L331 of SEQ ID NO: 19, corresponding to amino acid residues 73 to 382 of SEQ ID NO: 1.

4. A crystal as defined in claim 3, which comprises a binding pocket provided by residues E175, D135 and H301 of SEQ ID NO: 19, corresponding to E226, D186 and H351 of SEQ ID NO: 1.

5. A crystal as defined in claim 3, which comprises a disulfide bridge between residues C116 and C140 of SEQ ID NO: 19, corresponding to C167 and C191 of SEQ ID NO: 1.

6. A co-crystal comprising the crystal as defined in claim 1 bound to a binding ligand, such as an isoglutaminyl cyclase inhibitor.

7. A method of preparing the crystal of human isoglutaminyl cyclase as described in claim 1, which comprises the steps of:
(a) providing a solution having said human isoglutaminyl cyclase, optionally in the presence of a known isoglutaminyl cyclase inhibitor, in a suitable buffer such as 25 mM Bis-Tris pH 6.8/100 mM NaCl buffer;
(b) mixing the solution with a crystallization solution comprising 0.1 M sodium citrate, 0.1 M ammonium sulfate and 13% (w/v) 35000 PEG; and
(c) incubating the mixture under conditions to promote hanging drop vapor diffusion for a time sufficient to produce the crystal of human isoglutaminyl cyclase.

8. A method of preparing the co-crystal as defined in claim 6, which comprises the steps of:
(a) providing a solution having said human isoglutaminyl cyclase in the presence of a binding ligand, such as an isoglutaminyl cyclase inhibitor, in a suitable buffer such as 25 mM Bis-Tris pH 6.8/100 mM NaCl buffer;
(b) mixing the solution with a crystallization solution comprising 0.1 M sodium citrate, 0.1 M ammonium sulfate and 13% (w/v) 35000 PEG; and
(c) incubating the mixture under conditions to promote hanging drop vapor diffusion for a time sufficient to produce the co-crystal of human isoglutaminyl cyclase bound to a binding ligand, such as an isoglutaminyl cyclase inhibitor.

9. A crystal or co-crystal comprising human isoglutaminyl cyclase obtainable by the crystallisation method as defined in claim 7.

10. The crystal of claim 1, wherein said polypeptide forms a decamer within the unit cell and is characterized according to the coordinates of FIG. 1.

* * * * *